US009574189B2

(12) United States Patent
Franch et al.

(10) Patent No.: US 9,574,189 B2
(45) Date of Patent: Feb. 21, 2017

(54) ENZYMATIC ENCODING METHODS FOR EFFICIENT SYNTHESIS OF LARGE LIBRARIES

(75) Inventors: Thomas Franch, Snekkersten (DK); Mikkel Dybro Lundorf, København Ø (DK); Søren Nyboe Jacobsen, Frederiksberg (DK); Eva Kampmann Olsen, Herlev (DK); Anne Lee Andersen, Ringsted (DK); Anette Holtmann, Ballerup (DK); Anders Holm Hansen, København NV (DK); Anders Malling Sørensen, København NV (DK); Anne Goldbech, København NV (DK); Daen de Leon, København S (DK); Ditte Kievsmose Kaldor, København NV (DK); Frank Abildgaard Sløk, Allerød (DK); Gitte Nystrup Husemoen, Valby (DK); Johannes Dolberg, København K (DK); Kim Birkebæ Jensen, Rødovre (DK); Lene Pedersen, København Ø (DK); Mads Nørregaard-Madsen, Birkerød (DK); Michael Anders Godskesen, Vedbæk (DK); Sanne Schrøder Glad, Ballerup (DK); Søren Neve, Lyngby (DK); Thomas Thisted, Frederikssund (DK); Tine Titilola Akinleminu Kronborg, Værløse (DK); Christian Klarner Sams, Værløse (DK); Jakob Felding, Charlottenlund (DK); Per-Ola Freskgård, Norrköpping (SE); Alex Haahr Gouliaev, Veksø Sjælland (DK); Henrik Pedersen, Bagsværd (DK)

(73) Assignee: Nuevolution A/S, Copenhagen (DK)

( * ) Notice: Subject to any disclaimer, the term of this patent is extended or adjusted under 35 U.S.C. 154(b) by 1724 days.

(21) Appl. No.: 12/095,778

(22) PCT Filed: Dec. 1, 2006

(86) PCT No.: PCT/DK2006/000685
§ 371 (c)(1),
(2), (4) Date: Dec. 15, 2008

(87) PCT Pub. No.: WO2007/062664
PCT Pub. Date: Jun. 7, 2007

(65) Prior Publication Data
US 2009/0264300 A1    Oct. 22, 2009

Related U.S. Application Data

(60) Provisional application No. 60/741,490, filed on Dec. 2, 2005.

(30) Foreign Application Priority Data

Dec. 1, 2005 (DK) ................................ 2005 01704

(51) Int. Cl.
C12N 15/10 (2006.01)
C40B 40/08 (2006.01)
C40B 50/04 (2006.01)
C40B 50/06 (2006.01)

(52) U.S. Cl.
CPC ....... *C12N 15/1068* (2013.01); *C12N 15/1089* (2013.01); *C40B 40/08* (2013.01); *C40B 50/04* (2013.01); *C40B 50/06* (2013.01)

(58) Field of Classification Search
None
See application file for complete search history.

(56) References Cited

U.S. PATENT DOCUMENTS

| | | |
|---|---|---|
| 4,822,731 A | 4/1989 | Watson et al. |
| 5,013,830 A | 5/1991 | Ohtsuka et al. |
| 5,047,519 A | 9/1991 | Hobbs, Jr. et al. |
| 5,324,829 A | 6/1994 | Bahl et al. |
| 5,432,272 A | 7/1995 | Benner |
| 5,437,977 A | 8/1995 | Segev |
| 5,449,613 A | 9/1995 | Dordick et al. |
| 5,451,503 A | 9/1995 | Hogan et al. |
| 5,473,060 A | 12/1995 | Gryaznov et al. |
| 5,474,796 A | 12/1995 | Brennan |
| 5,476,930 A | 12/1995 | Letsinger et al. |
| 5,503,805 A | 4/1996 | Sugarman et al. |

(Continued)

FOREIGN PATENT DOCUMENTS

| | | |
|---|---|---|
| DE | 19646372 | 6/1997 |
| DE | 196 42 751 A1 | 4/1998 |

(Continued)

OTHER PUBLICATIONS

Millward, S.W. et al. "A General Route for Post-Translational Cyclization of mRNA Display Libraries", *Journal of the American Chemical Society:* vol. 127, 14142-14143, (2005).

(Continued)

*Primary Examiner* — Christopher M Gross
(74) *Attorney, Agent, or Firm* — Merchant & Gould P.C.

(57) ABSTRACT

Disclosed is a method for obtaining a bifunctional complex comprising a molecule linked to a single stranded identifier oligonucleotide, wherein a nascent bifunctional complex comprising a chemical reaction site and a priming site for enzymatic addition of a tag is a) reacted at the chemical reaction site with one or more reactants, and b) reacted enzymatically at the priming site with one or more tag(s) identifying the reactant(s).

38 Claims, 61 Drawing Sheets

(56) References Cited

U.S. PATENT DOCUMENTS

Figure 1:
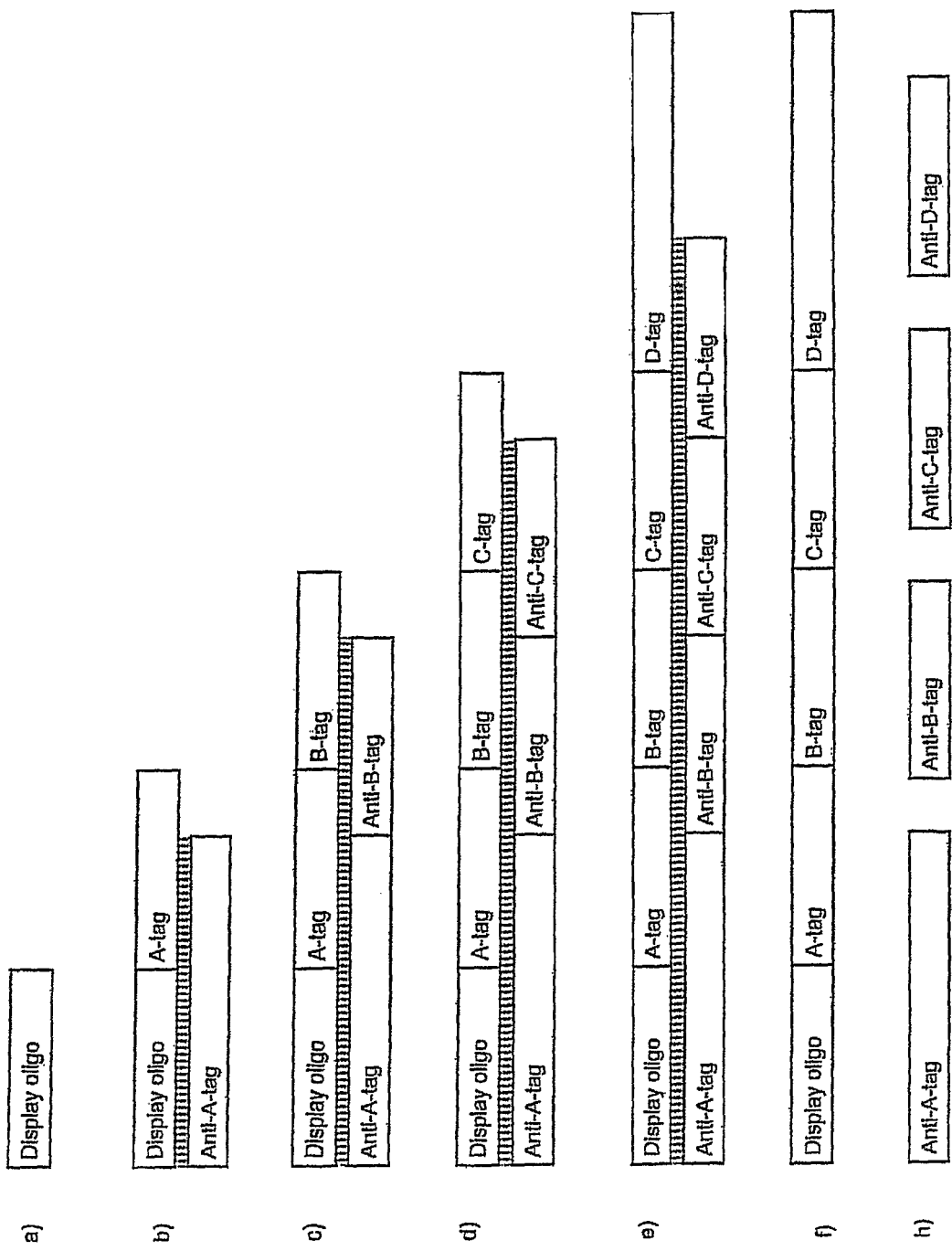

| | | |
|---|---|---|
| 5,571,677 A | 11/1996 | Gryaznov |
| 5,571,903 A | 11/1996 | Gryaznov et al. |
| 5,573,905 A | 11/1996 | Lerner et al. |
| 5,604,097 A | 2/1997 | Brenner |
| 5,635,400 A | 6/1997 | Brenner |
| 5,639,603 A | 6/1997 | Dower et al. |
| 5,643,722 A | 7/1997 | Rothschild et al. |
| 5,646,265 A | 7/1997 | McGee |
| 5,654,413 A | 8/1997 | Brenner |
| 5,656,739 A | 8/1997 | Cubicciotti |
| 5,663,046 A | 9/1997 | Baldwin et al. |
| 5,665,975 A | 9/1997 | Kedar et al. |
| 5,670,633 A | 9/1997 | Cook et al. |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A | 3/1998 | Lerner et al. |
| 5,739,314 A | 4/1998 | Roy et al. |
| 5,739,386 A | 4/1998 | Holmes |
| 5,741,643 A | 4/1998 | Gryaznov et al. |
| 5,763,175 A | 6/1998 | Brenner |
| 5,763,263 A | 6/1998 | Dehlinger |
| 5,770,358 A | 6/1998 | Dower et al. |
| 5,770,455 A | 6/1998 | Cargill et al. |
| 5,780,613 A | 7/1998 | Letsinger et al. |
| 5,789,162 A | 8/1998 | Dower et al. |
| 5,789,172 A | 8/1998 | Still et al. |
| 5,795,976 A | 8/1998 | Oefner et al. |
| 5,804,563 A | 9/1998 | Still et al. |
| 5,817,795 A | 10/1998 | Gryaznov et al. |
| 5,824,471 A | 10/1998 | Mashal et al. |
| 5,830,658 A | 11/1998 | Gryaznov et al. |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,880,972 A | 3/1999 | Horlbeck |
| 5,942,609 A | 8/1999 | Hunkapiller |
| 5,948,648 A | 9/1999 | Khan et al. |
| 6,001,579 A | 12/1999 | Still et al. |
| 6,056,926 A | 5/2000 | Sugarman et al. |
| 6,060,596 A | 5/2000 | Lerner et al. |
| 6,087,112 A | 7/2000 | Dale |
| 6,090,912 A | 7/2000 | Lebl et al. |
| 6,096,500 A | 8/2000 | Oprandy et al. |
| 6,096,875 A | 8/2000 | Khan et al. |
| 6,127,533 A | 10/2000 | Cook et al. |
| 6,132,970 A | 10/2000 | Stemmer |
| 6,140,489 A | 10/2000 | Brenner |
| 6,140,493 A | 10/2000 | Dower et al. |
| 6,143,497 A | 11/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar et al. |
| 6,172,214 B1 | 1/2001 | Brenner |
| 6,194,550 B1 | 2/2001 | Gold et al. |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,287,765 B1 | 9/2001 | Cubicciotti et al. |
| 6,297,053 B1 | 10/2001 | Stemmer |
| 6,306,587 B1 | 10/2001 | Royer et al. |
| 6,352,828 B1 | 3/2002 | Brenner |
| 6,416,949 B1 | 7/2002 | Dower et al. |
| 6,429,300 B1 | 8/2002 | Kurz et al. |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,915,201 B2 | 3/2011 | Franch et al. |
| 7,998,904 B2 | 8/2011 | Liu et al. |
| 8,206,901 B2 | 6/2012 | Freskgard et al. |
| 2002/0048760 A1 | 4/2002 | Drmanac et al. |
| 2002/0055125 A1 | 5/2002 | Charych et al. |
| 2002/0072887 A1 | 6/2002 | Szalma et al. |
| 2002/0081714 A1 | 6/2002 | Jain et al. |
| 2002/0115068 A1 | 8/2002 | Tomlinson et al. |
| 2002/0127598 A1 | 9/2002 | Zhou et al. |
| 2002/0142335 A1 | 10/2002 | Strittmatter |
| 2003/0004122 A1 | 1/2003 | Beigelman et al. |
| 2003/0050453 A1 | 3/2003 | Sorge |
| 2003/0113738 A1* | 6/2003 | Liu et al. ............ 435/6 |
| 2003/0182068 A1 | 9/2003 | Battersby et al. |
| 2003/0186233 A1 | 10/2003 | Chesnut et al. |
| 2003/0187240 A1 | 10/2003 | Cook et al. |
| 2004/0049008 A1 | 3/2004 | Pedersen et al. |
| 2004/0110213 A1 | 6/2004 | Namsaraev |
| 2004/0161741 A1 | 8/2004 | Rabani et al. |
| 2004/0185484 A1 | 9/2004 | Costa et al. |
| 2004/0191812 A1 | 9/2004 | Davydova et al. |
| 2004/0197802 A1* | 10/2004 | Dahl ............... C12N 15/1096 435/6.11 |
| 2004/0197804 A1 | 10/2004 | Keefe et al. |
| 2004/0197845 A1 | 10/2004 | Hassibi et al. |
| 2004/0209282 A1 | 10/2004 | Ault-Riche et al. |
| 2005/0025766 A1 | 2/2005 | Liu |
| 2005/0042669 A1 | 2/2005 | Liu |
| 2005/0130173 A1 | 6/2005 | Leamon et al. |
| 2005/0142583 A1 | 6/2005 | Liu et al. |
| 2005/0158765 A1 | 7/2005 | Morgan et al. |
| 2005/0170376 A1 | 8/2005 | Liu et al. |
| 2006/0099592 A1 | 5/2006 | Freskgard et al. |
| 2006/0121470 A1 | 6/2006 | Pedersen |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0224607 A1 | 9/2007 | Morgan et al. |
| 2008/0193983 A1 | 8/2008 | Gouliaev et al. |
| 2008/0305957 A1 | 12/2008 | Thisted et al. |
| 2009/0035824 A1 | 2/2009 | Liu et al. |
| 2009/0143232 A1 | 6/2009 | Pedersen et al. |
| 2009/0149347 A1 | 6/2009 | Liu et al. |
| 2009/0239211 A1 | 9/2009 | Freskgard et al. |
| 2009/0264300 A1 | 10/2009 | Franch et al. |
| 2010/0016177 A1 | 1/2010 | Pedersen et al. |
| 2011/0230419 A1 | 9/2011 | Lundorf et al. |
| 2012/0028812 A1 | 2/2012 | Freskgard et al. |
| 2014/0179539 A1* | 6/2014 | Lohman ............... C12Q 1/6862 506/7 |

FOREIGN PATENT DOCUMENTS

| | | |
|---|---|---|
| EP | 0324616 | 7/1989 |
| EP | 0604552 | 4/1993 |
| EP | 0542770 | 5/1993 |
| EP | 0643778 | 10/1993 |
| EP | 0695305 | 10/1994 |

(56) References Cited

FOREIGN PATENT DOCUMENTS

| | | |
|---|---|---|
| EP | 0776330 | 10/1996 |
| EP | 0766826 | 4/1997 |
| EP | 0773227 | 5/1997 |
| EP | 0 778 280 B1 | 6/1997 |
| EP | 0879219 | 11/1998 |
| EP | 0 962 527 B1 | 12/1999 |
| EP | 1324045 | 7/2003 |
| EP | 1 402 024 B1 | 3/2004 |
| EP | 1 483 585 B1 | 12/2004 |
| EP | 1514938 | 3/2005 |
| EP | 1533385 | 5/2005 |
| EP | 1 828 381 B1 | 9/2007 |
| EP | 1 832 567 A2 | 9/2007 |
| EP | 2 305 808 | 4/2011 |
| WO | 9005785 | 5/1990 |
| WO | 9105058 | 4/1991 |
| WO | WO 91/19818 | 12/1991 |
| WO | WO 92/00091 | 1/1992 |
| WO | WO 92/02536 | 2/1992 |
| WO | WO 92/22875 | 12/1992 |
| WO | 9303172 | 2/1993 |
| WO | WO 93/06121 | 4/1993 |
| WO | WO 93/20242 | 10/1993 |
| WO | 9408051 | 4/1994 |
| WO | WO 94/13623 | 6/1994 |
| WO | WO 94/24143 | 10/1994 |
| WO | WO 95/04160 | 2/1995 |
| WO | WO 95/06293 | 3/1995 |
| WO | 9512608 | 5/1995 |
| WO | 9603418 | 2/1996 |
| WO | 9609316 | 3/1996 |
| WO | 9611878 | 4/1996 |
| WO | 9612014 | 4/1996 |
| WO | 9624847 | 8/1996 |
| WO | 9635699 | 11/1996 |
| WO | 9640201 | 12/1996 |
| WO | WO 96/41011 | 12/1996 |
| WO | 9711958 | 4/1997 |
| WO | 9719039 | 5/1997 |
| WO | WO 97/27317 | 7/1997 |
| WO | WO 97/35198 | 9/1997 |
| WO | WO 98/01562 | 1/1998 |
| WO | 9831700 | 7/1998 |
| WO | 9847613 | 10/1998 |
| WO | 9856904 | 12/1998 |
| WO | 9858256 | 12/1998 |
| WO | 9942605 | 8/1999 |
| WO | WO 99/51546 | 10/1999 |
| WO | WO 99/51773 | 10/1999 |
| WO | 9964378 | 12/1999 |
| WO | 0021909 | 4/2000 |
| WO | 0023458 | 4/2000 |
| WO | WO00/20639 | 4/2000 |
| WO | WO 00/20639 | 4/2000 |
| WO | WO 00/23456 | 4/2000 |
| WO | 0024882 | 5/2000 |
| WO | 0032823 | 6/2000 |
| WO | 0040695 | 7/2000 |
| WO | 0047775 | 8/2000 |
| WO | 0061775 | 10/2000 |
| WO | 0100876 | 1/2001 |
| WO | WO 01/07657 | 2/2001 |
| WO | WO 01/07690 | 2/2001 |
| WO | WO 01/79420 * | 4/2001 |
| WO | WO 01/53539 | 7/2001 |
| WO | 0156955 | 8/2001 |
| WO | WO 01/90414 | 11/2001 |
| WO | 0203067 | 1/2002 |
| WO | WO 02/10186 | 2/2002 |
| WO | WO 02/34948 | 5/2002 |
| WO | WO 02/40664 | 5/2002 |
| WO | 02074929 | 9/2002 |
| WO | WO 02/074978 | 9/2002 |
| WO | WO 02/083951 | 10/2002 |
| WO | WO02090581 | 11/2002 |
| WO | 02102820 | 12/2002 |
| WO | 02103008 | 12/2002 |
| WO | WO 02/099078 | 12/2002 |
| WO | WO 03/025567 | 3/2003 |
| WO | WO 03/062417 | 7/2003 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03078627 | 9/2003 |
| WO | WO 03/076943 | 9/2003 |
| WO | 03082901 | 10/2003 |
| WO | 03106679 | 12/2003 |
| WO | 04001042 | 12/2003 |
| WO | 2004009814 | 1/2004 |
| WO | WO 2004/007529 | 1/2004 |
| WO | 2004013070 | 2/2004 |
| WO | 2004016767 | 2/2004 |
| WO | 2004024929 | 3/2004 |
| WO | 2004039962 | 5/2004 |
| WO | 2004042019 | 5/2004 |
| WO | WO 2004/039825 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 | 11/2004 |
| WO | 2004110964 | 12/2004 |
| WO | 2005003778 | 1/2005 |
| WO | WO 2005/008240 | 1/2005 |
| WO | 2005026387 | 3/2005 |
| WO | 2005058479 | 7/2005 |
| WO | 2005078122 | 8/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | WO 2006/128138 | 11/2006 |
| WO | 2006135786 | 12/2006 |
| WO | WO 2006/130669 | 12/2006 |
| WO | WO 2006/133312 | 12/2006 |
| WO | WO 2006/135654 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | 2007053358 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO2008/094599 | 8/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

Millward, S.W. et al. "Design of Cyclic Peptides That Bind Protein Surfaces with Antibody-Like Affinity", *ACS Chemical Biology:* vol. 2, No. 9, 625-634, (2007).

Giebel, L.B. et al. "Screening of Cyclic Peptide Phage Libraries Identifies Ligands That Bind Streptavidin with High Affinities", *Biochemistry:* vol. 34, No. 47; 15430-15435, (1995).

Ladner, R.C. "Constrained peptides as binding entities", Elsevier Science Ltd., *Trends in Biotechnology:* vol. 13, 426-430, (1995).

Koivunen, E. et al. "Phage Libraries Displaying Cyclic Peptides with Different Ring Sizes: Ligand Specificities of the RGD-Directed Integrins", *Bio/Technology:* vol. 13, 265-270, (1995).

Office Action in European patent application No. 10184311.8, dated Mar. 19, 2012, with Annex.

(56) References Cited

OTHER PUBLICATIONS

Office Action in Israel patent application No. 207672, dated Jan. 15, 2012, with English translation.
Response to OA in Israel patent application No. 207672, dated Jun. 14, 2012.
Office Action in Israel patent application No. 207673, dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application No. 200380104764.5, dated Jul. 16, 2012.
Office Action in Japanese patent application No. P2010-226107, dated Jul. 10, 2012, with English translation.
Office Action in European patent application No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.
Abravaya et al. "Detection of point mutations with a modified ligase chain reaction (GAP-LCR)", Nucleic Acids Research, vol. 23, No. 4, pp. 675-682 (1995).
Acinas, et al. "PCR-Induced Sequence Artifacts and Bias: Insights from Comparison of Two 16S rRNA Clone Libraries Constructed from the same Sample", Applied and Environmental Microbiology, vol. 71, No. 12, pp. 8966-8969 (2005).
Annex I: Vipergen Technology Paper—The YoctoReactor drug discovery technology platform. 2 pages.
Annex II: Vipergen Technology Paper—The YoctoReactor drug discovery technology platform. 2 pages. Aug. 2008.
Australian Patents Act 19909—Sectino 32 Regulation 3.6, (Request for a Determination of Dispute between Applicants) and 3.7 Application to Commisioner for Declaration of an Eligible Person.
Barany, "Genetic disease detection and DNA amplification using cloned thermostable ligase", Proc. Natl. Acad. Sci., vol. 88, pp. 189-193 (1991).
Bittker, et al. "Nucleic Acid Evolution and Minimization by Non-homologous Random Recombination", Nature Biotechnology, vol. 20, pp. 1024-1029 (Oct. 2002).
Borman, "Combinatorial chemists focus on small molecules, molecular recognition, and automation", Chemical & Engineering News, pp. 29-54 (Feb. 12, 1996).
Brennan, et al. "Using T4 RNA Ligase with DNA Substrates", Methods in Enzymology, vol. 100, pp. 38-52 (1983).
Braasch, et al. "Locked nucleic acid (LNA): fine-tuning the recognition of DNA and RNA", Chemistry & Biology, vol. 8, pp. 1-7 (2001).
Broude, "Stem-loop oligonucleotides: a robust tool for molecular biology and biotechnology", TRENDS in Biotechnology, vol. 20, No. 6, pp. 249-256 (Jun. 2002).
Buller, "Design and synthesis of a novel DNA-encoded chemical library using Diels-Alder cycloadditions", Bioorg Med Chem Lett., vol. 18, pp. 5926-5931 (2008).
Buller, "Discovery of TNF Inhibitors from a DNA-Encoded Chemical Library based on Diels-Alder Cycloaddition", Chemistry & Biology, vol. 16, pp. 1075-1086 (2009).
Buller, "Drug Discovery with DNA-Encoded Chemical Libraries", Bioconjugate Chem., vol. 21, No. 9, pp. 1571-1580 (2010).
Bunin, et al. "Synthesis and Evaluation of 1,4-Benzodiazepine Libraries", Methods in Enzymology, vol. 267, pp. 448-465 (1996).
Bunin, et al. "The combinatorial synthesis and chemical and biological evaluation of a 1,4-benzodiazepine library", Proc. Natl. Acad. Sci. USA, vol. 91, pp. 4708-4712 (May 1994).
Buskirk, et al. "Engineering a Ligand-Dependent RNA Transcriptional Activator", Chemistry & Biology, vol. 11, pp. 1157-1163 (2004). This work is featured in a Research Highlight in Nature Methods, vol. 1, pp. 6-7 (2004).
Canne, et al. "Chemical Protein Synthesis by Solid Phase Ligation of Unprotected Peptide Segments", J. Am. Chem. Soc., vol. 121, pp. 8720-8727 (1999).
Clark, et al. "Design, synthesis and selection of DNA-encoded small-molecule libraries", Nature Chemistry Biology, vol. 5, pp. 647-654 (2009).
Clark, "Selecting chemicals: the emerging utility of DNA-encoded libraries", Current Opinion in Chemical Biology, vol. 14, pp. 396-403 (2010).
Costantino, et al. "Privileged Structures as Leads in Medicinal Chemistry", Current Medicinal Chemistry, vol. 13, pp. 65-85 (2006).
Cotton, et al. "Reactivity of cytosine and thymine in single-base-pair mismatches with hydroxylamine and osmium tetroxide and its application to the study of mutations", Proc Natl. Acad. Sci. USA, vol. 85, pp. 4397-4401 (Jun. 1988).
Czarnik, "Encoding strategies in combinatorial chemistry", Proc. Natl. Acad. Sci. USA, vol. 94, pp. 12738-12739 (Nov. 1997).
"Dokl Akad Nauk SSSR", vol. 258, pp. 1242-1245, Krynetskya NF Tumanov YV (1981).
Dolinnaya, et al. "Chemical ligation as a method for the assembly of double-stranded nucleic acids: Modifications and local structure studies", Russian Chemical Bulletin, vol. 45, No. 8, pp. 1787-1809 (Aug. 1996).
Dolinnaya, et al. "Structural and kinetic aspects of chemical reactions in DNA duplexes. Information on DNA local structure obtained from chemical ligation data", Nucleic Acids Research, vol. 19, No. 11, 3073-3080 (1991).
Doyon, et al. "Highly Sensitive in Vitro Selections for DNA-Linked Synthetic Small Molecules with Protein Binding Affinity and Specificity", J. Am. Chem. Soc, vol. 125, pp. 12372-12373 (2003).
Drabovich, et al. "Selection of Smart Small-Molecule Ligands: The Proof of Principle", Analytical Chemistry, vol. 81, No. 1, pp. 490-494 (2009).
Drews, "Drug Discovery: A Historical Perspective", Science vol. 287, pp. 1960-1964 (2000).
Ecker, et al. "Rational screening of oligonucleotide combinatorial libraries for drug discovery", Nucleic Acids Research, vol. 21, No. 8, pp. 1853-1856 (1993).
Fack, et al. "Heteroduplex mobility assay (HMA) pre-screening: An improved strategy for the rapid identification of inserts selected from phage-displayed peptide libraries", Molecular Diversity, vol. 5, pp. 7-12 (2000).
Fegan, et al. "Rigid cyanine dye nucleic acid labels", Chem. Commun., pp. 2004-2006 (2008).
Furka, et al. "Combinatorial Libraries by Portioning and Mixing", Combinatorial Chemistry & High Throughput Screening, vol. 2, pp. 105-122 (1999).
Gorin, et al. "Reactivity-Dependent PCR: Direct, Solution-Phase in Vitro Selection for Bond Formation", J. Am. Chem., vol. 131, pp. 9189-9191 (2009).
Grange, et al. "Detection of point mutations in type I collagen by RNase digestion of RNA/RNA hybrids", Nucleic Acids Research, vol. 18, No. 14, pp. 4227-4236 (1990).
Gruen, et al. "An in vivo selection system for homing endonuclease activity", Nucleic Acids Research, vol. 30, No. 7 e29, 6 pages (2002).
Gumport, et al. "T4 RNA Ligase as a Nucleic Acid Synthesis and Modification Reagent", Elsevier North Holland, Inc., pp. 314-345 (1981).
Guo, et al. "Preparation of Encoded Combinatorial Libraries for Drug Discovery", Methods in Molecular Biology, Combinatorial Library Methods and Protocols, pp. 23-39.
Hansen, et al. "A Yoctoliter-Scale DNA Reactor for Small-Molecule Evolution", J. Am. Chem. Soc., vol. 131, pp. 1322-1327 (2009).

(56) References Cited

OTHER PUBLICATIONS

Harada, et al. In vitro selection of optimal DNA substrates for T4 RNA ligase, Proc. Natl. Acad. Sci. USA, vol. 90, pp. 1576-1579 (Feb. 1993).
Harada, et al. "Unexpected substrate specificity of T4 DNA ligase revealed by in vitro selection", Nucleic Acids Research, vol. 21, No. 10, pp. 2287-2291 (1993).
Harada, et al. "In Vitro Selection of Optimal DNA Substrates for Ligation by a Water-Soluble Carbodiimide", J Mol Evol., vol. 38, pp. 558-560 (1994).
Herpin, et al. "Synthesis of a 10 000 Member 1,5-Benzodiazepine-2-one Library by the Directed Sorting Method", J. Comb. Chem., vol. 2, pp. 513-521 (2000).
Higgins, et al. "Addition of oligonucleotides to the 5'-terminus of DNA by T4 RNA ligase", Nucleic Acids Research, vol. 6, No. 3, pp. 1013-1024 (Mar. 1979).
Higgins, et al. "DNA-Joining Enzymes: A Review", Methods in Enzymology, vol. 68, pp. 50-71 (1979).
Hinton, et al. "T4 RNA Ligase Joins 2'-Deoxyribonucleoside 3', 5'-Bisphosphates to Oligodeoxyribonucleotides", Biochemistry, vol. 17, No. 24, pp. 5091-5097 (1978).
Holmes, "Model Studies for New o-Nitrobenzyl Photolabile Linkers: Substituent Effects on the Rates of Photochemical Cleavage", J. Org. Chem., vol. 62, pp. 2370-2380 (1997).
Housby, et al. "Fidelity of DNA ligation: a novel experimental approach based on the polymerisation of libraries of oligonucleotides", Nucleic Acids Research, vol. 26, No. 18, pp. 4259-4266 (1998).
Hsu, et al. "Detection of DNA point mutations with DNA mismatch repair enzymes" Carcinogenesis, vol. 15, No. 8, pp. 1657-1662 (1994).
Ito, et al. Tag-Reporter and Resin Capture-Release Strategy in Oligosaccharide Synthesis. Chem. Eur. J., vol. 8, No. 14, pp. 3076-3084 (2002).
Janda, "Tagged versus untagged libraries: Methods for the generation and screening of combinatorial chemical libraries", Proc. Natl. Acad. Sci. USA, vol. 91, pp. 10779-10785 (Nov. 1994).
Jäschke, et al. "Synthesis and properties of oligodeoxyribonucleotide-polyethylene glycol conjugates", Nucleic Acids Research, vol. 22, No. 22, pp. 4810-4817 (1994).
Kanagawa, Bias and Artifacts in Multitemplate Polymerase Chain Reactions (PCR), Journal of Bioscience and Bioengineering, vol. 96, No. 4, pp. 317-323 (2003).
Kanan, et al. "Reaction Discovery Enabled by DNA-Templated Synthesis and In Vitro Selection", Supplementary Information, pp. 1-20 (2004).
Kinoshita, et al. "Enzymatic Synthesis of Code Regions for Encoded Combinatorial Chemistry (ECC)", Nucleic Acids Symposium Series, vol. 34, pp. 201-202 (1995).
Kinoshita, et al. "Strand Ligation in a Double-stranded DNA by T4 RNA Ligase", Chemistry Letters, vol. 9, pp. 797-798 (1996).
Krug, et al. "Reversal of T4 RNA Ligase", Biochemistry, vol. 21, No. 8, pp. 1858-1864 (1982).
Kurz, et al. "cDNA—Protein Fusions: Covalent Protein—Gene Conjugates for the In Vitro Selection of Peptides and Proteins", Chembiochem, vol. 2, pp. 666-672, (2001).
Lebl, "Parallel Personal Comments on "Classical" Papers in Combinatorial Chemistry", J. Comb. Chem., vol. 1, pp. 3-24 (1999).
Liu, "The Chemistry and Chemical Biology of Molecular Evolution", Liu Group Research Summary from the website of Professor David R. Liu, obtained from the website in Feb. 2005.
Liu, "The Chemistry and Chemical Biology of Molecular Evolution", website of Dr. D. R. Liu, publicly available Mar. 1, 2001. http://web.archive.org/web/20010301175107/http://evolve.havard.edu.
Liu, "The Chemistry and Chemical Biology of Molecular Evolution", website of Dr. D. R. Liu, publicly available Oct. 15, 2003. http://web.archive.org/web/20031015144255/http://evolve.havard.edu.
Liu, "The Chemistry and Chemical Biology of Molecular Evolution", website of Dr. D. R. Liu, publicly available Nov. 20, 2002. http://web.archive.org/web/20021120104204/http://evolve.havard.edu.
Liu, "The Chemistry of Molecular Evolution", website of Dr. D. R. Liu, publicly available Oct. 15, 2000. http://web.archive.org/web/20001015144553/http://evolve.havard.edu.
Liu, et al. "Denaturing high perfomance liquid chromatography (DHPLC) used in the detection of germline and somatic mutations", Nucleic Acids Research, vol. 26, No. 6, pp. 1396-1400 (1998).
Lobanov. TRENDS in Biotechnology, vol. 20, No. 2, pp. 86-87 (Feb. 2002).
Lockhart, et al. "Expression monitoring by hybridization to high-density oligonucleotide arrays", Nature Biotechnology, vol. 14, pp. 1675-1680 (Dec. 1996).
Maclean, et al. "Encoded Combinatorial Chemistry: Synthesis and screening of a library of highly functionalized pyrrolidines", Proc. Natl. Acad. Sci. USA, vol. 94, pp. 2805-2810 (Apr. 1997).
Magliery, et al. "Expanding the Genetic Code In Vitro and In Vivo", The Genetic Code and the Origin of Life, Ed. Ribas de Pouplana, L. Landes Bioscience, in Press, pp. 221-249 (2004).
Makara, et al. "Improving success rates for lead generation using affinity binding technologies", Current Opinion in Biotechnology, vol. 16, pp. 666-673 (2005).
Mannocci, "DNA-encoded affinity maturation libraries", $2^{nd}$ International Symposium on DNA Encoded Chemical Libraries, 23 pages (Aug. 20, 2010).
Mannocci, "DNA-Encoded Chemical Libraries", Diss. ETH No. 18153, 172 pages (2009).
Margulies, et al., "Genome sequencing in microfabricated high-density picolitre reactors", Nature, vol. 437, pp. 376-380 (2005).
Mashal, et al. "Detection of mutations by cleavage of DNA heteroduplexes with bacteriophage resolvases", Nature Genetics, vol. 9, pp. 177-183 (1995).
Matsuda, et al. "Low Fidelity DNA Synthesis by Human DNA Polymerase-η", Nature, vol. 404, pp. 1011-1013 (Apr. 27, 2000).
Matsuura, et al., "Construction of glyco-clusters by self-organization of site-specifically glycosylated oligonucleotides and their cooperative amplification of lectin-recognition." Journal of the American Chemical Society, vol. 123, No. 2, pp. 357-358 (2001).
McCoy, et al. "T4 Ribonucleic Acid Ligase Joins Single-Strand Oligo(deoxyribonucleotides)", Biochemistry, vol. 19, No. 4, pp. 635-642 (1980).
McGregor, et al. "Interaction-Dependent PCR: Identification of Ligand-Target Pairs from Libraries of Ligands and Libraries of Targets in a Single Solution-Phase Experiment", J. Am. Chem. Soc., vol. 132, pp. 15522-15524 (2010).
Melkko, et al. "Lead discovery by DNA-encoded chemical libraries", Drug Discovery Today, vol. 12, Nos. 11/12, pp. 465-471 (Jun. 2007).
Miller, "DNA as a template for reaction discovery", Nature Biotechnology, vol. 22, No. 11, pp. 1378-1379 (Nov. 2004).
Mudrakovskaya, et al. "Solid-Phase Enzymatic Synthesis of Oligoribonucleotides", Bioorg Khim, vol. 17, No. 6, pp. 469-472 (1991).
Myers, et al. "Detection of single base substitutions by ribonuclease cleavage at mismatches in RNA:DNA duplexes", Science, vol. 230, pp. 1242-1246 (1985).
Nielsen, "Combinatorial chemistry and automation", DDT, vol. 1, No. 11, pp. 458-460 (Nov. 1996).
Nishigaki, et al. "Y-ligation: an efficient method for ligating single-stranded DNAs and RNAs with T4 RNA ligase", Molecular Diversity, vol. 4, pp. 187-190 (1998).
O'Donovan, et al. "Blind analysis of denaturing high-performance liquid chromatography as a tool for mutation detection", Genomics, vol. 52:44-49 (1998).
Ohlmeyer, et al. "Complex synthetic chemical libraries indexed with molecular tags". Proc. Natl. Acad. Sci. USA. vol. 90, pp. 10922-10926 (Dec. 1993).
Persichetti, et al. "Cross-Linked Enzyme Crystals (CLECs) of Thermolysin in the Synthesis of Peptides", J. Am. Chem. Soc., vol. 117, pp. 2732-2737 (1995).

(56) References Cited

OTHER PUBLICATIONS

Pochet, et al. "Solid-Supported Ligation Primer", Nucleic Acids Research, vol. 16, No. 4, p. 1619 (1988).
Polsky-Cynkin, et al., "Use of DNA Immobilized on Plastic and Agarose Supports to Detect DNA by Sandwich Hybridization", Clin. Chem., vol. 31, No. 9, pp. 1438-1443 (1985).
Romaniuk, et al. "Joining of RNA molecules with RNA ligase", Methods in Enzymology, vol. 100, pp. 52-59 (1983).
Saiki, et al. "Genetic analysis of amplified DNA with immobilized sequence-specific oligonucleotide probes", Proc. Natl. Acad. Sci. USA, vol. 86, pp. 6230-6234 (Aug. 1989).
Sarmento, et al. "Cardosins A and B, Two New Enzymes Available for Peptide Synthesis", Journal of Molecular Catalysis B: Enzymatic, vol. 5, pp. 327-330 (1998).
Scheuermann, et al. "DNA-encoded chemical libraries: A tool for drug discovery and for chemical biology", ChemBioChem, vol. 11, No. 7, pp. 931-937 (2010).
Schmidt, et al., "Information transfer from DNA to peptide nucleic acids by template-directed syntheses", Nucleic Acids Research, vol. 25, No. 23, pp. 4792-4796 (1997).
Schmitz, et al. "Solid-Phase Enzymatic Synthesis of Oligonucleotides", Organic Letters, vol. 1, No. 11, pp. 1729-1731 (1999).
Schoenleber, et al. "Photochemical Release of Amines by C,N-Bond Cleavage", Synlett, No. 4, pp. 501-504 (2003).
Schultz, et al. "The Combinatorial Library: A Multifunctional Resource", Biotechnol. Prog., vol. 12, pp. 729-743 (1996).
Sharifian, "Errors induced during PCR amplification", 53 pages (May 30, 2010).
Snyder, et al. "Ordered Multistep Synthesis in a Single Solution Directed by DNA Templates", Angew. Chem. Int. Ed, vol. 44, pp. 7379-7382 (2005).
Still, "Career-In-Review (CIR)", BJ Wright, Synthesis Literacy Group, Columbia University Chemistry, 22 pages (Mar. 30, 2007).
Tan, et al. Natural-product inhibitors of human DNA ligase I, Biochem. J., vol. 314, pp. 993-1000 (1996).
Tan, et al. "Ligand discovery using encoded combinatorial libraries", Current Opinion in Drug Discovery & Development, vol. 3, No. 4, pp. 439-453 (2000).
Tessier, et al. "Ligation of Single-Stranded Oligodeoxyribonucleotides by T4 RNA Ligase", Analytical Biochemistry, vol. 158, pp. 171-178 (1986).
Tse, et al. "Translation of DNA into a Library of 13,000 Synthetic Small-Molecule Macrocycles Suitable for In Vitro Selection", J Am. Chem. Soc., vol. 130, No. 46, pp. 15611-15626 (2008).
Uhlenbeck, et al. "T4 RNA Ligase", The Enzymes, vol. XV, pp. 31-58 (1982).
Unknown, "Science & Technology: Concentrates", Chem. & Eng. News, vol. 82, No. 40, p. 31 (2004).
Vágner, et al. "Enzyme-mediated spatial segregation on individual polymeric support beads: Application to generation and screening of encoded combinatorial libraries", Proc. Natl. Acad. Sci. USA, vol. 93, pp. 8194-8199 (Aug. 1996).
Vaisman, et al. "Human DNA Polymerase ι Promiscuous Mismatch Extension", The Journal of Biological Chemistry, vol. 276, No. 33, pp. 30615-30622 (2001).
Vratskikh, et al. "Solid-phase synthesis of oligoribonucleotides using T4 RNA ligase and T4 polynucleotide kinase", Biochimie, vol. 77, pp. 227-232 (1995).
Wagner, et al. "Mutation detection using immobilized mismatch binding protein (MutS)" Nucleic Acids Research, vol. 23, No. 19, pp. 3944-3948 (1995).
Walder, et al. "Complementary Carrier Peptide Synthesis: General Strategy and Implications for Prebiotic Origin of Peptide Synthesis", Proc. Natl. Acad. Sci. USA, vol. 76, No. 1, pp. 51-55 (Jan. 1979).
Washington, et al. "Mismatch Extension Ability of Yeast and Human DNA Polymerase η", The Journal of Biological Chemistry, vol. 276, No. 3, pp. 2263-2266 (2001).
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Dec. 16, 2003.
Website of prof. David R. Liu, publicly available Feb. 10, 2004.
Website of prof. David R. Liu, publicly available Feb. 15, 2001.
Website of prof. David R. Liu, publicly available Feb. 8, 2003.
Website of prof. David R. Liu, publicly available Jun. 4, 2002.
Website of prof. David R. Liu, publicly available Jun. 6, 2003.
Website of prof. David R. Liu, publicly available Mar. 27, 2003.
Website of prof. David R. Liu, publicly available Mar. 31, 2001.
Website of prof. David R. Liu, publicly available Nov. 29, 2002.
Website of prof. David R. Liu, publicly available Nov. 30, 2001.
Website of prof. David R. Liu, publicly available Oct. 17, 2002.
Weiss, et al. "Enzymatic Breakage and Joining of Deoxyribonucleic Acid, I. Repair of Single-Strand Breaks in DNA by an Enzyme System From *Escherichia coli* Infected With T4 Bacteriophage" Proc. Natl. Acad. Sci. USA, vol. 57, pp. 1021-1028 (1967).
Winzeler, et al. "Fluorescence-Based Expression Monitoring Using Microarrays", Methods Enzymol., vol. 306, pp. 3-18 (1999).
Zhu, et al. "A Primer-dependent Polymerase Function of Pseudomonas aeruginosa ATP-dependent DNA ligase (LigD)", The Journal of Biological Chemistry, vol. 280, No. 1, pp. 418-427 (2005).
International Search Report from PCT No. PCT/DK02/00419 dated Jun. 25, 2003.
International Preliminary Examination Report from PCT No. PCT/DK02/00419 dated Jan. 28, 2004.
European Office Action from European Application No. EP 02740409.4 dated Sep. 1, 2005.
Reply to European Office Action from European Applicant No. 02740409.4 dated Jun. 16, 2006.
Intent to Grant from European Application No. EP 02740409.4 printed Oct. 13, 2006.
Decision to Grant from European Application No. EP 02740409.4 dated Jul. 26, 2007.
Extended European Search Report from European Application No. 07114663.3 dated May 25, 2009.
Extended European Search Report from European Application No. 10 18 4311 dated Feb. 28, 2011.
International Search Report from PCT No. PCT/DK03/00172 dated Nov. 3, 2003.
Office Action from European Application No. 03709676.5 dated Feb. 23, 2005.
Reply to 1st Office Action from European Application No. 30709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 9, 2006.
Amendment after Intention to Grant from European Application No. 03709676.5 dated Nov. 16, 2007.
Decision to Grant from European Application No. 03709676.5 dated Oct. 23, 2008.
European Search Report from European Application No. 08 16 9346 mailed Apr. 13, 2010.
Response filed in European Application No. 08169346.7 mailed Mar. 23, 2011.
1st Office Action from European Application No. 08169346.7 mailed Apr. 19, 2011.
International Search Report from PCT Application No. PCT/DK03/00516 mailed Feb. 18, 2004.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.

(56) References Cited

OTHER PUBLICATIONS

Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report for PCT Application No. PCT/DK03/00921 Jun. 22, 2004.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00417 mailed Feb. 10, 2004.
1st Office Action for European Application No. 03729906.6 mailed May 17, 2006.
Reply to 1st Office Action for European Application No. 03729906.6 mailed Mar. 9, 2007.
2nd Office Action for European Application No. 30729906.6 mailed Sep. 22, 2009.
Reply to 2nd Office Action for European Application No. 03729906.6 mailed May 6, 2010.
International Search Report for PCT Application No. PCT/DK2004/000116 mailed Aug. 23, 2004.
1st Office Action for European Application No. 04713515.7 mailed Oct. 19, 2006.
Reply to 1st Office Action for European Application No. 04713515.7 mailed Aug. 20, 2007.
2nd Office Action for European Application No. 04713515.7 mailed Mar. 31, 2008.
Reply to 2nd Office Action for European Application No. 04713515.7 mailed Dec. 5, 2008.
3rd Office Action for European Application No. 04713515.7 mailed Sep. 6, 2010.
Reply to 3rd Office Action for European Application No. 04713515.7 mailed Jun. 21, 2011.
International Search Report for International Application No. PCT/DK2004/000117 mailed Aug. 19, 2004.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/2004/000195 mailed Dec. 27, 2004.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European Application No. 09154197 mailed Sep. 15, 2010.
International Search Report for International Application No. PCT/DK03/00739 mailed Aug. 30, 2004.
Amendment after ESR for European Application No. 03757752.5 dated Feb. 14, 2006.
1st Office Action for European Application No. 03757752.5 dated Mar. 16, 2006.
Reply to 1st Office Action for European Application No. 03757752.5 dated Jan. 12, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
Australian Application No. 2003273792.
Examination Report for Australian Application No. 2003273792 dated May 6, 2011.
International Search Report for PCT/DK2004/000630 mailed Feb. 14, 2005.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Amendment after Grant for European Application No. 04762850.8 dated Jul. 17, 2009.
Decision to Grant for European Application No. 04762850.8 dated Oct. 8, 2009.
International Search Report for International Application No. PCT/DK2005/000199 mailed Jan. 23, 2006.
1st Office Action for European Application No. 05715120.1 dated Apr. 12, 2007.
Reply to 1st Office Action for European Application No. 05715120.1 dated Feb. 1, 2008.

(56) References Cited

OTHER PUBLICATIONS

2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000106 mailed Sep. 12, 2005.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for International Application No. PCT/DK2006/000685 mailed Jun. 14, 2007.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 mailed May 24, 2011.
Invitation to Identify Subject Matter for European Application No. 10 192 717.6 dated Jun. 1, 2011.
International Search Report for International Application No. PCT/DK2009/050129 mailed Aug. 21, 2009.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
Office Action in European application No. 07114663.3, dated Sep. 12, 2011.
Response to European Search Report in European application No. 10184311.8, dated Feb. 6, 2012.
Response to Office Action in European application No. 08169346.7, dated Feb. 10, 2012.
Office Action in European application No. 08169346.7, dated Feb. 24, 2012.
Annex to Office Action in European application No. 08169346.7, dated Feb. 24, 2012.
Response to Office Action in European application No. 09154197.9, dated Aug. 5, 2011.
Office Action in European application No. 09154197.9, dated Sep. 12, 2011.
Annex to Office Action in European application No. 09154197.9, dated Sep. 12, 2011.

European Search Report in European application No. 10183942.1, dated Feb. 6, 2012.
European Search Opinion in European application No. 10183942.1 dated Feb. 6, 2012.
Communication re partial European Search Report in European application No. 10184069.2, dated Feb. 10, 2012.
Partial European Search Report in European application No. 10184069.2, dated Feb. 10, 2012.
Response to Invitation in European application No. 10192717.6, dated Aug. 5, 2011.
Communication re European Search Report in European application No. 10192717.6, dated Oct. 7, 2011.
Partial European Search Report in European application No. 10192717.6, dated Oct. 7, 2011.
Response to Partial European Search Report in European application No. 10192717.6, dated Dec. 8, 2011.
European Search Report in European application No. 10192717.6, dated Jan. 25, 2012.
European Search Opinion in European application No. 10192717.6, dated Jan. 25, 2012.
International Search Report in PCT/DK2011/000031, dated Aug. 23, 2011.
Australian Patents Act 1990—Sectino 32 Regulation 3.6, (Request for a Determination of Dispute between Applicants) and 3.7 Application to Commissioner for Declaration of an Eligible Person.
Opposition against EP 1558744 filed by Strawman Limited on Mar. 12, 2012.
Opposition against EP 1558744 filed by HGF on Mar. 14, 2012.
Nemoto, N et al. "In vitro virus: bonding of mRNA bearing puromycin at the 3′-terminal end to the C-terminal end of its encoded protein on the ribosome in vitro". FEBS Lett. Sep. 8, 1997;414(2):405-8.
Roberts, RW et al. "RNA-peptide fusions for the in vitro selection of peptides and proteins". Proc Natl Acad Sci U S A. Nov. 11, 1997;94(23):12297-302.
Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000, pp. 1-5.
Kurz, M et al. Psoralen photo-crosslinked mRNA-puromycin conjugates: a novel template for the rapid and facile preparation of mRNA-protein fusions. Nucleic Acids Res. Sep. 15, 2000:28(18):E83.
Keiler et al. "Role of a peptide tagging system in degradation of proteins synthesized from damaged messenger RNA". Science. Feb. 16, 1996;271(5251):990-3.
Benner, SA. "Expanding the genetic lexicon: incorporating non-standard amino acids into proteins by ribosome-based synthesis" Trends Biotechnol. May 1994;12(5):158-63.
Mendel, D. "Site-directed mutagenesis with an expanded genetic code". Annu. Rev. Biophys. Biomol. Struc. 1995. 24:435-462.
Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.
Liu DR et al. "Progress toward the evolution of an organism with an expanded genetic code". Proc Natl Acad Sci USA. Apr. 27, 1999;96(9):4780-5.
Liu, R et al. "Optimized synthesis of RNA-protein fusions for in vitro protein selection". Methods Enzymol. 2000;318:268-93.
Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.
Ellman J.A., et al. "Biosynthetic method for introducing Unnatural Amino acids site specifically into proteins". Methods Enzymol. 202, 301-336 (1992).
José Salas et al. "Biosynthetic Polydeoxynucleotides as Direct Templates for Polypeptide Synthesis". J. of Biological Chemistry, vol. 243, No. 6, 1968, p. 1012-1015.
Walder JA, Walder RV, Heller MJ, Freier SM, Letsinger RL, Klotz IM. "Complementary earner peptide synthesis: general strategy and

(56) References Cited

OTHER PUBLICATIONS implications for prebiotic origin of peptide synthesis". Proc Natl Acad Sci U S A. Jan. 1979;76(1):51-5.
Bruick et al. "Template-directed ligation of peptides to oligonucleotides" Chemistry and Biology, vol. 3, No. 1, Jan. 1996, p. 49-56.
Tamura K, Schimmel P. "Oligonucleotide-directed peptide synthesis in a ribosome- and ribozyme-free system". Proc Natl Acad Sci U S A. Feb. 13, 2001;98(4):1393-7.
Lewis RJ, Hanawalt PC. "Ligation of oligonucleotides by pyrimidine dimers—a missing 'link' in the origin of life?" 22;298(1982):393-6.
Liu J, Taylor JS. "Template-directed photo ligation of oligodeoxyribonucl otides via 4-thiothymidine". Nucleic Acids Res Jul. 1, 1998;26(13):3300-4.
Fujimoto et al. "Template-directed photoreversible ligation of deoxyol gonucleotides via 5-Vinyldeoxyuridine" J. Am. Soc. 2000, 122, 5646-5647.
Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000 , 41:33:6451-6454.
Kenzo Fujimoto, Naoki Ogawa, Masayuki Hayashi, Shigeo Matsuda & Isao Saito "Template directed photochemical synthesis of branched oligodeoxynucleotides via 5-carboxyvinyldeoxyuridine". Tetrahedron letters 2000, 41:49:9437-40.
Gryanov et al. "Chemical Ligation of oligonucleotides in the presence and absence of a template". J. Amer. Chem. Soc. 1993, 115, 3808-9.
Gryaznov SM, Letsinger RL. "Template controlled coupling and recombination of oligonucleotide blocks containing thiophosphoryl groups". Nucleic Acids Res. Mar. 25, 1993;21(6):1403-8.
Gryaznov SM, Schultz R. Chaturvedi SK, Letsinger RL. "Enhancement of selectivity in recognition of nucleic acids via chemical autoligation". Nucleic Acids Res. Jun. 25, 1994;22(12):2366-9.
Herrlein MK, Letsinger RL. "Selective chemical autoligation on a double-stranded DNA template". Nucleic. Acids Res. Nov. 25, 1994;22(23):5076-8.
Letsinger, RL; Wu, T; Elghanian, R "Chemical and photochemical ligation of oligonucleotide blocks". Nucleosides and nucleotides, 16(5&6), 643-652 (1997).
Visscher J, Schwartz AW "Template-directed synthesis of acyclic oligonucleotide analogues". J Mol Evol. Dec. 1988-Feb. 1989;28(1-2):3-6.
Visscher J, Bakker CG, van der Woerd R, Schwartz AW "Template-directed oligomerization catalyzed by a polynucleotide analog". Science. Apr. 21, 1989;244(4902):329-31.
Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.
Zhan, ZJ and Lynn, DG "Chemical Amplification through template-directed synthesis". J. Am Chem. Soc. 1997, 119, 12420-1.
Bruick RK, Koppitz M, Joyce GF, Orgel LE. "A simple procedure for constructing 5'-amino-terminated oligodeoxynucleotides in aqueous solution Nucleic Acids Res". Mar. 15, 1997;25(6):1309-10.
Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.
Xu, Y and Kool, E "Rapid and Selective selenium-mediated autoligation of DNA strands". J. Am. Chem. Soc. 2000, 122, 9040-1 Pub. on web Aug. 31, 2000.
Xu Y, Karalkar NB, Kool ET. "Nonenzymatic autoligation in direct three-color detection of RNA and DNA point mutations". Nat Biotechnol. Feb. 2001;19(2):148-52.
Li X, Zhan ZY, Knipe R, Lynn DG. "DNA-catalyzed polymerization". J Am Chem Soc. Feb. 6, 2002;124(5):746-7.

Czlapinski, JL and Sheppard, TL. "Nucleic acid template-directed assembly of metallosalen-DNA conjugates". J Am Chem Soc. Sep. 5, 2001;123(35):8618-9 published on the web Aug. 10, 2001.
Leitzel JC, Lynn DG "Template-directed ligation: from DNA towards different versatile templates". Chem Rec. 2001;1(1):53-62. Published online Jan 30, 2001.
Schmidt JG, Nielsen PE, Orgel LE. "Information transfer from DNA to peptide nucleic acids to RNA by template-directed syntheses". Nucleic Acids Res. Dec. 1, 1997;25(23):4792-4796.
Dower, WJ et al. "In vitro selection as a powerful tool for the applied evolution of proteins and peptides".Current Opinion in Chemical Biology, 2002, 6:390-398.
Brenner, S and Lerner, RA . "Encoded combinatorial chemistry" Proc. Natl. Acad. Sci. USA. vol. 89, p. 5381-3, Jun. 1992.
Gartner, Z; Liu, DR "The generality of DNA-templated synthesis as a basis for evolving non-natural small molecules". J Am Chem Soc. Jul. 18, 2001;123(28):6961-3.
David Liu. "Expanding the reaction scope of DNA-templated synthesis" Angew. Chem. Int. Ed. 2002, 41, No. 10 pp. 1796-1800. Published May 15, 2002.
Gartner, ZJ et al. "Multistep small-molecule synthesis programmed by DNA templates". J. Am. Chem. Soc. vol. 124, No. 35, 2002, 10304-10306.
Calderone, CT et al. "Directing otherwise incompatible reactions in a single solution by using DNA-templated organic synthesis". Angew Chem Int Ed. 2002. 41, No. 21. 4104-4108.
Bittker, JA; Phillips, KJ and Liu, DR "Recent advances in the in vitro evolution of nucleic acids". Curr Opin Chem Biol. Jun. 2002;6(3):367-74. Review. Pub. on the web Mar. 20, 2002.
Summerer,D and Marx, A "DNA-templated synthesis: more versatile than expected". Angew Chem Int Ed Engl. Jan. 4, 2002;41(1):89-90. Review.
Gartner, ZJ et al. "Two enabling architectures for DNA-templated organic synthesis". Angew. Chem. Int. Ed. 2003, 42, No. 12, 1370-1375.
Rosenbaum, DM et al. "Efficient and sequence-specific DNA-templated polymerization of peptide nucleic acid aldehydes". J. Am. Chem. Soc. vol. 125, No. 46, 2003, 13924-13925.
Li, X et al. "Stereoselectivity in DNA-templated organic synthesis and its origins". J. Am. Chem. Soc. vol. 125, No. 34, 2003, 10188-10189.
Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994, pp. 1385-1401.
Otto, S et al. S"Recent developments in dynamic combinatorial chemistry". Current opinion in Chemical Biology 2002, 6: 321-327.
Pavia, MR. "The Chemical generation of molecular diversity". http://www.netsci.org/Science/Combichem/feature01.html, pp. 1-10, Nov. 2, 2004.
Braun, E, et al. "DNA-templated assembly and electrode attachment of a conducting silver wire". Nature, vol. 391, Feb. 19, 1998, 775-778.
Tanaka, K et al. "Synthesis of a novel nucleoside for alternative DNA base pairing through metal complexation" J. Org. Chem. 1999, 64, 5002-5003.
Beger, M et al. "Universal bases for hybridization, replication and chain termination", Nucleic acids research, Oxford University Press, vol. 28, No. 15, pub. Aug. 1, 2000, p. 2911-2914.
Weizman, H et al. "2,2'-Bipyridine ligandoside: a novel building block for modifying DNA with intra-duplex metal complexes". J. Am. Chem. Soc. 2001, 123, 3375-3376.
Frutos, AG et al. "Demonstration of a word design strategy for DNA computing on surfaces". Nucleic Acids Research, 1997, vol. 25, No. 23, 4748-4757.
Loweth, CJ et al. "DNA-based assembly of gold nanocrystals". Angew. Chem. Int. Ed. 1999, 38, No. 12. 1808-1812.
Elghanian, R et al. "Selective colorimetric detection of polynucleotides based on the distance-dependent optical properties of gold nanoparticles". Science, vol. 277, Aug. 22, 1997.
Storhoff, JJ and Mirkin, CA. "Programmed Materials Synthesis with DNA". Chem Rev. Jul. 14, 1999;99(7):1849-1862.

(56) References Cited

OTHER PUBLICATIONS

Mirkin CA. "Programming the assembly of two- and three-dimensional architectures with DNA and nanoscale inorganic building blocks". Inorg Chem. May 29, 2000;39(11):2258-72.
Waybright SM, Singleton CP, Wachter K, Murphy CJ, Bunz UH. "Oligonucleotide-directed assembly of materials: defined oligomers". J Am Chem Soc. Mar. 7, 2001;123(9):1828-33. Pub. on web Feb. 7, 2001.
Bruce Smith and Markus Krummenacker "DNA-guided assembly of proteins as a pathway to an assembler" (http://www.wadsworth.org/albcon97/abstract/krummena.htm) The 1997 Albany Conference: Biomolecular Motors and Nanomachines.
DeWitt, SH et al. "Diversomers: an approach to nonpeptide, nonoligomeric chemical diversity". Proc. Natl. Acad. Sci, USA, vol. 90, pp. 6909-6913, Aug. 1993.
Nielsen, J et al. "Synthetic methods for the implementation of encoded combinatorial chemistry". J. Am. Chem. Soc. 1993, 115, 9812-9813.
Zuckermann, RN et al "Discovery of nanomolar ligands for 7-transmembrane G-protein-coupled receptors from a diverse N-(substituted) glycine peptoid library". J. Med. Chem. 1994, 37, 2678-2685.
Luo, P et al. "Analysis of the structure and stability of a backbone-modified oligonucleotide: implications for avoiding product inhibition in catalytic template-directed synthesis". J. Am. Chem. Soc. 1998, 120, 3019-3031.
Luther, A et al. "Surface-promoted replication and exponential amplification of DNA analogues". Nature, vol. 396, Nov. 19, 1998, 245-248.
Klekota, B et al. "Selection of DNA-Binding Compounds via Multistage Molecular Evolution". Tetrahedron 55 (1999) 11687-11697.
Furlan, RLE et al. "Molecular amplification in a dynamic combinatorial library using non-covalent interactions". Chem. Commun., 2000, 1761-1762.
Ramström, O et al. "In situ generation and screening of a dynamic combinatorial carbohydrate library against concanavalin A". ChemBioChem, 2000, 1, 41-48.
Cousins, GRL et al. "Identification and Isolation of Receptor for N-Methyl Alkylammonium Salts: Molecular Amplification in a Pseudo-peptide Dynamic Combinatorial Library". Angew. Chem. Int. Ed., 2001, 40, No. 2, 423-427.
Roberts, SI et al. "Simultaneous selection, amplification and isolation of a pseudo-peptide receptor by an immobilised N-methyl ammonium ion template". Chem. Commun., 2002, 938-939.
Furka, A "Combinatorial Chemistry: 20 years on . . . " Drug discovery today vol. 7, No. 1, p. 1-4, 2002.
Needels, CM et al. "Generation and screening of an oligonucleotide-encoded synthetic peptide library" Proc. Natl. Acad. Sci., USA, vol. 90, pp. 10700-10704. Nov. 1993, Chemistry.
Kerr, JM et al. "Encoded Combinatorial Peptide Libraries Containing Non-Natural Amino Acids" J. Am. Chem. Soc., USA. 1993, 115, 2529.
Nestler, HP et al. A general Method for Molecular Tagging of Encoded Combinatorial Chemistry Libraries J. Org. Chem., 1994, 59, 4723-4724.
Baldwin, JJ et al. "Synthesis of a Small Molecule Combinatorial Library Encoded with Molecular Tags" J. Am. Chem. Soc. 1995, 117, 5588-5589.
Nikolaiev. v et al. "Peptide-Encoding for structure determination of nonsequenceable polymers within libraries synthesized and tested on solid-phase supports" Peptide Research, vol. 6, No. 3, 1993. pp. 161-170.
"The Nucleus", Jan. 2004, vol. LXXXII, No. 5, R. Grubina; "Summer Research Report: R. Grubina on DNA Templated Synthesis for Small Molecule Library", p. 10-14.
Nazarenko et al., "A closed tube format for amplification and detection of DNA based on energy transfer", Nucleic Acids Research, 1997, vol. 25, No. 12, p. 2516-2521.

Chan et al., "Intra-tRNA distance measurements for nucleocapsid protein-dependent tRNA unwinding during priming of HIV reverse transcription", PNAS vol. 96, p. 459-464, Jan. 1999.
DNA-templated synthesis as a basis for the evolution of synthetic molecules. Liu DR, Gartner ZJ, Kanan MW, Calderone CT Abstracts of Papers of the American Chemical Society 225: 612-ORGN , Part 2, Mar. 2003.
Rodriguez et al., "Template-directed extension of a guanosine 5'-phosphate covalently attached to an oligodeoxycytidylate template", J Mol Evol (1991) 33:477-482.
Inoue et al, Oligomerization of (Guanosine 5'-phosphor)-2-methylimidazolide on Poly(C), J. Mol. Biol. (1982), 162, 201-217.
C. B. Chen et al., "Template-directed synthesis on Oligodeoxycytidylate and Polydeoxycytidylate templates" J. Mol. Biol. 1985, 181, 271.
H. Rembold et al.. "Single-strand regions of Poly(G) act as templates for oligo(C) synthesis" J. Mol. Evol. 1994, 38, 205.
T. Inoue et al., "A nonenzymatic RNA polymerase model", Science 1983, 219, p. 859-862.
O. L. Acevedo et al., "Non-enzymatic transcription of an oligonucleotide 14 residues long", J. Mol. Biol. 1987, 197, p. 187-193.
C. Böhler et al., "Template switching between PNA and RNA oligonucleotides", Nature 1995, 376, 578-581.
Acevedo et al., "Template-directed oligonucleotide ligation on hydroxylapatite", Nature vol. 321, Jun. 19, 1986, p. 790-792.
Piccirilli, "RNA seeks its maker", Nature vol. 376, Aug. 17, 1995, p. 548-549.
A. W. Schwartz et al., "Template-directed synthesis of novel, nucleic acid-like structures", Science 1985, 228, 585-7.
Halpin et al.: DNA display III. Solid-phase organic synthesis on unprotected DNA. PLoS Biol. Jul. 2004;2(7):E175. Epub Jun. 22, 2004.
Halpin et al.: DNA display II. Genetic manipulation of combinatorial chemistry libraries for small-molecule evolution, PLoS Biol. Jul. 2004;2(7):E174. Epub Jun. 22, 2004.
Halpin et al.: DNA display I. Sequence-encoded routing of DNA populations. PLoS Biol. Jul. 2004;2(7):E173. Epub Jun. 22, 2004.
Doyon, et al., "Highly Sensitive In Vitro Selections for DNA-Linked Synthetic Small Molecules with Protein Binding Affinity and Specificity", J. Am. Chem. Soc. 125, 12372-12373 (2003).
Li, X , et al., "Translation of DNA into Synthetic N-Acyloxazolidines"., J. Am. Chem. Soc. 126, 5090-5092 (2004).
Li, X, et al., "DNA-Templated Organic Synthesis: Nature's Strategy for Controlling Chemical Reactivity Applied to Synthetic Molecules", Angew. Chem. Int. Ed. 43, 4848-4870 (2004).
Gartner, Z. J., et al., "DNA-Templated Organic Synthesis and Selection of a Library of Macrocycles"; Science 305, 1601-1605 (2004).
Calderone, C. T., "Nucleic Acid-Templated Synthesis as a Model System for Ancient Translation", Curr. Opin. Chem. Biol. 8, 645-653 (2004).
Sakurai, K , "DNA-Templated Functional Group Transformations Enable Sequence-Programmed Synthesis Using Small-Molecule Reagents", J. Am. Chem. Soc. 127, 1660-1661 (2005).
David R. Liu , "Translating DNA into synthetic Molecules", PLoS Biology, Jul. 2004, vol. 2, Iss. 7, p. 905-6.
David R. Liu, "The Development of Amplifiable and Evolvable Unnatural Molecules", Harvard Univ. Cambridge MA Dept of Chemistry and Chemical Biology, Report dated Aug. 4, 2003 No. A104614, approved for public release.
Liu, "David R. Liu, Assistant Professor of Chemistry" (personal website), publicly available Mar. 11, 2000, available online at http://web.archive.org/web/20000311112631/http://evolve.harvard.edu/.
Liu, "David R. Liu, Assistant Professor of Chemistry" (personal website), publicly available Oct. 15, 2000, available online at http://web.archive.org/web/0001015144552/http://evolve.harvard.edu.
Liu, "David R. Liu, Assistant Professor of Chemistry" (personal website), publicly available Mar. 1, 2001, available online at http://web.archive.org/web/20010301175107/http://evolve.harvard.edu/.

(56) References Cited

OTHER PUBLICATIONS

Liu, "David R. Liu, Assistant Professor of Chemistry" (personal website), publicly available Apr. 19, 2001, available online at http://web.archive.org/web/20010419064232/http://evolve.harvard.edu/.
Liu, "David R. Liu, Assistant Professor of Chemistry" (personal website), publicly available Sep. 23, 2001, available online at http://web.archive.org/web/20010923021615/http://evolve.harvard.edu/.
Liu, "David R. Liu, Assistant Professor of Chemistry" (personal website), publicly available Sep. 24, 2002, available online at http://web.archive.org/web/20020924154032/http://evolve.harvard.edu/.
Liu. "David R. Liu. Assistant Prolessor of Chemistry" (personal website), publicly available Nov. 20, 2002, available online at http://web.archive.org/web/20021120104204/http://evolve.harvard.edu/.
Liu, "David R. Liu. Assistant Professor of Chemistry" (personal website), publicly available Oct. 15, 2003, available online at http://web.archive.org/web/20031015114255/http://evolve.harvard.edu/.
Kanan, M.W et al. "Reaction discovery enabled by DNA-templated synthesis and in vitro selection" Nature, vol. 431, Sep. 30, 2004, pp. 545-549 and suppl pp. 1-20.
"Finding reactions in a haystack: Try'em all, see what works" Meeting American Chemical Society, Sep. 10, 2004, vol. 305, Science.
Fredriksson et al., "Protein detection using proximity-dependent DNA ligation assays", Nature Biotechnology, vol. 20, p. 473-477, May 2002.
Lowe et al., "Combinatorial Libraries for Studying Molecule Recognition", URL: http://www.iupac.org/symposia/proceedings/phuket97/lowe.html, downloaded in Jun. 2005, pp. 1-7.
Czarnik et al., "Encoding methods for combinatorial chemistry", Current Opinion in Chemical Biology vol. 1, Iss 1, Jun. 1997, p. 60-66.
Battersby et al., "Optical encoding of micro-beads for gene screening: alternatives to micro-arrays", Drug Discovery Today, vol. 6, Supp 1, Jun. 1, 2001, p. 19-26.
Shchepinov et al., "Trityl tags for encoding in combinatorial synthesis", Tetrahedron 56 (2000) 2713-2724.
Geysen et al., "Combinatorial Compound Libraries for Drug Discovery: An Ongoing Challenge", Nature Reviews, Drug Discovery, vol. 2, Mar. 2003, p. 222-230.
Bonora et al.; Large Scale, PEG-supported DNA Synthesis; Nucleotided & Nucleotides, 10 (1-3), (1991).
Colombo R. et al.; Synthesis of leucin-enkephalin and methionineenkephalin . . . Hoppe-Seyler's Z.Physiol.Chem. vol. 363 (1981).
Denapoli et al; PEG-Supported Synthesis of Cyclic Oligodeoxyribonucleotides; Nucleosides & Nucleotides; vol. 12 No. 1; 1993.
Douglas et al.; Polymer-supported solution synthesis of oligosaccharides; J.Am. Chem.Soc; vol. 113 (1991).
E. Bayer et al.; Liquid Phase Synthesis of Peptides; Nature vol. 7; 237; Jun. 16, 1972.
Mutter M. et al, ; Functionalized polyethylene glycols and polypeptides in organic synhesis and catalysis Reactive Polymers, vol. 6 (1987), pp. 99-107.
Enzymes in Nonaqueous Solvents; Applications in Carbohydrate and Peptide Preparation; Shui-Tein Chen et.al.; Methods of Biotechnology; vol. 15; p. 373-374, 2001.
Quality Systems, DNA Phosphoramidites & CPG's; pp. 1-4, Mar. 18, 2010 http://www.qualitysystems.com.tw/proligo/dna%20phosphoamidites%20&%20cpg's.htm.
Kahn, Jason, DNA Ligases; pp. 1-4, 2009, http://adnadn.umd.edu/biochem/kahn/molmachines/replication/DNA%20Ligase.htm.

Dryer, et al., "Enzyme Catalysis in Nonaqueous Media: Past, Present, and Future", pp. 791, 819-820 in Ramesh N. Patel, ed., *Biocatalysis in the Pharmaceutical and Biotechnology Industries;* (CRC Press 2006).
Abstract only, Synthesis of DNA Dumbbells: Chemical vs. Enzymatic Ligation of Self-Complementary Oligonucleotides; Carols S. Lim; C. Anthony Hunt; Nucleotides and Nucleic Acids; vol. 16, Issue 1 & Jan. 2, 1997; pp. 41-51.
Xu, et al., A Novel 5'-Iodonucleoside Allows Efficient Nonenzymatic Ligation of Single-stranded and Duplex DNAs, Tetrahedron Letters, vol. 38, No. 32, pp. 5595-5598, 1997.
High sequence fidelity in a non-enzymatic DNA autoligation reaction; Y. Xu and E.T. Kooi; 1999; Nucleic Acids Research, 1999 vol. 27, No. 3; pp. 875-881.
Abstract only, Enzyme Engineering for Nonaqueous Solvents: Random Mutagenesis to Enhance Activity of Subtilisin E in Polar Organic Media; Keqin Chen & Frances H. Arnold; Bio/Technology 9, 1073-1077 (1991).
An orthogonal oligonucleotide protecting group strategy that enables assembly of repetitive or highly structured DNAs; Ulf M. Lindstöm and Erik T. Kool; Nucleic Acids Res. 2002 Oct. 1, 2002; 30(19), e101.
As Fast and Selective as Enzymatic Ligations: Upaired Nucleobases Increase the Selectivity of DNA-Controlled Native Chemical PNA Ligation; Simon Ficht et. al.; ChemBioChem: vol. 6 Issue 11 (2005), pp. 2098-2103.
Wikipedia, "Organic Chemistry"; [accessed Dec. 10, 2009] http://en.wikipedia.org/wiki/Organic_chemistry (10 pages).
Evolution of DNA and RNA as catalysts for chemical reactions; Andres Jäschke and Burckhard Seelig; Current Opinion in Chemical Biology 2000; vol. 4; pp. 257-262.
Direct Evolution Process for Robust Enzyme Catalysis in Organic Solvents; Dan Robertson; Report Date: Sep. 1996, pp. 1-14.
Circular RNA oligonucleotides. Synthesis, nucleic acid binding properties, and a comparison with circular DNAs; Shaohui Wang and Eric T. Kool; Nucleic Acids Research, 1994, vol. 22, No. 12; 1994; pp. 2326-2333.
Chemicall reactions within DNA duplexes; Cyanogen bromide as an effective oligodeoxyribonucleotide coupling agent; N.I. Sokolova et al.; FEBS Letters, vol. 232, No. 1, pp. 153-155; May 1988.
A new affinity reagent for the site-specific, covalent attachment of DNA to active-site nucleophiles: application to the EcoRI and Rsrl restriction and modification enzymes; Andrei A. Purmal et al.; Nucleic Acids Research; vol. 20, No. 14; 1992; pp. 3713-3719.
Nonenzymatic ligation of double-helical DNA by alternate-strand triple helix formation; Kevin J. Luebke and Peter B. Dervan; Nucleic Acids Research, vol. 20, No. 12; 1992; pp. 3005-3009.
Ligation of oligonucleotides to nucleic acids or proteins via disulfide bonds; Barbara C.F. Chu and Leslie E. Orgel; Nucleic Acids Research; vol. 16, No. 9, 1988; pp. 3671-3691.
DNA Ligases: Progress and Prospects; Stewart Shuman; pp. 1-7, Feb. 10, 2009 http://jbc.org/content/284/26/17365.full.
Answers.com; "Ligase"; http://www.answers.com/topic/ligase, [accessed Dec. 10, 2009].
Biotransformations in organic synthesis; Wendy A. Loughlin; Bioresource Technology 74 (2000); pp. 49-62.
The Fidelity of Template-Directed Oligonucleotide Ligation and the Inevitability of Polymerase Function; Kenneth D. James and Andrew D. Ellington; Origins of Life and Evolution of the Biosphere 29; 1999 Kluwer Academic Publishers; pp. 375-390.
Enzymes in organic synthesis 22. Effects of organic solvents on horse liver alcohol dehydrogense-catalyzed reduction; J. Bryan Jones and Harold M. Schwartz; Can. J. Chem. 1982; vol. 60, pp. 335-338.
The ligase chain reaction in PCR world; F. Barany; Genome Res. 1991; 1: 5-16.
Branch capture reactions: displacers derived from asymmetric PCR; Daphne M. Wong; et al; 1991; Nucleic Acids Research; vol. 19; No. 9; pp. 2251-2259.
The TaqI star reaction: strand preferences reveal hydrogen-bond donor and acceptor sites in canonical sequence recognition; F. Barany; 1988; Gene vol. 65; pp. 149-165.

(56) References Cited

OTHER PUBLICATIONS

DNA-ligases; Stanley Tabor; Current Protocols in Molecular Biology (1987) pp. 3.14.1-3.14.4, Supplement B, John Wiley & Sons Inc.
DNA Ligase: Structure, Mechanism, and Function; The joining of DNA chains by DNA ligase is an essential component of DNA repair, replication, and recmobination I.R. Lehman; Science vol. 186; 1974; pp. 790-797.
Abstract only, Development and trends in enzyme catalysis in nonconventional medai; Sajja Hari Krishna; Biotechnology Advances; vol. 20; Issues 3-4; Nov. 2002; pp. 239-267.
Enzyme Activity in Organic Solvent as a function of Water Activity Determined by Membrane Inlet Mass Spectometry; Hans Degn et al.; Biotechnology Techniques vol. 6; No. 2; Mar./Apr. 1992; pp. 161-164—p. 161.
Abstract only, Stabilization of Enzyme Activity by an Organic Solvent; Shigeki Takemori et al., Nature 215, 417-419 (Jul. 22, 1967).
Abstract only, Why are enzymes less active in organic solvent than in water?; Alexander M. Klibanov; Trends in Biotechnology; vol. 15, Issue 3, 97-101; Mar. 1, 1997.
Design, synthesis and use of binary encoded synthetic chemical libraries; John J. Baldwin; Molecular Divesity 2 (1996); pp. 81-88.
Total synthesis of marine natural products without using protecting groups; Phil S. Baran et al; Nature vol. 446; Mar. 22, 2007; pp. 404-408.
DNA-encoded chemical libraries; Jörg Scheuermann, et al.; Journal of Biotechnology 126 (2006) 568-581.
Wikipedia, "Protecting Group"; hhtp://en.wikipedia.org/wiki/Protecting_group#Orthogonal_protection; [accessed Apr. 15, 2010].
Shabarova, et al., "Chemical ligation of DNA: the first non-enzymatic assembly of a biologically active gene", Nucl. Acids Res., 19;4247-51 (1991).
Lim and Hunt. "Synthesis of DNA Dumbbells: Chemical vs. Enzymatic Ligation of Self-Complementary Oligonucleotides", Nucleosides, Nucleotides and Nucleic Acids, 16(1&2): 41-51 (1997).
Anonymous, DCI—A Logical Alternative Activator, Glen Research Report, vol. 10, 1997 (December issue), pp. 1-2.
Anonymous, Preparing Oligonucleotides for Antisensen Experiments, Glen Research Report, vol. 10, 1997 (December issue), p. 3.
Anonymous, Cytofectin GSV Transfection Protocol, Glen Research Report, vol. 10, 1997 (December issue), pp. 4-6.
Anonymous, New Fluorescent Reagents—Tamra CPG, Fluorescein-dt, Glen Research Report, vol. 10, 1997 (December issue), p. 7.
Anonymous, Universal Support Replaces Individual Columns, Glen Research Report, vol. 10, 1997 (December issue), p. 8.
Anonymous, Q-Supports Reduce Cleavage Time to 2 Minutes, Glen Research Report, vol. 10, 1997 (December issue), p. 9.
Anonymous, More Novel Monomers-4-Thio-dU, 5'-Amino-dT, 2'-F-Pyrimidines, Glen Research Report, vol. 10, 1997 (December issue), p. 10.
Anonymous, 5,6-Dihydro-Pyrimidines, 2'-Phosphoramidites, Glen Research Report, vol. 10, 1997 (December issue), p. 11.
Anonymous, Non-Enzymatic Ligation of Single-Stranded and Duplex DNA, Glen Research Report, vol. 10, 1997 (December issue), p. 12.
Porco, Jr., "Synthesis Undressed", Nature 446, 383-5 (Mar. 22, 2007).
Abstract only, Agarwal, et al., Total Synthesis of the gene for an alanine transfer ribonucleic acid from yeast, Nature, 227, 27-34 (1970).
Whitesides, et al., Enzymes as Catalysts in Organic Synthesis, Aldrichimica Acta., vol. 16, No. 2, pp. 27-34, 1983.
Robinson, A Synthesis of Tropinone, Journal of the Chemical Society Transactions, vol. 111, pp. 762-768, 1917.
Coe, et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Furka et al., "General method for rapid synthesis of multicomponent peptide mixtures", Int. J. Peptide Protein Res., 37, 1991, 487-493.
Gallop et al., "Applications of Combinatorial Technologies to Drug Discovery. 1. Background and Peptide Combinatorial Libraries", Journal of Medicinal Chemistry, 1994, vol. 37, No. 9, pp. 1233-1251.
Guillen Schlippe, et al.,"In Vitro Selection of Highly Modified Cyclic Peptides That Act as Tight Binding Inhibitors", J. Am. Chem. Soc., 2012, 134, 10469-10477.
Han, et al., "Liquid-phase combinatorial synthesis", Proc. Natl. Acad. Sci. USA, vol. 92, pp. 6419-6423, Jul. 1995.
www.wikipedia.org/wiki/DNA-encoded chemical library, Oct. 2, 2012, pp. 1-12.
http://www2.umt.edu/medchem/teaching/medchem/mclect14.htm, Thompson C. M., Medicinal Chemistry, lecture 14, Pharmaceutical Sciences 621 & Chemistry 569, 1996.
Li, et al., "Kinetics of RNA degradation by specific base catalysis of transesterification involving the 2'-hydroxyl group", J. Am. Chem. Soc., 1999, 121, pp. 5364-5372.
Ma, et al., "In Vitro Selection of Unnatural Cyclic Peptide Libraries via mRNA Display", Book Ribosome Display and Related Technologies, ch. 21, pp. 367-390, 2012.
Maclean, et al., "Glossary of terms used in combinatorial chemistry", Pure Appl. Chem., vol. 71, No. 12, pp. 2349-2365, 1999.
Meier, et al., "Combinatorial Methods, Automated Synthesis and High-Throughput Screening in Polymer Research: The Evolution Continues", Macromol. Rapid Commun., 2004, 25, 21-33.
Chorghade, "Drug discovery and development", 2006, ISBN-13: 978-0-471-39848-6, Published by John Wiley & Sons, Inc., Hoboken, New Jersey.
Needels, et al., "Generation and screening of an oligonucleotide-encoded synthetic peptide library", Proc. Natl. Acad. Sci. USA, vol. 90, pp. 10700-10704, Nov. 1993.
Ni, et al., "Versatile Approach to Encoding Combinatorial Organic Syntheses Using Chemically Robust Secondary Amine Tags", J. Med. Chem. 1996, 39, 1601-1608.
Nicolaou, et al., "Radiofrequency Encoded Combinatorial Chemistry", Angew. Chem. Int. Ed. Engl., 1995, 34, No. 20, pp. 2289-2291.
Noren, et al., "A general method for site-specific incorporation of unnatural amino acids into proteins", Science, American Association for the advancement of science, Washington, DC, vol. 244, 1989, pp. 182-188.
Starck, et al., "The puromycin route to assess stereo- and regiochemical constraints on peptide bond formation in eukaryotic ribosomes", J. Am. Chem. Soc., 2003, 125, 8090-8091.
Studer, et al., "Fluorous Synthesis: A Fluorous-Phase Strategy for Improving Separation Efficiency in Organic Synthesis", 1997, Science, 275, pp. 823-826.
Terrett, et al., "Combinatorial synthesis—The design of compound libraries and their application to drug discovery", Tetrahedron, 1995, vol. 51, No. 30., pp. 8135-8173.
Website: "Combinatorial Chemistry", http://www.ukessays.co.uk/essays/chemistry/combinatorial-chemistry.php, Oct. 29, 2012, pp. 1-11.
Wermuth, et al., "Glossary of terms used in medical chemistry", Pure & Appl. Chem, 1998, vol. 70, No. 5, pp. 1129-1143.
Ymane, et al., "Discrimination between D- and L-Tyrosyl transfer ribonucleic acids in peptide chain elongation", Biochemistry, vol. 20, No. 25, Dec. 8, 1981, pp. 7059-7064.
Lipinski et al., "Experimental and computational approaches to estimate solubility and permeability in drug discovery and development settings", Adv. Drug Deliv. Rev., vol. 46 (1-3), 2001, pp. 3-26.

(56) References Cited

OTHER PUBLICATIONS

Lipinski, "Lead- and drug-like compounds: the rule-of-five revolution", Drug Discovery Today: Technologies, vol. 1, No. 4, 2004, pp. 337-341.
Kleiner, et al., "Small-molecule discovery from DNA-encoded chemical libraries", Chem. Soc. Rev., 2011, 40, pp. 5707-5717.
http://en.wikipedia.org/wiki/Scaffold_protein, Oct. 21, 2013.
Balkenhohl, et al., "Combinatorial synthesis of small organic molecules", Angew Chem Int. Ed Engl., 1996, 35, pp. 2288-2337.
Strachan, "Human Molecular Genetics", 2nd edition, textbook published by Wiley-Liss, 1999.
Barrio, et al., "Synthesis of modified nucleoside 3',5'-bisphophates and their incorporation into oligoribonucleotides with T4 RNA Ligase", Biochemistry, vol. 17, No. 11, 1978.
Chan, et al., "Altered DNA ligase I activity in Bloom's syndrome cells", Nature, vol. 325, pp. 357-359, 1987.
Cranston, et al., "Studies on ribonucleic acid ligase", J.Biol.Chem., vol. 249, pp. 7447-7456, 1974.
England, et al., "Enzymatic oligoribonucleotide synthesis with T4 RNA ligase", American Chemical Society, vol. 17, No. 11., 1978.
Gassen, et al., "Synthesis by polymer-bound ribonuclease of the termination codons U-A-A, U-A-G, and U-G-A" Biochemical and Biophysical Research Communications, vol. 44, No. 6, pp. 1410-1415, 1971.
Haseth, et al., "Interaction of *Escherichia coli* host factor protein with oligoriboadenylates", Biochemistry, 19, pp. 6138-6146, 1980.
Hoffman, et al., "Polynucleotide phosphorylase covalently bound to cellulose and iths use in the preparation of homopolynucleotides", Biochemical and Biophysical Research Communications, vol. 41, No. 3, pp. 710-714, 1970.
Kiebom, "Enzymes that do not work in organic solvents: Too polar substrates give too tight enzyme-product complexes", Recl. Trav. Chim. Pays-Bas, 107, pp. 347-348, 1988.
Middleton, et al., "Synthesis and purification of oligoribonucleotides using T4 RNA ligase and reverse-phase chromatography", Analytical Biochemistry, 144, pp. 110-117, 1985.
Narang, "DNA synthesis", Tetrahedron, vol. 39, No. 1, pp. 3-22, 1983.
Neilson, et al., "Synthesis of biologically active portions of an intercistronic region by use of a new 3'-phosphate incorporation method to protect 3'-OH and their binding to ribosomes", Eur. J. Biochem., 99, pp. 429-439, 1979.
Ochoa, et al., "Enzymatic synthesis of polynucleotides", J.Biol. Chem., vol. 236, 12, pp. 3303-3311, 1961.
Willis, et al., "DNA ligase I deficiency in Bloom's syndrome", Nature, vol. 325, pp. 355-357, 1987.
d'Angelo, et al., "HIV-1 integrase: the next target for AIDS therapy?", Pathol. Biol. 2001, 49, pp. 237-246.
http://www.piercenet.com/method/avidin-biotin-interaction retrieved Nov. 5, 2013.
Schreiber, "The small-molecule approach to biology—Chemical genetics and diversity-oriented organic synthesis make possible the systematic exploration of biology", C&EN, Mar. 3, 2003, pp. 51-61.
Balasubramanian, "The science of chemical discovery: probing the unknown with new technologies", DDT, vol. 5, No. 12, Dec. 2000, pp. 533-534.
Wills, et al., "Recent developments in linker design and application", Current Opinion in Chemical Biology, 2003, 7, pp. 346-352.
Balasubramanian, "Solid phase chemical technologies for combinatorial chemistry", J. Cell. Biochem. Suppl., 37, 2001, pp. 28-33.
Bain et al., "Regioselective Ligation of Oligoribonucleotides using DNA Splints", Nucl. Acids Res., vol. 20, No. 16, 4372, 1992.
Boger & Goldberg, "Chapter 10: Multi-step Solution Phase Combinatorial Synthesis" in Combinatorial Chemistry, ed. Hicham Fenniri, Oxford University Press (Oxford, England), 2000, pp. 303-326.
Cheng et al., "Novel Solution Phase Strategy for the Synthesis of Chemical Libraries Containing Small Organic Molecules", J. Am. Chem. Soc., vol. 118, 2567-2573, 1996.
Clark et al., "Design, Synthesis and Selection of DNA-encoded Small-molecule Libraries", Nat. Chem. Biol., vol. 5, No. 9, 647-654, 2009.
Curran, "Strategy-Level Separations in Organic Synthesis: From Planning to Practise", Angew. Chem. Int. Ed., vol. 37, 1174-1196, 1998.
Declaration by Dr. Dennis Benjamin (including curriculum vitae) Sep. 11, 2013.
Frutos et al. "Enzymatic Ligation Reactions of DNA "Words" on Surfaces for DNA Computing", J. Am. Chem. Soc., vol. 120, No. 40, 10277-10282, 1998.
Gait, "Chapter 1: An Introduction to Modern Methods of DNA Synthesis": Van Boom & Wreesman, "Chapter 7: Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4), 2002.
Glen Research Report, "Advances in RNA Synthesis and Structural Analysis", vol. 11, No. 2, Dec. 1998.
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries," PNAS USA, vol. 91, 10779-10785, 1994.
Kelemen et al., "Hypersensitive Substrate for Ribonucleases", Nucl. Acids. Res., vol. 27, No. 18, 3696-3701, 1999.
Kempe et al., "Chemical and Enzymatic Biotin-labeling of Oligodeoxyribonucleotides", Nucl. Acids Res., vol. 13, No. 1, 45-57, 1985.
Kinoshita et al., "Enzymatic Synthesis of Sequencing Primers Based on a Library of Tetramers", Chem. Express, No. 7, 149-152, 1992.
Kinoshita et al., "Strand Ligation in a double-stranded DNA by T4 RNA Ligase", Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Moore et al. "Site-specific Modification of Pre-mRNA: the 2'-Hydroxyl Groups at the Splice Sites", Science, vol. 256, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).
Nielsen et al., "Toward Chemical Implementation of Encoded Combinatorial Libraries", Methods: A Companion to Meth: Enzymol., vol. 6, 361-371, 1994.
Roux, "Optimization and troubleshooting in PCR", PCR Methods Appl., S185-S194, 1995.
Schmitz et al., "Solid-phase Enzymatic Synthesis of Oligonucleotides", Org. Lett., vol. 1, 1729-1731, 1999.
Seelig et al., "Site-Specific Modification of Enzymatically Synthesized RNA: Transcription Initiation and Diels-Alder Reaction", Tetrahed. Lett., vol. 38, 7729-7732, 1997.

(56) References Cited

OTHER PUBLICATIONS

Seo et al., "Click Chemistry to Construct Fluorescent Oligonucelotides for DNA Sequencing", J. Org. Chem., vol. 68, 609-612, 2003.
Sherlin et al., "Chemical and Enzymatic Synthesis of tRNAs for High-throughput Crystallization", RNA, vol. 7, 1671-1678, 2001.
Tabuchi et al., "An Efficient Ligation Method in the Making of an in vitro Virus for in vitro Protein Evolution," Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed in the Surface of Encoded Bacteriophage", Chem. Biol., vol. 10, 847-858, Sep. 2003.
Wojczewski et al., "Fluorescent Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series vol. 12, Pergamon, Elsevier Science Lrd. (Oxford, England) 1994, pp. Xiii-xv, 1-40, and 329-334.
Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.
Further submissions re EP 1558744 submitted Nov. 6, 2013 by proprietor.
Opposition minutes dated Dec. 13, 2013 of oral proceedings re European Patent No. 1558744.
Written Decision re European Patent No. 1558744 of Dec. 13, 2013.
Response to 1st Office Action of Jul. 30, 2012 in EP 10192716.8 submitted May 28, 2013.
Response to 2nd Office Action of Feb. 6 in EP 10184311.8 submitted Dec. 8, 2013.
1st Office Action dated Nov. 20, 2013 re patent application No. 201210222023.8 in China.
Notice of Allowance dated Jan. 19, 2012 re U.S. Appl. No. 10/525,817.
RCE dated Mar. 19, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
Restriction Requirement of Jun. 25, 2008 re U.S. Appl. No. 11/402,957.
Response submitted Aug. 25, 2008 to Restriction Requirement re U.S. Appl. No. 11/402,957.
Non-final Rejection dated Nov. 28, 2008 re U.S. Appl. No. 11/402,957.
Response submitted May 14, 2009 to Non-final Rejection re U.S. Appl. No. 11/402,957.
Non-final Rejection dated Jul. 6, 2009 re U.S. Appl. No. 11/402,957.
Response submitted Dec. 7, 2009 to Non-final Rejection re U.S. Appl. No. 11/402,957.
Final Rejection dated Feb. 16, 2010 re U.S. Appl. No. 11/402,957.
Response submitted Jul. 28, 2010 to Final Rejection re U.S. Appl. No. 11/402,957.
Notice of Appeal dated Aug. 16, 2010 re U.S. Appl. No. 11/402,957.
Notice of Allowance dated Sep. 2, 2010 re U.S. Appl. No. 11/402,957.
RCE dated Dec. 2, 2010 re U.S. Appl. No. 11/402,957.
Second Notice of Allowance dated Apr. 29, 2011 re U.S. Appl. No. 11/402,957.
RCE dated Jul. 28, 2011 re U.S. Appl. No. 11/402,957.
Third Notice of Allowance dated Oct. 31, 2011 re U.S. Appl. No. 11/402,957.
RCE dated Dec. 12, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Response to Non-final rejection submitted Sep. 23, 2013 re U.S. Appl. No. 11/402,957.
Notice of Allowance dated Dec. 5, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
Non-final rejection dated Nov. 15, 2013 re U.S. Appl. No. 13/455,223.
First Restriction Requirement dated Feb. 4, 2009 re U.S. Appl. No. 10/572,644.
Reponse submitted Jul. 29, 2009 to First Restriction Requirement re U.S. Appl. No. 10/572,644.
Non-final rejection dated Oct. 29, 2009 re U.S. Appl. No. 10/572,644.
Response submitted Apr. 28, 2010 to Non-final rejection re U.S. Appl. No. 10/572,644.
Second Restriction Requirement dated Jul. 21, 2010 re U.S. Appl. No. 10/572,644.
Response submitted Jan. 19, 2011 to Second Restriction Requirement re U.S. Appl. No. 10/572,644.
Non-final rejection dated Mar. 31, 2011 re U.S. Appl. No. 10/572,644.
Response submitted Sep. 30, 2011 to Non final rejection re U.S. Appl. No. 10/572,644.
Final rejection dated Jan. 9, 2012 re U.S. Appl. No. 10/572,644.
Notice of Appeal filed Jul. 6, 2012 re U.S. Appl. No. 10/572,644.
RCE of Sep. 6, 2012 re U.S. Appl. No. 10/572,644.
Non-final rejection dated Mar. 30, 2009 re U.S. Appl. No. 10/593,868.
Response submitted Jul. 28, 2009 to Non-final rejection re U.S. Appl. No. 10/593,868.
Notice of Allowance dated Nov. 16, 2009 re U.S. Appl. No. 10/593,868.
Amendments after Notice of Allowance Feb. 16, 2010 re U.S. Appl. No. 10/593,868.
Issue Notification dated Apr. 7, 2010 re U.S. Appl. No. 10/593,868.
Restriction Requirement dated Apr. 7, 2011 re U.S. Appl. No. 10/589,551.
Response submitted Oct. 7, 2011 to Restriction Requirement re U.S. Appl. No. 10/589,551.
Non-final rejection dated Oct. 26, 2011 re U.S. Appl. No. 10/589,551.
Adang, et al., "The Contribution of Combinatorial Chemistry to Lead Generation: An Interim Analysis", Current Medicinal Chemistry, 2001, 8, 985-998.
Affleck, "Solutions for library encoding to create collections of discrete compounds", Current Opinion in Chemical Biology, 2001, 5:257-263.
Bain, et al., "Biosynthetic site-specific incorporation of a non-natural amino acid into a polypeptide", J. Am. Chem. Soc., 1989, 111, 8013-8014.
Barnes, et al., "Recent developments in the encoding and deconvolution of combinatorial libraries", Current Opinion in Chemical Biology 2000, 4:346-350.
Chen, et al., "Total Synthesis of Naturally Occurring Prostaglandin F2α on a Non-Cross-Linked Polystyrene Support", Tetrahedron Letters, 39, (1998), 3943-3946.
Chen, C.B., et al., "Template-directed synthesis on Oligodeoxycytidylate and Polydeoxycytidylate templates", J. Mol. Biol., 1985,181, 271-279.
Response to Office Action in EP 07114663.3 dated May 17, 2013.
3rd Office Action in European patent application No. 07114663.3 dated Jun. 3, 2013.
Response to 2nd Office Action of Feb. 24, 2012 in EP 08169346.7 submitted Dec. 21, 2012.
3rd Office Action dated Jan. 29, 2013 in EP 08169346.7.
Reply to 5th Office Action dated May 31, 2012 in EP 03766117.0 submitted Mar. 11, 2013.
6th Office Action from European Application No. 03766117.0 dated Mar. 26, 2013.

(56) References Cited

OTHER PUBLICATIONS

Reply to 6th Office Action dated Mar. 26, 2013 in EP 03766117.0 submitted Jan. 8, 2014.
Decision to Grant dated Oct. 10, 2013 re European patent appliction No. 09154197.9.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
European Search Report dated Feb. 6, 2012 & Search Opinion.
Response to ESR of Feb. 6, 2012 re European Patent Application No. 10183942.1 submitted Jan. 9, 2013.
1st Office Action for European Patent Application No. 10183942.1 dated Feb. 11, 2013.
Decision to Grant EP 10183942.1 dated Nov. 14, 2013.
Communication re Partial European Seach Report dated Feb. 10, 2012.
Partial European Search Report dated Feb. 3, 2012.
European Search Report issued Jun. 6, 2012 re EP 10184069.2.
Response dated Apr. 12, 2013 to European Search Report issued in European Patent Application No. 10184069.2.
1st Office Action for European Patent Application No. 10184069.2 dated Jul. 3, 2013.
Invitation to identify subject matter for search Response to ESR dated Jan. 25, 2012 submitted Dec. 5, 2012.
Invitation to identify subject matter for search Office Action dated Jul. 16, 2013 re European patent application No. 10192717.6.
Communication pursuant to Rule 161(1) and 162 for European Application No. 11720372.9 dated Dec. 12, 2012.
Notice of Allowance of Sep. 3, 2012 re Chinese patent application No. 200380104764.5.
Office Action in Israeli patent application No. 207672 dated May 28, 2013.
Office Action in Israeli patent application No. 207673 dated May 28, 2013.
Restriction Requirement dated Apr. 6, 2005 re U.S. Appl. No. 10/175,539.
Response to Restriction Requirement submitted May 6, 2005 re U.S. Appl. No. 10/175,539.
Non-final Rejection dated Oct. 13, 2005 re U.S. Appl. No. 10/175,539.
Response submitted Apr. 13, 2006 to Non-final Rejection re U.S. Appl. No. 10/175,539.
Final Rejection dated May 19, 2006 re U.S. Appl. No. 10/175,539.
Notice of Appeal filed Nov. 20, 2006 re U.S. Appl. No. 10/175,539.
RCE submitted Feb. 20, 2007 re U.S. Appl. No. 10/175,539.
Non-final Rejection dated May 14, 2007 re U.S. Appl. No. 10/175,539.
Response submitted Sep. 13, 2007 to Non-final Rejection to U.S. Appl. No. 10/175,539.
Quayle Action dated Nov. 27, 2007 re U.S. Appl. No. 10/175,539.
Response submitted Feb. 27, 2008 to Quayle Action re U.S. Appl. No. 10/175,539.
Notice of Allowance dated May 30, 2008 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Issue Notification dated May 12, 2010 re U.S. Appl. No. 10/175,539.
Non-final Rejection dated Oct. 27, 2009 re U.S. Appl. No. 12/330,709.
Response submitted Apr. 21, 2010 to Non-final Rejection re U.S. Appl. No. 12/330,709.
Supplemental response submitted Jun. 2, 2010 re U.S. Appl. No. 12/330,709.
Ex parte Quyale Action dated Jul. 27, 2010 re U.S. Appl. No. 12/330,709.
Response of Jan. 10, 2011 to Ex parte Quayle Action re U.S. Appl. No. 12/330,709.
Notice of Allowance dated Mar. 3, 2011 re U.S. Appl. No. 12/330,709.
RCE filed Jun. 2, 2011 re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Final rejection dated Oct. 28, 2013 re U.S. Appl. No. 12/330,709.
Non-final Rejection dated Feb. 8, 2007 re U.S. Appl. No. 10/507,121.
Response submitted Jun. 7, 2007 to Non-final Rejection re U.S. Appl. No. 10/507,121.
Final Rejection dated Sep. 7, 2007 re U.S. Appl. No. 10/507,121.
RCE filed Feb. 13, 2008 re U.S. Appl. No. 10/507,121.
Notice of Allowance dated Mar. 20, 2008 re U.S. Appl. No. 10/507,121.
Issue Notification for U.S. Appl. No. 10/507,121 dated Jul. 30, 2008.
Non-final Rejection dated Jan. 27, 2010 re U.S. Appl. No. 12/179,323.
Response submitted Jun. 24, 2010 to Non-final Rejection re U.S. Appl. No. 12/179,323.
Final Rejection dated Sep. 15, 2010 re U.S. Appl. No. 12/179,323.
Notice of Appeal submitted Mar. 15, 2011 re U.S. Appl. No. 12/179,323.
RCE submitted Oct. 17, 2011 re U.S. Appl. No. 12/179,323.
Non-final Rejection dated Jul. 3, 2013 re U.S. Appl. No. 12/179,323.
First Restriction Requirement dated Apr. 4, 2008 re U.S. Appl. No. 10/523,006.
Response to first Restriction Requirement submitted Oct. 1, 2008 re U.S. Appl. No. 10/523,006.
Second Restriction Requirement dated Dec. 9, 2009 re U.S. Appl. No. 10/523,006.
Response to second Restriction Requirement submitted May 5, 2010 re U.S. Appl. No. 10/523,006.
Third Restriction Requirement dated Aug. 3, 2010 re U.S. Appl. No. 10/523,006.
Response to third Restriction Requirement submitted Feb. 1, 2011 re U.S. Appl. No. 10/523,006.
Non-final Rejection dated Mar. 16, 2011 re U.S. Appl. No. 10/523,006.
Response submitted Sep. 16, 2011 to non-final rejection re U.S. Appl. No. 10/523,006.
Final rejection dated Feb. 6, 2012 re U.S. Appl. No. 10/523,006.
RCE submitted Aug. 6, 2012 re U.S. Appl. No. 10/523,006.
Response submitted Oct. 11, 2013 re U.S. Appl. No. 10/523,006.
Restriction Requirement dated Aug. 2, 2010 re U.S. Appl. No. 10/539,288.
Response to Restriction Requirement submitted Jan. 31, 2011 re U.S. Appl. No. 10/539,288.
Non-final Rejection dated Apr. 25, 2011 re U.S. Appl. No. 10/539,288.
Response after Non-final rejection submitted Oct. 25, 2011 re U.S. Appl. No. 10/539,288.
Final rejection dated Dec. 22, 2011 re U.S. Appl. No. 10/539,288.
Notice of Appeal filed Jun. 18, 2012 re U.S. Appl. No. 10/539,288.
RCE filed Aug. 20, 2012 re U.S. Appl. No. 10/539,288.
Non final rejection dated Sep. 21, 2012 re U.S. Appl. No. 10/539,288.
Response after Non-final rejection submitted Feb. 28, 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Non final rejection dated Nov. 15, 2013 re U.S. Appl. No. 10/539,288.
Restriction Requirement dated Jan. 4, 2008 re U.S. Appl. No. 10/518,056.

(56) References Cited

OTHER PUBLICATIONS

Response to Restriction Requirement submitted Jun. 2, 2008 re U.S. Appl. No. 10/518,056.
Non-final Rejection dated Oct. 8, 2008 re U.S. Appl. No. 10/518,056.
Response after Non-final Rejection submitted Feb. 17, 2009 re U.S. Appl. No. 10/518,056.
Final Rejection dated May 27, 2009 re U.S. Appl. No. 10/518,056.
Notice of Appeal filed Oct. 27, 2009 re U.S. Appl. No. 10/518,056.
Amendments after Notice of Appeal submitted Nov. 17, 2009 re U.S. Appl. No. 10/518,056.
Advisory Action dated Jan. 7, 2010 re U.S. Appl. No. 10/518,056.
RCE filed Mar. 22, 2010 re U.S. Appl. No. 10/518,056.
Non-final Rejection mailed Mar. 31, 2008 re U.S. Appl. No. 10/545,795.
Response after Non-final Rejection submitted Sep. 30, 2008.
Final Rejection dated Jan. 27, 2009 re U.S. Appl. No. 10/545,795.
Notice of Appeal filed Jul. 27, 2009 re U.S. Appl. No. 10/545,795.
Amendments after Notice of Appeal submitted Sep. 28, 2009 re U.S. Appl. No. 10/545,795.
Advisory Action dated Sep. 29, 2009 re U.S. Appl. No. 10/545,795.
Second amendment after Notice of Appeal submitted Sep. 28, 2009 re U.S. Appl. No. 10/545,795.
Advisory Action dated Oct. 21, 2009 re U.S. Appl. No. 10/545,795.
RCE submitted Oct. 27, 2009 re U.S. Appl. No. 10/545,795.
Non-final Rejection dated Nov. 16, 2009 re U.S. Appl. No. 10/545,795.
Non-final Rejection dated Mar. 30, 2010 re U.S. Appl. No. 10/545,795.
Interview summary dated Jul. 15, 2010 re U.S. Appl. No. 10/545,795.
Interview summary dated Jul. 30, 2010 re U.S. Appl. No. 10/545,795.
Response after Non-final Rejection dated Aug. 30, 2010 re U.S. Appl. No. 10/545,795.
Final Rejection dated Feb. 1, 2011 re U.S. Appl. No. 10/545,795.
Notice of Appeal filed Jul. 27, 2011 re U.S. Appl. No. 10/545,795.
Restriction Requirement dated Jul. 31, 2008 re U.S. Appl. No. 10/546,538.
Response to Restriction Requirement filed Dec. 24, 2008 re U.S. Appl. No. 10/546,538.
Non-final Rejection dated Jun. 10, 2009 re U.S. Appl. No. 10/546,538.
Response after Non-final Rejection submitted Dec. 9, 2009 re U.S. Appl. No. 10/546,538.
Final Rejection dated Jun. 8, 2010 re U.S. Appl. No. 10/546,538.
Notice of Appeal filed Dec. 8, 2010 re U.S. Appl. No. 10/546,538.
Appeal dismissed dated Jul. 20, 2011 re U.S. Appl. No. 10/546,538.
Restriction requirement mailed Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.
Response of Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Restriction Requirement of Apr. 21, 2008 re U.S. Appl. No. 10/549,619.
Response filed Sep. 22, 2008 to Restriction Requirement re U.S. Appl. No. 10/549,619.
Non-final Rejection Apr. 28, 2009 re U.S. Appl. No. 10/549,619.
Response after Non-final Rejection submitted Oct. 26, 2009 re U.S. Appl. No. 10/549,619.
Interview summary Mar. 3, 2010 re U.S. Appl. No. 10/549,619.
Notice of Allowance Jul. 7, 2010 re U.S. Appl. No. 10/549,619.
Amendments after Notice of Allowance Oct. 6, 2010 re U.S. Appl. No. 10/549,619.
Second amendment after Notice of Allowance Oct. 21, 2012 re U.S. Appl. No. 10/549,619.
Issue Notification of Mar. 9, 2011 re U.S. Appl. No. 101549,619.
First Restriction Requirement dated May 9, 2007 re U.S. Appl. No. 10/525,817.
Response submitted to First Restriction Requirement Sep. 10, 2007 re U.S. Appl. No. 10/525,817.
Second Restriction Requirement dated Nov. 28, 2007 re U.S. Appl. No. 10/525,817.
Response to second Restriction Requirement submitted Feb. 29, 2008 re U.S. Appl. No. 10/525,817.
Third Restriction Requirement dated Jul. 7, 2009 re U.S. Appl. No. 10/525,817.
Response to third Restriction Requirement submitted Oct. 5, 2009 re U.S. Appl. No. 10/525,817.
Non-final rejection dated Apr. 1, 2010 re U.S. Appl. No. 10/525,817.
Supplemental Non-final Action dated Apr. 5, 2010 re U.S. Appl. No. 10/525,817.
Response submitted Jul. 27, 2010 to Non-final Action Apr. 5, 2010 re U.S. Appl. No. 10/525,817.
Non-final rejection Jan. 5, 2011 re U.S. Appl. No. 10/525,817.
Interview Summary dated Jul. 1, 2011 re U.S. Appl. No. 10/525,817.
Response submitted Jul. 5, 2011 to Non-final Action re U.S. Appl. No. 10/525,817.
Examiner's amendment communication dated Dec. 5, 2011 re U.S. Appl. No. 10/525,817.
Notice of Allowance dated Oct. 14, 2011 re U.S. Appl. No. 10/525,817.
U.S. Appl. No. 10/525,817, filed Sep. 15, 2005, Method for the Synthesis of a Bifunctional Complex.
U.S. Appl. No. 11/402,957, filed Apr. 13, 2006, Method for Selecting a Chemical Entity From a Tagged Library.
U.S. Appl. No. 12/330,709, filed Dec. 9, 2008, Templated Molecules and Methods for Using Such Molecules.
U.S. Appl. No. 12/179,323, filed Jul. 24, 2008, Method for Synthesising Templated Molecules.
U.S. Appl. No. 10/523,006, filed Dec. 16, 2005, Multi-step synthesis of templated molecules.
U.S. Appl. No. 10/539,288, filed Jan. 28, 2008, Quasirandom Structure and Function Guided Synthesis Methods.
U.S. Appl. No. 13/179,283, filed Jul. 8, 2011, Method for Producing Second-Generation Library.
U.S. Appl. No. 10/572,644, filed Aug. 25, 2008, Method for Obtaining Structural Information Concerning an Encoded Molecule and Method for Selecting Compounds.
Blondal et al., "Isolation and characterization of a thermostable RNA ligase 1 from a Thermus scotoductus bacteriophage TS2126 with good single-stranded DNA ligation properties", Nucl. Acids. Res. 2005, vol. 33, No. 1, pp. 135-142.
Brennan & Gumport, "T4 RNA ligase catalyzed synthesis of base analogue-containing oligodeoxyribonucleotides and a characterization of their thermal stabilities", Nucleic Acids Res., 1985, vol. 13, No. 24, pp. 8665-8684.
Cummins et al., "Characterization of fully 2'-modified oligoribonucleotide hetero- and homoduplex hybridization and nuclease sensitivity", Nucl. Acids Res. 1995, vol. 23, No. 11, pp. 2019-2024.
Inoue et al., "Synthesis and hybridization studies on two complementary nona(2'-O-methyl)ribonucleotides", Nucleic Acids Res. 1987, vol. 15, No. 15, pp. 6131-6148.
Lesnik et al., "Oligodeoxynucleotides containing 2'-O-modified adenosine: Synthesis and effects on stability of DNA: RNA duplexes", Biochemistry, 1993, vol. 32, pp. 7832-7838.
Verma et al., "Functional tuning of nucleic acids by chemical modifications: tailored oligonucleotides as drugs, devices, and diagnostics", Chem Rec. 2003, 3(1), pp. 51-60.
Communication (office action) by the European Patent Office dated Mar. 24, 2016 in relation to European Patent Application No. 10741877.4.
Glen Research (Catalogue No. 10-1014-XX)—Mar. 8, 2005 + Material Safety Data Sheet on Catalogue No. 10-1014-xx—Sep. 11, 2004.

(56) References Cited

OTHER PUBLICATIONS

Glen Research (Catalogue No. 10-1054-XX)—Mar. 8, 2005 + Material Safety Data Sheet on Catalogue No. 10-1054-xx—Oct. 28, 2004.
Glen Research (Catalogue No. 10-1092-XX)—Apr. 28, 2005 + Material Safety Data Sheet on Catalogue No. 10-1092-xx—Oct. 28, 2004.
Glen Research (Catalogue No. 10-1590-XX)—Aug. 21, 2008 + Further Info on 10-1590-xx—Dec. 12, 2008.
Han et al., "Quantum-dot-tagged microbeads for multiplexed optical coding of biomolecules", Nature Biotechnology, 2001, vol. 19, pp. 631-635.
Korshun et al., "5-(1-Pyrenylethynyl)-2'-Deoxyuridine, A N ovel Fluorescent Nucleosideanalog", Bioorganiceskaa himia, 22(12), 1996, pp. 923-925. (English abstract only).
Mullah et al., "Efficient synthesis of double dye-labeled oligodeoxyribonucleotide probes and their application in a real time PCR assay", Nucleic Acids Research, 1998, vol. 26, No. 4, pp. 1026-1031.
Thelwell, "Mode of action and application of Scorpion primers to mutation detection", Nucleic Acids Research, 2000, vol. 28, No. 19, pp. 3752-3761.
Third Party observation filed with the European Patent Office on Mar. 14, 2016 in relation to European Patent Application No. 10741877.4 (X-Chem Inc.).
Wagner, "Gene inhibition using antisense oligodeoxynucleotides", Nature, 1994, vol. 372, pp. 333-335.
Wagner, "Antisense gene inhibition by oligonucleotides containing C-5 propyne pyrimidines", Science, 1993, vol. 260, pp. 1510-1513.
Yamana et al., "Synthesis and Binding Properties of Oligonucleotides Containing an Azobenzene Linker", Nucleosides & Nucleotides, 1998, vol. 17, No. 1-3, pp. 233-242.
Zammatteo et al., "Amination of polystyrene microwells: Application to the covalent grafting of DNA probes for hybridization assays", Analytical Biochemistry, 236, pp. 85-94, 1996.

* cited by examiner a) 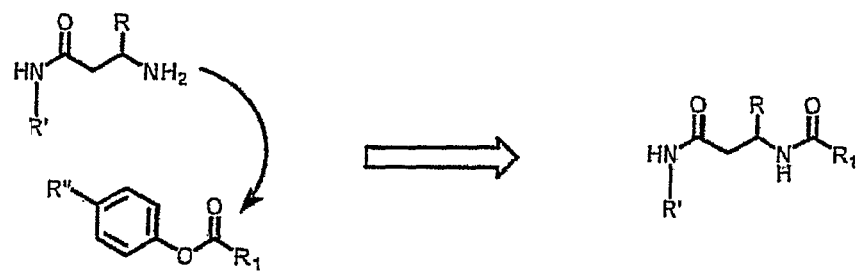
b) 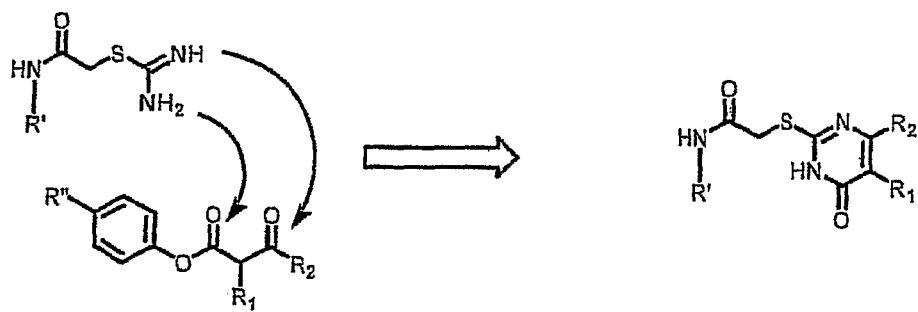
Fig. 13

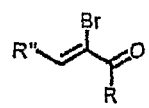 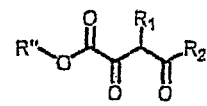
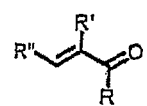 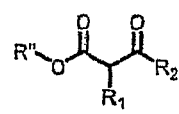
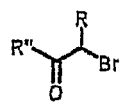 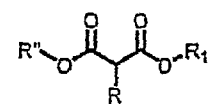
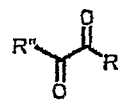 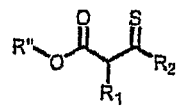 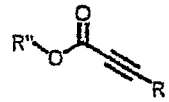
Fig. 14

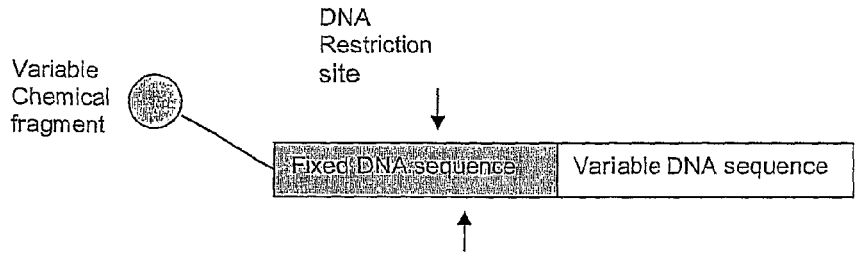

Step 1:
Following parallel chemical reactions, a sample or a pool of samples from n reactions comprising a total of ~ 100 pmol of DNA is subtracted for ES-MS analysis.

Step2:
Add 500 pmol of Biotinylated antisense DNA complementary to the fixed sequence and add EcoRI Restriction buffer [90 mM HCl, 10 mM MgCl2, 50 mM NaCl, pH7.5] in a total volume of 100 ul.
Denature sample at 90 oC for 2 min and cool sample to 37oC. Add 20 units of EcoRI and incubate for a minimum of 2 hours.

Step3:
Prepare Streptavidine beads by washing 50 ul of SA-bead
slurry (Amersham) with 1 ml of 25 mM $NH_4$-acetate (pH 7.25) X 3 and transfer the slurry to a Spin-X column with cellulose-acetate filter (Corning cat#8160/8161).
Add the *EcoRI* restriction sample and
incubate at 30 oC for 15 min. Wash 3 times with 500 ul of $NH_4$-acetate buffer

Step4
The 12 nt DNA seqment with attached chemical building block(s)Is eluted by addition of 50 ul of H2O at 80 oC for 30 sec followed removal of SA-beads using immediate spin-filtration.

Step5
The sample is dried down and redissolved in 50 ul ES-MS buffer Containing 25 mM imidazole/25mM piperidine in a 50:50 mixture of H2O/Acetonitril before applying the sample to the ES-MS for analysis

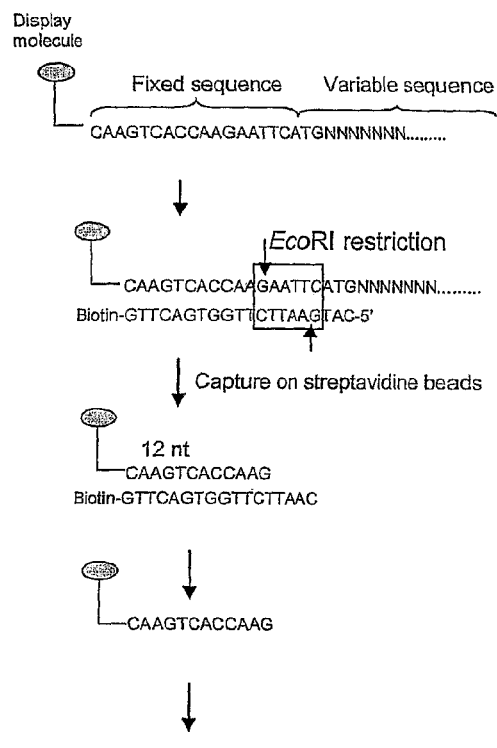

Fig. 55

Library Mimic (general)

Step1: Add oligonucleotide complementary to a control mimic sequence. Purify using handle on complementary oligonucleotide, such as a biotin group, and a suitable method, such as interaction to SA-beads
Step2: Elute mimic and evaluate by analytical tool such as MALDI- or Electrospray MS

Fig. 58

Fig. 58 (cont.)

ENZYMATIC ENCODING METHODS FOR EFFICIENT SYNTHESIS OF LARGE LIBRARIES

This application is a non-provisional of U.S. provisional application Ser. No. 60/741,490 filed on Dec. 2, 2005, which is hereby incorporated by reference in its entirety. All patent and non-patent references cited in U.S. provisional application Ser. No. 60/741,490, or in the present application, are also hereby incorporated by reference in their entirety.

TECHNICAL FIELD OF THE INVENTION

The present invention relates to bifunctional complexes and methods for synthesising such complexes, as well as to methods for split-and-mix synthesis of different molecules each linked to a single stranded identifier oligonucleotide comprising a plurality of tags identifying the molecule and/or the chemical entities having participated in the synthesis of the molecule. The invention also relates to a method for generating a library of different bifunctional complexes and methods for selecting molecules and/or identifying molecules having a desirable property, such as affinity for a target compound.

BACKGROUND OF THE INVENTION

Synthesis methods known as split-and-mix, or split-and-recombine, are known and have been used for the synthesis of different molecules. Split-and-mix methods for synthesising polypeptides and other biochemical polymers have been disclosed e.g. in U.S. Pat. No. 5,723,598 directed to the generation of a library of bifunctional complexes comprising a polypeptide and an identifier oligonucleotide comprising tags in the form of a sequence of nucleotides identifying the amino acids which participated in the formation of the polypeptide. The methods are directed to chemical linkage of tags and do not disclose enzymatic linkage, such as ligation, of the nucleotide tags making up the identifier oligonucleotide.

WO 00/23458 discloses a split-and-mix method in which nucleic acid tags are involved in both molecule synthesis and molecule identification.

WO 2004/039825 and WO 2005/058479 disclose split-and-mix methods wherein tags in the form of identifier oligonucleotides are linked enzymatically. The prior art methods do not disclose ligation of a double-stranded oligonucleotide substrate comprising a plurality of tags and complementary anti-tags at least partly hybridised to each other, wherein said ligation results in the formation of an identifier oligonucleotide comprising a plurality of consecutive nucleotides in the form of covalently linked tags, whereas the anti-tags of the double-stranded oligonucleotide substrate are not affected by the action of the ligase, i.e. no anti-tags become covalently linked as a result of the enzymatic ligation of the tag part of the double-stranded oligonucleotide substrate.

Reference is also made to WO2006/053571 disclosing methods for molecule synthesis.

SUMMARY OF THE INVENTION

There is a need for improved methods for split-and-mix synthesis of libraries of small molecules for e.g. pharmaceutical and other purposes. The small molecules can initially be synthesised as part of a bifunctional complex further comprising an identifier oligonucleotide identifying the reactants which have participated in the synthesis of the small molecule.

The methods of the present invention employs a ligation step wherein the substrate for the ligase is in a double stranded form and wherein the substrate comprises a plurality of tags and at least one or more anti-tags wherein tags and anti-tag(s) is/are at least partly hybridised to each other. The tags are covalently linked as a result of the action of an enzyme comprising a ligase activity on the double stranded substrate, but no anti-tags are covalently linked as a result of said ligase action.

The method facilitates separation of ligated tags and discrete, non-ligated anti-tags because of the size and molecular weight difference between (i) the afore-mentioned single stranded identifier oligonucleotide comprising a plurality of covalently linked tags and (ii) discrete, non-ligated anti-tags. The identifier oligonucleotide comprising the ligated tags will typically have a length at least about 3 times the length of the individual anti-tags.

Figure 6:
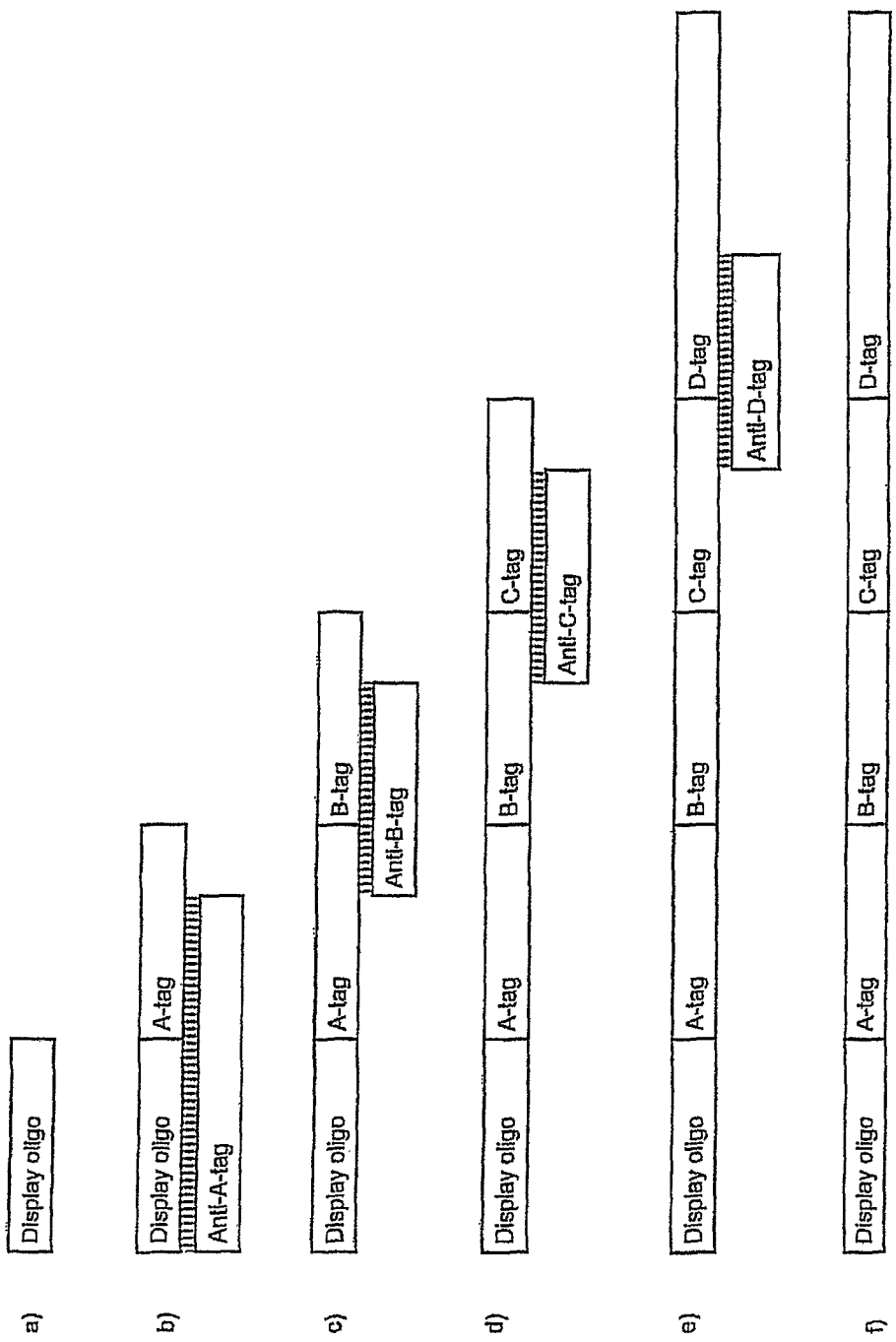

In one embodiment, the tags comprise a 5' phosphate, or a variant ligatable reactive group, whereas anti-tags do not. Therefore, the growing bifunctional complex will comprise a covalently linked "top"-strand to which a number, such as one or more, of shorter and non-ligated anti-tag(s) is/are hybridised/annealed. This enables removal of anti-tag(s), e.g. after all tag additions have been performed (FIG. 1) or after each tag addition has been performed (FIG. 6).

Removal of anti-tags generally increases fidelity and allows extension after purification of the single-stranded oligonucleotide identifier comprising a plurality of ligated tags. Said extension makes possible the use of selection-specific sequences, which improves robustness towards contamination, which is a well-known phenomena when e.g. PCR amplifications are performed. Also, diversification-sequences can be used which diversifies otherwise undistinguishable tag combinations. This makes it possible to identify tag combination sequences which may arise during PCR from a single tag combination. It is advantageous to identify such sequences as they may otherwise be interpreted as arising from several molecular entities containing the same tag combination, thus indicating that the specific tag combination corresponds to a small molecule with relatively high ability to be retained during subsequent selection procedures.

Also, because of the design of the tags, cross-hybridization between single stranded tags can be reduced or essentially eliminated. This greatly improves the purification process of the bifunctional complexes comprising single stranded identifier oligonucleotides following the synthesis reactions. One problem associated with purification of bifunctional complexes comprising double stranded identifier oligonucleotides is that such identifiers are prone to illegitimate hybridization when renaturing conditions are resumed following a purification process under denaturing conditions.

In order to achieve a minimum degree of cross-hybridization between tags in an identifier oligonucleotide, the tags can be designed using a computer algorithm to maximize or optimize the number of mismatches between any oligo pair, e.g. resulting in a minimum of seven mismatches between any two tag tags. This maximizes or optimize fidelity of hybridization and enables use of sorting methods, such as the ones disclosed e.g. in WO 00/23458 (Harbury). Moreover, it increases robustness of decoding by sequencing, e.g. the tag information can be decoded even if sequencing errors occur.

It is also possible to perform a quenching reaction with the reactants and tags. After reactant reactions resulting in the synthesis of the molecule, excess reactants are rendered un-reactive, e.g., by adding a quencher in the form e.g. of a reactant which reacts with excess reactants, e.g. by raising pH, etc, or by removal of a reactant which is critical for the reaction, etc. This can be done e.g. prior to, after or in parallel with deprotection of reacted reactants.

The same principle can be applied to the tags. Unreacted tags can be rendered unreactive at one or more tag reaction site(s), e.g., by dephosphorylation of tags containing 5' phosphates. Advantages associated with these steps include higher fidelity and the possible omission of purification steps between reaction cycles.

The same principle can also be applied to the chemical reaction site on the growing complexes.

In one embodiment of the present invention there is provided a method for the synthesis of a bifunctional complex comprising a molecule and a single stranded oligonucleotide identifier attached to the molecule, said method comprising the steps of
  i) providing a display oligonucleotide attached to
    a) one or more chemical reaction site(s) comprising one or more reactive groups and
    b) one or more priming site(s) for enzymatic addition of a tag,
  ii) providing a first reactant comprising one or more chemical entities and one or more reactive groups capable of reacting with
    c) the one or more chemical reaction site(s) of the display oligonucleotide, and/or
    d) one or more reactive groups of at least a first further reactant comprising one or more chemical entities, wherein said first further reactant is provided simultaneously or sequentially in any order with the first reactant,
  iii) providing a first oligonucleotide tag capable of hybridising to part of a first oligonucleotide anti-tag, wherein the first oligonucleotide tag identifies the first reactant and, optionally, the further first reactant,
  iv) providing a first oligonucleotide anti-tag capable of hybridising to at least part of the first oligonucleotide tag provided in step iii) and to at least part of the display oligonucleotide provided in step i),
  v) reacting the first reactant provided in step ii) with c) the one or more chemical reaction site(s) of the display oligonucleotide and/or with d) the one or more reactive groups of the first further reactant comprising one or more chemical entities,
    wherein the reaction of complementary reactive groups result in the formation of a covalent bond, and
    wherein one or more reactive group reactions of step v) result in the formation of one or more covalent bond(s) between the one or more chemical reaction site(s) of the display oligo and at least one chemical entity of at least one reactant selected from the group consisting of the first reactant and the further first reactant,
  vi) hybridising the anti-tag to the display oligonucleotide and to the first oligonucleotide tag,
    wherein method steps v) and vi) are simultaneous or sequential in any order,
  vii) enzymatically ligating the display oligonucleotide and the first oligonucleotide tag,
  viii) providing a second reactant comprising one or more chemical entities and one or more reactive groups capable of reacting with
    c) the one or more chemical reaction site(s) of the display oligonucleotide, and/or
    d) one or more reactive groups of one or more reactant(s) having reacted in a previous synthesis round, and/or
    e) one or more reactive groups of a second further reactant comprising one or more chemical entities, wherein said second further reactant is provided simultaneously or sequentially in any order with the second reactant,
  ix) providing a second oligonucleotide tag capable of hybridising to part of a second oligonucleotide anti-tag, wherein the second oligonucleotide tag identifies the second reactant and, optionally, the further second reactant,
  x) providing a second oligonucleotide anti-tag capable of hybridising to part of the first oligonucleotide tag provided in step iii) and to part of the second oligonucleotide tag provided in step ix),
  xi) reacting the second reactant provided in step viii) with
    c) the one or more chemical reaction site(s) of the display oligonucleotide and/or d) one or more reactive groups of one or more reactant(s) having reacted in a previous synthesis round and/or e) one or more reactive groups of a further second reactant comprising one or more chemical entities,
    wherein the reaction of complementary reactive groups result in the formation of a covalent bond, and
    wherein one or more reactive group reactions of step xi) result in
    f) the formation of one or more covalent bond(s) between the one or more chemical reaction site(s) and at least one chemical entity of at least one reactant selected from the group consisting of the second reactant and the further second reactant, and/or
    g) the formation of one or more covalent bond(s) between a reactant having reacted in a previous synthesis round and at least one chemical entity of at least one reactant selected from the group consisting of the second reactant and the further second reactant,
  xii) hybridising the anti-tag to the first oligonucleotide tag and the second oligonucleotide tag,
    wherein method steps xi) and xii) are simultaneous or sequential in any order,
  xiii) enzymatically ligating the first and second oligonucleotide tags in the absence of ligation the first and second anti-tag oligonucleotides, and optionally
  xiv) displacing unligated anti-tags from the bifunctional complex comprising a molecule and a single stranded oligonucleotide identifier comprising tags identifying the reactants which participated in the synthesis of the molecule.

It is clear from the above that the claimed method for synthesis of a bifunctional molecule covers a number of alternative embodiments—as well as combinations of a number of such alternative embodiments. The below overview aim to specifically disclose a number of alternative embodiments and combinations thereof.

In step ia) there is provided a display oligonucleotide. In one embodiment the display oligonucleotide has one chemical reaction site comprising one or more reactive groups. A chemical reaction site comprising more than one reactive group can be used for the synthesis of both linear molecules, branched molecules, cyclical molecules and the chemical reaction site can be in the form of a scaffold for the synthesis of small, scaffolded molecules.

In another embodiment, the display oligonucleotide has more than one chemical reaction site each comprising one or more reactive groups.

For each of the above alternatives the display oligonucleotide can have one or more priming sites. Accordingly, as far as step i) is concerned, the following alternatives are provided:

A display oligonucleotide comprising one chemical reaction site and one priming site;
A display oligonucleotide comprising more than one chemical reaction site and one priming site;
A display oligonucleotide comprising one chemical reaction site and more than one priming site; and
A display oligonucleotide comprising more than one chemical reaction site and more than one priming site.

Each of the above-mentioned sites can have one or more reactive groups. When more sites are provided, there is also provided an embodiment wherein one site has one reactive group whereas the remaining sites have more than one reactive group.

In step ii) there is provided a first reactant comprising one or more chemical entities, wherein each entity has one or more reactive groups. Accordingly, as far as step ii) is concerned, the following alternatives are provided:

A first reactant comprising one chemical entity having one reactive group;
A first reactant comprising more than one chemical entity each having one reactive group;
A first reactant comprising one chemical entity each having more than one reactive group; and
A first reactant comprising more than one chemical entity each having more than one reactive group.

In one embodiment, a display oligonucleotide selected from the group consisting of a display oligonucleotide comprising one chemical reaction site and one priming site; a display oligonucleotide comprising more than one chemical reaction site and one priming site; a display oligonucleotide comprising one chemical reaction site and more than one priming site; and a display oligonucleotide comprising more than one chemical reaction site and more than one priming site, is reacted with a first reactant selected from the group consisting of a first reactant comprising one chemical entity having one reactive group; a first reactant comprising more than one chemical entity each having one reactive group; a first reactant comprising one chemical entity each having more than one reactive group; and a first reactant comprising more than one chemical entity each having more than one reactive group.

Step ii) also allows a reaction to occur between a first reactant and a further first reactant, wherein the reaction product reacts, simultaneously or sequentially in any order, with a chemical reaction site of a display molecule. Accordingly, there is also provided in step ii):

A first further reactant comprising one chemical entity having one reactive group;
A first further reactant comprising more than one chemical entity each having one reactive group;
A first further reactant comprising one chemical entity having more than one reactive group; and
A first further reactant comprising more than one chemical entity each having more than one reactive group.

Consequently, there is provided in one embodiment a reaction between a first reactant selected from the group consisting of a first reactant comprising one chemical entity having one reactive group; a first reactant comprising more than one chemical entity each having one reactive group; a first reactant comprising one chemical entity having more than one reactive group; and a first reactant comprising more than one chemical entity each having more than one reactive group, and a first further reactant selected from the group consisting of a first further reactant comprising one chemical entity having one reactive group; a first further reactant comprising more than one chemical entity each having one reactive group; a first further reactant comprising one chemical entity having more than one reactive group; and a first further reactant comprising more than one chemical entity each having more than one reactive group.

In step viii) there is provided a second reactant comprising one or more chemical entities, wherein each entity has one or more reactive groups. Accordingly, as far as step ii) is concerned, the following alternatives are provided:

A second reactant comprising one chemical entity having one reactive group;
A second reactant comprising more than one chemical entity each having one reactive group;
A second reactant comprising one chemical entity each having more than one reactive group; and
A second reactant comprising more than one chemical entity each having more than one reactive group.

In one embodiment, a display oligonucleotide selected from the group consisting of a display oligonucleotide comprising one chemical reaction site and one priming site; a display oligonucleotide comprising more than one chemical reaction site and one priming site; a display oligonucleotide comprising one chemical reaction site and more than one priming site; and a display oligonucleotide comprising more than one chemical reaction site and more than one priming site, wherein one or more chemical reaction sites have reacted with one or more reactants in a first or previous reaction round, is reacted with a second reactant selected from the group consisting of a second reactant comprising one chemical entity having one reactive group; a second reactant comprising more than one chemical entity each having one reactive group; a second reactant comprising one chemical entity each having more than one reactive group; and a second reactant comprising more than one chemical entity each having more than one reactive group.

Step viii) also allows a reaction to occur between a second reactant and a further second reactant, wherein the reaction product reacts, simultaneously or sequentially in any order, with a chemical reaction site of a display molecule, or a reactive group of a reactant having reacted with one or more chemical reaction sites of the display oligonucleotide in a previous reaction round. Accordingly, there is also provided in step viii):

A second further reactant comprising one chemical entity having one reactive group;
A second further reactant comprising more than one chemical entity each having one reactive group;
A second further reactant comprising one chemical entity having more than one reactive group; and
A second further reactant comprising more than one chemical entity each having more than one reactive group.

Consequently, there is provided in one embodiment a reaction between a second reactant selected from the group consisting of a second reactant comprising one chemical entity having one reactive group; a second reactant comprising more than one chemical entity each having one reactive group; a second reactant comprising one chemical entity having more than one reactive group; and a second reactant comprising more than one chemical entity each having more than one reactive group, and a second further reactant selected from the group consisting of a second further reactant comprising one chemical entity having one reactive group; a second further reactant comprising more than one chemical entity each having one reactive group; a second further reactant comprising one chemical entity having more than one reactive group; and a second further reactant comprising more than one chemical entity each having more than one reactive group.

In one embodiment, a reactant having reacted in a previous reaction round with one or more chemical reaction sites of a display oligonucleotide, or a reactant having previously reacted with a reactant having reacted with said one or more chemical reaction sites, is to be regarded as a chemical reaction site capable of reacting with one or more reactants provided in a subsequent reaction round.

When a library of different bifunctional complexes are synthesised by split-and-mix methods according to the present invention, the composition of nascent bifunctional complexes obtained in step vii) is split (divided) into a plurality of different compartments. In each different compartment, a different second reactant is provided, c.f. step viii) above. Also, in each different compartment a second oligonucleotide tag is added, c.f. step ix) above, said second oligonucleotide tag identifying in each different compartment the second reactant, and optionally also the further second reactant, provided in the same compartment as the second oligonucleotide tag.

In each different compartment a suitable anti-tag is provided, c.f. step x) above, and hybridised to at least partly complementary tags, c.f. step xii) above.

The reaction cited in step xi) herein above takes place in each different compartment, resulting in the synthesis in each different compartment of different nascent bifunctional complexes comprising the result (reaction product in the form of a molecule or molecule precursor) of a reaction involving the first and second reactants, and optionally also the further first reactant and/or the further second reactant, wherein said reaction product of the nascent bifunctional product is linked to a corresponding identifier oligonucleotide comprising the first and second oligonucleotide tags, c.f. step xiv). At the end of each synthesis round, the generated, nascent or final bifunctional complex is optionally separated from unligated anti-tags. However, this separation step can also be carried out only once, after the final synthesis round.

The different bifunctional complexes from a given round of synthesis are combined and split in order to initiate a new synthesis round, c.f. steps viii) to xii) above, which are repeated for a different reactant and optionally a different further reactant.

Taking the above library synthesis steps into consideration, the present invention is in one embodiment directed to a method for the synthesis of a plurality of different bifunctional complexes, said method comprising the steps of i) providing a plurality of display oligonucleotides each attached to
  a) one or more chemical reaction site(s) comprising one or more reactive groups and
  b) one or more priming site(s) for enzymatic addition of a tag, ii) providing a plurality of first reactants each comprising one or more chemical entities and one or more reactive groups, each first reactant being capable of reacting with
  c) the one or more chemical reaction site(s) of the display oligonucleotide, and/or
  d) one or more reactive groups of a first further reactant comprising one or more chemical entities, wherein said first further reactant is provided simultaneously or sequentially in any order with the first reactant, iii) providing a plurality of first oligonucleotide tags each capable of hybridising to part of a first oligonucleotide anti-tag, wherein each first oligonucleotide tag identifies a first reactant and, optionally, a further first reactant, iv) providing a plurality of first oligonucleotide anti-tags each capable of hybridising to at least part of a first oligonucleotide tag provided in step iii) and to at least part of a display oligonucleotide provided in step i), v) reacting each of the first reactants provided in step ii) with c) the one or more chemical reaction site(s) of the display oligonucleotides and/or with d) the one or more reactive groups of a first further reactant comprising one or more chemical entities,
  wherein the reaction of complementary reactive groups result in the formation of a covalent bond, and
  wherein one or more reactive group reactions of step v) result in the formation of one or more covalent bond(s) between the one or more chemical reaction site(s) of the display oligonucleotides and at least one chemical entity of at least one reactant selected from the group consisting of a first reactant and a further first reactant, vi) hybridising anti-tags to display oligonucleotides and to first oligonucleotide tags,
  wherein method steps v) and vi) are simultaneous or sequential in any order, vii) enzymatically ligating display oligonucleotides and first oligonucleotide tags, viii) dividing the plurality of nascent bifunctional complexes obtained in step vii) into a plurality of different compartments, ix) providing in each different compartment a plurality of different second reactants each comprising one or more chemical entities and one or more reactive groups capable of reacting with
  c) the one or more chemical reaction site(s) of each of the display oligonucleotides, and/or
  d) one or more reactive groups of one or more reactant(s) having reacted in a previous synthesis round, and/or
  e) one or more reactive groups of a second further reactant comprising one or more chemical entities, wherein said second further reactants are provided simultaneously or sequentially in any order with the second reactants, x) providing in each different compartment a plurality of second oligonucleotide tags each capable of hybridising to part of a second oligonucleotide anti-tag, wherein different second oligonucleotide tags are provided in each different compartment, and wherein each different second oligonucleotide identifies a different second reactant and, optionally, a further second reactant which may be the same or a different further second reactant in each different compartment, xi) providing in each different compartment a plurality of second oligonucleotide anti-tags capable of hybridising to part of a first oligonucleotide tag provided in step iii) and to part of a second oligonucleotide tag provided in step x), xii) reacting in each different compartment each of the different second reactants provided in step ix) with c) the one or more chemical reaction site(s) of a display oligonucleotide and/or d) one or more reactive groups of one or more reactant(s) having reacted in a previous synthesis round and/or e) one or more reactive groups of a further second reactant comprising one or more chemical entities,
   wherein said one or more reactions result in the formation of different bifunctional complexes in each different compartment,
   wherein the reaction of complementary reactive groups result in the formation of a covalent bond, and
   wherein one or more reactive group reactions of step xii) result in
   f) the formation of one or more covalent bond(s) between the one or more chemical reaction site(s) and at least one chemical entity of at least one reactant selected from the group consisting of second reactants and further second reactants, and/or
   g) the formation of one or more covalent bond(s) between a reactant having reacted in a previous synthesis round and at least one chemical entity of at least one reactant selected from the group consisting of second reactants and further second reactants,
xiii) hybridising anti-tags to first oligonucleotide tags and second oligonucleotide tags in each different compartment,
   wherein method steps xii) and xiii) are simultaneous or sequential in any order,
xiv) enzymatically ligating in each different compartment first and second oligonucleotide tags in the absence of ligation first and second anti-tag oligonucleotides, and optionally
xv) displacing in each compartment unligated anti-tags from bifunctional complexes comprising a molecule and a single stranded oligonucleotide identifier comprising tags identifying the one or more reactants which participated in the synthesis of the molecule.

The above steps viii) to xv) can be repeated once or more than once using different reactants and tags identifying said different reactants. Prior to the repetition of the aforementioned steps the synthesised bifunctional complexes are combined and split into different reaction compartments.

As will be clear from the above, the present invention in one embodiment allows for efficient, enzymatic ligation of a plurality of single-stranded tags making up one strand only of an at least partly double stranded, identifier oligonucleotide hybridisation complex (at least at the time of ligation), wherein anti-tags at least partly hybridised to the tags are not ligated and can easily be disposed of after each synthesis round (FIG. 6) or after molecule synthesis have been completed (FIG. 1).

None of the prior art methods disclose the formation of a double stranded, identifier oligonucleotide precursor comprising complementary tags and anti-tags which are at least partly hybridised to each other, but not covalently linked. That is, prior to ligation, a tag can initially be hybridised to an anti-tag of the complementary strand of the double stranded, identifier oligonucleotide precursor, but not covalently linked to either such an anti-tag, or to another tag forming part of the same strand of the double stranded, identifier oligonucleotide precursor.

Likewise, an anti-tag can initially be hybridised to a tag of the complementary strand of the double stranded, identifier oligonucleotide precursor, but not covalently linked to either such a tag, or to another anti-tag forming part of the same strand of the double stranded, identifier oligonucleotide precursor.

In a further aspect of the invention there is provided a method for obtaining a bifunctional complex comprising a molecule and an identifier oligonucleotide. Initially, a nascent bifunctional complex comprising one or more chemical reaction site(s) and one or more priming site(s) for enzymatic addition of a tag is reacted a) at the chemical reaction site with one or more reactant(s) in the form of chemical entities and b) reacted at the priming site with one or more identifier oligonucleotide tag(s) identifying the reactant(s) which have reacted—or are going to react—with each other and/or with the chemical reaction site, wherein tag ligation results in the formation only of a single stranded identifier oligonucleotide comprising a plurality of tags, whereas no anti-tag at least partly hybridised the one or more tags are ligated to a neighbouring anti-tag.

There is also provided a bifunctional complex as disclosed herein. In one aspect, the bifunctional complex is an intermediate bifunctional complex comprising a molecule precursor and a single stranded identifier oligonucleotide identifying the molecule precursor, wherein the single stranded identifier comprises a plurality of covalently linked tags which are at least partly hybridised to one or more corresponding anti-tag(s), wherein, when more anti-tags are present, said anti-tags are not covalently linked to each other.

In another aspect there is provided a bifunctional complex comprising a molecule and a single stranded identifier oligonucleotide identifying the molecule, wherein the single stranded identifier comprises a plurality of covalently linked tags which are at least partly hybridised to one or more corresponding anti-tag(s), wherein, when more anti-tags are present, said anti-tags are not covalently linked.

In a still further aspect there is provided a bifunctional complex comprising a molecule and a single stranded identifier oligonucleotide identifying the molecule, wherein the single stranded identifier comprises a plurality of covalently linked tags.

There is also provided a method for synthesising a library of different bifunctional complexes. The lack of a covalent link between a reactant and a tag means that a library can be produced by a split-and-mix strategy. In a first step a display oligonucleotide or a nascent bifunctional complex is dispensed in separate compartments and subsequently exposed to a different reactant in each or at least the majority of the compartments. The reactant reacts in each compartment with at least one reactive group of the chemical reaction site and a tag identifying the reactant is added by enzymatic action at the priming site. In one embodiment of the invention, the tag is added to the priming site by enzymatic ligation.

There is also provided a method for partitioning a library or composition of different bifunctional complexes, said partitioning resulting in the selection of bifunctional complexes comprising molecules having one or more desirable characteristics. The partitioning of bifunctional complexes can occur as a result of the differential affinity of the molecule(s) of different bifunctional complexes for the same or different targets, such as the targets disclosed herein. Alternatively, and/or in combination with the above, partitioning of bifunctional complexes can occur based on tag features, such as e.g. tag nucleotide sequences and/or physical properties capable of distinguishing different tags and/or identifier oligonucleotides from each other.

Whereas an initially generated library is often termed a "naïve library", the library obtained after partitioning is often termed an "intelligent" or "enriched" library. The partitioning can be carried out once or more than once using the same or different partitioning parameters, such as binding affinity to a target compound under predetermined assaying conditions.

In a further aspect there is provided a pharmaceutical composition comprising the molecule, or a variant of the molecule, of the bifunctional complex—wherein preferably the molecule is not linked to the identifier oligonucleotide of the bifunctional complex. The terms "molecule", "compound", "chemical compound", "reaction product", "bioactive agent" and "bioactive species" are used interchangably herein when referring to a product obtained by the methods of the present invention, or a variant of such a product obtained e.g. when a "lead compound" or "drug lead" is being optimised for pharmaceutical uses. A "bioactive agent" or a "bioactive species" is typically a molecule which exerts a biologically relevant activity, such as e.g. a biologically relevant binding affinity for a target compound.

There is also provided the use of a bifunctional complex according to the invention in the manufacture of a medicament for the treatment of a clinical indication in an individual in need thereof.

DEFINITIONS

α-peptide: Peptide comprising or essentially consisting of at least two ☐-amino acids linked to one another by a linker including a peptide bond.

Amino acid: Entity comprising an amino terminal part ($NH_2$) and a carboxy terminal part (COOH) separated by a central part comprising a carbon atom, or a chain of carbon atoms, comprising at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b) (2) belong to the group of amino acids listed herein below. Non-natural amino acids are those not listed in the below table. Examples of non-natural amino acids are those listed e.g. in 37 C.F.R. section 1.822(b) (4), all of which are incorporated herein by reference. Further examples of non-natural amino acids are listed herein below. Amino acid residues described herein can be in the "D" or "L" isomeric form.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |

-continued

| Symbols | | |
|---|---|---|
| 1-Letter | 3-Letter | Amino acid |
| N | Asn | asparagine |
| C | Cys | cysteine |

Amino acid precursor: Moiety capable of generating an amino acid residue following incorporation of the precursor into a peptide.

Amplifying: Any process or combination of process steps that increases the number of copies of an identifier oligonucleotide. Amplification of identifier oligonucleotides can be carried out by any state of the art method including, but not limited to, a polymerase chain reaction to increase the copy number of each identifier oligonucleotide by using the identifier oligonucleotide(s) as template(s) for synthesising additional copies of the identifier oligonucleotides. Any amplification reaction or combination of such reactions known in the art can be used as appropriate as readily recognized by those skilled in the art. Accordingly, identifier oligonucleotides can be amplified using a polymerase chain reaction (PCR), a ligase chain reaction (LCR), by in vivo amplification of identifier oligonucleotides cloned in DNA chromosomal or extra-chromosomal elements including vectors and plasmids, and the like. The amplification method should preferably result in the proportions of the amplified mixture of identifier oligonucleotides being essentially representative of the proportions of identifier oligonucleotides of different sequences in a mixture prior to said amplification.

Base: Nitrogeneous base moiety of a natural or non-natural nucleotide, or a derivative of such a nucleotide comprising alternative sugar or phosphate moieties. Base moieties include any moiety that is different from a naturally occurring moiety and capable of complementing one or more bases of the opposite nucleotide strand of a double helix.

Bifunctional complex: Molecule linked to an identifier oligonucleotide capable of identifying the molecule and/or the reactants having participated in the synthesis of the molecule. An "intermediate bifunctional complex" wherein the chemical reaction site or the (precursor) molecule part will undergo further reactions with reactants or chemical entities in order to synthesise a "final" molecule is also termed a "nascent bifunctional complex".

Binding region: Region on a string of consecutive nucleotides to which an enzyme can bind, e.g. when ligating different oligonucleotides (e.g. in case of a ligase) or prior to a fill-in reaction (e.g. in case of a polymerase).

Catalyst: Moiety acting on a starting compound or a set of starting compounds and speeding up chemical reactions involving such compound(s).

Chemical entity: Functional chemical group, or reactant, which, when reacted, becomes covalently attached to a site, such as a chemical reaction site, for example a site on a molecule, such as a scaffold at which site one or more reactive groups can be e.g. reacted, substituted or added. Chemical entities and reactants are used interchangably herein in bond-forming reactions resulting in the formation of a molecule, or a molecule precursor. For example, a carbon atom that is part of the scaffold can be bound to a methyl group chemical entity. This site may also be within the scaffold; for example, a hydrogen atom on a carbon atom within a ring can be a chemical entity. Chemical entities can preferably be modified or replaced by other chemical entities or derived substituents using one step or two step chemical processes. Protection and de-protection steps may also be required. In an embodiment of the methods of the invention, this modification can be done independently at each chemical entity, without the need to add protecting groups at the other chemical entities. Chemical entities may comprise substituents capable of anomalous scattering. The chemical entity either forms part of a reactant or is used herein interchangably with the term "reactant". The chemical entity can comprise or be linked to a reactive group capable of reacting with reactive groups of other chemical entities or reactants. Chemical entities that can be used in some aspects of the present invention include, but are not limited to H, benzyl halide, benzyl alcohol, allyl halide, allyl alcohol, carboxylic acid, aryl amine, heteroaryl amine, benzyl amine, aryl alkyl amine, alkyl amino, phenol, aryl halide, heteroaryl halide, heteroaryl chloride, aryl aldehyde, heteroaryl aldehyde, aryl alkyl aldehyde, alkyl aldehyde, aryl, heteroaryl, alkyl, aryl alkyl, ketone, arylthiol, heteroaryl thiol, urea, imide, aryl boronic acid, ester, carbamate, tert-butyl carbamate, nitro, aryl methyl, heteroaryl methyl, vinyl methyl, 2- or 2,2-substituted vinyls, 2-substituted alkynes, acyl halide, aryl halide, alkyl halide, cycloalkyl halide, sulfonyl halide, carboxylic anhydride, epoxide, and sulfonic acid. In some embodiments, the chemical entities may include, but are not limited to benzyl bromide, benzyl alcohol, allyl bromide, allyl alcohol, carboxylic acid, aryl amine, heteroaryl amine, benzyl amine, aryl alkyl amine, phenol, aryl bromide, heteroaryl bromide, heteroaryl chloride, aryl aldehyde, heteroaryl aldehyde, aryl alkyl aldehyde, ketone, arylthiol, heteroaryl thiol, urea, imide, and aryl boronic acid. Halide may include, for example, iodide, bromide, fluoride, and chloride. Halide may include halides capable of anomalous scattering, such as, for example, bromide or iodide. By convention, a chemical entity can be considered as either "direct" chemical entities or "latent" chemical entities, with some having the capacity to function as either. A direct chemical entity is a functional group or moiety that can react directly with another functional group or moiety without prior modification or that can be rendered reactive by the addition of reagents and/or catalysts typically, but not necessarily, in a single-pot reaction. Examples of a direct chemical entity include, but are not limited to: the Br in a benzyl bromide, carboxylic acid, amine, phenol, the Br in an aryl bromide, aldehyde, thiol, boronic acid or ester, and the like. A latent chemical entity is a functional group or moiety that requires prior modification, either in a separate step after which it may or may not be isolated, or generated in situ to afford a more reactive species (i.e., obtaining a direct chemical entity). A latent chemical entity may also comprise a moiety that by virtue of its proximity or connectivity to a functional group or other moiety is rendered reactive. Examples of a latent chemical entity include, but are not limited to: nitro (which can be reduced to an amine), aryl methyl (which can be converted to aryl bromomethyl or to aryl carboxylic acid), olefin (which can undergo oxidative cleavage to afford an epoxide, an aldehyde or carboxylic acid), and the like. The adoption of the above convention serves to illustrate the scope of chemical moieties regarded as chemical entities within the present invention. Additional chemical entities are within the scope of this invention and are evident to those trained in the art and having access to the chemical literature.

Chemical group: Entity of a reactant or chemical entity participating in the synthesis of a molecule.

Chemical reaction site: Site of a nascent bifunctional complex reacted with at least one reactant or chemical entity during the synthesis of a molecule.

Cleavable linker: Residue or bond capable of being cleaved under predetermined conditions.

Cleaving: Breaking a chemical bond. The bond can be a covalent bond or a non-covalent bond.

Complementary binding partners: Binding partners capable of reacting with each other. Binding partner and reactant are used interchangably herein.

Complementary reactive groups: Reactive groups capable of reacting with each other.

Contacting: Bringing e.g. corresponding reactive groups or corresponding binding partners or hybridization partners into reactive contact with each other. The reactive contact is evident from a reaction between the partners, or the formation of a bond, or hybridization, between the partners.

Cycle of reaction: The methods of the present invention employ split-n-mix strategies for molecule synthesis. A reaction cycle involves a reaction of a reactant or chemical entity with another reactant or chemical entity or with the chemical reaction site and the reaction of a tag with another tag or with the priming site. In other words, a reaction cycle involves both a molecule specific reaction and a tag specific reaction.

Enzyme: Any polypeptide capable of speeding up chemical reactions. Enzymes act as catalysts for a single reaction and converts a starting compound or a specific set of starting compounds into specific products. Examples are ligases and polymerases.

Hybridisation: The ability of complementary nucleotides to form an association through hydrogen bonding.

Identifier oligonucleotide: The identifier oligonucleotide can be single stranded or, in an initial state, at least partly hybridised to one or more discrete anti-tags. The oligonucleotide identifier (s) can be linear or branched. The nucleotides of the identifier oligonucleotide can be natural and/or non-natural nucleotides, including nucleotide derivatives. The length can vary as long as the identifier is long enough (i.e. contains a sufficient number of nucleotides) to identify the molecule part of the bifunctional complex to which the identifier oligonucleotide is linked, or the reactants having participated in the synthesis of the molecule.

Interacting: Used interchangably with contacting. Bringing species such as e.g. corresponding binding partners into reactive contact with each other. The reaction can be mediated by recognition groups forming corresponding binding partners by means of covalent or non-covalent bonds.

Library: A composition of different moieties, such as small molecules or bifunctional complexes comprising different small molecules each linked to a specific identifier oligonucleotide identifying the small molecule.

Linker: A residue or chemical bond separating at least two species. The species can be retained at an essentially fixed distance, or the linker can be flexible and allow the species some freedom of movement in relation to each other. The link can be a covalent bond or a non-covalent bond.

Molecule: A chemical reaction site, such as a scaffold, which has reacted with one or more reactants. The molecule can form part of a bifunctional complex further comprising an identifier oligonucleotide capable of identifying the molecule or the reactants which have reacted in the method for synthesising the molecule. The molecule is also termed a "display molecule". The molecule part of the bifunctional complex can be linked covalently to the priming site of the bifunctional complex and/or to a single stranded identifier oligonucleotide comprising a plurality of covalently linked tags. A "molecule" is any chemical entity, or part thereof, selected or designed to be part of a synthetic precursor to lead candidate or drug candidate. The molecule comprises one, two, or three or more chemical substituents, also called "chemical entities". A molecule preferably exhibits properties of desirable lead compounds, including, for example, a low molecular complexity (low number of hydrogen bond donors and acceptors, low number of rotatable bonds, and low molecular weight), and low hydrophobicity. Because the molecule is small, one of ordinary skill in the art may further develop or elaborate the molecule into a lead or drug candidate by modifying the molecule, either at the chemical entities or at the core structure, to have desirable drug characteristics, including, for example, by meeting the Lipinski rule of five. Preferred molecule properties include lead-like properties and are known to those of ordinary skill in the art and are described in Teague, S. J., et al., Agnew. Chem. Int. Ed. 38:3743-3748, 1999; Oprea, T. I., et al., J. Chem. Inf. Comput. Sci. 41:1308-1315, 2001; and Hann, M. M. et al., J. Chem. Inf. Comput. Sci. 41:856-864, 2001. Desirable molecules include, but are not limited to, for example, molecules having many or all of the following general properties: MW<about 1000, MW<about 500, MW<about 350, MW<about 300, or MW<about 250, a clog P<about 3, less than about 5 rings, and an Log P<about 5 or <about 4. Other general properties may include less than about 15, such as 12, for example 10 nonterminal single bonds, less than about 10, such as 8, for example 6 hydrogen bond donors, and less than about 10, such as 8, for example 6 hydrogen bond acceptors. Thus, molecules are designed so that more complexity and weight can be added during development and building out of the compound into a lead candidate, while maintaining the general properties. Molecules may comprise scaffolds comprising cyclic or non-cyclic structures. Examples of non-cyclic scaffolds, include, but are not limited to, hypusine, putrescine, gamma-aminobutyric acid, and 2-hydroxyputresine. Generally, the scaffold portion of a molecule may comprise 1) a cyclic structure, including any of the cyclic structures described herein, with 2) one or more of the chemical entities disclosed herein.

Nascent bifunctional complex: Also referred to as a growing complex; specifies an initial or intermediate complex to be processed according to the methods of the present invention. An intermediate complex designates an initial complex that has been subjected to one or more rounds of reactant reaction and tag addition.

Natural nucleotide: Any of the four deoxyribonucleotides, dA, dG, dT, and dC (constituents of DNA) and the four ribonucleotides, A, G, U, and C (constituents of RNA) are natural nucleotides. Each natural nucleotide comprises a sugar moiety (ribose or deoxyribose), a phosphate moiety, and a natural/standard base moiety. Natural nucleotides bind to complementary nucleotides according to well-known base pairing rules, such as e.g. Watson & Crick type base pairing, where adenine (A) pairs with thymine (T) or uracil (U); and where guanine (G) pairs with cytosine (C), wherein corresponding base-pairs are part of complementary, anti-parallel nucleotide strands. The base pairing results in a specific hybridization between predetermined and complementary nucleotides. The base pairing is the basis by which enzymes are able to catalyze the synthesis of an oligonucleotide complementary to the template oligonucleotide. In this synthesis, building blocks (normally the triphosphates of ribo or deoxyribo derivatives of A, T, U, C, or G) are directed by a template oligonucleotide to form a complementary oligonucleotide with the correct, complementary sequence. The recognition of an oligonucleotide sequence by its complementary sequence is mediated by corresponding and interacting bases forming base pairs. In nature, the specific interactions leading to base pairing are governed by the size of the bases and the pattern of hydrogen bond donors and acceptors of the bases. A large purine base (A or G) pairs with a small pyrimidine base (T, U or C). Additionally, base pair recognition between bases is influenced by hydrogen bonds formed between the bases. In the geometry of the Watson-Crick base pair, a six membered ring (a pyrimidine in natural oligonucleotides) is juxtaposed to a ring system composed of a fused, six membered ring and a five membered ring (a purine in natural oligonucleotides), with a middle hydrogen bond linking two ring atoms, and hydrogen bonds on either side joining functional groups appended to each of the rings, with donor groups paired with acceptor groups.

Figure 2:
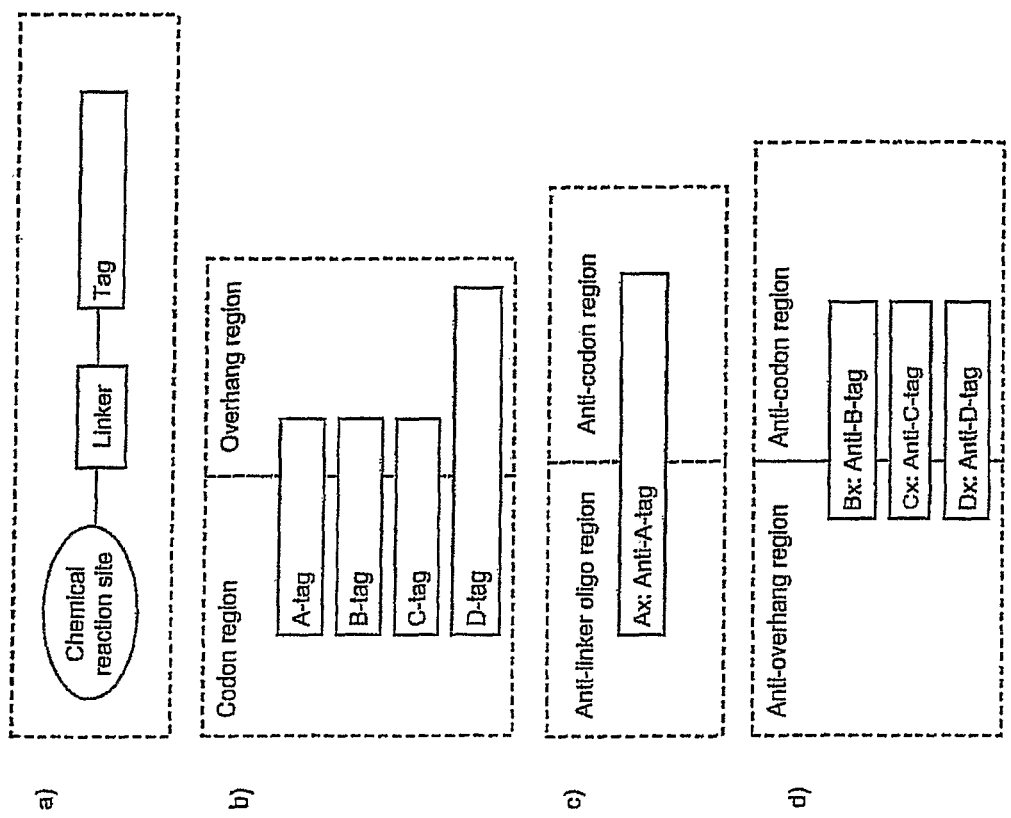

Non-natural base pairing: Base pairing among non-natural nucleotides, or among a natural nucleotide and a non-natural nucleotide. Examples are described in U.S. Pat. No. 6,037,120, wherein eight non-standard nucleotides are described, and wherein the natural base has been replaced by a non-natural base. As is the case for natural nucleotides, the non-natural base pairs involve a monocyclic, six membered ring pairing with a fused, bicyclic heterocyclic ring system composed of a five member ring fused with a six membered ring. However, the patterns of hydrogen bonds through which the base pairing is established are different from those found in the natural AT, AU and GC base pairs. In this expanded set of base pairs obeying the Watson-Crick hydrogen-bonding rules, A pairs with T (or U), G pairs with C, iso-C pairs with iso-G, and K pairs with X, H pairs with J, and M pairs with N (FIG. 2). Nucleobases capable of base pairing without obeying Watson-Crick hydrogen-bonding rules have also been described (Berger et al., 2000, Nucleic Acids Research, 28, pp. 2911-2914).

Non-natural nucleotide: Any nucleotide not falling within the above definition of a natural nucleotide.

Nucleotide: The term nucleotides as used herein refers to both natural nucleotides and non-natural nucleotides. Nucleotides can differ from natural nucleotides by having a different phosphate moiety and/or a different sugar moiety and/or a different base moiety from the natural nucleotide. Accordingly, nucleotides can form part of an identifier oligonucleotide when they are linked to each other by a natural bond in the form of a phosphodiester bond, or a non-natural bond, such as e.g. a peptide bond as in the case of PNA (peptide nucleic acids).

Nucleotide derivative: Nucleotide further comprising an appended molecular entity. The nucleotides can be derivatized on the bases and/or the ribose/deoxyribose unit and/or the phosphate. Preferred sites of derivatization on the bases include the 8-position of adenine, the 5-position of uracil, the 5- or 6-position of cytosine, and the 7-position of guanine. The nucleotide-analogs described below can be derivatized at the corresponding positions (Benner, U.S. Pat. No. 6,037,120). Other sites of derivatization can be used, as long as the derivatization does not disrupt base pairing specificity. Preferred sites of derivatization on the ribose or deoxyribose moieties are the 5', 4' or 2' positions. In certain cases it can be desirable to stabilize the nucleic acids towards degradation, and it can be advantageous to use 2'-modified nucleotides (U.S. Pat. No. 5,958,691). Again, other sites can be employed, as long as the base pairing specificity is not disrupted. Finally, the phosphates can be derivatized. Preferred derivatizations are phosphorothiote. Nucleotide analogs (as described below) can be derivatized similarly to nucleotides. It is clear that the various types of modifications mentioned herein above, including i) derivatization and ii) substitution of the natural bases or natural backbone structures with non-natural bases and alternative, non-natural backbone structures, respectively, can be applied once or more than once within the same nucleic acid molecule.

Oligonucleotide: The term oligonucleotide comprises oligonucleotides of both natural and/or non-natural nucleotides, including any combination thereof. The natural and/or non-natural nucleotides can be linked by natural phosphodiester bonds or by non-natural bonds. Oligonucleotides have at least 2 nucleotides, such as 3 or more nucleotides.

Oligomer: Molecule comprising a plurality of monomers that can be identical, of the same type, or different. Oligomers can be homooligomers comprising a plurality of identical monomers, oligomers comprising different monomers of the same type, or heterooligomers comprising different types of monomers, wherein each type of monomer can be identical or different.

Partitioning: Process whereby molecules, or complexes comprising such molecules linked to an identifier oligonucleotide, are preferentially bound to a target molecule and separated from molecules, or complexes comprising such molecules linked to an identifier oligonucleotide, that do not have an affinity for—and is consequently not bound to—such target molecules. Partitioning can be accomplished by various methods known in the art. The only requirement is a means for separating molecules bound to a target molecule from molecules not bound to target molecules under the same conditions. The choice of partitioning method will depend on properties of the target and of the synthesised molecule and can be made according to principles and properties known to those of ordinary skill in the art.

Peptide: Plurality of covalently linked amino acid residues defining a sequence and linked by amide bonds. The term is used analogously with oligopeptide and polypeptide. The amino acids can be both natural amino acids and non-natural amino acids, including any combination thereof. The natural and/or non-natural amino acids can be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Plurality: At least two.

Polymer: Molecules characterised by a sequence of covalently linked residues each comprising a functional group, including H. Polymers according to the invention comprise at least two residues.

Precursor entity: Chemical entity further comprising a precursor moiety which is cleaved or modified when the chemical entity is reacted with another chemical entity.

Priming site: Site on a display oligonucleotide or a nascent bifunctional complex to which at least on tag is added chemically or enzymatically or otherwise during the synthesis of the molecule. At least one tag is added enzymatically.

Reactive group: Part of a reactant and linked to the chemical entity of the reactant. Complementary reactive groups brought into reactive contact with each other are capable of forming a chemical bond linking two binding partners. Reaction of reactants comprising complementary reactive groups result in the formation of a chemical bond between the reactants or the chemical entities of each reactant.

Recognition group: Part of a tag and involved in the recognition of complementary recognitions groups of e.g. a complementary oligonucleotide. Preferred recognition groups are natural and non-natural nitrogeneous bases of a natural or non-natural nucleotide.

Recombine: A recombination process recombines two or more sequences by a process, the product of which is a sequence comprising sequences from each of the two or more sequences. When involving nucleotides, the recombination involves an exchange of nucleotide sequences between two or more nucleotide molecules at sites of identical nucleotide sequences, or at sites of nucleotide sequences that are not identical, in which case the recombination can occur randomly. One type of recombination among nucleotide sequences is referred to in the art as gene shuffling.

Residue: A molecule comprises a plurality of linked residues, wherein each residue comprises a functional group. A polymer comprises a sequence of covalently linked residues, wherein each residue comprises a functional group.

Ribose derivative: Ribose moiety forming part of a nucleoside capable of being enzymatically incorporated into a template or complementing template. Examples include e.g. derivatives distinguishing the ribose derivative from the riboses of natural ribonucleosides, including adenosine (A), guanosine (G), uridine (U) and cytidine (C). Further examples of ribose derivatives are described in e.g. U.S. Pat. No. 5,786,461. The term covers derivatives of deoxyriboses, and analogously with the above-mentioned disclosure, derivatives in this case distinguishes the deoxyribose derivative from the deoxyriboses of natural deoxyribonucleosides, including deoxyadenosine (dA), deoxyguanosine (dG), deoxythymidine (dT) and deoxycytidine (dC).

Scaffold: Structural entity comprising one or more reactive groups, preferably more reactive groups, with which one or more reactants can react. A "scaffold" or "core scaffold" is a molecule that generally does not include chemical entities, as described herein, but may include internal chemical entities, such as atoms that are part of one of the central rings. A molecule comprises a scaffold and at least one chemical entity. Non-limiting examples of a scaffold include any cyclic or non-cyclic structure, such as, but not limited to, those disclosed herein. In some embodiments of the invention, a scaffold is the portion of a molecule lacking one or more chemical entities. Compounds of the invention include those comprising a scaffold and one or more chemical entities. A scaffold preferably exhibits properties of desirable lead compounds, including, for example, a low molecular complexity (low number of hydrogen bond donors and acceptors, low number of rotatable bonds, and low molecular weight), and low hydrophobicity. Because a scaffold is small, one of ordinary skill in the art may further develop or elaborate the core into a lead or drug candidate by modifying the core to have desirable drug characteristics, including, for example, by meeting the Lipinski rule of five. Preferred core properties include lead-like properties and are known to those of ordinary skill in the art and are described in Teague, S. J., et al., Agnew. Chem. Int. Ed. 38:3743-3748, 1999; Oprea, T. I., et al., J. Chem. Inf. Comput. Sci. 41:1308-1315, 2001; and Hann, M. M. et al., J. Chem. Inf. Comput. Sci. 41:856-864, 2001. Thus, scaffolds are designed so that more complexity and weight can be added during development and building out of the molecule into a lead candidate, while maintaining the general properties.

Selectively cleavable linker: A selectively cleavable linkers are not cleavable under conditions wherein cleavable linkers is cleaved.

Specific recognition: The specific interaction of e.g. a nucleotide of a tag with preferably one predetermined nucleotide of an anti-tag constitutes a specific recognition. A specific recognition occurs when the affinity of a tag nucleotide recognition group for an anti-tag nucleotide recognition group results in the formation of predominantly only one type of corresponding binding partners. Simple mis-match incorporation does not exclude a specific recognition of corresponding binding partners.

Subunit: Monomer of a tag, such as e.g. a nucleotide.

Support: Solid or semi-solid member to which e.g. tags can be attached. Examples of supports includes planar surfaces including silicon wafers as well as beads.

Tag: Part of an identifier oligonucleotide. A tag is a string of consecutive nucleotides capable of identifying a particular reactant having reacted during the method of synthesising the molecule to which the identifier oligonucleotide is linked. A tag can be an element of an identifier, such as an identifier oligonucleotide, comprising one or more recognition group(s) capable of recognising one or more predetermined, complementary recognition group(s). The recognition can be generated by and/or result in the formation of a covalent bond or a non-covalent bond between corresponding pairs of recognition groups capable of interacting with one another. The recognition groups can be nucleobases in a strand of consecutive nucleotides, such as an oligonucleotide.

Tag complementation: Contacting a tag with a predetermined, complementary tag (anti-tag) comprising recognition group(s) capable of recognising the recognition groups(s) of the tag. Hybridisation of complementary oligonucleotides (anti-tags) represents one example of a tag complementation. The complementation occurs when a tag is brought into reactive contact with a predetermined, complementary tag capable of recognising the recognition group(s) of the tag. When the tag and the complementary tag (anti-tag) both comprises nucleotides, predetermined sets of nucleotides are capable of complementing each other by means of hydrogen bonds formed between the base moieties of the tags and the anti-tags capable of hybridising thereto.

Target molecule: Any compound of interest for which a templated molecule in the form of a ligand is desired. A target molecule can be a protein, fusion protein, peptide, enzyme, nucleic acid, nucleic acid binding protein, carbohydrate, polysaccharide, glycoprotein, hormone, receptor, receptor ligand, cell membrane component, antigen, antibody, virus, virus component, substrate, metabolite, transition state analog, cofactor, inhibitor, drug, controlled substance, dye, nutrient, growth factor, toxin, lipid, glycolipid, etc., without limitation.

Variant: Molecule exhibiting a certain degree of identity or homology—either physically or functionally—to a predetermined molecule.

The term "hydrido" denotes a single hydrogen atom (H). This hydrido radical may be attached, for example, to an oxygen atom to form a hydroxyl radical or two hydrido radicals may be attached to a carbon atom to form a methylene ($-CH_2-$) radical.

Where the term "alkyl" is used, either alone or within other terms such as "haloalkyl" and "alkylsulfonyl", it embraces linear or branched radicals having one to about twenty carbon atoms or, preferably, one to about twelve carbon atoms. Preferred alkyl radicals are "lower alkyl" radicals having one to about ten carbon atoms, such as lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Branched chain isomers of straight chain alkyl groups, include, but are not limited to, the following which are provided by way of example: $-CH(CH_3)_2$, $-CH(CH_3)$ $(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)$ $(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)$ $(CH_2CH_3)$, $-CH_2CH_2CH(CH_3)_2$, $-CH_2CH_2CH(CH_3)$ $(CH_2CH_3)$, $-CH_2CH_2CH(CH_2CH_3)_2$, $-CH_2CH_2C(CH_3)_3$, $-CH_2CH_2C(CH_2CH_3)_3$, $-CH(CH_3)CH_2CH(CH_3)_2$, $-CH(CH_3)CH(CH_3)CH(CH_3)CH(CH_3)_2$, $-CH(CH_2CH_3)CH(CH_3)CH(CH_3)$ $(CH_2CH_3)$, and others. When substituted, the "alkyl" or "lower alkyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "alkenyl" embraces linear or branched radicals having at least one carbon-carbon double bond of two to about twenty carbon atoms, such as from two to about twelve carbon atoms, for example from two to about eight carbon atoms. Preferred alkyl radicals are "lower alkenyl" radicals having two to about six carbon atoms. Examples of such radicals include ethenyl, n-propenyl, butenyl, and the like. When substituted, the "alkenyl" or "lower alkenyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" preferably embraces radicals having 1-6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The "haloalkyl" or "lower haloalkyl" can optionally be further substituted. When further substituted, the "haloalkyl" or "lower haloalkyl" can further comprise one or more radicals selected from the group of radicals consisting of hydroxy, primary amine, carboxy, acid chloride, sulfonyl chloride, sulphonate, nitro, cyano, isothiocyanate, phosphonyl, sulphonyl, sulfamyl, carbonyl, and thiolyl.

The term "hydroxyalkyl" embraces linear or branched alkyl radicals having from one to about ten carbon atoms any one of which may be substituted with one or more hydroxyl radicals. Hydroxyalkyl radicals can be "lower hydroxyalkyl" radicals preferably having one to six carbon atoms and one or more hydroxyl radicals. Examples of such radicals include hydroxymethyl, hydroxyethyl, hydroxypropyl, hydroxybutyl and hydroxyhexyl. The "hydroxyalkyl" or "lower hydroxyalkyl" can optionally be further substituted.

When further substituted, the "hydroxyalkyl" or "lower hydroxyalkyl" can further comprise one or more radicals selected from the group of radicals consisting of primary amine, carboxy, acid chloride, sulfonyl chloride, sulphonate, nitro, cyano, isothiocyanate, halogen, phosphonyl, sulphonyl, sulfamyl, carbonyl, and thiolyl.

The terms "alkoxy" and "alkoxyalkyl" embrace linear or branched oxy-containing radicals each having alkyl portions of one to about ten carbon atoms, such as methoxy radical. Alkoxy radicals can be "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. Alkoxyalkyl radicals can be "lower alkoxyalkyl" radicals having one to six carbon atoms and one or two alkoxy radicals. Examples of such radicals include methoxymethyl, methoxyethyl, ethoxyethyl, methoxybutyl and metoxypropyl. The alkyl in said "alkoxyalkyl" can be substituted with one or more of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. When e.g. the above "alkoxyl" or "alkoxyalkyl" radicals are substituted with one or more halo atoms, such as fluoro, chloro or bromo, "haloalkoxy" or "haloalkoxyalkyl" radicals are provided. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one, two or three rings wherein such rings may be attached together in a pendent manner or may be fused. When substituted, "aryl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of "aryl" include aromatic radicals such as phenyl, pentafluorphenyl, naphthyl, tetrahydronaphthyl, indane and biphenyl.

The term "heterocyclic" embraces saturated, partially saturated and unsaturated heteroatom-containing ring-shaped radicals, where the heteroatoms may be selected from nitrogen, sulfur and oxygen. When substituted, "heterocyclic" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of saturated heterocyclic radicals include e.g. saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g. thiazolidinyl, etc.]. Examples of partially saturated heterocyclic radicals include dihydrothiophene, dihydropyran, dihydrofuran and dihydrothiazole.

The term "heteroaryl" embraces unsaturated heterocyclic radicals. When substituted, "heteroaryl" can comprise one or more radicals selected from the group of radicals consisting of hydroxy, primary amine, secondary amine, carboxy, acid chloride, sulfonyl chloride, sulphonate, nitro, cyano, isothiocyanate, halogen, phosphonyl, sulphonyl, sulfamyl, carbonyl, and thiolyl. Examples of unsaturated heterocyclic radicals, also termed "heteroaryl" radicals, include e.g. unsaturated 5 to 6 membered heteromonocyclic group containing 1 to 4 nitrogen atoms, for example, pyrrolyl, pyrrolinyl, imidazolyl, pyrazolyl 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term "heteroaryl" or "unsaturated heterocyclic radical" also embraces radicals where heterocyclic radicals are fused with aryl radicals. Examples of such fused bicyclic radicals include benzofuran, benzothiophene, and the like. Said "heterocyclic group" can be substituted with one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl, said substitution generating a substituted "heteroaryl", optionally a substituted "heteroaryl" fused with an "aryl" radical which can be substituted or un-substituted. When substituted, the "aryl" is substituted as described herein above. Preferred heterocyclic radicals include five to ten membered fused or unfused radicals. More preferred examples or heteroaryl radicals include benzofuryl, 2,3-dihydrobenzofuryl, benzotrienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl.

The term "sulfonyl", whether used alone or linked to other terms such as alkylsulfonyl, denotes respectively divalent radicals —$SO_2$—.

"Alkylsulfonyl" embraces alkyl radicals attached to a sulfonyl radical, where alkyl can be substituted is defined as above. Alkylsulfonyl radicals can be "lower alkylsulfonyl" radicals having one to six carbon atoms. Examples of such lower alkylsulfonyl radicals include methylsulfonyl, ethylsulfonyl and propylsulfonyl.

The term "arylsulfonyl" embraces aryl radicals as defined above, including substituted aryl radicals, attached to a sulfonyl radical. Examples of such radicals include phenylsulfonyl.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$).

The terms "N-alkylaminosulfonyl" and "N,N-dialkylaminosulfonyl" denote sulfamyl radicals substituted respectively, with one alkyl radical, or two alkyl radicals, optionally substituted alkyl radicals as described herein above. Alkylaminosulfonyl radicals can be "lower alkylaminosulfonyl" radicals having one to six carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical, optionally substituted aryl and/or alkyl radicals as described herein above. N-alkyl-N-arylaminosulfonyl radicals can be "lower N-alkyl-N-arylsulfonyl" radicals having alkyl radicals of one to six carbon atoms. Examples of such lower N-alkyl-N-aryl aminosulfonyl radicals include N-methyl-phenylaminosulfonyl and N-ethyl-phenylaminosulfonyl.

The terms "carboxy" or "carboxyl", whether used alone or with other terms, such as "carboxyalkyl", denotes —CO$_2$H.

The term "carboxyalkyl" or "alkanoyl" embraces radicals having a carboxy radical as defined above, attached to an alkyl radical as described herein above. When substituted, the "alkyl" or "lower alkyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of "carboxyalkyl" radicals include formyl, acetyl, propionyl (propanoyl), butanoyl (butyryl), isobutanoyl (isobutyryl), valeryl (pentanoyl), isovaleryl, pivaloyl, hexanoyl or the like.

The term "carbonyl", whether used alone or with other terms, such as "alkylcarbonyl", denotes —(C=O)—.

The term "alkylcarbonyl" embraces radicals having a carbonyl radical substituted with an alkyl radical. Alkylcarbonyl radicals can be "lower alkylcarbonyl" radicals having from one to six carbon atoms. Examples of such radicals include methylcarbonyl and ethylcarbonyl. When substituted, the "alkyl" or "lower alkyl" of the "alkylcarbonyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, and thiolyl.

The term "alkylcarbonylalkyl", denotes an alkyl radical substituted with an "alkylcarbonyl" radical as described herein above. Both the alkyl and the alkylcarbonyl can be substituted as described herein above.

The term "alkoxycarbonyl" means a radical containing an alkoxy radical, as defined above, attached via an oxygen atom to a carbonyl radical. "Lower alkoxycarbonyl" embraces alkoxy radicals preferably having from one to six carbon atoms. Examples of "lower alkoxycarbonyl" ester radicals include substituted or unsubstituted methoxycarbonyl, ethoxycarbonyl, propoxycarbonyl, butoxycarbonyl and hexyloxycarbonyl.

The term "alkoxycarbonylalkyl" embraces radicals having "alkoxycarbonyl", as defined above substituted to an optionally substituted alkyl radical. Alkoxycarbonylalkyl radicals can be "lower alkoxycarbonylalkyl" having lower alkoxycarbonyl radicals as defined above attached to one to six carbon atoms. Examples of such lower alkoxycarbonylalkyl radicals include methoxycarbonylmethyl, tert-butoxycarbonylethyl, and methoxycarbonylethyl.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$.

The terms "N-alkylaminocarbonyl" and "N,N-dialkylaminocarbonyl" denote aminocarbonyl radicals which have been substituted with one alkyl radical and with two alkyl radicals, respectively. The alkyl radicals can be substituted as described herein above. "Lower alkylaminocarbonyl" comprises lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical, wherein such radicals can be substituted as described herein above.

The term "aminocarbonylalkyl" embraces optionally substituted alkyl radicals substituted with aminocarbonyl radicals.

The term "N-cycloalkylaminocarbonyl" denotes aminocarbonyl radicals which have been substituted with at least one optionally substituted cycloalkyl radical. "Lower cycloalkylaminocarbonyl" comprises lower cycloalkyl radicals of three to seven carbon atoms, attached to an aminocarbonyl radical.

The term "aminoalkyl" embraces alkyl radicals substituted with one or more amino radicals. The alkyl radicals can be further substituted by one or more radicals selected from the group of radicals consisting of hydroxy, carboxy, acid chloride, sulfonyl chloride, sulphonate, nitro, cyano, isothiocyanate, halogen, phosphonyl, sulphonyl, sulfamyl, carbonyl, and thiolyl.

The term "alkylaminoalkyl" embraces aminoalkyl radicals having the nitrogen atom substituted with an optionally substituted alkyl radical.

The term "amidino" denotes an —C(=NH)—NH$_2$ radical.

The term "cyanoamidino" denotes an —C(=N—CN)—NH$_2$ radical.

The term "heterocyclicalkyl" embraces heterocyclic-substituted alkyl radicals. The alkyl radicals can themselves be substituted by one or more radicals selected from the group of radicals consisting of hydroxy, primary amino, carboxy, acid chloride, sulfonyl chloride, sulphonate, nitro, cyano, isothiocyanate, halogen, phosphonyl, sulphonyl, sulfamyl, carbonyl, and thiolyl. Heterocyclicalkyl radicals can be "lower heterocyclicalkyl" radicals preferably having from one to six carbon atoms and a heterocyclic radical. Examples include such radicals as pyrrolidinylmethyl, pyridylmethyl and thienylmethyl.

The term "aralkyl" embraces aryl-substituted alkyl radicals. The alkyl radicals can themselves be substituted by one or more radicals selected from the group of radicals consisting of hydroxy, primary amino, carboxy, acid chloride, sulfonyl chloride, sulphonate, nitro, cyano, isothiocyanate, halogen, phosphonyl, sulphonyl, sulfamyl, carbonyl, and thiolyl. Aralkyl radicals can be "lower aralkyl" radicals having aryl radicals attached to alkyl radicals having from one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, halkoalkyl and haloalkoxy. The terms benzyl and phenylmethyl are interchangeable.

The term "cycloalkyl" embraces radicals having three to ten carbon atoms. Cycloalkyl radicals can be "lower cycloalkyl" radicals having three to seven carbon atoms. Examples include radicals such as cyclopropyl, cyclobutyl, cyclopentyl, cyclohexyl and cycloheptyl. The "cycloalkyl" can optionally be substituted by one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "cycloalkenyl" embraces unsaturated cyclic radicals having three to ten carbon atoms. The "cycloalkenyl" can optionally be substituted by one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples include cyclobutenyl, cyclopentenyl, cyclohexenyl and cycloheptenyl, which can optionally be substituted as described above.

The term "alkylthio" embraces radicals containing a linear or branched alkyl radical, of one to ten carbon atoms, attached to a divalent sulfur atom. An example of "alkylthio" is methylthio, ($CH_3$—S—). The alkyl radical can be substituted as described herein above.

The term "alkylsulfinyl" embraces radicals containing a linear or branched alkyl radical, of one to ten carbon atoms, attached to a divalent —S(=O)— atom. The alkyl radical can be substituted as described herein above.

The term "aminoalkyl" embraces alkyl radicals substituted with amino radicals. The alkyl radicals can be further substituted by one or more radicals selected from the group of radicals consisting of hydroxy, carboxy, acid chloride, sulfonyl chloride, sulphonate, nitro, cyano, isothiocyanate, halogen, phosphonyl, sulphonyl, sulfamyl, carbonyl, and thiolyl. Aminoalkyl radicals can be "lower aminoalkyl" having from one to six carbon atoms. Examples include aminomethyl, aminoethyl and aminobutyl which can optionally be further substituted as described above.

The term "alkylaminoalkyl" embraces aminoalkyl radicals having the nitrogen atom substituted with at least one alkyl radical. Alkylaminoalkyl radicals can be "lower alkylaminoalkyl" having one to six carbon atoms attached to a lower aminoalkyl radical as described above. The alkyl radical can be substituted as described herein above.

The terms "N-alkylamino" and "N,N-dialkylamino" denote amino groups which have been substituted with one alkyl radical and with two alkyl radicals, respectively. The alkyl radical can be substituted as described herein above. Alkylamino radicals can be "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "arylamino" denotes amino groups which have been substituted with one or two aryl radicals, such as N-phenylamino. The "arylamino" radicals may be further substituted on the aryl ring portion of the radical. Substitutions can include one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

The term "aralkylamino" denotes amino groups which have been substituted with one or two aralkyl radicals, such as N-benzylamino. The "aralkylamino" radicals may be further substituted on the aryl ring portion of the radical. Substitutions can include one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

The terms "N-alkyl-N-arylamino" and "N-aralkyl-N-alkylamino" denote amino groups which have been substituted with one aralkyl and one alkyl radical, or one aryl and one alkyl radical, respectively, to an amino group. The aralkyl and/or alkyl and/or aryl radicals can be substituted as described herein above.

The terms "N-arylaminoalkyl" and "N-aralkylaminoalkyl" denote amino groups which have been substituted with one aryl radicals or one aralkyl radical, respectively, and having the amino group attached to an alkyl radical. The aralkyl and/or alkyl and/or aryl radicals can be substituted as described herein above. Arylaminoalkyl radicals can be "lower arylaminoalkyl" having the arylamino radical attached to one to six carbon atoms. Examples of such radicals include N-phenylaminomethyl and N-phenyl-N-methylaminomethyl.

The terms "N-alkyl-N-arylaminoalkyl", and "N-aralkyl-N-alkylaminoalkyl" denote N-alkyl-N-arylamino and N-alkyl-N-aralkylamino groups, respectively, and having the amino group attached to alkyl radicals which can be substituted as described herein above.

The term "acyl", whether used alone, or within a term such as "acylamino", denotes a radical provided by the residue after removal of hydroxyl from an organic acid.

The term "acylamino" embraces an amino radical substituted with an acyl group. An examples of an "acylamino" radical is acetylamino or acetamido ($CH_3C(=O)$—NH—) where the amine may be further substituted with alkyl, aryl or aralkyl, wherein said alkyl, aryl or aralkyl can be substituted as described herein above.

The term "arylthio" embraces aryl radicals of six to ten carbon atoms, attached to a divalent sulfur atom. The aryl can be substituted as described herein above. An example of "arylthio" is phenylthio.

The term "aralkylthio" embraces aralkyl radicals as described above, attached to a divalent sulfur atom. The aralkyl radicals can be further substituted as described herein above. An example of "aralkylthio" is benzylthio.

The term "aryloxy" embraces aryl radicals, as defined above, attached to an oxygen atom. The aryl can be substituted as described herein above. Examples of such radicals include phenoxy.

The term "aralkoxy" embraces oxy-containing aralkyl radicals attached through an oxygen atom to other radicals. The aralkyl can be substituted as described herein above. Aralkoxy radicals can be "lower aralkoxy" radicals having phenyl radicals attached to lower alkoxy radical as described above.

The term "haloaralkyl" embraces aryl radicals as defined above attached to haloalkyl radicals. The aryl can be further substituted as described herein above.

The term "carboxyhaloalkyl" embraces carboxyalkyl radicals as defined above having halo radicals attached to the alkyl portion. The alkyl portion can be further substituted as described herein above.

The term "alkoxycarbonylhaloalkyl" embraces alkoxycarbonyl radicals as defined above substituted on a haloalkyl radical. The haloalkyl radical can be further substituted by one or more of hydroxy, amino, carboxy, acid chloride, sulfonyl chloride, sulphonate, nitro, cyano, isothiocyanate, phosphonyl, sulphonyl, sulfamyl, carbonyl, and thiolyl.

The term "aminocarbonylhaloalkyl" embraces aminocarbonyl radicals as defined above substituted on an optionally substituted haloalkyl radical wherein the alkyl is substituted by one or more of hydroxy, amino, carboxy, acid chloride, sulfonyl chloride, sulphonate, nitro, cyano, isothiocyanate, phosphonyl, sulphonyl, sulfamyl, carbonyl, and thiolyl.

The term "alkylaminocarbonylhaloalkyl" embraces alkylaminocarbonyl radicals as defined above substituted on an optionally substituted haloalkyl radical as described above.

The term "alkoxycarbonylcyanoalkenyl" embraces alkoxycarbonyl radicals as defined above, and a cyano radical, both substituted on an optionally substituted alkenyl radical.

The term "carboxyalkylaminocarbonyl" embraces aminocarbonyl radicals substituted with carboxyalkyl radicals, as defined above. The carboxyalkyl can be further substituted. Substitutions can include one or more of hydroxy, amino, acid chloride, sulfonyl chloride, sulphonate, nitro, cyano, isothiocyanate, halogen, phosphonyl, sulphonyl, sulfamyl, carbonyl, and thiolyl.

The term "aralkoxycarbonylalkylaminocarbonyl" embraces aminocarbonyl radicals substituted with aryl-substituted alkoxycarbonyl radicals, as defined above.

The term "cycloalkylalkyl" embraces cycloalkyl radicals having three to ten carbon atoms attached to an alkyl radical, as defined above. Cycloalkylalkyl radicals can be "lower cycloalkylalkyl" radicals having cycloalkyl radicals attached to lower alkyl radicals as defined above. Examples include radicals such as cyclopropylmethyl, cyclobutylmethyl, and cyclohexylethyl.

The term "aralkenyl" embraces optionally substituted aryl radicals attached to alkenyl radicals having two to ten carbon atoms, such as phenylbutenyl, and phenylethenyl or styryl. When substituted the aryl can be substituted with one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

BRIEF DISCLOSURE OF THE FIGURES

FIG. 1. A tag addition process employing linkage of top strand tags only. (a) The initial bifunctional complex. (b-e) Addition of tags A to D. (f) The top strand containing tags A to D. (h) The individual anti-tags Ax to Dx. The polarity of overhangs is such that B, C, and D tags contact their cognant anti-tag and the anti-tag cognate to the following tag, e.g. a B-tag contacts an anti-B-tag and an anti-C-tag.

FIG. 2. One possible type of tag layout. (a) The initial bifunctional complex containing a chemical reaction site, a linker moiety, and a tag region (linker tag). (b) Tags A, B, C, and D containing a tag region and an overhang region. (c) The anti-A-tag containing an anti-linker tag region and an anti-A-tag region. (d) Anti-tags Ax, Bx, Cx, and Dx containing an anti-overhang region and an anti-tag region.

Figure 3:
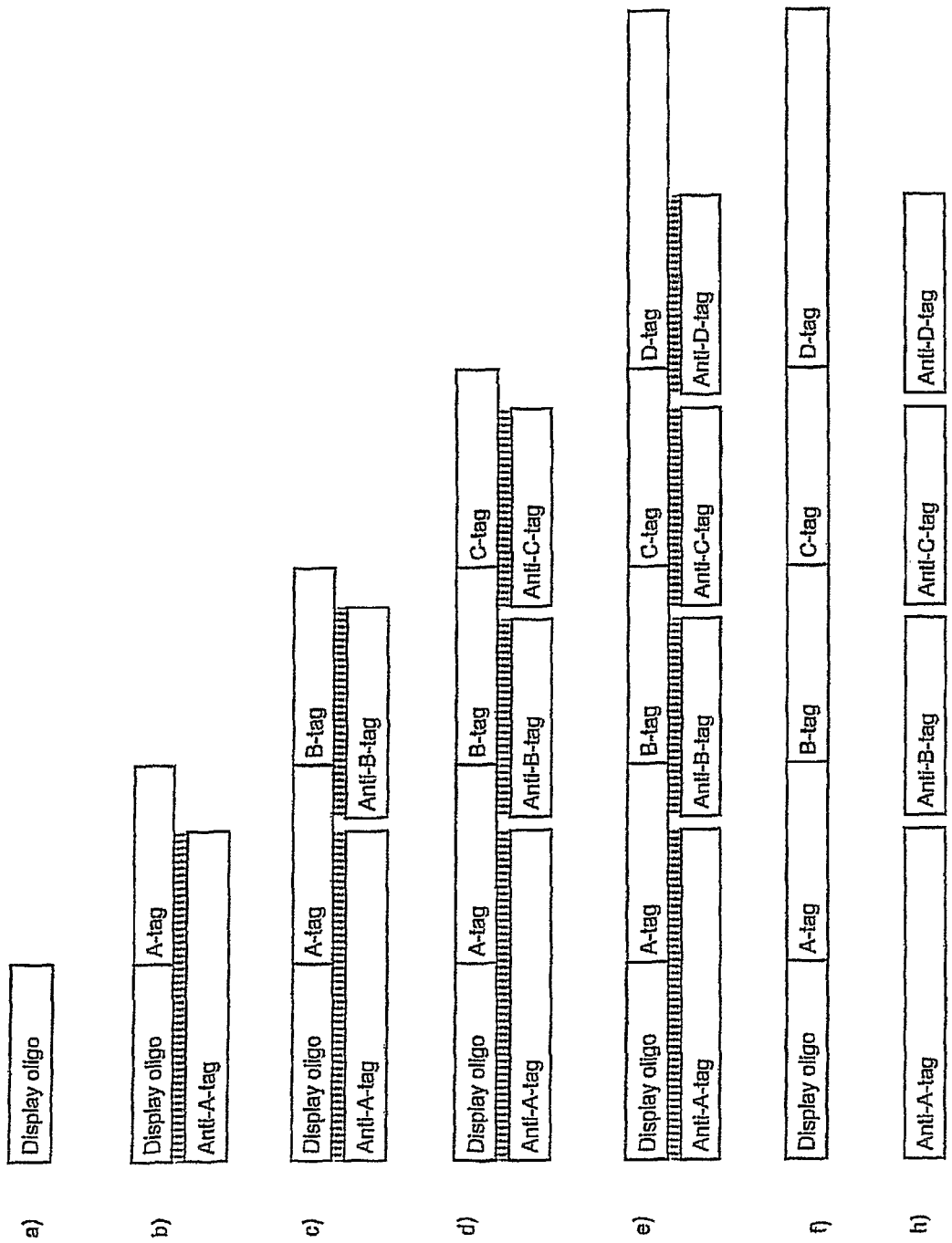

FIG. 3. A tag addition process employing linkage of top strand tags only and using non-abutting anti-tags, i.e., the anti-tags are separated from each other. (a) The initial bifunctional complex. (b-e) Addition of tags A to D. (f) The top strand containing tags A to D. (h) The individual anti-tags Ax to Dx. The polarity of overhangs is such that B, C, and D tags contact their cognant anti-tag and the anti-tag cognate to the following tag, e.g. a B-tag contacts an anti-B-tag and an anti-C-tag.

Figure 4:
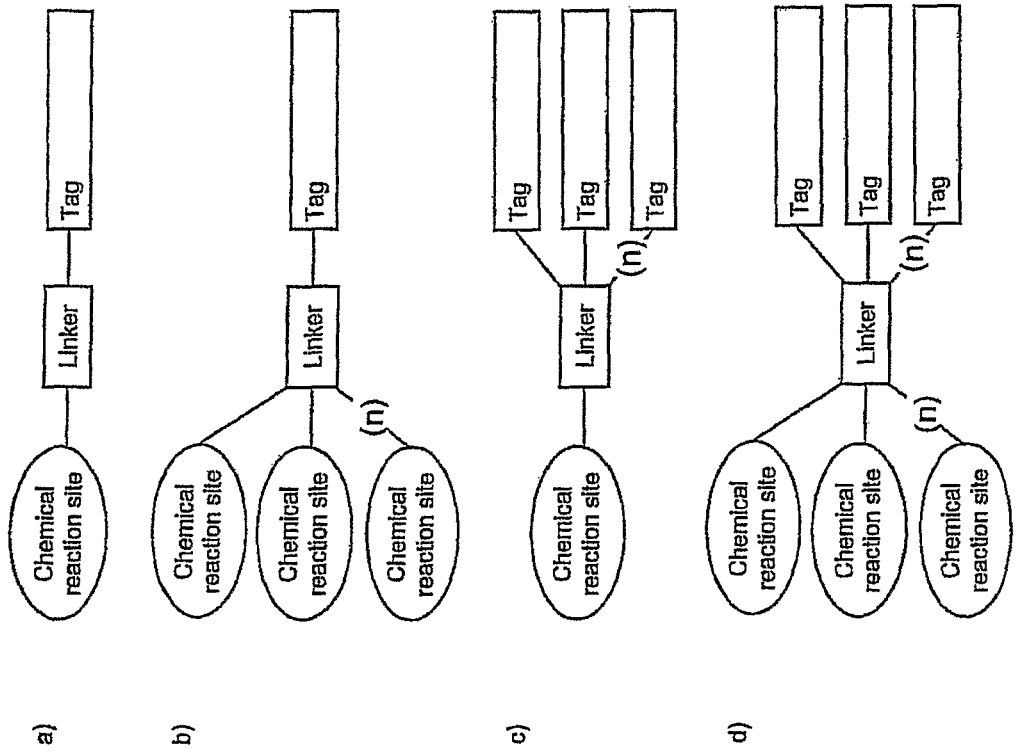

FIG. 4. Different possible designs of the initial bifunctional complex. (a) a single chemical reaction site is attached to a single linker tag via a non-branched linker. (b) A number (n) of chemical reaction sites are attached to a single linker tag via a branched linker. (c) A single chemical reaction site is attached to a number (n) of linker tags via a branched linker. (d) A number (n) of chemical reaction sites are attached to a number (n) of linker tags via a branched linker.

Figure 5:
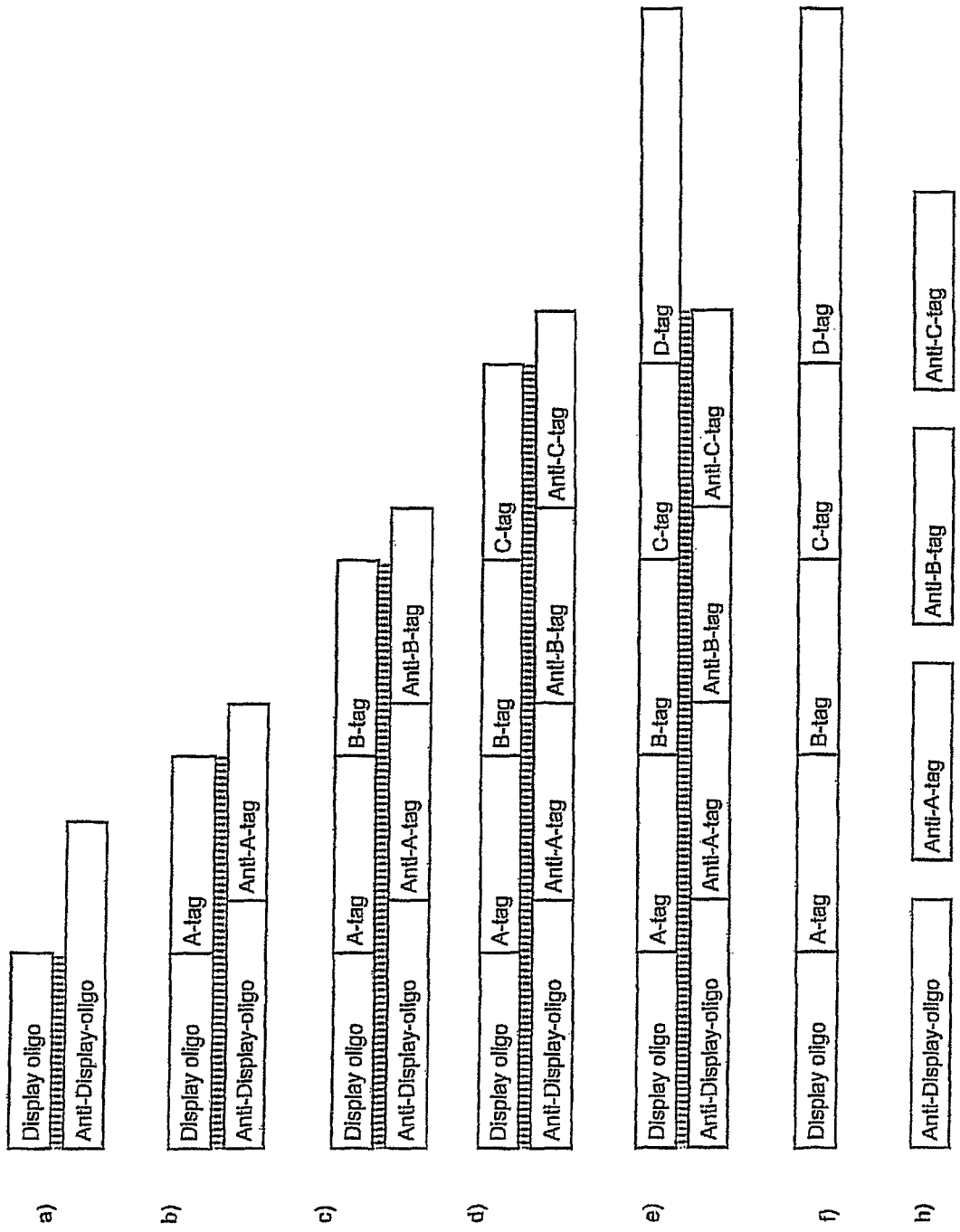

FIG. 5. A tag addition process employing linkage of top strand tags only. (a) The initial bifunctional complex. (b-e) Addition of tags A to D. (f) The top strand containing tags A to D. (h) The individual anti-tags Ax to Dx. The polarity of overhangs is such that B, C, and D tags contact their cognant anti-tag and the anti-tag cognate to the previous tag (compare with FIG. 1), e.g. a B-tag contacts an anti-B-tag and an anti-A-tag.

FIG. 6. A tag addition process employing linkage of top strand tags only and removal of anti-tags after each cycle of tag addition. (a) The initial bifunctional complex. (b-e) Addition of tags A to D. (f) The top strand containing tags A to D. The polarity of overhangs is such that B, C, and D tags contact their cognant anti-tag and the anti-tag cognate to the following tag, e.g. a B-tag contacts an anti-B-tag and an anti-C-tag.

Figure 7:
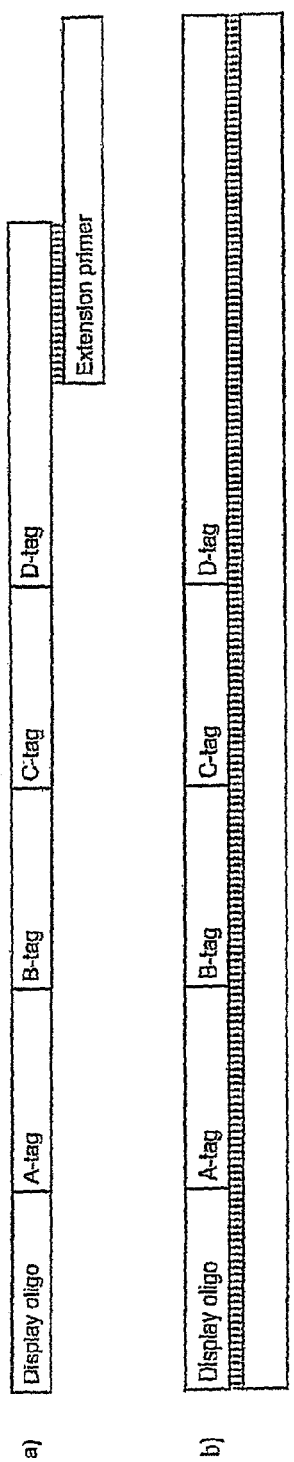

FIG. 7. The primer extension process. (a) An extension primer is annealed to the single tag strand containing tags. (b) Extension of the primer results in a double-stranded tag.

Figure 8:
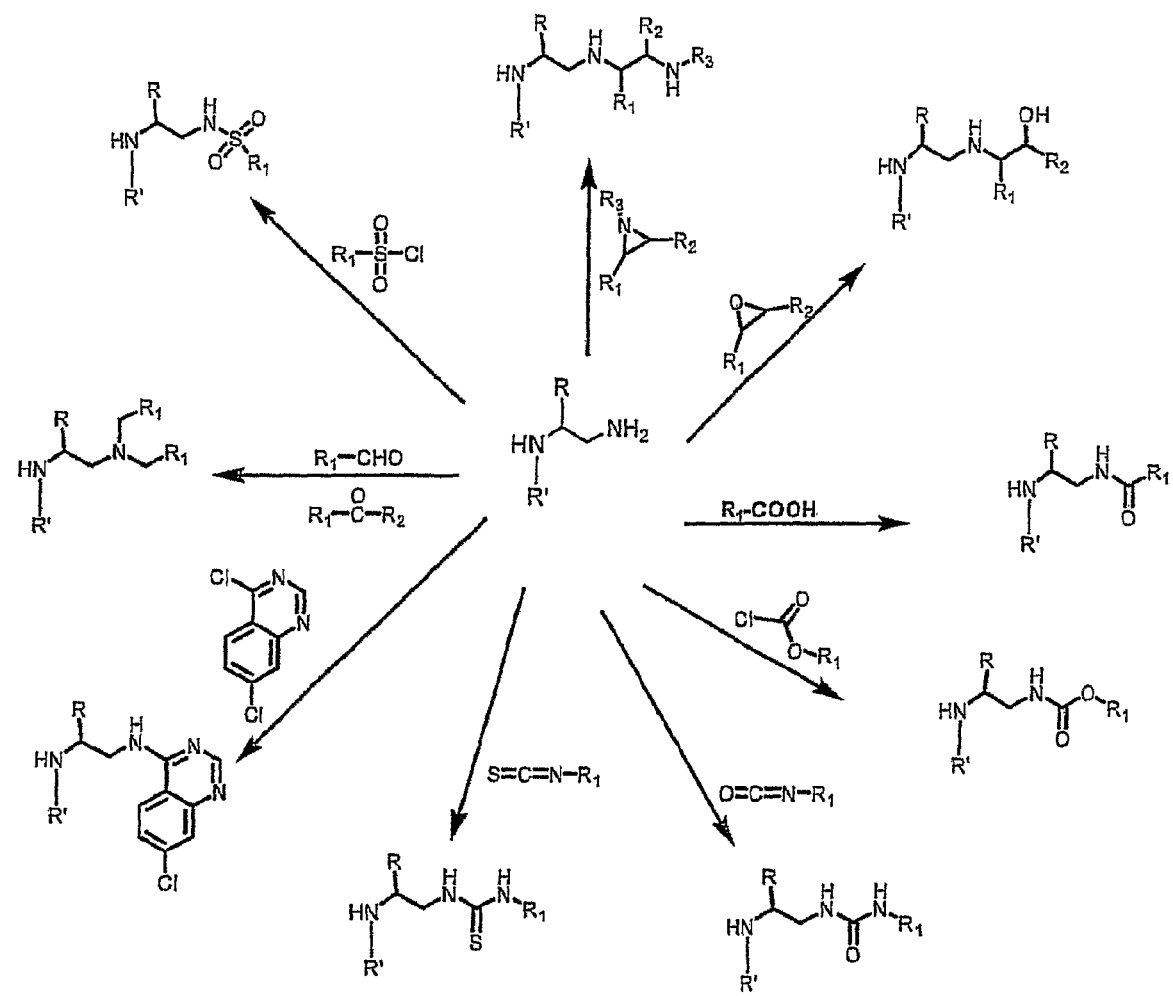

FIG. 8. Examples of chemical reactions using an amine as a chemical reaction site.

Figure 9:
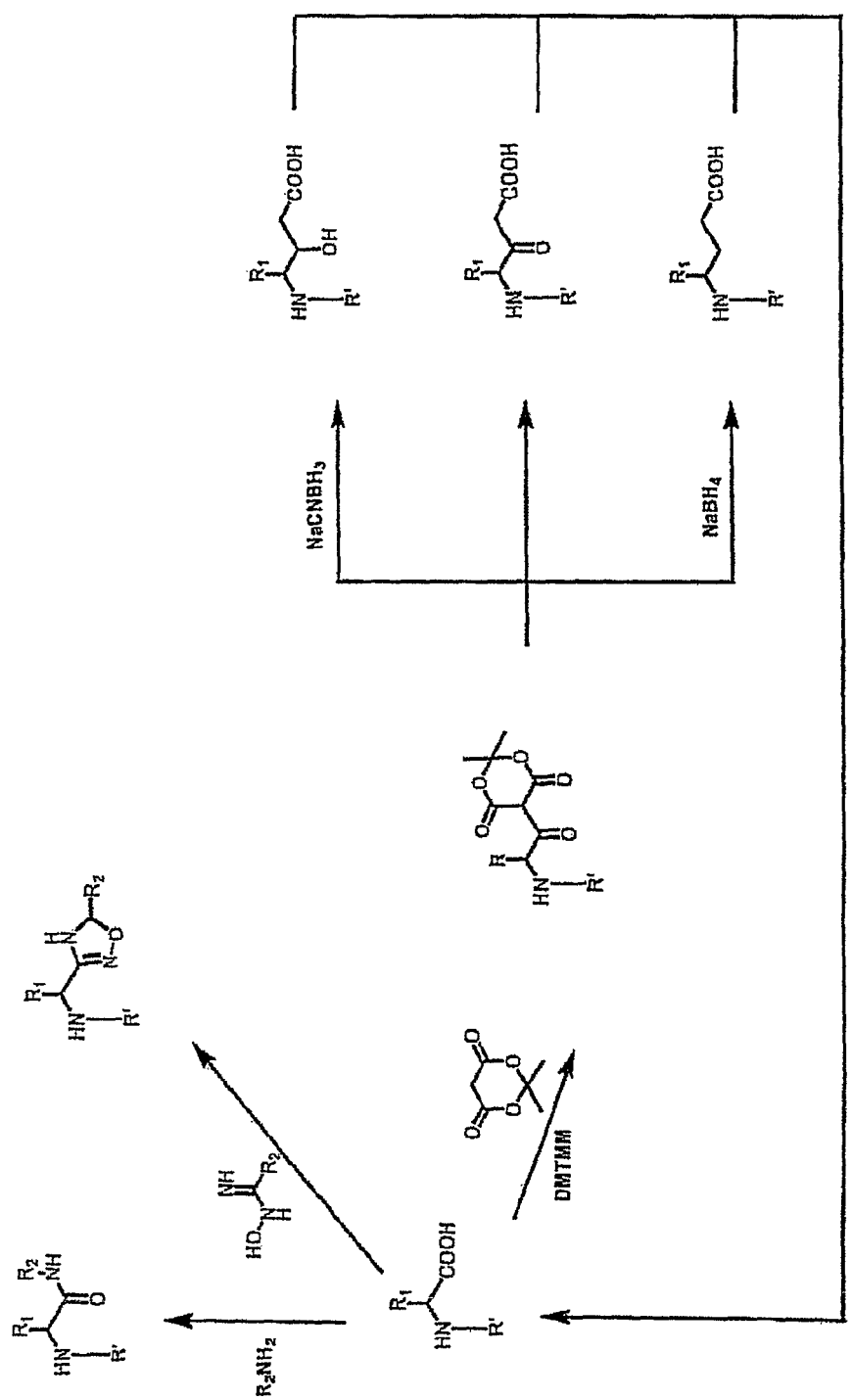

FIG. 9. Examples of chemical reactions using an acid as a chemical reaction site.

Figure 10:
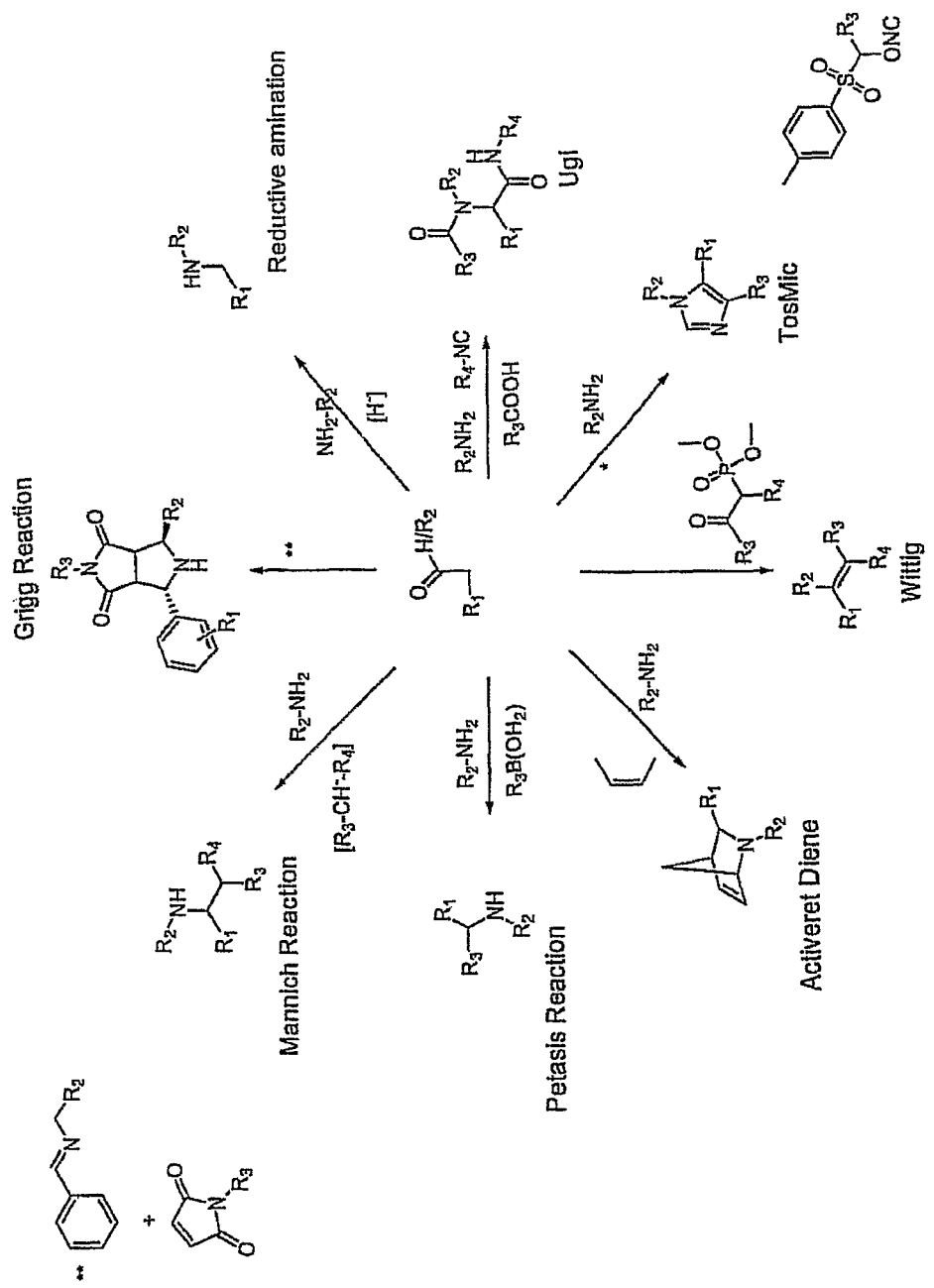

FIG. 10. Examples of chemical reactions using an aldehyde or a ketone as a chemical reaction site.

Figure 11:
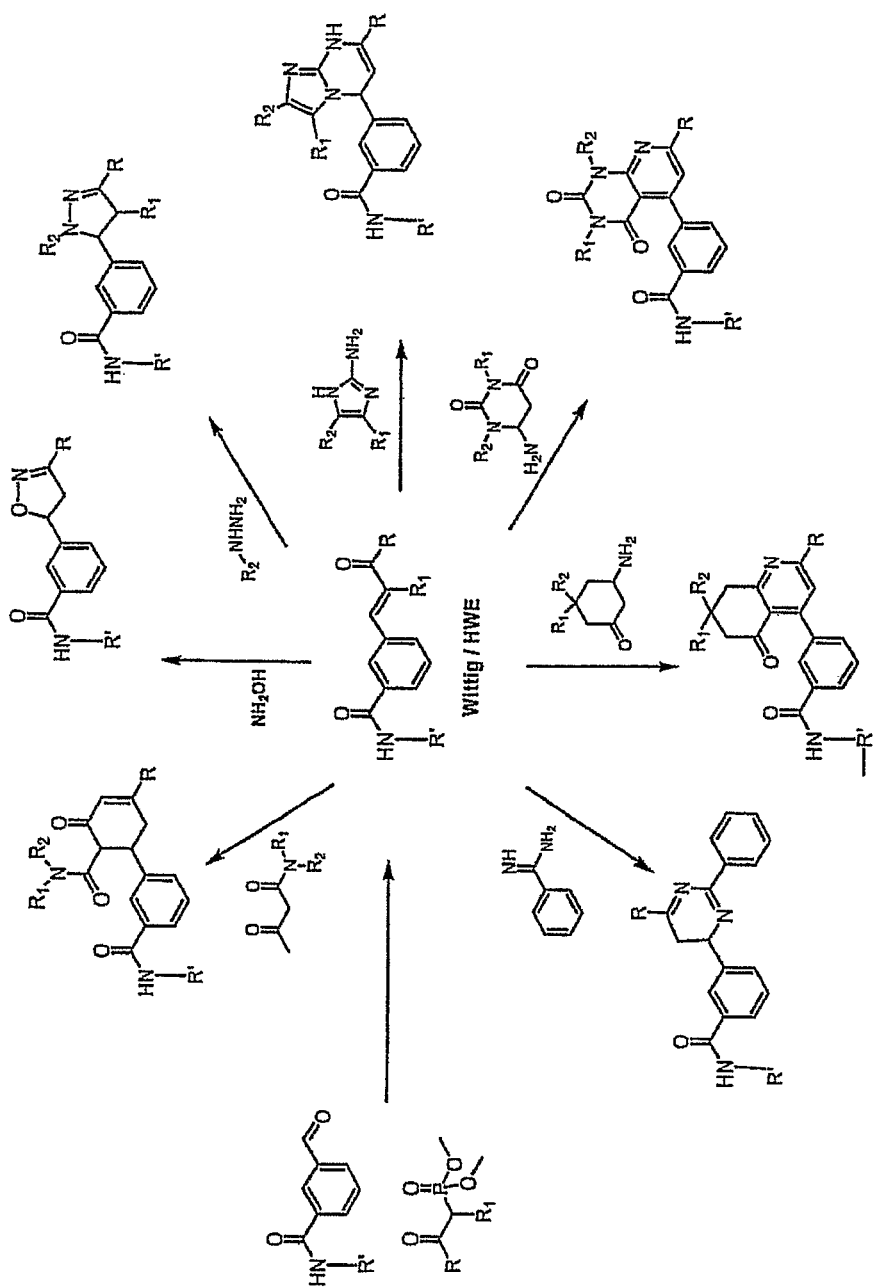

FIG. 11. Examples of chemical reactions using Wittig or Horner-Wadsworth-Emmons reaction substrates.

Figure 12:
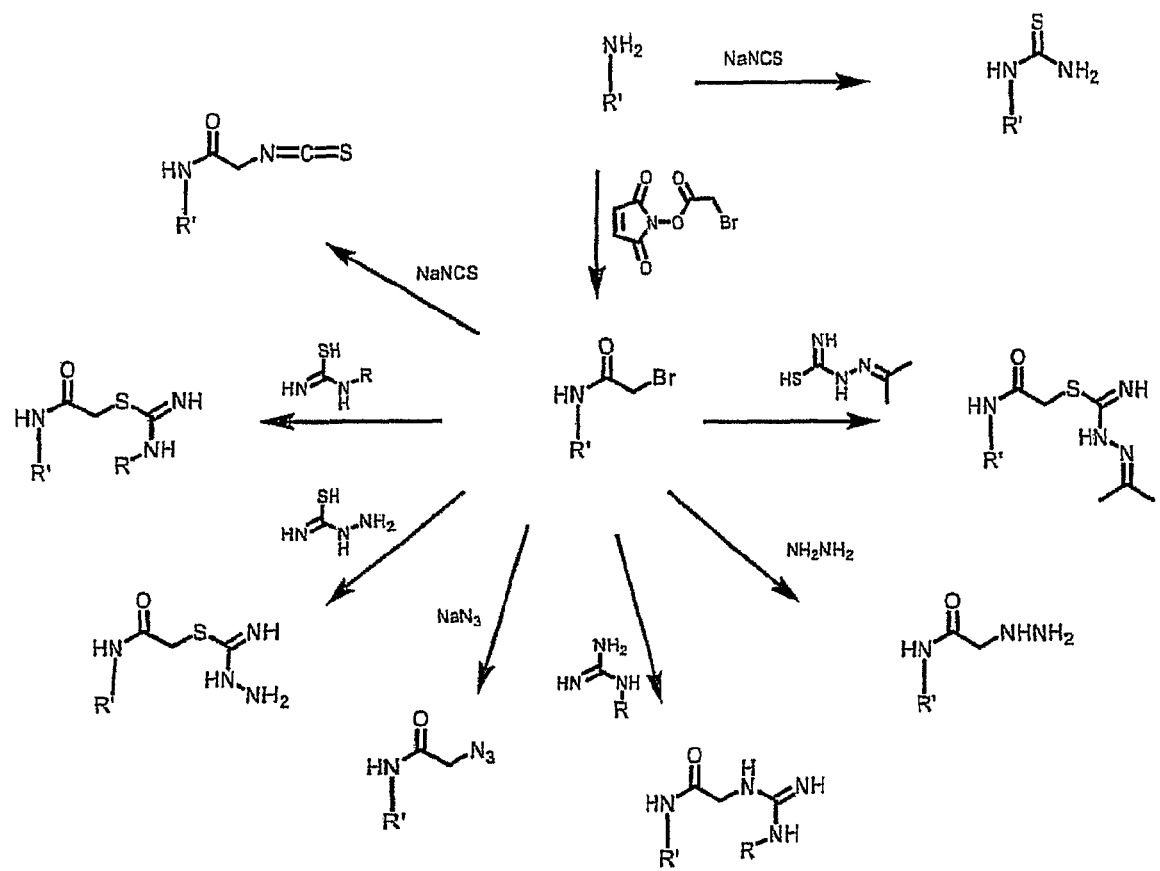

FIG. 12. Examples of chemical reactions generating a dinucleophile.

FIG. 13. Examples of monofunctional versus multifunctional reactions. (a) monofunctional reaction. (b) bifunctional reaction generating a heterocyclic molecule.

FIG. 14. Examples of bifunctional electrophiles.

Figure 15:
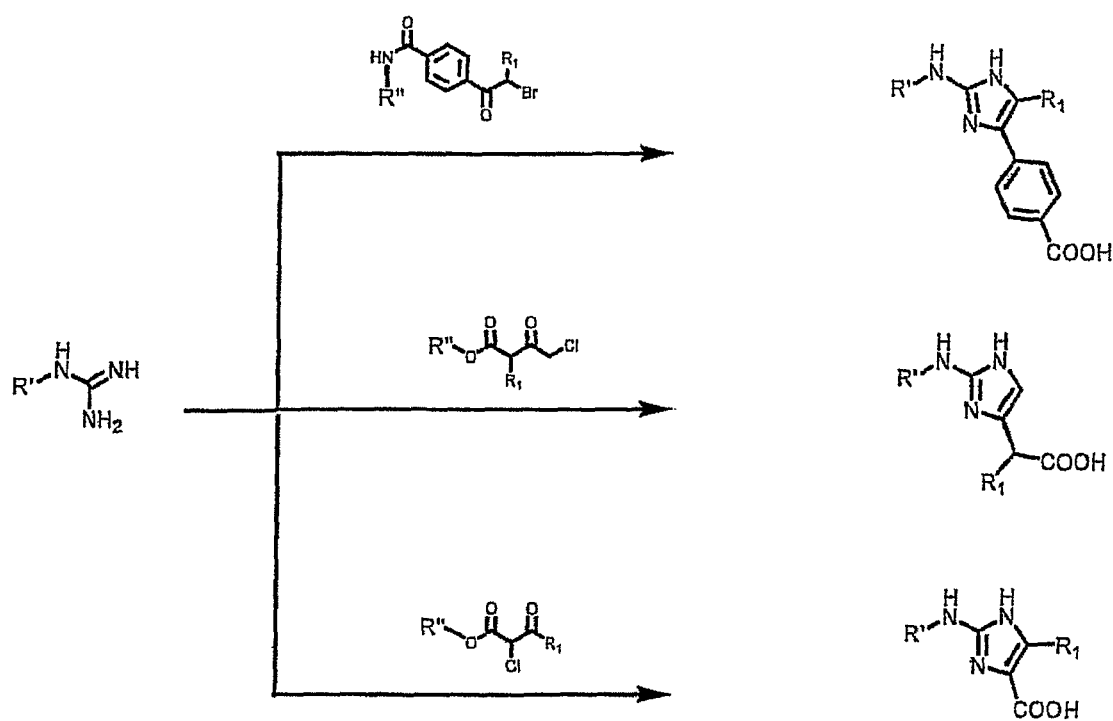

FIG. 15. Examples of chemical reactions of 1,2-dielectrophiles.

Figure 16:
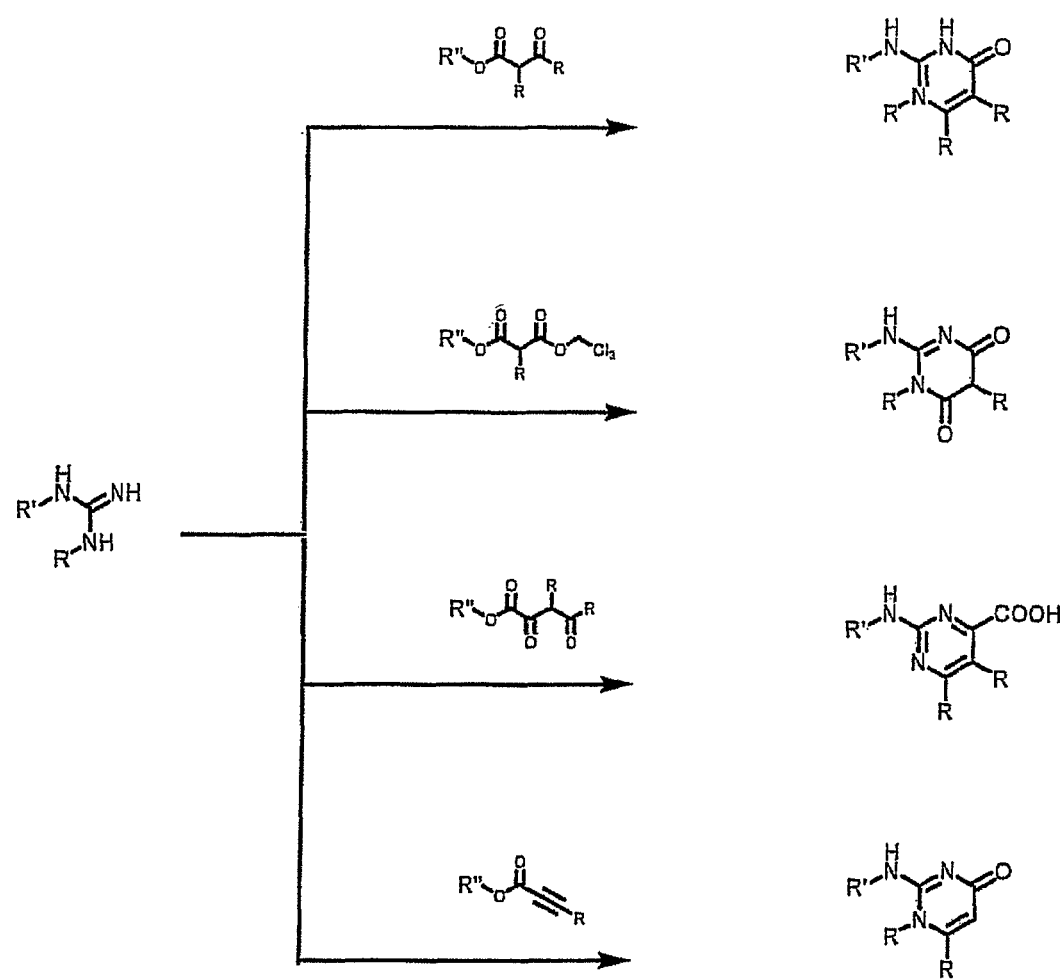

FIG. 16. Examples of chemical reactions of 1,3-dielectrophiles.

Figure 17:

FIG. 17. Examples of transformations of building blocks (reactants) into heterocycles.

Figure 18:
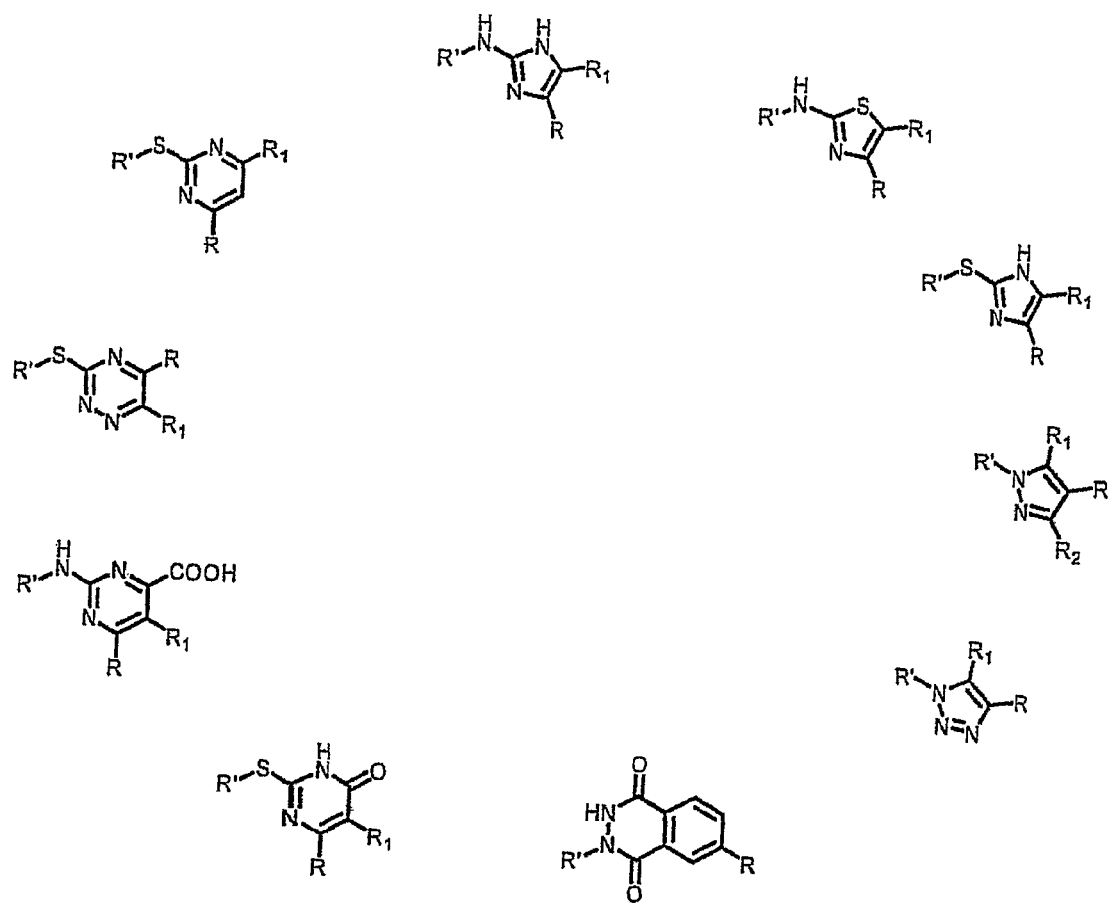

FIG. 18. Examples of heterocyclic structures generated using bifunctional reactions.

Figure 19:
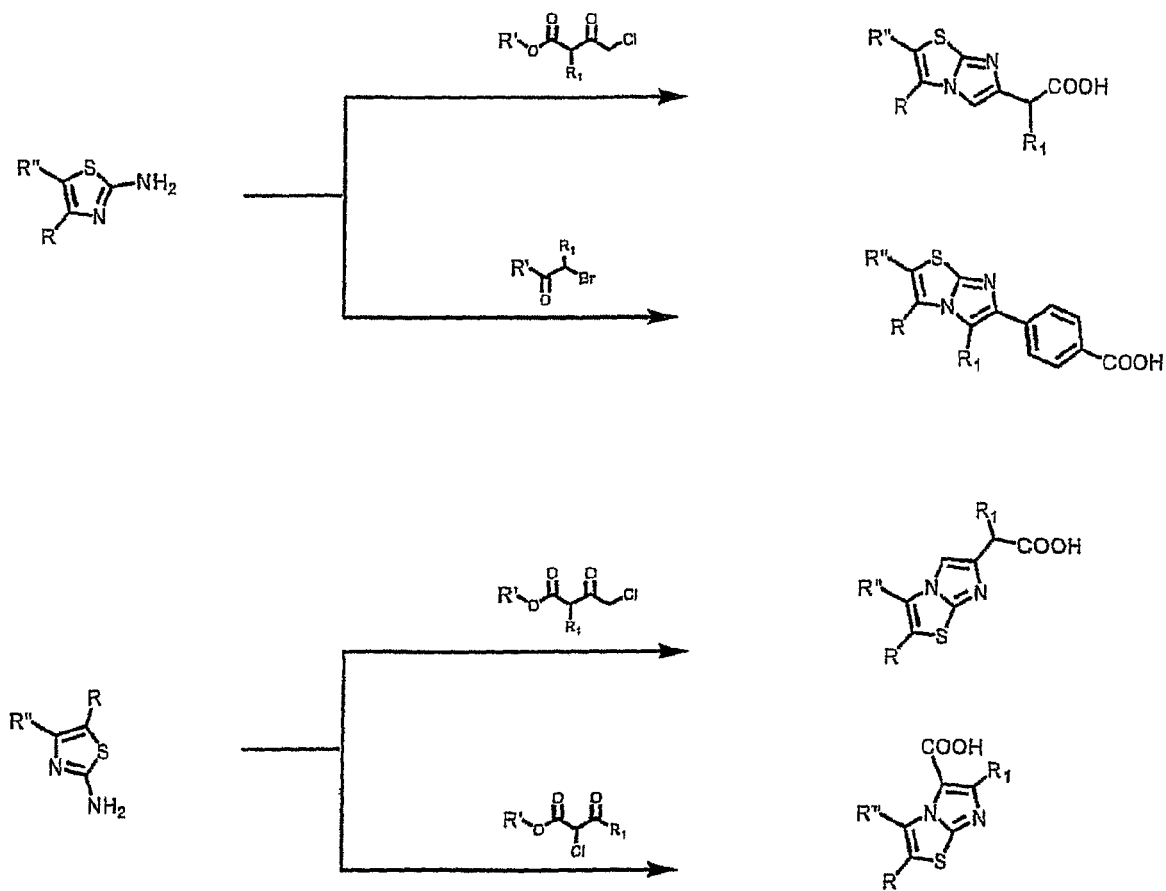

FIG. 19. Examples of chemical reactions generating bicyclic structures (I).

Figure 20:
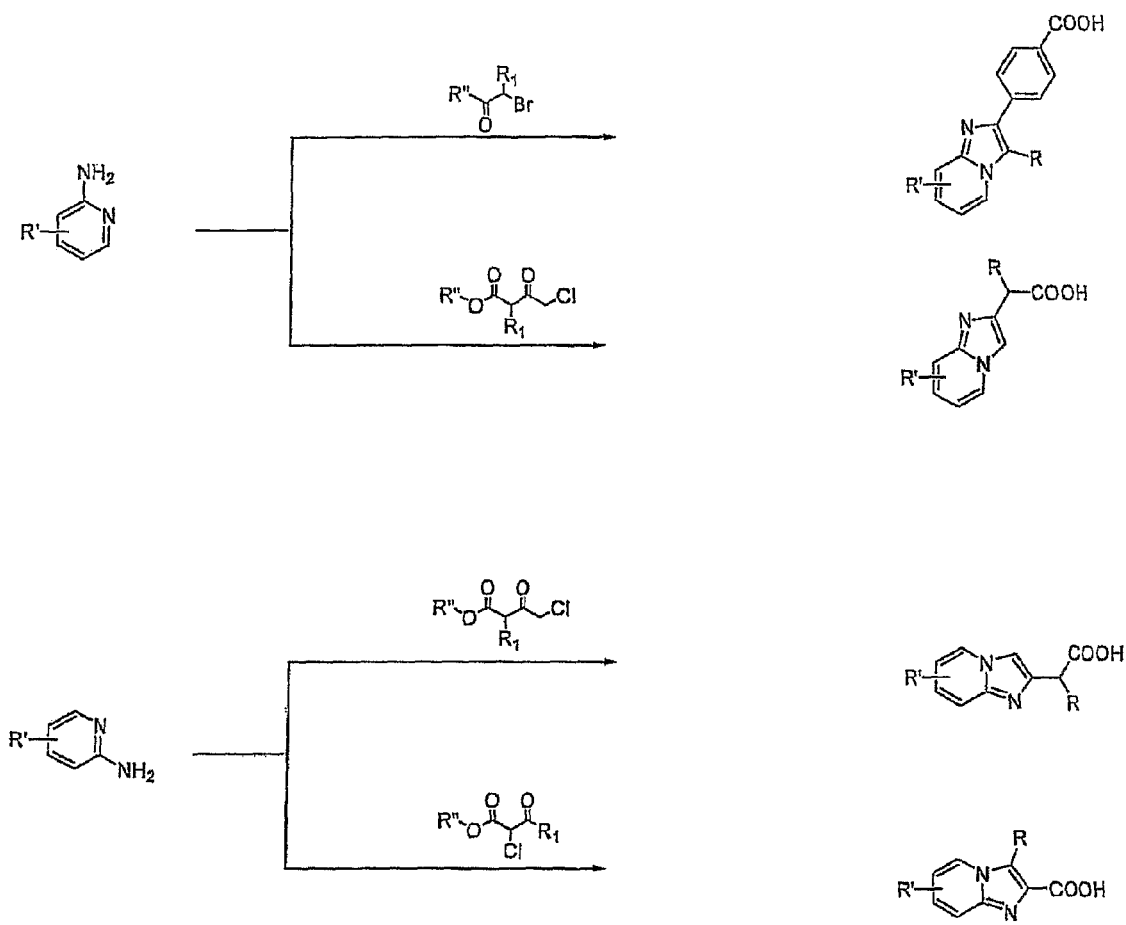

FIG. 20. Examples of chemical reactions generating bicyclic structures (II).

Figure 21:
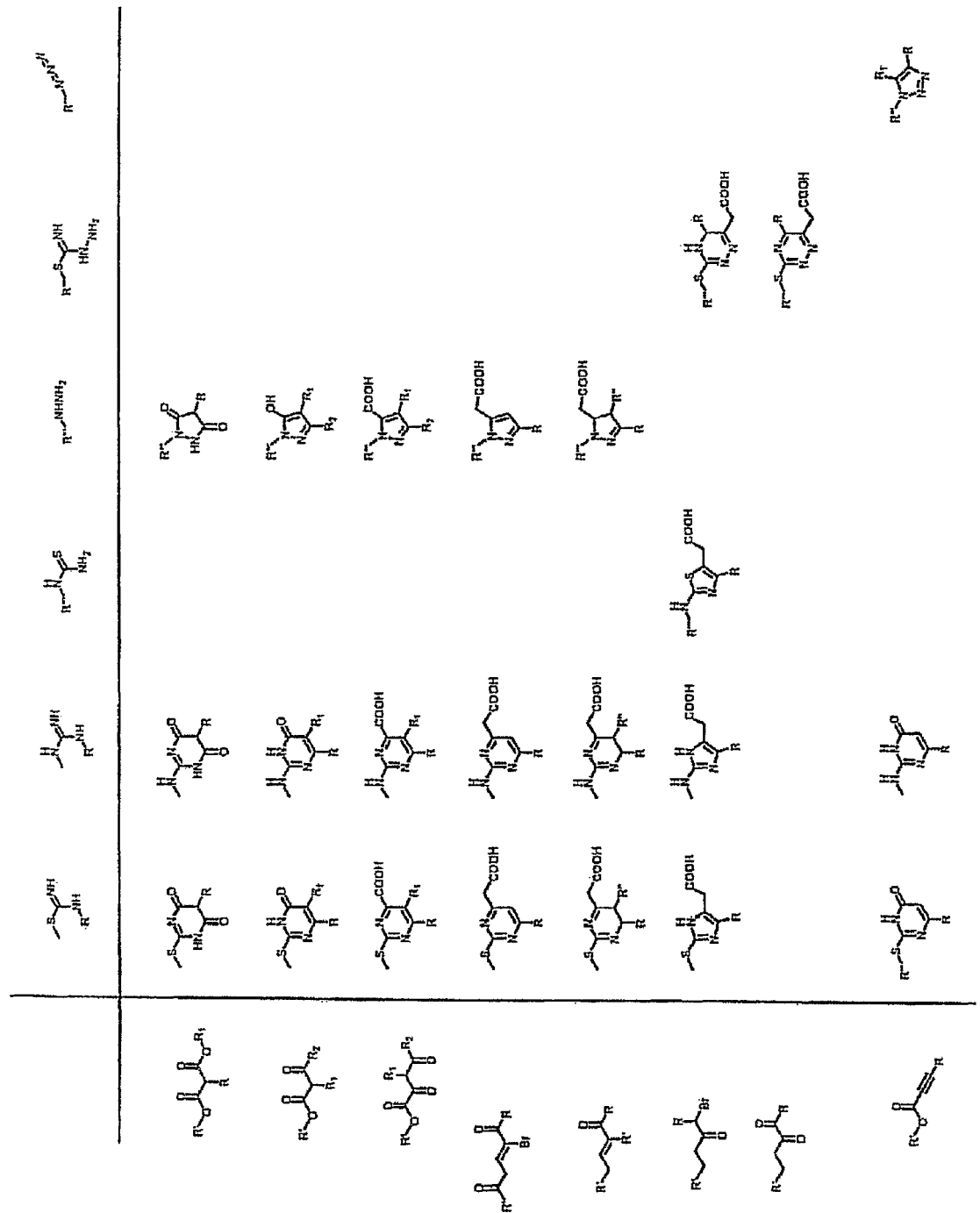

FIG. 21. Examples of chemical reaction matrix illustrating how building blocks (reactants) (rows and columns) can be combined to form cyclic structures.

Figure 22:
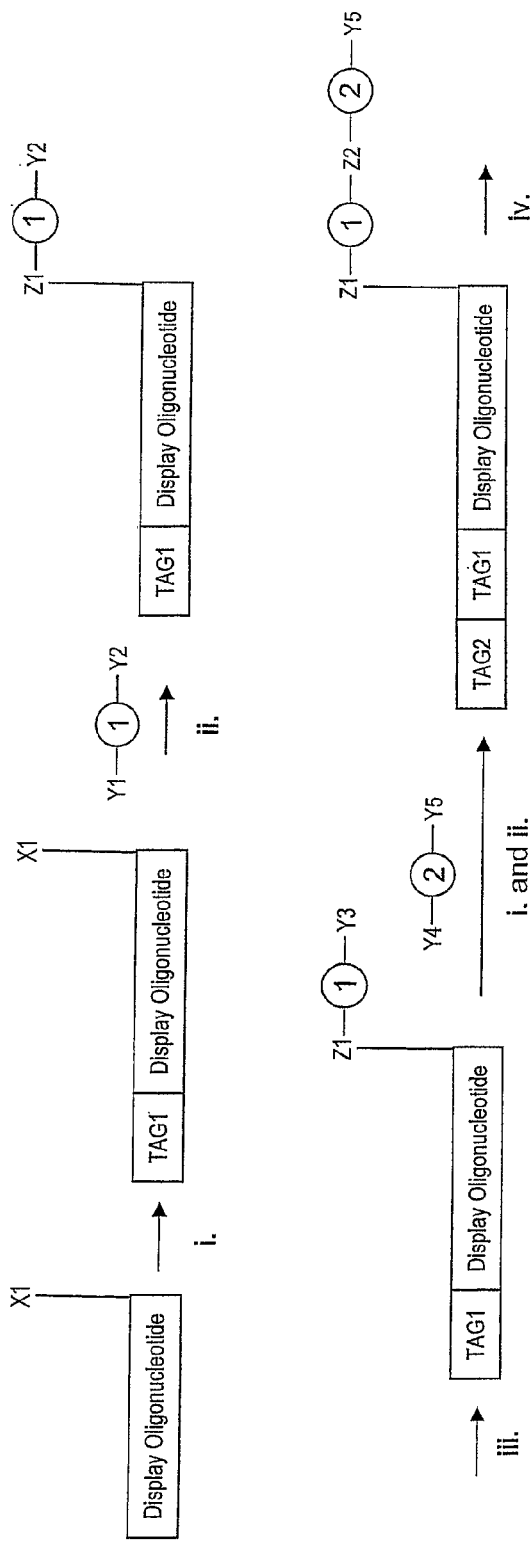
Figure 23:
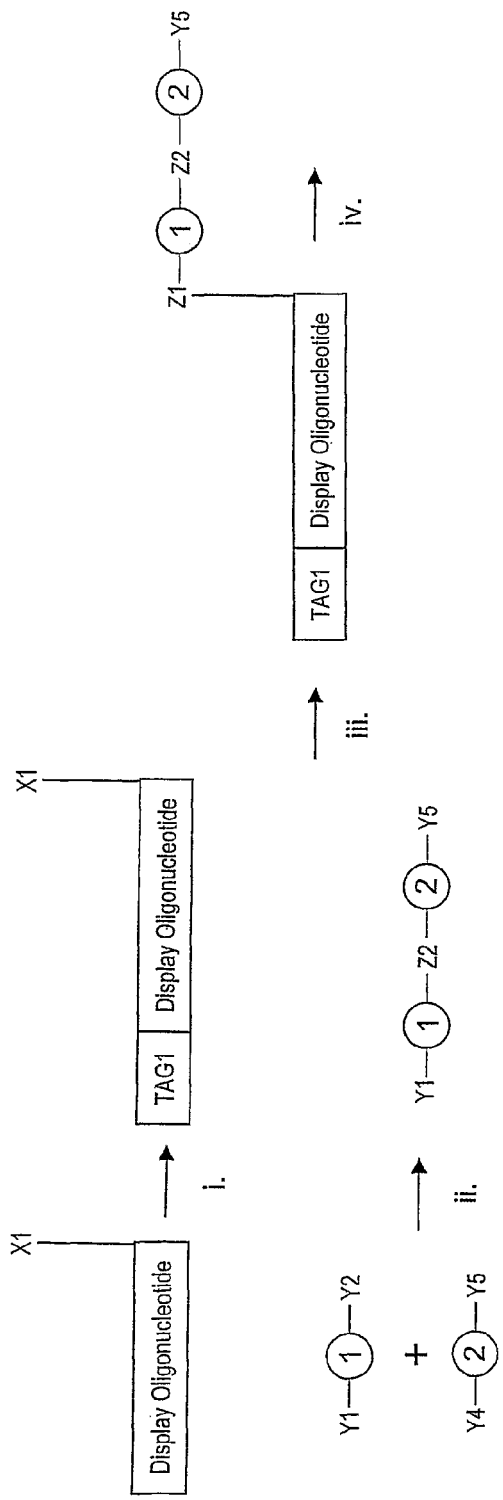

FIGS. 22-23. The figures serve to illustrate the formation of molecules/product structures formed by the process.

The figures represent examples, which are not meant to limit the scope of the invention. In FIG. 22, the following steps are illustrated:

Step i.: E.g. enzymatical ligation of one oligonucleotide tag to the display oligonucleotide.

Step ii.: E.g. Reacting one reactant with the chemical reaction site in the formation of one or more covalent bonds.

Step iii.: Reactive groups may optionally be transformed into other reactive groups, such as for example but not limited to the deprotection of one reactive group into another reactive group, for example deprotection of a amino protection group, whereby a reactive amine will be formed, for example deprotection of an ester, whereby a reactive carboxylic acid will be formed, for example oxidation of a 1,2-diol using periodate, whereby a reactive aldehyde will be formed.

Step iv.: Optionally repeat step iii., optionally repeat step i. and ii. Optionally, conduct further repetition of step iv. and other steps in accordance with and as described and claimed by this invention.

FIG. 23. Reactants may be reacted prior to (step ii) reactions with the chemical reaction site (step iii).

Figure 24:
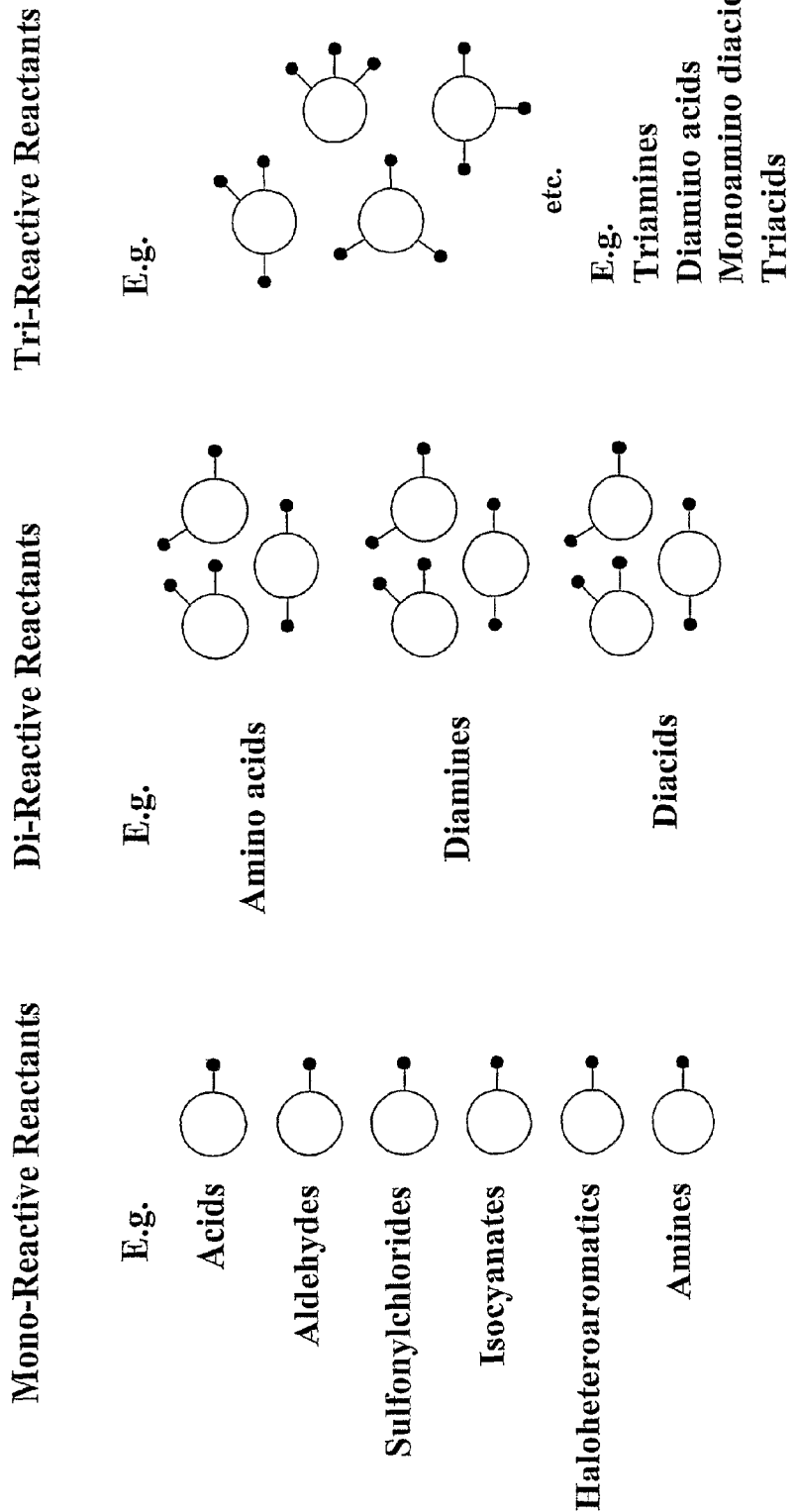
Figure 25:
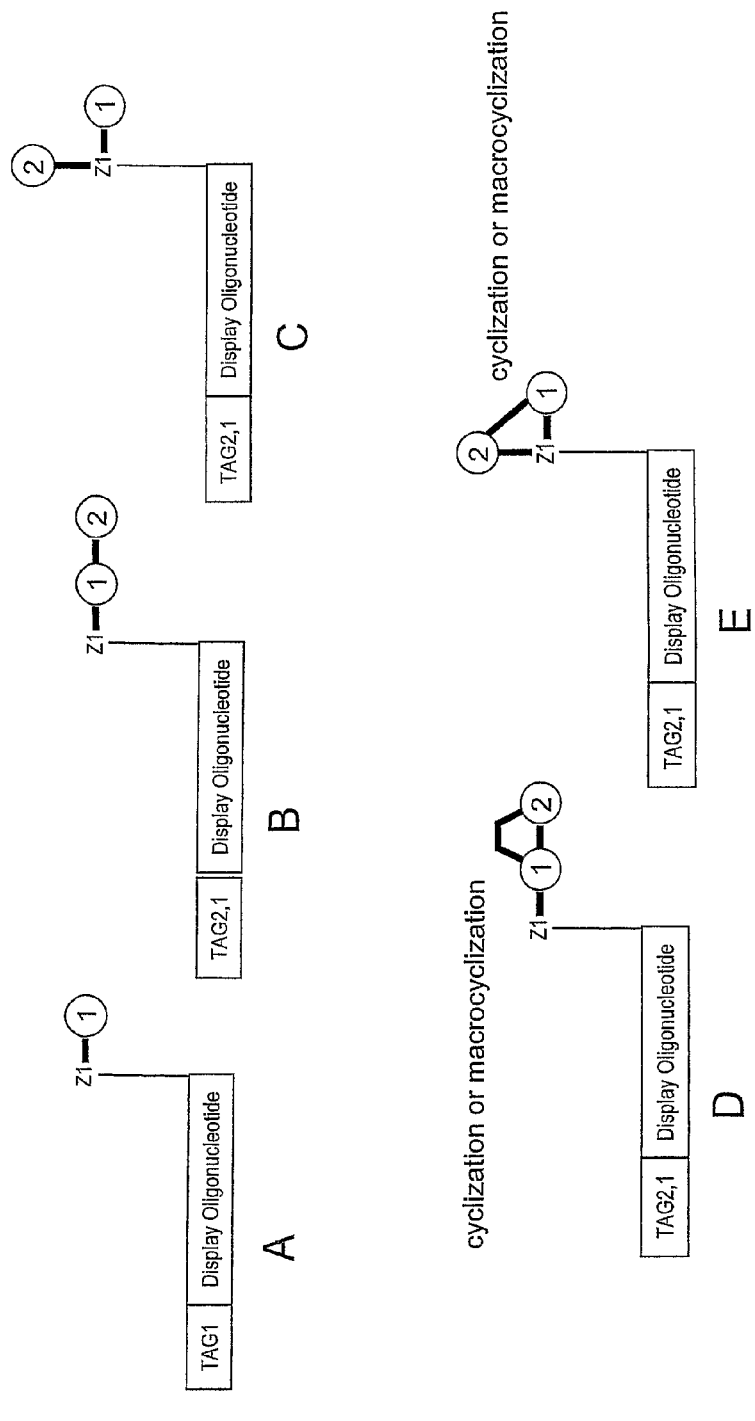
Figure 26:
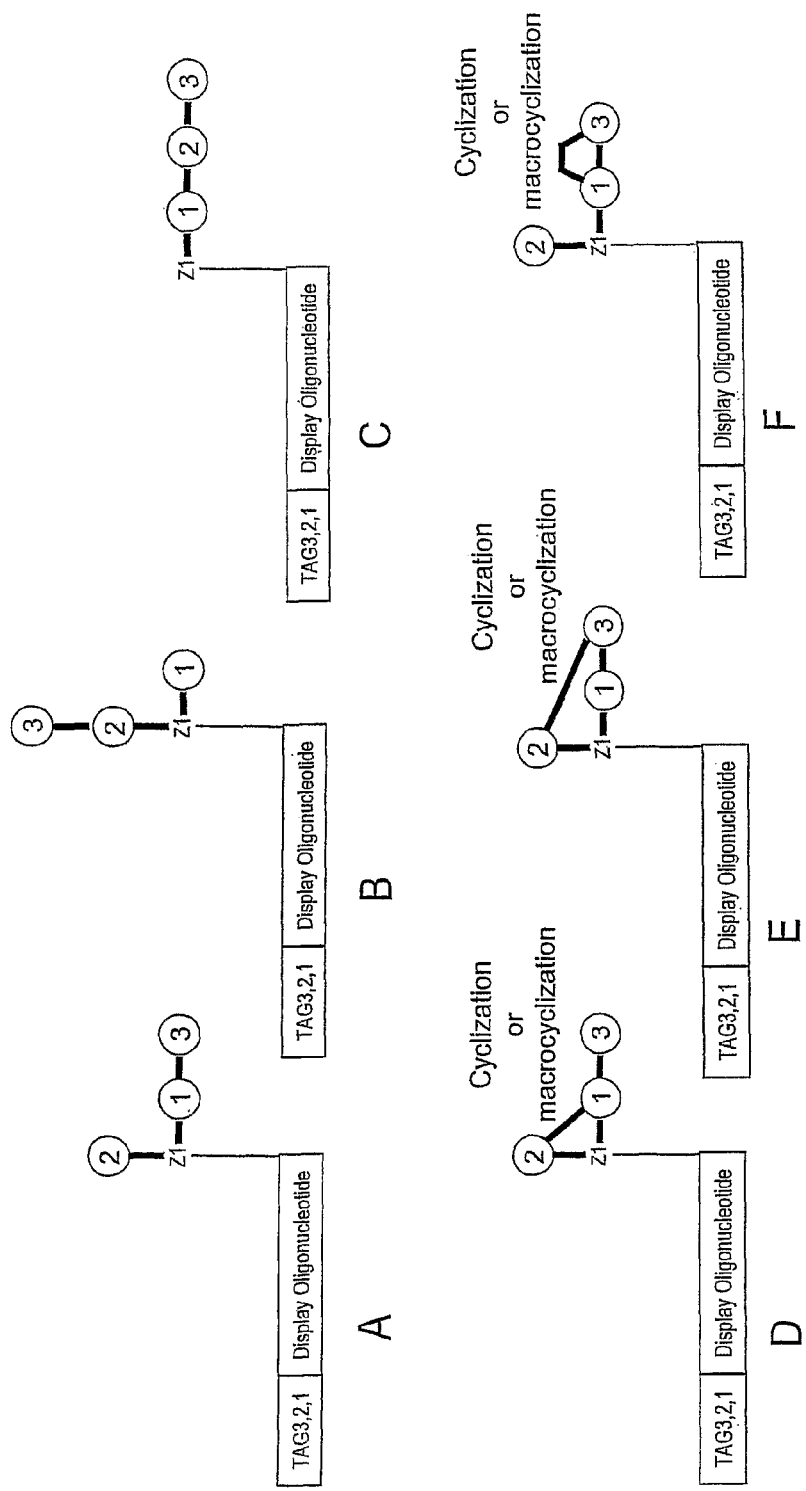
Figure 27:
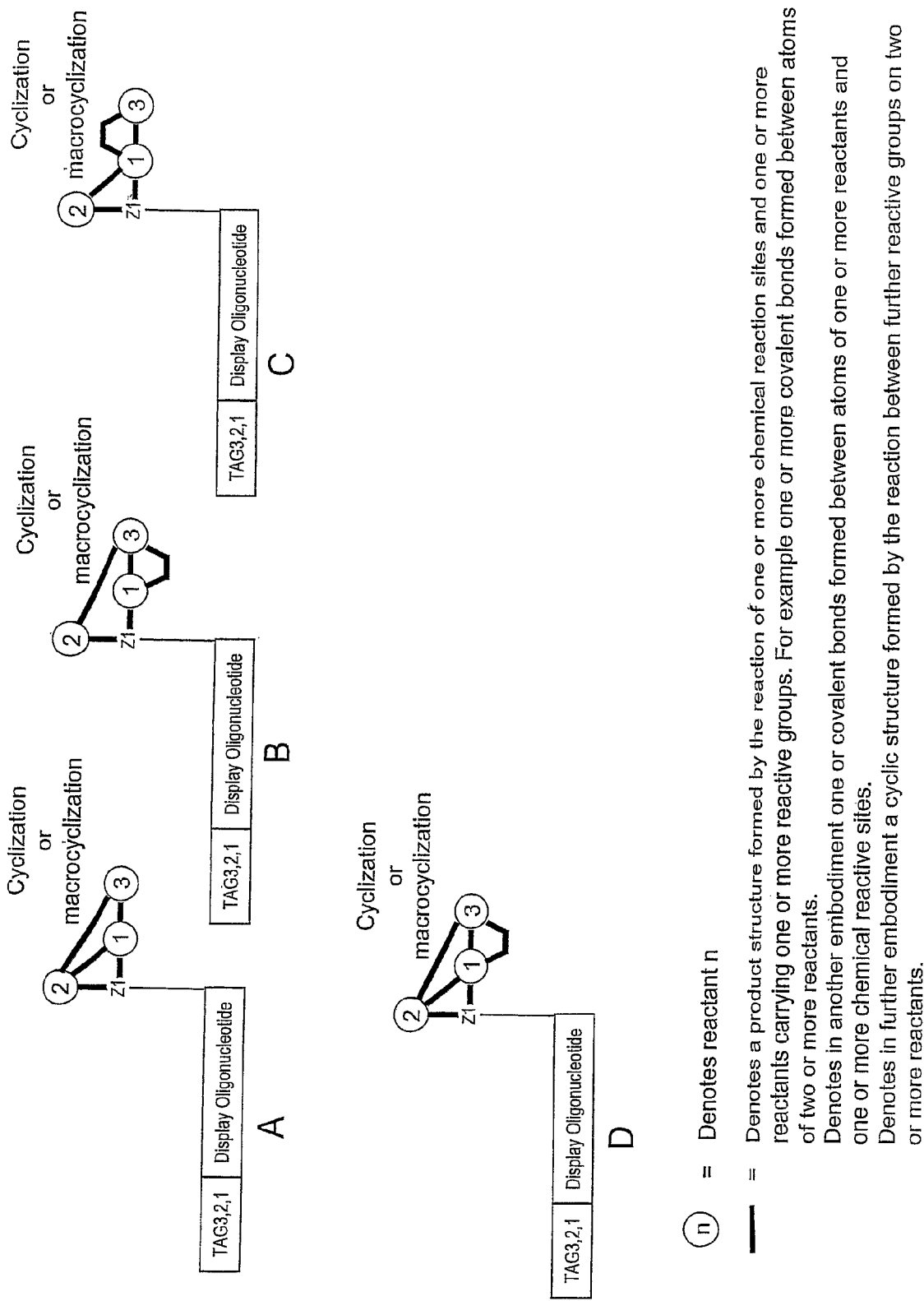
Figure 28:
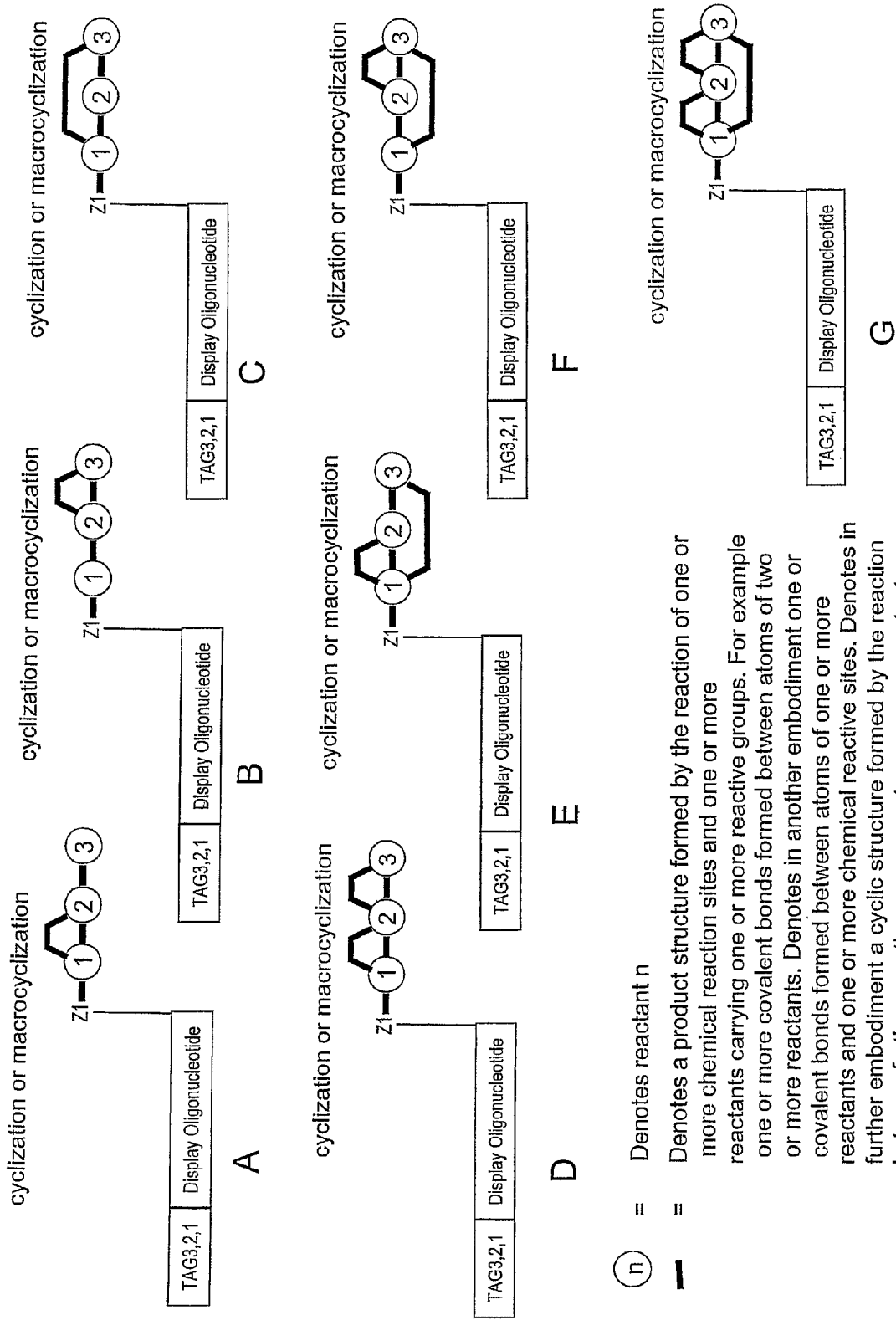
Figure 29:
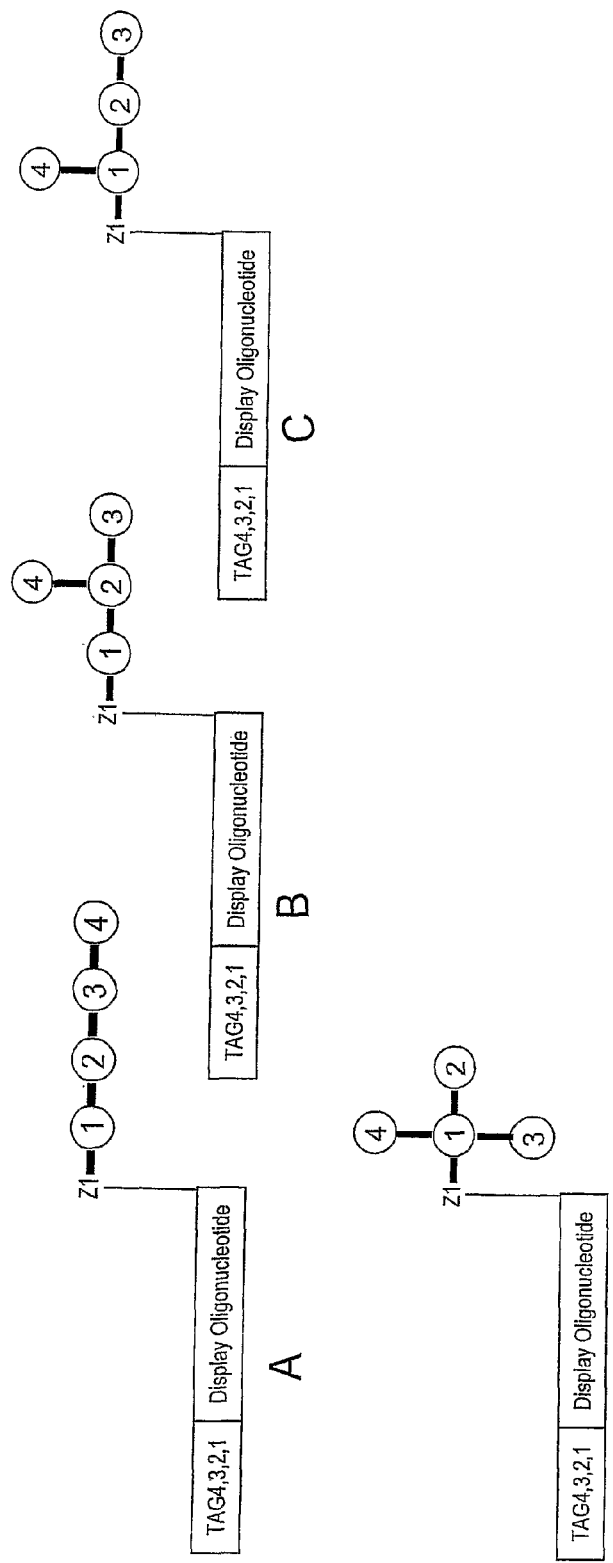
Figure 30:
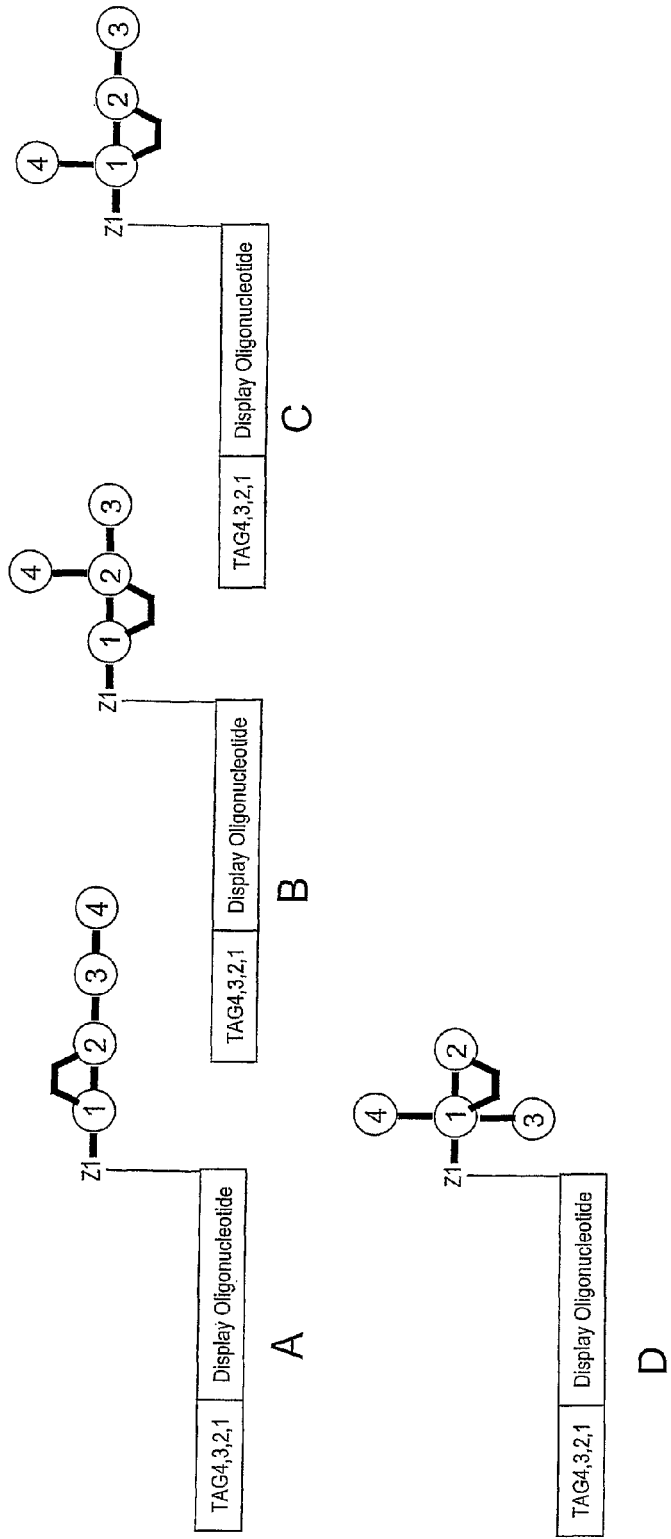
Figure 31:
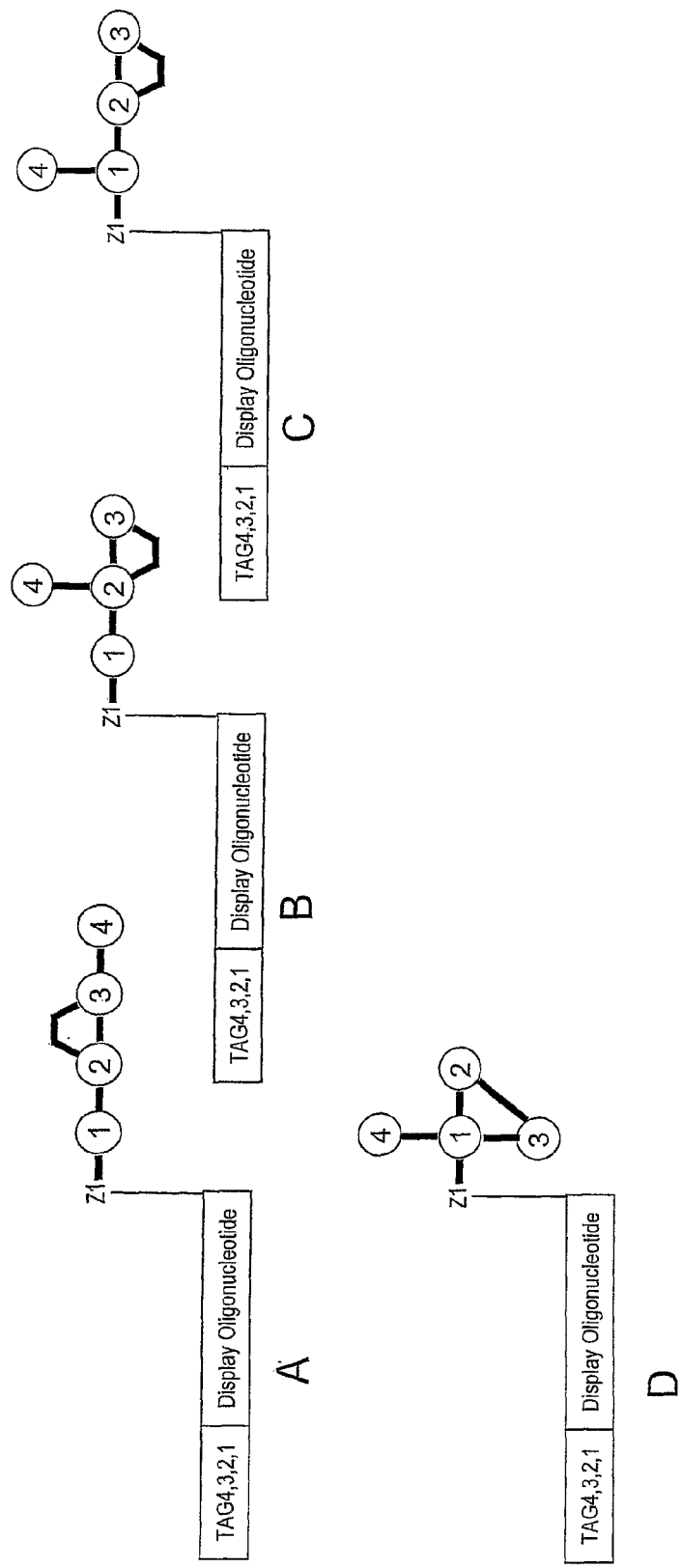
Figure 32:
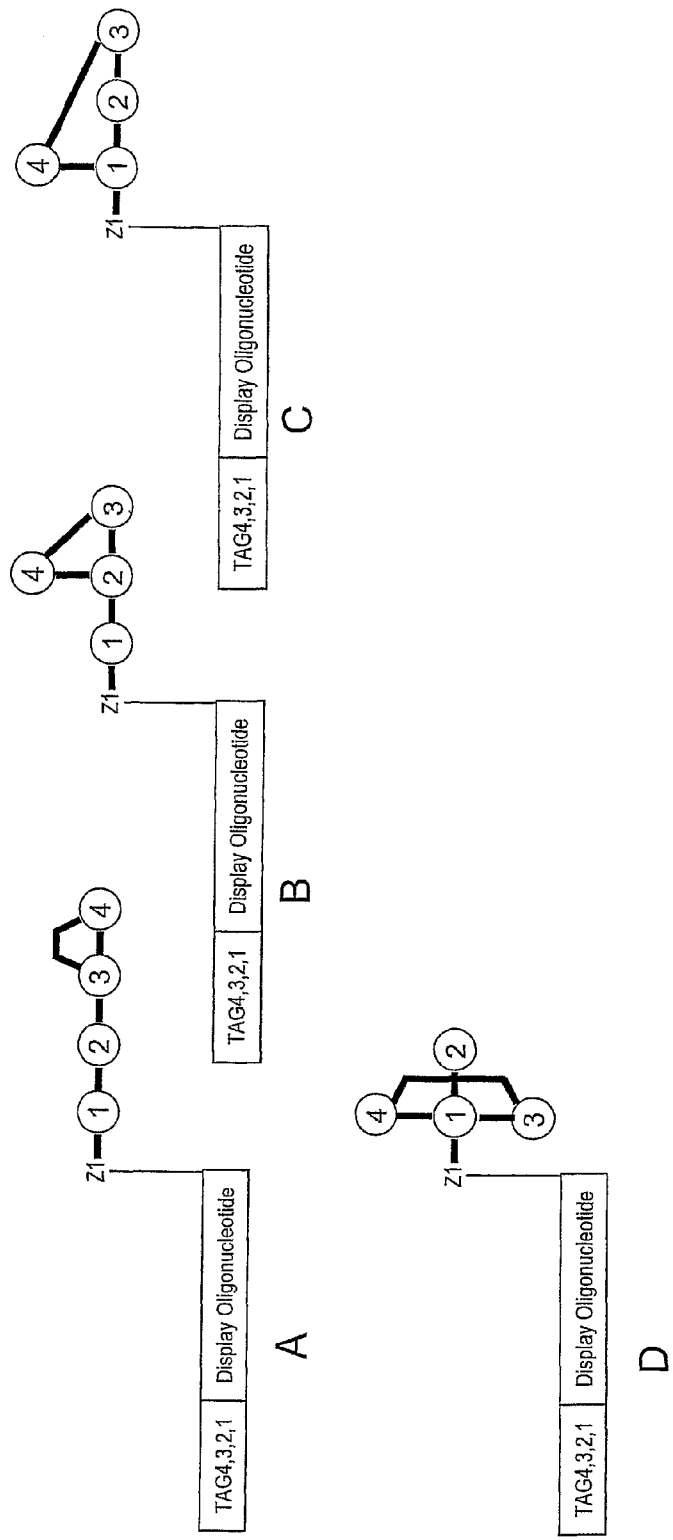
Figure 33:
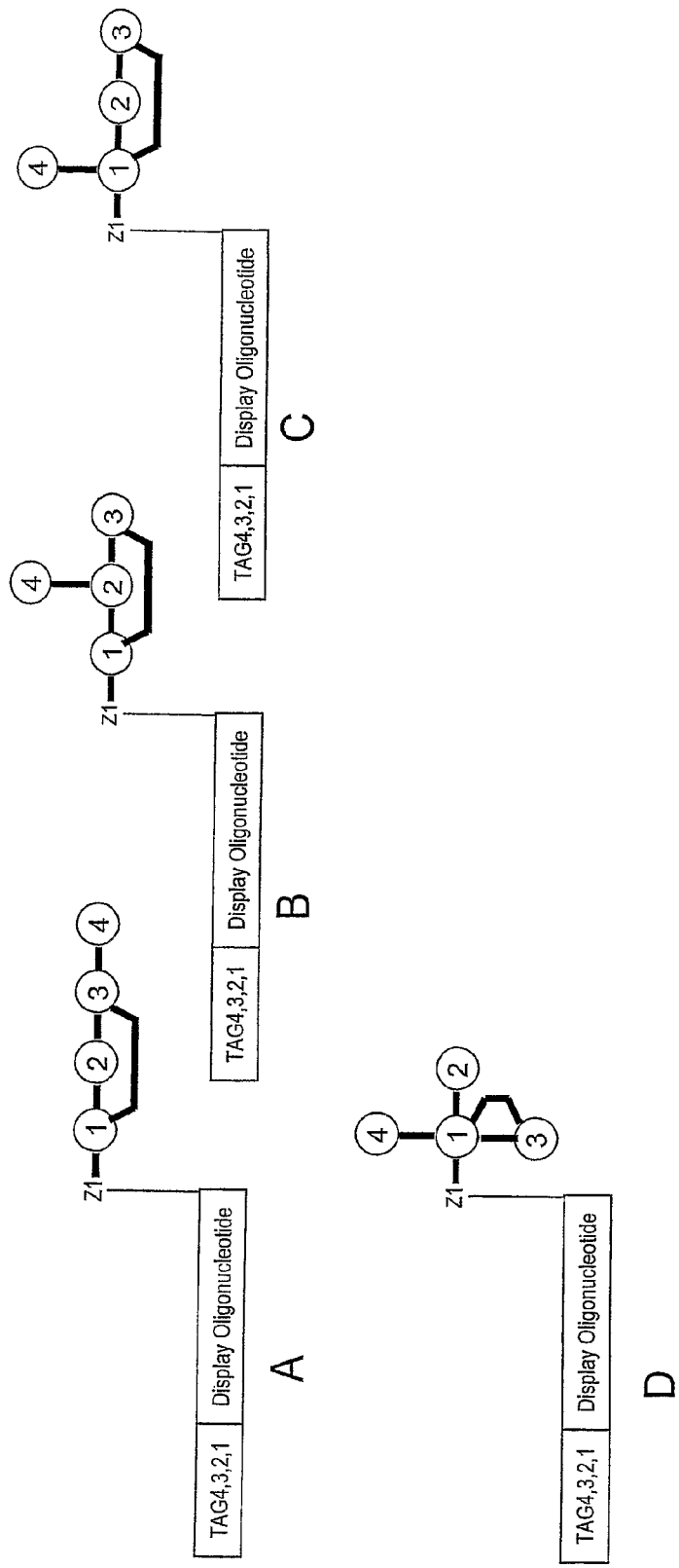
Figure 34:
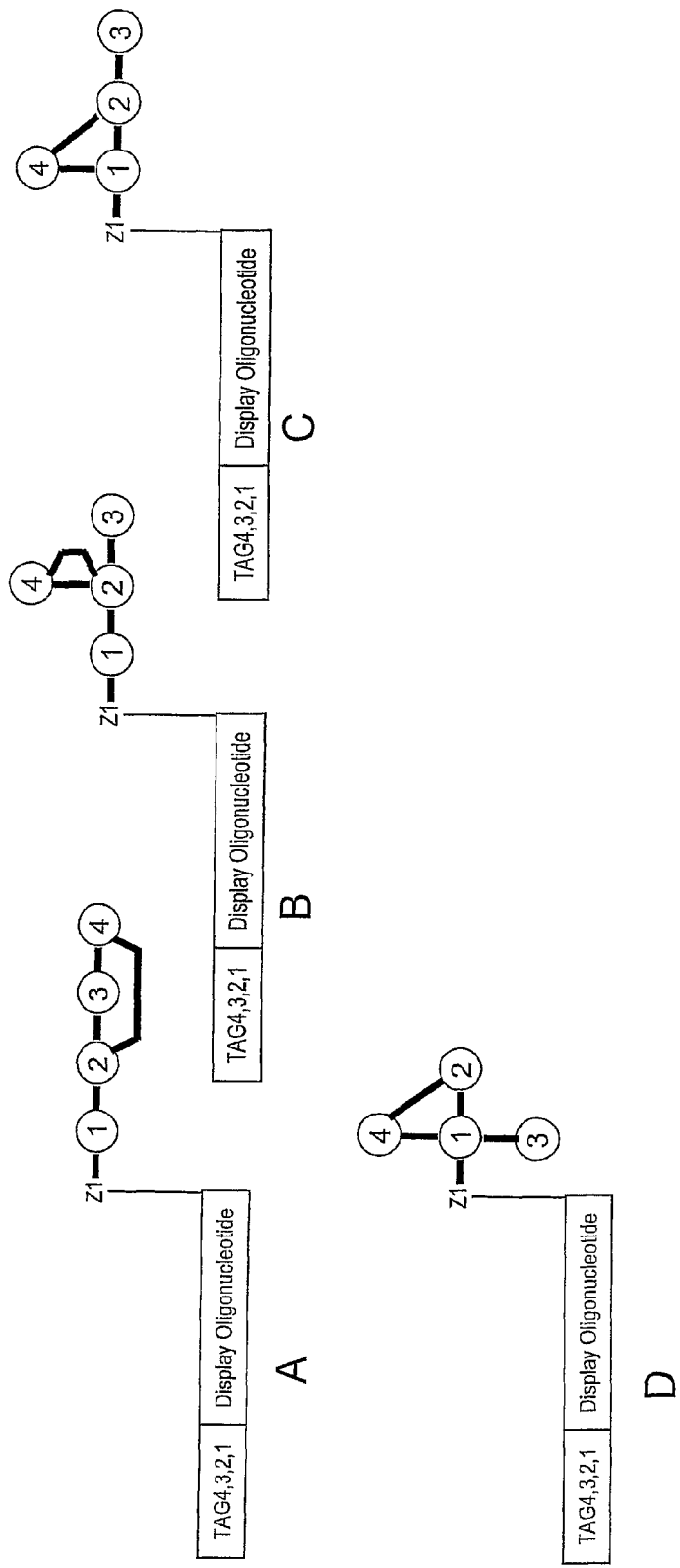
Figure 35:
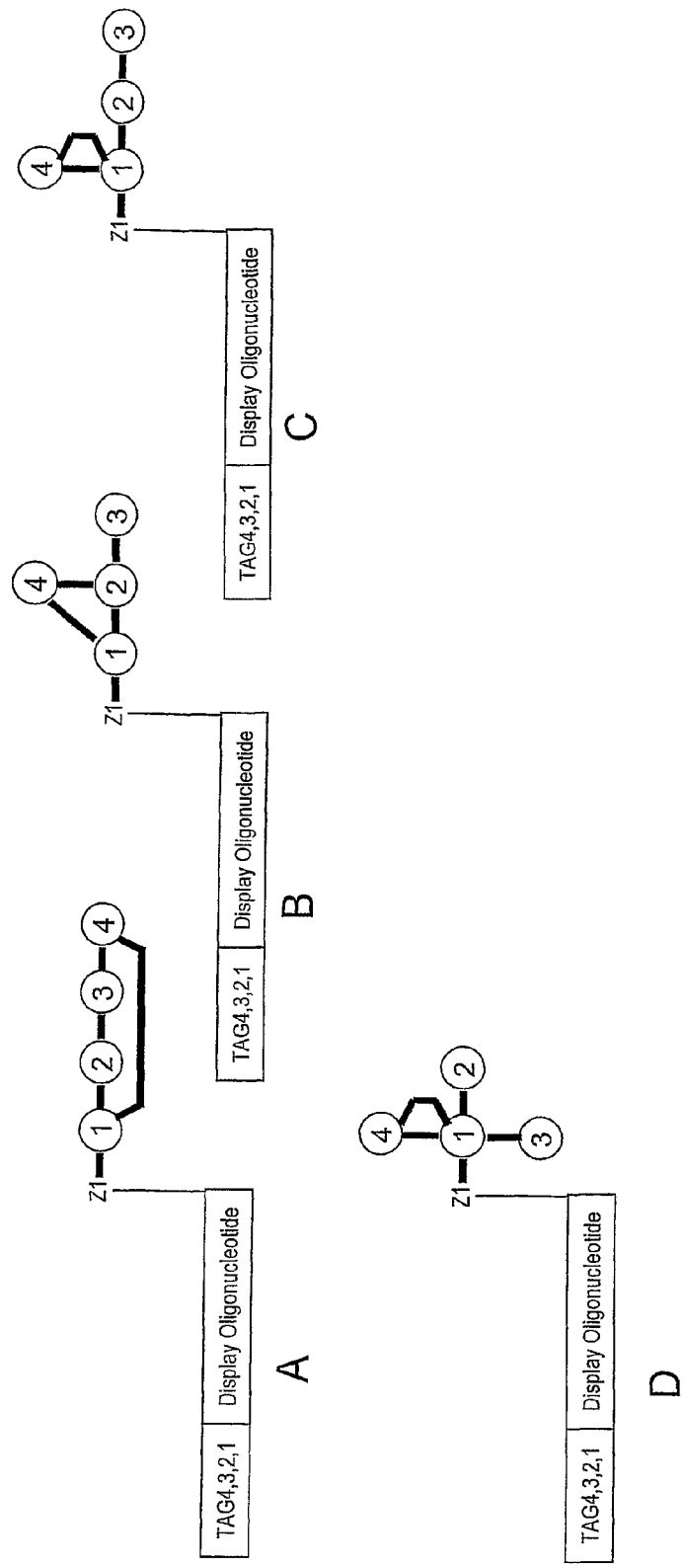
Figure 36:
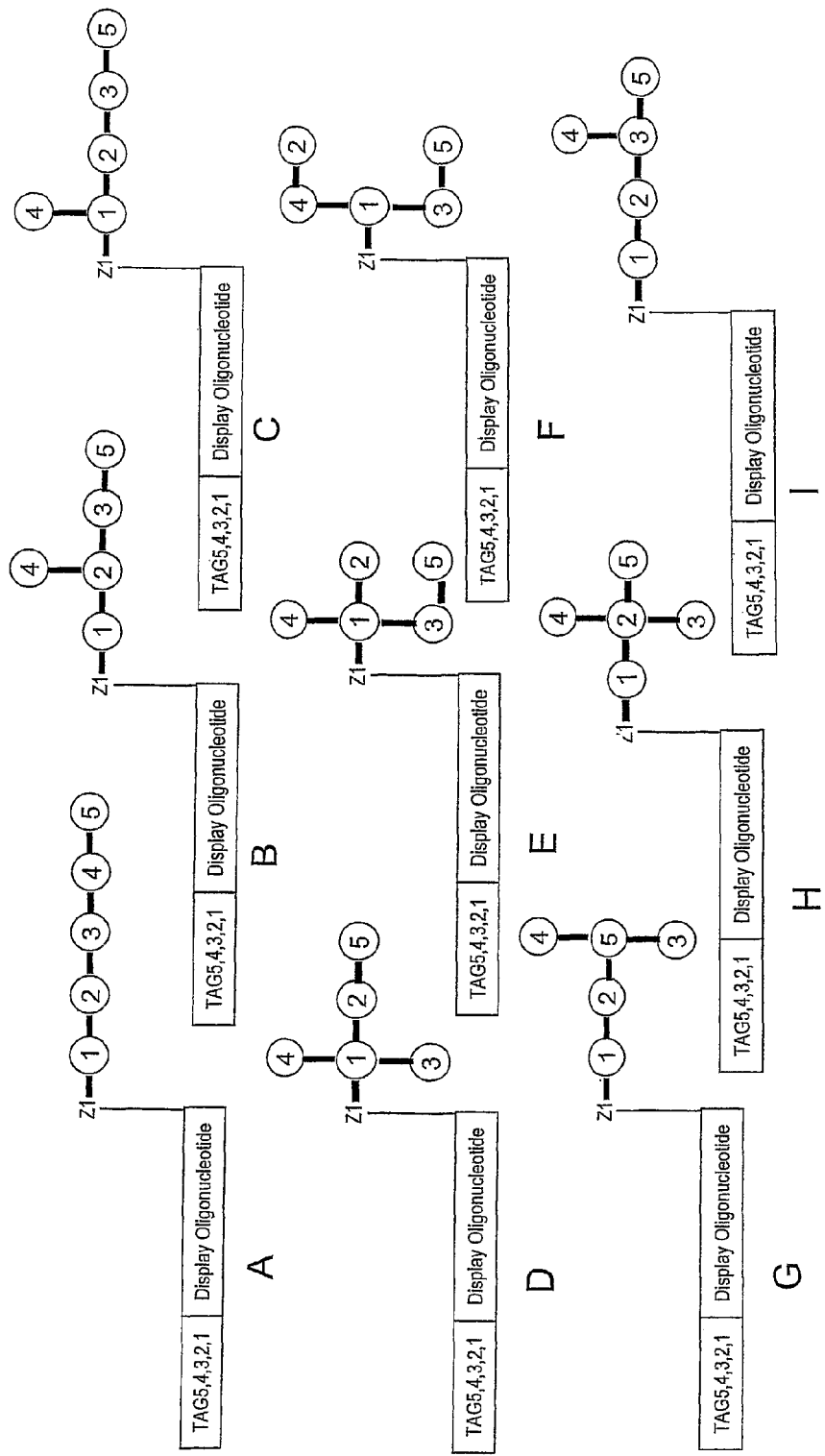

FIG. 24 The figure serves to illustrate example reactants comprising one or more chemical entities and one or more reactive groups. The invention is not limited to the use of the reactants shown. Reactants may furthermore be protected by use of one or more protection groups.

Reactants within a group comprising one or more identical reactive groups may comprise different chemical entities, which may be focused around specific core structures or which may be diverse (different) or the group may comprise a combination of focused and diverse chemical entities.

Reactants in different groups of reactive groups may be focused around specific core structures or may be diverse (different) or the groups may comprise a combination of focused and diverse chemical entities.

FIGS. 25-36. Circles with a number inside, denotes reactants. The figures serve to illustrate various product structures formed by the use of reactants in various ways. Emphasized (thick) lines denotes a product structure formed by the reaction of one or more reactive groups on one or more reactants and a product structure formed by the reaction of one or more reactive groups on one or more reactants and one or more chemical reaction sites. The product structure does not need to comprise atoms (direct covalent linkage of two reactants). The product structure may also comprise one or more bonds and one or more atoms. The product structure may be cyclic or linear or branched or combinations thereof. The product structure may for example also comprise product structure examples as described elsewhere by this invention. Product structures represented by thick lines may be the same or different.

FIGS. 37-50. In some figures a pyrimidine product structure is used as an example for a heteroaromatic chemical structure e.g. an azine, such as for example a pyridine, a pyrimidine, a pyrazine, a pyridazine, a purine and for example benzo and azolo variants thereof. Azine product structure examples are also exemplified elsewhere in this invention.

Definitions used:
CRS: Chemical Reactive Site

Chemical entities are denoted/illustrated by R groups, which may have numbers such as R1, R2, R3, R4, R5, R6, R7, R8, R9, R10. Chemical entities may also be shown as a circle with an R group inside. Such circles may optionally represent a cyclic structure, e.g. R1 may be a cyclic structure such as e.g. a cyclic diamino acid, for example but not limited to the product following the use of piperidine 2-carboxylic acid as reactant, whereby two amino groups may react with similar or different electrophiles, such as for example reaction with aldehydes under reductive amination conditions to form an alkylated amine, for example reaction with a sulfonyl chloride to form sulfonamides, for example acylation by reaction with carboxylic acids under for example EDC/NHS or DMTMM coupling conditions to form carboxamides, for example reaction with haloazines to form aminoazines, and the carboxylic acid of the diamino-acid may undergo an acylation reaction to form an amide. Although illustrated by circles, the back bone/core/scaffolded structure may in fact be either cyclic or non-cyclic, including branched, linear, cyclic structures or a combination thereof.

Amino groups may be primary amines, secondary amines, tertiary amines. Amide groups may be primary, secondary, tertiary amides. When the circle represents a cyclic structure, amines may be endocyclic or exocyclic.

Het: means a heterocyclic product structure for example an azine, an azole, a purine, and other heterocyclic systems as defined elsewhere in the invention. Aromatic rings with an N inside the ring are by definition equivalent to Het. Pyrimidine structures are also equivalent to the definition of Het and the pyrimidine structure is only used to illustrate the example and not to limit the scope of this invention.

Figure 37:
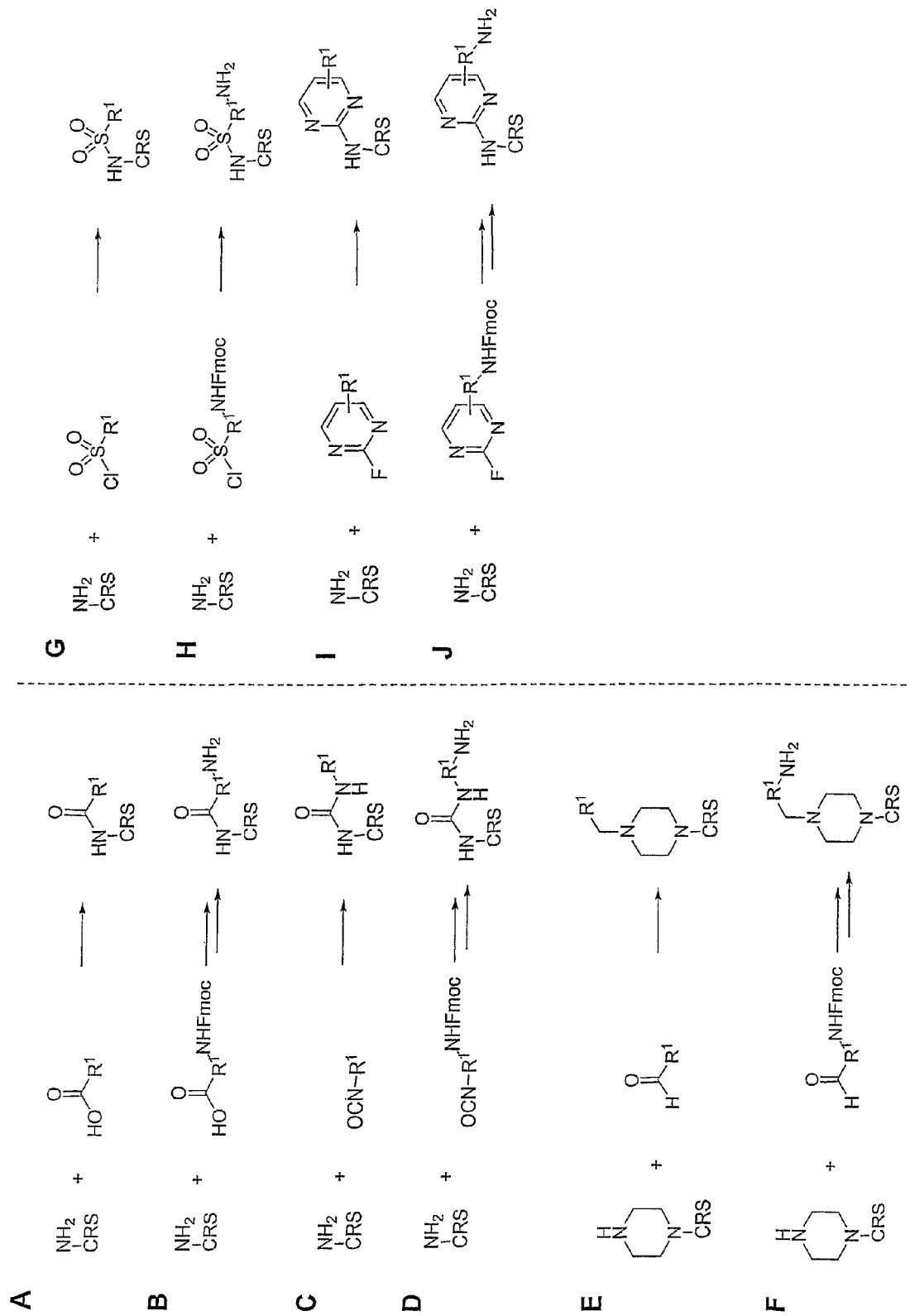
Figure 38:
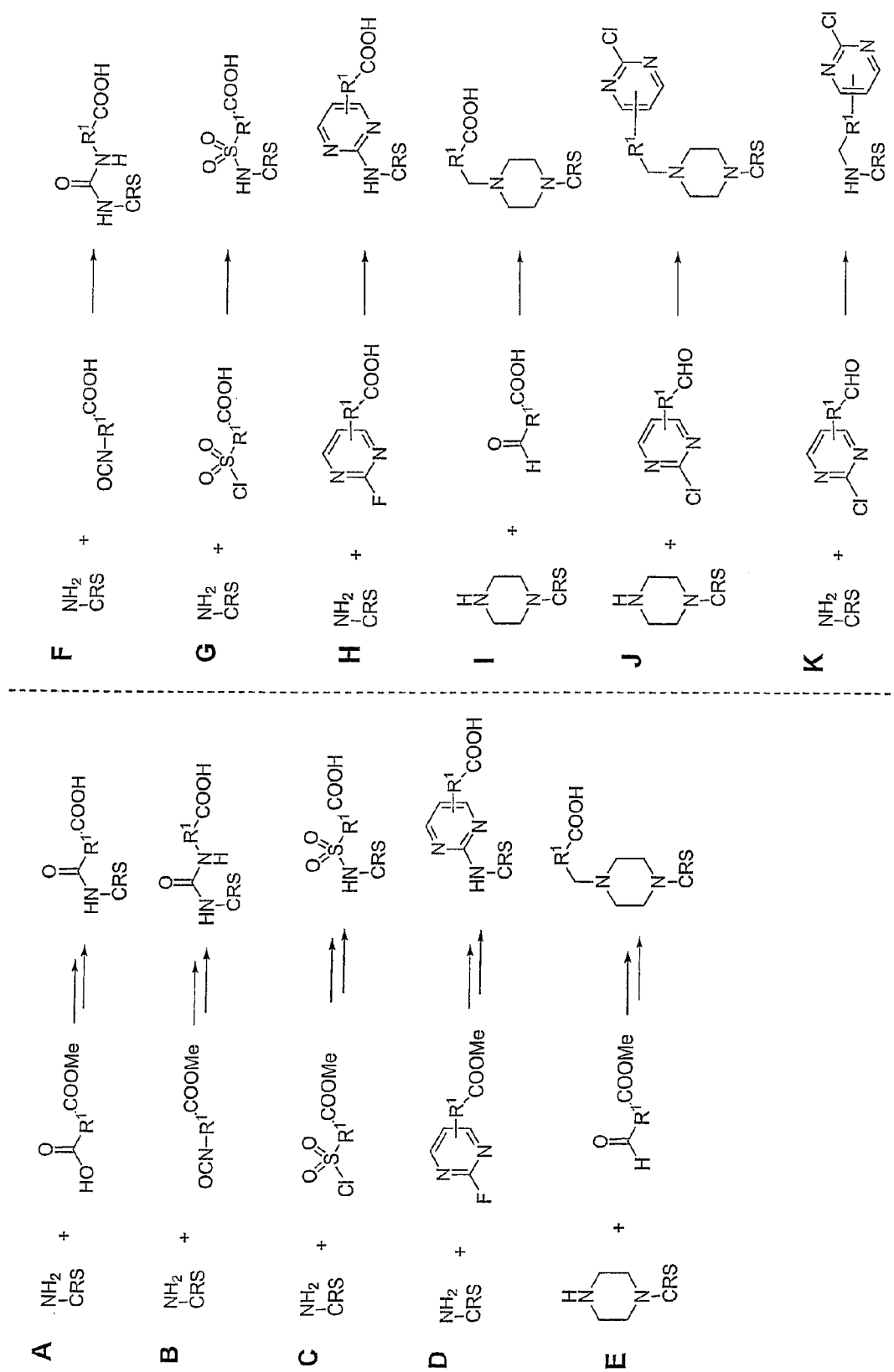
Figure 39:
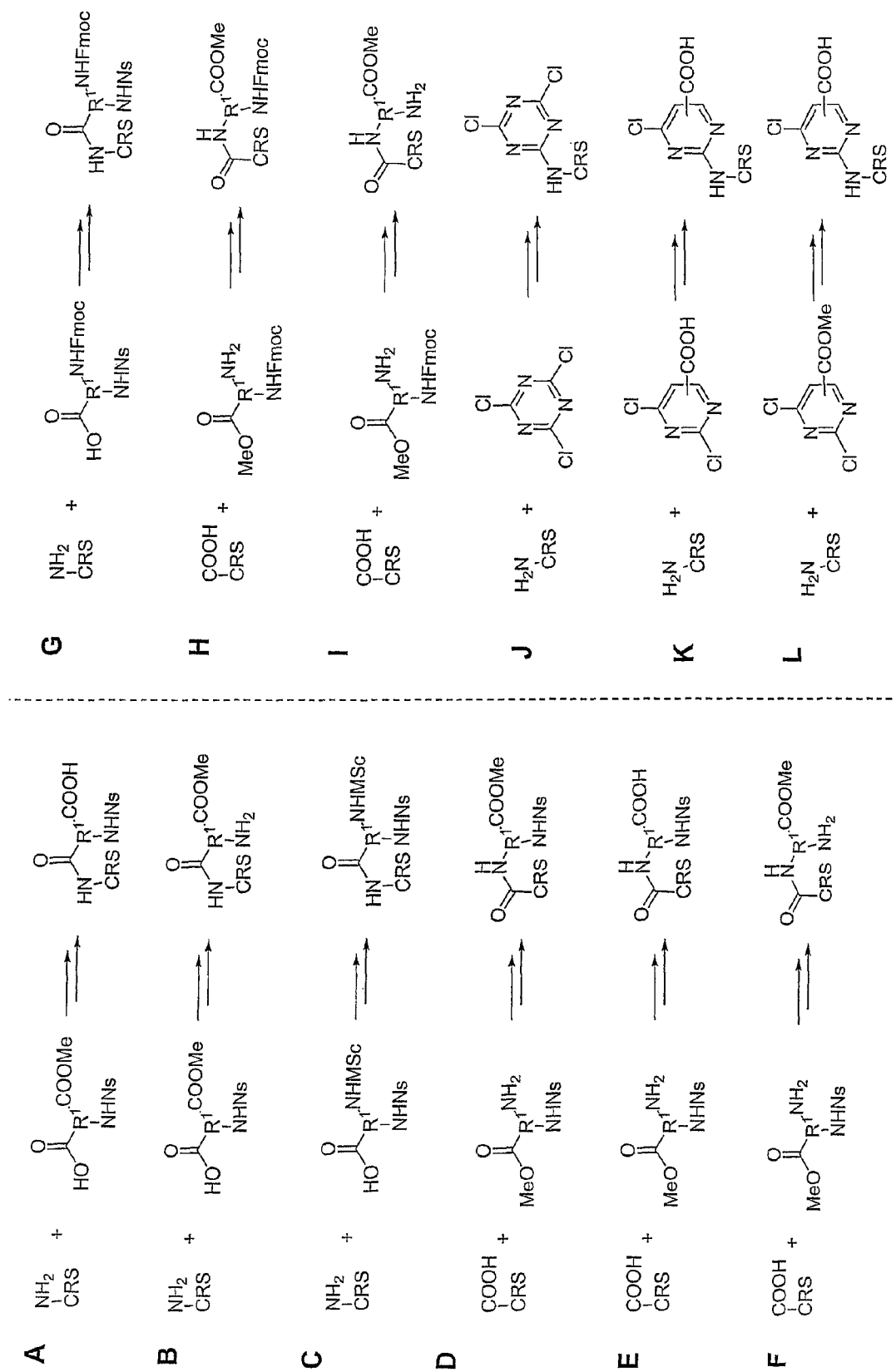
Figure 40:
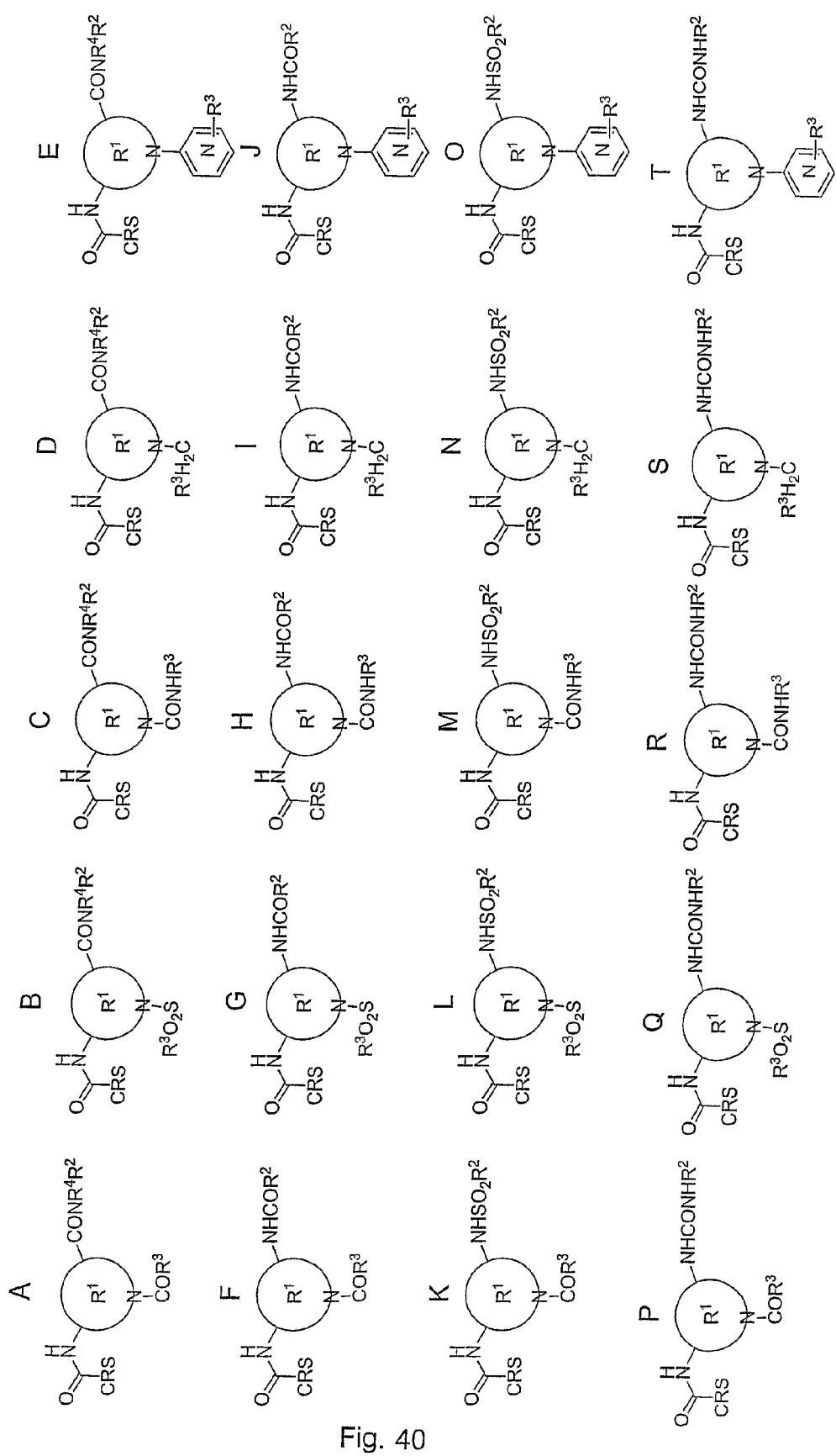
Figure 41:
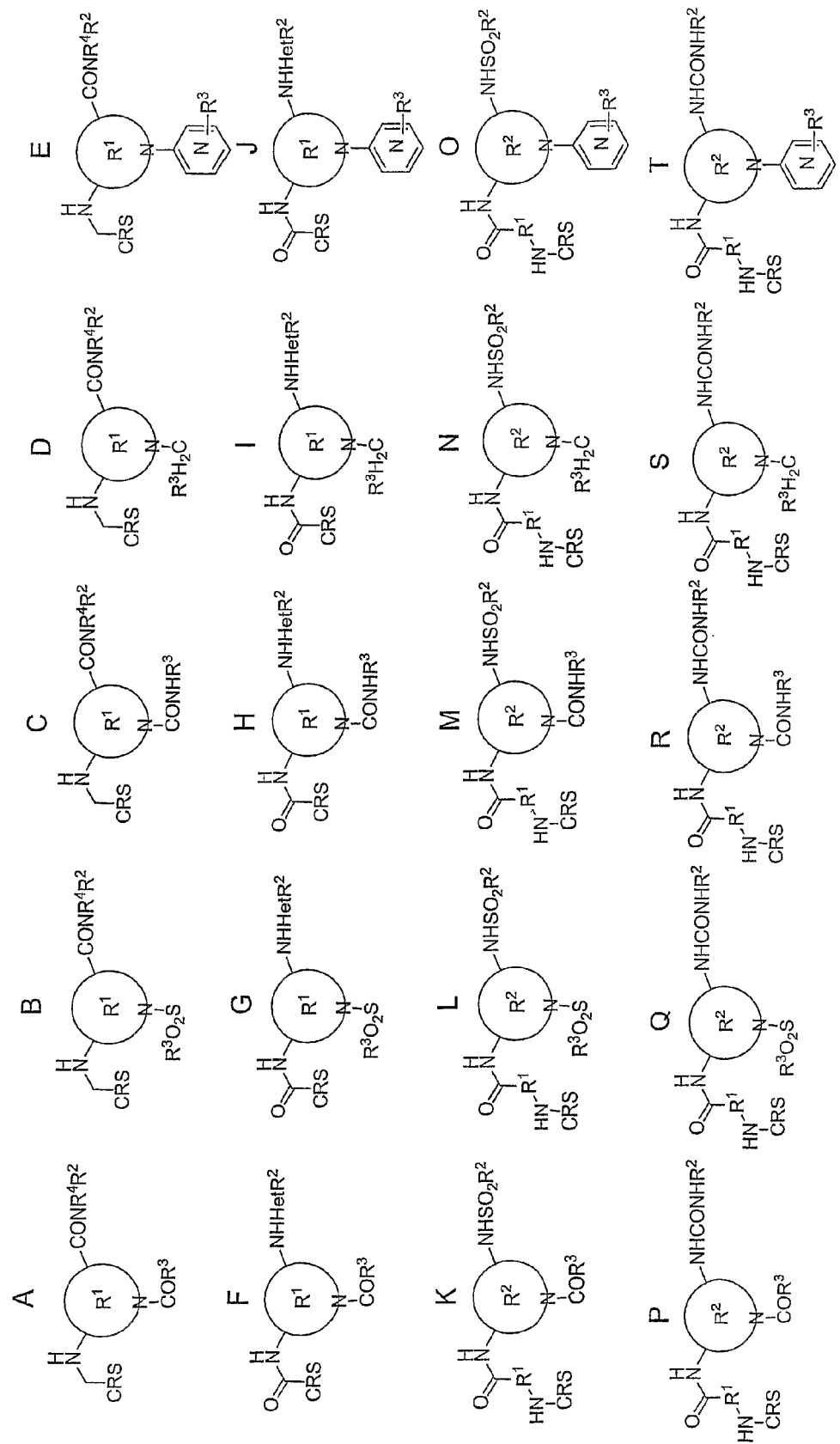
Figure 42:
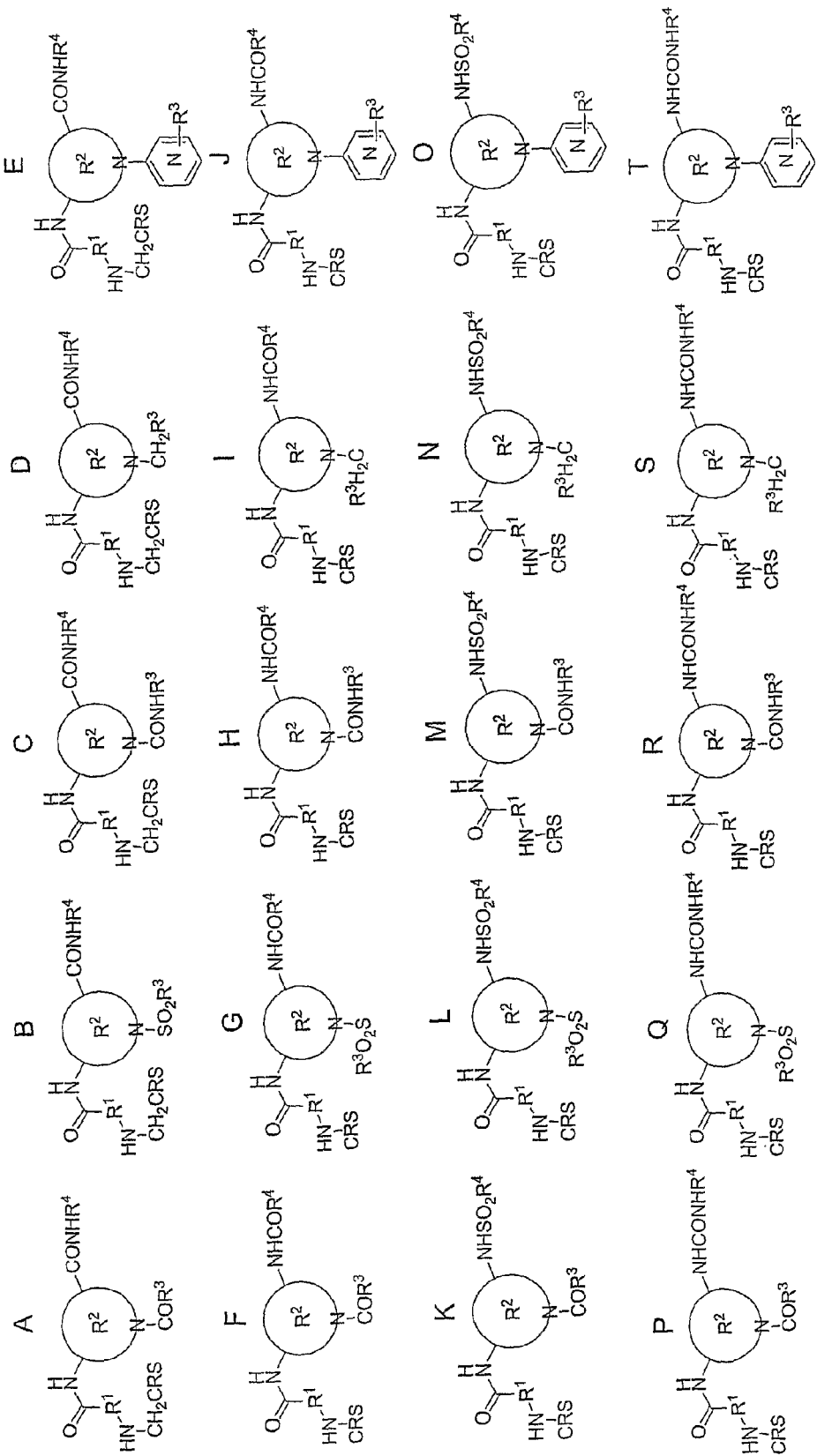
Figure 43:
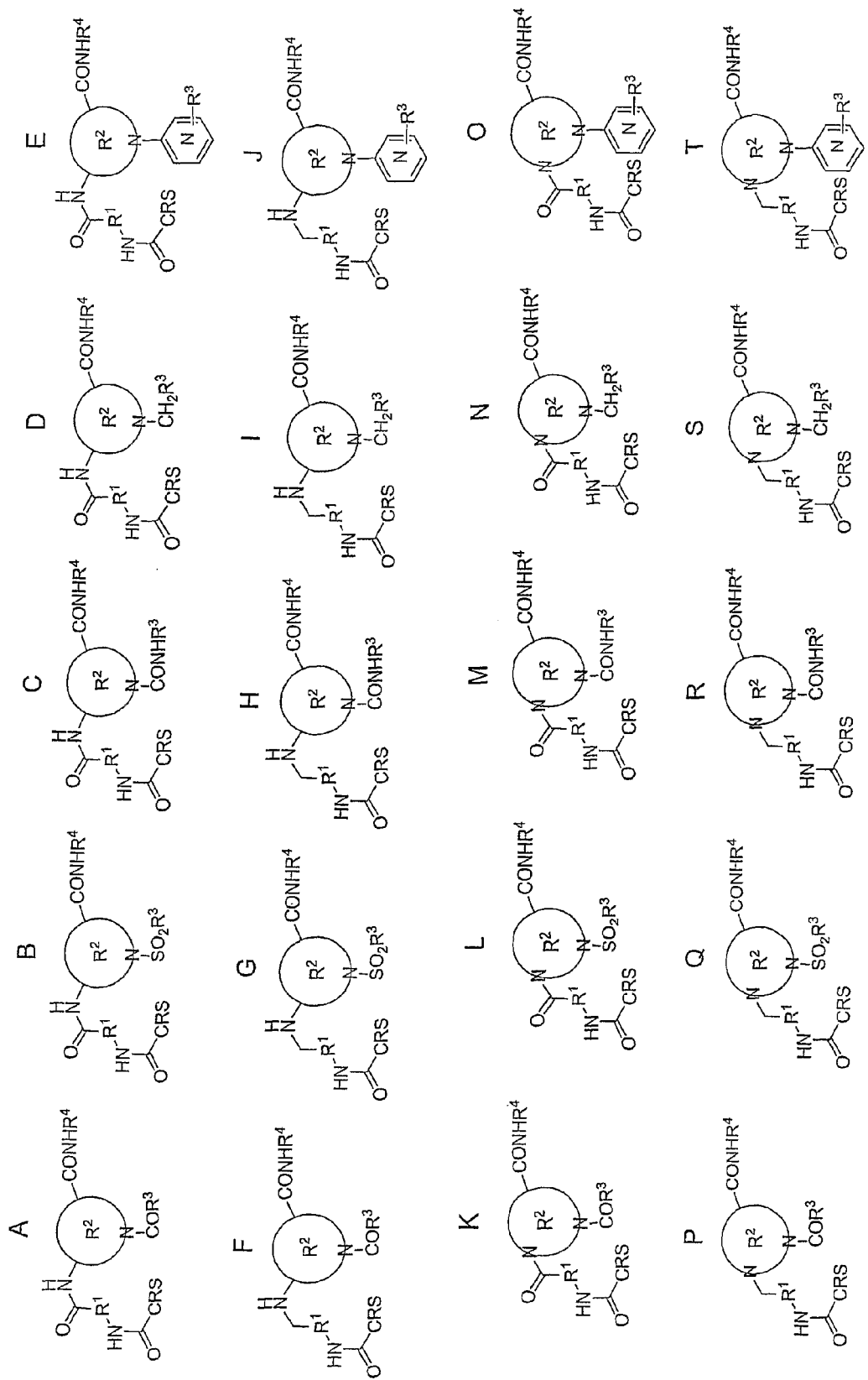
Figure 44:
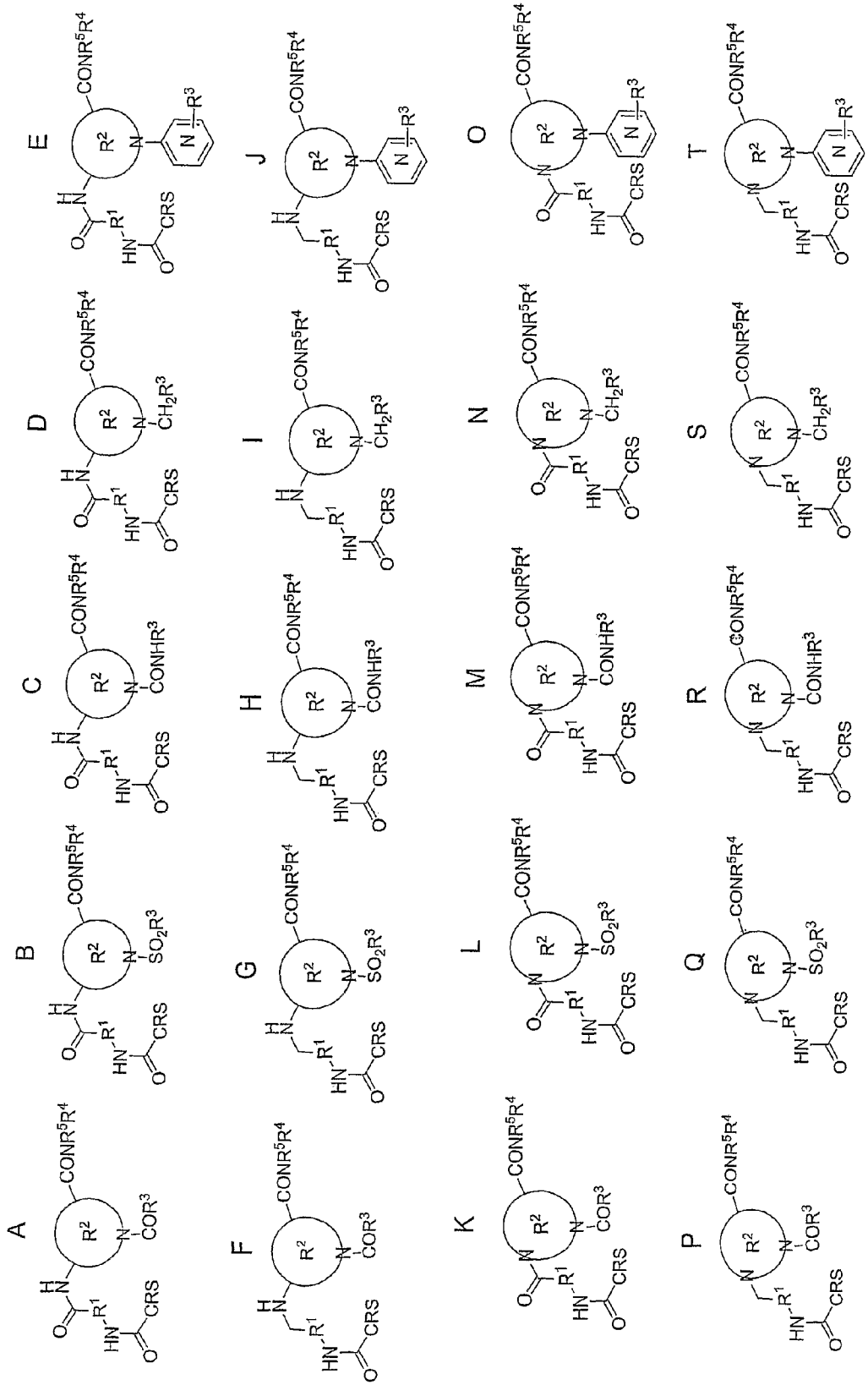
Figure 45:
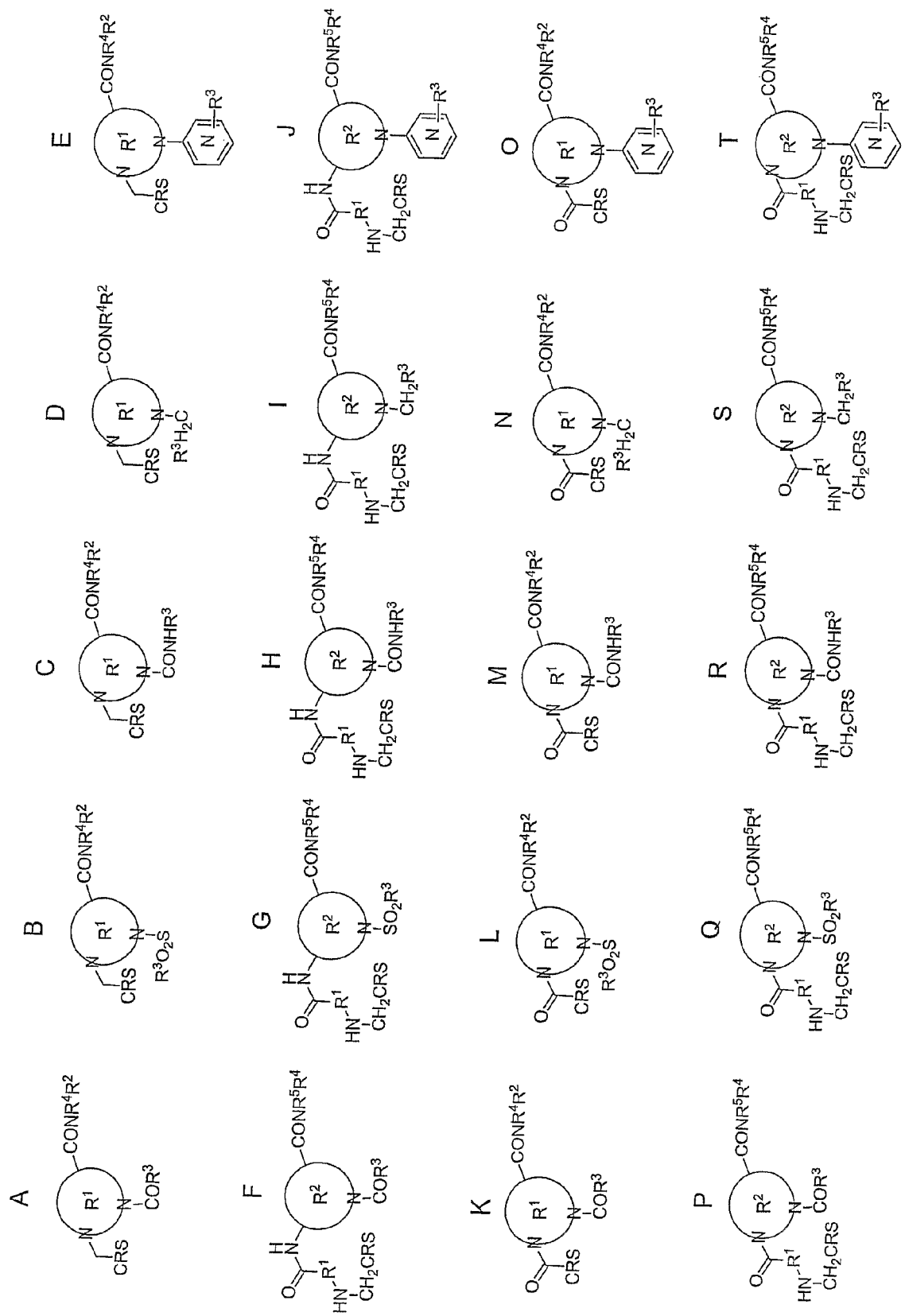
Figure 46:
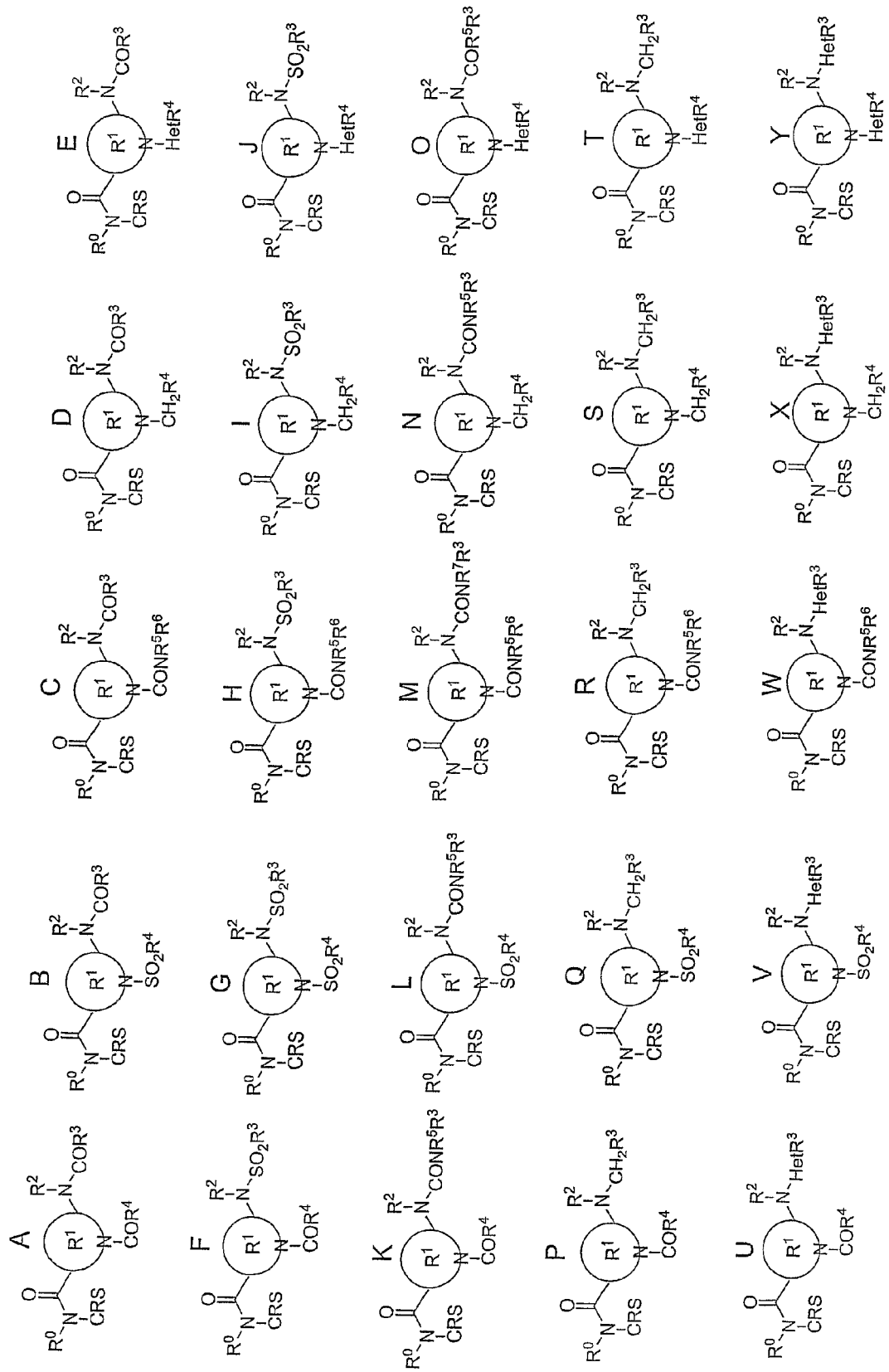
Figure 47:
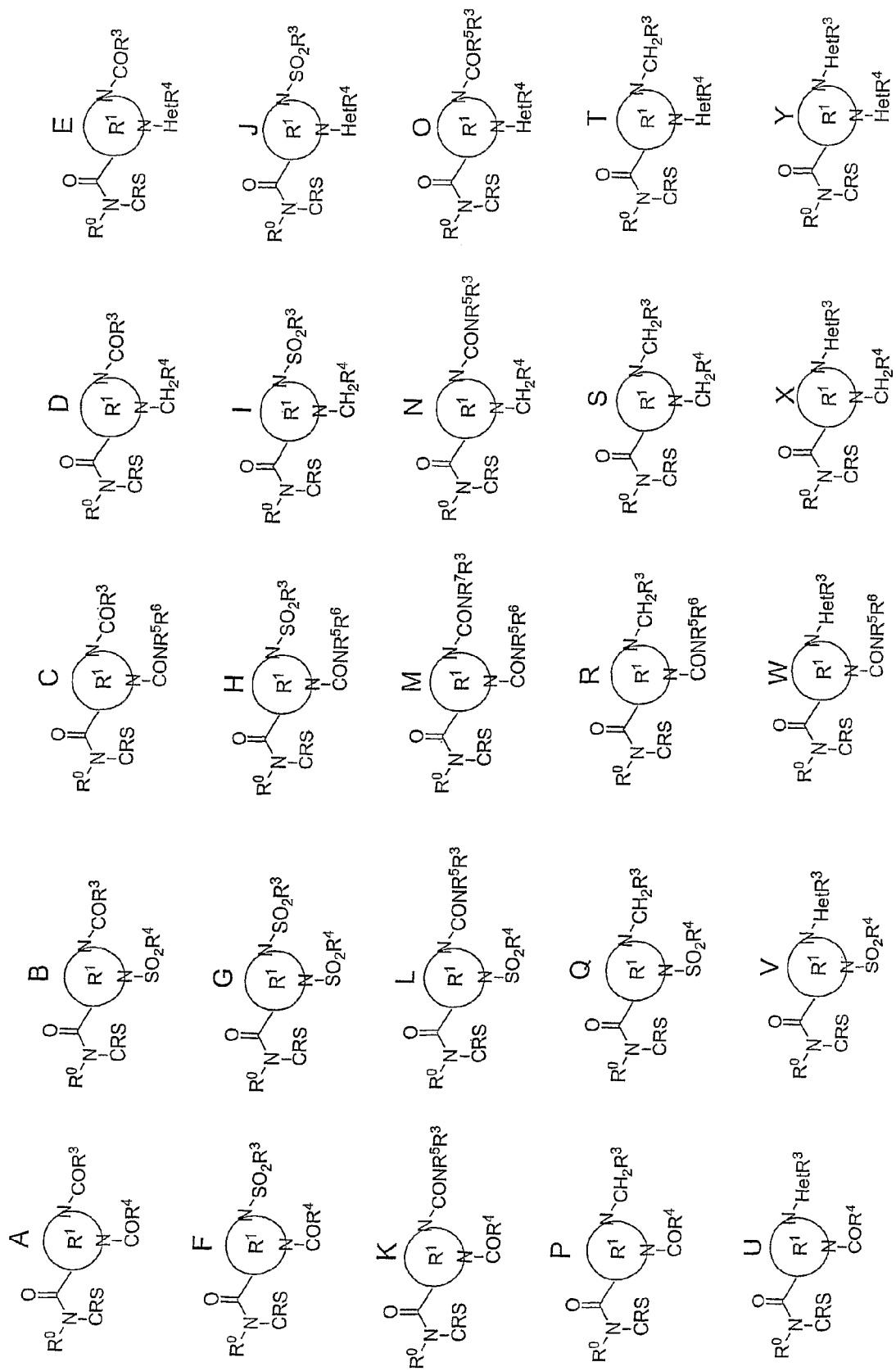
Figure 48:
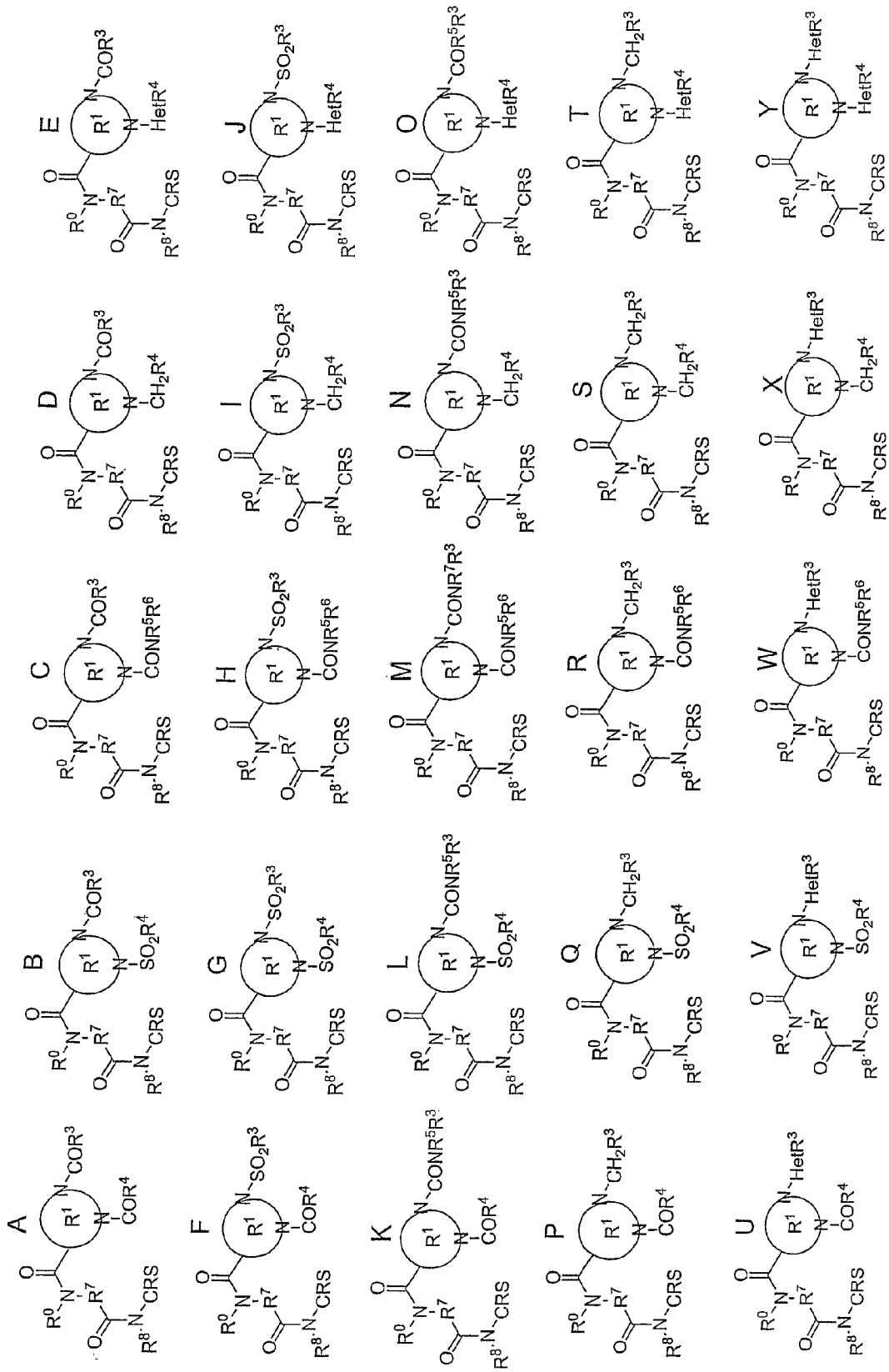
Figure 49:
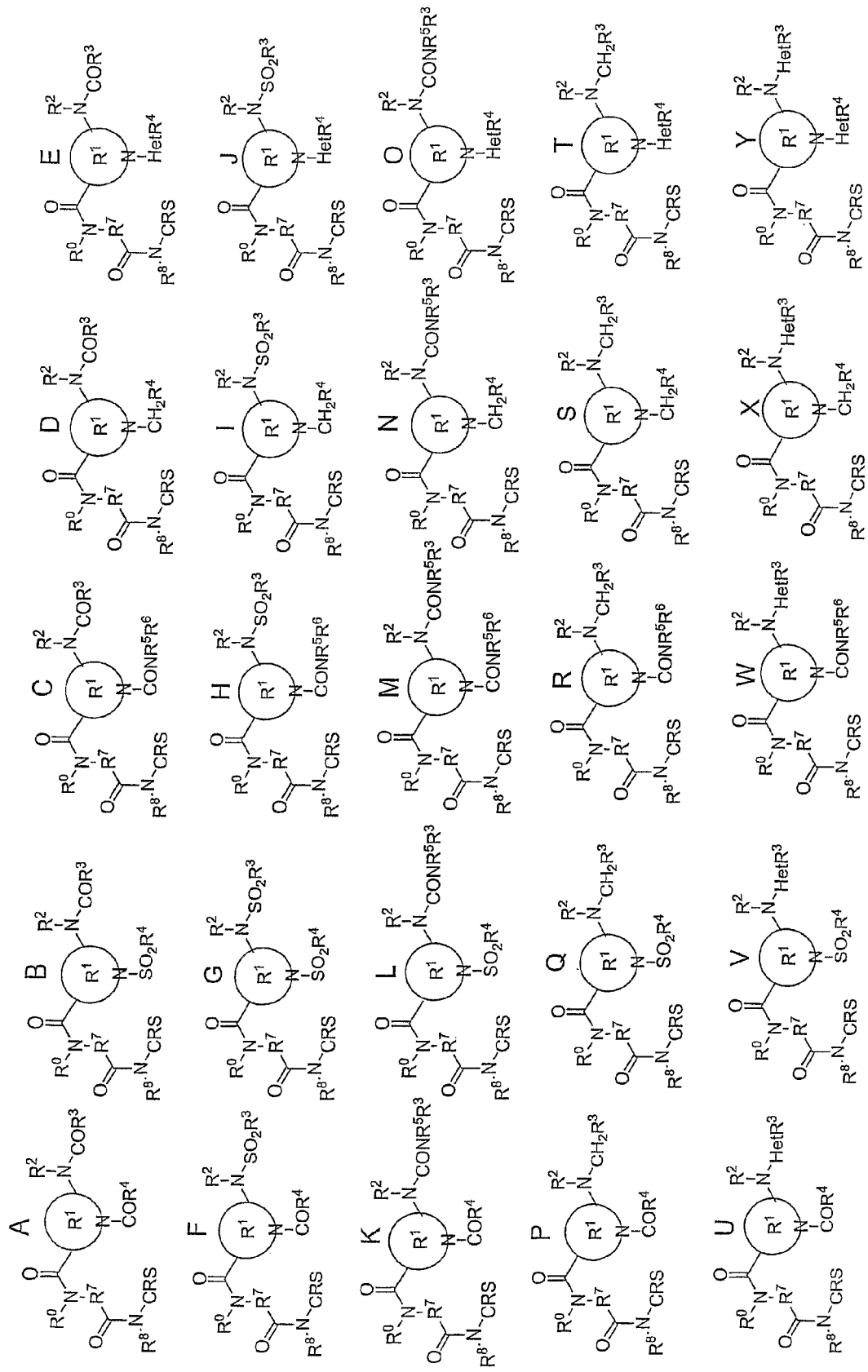
Figure 50:
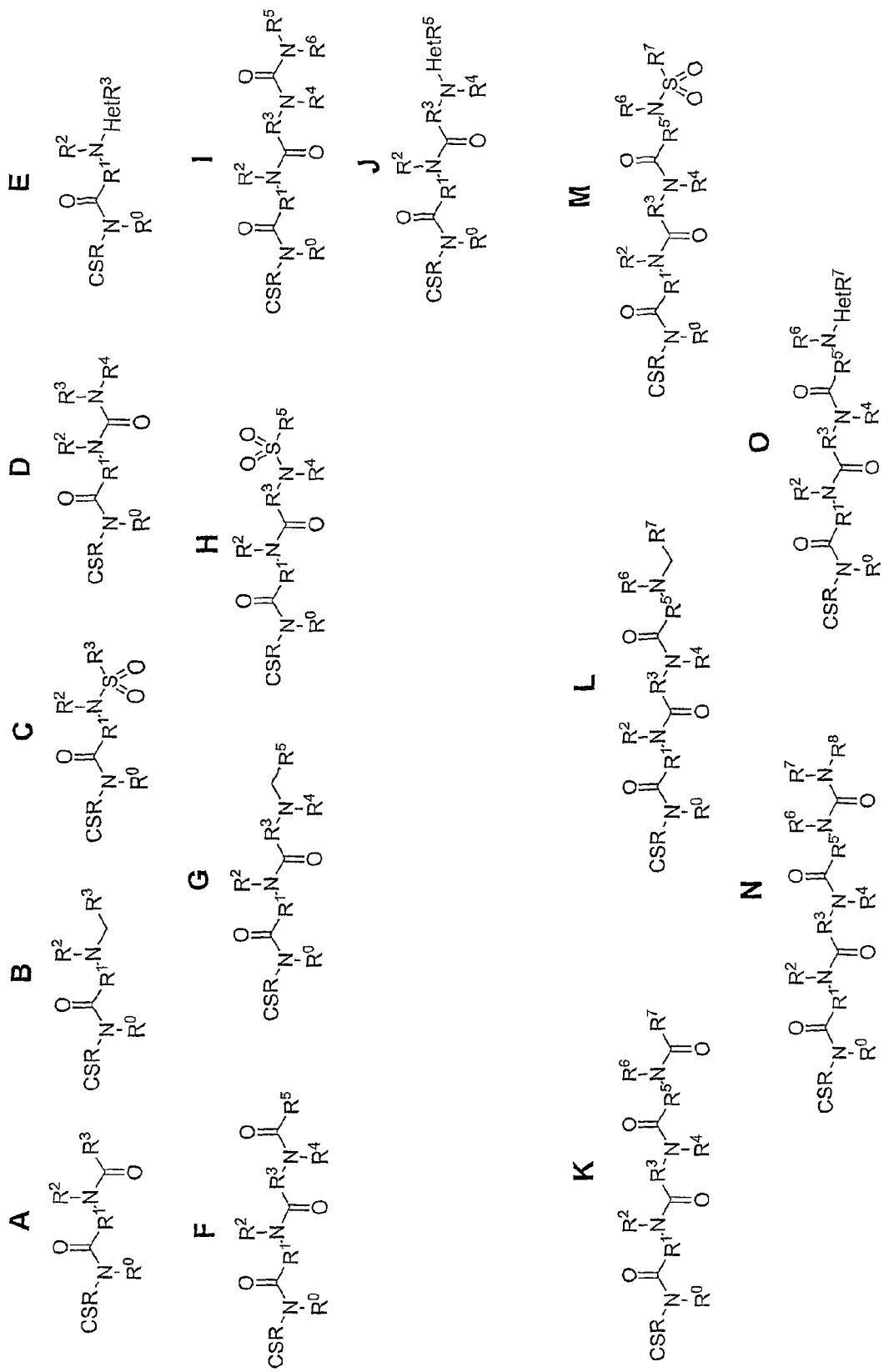

FIGS. 37-39. The figure describes various example product structures formed by use of at least one reactant. In some examples reactants comprising further reactive groups may react with further reactants to form linear, branched, cyclic, macrocyclic structures or a combination thereof or undergo intramolecular cyclization through the reaction with further reactive groups on R1, including reactive groups not shown but comprised by R1.

FIGS. 40-50. The figure describes various product structures formed by use of 1-5 reactants, for example one reactant, for example 2 reactants, for example 3 reactants, for example 4 reactants, for example 5 reactants. In some examples reactants comprising further reactive groups may react with further reactants to form linear, branched, cyclic or macrocyclic structures or undergo intramolecular cyclization through the reaction with further reactive groups on Rn-groups, including reactive groups not shown but comprised by Rn-groups (where n is an integer). The invention may also use more than five reactants, such as six reactants, for example seven reactants, for example eight reactants, for example nine reactants, for example ten reactants. In another embodiment, 11-20 reactants are used, such as 11-15 reactants, for example 16-20 reactants.

Figure 51:
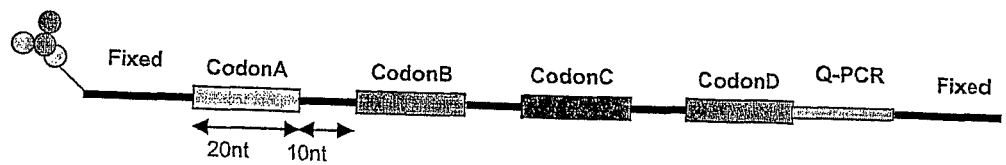

FIG. 51. The figure illustrates a member of a tetramer library consisting of bifunctional molecules each comprising 4 DNA codon elements (tags) covalently linked to the cognate chemical fragments. The overall structure of the bifunctional molecules is shown. Each 20 nt/bp codon is spaced by a 10 nt fixed region and the tags A-D is flanked by fixed sequences useful for amplification by PCR.

Figure 52:
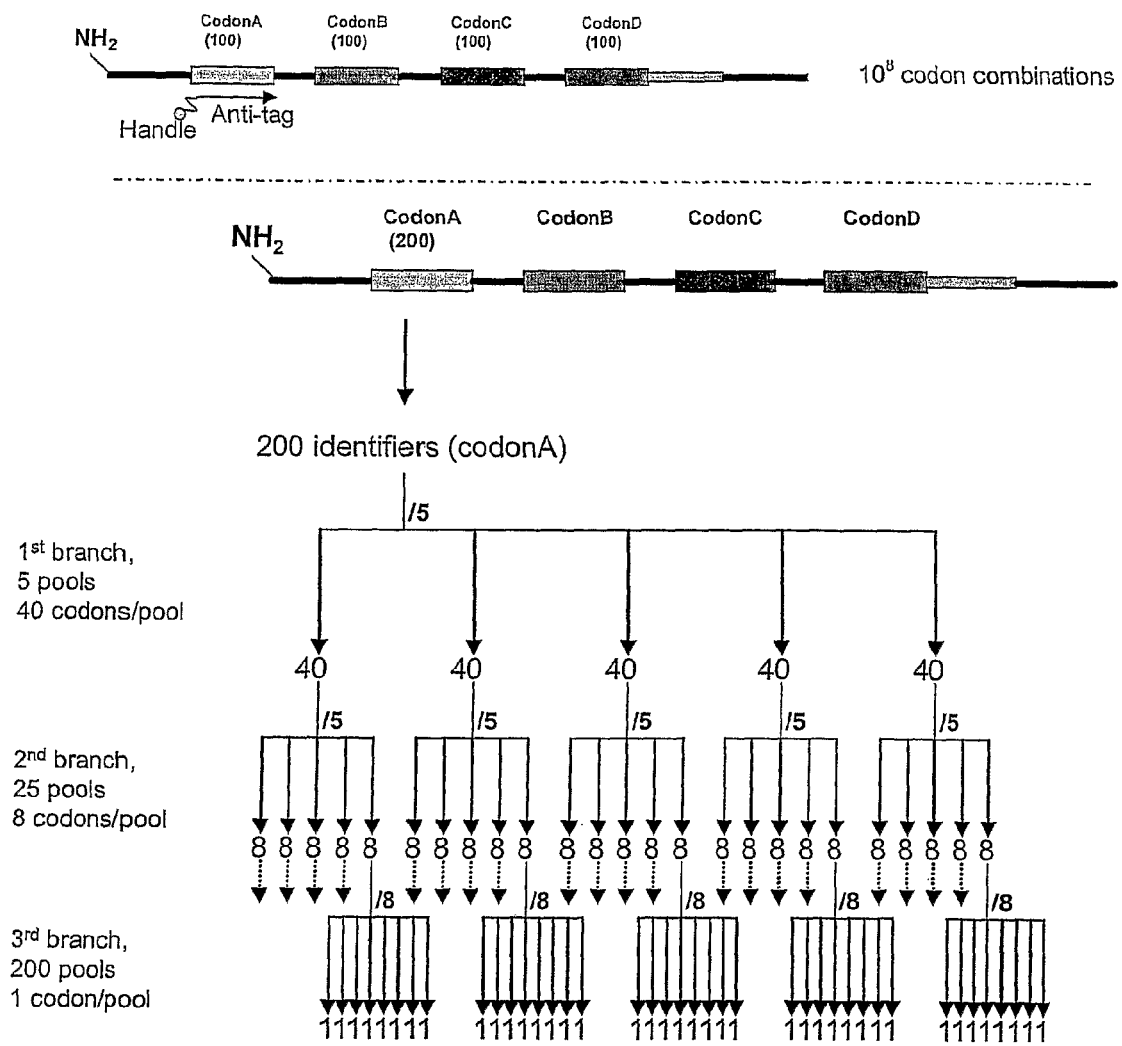

FIG. 52. Panel A illustrates a single stranded identifier oligonucleotide linked to a reactive entity (chemical reaction site). Panel B illustrates iterative steps of subtraction of specifically formed duplexes between the anti-tags supplied and the corresponding identifier codon sequences.

Figure 53:
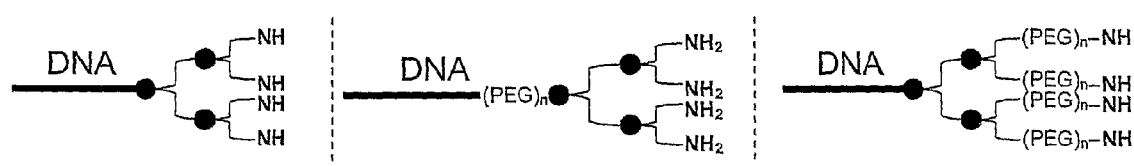

FIG. 53. Illustration of a simple quadruple amino-DNA tag enabling synthesis and display of the same encoded molecule attached to a single encoding tag. It may be desirable to include spacing groups such as polyethylene glycol (PEG) units at any point in the synthesis process (chosen by the experimenter) for improved synthesis and display of the synthetic molecule.

Figure 54:
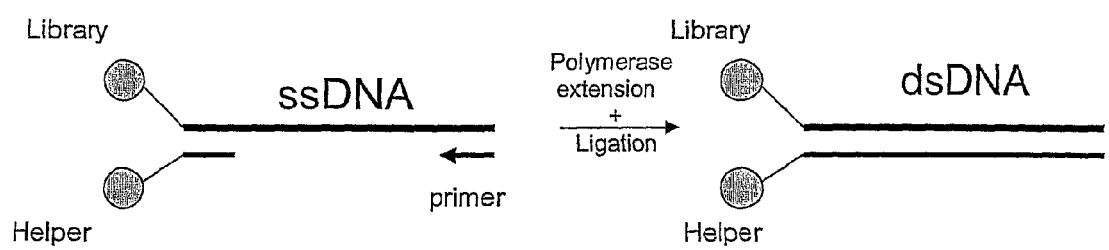

FIG. 54. The figure depicts a scheme for the addition, by hybridization, of a helper molecule covalently linked to a DNA sequence complementary to the region of DNA of the bifunctional library molecule that is proximal to the displayed molecule. Hybridization of a second primer followed by polymerase extension and ligation will produce dsDNA displaying both the encoded library molecule and the helper molecule FIG. 55. In a split and mix library generation procedure n chemical reactions are conducted producing n chemical fragments linked to N different tags producing intermediates with a common structure.

Figure 56:
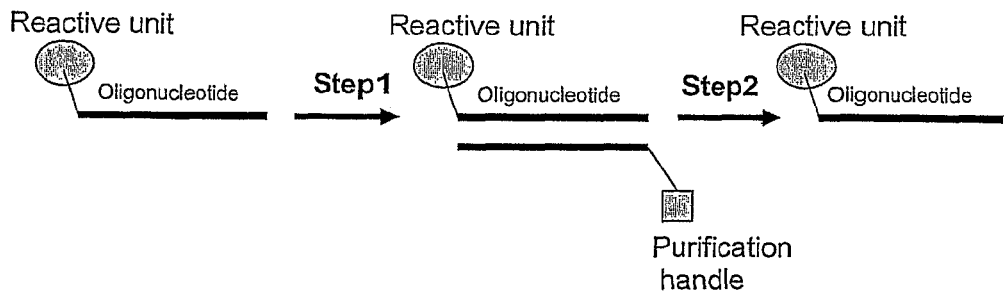

FIG. 56. The figure illustrates an alternative method for the purification of the control mimics in the library is to include a selective cleavable linker connecting a handle for purification and the reactive chemical unit.

Figure 57:

FIG. 57. The figure illustrates an alternative method for the purification of the control mimics in a library. A selectively cleavable linker connecting a handle for purification and the reactive chemical unit is included. The reactive unit (site) is any suitable reactive groups, for example, but not limited to, an amino, thiol, carboxylic-acid or aldehyde-group. The oligonucleotide moiety is optional but provides an excellent handle for molecular weight analysis using MS. The cleavable linker (optionally) is selectively cleavable by any means such as e.g. by enzymatic, chemical or photo-cleavable methods. The purification (optional) may be any unit capable of being selectively recovered.

Figure 58:
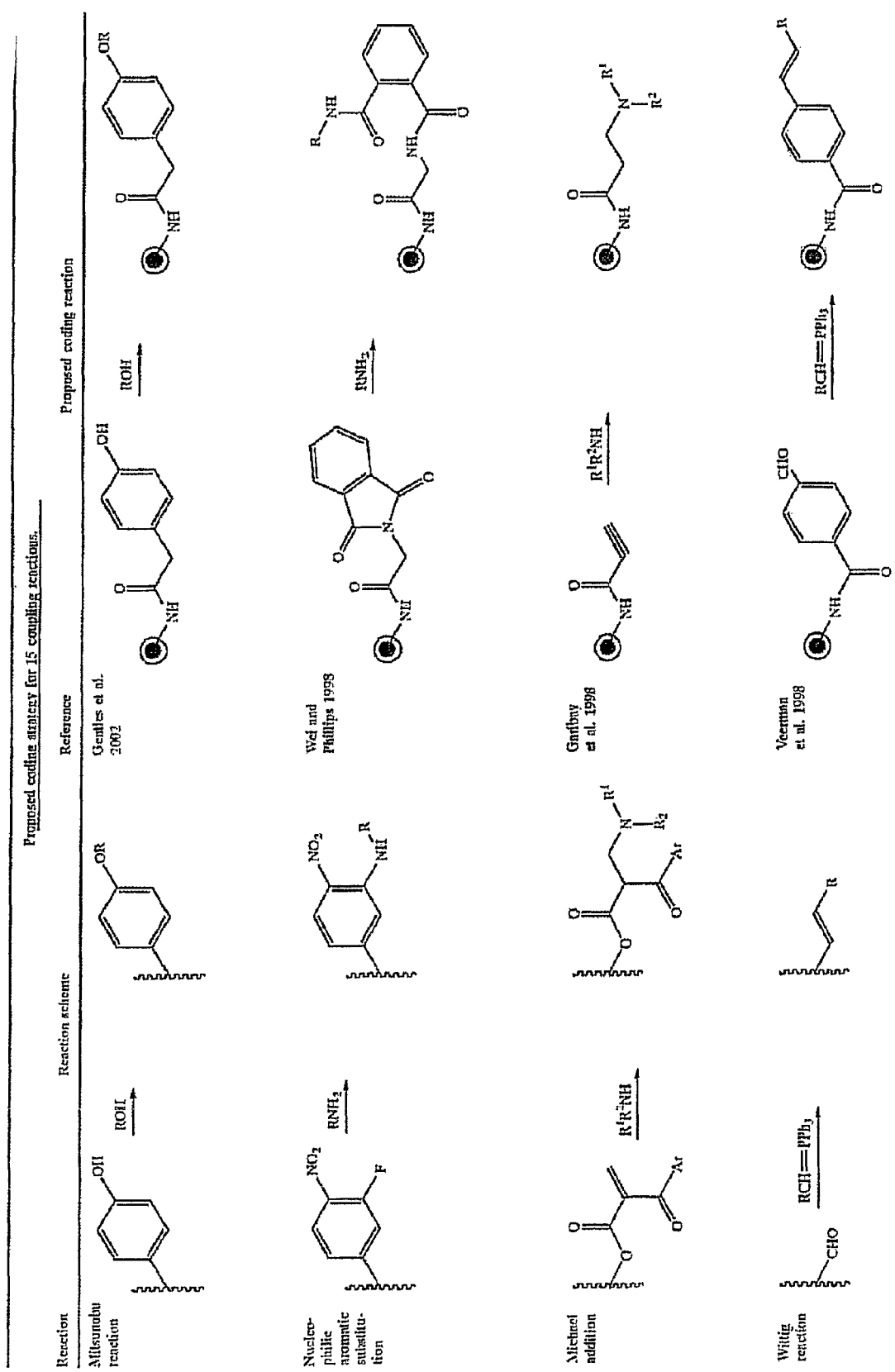
Figure 58:
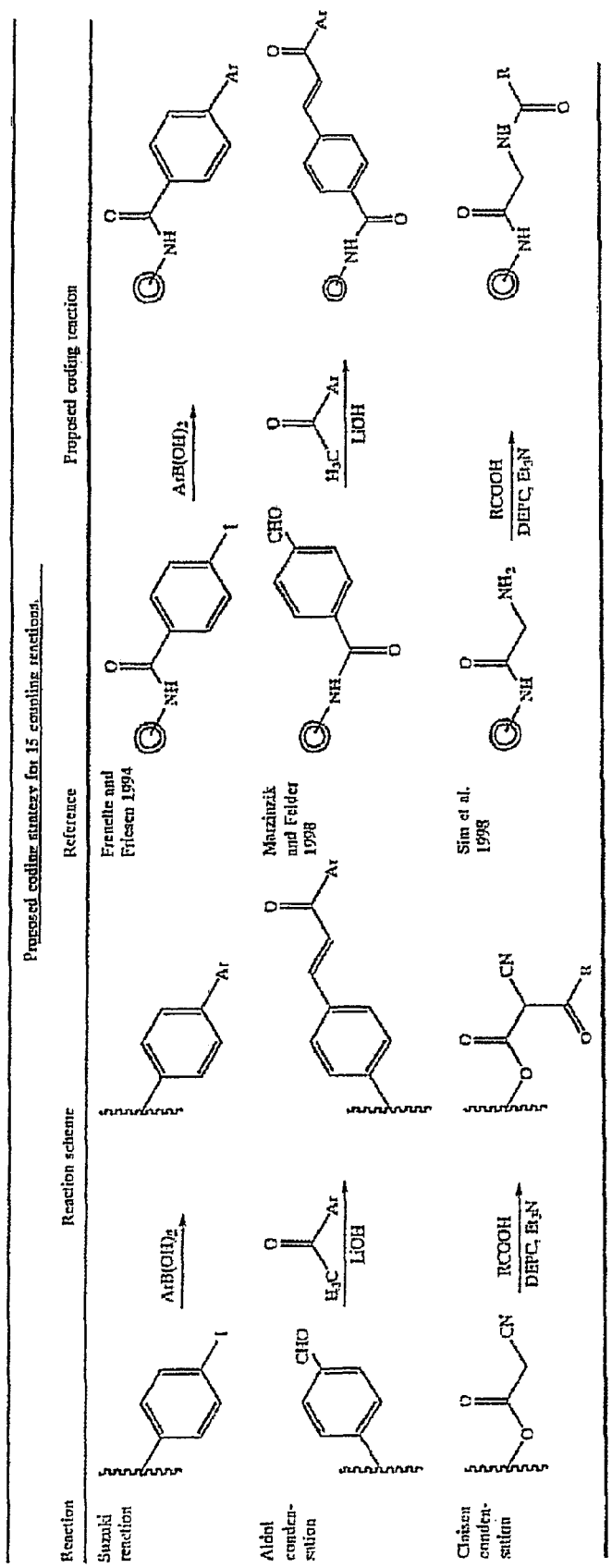

FIG. 58. The figure illustrates exemplary reaction chemistries applicable to the present invention.

DISCLOSURE OF THE INVENTION

The methods and products pertaining to the present invention are further disclosed in more detail herein below. The examples demonstrating the utility of the present invention should not be construed as a limitation of the scope of protection conferred by the patent claims.

Nucleotides

A tag comprises recognition units, i.e. units which can be recognized by recognition groups. The recognition units making up a tag possesses information so as to identify a reactant having participated in the synthesis of the molecule. Generally, it is preferred that the tag comprises or consists of a sequence of nucleotides.

Individual tags can be distinguished from each other e.g. by a difference in only a single nucleotide position, such as a deletion, an insertion or a mutation. However, to facilitate a subsequent decoding process it is in general desirable to have two or more differences in the nucleotide sequence of any two tags.

In the event two or more reactants are reacted with the chemical reactive site, the tags of the identifier oligonucleotide can be separated by a constant region or a binding region. One function of the binding region can be to establish a platform at which an enzyme, such as polymerase or ligase can recognise as a substrate. Depending on the molecule formed, the identifier oligonucleotide can comprise further tags, such as 2, 3, 4, 5, or more tags. Each of the further tags can be separated by a suitable binding region.

All or at least a majority of the tags of the identifier oligonucleotide can be separated from a neighbouring tag by a binding sequence. The binding region may have any suitable number of nucleotides, e.g. 1 to 20. The binding region, if present, may serve various purposes besides serving as a substrate for an enzyme. In one setup of the invention, the binding region identifies the position of the tag. Usually, the binding region either upstream or downstream of a tag comprises information which allows determination of the position of the tag. In another setup, the binding regions have alternating sequences, allowing for addition of reactants from two pools in the formation of the library. Moreover, the binding region may adjust the annealing temperature to a desired level.

A binding region with high affinity can be provided by one or more nucleobases forming three hydrogen bonds to a cognate nucleobase. Examples of nucleobases having this property are guanine and cytosine. Alternatively, or in addition, the binding region can be subjected to backbone modification. Several backbone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The identifier oligonucleotide can optionally further comprise flanking regions around the tag. The flanking region can encompass a signal group, such as a fluorophor or a radio active group to allow for detection of the presence or absence of a complex or the flanking region may comprise a label that can be detected, such as biotin. When the identifier comprises a biotin moiety, the identifier may easily be recovered.

The flanking regions can also serve as priming sites for amplification reactions, such as PCR. Usually, the last cycle in the formation of the bifunctional complex includes the incorporation of a priming site. A region of the bifunctional complex close to the molecule, such as a nucleic acid sequence between the molecule and the tag coding for the scaffold molecule, is usually used for another priming site, thereby allowing for PCR amplification of the coding region of the bifunctional complex.

Apart from a combination of the nucleotides coding for the identity of the reactant, a tag may comprise further nucleotides, such as a framing sequence. The framing sequence can serve various purposes, such as acting as a further annealing region for anti-tags and/or as a sequence informative of the point in time of the synthesis history of the molecule being synthesised.

In certain embodiments, a tag codes for several different reactants. In a subsequent identification step, the structure of the molecule can never-the-less be deduced by taking advantage of the knowledge of the different attachment chemistries, steric hindrance, deprotection of orthogonal protection groups, etc. In another embodiment, the same tag is used for a group of reactants having a common property, such as a lipophilic nature, molecular weight, or a certain attachment chemistry, etc. In a still further embodiment, each tag is unique, i.e. a similar combination of nucleotides does not identify another reactant. The same of different synthesis methods can employ the same or different type of tags as disclosed herein above.

In some embodiments it can be advantageous to use several different tags for the same reactant. Accordingly, two or more tags identifying the same reactant can optionally carry further information relating to e.g. different reaction conditions.

The identifier oligonucleotide of the final bifunctional complex comprises all the tags necessary for identifying the corresponding molecule. All or part of the sequence of each tag is used to decipher the structure of the reactants that have participated in the formation of the molecule, i.e. the reaction product.

The order of the tags can also be used to determine the order of incorporation of the reactants. This can be of particular interest e.g. when a linear polymer is formed, because the exact sequence of the polymer can be determined by decoding the encoding sequence. Usually, to facilitate the decoding step, tags will further comprise a constant region or a binding region together with the tag sequence identifying a given reactant. The constant region may contain information about the position of the reactant in a synthesis pathway resulting in the synthesis of the molecule.

The identifier oligonucleotide of the bifunctional complex is in a preferred aspect of the invention amplifiable. The capability of being amplified allows for the use of a low amount of bifunctional complex during a selection process. In one embodiment the tag is a sequence of nucleotides which can be amplified using standard techniques like PCR. When two or more tags are present in a linear identifying oligonucleotide, said oligonucleotide generally comprises a certain backbone structure, so as to allow an enzyme to recognise the oligonucleotide as substrate. As an example the back bone structure can be DNA or RNA.

The priming site of a nascent bifunctional complex is capable of receiving a tag. When the tag comprises a polynucleotide sequence, the priming site generally comprises a 3'-OH or 5'-phosphate group, or functional derivatives of such groups. Enzymes which can be used for enzymatic addition of a tag to the priming site include an enzyme selected from polymerase, ligase, and recombinase, and a combination of these enzymes. In some embodiments, an enzyme comprising ligase activity is preferred.

The display oligonucleotide provided in step i) of the above-cited method should be long enough to allow for hybridisation of an anti-tag thereto, c.f. step iv). A desirable length of the display oligonucleotide is from about 3 consecutive nucleotides to about 25 consecutive nucleotides, although longer display oligonucleotides can also be provided. Accordingly, the display oligonucleotide preferably has from 5 to about 20 consecutive nucleotides, for example from 10 to 20 consecutive nucleotides, such as 6 nucleotides, for example 7 nucleotides, such as 8 nucleotides, for example 9 nucleotides, such as 10 nucleotides, for example 11 nucleotides, such as 12 nucleotides, for example 13 nucleotides, such as 14 nucleotides, for example 15 nucleotides, such as 16 nucleotides, for example 17 nucleotides, such as 18 nucleotides, for example 19 nucleotides.

Likewise, the each tag should be long enough to allow for hybridisation of one or two anti-tag(s) thereto, c.f. step iii). A desirable length of a tag is from about 3 consecutive nucleotides to about 25 consecutive nucleotides, although longer tags can also be provided. Accordingly, the tags preferably have from 5 to about 20 consecutive nucleotides, such as 6 nucleotides, for example 7 nucleotides, such as 8 nucleotides, for example 9 nucleotides, such as 10 nucleotides, for example 11 nucleotides, such as 12 nucleotides, for example 13 nucleotides, such as 14 nucleotides, for example 15 nucleotides, such as 16 nucleotides, for example 17 nucleotides, such as 18 nucleotides, for example 19 nucleotides.

Likewise, the each anti-tag should be long enough to allow for hybridisation of one or two tag(s) thereto, c.f. step iv). A desirable length of an anti-tag is from about 3 consecutive nucleotides to about 25 consecutive nucleotides, although longer anti-tags can also be provided. Accordingly, the anti-tags preferably have from 5 to about 20 consecutive nucleotides, such as 6 nucleotides, for example 7 nucleotides, such as 8 nucleotides, for example 9 nucleotides, such as 10 nucleotides, for example 11 nucleotides, such as 12 nucleotides, for example 13 nucleotides, such as 14 nucleotides, for example 15 nucleotides, such as 16 nucleotides, for example 17 nucleotides, such as 18 nucleotides, for example 19 nucleotides.

All or some of the nucleotides of a tag, or an anti-tag, can be involved in the identification of a corresponding reactant. In other words, decoding of an identifier oligonucleotide can be performed by determining the sequence of all or only a part of the identifier oligonucleotide.

In some embodiments of the invention, each tag and each anti-tag constitutes what is often referred to as a "codon" and an "anti-codon", respectively. These terms are often used in the prior art even though the methods employ split-n-mix technology and not templated reactions. In some embodiments, each tag and each anti-tag comprises one or more "codon(s)" or "anti-codon(s)", respectively, which identifies the corresponding reactant involved in the synthesis of a molecule.

The single-stranded over-hangs resulting from hybridisation of tags and anti-tags can be of any suitable length as long as the over-hang allows for hybridisation of a tag or an anti-tag to the over-hang, c.f. steps vi) and xii). A desirable length for an overhang is from about 3 consecutive nucleotides to about 25 consecutive nucleotides, although longer over-hangs can also be provided for. Accordingly, the over-hangs preferably have from 5 to about 20 consecutive nucleotides, such as 6 nucleotides, for example 7 nucleotides, such as 8 nucleotides, for example 9 nucleotides, such as 10 nucleotides, for example 11 nucleotides, such as 12 nucleotides, for example 13 nucleotides, such as 14 nucleotides, for example 15 nucleotides, such as 16 nucleotides, for example 17 nucleotides, such as 18 nucleotides, for example 19 nucleotides.

The identifier oligonucleotide resulting from tag ligation can include or exclude the display oligonucleotide and preferably has a length of from 6 to about 300 consecutive nucleotides, for example from 6 to about 250 consecutive nucleotides, such as from 6 to about 200 consecutive nucleotides, for example from 6 to about 150 consecutive nucleotides, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100 consecutive nucleotides.

The length of the identifier oligonucleotide will depend of the length of the individual tags as well as on the number of tags ligated. In some embodiments of the invention it is preferred that the identifier oligonucleotide is attached to a solid or semi-solid support.

The identifier oligonucleotide preferably comprises a string of consecutive nucleotides comprising from 2 to 10 tags, for example from 3 to 10 tags, such as from 4 to 10 tags, for example from 5 to 10 tags, such as from 6 to 10 tags, for example from 7 to 10 tags, such as from 8 to 10 tags, for example from 2 to 9 tags, such as from 2 to 8 tags, for example from 2 to 7 tags, such as from 2 to 6 tags, for example from 2 to 5 tags, such as from 2 to 4 tags, for example 2 or 3 tags, such as from 3 to 9 tags, such as from 3 to 8 tags, for example from 3 to 7 tags, such as from 3 to 6 tags, for example from 3 to 5 tags, such as from 3 to 4 tags, for example from 4 to 9 tags, such as from 4 to 8 tags, for example from 4 to 7 tags, such as from 4 to 6 tags, for example from 4 to 5 tags, such as from 5 to 9 tags, such as from 5 to 8 tags, for example from 5 to 7 tags, such as 5 or 6 tags, for example 2, 3, 4 or 5 tags, such as 6, 7 or 8 tags, for example 9 or 10 tags.

The display oligonucleotide and/or the tags employed in the methods of the present invention in one embodiment preferably comprise or essentially consist of nucleotides selected from the group consisting of deoxyribonucleic acids (DNA), ribonucleic acids (RNA), peptide nucleic acids (PNA), locked nucleic acids (LNA), and morpholinos sequences, including any analog or derivative thereof.

In another embodiment, the display oligonucleotide and/or the tags employed in the methods of the present invention preferably comprise or essentially consist of nucleotides selected from the group consisting of DNA, RNA, PNA, LNA and morpholinos sequence, including any analog or derivative thereof, and the anti-tags preferably comprise or essentially consist of nucleotides selected from the group consisting of DNA, RNA, PNA, LNA and morpholinos sequences, including any analog or derivative thereof.

The nucleic acids useful in connection with the present invention include, but is not limited to, nucleic acids which can be linked together in a sequence of nucleotides, i.e. an oligonucleotide. However, in one embodiment and in order to prevent ligation of anti-tags, c.f. step xiv) and xv), end-positioned nucleic acids of anti-tags do not contain a reactive group, such as a 5'-P or a 3'-OH reactive group, capable of being linked by e.g. an enzyme comprising ligase activity. The priming site of the display oligonucleotide preferably comprises a 3'-OH or 5'-phosphate group, or functional derivatives of such groups, capable of being linked by an enzyme comprising ligase activity.

Each nucleotide monomer is normally composed of two parts, namely a nucleobase moiety, and a backbone. The back bone may in some cases be subdivided into a sugar moiety and an internucleoside linker. The nucleobase moiety can be selected among naturally occurring nucleobases as well as non-naturally occurring nucleobases. Thus, "nucleobase" includes not only known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-natural" nucleobases described in U.S. Pat. No. 5,432,272.

The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases. Examples of suitable specific pairs of nucleobases are shown below:

Natural Base Pairs

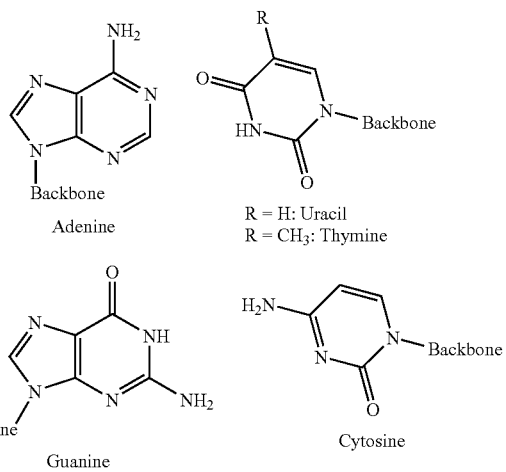

Synthetic Base Pairs

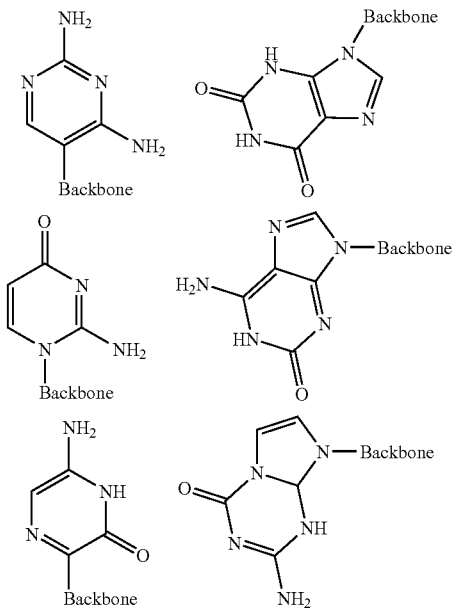

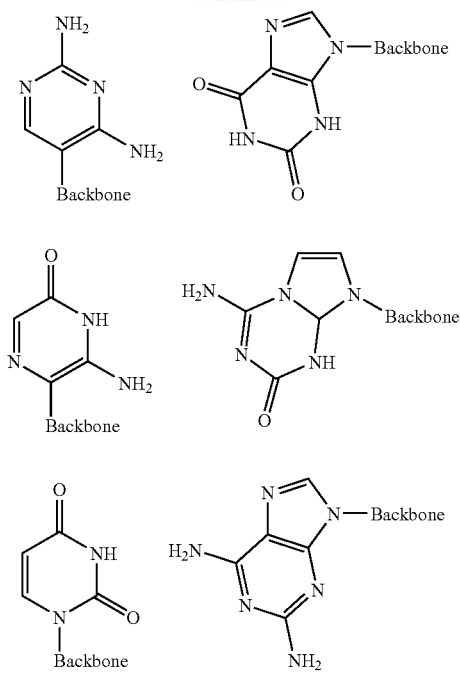
Synthetic purine bases pairring with natural pyrimidines
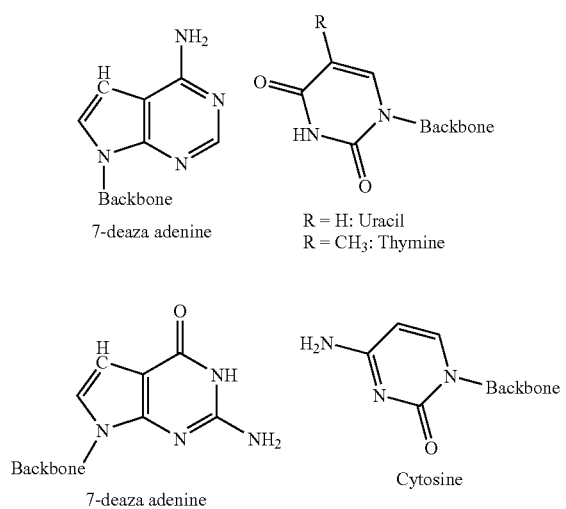
Suitable examples of backbone units are shown below (B denotes a nucleobase):
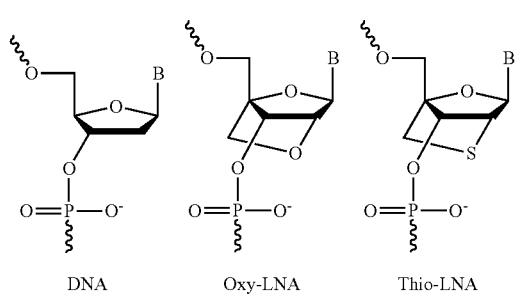
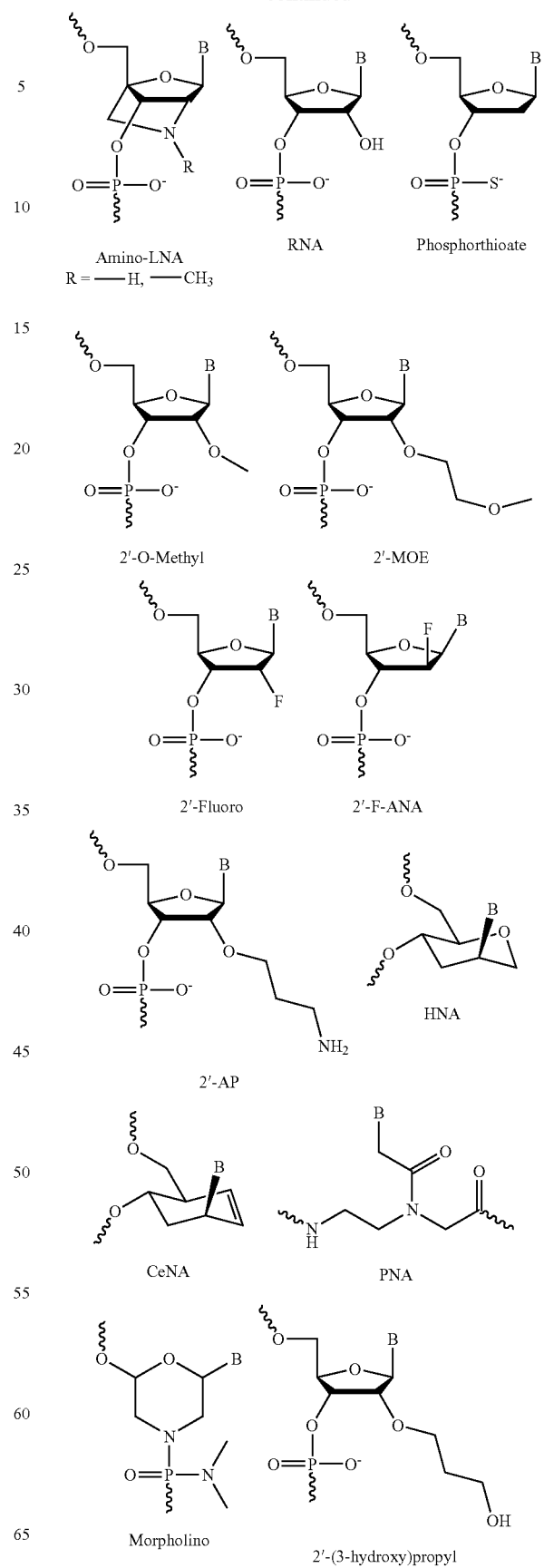

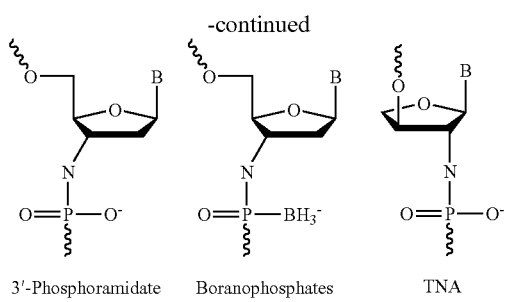

3'-Phosphoramidate   Boranophosphates   TNA

The sugar moiety of the backbone is suitably a pentose, but can be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage can be the natural occurring phosphodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine.

It is within the capability of the skilled person in the art to construct the desired design of an oligonucleotide. When a specific annealing temperature is desired it is a standard procedure to suggest appropriate compositions of nucleic acid monomers and the length thereof. The construction of an appropriate design can be assisted by software, such as Vector NTI Suite or the public database at the internet address http://www.nwfsc.noaa.gov/protocols/oligoTMcalc.html. The conditions which allow hybridisation of two oligonucleotides are influenced by a number of factors including temperature, salt concentration, type of buffer, and acidity. It is within the capabilities of the person skilled in the art to select appropriate conditions to ensure that the contacting between two oligonucleotides is performed at hybridisation conditions. The temperature at which two single stranded oligonucleotides forms a duplex is referred to as the annealing temperature or the melting temperature. The melting curve is usually not sharp indicating that the annealing occurs over a temperature range.

Oligonucleotides in the form of tags, anti-tags and display oligonucleotides can be synthesized by a variety of chemistries as is well known. For synthesis of an oligonucleotide on a substrate in the direction of 3' to 5', a free hydroxy terminus is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether. The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide in the direction of 5' to 3', a free hydroxy terminus on the linker is required as before. However, the blocked nucleotide to be added has the blocking chemistries reversed on its 5' and 3' termini to facilitate addition in the opposite orientation. A nucleotide with a free 3' hydroxyl and 5' DMT ether is first blocked at the 3' hydroxy terminus by reaction with TBS-Cl in imidazole to form a TBS ester at the 3' terminus. Then the DMT-blocked 5' terminus is deblocked with DCA in DCM as before to form a free 5' hydroxy terminus. The reagent (N,N-diisopropylamino) (cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-Cl adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

The identifier oligonucleotide part of a bifunctional complex is formed by addition of a tag or more than one tag to a priming site and/or to a previously added tag using one or more enzymes such as enzymes possessing ligase activity. When one or more further tag(s) are attached to a tag which was added to a nascent bifunctional complex in a previous synthesis round, the addition can produce a linear or a branched identifier oligonucleotide. Preferably, at least one tag of the identifier is attached to the priming site and/or to another tag by an enzymatically catalysed reaction, such as a ligation. Further tag(s) can in principle be attached using chemical means or enzymatic means. In one embodiment, all tags are attached using an enzymatically catalysed reaction.

The identifier oligonucleotide part of the bifunctional complex is preferably amplifiable. This means that the tags form a sequence of nucleotides capable of being amplified e.g. using a polymerase chain reaction (PCR) techniques.

The tags can be "unique" for a single predetermined reactant, or a given tag can in principle code for several different reactants, in which case the structure of the synthesised molecule can optionally be deduced by taking into account factors such as different attachment chemistries, steric hindrance and deprotection of orthogonal protection groups. It is also possible to use the same or similar tags for a group of reactants having at least one common property in common, such as e.g. lipophilic nature, molecular weight and attachment chemistry.

In one embodiment, two or more tags identifying the same reactant comprise further information related to different reaction conditions used for reacting said reactant. Individual tags can be distinguished from each other by only a single nucleotide, or by two or more nucleotides. For example, when the tag or anti-tag length is 5 nucleotides, more than 100 nucleotide combinations exist in which two or more differences appear between any two tags.

Multiple Encoding

In one embodiment, multiple encoding implies that two or more tags are provided in the identifier prior to or subsequent to a reaction between the chemical reactive site and two or more reactants. Multiple encoding has various advantages, such as allowing a broader range of reactions possible, as many compounds can only be synthesis by a three (or more) component reaction because an intermediate between the first reactant and the chemical reactive site is not stable. Other advantages relates to the use of organic solvents and the availability of two or more reactants in certain embodiments.

Thus in a certain aspect of the invention, it relates to a method for obtaining a bifunctional complex comprising a molecule part and a identifier oligonucleotide, wherein the molecule is obtained by reaction of a chemical reactive site with two or more reactants and the identifier oligonucleotide comprises tag(s) identifying the reactants.

In a certain aspect of the invention, a first reactant forms an intermediate product upon reaction with the chemical reactive site and a second reactant reacts with the intermediate product to obtain the molecule or a precursor thereof. In another aspect of the invention, two or more reactants react with each other to form an intermediate product and the chemical reactive site reacts with this intermediate product to obtain the molecule or a precursor thereof. The intermediate product can be obtained by reacting the two or more reactants separately and then in a subsequent step reacting the intermediate product with the chemical reactive site. Reacting the reactants in a separate step provide for the possibility of using conditions the tags would not withstand. Thus, in case the identifier oligonucleotide comprises nucleic acids, the reaction between the reactant can be conducted at conditions that otherwise would degrade the nucleic acid.

The reactions can be carried out in accordance with the scheme shown below. The scheme shows an example in which the identifying tags for two reactants and the chemical reactive site (scaffold) attached to the chemical reaction site are provided in separate compartments. The compartments are arranged in an array, such as a microtiter plate, allowing for any combination of the different acylating agents and the different alkylating agents.

Starting Situation:

|  | Alkylating agents | | | |
| --- | --- | --- | --- | --- |
| Acylating agents | A | B | C | ... |
| 1 | Tagx11-X | Tagx12-X | Tagx13-X | ... |
| 2 | Tagx21-X | Tagx22-X | Tagx23-X | ... |
| 3 | Tagx31-X | Tagx32-X | Tagx33-X | ... |
| ... | ... | ... | ... | ... |

X denotes a chemical reaction site such as a scaffold.

The two reactants are either separately reacted with each other in any combination or subsequently added to each compartment in accordance with the tags of the identifier oligonucleotide or the reactants can be added in any order to each compartment to allow for a direct reaction. The scheme below shows the result of the reaction.

Plate of Products

|  | Alkylating agents | | | |
| --- | --- | --- | --- | --- |
| Acylating agents | A | B | C | ... |
| 1 | Tagx11-XA1 | Tagx12-XB1 | Tagx13-XC1 | ... |
| 2 | Tagx21-XA2 | Tagx22-XB2 | Tagx23-XC2 | ... |
| 3 | Tagx31-XA3 | Tagx32-XB3 | Tagx33-XC3 | ... |
| ... | ... | ... | ... | ... |

As an example XA2 denotes molecule XA2 in its final state, i.e. fully assembled from fragments X, A and 2.

The identifier oligonucleotide comprising the two or more tags identifying the reactants, can in principle be prepared in any suitable way either before or after the reaction. In one embodiment of the invention, each of the identifier oligonucleotides are synthesised by standard phosphoramidite chemistry. In another aspect the tags are pre-prepared and assembled into the final identifier oligonucleotide by chemical or enzymatic ligation.

Various possibilities for chemical ligation exist. Suitable examples include that
a) a first oligonucleotide end comprises a 3'-OH group and the second oligonucleotide end comprises a 5'-phosphor-2-imidazole group. When reacted a phosphodiester internucleoside linkage is formed,
b) a first oligonucleotide end comprising a phosphoimidazolide group and the 3'-end and a phosphoimidazolide group at the 5'- and. When reacted together a phosphodiester internucleoside linkage is formed,
c) a first oligonucleotide end comprising a 3'-phosphorothioate group and a second oligonucleotide comprising a 5'-iodine. When the two groups are reacted a 3'-O—P(=O)(OH)—S-5' internucleoside linkage is formed, and
d) a first oligonucleotide end comprising a 3'-phosphorothioate group and a second oligonucleotide comprising a 5'-tosylate. When reacted a 3'-O—P(=O) (OH)—S-5' internucleoside linkage is formed.

Enzymes

The identifier oligonucleotide of a nascent bifunctional complex involves the addition of at least one tag to a priming site using one or more enzymes. Further tags can be attached to a previous tag so as to produce a linear or branched identifier oligonucleotide. One or more enzymes are used for at least one reaction involving one or more identifier oligonucleotide tags. Enzymes are in general substrate specific, entailing that the enzymatic addition of a tag to a priming site, or to another tag, is not likely to interfere with the synthesis of a molecule. Enzymes can be active in both aqueous and organic solvents.

As long as at least one tag of the identifier is attached to the priming site or to another tag by an enzymatic reaction, further tags can be added using either chemical means or the same or different enzymatic means. In one embodiment, all of the tags are added to the priming site and/or to each other using the same or different enzymatically catalysed reaction(s).

In one embodiment, addition of a tag to the priming site, or to a tag having reacted with the priming site or another tag in a previous synthesis round, can involve an enzymatic extension reaction. The extension reaction can be performed by a polymerase or a ligase, or a combination thereof. The extension using a polymerase is suitably conducted using a tag hybridised to an anti-tag oligonucleotide as template. The substrate is usually a blend of triphosphate nucleotides selected from the group comprising dATP, dGTP, dTTP, dCTP, rATP, rGTP, rTTP, rCTP, rUTP.

In a different embodiment, a ligase is used for the addition of a tag using one or more oligonucleotides as substrates. The ligation can be performed in a single stranded or a double stranded state depending on the enzyme used. In general it is preferred to ligate tags in a double stranded state, i.e. tag oligonucleotides to be ligated together are kept together by a complementing oligonucleotide (anti-tag), which complements the ends of the two tag oligonucleotides to be ligated.

Substrates for ligases are oligo- and polynucleotides, i.e. nucleic acids comprising two or more nucleotides. An enzymatic ligation can be performed in a single or double stranded fashion. When a single stranded ligation is performed, a 3' OH group of a first nucleic acid is ligated to a 5' phosphate group of a second nucleic acid. A double stranded ligation uses a third oligonucleotide complementing a part of the 3' end and 5' end of the first and second nucleic acid to assist in the ligation. Generally, it is preferred to perform a double stranded ligation. Only tags are ligated. Anti-tags are not ligated as they do not, in one embodiment, comprise a reactive group, such as a 5'-P or a 3'-OH, or variants or derivatives thereof, enabling enzymatic ligation. In another embodiment, anti-tags do not abut to each other but are physically separated by hybridisation to parts of tag oligonucleotides which are separated from each other. This is illustrated in FIG. 3.

In some embodiments of the invention, a combination of polymerase transcription and ligational coupling is used. As an example, a gap in an otherwise double stranded nucleic acid can be filled-in by a polymerase and a ligase can ligate the tag portion of the extension product.

Examples of suitable polymerases include DNA polymerase, RNA polymerase, Reverse Transcriptase, DNA ligase, RNA ligase, Taq DNA polymerase, Pfu polymerase, Vent polymerase, HIV-1 Reverse Transcriptase, Klenow fragment, or any other enzyme that will catalyze the incorporation of complementing elements such as mono-, di- or polynucleotides. Other types of polymerases that allow mismatch extension could also be used, such for example DNA polymerase η (Washington et al., (2001) JBC 276: 2263-2266), DNA polymerase τ (Vaisman et al., (2001) JBC 276: 30615-30622), or any other enzyme that allow extension of mismatched annealed base pairs.

Suitable examples of ligases include Taq DNA ligase, T4 DNA ligase, T4 RNA ligase, T7 DNA ligase, and *E. coli* DNA ligase. The choice of the ligase depends, among other things, on the design of the ends to be joined together. Thus, if the ends are blunt, T4 RNA ligase can be preferred, while a Taq DNA ligase can be preferred for a sticky end ligation, i.e. a ligation in which an overhang on each end is a complement to each other.

Chemical Reaction Site, Reactants and Reactive Groups

The chemical reaction site can comprise a single reactive group or two or more reactive groups. In preferred embodiments, the chemical reaction site comprises 3 or more reactive groups. The plurality of reactive groups of a chemical reaction site can each react with one or more reactants each comprising one or more reactive groups linked to one or more chemical entities.

Reactive groups of the chemical reaction site are in principle no different from reactive groups of complementary reactants capable of reacting with each other under conditions allowing such a reaction to occur. Examples of reactive groups of chemical reaction sites and complementary reactants are listed e.g. in FIG. 58 and in the detailed disclosure of the invention herein below.

Chemical reaction site reactive groups can be selected a variety of from well known reactive groups, such as e.g. hydroxyl groups, thiols, optionally substituted or activated carboxylic acids, isocyanates, amines, esters, thioesters, and the like. Further non-limiting examples of reactive group reactions are e.g. Suzuki coupling, Heck coupling, Sonogashira coupling, Wittig reaction, alkyl lithium-mediated condensations, halogenation, SN2 displacements (for example, N, O, S), ester formation, and amide formation, as well as other reactions and reactive groups that can be used to generate chemical entities, such as those presented herein.

In general, the chemical reaction site and reactants capable of reacting with the chemical reaction site, i.e. complementary reactants, can in principle be any chemical compounds which are complementary, that is the reactive groups of the entities in question must be able to react. Typically, a reactant can have a single reactive group or more than one reactive group, such as at least two reactive groups, although it is possible that some of the reactants used will have more than two reactive groups each. This will be the case when branched molecules are synthesised.

The number of reactive groups on present on a reactant and/or a chemical reaction site is suitably from 1 to 10, for example 1, such as 2, for example 3, such as 4, for example 5, such as 6, for example 7, such as 8, for example 9, such as from 2 to 4, for example from 4 to 6, such as from 6 to 8, for example from 8 to 10, such as from 2 to 6, for example from 6 to 10, such as from 3 to 6, for example from 6 to 9, such as from 4 to 6, for example from 6 to 10 reactive groups present on the chemical reaction site and/or a reactant capable of reacting with the chemical reaction site and/or with another reactant.

Reactive groups on two different reactants should be complementary, i.e., capable of reacting to form a covalent bond, optionally with the concomitant loss of a small molecular entity, such as water, HCl, HF, and so forth.

Two reactive groups are complementary if they are capable of reacting together to form a covalent bond. Complementary reactive groups of two reactants can react, for example, via nucleophilic substitution, to form a covalent bond. In one embodiment, one member of a pair of complementary reactive groups is an electrophilic group and the other member of the pair is a nucleophilic group. Examples of suitable electrophilic reactive groups include reactive carbonyl groups, such as acyl chloride groups, ester groups, including carbonylpentafluorophenyl esters and succinimide esters, ketone groups and aldehyde groups; reactive sulfonyl groups, such as sulfonyl chloride groups, and reactive phosphonyl groups. Other electrophilic reactive groups include terminal epoxide groups, isocyanate groups and alkyl halide groups. Suitable nucleophilic reactive groups include, but is not limited to, primary and secondary amino groups and hydroxyl groups and carboxyl groups.

Accordingly, complementary electrophilic and nucleophilic reactive groups include any two groups which react via nucleophilic substitution under suitable conditions to form a covalent bond. A variety of suitable bond-forming reactions are known in the art. See, for example, March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Collman et al., Principles and Applications of Organotransition Metal Chemistry, University Science Books, Mill Valley, Calif. (1987), Chapters 13 to 20; each of which is incorporated herein by reference in its entirety.

Further suitable complementary reactive groups are set forth herein below. One of skill in the art can readily determine other reactive group pairs that can be used in the present method, such as, but not limited to, reactive groups capable of facilitating the reactions illustrated in Table 1.

In some embodiments, the reactive groups of the chemical reaction site and/or the reactive group(s) of one or more reactants reacting with each other and/or with the chemical reaction site are preferably selected from the group consisting of:

a) activated carboxyl groups, reactive sulfonyl groups and reactive phosphonyl groups, or a combination thereof, and complementary primary or secondary amino groups; the complementary reactive groups react under suitable conditions to form amide, sulfonamide and/or phosphonamidate bonds;

b) epoxide groups and complementary primary and/or secondary amino groups; a reactant comprising one or more epoxide reactive group(s) can react with one or more amine-group(s) of a complementary reactant under suitable conditions to form one or more carbon-nitrogen bond(s), resulting e.g. in a beta-amino alcohol;

c) aziridine groups and complementary primary or secondary amino groups; under suitable conditions, a reactant comprising one or more aziridine-group(s) can react with one or more amine-group(s) of a complementary reactant to form one or more carbon-nitrogen bond(s), resulting e.g. in a 1,2-diamine;

d) isocyanate groups and complementary primary or secondary amino groups, a reactant comprising one or more isocyanate-group(s) can react with one or more amino-group(s) of a complementary reactant under suitable conditions to form one or more carbon-nitrogen bond(s), resulting e.g. in a urea group;

e) isocyanate groups and complementary hydroxyl groups; a reactant comprising one or more isocyanate-group(s) can react with a complementary reactant comprising one or more hydroxyl-groups under suitable conditions to form one or more carbon-oxygen bond(s), resulting e.g. in a carbamate group.

f) amino groups and complementary carbonyl groups; a reactant comprising one or more amino groups can react with a complementary reactant comprising one or more carbonyl-group(s), such as aldehyde and/or a ketone group(s); the amines can react with such groups via reductive amination to form e.g. a carbon-nitrogen bond;

g) phosphorous ylide groups and complementary aldehyde and/or ketone groups; A reactant comprising a phosphorus-ylide-group can react with an aldehyde and/or a ketone-group of a complementary reactant under suitable conditions to form e.g. a carbon-carbon double bond, resulting e.g. in an alkene;

h) complementary reactive groups can react via cycloaddition to form a cyclic structure; an example of such complementary reactive groups are alkynes and organic azides, which can react under suitable conditions to form a triazole ring structure—suitable conditions for such reactions are known in the art and include those disclosed in WO 03/101972, the entire contents of which are incorporated by reference herein;

i) the complementary reactive groups are alkyl halide groups and one or more nucleophile group(s), such as, but not limited to, nucleophile groups selected from the group consisting of amino groups, hydroxyl groups and carboxyl group; such groups react under suitable conditions to form a carbon-nitrogen bond (alkyl halide plus amine) or carbon oxygen bond (alkyl halide plus hydroxyl or carboxyl group);

j) the complementary functional groups are halogenated heteroaromatic groups and one or more nucleophile group(s), the reactants are linked under suitable conditions via aromatic nucleophilic substitution; suitable halogenated heteroaromatic groups include chlorinated pyrimidines, triazines and purines, which react with nucleophiles, such as amines, under mild conditions in aqueous solution.

As will be clear from the above, a large variety of chemical reactions may optionally be used for the formation of one or more covalent bonds between a reactant and one or more chemical reaction sites and a large variety of chemical reactions may optionally be used for the formation of one or more covalent bonds between one or more reactants.

Thus, reactions such as those listed in March's Advanced Organic Chemistry, Organic Reactions, Organic Syntheses, organic text books, journals such as Journal of the American Chemical Society, Journal of Organic Chemistry, Tetrahedron, etc., and Carruther's Some Modern Methods of Organic Chemistry can be used. The chosen reactions preferably are compatible with nucleic acids such as DNA or RNA or are compatible with the modified nucleic acids used as the template. Reactions useful in stage 1 and stage 2 synthesis include, for example, substitution reactions, carbon-carbon bond forming reactions, elimination reactions, acylation reactions, and addition reactions. An illustrative but not exhaustive list of aliphatic nucleophilic substitution reactions useful in the present invention includes, for example, SN2 reactions, SN1 reactions, SNi reactions, allylic rearrangements, nucleophilic substitution at an aliphatic trigonal carbon, and nucleophilic substitution at a vinylic carbon. Specific aliphatic nucleophilic substitution reactions with oxygen nucleophiles include, for example, hydrolysis of alkyl halides, hydrolysis of gen-dihalides, hydrolysis of 1,1,1-trihalides, hydrolysis of alkyl esters or inorganic acids, hydrolysis of diazo ketones, hydrolysis of acetal and enol ethers, hydrolysis of epoxides, hydrolysis of acyl halides, hydrolysis of anhydrides, hydrolysis of carboxylic esters, hydrolysis of amides, alkylation with alkyl halides (Williamson Reaction), epoxide formation, alkylation with inorganic esters, alkylation with diazo compounds, dehydration of alcohols, transetherification, alcoholysis of epoxides, alkylation with onium salts, hydroxylation of silanes, alcoholysis of acyl halides, alcoholysis of anhydrides, esterfication of carboxylic acids, alcoholysis of carboxylic esters (transesterfication), alcoholysis of amides, alkylation of carboxylic acid salts, cleavage of ether with acetic anhydride, alkylation of carboxylic acids with diazo compounds, acylation of carboxylic acids with acyl halides; acylation of caripoxylic acids with carboxylic acids, formation of oxoniiim salts, preparation of peroxides and hydroperoxides, preparation of inorganic esters (e.g., nitrites, nitrates, sulfonates), preparation of alcohols from amines, and preparation of mixed organic-inorganic an hydrides.

Specific aliphatic nucleophilic substitution reactions with sulfur nucleophiles, which tend to be better nucleophiles than their oxygen analogs, include, for example, attack by SH at an alkyl carbon to form thiols, attack by S at an alkyl carbon to form thioethers, attack by SH or SR at an acyl carbon, formation of disulfides, formation of Bunte salts, alkylation of sulfuric acid salts, and formation of alkyl thiocyanates.

Aliphatic nucleophilic substitution reactions with nitrogen nucleophiles include, for example, alkylation of amines, N-ar[gamma]lation of amines, replacement of a hydroxy by an amino group, transamination, transamidation, alkylation of amines with diazo compounds, animation of epoxides, amination of oxetanes, amination of aziridines, amination of alkanes, formation of isocyanides, acylation of amines by acyl halides, acylation of amines by anhydrides, acylation of amines by carboxylic acids, acylation of amines by carboxylic esters, acylation of amines by amides, acylation of amines by other acid derivatives, N-alkylation or N-arylation of amides and imides, N-acylation of amides and imides, formation of aziridines from epoxides, formation of nitro compounds, formation of azides, formation of isocyanates and isothiocyanates, and formation of azoxy compounds. Aliphatic nucleophilic substitution reactions with halogen nucleophiles include, for example, attack at an alkyl carbon, halide exchange, formation of alkyl halides from esters of sulfuric and sulfonic acids, formation of alkyl halides from alcohols, formation of alkyl halides from ethers, formation of halohydrins from epoxides, cleavage of carboxylic esters with lithium iodide, conversion of diazo ketones to alpha-halo ketones, conversion of amines to halides, conversion of tertiary amines to cyanamides (the von Braun reaction), formation of acyl halides from carboxylic acids, and formation of acyl halides from acid derivatives.

Aliphatic nucleophilic substitution reactions using hydrogen as a nucleophile include, for example, reduction of alkyl halides, reduction of tosylates, other sulfonates, and similar compounds, hydrogenolysis of alcohols, hydrogenolysis of esters (Barton-McCombie reaction), hydrogenolysis of nitriles, replacement of alkoxyl by hydrogen, reduction of epoxides, reductive cleavage of carboxylic esters, reduction of a C—N bond, desulfurization, reduction of acyl halides, reduction of carboxylic acids, esters, and anhydrides to aldehydes, and reduction of amides to aldehydes.

Although certain carbon nucleophiles may be too nucleophilic and/or basic to be used in certain embodiments of the invention, aliphatic nucleophilic substitution reactions using carbon nucleophiles include, for example, coupling with silanes, coupling of alkyl halides (the Wurtz reaction), the reaction of alkyl halides and sulfonate esters with Group I (I A), and II (II A) organometallic reagents, reaction of alkyl halides and sulfonate esters with organocuprates, reaction of alkyl halides and sulfonate esters with other organometallic reagents; allylic and propargylic coupling with a halide substrate, coupling of organometallic reagents with esters of sulfuric and sulfonic acids, sulfoxides, and sulfones, coupling involving alcohols, coupling of organometallic reagents with carboxylic esters, coupling of organometallic reagents with compounds containing an ester linkage, reaction of organometallic reagents with epoxides, reaction of organometallics with aziridine, alkylation at a carbon bearing an active hydrogen, alkylation of ketones, nitriles, and carboxylic esters, alkylation of carboxylic acid salts, alkylation at a position alpha to a heteroatom (alkylation of 1,3-dithianes), alkylation of dihydro-l,3-oxazine (the Meyers synthesis of aldehydes, ketones, and carboxylic acids), alkylation with trialkylboranes, alkylation at an alkynyl carbon, preparation of nitriles, direct conversion of alkyl halides to aldehydes and ketones, conversion of alkyl halides, alcohols, or alkanes to carboxylic acids and their derivatives, the conversion of acyl halides to ketones with organometallic compounds, the conversion of anhydrides, carboxylic esters, or amides to ketones with organometallic compounds, the coupling of acyl halides, acylation at a carbon bearing an active hydrogen, acylation of carboxylic esters by carboxylic esters (the Claisen and Dieckmann condensation), acylation of ketones and nitriles with carboxylic esters, acylation of carboxylic acid salts, preparation of acyl cyanides, and preparation of diazo ketones, ketonic decarboxylation. Reactions which involve nucleophilic attack at a sulfonyl sulfur atom may also be used in the present invention and include, for example, hydrolysis of sulfonic acid derivatives (attack by OH), formation of sulfonic esters (attack by OR), formation of sulfonamides (attack by nitrogen), formation of sulfonyl halides (attack by halides), reduction of sulfonyl chlorides (attack by hydrogen), and preparation of sulfones (attack by carbon).

Aromatic electrophilic substitution reactions may also be used in stage 1 and stage 2 synthesis schemes. Hydrogen exchange reactions are examples of aromatic electrophilic substitution reactions that use hydrogen as the electrophile. Aromatic electrophilic substitution, reactions which use nitrogen electrophiles include, for example, nitration and nitro-dehydrogenation, nitrosation of nitroso-de-hydrogenation, diazonium coupling, direct introduction of the diazonium group, and amination or amino-dehydrogenation. Reactions of this type with sulfur electrophiles include, for example, sulfonation, sulfo-dehydrogenation, halosulfonation, halosulfo-dehydrogenation, sulfurization, and sulfonylation. Reactions using halogen electrophiles include, for example, halogenation, and halo-dehydrogenation. Aromatic electrophilic substitution reactions with carbon electrophiles include, for example, Friedel-Crafts alkylation, alkylation, alkyl-dehydrogenation, Friedel-Crafts arylation (the Scholl reaction), Friedel-Crafts acylation, formylation with disubstituted formamides, formylation with zinc cyanide and HCl (the Gatterman reaction), formylation with chloroform (the Reimer-Tiemami reaction), other formylations, formyl-dehydrogenation, carboxylation with carbonyl halides, carboxylation with carbon dioxide (the Kolbe-Schmitt reaction), amidation with isocyanates, [Lambda]/-alkylcarbamoyl-dehydrogenation, hydroxyalkylation, hydroxyalkyl-dehydrogenation, cyclodehydration of aldehydes and ketones, haloalkylation, halo-dehydrogenation, aminoalkylation, amidoalkylation, dialkylaminoalkylation, dialkylamino-dehydrogenation, thioalkylation, acylation with nitriles (the Hoesch reaction), cyanation, and cyano-de hydrogenation. Reactions using oxygen electrophiles include, for example, hydroxylation and hydroxy-dehydrogenation.

Rearrangement reactions include, for example, the Fries rearrangement, migration of a nitro group, migration of a nitroso group (the Fischer-Hepp Rearrangement), migration of an arylazo group, migration of a halogen (the Orton rearrangement), migration of an alkyl group, etc. Other reaction on an aromatic ring include the reversal of a Friedel-Crafts alkylation, decarboxylation of aromatic aldehydes, decarboxylation of aromatic acids, the Jacobsen reaction, deoxygenation, desulfonation, hydro-desulfonation, dehalogenation, hydro-dehalogenation, and hydrolysis of organometallic compounds.

Aliphatic electrophilic substitution reactions are also useful. Reactions using the SEl, SE2 (front), SE2 (back), SEi, addition-elimination, and cyclic mechanisms can be used in the present invention. Reactions of this type with hydrogen as the leaving group include, for example, hydrogen exchange (deuterio-de-hydrogenation, deuteriation), migration of a double bond, and keto-enol tautomerization. Reactions with halogen electrophiles include, for example, halogenation of aldehydes and ketones, halogenation of carboxylic acids and acyl halides, and halogenation of sulfoxides and sulfones. Reactions with nitrogen electrophiles include, for example, aliphatic diazonium coupling, nitrosation at a carbon bearing an active hydrogen, direct formation of diazo compounds, conversion of amides to alpha-azido amides, direct amination at an activated position, and insertion by nitrenes. Reactions with sulfur or selenium electrophiles include, for example, sulfenylation, sulfonation, and selenylation of ketones and carboxylic esters. Reactions with carbon electrophiles include, for example, acylation at an aliphatic carbon, conversion of aldehydes to beta-keto esters or ketones, cyanation, cyano-de-hydrogenation, alkylation of alkanes, the Stork enamine reaction, and insertion by carbenes. Reactions with metal electrophiles include, for example, metalation with organometallic compounds, metalation with metals and strong bases, and conversion of enolates to silyl enol ethers. Aliphatic electrophilic substitution reactions with metals as leaving groups include, for example, replacement of metals by hydrogen, reactions between organometallic reagents and oxygen, reactions between organometallic reagents and peroxides, oxidation of trialkylboranes to borates, conversion of Grignard reagents to sulfur compounds, halo-demetalation, the conversion of organometallic compounds to amines, the conversion of organometallic compounds to ketones, aldehydes, carboxylic esters and amides, cyano-de-metalation, transmetalation with a metal, transmetalation with a metal halide, transmetalation with an organometallic compound, reduction of alkyl halides, metallo-de-halogenation, replacement of a halogen by a metal from an organometallic compound, decarboxylation of aliphatic acids, cleavage of aikoxides, replacement of a carboxyl group by an acyl group, basic cleavage of beta-keto esters and beta-diketones, haloform reaction, cleavage of non-enolizable ketones, the Haller-Bauer reaction, cleavage of alkanes, decyanation, and hydro-de-cyanation. Electrophilic substitution reactions at nitrogen include, for example, diazotization, conversion of hydrazines to azides, N-nitrosation, N-nitroso-de-hydrogenation, conversion of amines to azo compounds, N-halogenation, N-halo-de-hydrogenation, reactions of amines with carbon monoxide, and reactions of amines with carbon dioxide. Aromatic nucleophilic substitution reactions may also be used in the present invention. Reactions proceeding via the SNAr mechanism, the SNI mechanism, the benzyne mechanism, the SRN1 mechanism, or other mechanism, for example, can be used. Aromatic nucleophilic substitution reactions with oxygen nucleophiles include, for example, hydroxy-de-halogenation, alkali fusion of sulfonate salts, and replacement of OR or OAr. Reactions with sulfur nucleophiles include, for example, replacement by SH or SR. Reactions using nitrogen nucleophiles include, for example, replacement by NH2, NHR, or NR2, and replacement of a hydroxy group by an amino group: Reactions with halogen nucleophiles include, for example, the introduction halogens. Aromatic nucleophilic substitution reactions with hydrogen as the nucleophile include, for example, reduction of phenols and phenolic esters and ethers, and reduction of halides and nitro compounds. Reactions with carbon nucleophiles include, for example, the Rosenmund-von Braun reaction, coupling of organometallic compounds with aryl halides, ethers, and carboxylic esters, arylation at a carbon containing an active hydrogen, conversions of aryl substrates to carboxylic acids, their derivatives, aldehydes, and ketones, and the Ullmann reaction. Reactions with hydrogen as the leaving group include, for example, alkylation, arylation, and amination of nitrogen heterocycles. Reactions with N2<+> as the leaving group include, for example, hydroxy-de-diazoniation, replacement by sulfur-containing groups, iodo-de-diazoniation, and the Schiemann reaction. Rearrangement reactions include, for example, the von Richter rearrangement, the Sommelet-Hauser rearrangement, rearrangement of aryl hydroxylamines, and the Smiles rearrangement. Reactions involving free radicals can also be used, although the free radical reactions used in nucleotide-templated chemistry should be carefully chosen to avoid modification or cleavage of the nucleotide template. With that limitation, free radical substitution reactions can be used in the present invention. Particular free radical substitution reactions include, for example, substitution by halogen, halogenation at an alkyl carbon, allylic halogenation, benzylic halogenation, halogenation of aldehydes, hydroxylation at an aliphatic carbon, hydroxylation at an aromatic carbon, oxidation of aldehydes to carboxylic acids, formation of cyclic ethers, formation of hydroperoxides, formation of peroxides, acyloxylation, acyloxy-de-hydrogenation, chlorosulfonation, nitration of alkanes, direct conversion of aldehydes to amides, amidation and amination at an alkyl carbon, simple coupling at a susceptible position, coupling of alkynes, arylation of aromatic compounds by diazonium salts, arylation of activated alkenes by diazonium salts (the Meerwein arylation), arylation and alkylation of alkenes by organopalladium compounds (the Heck reaction), arylation and alkylation of alkenes by vinyltin compounds (the StHle reaction), alkylation and arylation of aromatic compounds by peroxides, photochemical arylation of aromatic compounds, alkylation, acylation, and carbalkoxylation of nitrogen heterocycles. Particular reactions in which N2<+> is the leaving group include, for example, replacement of the diazonium group by hydrogen, replacement of the diazonium group by chlorine or bromine, nitro-de-diazoniation, replacement of the diazonium group by sulfur-containing groups, aryl dimerization with diazonium salts, methylation of diazonium salts, vinylation of diazonium salts, arylation of diazonium salts, and conversion of diazonium salts to aldehydes, ketones, or carboxylic acids. Free radical substitution reactions with metals as leaving groups include, for example, coupling of Grignard reagents, coupling of boranes, and coupling of other organometallic reagents. Reaction with halogen as the leaving group are included. Other free radical substitution reactions with various leaving groups include, for example, desulfurization with Raney Nickel, conversion of sulfides to organolithium compounds, decarboxylase dimerization (the Kolbe reaction), the Hunsdiecker reaction, decarboxylative allylation, and decarbonylation of aldehydes and acyl halides.

Reactions involving additions to carbon-carbon multiple bonds are also used in the stage 1 and stage 2 synthesis schemes. Any mechanism may be used in the addition reaction including, for example, electrophilic addition, nucleophilic addition, free radical addition, and cyclic mechanisms. Reactions involving additions to conjugated systems can also be used. Addition to cyclopropane rings can also be utilized. Particular reactions include, for example, isomerization, addition of hydrogen halides, hydration of double bonds, hydration of triple bonds, addition of alcohols, addition of carboxylic acids, addition of H2S and thiols, addition of ammonia and amines, addition of amides, addition of hydrazoic acid, hydrogenation of double and triple bonds, other reduction of double and triple bonds, reduction of the double and triple bonds of conjugated systems, hydrogenation of aromatic rings, reductive cleavage of cyclopropanes, hydroboration, other hydrometalations, addition of alkanes, addition of alkenes and/or alkynes to alkenes and/or alkynes (e.g., pi-cation cyclization reactions, hydro-alkenyl-addition), ene reactions, the Michael reaction, addition of organometallics to double and triple bonds not conjugated to carbonyls, the addition of two alkyl groups to an alkyne, 1,4-addition of organometallic compounds to activated double bonds, addition of boranes to activated double bonds, addition of tin and mercury hydrides to activated double bonds, acylation of activated double bonds and of triple bonds, addition of alcohols, amines, carboxylic esters, aldehydes, etc., carbonylation of double and triple bonds, hydrocarboxylation, hydroformylation, addition of aldehydes, addition of HCN, addition of silanes, radical addition, radical cyclization, halogenation of double and triple bonds (addition of halogen, halogen), halolactonization, halolactamization, addition of hypohalous acids and hypohalites (addition of halogen, oxygen), addition of sulfur compounds (addition of halogen, sulfur), addition of halogen and an amino group (addition of halogen, nitrogen), addition of NOX and NO2X (addition of halogen, nitrogen), addition of XN3 (addition of halogen, nitrogen), addition of alkyl halides (addition of halogen, carbon), addition of acyl halides (addition of halogen, carbon), hydroxylation (addition of oxygen, oxygen) (e.g., asymmetric dihydroxylation reaction with OSO4), dihydroxylation of aromatic rings, epoxidation (addition of oxygen, oxygen) (e.g., Sharpless asymmetric epoxidation), photooxidation of dienes (addition of oxygen, oxygen), hydroxysulfenylation (addition of oxygen, sulfur), oxyamination (addition of oxygen, nitrogen), diamination (addition of nitrogen, nitrogen), formation of aziridines (addition of nitrogen), aminosulferiylation (addition of nitrogen, sulfur), acylacyloxylation and acylamidation (addition of oxygen, carbon or nitrogen, carbon), 1,3-dipolar addition; (addition of oxygen, nitrogen, carbon), Diels-Alder reaction, heteroatom Diels-Alder reaction, all carbon 3+2 cycloadditions, dimerization of alkenes, the addition of carbenes and carbenoids to double and triple bonds, trimerization and tetramerization of alkynes, and other cycloaddition reactions.

In addition to reactions involving additions to carbon-carbon multiple bonds, addition reactions to carbon-hetero multiple bonds can be used in nucleotide-templated chemistry. Exemplary reactions include, for example, the addition of water to aldehydes and ketones (formation of hydrates), hydrolysis of carbon-nitrogen double bond, hydrolysis of aliphatic nitro compounds, hydrolysis of nitriles, addition of alcohols and thiols to aldehydes and ketones, reductive alkylation of alcohols, addition of alcohols to isocyanates, alcoholysis of nitriles, formation of xanthates, addition of H2S and thiols to carbonyl compounds, formation of bisulfite addition products, addition of amines to aldehydes and ketones, addition of amides to aldehydes, reductive alkylation of ammonia or amines, the Mannich reaction, the addition of amines to isocyanates, addition of ammonia or amines to nitriles, addition of amines to carbon disulfide and carbon dioxide, addition of hydrazine derivative to carbonyl compounds, formation of oximes, conversion of aldehydes to nitriles, formation of gem-dihalides from aldehydes and ketones, reduction of aldehydes and ketones to alcohols, reduction of the carbon-nitrogen double bond, reduction of nitriles to amines, reduction of nitriles to aldehydes, addition of Grignard reagents and organolithium reagents to aldehydes and ketones, addition of other organometallics to aldehydes and ketones, addition of trialkylallylsilanes to aldehydes and ketones, addition of conjugated alkenes to aldehydes (the Baylis-Billmah reaction), the Reformatsky reaction, the conversion of carboxylic acid salts to ketones with organometallic compounds, the addition of Grignard reagents to acid derivatives, the addition of Organometallic compounds to CO2 and CS2, addition of organometallic compounds to C=IM compounds, addition of carbenes and diazoalkanbs to C=N compounds, addition of Grignard reagents to nitriles and isocyanates, the Aldol reaction, Mukaiyama Aldol and related reactions, Aldol-type reactions between carboxylic esters or amides and aldehydes or ketones, the Knoevenagel reaction (e.g., the Nef reaction, the Favorskii reaction), the Peterson alkenylation reaction, the addition of active hydrogen compounds to CO2 and CS2, the Perkin reaction, Darzens glycidic ester condensation, the Tollens reaction, the Wittig reaction, the Tebbe alkenylation, the Petasis alkenylation, alternative alkenylations, the Thorpe reaction, the Thorpe-Ziegler reaction, addition of silanes, formation of cyanohydrins, addition of HCN to C=N and C—N bonds, the Prins reaction, the benzoin condensation, addition of radicals to C=O, C=S, C=N compounds, the Ritter reaction, acylation of aldehydes and ketones, addition of aldehydes to aldehydes, the addition of isocyanates to isocyanates (formation of carbodiimides), the conversion of carboxylic acid salts to nitriles, the formation of epoxides from aldehydes and ketones, the formation of episulfides and episulfones, the formation of beta-lactones and oxetanes (e.g., the Paterno-Buchi reaction), the formation of beta-lactams, etc. Reactions involving addition to isocyanides include the addition of water to isocyanides, the Passerini reaction, the Ug reaction, and the formation of metalated aldimines. Elimination reactions, including alpha, beta, and gamma eliminations, as well as extrusion reactions, can be performed using nucleotide-templated chemistry, although the strength of the reagents and conditions employed should be considered. Preferred elimination reactions include reactions that go by EI, E2, EIcB, or E2C mechanisms. Exemplary reactions include, for example, reactions in which hydrogen is removed from one side (e.g., dehydration of alcohols, cleavage of ethers to alkenes, the Chugaev reaction, ester decomposition, cleavage of quarternary ammonium hydroxides, cleavage of quaternary ammonium salts with strong bases, cleavage of amine oxides, pyrolysis of keto-ylids, decomposition of toluene-p-sulfonylhydrazones, cleavage of sulfoxides, cleavage of selenoxides, cleavage of sulformes, dehydrogalogenation of alkyl halides, dehydrohalogenation of acyl halides, dehydrohalogenation of sulfonyl halides, elimination of boranes, conversion of alkenes to alkynes, decarbonylation of acyl halides), reactions in which neither leaving atom is hydrogen (e.g., deoxygenation of vicinal diols, cleavage of cyclic thionocarbonates, conversion of epoxides to episulfides and alkenes, the Ramberg-Backlund reaction, conversion of aziridines to alkenes, dehalogenat[iota]on of vicinal dihalides, dehalogenation of alpha-halo acyl halides, and elimination of a halogen and a hetero group), fragmentation reactions (i.e., reactions in which carbon is the positive leaving group or the electrofuge, such as, for example, fragmentation of gamma-amino and gamma-hydroxy halides, fragmentation of 1,3-diols, decarboxylation of beta-hydroxy carboxylic acids, decarboxylation of (3-lactones, fragmentation of alpha-beta-epoxy hydrazones, elimination of CO from bridged bicyclic compounds, and elimination Of CO2 from bridged bicyclic compounds), reactions in which C=N or C≡N bonds are formed (e.g., dehydration of aldoximes or similar compounds, conversion of ketoximes to nitriles, dehydration of unsubstituted amides, and conversion of N-alkylformamides to isocyanides), reactions in which C=O bonds are formed (e.g., pyrolysis of beta-hydroxy alkenes), and reactions in which N=N bonds are formed (e.g., eliminations to give diazoalkenes). Extrusion reactions include, for example, extrusion of N2 from pyrazolines, extrusion of N2 from pyrazoles, extrusion of N from triazolines, extrusion of CO, extrusion Of CO2, extrusion Of SO2, the Story synthesis, and alkene synthesis by twofold extrusion.

Rearrangements, including, for example, nucleophilic rearrangements, electrophilic rearrangements, prototropic rearrangements, and free-radical rearrangements, can also be performed using stage 1 and stage 2 synthesis schemes. Both 1,2 rearrangements and non-1,2 rearrangements can be performed. Exemplary reactions include, for example, carbon-to-carbon migrations of R, H, and Ar (e.g., Wagner-Meerwein and related reactions, the Pinacol rearrangement, ring expansion reactions, ring contraction reactions, acid-catalyzed rearrangements of aldehydes and ketones, the dienone-phenol rearrangement, the Favorskii rearrangement, the Arndt-Eistert synthesis, homologation of aldehydes, and homologation of ketones), carbon-to-carbon migrations of other groups (e.g., migrations of halogen, hydroxyl, amino, etc.; migration of boron; and the Neber rearrangement), carbon-to-nitrogen migrations of R and Ar (e.g., the Hofmann rearrangement, the Curtius rearrangement, the Lossen rearrangement, the Schmidt reaction, the Beckman rearrangement, the Stieglits rearrangement, and related rearrangements), carbon-to-oxygen migrations of R and Ar (e.g., the Baeyer-Villiger rearrangement and rearrangment of hydroperoxides), nitrogen-to-carbon, oxygen-to-carbon, and sulfur-to-carbon migration (e.g., the Stevens rearrangement, and the Wittig rearrangement), boron-to-carbon migrations (e.g., conversion of boranes to alcohols (primary or otherwise), conversion of boranes to aldehydes, conversion of boranes to carboxylic acids, conversion of vinylic boranes to alkenes, formation of alkynes from boranes and acetylides, formation of alkenes from boranes and acetylides, and formation of ketones from boranes and acetylides), electrocyclic rearrangements (e.g., of cyclobutenes and 1,3-cyclohexadienes, or conversion of stilbenes to phenanthrenes), sigmatropic rearrangements (e.g., (1,j) sigmatropic migrations of hydrogen, (lj) sigmatropic migrations of carbon, conversion of vinylcyclopropanes to cyclopentenes, the Cope rearrangement, the Claisen rearrangement, the Fischer indole synthesis, (2,3) sigmatropic rearrangements, and the benzidine rearrangement), other cyclic rearrangements (e.g., metathesis of alkenes, the di-n-methane and related rearrangements, and the Hofmann-Loffler and related reactions), and non-cyclic rearrangements (e.g., hydride shifts, the Chapman rearrangement, the Wallach rearrangement, and dybtropic rearrangements). Oxidative and reductive reactions may also be performed using stage 1 and stage 2 synthesis schemes. Exemplary reactions may involve, for example, direct electron transfer, hydride transfer, hydrogen-atom transfer, formation of ester intermediates, displacement mechanisms, or addition-elimination mechanisms. Exemplary oxidations include, for example, eliminations of hydrogen (e.g., aromatization of six-membered rings, dehydrogenations yielding carbon-carbon double bonds, oxidation or dehydrogenation of alcohols to aldehydes and ketones, oxidation of phenols and aromatic amines to quinones, oxidative cleavage of ketones, oxidative cleavage of aldehydes, oxidative cleavage of alcohols, ozonolysis, oxidative cleavage of double bonds and aromatic rings, oxidation of aromatic side chains, oxidative decarboxylation, and bisdecarboxylation), reactions involving replacement of hydrogen by oxygen (e.g., oxidation of methylene to carbonyl, oxidation of methylene to OH, CO2R, or OR, oxidation of arylmethanes, oxidation of ethers to carboxylic esters and related reactions, oxidation of aromatic hydrocarbons to quinones, oxidation of amines or nitro compounds to aldehydes, ketones, or dihalides, oxidation of primary alcohols to carboxylic acids or carboxylic esters, oxidation of alkenes to aldehydes or ketones, oxidation of amines to nitroso compounds and hydroxylamines, oxidation of primary amines, oximes, azides, isocyanates, or nitroso compounds, to nitro compounds, oxidation of thiols and other sulfur compounds to sulfonic acids), reactions in which oxygen is added to the substrate (e.g., oxidation of alkynes to alpha-diketones, oxidation of tertiary amines to amine oxides, oxidation of thioesters to sulfoxides and sulfones, and oxidation of carboxylic acids to peroxy acids, and oxidative coupling reactions (e.g., coupling involving carbanoins, dimerization of silyl enol ethers or of lithium enolates, and oxidation of thiols to disulfides).

Exemplary reductive reactions include, for example, reactions involving replacement of oxygen by hydrogen {e.g., reduction of carbonyl to methylene in aldehydes and ketones, reduction of carboxylic acids to alcohols, reduction of amides to amines, reduction of carboxylic esters to ethers, reduction of cyclic anhydrides to lactones and acid derivatives to alcohols, reduction of carboxylic esters to alcohols, reduction of carboxylic acids and esters to alkanes, complete reduction of epoxides, reduction of nitro compounds to amines, reduction of nitro compounds to hydroxylamines, reduction of nitroso compounds and hydroxylamines to amines, reduction of oximes to primary amines or aziridines, reduction of azides to primary amines, reduction of nitrogen compounds, and reduction of sulfonyl halides and sulfonic acids to thiols), removal of oxygen from the substrate {e.g., reduction of amine oxides and azoxy compounds, reduction of sulfoxides and sulfones, reduction of hydroperoxides and peroxides, and reduction of aliphatic nitro compounds to oximes or nitrites), reductions that include cleavage {e.g., de-alkylation of amines and amides, reduction of azo, azoxy, and hydrazo compounds to amines, and reduction of disulfides to thiols), reductive coupling reactions {e.g., bimolecular reduction of aldehydes and ketones to 1,2-diols, bimolecular reduction of aldehydes or ketones to alkenes, acyloin ester condensation, reduction of nitro to azoxy compounds, and reduction of nitro to azo compounds), and. reductions in which an organic substrate is both oxidized and reduced {e.g., the Cannizzaro reaction, the Tishchenko reaction, the Pummerer rearrangement, and the Willgerodt reaction).

In one embodiment, a reactive group may comprise a nitrogen atom such as for example an amine, an isocyanate, an isocyanide, a hydroxylamine, a hydrazine, a nitrile, an amide, a lactam, an imine, an azo group, a nitro group, a nitroso group, an amidine group, a guanidine group, a carbamate, an azide, which may optionally be substituted by one or more substituents depending on the type of reactive group.

In one embodiment, a reactive group may comprise an oxygen atom such as for example a hydroxyl group, an ether, a ketone, an aldehyde, a hemiacetal, a hemiketal, an acetal, a ketal, a carboxylic acid, a carboxylic acid ester, an ortho ester, a carbonate, a carbamate, a lactam, a lactone, a hydroxylamine, which may optionally be substituted by one or more substituents depending on the type of reactive group.

In one embodiment, a reactive group may comprise a sulfur atom such as for example a thiol, a disulfide, a sulfide, a sulfoxide, a sulfin amide, a sulfonamide, a sulfone, a sultam, a sultone, a thioketone, a thioaldehyde, a dithioacetal, a carboxylic acid thioester, a thiocarbonate, a thiocarbamate, a isothiocyanate, which may optionally be substituted by one or more substituents depending on the type of reactive group.

In one embodiment, a reactive group may comprise a halogen such as for example fluorine, chlorine, bromine, iodine, for example alkylchloride, alkylbromide, alkyliodide, alkenylchloride, alkenylbromide, alkenyliodide, alkynylchloride, alkynylbromide, alkynyliodide, arylfluoride, arylchloride, arylbromide, aryliodide, hetarylfluoride, hetarylchloride, hetarylbromide, hetaryliodide, carbonylfluoride, carbonylchloride, carbonylbromide, carbonyliodide, sulfonylfluoride, sulfonylchloride, sulfonylbromide, sulfonyliodide, which may optionally be substituted by one or more substituents depending on the type of reactive group.

In one embodiment, a reactive group may comprise a carbon atom such as for example an alkene, an alpha,beta-unsaturated ketone, an alpha,beta-unsaturated aldehyde, an alpha,beta-unsaturated carboxylic acid ester, an alpha,beta-unsaturated carboxylic acid amide, an alpha,beta-unsaturated sulfoxide, an alpha,beta-unsaturated sulfone, an alpha,beta-unsaturated sulfonamide, an alpha,beta-unsaturated sulfonylchloride, a nitro alkene, such as a vinylogous nitro group (alpha,beta-unsaturated nitroalkene), an alkyne, an arene, a hetarene, a nitrile, an amide, a lactam, an imine, a nitroalkyl group, a nitroaryl group, an amidine group, a carbamate, a ketone, an aldehyde, a hemiacetal, a hemiketal, an acetal, a ketal, a carboxylic acid, a carboxylic acid ester, an ortho ester, a carbonate, a carbamate, a lactam, a lactone, a carbosulfone, a carbosultam, a carbosultone, a thioketone, a thioaldehyde, a dithioacetal, a carboxylic acid thioester, a thiocarbonate, a thiocarbamate, an alkylchloride, an alkylbromide, an alkyliodide, an alkenylchloride, an alkenylbromide, an alkenyliodide, an alkynylchloride, an alkynylbromide, an alkynyliodide, an arylfluoride, an arylchloride, an arylbromide, an aryliodide, an hetarylfluoride, an hetarylchloride, an hetarylbromide, an hetaryliodide, an carbonylfluoride, an carbonylchloride, an carbonylbromide, an carbonyliodide, an isocyanate, an isothiocyanate, an isocyanide, a alkylphosphonium group such as for example alkyltriphenylphosphonium chloride, for example alkyltriphenylphosphonium bromide, for example alkyltriphenylphosphonium iodide, which may optionally be substituted by one or more substituents depending on the type of reactive group.

Reactive groups may also comprising further functional groups as described in Comprehensive Organic Functional Group Transformations, Eds. A. R. Katritsky, O. Meth-Cohn, C. W. Rees, Pergamon, Elsevier 1995 Volumes 1-6, which are hereby incorporated by reference.

A chemical reactive site may comprise one or more reactive groups for example chemical reactive sites comprising 1-10 reactive groups, for example one reactive group, for example two reactive groups, for example three reactive groups, for example four reactive groups, for example five reactive groups.

A reactant may comprise one or more reactive groups for example reactants comprising 1-10 reactive groups, for example one reactive group, for example two reactive groups, for example three reactive groups, for example four reactive groups, for example five reactive groups.

In one embodiment, a reactant comprises two reactive groups, such as for example a diamine, an aminoketone, an aminoalcohol, an aminothiol, an aminoacid, such as for example an amino carboxylic acid, an aminoacid ester such as for example and amino carboxylic acid ester, an aminoacid amide such as for example an amino carboxylic acid amide, an amino chloroazine such as for example an amino chloropyridine, for example an amino chloropyrimidine, an amino chloropyridazine, an amino chloropyrazine, an amino fluoroazine such as for example an amino fluoropyridin, for example an amino fluoropyrimidine, an amino fluoropyridazine, an amino fluoro pyrazine, an Fmoc protected diamine, an Fmoc protected aminoketone, an Fmoc protected aminoalcohol, an Fmoc protected aminoacid such as for example an Fmoc protected amino carboxylic acid, an Fmoc protected aminoacid ester such as for example an Fmoc protected amino carboxylic acid ester, an Fmoc protected aminoacid amide such as for example an Fmoc protected amino carboxylic acid amide, an Fmoc protected aminoisocyanate, an Fmoc protected amino chloroazine such as for example an Fmoc protected amino chloropyridine, for example an Fmoc protected amino chloropyrimidine, an Fmoc protected amino chloropyridazine, an Fmoc protected amino chloropyrazine, an Fmoc protected amino fluoroazine such as for example an Fmoc protected amino fluoropyridin, for example an Fmoc protected amino fluoropyrimidine, an Fmoc protected amino fluoropyridazine, an Fmoc protected amino fluoro pyrazine, an Fmoc protected aminosulfonylchloride, an Fmoc protected aminoaldehyde, an Fmoc protected aminoisocyanate, an MSc protected diamine, an MSc protected aminoketone, an MSc protected aminoalcohol, an MSc protected aminoacid, an MSc protected aminoacid such as for example an MSc protected amino carboxylic acid, an MSc protected aminoacid ester such as for example an MSc protected amino carboxylic acid ester, an MSc protected aminoacid amide such as for example an MSc protected amino carboxylic acid amide, an MSc protected aminoisocyanate, an MSc protected amino chloroazine such as for example an MSc protected amino chloropyridine, for example an MSc protected amino chloropyrimidine, an MSc protected amino chloropyridazine, an MSc protected amino chloropyrazine, an MSc protected amino fluoroazine such as for example an MSc protected amino fluoropyridin, for example an MSc protected amino fluoropyrimidine, an MSc protected amino fluoropyridazine, an MSc protected amino fluoro pyrazine, an MSc protected aminosulfonylchloride, an MSc protected aminoaldehyde, an MSc protected aminoisocyanate, a 4-pentenoyl protected diamine, a 4-pentenoyl protected aminoketone, a 4-pentenoyl protected aminoalcohol, a 4-pentenoyl protected aminoacid such as for example a 4-pentenoyl protected amino carboxylic acid, a 4-pentenoyl protected aminoacid ester such as for example a 4-pentenoyl protected amino carboxylic acid ester, a 4-pentenoyl protected aminoacid amide such as for example a 4-pentenoyl protected amino carboxylic acid amide, a 4-pentenoyl protected aminoisocyanate, a 4-pentenoyl protected amino chloroazine such as for example a 4-pentenoyl protected amino chloropyridine, for example an 4-pentenoyl protected amino chloropyrimidine, a 4-pentenoyl protected amino chloropyridazine, a 4-pentenoyl protected amino chloropyrazine, a 4-pentenoyl protected amino fluoroazine such as for example a 4-pentenoyl protected amino fluoropyridin, for example a 4-pentenoyl protected amino fluoropyrimidine, a 4-pentenoyl protected amino fluoropyridazine, a 4-pentenoyl protected amino fluoro pyrazine, a 4-pentenoyl protected aminosulfonylchloride, a 4-pentenoyl protected aminoaldehyde, a 4-pentenoyl protected aminoisocyanate, a Boc protected diamine, a Boc protected aminoketone, a Boc protected aminoalcohol, a Boc protected aminoacid such as for example a Boc protected amino carboxylic acid, a Boc protected aminoacid ester such as for example a Boc protected amino carboxylic acid ester, a Boc protected aminoacid amide such as for example a Boc protected amino carboxylic acid amide, a Boc protected aminoisocyanate, a Boc protected amino chloroazine such as for example an Boc protected amino chloropyridine, for example a Boc protected amino chloropyrimidine, a Boc protected amino chloropyridazine, a Boc protected amino chloropyrazine, a Boc protected amino fluoroazine such as for example a Boc protected amino fluoropyridin, for example an Boc protected amino fluoropyrimidine, an Boc protected amino fluoropyridazine, an Boc protected amino fluoro pyrazine, a o-Ns protected diamine, a o-Ns protected aminoketone, a o-Ns protected aminoalcohol, a o-Ns protected aminoacid such as for example a o-Ns protected amino carboxylic acid, a o-Ns protected aminoacid ester such as for example a o-Ns protected amino carboxylic acid ester, a o-Ns protected aminoacid amide such as for example a o-Ns protected amino carboxylic acid amide, a o-Ns protected aminoisocyanate, a o-Ns protected amino chloroazine such as for example an o-Ns protected amino chloropyridine, for example a o-Ns protected amino chloropyrimidine, a o-Ns protected amino chloropyridazine, a o-Ns protected amino chloropyrazine, a o-Ns protected amino fluoroazine such as for example a o-Ns protected amino fluoropyridin, for example an o-Ns protected amino fluoropyrimidine, an o-Ns protected amino fluoropyridazine, an o-Ns protected amino fluoro pyrazine, a p-Ns protected diamine, a p-Ns protected aminoketone, a p-Ns protected aminoalcohol, a p-Ns protected aminoacid such as for example a p-Ns protected amino carboxylic acid, a p-Ns protected aminoacid ester such as for example a p-Ns protected amino carboxylic acid ester, a p-Ns protected aminoacid amide such as for example a p-Ns protected amino carboxylic acid amide, a p-Ns protected aminoisocyanate, a p-Ns protected amino chloroazine such as for example an p-Ns protected amino chloropyridine, for example a p-Ns protected amino chloropyrimidine, a p-Ns protected amino chloropyridazine, a p-Ns protected amino chloropyrazine, a p-Ns protected amino fluoroazine such as for example a p-Ns protected amino fluoropyridin, for example an p-Ns protected amino fluoropyrimidine, an p-Ns protected amino fluoropyridazine, an p-Ns protected amino fluoro pyrazine, a allyl carbamate protected diamine, a allyl carbamate protected aminoketone, a allyl carbamate protected aminoalcohol, a allyl carbamate protected aminoacid such as for example a allyl carbamate protected amino carboxylic acid, a allyl carbamate protected aminoacid ester such as for example a allyl carbamate protected amino carboxylic acid ester, a allyl carbamate protected aminoacid amide such as for example a allyl carbamate protected amino carboxylic acid amide, a allyl carbamate protected aminoisocyanate, a allyl carbamate protected amino chloroazine such as for example an allyl carbamate protected amino chloropyridine, for example a allyl carbamate protected amino chloropyrimidine, a allyl carbamate protected amino chloropyridazine, a allyl carbamate protected amino chloropyrazine, a allyl carbamate protected amino fluoroazine such as for example a allyl carbamate protected amino fluoropyridin, for example an allyl carbamate protected amino fluoropyrimidine, an allyl carbamate protected amino fluoropyridazine, an allyl carbamate protected amino fluoro pyrazine, a benzyl carbamate protected diamine, a benzyl carbamate protected aminoketone, a benzyl carbamate protected aminoalcohol, a benzyl carbamate protected aminoacid such as for example a benzyl carbamate protected amino carboxylic acid, a benzyl carbamate protected aminoacid ester such as for example a benzyl carbamate protected amino carboxylic acid ester, a benzyl carbamate protected aminoacid amide such as for example a benzyl carbamate protected amino carboxylic acid amide, a benzyl carbamate protected aminoisocyanate, a benzyl carbamate protected amino chloroazine such as for example an benzyl carbamate protected amino chloropyridine, for example a benzyl carbamate protected amino chloropyrimidine, a benzyl carbamate protected amino chloropyridazine, a benzyl carbamate protected amino chloropyrazine, a benzyl carbamate protected amino fluoroazine such as for example a benzyl carbamate protected amino fluoropyridin, for example an benzyl carbamate protected amino fluoropyrimidine, an benzyl carbamate protected amino fluoropyridazine, an benzyl carbamate protected amino fluoro pyrazine, a Fmoc protected aminofluorotriazine such as for example a Fmoc protected aminofluoro-1,2,3-triazine, for example a Fmoc protected aminofluoro-1,2,4-triazine, for example a Fmoc protected aminofluoro-1,3,5-triazine, a Fmoc protected aminochlorotriazine such as for example a Fmoc protected aminochloro-1,2,3-triazine, for example a Fmoc protected aminochloro-1,2,4-triazine, for example a Fmoc protected aminochloro-1,3,5-triazine, a MSc protected aminofluorotriazine such as for example a MSc protected aminofluoro-1,2,3-triazine, for example a MSc protected aminofluoro-1,2,4-triazine, for example a MSc protected aminofluoro-1,3,5-triazine, a MSc protected aminochlorotriazine such as for example a MSc protected aminochloro-1,2,3-triazine, for example a MSc protected aminochloro-1,2,4-triazine, for example a MSc protected aminochloro-1,3,5-triazine, a o-Ns protected aminofluorotriazine such as for example a o-Ns protected aminofluoro-1,2,3-triazine, for example a o-Ns protected aminofluoro-1,2,4-triazine, for example a o-Ns protected aminofluoro-1,3,5-triazine, a o-Ns protected aminochlorotriazine such as for example a o-Ns protected aminochloro-1,2,3-triazine, for example a o-Ns protected aminochloro-1,2,4-triazine, for example a o-Ns protected aminochloro-1,3,5-triazine, a p-Ns protected aminofluorotriazine such as for example a p-Ns protected aminofluoro-1,2,3-triazine, for example a p-Ns protected aminofluoro-1,2,4-triazine, for example a p-Ns protected aminofluoro-1,3,5-triazine, a p-Ns protected aminochlorotriazine such as for example a p-Ns protected aminochloro-1,2,3-triazine, for example a p-Ns protected aminochloro-1,2,4-triazine, for example a p-Ns protected aminochloro-1,3,5-triazine, a allyl carbamate protected aminofluorotriazine such as for example a allyl carbamate protected aminofluoro-1,2,3-triazine, for example a allyl carbamate protected aminofluoro-1,2,4-triazine, for example a allyl carbamate protected aminofluoro-1,3,5-triazine, a allyl carbamate protected aminochlorotriazine such as for example a allyl carbamate protected aminochloro-1,2,3-triazine, for example a allyl carbamate protected aminochloro-1,2,4-triazine, for example a allyl carbamate protected aminochloro-1,3,5-triazine, a benzyl carbamate protected aminofluorotriazine such as for example a benzyl carbamate protected aminofluoro-1,2,3-triazine, for example a benzyl carbamate protected aminofluoro-1,2,4-triazine, for example a benzyl carbamate protected aminofluoro-1,3,5-triazine, a benzyl carbamate protected aminochlorotriazine such as for example a benzyl carbamate protected aminochloro-1,2,3-triazine, for example a benzyl carbamate protected aminochloro-1,2,4-triazine, for example a benzyl carbamate protected aminochloro-1,3,5-triazine, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises two reactive groups, such as for example a mercaptoaldehyde, a hydroxyaldehyde, a formylalkyl carboxylic acid, a formyl aryl carboxylic acid, a formyl hetaryl carboxylic acid, a formyl alkylaryl carboxylic acid, a formyl alkylhetaryl carboxylic acid, a formyl arylalkyl carboxylic acid, a formyl hetarylalkyl carboxylic acid, a formylalkyl carboxylic acid ester, a formyl aryl carboxylic acid ester, a formyl hetaryl carboxylic acid ester, a formyl alkylaryl carboxylic acid ester, a formyl alkylhetaryl carboxylic acid ester, a formyl arylalkyl carboxylic acid ester, a formyl hetarylalkyl carboxylic acid ester, a formylalkyl sulfonyl chloride, a formyl aryl sulfonyl chloride, a formyl hetaryl sulfonyl chloride, a formyl alkylaryl sulfonyl chloride, a formyl alkylhetaryl sulfonyl chloride, a formyl arylalkyl sulfonyl chloride, a formyl hetarylalkyl sulfonyl chloride, a formylalkyl isocyanate, a formyl aryl isocyanate, a formyl hetaryl isocyanate, a formyl alkylaryl isocyanate, a formyl alkylhetaryl isocyanate, a formyl arylalkyl isocyanate, a formyl hetarylalkyl isocyanate, a formylalkyl isocyanide, a formyl aryl isocyanide, a formyl hetaryl isocyanide, a formyl alkylaryl isocyanide, a formyl alkylhetaryl isocyanide, a formyl arylalkyl isocyanide, a formyl hetarylalkyl isocyanide, a formyl chloroazine such as for example a formyl chloropyridine, for example a formyl chloropyrimidine, a formyl chloropyridazine, a formyl chloropyrazine, a formyl fluoroazine such as for example a formyl fluoropyridin, for example a formyl fluoropyrimidine, a formyl fluoropyridazine, a formyl fluoro pyrazine, a formyl fluorotriazine, a formylchlorotriazine, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises two reactive groups, such as for example a dicarboxylic acid, a alkoxycarbonylalkyl carboxylic acid, a alkoxycarbonyl aryl carboxylic acid, a alkoxycarbonyl hetaryl carboxylic acid, a alkoxycarbonyl alkylaryl carboxylic acid, a alkoxycarbonyl alkylhetaryl carboxylic acid, a alkoxycarbonyl arylalkyl carboxylic acid, a alkoxycarbonyl hetarylalkyl carboxylic acid, a carboxyalkyl sulfonyl chloride, a carboxy aryl sulfonyl chloride, a carboxy hetaryl sulfonyl chloride, a carboxy alkylaryl sulfonyl chloride, a carboxy alkylhetaryl sulfonyl chloride, a carboxy arylalkyl sulfonyl chloride, a carboxy hetarylalkyl sulfonyl chloride, a alkoxycarbonylalkyl sulfonyl chloride, a alkoxycarbonyl aryl sulfonyl chloride, a alkoxycarbonyl hetaryl sulfonyl chloride, a alkoxycarbonyl alkylaryl sulfonyl chloride, a alkoxycarbonyl alkylhetaryl sulfonyl chloride, a alkoxycarbonyl arylalkyl sulfonyl chloride, a alkoxycarbonyl hetarylalkyl sulfonyl chloride, a alkoxycarbonylalkyl isocyanate, a alkoxycarbonyl aryl isocyanate, a alkoxycarbonyl hetaryl isocyanate, a alkoxycarbonyl alkylaryl isocyanate, a alkoxycarbonyl alkylhetaryl isocyanate, a alkoxycarbonyl arylalkyl isocyanate, a alkoxycarbonyl hetarylalkyl isocyanate, a alkoxycarbonyl chloroazine such as for example a alkoxycarbonyl chloropyridine, for example a alkoxycarbonyl chloropyrimidine, a alkoxycarbonyl chloropyridazine, a alkoxycarbonyl chloropyrazine, a alkoxycarbonyl fluoroazine such as for example a alkoxycarbonyl fluoropyridin, for example a alkoxycarbonyl fluoropyrimidine, a alkoxycarbonyl fluoropyridazine, a alkoxycarbonyl fluoro pyrazine, a alkoxycarbonyl fluorotriazine, a alkoxycarbonylchlorotriazine, a carboxycarbonyl chloroazine such as for example a carboxycarbonyl chloropyridine, for example a carboxycarbonyl chloropyrimidine, a carboxycarbonyl chloropyridazine, a carboxycarbonyl chloropyrazine, a carboxycarbonyl fluoroazine such as for example a carboxycarbonyl fluoropyridin, for example a carboxycarbonyl fluoropyrimidine, a carboxycarbonyl fluoropyridazine, a carboxycarbonyl fluoro pyrazine, a carboxycarbonyl fluorotriazine, a carboxycarbonylchlorotriazine, a chlorosulfonyl chloroazine such as for example a chlorosulfonyl chloropyridine, for example a chlorosulfonyl chloropyrimidine, a chlorosulfonyl chloropyridazine, a chlorosulfonyl chloropyrazine, a chlorosulfonyl fluoroazine such as for example a chlorosulfonyl fluoropyridin, for example a chlorosulfonyl fluoropyrimidine, a chlorosulfonyl fluoropyridazine, a chlorosulfonyl fluoro pyrazine, a chlorosulfonyl fluorotriazine, a chlorosulfonylchlorotriazine, a dihaloazine such as for example a dihalopyridin, for example a dihalopyrimidine, a dihalopyridazine, a dihalo pyrazine, a dihalotriazine, a dihalotriazine such as for example a dihalo-1,2,3-triazine, for example a dihalo-1,2,4-triazine, for example a dihalo-1,3,5-triazine, a dichloroazine such as for example a dichloropyridin, for example a dichloropyrimidine, a dichloropyridazine, a dichloro pyrazine, a dichlorotriazine, a dichlorotriazine such as for example a dichloro-1,2,3-triazine, for example a dichloro-1,2,4-triazine, for example a dichloro-1,3,5-triazine, a difluoroazine such as for example a difluoropyridin, for example a difluoropyrimidine, a difluoropyridazine, a difluoropyrazine, a difluorotriazine, a difluorotriazine such as for example a difluoro-1,2,3-triazine, for example a difluoro-1,2,4-triazine, for example a difluoro-1,3,5-triazine, a chlorofluoroazine such as for example a chlorofluoropyridin, for example a chlorofluoropyrimidine, a chlorofluoropyridazine, a chlorofluoro pyrazine, a chlorofluorotriazine, a chlorofluorotriazine such as for example a chlorofluoro-1,2,3-triazine, for example a chlorofluoro-1,2,4-triazine, for example a chlorofluoro-1,3,5-triazine, wherein such reactive groups may optionally be protected by further protection groups, for example carboxylic acid protection such as methyl ester, ethyl ester, t-butyl ester, 2,2,2-trichloroethyl ester, methylsulfonylethyl ester, benzyl ester, p-methoxy benzyl ester, o-nitrobenzyl ester, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises two reactive groups, such as for example an alpha,beta-unsaturated aldehyde, an alpha,beta-unsaturated sulfonyl chloride, an alpha,beta-unsaturated carboxylic acid, an alpha,beta-unsaturated carboxylic acid ester, an alpha,beta-unsaturated isocyanate, an alpha,beta-unsaturated ketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example a triamine, a diamino carboxylic acid, an amino dicarboxylic acid, a tricarboxylic acid, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example trihalotriazine for example trichlorotriazine, trifluorotriazine, dichlorofluorotriazine, difluorochlorotriazine, such as for example formyl dihaloazines, carboxy dihaloazines, chlorosulfonyl dihaloazines, isocyanato dihaloazines, amino dihaloazines, trihaloazinylazine, dihaloazinylhaloazine, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example a diamino aldehyde, an amino dialdehyde, a trialdehyde, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example a diformyl carboxylic acid, a formyl dicarboxylic acid, a formyl amino carboxylic acid, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example an alpha,beta-unsaturated aminoaldehyde, an alpha,beta-unsaturated aminosulfonyl chloride, an alpha,beta-unsaturated aminocarboxylic acid, an alpha,beta-unsaturated aminocarboxylic acid ester, an alpha,beta-unsaturated aminoisocyanate, an alpha,beta-unsaturated aminoketone, an alpha,beta-unsaturated aminocarboxylic acid amide, an alpha,beta-unsaturated aminosulfoxide, an alpha,beta-unsaturated aminosulfone, an alpha,beta-unsaturated aminosulfonamide, an alpha,beta-unsaturated aminosulfonylchloride, a nitro aminoalkene, such as comprising a vinylogous nitro group (alpha,beta-unsaturated nitroaminoalkene), an alpha,beta-unsaturated formylaldehyde, an alpha,beta-unsaturated formylsulfonyl chloride, an alpha,beta-unsaturated formylcarboxylic acid, an alpha,beta-unsaturated formylcarboxylic acid ester, an alpha,beta-unsaturated formylisocyanate, an alpha, beta-unsaturated formylketone, an alpha,beta-unsaturated formylcarboxylic acid amide, an alpha,beta-unsaturated formylsulfoxide, an alpha, beta-unsaturated formylsulfone, an alpha, beta-unsaturated formylsulfonamide, an alpha,beta-unsaturated formylsulfonylchloride, a nitro formylalkene, such as comprising a vinylogous nitro group (alpha,beta-unsaturated nitroformylalkene), wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example an alpha,beta-unsaturated carboxyaldehyde, an alpha,beta-unsaturated carboxysulfonyl chloride, an alpha,beta-unsaturated carboxycarboxylic acid, an alpha,beta-unsaturated carboxycarboxylic acid ester, an alpha,beta-unsaturated carboxyisocyanate, an alpha,beta-unsaturated carboxyketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example an alpha,beta-unsaturated alkoxycarbonylaldehyde, an alpha,beta-unsaturated alkoxycarbonylsulfonyl chloride, an alpha,beta-unsaturated alkoxycarbonylcarboxylic acid, an alpha, beta-unsaturated alkoxycarbonylcarboxylic acid ester, an alpha,beta-unsaturated alkoxycarbonylisocyanate, an alpha,beta-unsaturated alkoxycarbonylketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

In a further embodiment, a reactant comprises three reactive groups, such as for example an alpha,beta-unsaturated formylaldehyde, an alpha,beta-unsaturated formylsulfonyl chloride, an alpha,beta-unsaturated formylcarboxylic acid, an alpha,beta-unsaturated formylcarboxylic acid ester, an alpha,beta-unsaturated formylisocyanate, an alpha,beta-unsaturated formylketone, wherein such reactive groups may optionally be protected by protection groups, for example amino protection groups such as for example Fmoc, for example MSc, for example Boc, for example 4-pentenoyl, for example o-Ns, for example p-Ns, for example allyl carbamate, for example benzyl carbamate and a combination thereof, for example carboxylic acid protection such as methyl ester, ethyl ester, t-butyl ester, 2,2,2-trichloroethyl ester, benzyl ester, p-methoxy benzyl ester, o-nitrobenzyl ester, methylsulfonylethyl ester, for example aldehyde protection such as an acetal or the aldehyde may optionally be masked as a 1,2-diol and a combination thereof, wherein such reactants may optionally be substituted by one or more substituents.

Further reactive group reactions are illustrated herein below. The illustrations should not be construed as limiting the scope of the present invention in any way.

Nucleophilic Substitution Using Activation of Electrophiles

A. Acylating Monomer Building Blocks (Reactants)—Principle

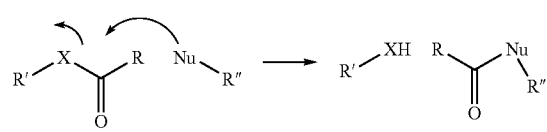

X = O, S   Nu = Oxygen-, Nitrogen-, Sulfur- and Carbon Nucleophiles

B. Acylation

Amide Formation by Reaction of Amines with Activated Esters

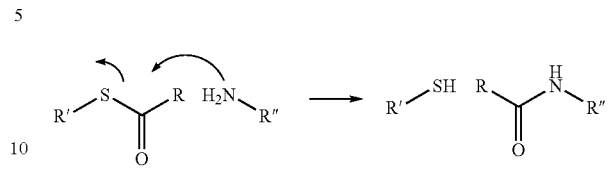

C. Acylation

Pyrazolone Formation by Reaction of Hydrazines with Alpha-Ketoesters

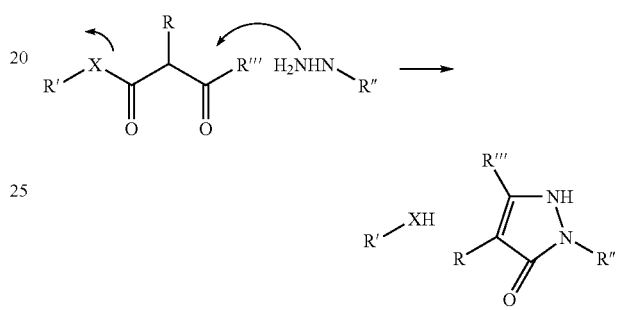

D. Acylation

Isoxazolone Formation by Reaction of Hydroxylamines with Alpha-Ketoesters

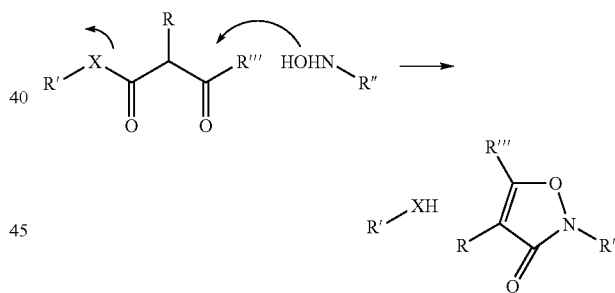

E. Acylation

Pyrimidine Formation by Reaction of Thioureas with Alpha-Ketoesters

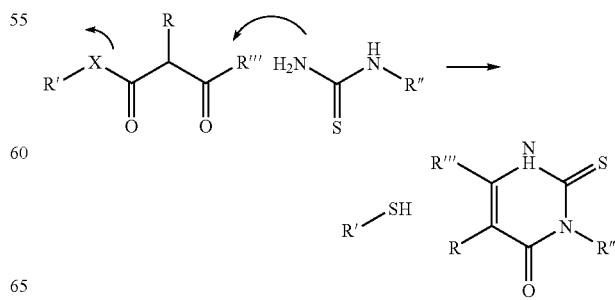

F. Acylation
Pyrimidine Formation by Reaction of Ureas with Malonates

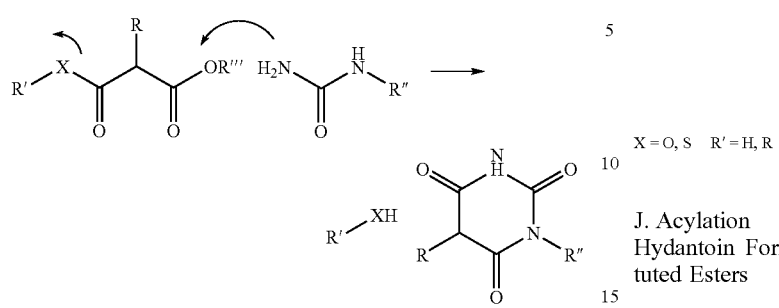

G. Acylation
Coumarine or Quinolinon Formation by a Heck Reaction Followed by a Nucleophilic Substitution

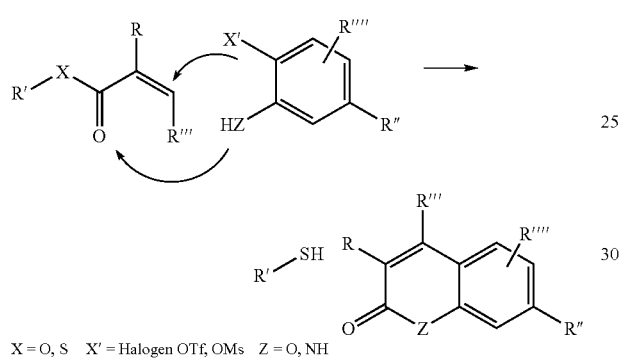

X = O, S   X' = Halogen OTf, OMs   Z = O, NH

H. Acylation
Phthalhydrazide formation by reaction of Hydrazines and Phthalimides

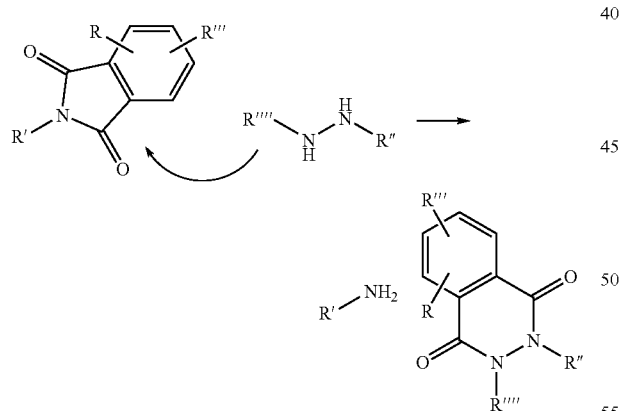

I. Acylation
Diketopiperazine Formation by Reaction of Amino Acid Esters

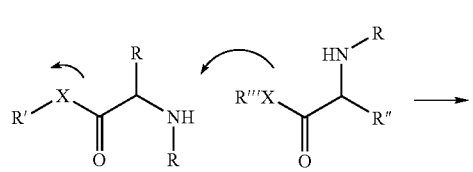

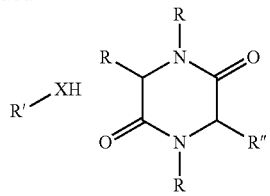

X = O, S   R' = H, R

J. Acylation
Hydantoin Formation by Reaction of Urea and α-Substituted Esters

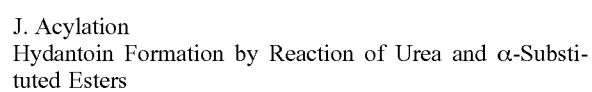

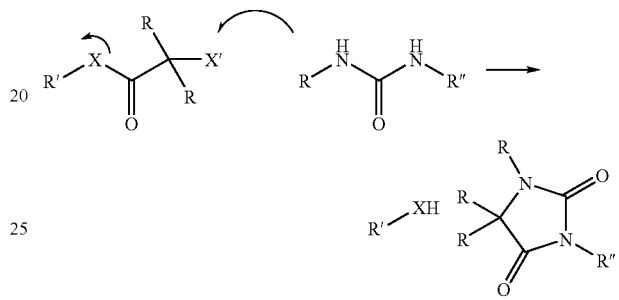

X = O, S
X' = Hal, OTos, OMs, etc.

K. Alkylating Monomer Building Blocks (Reactants)—Principle
Alkylated Compounds by Reaction of Sulfonates with Nucleofiles

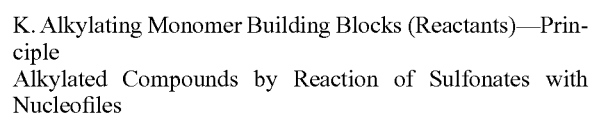

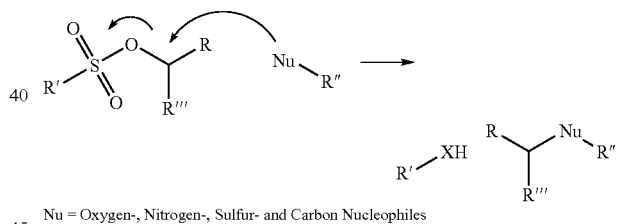

Nu = Oxygen-, Nitrogen-, Sulfur- and Carbon Nucleophiles

L. Vinylating Monomer Building Blocks (Reactants)—Principle

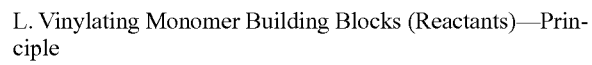

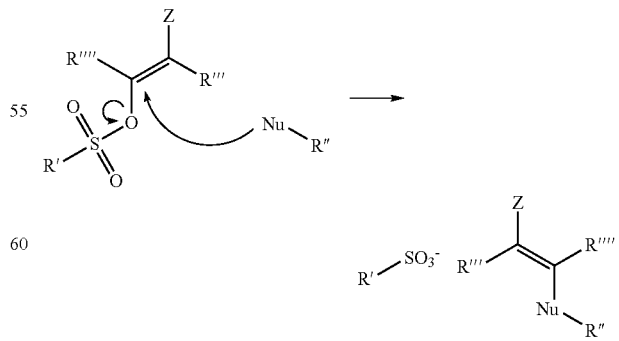

Z = CN, COOR, COR, NO$_2$, SO$_2$R, S(=O)R, SO$_2$NR, F
Nu = Oxygen-, Nitrogen-, Sulfur- and Carbon Nucleophiles M. Heteroatom Electrophiles
Disulfide Formation by Reaction of Pyridyl Disulfide with Mercaptanes

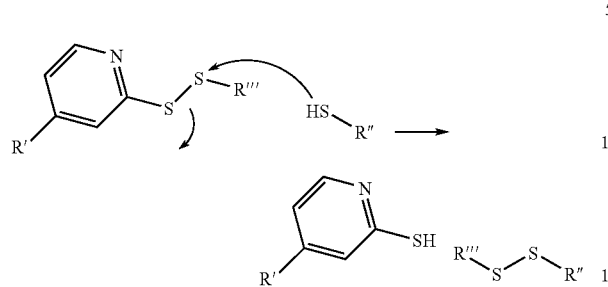

N. Acylation
Benzodiazepinone Formation by Reaction of Amino Acid Esters and Amino Ketones

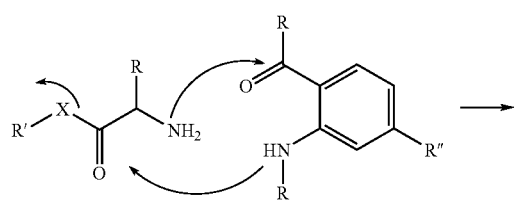

X = O, S

Addition to Carbon-Hetero Multiple Bonds:
O. Wittig/Horner-Wittig-Emmons Reagents
Substituted Alkene Formation by Reaction of Phosphonates with Aldehydes or Ketones

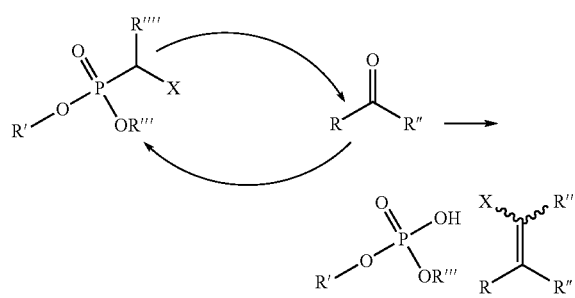

X = EWG

Transition Metal Catalysed Reactions
P. Arylation
Biaryl Formation by the Reaction of Boronates with Aryls or Heteroaryls

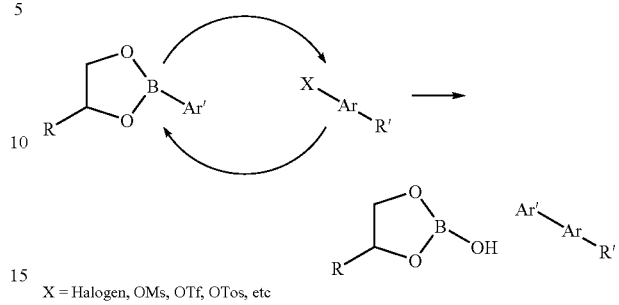

X = Halogen, OMs, OTf, OTos, etc

Q. Arylation
Biaryl Formation by the Reaction of Boronates with Aryls or Heteroaryls

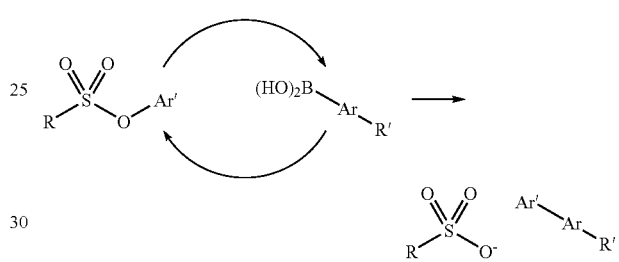

R. Arylation
Vinylarene Formation by the Reaction of Alkenes with Aryls or Heteroaryls

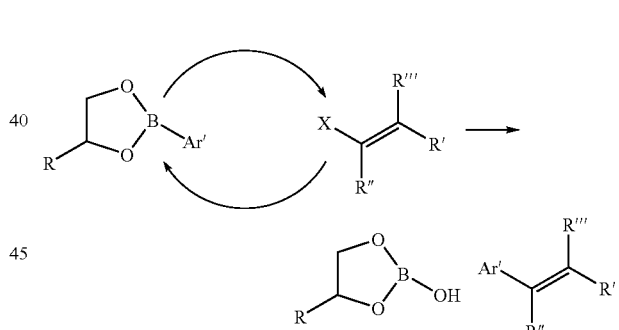

X = Halogen, OMs, OTf, OTos, etc

S. Alkylation
Alkylation of Arenes/Hetarens by the Reaction with Alkyl Boronates

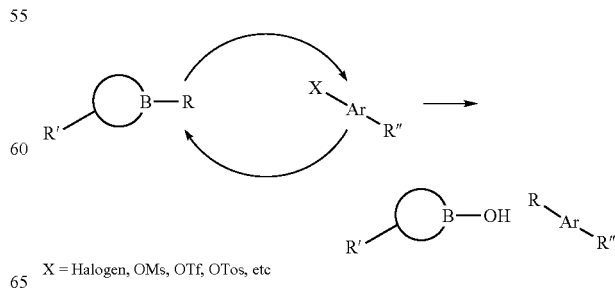

X = Halogen, OMs, OTf, OTos, etc

T. Alkylation

Alkylation of Arenas/Hetarenes by Reaction with Enolethers

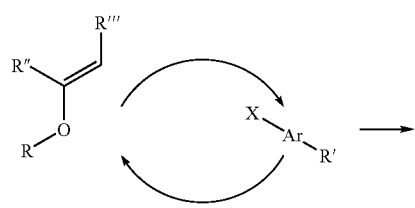

X = Halogen, OMs, OTf, OTos, etc

Nucleophilic Substitution Using Activation of Nucleophiles
U. Condensations
Alkylation of Aldehydes with Enolethers or Enamines

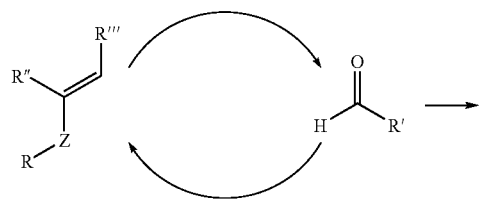

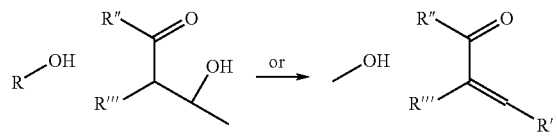

Z = NR, O; X = Halogen, OMs, OTf, OTos, etc

V. Alkylation
Alkylation of Aliphatic Halides or Tosylates with Enolethers or Enamines

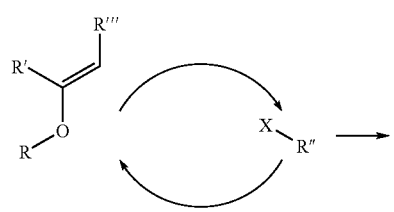

X = Halogen, OMs, OTf, OTos, etc

Cycloadditions
W. [2+4] Cycloadditions

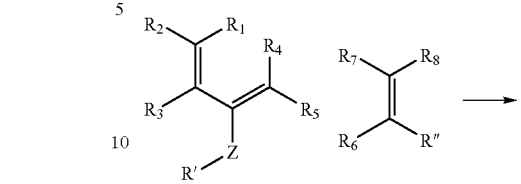

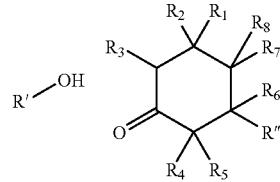

X. [2+4] Cycloadditions

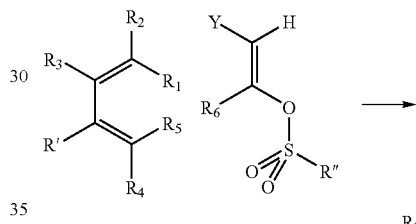

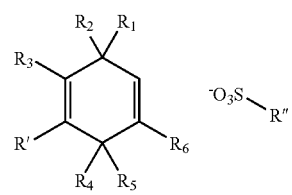

Y, CN, COOR, COR, $NO_2$, $SO_2R$, $S(=O)R$, $SO_2NR_2$, F

Y. [3+2] Cycloadditions

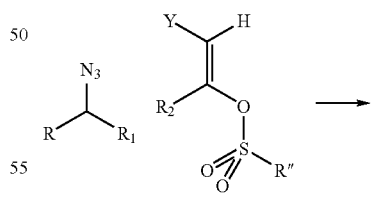

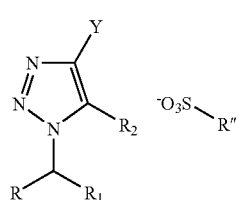

Y, CN, COOR, COR, $NO_2$, $SO_2R$, $S(=O)R$, $SO_2NR_2$, F

Z. [3+2] Cycloadditions

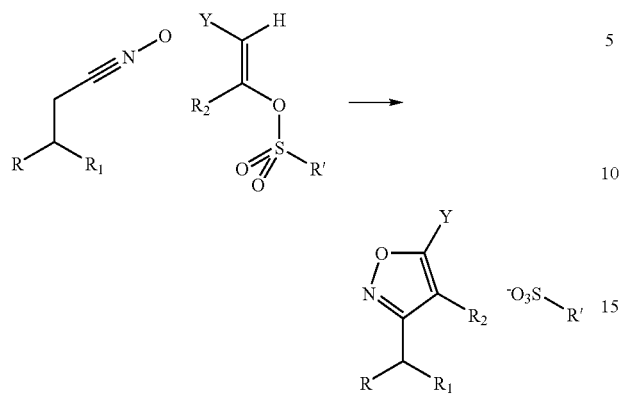

Y, CN, COOR, COR, NO₂, SO₂R, S(=O)R, SO₂NR₂, F

The synthesis of the molecule can involve one or more of the below illustrated reactions.

Examples of nucleophilic substitution reactions involved in one or more molecule synthesis steps.

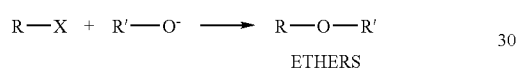
ETHERS

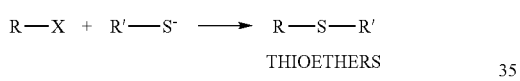
THIOETHERS

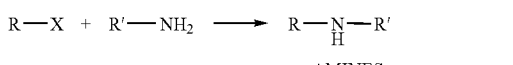
sec-AMINES

tert-AMINES

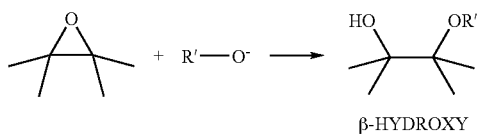
β-HYDROXY ETHERS

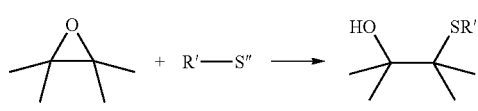
β-HYDROXY THIOETHERS

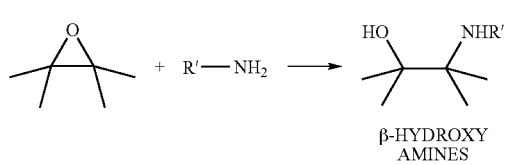
β-HYDROXY AMINES

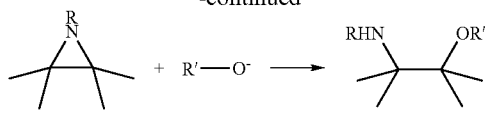
β-AMINO ETHERS

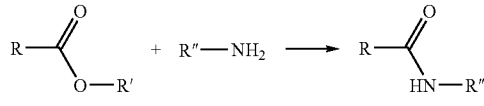
AMIDES

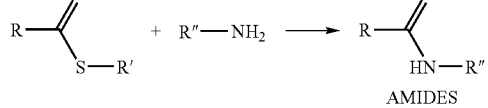
AMIDES

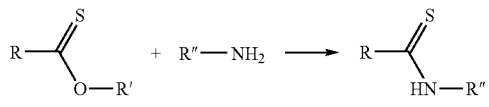
THIOAMIDES

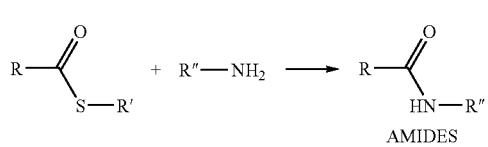
AMIDES

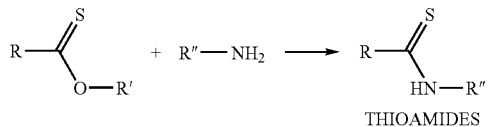
THIOAMIDES

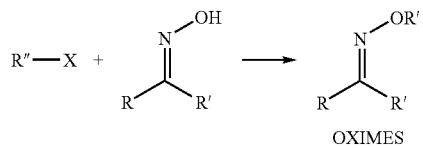
OXIMES

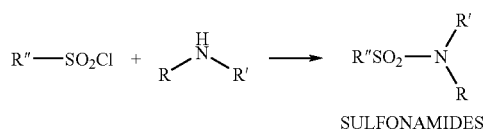
SULFONAMIDES

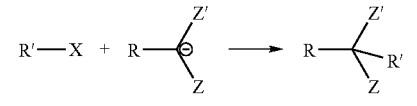
DI- AND TRI-FUNCTIONAL COMPOUNDS

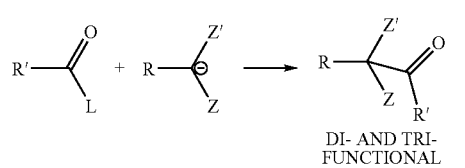
DI- AND TRI-FUNCTIONAL COMPOUNDS

Z', Z = COOR, CHO, COR, CONR"₂, COO⁻, NO₂, SOR, SO₂R, SO₂NR"₂, CN, ect.

Aromatic nucleophilic substitutions

SUBSTITUTED AROMATIC COMPOUNDS

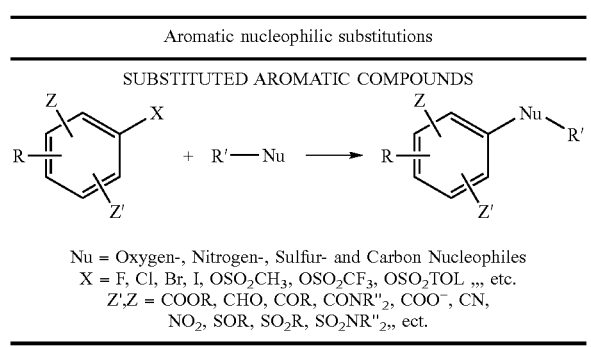

Nu = Oxygen-, Nitrogen-, Sulfur- and Carbon Nucleophiles
X = F, Cl, Br, I, $OSO_2CH_3$, $OSO_2CF_3$, $OSO_2TOL$ ,,, etc.
Z',Z = COOR, CHO, COR, $CONR''_2$, $COO^-$, CN, $NO_2$, SOR, $SO_2R$, $SO_2NR''_2$, ect.

Transition metal catalysed reactions

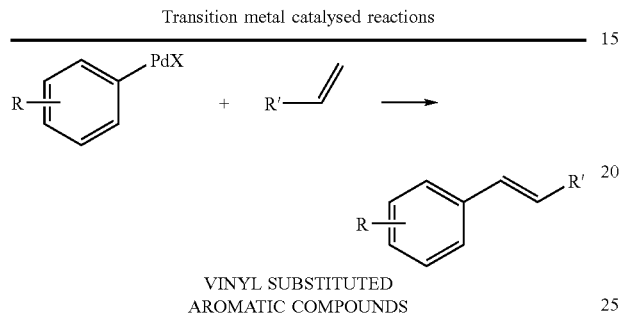

VINYL SUBSTITUTED AROMATIC COMPOUNDS

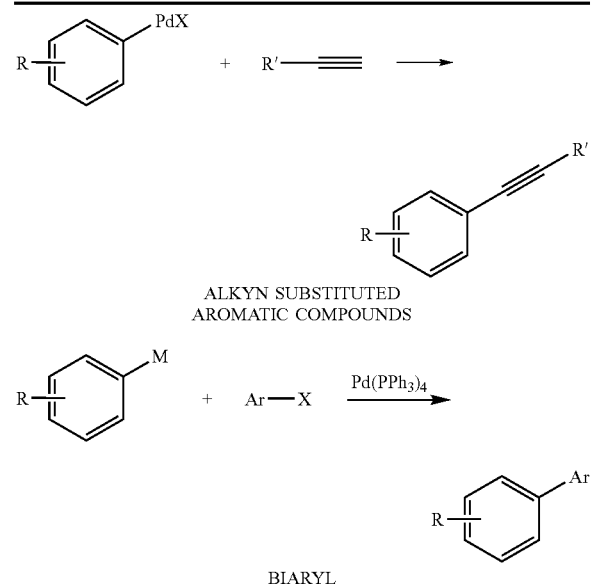

ALKYN SUBSTITUTED AROMATIC COMPOUNDS

BIARYL COMPOUNDS

Addition to Carbon-Carbon Multiple Bonds

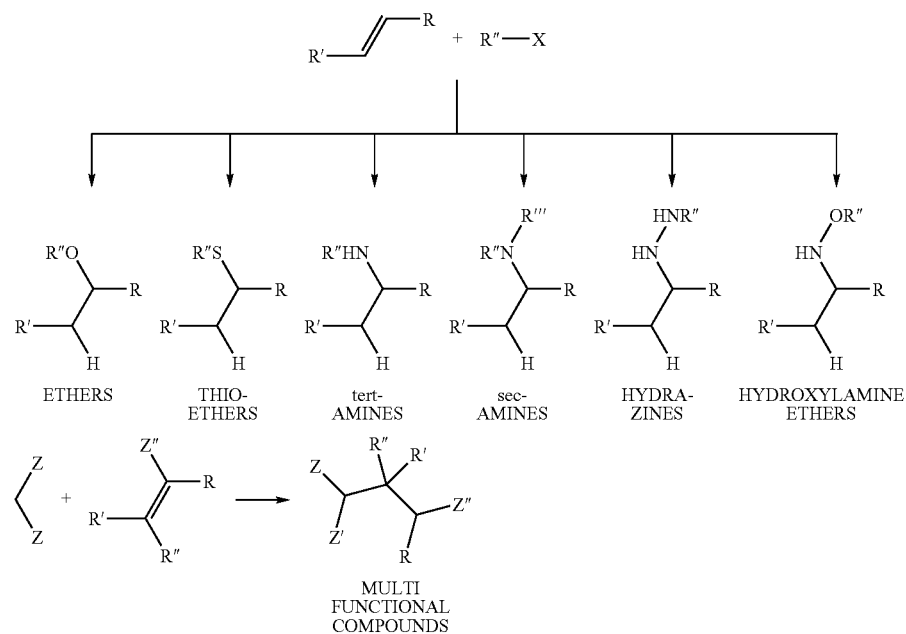

ETHERS — THIO-ETHERS — tert-AMINES — sec-AMINES — HYDRA-ZINES — HYDROXYLAMINE ETHERS

MULTI FUNCTIONAL COMPOUNDS

Z = H, Alkyl, Z', Ar
Z'' = COOR, CHO, COR, $CONR''_2$, CN, $NO_2$, SOR, $SO_2R$, $SO_2NR''_2$, , ect.
Z' = Z''
R = R', = R'', = Z

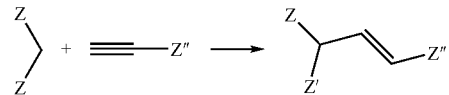

DI- AND TRI-FUNCTIONAL ALKENES

Z = H, Alkyl, Ar
Z'' = Z', Alkyl, Ar,
Z' = COOR, CHO, COR, $CONR''_2$, CN, $NO_2$, SOR, $SO_2R$, $SO_2NR''_2$, ect.

Cycloaddition to Multiple Bounds

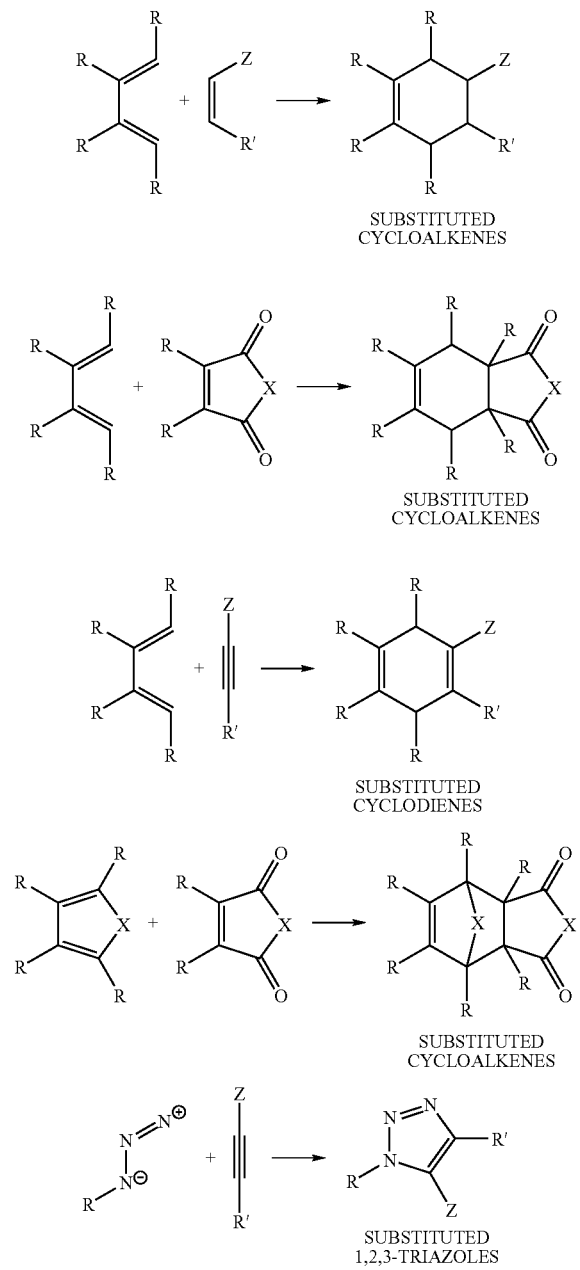

Z = COOR, CHO, COR, COOH, COAr CN, NO₂, Ar, CH₂OH, CH₂NH₂, CH₂CN, SOR, SO₂R etc.
R = H, Alkyl, Ar, Z
X = O, NR, CR₂, S, Addition to Carbon-Hetero Multiple Bonds

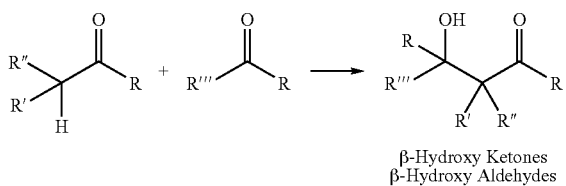

β-Hydroxy Ketones
β-Hydroxy Aldehydes

-continued

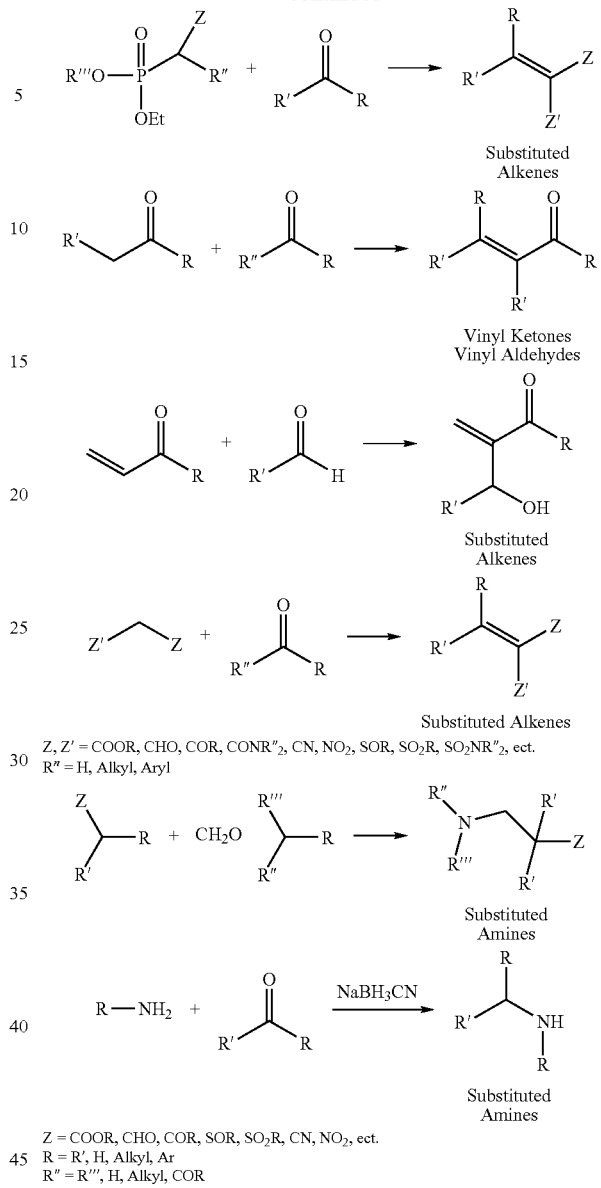

Substituted Alkenes

Vinyl Ketones
Vinyl Aldehydes

Substituted Alkenes

Substituted Alkenes

Z, Z' = COOR, CHO, COR, CONR"₂, CN, NO₂, SOR, SO₂R, SO₂NR"₂, ect.
R" = H, Alkyl, Aryl Substituted Amines Substituted Amines Z = COOR, CHO, COR, SOR, SO₂R, CN, NO₂, ect.
R = R', H, Alkyl, Ar
R" = R''', H, Alkyl, COR In the above illustrated chemical reactions, R, R', R", R''', R'''', R1, R2, R3, R4, R5, R6, R7, R8, respectively, are selected independently from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl, carboxy, substituted and unsubstituted carboxyalkyl, carbonyl, substituted and unsubstituted alkylcarbonyl, substituted and unsubstituted alkylcarbonylalkyl, substituted and unsubstituted alkoxycarbonyl, substituted and unsubstituted alkoxycarbonylalkyl, aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl, substituted and unsubstituted aminoalkyl, substituted and unsubstituted alkylaminoalkyl, amidino, cyanoamidino, substituted and unsubstituted heterocyclicalkyl, substituted and unsubstituted aralkyl, substituted and unsubstituted cycloalkyl, substituted and unsubstituted cycloalkenyl, substituted and unsubstituted alkylthio, substituted and unsubstituted alkylsulfinyl, substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl, acyl, acylamino, substituted and unsubstituted arylthio, substituted and unsubstituted aralkylthio, substituted and unsubstituted aryloxy, substituted and unsubstituted aralkoxy, substituted and unsubstituted haloaralkyl, substituted and unsubstituted carboxyhaloalkyl, substituted and unsubstituted alkoxycarbonylhaloalkyl, substituted and unsubstituted aminocarbonylhaloalkyl, substituted and unsubstituted alkylaminocarbonylhaloalkyl, substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

Further reaction schemes in accordance with the present invention are disclosed herein below.

A. Acylation Reactions

General route to the formation of acylating reactants and the use of these:

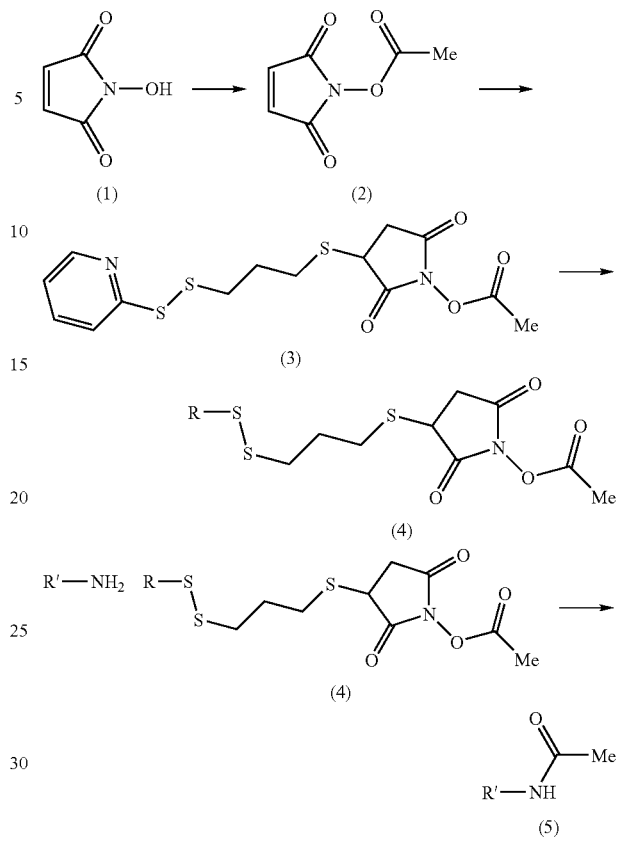

N-hydroxymaleimide (1) may be acylated by the use of an acylchloride e.g. acetylchloride or alternatively acylated in e.g. THF by the use of dicyclohexylcarbodiimide or diisopropylcarbodiimide and acid e.g. acetic acid. The intermediate may be subjected to Michael addition by the use of excess 1,3-propanedithiol, followed by reaction with either 4,4'-dipyridyl disulfide or 2,2'-dipyridyl disulfide. This intermediate (3) may then be loaded onto an oligonucleotide carrying a thiol handle to generate the reactant (4). Obviously, the intermediate (2) can be attached to the oligonucleotide using another linkage than the disulfide linkage, such as an amide linkage and the N-hydroxymaleimide can be distanced from the oligonucleotide using a variety of spacers.

The reactant (4) may be reacted with an identifier oligonucleotide comprising a recipient amine group e.g. by following the procedure: The reactant (4) (1 nmol) is mixed with an amino-oligonucleotide (1 nmol) in hepes-buffer (20 μL of a 100 mM hepes and 1 M NaCl solution, pH=7.5) and water (39 uL). The oligonucleotides are annealed together by heating to 50° C. and cooling (2° C./second) to 30° C. The mixture is then left o/n at a fluctuating temperature (10° C. for 1 second then 35° C. for 1 second), to yield the product (5).

In more general terms, the reactants indicated below is capable of transferring a chemical entity (CE) to a recipient nucleophilic group, typically an amine group. The bold lower horizontal line illustrates the reactant and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

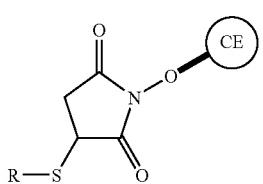

Another reactant which may form an amide bond is

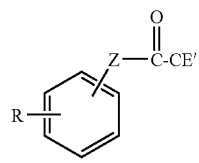

R may be absent or $NO_2$, $CF_3$, halogen, preferably Cl, Br, or I, and Z may be S or O. This type of reactant is disclosed in Danish patent application No. PA 2002 0951 and US provisional patent application filed 20 Dec. 2002 with the title "A reactant capable of transferring a functional entity to a recipient reactive group". The content of both patent application are incorporated herein in their entirety by reference.

A nucleophilic group can cleave the linkage between Z and the carbonyl group thereby transferring the chemical entity —(C=O)—CE' to said nucleophilic group.

CE and CE' are preferably selected from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl,
carboxy, substituted and unsubstituted carboxyalkyl,
carbonyl, substituted and unsubstituted alkylcarbonyl, substituted and unsubstituted alkylcarbonylalkyl,
substituted and unsubstituted alkoxycarbonyl, substituted and unsubstituted alkoxycarbonylalkyl,
aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl,
substituted and unsubstituted aminoalkyl, substituted and unsubstituted alkylaminoalkyl,
amidino,
cyanoamidino,
substituted and unsubstituted heterocyclicalkyl,
substituted and unsubstituted aralkyl,
substituted and unsubstituted cycloalkyl,
substituted and unsubstituted cycloalkenyl,
substituted and unsubstituted alkylthio,
substituted and unsubstituted alkylsulfinyl,
substituted and unsubstituted N-alkylamino, substituted and unsubstituted N,N-dialkylamino,
substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-alkyl-N-arylaminoalkyl, substituted and unsubstituted N-aralkyl-N-alkylaminoalkyl,
acyl, acylamino,
substituted and unsubstituted arylthio, substituted and unsubstituted aralkylthio,
substituted and unsubstituted aryloxy, substituted and unsubstituted aralkoxy,
substituted and unsubstituted haloaralkyl,
substituted and unsubstituted carboxyhaloalkyl,
substituted and unsubstituted alkoxycarbonylhaloalkyl, substituted and unsubstituted aminocarbonylhaloalkyl, substituted and unsubstituted alkylaminocarbonylhaloalkyl,
substituted and unsubstituted alkoxycarbonylcyanoalkenyl,
substituted and unsubstituted carboxyalkylaminocarbonyl,
substituted and unsubstituted aralkoxycarbonylalkylaminocarbonyl,
substituted and unsubstituted cycloalkylalkyl, and
substituted and unsubstituted aralkenyl.

B. Alkylation

General route to the formation of alkylating/vinylating reactants and use of these:

Alkylating Reactants may have the Following General Structure:

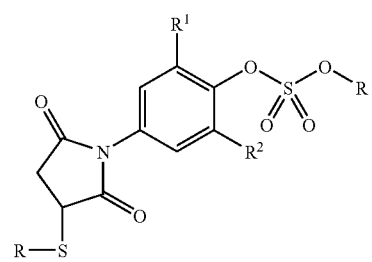

-continued

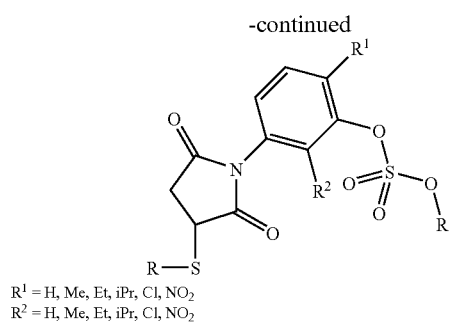

$R^1$ = H, Me, Et, iPr, Cl, $NO_2$
$R^2$ = H, Me, Et, iPr, Cl, $NO_2$ $R^1$ and $R^2$ may be used to tune the reactivity of the sulphate to allow appropriate reactivity. Chloro and nitro substitution will increase reactivity. Alkyl groups will decrease reactivity. Ortho substituents to the sulphate will due to steric reasons direct incoming nucleophiles to attack the R-group selectively and avoid attack on sulphur.

An example of the formation of an alkylating reactant and the transfer of a functional entity is depicted below:

3-Aminophenol (6) is treated with maleic anhydride, followed by treatment with an acid e.g. $H_2SO_4$ or $P_2O_5$ and heated to yield the maleimide (7). The ring closure to the maleimide may also be achieved when an acid stable O-protection group is used by treatment with $Ac_2O$, with or without heating, followed by O-deprotection. Alternatively reflux in $Ac_2O$, followed by O-deacetylation in hot water/dioxane to yield (7).

Further treatment of (7) with $SO_2Cl_2$, with or without triethylamine or potassium carbonate in dichloromethane or a higher boiling solvent will yield the intermediate (8), which may be isolated or directly further transformed into the aryl alkyl sulphate by the quench with the appropriate alcohol, in this case MeOH, whereby (9) will be formed.

The organic moiety (9) may be connected to an oligonucleotide, as follows: A thiol carrying oligonucleotide in buffer 50 mM MOPS or hepes or phosphate pH 7.5 is treated with a 1-100 mM solution and preferably 7.5 mM solution of the organic reactant (9) in DMSO or alternatively DMF, such that the DMSO/DMF concentration is 5-50%, and preferably 10%. The mixture is left for 1-16 h and preferably 2-4 h at 25° C. to give the alkylating agent in this case a methylating reactant (10).

The reaction of the alkylating reactant (10) with an amine bearing nascent bifunctional complex may be conducted as follows: The bifunctional complex (1 nmol) is mixed the reactant (10) (1 nmol) in hepes-buffer (20 μL of a 100 mM hepes and 1 M NaCl solution, pH=7.5) and water (39 uL). The oligonucleotides are annealed to each other by heating to 50° C. and cooled (2° C./second) to 30° C. The mixture is then left o/n at a fluctuating temperature (10° C. for 1 second then 35° C. for 1 second), to yield the methylamine reaction product (11).

In more general terms, a reactant capable of transferring a chemical entity to a receiving reactive group forming a single bond is

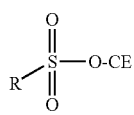

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold.

CE is defined as herein above under section A (acylation reactions).

C. Vinylation Reactions

A vinylating reactant may be prepared and used similarly as described above for an alkylating reactant. Although instead of reacting the chlorosulphonate (8 above) with an alcohol, the intermediate chlorosulphate is isolated and treated with an enolate or O-trialkylsilylenolate with or without the presence of fluoride. E.g.

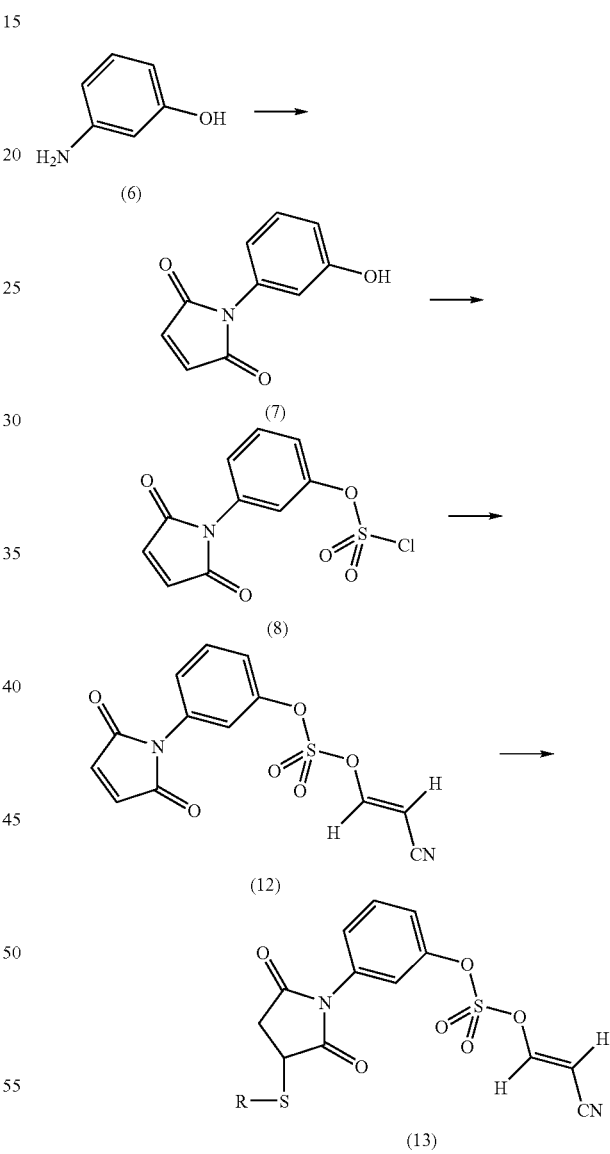

Formation of an Exemplary Vinylating Reactant (13):

The thiol carrying oligonucleotide in buffer 50 mM MOPS or hepes or phosphate pH 7.5 is treated with a 1-100 mM solution and preferably 7.5 mM solution of the organic moiety (12) in DMSO or alternatively DMF, such that the DMSO/DMF concentration is 5-50%, and preferably 10%. The mixture is left for 1-16 h and preferably 2-4 h at 25° C. to give the vinylating reactant (13).

The sulfonylenolate (13) may be used to react with amine carrying scaffold to give an enamine (14a and/or 14b) or e.g. react with a carbanion to yield (15a and/or 15b). E.g.

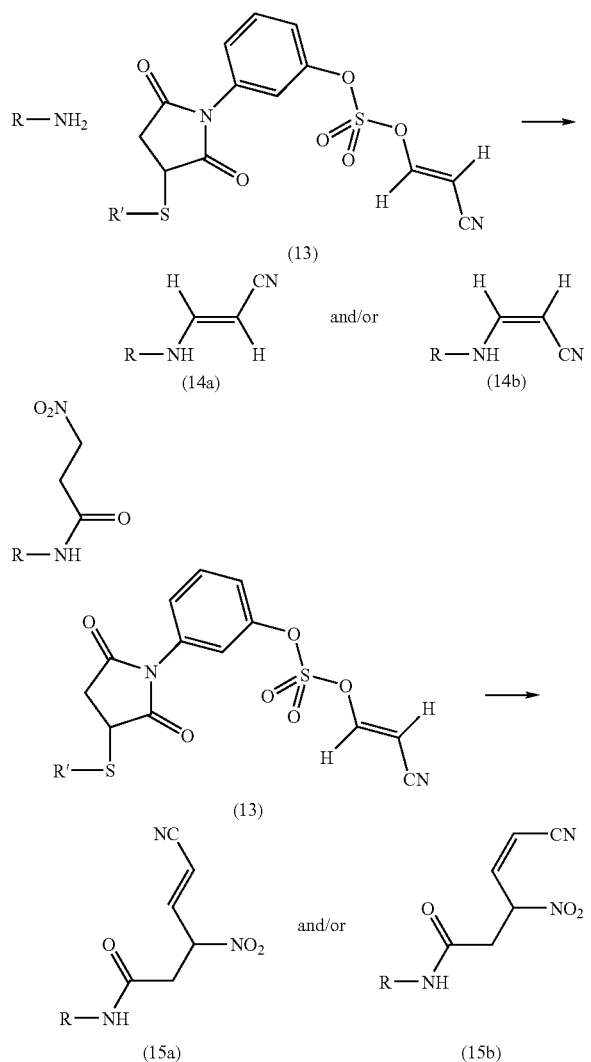

The reaction of the vinylating reactant (13) and an amine or nitroalkyl carrying identifier may be conducted as follows:

The amino-oligonucleotide (1 nmol) or nitroalkyl-oligonucleotide (1 nmol) identifier is mixed with the reactant (1 nmol) (13) in 0.1 M TAPS, phosphate or hepes-buffer and 300 mM NaCl solution, pH=7.5-8.5 and preferably pH=8.5. The oligonucleotides are annealed to the template by heating to 50° C. and cooled (2° C./second) to 30° C. The mixture is then left o/n at a fluctuating temperature (10° C. for 1 second then 35° C. for 1 second), to yield reaction product (14a/b or 15a/b). Alternative to the alkyl and vinyl sulphates described above may equally effective be sulphonates as e.g. (31) (however with R" instead as alkyl or vinyl), described below, prepared from (28, with the phenyl group substituted by an alkyl group) and (29), and be used as alkylating and vinylating agents.

Another reactant capable of forming a double bond by the transfer of a chemical entity to a recipient aldehyde group is shown below. A double bond between the carbon of the aldehyde and the chemical entity is formed by the reaction.

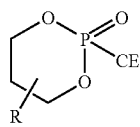

The above reactant is comprised by the Danish patent application No. DK PA 2002 01952 and the US provisional patent application filed 20 Dec. 2002 with the title "A reactant capable of transferring a functional entity to a recipient reactive group forming a C=C double bond". The content of both patent applications are incorporated herein in their entirety by reference.

CE is defined as herein above under section A (acylation reactions).

D. Alkenylidation Reactions

General route to the formation of Wittig and HWE reactants and use of these:

Commercially available compound (16) may be transformed into the NHS ester (17) by standard means, i.e. DCC or DIC couplings. An amine carrying oligonucleotide in buffer 50 mM MOPS or hepes or phosphate pH 7.5 is treated with a 1-100 mM solution and preferably 7.5 mM solution of the organic compound in DMSO or alternatively DMF, such that the DMSO/DMF concentration is 5-50%, and preferably 10%. The mixture is left for 1-16 h and preferably 2-4 h at 25° C. to give the phosphine bound precursor reactant (18). This precursor reactant is further transformed by addition of the appropriate alkylhalide, e.g. N,N-dimethyl-2-iodoacetamide as a 1-100 mM and preferably 7.5 mM solution in DMSO or DMF such that the DMSO/DMF concentration is 5-50%, and preferably 10%. The mixture is left for 1-16 h and preferably 2-4 h at 25° C. to give the reactant (19). As an alternative to this, the organic compound (17) may be P-alkylated with an alkylhalide and then be coupled onto an amine carrying oligonucleotide to yield (19).

An aldehyde carrying identifier (20), may be formed by the reaction between the NHS ester of 4-formylbenzoic acid and an amine carrying oligonucleotide, using conditions similar to those described above. The identifier (20) reacts with (19) under slightly alkaline conditions to yield the alkene (21).

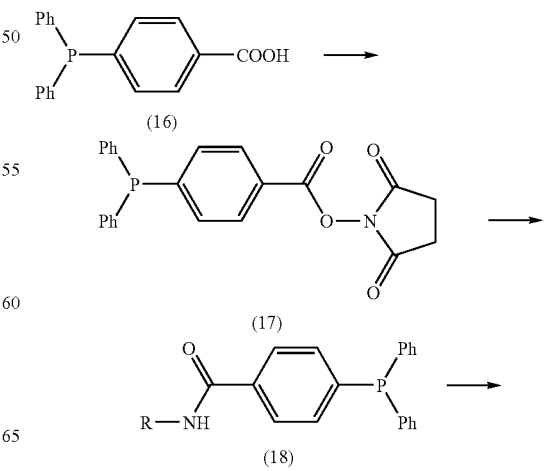

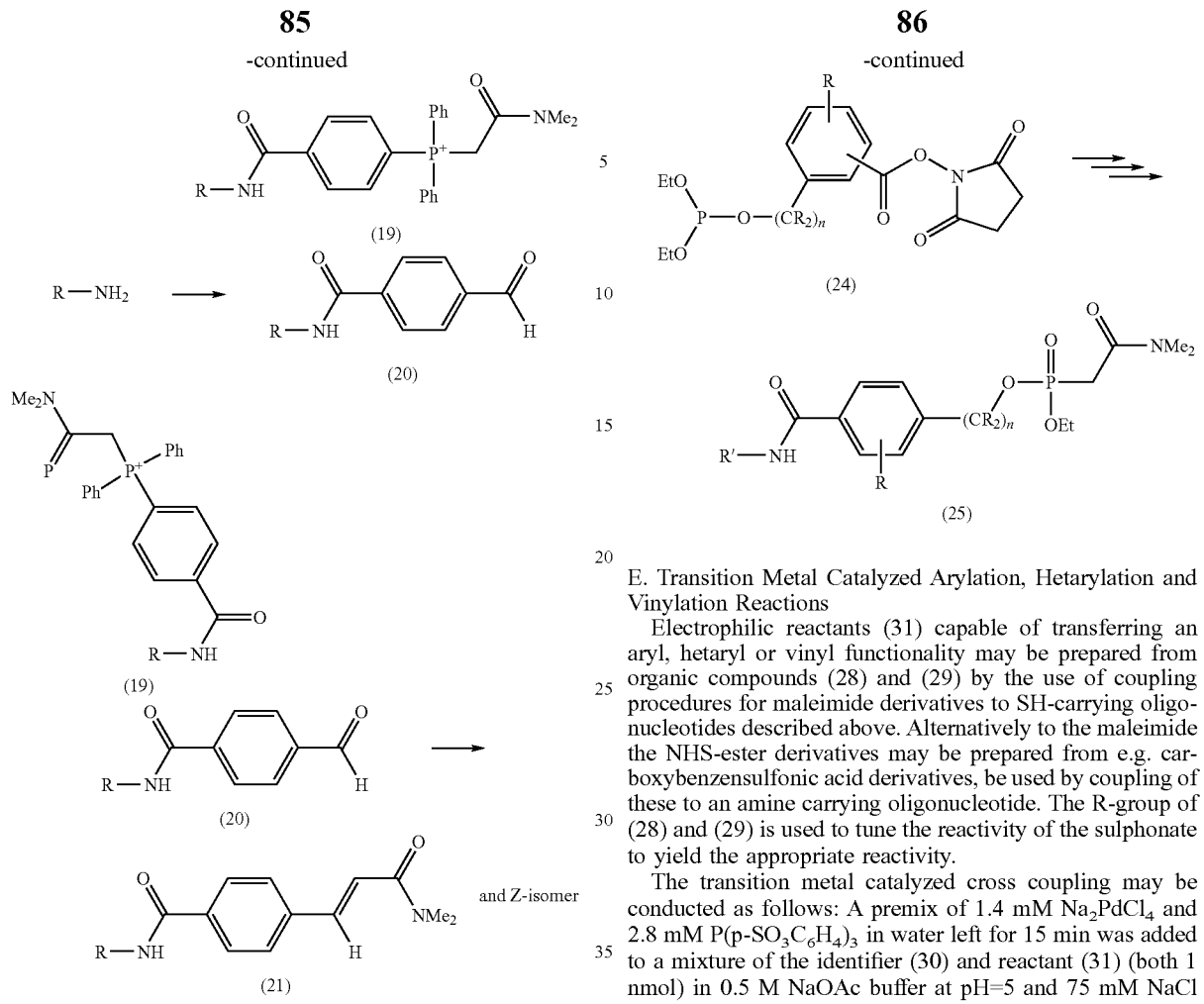

The reaction of monomer reactants (19) and identifier (20) may be conducted as follows: The identifier (20) (1 nmol) is mixed with reactant (19) (1 nmol) in 0.1 M TAPS, phosphate or hepes-buffer and 1 M NaCl solution, pH=7.5-8.5 and preferably pH=8.0. The reaction mixture is left at 35-65° C. preferably 58° C. over night to yield reaction product (21).

As an alternative to (17), phosphonates (24) may be used instead. They may be prepared by the reaction between diethylchlorophosphite (22) and the appropriate carboxy carrying alcohol. The carboxylic acid is then transformed into the NHS ester (24) and the process and alternatives described above may be applied. Although instead of a simple P-alkylation, the phosphite may undergo Arbuzov's reaction and generate the phosphonate. Reactant (25) benefits from the fact that it is more reactive than its phosphonium counterpart (19).

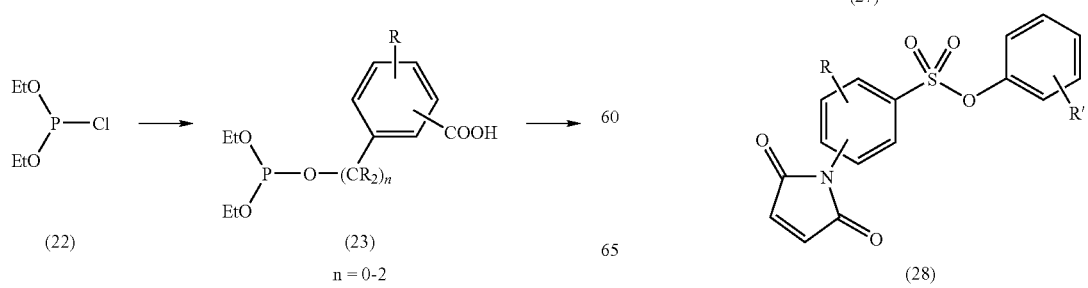

n = 0-2

E. Transition Metal Catalyzed Arylation, Hetarylation and Vinylation Reactions

Electrophilic reactants (31) capable of transferring an aryl, hetaryl or vinyl functionality may be prepared from organic compounds (28) and (29) by the use of coupling procedures for maleimide derivatives to SH-carrying oligonucleotides described above. Alternatively to the maleimide the NHS-ester derivatives may be prepared from e.g. carboxybenzensulfonic acid derivatives, be used by coupling of these to an amine carrying oligonucleotide. The R-group of (28) and (29) is used to tune the reactivity of the sulphonate to yield the appropriate reactivity.

The transition metal catalyzed cross coupling may be conducted as follows: A premix of 1.4 mM $Na_2PdCl_4$ and 2.8 mM $P(p-SO_3C_6H_4)_3$ in water left for 15 min was added to a mixture of the identifier (30) and reactant (31) (both 1 nmol) in 0.5 M NaOAc buffer at pH=5 and 75 mM NaCl (final [Pd]=0.3 mM). The mixture is then left o/n at 35-65° C. preferably 58° C., to yield reaction product (32).

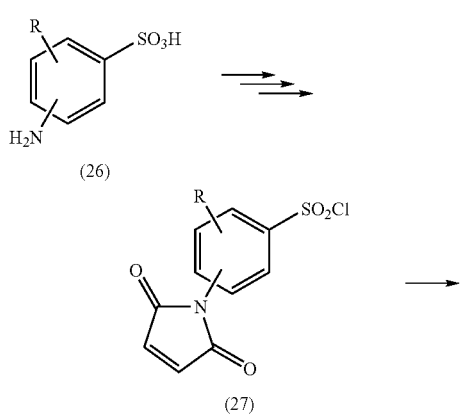

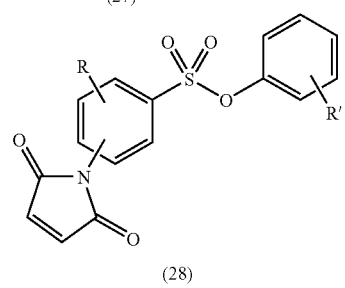

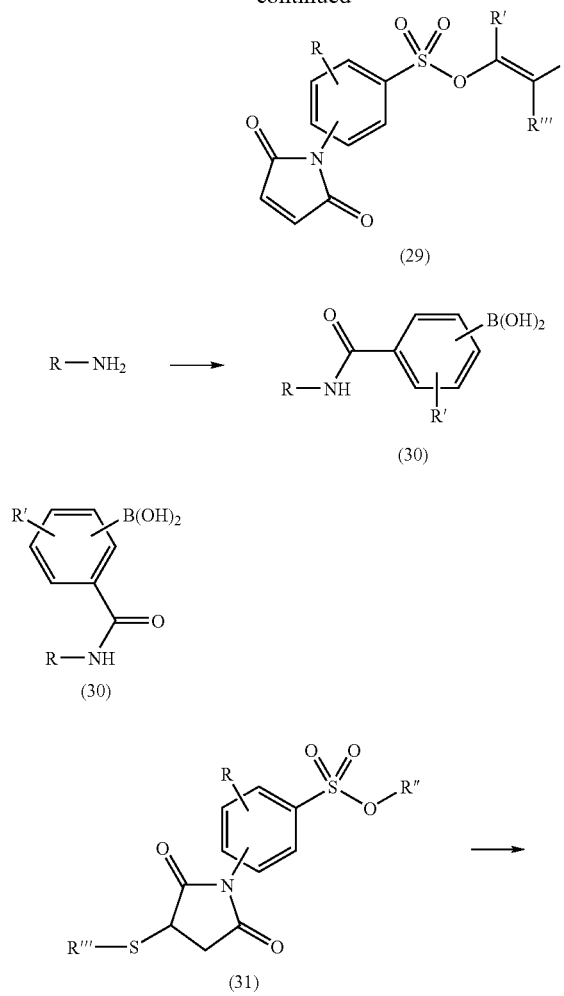

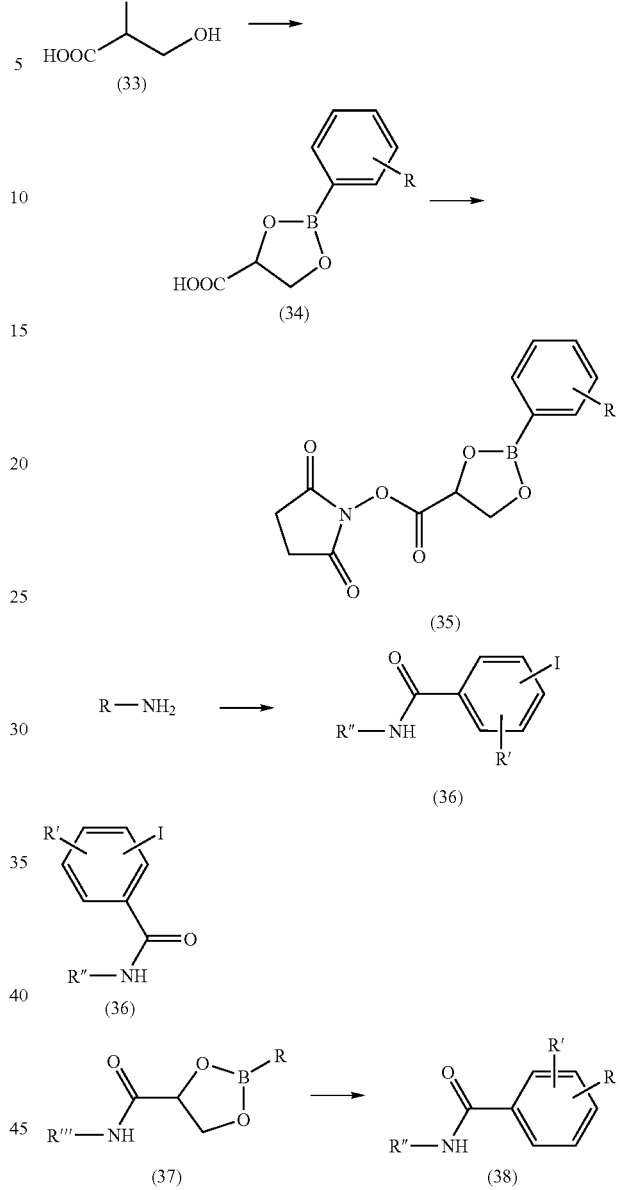

Corresponding nucleophilic monomer reactants capable of transferring an aryl, hetaryl or vinyl functionality may be prepared from organic compounds of the type (35). This is available by estrification of a boronic acid by a diol e.g. (33), followed by transformation into the NHS-ester derivative. The NHS-ester derivative may then be coupled to an oligonucleotide, by use of coupling procedures for NHS-ester derivatives to amine carrying oligonucleotides described above, to generate reactant type (37). Alternatively, maleimide derivatives may be prepared as described above and loaded onto SH-carrying oligonucleotides.

The transition metal catalyzed cross coupling is conducted as follows: A premix of 1.4 mM $Na_2PdCl_4$ and 2.8 mM $P(p\text{-}SO_3C_6H_4)_3$ in water left for 15 min was added to a mixture of the identifier (36) and the reactant (37) (both 1 nmol) in 0.5 M NaOAc buffer at pH=5 and 75 mM NaCl (final [Pd]=0.3 mM). The mixture is then left o/n at 35-65° C. preferably 58° C., to yield template bound (38).

F. Reactions of Enamine and Enolether Monomer Reactants

Reactants loaded with enamines and enolethers may be prepared as follows: For Z=NHR (R=H, alkyl, aryl, hetaryl), a 2-mercaptoethylamine may be reacted with a dipyridyl disulfide to generate the activated disulfide (40), which may then be condensed to a ketone or an aldehyde under dehydrating conditions to yield the enamine (41). For Z=OH, 2-mercaptoethanol is reacted with a dipyridyl disulfide, followed by O-tosylation (Z=OTs). The tosylate (40) may then be reacted directly with an enolate or in the presence of fluoride with a O-trialkylsilylenolate to generate the enolate (41).

The enamine or enolate (41) may then be coupled onto an SH-carrying oligonucleotide as described above to give the reactant (42).

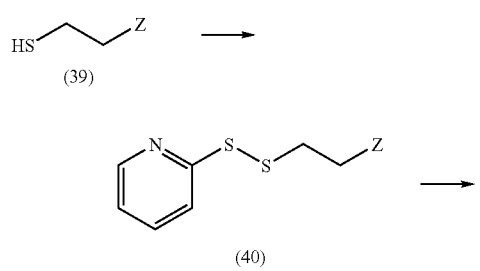

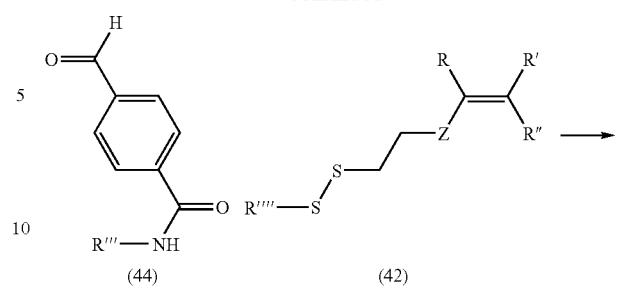

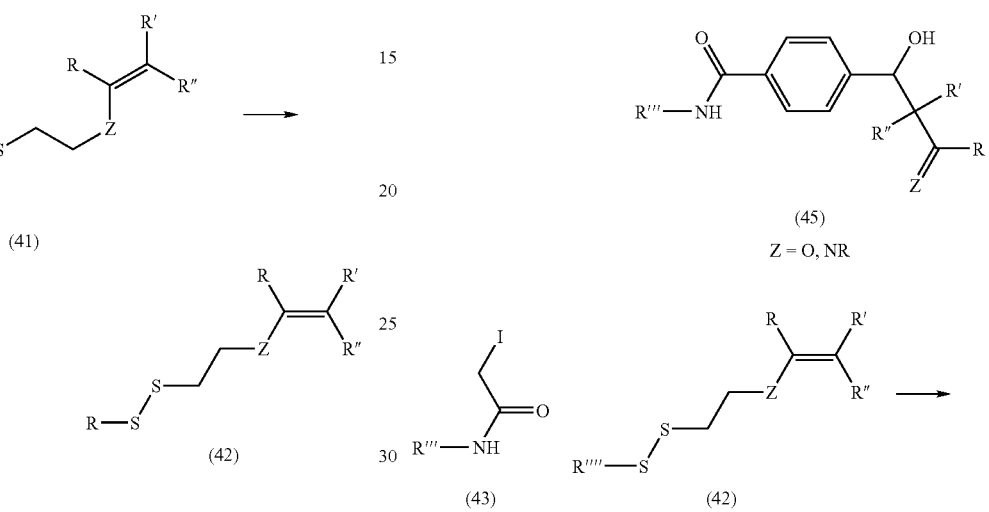

The reactant (42) may be reacted with a carbonyl carrying identifier oligonucleotide like (44) or alternatively an alkylhalide carrying oligonucleotide like (43) as follows: The reactant (42) (1 nmol) is mixed with the identifier (43) (1 nmol) in 50 mM MOPS, phosphate or hepes-buffer buffer and 250 mM NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield reaction product (46), where Z=O or NR. For compounds where Z=NR slightly acidic conditions may be applied to yield product (46) with Z=O.

The reactant (42) (1 nmol) is mixed with the identifier (44) (1 nmol) in 0.1 M TAPS, phosphate or hepes-buffer buffer and 300 mM NaCl solution, pH=7.5-8.5 and preferably pH=8.0. The reaction mixture is left at 35-65° C. preferably 58° C. over night or alternatively at a fluctuating temperature (10° C. for 1 second then 35° C. for 1 second) to yield reaction product (45), where Z=O or NR. For compounds where Z=NR slightly acidic conditions may be applied to yield product (45) with Z=O.

Enolethers type (13) may undergo cycloaddition with or without catalysis. Similarly, dienolethers may be prepared and used, e.g. by reaction of (8) with the enolate or trialkylsilylenolate (in the presence of fluoride) of an α,β-unsaturated ketone or aldehyde to generate (47), which may be loaded onto an SH-carrying oligonucleotide, to yield monomer reactant (48).

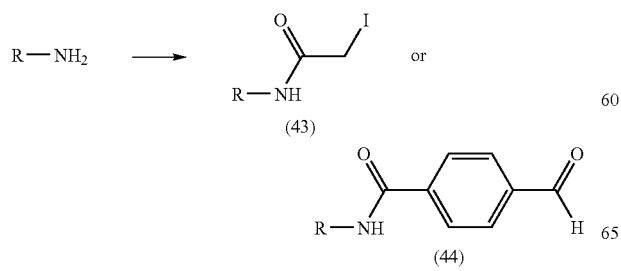

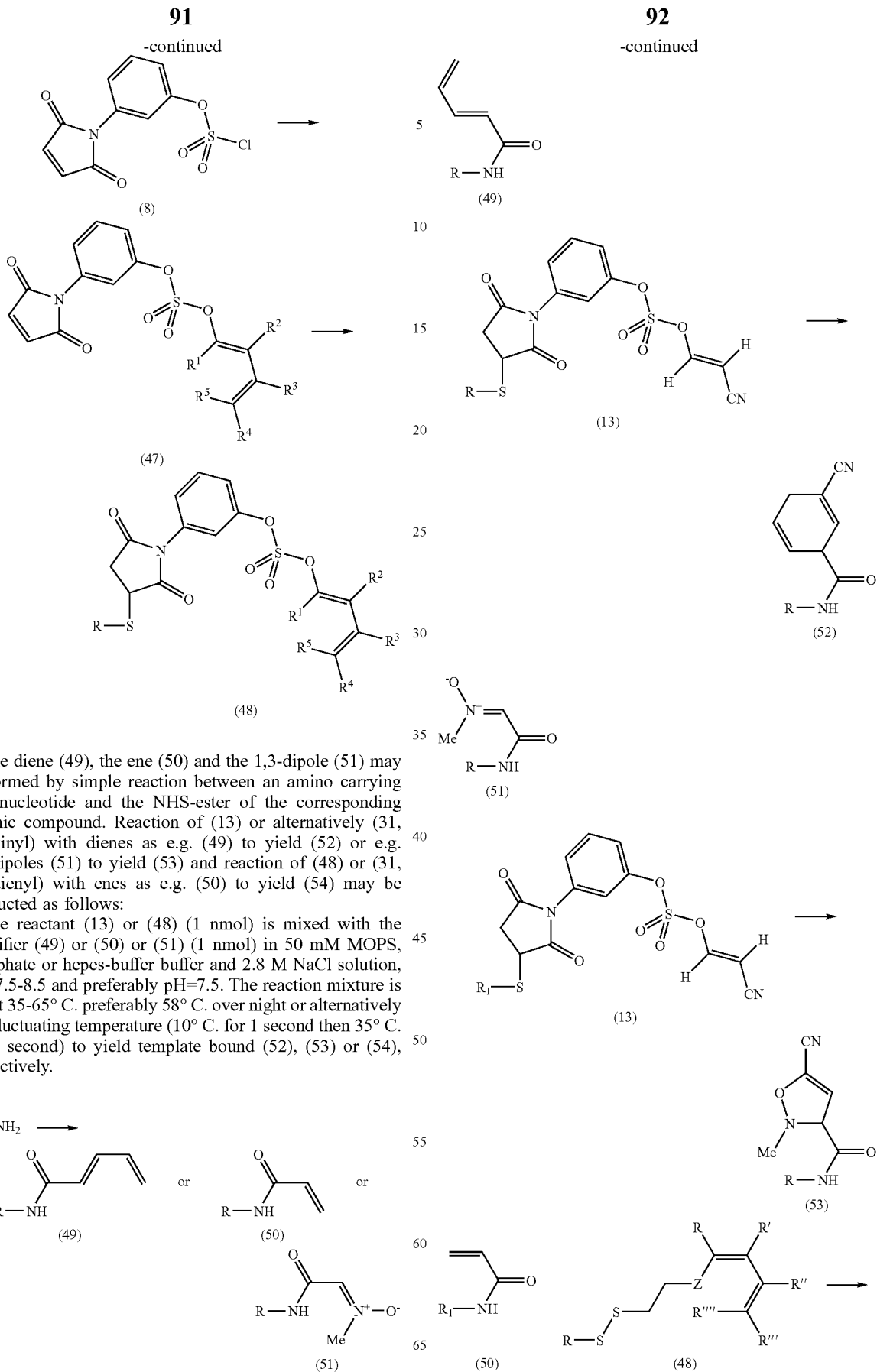

The diene (49), the ene (50) and the 1,3-dipole (51) may be formed by simple reaction between an amino carrying oligonucleotide and the NHS-ester of the corresponding organic compound. Reaction of (13) or alternatively (31, R″=vinyl) with dienes as e.g. (49) to yield (52) or e.g. 1,3-dipoles (51) to yield (53) and reaction of (48) or (31, R″=dienyl) with enes as e.g. (50) to yield (54) may be conducted as follows:

The reactant (13) or (48) (1 nmol) is mixed with the identifier (49) or (50) or (51) (1 nmol) in 50 mM MOPS, phosphate or hepes-buffer buffer and 2.8 M NaCl solution, pH=7.5-8.5 and preferably pH=7.5. The reaction mixture is left at 35-65° C. preferably 58° C. over night or alternatively at a fluctuating temperature (10° C. for 1 second then 35° C. for 1 second) to yield template bound (52), (53) or (54), respectively.

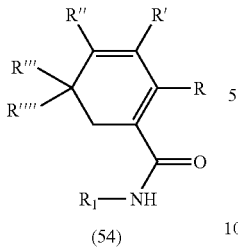

(54)

Cross-Link Cleavage Reactants

It may be advantageous to split the transfer of a chemical entity to a recipient reactive group into two separate steps, namely a cross-linking step and a cleavage step because each step can be optimized. A suitable reactant for this two step process is illustrated below:

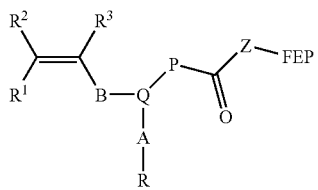

Initially, a reactive group appearing on the functional entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, $H^+$, or a Lewis acid. The cleavage results in a transfer of the group HZ-FEP- to the recipient moiety, such as a scaffold.

In the above formula

Z is O, S, $NR^4$

Q is N, $CR^1$

P is a valence bond, O, S, $NR^4$, or a group $C_{5-7}$arylene, $C_{1-6}$alkylene, $C_{1-6}$O-alkylene, $C_{1-6}$S-alkylene, $NR^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, B is a group comprising D-E-F, in which D is a valence bond or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, E is, when present, a valence bond, O, S, $NR^4$, or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —$NHNHR^6$, —C(O)$R^6$, —$SnR^6{}_3$, —B(O$R^6$)$_2$, —P(O) (O$R^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —CO$R^6$, —CN, —OSi$R^6{}_3$, —O$R^6$ and —$NR^6{}_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —O$R^3$—Si$R^3{}_3$ $R^9$ is =O, —F, —Cl, —Br, —I, —CN, —$NO_2$, —O$R^6$, —$NR^6{}_2$, —$NR^6$—C(O)$R^8$, —$NR^6$—C(O)O$R^8$, —$SR^6$, —S(O)$R^6$, —S(O)$_2R^6$, —COO$R^6$, —C(O)$NR^6{}_2$ and —S(O)$_2NR^6{}_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous $I_2$.

Reactant Reactions and Molecules Generated by such Reactions

A reactant can participate in a reaction with the chemical reaction site and/or in a reaction with other reactants and contributes to the a chemical structure of the final molecule. The reaction between the chemical reaction site and the one or more reactants, or between individual reactants, can take place under suitable conditions that favours the reaction.

Generally, a molecule is formed by reacting several chemical entities with each other and/or with a chemical reaction site, such as a scaffold moiety comprising a plurality of reactive groups or sites. In one embodiment of the invention, a nascent bifunctional complex is reacted with one or more reactants and with the respective tag(s) more than once preferably using a split-and-mix technique. The reactions can be repeated as often as necessary in order to obtain a molecule as one part of the bifunctional complex and an identifying oligonucleotide comprising the tags identifying the reactants which participated in the formation of the molecule.

The synthesis of a molecule according to the methods of the present invention can proceed via particular type(s) of coupling reaction(s), such as, but not limited to, one or more of the reactive group reactions cited herein above. In some embodiments, combinations of two or more reactive group reactions will occur, such as combinations of two or more of the reactive group reactions discussed above, or combinations of the reactions disclosed in Table 1. For example, reactants can be joined by a combination of amide bond formation (amino and carboxylic acid complementary groups) and reductive amination (amino and aldehyde or ketone complementary groups).

The reaction of the reactant(s) with each other and/or with the chemical reaction site on the one hand and the reaction of tag(s) with each other and/or with the priming site on the other hand may occur sequentially in any order or simultaneously. The choice of order can be influenced by e.g. type of enzyme, reaction conditions used, and the type of reactant(s). The chemical reaction site can comprise a single or multiple reactive groups capable of reacting with one or more reactants. In a certain aspect the chemical reaction site comprises a scaffold having one or more reactive groups attached.

A round or cycle of reaction can imply that a) a single reactant is reacted with the chemical reaction site, such as a scaffold, or with one or more reactant(s) having reacted with the chemical reaction site during a previous reaction round, and b) that the respective oligonucleotide tag identifying the reactant is reacted with another tag or with the priming site. However, a round or cycle of reaction can also imply that a) multiple reactants are reacted with the chemical reaction site, such as a scaffold, or with one or more reactant(s) having reacted with the chemical reaction site during a previous reaction round, and b) that respective oligonucleotide tags identifying the reactants are reacted with each other and/or with another tag and/or with the priming site. At least one tag reaction resulting in the tag being attached to another tag or to the priming site involves one or more enzymes.

A reactant comprising one or more chemical entities and one or more reactive groups can have any chemical structure. At least one reactive group, or a precursor thereof, reacts with the chemical reaction site or one or more reactive group(s) of one or more other reactants. A "bridging molecule" can act to mediate a connection or form a bridge between two reactants or between a reactant and a chemical reaction site.

The invention can be performed by reacting a single reactant with the nascent bifunctional complex and add the corresponding tag. However, it may be preferred to build a molecule comprising the reaction product of two of more reactants. Thus, in a certain aspect of the invention a method is devised for obtaining a bifunctional complex composed of a molecule part and a single stranded identifier oligonucleotide, said molecule part being the reaction product of reactants and the chemical reaction site of the initial complex.

In one embodiment of the invention, parallel syntheses are performed so that a tag is enzymatical linked to a nascent bifunctional complex in parallel with a reaction between a chemical reaction site and a reactant. In each round the addition of the tag is followed or preceded by a reaction between reactant and the chemical reaction site. In each subsequent round of parallel syntheses the reaction product of the previous reactions serves as the chemical reaction site and the last-incorporated tag provides for a priming site which allows for the enzymatical addition a tag. In other aspects of the invention, two or more tags are provided prior to or subsequent to reaction with the respective reactants.

The single stranded identifier oligonucleotide comprising covalently ligated tags can be transformed to a double stranded form by an extension process in which a primer is annealed to the 3' end of the single stranded identifier oligonucleotide and extended using a suitable polymerase. The double strandness can be an advantage during subsequent selection processes.

Reactants comprising chemical entities and reactive groups can be synthesised e.g. as disclosed by Dolle et al. (Dolle, R. E. Mol. Div.; 3 (1998) 199-233; Dolle, R. E. Mol. Div.; 4 (1998) 233-256; Dolle, R. E.; Nelson, K. H., Jr. *J. Comb. Chem.;* 1 (1999) 235-282; Dolle, R. E. *J. Comb. Chem.;* 2 (2000) 383-433; Dolle, R. E. *J. Comb. Chem.;* 3 (2001) 477-517; Dolle, R. E. *J. Comb. Chem.;* 4 (2002) 369-418; Dolle, R. E. *J. Comb. Chem.;* 5 (2003) 693-753; Dolle, R. E. *J. Comb. Chem.;* 6 (2004) 623-679; Dolle, R. E. *J. Comb. Chem.;* 7 (2005) 739-798; Dolle, R. E.; Le Bourdonnec, B.; Morales, G. A.; Moriarty, K. J.; Salvino, J. M., *J. Comb. Chem.;* 8 (2006) 597-635 and references cited therein. (incorporated by reference herein in their entirety).

Reactants may furthermore be formed by use of solid phase synthesis or by in solution synthesis. Reactants may also be commercially available. Reactants may be produced by conventional organic synthesis, parallel synthesis or combinatorial chemistry methods.

Protection Groups

Reactive groups may optionally be protected using protection group chemistries as e.g. described by Green T. W. and Wuts P. G. M in Protection Groups in Organic Synthesis, Wiley, 1999, ISBN: 0-471-16019-9 which is hereby incorporated by reference.

In one embodiment amines may optionally be protected as carbamates, such as for example methyl carbamate, ethyl carbamate, t-butyl carbamate (Boc), 9-fluorenylmethyl carbamate (Fmoc), 2,2,2-trichlorethyl carbamate, 2-trimethylsilylethyl carbamate, vinyl carbamate, allyl carbamate, benzyl carbamate, p-methoxybenzyl carbamate, p-nitrobenzyl carbamate, m-nitrophenyl carbamate, 3,5-dimethoxybenzyl carbamate, alpha-methylnitropiperonyl carbamate, o-nitrophenyl carbamate, 3,4-dimethoxy-6-nitro carbamate, phenyl (o-nitrophenyl)methyl carbamate, 2-(2-nitrophenyl)ethyl carbamate, 6-nitroveratryl carbamate, 4-methoxyphenacyl carbamate, methylsulfonylethyl carbamate (MSc), which may optionally be deprotected as appropriate according to literature procedures as described by Green T. W. and Wuts P. G. M in *Protection Groups in Organic Synthesis*, Wiley, 1999.

In another embodiment amines may optionally be protected as amides, such as for example trifluoroacetamide, trichloroacetamide, 4-pentenoic acid amide, o-(benzoyloxymethyl)benzamide, 2-(acetoxymethyl)benzamide, N-phthalimide, N-tetrachlorophthalimide, a nosyl (Ns) protection group, such as for example an o-nitrophenylsulfonamide (o-Ns), for example an p-nitrophenylsulfonylsulfonamide (p-Ns), which may optionally be deprotected as appropriate according to literature procedures as described by Green T. W. and Wuts P. G. M in *Protection Groups in Organic Synthesis*, Wiley, 1999.

In a further embodiment amines may optionally be protected as triphenylmethyl amine (trityl, Trt), di(p-methoxyphenyl)phenylmethyl (DMT) amine, which may optionally be deprotected as appropriate according to literature procedures as described by Green T. W. and Wuts P. G. M in *Protection Groups in Organic Synthesis*, Wiley, 1999.

In one embodiment carboxylic acids may optionally be protected such as for example methyl ester, ethyl ester, t-butyl ester, benzyl ester, p-methoxy benzyl ester, 9-fluorenylmethyl ester, methoxy methyl ester, benzyloxy methyl ester, cyanomethyl ester, phenacyl ester, p-methoxy phenacyl ester, 2,2,2-trichloroethyl ester, vinyl ester, allyl ester, triethylsilyl ester, t-butyldimethylsilyl ester, phenyldimethylsilyl ester, triphenylmethyl ester, di(p-methoxyphenyl) phenylmethyl ester, methyl sulfonylethyl ester, which may optionally be deprotected as appropriate according to literature procedures as described by Green T. W. and Wuts P. G. M in *Protection Groups in Organic Synthesis*, Wiley, 1999.

In one embodiment hydroxyl groups may optionally be protected such as for example methyl ether, methoxymethyl ether, benzyloxymethyl ether, p-methoxybenzyloxymethyl ether, o-nitrobenzyloxymethyl ether, tetrahydropyranyl ether, tetrahydrofuranyl ether, ethoxyethyl ether, 2,2,2-trichloroethyl ether, allyl ether, vinyl ether, benzyl ether, p-methoxybenzyl ether, o-nitrobenzyl ether, triphenylmethyl ether, di(p-methoxyphenyl)phenylmethyl ether, which may optionally be deprotected as appropriate according to literature procedures as described by Green T. W. and Wuts P. G. M in *Protection Groups in Organic Synthesis*, Wiley, 1999.

In another embodiment hydroxyl groups may optionally be protected such as for example formic acid ester, acetic acid ester, trichloroacetic acid ester, trifluoroacetic acid ester, which may optionally be deprotected as appropriate according to literature procedures as described by Green T. W. and Wuts P. G. M in *Protection Groups in Organic Synthesis*, Wiley, 1999.

In a further embodiment hydroxyl groups may optionally be protected such as for example methyl carbonates, methoxymethyl carbonates, 9-fluorenylmethyl carbonates, ethyl carbonates, 2,2,2-trichloroethyl carbonates, allyl carbonates, vinyl carbonates, t-butyl carbonates, benzyl carbonates, p-methoxybenzyl carbonates, tosylate, which may optionally be deprotected as appropriate according to literature procedures as described by Green T. W. and Wuts P. G. M in *Protection Groups in Organic Synthesis*, Wiley, 1999.

In one embodiment carbonyl groups may optionally be protected such as for example dimethyl acetal and ketal, dibenzyl acetal and ketal, 1,3-dioxanes, 1,3-dioxolanes, 1,3-dithiane, 1,3-dithiolane, S,S'-dimethyl thioacetal and ketal, which may optionally be deprotected as appropriate according to literature procedures as described by Green T. W. and Wuts P. G. M in *Protection Groups in Organic Synthesis*, Wiley, 1999.

In another embodiment aldehydes may optionally be masked as 1,2-diols, which may optionally be demasked by use of periodate. For example:

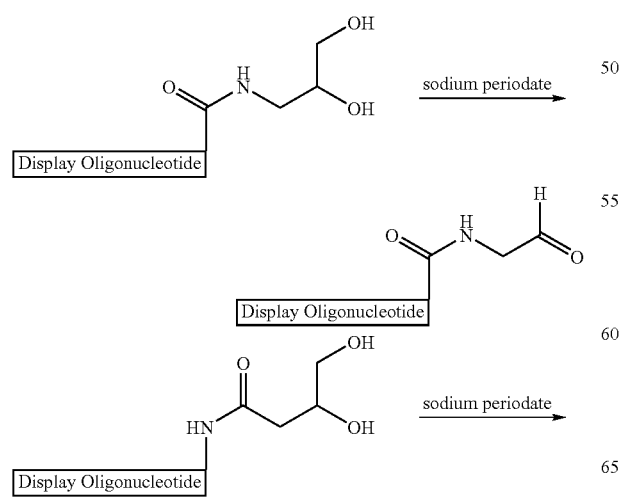

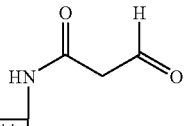

1. Dry down 1-20 nmol diol functionalised oligo
2. Add 25 μl $NaIO_4$ (50 mM in Sodium Acetate Buffer pH 4)
3. Shake at 25° C. for 30 min.
4. Add 25 μl 700 mM Phosphate buffer pH 6.7
5. Purify by P6 spin column
6. Dry down the aldehyde functionalized oligo (temperature max. 45° C.)

The following procedures may be applied for deprotection of protection groups. Other methods may also be applied as described in the literature and by Green T. W. and Wuts P. G. M in *Protection Groups in Organic Synthesis*, Wiley, 1999:

Procedure for tBu Ester and N-Boc Deprotection
1. Dry down functionalised oligo in an PCR tube
2. Add 20 μL 37.5 mM NaOAc and 5 μL 1 M $MgCl_2$
3. Incubate at 70° C. ON (Lid 100° C.) in PCR-machine
4. Add 45 μL $H_2O$
5. Purify by P6 spin column Procedure Fmoc Deprotection in Water
1. Dry down oligo
2. Add 6% piperidine/$H_2O$ 10 μL
3. Shake 30 min at 25° C.
4. Add 40 μL $H_2O$
5. Purify by P6 spin column Procedure Msc Deprotection in Water
1. Dry down oligo
2. Dissolve in 25 μL Sodium Borate Buffer (0.1 M, pH=10)
3. Shake 3 h at 40° C.
4. Add 25 μL Water
5. Purify by P6 spin column Deprotection of tBu, Me and Et Esters
1. Dry down oligo in an PCR tube
2. Add 20 μL 100 mM LiOH, seal tube
3. Incubate at 80° C. in PCR machine for 30 minutes
4. Add 40 μL 100 mM NaOAc buffer pH 5
5. Purify by P6 spin column Procedure for Fmoc Deprotection on DEAE Sepharose
1) 100 μL DEAE suspension is pipetted into a filtertube and drained by vacuum.
2) Add water (200 μL) and drain.
3) Bind solution ($H_2O$ (200 μL)) is added. Shake 10 min 600 rpm, then drain.
4) Bind solution ($H_2O$ (100 uL) is added. No drain!
5) Oligo dissolved in $H_2O$ (max. 50 μL) is added. Shake 10 min 600 rpm, then drain.
6) $H_2O$ is added (200 μL). Drain.
7) DMF is added (200 μL). Drain.
8) Repeat step 11 twice.
9) 10% piperidine/DMF (250 μL) is added. Shake 5 min 600 rpm. Spin 1000 g 1 min.
10) Repeat step 13.
11) DMF is added (200 μL). Drain.
12) Repeat step 15 twice
13) $H_2O$ is added (200 μL). Drain.
14) Repeat step 17

15) Release solution is added (35 µL, 2M TEAB). Shake 10 min 600 rpm. Spin at 1000 g for 1 min, collect the solvent in an eppendorf tube.
16) Repeat step 19.
17) Combine the solvents from step 19 and 20, then spin column filtrate the sample.

Procedure for Ns Deprotection on DEAE Sepharose
1) 100 µL DEAE suspension is pipetted into a filtertube and drained by vacuum.
2) Add water (200 µL) and drain.
3) Bind solution ($H_2O$ (200 µL)) is added. Shake 10 min 600 rpm, then drain.
4) Bind solution ($H_2O$ (100 µL) is added. No drain!
5) Oligo dissolved in $H_2O$ (max. 50 µL) is added. Shake 10 min 600 rpm, then drain.
6) $H_2O$ is added (200 µL). Drain.
7) DMF (dry) is added (200 µL). Drain.
8) Repeat step 7 twice.
9) 0.5M mercaptoanisol and 0.25M DIPEA in DMF (dry) (200 µL; freshly prepared) is added. Shake 24 h at 25° C., 600 rpm. No drain!
10) 0.3 M AcOH in DMF is added (200 µL). Shake 5 min 600 rpm, then drain.
11) DMF is added (200 µL). Drain.
12) Repeat step 11 twice.
13) $H_2O$ is added (200 µL). Drain.
14) Repeat step 13
15) Release solution is added (35 µL, 2M TEAB). Shake 10 min 600 rpm. Spin at 1000 g for 1 min, collect the solvent in an eppendorf tube.
16) Repeat step 15.
17) Combine the solvents from step 14 and 15, then spin column filtrate the sample.

Procedure for Ns Deprotection on DEAE Sepharose (Parallel Format)
1) 20 µL DEAE suspension is pipetted into each well and drained by vacuum. (The capacity of the DEAE suspension is 0.5 nmol/µL oligo use min 20 µL for >10 nmol oligo)
2) Add water (100 µL per well) and drain.
3) Bind solution ($H_2O$ (100 µL per well)) is added. Shake 10 min 600 rpm, then drain.
4) Oligo dissolved in $H_2O$ (max. 100 µL per well) is added. Shake 10 min 600 rpm, then drain.
5) $H_2O$ is added (100 µL per well). Drain.
6) DMF (dry) is added (100 µL per well). Drain.
7) Repeat step 6 twice.
8) 0.5M mercaptoanisol and 0.25M DIPEA in DMF (dry) (100 µL per well; freshly prepared) is added. Shake 24 h at 25° C., 600 rpm. No drain!
9) 0.3 M AcOH in DMF is added (100 µL per well). Shake 5 min 600 rpm, then drain.
10) DMF is added (100 µL per well). Drain.
11) Repeat step 10 twice
12) $H_2O$ is added (100 µL per well). Drain.
13) Repeat step 12
14) Release solution is added (50 µL per well, 2M TEAB). Shake 10 min 600 rpm. Spin at 1000 g for 1 min, collect the solvent in a 96 well plate.
15) Repeat step 14.
16) Combine the solvents from step 14 and 15, then evaporate samples to ~50 µL per well and spin column filtrate the samples.

A reactant can include one or more functional groups in addition to the reactive group or groups employed to generate the molecule being synthesised by the methods of the present invention. One or more of the functional groups can be protected to prevent undesired reactions of these functional groups. Suitable protecting groups are known in the art for a variety of functional groups (see e.g. Greene and Wuts, Protective Groups in Organic Synthesis, second edition, New York: John Wiley and Sons (1991), incorporated herein by reference). Useful protecting groups include t-butyl esters and ethers, acetals, trityl ethers and amines, acetyl esters, trimethylsilyl ethers, trichloroethyl ethers and esters and carbamates.

The reactive groups of the reactants and/or the chemical reaction site can also be in a pro-form that has to be activated before a reaction with (another) reactant can take place. As an example, the reactive groups can be protected, c.f. above, with a suitable group, which needs to be removed before a reaction with the reactant can proceed. Accordingly, a reactant can comprise one or more reactive group(s) or precursors of such groups, wherein the precursors can be activated or processed to generate the reactive group. Also, the reactant itself can be a precursor for the structural entity which is going to be incorporated into the display molecule.

Examples of further protection groups include "N-protected amino" and refers to protecting groups protecting an amino group against undesirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

Also, the term "O-protected carboxy" refers to a carboxylic acid protecting ester or amide group typically employed to block or protect the carboxylic acid functionality while the reactions involving other functional sites of the compound are performed. Carboxy protecting groups are disclosed in Greene, "Protective Groups in Organic Synthesis" (1981). Additionally, a carboxy protecting group can be used as a prodrug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667.

In some embodiments, the reaction between reactants or between a reactant and the chemical reaction site can involve a further reactant, such as a "bridging-molecule", mediating a connection between the reactant and the chemical reaction site.

Scaffolds and Small Molecules

In some embodiments, the chemical reaction site comprises one or more scaffolds each having one or more reactive groups attached thereto. The one or more reactive groups can e.g. be any of the groups cited herein above under the heading "Chemical reaction site and reactive groups".

Examples of scaffold structures are e.g. benzodiazepines, steroids, hydantiones, piperasines, diketopiperasines, morpholines, tropanes, cumarines, qinolines, indoles, furans, pyrroles, oxazoles, amino acid precursors, and thiazoles. Further examples are provided herein below.

When the synthesis methods employ scaffolds, a reactant comprising only one reactive group can be used in the end position of the scaffolded molecule being synthesised, whereas reactants comprising two or more reactive groups are suitably incorporated into the body part and/or a branching portion of a scaffolded molecule optionally capable of being reacted with further reactants. Two or more reactive groups can be present on a scaffold having a core structure on which the molecule is being synthesised. This create the basis for synthesising multiple variants of compounds of the same class or compounds sharing certain physical or functional traits. The variants can be formed e.g. through reaction of reactive groups of the scaffold with reactive groups of one or more reactants, optionally mediated by fill-in groups ("bridging molecules") and/or catalysts.

The small molecules of the compound libraries of the present invention can be linear, branched or cyclical, or comprise structural elements selected from a combination of the aforementioned structures. When comprising a ring system, the small molecules can comprise a single ring or a fused ring system. One or more heteroatoms can be present in either the single ring system or the fused ring system.

"Single ring" refers to a cycloalkyl, heterocycloalkyl, aryl, or heteroaryl ring having about three to about eight, or about four to about six ring atoms. A single ring is not fused by being directly bonded at more than one ring atom to another closed ring.

"Fused ring" refers to fused aryl or cyclyl ring. For example, about six or less, about five or less, about four or less, about three or less, or about two rings can be fused. Each ring can be independently selected from the group consisting of aryl, heteroaryl, cycloalkyl, heterocycloalkyl, cycloalkenyl, and heterocycloalkenyl rings, each of which ring may independently be substituted or unsubstituted, having about four to about ten, about four to about thirteen, or about four to about fourteen ring atoms.

The number of rings in a small molecule refers to the number of single or fused ring systems. Thus, for example a fused ring can be considered to be one ring. As non-limiting examples, a phenyl ring, naphthalene, and norbornane, for purposes of the present invention, are all considered to be one ring, whereas biphenyl, which is not fused, is considered to be two rings.

A "heteroatom" refers to N, O, S, or P. In some embodiments, heteroatom refers to N, O, or S, where indicated. Heteroatoms shall include any oxidized form of nitrogen, sulfur, and phosphorus and the quaternized form of any basic nitrogen.

Accordingly, examples of small molecule ring systems are:

"Aryl", used alone or as part of a larger moiety as in "aralkyl", refers to aromatic rings having six ring carbon atoms.

"Fused aryl," refers to fused about two to about three aromatic rings having about six to about ten, about six to about thirteen, or about six to about fourteen ring carbon atoms.

"Fused heteroaryl" refers to fused about two to about three heteroaryl rings wherein at least one of the rings is a heteroaryl, having about five to about ten, about five to about thirteen, or about five to about fourteen ring atoms.

"Fused cycloalkyl" refers to fused about two to about three cycloalkyl rings having about four to about ten, about four to about thirteen, or about four to about fourteen ring carbon atoms.

"Fused heterocycloalkyl" refers to fused about two to about three heterocycloalkyl rings, wherein at least one of the rings is a heterocycloalkyl, having about four to about ten, about four to about thirteen, or about four to about fourteen ring atoms.

"Heterocycloalkyl" refers to cycloalkyls comprising one or more heteroatoms in place of a ring carbon atom.

"Lower heterocycloalkyl" refers to cycloalkyl groups containing about three to six ring members.

"Heterocycloalkenyl" refers to cycloalkenyls comprising one or more heteroatoms in place of a ring carbon atom. "Lower heterocycloalkenyl" refers to cycloalkyl groups containing about three to about six ring members. The term "heterocycloalkenyl" does not refer to heteroaryls.

"Heteroaryl" refers to aromatic rings containing about three, about five, about six, about seven, or about eight ring atoms, comprising carbon and one or more heteroatoms.

"Lower heteroaryl" refers to heteroaryls containing about three, about five, or about six ring members.

Exemplary preferred scaffold structures can e.g. be selected from the group consisting of quinazoline, tricyclic quinazoline, purine, pyrimidine, phenylamine-pyrimidine, phthalazine, benzylidene malononitrile, amino acid, tertiary amine, peptide, lactam, sultam, lactone, pyrrole, pyrrolidine, pyrrolinone, oxazole, isoxazole, oxazoline, isoxazoline, oxazolinone, isoxazolinone, thiazole, thiozolidinone, hydantoin, pyrazole, pyrazoline, pyrazolone, imidazole, imidazolidine, imidazolone, triazole, thiadiazole, oxadiazole, benzofuran, isobenzofuran, dihydrobenzofuran, dihydroisobenzofuran, indole, indoline, benzoxazole, oxindole, indolizine, benzimidazole, benzimidazolone, pyridine, piperidine, piperidinone, pyrimidinone, piperazine, piperazinone, diketopiperazine, metathiazanone, morpholine, thiomorpholine, phenol, dihydropyran, quinoline, isoquinoline, quinolinone, isoquinolinone, quinolone, quinazolinone, quinoxalinone, benzopiperazinone, quinazolinedione, benzazepine and azepine.

Further exemplary scaffold structures linked to the display oligonucleotides are selected from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl,
carboxy, substituted and unsubstituted carboxyalkyl,
carbonyl, substituted and unsubstituted alkylcarbonyl, substituted and unsubstituted alkylcarbonylalkyl,
substituted and unsubstituted alkoxycarbonyl, substituted and unsubstituted alkoxycarbonylalkyl,
aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N- dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl, substituted and unsubstituted aminoalkyl, substituted and unsubstituted alkylaminoalkyl, amidino, cyanoamidino, substituted and unsubstituted heterocyclicalkyl, substituted and unsubstituted aralkyl, substituted and unsubstituted cycloalkyl, substituted and unsubstituted cycloalkenyl, substituted and unsubstituted alkylthio, substituted and unsubstituted alkylsulfinyl, substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl, acyl, acylamino, substituted and unsubstituted arylthio, substituted and unsubstituted aralkylthio, substituted and unsubstituted aryloxy, substituted and unsubstituted aralkoxy, substituted and unsubstituted haloaralkyl, substituted and unsubstituted carboxyhaloalkyl, substituted and unsubstituted alkoxycarbonylhaloalkyl, substituted and unsubstituted aminocarbonylhaloalkyl, substituted and unsubstituted alkylaminocarbonylhaloalkyl, substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

The same or different scaffolds comprising a plurality of sites for functionalization react with one or more identical or different reactants in order to generate a compound library comprising different small molecules. As used herein, the term "scaffold reactive group" refers to a chemical moiety that is capable of reacting with the reactive group of a reactant or chemical entity during the synthesis if the small molecule. Preferred scaffold reactive groups include, but are not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, amino acid, aryl, cycloalkyl, heterocyclyl, heteroaryl, etc. One of skill in the art will be aware of other common functional groups that are encompassed by the present invention.

As used herein, the term "chemical entity reactive group" refers to a chemical moiety of a reactant capable of reacting with one or more scaffold reactive groups. Preferred reactive groups of a reactant include, but are not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, amino acid, aryl, cycloalkyl, heterocyclyl, heteroaryl, etc. One of skill in the art will be aware of other common functional groups that are encompassed by the present invention.

The small molecule compounds of the present invention can be prepared using a variety of synthetic reactions. Suitable reaction chemistries are preferably selected from the following group: Amine acylation, reductive alkylation, aromatic reduction, aromatic acylation, aromatic cyclization, aryl-aryl coupling, [3+2]cycloaddition, Mitsunobu reaction, nucleophilic aromatic substitution, sulfonylation, aromatic halide displacement, Michael addition, Wittig reaction, Knoevenagel condensation, reductive amination, Heck reaction, Stille reaction, Suzuki reaction, Aldol condensation, Claisen condensation, amino acid coupling, amide bond formation, acetal formation, Diels-Alder reaction, [2+2]cycloaddition, enamine formation, esterification, Friedel Crafts reaction, glycosylation, Grignard reaction, Horner-Emmons reaction, hydrolysis, imine formation, metathesis reaction, nucleophilic substitution, oxidation, Pictet-Spengler reaction, Sonogashira reaction, thiazolidine formation, thiourea formation and urea formation.

Accordingly, the reactants and scaffolds of the present invention are those that enable the reactions above to occur. These include, but are not limited to, nucleophiles, electrophiles, acylating agents, aldehydes, carboxylic acids, alcohols, nitro, amino, carboxyl, aryl, heteroaryl, heterocyclyl, boronic acids, phosphorous ylides, etc. One of skill in the art can envision other synthetic reactions and reactive components useful in the present invention.

FIG. 58 highlights several reactions that can be used to prepare the small molecule compounds of the present invention, and the corresponding coding reactions and reactive components. In FIG. 58, one of skill in the art will understand that radicals R, $R_1$ and $R_2$ can be any of the above described groups, such as, for example, hydrogen, alkyl, cycloalkyl, heterocyclyl, aryl and heteroaryl, all optionally substituted as disclosed herein above. One of skill in the art will further understand that radical Ar is an aryl, which can be, for example, phenyl, naphthyl, pyridyl and thienyl. In addition, one of skill in the art will understand that radical X can be, for example, hydrogen, halogen alkyl, cycloalkyl, heterocyclyl, aryl and heteroaryl.

Contacting a scaffold with one or more reactants results in the conversion of the scaffold into a small molecule, or an intermediate scaffold structure to be further reacted or modified.

Accordingly, in one embodiment of the present invention, reactants comprising one or more reactive groups, react with one or more, preferably more, such as 2, 3, 4, 5, 6, 7, 8, 9, 10, or from 10 to 20, reactive groups of a scaffold comprising a plurality of such reactive groups, by one or more reactions selected from the group consisting of amine acylation, reductive alkylation, aromatic reduction, aromatic acylation, aromatic cyclization, aryl-aryl coupling, [3+2] cycloaddition, Mitsunobu reaction, nucleophilic aromatic substitution, sulfonylation, aromatic halide displacement, Michael addition, Wittig reaction, Knoevenagel condensation, reductive amination, Heck reaction, Stille reaction, Suzuki reaction, Aldol condensation, Claisen condensation, amino acid coupling, amide bond formation, acetal formation, Diels-Alder reaction, [2+2]cycloaddition, enamine formation, esterification, Friedel Crafts reaction, glycosylation, Grignard reaction, Horner-Emmons reaction, hydrolysis, imine formation, metathesis reaction, nucleophilic substitution, oxidation, Pictet-Spengler reaction, Sonogashira reaction, thiazolidine formation, thiourea formation and urea formation, wherein said scaffold preferably comprises a structural component selected from the group consisting of a cyclic or bicyclic hydrocarbon, a steroid, a sugar, a heterocyclic structure, a polycyclic aromatic molecule, an amine, an amino acid, a multi-functional small molecule, a peptide or a polymer having various substituents at defined positions.

Suitable scaffolds of the present invention include, but are not limited to, quinazoline, tricyclic quinazoline, purine, pyrimidine, phenylamine-pyrimidine, phthalazine, benzylidene malononitrile, amino acid, tertiary amine, peptide, polymer, aromatic compounds containing ortho-nitro fluoride(s), aromatic compounds containing para-nitro fluoride(s), aromatic compounds containing ortho-nitro chloromethyl, aromatic compounds containing ortho-nitro bromomethyl, lactam, sultam, lactone, pyrrole, pyrrolidine, pyrrolinone, oxazole, isoxazole, oxazoline, isoxazoline, oxazolinone, isoxazolinone, thiazole, thiozolidinone, hydantoin, pyrazole, pyrazoline, pyrazolone, imidazole, imidazolidine, imidazolone, triazole, thiadiazole, oxadiazole, benzofuran, isobenzofuran, dihydrobenzofuran, dihydroisobenzofuran, indole, indoline, benzoxazole, oxindole, indolizine, benzimidazole, benzimidazolone, pyridine, piperidine, piperidinone, pyrimidinone, piperazine, piperazinone, diketopiperazine, metathiazanone, morpholine, thiomorpholine, phenol, dihydropyran, quinoline, isoquinoline, quinolinone, isoquinolinone, quinolone, quinazolinone, quinoxalinone, benzopiperazinone, quinazolinedione, benzazepine and azepine, and wherein said scaffold preferably comprises at least two scaffold reactive groups selected from the group consisting of hydroxyl, carboxyl, amino, thiol, aldehyde, halogen, nitro, cyano, amido, urea, carbonate, carbamate, isocyanate, sulfone, sulfonate, sulfonamide, sulfoxide, etc., for reaction with said one or more reactants.

The compound libraries can be partitioned or enriched with the selection of possible "lead candidates" or "drug candidates" as a result. The identification of "lead candidates" or "drug candidates" typically result when an association is formed between a small molecule member of the compound library and a target compound.

A "library" is a collection of library compounds, such as a collection of different small molecules. The library can be virtual, in that it is an in silico or electronic collection of structures used for computational analysis as described herein. The library is preferably physical, in that the set of small molecules are synthesized, isolated, or purified.

A "lead candidate" is a library compound, such as a small molecule, that binds to a biological target molecule and is designed to modulate the activity of a target protein. A lead candidate can be used to develop a drug candidate, or a drug to be used to treat a disorder or disease in an animal, including, for example, by interacting with a protein of said animal, or with a bacterial, viral, fungal, or other organism that can be implicated in said animal disorder or disease, and that is selected for further testing either in cells, in animal models, or in the target organism. A lead candidate may also be used to develop compositions to modulate plant diseases or disorders, including, for example, by modulating plant protein activity, or by interacting with a bacterial, viral, fungal, or other organism implicated in said disease or disorder.

A "drug candidate" is a lead candidate that has biological activity against a biological target molecule and has ADMET (absorption, distribution, metabolism, excretion and toxicity) properties appropriate for it to be evaluated in an animal, including a human, clinical studies in a designated therapeutic application.

A "compound library" is a group comprising more than one compound, such as more than one different small molecule, used for drug discovery. The compounds in the library can be small molecules designed to be linked to other compounds or small molecules, or the compounds can be small molecules designed to be used without linkage to other small molecules.

A "plurality" is more than one of whatever noun "plurality" modifies in the sentence.

The term "obtain" refers to any method of obtaining, for example, a small molecule, a library of such different small molecules, or a target molecule. The method used to obtain such compounds, biological target molecules, or libraries, may comprise synthesis, purchase, or any means the compounds, biological target molecules, or libraries can be obtained.

By "activity against" is meant that a compound may have binding activity by binding to a biological target molecule, or it may have an effect on the enzymatic or other biological activity of a target, when present in a target activity assay. Biological activity and biochemical activity refer to any in vivo or in vitro activity of a target biological molecule. Non-limiting examples include the activity of a target molecule in an in vitro, cellular, or organism level assay. As a non-limiting example with an enzymatic protein as the target molecule, the activity includes at least the binding of the target molecule to one or more substrates, the release of a product or reactant by the target molecule, or the overall catalytic activity of the target molecule. These activities can be accessed directly or indirectly in an in vitro or cell based assay, or alternatively in a phenotypic assay based on the effect of the activity on an organism. As a further non-limiting example wherein the target molecule is a kinase, the activity includes at least the binding of the kinase to its target polypeptide and/or other substrate (such as ATP as a non-limiting example) as well as the actual activity of phosphorylating a target polypeptide.

Obtaining a crystal of a biological target molecule in association with or in interaction with a test small molecule includes any method of obtaining a compound in a crystal, in association or interaction with a target protein. This method includes soaking a crystal in a solution of one or more potential compounds, or ligands, or incubating a target protein in the presence of one or more potential compounds, or ligands.

By "or" is meant one, or another member of a group, or more than one member. For example, A, B, or C, may indicate any of the following: A alone; B alone; C alone; A and B; B and C; A and C; A, B, and C.

"Association" refers to the status of two or more molecules that are in close proximity to each other. The two molecules can be associated non-covalently, for example, by hydrogen-bonding, van der Waals, electrostatic or hydrophobic interactions, or covalently.

"Active Site" refers to a site in a target protein that associates with a substrate for target protein activity. This site may include, for example, residues involved in catalysis, as well as residues involved in binding a substrate. Inhibitors may bind to the residues of the active site.

"Binding site" refers to a region in a target protein, which, for example, associates with a ligand such as a natural substrate, non-natural substrate, inhibitor, substrate analog, agonist or antagonist, protein, co-factor or small molecule, as well as, optionally, in addition, various ions or water, and/or has an internal cavity sufficient to bind a small molecule and can be used as a target for binding drugs. The term includes the active site but is not limited thereby.

"Crystal" refers to a composition comprising a biological target molecule, including, for example, macromolecular drug receptor targets, including protein, including, for example, but not limited to, polypeptides, and nucleic acid targets, for example, but not limited to, DNA, RNA, and ribosomal subunits, and carbohydrate targets, for example, but not limited to, glycoproteins, crystalline form. The term "crystal" includes native crystals, and heavy-atom derivative crystals, as defined herein. The discussion below often uses a target protein as a exemplary, and non-limiting example. The discussion applies in an analogous manner to all possible target molecules.

"Alkyl" and "alkoxy" used alone or as part of a larger moiety refers to both straight and branched chains containing about one to about eight carbon atoms. "Lower alkyl" and "lower alkoxy" refer to alkyl or alkoxy groups containing about one to about four carbon atoms.

"Cyclyl", "cycloalkyl", or "cycloalkenyl" refer to cyclic alkyl or alkenyl groups containing from about three to about eight carbon atoms. "Lower cyclyl," "lower cycloalkyl." or "lower cycloalkenyl" refer to cyclic groups containing from about three to about six carbon atoms.

"Alkenyl" and "alkynyl" used alone or as part of a larger moiety shall include both straight and branched chains containing about two to about eight carbon atoms, with one or more unsaturated bonds between carbons. "Lower alkenyl" and "lower alkynyl" include alkenyl and alkynyl groups containing from about two to about five carbon atoms.

"Halogen" means F, Cl, Br, or I.

"Linker group" of a bifunctional complex means an organic moiety that connects two parts of the bifunctional complex, typically the small molecule and the oligonucleotide identifier. Linkers are typically comprised of an atom such as oxygen or sulfur, a unit such as —NH— or —CH$_2$—, or a chain of atoms, such as an alkylidene chain. The molecular mass of a linker is typically in the range of about 14 to about 200. Examples of linkers are known to those of ordinary skill in the art and include, but are not limited to, a saturated or unsaturated C$_{1-6}$ alkylidene chain which is optionally substituted, and wherein up to two saturated carbons of the chain are optionally replaced by —C(=O)—, —CONH—, CONHNH—, —CO$_2$—, —NHCO$_2$—, —O—, —NHCONH—, —O(C=O)—, —O(C=O)NH—, —NHNH—, —NHCO—, —S—, —SO—, —SO$_2$—, —NH—, —SO$_2$NH—, or NHSO$_2$—.

An Log P value can be, for example, a calculated Log P value, for example, one determined by a computer program for predicting Log P, the log of the octanol-water partition coefficient commonly used as an empirical descriptor for predicting bioavailability (e.g. Lipinski's Rule of 5; Lipinski, C. A.; Lombardo, F.; Dominy, B. W.; Feeney, P. J. (1997) Experimental and computational approaches to estimate solubility and permeability in drug discovery and development settings. Adv. Drug Delivery Rev. 23, 3-25). The calculated log P value may, for example, be the Slog P value. Slog P is implemented in the MOE software suite from Chemical Computing Group, www.chemcomp.com. Slog P is based on an atomic contribution model (Wildman, S. A., Crippen, G. M.; Prediction of Physicochemical Parameters by Atomic Contributions; J. Chem. Inf. Comput. Sci., 39(5), 868-873 (1999)).

Linker Moiety of a Bifunctional Complex

The nascent bifunctional complex comprising a chemical reaction site and a priming site for enzymatic addition of a tag can also comprise a linking moiety connecting the chemical reaction site and the priming site.

In some embodiments it is preferable that the linker ensures that a reactive group or a building block (reactant) or an encoded molecule is spaced away from the tag. In some embodiments it is also preferable that the linker ensures that a reactive group, a building block (reactant) or an encoded molecule can efficiently interact with another object such as a target used for screening/affinity selection.

The linker may be composed of one or more atoms. The linker may include monomer units such as a peptide, protein, carbohydrates and substituted carbohydrates, a nucleotide, or any unit synthesized using organic and/or inorganic chemistry such as ethylenglycol; 1,3-propylenglycol; 1,4-propylenglycol; 1,5-pentylenglycol. Any unit may be in substituted form, e.g., 1,3.propylenglycol hydroxyl-substituted at the 2 position (Propane-1,2,3-triol). The linker may also include a polymer such as an organic polymer, e.g. a polyethylenglycol, a polypeptide, or an oligonucleotide, polyvinyl, acetylene or polyacetylene, aryl/hetaryl and substituted aryl/hetaryl, ethers and polyethers such as e.g. polyethylenglycol and substituted polyethers, amines, polyamines and substituted polyamines, single- or double-stranded oligonucleotides, and polyamides and natural and unnatural polypeptides. The linker may contain any combination of monomeric and polymeric units. The linker may also contain branching units. The linker may be flexible or rigid and contain flexible and/or rigid parts. The linker may be attached to one or more reactive groups by one or more atoms. Moreover, the linker may contain one or more reactive groups. The linker may be attached to the tag via one or more atoms, e.g. via a phosphate group.

The attachment point may be anywhere on the tags such as a 5' or 3' phosphate, a 5' or 3' OH, carbon, oxygen or nitrogen on one or more nucleotides. The linker may be attached one or more tags such as both strands of a double stranded tag. The linker may be attached to the tag by one or more covalent bonds and/or one or more noncovalent bonds, e.g. the linker may include a biotin moiety which can bind noncovalently to a streptavidin molecule attached to the tag. Preferably the length of the linker is in the range of 1-50 angstrom, more preferably 5-30 angstrom, most preferably 10-25 angstrom. Preferably, the linker separates the linker-tag attachment point from a reactive group by 5-50 atomic bonds, more preferably, by 10-30 atomic bonds, most preferably by 15-25 atomic bonds. Preferably, the linker is prepared from Diisopropyl-phosphoramidous acid 2-cyanoethyl ester 2-[2-(2-{2-[2-(2-{[(4-methoxy-phenyl)-diphenyl-methyl]-amino}-ethoxy)-ethoxy]-ethoxy}-ethoxy)-ethoxy]-ethyl ester or similar compound. Preferably, the linker contains the structure 2-[2-(2-{2-[2-(2-Amino-ethoxy)-ethoxy]-ethoxy}-ethoxy)-ethoxy]-ethanol.

Cleavable linkers can be cleaved in any number of ways, e.g., by photolysis or increased temperature, or by the addition of acid, base, enzymes, ribozymes, other catalysts, or any other agents.

To maintain a physical link between the identifier and the encoded molecule (in the case of stage 2 synthesis, the template and the encoded molecule), at least one non-cleavable linker is needed. The non-cleavable linker may of course be cleavable under certain conditions, but is non-cleavable under the conditions that lead to the bi-functional molecule employed in the screening. This non-cleavable linker is preferably flexible, enabling it to expose the encoded molecule in an optimal way.

Under certain conditions it may desirable to be able to cleave the linker before, during or after the screening of the library has been done, for example in order to perform a mass spectrometric analysis of the encoded molecule without the identifier attached, or to perform other types of assays on the free encoded molecule.

The linking moiety in one embodiment separates the priming site from the chemical reaction site so as to allow an enzyme to perform the tag addition and provide for a hybridisation region. The linking moiety can be a nucleic acid sequence, such as an oligonucleotide. The length of the oligonucleotide is preferably suitable for hybridisation with a complementing oligonucleotide, i.e. the number of nucleotides in the linking moiety is suitably 2 or more, such as 3 or more, for example 4 or above, such as 5 or more, for example 6 or more, such as 7 or more, for example 8 or more nucleotides.

In a certain embodiment, the linking moiety is attached to the chemical reaction site via a spacer comprising a selectively cleavable linker to enable release of the molecule from the identifier oligonucleotide in a step subsequent to the formation of the final bifunctional complex. The cleavable linker can be selectively cleavable, i.e. conditions can be selected that only cleave that particular linker.

The cleavable linkers can be selected from a variety chemical structures. Examples of linkers includes, but are not limited to, linkers having an enzymatic cleavage site, linkers comprising a chemical degradable component, linkers cleavable by electromagnetic radiation.

Examples of Linkers Cleavable by Electromagnetic Radiation (Light)
o-nitrobenzyl
    p-alkoxy

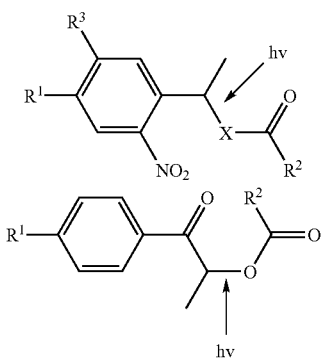

o-nitrobenzyl in Exo Position

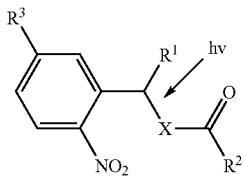

For more details see Holmes C P. J. Org. Chem. 1997, 62, 2370-2380
3-nitrophenyloxy

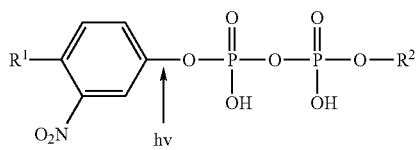

For more details see Rajasekharan Pillai, V. N. Synthesis. 1980, 1-26

Dansyl Derivatives:

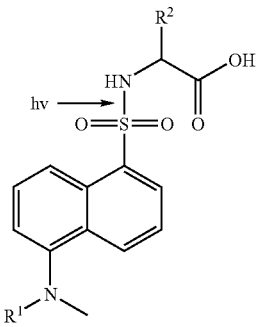

For more details see Rajasekharan Pillai, V. N. Synthesis. 1980, 1-26
Coumarin Derivatives

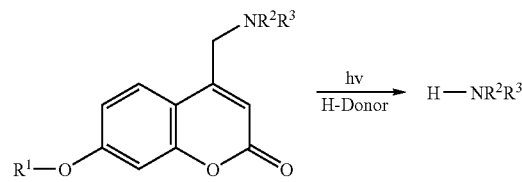

For more details see R. O, Schoenleber, B. Giese. Synlett 2003, 501-504

$R^1$ and $R^2$ can be any molecule or chemical entity (CE) such as those exemplified herein above under section A (acylation reactions), respectively. Moreover, $R^1$ and $R^2$ can be either the target or a solid support, respectively. $R^3$ can be e.g. H or $OCH_3$ independently of $R^1$ and $R^2$. If X is O then the product will be a carboxylic acid. If X is NH the product will be a carboxamide One specific example is the PC Spacer Phosphoramidite (Glen research catalog #10-4913-90) which can be introduced in an oligonucleotide during synthesis and cleaved by subjecting the sample in water to UV light (~300-350 nm) for 30 seconds to 1 minute.

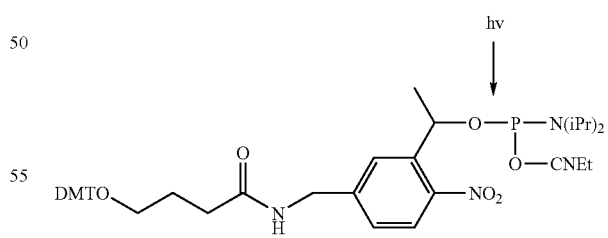

DMT=4,4'-Dimethoxytrityl
iPr=Isopropyl
CNEt=Cyanoethyl

The above PC spacer phosphoamidite is suitable incorporated in a library of complexes at a position between the identifier and the potential drug candidate. The spacer can be cleaved according to the following reaction.

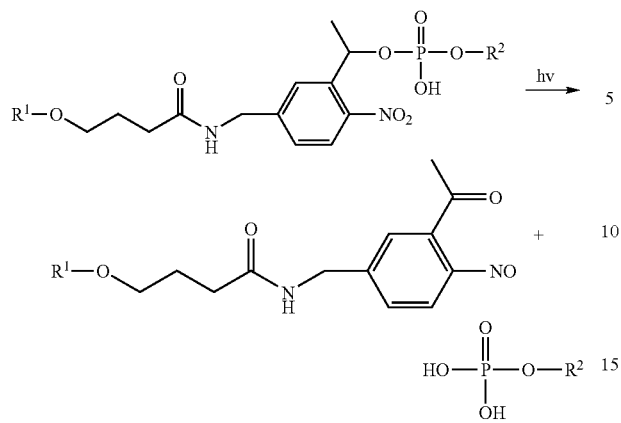

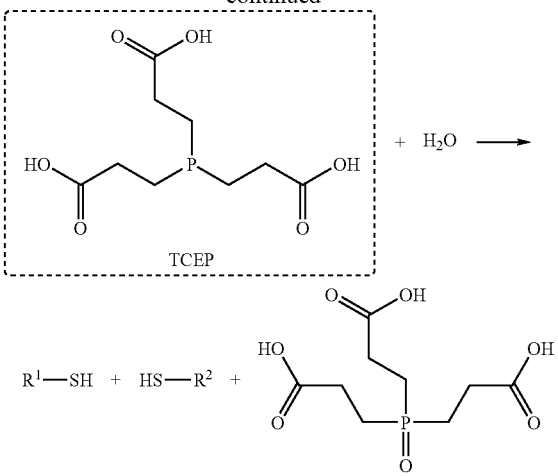

R[1] and R[2] can be any molecule or chemical entity (CE) such as those exemplified herein above under section A (acylation reactions). Moreover, R[1] and R[2] can be either the target or a solid support, respectively. In a preferred aspect R[2] is an oligonucleotide identifier and the R[1] is the molecule. When the linker is cleaved a phosphate group is generated allowing for further biological reactions. As an example, the phosphate group can be positioned in the 5' end of an oligonucleotide allowing for an enzymatic ligation process to take place.

Examples of Linkers Cleavable by Chemical Agents:

Ester linkers can be cleaved by nucleophilic attack using e.g. hydroxide ions. In practice this can be accomplished by subjecting the target-ligand complex to a base for a short period.

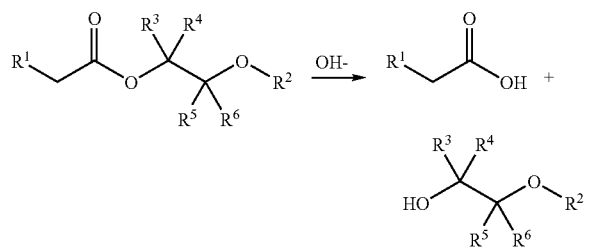

R[1] and R[2] can be the either of be the potential drug candidate or the identifier, respectively. R[4-6] can be any of the following: H, CN, F, $NO_2$, $SO_2NR_2$.

Disulfide linkers can efficiently be cleaved/reduced by Tris (2-carboxyethyl) phosphine (TCEP). TCEP selectively and completely reduces even the most stable water-soluble alkyl disulfides over a wide pH range. These reductions frequently required less than 5 minutes at room temperature. TCEP is a non-volatile and odorless reductant and unlike most other reducing agents, it is resistant to air oxidation. Trialkylphosphines such as TCEP are stable in aqueous solution, selectively reduce disulfide bonds, and are essentially unreactive toward other functional groups commonly found in proteins.

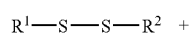

More details on the reduction of disulfide bonds can be found in Kirley, T. L. (1989), Reduction and fluorescent labeling of cyst(e)ine-containing proteins for subsequent structural analysis, *Anal. Biochem.* 180, 231 and Levison, M. E., et al. (1969), Reduction of biological substances by water-soluble phosphines: Gamma-globulin. *Experentia* 25, 126-127.

Linkers Cleavable by Enzymes

The linker connecting the potential drug candidate with the identifier or the solid support and the target can include a peptide region that allows a specific cleavage using a protease. This is a well-known strategy in molecular biology. Site-specific proteases and their cognate target amino acid sequences are often used to remove the fusion protein tags that facilitate enhanced expression, solubility, secretion or purification of the fusion protein.

Various proteases can be used to accomplish a specific cleavage. The specificity is especially important when the cleavage site is presented together with other sequences such as for example the fusion proteins. Various conditions have been optimized in order to enhance the cleavage efficiency and control the specificity. These conditions are available and know in the art.

Enterokinase is one example of an enzyme (serine protease) that cut a specific amino acid sequence. Enterokinase recognition site is Asp-Asp-Asp-Asp-Lys (DDDDK), and it cleaves C-terminally of Lys. Purified recombinant Enterokinase is commercially available and is highly active over wide ranges in pH (pH 4.5-9.5) and temperature (4-45° C.).

The nuclear inclusion protease from tobacco etch virus (TEV) is another commercially available and well-characterized proteases that can be used to cut at a specific amino acid sequence. TEV protease cleaves the sequence Glu-Asn-Leu-Tyr-Phe-Gln-Gly/Ser (ENLYFQG/S) between Gln-Gly or Gln-Ser with high specificity.

Another well-known protease is thrombin that specifically cleaves the sequence Leu-Val-Pro-Arg-Gly-Ser (LVPAGS) between Arg-Gly. Thrombin has also been used for cleavage of recombinant fusion proteins. Other sequences can also be used for thrombin cleavage; these sequences are more or less specific and more or less efficiently cleaved by thrombin. Thrombin is a highly active protease and various reaction conditions are known to the public.

Activated coagulation factor FX (FXa) is also known to be a specific and useful protease. This enzyme cleaves C-terminal of Arg at the sequence Ile-Glu-Gly-Arg (IEGR).

FXa is frequently used to cut between fusion proteins when producing proteins with recombinant technology. Other recognition sequences can also be used for FXa.

Other types of proteolytic enzymes can also be used that recognize specific amino acid sequences. In addition, proteolytic enzymes that cleave amino acid sequences in an un-specific manner can also be used if only the linker contains an amino acid sequence in the complex molecule.

Other type of molecules such as ribozymes, catalytically active antibodies, or lipases can also be used. The only prerequisite is that the catalytically active molecule can cleave the specific structure used as the linker, or as a part of the linker, that connects the encoding region and the displayed molecule or, in the alternative the solid support and the target. Also, a variety of endonucleases are available that recognize and cleave a double stranded nucleic acid having a specific sequence of nucleotides.

Molecules

A molecule can be formed by the reaction of one or more reactive groups on one or more reactants or a molecule can be formed by the reaction of one or more reactive groups on one or more reactants and one or more chemical reaction sites.

A molecule can comprise one or more atoms and one or more bonds, wherein such bonds between atoms may optionally be single bonds, double bonds or triple bonds and a combination thereof, wherein such atoms may comprise carbon, silicon, nitrogen, phosphorous, oxygen, sulfur, selenium, fluorine, chlorine, bromine, iodine, borane, stannane, lithium, sodium, potassium, kalium, calcium, barium, strontium, including any combination thereof. In further embodiments, a molecule may comprise other atoms in the periodic system.

In one or more embodiments, a reactive group may comprise one or more atoms and one or more bonds, wherein such bonds between atoms may optionally be single bonds, double bonds or triple bonds and a combination thereof, wherein such atoms may comprise carbon, silicon, nitrogen, phosphorous, oxygen, sulfur, selenium, fluorine, chlorine, bromine, iodine, borane, stannane, lithium, sodium, potassium, kalium, calcium, barium, strontium. In further embodiments, a molecule may comprise other atoms in the periodic system.

In one or more embodiments, a chemical reaction site may comprise one or more atoms and one or more bonds, wherein such bonds between atoms may optionally be single bonds, double bonds or triple bonds and a combination thereof, wherein such atoms may comprise carbon, silicon, nitrogen, phosphorous, oxygen, sulfur, selenium, fluorine, chlorine, bromine, iodine, borane, stannane, lithium, sodium, potassium, kalium, calcium, barium, strontium. In further embodiments, a molecule may comprise other atoms in the periodic system.

In one or more embodiments, the molecule comprisings the molecule, which can be formed following the reaction of one or more reactants with one or more chemical reaction sites, where the molecule is linked through a linker to a display oligonucleotide optionally covalently linked to one or more tags.

In one or more embodiments, the molecule comprisings the chemical motif formed by reaction of reactive groups comprising atoms participating in the reaction between one or more reactive groups on one or more reactants and one or more chemical reaction sites.

In one embodiment, the molecule comprisings a carboxamide. In another embodiment, the molecule comprisings a sulfonamide. In a further embodiment, the molecule comprisings a urea group. In further embodiments, the molecule comprisings an amine. In another embodiment, the molecule comprisings an ether. In a further embodiment, the molecule comprisings an ester for example an carboxylic acid ester. In a further embodiment, the molecule comprisings an alkene. In a further embodiment, the molecule comprisings an alkyne. In a further embodiment, the molecule comprisings an alkane. In a further embodiment, the molecule comprisings a thioether. In a further embodiment, the molecule comprisings a sulfone. In a further embodiment, the molecule comprisings a sulfoxide. In a further embodiment, the molecule comprisings a sulfonamide. In a further embodiment, the molecule comprisings a carbamate. In a further embodiment, the molecule comprisings a carbonate. In a further embodiment, the molecule comprisings a 1,2-diol. In a further embodiment, the molecule comprisings a 1,2-dioxoalkane. In a further embodiment, the molecule comprisings a ketone. In a further embodiment, the molecule comprisings an imine. In a further embodiment, the molecule comprisings a hydrazone. In a further embodiment, the molecule comprisings an oxime. In a further embodiment, the molecule comprisings an aminohetarene.

In one embodiment the molecule comprising a cyclic structure such as a 3-40 member ring, such as for example an 18-40 member ring, such as for example a 3-7 member ring, for example an 8-24 member ring, for example an 8-18 member ring, for example an 8-14 member ring, for example a 5-7 member ring, such as for example a 3 member ring, for example a 4 member ring, for example a 5 member ring, for example a 6 member ring, for example a 7 member ring, for example an 8 member ring, for example a 9 member ring, for example a 10 member ring, for example an 11 member ring, for example a 12 member ring, for example a 13 member ring, for example a 14 member ring, for example a 15 member ring, for example a 16 member ring, for example a 17 member ring, for example an 18 member ring.

In one embodiment the molecule comprisings a cyclic structure, for example an aliphatic ring, for example an aromatic ring, for example a partially unsaturated ring and a combination thereof.

In one embodiment the molecule comprising a 3 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 4 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 5 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 6 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 7 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising an 8 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 9 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 10 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising an 11 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 12 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 13 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 14 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 15 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 16 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising a 17 member ring comprising one or more carbon ring atoms and optionally one or more heteroatoms, for example one or more oxygen ring atoms, for example one or more nitrogen ring atoms, for example one or more sulfur ring atoms.

In one embodiment the molecule comprising an 18 member ring comprising one or more carbon ring atoms and optionally one or more heteroatoms, for example one or more oxygen ring atoms, for example one or more nitrogen ring atoms, for example one or more sulfur ring atoms.

In one embodiment a molecule comprises for example a fully unsaturated ring structure, for example a fully saturated ring structure, for example a partly saturated ring structure, wherein such ring structure may comprise a pyrrole, a tetrahydrofuran, a tetrahydropyran, a furan, a thiophene, a pyrazole, an imidazole, a furazan, an oxazole, an isoxazole, a thiazole, an isothiazole, a 1,2,3-triazole, a 1,2,4-triazole, an 1,2,3-oxadiazole, 1,2,4-oxadiazole, 1,3,4-oxadiazole, a tetrazole, a pyridine, a pyridazine, a pyrimidine, a pyrazine, a piperidine, a piperazine, a morpholine, a thiomorpholine, an indole, an isoindole, an indazole, a purine, an indolizine, a quinoline, an isoquinoline, a quinazoline, a pteridine, a quinolizine, a carbazole, a phenazine, a phenothiazine, a phenanthridine, a chroman an oxolane, a dioxine, an aziridine, an oxirane, an azetidine, an azepine, which may optionally be substituted by one or more substituents.

In one embodiment a molecule comprises for example a fully unsaturated ring structure, for example a fully saturated ring structure, for example a partly saturated ring structure, wherein such ring structure may comprise a benzopyrrole, a benzotetrahydrofuran, a benzotetrahydropyran, a benzofuran, a benzothiophene, a benzopyrazole, an benzoimidazole, a benzofurazan, an benzooxazole, an benzoisoxazole, a benzothiazole, an benzoisothiazole, a benzo1,2,3-triazole, a benzopyridine, a benzopyridazine, a benzopyrimidine, a benzopyrazine, a benzopiperidine, a benzopiperazine, a benzomorpholine, a benzothiomorpholine, an benzoindole, an benzoisoindole, an benzoindazole, an benzoindolizine, a benzoquinoline, a benzoisoquinoline, a benzoquinazoline, a benzopteridine, a benzoquinolizine, a benzocarbazole, a benzophenazine, a benzophenothiazine, a benzophenanthridine, a benzochroman an benzooxolane, a benzodioxine, a benzoazetidine, a benzoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a pyridopyrrole, a pyridotetrahydrofuran, a pyridotetrahydropyran, a pyridofuran, a pyridothiophene, a pyridopyrazole, an pyridoimidazole, a pyridofurazan, an pyridooxazole, an pyridoisoxazole, a pyridothiazole, an pyridoisothiazole, a pyrido1,2,3-triazole, a pyridopyridine, a pyridopyridazine, a pyridopyrimidine, a pyridopyrazine, a pyridopiperidine, a pyridopiperazine, a pyridomorpholine, a pyridothiomorpholine, an pyridoindole, an pyridoisoindole, an pyridoindazole, an pyridoindolizine, a pyridoquinoline, a pyridoisoquinoline, a pyridoquinazoline, a pyridopteridine, a pyridoquinolizine, a pyridocarbazole, a pyridophenazine, a pyridophenothiazine, a pyridophenanthridine, a pyridochroman an pyridooxolane, a pyridodioxine, a pyridoazetidine, a pyridoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a pyrrolopyrrole, a pyrrolotetrahydrofuran, a pyrrolotetrahydropyran, a pyrrolofuran, a pyrrolothiophene, a pyrrolopyrazole, an pyrroloimidazole, a pyrrolofurazan, an pyrrolooxazole, an pyrroloisoxazole, a pyrrolothiazole, an pyrroloisothiazole, a pyrrolo1,2,3-triazole, a pyrrolopyridine, a pyrrolopyridazine, a pyrrolopyrimidine, a pyrrolopyrazine, a pyrrolopiperidine, a pyrrolopiperazine, a pyrrolomorpholine, a pyrrolothiomorpholine, an pyrroloindole, an pyrroloisoindole, an pyrroloindazole, an pyrroloindolizine, a pyrroloquinoline, a pyrroloisoquinoline, a pyrroloquinazoline, a pyrrolopteridine, a pyrroloquinolizine, a pyrrolocarbazole, a pyrrolophenazine, a pyrrolophenothiazine, a pyrrolophenanthridine, a pyrrolochroman an pyrrolooxolane, a pyrrolodioxine, a pyrroloazetidine, a pyrroloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a furopyrrole, a furotetrahydrofuran, a furotetrahydropyran, a furofuran, a furothiophene, a furopyrazole, an furoimidazole, a furofurazan, an furooxazole, an furoisoxazole, a furothiazole, an furoisothiazole, a furo1,2,3-triazole, a furopyridine, a furopyridazine, a furopyrimidine, a furopyrazine, a furopiperidine, a furopiperazine, a furomorpholine, a furothiomorpholine, an furoindole, an furoisoindole, an furoindazole, an furoindolizine, a furoquinoline, a furoisoquinoline, a furoquinazoline, a furopteridine, a furoquinolizine, a furocarbazole, a furophenazine, a furophenothiazine, a furophenanthridine, a furochroman an furooxolane, a furodioxine, a furoazetidine, a furoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a thienopyrrole, a thienotetrahydrofuran, a thienotetrahydropyran, a thienofuran, a thienothiophene, a thienopyrazole, an thienoimidazole, a thienofurazan, an thienoooxazole, an thienoisoxazole, a thienothiazole, an thienoisothiazole, a thieno1,2,3-triazole, a thienopyridine, a thienopyridazine, a thienopyrimidine, a thienopyrazine, a thienopiperidine, a thienopiperazine, a thienomorpholine, a thienothiomorpholine, an thienoindole, an thienoisoindole, an thienoindazole, an thienoindolizine, a thienoquinoline, a thienoisoquinoline, a thienoquinazoline, a thienopteridine, a thienoquinolizine, a thienocarbazole, a thienophenazine, a thienophenothiazine, a thienophenanthridine, a thienochroman an thienooxolane, a thienodioxine, a thienoazetidine, a thienoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a imidazopyrrole, a imidazotetrahydrofuran, a imidazotetrahydropyran, a imidazofuran, a imidazothiophene, a imidazopyrazole, an imidazoimidazole, a imidazofurazan, an imidazoooxazole, an imidazoisoxazole, a imidazothiazole, an imidazoisothiazole, a imidazo1,2,3-triazole, a imidazopyridine, a imidazopyridazine, a imidazopyrimidine, a imidazopyrazine, a imidazopiperidine, a imidazopiperazine, a imidazomorpholine, a imidazothiomorpholine, an imidazoindole, an imidazoisoindole, an imidazoindazole, an imidazoindolizine, a imidazoquinoline, a imidazoisoquinoline, a imidazoquinazoline, a imidazopteridine, a imidazoquinolizine, a imidazocarbazole, a imidazophenazine, a imidazophenothiazine, a imidazophenanthridine, a imidazochroman an imidazooxolane, a imidazodioxine, a imidazoazetidine, a imidazoazepine, which may optionally be substituted by one or more substituents.

In one embodiment a molecule comprises for example a fully unsaturated ring structure, for example a fully saturated ring structure, for example a partly saturated ring structure, wherein such ring structure may comprise a pyrazolopyrrole, a pyrazolotetrahydrofuran, a pyrazolotetrahydropyran, a pyrazolofuran, a pyrazolothiophene, a pyrazolopyrazole, an pyrazoloimidazole, a pyrazolofurazan, an pyrazoloooxazole, an pyrazoloisoxazole, a pyrazolothiazole, an pyrazoloisothiazole, a pyrazolo-1,2,3-triazole, a pyrazolopyridine, a pyrazolopyridazine, a pyrazolopyrimidine, a pyrazolopyrazine, a pyrazolopiperidine, a pyrazolopiperazine, a pyrazolomorpholine, a pyrazolothiomorpholine, an pyrazoloindole, an pyrazoloisoindole, an pyrazoloindazole, an pyrazoloindolizine, a pyrazoloquinoline, a pyrazoloisoquinoline, a pyrazoloquinazoline, a pyrazolopteridine, a pyrazoloquinolizine, a pyrazolocarbazole, a pyrazolophenazine, a pyrazolophenothiazine, a pyrazolophenanthridine, a pyrazolochroman an pyrazolooxolane, a pyrazolodioxine, a pyrazoloazetidine, a pyrazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a oxazolopyrrole, a oxazolotetrahydrofuran, a oxazolotetrahydropyran, a oxazolofuran, a oxazolothiophene, a oxazolopyrazole, an oxazoloimidazole, a oxazolofurazan, an oxazoloooxazole, an oxazoloisoxazole, a oxazolothiazole, an oxazoloisothiazole, a oxazolo1,2,3-triazole, a oxazolopyridine, a oxazolopyridazine, a oxazolopyrimidine, a oxazolopyrazine, a oxazolopiperidine, a oxazolopiperazine, a oxazolomorpholine, a oxazolothiomorpholine, an oxazoloindole, an oxazoloisoindole, an oxazoloindazole, an oxazoloindolizine, a oxazoloquinoline, a oxazoloisoquinoline, a oxazoloquinazoline, a oxazolopteridine, a oxazoloquinolizine, a oxazolocarbazole, a oxazolophenazine, a oxazolophenothiazine, a oxazolophenanthridine, a oxazolochroman an oxazolooxolane, a oxazolodioxine, a oxazoloazetidine, a oxazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a isoxazolopyrrole, a isoxazolotetrahydrofuran, a isoxazolotetrahydropyran, a isoxazolofuran, a isoxazolothiophene, a isoxazolopyrazole, an isoxazoloimidazole, a isoxazolofurazan, an isoxazoloooxazole, an isoxazoloisoxazole, a isoxazolothiazole, an isoxazoloisothiazole, a isoxazolo1,2,3-triazole, a isoxazolopyridine, a isoxazolopyridazine, a isoxazolopyrimidine, a isoxazolopyrazine, a isoxazolopiperidine, a isoxazolopiperazine, a isoxazolomorpholine, a isoxazolothiomorpholine, an isoxazoloindole, an isoxazoloisoindole, an isoxazoloindazole, an isoxazoloindolizine, a isoxazoloquinoline, a isoxazoloisoquinoline, a isoxazoloquinazoline, a isoxazolopteridine, a isoxazoloquinolizine, a isoxazolocarbazole, a isoxazolophenazine, a isoxazolophenothiazine, a isoxazolophenanthridine, a isoxazolochroman an isoxazolooxolane, a isoxazolodioxine, a isoxazoloazetidine, a isoxazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a thiaazolopyrrole, a thiaazolotetrahydrofuran, a thiaazolotetrahydropyran, a thiaazolofuran, a thiaazolothiophene, a thiaazolopyrazole, an thiaazoloimidazole, a thiaazolofurazan, an thiaazoloooxazole, an thiaazoloisoxazole, a thiaazolothiazole, an thiaazoloisothiazole, a thiaazolo1,2,3-triazole, a thiaazolopyridine, a thiaazolopyridazine, a thiaazolopyrimidine, a thiaazolopyrazine, a thiaazolopiperidine, a thiaazolopiperazine, a thiaazolomorpholine, a thiaazolothiomorpholine, an thiaazoloindole, an thiaazoloisoindole, an thiaazoloindazole, an thiaazoloindolizine, a thiaazoloquinoline, a thiaazoloisoquinoline, a thiaazoloquinazoline, a thiaazolopteridine, a thiaazoloquinolizine, a thiaazolocarbazole, a thiaazolophenazine, a thiaazolophenothiazine, a thiaazolophenanthridine, a thiaazolochroman an thiaazolooxolane, a thiaazolodioxine, a thiaazoloazetidine, a thiaazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a isothiaazolopyrrole, a isothiaazolotetrahydrofuran, a isothiaazolotetrahydropyran, a isothiaazolofuran, a isothiaazolothiophene, a isothiaazolopyrazole, an isothiaazoloimidazole, a isothiaazolofurazan, an isothiaazolooxazole, an isothiaazoloisoxazole, a isothiaazolothiazole, an isothiaazoloisothiazole, a isothiaazolo1,2,3-triazole, a isothiaazolopyridine, a isothiaazolopyridazine, a isothiaazolopyrimidine, a isothiaazolopyrazine, a isothiaazolopiperidine, a isothiaazolopiperazine, a isothiaazolomorpholine, a isothiaazolothiomorpholine, an isothiaazoloindole, an isothiaazoloisoindole, an isothiaazoloindazole, an isothiaazoloindolizine, a isothiaazoloquinoline, a isothiaazoloisoquinoline, a isothiaazoloquinazoline, a isothiaazolopteridine, a isothiaazoloquinolizine, a isothiaazolocarbazole, a isothiaazolophenazine, a isothiaazolophenothiazine, a isothiaazolophenanthridine, a isothiaazolochroman an isothiaazolooxolane, a isothiaazolodioxine, a isothiaazoloazetidine, a isothiaazoloazepine, which may optionally be substituted by one or more substituents.

In one embodiment a molecule comprises for example a fully unsaturated ring structure, for example a fully saturated ring structure, for example a partly saturated ring structure, wherein such ring structure may comprise a isothiaazolopyridine, a isothiaazolopyridazine, a isothiaazolopyrimidine, a isothiaazolopyrazine, a isothiazolotriazine, a pyrimidinopyridine, a pyrimidinopyridazine, a pyrimidinopyrimidine, a pyrimidinopyrazine, a pyrimidinotriazine, a pyrazinopyridine, a pyrazinopyridazine, a pyrazinopyrimidine, a pyrazinopyrazine, a pyrazinotriazine, a pyridazinopyridine, a pyridazinopyridazine, a pyridazinopyrimidine, a pyridazinopyrazine, a pyridazinotriazine, a triazinopyridine, a triazinopyridazine, a triazinopyrimidine, a triazinopyrazine, a triazinotriazine, which may optionally be substituted by one or more substituents.

In one embodiment the molecule may comprising a lactone, a lactam, a 2-hydroxy tetrahydrofuran, a 2-alkoxy tetrahydrofuran, a 2-hydroxy tetrahydropyran, a 2-alkoxy tetrahydropyran, a benzene, a naphthalene, a phenanthrene, an anthracene, a cyclopentane, a cyclopentene, a cyclohexane, a cyclohexene, a 1,3-cyclohexadiene, a 1,4-cyclohexadiene, a cyclopentadiene, which may optionally be substituted by one or more substituents.

In one embodiment the molecule may comprising a monocyclic system, a bicyclic system, a tricyclic system, a spirocyclic system, a fused bicyclic system, wherein such cyclic systems may optionally comprise carbon atoms, silicon atoms, nitrogen atoms, phosphorous atoms, oxygen atoms, sulfur atoms, wherein such cyclic systems may optionally be substituted by one or more substituents.

In a further embodiment, two or more cyclic structures may optionally be linked by one or more bonds comprising single bonds, double bonds, triple bonds and a combination thereof, wherein such cyclic systems may optionally comprise carbon atoms, silicon atoms, nitrogen atoms, phosphorous atoms, oxygen atoms, sulfur atoms, wherein such cyclic systems may optionally be substituted by one or more substituents.

Resynthesis of Bifunctional Complexes

In some embodiments unique bifunctional complexes are resynthesized following synthesis and analysis of a library. The unique bifunctional complexes may be identified by unique codon sequences. It is then possible to mix the bifunctional complexes and then enrich certain bifunctional complexes according to e.g. affinity for a target, e.g. by performing an affinity selection. Such enriched bifunctional complexes can then be identified e.g. by quantitative PCR, hybridization or a similar method.

Also provided in the present invention is a method to obtain information on display molecules in their free form, i.e. without an identifier oligonucleotide. A display molecule can be synthesized from an initial nascent bifunctional complex with a cleavable linker. The identifier or tag of this complex may have any composition, e.g. it may be an oligonucleotide of any length or sequence, for example an oligo nucleotide of 10-40 nucleotides in length. During synthesis the nascent bifunctional complex can be purified by gel filtration (size exclusion) because the mass of the tag employed, e.g. from 3000 to 12000 dalton allows separation of the nascent bifunctional complex from reactants, buffer components and other molecular entities of small mass, which typically have masses less than 1000 dalton. Furthermore, the use of an oligonucleotide tag allows the amount of material retained during synthesis of the bifunctional complex to be estimated by measuring e.g. the optical density (OD) of the DNA by measuring absorbance at 260 nm. Alternatively, an oligonucleotide tag with an easily measurable label such as phosphor-32 or fluorescent groups is used. Following synthesis and subsequent purification of the bifunctional complex, the cleavable linker is cleaved e.g. by electromagnetic radiation, whereby the display molecule is released. The tag can then be removed from the solution containing the display molecule, e.g. by hybridizing the tag to a complementary anti-tag oligonucleotide attached to a solid phase which can easily be removed from the solution. The display molecule can then be used in any assay determining some property of the display molecule such as Ki determination versus an enzyme, Kd determination versus a protein or other target, or determination of any in vitro or biological parameter such as the activated partial thromboplastin time (aPTT). Removal of the tag is advantageous if the assay used to measure some property of the display molecule is sensitive to the presence of DNA. One advantage of the describe method is that the synthesis scale is on the order of nanomoles. Only a small amount of each building block (reactant) used to synthesize the bifunctional complex is therefore required. Also the building blocks (reactants) used to synthesize the display molecule may be labelled by any method e.g. by radioactive atoms; for example the display molecule may be synthesized using on or more building blocks (reactants) containing a hydrogen-3 or carbon-14 atom. In this way a released display molecule may be used in an assay which measures some property of the display molecule by measuring the amount of label present. For example, the display molecule may be applied on one side of a layer of confluent CaCo-2 cells. Following a period of incubation the presence of label (reflecting the presence of display molecule) may be measured at each side of the confluent cell layer. Said measurements can be informative of the bioavailability of the display molecule. In another example the display molecule is applied to plasma proteins, e.g. human plasma proteins and the fraction of display molecule bound to plasma protein can be determined.

Library Synthesis and Further Processing Steps

When a library of different bifunctional complexes are synthesised, split-and-mix synthesis methods are employed. A plurality of nascent bifunctional complexes obtained after a first synthesis round are divided ("split") into multiple fractions. In each fraction, the nascent bifunctional complex is reacted sequentially or simultaneously with a different reactant and a corresponding oligonucleotide tag which identifies each different reactant.

The molecules (linked to their respective identifier oligonucleotides) produced in each of the fractions as disclosed herein above and in claim 1, are combined ("pooled") and then divided again into multiple fractions. Each of these fractions is then reacted with a further unique (fraction-specific) reactant and a further oligonucleotide tag identifying the reactant. The number of unique molecules present in the product library is a function of the number of different reactants used in each round of the synthesis and the number of times the pooling and dividing process is repeated.

When a library of different bifunctional complexes are synthesised, the method comprises the steps of providing in separate compartments nascent bifunctional complexes, each comprising a chemical reaction site and a priming site for enzymatic addition of a tag, and performing in any order reaction in each compartment between the chemical reaction site and one or more reactants, and enzymatically adding the priming site one or more tags identifying the one or more reactants having participated in the synthesis of a molecule or an intermediate thereof.

The nascent bifunctional complexes in each compartment can be identical or different. In the event the nascent bifunctional complex differs at the chemical reaction site, the nascent bifunctional complex suitably comprises a tag identifying the structure of the chemical reaction site. Similar, the reactants applied in each compartment can be identical or different as the case may be. Also, the reaction conditions in each compartment can be similar or different.

Accordingly, the contents of any two or more compartments can be mixed and subsequently split into an array of compartments for a new round of reaction. Thus, in any round subsequent to the first round, the end product of a preceding round of reaction is used as the nascent bifunctional complex to obtain a library of bifunctional complexes, in which each member of the library comprises a reagent specific reaction product and respective tags which codes for the identity of each of the reactants that have participated in the formation of the reaction product.

In some embodiments, it is preferred to add the tag to the nascent bifunctional complex prior to the reaction, because it can be preferable to apply conditions for the reaction which are different form the conditions used by the enzyme. Generally, enzyme reactions are conducted in aqueous media, whereas the reaction between the reactant and the chemical reaction site for certain reactions is favoured by an organic solvent. An appropriate approach to obtain suitable condition for both reactions is to conduct the enzyme reaction in an aqueous media, lyophilize and subsequent dissolve or disperse in a media suitable of the reaction at the chemical reactive site to take place. In an alternative approach, the lyophilization step can be dispensed with as the appropriate reaction condition can be obtained by adding a solvent to the aqueous media. The solvent can be miscible with the aqueous media to produce a homogeneous reaction media or immiscible to produce a bi-phasic media.

Libraries of the present invention can be virtual libraries, in that they are collections of computational or electronic representations of molecules. The libraries may also be "wet" or physical libraries, in that they are collection of molecules that are actually obtained through, for example, synthesis or purification, or they can be a combination of wet and virtual, with some of the molecules having been obtained and others remaining virtual, or both.

Libraries of the present invention may, for example, comprise at least about 10, at least about 50, at least about 100, at least about 500, at least about 750, at least about 1,000, or at least about 2,500 molecules or compounds.

Libraries of the present invention may also include subsets of larger libraries, i.e. enriched libraries comprising at least two members of a larger (naïve) library.

In various embodiments, at least about 40%, at least about 50%, at least about 75%, at least about 90%, or at least about 95% of the molecules of the libraries of the present invention have less than six, less than five, or, for example, less than four hydrogen bond acceptors.

In various embodiments, at least about 40%, at least about 50%, at least about 75%, at least about 90%, or at least about 95% of the molecules of the libraries of the present invention have less than six, less than five, or, for example, less than four hydrogen bond donors.

In various embodiments, at least about 40%, at least about 50%, at least about 75%, at least about 90%, or at least about 95% of the molecules or compounds of the libraries of the present invention have a calculated Log P value of less than six, less than five, or, for example, less than four.

In various embodiments, at least about 40%, at least about 50%, at least about 75%, at least about 90%, or at least about 95% of the molecules or compounds of the libraries of the present invention have a molecular weight of less than about 500, such as less than about 350, for example, less than about 300, less than about 250, or less than about 200 Daltons.

Also included in the scope of the present invention are methods and computer processor executable instructions on one or more computer readable storage devices wherein the instructions cause representation and/or manipulation, via a computer output device, of a molecule library of the present invention. Also, methods for performing such representation and/or manipulation of a molecule library having been produced by the methods of the present invention are within the scope of the present invention.

For example, the processor executable instructions are provided on one or more computer readable storage devices wherein the instructions cause representation and/or manipulation, via a computer output device, of a library of the present invention, such as, for example, a library of scaffolded molecules, the library may comprise a plurality of molecules, wherein each molecule comprises a scaffolded part and one or more chemical entities.

The present invention also provides processor executable instructions on one or more computer readable storage devices wherein the instructions cause representation and/or manipulation, via a computer output device, of a combination of structures for analysis, wherein the combination comprises the structure of one or more members of a library of the present invention, and a biological target molecule.

In one embodiment of the invention the structure of the one or more members of the library can be represented or displayed as interacting with at least a portion of a substrate binding pocket structure of a biological target molecule. The processor executable instructions may optionally include one or more instructions directing the retrieval of data from a computer readable storage medium for the representation and/or manipulation of a structure or structures described herein.

In another aspect of the invention, combinations are provided. For example, provided in the present invention is a combination of structures for analysis, comprising a molecule library of the present invention, and a biological target molecule, wherein the structures comprise members of the library, the target molecule, and combinations thereof.

Also provided in the present invention is a combination of structures for analysis, comprising a member of a molecule library of the present invention and a biological target molecule, wherein the structures comprise the library member, the biological target molecule, and combinations thereof. The combination can be virtual, for example, computational representations, or actual or wet, for example, physical entities. In one example, at least one member of the library binds to a portion of a ligand binding site of the target molecule. In some aspects of the combination, the concentration ratio of library members to target molecules is in a ratio of, for example about 50,000, about 25,000, about 10,000, about 1,000, about 100, or about 10 mol/mol. In some aspects of the combination, the concentration of library members is close to, at, or beyond the solubility point of the solution.

The present invention also provides a mixture for analysis by x-ray crystallography, comprising a plurality of molecules or compounds selected from a library of the present invention and a biological target molecule. The biological target molecule, may, for example, be a protein, or a nucleic acid. The biological target molecule may, for example, be crystalline.

Methods of designing novel compounds or lead candidates are also provided in the present invention. For example, in one embodiment of the present invention, a method is provided of designing a lead candidate having activity against a biological target molecule, comprising obtaining a library of the present invention, determining the structures of one or more, and in some embodiments of the invention at least two, members of the library in association with the biological target molecule, and selecting information from the structures to design at least one lead candidate.

The method can further comprise the step of determining the structure of the lead candidate in association with the biological target molecule. In one embodiment, the method further comprises the step of designing at least one second library of compounds wherein each compound of the second library comprises a scaffold and two or more chemical entities; and each compound of the second library is different. In one embodiment of the invention, the scaffold of the compounds of the second library and the scaffold of the lead candidate is the same. In one embodiment, the method further comprises the steps of obtaining the second library; and determining the structures of one or more, and in some embodiments of the invention at least two, compounds of the second library in association with the biological target molecule. The biological target molecule can be, for example, a protein or, for example, a nucleic acid. The biological target molecule may, for example, be crystalline.

The method can, for example, comprise preparing a plurality of mixtures of the biological target molecule with at least one of the molecules. The method can also, for example, comprise preparing a mixture of the biological target molecule with a plurality of the molecules.

The method can, for example, further comprise the step of assaying the biological activity of one or more, and in some embodiments of the invention at least two, molecules against the biological target molecule. The assay may, for example, be a biochemical activity assay, or, for example, a biophysical assay, such as, for example, a binding assay, including, for example, but not limited to, an assay that comprises the use of mass spectroscopy. The biological activity assay may, for example, be conducted before, after, or simultaneously with obtaining the structure of the molecule in association with the biological target molecule.

In one example, a subset of the molecules or compounds assayed in the biological activity assay are selected for the structure determination step. In another example, a subset of the molecules or compounds used in the structure determination step are assayed in the biological activity assay. In one embodiment of the invention, the structure is determined using a method comprising X-ray crystallography. In one example, the method can further comprise the step of analyzing the binding of one or more, and in some embodiments of the invention at least two, molecules to the biological target molecule using a computational method.

In another example, the method can further comprise the steps of selecting or otherwise using information about the structures to design at least one second library, wherein the second library is derived from at least one molecule of the molecule library; and comprises compounds having modifications in at least one of the chemical entities of the scaffolded molecule. The method can, for example, further comprise the step of assaying the biological activity of one or more, and in some embodiments of the invention at least two, of the compounds against the biological target molecule.

The present invention also provides a method of designing a lead candidate having activity against a biological target molecule, comprising obtaining a library of bifunctional complexes of the present invention, determining the structures of at least one compound of the library in association with the biological target molecule, and selecting information from the structure to design at least one lead candidate.

The present invention also comprises methods where the molecule library can be screened against a first biological target molecule and eventually developed for activity against a second biological molecule. In some aspects of the invention, molecules or compounds found to have activity toward one biological target molecule can be screened against other biological target molecules where they may, for example, have the same or even enhanced activity. The second biological target molecule may, for example, be a related protein, and may, for example, be from the same protein family, for example, a protease, phosphatase, nuclear hormone receptor, or kinase family.

Thus, provided in the present invention is a method of designing a candidate compound having activity against a second biological target molecule, comprising obtaining a lead candidate of the present invention, determining the interaction of the lead candidate with a second biological target molecule; and designing at least one second library of compounds wherein each compound of the second library comprises a scaffold found in the lead candidate and modifications in at least one of the chemical entities on the scaffold.

In other methods of the invention, the molecule libraries are used in binding or biological activity assays before crystallization, and those molecules or compounds exhibiting a certain threshold of activity are selected for crystallization and structure determination. The binding or activity assay may also be performed at the same time as, or after, crystallization. Because of the ability to determine any complex structure, the threshold for determining whether a particular molecule is a hit can be set to be more inclusive than traditional high throughput screening assays, because obtaining a large number of false positives would not greatly negatively affect the process. For example, weak binders from a binding assay can be used in crystallization, and any false-positives easily weeded out. In other methods of the invention, the binding or biological activity assays can be performed after crystallization, and the information obtained, along with the structural data, used to determine the direction of the follow-up combinatorial library.

In one embodiment of the present invention, derivative compounds are selected from each library, wherein each such library comprises molecules with modifications at one chemical entity, resulting in a derived substituent, and for each library, the chemical entity that is modified is a different chemical entity, a new derivative compound is selected having the best-scoring chemical entities in one compound. This selected derivative compound can be used as the basis of a new round of library design and screening, or can be the basis of a more traditional combinatorial library. The selected derivative compound may also be subjected to computational elaboration, in that it may serve as the basis for the individual design of an improved compound for screening. The cycle continues until a new derivative compound is obtained that can be considered to be a lead compound, having a desired $IC_{50}$, and other desirable lead compound properties.

The present invention also provides methods for designing the molecule and compound libraries of the present invention. Provided in the present invention is a method of designing a molecule library for drug discovery, comprising screening or reviewing a list of synthetically accessible or commercially available molecules, and selecting molecules for the library wherein each of the molecules comprises: two or more chemical entities and preferably less than 25 non-hydrogen atoms. The molecules of the library may, for example, comprise, in their scaffold, at least one single or fused ring system. The molecules of the library may, for example, comprise in their scaffold at least one hetero atom on at least one ring system.

Also provided in the present invention is a method of screening for a molecule for use as a base molecule for library design, comprising obtaining a library of the present invention, screening the library for members having binding activity against a biological target molecule; and selecting a molecule of member (s) with binding activity to use as a base molecule for library design.

Also provided in the present invention are lead candidates and candidate compounds obtained by the methods of the present invention, libraries obtained by the methods of the present invention, and libraries comprising compounds with molecules selected by the methods of the present invention.

The present invention also provides a method of designing a lead candidate having biophysical or biochemical activity against a biological target molecule, comprising obtaining the structure of the biological target molecule bound to a molecule, wherein the molecule comprises a substituent having anomalous dispersion properties, synthesizing a lead candidate molecule comprising the step of replacing a chemical entity or derived substituent on the compound with a substituent comprising a functionalized carbon, nitrogen, oxygen, sulfur, or phosphorus atom, and assaying the lead candidate molecule for biophysical or biochemical activity against the biological target molecule.

The present invention also provides a method of designing a lead candidate having biophysical or biochemical activity against a biological target molecule, comprising combining a biological target molecule with a mixture comprising one or more, and in some embodiments of the invention at least two, molecules or compounds, wherein at least one of the molecules or compounds comprises a substituent having anomalous dispersion properties, identifying a molecule bound to the biological target molecule using the anomalous dispersion properties of the substituent, synthesizing a lead candidate molecule comprising the step of replacing the anomalous dispersion substituent with a substituent comprising a functionalized carbon or nitrogen atom, and assaying the lead candidate molecule for biophysical or biochemical activity against the biological target molecule.

Design of Libraries

A vast number of different libraries may be designed that can be synthesized by methods of the present invention. The library may be designed using a number of approaches known to a person skilled in the art. Library design (i.e. the choice of reactants, linker, and tags which shall be used for the synthesis of a library) may consist of a number of steps including but not limited to:

I. Choosing the linker type, e.g., the linker may be chosen to have a single chemical reaction site, two chemical reaction sites or more. The chemical reaction site may be chosen to be an amine, an acid, an aldehyde or a C—X group where X is a halogen.

II. Choosing the number of reactants to be used at each cycle during library synthesis III. Choosing the type of reactants such as
 a. reactants with a single reactive group such as a —COOH group, an amine, an isocyanate, a sulfonyl halogen, an aldehyde or a C—X group where X is a halogen, and/or
 b. reactants with two reactive groups chosen from the group of a —COOH group, an amine, an isocyanate, a sulfonyl halogen, an aldehyde or a C—X group where X is a halogen, and/or
 c. reactants with three reactive groups chosen from the group of a —COOH group, an amine, an isocyanate, a sulfonyl halogen, an aldehyde or a C—X group where X is a halogen.
 d. reactants with four reactive groups chosen from the group of a —COOH group, an amine, an isocyanate, a sulfonyl halogen, an aldehyde or a C—X group where X is a halogen.
 e. reactants with five reactive groups chosen from the group of a —COOH group, an amine, an isocyanate, a sulfonyl halogen, an aldehyde or a C—X group where X is a halogen.
 f. reactants with six reactive groups chosen from the group of a —COOH group, an amine, an isocyanate, a sulfonyl halogen, an aldehyde or a C—X group where X is a halogen.
 g. All or some of the reactive group may be appropriately protected using a protection group known to a person skilled in the art such as an fmoc group, a nosyl group, an msec group, a boc group or a tBu group (see general procedures for details).

IV. Choosing the number of each type of reactants to be used at each cycle during library synthesis.

V. Analyzing reactants with regards to properties such as molecular weight, octanol/water and water/gas log Ps, log S, log BB, overall CNS activity, Caco-2 and MDCK cell permeabilities, human oral absorption, log Khsa for human serum albumin binding, and log IC50 for HERG K+-channel blockage logD, number of hydrogen bond donors or acceptors, rotational bonds, polar surface area, Lipinski Rule-of-Five violations, drug-likeness or lead-likeness etc. Said properties may be predicted e.g. using a computer program such as qikprop (www.schrodinger.com) or determined in an assay by a person skilled in the art.

VI. Comparing reactants with other reagents with regards to structural of functional similarity VII. Enumerating the library to be synthesized, i.e., virtually (e.g. using a computer) constructing all possible encoded molecules.
 a. Analyzing said molecules with regards to properties such as molecular weight, octanol/water and water/gas log Ps, log S, log BB, overall CNS activity, Caco-2 and MDCK cell permeabilities, human oral absorption, log Khsa for human serum albumin binding, and log IC50 for HERG K+-channel blockage logD, number of hydrogen bond donors or acceptors, rotational bonds, polar surface area, Lipinski Rule-of-Five violations, drug-likeness or lead-likeness etc. Said properties may be predicted e.g. using a computer program such as qikprop (www.schrodinger.com) or determined in an assay by a person skilled in the art.

b. Comparing said molecules with other molecules with regards to structural of functional similarity VIII. Testing the reaction efficiency of reactants before using them for library synthesis.

IX. Generating one or more encoded molecules using reactants from an initial list of reactants to be used for the synthesis of a specific library, subjecting said encoded molecule(s) to one or more assays, and adjusting said list of reactants (i.e. removing reactants from the list or adding reactants to the list) based on the results of said assays.

X. Choosing reactants based on prior information regarding a target or a related molecule on which a library is intended to be screened. The related molecule may be one or more parts of a target, a molecule derived from a target e.g. by mutation, a molecule which is related to the target e.g. another member of the target family, a target homolog etc. Said prior information may be a. structural information obtained by x-ray crystallography or NMR or another method b. structural information obtained by x-ray crystallography or NMR or another method in the presence of ligand and/or cofactor c. structural information obtained by x-ray crystallography or NMR or another method in the presence of a molecule or fragment such as a reactant or a reactant analog d. information obtained by mutagenesis followed by an assay which can be performed by a person skilled in the art.

e. structure-activity information obtained e.g. by synthesis of a series of molecules followed by testing of the molecules in an appropriate assay. Such information may suggest reactants which are identical or similar to parts of said tested molecules.

XI. Choosing reactants based on prior information obtained by synthesis of a library followed by screening of the library and analyses of the screening results. Said library being synthesized by the methods described by the current invention or related methods for synthesizing bifunctional molecules such but not limited to those described in Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, and Hansen et al WO 06/048025.

In some embodiments it is preferred that each display molecule has the same general structure. In other embodiments it is preferred that display molecules may have different general structures, e.g. be composed from a different number of chemical entities:

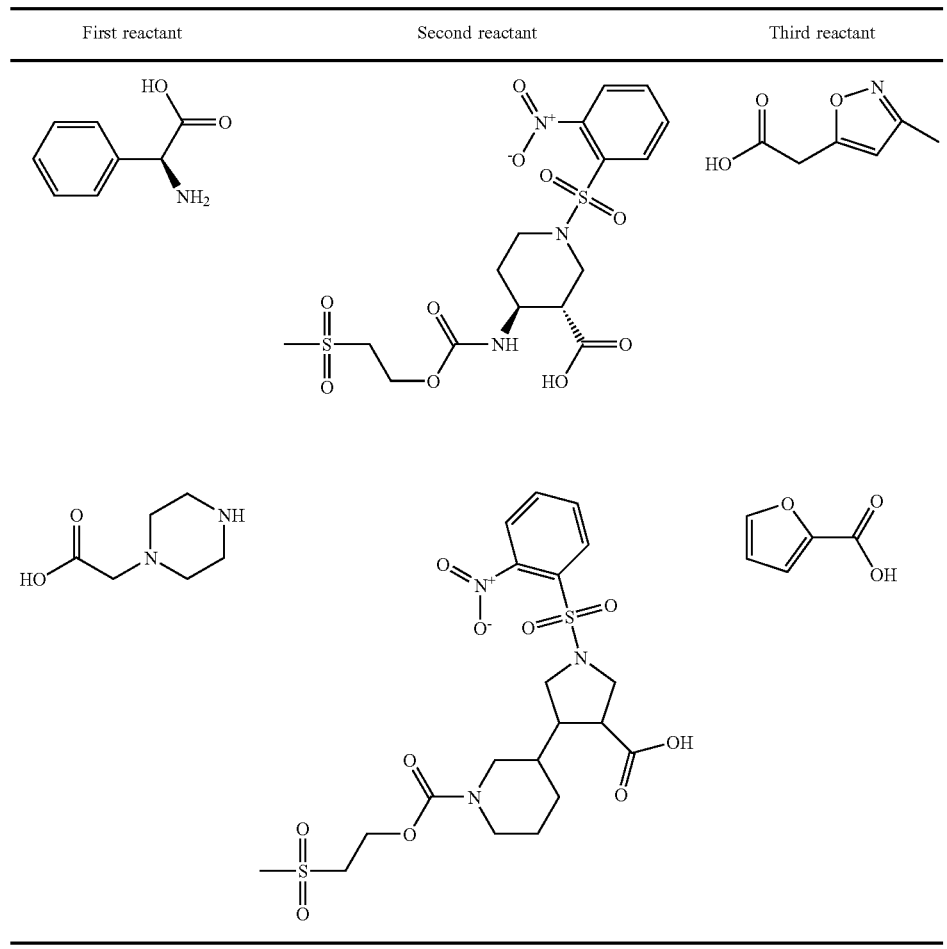

| Fourth reactant | Fifth reactant | Final product |
|---|---|---|

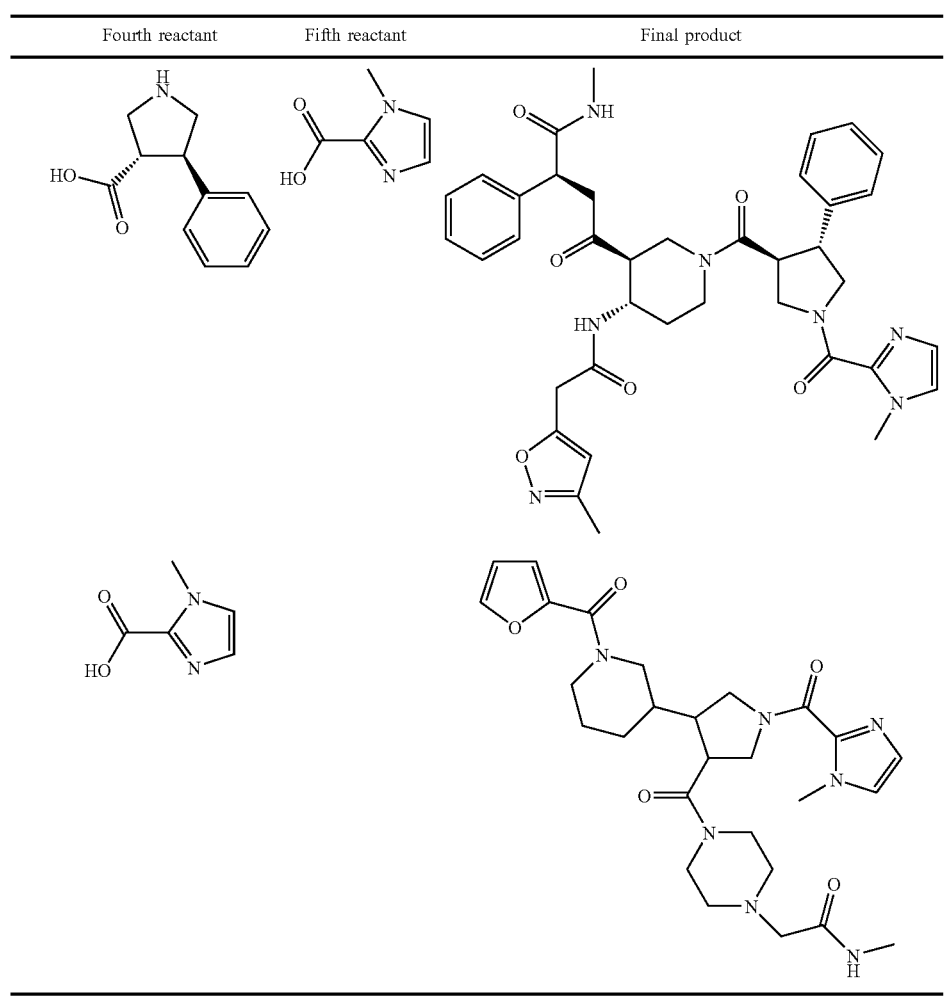

This can be achieved e.g. by subjecting to library to a final reactant reaction step. The reactant can only react with display molecules that have a corresponding reactive group. Thus, the finalized library may contain display molecules of different general structures, e.g., be composed of a different number of entities.

Preferred Split-and-Mix Methods

In preferred embodiments there are provided methods for preparing a large combinatorial library of compounds which has the advantages of (i) massive parallel synthesis of subunits and known, addressable library positions, (ii) adaptable to virtually any oligomer or small-molecule chemistry, (iii) a relatively large area for synthesis of each library member, (iv) capable of being screened either as a mixture or as individual library compounds in either solution phase or solid phase, and (v) capable of amplifying and modifying selected library compounds.

The principle advantage of the below-disclosed embodiments is that the tag directs and encodes the synthesis of the compound to which it is covalently attached (not merely reporting on the synthetic history of individual compounds), the tag can be used to create library subpopulations based on hybridization, the types of compounds that are synthesized are not limited to polypeptides and polynucleotides, the number of compounds that can be produced far exceeds that of traditional combinatorial libraries and the tag comprises or consists of a nucleic acid molecule which can be amplified biochemically and improved by genetic recombination, and in vitro evolution. The nucleic acid molecule can comprise any of the nucleotides disclosed herein above.

In one aspect of the present invention, the below disclosed split-n-mix methods are carried out subsequently to the above-disclosed methods for obtaining a bifunctional complex comprising a molecule and an identifier oligonucleotide, wherein, initially, a nascent bifunctional complex comprising one or more chemical reaction site(s) and one or more priming site(s) for enzymatic addition of a tag is reacted, in any order, a) at the chemical reaction site with one or more reactant(s) in the form of reactants or chemical entities and b) reacted at the priming site with one or more identifier oligonucleotide tag(s) identifying the reactant(s) which have reacted—or are going to react—with each other and/or with the chemical reaction site, wherein tag ligation results in the formation only of a single stranded identifier oligonucleotide comprising a plurality of tags, whereas no anti-tag at least partly hybridised the one or more tags are ligated to a neighbouring anti-tag. Subsequently to this method, the below disclosed embodiments are carried out, optionally after having selected desirable bifunctional complexes from the first synthesis method, and further optionally after having amplified the identifier oligonucleotide of one or more of said selected bifunctional complexes. The amplification can be carried out when the identifier oligonucleotide is attached to the molecule of the bifunctional complex, or the amplification can occur after the identifier oligonucleotide has been released from the remaining part of the bifunctional complex.

Accordingly, in one embodiment there is provided further method steps and compositions for further iterative synthesis and further screening of a plurality of compounds wherein a nucleic acid tag directs and encodes the synthesis of the compound to which it is covalently attached, and the tag is a DNA molecule which can be amplified biochemically.

The further methods of the present invention provide for synthesis of a plurality of compounds in a combinatorial library by way of a split and combine synthesis strategy, wherein synthesis is directed by the nucleic acid tag. The library can be provided in solution or attached to a solid support.

The nucleic acid tags useful in the methods of the present invention comprise nucleic acid sequences having a plurality of different first hybridization sequences, a mixture of different second hybridization sequences, and a chemical reaction site.

The present invention further provides a library of nucleic acid tags, also termed nucleic acid supports for use in directing the synthesis of a plurality of compounds wherein each tag has a first segment having a selected one of a plurality of different first hybridization sequences, a mixture of different second hybridization sequences, and a chemical reaction site; and a second segment having a selected one of a plurality of different second hybridization sequences and a mixture of different first hybridization sequences.

The further methods of the present invention provide subsets of nucleic acid tags generated by base-specific duplex formation between each different first or second hybridization sequence and a complementary oligonucleotides or oligonucleotide analogs. The chemical reaction sites in each of the subsets are reacted with a selected reagent to form a reagent-specific compound intermediate.

The further methods of the present invention also provide that the steps of formation of subsets of nucleic acid sequences by base-specific duplex formation be repeated and a chemical subunit added to the chemical reaction site or last added chemical subunit within each subset until synthesis of the plurality of compounds is complete.

In an exemplary aspect of the present invention, the nucleic acid tags include alternating spacer and hybridization sequences, wherein the spacer sequences are the same for all subsets of nucleic acid sequences and the hybridization sequences are different for each subset of nucleic acid sequences.

In a related aspect, the spacer sequence portion of each nucleic acid sequence has a restriction enzyme site which is unique to a given spacer sequence.

The methods of the present invention provide for the synthesis of small molecules with different chemical sequences, catalysts useful for the synthesis of complex molecules from simple substrates, inorganic compounds with useful properties as materials, non-ribosomally produced polypeptides, peptoids, polyketide-based natural products or subunit oligomers, e.g., polypeptides, polynucleotides etc. as disclosed herein above.

In one embodiment, the invention provides compound libraries wherein the compounds of such libraries can be subjected to enrichment for one or more desired activities on a continuously amplifying population.

In the methods of the present invention compounds having one or more desired activities are enriched to yield a subpopulation of nucleic acid sequences. The enriched subpopulation (s) of nucleic acid sequences serve as the starting material for repeating the step-wise synthesis of additional compounds.

Alternatively, the enriched subpopulation of nucleic acid sequences is amplified by nonspecific polymerase chain reaction (PCR), and a new chemical reaction site added prior to repeating the step-wise synthesis of additional compounds.

A process termed "polynucleotide or gene shuffling" may also be applied to the present invention. In such a process, the enriched subpopulation of nucleic acid sequences is treated with one or more restriction enzymes under conditions effective to produce a partial digest by cleavage at a sequence-specific restriction enzyme site within each spacer sequence. The partially digested nucleic acid sequences are rejoined and a new chemical reaction site added prior to repeating the step-wise synthesis of additional compounds.

Compound libraries which are synthesized under the direction of compound-specific synthesis-directing nucleic acid tags are also provided by the present invention. In this aspect, the nucleic acid sequences which direct the synthesis of the compounds can be subjected to genetic recombination or in vitro evolution by repeated cycles of enrichment and step-wise synthesis; enrichment, PCR amplification and step-wise synthesis; or enrichment, partial digestion, rejoining of fragments and stepwise synthesis to yield a highly enriched subpopulation of synthesis-directing nucleic acid sequences.

Preferably, subpopulations of enriched compounds are produced by the methods of the present invention by selecting for activities which include, but are not limited to, modulation of enzymatic activity, modulation of non-enzymatic catalytic activity, modulation of protein-protein interactions and modulation of receptor/ligand interactions, etc.

The invention also provides a method for library splitting on the basis of sequence hybridization post-synthesis. In this aspect, a complete library is synthesized, split by hybridization based on the different sequence directing nucleic acid tag attached to each library member and further step performed on the split library.

The invention also provides a method for library splitting on the basis of sequence hybridization following enrichment of certain bifunctional complexes, e.g. by affinity selection. In this aspect, a complete library is synthesized, subjected to affinity selection and split by hybridization based on the different sequence directing nucleic acid tag attached to each library member. Then further steps may be performed on the split library such as decoding tags of individual split library pools by sequencing.

Preferred types of compounds in the compound libraries of the present invention include, but are not limited to, small molecules with different chemical sequences, catalysts useful for the synthesis of complex molecules from simple substrates, inorganic compounds with useful properties as materials, non-ribosomally produced polypeptides, peptoids, polyketide-based natural products or subunit oligomers, e.g., polypeptides, polynucleotides etc.

Further, the invention provides a method to perform all genetic manipulations possible with natural biopolymers (through the manipulation of DNA instructions) on such DNA templated combinatorial libraries of compounds as a means to provide a method to identify useful compounds from large combinatorial libraries of compounds, as described above.

These and other objects and features of the invention will become more fully apparent when the following detailed description of the invention is read in conjunction with the accompanying drawings.

DEFINITIONS

The term "combinatorial library" is defined herein to mean a library of molecules containing a large number, typically between 10e3 and at least 10e6, such as 10e8, for example 10e10 different compounds typically characterized by different sequences of subunits, or a combination of different sequences of side chains and linkages.

The term "combinatorial library of subunit oligomers" is defined herein to mean a set of oligomers containing substantially each sequence permutation that can be formed by placing a selected one of a number of different subunits at each of a selected number of residue positions.

"Different-sequence oligomer compounds" are oligomers, such as oligonucleotides, oligonucleotide analogs, oligopeptides, oligopeptide analogs, oligosaccharides, or lipopeptides with different permutations of lipid and/or sequences in the peptide moieties, glycopeptides with different sequence permutations in the saccharide and/or peptide moieties, non-biological oligomers with different-sequence permutations, or different-substituent compounds in a small molecule library.

The terms "base-specific duplex formation" or "specific hybridization" refer to temperature, ionic strength and/or solvent conditions effective to produce sequence-specific pairing between a single-stranded oligonucleotide and its complementary-sequence nucleic acid strand, for a given length oligonucleotide. Such conditions are preferably stringent enough to prevent or largely prevent hybridization of two nearly-complementary strands that have one or more internal base mismatches. Preferably the region of identity between two sequence s forming a base-specific duplex is greater than about 5 bp, more preferably the region of identity is greater than 10 bp.

The terms "polymerase chain reaction" and "PCR" refer to a process of amplifying one or more specific nucleic acid sequences, wherein (i) oligonucleotide primers which determine the ends of the sequences to be amplified are annealed to single-stranded nucleic acids in a test sample, (ii) a nucleic acid polymerase extends the 3' ends of the annealed primers to create a nucleic acid strand complementary in sequence to the nucleic acid to which the primers were annealed, (iii) the resulting double-stranded nucleic acid is denatured to yield two single-stranded nucleic acids, and (iv) the processes of primer annealing, primer extension, and product denaturation are repeated enough times to generate easily identified and measured amounts of the sequences defined by the primers. The sequential annealing, extension and denaturation steps are controlled by varying the temperature of the reaction container, normally in a repeating cyclical manner. Annealing and extension are typically carried out between 40-80 C, whereas denaturation requires temperatures between about 80 and 100 C. A "thermal cycler", such as Perkin Elmer Model 9600, is typically used to regulate the reactions.

The terms "oligonucleotides" or "oligos" as used herein refer to nucleic acid oligomers containing between about 3 and typically up to about 150, such as from about 5 to about 100 nucleic acid subunits, for example from about 5 to about 80 nucleic acid subunits. In the context of oligos which direct the synthesis of the library compounds of the present invention, the oligos may include or be composed primarily of nucleotide analog subunits, or other subunits capable of forming sequence-specific Watson-Crick base pairing, when assembled in a linear polymer, with the proviso that the free ends of the oligos are ribonucleotide or deoxyribonucleotide subunits capable of providing a suitable substrate for strand-directed polymerization in the presence of a DNA polymerase and one or more nucleotide triphosphates, e.g., conventional deoxyribonucleotides with free 3'OH groups. A "known sequence oligo" is an oligo whose nucleic acid sequence is known.

The term "oligonucleotide analog" is defined herein to mean a nucleic acid that has been modified and which is capable of some or all of the chemical or biological activities of the oligonucleotide from which it was derived. An oligonucleotide analog will generally contain phosphodiester bonds, although in some cases, oligonucleotide analogs are included that may have alternate backbones. (See, E. G., several nucleic acid analogs described in Rawls, C & E News, Jun. 2, 1997, page 35). Modifications of the ribose-phosphate backbone may facilitate the addition of additional moieties such as labels, or can be done to increase the stability and half-life of such molecules. In addition, mixtures of naturally occurring nucleic acids and analogs can be made. Alternatively, mixtures of different nucleic acid analogs, and mixtures of naturally occurring nucleic acids and analogs can be made. The oligonucleotides can be single stranded or double stranded, as specified, or contain portions of both double stranded or single stranded sequence. The oligonucleotide can be DNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The "subunit oligomers" produced by the methods of the present invention typically have 3 to 20 residue positions at which the subunit assumes one of a plurality of possible forms, e.g., different nucleic acid or amino acid side chains.

"Different-sequence small-molecule compounds" are small organic molecules, typically, but not necessarily, having a common parent structure, such as a ring structure, and a plurality of different R group substituents or ring-structure modifications, each of which takes a variety of forms, e.g., different R groups. Such compounds are usually non-oligomeric (that is, do not consist of sequences of repeating similar subunits) and can be similar in terms of basic structure and functional groups, but vary in such aspects as chain length, ring size or number, or patterns of substitution.

The term "chemical reaction site" as used herein refers to a chemical component capable of forming a variety of chemical bonds including, but not limited to; amide, ester, urea, urethane, carbon-carbonyl bonds, carbon-nitrogen bonds, carbon-carbon single bonds, olefin bonds, thioether bonds, and disulfide bonds.

The terms "nucleic acid tag" and "nucleic acid support" are defined herein to mean the nucleic acid sequences which comprise a plurality of different first hybridization sequences, a mixture of different second hybridization sequences, and a chemical reaction site. Such "nucleic acid tags" are capable of directing the synthesis of the combinatorial library of the present invention and are also termed "synthesis-directing nucleic acid tags".

The term "tag-directed synthesis" refers to the fact that the plurality of compounds synthesized by the methods of the present invention is directed by the nucleic acid tag.

The term "continuously amplifying population" refers to the continuously increasing plurality of compounds produced by the iterative methods of the present invention.

The term "genetic recombination" refers to enrichment of the plurality of compounds produced by the methods of the present invention for those compounds having one or more desired activities by performing the steps of enrichment, partial digestion, rejoining the partially digested sequences and further stepwise synthesis to yield a highly enriched subpopulation of nucleic acid sequences which are bound to compounds having one or more desired activities.

The term "nucleic acid tag(s)" are used interchangably herein below with identifier oligonucleotide(s) comprising a plurality of nucleic acid tags.

In another aspect, the invention provides combinatorial compound libraries which can be subjected to genetic recombination or in vitro evolution by repeated cycles of enrichment and step-wise synthesis, enrichment, PCR amplification and step-wise synthesis or enrichment, partial digestion, reformation and stepwise synthesis to yield a highly enriched subpopulation of nucleic acids which are bound to compounds having one or more desired activities.

The term "selection for a desired activity" means evaluating one or more of the plurality of compounds produced by the methods of the invention for the ability to modulate a chemical or biological reaction.

The term "receptor" refers to a molecule that has an affinity for a given ligand which can be naturally occurring or synthetic molecule. Receptors can be attached, covalently or noncovalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

The term "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

The term "modulate" as used herein refers to a change in a particular biological activity.

Modulation may relate to an increase or a decrease in biological activity, binding characteristics, or any other biological, functional, or immunological property of the molecule.

The term "agonist" as used herein, refers to a molecule which is capable of modulating a biological activity of, e.g., a receptor by inducing, increasing, or prolonging the duration of the biological activity mediated by the receptor. Agonists may themselves be polypeptides, nucleic acids, carbohydrates, lipids, or derivatives thereof, or any other molecules which bind to and modulate the activity of the receptor.

The term "antagonist" as used herein, refers to a molecule which, when bound to, e.g., a receptor modulates the activity of the receptor by blocking, decreasing, or shortening the duration of the biological activity mediated by the receptor.

Antagonists may themselves be polypeptides, nucleic acids, carbohydrates, lipids, or derivatives thereof, or any other molecules which bind to and modulate the activity of the receptor.

Other terms used herein should be construed to take on meanings customary in the art, unless otherwise defined herein.

Templated Resynthesis of Libraries of Bifunctional Molecules

Methods disclosed herein allows for the synthesis of libraries of bifunctional molecules and for the subsequent partitioning such as affinity selection of libraries for the purpose of the identification of library molecules with a desired function.

In some cases it may be beneficial that the identifier tag information that is amplified following the partioning step can be used to direct the re-synthesis of the first library for subsequent further partitioning and identification of desired molecules.

Consequently, following an initial split-and-mix synthesis of a library of bifunctional molecules according to the present invention and as disclosed herein and a subsequent partitioning step and optionally amplification of the identifier tags (identifier oligonucleotides) of selected molecules, the tags or tag amplification product(s) can be used as a template for the re-synthesis of the first library or a subset of the first library using any process that allows the information of the amplified identifier to direct a templated synthesis of the library.

Following templated synthesis, the generated second library can be partitioned and the template amplified for identification of desired molecules by e.g. sequencing of the isolated identifiers (templates). Alternatively the amplified template can be used to template the synthesis of a third library being identical to or a subset of the first or the second library using any process that allows the templated synthesis of a library of bifunctional molecules. The process of library resynthesis, partitioning and template amplification can be iterated any number of times such as 1 time, 2 times, 3 times, 4 times, 5 times, 6 times, 7 times, 8 times, 9 times, 10 times or more than 10 times.

Methods that can be used for templated library resynthesis includes but is not limited to (Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, Hansen et al WO 06/048025. In the method disclosed by Harbury and Halpin, free reactants are loaded on the reactive site on the identifier in solution or attached to a solid-support. This method of reactant loading in free form is similar to the methods disclosed herein. Consequently, the building block reactants applied for a first library of bifunctional molecules is directly applicable to the templated process described by Halpin and Harbury for second library synthesis. Other methods for templated synthesis listed above (Rasmussen (2006) WO 06/053571A2, Liu et al. (2002), WO 02/074929 A2; Pedersen et al. (2002) WO 02/103008 A2; Pedersen et al. (2003) WO03/078625 A2; Hansen et al WO 06/048025 A1, requires the pre-attachment of reactants to oligonucleotides prior to the chemical reactions required for the templated synthesis of a second library. Thus, none of the building block reactants applied in a first library synthesis using the method disclosed herein is directly applicable to the synthesis of a second library without prior modification of the reactants and/or appendage to an oligonucleotide.

The following example is included to illustrate the principle of templated resynthesis of a library using templates that are amplified from a pool of identifiers isolated from the screening of a first library of bifunctional molecules.

Synthesis of a first library is conducted as described elsewhere in the claims and in example 1 producing a library consisting of app 65.000 different bifunctional molecules. The tetramer library consists of bifunctional molecules each comprising 4 DNA codon elements (tags) covalently linked to the cognate chemical fragments. The overall structure of the bifunctional molecules is shown in FIG. 51. Each 20 nt/bp codon is spaced by a 10 nt fixed region and the tags A-D is flanked by fixed sequences useful for amplification by PCR.

The 65.000 member library was screened against thrombin and the isolated DNA was amplified as described in example 1 using proof-reading PCR and the forward and reverse primers 5'-CAAGTCACCAAGAATTCATG and 5'-AAGGAACATCATCATGGAT. The PCR product was used as template for large-scale 96 wells proof-reading PCR (Pwo Master-mix, Roche) using a similar primer pair except that the forward primer contained the $NH_2$-PEG unit described in example 1 and the reverse primer contained a 5'-biotin group. Following PCR, the content of all wells was pooled, extracted twice with phenol and once with chloroform before ethanol/acetate precipitation of the DNA. Following centrifugation the DNA pellet was washed twice using 70% ethanol, dried and redissolved in 100 ul of 25 mM $NH_4$-acetate pH 7.25.100 ul SA-beads (Amersham) is washed 3 times with 25 mM $NH_4$-acetate buffer before mixing with the DNA sample and incubation for 10 min at RT. The sample is washed 3 times with ammonium-acetate buffer. The non-biotinylated topstrand comprising the 5' Amino-PEG unit was eluted by adding 200 ul of $H_2O$ at 90° C. for 30 seconds before immediate spin removal of the SA-beads using a SpinX column (Corning). The singlestranded template is incubated with another 100 ul of SA-beads and incubated for 10 min at RT before SA-bead removal using SpinX column. The unbound fraction is purified on a microspin 6 column (Bio-rad). This sample containing a singlestranded template with terminal Amino-PEG unit was used for the templated resynthesis of the second library essentially according to the method of Halpin and Harbury: DNA Display I. Sequence-Encoded Routing of DNA Populations, *PLoS Biol.* 2004 July; 2(7): e173. DNA Display II. Genetic Manipulation of Combinatorial Chemistry Libraries for Small-Molecule Evolution, *PLoS Biol.* 2004 July; 2(7): e174. DNA Display III. Solid-Phase Organic Synthesis on Unprotected DNA, *PLoS Biol.* 2004 Jul. 2(7): e175.

In brief, the singlestranded template is allocated according to the codon sequence in position A into specific compartments by hybridization to a complementary anti-tag immobilised to a solid-support. Consequently, 16 different anti-tags each capable of hybridizing specifically to one A-codon tag is immobilised on solid-support, placed in individual housings and connected in series. The template is pumped through the compartments in a circular system until the templates are allocated in their cognate compartments. Subsequently, each template is transferred to a DEAE column for chemical reaction with a codon specific building block (reactant) according to Table 1.4A. Following chemical transformation and deprotection, all templates are collected from the DEAE column, pooled and redistributed into specific codon B compartments in a process similar to that described above for position A. Consequently the allocation, chemical reaction, deprotection, pooling steps can be iterated for codon positions A to D ultimately producing a library a bifunctional molecules using the same building block/codon combinations as for the initial library enabling the resynthesis of this library based on the identifier/template bias created from the partitioning of the first library. Templated Synthesis of a Library of Bifunctional Complexes Using Identifier Allocation by Sequential Identifier Subtraction.

Several methods have been disclosed for the templated synthesis of a library of bifunctional molecules such as (Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, Hansen et al WO 06/048025. All methods except for DNA-display (Harbury and Halpin) employ the pre-attachment of reactants to specific oligonucleotide sequences capable of hybridising to a specific codon on the template. This pre-attachment is time- and resource consuming and limits the number of commercially available reactants for library generation. In contrast, the chemical transformation using free-form reactants (Halpin and Harbury) dramatically increase building block access, number of chemical reactions available for library generation and reduce time and resources necessary for preparation of reactants. Consequently, the free-form reactant offers a clear advantage for the fast access to and diversity of chemical transformations. However, the method disclosed by Halpin and Harbury requires specific allocation of the identifier templates into discrete compartments. This allocation is conducted by passing the pool of identifier templates through a series of compartments comprising compartment specific anti-tags oligonucleotides attached to a solid-support. Such compartment specific allocation is difficult due to problems with unspecific template allocation resulting in a template being fortuitously trapped in compartments with a non-cognate anti-tag. Ultimately, this results in an illegal reactant/codon combination and a reduced fidelity in translation of the template. Furthermore, the single stranded form of DNA is energetically disfavoured and a complex ssDNA template will tend to take up secondary structure which may result in template loss during an allocation step due to lack of hybridisation to a cognate anti-tag. Also, the hybridisation between two complementary oligonucleotide sequences may be impeded to some extent by the covalent attachment of one oligonucleotide component (anti-tag) to a solid-support compared to a similar duplex formation performed in solution.

The issues above could be resolved by performing the hybridization between a specific anti-tag or a subset pool of anti-tags and the complementary identifier sequence(s) in solution. This allows the experimenter to remove secondary structures in the template f. ex by a heat denaturation step prior to anti-tag hybridization for improved hybridization kinetics. Subsequently, the anti-tag/identifier duplexes needs to be retracted from the remaining unbound fraction of identifiers in a first allocation step using a handle supplied on the anti-tag such as a biotin-group for specific isolation using SA(streptavidin)-beads. Following retraction of the first subset of identifiers the remaining pool of unbound identifiers is denatured before addition of the next specific anti-tag or subset of anti-tags and the process of identifier subset isolation is iterated until all identifiers are allocated on their sequence specific subset SA-beads.

Obviously, an iterative process involving fishing out single specific codon identifier sequences may become unfeasible for large codon sets. Consequently, the entire pool of individual (single) anti-tag sequences complementary to the pool of codons at one position such as position A in the template shown in the figure below, can be subdivided into a subset pool of anti-tags. The subset pools can then be used for sequential subtraction of identifier templates into discrete pools. Following elution of identifiers from each retracted sub-pool the single-stranded identifiers are hybridised to a smaller subset of anti-tags than used for initial round of allocation or using a single anti-tag from the corresponding first round subset. The sequential subtraction can be iterated until each identifier is allocated in separate compartments according to its unique first codon sequence.

The example below (see FIG. 52) is included to illustrate the use of sequential subtraction. Initially, 10 subset pools a-j each comprising 10 anti-tag totalling 100 anti-tag sequences for codon position A is prepared carrying a purification handle (f. ex a biotin-group).

i) A singlestranded identifier with a reactive entity is provided.
ii) $1^{st}$ capture: combine anti-tags complementary to codon position A in different 10 different pools (a-n) each having 10 anti-tags:
(a) 1-10, (b) 11-20, (c) 21-30, (d) 31-40, (e) 41-50, (f) 51-60, (g) 61-70, (h) 71-80, (i) 81-90, (j) 91-100.
iii) Add pool a to identifier and hybridize anti-tags to the cognate subset of identifiers in solution or on solid support. The bound fraction is subtracted from the pool using the anti-tag handle.
iv) The fraction of unbound identifiers is hybridized to pool b and subtracted from the identifier pool as above
v) Continue the identifier subset subtraction using anti-tag pool a to j.
vi) Elute single-stranded identifier into pool a to j
vii) $2^{nd}$ capture: The subset capture method described above is used for each subset a to j applying single anti-tags. Consequently, from pool a, anti-tag 1 is used as a first hybridizing anti-tag allowing specific subtraction of identifiers with a codon 1 at position A. The unbound pool of identifiers is subsequently hybridized with anti-tag 2 for specific subtraction of identifiers with codon 2 at position A.
viii) Repeat identifier subset allocation using all 10 single anti-tag within specific subgroup allowing specific (single) allocation of identifiers in 100 subset groups.
ix) Chemical reaction using specific reactant/codon combinations and subsequent deprotection
x) Pool identifiers and repeat routing principle for codon position B In the example above, two branch allocations are conducted for each specific identifier (ie each codon sequence is subset allocated twice). In the first round each identifier is allocated as a subset pool followed by a second specific allocation for each unique codon. However, the experimenter may choose any number of branches, any number of subset pools at each branch and any number of anti-tags in each subset pool. Furthermore, the specific routing conducted for one position is custom-made for that codon position and, consequently, the experimenter can re-use the branch-profile from one position to any of the remaining positions or may apply a branch profile that is unique for a codon position.

Also, the experimenter may use any number of branches such as 1, 2, 3, 4, 5, 6, 7, 8, 9, 10 or more than 10 branches in the routing protocol. Furthermore, the experimenter can use any number of subset pools such as any number between 1 and 1.000 or more than 1.000. Also the experimenter can use any number of anti-tags in each subset pool such as any number between 1 and 1.000 or more than 1.000.

The use of multiple branches increase the specificity of the allocation step, because the level of unspecific allocation is reduced when conducting more than a single allocation round as described Halpin and Harbury WO 00/23458. In the example below, a principle for sub-allocation of 200 different codons at position for a pool of identifier templates is described using 3 branches. In the first branch 5 pools of anti-tags each comprising 40 unique anti-tags is used for the sequential subtraction of identifiers into their cognate sub-pools. Following elution of identifiers in each sub-pool, the second branch of allocation is conducted using a subset of 5 pools of 8 anti-tags each, for the specific retrieval of subsets within their respective $1^{st}$ branch subset producing a total of 25 sub-pools. Following identifier elution, the $3^{rd}$ branch of subset allocation is conducted using each unique anti-tag individually for identifier retrieval subtracted from their cognate subset pool from the $2^{nd}$ branch resulting in specific single allocation of identifiers containing a unique codon at position A. Subsequently, the identifiers can be eluted e.g. in H2O as described herein elsewhere and prepared for chemical transformation using a codon-specific reactant, reacted, optionally purified, optionally deprotected and pooled before re-allocation according to the next codon position of the identifier template. The process is iterated any number of times dependent on the number of chemical reactant that need to be reacted and the number of codon positions. Chemical reactions can be conducted by any means compatible with the presence of DNA including methods described herein and using methods referred in this document The method described here, make use of iterative steps of subtraction of specifically formed duplexes between the anti-tags supplied and the corresponding identifier codon sequences. The method relies on efficient retrieval of the duplexes which can be done using any means useful for isolation of DNA duplexes. Consequently, any entity capable of being linked to an anti-tag and useful as handle for purification purposes may be used for the allocation steps described herein. Specifically, the anti-tags may be supplied with a handle for purification of the duplexex, such as a biotin-group for interaction with streptavidine-beads or derivatives thereof, a dinitrophenol (DNP) for purification using DNP-specific antibodies (f.ex covalently attached to a solid-support) or having a chemical entity f.ex a thiol-group capable of reacting forming a covalent link with a solid-support such as 2-pyridin-activated thio-sepharose (Amersham Biosciences).

In principle, the anti-tag or pool of anti-tags may be linked covalently, or non-covalently to a solid-support prior to hybridization of the identifier templates.

Templated Resynthesis
Step 1: Construction of Anti-Tag Columns 16 different twenty-base capture oligonucleotides were synthesized using standard phosphoramidite chemistry, with the addition of a C12-methoxytritylamine modifier at the 5'-end (Glen Research #10-1912, DNA technology, Aarhus Denmark). The HPLC purified oligonucleotides were loaded on a DEAE column and reacted with Fmoc-amino-PEG24 carboxylic-acid (Quanta BioDesign, ltd) using DMT-MM as activating agent. Excess Fmoc-Amino-PEG linker was removed by collecting the oligonucleotide on a DEAE column followed by Fmoc deprotection by two 1-ml treatments with 20% piperidine in DMF, one for 3 min and one for 17 min. Following elution from DEAE, the oligonucleotides were purified by microspin column gelfiltration (biorad) and analysed on ES-MS. The oligonucleotides were covalently attached to a sepharose resin by incubation with one volume equivalent of drained NHS-activated Sepharose (Amersham Biosciences #17-0906-01). The suspension was rotated at 37° C. ON before addition of 1 M Tris-HCl and incubation ON. The product resin was washed and could be stored at 4° C. or −20° C.

The derivatized resins were loaded into empty DNA synthesis column housings (#CL-1502-1; Biosearch Technologies, Novato, Calif., United States).

Step 2: ssDNA Template Hybridization.

Approximately 250 μl of DEAE Sepharose suspension was pipetted into an empty Glen Research column housing and washed with 20 ml of H₂O followed by 12 ml of DEAE bind buffer (10 mM acetic acid and 0.005% Triton X-100) using a syringe or a syringe barrel, a male-male luer adapter, and a vacuum manifold. The template DNA was loaded onto the washed chemistry column in 1 ml of DEAE bind buffer at approximately 1 ml/min. Anticodon columns were connected in series to the DEAE column using male tapered luer couplers, capillary tubing, silicone tubing, and tubing connectors. Approximately 3 ml of hybridization buffer containing 1 nmol of each oligonucleotide complementary to the noncoding regions was cyclically pumped over the system at 0.5 ml/min for 1 h at 70° C., 10 min at 37° C., and 1 h in a 46-° C. water bath within a 37-° C. room. Hybridized DNA was transferred back to fresh individual DEAE columns for loading of the specific reactants, Step 3: Chemical Reactions at Position A Chemical reaction on the reactive amino-group on the template was carried out essentially as described in Halpin and Harbury (PLoS, 2004). To accomplish amino acid additions, columns were washed with 3 ml of DMF and subsequently incubated with 50 mM Fmoc protected-AA shown in table 1.4 and 50 mM DMT-MM in 100 ul of coupling mix containing 2% DEA in DIPEA/H2O (95:5) for 10 min. Excess reagent was washed away with 3 ml DMF, and the coupling procedure was repeated. The Fmoc-protecting group was then removed by two 1-ml treatments with 20% piperidine in DMF, one for 3 min and one for 17 min. Finally, the columns were washed with 3 ml of DMF followed by 3 ml of DEAE Bind Buffer (10 mM acetic acid, 0.005% Triton X-100). Identifier templates were eluted with 2 ml of Basic Elute Buffer (1.5 M NaCl, 10 mM NaOH, and 0.005% Triton X-100) heated to 80° C. The DNA was pooled, precipitated with ethanol/acetate, redissolved and reloaded on a fresh DEAE column.

Subsequent Re-Allocation According to Codon B, C and D.

Construction of anti-tag columns, ssDNA template allocation and transfer to specific DEAE columns for position B, C and D reactions was accomplished using the protocol described above for codon A.

Chemical Reaction at Position B

Building block reactants according to Table 1.4B was reacted using 50 mM of reactant, 50 mM DMT-MM in 100 ul of coupling mix containing 2% DIPEA (N,N'-Diisopropyethylamin) in DMF/H2O (95:5) for 10 min. Excess reagent was washed away with 3 ml DMF, and the coupling procedure was repeated. The Msec protection group was removed by addition of 20% piperidine in H2O for 10 min. The process was repeated once.

Chemical Reactions at Position C

Building blocks (reactants) for position C is listed in Table 1.4C i) Acylation reactions: Conducted as described above.

ii) Isocyanate addition: The DNA on DEAE was washed with 0.5 ml of a buffer containing 100 mM sodium borate and 100 mM sodium phosphate pH 8.0 and subsequently incubated with 50 mM of specific isocyanate reactant in CH3CN in the above buffer in a total volume of 100 ul. The reaction was incubated at 50° C. ON.

iii) Sulphonylation: The DNA on DEAE was washed using 100 mM Na-borate pH 9. Subsequently 10 ul of 100 mM of sulphonylation reactant in THF is mixed with 40 ul of 100 mM Na-borate buffer pH 9 and incubated at 30° C. ON.

Following transformations all resins are washed and the templated molecules are Ns deprotected by incubation in a solution of 0.25 M mercaptoanisol and 0.25 M DIPEA (N,N'-Diisopropylethylamine) in DMF and incubated ON at 25° C. in an eppendorph thermoshaker at 600 rpm. Then the material on DEAE was washed with 0.3M AcOH in DMF, then twice with DMF before elution.

Chemical Reactions at Position D

Building blocks (reactants) for position D are listed in Table 1.4D

Acylation, isocyanate addition and sulphonylation was carried out as described above.

iv) Nucleophilic aromatic substitution: DNA on DEAE was washed once with 0.5 ml 100 mM Na-borate buffer pH 9.0. 25 ul of the reactant in (100 mM in DMSO) was mixed with 25 ul of 100 mM Na-borate pH 9.0 was added and the reaction incubated at 90° C. ON v) Reductive amination: DNA on the DEAE resin was washed with 0.5 ml of 200 Na-acetate buffer pH 5.0 in 90% DMF followed by incubation of 10 ul of 200 mM reactant in DMSO dissolved in 40 ul of 200 mM Na-acetate buffer pH 5.0 in 90% DMF and subsequent incubation at 30° C. for 1 hour. Subsequently 25 ul of freshly prepared 140 mM NaCNBH₃ in Na-acetate buffer pH 5.0 was added followed by incubation ON at 30° C.

Following the final chemical reactions, all samples are subjected to an Fmoc deprotection reaction using piperidine as described above (position A). The DNA is eluted from the DEAE columns, pooled and precipitated using ethanol/acetate. Following centrifugation the pellet is washed twice with 70% ethanol, dried and redissolved in H2O.

Prior to iterating the affinity selections on trombin, the singlestranded library of bifunctional molecules is converted to a doublestranded form by polymerase extension as described in example 1.

A. An Exemplary Encoding Scheme

The encoding scheme described below represents one of many different possible embodiments of the encoding schemes encompassed by the present invention in combination with the split-and-mix synthesis methods disclosed herein elsewhere. All of the possible encoding schemes that are encompassed under this invention are based on differential hybridization to nucleic acid tags during a split-and-recombine synthesis.

1. The Solid Support.

In the present invention, the conventional solid support (typically a polystyrene/polymethylacrylate bead, or a polyethyleneglycol hybrid thereof) has been replaced with a nucleic acid sequence.

In an exemplary embodiment the nucleic acid tag comprises or consists of at least 220 basepairs and more preferably contains 420 base pairs. In some cases the nucleic acid tag contains more than 420 base pairs.

In another exemplary embodiment the nucleic acid tag comprises or consists of from about 40 to 160 basepairs, such as from 60 to 80 basepairs, for example from 80 to 100 basepairs, such as from 100 to 120 basepairs, for example from 120 to 140 basepairs, such as from 140 to 160 basepairs. In some cases the nucleic acid tag contains more than 160 basepairs, such as more than 200 base pairs.

In one exemplary embodiment, the nucleic acid tag consists of 21 regions of twenty base pairs. Eleven of these regions are denoted C,→C", wherein, C is an abbreviation for "constant" and refers to the "spacer" sequences described above. In this embodiment, the ten remaining regions are denoted V,→V, o wherein, V is an abbreviation for "variable" and refers to the hybridization sequences which are different for each group of subsets of nucleic acid sequences. In this embodiment, every V region is bordered by two different C regions.

In one exemplary embodiment, the nucleic acid tag consists of 3 regions of twenty base pairs and 4 regions of ten nucleotides. The 4 regions of ten nucleotides are denoted C,→C", wherein, C is an abbreviation for "constant" and refers to the "spacer" sequences described above. In this embodiment, the 3 regions of twenty nucleotides are denoted V,→V, o wherein, V is an abbreviation for "variable" and refers to the hybridization sequences which are different for each group of subsets of nucleic acid sequences. In this embodiment, every V region is bordered by two different C regions.

In one exemplary embodiment, the nucleic acid tag consists of 4 regions of twenty base pairs and 5 regions of ten nucleotides. The 5 regions of ten nucleotides are denoted C,→C", wherein, C is an abbreviation for "constant" and refers to the "spacer" sequences described above. In this embodiment, the 4 regions of twenty nucleotides are denoted V,→V, o wherein, V is an abbreviation for "variable" and refers to the hybridization sequences which are different for each group of subsets of nucleic acid sequences. In this embodiment, every V region is bordered by two different C regions.

The pool of nucleic acid tags is degenerate, meaning that almost all of the nucleic acid tags differ from one another in nucleotide sequence. The nucleotide differences between different nucleic acid tags reside entirely in the hybridization sequences. For example, in one embodiment in the V, region, ten different twenty base-pair sequences are present. In another embodiment in the V, region, 100 different twenty base-pair sequences are present. Each unique twenty base-pair sequence can be referred to as a "ZIP code". Thus ten different "ZIP codes", denoted a, b, c, . . . j, appear in the V, region of the different nucleic acid tags. Likewise, ten more unique "ZIP codes", denoted a2, b2, c2 . . . j2, appear in the V2 region of the different nucleic acid tags. A third set of 10 or 100 unique ZIP codes appears in the V3 region, etc.

In this embodiment, all of the DNA tags share the same twenty base-pair sequence in designated spacer regions, i.e., the c, spacer region is denoted z. A different 20 base-pair sequence, z2, appears in the C2 region of every DNA tag. Accordingly in an embodiment where the nucleic acid tag contains 420 base pairs, in regions C3→C", all of the tags have the spacer sequences Z3→Z, respectively.

Thus each 420 base pair nucleic acid tag consists of an ordered assembly composed of 111 different twenty base-pair reactants, the 100 ZIP codes (a"b"c, . . . d5, e5, 5, . . . hlo ilo, jio) and the 11 spacer regions (z, . . . z'). The 111 twenty base-pair reactants have the following properties: (i) micromolar concentrations of all 111 sequences hybridize to their complementary DNA sequences efficiently in solution at a specified temperature designated Tm, and (ii) the 111 sequences are orthogonal to each other with respect to hybridization, meaning that none of the 111 sequences cross-hybridizes efficiently with another of the 111 sequences, or with the complement to any of the other 111 sequences, at the temperature Tm.

The degenerated identifier oligonucleotides comprising a plurality of nucleic acid tags can be assembled from their constituent reactants e.g. by the primeness PCR assembly method described by Stemmer et al., Gene 164 (1): 49-53 (1995).

However, the identifier oligonucleotides comprising a plurality of tags can also be provided as described herein above by step-wise ligation of tags. In one embodiment of this method, both tags and anti-tags are ligated. In another embodiment, tags are ligated using one or more "splints" capable of hybridising to the tags to be ligated.

2. The Chemical Reaction Site

The 5'alcohol of the 5'base of the nucleic acid tag is modified with a commercially available reagent which introduces a phosphate group tethered to a linear spacer, e.g., a 12-carbon and terminated with a primary amine group (e.g., Glen Research catalog#10-1912-xx or numerous other reagents which are available for introducing thiols or other chemical reaction sites into synthetic DNA).

The primary amine represents the chemical reaction site on which the compound library is synthesized. Many different types of chemical reaction sites (in addition to primary amines) can be introduced at the 5'terminus of the nucleic acid tag. Exemplary chemical reaction sites include, but are not limited to, chemical components capable of forming amide, ester, urea, urethane, carbon-carbonyl bonds, carbon-nitrogen bonds, carbon-carbon single bonds, olefin bonds, thioether bonds, and disulfide bonds. In the case of enzymatic synthesis, co-factors can be supplied as are required for effective catalysis. Such co-factors are known to those of skill in the art. An exemplary cofactor is the phosphopantetheinyl group useful for polyketide synthesis.

B. Carrying Out a DNA-Templated Split

The compound library can be split into subsets at each step of the split-and-recombine combinatorial synthesis by differential hybridization of the nucleic acid tag to complementary oligonucleotides or oligonucleotide analogs bound to a solid support, e.g., polystyrene beads.

In a preferred embodiment, the hybridization sequence of each nucleic acid tag comprises at least 10 nucleotides.

The reagents described below are used to carry out the first step of an exemplary encoded split and are analogous to those used to carry out subsequent splits.

Oligonucleotides or oligonucleotide analogs which represent the complementary sequences to each of the hybridization sequences of the nucleic acid tags are synthesized. The 5' alcohols of the 5'bases of the each oligonucleotide or oligonucleotide analog are modified with a commercially available reagent which introduces a phosphate group tethered to a linear spacer, having for example six carbons and terminated with a thiol group (Glen Research catalog#10-1926-xx). Each of the thiol-bearing oligonucleotides or oligonucleotide analogs is immobilized through a thioether linkage to a macroporous resin (e.g., polystyrene, MPS; Biopore catalog#NH-2CM, L-970317) bearing electrophilic bromoacetamide groups (the preparation of which is described below). Thus a number of affinity resins result, each bearing a unique oligonucleotide or oligonucleotide analog. Each of the affinity resins is loaded into its own column with luerlock fittings at either end and the columns connected in a linear sequence.

Numerous variants on the DNA encoding strategy, the attachment of chemical reaction sites to the DNA, and the specific chemistry or biochemistry used to construct the compound library are possible. Variation in the specific resins used to carry out the library splits, and to perform the chemical/biochemical coupling steps are also possible.

By way of application to the exemplary embodiment described above, the nucleic acid tag comprises 420 base pairs and 10 hybridization sequences. In this case, 10 different affinity resins and corresponding columns are used to form 10 subsets of nucleic acid sequences in each step of the synthesis of the compound library.

An exemplary first nucleic acid-encoded split is performed by contacting, i.e. pumping a high-salt aqueous solution containing the entire pool of different nucleic acid tags cyclically over the linear sequence of affinity columns under high stringency conditions [See, e.g., Southern, E M et al., Nucl Acids Res. 22 (8) 1368-1373 (1994)], using a peristaltic pump for a time sufficient for all of the specific hybridization sequences of each DNA to hybridize to the oligonucleotide or oligonucleotide analogs bound to the columns. The DNA encoded split is completed simply by breaking the luer-lock linkages between the affinity columns. At this point the different DNA tags have been divided into physically separate subsets on the basis of the specific hybridization sequence in the V region of each tag.

To carry out the DNA-templated split for the second and subsequent synthetic steps, new affinity columns are prepared which display oligonucleotides corresponding to additional groups of different hybridization sequences bound to the polystyrene resin. These columns separate the DNA tags into additional subsets on the basis of which of possible nucleic acid sequences is present in the hybridization region of each nucleic acid tag. In a preferred embodiment at least 5 separate hybridization steps are preformed. In an even more preferred embodiment at least 10 separate hybridization steps are preformed.

The MPS resin described above is prepared from commercially available chloromethyl MPS resin in four steps (Biopore catalog#NH-2CM, L-970317): (i) the chloromethyl MPS resin is coupled to thioglycolic acid (ii) the N-hydroxy succinimide active ester of the coupled thioglycolic acid is prepared (iii) a Jeffamine 1500 molecular weight diamine (Fluke chemical#14535) is coupled to the resin by formation of an amide bond with the thioglycolic active ester (iv) the second amine of the coupled Jeffamine is acetylated with bromoacetic anhydride to produce the final bromoacetamide functionalized MPS resin.

Chemical Coupling

Each subset of nucleic acid tags formed by hybridization as described above is subjected to a different synthetic coupling reaction.

By way of example, a polypeptide can be formed by the methods of the present invention, as described below.

For synthesis of a polypeptide on the linker substrate in the direction of carboxy to amino terminus, a free amino terminus on the linker is required that can be conveniently blocked and deblocked as needed. A preferred amino terminus blocking group is a fluorenylmethoxycarbonyl group (FMOC).

For example, to couple an Fmoc-protected amino-acid to the to the primary amine "chemical reaction site" which is covalently attached to the synthesis-directing nucleic acid sequence or tag, the following steps are carried out: (i) the DNA tags hybridized to the affinity columns are transferred onto columns, e.g., hydroxyapatite resin columns (Bio-Rad Macro-Prep Ceramic Hyroxyapatite TYPE II catalog#1588200) with elution in 300 M CaCl or DEAE Sepharose fas (Pharmacia 17-0709-01) with elution in 10 mM acetate at pH 5.0 with 0.005% triton). The DNA tags remain non-covalently bound to the hydroxyapatite or sepharose resin in numerous organic solvents (for example DMF, acetonitrile, ethanol, and mixtures of those solvents with water). Thus organic reagents can be flowed over the columns and reacted with the chemical reaction sites on the DNA tags in the same manner that conventional solid phase chemical synthesis is carried out. Accordingly, a different Fmoc-protected amino-acid preactivated with N (1H-benzotriazol-1-yl) (dimethylamino) methylene-N-methylmethanaminium tetrafluoroborate (TBTU) or as an N-hydroxy succimnimide ester in DMF is flowed over each hydroxyapatite or sepharose column, resulting in the acylation of the primary amines of the DNA tags on each of the hydroxyapatite or sepharose columns with an Fmoc-protected amino acid [Albericio, F. and Carpino L A, Methods in Enzymology 289: 104-26 (1997)]. Following acylation, the Fmoc group is removed from the newly added amino acid by flowing a piperidine/DMF solution over the hydroxyapatite or sepharose columns, thus presenting a new primary amine ready for the next coupling step.

Numerous methods for modification of DNA are known to those of skill in the art and readily incorporated into the methods described herein [See, e.g., Chu, B C, et al. Nucleic Acids Research 11 (18): 6513-6529 (1983)]. By way of further example, nucleotides can be synthesized by various methods known to those of skill in the art. [See e.g., "Oligonucleotide Synthesis: A Practical Approach", ed. M. J. Gait, JRL Press, New York, N.Y. (1990)].

An entire compound library is synthesized by carrying out alternate rounds of DNAtemplated library splitting and chemical and/or biochemical coupling to each subsets of nucleic acid tags.

The plurality of chemical compounds produced by the methods of the present invention are linked to nucleic acid sequence tags which facilitate identification of the chemical structure.

Conventional DNA sequencing methods are readily available and useful for a determination of the sequence of the synthesis-directing nucleic acid tags. See, e.g., Maniatis et al., eds, MOLECULAR CLONING: A LABORATORY MANUAL, Second Edition, Cold Spring Harbor, N.Y. (1989).

III. Selection, Amplification and Enrichment

The compound library can be screened for a desired activity, for example the ability to catalyze a particular reaction or to bind with high affinity to an immobilized receptor. In most cases, the subpopulation of molecules with the desired activity, as well as their nucleic acid tags, are physically partitioned away from siblings during the selection. Following selection, the nucleic acid tags attached to the selected molecules are amplified by the polymerase chain reaction [PCR] [Saiki et al, Science 239 (4839) 487-491 (1988)]. The 5'hydroxyl of the 5'-end primer used to PCR amplify the coding strand is modified with a phosphate group tethered to a fresh primary amine chemical reaction site. After amplification, the coding strand is separated from the non-coding strand. Because the nucleic acid tags direct the library synthesis in the present invention, rather than merely reporting on the synthetic history of individual compounds, the coding strands amplified from the first library can be used to direct the construction of a second generation compound library. Iteration of this procedure, by carrying out multiple rounds of selection, DNA tag amplification, and library resynthesis, allows individual desirable compounds to "evolve" from extremely complex libraries.

A. Screening Library for a Desired Activity

An entire compound library or individual library members produced by the methods of the present invention can be evaluated for one or more desired activities in screening assays capable of distinguishing compounds which modulate an activity or possess a desired structural or functional property.

Exemplary assays and functional analyses include, but are not limited to, enzymatic assays, non-enzymatic catalytic assays, protein-protein binding assays, receptor/ligand binding assays and cell-based assays. More specifically, exemplary cell-based methods provided by the present invention are based on; (1) differential binding of library compounds to a cell surface (i.e. binding to cancer cell and not a non-cancer cell), (2) binding of library compounds to components of a cell extract (e.g., binding to a cell fraction produced by separating an entire cell extract on a sucrose gradient), (3) library compounds capable of endocytosis by a cell, and (4) in vivo localization and binding properties of library compounds by injecting the library into an animal. [See, e.g., Arap, W., et al., Science 279 (5349): 377-80. (1998) which describes in vivo selection of phage display libraries to isolate peptides that home specifically to tumor blood vessels As will be appreciated by those of skill in the art, such assays can be preformed on entire libraries of compounds synthesized by the methods described herein or sub populations derived therefrom.

The number of possible receptor molecules for which ligands can be synthesized and identified by the methods of the present invention is virtually unlimited. Exemplary receptor molecules include, but are not limited to antibodies, growth factors, hormones, enzyme substrates, interferons, interleukins, intracellular and intercellular messengers, lectins, cellular adhesion molecules, and the like. Additional exemplary ligands include, but are not limited to, carbohydrates, non-protein organic compounds, metals, peptide mimetics, non-ribosomally produced polypeptides, conotoxins and polyketides, etc.

Desired compounds produced by the nucleic acid tag-directed combinatorial library methods of the present invention include, but are not limited to, small organic molecules, polyketides, subunit oligomers and catalysts for the synthesis of complex molecules from simple substrates, e.g., transition metal mediated reactions termed "domino" reactions which are highly efficient processes that allow for production of large libraries of complex structures in relatively few steps beginning with simple precursors. [See, e.g., Tietze and Lieb, Curr Opin Chem Biol 2: 63-371 (1998)].

B. In Vitro Evolution of Selected Compounds-Gene Shuffling

In addition to allowing amplification of selected library members, the present invention permits evolution of the encoded compound libraries. More specifically, genetic recombination between the nucleic acid tags which encode selected subpopulations of compounds is carried out in vitro by mutagenesis or random fragmentation of the nucleic acid tag sequence, followed by the generation of related nucleic acid sequences ["gene shuffling", Stemmer, Nature, 370: 389391 (1994); U.S. Pat. No. 5,811,238 (1998)], and subsequent step-wise synthesis of additional compounds.

In one embodiment of the invention, a unique restriction site is introduced into each specific hybridization sequence. By way of example, partial digestion of a library with 11 specific hybridization sequences is accomplished by partial digestion with 11 corresponding restriction enzymes, followed by a primeness PCR reassembly reaction, allowing the nucleic acid tags for compounds that have been selected out of the library to be recombined with one another and further synthetic steps carried out. By analogy to gene shuffling for protein synthesis [Crameri, et al., Nature 391 (6664): 288-291 (1998)], the ability to carry out genetic recombination of compound libraries vastly increases the efficiency with which the diversity in the compound libraries can be explored and optimized.

Accordingly, the invention provides for polynucleotide shuffling to yield a population of variant nucleic acid sequences, capable of directing the synthesis of structurally-related, and/or functionally-related molecules, and/or variants thereof to create compounds having one or more desired activities. For example, molecules capable of binding to the 5'untranslated region (UTR) of mRNA can be identified in this manner.

It is also contemplated that the method of this invention can be used for the in vitro amplification of a selected subpopulations of synthesis directing nucleic acid tags by PCR, either prior to or following "gene shuffling".

General Selection Steps and Further Down-Stream Processing Steps

Once a library of bifunctional complexes have been synthesised it is possible to select and/or screen and/or partition and/or purify the library in order to identify or isolate desirable compounds therefrom. The compounds in one embodiment are small scaffolded molecules.

The partitioning may be based one or more features or properties of a molecule. Such a feature may be associated with or reside in a bifunctional molecule or a part of or a combination of parts of the encoded small molecule, the linker, the identifier. Partitioning may be based a structural, chemical, or electronic feature of a molecule. Partitioning may be based on a feature of a molecule or one or more parts of the molecule such as affinity for a target, hydrophobicity, hydrophilicity, charge distribution, size, mass, volume, conductivity, electric resistance, reactivity under certain conditions such as bond formation to a target, effect of the molecule such as induction of a signal in a system, e.g. a biochemical system, a biological system such as cell or a whole organism. The feature may be present in the molecule or it may be induced by the addition of a cofactor, e.g. a metal ion to the molecule.

A number of screening methods exist, for the identification of molecules, e.g. organic molecules such as the encoded molecule part of a bifunctional complex or the tag part of a bifunctional complex, with desired characteristics. Different types of selection or screening protocols are described in (Rasmussen (2006) WO 06/053571A2, Liu et al. (2002), WO 02/074929 A2; Pedersen et al. (2002) WO 02/103008 A2; Pedersen et al. (2003) WO03/078625 A2; Lerner et al., EP 0643778 B1, Encoded combinatorial chemical libraries; Dower et al., EP 0604552 B1; Freskgard et al., WO 2004/039825 A2; Morgan et al., 2005, WO 2005/058479; Harbury and Halpin, WO 00/23458). For example, affinity selections may be performed according to the principles used in library-based selection methods such as phage display, polysome display, and mRNA-fusion protein displayed peptides. The template-directed synthesis of the invention permits selection procedures analogous to other display methods such as phage display (Smith (1985) SCIENCE 228: 1315-1317). Phage display selection has been used successfully on peptides (Wells et al. (1992) CURR. OP. STRUCT. BIOL. 2: 597-604), proteins (Marks et al. (1992) J. BIOL. CHEM. 267: 16007-16010) and antibodies (Winter et al. (1994) ANNU. REV. IMMUNOL. 12: 433-455). Similar selection procedures also are exploited for other types of display systems such as ribosome display Mattheakis et al. (1994) PROC. NATL. ACAD. Sci. 91: 9022-9026) and mRNA display (Roberts, et al. (1997) PROC. NATL. ACAD. Sci. 94:12297-302).

The invention also relates to a method for identifying a molecule having a preselected property, comprising the steps of: subjecting the library produced according to the method indicated above to a condition, wherein a molecule or a subset of molecules having a predetermined property is partitioned from the remainder of the library, and identifying the molecule(s) having a preselected function by decoding the identifier oligonucleotide of the complex.

The above method, generally referred to as selection or screening, involves that a library is subjected to a condition in order to select molecules having a property which is responsive to this condition. The condition may involve the exposure of the library to a target. The bifunctional complexes having an affinity towards this target can be partitioned form the remainder of the library by removing non-binding complexes and subsequent eluting under more stringent conditions the complexes that have bound to the target. Alternatively, the identifier oligonucleotide of the bifunctional complex can be cleaved from the molecule after the removal of non-binding complexes and the identifier oligonucleotide can be recovered and decoded to identify the molecule.

Specific screening methods employing bifunctional molecules for the identification of organic molecules with desired characteristics include but are not limited to:

i. Affinity selection on immobilised target molecules. In this approach the target molecules (e.g., DNA, RNA, protein, peptide, carbohydrate, organic or inorganic molecule, supramolecular structure or any other molecule, is immobilized covalently or non-covalently to a solid support such as beads, the bottom of a well of a microtiter plate, a reagent tube, a chromatographic column, or any other type of solid support. A library of bifunctional molecules are now incubated with the immobilized target molecule, excess non-bound bi-functional molecules are washed off by the replacing supernatant or column buffer with buffer not containing bi-functional molecules one or more times. After washing the bound bi-functional molecules are released from solid support by addition of reagents, specific ligands or the like that results in the elution of the bi-functional molecule, or the pH is increased or decreased to release the bound bi-functional molecules, or the identifier of the bi-functional molecule, e.g., one or both strands of the identifier, is released from the encoded molecule with a reagent, pH change or light-induced cleavage. The recovered identifiers can now optionally be amplified by PCR, optionally cloned and sequenced to reveal the structure of the ligands encoded by the identifier. As an alternative, the identifiers or bi-functional molecules comprising identifiers, are not released from solid support, but rather the identifiers are optionally amplified by PCR and/or analyzed directly while still immobilised on solid support. Selection of binding molecules from a library can be performed in any format to identify optimal binding molecules. Binding selections typically involve immobilizing the desired target molecule, adding a library of potential binders, and removing non-binders by washing. When the molecules showing low affinity for an immobilized target are washed away, the molecules with a stronger affinity generally remain attached to the target. The enriched population remaining bound to the target after stringent washing is preferably eluted with, for example, acid, chaotropic salts, heat, competitive elution with a known ligand or by proteolytic release of the target and/or of template molecules. The eluted templates are suitable for PCR, leading to many orders of amplification, whereby essentially each selected template becomes available at a greatly increased copy number for cloning, sequencing, and/or further enrichment or diversification. In a binding assay, when the concentration of ligand is much less than that of the target (as it would be during the selection of a DNA-templated library), the fraction of ligand bound to target is determined by the effective concentration of the target protein. The fraction of ligand bound to target is a sigmoidal function of the concentration of target, with the midpoint (50% bound) at [target]=Kd of the ligand-target complex. This relationship indicates that the stringency of a specific selection-the minimum ligand affinity required to remain bound to the target during the selection—is determined by the target concentration. Therefore, selection stringency is controllable by varying the effective concentration of target. The target molecule (peptide, protein, DNA or other antigen) can be immobilized on a solid support, for example, a container wall, a wall of a microtiter plate well. The library preferably is dissolved in aqueous binding buffer in one pot and equilibrated in the presence of immobilized target molecule. Non-binders are washed away with buffer. Those molecules that may be binding to the target molecule through their attached DNA templates rather than through their synthetic moieties can be eliminated by washing the bound library with unfunctionalized templates lacking PCR primer binding sites. Remaining bound library members then can be eluted, for example, by denaturation. The target molecule can be immobilized on beads, particularly if there is doubt that the target molecule will adsorb sufficiently to a container wall, as may be the case for an unfolded target eluted from an SDS-PAGE gel. The derivatized beads can then be used to separate high-affinity library members from nonbinders by simply sedimenting the beads in a benchtop centrifuge. Alternatively, the beads clan be used to make an affinity column. In such cases, the library is passed through the column, one or more times to permit binding. The column then is washed to remove nonbinding library members. Magnetic beads are essentially a variant on the above; the target is attached to magnetic beads which are then used in the selection. There are many reactive matrices available for immobilizing the target molecule, including matrices bearing —NH2 groups or —SH groups. The target molecule can be immobilized by conjugation with NHS ester or maleimide groups covalently linked to Sepharose beads and the integrity of known properties of the target molecule can be verified. Activated beads are available with attachment sites for —NH2 or —COOH groups (which can be used for coupling). Alternatively, the target molecule is blotted onto nitrocellulose or PVDF. When using a blotting strategy, the blot should be blocked (e.g., with BSA or similar protein) after immobilization of the target to prevent nonspecific binding of library members to the blot.

ii. Affinity selection on target molecules in solution, followed by any means of isolation of the bi-functional molecules bound to the target, e.g. by immunoprecipitation of the target-bi-functional molecule complexes, capture of the complexes on nitrocellulose filter or by immobilisation of the target via a functionality on the target such as biotin or GST-tag or Histidine-tag or other useful means for immobilization as recognized by a person skilled in the art. A library of bi-functional molecules are incubated with target molecules (e.g. a protein). After complex formation of bi-functional molecules with target, the complex is isolated from non-complexes, for example by the addition of polyvalent antibodies against the target molecule and precipitation of antibody-target-bi-functional molecule complexes, or is precipitated by the addition of beads that bind the target molecules. The latter may for example be by addition of streptavidin-coated beads that bind to pre-biotinylated targets. The identifiers recovered by precipitation can now be characterised or amplified, e.g., by PCR, as described in (i). The sequence of the identifiers will reveal the identity of the encoded molecules that bind the target molecules.

iii. Affinity selection on target molecules in solution, followed by gel retardation, chromatographic separation e.g.

size exclusion chromatography, or separation by centrifugation e.g. in a $CsCl_2$-gradient. A library of bi-functional molecules are incubated with target molecules (e.g. a protein). After complex formation of bi-functional molecules with target, the complex is isolated from non-complexes, for example by gel electrophoresis or size exclusion chromatography, or any other chromatographic or non-chromatographic method that separates the target-bi-functional molecule complexes from non-complexed bi-functional molecules, for example based on the difference in size and/or charge. The tags of the bi-functional molecules of the column fraction or band on the gel that comprises target-bi-functional molecule complexes are now characterised or amplified, e.g., by PCR, as described above. The sequence of the tags will reveal the identity of the encoded molecules that bind the target molecules.

iv. Affinity selection on surfaces. Particles, preferably small particles, of solid material, e.g., metal particles, metal oxide particles, grinded plastic, wood, preformed carbon nanotubes, clay, glas, silica, bacterial biofilm or biofilm of other microorganism, cement, solid paint particles, laminate, stone, marble, quartz, textile, paper, skin, hair, cell membranes, industrial membranes, epiderm, or the like, is added to a solution comprising a library of bi-functional molecules. After incubation, one or more washing steps are performed, to remove unbound bi-functional molecules. Then, the bi-functional molecules bound to the surface, or the identifiers of the bi-functional molecules bound to the surface, are released as described above, and the identifiers characterised and/or amplified as described above.

v. Selection for intracellularisation. Bi-functional molecules are incubated with cells or micelles, or on one side of a lipid membrane, or on one side of a cell monolayer (e.g. CaCo2 cell monolayer), in order to allow the bi-functional molecule to pass or become immobilized into the membranes. Then, a number of washing steps are performed in order to remove bi-functional molecules that have not become immobilized or have passed the membrane. Identifiers from bi-functional molecules that have become immobilized or have passed the membrane are now amplified and/or characterized as described above. The encoded molecule of bi-functional molecules that have either become immobilized in the membrane or have passed the membrane, represent potential transporters for intracellularization, i.e. by attaching these encoded molecules (without the oligonucleotide tag) to e.g. non-oral drugs these may become orally available, because the transporter mediate their transport across the cell.

vi. Selection by phase partitioning. A two- or three phase system may be set up, wherein the bi-functional molecules will partition out according (at least in part) to the characteristics of the encoded molecules. Therefore, the principle allows the identification of encoded molecules that have particular preference for a certain kind of solvent. Again, the identifiers of the isolated bi-functional molecules can be amplified and/or characterised after the selection has occurred. It may be necessary to coat the nucleic acid component of the bi-functional molecule with e.g. DNA binding proteins, in order to ensure that the partitioning of the bi-functional molecule is significantly correlated with the characteristics of the encoded molecule of the bi-functional molecule.

vii. Selection for induced dimerisation of target molecules. In a preferred embodiment, encoded molecules are sought that induce the dimerization of target molecules. For example, small molecules with the potential to induce dimerization of protein receptors in the cell membrane may be applicable as therapeutics. Thus, a selection protocol for encoded molecules with the potential to induce dimerization of proteins A and B is as follows: A library of bi-functional molecules are incubated with proteins A and B. After incubation, the solution is applied to gel electrophoresis, ultra-centrifugation (e.g. CsCl-centrifugation), size exclusion chromatography, or any other kind of separation that separates the protein A-protein B-bi-functional molecule-complex from un-complexed protein A and B, and other undesired complexes, such as protein A-protein B-complex. Bi-functional molecules from the band or fraction corresponding to the size and/or charge of the protein A-protein B-bi-functional molecule-complex is recovered, and template identifiers are then amplified and/or characterised as described above. In this case, the encoded molecule would be resynthesized, and tested in a protein dimerisation assay for its effect on the dimerisation of protein A and B.

viii. Selection by iterative rounds of binding and elution. This is a modification of the methods reported previously (Doyon et al. (2003), J. Am. Chem. Soc., 125, 12372-12373, the content of which is incorporated herein by reference in its entirety). Bi-functional molecules are incubated with e.g. immobilised target molecule, e.g. a biotinylated enzyme immobilised on streptavidin beads. After washing one or more times, the bound bi-functional molecules are released from solid support by a change in pH, addition of a detergent such as SDS, or by addition of an excess of ligand that binds the target molecule (the ligand can be e.g. a small molecule, peptide, DNA aptamer or protein that is known to bind the target molecule). Alternatively, the bi-functional molecules may be released by degradation of the immobilised target (e.g. by nuclease or protease), denaturation of target by methods such as heat or induced conformational changes in target structure or the like. The recovered bi-functional molecules are now re-applied to e.g. immobilised target molecule, optionally after removal or degradation of the ligand or reagent used for elution in the previous step. Again, washing is performed, and the bound bi-functional molecules eluted. The process of incubation and binding, washing and elution can be repeated many times, until eventually only bi-functional molecules of high affinity remains. Then the tags of the bi-functional molecules are amplified and/or characterised. Using this kind of iterative binding and elution, enrichment factors higher than 1.000.000-fold can be obtained.

Targets may be immobilised on columns, on beads (batch selection), on the surface of a well, or target and ligands may interact in solution, followed by immunoprecipitation of the target (leading to immunoprecipitation of ligands bound to target). In one embodiment of iterative library partioning step(s) the target concentration is kept constant at all selection steps. In another embodiment it may be desirable to change the target concentration between or during each or some partitioning steps. Consequently, the experimenter can choose the affinity thresholds for molecule recovery based on the molecules affinity for the target by altering the target concentration. F. ex a first selection step may employ a target concentration in the range of 1-50 uM (or even higher if practically allowed). Following selection and isolation of the library pool enriched for ligands the library pool is incubated with a target in reduced concentration such as in the range of 0.01-5 uM. A reduction in target concentration will enable the experimenter to increase the recovery of the best ligands in a library compared to molecules of lower affinity thereby achieving a better or more exact ranking of isolated ligands from the library pool based on ligand affinity (i.e the number of specific DNA-tags isolated from the selection output correlate directly with molecule affinity for the target). In yet another embodiment, the ranking of ligands in a selection output is based on the off-rate of the target-molecule pair. Following the library incubation with immobilised target a specific ligand is added which saturate unbound target thus preventing rebinding of library molecules once released from it target binding site. This enables the experimenter to isolate library fractions eluted at different timepoints after target saturation resulting in primarily the isolation of molecules according to their off-rates (koff).

It is possible to perform a single or several rounds of selection against a specific target with a subsequently amplification of the selected variants. These obtained variants are then separately tested in a suitable assay. The selection condition can be stringent and specific to obtain binding molecules in one selection rounds. It can be advantageously to perform the method using a single round of selection because the number and diversity of the potential binders are larger compared to procedures using further selections where potential binders can be lost. In another embodiment the selection procedure involves several round of selection using increasing stringency conditions. Between each selection an amplification of the selected complex can be desirable.

x. Whole organism selection. A library of bi-functional molecules, optionally modified by e.g. coating proteins, is injected into a dead or living animal, for example a mouse. After incubation for a period of time (e.g two hours) in the animal, specific tissue or organs are recovered, and the bi-functional molecules associated with specific organs can be characterised, by e.g. PCR amplification and/or sequencing of the corresponding identifiers. As a specific example, a mouse carrying a tumor can be injected with a library of bi-functional molecules. After incubation, the tumor can be isolated from the animal. The bi-functional molecules associated with the tumor are potential therapeutics or diagnostics for that cancer.

The abovementioned target molecules may be any supramolecular structure (e.g. nanoclusters, multiprotein complex, ribosomes), macromolecule (e.g. DNA, RNA, protein, polymers such as carbohydrates, thiophenes, fibrin), or low molecular weight compound (e.g. cAMP, small peptide hormones, chelates, morphine, drug). After having performed any of the selections above, the identifiers can taken through one more round of the same or another selection protocol. This process can be repeated until an appropriately small number of different bi-functional molecules are recovered.

The selection may be performed in the presence of one or more specific ligands for site on a target. For example, if it is desired to avoid identification of ligands to a particular target site, known ligands to that site may be included during selections. The known ligand may then compete with bifunctional molecules for binding to the particular site thus reducing or eliminating binding of bifunctional molecules to the site. In this way, the bifunctional molecules will not be identified based on their with affinity to the particular target site.

After having performed any of the selections above, the tags of the output bi-functional molecules can be amplified by PCR or other means, sequenced and the chemical composition of the molecule identified.

Polyvalent Display and Other Means of Increasing the Likelihood of Identifying Encoded Molecules with Weak Characteristics.

Under certain conditions the requirements of an encoded molecule, in order to be isolated during the screening step, are too strong, and few or none of the encoded molecules of a library are expected to fulfil the requirements. Such requirements may be for example high affinity or high catalytic turn-over. The methods and success of multivalent display in affinity selections is evident from systems similar to that described here such as phage display as should be recognized by persons skilled in the art Thus, it may be desirable to employ a multivalent display mode, i.e., to generate libraries of multivalent encoded molecules (multiple encoded molecules attached to one tag). During a selection step in which for example an encoded molecule interacts weakly with a target protein, a multivalent encoded molecule may interact with multiple protein targets through the multiple copies of encoded molecules that it contains, and as a result, may bind with higher affinity because of the avidity effect. Likewise, in a screening or selection step for catalytic efficiency, a multivalent encoded molecule may generate more product in a given time, and may be isolated because of this.

A preferred means of generating libraries of multivalent encoded molecules each containing multiple copies of the same encoded molecule, is as follows: The DNA tag-piece (denoted "Display oligonucleotide" or "single-stranded identifier") employed for chemical reaction can be synthesised with 1 or more reactive handles using standard phosphoramidite chemistry. One strategy for the introduction of multivalent display involves the incorporation of doublers or treblers (such as Glen Research catalog No 10-1920-90 or 10-1922-90) one or more times forming dendrimer structures that can be capped by reactive handles f.ex amino-, acid-, Thiol- or aldehyde-group (or any chemical entity useful as starting point in a chemical reaction. This enables the formation of a single DNA sequence connected to any number of reactive handles such as 1, 2, 3, 4, 5, 6, 7, 8, 9, 10, 11, 12, 13, 14, 15, 16, 17, 18, 19, 20 or more reactive handles. FIG. 53 shows 3 examples of a simple quadruple amino-DNA tag enabling synthesis and display of the same encoded molecule attached to a single encoding tag. It may be desirable to include spacing groups such as polyethylene glycol (PEG) units at any point in the synthesis process (chosen by the experimenter) for improved synthesis and display of the synthetic molecule.

The multivalent encoded molecules can now be used in various screening or selection processes. For example, the multivalent encoded molecules may be added to an affinity column, to which target protein has been immobilised with an appropriately high density, so that multivalent encoded molecules may interact with several immobilised targets simultaneously. This will lead to the isolation of bi-functional molecules that contain encoded molecules with affinity for the immobilised target protein. The use of multivalent encoded molecules may be particularly advantageous to use when selecting for affinity to a homodimeric target molecule, or any other target that contains two or more identical binding sites. Relevant targets include membrane proteins such as the Epo-receptor, p53, HER2, Insulin Receptor, many interleukins, palindromic DNA- or RNA-sequences, or fibrin. Divalent encoded molecules containing identical encoded molecules are also appropriate for affinity selection on target molecules with one binding site, where the binding site is partly or fully symmetrical, and therefore allows two identical encoded molecules to interact.

In another embodiment the addition of a helper element comprising a helper molecule known to interact with the target, is linked to an oligonucleotide capable of hybridizing to a region on the DNA portion of the bi-functional library molecules may aid the isolation of a bifunctional molecule e.g. by increasing the overall affinity of the helper molecule/ bifunctional molecule complex for the target. FIG. 54 depicts a scheme for the addition, by hybridization, of a helper molecule covalently linked to a DNA sequence complementary to the region of DNA of the bifunctional library molecule that is proximal to the displayed molecule. Hybridization of a second primer followed by polymerase extention and ligation will produce dsDNA displaying both the encoded library molecule and the helper molecule Consequently, if a ligand is known for a binding site in a protein, this ligand may be coupled to the bi-functional molecule, in order to guide the encoded molecule to the target protein, and in order to increase the affinity of the bi-functional molecule (carrying the known ligand) for the target protein Similar approaches may be used for isolation of encoded molecules with affinity for a target binding site, where the binding site can be occupied by both the encoded molecule and the known ligand simultaneously. Finally, it may be desirable to increase the overall affinity of the bi-functional molecule for the target by linking a short oligonucleotide that is complementary to the tag of the bi-functional molecule to the target. The short oligonucleotide will then function as a helper moiety that increases the affinity of the bi-functional molecule for the target, by hybridisation of the short oligonucleotide to the bi-functional molecule.

Selections employing such bi-functional molecules to which have been attached a helper moiety may be applied to affinity selection against all kinds of targets, including protein-heterodimers as well as protein-homodimers, and thus molecular targets include HER2, Insulin-receptor, VEGF, EGF, IL-4, IL-2, TNF-alpha, the TATA-box of eukaryotic promoter regions, and many others.

In another embodiment, a target and the bifunctional molecules may be modified to allow screening. For example, an —SH group may be introduced in a protein target by mutagenesis of an amino acid to a cysteine. Correspondingly, a library of bifunctional molecules may be synthesized such that encoded molecules carry an —SH group. Alternatively, a library may following synthesis be reacted with a reactant that carries an —SH group. Screenings may then be performed under conditions that induce the formation of an S—S bond between the —SH of the target and the —SH of the encoded molecules of the library. In this way, the bifunctional molecules may be directed to a specific site on the target.

Dynamic combinatorial library of dimers or trimers of encoded molecules. The bi-functional molecules of a library may be designed in a way that leads to transient complex formation between 2, 3, or more bi-functional complexes during the screening process. This may be desirable, especially in cases where the libraries that have been generated are relatively small, or in cases where it is desirable to screen a large number of combinations of encoded molecules for synergistic effects. In order to generate transient complexes, the bifunctional molecules may be designed so as to comprise half of a transient interaction pair. For example, a short single stranded oligonucleotide region may be included in the design of the tag of the bi-functional molecules; if some of the bifunctional molecules carry a molecular entity "A" and some other bi-functional molecules of the library carry another molecular entity "B" that interacts transiently, i.e. forms a short-lived complex with, "A", then the two sets of bi-functional molecules of the library will form transient dimers of bi-functional molecules. These transient dimers may then be exposed to a screening process, for example affinity selection, where the dimers are then examined for ability to bind to a certain target. As an example, for each of the species of bi-functional molecules, half of the generated bi-functional molecules carry the oligo sequence 3'-ATGC-5' in the proximity of the encoded molecule, and the other half of the generated bifunctional molecules carry the oligo sequence 3'-GCTA-5'. When all the generated bi-functional molecules are incubated at appropriately low temperature, different combinations of dimers will transiently form, and allow for a feature displayed by the combination of the corresponding two encoded molecules to be selected for. This feature could be the binding of the two encoded molecules of the dimer to bind simultaneously to a target molecule. If appropriately designed, trimers may be (transiently) formed, by formation of triplex DNA between three bi-functional molecules. In this way, all the possible dimers (or trimers) of a pool of bi-functional molecules may be screened for the desired feature.

Once the screening of a library of bi-functional molecules has been done, the isolated bi-functional molecules may be identified. This can be done without DNA amplification or more preferably by use of PCR or other means of DNA amplification. Next, the structure of the molecules isolated can be identified from the tag sequence directly using techniques such as pyrosequencing described by Margulies, M. et al (Nature. 2005 Sep. 15; 437(7057):376-80) and incorporated herein by reference or by a probing technique described in WO2005093094 or other means of direct sequencing without cloning. Alternatively the tags can be cloned and sequenced by conventional means such as Sanger sequencing, mass spectrometry-based sequencing, single molecule sequencing, or sequencing by hybridisation to oligonucleotide arrays.

The characteristics of the encoded molecules thus identified may now be analyzed, either in its free form (after resynthesis by organic chemistry or after generation of the bi-functional molecule followed by cleavage of the linker that connects the encoded molecule and its identifier) or in its oligonucleotide-linked form (as a bi-functional molecule).

QC of Library Generation.

It may be desirable to test reaction efficiencies for the entire set- or a subset of chemical reactions. A simple method for evaluation of transformations efficiency is the use of Mass spectroscopy for analysis of library transformations. Consequently, a small sample of all reaction wells, a subset or of single wells may be collected and analysed directly by any analytical tool available such as MALDI-TOF MS or Electrospray MS. Alternatively the sample may be subjected to a number of methods for the aid of the analysis. In one embodiment it may be desirably to purify the identifier from unwanted DNA, chemical entities, buffers etc using methods such as HPLC/FPLC, gelfiltration, Ion-chromatography, Gel-electrophoresis or using immobilisation on solid-support followed by elution of the library product. Subsequently, the identifier DNA can be analysed using spectroscopic methods including but not limited to MALDI-TOF or ES-MS.

In some embodiments it may be necessary to apply additional methods for the simplification of the analytical step. Since each bifunctional molecules generated by the library generation process contains both a DNA part and a chemical part, all samples following the first pool event comprises both a heterogeneous DNA part (due to the sequence differences) and heterogeneous chemical part due the differences in the chemical composition. Consequently, in order to analyze the chemical reactions it may be desirable to separate the DNA portion of the bifunctional molecule from the chemical entity. Thus, one method for separation is the use of a selectively cleavable linker connecting the DNA and the small molecule allowing cleavage and subsequent (optional) removal of the DNA allowing analysis of the remaining chemical fragment.

Selectively cleavable linkers have been described elsewhere and are incorporated herein by reference Pedersen (Pedersen et al. (2002) WO 02/103008 A2). One example is the use of a photo-cleavable linkers or the use of chemically labile linkers such as a linker comprising and S—S bond which can be selectively cleaved by reducing agents such as DTT or TCEP.

In an alternative approach, a fixed DNA sequence of the DNA-tag that separates the chemical entity from the heterologous DNA encoding part may contain a restriction site recognized by a DNA restriction endonuclease. Consequently, DNA cleavage would produce a sample containing a small uniform DNA segment connected to a heterologous chemical entity. This fragment may be purified by several methods which include but is not restricted to gel-electrophoresis, HPLC or hybridization to a biotinylated DNA-oligonucleotide complementary to the DNA segment comprising the pool of chemical fragments followed by binding to streptavidine beads (SA-beads) and subsequent elution of the DNA fragments.

The example described below is included to describe one principle for the evaluation of transformation efficiencies during the generation of a library of bifunctional molecules: The example is used to illustrate one principle for quality control on one or more single reactions, a subset pool of reactions or a sample pool collected from all reactions In a split and mix library generation procedure n chemical reactions are conducted producing n chemical fragments linked to N different tags producing intermediates with a common structure depicted in FIG. 55.

The procedure depicted in FIG. 55 can be conducted at each round of chemical reaction to monitor reaction efficiencies. If any reactions is not run satisfactorily, all or only a subset of reactions can be iterated and subject to another round of analysis. Such a process using chemical reactions followed by QC on the transformation rates can be repeated any number of time until sufficient chemical turn-over is achieved and verified.

For some analysis it may be desirable to purify the sample by gel-electrophoresis or other means such as to harvest the ssDNA or dsDNA identifier comprising the chemical entity and purify this moiety from the remaining DNA in the sample such as unligated surplus tags. Alternatively it may be desirable to purify a singlestranded form of the identifier f. ex by gel-electrophoresis on UREA-PAGE prior to step 2 described above.

Another method for monitoring transformation efficiencies in library generation is to include one or more library mimics, a DNA molecule with a reactive entity, in the library synthesis step(s) containing a specific DNA sequence preferably unrelated to any sequence used for library tagging. The one or more mimics can be included as tracers to monitor single-, a subset pool or the entire pool of reactions at any synthesis or deprotection step during library generation. The mimics will be chemically transformed similar to the reactive entity on the identifier in the library generation process and can be included at any specific reaction step or at multiple reaction steps. As each mimic contains a unique DNA sequence, one or more mimics can be specifically subtracted from the library at any step and analysed for chemical transformations. This allows the experimenter to continuously analyse the chemical reaction within the library synthesis by examination of the included control mimics. The methods for mimic isolation includes, but is not limited to, purification by UREA-PAGE, HPLC/FPLC or purification using binding to a complementary nucleic acids strand, PNA, LNA or molecule with equivalent specific hybridization function, that carries a handle, such as a biotin group, useful for purification such as on SA-beads as described above (FIG. 56). Subsequently the mimics can be analysed by any suitable analytical tool such as MALDI- or Electrospray MS.

An alternative method for the purification of the control mimics in the library is to include a selective cleavable linker connecting a handle for purification and the reactive chemical unit. FIG. 57 depicts the general principle. The reactive unit (site) is any suitable reactive groups for example but not limited to an amino, thiol, carboxylic-acid or aldehyd-group. The oligonucleotide moiety is optional but provides an excellent handle for molecular weight analysis using MS. The cleavable linker (optionally) is selectively cleavable by any means such as e.g. by enzymatic, chemical or photocleavable methods. The purification (optional) may be any unit capable of being selectively recovered.

Templated Synthesis:

In some embodiments it may be desirable to amplify, by PCR or other means, the tags recovered from a selection step and use the amplified material as template for a subsequent synthesis of a library of bifunctional molecules. Methods for templated synthesis of bifunctional molecules include, but is not restricted to methods disclosed in (Rasmussen (2006) WO 06/053571A2, Liu et al. (2002), WO 02/074929 A2; Pedersen et al. (2002) WO 02/103008 A2; Pedersen et al. (2003) WO03/078625 A2; Harbury and Halpin, WO 00/23458, and further methods described herein. Alternatively the amplified tags may be used for the partitioning of a library of bifunctional molecules prior to selection on a target. This step will enrich a subset of the library by hybridization with the matching tag and the selection procedure(s) can be iterated with this library subset.

Such pre-selection partitioning of libraries of bifunctional molecules can be accomplished by various methods which include but is not restricted to techniques disclosed in Brenner and Lerner (1992, Proc, Natl. Acad. Sci. 89:5381-83 Lerner et al., EP 0643778 B1; EP 0604552 B1; WO2004099441)

The templated library re-synthesis or subset partitioning followed by selection and amplification (optional) step(s) described above may be iterated any number of times. Preferably, the processes are iterated until sufficient sequence bias is achieved for easy identification of ligands form tag sequencing.

The characteristics of the encoded molecules thus identified may now be analyzed, either in its free form (after resynthesis by organic chemistry or after generation of the bi-functional molecule followed by cleavage of the linker that connects the encoded molecule and its identifier) or in its oligonucleotide-linked form (as a bi-functional molecule).

Once the library has been formed in accordance with the methods disclosed herein, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor. In addition to bioactive species produced as disclosed herein above, bioactive species prepared in accordance with method A and B below, can be screened according to the present invention.

A. Molecules can be single compounds in their final "state", which are tagged individually and separately. E.g. single compounds may individually be attached to a unique tag. Each unique tag holds information on that specific compound, such as e.g. structure, molecular mass etc.

B. A molecule can be a mixture of compounds, which can be considered to be in their final "state". These molecules are normally tagged individually and separately, i.e. each single compound in a mixture of compounds can be attached to the same tag. Another tag can be used for another mixture of compounds. Each unique tag holds information on that specific mixture, such as e.g. spatial position on a plate.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-10 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc. The target can also be for example, a surface (such as metal, plastic, composite, glass, ceramics, rubber, skin, or tissue); a polymer; a catalyst; or a target biomolecule such as a nucleic acid, a protein (including enzymes, receptors, antibodies, and glycoproteins), a signal molecule (such as cAMP, inositol triphosphate, peptides, or prostaglandins), a carbohydrate, or a lipid. Binding assays can be advantageously combined with activity assays for the effect of a reaction product on a function of a target molecule.

The libraries of the present invention can contain molecules that could potentially bind to any known or unknown target. The binding region of a target molecule could include a catalytic site of an enzyme, a binding pocket on a receptor (for example, a G-protein coupled receptor), a protein surface area involved in a protein-protein or protein-nucleic acid interaction (preferably a hot-spot region), or a specific site on DNA (such as the major groove). The natural function of the target could be stimulated (agonized), reduced (antagonized), unaffected, or completely changed by the binding of the reaction product. This will depend on the precise binding mode and the particular binding site the reaction product occupies on the target Functional sites (such as protein-protein interaction or catalytic sites) on proteins often are more prone to bind molecules than are, other more neutral surface areas on a protein. In addition, these functional sites normally contain, a smaller region that seems to be primarily responsible for the binding energy: the so-called, hot-spot regions (Wells, et al. (1993) RECENT, PROG. HORMONE RES. 48: 253-262). This phenomenon facilitates selection for molecules affecting the biological function of a certain target The linkage between the template molecule and reaction product allows rapid identification of binding molecules using various selection strategies. This invention broadly permits identifying binding molecules for any known target molecule. In addition, novel unknown targets can be discovered by isolating binding molecules against unknown antigens (epitopes) and using these binding molecules for identification and validation. In another preferred embodiment, the target molecule is designed to mimic a transition state of a chemical reaction; one or more reaction products resulting from the selection may stabilize the transition state and catalyze the chemical reaction.

The upper limit for the strength of the stringency conditions is the disintegration of the complex comprising the displayed molecule and the encoding region. Screening conditions are known to one of ordinary skill in the art.

Complexes having predetermined desirable characteristics can be partitioned away from the rest of the library while still attached to a nucleic acid identifier tag by various methods known to one of ordinary skill in the art. In one embodiment of the invention the desirable products are partitioned away from the entire library without chemical degradation of the attached nucleic acid such that the identifier nucleic acids are amplifiable. The part of the identifier comprising the tags may then be amplified, either still attached to the desirable chemical compound or after separation from the desirable chemical compound.

Library members that bind a target molecule can be released by denaturation, acid, or chaotropic salts. Alternatively, elution conditions can be more specific to reduce background or to select for a desired specificity. Elution can be accomplished using proteolysis to cleave a linker between the target molecule and the immobilizing surface or between the reaction product and the template. Also, elution can be accomplished by competition with a known competitive ligand for the target molecule. Alternatively, a PCR reaction can be performed directly in the presence of the washed target molecules at the end of the selection procedure. Thus, the binding molecules need not be elutable from the target to be selectable since only the template is needed for further amplification or cloning, not the reaction product itself. Indeed, some target molecules bind the most avid ligands so tightly that elution would be difficult.

In a certain embodiment, the desirable molecule acts on the target without any interaction between the coding sequences attached to the desirable display compound and the target. In one embodiment, the desirable chemical compounds bind to the target followed by a partition of the complex from unbound products by a number of methods. The methods include plastic binding, nitrocellulose filter binding, column chromatography, filtration, affinity chromatography, centrifugation, and other well known methods for immobilizing targets.

Briefly, the library is subjected to the partitioning step, which may include contact between the library and a column onto which the target is bound. All identifier sequences which do not encode for a reaction product having an activity towards the target will pass through the column. Additional undesirable chemical entities (e.g., entities which cross-react with other targets) can be removed by counter-selection methods. Desirable complexes are bound to the column and can be eluted by changing the conditions of the column (e.g., salt, etc.) or the identifier sequence associated with the desirable chemical compound can be cleaved off and eluted directly.

In a certain embodiment, the basic steps involve mixing the library of complexes with the immobilized target of interest. The target can be attached to a column matrix or microtitre wells with direct immobilization or by means of antibody binding or other high-affinity interactions. In another embodiment, the target and displayed molecules interact without immobilisation of the target. Displayed molecules that bind to the target will be retained on this surface, while nonbinding displayed molecules will be removed during a single or a series of wash steps. The identifiers of complexes bound to the target can then be separated by cleaving the physical connection to the synthetic molecule. It can be considered advantageously to perform a chromatography step after of (or) instead of the washing step. After the cleavage of the physical link between the synthetic molecule and the identifier, the identifier can be recovered from the media and optionally amplified before the decoding step.

In traditional elution protocols, false positives due to suboptimal binding and washing conditions are difficult to circumvent and may require elaborate adjustments of experimental conditions. However, an enrichment of more than 100 to 1000 is rarely obtained. The selection process used in example 7 herein alleviates the problem with false positive being obtained because the non-specific binding complexes to a large extent remain in the reaction chamber. The experiments reported herein suggest that an enrichment of more than 107 can be obtained.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group, or similar activated chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

To select for a molecule that binds a protein expressible on a cell surface, such as an ion channel or a transmembrane receptor, the cells themselves can be used as the selection agent. The library preferably is first exposed to cells not expressing the target molecule on their surfaces to remove library members that bind specifically or non specifically to other cell surface epitopes. Alternatively, cells lacking the target molecule are present in large excess in the selection process and separable (by fluorescence-activated cell sorting (FACS), for example) from cells bearing the target molecule. In either method, cells bearing the target molecule then are used to isolate library members bearing the target molecule (e.g., by sedimenting the cells or. by FACS sorting). For example, a recombinant DNA encoding the target molecule can be introduced into a cell line; library members that bind the transformed cells but not the untransformed cells are enriched for target molecule binders. This approach is also called subtraction, selection and has been used for phage display on antibody libraries (Hoogenboom et al. (1998) IMMUNOTECH 4: 20).

A selection procedure can also involve selection for binding to cell surface receptors that are internalized so that the. receptor together with the selected binding molecule passes into the cytoplasm, nucleus, or other cellular compartment, such as the Golgi or lysosomes. Depending on the dissociation rate constant for specific selected binding molecules, these molecules may localize primarily within the intracellular compartments. Internalized library members can be distinguished from molecules attached to the cell surface by washing the cells, preferably with a denaturant. More preferably, standard subcellular fractionation techniques are used to isolate the selected library members in a desired subcellular compartment.

An alternative selection protocol also includes a known, weak ligand affixed to each member of the library. The known ligand guides the selection by interacting with a defined part of the target molecule and focuses the selection on molecules that bind to the same region, providing a cooperative effect. This can be particularly useful for increasing the affinity of a ligand with a desired biological function but with too low a potency.

Other methods for selection or partitioning are also available for use with the present invention. These include, for example: immunoprecipitation (direct or indirect) where the target molecule is captured together with library members; mobility shift assays in agarose or polyacrylamide gels, where the selected library members migrate with the target molecule in a gel; cesium chloride gradient centrifugation to isolate the target molecule with library members; mass spectroscopy to identify target molecules labeled with library members. In general, any method where the library member/target molecule complex can be separated from library members not bound to the target is useful.

The selection process is well suited for optimizations, where the selection steps are made in series, starting with the selection of binding molecules and ending with an optimized binding molecule. The procedures in each step can be automated using various robotic systems.

Thus, the invention permits supplying a suitable library and target molecule to a fully automatic system which finally generates an optimized binding molecule. Under ideal conditions, this process should run without any requirement for external work outside the robotic system during the entire procedure.

The selection methods of the present invention can be combined with secondary selection or screening identify reaction products capable of modifying target molecule function upon binding. Thus, the methods, described herein can be employed to isolate or produce binding molecules that bind to and modify the function of any protein or, nucleic acid.

For example, nucleic acid-templated chemistry can be used to identify, isolate, or produce binding molecules (1) affecting catalytic activity of target enzymes by inhibiting catalysis or, modifying substrate binding; (2) affecting the functionality of protein receptors, by inhibiting binding to receptors. or by modifying the specificity of binding to receptors; (3) affecting the formation of protein multimers by disrupting the quaternary structure of protein subunits; or (4) modifying transport properties of a protein by disrupting transport of small molecules or ions.

Functional assays can be included in the selection process. For example, after selecting for binding activity, selected library members can be directly tested for a desired functional effect, such as an effect on cell signaling. This can, for example, be performed via FACS methodologies.

The binding molecules of the invention can be selected for other properties in addition to binding. For example, to select for stability of binding interactions in a desired working environment. If stability in the presence of a certain protease is desired, that protease can be part of the buffer medium used during selection. Similarly, the selection can be performed in serum or cell extracts or in any type of medium, aqueous or organic. Conditions that disrupt or degrade the template should however be avoided to allow subsequent amplification.

Selections for other desired properties, such as catalytic or other functional activities, can also be performed. Generally, the selection should be designed such that library members with the desired activity are isolatable on that basis from other library members. For example, library members can be screened for the ability to fold or otherwise significantly change conformation in the presence of a target molecule, such as a metal ion, or under particular pH or salinity conditions. The folded library members can be isolated by performing non-denaturing gel electrophoresis under the conditions of interest. The folded library members migrate to a different position in the gel and can subsequently be extracted from the gel and isolated.

Selection for catalytic activity may be performed by affinity selections on transition-state analog affinity columns (Baca et al. (1997) PROC. NATL. ACAD. Sci. USA 94 (19): 10063-8) or by function-based selection schemes (Pedersen et al. (1998) PROC. NATL. ACAD. Sci. USA 95 (18): 10523-8).

Similarly, reaction products that fluoresce in the presence of specific ligands may be selected by FACS based sorting of translated polymers linked through their DNA templates to beads. Those beads that fluoresce in the presence, but not in the absence, of the target ligand are isolated and, characterized. Useful beads with a homogenous population of nucleic acid-templates-on any bead can be prepared using, the split-ppol synthesis technique on the bead, such that each bead is exposed to only a single nucleotide sequence. Alternatively, a different asti-"template (each complementary to only a single, different template) can by synthesized on beads using a split-pool" technique, and then can anneal to capture a solution-phase library.

Biotin-terminated biopolymers can be selected for the actual catalysis of bond-. breaking reactions by passing these biopolymers over a resin linked through a substrate to avidin. Those biopolymers that catalyze substrate cleavage self-elute from a column charged with this resin. Similarly, biotin-terminated biopolymers can be selected for the catalysis of bond-forming reactions. One substrate is linked to resin and the second substrate is linked to avidin. Biopolymers that catalyze bond formation between the substrates are selected by their ability to react the substrates together, resulting in attachment of the biopolymer to the resin.

Library members can also be selected for their catalytic effects on synthesis of a polymer to which the template is or becomes attached. For example, the library member may influence the selection of monomer units to be polymerized as well as how the polymerization reaction takes place (e.g., stereochemistry, tacticity, activity). The synthesized polymers can be selected for specific properties, such as, molecular weight, density, hydrophobicity, tacticity, stereoselectivity, using standard techniques, such as, electrophoresis, gel filtration, centrifugal sedimentation, or partitioning into solvents of different hydrophobicities. The attached template that directed the synthesis of the polymer can then be identified.

Library members that catalyze virtually any reaction causing bond formation between two substrate molecules or resulting in bond breakage into two product molecules can be selected. To select for bond forming catalysts (for example, hetero Diels-Alder, Heck coupling, aldol reaction, or olefin metathesis catalysts), library members are covalently linked to one substrate through their 5'. amino or thiol termini. The other substrate of the reaction is synthesized as a derivative linked to biotin. When dilute solutions of library-substrate conjugate are combined with the substrate-biotin conjugate, those library members that catalyze bond formation cause the biotin group to become covalently attached to themselves. Active bond forming catalysts can then be separated from inactive library members by capturing the former with immobilized streptavidin and washing away inactive library members. In an analogous manner, library members that catalyze bond cleavage reactions such as retro-aldol reactions, amide hydrolysis, elimination reactions, or olefin dihydroxylation followed by periodate cleavage can be selected. In this case, library members are covalently linked to biotinylated substrates such that the bond breakage reaction causes the disconnection of the biotin moiety from the library members. Upon incubation under reaction conditions, active catalysts, but not inactive library members, induce the loss of their biotin groups. Streptavidin-linked beads can then be used to capture inactive polymers, while active catalysts are able to be eluted from the beads. Related bond formation and bond cleavage selections have been used successfully in catalytic RNA and DNA evolution (Jaschke et al. (2000) CURR. OPIN. CHEM. BIOL. 4: 257-62) Although these selections do not explicitly select for multiple turnover catalysis, RNAs and DNAs selected in this manner have in general proven to be multiple turnover catalysts when separated from their substrate moieties (Jaschke et al. (2000) CURR. OPIN. CHEM. BIOL. 4: 257-62; Jaeger et al. (1999) PROC. NATL. ACAD. Sci. USA 96: 14712-7; Bartel et al. (1993) SCIENCE 261:1411-8; Sen et al. (1998) CURR. OPIN. CHEM. BIOL. 2:680-7).

In addition to simply evolving active catalysts, the in vitro selections described above are used to evolve non-natural polymer libraries in powerful directions difficult to achieve using other catalyst discovery approaches. Substrate specificity among catalysts can be selected by selecting for active catalysts in the presence of the desired substrate and then selecting for inactive catalysts in the presence of one or more undesired substrates. If the desired and undesired substrates differ by their configuration at one or more stereocenters, enantioselective or diastereoselective catalysts can emerge from rounds of selection. Similarly, metal selectivity can be evolved by selecting for active catalysts in the presence of desired metals and selecting for inactive catalysts in the presence of undesired metals. Conversely, catalysts with broad substrate tolerance can be evolved by varying substrate structures between successive rounds of iteration.

Alternatively, following PCR amplification of DNA templates encoding selected synthetic molecules, additional rounds of translation, selection, and amplification can be conducted to enrich the library for high affinity binders. The stringency of the selection is gradually increased by increasing the salt concentration of the binding and washing buffers, decreasing the duration of binding, elevating the binding and washing temperatures, and increasing the concentration of washing additives such as template DNA or unrelated proteins.

Importantly, in vitro selections can also select for specificity in addition to binding affinity. Library screening methods for binding specificity typically require duplicating the entire screen for each target or non-target of interest. In contrast, selections for specificity can be performed in a single experiment by selecting for target binding as well as for the inability to bind one or more non-targets. Thus, the library can be pre-depleted by removing library members that bind to a non-target. Alternatively, or in addition, selection for binding to the target molecule can be performed in the presence of an excess of one or more non-targets. To maximize specificity, the non-target can be a homologous molecule. If the target molecule is a protein, appropriate non-target proteins include, for example, a generally promiscuous protein such as an albumin. If the binding assay is designed to target only a specific portion of a target molecule, the non-target can be a variation on the molecule in which that portion has been changed or removed.

Ultimately, a binding molecule identified using the present invention may be useful as a therapeutic and/or diagnostic agent. Once the selection is complete, the selected templates optionally can be amplified and sequenced. The selected reaction products, if present in sufficient quantity, can be separated from the templates, purified (e.g., by HPLC, column chromatography, or other chromatographic method), and further characterized.

Inherent in the present method is the selection of chemical entities on the basis of a desired function; this can be extended to the selection of small molecules with a desired function and specificity. Specificity can be required during the selection process by first extracting identifiers sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Amplification of Identifier Oligonucleotides

PCR amplification methods are described in detail in U.S. Pat. Nos. 4,683,192, 4,683,202, 4,800,159, and 4,965,188, and at least in PCR Technology: Principles and Applications for DNA Amplification, H. Erlich, ed., Stockton Press, New York (1989); and PCR Protocols: A Guide to Methods and Applications, Innis et al., eds., Academic Press, San Diego, Calif. (1990). The contents of all the foregoing documents are incorporated herein by reference.

The identifier oligonucleotide can be amplified using PCR with primers generating two unique cut-sites. These cut-sites can be used for multimerization of the coding region by cloning into a suitable vector for sequencing. This approach will allow simultaneously sequencing of many encoding regions. Alternatively, the PCR product is directly cloned into a suitable vector using for example TA cloning. In still another approach the identity of the molecule is established by applying the PCR product to a suitable microarray.

It is preferred that the oligonucleotide parts of the bifunctional complexes of the libraries of the invention have a common terminal sequence which can serve as a primer for PCR, as is known in the art. Such a common terminal sequence can be incorporated as the terminal end of a tag added in the final cycle of the library synthesis, or it can be added following library synthesis, for example, using the enzymatic ligation methods disclosed herein.

In embodiments in which PCR is to be used to amplify the identifier oligonucleotides of selected bifunctional complexes, the identifier oligonucleotides preferably include PCR primer sequences. For example, a PCR primer sequence can be included in the display oligonucleotide and/or it can be included with the first tag oligonucleotide. The identifier oligonucleotide can also include a capping PCR primer sequence that follows the tag sequences. The capping sequence can be ligated to the identifier oligonucleotide following the final cycle of library synthesis or it can be included in the tag oligonucleotide of the final cycle. In cases in which the PCR primer sequences are included in a tag oligonucleotide, these tag oligonucleotides will be longer than the tag oligonucleotides added in the other cycles, because they will include both a tag sequence and a PCR primer sequence.

In cases in which the capping sequence is added after the addition of the final reactant and the final tag oligonucleotide, the synthesis of a library as set forth herein will include the step of ligating the capping sequence to the identifier oligonucleotide, such that the oligonucleotide portion of substantially all of the library members terminates in a sequence that includes a PCR primer sequence.

PCR primer sequences suitable for use in the libraries of the invention are known in the art; suitable primers and methods are set forth, for example, in Innis et al., eds., PCR Protocols: A Guide to Methods and Applications, San Diego: Academic Press (1990), the contents of which are incorporated herein by reference in their entirety. Preferably, the capping sequence is added by ligation to the pooled fractions which are products of the final synthesis round. The capping sequence can be added using the enzymatic process used in the construction of the library.

As indicated above, the nucleotide sequence of the oligonucleotide tag as part of the methods of this invention, may be determined by the use of the polymerase chain reaction (PCR).

The nucleic acid sequence of an oligonucleotide tag can be determined by subjecting the oligonucleotide tag to a PCR reaction as follows. The appropriate sample is contacted with a PCR primer pair, each member of the pair having a preselected nucleotide sequence. The PCR primer pair is capable of initiating primer extension reactions by hybridizing to a PCR primer binding site on the identifier oligonucleotide tag. The PCR primer binding site is preferably designed into the identifier oligonucleotide tag. For example, a PCR primer binding site may be incorporated into the initial (display) oligonucleotide tag and the second PCR primer binding site may be in the final oligonucleotide tag. Alternatively, the second PCR primer binding site may be incorporated into the capping sequence as described herein. In preferred embodiments, the PCR primer binding site is at least about 5, 7, 10, 13, 15, 17, 20, 22, or 25 nucleotides in length.

The PCR reaction can be performed by mixing the PCR primer pair, preferably a predetermined amount thereof, with the identifier oligonucleotide, preferably a predetermined amount thereof, in a PCR buffer to form a PCR reaction admixture. The admixture is thermocycled for a number of cycles, which is typically predetermined, sufficient for the formation of a PCR reaction product. A sufficient amount of product is one that can be isolated in a sufficient amount to allow for DNA sequence determination.

PCR is typically carried out by thermocycling i.e. repeatedly increasing and decreasing the temperature of a PCR reaction admixture within a temperature range whose lower limit is about 30 C to about 55 C and whose upper limit is about 90 C to about 100 C. The increasing and decreasing steps can be continuous, but is preferably phasic with time periods of relative temperature stability at each of temperatures favoring polynucleotide synthesis, denaturation and hybridization.

The PCR reaction can be performed using any suitable method. Generally it occurs in a buffered aqueous solution, i.e. a PCR buffer, preferably at a pH of 7-9. Preferably, a molar excess of the primer is present. A large molar excess is preferred to improve the efficiency of the process.

The PCR buffer also contains the deoxyribonucleotide triphosphates (polynucleotide synthesis substrates) dATP, dCTP, dGTP and dTTP and a polymerase, typically thermostable, all in adequate amounts for primer extension (polynucleotide synthesis) reaction. The resulting solution (PCR mixture) is-heated to about 90 C-100 C for about 1 to 10 minutes, preferably from 1 to 4 minutes. After this heating period the solution is allowed to cool to 54 C, which is preferable for primer hybridization.

The synthesis reaction may occur at a temperature ranging from room temperature up to a temperature above which the polymerase no longer functions efficiently. Suitable enzymes for elongating the primer sequences include, for example, *E. coli* DNA polymerase I, Taq DNA polymerase, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5'direction along the template strand, until synthesis terminates, producing molecules of different lengths. The newly synthesized DNA strand and its complementary strand form a double-stranded molecule which can be used in the succeeding steps of the analysis process.

Ultra High-Throughput Methods

Tags and/or identifiers may be analyzed by an ultra high throughput method, such as ultra high throughput sequencing as described herein below. Often following a screen or affinity assay using encoded molecules e.g. phage display, DNA display, mRNA display, or other types of tagged compounds, the results of screening may be analyzed by sampling a limited number of tags, e.g. 1-100 tags. Tags may be analyzed by cloning individual tags e.g. by cloning in *E. coli* followed by preparation of plasmids or "colony PCR" and then sequencing using any method known in the art. However, it is often desirable to analyse a significantly larger number of tags to obtain more information from the screening which makes these traditional methods of cloning and sequencing cumbersome. For example, a single type of sequence corresponding to a specific combination of codons may dominate a small tag sample e.g. 40 of 100 tags may correspond to a single codon combination and the remaining tags may be different. If instead 1000 or 10000 tags are analysed it is expected that about 400 and 4000 sequences respectively correspond to the tag observed 40 of 100 times in the small sample. However the remaining 600 and 6000 sequences respectively may reveal several sequences that are observed more than once thus indicating that they have been preferentially enriched during the screening. Thus a potential wealth of information exists which is very cumbersome to access using traditional methods, e.g. e.g. by cloning in *E. coli* followed by preparation of plasmids or "colony PCR" and then sequencing. Several methods can be applied to analyze tags in an ultra high-throughput fashion. For example identifiers may be analyzed by an ultra high-throughput method similar to that described in patent WO01 20039 and Margulies M et al (Genome sequencing in microfabricated high-density picoliter reactors, Nature 2005). This method involves capture of individual PCR-derived fragments on their own beads and, within the droplets of an emulsion, clonally amplifying the individual fragment. Unlike in current sequencing technology, this approach does not require subcloning in bacteria or the handling of individual clones; the templates are handled in bulk within the emulsions. Sequencing can be done by synthesis simultaneously in open wells of a fibre-optic slide using a modified pyrosequencing protocol that is designed to take advantage of the small scale of the wells. The fibreoptic slides are manufactured by slicing of a fibre-optic block that is obtained by repeated drawing and fusing of optic fibres. At each iteration, the diameters of the individual fibres decrease as they are hexagonally packed into bundles of increasing cross-sectional sizes. Each fibre-optic core is 44 µm in diameter and surrounded by 2-3 µm of cladding; etching of each core creates reaction wells approximately 55 µm in depth with a centre-to-centre distance of 50 µm, resulting in a calculated well size of 75 pl (picoliters). The slide, containing approximately 1.6 million wells, is loaded with beads and mounted in a flow chamber designed to create a 300-mm high channel, above the well openings, through which the sequencing reagents flow The unetched base of the slide is in optical contact with a second fibre optic imaging bundle bonded to a charge-coupled device (CCD) sensor, allowing the capture of emitted photons from the bottom of each individual well. The combination of picoliter-sized wells, enzyme loading uniformity allowed by the small beads and enhanced solid support chemistry enables a method that extends the useful read length of sequencing-by-synthesis to more than 100 bases.

Identifiers may also be analyzed by an ultra high-throughput method similar to that described in WO/2005/093094. This method relates to "high-density fingerprinting", in which a panel of nucleic acid probes is annealed to nucleic acid information is desired, e.g. an identifier, with determination of the presence or absence of sequence complementary to a panel of probes, thus providing sequence information. The method involves hybridization of a panel of probes, each probe comprising one or more oligonucleotide molecules, in sequential steps determining for each probe if it hybridizes to the template or not, thus forming the "hybridization fingerprint" of the target. Preferably, the panel of probes and the length of the template strand are adjusted to ensure dense coverage of any given template strand with indicative probes' (probes which hybridize exactly once to the template strand). Probes may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or nucleotides long. Probes may contain any natural or unnatural nucleotide or analog. The obtained hybridization spectrum can then be compared with a reference database containing all expected identifier sequences. Before probing, identifiers or derived products may be immobilized in an array format. Then identifiers may be amplified e.g. using rolling-circle amplification or a related method. Thus individual identifier sequences are placed apart and amplified avoiding the need for traditional cumbersome cloning e.g. in *e. coli*.

Identifiers may also be analyzed by an ultra high-throughput method similar to that described in WO/2001/057248. By this method identifiers or amplified or modified identifiers may be immobilized in an array format. Primers may be annealed to the identifiers and the sequence of the identifiers may be determined by sequencing. Seqeuncing in an array format can be done by various methods recognized by those skilled in the art. For example, incorporation of fluorescently-labeled, 3'-blocked nucleotides can be done in the presence of a DNA polymerase. Nucleotide may be any natural or unnatural nucleotide or any nucleotide analog. The polymerase incorporates a base complementary to the target polynucleotide, but is prevented from further addition by the 3'-blocking group. The label of the incorporated base can then be determined and the blocking group removed by chemical cleavage to allow further polymerisation to occur. The fluorescent group can also be removed thus allowing detection of a new nucleotide incorporation at a specific array position. Prior to immobilization, a hairpin adaptor may be ligated to the identifier sequence such that a primer becomes covalently linked to the identifier.

The information carried by tags may be analyzed using a computer application, e.g. a word or text processing application, a spreadsheet application. Preferably, the tag information may be analyzed using a computer application which can translate the tag information into e.g. encoded structures. A computer application may preferably be used to analyze such encoded structures include quantitative and qualitative structure-activity relationship (SAR) analyses e.g. such as analyzing and/or clustering structural fingerprints common to enriched encoded structures. A simple but efficient method is to look for tag combinations which have been enriched by the screening process.

It may be found that only specific reactants or dimers formed by reactants, e.g., dimers formed by the first and the second reactant or the first and the third reactant are enriched by a screening process. Such a result may indicate that the screening process has not been optimized and steps can be taken to improve the screening process. If a large number of molecules with e.g. same or very similar target affinity exist in a library of bifunctional complexes it may be difficult or impossible to optimize the screening process so that it can discriminate sufficiently between them. The tag analysis may then identify a common reactant combination shared by the tags whereas one reactant position may be "undefined" i.e. it is not possible to determine which reactant is preferred at this position, e.g. the "C" position in the following list of tag combinations, where identifiers are composed of three tags (A-B-C): A2-B17-C13, A1-B1-C2, A1-B1-C14, A1-B1-C23, A1-B1-C17, A5-B278-C11. In this case is preferable to obtain significantly more tag sequences as this may enable discrimination of different but similar reactant combinations. This can be achieved by using ultra high-throughput tag sequencing methods as described.

Following screening or analyses of identifiers the pool of identifiers may be subjected to further methods which may aid analyses of the identifiers. Such methods may include partitioning the identifiers based on specific features of the identifiers such as a nucleotide sequence. For example a subset of identifiers may contain too many variants of a tag combination or it may contains too much noise, e.g. identifiers which are deemed uninteresting. In such cases nested PCR may be used to amplify only identifiers which contain specific tags. The resulting amplification product may then be processed e.g. sequencing, optionally in an ultra high-throughput fashion, to identify a common tag at an otherwise unresolved position. Alternatively, tag combinations may be enriched by partitioning single-stranded identifier oligonucleotides e.g. sequentially with anticodons corresponding to specific tags essentially performing an affinity selection/screening of the identifiers with or without encoded molecules. In this way it is possible to partition specific identifiers or identifier subsets.

Targets

The methods described herein may involve partitioning of molecules or bifunctional complexes according to their affinity for a target. Targets may be protein or non-protein as discussed elsewhere. In the case of protein targets a list of applicable targets may be obtained e.g. by accessing an public database such as a NCBI database (http://www.ncbi.nlm.nih.gov/entrez/guery.fcgi?db=Protein). In the case of human enzymes and receptors, targets may be retrieved from said database using e.g. "Human" and "Enzyme" or "Receptor" as query keywords. Moreover, a list of targets can be retrieved from the "Mode of Action" section of the Medtrack database (medtrack.com).

A target suitable for use with the methods described herein can be selected from the list consisting of:

1:) (2'-5')oligo(A) synthetase (EC 2.7.7.-), splice form 8-2—human; (2:) [3-methyl-2-oxobutanoate dehydrogenase [lipoamide]] kinase, mitochondrial precursor (Branched-chain alpha-keto acid dehydrogenase kinase) (BCKDHKIN) (BCKD-kinase); (3:) [Protein ADP-ribosylarginine] hydrolase (ADP-ribosylargininehydrolase) (ADP-ribose-L-arginine cleaving enzyme); (4:) 1,4-alpha-glucan branching enzyme; (5:) 11 beta-hydroxysteroid dehydrogenase type II; (6:) 11-beta-hydroxysteroid dehydrogenase 1 [*Homo sapiens*]; (7:) 130 kDa leucine-rich protein (LRP 130) (GP130) (Leucine-rich PPR motif-containing protein); (8:) 130 kDa phosphatidylinositol 4,5-biphosphate-dependent ARF1 GTPase-activating protein (PIP2-dependent ARF1 GAP) (ADP-ribosylation factor-directed GTPase-activating protein 1) (ARFGTPase-activating protein 1) (Development and differentiation-enhancing factor 1); (9:) 14-3-3 protein zeta/delta (Protein kinase C inhibitor protein 1) (KCIP-1); (10:) 15-hydroxyprostaglandin dehydrogenase [NAD+] (PGDH) (Prostaglandindehydrogenase 1); (11:) 17 beta hydroxysteroid dehydrogenase type 2; (12:) 17beta-hydroxysteroid dehydrogenase type 10/short chain L-3-hydroxyacyl-CoA dehydrogenase [*Homo sapiens*]; (13:) 17beta-hydroxysteroid dehydrogenase type 7 form 2 [*Homo sapiens*]; (14:) 1-acylglycerol-3-phosphate O-acyltransferase 1 [*Homo sapiens*]; (15:) 1-acylglycerol-3-phosphate O-acyltransferase 5 [*Homo sapiens*]; (16:) 1-aminocyclopropane-1-carboxylate synthase [*Homo sapiens*]; (17:) 1-phosphatidylinositol-4,5-bisphosphate phosphodiesterase gamma 2(Phosphoinositide phospholipase C) (PLC-gamma-2) (Phospholipase C-gamma-2) (PLC-IV); (18:) 2,4-dienoyl CoA reductase 1 precursor [*Homo sapiens*]; (19:) 2,4-dienoyl-CoA reductase, mitochondrial precursor (2,4-dienoyl-CoA reductase [NADPH]) (4-enoyl-CoA reductase [NADPH]); (20:) 2',5'-oligoadenylate synthetase 1 isoform 1 [*Homo sapiens*]; (21:) 2',5'-oligoadenylate synthetase 1 isoform 2 [*Homo sapiens*]; (22:) 2',5'-oligoadenylate synthetase 1 isoform 3 [*Homo sapiens*]; (23:) 2-5A-dependent ribonuclease (2-5A-dependent RNase) (Ribonuclease L) (RNase L) (Ribonuclease 4); (24:) 25-hydroxyvitamin D-1 alpha hydroxylase, mitochondrial precursor (Cytochrome P450 subfamily XXVIIB polypeptide 1) (Cytochrome p45027B1) (Calcidiol 1-monooxygenase) (25-OHD-1 alpha-hydroxylase) (25-hydroxyvitamin D(3) 1-alpha-hydroxylase) (VD31A hydroxylase) (P450C1 alpha) (P450VD1-alpha); (25:) 25-hydroxyvitamin D-1-alpha-hydroxylase [*Homo sapiens*]; (26:) 2'-5'oligoadenylate synthetase 3 [*Homo sapiens*]; (27:) 2'-5'-oligoadenylate synthetase-like isoform a [*Homo sapiens*]; (28:) 2'-5'-oligoadenylate synthetase-like isoform b [*Homo sapiens*]; (29:) 26S proteasome non- ATPase regulatory subunit 2 (26S proteasome regulatory subunit RPN1) (26S proteasome regulatory subunit S2) (26S proteasome subunit p97) (Tumor necrosis factor type 1 receptor-associated protein 2) (55.11 protein); (30:) 26S proteasome non-ATPase regulatory subunit 7 (26S proteasome regulatory subunit rpn8) (26S proteasome regulatory subunit S12) (Proteasome subunit p40) (Mov34 protein homolog); (31:) 2-acylglycerol O-acyltransferase 2 (MonoacylglycerolO-acyltransferase 2) (Acyl CoA:monoacylglycerol acyltransferase 2) (MGAT2) (hMGAT2) (Diacylglycerol acyltransferase 2-like protein 5) (Diacylglycerol O-acyltransferase candidate 5) (hDC5); (32:) 2-acylglycerol O-acyltransferase 3 (MonoacylglycerolO-acyltransferase 3) (Acyl CoA:monoacylglycerol acyltransferase 3) (MGAT3) (Diacylglycerol acyltransferase 2-like protein 7) (Diacylglycerol O-acyltransferase candidate 7) (hDC7); (33:) 2-amino-3-carboxymuconate-6-semialdehyde decarboxylase; (34:) 2-amino-3-ketobutyrate coenzyme A ligase, mitochondrial precursor (AKB ligase) (Glycine acetyltransferase); (35:) 2-amino-3-ketobutyrate-CoA ligase [*Homo sapiens*]; (36:) 2-aminoadipic 6-semialdehyde dehydrogenase [*Homo sapiens*]; (37:) 2-enoyl-CoA hydratase, 3-hydroxyacyl-CoA dehydrogenase, 3-oxoacyl-CoA thiolase, TFE beta=trifunctional enzyme beta subunit {N-terminal} [human, liver, Peptide Mitochondrial Partial, 16 aa]; (38:) 2-hydroxyacyl-CoA lyase 1 [*Homo sapiens*]; (39:) 2-hydroxyacylsphingosine 1-beta-galactosyltransferase (EC 2.4.1.45)—human; (40:) 2-hydroxyphytanoyl-CoA lyase (2-HPCL); (41:) 2-hydroxyphytanoyl-CoA lyase [*Homo sapiens*]; (42:) 2-oxoglutarate dehydrogenase E1 component, mitochondrial precursor (Alpha-ketoglutarate dehydrogenase); (43:) 2-oxoglutarate receptor 1 (Alpha-ketoglutarate receptor 1) (G-protein coupled receptor 80) (G-protein coupled receptor 99) (P2Y purinoceptor 15) (P2Y-like nucleotide receptor) (P2Y-like GPCR); (44:) "3 beta-hydroxysteroid dehydrogenase/delta 5→4-isomerase type 1(3Beta-HSD 1) (Trophoblast antigen FDO161G) [Includes: 3-beta-hydroxy-delta(5)-steroid dehydrogenase (3-beta-hydroxy-5-enesteroid dehydrogenase) (Progesterone reductase); Steroid delta-isomerase (Delta-5-3-ketosteroid isomerase)]."; (45:) "3 beta-hydroxysteroid dehydrogenase/ delta 5→4-isomerase type II (3Beta-HSD II) [Includes:) 3-beta-hydroxy-delta(5)-steroid dehydrogenase (3-beta-hydroxy-5-ene steroid dehydrogenase) (Progesterone reductase); Steroid delta-isomerase(Delta-5-3-ketosteroid isomerase)]."; (46:) 3' histone mRNA exonuclease 1 (3'-5' exonuclease ERI1) (Eri-1 homolog) (Histone mRNA 3' end-specific exoribonuclease) (Protein3'hExo) (HEXO); (47:) 3'(2'),5'-bisphosphate nucleotidase 1 (Bisphosphate 3'-nucleotidase 1) (PAP-inositol-1,4-phosphatase) (PIP); (48:) 3,2-trans-enoyl-CoA isomerase, mitochondrial precursor (Dodecenoyl-CoA isomerase) (Delta(3),delta(2)-enoyl-CoA isomerase) (D3,D2-enoyl-CoA isomerase); (49:) 3',5'-cyclic nucleotide phosphodiesterase (EC 3.1.4.17) 8B1-human; (50:) 3-hydroxy-3-methylglutaryl coenzyme A reductase; (51:) "3-hydroxyacyl-CoA dehydrogenase; peroxisomal enoyl-CoA hydratase[*Homo sapiens*]."; (52:) 3-hydroxybutyrate dehydrogenase precursor [*Homo sapiens*]; (53:) 3-hydroxybutyrate dehydrogenase type 2 (R-beta-hydroxybutyrate dehydrogenase) (Dehydrogenase/ reductase SDR family member 6) (Oxidoreductase UCPA); (54:) 3-hydroxybutyrate dehydrogenase, type 2 [*Homo sapiens*]; (55:) 3-hydroxyisobutyrate dehydrogenase [*Homo sapiens*]; (56:) 3-hydroxymethyl-3-methylglutaryl-Coenzyme A lyase (hydroxymethylglutaricaciduria) [*Homo sapiens*]; (57:) 3-keto-steroid reductase (Estradiol 17-beta-dehydrogenase 7) (17-beta-HSD 7) (17-beta-hydroxysteroid dehydrogenase 7); (58:) 3-mercaptopyruvate sulfurtransferase [*Homo sapiens*]; (59:) 3-methylcrotonyl-CoA carboxylase alpha subunit [*Homo sapiens*]; (60:) 3-methylcrotonyl-CoA carboxylase biotin-containing subunit [*Homo sapiens*]; (61:) 3-oxo-5 alpha-steroid 4-dehydrogenase 2 [*Homo sapiens*]; (62:) 3-oxo-5-beta-steroid 4-dehydrogenase (Delta(4)-3-ketosteroid 5-beta-reductase) (Aldo-keto reductase family 1 member D1); (63:) 3-oxoacid CoA transferase 1 precursor [*Homo sapiens*]; (64:) 3-oxoacyl-[acyl-carrier-protein] synthase, mitochondrial precursor (Beta-ketoacyl synthase); (65:) 3'-phosphoadenosine 5'-phosphosulfate synthase 1 [*Homo sapiens*]; (66:) 3'phosphoadenosine 5'-phosphosulfate synthase 2b isoform [*Homo sapiens*]; (67:) 40 kDa peptidyl-prolyl cis-trans isomerase (PPIase) (Rotamase) (Cyclophilin-40) (CYP-40) (Cyclophilin-related protein); (68:) 4a-carbinolamine dehydratase; (69:) 4-alpha-glucanotransferase (EC 2.4.1.25)/amylo-1,6-glucosidase (EC 3.2.1.33)-human; (70:) 4-aminobutyrate aminotransferase precursor [*Homo sapiens*]; (71:) 4-trimethylaminobutyraldehyde dehydrogenase (TMABADH) (Aldehydedehydrogenase 9A1) (Aldehyde dehydrogenase E3 isozyme) (Gamma-aminobutyraldehyde dehydrogenase) (R-aminobutyraldehydedehydrogenase); (72:) 5' nucleotidase, ecto [*Homo sapiens*]; (73:) 5'(3')-deoxyribonucleotidase, cytosolic type (Cytosolic 5',3'-pyrimidine nucleotidase) (Deoxy-5'-nucleotidase 1) (dNT-1); (74:) 5,10-methylenetetrahydrofolate reductase (NADPH) [*Homo sapiens*]; (75:) 5',3'-nucleotidase, cytosolic [*Homo sapiens*]; (76:) 5',3'-nucleotidase, mitochondrial precursor [*Homo sapiens*]; (77:) 52 kD Ro/SSA autoantigen [*Homo sapiens*]; (78:) 5-aminoimidazole-4-carboxamide ribonucleotide formyltransferase/IMP cyclohydrolase [*Homo sapiens*]; (79:) 5-aminolevulinate synthase, erythroid-specific, mitochondrial precursor (5-aminolevulinic acid synthase) (Delta-aminolevulinate synthase) (Delta-ALA synthetase) (ALAS-E); (80:) 5-aminolevulinate synthase, nonspecific, mitochondrial precursor (5-aminolevulinic acid synthase) (Delta-aminolevulinate synthase) (Delta-ALA synthetase) (ALAS-H); (81:) 5-beta steroid reductase [*Homo sapiens*]; (82:) 5-hydroxytryptamine 1A receptor (5-HT-1A) (Serotonin receptor 1A) (5-HT1A) (G-21); (83:) 5-hydroxytryptamine 1B receptor (5-HT-1B) (Serotonin receptor 1B) (5-HT1B) (5-HT-1D-beta) (Serotonin 1D beta receptor) (S12); (84:) 5-hydroxytryptamine 1D receptor (5-HT-1D) (Serotonin receptor 1D) (5-HT-1D-alpha); (85:) 5-hydroxytryptamine 1E receptor (5-HT-1E) (Serotonin receptor 1E) (5-HT1E) (S31); (86:) 5-hydroxytryptamine 1F receptor (5-HT-1F) (Serotonin receptor 1F); (87:) 5-hydroxytryptamine 2A receptor (5-HT-2A) (Serotonin receptor 2A) (5-HT-2); (88:) 5-hydroxytryptamine 2B receptor (5-HT-2B) (Serotonin receptor 2B); (89:) 5-hydroxytryptamine 2C receptor (5-HT-2C) (Serotonin receptor 2C) (5-HT2C) (5-HTR2C) (5HT-1C); (90:) 5-hydroxytryptamine 3 receptor precursor (5-HT-3) (Serotonin-gated ion channel receptor) (5-HT3R); (91:) 5-hydroxytryptamine 4 receptor (5-HT-4) (Serotonin receptor 4) (5-HT4); (92:) 5-hydroxytryptamine 5A receptor (5-HT-5A) (Serotonin receptor 5A) (5-HT-5); (93:) 5-hydroxytryptamine 6 receptor (5-HT-6) (Serotonin receptor 6); (94:) 5-hydroxytryptamine 7 receptor (5-HT-7) (Serotonin receptor 7) (5-HT-X) (5HT7); (95:) 5-methyltetrahydrofolate-homocysteine methyltransferase [*Homo sapiens*]; (96:) 5'-methylthioadenosine phosphorylase [*Homo sapiens*]; (97:) 5'-nucleotidase, cytosolic II [*Homo sapiens*]; (98:) 5'-nucleotidase, cytosolic III isoform 1 [*Homo sapiens*]; (99:) 6-phosphofructo-2-kinase (EC 2.7.1.105)/fructose-2,6-bisphosphate 2-phosphatase (EC 3.1.3.46)—human; (100:) "6-phosphofructo-2-kinase/fructose-2,6-biphosphatase 1(6

PF-2-K/Fru-2,6-P2ASE liver isozyme) [Includes: 6-phosphofructo-2-kinase; Fructose-2,6-bisphosphatase]."; (101:) 6-phosphofructo-2-kinase/fructose-2,6-biphosphatase 2 isoform a[*Homo sapiens*]; (102:) 6-phosphofructo-2-kinase/fructose-2,6-biphosphatase 2 isoform b[*Homo sapiens*]; (103:) "6-phosphofructo-2-kinase/fructose-2,6-biphosphatase 2(6 PF-2-K/Fru-2,6-P2ASE heart-type isozyme) (PFK-2/FBPase-2) [Includes:) 6-phosphofructo-2-kinase; Fructose-2,6-bisphosphatase]."; (104:) 6-phosphofructo-2-kinase/fructose-2,6-biphosphatase 4 [*Homo sapiens*]; (105:) 6-phosphofructo-2-kinase/fructose-2,6-biphosphatase 4 splice isoform 3 [*Homo sapiens*]; (106:) 6-phosphofructo-2-kinase/fructose-2,6-biphosphatase 4 splice isoform 4 [*Homo sapiens*]; (107:) 6-phosphofructo-2-kinase/fructose-2,6-biphosphatase 4 splice isoform 5 [*Homo sapiens*]; (108:) "6-phosphofructo-2-kinase/fructose-2,6-biphosphatase 4(6 PF-2-K/Fru-2,6-P2ASE testis-type isozyme) [Includes: 6-phosphofructo-2-kinase; Fructose-2,6-bisphosphatase]."; (109:) 6-phosphofructo-2-kinase/fructose-2,6-biphosphatase-4 isoform 2-[*Homo sapiens*]; (110:) 6-phosphofructokinase (EC 2.7.1.11), hepatic—human; (111:) 6-phosphofructokinase type C (Phosphofructokinase 1) (Phosphohexokinase) (Phosphofructo-1-kinase isozyme C) (PFK-C) (6-phosphofructokinase, platelet type); (112:) 6-phosphofructokinase, liver type (Phosphofructokinase 1) (Phosphohexokinase) (Phosphofructo-1-kinase isozyme B) (PFK-B); (113:) 6-phosphofructokinase, muscle type (Phosphofructokinase 1) (Phosphohexokinase) (Phosphofructo-1-kinase isozyme A) (PFK-A) (Phosphofructokinase-M); (114:) 6-phosphogluconolactonase (6PGL); (115:) 6-pyruvoyl tetrahydrobiopterin synthase (PTPS) (PTP synthase); (116:) 6-pyruvoyltetrahydropterin synthase [*Homo sapiens*]; (117:) 7,8-dihydro-8-oxoguanine triphosphatase (8-oxo-dGTPase) (Nucleosidediphosphate-linked moiety X motif 1) (Nudix motif 1); (118:) 72 kDa type IV collagenase precursor (72 kDa gelatinase) (Matrixmetalloproteinase-2) (MMP-2) (Gelatinase A) (TBE-1); (119:) 85 kDa calcium-independent phospholipase A2 (iPLA2) (Cal-PLA2) (Group VI phospholipase A2) (GVI PLA2); (120:) 8-hydroxyguanine-DNA glycosylase [*Homo sapiens*]; (121:) 8-oxo-7,8-dihydroguanosine triphophatase—human; (122:) 8-oxo-dGTPase [*Homo sapiens*]; (123:) 8-oxoguanine DNA glycosylase 1 [*Homo sapiens*]; (124:) 8-oxoguanine DNA glycosylase homolog 1 [*Homo sapiens*]; (125:) 8-oxoguanine DNA glycosylase isoform 1a [*Homo sapiens*]; (126:) 8-oxoguanine DNA glycosylase isoform 1b [*Homo sapiens*]; (127:) 8-oxoguanine DNA glycosylase isoform 1c [*Homo sapiens*]; (128:) 8-oxoguanine DNA glycosylase isoform 2a [*Homo sapiens*]; (129:) 8-oxoguanine DNA glycosylase isoform 2b [*Homo sapiens*]; (130:) 8-oxoguanine DNA glycosylase isoform 2c [*Homo sapiens*]; (131:) 8-oxoguanine DNA glycosylase isoform 2d [*Homo sapiens*]; (132:) 8-oxoguanine DNA glycosylase isoform 2e [*Homo sapiens*]; (133:) 92-kDa type IV collagenase [*Homo sapiens*]; (134:) 9-cis-retinol specific dehydrogenase [*Homo sapiens*]; (135:) A Transferase [*Homo sapiens*]; (136:) A/G-specific adenine DNA glycosylase (MutY homolog) (hMYH); (137:) ACAD 10 [*Homo sapiens*]; (138:) Ac-CoA carboxylase; (139:) ACE2 [*Homo sapiens*]; (140:) ACE-related carboxypeptidase ACE2 [*Homo sapiens*]; (141:) Acetoacetyl-CoA synthetase [*Homo sapiens*]; (142:) Acetolactate synthase [*Homo sapiens*]; (143:) acetolactate synthase homolog; (144:) Acetylcholine receptor protein subunit alpha precursor; (145:) Acetylcholine receptor protein subunit beta precursor; (146:) Acetylcholine receptor protein subunit delta precursor; (147:) Acetylcholine receptor protein subunit epsilon precursor; (148:) Acetylcholine receptor protein subunit gamma precursor; (149:) Acetylcholinesterase collagenic tail peptide precursor (AChE Qsubunit) (Acetylcholinesterase-associated collagen); (150:) acetylcholinesterase collagen-like tail subunit [*Homo sapiens*]; (151:) acetylcholinesterase collagen-like tail subunit isoform I precursor [*Homo sapiens*]; (152:) acetylcholinesterase collagen-like tail subunit isoform II [*Homo sapiens*]; (153:) acetylcholinesterase collagen-like tail subunit isoform III [*Homo sapiens*]; (154:) acetylcholinesterase collagen-like tail subunit isoform III precursor [*Homo sapiens*]; (155:) acetylcholinesterase collagen-like tail subunit isoform IV [*Homo sapiens*]; (156:) acetylcholinesterase collagen-like tail subunit isoform IV precursor [*Homo sapiens*]; (157:) acetylcholinesterase collagen-like tail subunit isoform V [*Homo sapiens*]; (158:) acetylcholinesterase collagen-like tail subunit isoform V precursor [*Homo sapiens*]; (159:) acetylcholinesterase collagen-like tail subunit isoform VI [*Homo sapiens*]; (160:) acetylcholinesterase collagen-like tail subunit isoform VII [*Homo sapiens*]; (161:) acetylcholinesterase collagen-like tail subunit isoform VIII [*Homo sapiens*]; (162:) acetylcholinesterase collagen-like tail subunit isoform VIII precursor [*Homo sapiens*]; (163:) acetylcholinesterase collagen-like tail subunit isoform VII precursor [*Homo sapiens*]; (164:) acetylcholinesterase collagen-like tail subunit isoform VI precursor [*Homo sapiens*]; (165:) acetylcholinesterase isoform E4-E5 precursor [*Homo sapiens*]; (166:) acetyl-CoA carboxylase (EC 6.4.1.2)—human; (167:) Acetyl-CoA carboxylase 1 (ACC-alpha) [Includes:) Biotin carboxylase]; (168:) acetyl-CoA carboxylase 1 [*Homo sapiens*]; (169:) Acetyl-CoA carboxylase 2 (ACC-beta) [Includes:) Biotin carboxylase]; (170:) acetyl-CoA carboxylase 2 [*Homo sapiens*]; (171:) Acetyl-CoA carboxylase 2 variant [*Homo sapiens*]; (172:) acetyl-CoA carboxylase alpha [*Homo sapiens*]; (173:) acetyl-CoA synthetase [*Homo sapiens*]; (174:) acetyl-Coenzyme A acetyltransferase 1 precursor [*Homo sapiens*]; (175:) acetyl-Coenzyme A acetyltransferase 2 [*Homo sapiens*]; (176:) acetyl-Coenzyme A acyltransferase 1 [*Homo sapiens*]; (177:) acetyl-Coenzyme A carboxylase alpha isoform 1 [*Homo sapiens*]; (178:) acetyl-Coenzyme A carboxylase alpha isoform 2 [*Homo sapiens*]; (179:) acetyl-Coenzyme A carboxylase alpha isoform 3 [*Homo sapiens*]; (180:) acetyl-Coenzyme A carboxylase alpha isoform 4 [*Homo sapiens*]; (181:) acetyl-Coenzyme A carboxylase beta [*Homo sapiens*]; (182:) Acetyl-coenzyme A synthetase 2-like, mitochondrial precursor (Acetate-CoA ligase 2) (Acetyl-CoA synthetase 2) (Acyl-CoA synthetase short-chain family member 1); (183:) Acetyl-coenzyme A synthetase, cytoplasmic (Acetate-CoA ligase) (Acyl-activating enzyme) (Acetyl-CoA synthetase) (ACS) (AceCS) (Acyl-CoA synthetase short-chain family member 2); (184:) acid alpha-glucosidase preproprotein [*Homo sapiens*]; (185:) acid phosphatase 1 isoform b [*Homo sapiens*]; (186:) acid phosphatase 1 isoform c [*Homo sapiens*]; (187:) acid phosphatase 1 isoform d [*Homo sapiens*]; (188:) acid phosphatase 6, lysophosphatidic [*Homo sapiens*]; (189:) acid phosphatase; (190:) aconitase 2 precursor [*Homo sapiens*]; (191:) Aconitate hydratase, mitochondrial precursor (Citrate hydro-lyase) (Aconitase); (192:) acrosin precursor [*Homo sapiens*]; (193:) ACSBG2 protein [*Homo sapiens*]; (194:) ACSL1 protein [*Homo sapiens*]; (195:) ACSL3 protein [*Homo sapiens*]; (196:) ACSL6 protein [*Homo sapiens*]; (197:) ACSM1 protein [*Homo sapiens*]; (198:) ACSS2 protein [*Homo sapiens*]; (199:) activating transcription factor 2 [*Homo sapiens*]; (200:) activation of Sentrin/SUMO protein AOS1 [*Homo sapiens*]; (201:) activation-induced cytidine deaminase [*Homo sapiens*]; (202:) activin A receptor, type IC [*Homo sapiens*]; (203:) activin A receptor, type IIA precursor [*Homo sapiens*]; (204:) activin A type IB receptor isoform a precursor [*Homo sapiens*]; (205:) activin A type IB receptor isoform b precursor [*Homo sapiens*]; (206:) activin A type IB receptor isoform c precursor [*Homo sapiens*]; (207:) activin A type IIB receptor precursor [*Homo sapiens*]; (208:) Activin receptor type IB precursor (ACTR-IB) (Serine/threonine-protein kinase receptor R2) (SKR2) (Activin receptor-like kinase 4) (ALK-4); (209:) Activin receptor type 1C precursor (ACTR-IC) (Activin receptor-like kinase 7) (ALK-7); (210:) Activin receptor type 2A precursor (Activin receptor type IIA) (ACTR-IIA) (ACTRIIA); (211:) Activin receptor type 2B precursor (Activin receptor type IIB) (ACTR-IIB); (212:) Activin receptor type-1 precursor (Activin receptor type I) (ACTR-I) (Serine/threonine-protein kinase receptor R1) (SKR1) (Activin receptor-like kinase 2) (ALK-2) (TGF-B superfamily receptor type 1) (TSR-I); (213:) acyl coenzyme A:cholesterol acyltransferase [*Homo sapiens*]; (214:) acyl coenzyme A:monoacylglycerol acyltransferase 3 [*Homo sapiens*]; (215:) acylamino acid-releasing enzyme [*Homo sapiens*]; (216:) Acylamino-acid-releasing enzyme (AARE) (Acyl-peptide hydrolase) (APH) (Acylaminoacyl-peptidase) (Oxidized protein hydrolase) (OPH) (DNF15S2 protein); (217:) Acyl-CoA dehydrogenase family member 8, mitochondrial precursor (ACAD-8) (Isobutyryl-CoA dehydrogenase) (Activator-recruited cofactor 42 kDa component) (ARC42); (218:) Acyl-CoA synthetase 3 [*Homo sapiens*]; (219:) acyl-CoA synthetase 4 [*Homo sapiens*]; (220:) Acyl-CoA synthetase bubblegum family member 2 [*Homo sapiens*]; (221:) acyl-CoA synthetase long-chain family member 1 [*Homo sapiens*]; (222:) acyl-CoA synthetase long-chain family member 1 isoform a [*Homo sapiens*]; (223:) acyl-CoA synthetase long-chain family member 1 isoform c [*Homo sapiens*]; (224:) acyl-CoA synthetase long-chain family member 3 [*Homo sapiens*]; (225:) Acyl-CoA synthetase long-chain family member 4 [*Homo sapiens*]; (226:) acyl-CoA synthetase long-chain family member 4 isoform 1 [*Homo sapiens*]; (227:) acyl-CoA synthetase long-chain family member 4 isoform 2 [*Homo sapiens*]; (228:) Acyl-CoA synthetase long-chain family member 5 [*Homo sapiens*]; (229:) acyl-CoA synthetase long-chain family member 5 isoform a [*Homo sapiens*]; (230:) acyl-CoA synthetase long-chain family member 5 isoform b [*Homo sapiens*]; (231:) acyl-CoA synthetase long-chain family member 6 isoform a [*Homo sapiens*]; (232:) acyl-CoA synthetase long-chain family member 6 isoform b [*Homo sapiens*]; (233:) acyl-CoA synthetase long-chain family member 6 isoform d [*Homo sapiens*]; (234:) acyl-CoA synthetase long-chain family member 6 isoform e [*Homo sapiens*]; (235:) Acyl-CoA synthetase medium-chain family member 3 [*Homo sapiens*]; (236:) Acyl-CoA synthetase short-chain family member 1 [*Homo sapiens*]; (237:) Acyl-CoA synthetase short-chain family member 2 [*Homo sapiens*]; (238:) acyl-CoA synthetase short-chain family member 2 isoform 1 [*Homo sapiens*]; (239:) acyl-CoA synthetase short-chain family member 2 isoform 2 [*Homo sapiens*]; (240:) acyl-CoA synthetase-like protein [*Homo sapiens*]; (241:) Acyl-CoA wax alcohol acyltransferase 1 (Long-chain-alcoholO-fatty-acyltransferase 1) (Diacylglycerol O-acyltransferase 2-like protein 3) (Diacyl-glycerol acyltransferase 2); (242:) Acyl-CoA wax alcohol acyltransferase 2 (Long-chain-alcoholO-fatty-acyltransferase 2) (Wax synthase) (hWS) (MultifunctionalO-acyltransferase) (Diacylglycerol O-acyltransferase 2-like protein4) (Diacylglycerol O-acyltransferase candidate 4) (hDC4); (243:) acyl-Coenzyme A dehydrogenase family, member 10 [*Homo sapiens*]; (244:) Acyl-Coenzyme A dehydrogenase family, member 11 [*Homo sapiens*]; (245:) acyl-Coenzyme A dehydrogenase family, member 8 [*Homo sapiens*]; (246:) acyl-Coenzyme A dehydrogenase, C-2 to C-3 short chain precursor[*Homo sapiens*]; (247:) acyl-Coenzyme A dehydrogenase, C-4 to C-12 straight chain [*Homo sapiens*]; (248:) acyl-Coenzyme A dehydrogenase, long chain precursor [*Homo sapiens*]; (249:) acyl-Coenzyme A dehydrogenase, short/branched chain precursor [*Homo sapiens*]; (250:) acyl-Coenzyme A oxidase 2, branched chain [*Homo sapiens*]; (251:) acyl-Coenzyme A oxidase 3, pristanoyl [*Homo sapiens*]; (252:) acyl-Coenzyme A oxidase isoform a [*Homo sapiens*]; (253:) acyl-Coenzyme A oxidase isoform b [*Homo sapiens*]; (254:) Acyl-coenzyme A thioesterase 8 (Acyl-CoA thioesterase 8) (Peroxisomal acyl-coenzyme A thioester hydrolase 1) (PTE-1) (Peroxisomal long-chain acyl-coA thioesterase 1) (HIV-Nef-associated acyl coA thioesterase) (Thioesterase II) (hTE) (hACTEIII) (hACTE-III) (PTE-2); (255:) acyl-malonyl condensing enzyme [*Homo sapiens*]; (256:) acyl-malonyl condensing enzyme 1 [*Homo sapiens*]; (257:) acyloxyacyl hydrolase precursor [*Homo sapiens*]; (258:) acyloxyacyl hydrolase; (259:) ADAM 10 precursor (A disintegrin and metalloproteinase domain 10) (Mammalian disintegrin-metalloprotease) (Kuzbanian protein homolog) (CDw156c antigen); (260:) ADAM 17 precursor (A disintegrin and metalloproteinase domain 17) (TNF-alpha-converting enzyme) (TNF-alpha convertase) (Snake venom-like protease) (CD156b antigen); (261:) ADAM metallopeptidase domain 10 [*Homo sapiens*]; (262:) ADAM metallopeptidase domain 12 isoform 1 preproprotein [*Homo sapiens*]; (263:) ADAM metallopeptidase domain 12 isoform 2 preproprotein [*Homo sapiens*]; (264:) ADAM metallopeptidase domain 17 preproprotein [*Homo sapiens*]; (265:) ADAM metallopeptidase domain 19 isoform 1 preproprotein [*Homo sapiens*]; (266:) ADAM metallopeptidase domain 19 isoform 2 preproprotein [*Homo sapiens*]; (267:) ADAM metallopeptidase domain 33 isoform alpha preproprotein [*Homo sapiens*]; (268:) ADAM metallopeptidase domain 33 isoform beta preproprotein [*Homo sapiens*]; (269:) ADAM metallopeptidase with thrombospondin type 1 motif, 12preproprotein [*Homo sapiens*]; (270:) ADAM metallopeptidase with thrombospondin type 1 motif, 13 isoform1 preproprotein [*Homo sapiens*]; (271:) ADAM metallopeptidase with thrombospondin type 1 motif, 13 isoform2 preproprotein [*Homo sapiens*]; (272:) ADAM metallopeptidase with thrombospondin type 1 motif, 13 isoform3 preproprotein [*Homo sapiens*]; (273:) ADAM metallopeptidase with thrombospondin type 1 motif, 1 preproprotein [*Homo sapiens*]; (274:) ADAM metallopeptidase with thrombospondin type 1 motif, 2 isoform 1 preproprotein [*Homo sapiens*]; (275:) ADAM metallopeptidase with thrombospondin type 1 motif, 2 isoform 2 [*Homo sapiens*]; (276:) ADAM metallopeptidase with thrombospondin type 1 motif, 3proprotein [*Homo sapiens*]; (277:) ADAM metallopeptidase with thrombospondin type 1 motif, 4preproprotein [*Homo sapiens*]; (278:) ADAM metallopeptidase with thrombospondin type 1 motif, 5preproprotein [*Homo sapiens*]; (279:) ADAM metallopeptidase with thrombospondin type 1 motif, 8preproprotein [*Homo sapiens*]; (280:) ADAM10 [*Homo sapiens*]; (281:) ADAMTS-13 precursor (A disintegrin and metalloproteinase with thrombospondin motifs 13) (ADAM-TS13) (ADAM-TS13) (von Willebrand factor-cleaving protease) (vWF-cleaving protease) (vWF-CP); (282:) ADAMTS-14 precursor (A disintegrin and metalloproteinase with thrombospondin motifs 14) (ADAM-TS14) (ADAM-TS14); (283:) ADAMTS-2 precursor (A disintegrin and metalloproteinase with thrombospondin motifs 2) (ADAM-TS 2) (ADAM-TS2) (Procollagen I/II amino propeptide-processing enzyme) (Procollagen I N-proteinase) (PC I-NP) (Procollagen N-endopeptidase) (pNPI); (284:) ADAMTS-3 precursor (A disintegrin and metalloproteinase with thrombospondin motifs 3) (ADAM-TS 3) (ADAM-TS3) (Procollagen II amino propeptide-processing enzyme) (Procollagen II N-proteinase) (PC II-NP); (285:) adaptor-related protein complex 2, alpha 1 subunit isoform 1 [*Homo sapiens*]; (286:) adaptor-related protein complex 2, alpha 1 subunit isoform 2 [*Homo sapiens*]; (287:) Adenine phosphoribosyltransferase (APRT); (288:) adenine phosphoribosyltransferase isoform a [*Homo sapiens*]; (289:) adenine phosphoribosyltransferase isoform b [*Homo sapiens*]; (290:) Adenosine A1 receptor; (291:) Adenosine A2a receptor; (292:) Adenosine A2b receptor; (293:) Adenosine A3 receptor; (294:) adenosine deaminase [*Homo sapiens*]; (295:) adenosine deaminase variant [*Homo sapiens*]; (296:) adenosine deaminase, RNA-specific isoform a [*Homo sapiens*]; (297:) adenosine deaminase, RNA-specific isoform b [*Homo sapiens*]; (298:) adenosine deaminase, RNA-specific isoform c [*Homo sapiens*]; (299:) adenosine deaminase, RNA-specific isoform d [*Homo sapiens*]; (300:) adenosine kinase isoform a [*Homo sapiens*]; (301:) adenosine kinase isoform b [*Homo sapiens*]; (302:) adenosine monophosphate deaminase 1 (isoform M) [*Homo sapiens*]; (303:) adenylate cyclase (EC 4.6.1.1)—human (fragment); (304:) adenylate cyclase 2 [*Homo sapiens*]; (305:) adenylate cyclase 3 [*Homo sapiens*]; (306:) adenylate cyclase 5 [*Homo sapiens*]; (307:) adenylate cyclase 6 isoform a [*Homo sapiens*]; (308:) adenylate cyclase 6 isoform b [*Homo sapiens*]; (309:) adenylate cyclase 7 [*Homo sapiens*]; (310:) adenylate cyclase 8 [*Homo sapiens*]; (311:) adenylate cyclase 9 [*Homo sapiens*]; (312:) adenylate cyclase activating polypeptide 1 (pituitary) receptor type I precursor [*Homo sapiens*]; (313:) Adenylate cyclase type 1 (Adenylate cyclase type 1) (ATP pyrophosphate-lyase 1) (Ca(2+)/calmodulin-activated adenylylcyclase); (314:) Adenylate cyclase type 2 (Adenylate cyclase type 11) (ATP pyrophosphate-lyase 2) (Adenylyl cyclase 2); (315:) Adenylate cyclase type 3 (Adenylate cyclase type III) (Adenylatecyclase, olfactive type) (ATP pyrophosphate-lyase 3) (Adenylylcyclase 3) (AC-III) (AC3); (316:) Adenylate cyclase type 4 (Adenylate cyclase type IV) (ATP pyrophosphate-lyase 4) (Adenylyl cyclase 4); (317:) Adenylate cyclase type 5 (Adenylate cyclase type V) (ATP pyrophosphate-lyase 5) (Adenylyl cyclase 5); (318:) Adenylate cyclase type 6 (Adenylate cyclase type VI) (ATP pyrophosphate-lyase 6) (Ca(2+)-inhibitable adenylyl cyclase); (319:) Adenylate cyclase type 8 (Adenylate cyclase type VIII) (ATP pyrophosphate-lyase 8) (Ca(2+)/calmodulin-activated adenylylcyclase); (320:) Adenylate cyclase type 9 (Adenylate cyclase type IX) (ATP pyrophosphate-lyase 9) (Adenylyl cyclase 9); (321:) adenylate kinase 1 [*Homo sapiens*]; (322:) adenylate kinase 2 isoform a [*Homo sapiens*]; (323:) adenylate kinase 2 isoform b [*Homo sapiens*]; (324:) Adenylate kinase isoenzyme 1 (ATP-AMP transphosphorylase) (AK1) (Myokinase); (325:) Adenylate kinase isoenzyme 2, mitochondrial (ATP-AMP transphosphorylase); (326:) Adenylate kinase isoenzyme 5 (ATP-AMP transphosphorylase); (327:) Adenylate kinase isoenzyme 6 (ATP-AMP transphosphorylase 6); (328:) Adenylosuccinate lyase (Adenylosuccinase) (ASL) (ASASE); (329:) adenylosuccinate lyase [*Homo sapiens*]; (330:) adenylosuccinate synthase [*Homo sapiens*]; (331:) adhesion regulating molecule 1 precursor [*Homo sapiens*]; (332:) adiponectin precursor [*Homo sapiens*]; (333:) Adiponectin receptor protein 1 (Progestin and adipoQ receptor family member I); (334:) Adiponectin receptor protein 2 (Progestin and adipoQ receptor family member 11); (335:) "Adiponutrin (iPLA2-epsilon) (Calcium-independent phospholipase A2-epsilon) (Patatin-like phospholipase domain-containing protein3) [Includes:) Triacylglycerol lipase; AcylglycerolO-acyltransferase]."; (336:) ADP-ribosyl cyclase 1 (Cyclic ADP-ribose hydrolase 1) (cADPr hydrolase 1) (Lymphocyte differentiation antigen CD38) (T10) (Acutelymphoblastic leukemia cells antigen CD38); (337:) ADP-ribosylarginine hydrolase [*Homo sapiens*]; (338:) ADP-ribosylation factor binding protein 2 [*Homo sapiens*]; (339:) ADP-ribosyltransferase 5 precursor [*Homo sapiens*]; (340:) adrenal gland protein AD-004 [*Homo sapiens*]; (341:) Adrenocorticotropic hormone receptor (ACTH receptor) (ACTH-R) (Melanocortin receptor 2) (MC2-R) (Adrenocorticotropin receptor); (342:) Adrenomedullin receptor (AM-R); (343:) advanced glycosylation end product-specific receptor isoform 1 precursor [*Homo sapiens*]; (344:) advanced glycosylation end product-specific receptor isoform 2precursor [*Homo sapiens*]; (345:) aggrecanase 1 [*Homo sapiens*]; (346:) AHCYL1 protein [*Homo sapiens*]; (347:) AICAR formyl transferase/IMP cyclohydrolase bifunctional enzyme; (348:) AK001663 hypothetical protein [*Homo sapiens*]; (349:) A-kinase anchor protein 10 precursor [*Homo sapiens*]; (350:) A-kinase anchor protein 5 (A-kinase anchor protein 79 kDa) (AKAP79) (cAMP-dependent protein kinase regulatory subunit 11 high affinity-binding protein) (H21); (351:) A-kinase anchor protein 7 isoform alpha [*Homo sapiens*]; (352:) A-kinase anchor protein 7 isoform beta [*Homo sapiens*]; (353:) A-kinase anchor protein 7 isoform gamma [*Homo sapiens*]; (354:) A-kinase anchor protein 8 [*Homo sapiens*]; (355:) alanyl-tRNA synthetase [*Homo sapiens*]; (356:) albumin precursor [*Homo sapiens*]; (357:) Alcohol dehydrogenase [NADP+] (Aldehyde reductase) (Aldo-ketoreductase family 1 member A1); (358:) Alcohol dehydrogenase 1 B (Alcohol dehydrogenase beta subunit); (359:) alcohol dehydrogenase 1B (class I), beta polypeptide [*Homo sapiens*]; (360:) Alcohol dehydrogenase 4 (Alcohol dehydrogenase class II pi chain); (361:) Alcohol dehydrogenase class 4 mu/sigma chain (Alcohol dehydrogenase class IV mu/sigma chain) (Retinol dehydrogenase) (Gastric alcohol dehydrogenase); (362:) alcohol dehydrogenase pi subunit; (363:) alcohol dehydrogenase, iron containing, 1 isoform 1 [*Homo sapiens*]; (364:) alcohol dehydrogenase, iron containing, 1 isoform 2 [*Homo sapiens*]; (365:) "alcohol sulfotransferase; hydroxysteroid sulfotransferase [*Homo sapiens*]."; (366:) aldehyde dehydrogenase (NAD+) [*Homo sapiens*]; (367:) aldehyde dehydrogenase 1 (EC 1.2.1.3); (368:) aldehyde dehydrogenase 1 family, member L1 [*Homo sapiens*]; (369:) aldehyde dehydrogenase 1A1 [*Homo sapiens*]; (370:) aldehyde dehydrogenase 1A2 isoform 1 [*Homo sapiens*]; (371:) aldehyde dehydrogenase 1A2 isoform 2 [*Homo sapiens*]; (372:) aldehyde dehydrogenase 1A2 isoform 3 [*Homo sapiens*]; (373:) Aldehyde dehydrogenase 1A3 (Aldehyde dehydrogenase 6) (Retinaldehyde dehydrogenase 3) (RALDH-3); (374:) aldehyde dehydrogenase 1B1 precursor [*Homo sapiens*]; (375:) aldehyde dehydrogenase 2 (EC 1.2.1.3); (376:) aldehyde dehydrogenase 3 family, member A1 [*Homo sapiens*]; (377:) aldehyde dehydrogenase 4A1 precursor [*Homo sapiens*]; (378:) aldehyde dehydrogenase 5A1 precursor, isoform 1 [*Homo sapiens*]; (379:) aldehyde dehydrogenase 5A1 precursor, isoform 2 [*Homo sapiens*]; (380:) aldehyde dehydrogenase 6A1 precursor [*Homo sapiens*]; (381:) aldehyde dehydrogenase 8A1 isoform 1 [*Homo sapiens*]; (382:) aldehyde dehydrogenase 8A1 isoform 2 [*Homo sapiens*]; (383:) aldehyde dehydrogenase 9A1 [*Homo sapiens*]; (384:) Aldehyde dehydrogenase, dimeric NADP-preferring (ALDH class 3) (ALDHIII); (385:) Aldehyde dehydrogenase, mitochondrial precursor (ALDH class 2) (ALDHI) (ALDH-E2); (386:) Aldehyde Reductase; (387:) Aldo-keto reductase family 1 member C3(Trans-1,2-dihydrobenzene-1,2-diol dehydrogenase) (3-alpha-hydroxysteroid dehydrogenase type 2) (3-alpha-HSD type 2) (3-alpha-HSD type 11, brain) (Prostaglandin F synthase) (PGFS) (Estradiol 17-beta-dehydrogenase) (17-beta-hydroxysteroid dehydrogenase type 5) (17-beta-HSD 5) (Chlordecone reductase homolog HAKRb) (HA1753) (Dihydrodiol dehydrogenase type I) (Dihydrodiol dehydrogenase 3) (DD3) (DD-3); (388:) aldo-keto reductase family 1, member A1 [Homo sapiens]; (389:) aldo-keto reductase family 1, member B1 [Homo sapiens]; (390:) aldo-keto reductase family 1, member C1 [Homo sapiens]; (391:) aldo-keto reductase family 1, member C2 [Homo sapiens]; (392:) aldo-keto reductase family 1, member C3 [Homo sapiens]; (393:) aldo-keto reductase family 1, member C4 [Homo sapiens]; (394:) aldo-keto reductase family 1, member D1 [Homo sapiens]; (395:) aldolase A [Homo sapiens]; (396:) aldolase B [Homo sapiens]; (397:) Aldose reductase (AR) (Aldehyde reductase); (398:) Aldose Reductase (E.C.1.1.1.21) Mutant With Cys 298 Replaced By Ser (C298s) Complex With Nadph; (399:) Aldose Reductase (E.C.1.1.1.21) Mutant With Tyr 48 Replaced By His(Y48h) Complexed With Nadp+ And Citrate; (400:) ALK tyrosine kinase receptor precursor (Anaplastic lymphoma kinase) (CD246 antigen); (401:) Alkaline ceramidase 1 (Alkaline CDase-1) (Alk CDase 1) (Acylsphingosine deacylase 3) (N-acylsphingosine amidohydrolase 3); (402:) Alkaline phosphatase, placental type precursor (PLAP-1) (Reganisozyme); (403:) Alkaline phosphatase, tissue-nonspecific isozyme precursor (AP-TNAP) (Liver/bone/kidney isozyme) (TNSALP); (404:) Alkaline phytoceramidase (aPHC) (Alkaline ceramidase) (Alkalinedihydroceramidase SB89); (405:) alkaline phytoceramidase [Homo sapiens]; (406:) alkyldihydroxyacetone phosphate synthase precursor [Homo sapiens]; (407:) Alkyldihydroxyacetonephosphate synthase, peroxisomal precursor (Alkyl-DHAP synthase) (Alkylglycerone-phosphate synthase) (Aging-associated protein 5); (408:) alpha (1, 2) fucosyltransferase [Homo sapiens]; (409:) alpha 1 type I collagen preproprotein [Homo sapiens]; (410:) alpha 1 type II collagen isoform 1 precursor [Homo sapiens]; (411:) alpha 1 type II collagen isoform 2 precursor [Homo sapiens]; (412:) alpha 1,2-mannosidase [Homo sapiens]; (413:) alpha 1,4-galactosyltransferase [Homo sapiens]; (414:) alpha 2,3-sialyltransferase III isoform A7 [Homo sapiens]; (415:) alpha 2,3-sialyltransferase III isoform A8 [Homo sapiens]; (416:) alpha 2,3-sialyltransferase III type D2+26 [Homo sapiens]; (417:) alpha galactosidase A; (418:) alpha isoform of regulatory subunit A, protein phosphatase 2 [Homo sapiens]; (419:) alpha isoform of regulatory subunit B55, protein phosphatase 2 [Homo sapiens]; (420:) alpha mannosidase 11; (421:) Alpha platelet-derived growth factor receptor precursor (PDGF-R-alpha) (CD140a antigen); (422:) alpha(1,2)fucosyltransferase [Homo sapiens]; (423:) Alpha-(1,3)-fucosyltransferase (Galactoside 3-L-fucosyltransferase) (Fucosyltransferase 6) (FUCT-VI); (424:) alpha/beta hydrolase domain containing protein 1 [Homo sapiens]; (425:) alpha-1 antitrypsin [Homo sapiens]; (426:) alpha-1 antitrypsin variant [Homo sapiens]; (427:) alpha-1,3(6)-mannosylglycoprotein beta-1,6-N-acetyl-glucosaminyltransferase [Homo sapiens]; (428:) Alpha-1,4-N-acetylglucosaminyltransferase (Alpha4GnT); (429:) Alpha-1A adrenergic receptor (Alpha 1A-adrenoceptor) (Alpha1A-adrenoreceptor) (Alpha-1C adrenergic receptor) (Alpha adrenergic receptor 1c); (430:) Alpha-1-antichymotrypsin precursor (ACT) [Contains:Alpha-1-antichymotrypsin His-Pro-less]; (431:) Alpha-1B adrenergic receptor (Alpha 1B-adrenoceptor) (Alpha1B-adrenoreceptor); (432:) Alpha-1D adrenergic receptor (Alpha 1D-adrenoceptor) (Alpha1D-adrenoreceptor) (Alpha-1A adrenergic receptor) (Alpha adrenergic receptor 1a); (433:) Alpha-2A adrenergic receptor (Alpha-2A adrenoceptor) (Alpha-2A adreno receptor) (Alpha-2AAR) (Alpha-2 adrenergic receptor subtype C10); (434:) Alpha-2B adrenergic receptor (Alpha-2B adrenoceptor) (Alpha-2B adrenoreceptor) (Alpha-2 adrenergic receptor subtype C2); (435:) Alpha-2C adrenergic receptor (Alpha-2C adrenoceptor) (Alpha-2C adrenoreceptor) (Alpha-2 adrenergic receptor subtype C4); (436:) Alpha-2-macroglobulin precursor (Alpha-2-M); (437:) alpha-2-macroglobulin precursor [Homo sapiens]; (438:) alpha-2-plasmin inhibitor [Homo sapiens]; (439:) alpha2-subunit of soluble guanylyl cyclase [Homo sapiens]; (440:) alpha-aminoadipate semialdehyde synthase [Homo sapiens]; (441:) "Alpha-aminoadipic semialdehyde synthase, mitochondrial precursor (LKR/SDH) [Includes:) Lysine ketoglutarate reductase (LOR) (LKR); Saccharopine dehydrogenase (SDH)]."; (442:) Alpha-enolase (2-phospho-D-glycerate hydro-lyase) (Non-neuralenolase) (NNE) (Enolase 1) (Phosphopyruvate hydratase) (C-myc promoter-binding protein) (MBP-1) (MPB-1) (Plasminogen-binding protein); (443:) alpha-galactosidase A [Homo sapiens]; (444:) alpha-galactosidase A precursor (EC 3.2.1.22); (445:) Alpha-galactosidase A precursor (Melibiase) (Alpha-D-galactoside-galactohydrolase) (Alpha-D-galactosidase A) (Agalsidase alfa); (446:) alpha-galactosidase; (447:) alpha-keto acid dehydrogenase precursor; (448:) "alpha-ketoglutarate dehydrogenase complex dihydrolipoylsuccinyltransferase; KGDHC E2k component [Homo sapiens]."; (449:) alpha-KG-E2 [Homo sapiens]; (450:) Alpha-lactalbumin precursor (Lactose synthase B protein); (451:) alpha-L-iduronidase precursor [Homo sapiens]; (452:) Alpha-L-iduronidase precursor; (453:) alpha-methylacyl-CoA racemase isoform 1 [Homo sapiens]; (454:) alpha-methylacyl-CoA racemase isoform 2 [Homo sapiens]; (455:) alpha-N-acetylgalactosaminidase precursor [Homo sapiens]; (456:) alpha-N-acetylglucosaminidase precursor [Homo sapiens]; (457:) alpha-N-acetylglucosaminidase; (458:) Alpha-N-acetyl-neuraminide alpha-2,8-sialyltransferase (Ganglioside GD3 synthase) (Ganglioside GT3 synthase) (Alpha-2,8-sialyltransferase 8A) (ST8Sia I); (459:) alpha-synuclein isoform NACP112 [Homo sapiens]; (460:) alpha-synuclein isoform NACP140 [Homo sapiens]; (461:) amiloride binding protein [Homo sapiens]; (462:) Amiloride binding protein 1 (amine oxidase (copper-containing))[Homo sapiens]; (463:) amiloride binding protein 1 precursor [Homo sapiens]; (464:) amiloride-binding protein 1 (amine oxidase (copper-containing))[Homo sapiens]; (465:) amiloride-binding protein; (466:) Amiloride-sensitive amine oxidase [copper-containing] precursor (Diamine oxidase) (DAO) (Amiloride-binding protein) (ABP) (Histaminase) (Kidney amine oxidase) (KAO); (467:) amine oxidase (flavin containing) domain 2 isoform b [Homo sapiens]; (468:) amine oxidase (flavin-containing) [Homo sapiens]; (469:) Amine oxidase [flavin-containing] A (Monoamine oxidase type A) (MAO-A); (470:) amine oxidase, copper containing 2 (retina-specific) [Homo sapiens]; (471:) amine oxidase, copper containing 2 isoform a [Homo sapiens]; (472:) amine oxidase, copper containing 2 isoform b [Homo sapiens]; (473:) Amine oxidase, copper containing 3 (vascular adhesion protein 1)[Homo sapiens]; (474:) amine oxidase, copper containing 3 precursor [Homo sapiens]; (475:) amino-acid N-acetyltransferase (EC 2.3.1.1)-human; (476:) aminoacylase 1 [Homo sapiens]; (477:) aminoadipate-semialdehyde dehydrogenase-phosphopantetheinyltransferase [Homo sapiens]; (478:) aminoadipate-semialdehyde synthase [Homo sapiens]; (479:) aminocarboxymuconate semialdehyde decarboxylase [Homo sapiens]; (480:) aminolevulinate delta-synthase 1 [Homo sapiens]; (481:) aminolevulinate, delta, synthase 1 [Homo sapiens]; (482:) Aminolevulinate, delta-, synthase 1 [Homo sapiens]; (483:) aminolevulinate, delta-, synthase 2 isoform a [Homo sapiens]; (484:) aminolevulinate, delta-, synthase 2 isoform b [Homo sapiens]; (485:) aminolevulinate, delta-, synthase 2 isoform c [Homo sapiens]; (486:) aminolevulinate, delta-, synthase 2 isoform d [Homo sapiens]; (487:) aminomethyltransferase (glycine cleavage system protein T) [Homo sapiens]; (488:) Aminopeptidase N (hAPN) (Alanyl aminopeptidase) (Microsomalaminopeptidase) (Aminopeptidase M) (gp150) (Myeloid plasma membrane glycoprotein CD13) (CD13 antigen); (489:) Aminopeptidase O (AP-O); (490:) aminopeptidase puromycin sensitive [Homo sapiens]; (491:) AMP deaminase 3 (AMP deaminase isoform E) (Erythrocyte AMP deaminase); (492:) AMP-activated protein kinase alpha 2 catalytic subunit [Homo sapiens]; (493:) AMP-activated protein kinase beta 1 non-catalytic subunit [Homo sapiens]; (494:) AMP-activated protein kinase beta 2 non-catalytic subunit [Homo sapiens]; (495:) AMP-activated protein kinase gamma2 subunit isoform a [Homo sapiens]; (496:) AMP-activated protein kinase gamma2 subunit isoform b [Homo sapiens]; (497:) AMP-activated protein kinase gamma2 subunit isoform c [Homo sapiens]; (498:) AMP-activated protein kinase, noncatalytic gamma-1 subunit isoform1 [Homo sapiens]; (499:) AMP-activated protein kinase, noncatalytic gamma-1 subunit isoform2 [Homo sapiens]; (500:) AMP-activated protein kinase, non-catalytic gamma-3 subunit [Homo sapiens]; (501:) AMP-binding enzyme, 33217 [Homo sapiens]; (502:) amphiregulin preproprotein [Homo sapiens]; (503:) "amylase, alpha 1A; salivary precursor [Homo sapiens]."; (504:) Amylo-1,6-glucosidase, 4-alpha-glucanotransferase (glycogen debranching enzyme, glycogen storage disease type III) [Homo sapiens]; (505:) amylo-1,6-glucosidase, 4-alpha-glucanotransferase isoform 1 [Homo sapiens]; (506:) amylo-1,6-glucosidase, 4-alpha-glucanotransferase isoform 2 [Homo sapiens]; (507:) amylo-1,6-glucosidase, 4-alpha-glucanotransferase isoform 3 [Homo sapiens]; (508:) "Amyloid beta A4 protein precursor (APP) (ABPP) (Alzheimer disease amyloid protein) (Cerebral vascular amyloid peptide) (CVAP) (Protease nexin-II) (PN-II) (APPI) (PreA4) [Contains:) Soluble APP-alpha (S-APP-alpha); Soluble APP-beta (S-APP-beta); C99; Beta-amyloid protein 42 (Beta-APP42); Beta-amyloid protein 40(Beta-APP40); C83; P3(42); P3(40); Gamma-CTF (59) (Gamma-secretase C-terminal fragment 59) (Amyloid intracellular domain 59) (AID(59)); Gamma-CTF(57) (Gamma-secretase C-terminal fragment 57) (Amyloid intracellular domain 57) (AID(57)); Gamma-CTF(50) (Gamma-secretase C-terminal fragment 50) (Amyloid intracellular domain 50) (AID(50)); C31]."; (509:) amyloid beta A4 protein precursor, isoform a [Homo sapiens]; (510:) amyloid beta A4 protein precursor, isoform b [Homo sapiens]; (511:) amyloid beta A4 protein precursor, isoform c [Homo sapiens]; (512:) Amyloid beta precursor protein binding protein 1 [Homo sapiens]; (513:) amyloid beta precursor protein-binding protein 1 isoform a [Homo sapiens]; (514:) amyloid beta precursor protein-binding protein 1 isoform b [Homo sapiens]; (515:) amyloid beta precursor protein-binding protein 1 isoform c [Homo sapiens]; (516:) amyloid precursor protein-binding protein 1 (APP-B1) [Homo sapiens]; (517:) amyloid precursor protein-binding protein 1; (518:) anaphase promoting complex subunit 1 [Homo sapiens]; (519:) anaphase promoting complex subunit 10 [Homo sapiens]; (520:) Anaphase-promoting complex subunit 11 (APC11) (Cyclosome subunit 11) (Hepatocellular carcinoma-associated RING finger protein); (521:) anaphase-promoting complex subunit 2 [Homo sapiens]; (522:) anaphase-promoting complex subunit 4 [Homo sapiens]; (523:) anaphase-promoting complex subunit 5 [Homo sapiens]; (524:) anaphase-promoting complex subunit 7 [Homo sapiens]; (525:) Androgen receptor (Dihydrotestosterone receptor); (526:) androgen receptor isoform 1 [Homo sapiens]; (527:) androgen receptor isoform 2 [Homo sapiens]; (528:) androgen-regulated short-chain dehydrogenase/reductase 1 [Homo sapiens]; (529:) Angiogenin precursor (Ribonuclease 5) (RNase 5); (530:) Angiopoietin-1 receptor precursor (Tyrosine-protein kinase receptor TIE-2) (hTIE2) (Tyrosine-protein kinase receptor TEK) (p140 TEK) (Tunica interna endothelial cell kinase) (CD202b antigen); (531:) angiotensin converting enzyme (EC 3.4.15.1); (532:) angiotensin converting enzyme 2 [Homo sapiens]; (533:) angiotensin converting enzyme precursor (EC 3.4.15.1); (534:) angiotensin converting enzyme-like protein [Homo sapiens]; (535:) angiotensin I converting enzyme (peptidyl-dipeptidase A) 1 [Homo sapiens]; (536:) Angiotensin I converting enzyme (peptidyl-dipeptidase A) 2 [Homo sapiens]; (537:) angiotensin I converting enzyme [Homo sapiens]; (538:) angiotensin I converting enzyme 2 precursor [Homo sapiens]; (539:) angiotensin I converting enzyme isoform I precursor [Homo sapiens]; (540:) angiotensin I converting enzyme isoform 1 precursor variant [Homo sapiens]; (541:) angiotensin I converting enzyme isoform 2 precursor [Homo sapiens]; (542:) angiotensin I converting enzyme isoform 3 precursor [Homo sapiens]; (543:) "angiotensin I converting enzyme precursor; dipeptidylcarboxypeptidase 1 [Homo sapiens]."; (544:) "angiotensin I converting enzyme precursor; dipeptidylcarboxypeptidase 1; kinase II [Homo sapiens]."; (545:) angiotensin 1-converting enzyme [Homo sapiens]; (546:) angiotensin I-converting enzyme precursor (EC 3.4.15.1); (547:) angiotensin II receptor type-1 (clone HATR1GH)—human (fragment); (548:) angiotensin II receptor, type 1 [Homo sapiens]; (549:) angiotensin 11 receptor, type 2 [Homo sapiens]; (550:) angiotensin-converting enzyme [Homo sapiens]; (551:) angiotensin-converting enzyme 2 [Homo sapiens]; (552:) Angiotensin-converting enzyme 2 precursor (ACE-related carboxypeptidase) (Angiotensin-converting enzyme homolog) (ACEH); (553:) Angiotensin-converting enzyme, somatic isoform precursor (Dipeptidyl carboxypeptidase I) (Kininase II) (CD143 antigen)[Contains:) Angiotensin-converting enzyme, somatic isoform, soluble form]; (554:) Angiotensin-converting enzyme, testis-specific isoform precursor (ACE-T) (Dipeptidyl carboxypeptidase I) (Kininase II) [Contains:Angiotensin-converting enzyme, testis-specific isoform, soluble form]; (555:) "Angiotensinogen precursor [Contains:) Angiotensin-1 (Angiotensin I) (Ang I); Angiotensin-2 (Angiotensin II) (Ang II); Angiotensin-3(Angiotensin III) (Ang III) (Des-Asp[1]-angiotensin II)]."; (556:) angiotensinogen preproprotein [Homo sapiens]; (557:) Annexin A4 (Annexin IV) (Lipocortin IV) (Endonexin I) (Chromobindin-4) (Protein II) (P32.5) (Placental anticoagulant protein II) (PAP-II) (PP4-X) (35-beta calcimedin) (Carbohydrate-binding protein P33/P41) (P33/41); (558:) Annexin A5 (Annexin V) (Lipocortin V) (Endonexin II) (CalphobindinI) (CBP-I) (Placental anticoagulant protein I) (PAP-I) (PP4) (Thromboplastin inhibitor) (Vascular anticoagulant-alpha) (VAC-alpha) (Anchorin CII); (559:) anthracycline-associated resistance ARX [Homo sapiens]; (560:) Anthrax toxin receptor 1 precursor (Tumor endothelial marker 8); (561:) Anthrax toxin receptor 2 precursor (Capillary morphogenesis gene 2protein) (CMG-2); (562:) Anti-Muellerian hormone type-2 receptor precursor (Anti-Muellerian hormone type II receptor) (AMH type II receptor) (MIS type II receptor) (MISRII) (MRII); (563:) antioxidant enzyme AOE37-2 [*Homo sapiens*]; (564:) antioxidant enzyme B166 [*Homo sapiens*]; (565:) AP2-associated protein kinase 1 (Adaptor-associated kinase 1); (566:) APC11 anaphase promoting complex subunit 11 isoform 1 [*Homo sapiens*]; (567:) APC11 anaphase promoting complex subunit 11 isoform 2 [*Homo sapiens*]; (568:) Apelin receptor (G-protein coupled receptor APJ) (Angiotensin receptor-like 1) (HG11); (569:) APEX nuclease (multifunctional DNA repair enzyme) [*Homo sapiens*]; (570:) APEX nuclease (multifunctional DNA repair enzyme) 1 [*Homo sapiens*]; (571:) APG10 autophagy 10-like [*Homo sapiens*]; (572:) APG12 autophagy 12-like [*Homo sapiens*]; (573:) Apg3p [*Homo sapiens*]; (574:) APG4 autophagy 4 homolog B isoform a [*Homo sapiens*]; (575:) APG4 autophagy 4 homolog β isoform b [*Homo sapiens*]; (576:) APG5 autophagy 5-like [*Homo sapiens*]; (577:) APG7 autophagy 7-like [*Homo sapiens*]; (578:) APOBEC1 complementation factor (APOBEC1-stimulating protein); (579:) apobec-1 complementation factor isoform 1 [*Homo sapiens*]; (580:) apobec-1 complementation factor isoform 2 [*Homo sapiens*]; (581:) apobec-1 complementation factor isoform 3 [*Homo sapiens*]; (582:) APOBEC-1 stimulating protein [*Homo sapiens*]; (583:) Apolipoprotein A-I precursor (Apo-AI) (ApoA-I) [Contains:Apolipoprotein A-I (1-242)]; (584:) apolipoprotein A-II preproprotein [*Homo sapiens*]; (585:) apolipoprotein B mRNA editing enzyme [*Homo sapiens*]; (586:) apolipoprotein B mRNA editing enzyme catalytic polypeptide-like 3G[*Homo sapiens*]; (587:) apolipoprotein B mRNA editing enzyme complex-1 [*Homo sapiens*]; (588:) apolipoprotein B mRNA editing enzyme, catalytic polypeptide 1; (589:) apolipoprotein B mRNA editing enzyme, catalytic polypeptide-like 2 [*Homo sapiens*]; (590:) apolipoprotein B mRNA editing enzyme, catalytic polypeptide-like 2variant [*Homo sapiens*]; (591:) Apolipoprotein B mRNA editing enzyme, catalytic polypeptide-like 3A[*Homo sapiens*]; (592:) apolipoprotein B mRNA editing enzyme, catalytic polypeptide-like 3B[*Homo sapiens*]; (593:) apolipoprotein B mRNA editing enzyme, catalytic polypeptide-like 3C [*Homo sapiens*]; (594:) apolipoprotein B mRNA editing enzyme, catalytic polypeptide-like 3C variant [*Homo sapiens*]; (595:) apolipoprotein B mRNA editing enzyme, catalytic polypeptide-like 3D[*Homo sapiens*]; (596:) Apolipoprotein B mRNA editing enzyme, catalytic polypeptide-like 3F[*Homo sapiens*]; (597:) apolipoprotein B mRNA editing enzyme, catalytic polypeptide-like 3F isoform a [*Homo sapiens*]; (598:) apolipoprotein B mRNA editing enzyme, catalytic polypeptide-like 3F isoform b [*Homo sapiens*]; (599:) apolipoprotein B mRNA editing enzyme, catalytic polypeptide-like 3G[*Homo sapiens*]; (600:) Apolipoprotein B mRNA editing enzyme, catalytic polypeptide-like 3H[*Homo sapiens*]; (601:) apolipoprotein B mRNA editing enzyme, catalytic polypeptide-like 4(putative) [*Homo sapiens*]; (602:) apolipoprotein B precursor [*Homo sapiens*]; (603:) apolipoprotein C-II precursor [*Homo sapiens*]; (604:) apolipoprotein D precursor [*Homo sapiens*]; (605:) apolipoprotein E precursor [*Homo sapiens*]; (606:) apoptotic caspase Mch5-beta [*Homo sapiens*]; (607:) apoptotic cysteine protease Mch5 isoform alpha; (608:) apoptotic cysteine protease proMch4; (609:) aprataxin isoform a [*Homo sapiens*]; (610:) aprataxin isoform b [*Homo sapiens*]; (611:) aprataxin isoform c [*Homo sapiens*]; (612:) aprataxin isoform d [*Homo sapiens*]; (613:) apurinic/apyrimidinic endonuclease; (614:) aquaporin 12A [*Homo sapiens*]; (615:) arachidonate 12-lipoxygenase [*Homo sapiens*]; (616:) arachidonate 15-lipoxygenase [*Homo sapiens*]; (617:) arachidonate 5-lipoxygenase [*Homo sapiens*]; (618:) arachidonate 5-lipoxygenase-activating protein [*Homo sapiens*]; (619:) Archaemetzincin-1 (Archeobacterial metalloproteinase-like protein 1); (620:) Archaemetzincin-2 (Archeobacterial metalloproteinase-like protein2); (621:) arginase, type I [*Homo sapiens*]; (622:) Arginine decarboxylase (ARGDC) (ADC) (Ornithine decarboxylase-like protein) (ODC-paralogue) (ODC-p); (623:) arginine decarboxylase [*Homo sapiens*]; (624:) arginine methyltransferase 6 [*Homo sapiens*]; (625:) argininosuccinate lyase isoform 1 [*Homo sapiens*]; (626:) argininosuccinate lyase isoform 2 [*Homo sapiens*]; (627:) argininosuccinate lyase isoform 3 [*Homo sapiens*]; (628:) arginyl aminopeptidase (aminopeptidase B) [*Homo sapiens*]; (629:) arginyltransferase 1 isoform 1 [*Homo sapiens*]; (630:) arginyltransferase 1 isoform 2 [*Homo sapiens*]; (631:) Ariadne homolog, ubiquitin-conjugating enzyme E2 binding protein, 1(*Drosophila*) [*Homo sapiens*]; (632:) ariadne ubiquitin-conjugating enzyme E2 binding protein homolog 1 [*Homo sapiens*]; (633:) aromatase cytochrome P-450; (634:) aromatic decarboxylase [*Homo sapiens*]; (635:) Aromatic-L-amino-acid decarboxylase (MDC) (DOPA decarboxylase) (DDC); (636:) Arsenite methyltransferase (S-adenosyl-L-methionine:arsenic(III)methyltransferase) (Methylarsonite methyltransferase); (637:) Aryl hydrocarbon receptor precursor (Ah receptor) (AhR); (638:) Arylacetamide deacetylase (AADAC); (639:) arylalkylamine N-acetyltransferase [*Homo sapiens*]; (640:) arylamide acetylase 2 [*Homo sapiens*]; (641:) Arylamine N-acetyltransferase 1 (Arylamide acetylase 1) (Monomorphic arylamine N-acetyltransferase) (MNAT) (N-acetyltransferase type 1) (NAT-1); (642:) "Arylsulfatase A precursor (ASA) (Cerebroside-sulfatase) [Contains:Arylsulfatase A component B; Arylsulfatase A component C]."; (643:) arylsulfatase A precursor [*Homo sapiens*]; (644:) arylsulfatase β isoform 1 precursor [*Homo sapiens*]; (645:) arylsulfatase β isoform 2 precursor [*Homo sapiens*]; (646:) Arylsulfatase B precursor (ASB) (N-acetylgalactosamine-4-sulfatase) (G4S); (647:) Arylsulfatase E precursor (ASE); (648:) Arylsulfatase F precursor (ASF); (649:) Asialoglycoprotein receptor 1 (ASGPR 1) (ASGP-R1) (Hepatic lectin H1); (650:) Asialoglycoprotein receptor 2 (ASGP-R2) (ASGPR2) (Hepatic lectin H2); (651:) asparagine-linked glycosylation 12 [*Homo sapiens*]; (652:) aspartate aminotransferase 1 [*Homo sapiens*]; (653:) aspartate aminotransferase 2 precursor [*Homo sapiens*]; (654:) aspartoacylase [*Homo sapiens*]; (655:) aspartylglucosaminidase precursor [*Homo sapiens*]; (656:) aspartyl-tRNA synthetase [*Homo sapiens*]; (657:) Astacin-like metalloendopeptidase precursor (Oocyte astacin) (Ovastacin); (658:) ataxin 3 isoform 1 [*Homo sapiens*]; (659:) ataxin 3 isoform 2 [*Homo sapiens*]; (660:) ataxin 3 isoform 3 [*Homo sapiens*]; (661:) Ataxin-3 (Machado-Joseph disease protein 1) (Spinocerebellar ataxia type 3 protein); (662:) ATP citrate lyase isoform 1 [*Homo sapiens*]; (663:) ATP citrate lyase isoform 2 [*Homo sapiens*]; (664:) ATP specific succinyl CoA synthetase beta subunit precursor [*Homo sapiens*]; (665:) ATP sulfurylase/APS kinase [*Homo sapiens*]; (666:) ATP sulfurylase/APS kinase isoform SK2 [*Homo sapiens*]; (667:) ATP synthase mitochondrial F1 complex assembly factor 1 isoform 1 precursor [*Homo sapiens*]; (668:) ATP synthase mitochondrial F1 complex assembly factor 1 isoform 2 precursor [*Homo sapiens*]; (669:) ATP synthase mitochondrial F1 complex assembly factor 2 [*Homo sapiens*]; (670:) ATPase, Ca++ transporting, cardiac muscle, slow twitch 2 isoform 1 [*Homo sapiens*]; (671:) ATPase, Ca++ transporting, cardiac muscle, slow twitch 2 isoform 2 [*Homo sapiens*]; (672:) ATPase, Ca++ transporting, fast twitch 1 isoform a [*Homo sapiens*]; (673:) ATPase, Ca++transporting, fast twitch 1 isoform b [*Homo sapiens*]; (674:) ATPase, Cu++transporting, alpha polypeptide [*Homo sapiens*]; (675:) ATPase, Cu++transporting, beta polypeptide isoform a [*Homo sapiens*]; (676:) ATPase, Cu++ transporting, beta polypeptide isoform b [*Homo sapiens*]; (677:) ATPase, H+ transporting, lysosomal 14 kD, V1 subunit F [*Homo sapiens*]; (678:) ATPase, H+ transporting, lysosomal 21 kDa, V0 subunit b isoform 1 [*Homo sapiens*]; (679:) ATPase, H+ transporting, lysosomal 21 kDa, V0 subunit b isoform 2 [*Homo sapiens*]; (680:) ATPase, H+ transporting, lysosomal 42 kDa, V1 subunit C1 isoform A[*Homo sapiens*]; (681:) ATPase, H+ transporting, lysosomal 42 kDa, V1 subunit C1 isoform B[*Homo sapiens*]; (682:) ATPase, H+ transporting, lysosomal 50/57 kDa, V1 subunit H [*Homo sapiens*]; (683:) ATPase, H+ transporting, lysosomal 50/57 kDa, V1 subunit H isoform 1 [*Homo sapiens*]; (684:) ATPase, H+ transporting, lysosomal 50/57 kDa, V1 subunit H isoform 2 [*Homo sapiens*]; (685:) ATPase, H+ transporting, lysosomal 56/58 kDa, V1 subunit B1 [*Homo sapiens*]; (686:) ATPase, H+ transporting, lysosomal 70 kD, V1 subunit A, isoform 1 [*Homo sapiens*]; (687:) ATPase, H+ transporting, lysosomal 9 kDa, V0 subunit e1 [*Homo sapiens*]; (688:) ATPase, H+ transporting, lysosomal accessory protein 1 precursor[*Homo sapiens*]; (689:) ATPase, H+ transporting, lysosomal V0 subunit a isoform 1 [*Homo sapiens*]; (690:) ATPase, H+ transporting, lysosomal V0 subunit a4 [*Homo sapiens*]; (691:) ATPase, H+ transporting, lysosomal, V0 subunit c [*Homo sapiens*]; (692:) ATPase, H+ transporting, lysosomal, V0 subunit d1 [*Homo sapiens*]; (693:) ATPase, H+ transporting, lysosomal, V1 subunit G2 isoform a [*Homo sapiens*]; (694:) ATPase, H+ transporting, lysosomal, V1 subunit G2 isoform b [*Homo sapiens*]; (695:) ATPase, H+ transporting, lysosomal, V1 subunit G3 isoform a [*Homo sapiens*]; (696:) ATPase, H+ transporting, lysosomal, V1 subunit G3 isoform b [*Homo sapiens*]; (697:) ATPase, H+/K+ exchanging, alpha polypeptide [*Homo sapiens*]; (698:) ATPase, H+/K+ exchanging, beta polypeptide [*Homo sapiens*]; (699:) ATP-binding cassette sub-family B member 1 [*Homo sapiens*]; (700:) ATP-binding cassette transporter sub-family C member 8(Sulfonylurea receptor 1); (701:) ATP-binding cassette transporter sub-family C member 9(Sulfonylurea receptor 2); (702:) ATP-citrate synthase (ATP-citrate (pro-S-)-lyase) (Citrate cleavage enzyme); (703:) ATP-dependent DNA helicase 2 subunit 1 (ATP-dependent DNA helicaseII 70 kDa subunit) (Lupus Ku autoantigen protein p70) (Ku70) (70 kDa subunit of Ku antigen) (Thyroid-lupus autoantigen) (TLAA) (CTCbox-binding factor 75 kDa subunit) (CTCBF) (CTC75) (DNA-repair protein XRCC6); (704:) ATP-dependent DNA helicase 2 subunit 2 (ATP-dependent DNA helicaseII 80 kDa subunit) (Lupus Ku autoantigen protein p86) (Ku86) (Ku80) (86 kDa subunit of Ku antigen) (Thyroid-lupus autoantigen) (TLAA) (CTC box-binding factor 85 kDa subunit) (CTCBF) (CTC85) (Nuclear factor IV) (DNA-repair protein XRCC5); (705:) ATP-dependent DNA helicase II [*Homo sapiens*]; (706:) ATP-dependent DNA helicase 11, 70 kDa subunit [*Homo sapiens*]; (707:) Atrial natriuretic peptide clearance receptor precursor (ANP-C) (ANPRC) (NPR-C) (Atrial natriuretic peptide C-type receptor); (708:) Atrial natriuretic peptide receptor A precursor (AN P-A) (AN PRA) (GC-A) (Guanylate cyclase) (NPR-A) (Atrial natriuretic peptide A-type receptor); (709:) Atrial natriuretic peptide receptor B precursor (ANP-B) (ANPRB) (GC-B) (Guanylate cyclase B) (NPR-B) (Atrial natriuretic peptide B-type receptor); (710:) Atrial natriuteric peptide-converting enzyme (pro-ANP-converting enzyme) (Corin) (Heart-specific serine proteinase ATC2) (Transmembrane protease, serine 10); (711:) Attractin precursor (Mahogany homolog) (DPPT-L); (712:) AU RNA-binding protein/enoyl-Coenzyme A hydratase precursor [*Homo sapiens*]; (713:) Autocrine motility factor receptor precursor, isoform 1 (AMF receptor); (714:) Autocrine motility factor receptor, isoform 2 (AMF receptor) (gp78); (715:) autoimmune regulator AIRE isoform 1 [*Homo sapiens*]; (716:) autoimmune regulator AIRE isoform 2 [*Homo sapiens*]; (717:) Autophagy-related protein 10 (APG10-like); (718:) Autophagy-related protein 3 (APG3-like) (hApg3) (Protein PC3-96); (719:) Autophagy-related protein 7 (APG7-like) (Ubiquitin-activating enzyme E1-like protein) (hAGP7); (720:) autotaxin isoform 1 preproprotein [*Homo sapiens*]; (721:) autotaxin isoform 2 preproprotein [*Homo sapiens*]; (722:) Azurocidin precursor (Cationic antimicrobial protein CAP37) (Heparin-binding protein) (HBP); (723:) azurocidin, PUP=elastase homlog [human, Peptide Partial, 21 aa]; (724:) B- and T-lymphocyte attenuator precursor (B- and T-lymphocyte-associated protein) (CD272 antigen); (725:) B1 bradykinin receptor (BK-1 receptor) (B1R); (726:) B2 bradykinin receptor (BK-2 receptor) (B2R); (727:) B3GAT1 [*Homo sapiens*]; (728:) B3GAT2 [*Homo sapiens*]; (729:) B3GAT2 protein [*Homo sapiens*]; (730:) B3GAT3 protein [*Homo sapiens*]; (731:) baculoviral IAP repeat-containing 6 [*Homo sapiens*]; (732:) Baculoviral IAP repeat-containing protein 6 (Ubiquitin-conjugating BIR-domain enzyme apollon); (733:) Basic fibroblast growth factor receptor 1 precursor (FGFR-1) (bFGF-R) (Fms-like tyrosine kinase 2) (c-fgr) (CD331 antigen); (734:) BDNF/NT-3 growth factors receptor precursor (Neurotrophic tyrosine kinase receptor type 2) (TrkB tyrosine kinase) (GP145-TrkB) (Trk-B); (735:) beclin 1 [*Homo sapiens*]; (736:) beta adrenergic receptor kinase 1 [*Homo sapiens*]; (737:) beta adrenergic receptor kinase 2 [*Homo sapiens*]; (738:) beta amyloid cleaving enzyme 2 [*Homo sapiens*]; (739:) beta isoform of regulatory subunit A, protein phosphatase 2 isoform a [*Homo sapiens*]; (740:) beta isoform of regulatory subunit A, protein phosphatase 2 isoform b [*Homo sapiens*]; (741:) beta isoform of regulatory subunit B55, protein phosphatase 2 isoform a [*Homo sapiens*]; (742:) beta isoform of regulatory subunit B55, protein phosphatase 2 isoform b [*Homo sapiens*]; (743:) beta isoform of regulatory subunit B55, protein phosphatase 2 isoform c [*Homo sapiens*]; (744:) beta isoform of regulatory subunit B55, protein phosphatase 2 isoform d [*Homo sapiens*]; (745:) beta isoform of regulatory subunit B56, protein phosphatase 2A[*Homo sapiens*]; (746:) Beta klotho (BetaKlotho) (Klotho beta-like protein); (747:) Beta platelet-derived growth factor receptor precursor (PDGF-R-beta) (CD140b antigen); (748:) beta(1,6)-N-acetylglucosaminyltransferase V isoform 1 [*Homo sapiens*]; (749:) beta(1,6)-N-acetylglucosaminyltransferase V isoform 2 [*Homo sapiens*]; (750:) Beta,beta-carotene 9',10'-dioxygenase (Beta-carotene dioxygenase 2) (B-diox-II); (751:) Beta-1 adrenergic receptor (Beta-1 adrenoceptor) (Beta-1adrenoreceptor); (752:) beta-1,3 galactosyltransferase-V [*Homo sapiens*]; (753:) Beta-1,3-galactosyl-O-glycosyl-glycoprotein beta-1,6-N-acetylglucosaminyltransferase (Core 2 branching enzyme) (Core2-GlcNAc-transferase) (C2GNT) (Core 2 GNT); (754:) beta-1,3-galactosyl-O-glycosyl-glycoprotein beta-1,6-N-acetylglucosaminyltransferase [*Homo sapiens*]; (755:) beta-1,3-galactosyltransferase [*Homo sapiens*]; (756:) Beta-1,3-galactosyltransferase 5 (Beta-1,3-GalTase 5) (Beta3Gal-T5) (b3Gal-T5) (UDP-galactose:beta-N-acetylglucosamine beta-1,3-galactosyltransferase 5) (UDP-Gal:beta-GlcNAcbeta-1,3-galactosyltransferase 5) (Beta-3-

Gx-T5); (757:) Beta-1,3-glucosyltransferase (Beta3Glc-T) (Beta-3-glycosyltransferase-like); (758:) Beta-1,3-glucuronyltransferase 1 (glucuronosyltransferase P) [Homo sapiens]; (759:) beta-1,3-glucuronyltransferase 1 [Homo sapiens]; (760:) Beta-1,3-glucuronyltransferase 3 (glucuronosyltransferase 1) [Homo sapiens]; (761:) beta-1,3-glucuronyltransferase 3 [Homo sapiens]; (762:) beta1,3-N-acetylglucosaminyltransferase 5 [Homo sapiens]; (763:) beta-1,3-N-acetylglucosaminyltransferase 6 [Homo sapiens]; (764:) "Beta-1,4-galactosyltransferase 1 (Beta-1,4-GalTase 1) (Beta4Gal-T1) (b4Gal-T1) (UDP-galactose:beta-N-acetylglucosamine beta-1,4-galactosyltransferase 1) (UDP-Gal:beta-GlcNAcbeta-1,4-galactosyltransferase 1) [Includes:] Lactose synthase Aprotein; N-acetyllactosamine synthase (NaI synthetase); Beta-N-acetylglucosaminylglycopeptide beta-1,4-galactosyltransferase; Beta-N-acetylglucosaminyl-glycolipid beta-1,4-galactosyltransferase]."; (765:) Beta-1,4-galactosyltransferase 6 (Beta-1,4-GalTase 6) (Beta4Gal-T6) (b4Gal-T6) (UDP-galactose:beta-N-acetylglucosamine beta-1,4-galactosyltransferase 6) (UDP-Gal:beta-GlcNAcbeta-1,4-galactosyltransferase 6) [Includes:) Lactosylceramidesynthase (LacCer synthase) (UDP-Gal:glucosylceramide beta-1,4-galactosyltransferase)]; (766:) beta-1,4-N-acethylgalactosaminyltransferase [Homo sapiens]; (767:) beta-1,4-N-acetyl-galactosaminyl transferase 1 [Homo sapiens]; (768:) beta-1,6-N-acetylglucosaminyltransferase [Homo sapiens]; (769:) beta-1,6-N-acetylglucosaminyltransferase 2 [Homo sapiens]; (770:) beta-1,6-N-acetylglucosaminyltransferase 3 [Homo sapiens]; (771:) beta-1,6-N-acetylglucosaminyltransferase; (772:) Beta-2 adrenergic receptor (Beta-2 adrenoceptor) (Beta-2adrenoreceptor); (773:) Beta-3 adrenergic receptor (Beta-3 adrenoceptor) (Beta-3adrenoreceptor); (774:) beta-adrenergic-receptor kinase (EC 2.7.1.126) 2—human; (775:) Beta-Ala-His dipeptidase precursor (Carnosine dipeptidase 1) (CNDP dipeptidase 1) (Serum carnosinase) (Glutamate carboxypeptidase-like protein 2); (776:) beta-carotene 15,15'-monooxygenase 1 [Homo sapiens]; (777:) beta-carotene dioxygenase 2 isoform a [Homo sapiens]; (778:) beta-carotene dioxygenase 2 isoform b [Homo sapiens]; (779:) beta-D-galactosidase precursor (EC 3.2.1.23); (780:) Beta-galactosidase precursor (Lactase) (Acid beta-galactosidase); (781:) beta-galactosidase related protein precursor; (782:) Beta-galactosidase-related protein precursor (Beta-galactosidase-like protein) (S-Gal) (Elastin-binding protein) (EBP); (783:) Beta-hexosaminidase alpha chain precursor (N-acetyl-beta-glucosaminidase) (Beta-N-acetyl-hexosaminidase) (Hexosaminidase A); (784:) "Beta-hexosaminidase beta chain precursor (N-acetyl-beta-glucosaminidase) (Beta-N-acetylhexosaminidase) (Hexosaminidase B) (Cervical cancer proto-oncogene 7) (HCC-7)[Contains:) Beta-hexosaminidase beta-B chain; Beta-hexosaminidase beta-A chain]."; (785:) beta-hexosaminidase beta-chain {R to Q substitution at residue 505, internal fragment} {EC 3.2.1.53} [human, skin fibroblasts, Peptide Partial Mutant, 23 aa]; (786:) betaine-homocysteine methyltransferase [Homo sapiens]; (787:) beta-mannosidase [Homo sapiens]; (788:) beta-polymerase; (789:) Beta-secretase 1 precursor (Beta-site APP cleaving enzyme 1) (Beta-site amyloid precursor protein cleaving enzyme 1) (Membrane-associated aspartic protease 2) (Memapsin-2) (Aspartyl protease 2) (Asp 2) (ASP2); (790:) Beta-secretase 2 precursor (Beta-site APP-cleaving enzyme 2) (Aspartyl protease 1) (Asp 1) (ASP1) (Membrane-associated aspartic protease 1) (Memapsin-1) (Down region aspartic protease); (791:) beta-site APP cleaving enzyme [Homo sapiens]; (792:) beta-site APP cleaving enzyme 1-432 [Homo sapiens]; (793:) beta-site APP cleaving enzyme 1-457 [Homo sapiens]; (794:) beta-site APP cleaving enzyme 1-476 [Homo sapiens]; (795:) beta-site APP cleaving enzyme isoform 1-127 [Homo sapiens]; (796:) beta-site APP cleaving enzyme type B [Homo sapiens]; (797:) beta-site APP cleaving enzyme type C [Homo sapiens]; (798:) beta-site APP-cleaving enzyme [Homo sapiens]; (799:) Beta-site APP-cleaving enzyme 1 [Homo sapiens]; (800:) beta-site APP-cleaving enzyme 1 isoform A preproprotein [Homo sapiens]; (801:) beta-site APP-cleaving enzyme 1 isoform B preproprotein [Homo sapiens]; (802:) beta-site APP-cleaving enzyme 1 isoform C preproprotein [Homo sapiens]; (803:) beta-site APP-cleaving enzyme 1 isoform D preproprotein [Homo sapiens]; (804:) Beta-site APP-cleaving enzyme 2 [Homo sapiens]; (805:) beta-site APP-cleaving enzyme 2 isoform A preproprotein [Homo sapiens]; (806:) beta-site APP-cleaving enzyme 2 isoform B preproprotein [Homo sapiens]; (807:) beta-site APP-cleaving enzyme 2 isoform C preproprotein [Homo sapiens]; (808:) beta-site APP-cleaving enzyme 2, EC 3.4.23. [Homo sapiens]; (809:) beta-synuclein [Homo sapiens]; (810:) Beta-ureidopropionase (Beta-alanine synthase) (N-carbamoyl-beta-alanine amidohydrolase) (BUP-1); (811:) "Bifunctional 3'-phosphoadenosine 5'-phosphosulfate synthetase 1(PAPS synthetase 1) (PAPSS1) (Sulfurylase kinase 1) (SK1) (SK 1)[Includes:] Sulfate adenylyltransferase (Sulfate adenylatetransferase) (SAT) (ATP-sulfurylase); Adenylyl-sulfate kinase (Adenylylsulfate 3'-phosphotransferase) (APS kinase) (Adenosine-5'-phosphosulfate 3'-phosphotransferase) (3'-phosphoadenosine-5'-phosphosulfate synthetase)]."; (812:) "Bifunctional 3'-phosphoadenosine 5'-phosphosulfate synthetase 2(PAPS synthetase 2) (PAPSS 2) (Sulfurylase kinase 2) (SK2) (SK 2)[Includes:] Sulfate adenylyltransferase (Sulfate adenylatetransferase) (SAT) (ATP-sulfurylase); Adenylyl-sulfate kinase (Adenylylsulfate 3'-phosphotransferase) (APS kinase) (Adenosine-5'-phosphosulfate 3'-phosphotransferase) (3'-phosphoadenosine-5'-phosphosulfate synthetase)]."; (813:) bifunctional ATP sulfurylase/adenosine 5'-phosphosulfate kinase [Homo sapiens]; (814:) "Bifunctional coenzyme A synthase (CoA synthase) (NBP) (POV-2)[Includes:) Phosphopantetheine adenylyltransferase (Pantetheine-phosphate adenylyltransferase) (PPAT) (Dephospho-CoA pyrophosphorylase); Dephospho-CoA kinase (DPCK) (Dephospho coenzyme A kinase) (DPCOAK)]."; (815:) "Bifunctional heparan sulfate N-deacetylase/N-sulfotransferase 1(Glucosaminyl N-deacetylase/N-sulfotransferase 1) (NDST-1) ([Heparan sulfate]-glucosamine N-sulfotransferase 1) (HSNST1) (N-heparan sulfate sulfotransferase 1) (N-HSST 1) [Includes:Heparan sulfate N-deacetylase 1; Heparan sulfate N-sulfotransferase 1]."; (816:) "Bifunctional heparan sulfate N-deacetylase/N-sulfotransferase 2(Glucosaminyl N-deacetylase/N-sulfotransferase 2) (NDST-2) (N-heparan sulfate sulfotransferase 2) (N-HSST 2) [Includes:Heparan sulfate N-deacetylase 2; Heparan sulfate N-sulfotransferase 2]."; (817:) "Bifunctional heparan sulfate N-deacetylase/N-sulfotransferase 3(Glucosaminyl N-deacetylase/N-sulfotransferase 3) (NDST-3) (hNDST-3) (N-heparan sulfate sulfotransferase 3) (N-HSST 3)[Includes:) Heparan sulfate N-deacetylase 3; Heparan sulfate N-sulfotransferase 3]."; (818:) "Bifunctional heparan sulfate N-deacetylase/N-sulfotransferase 4(Glucosaminyl N-deacetylase/N-sulfotransferase 4) (NDST-4) (N-heparan sulfate sulfotransferase 4) (N-HSST 4) [Includes:Heparan sulfate N-deacetylase 4; Heparan sulfate N-sulfotransferase 4]."; (819:) "Bifunctional methylenetetrahydrofolate dehydrogenase/cyclohydrolase, mitochondrial precursor [Includes: NAD-dependent methylenetetrahydrofolate dehydrogenase; Methenyltetrahydrofolate cyclohydrolase]."; (820:) bifunctional phosphopantetheine adenylyl transferase/dephospho CoA kinase [Homo sapiens]; (821:) "Bifunctional protein NCOAT (Nuclear cytoplasmic O-GlcNAcase and acetyltransferase) (Meningioma-expressed antigen 5) [Includes:Beta-hexosaminidase (N-acetyl-beta-glucosaminidase) (Beta-N-acetylhexosaminidase) (Hexosaminidase C) (N-acetyl-beta-D-glucosaminidase) (O-GlcNAcase); Histoneacetyltransferase (HAT)]."; (822:) "Bifunctional UDP-N-acetylglucosamine-2-epimerase/N-acetylmannosamine kinase (UDP-GlcNAc-2-epimerase/ManAc kinase) [Includes:UDP-N-acetylglucosamine 2-epimerase (Uridine diphosphate-N-acetylglucosamine-2-epimerase) (UDP-GlcNAc-2-epimerase); N-acetylmannosamine kinase (ManAckinase)]."; (823:) bile acid beta-glucosidase [Homo sapiens]; (824:) bile acid CoA:) Amino acid N-acyltransferase; (825:) Bile acid CoA:amino acid N-acyltransferase (BAT) (BACAT) (Glycine N-choloyltransferase) (Long-chain fatty-acyl-CoA hydrolase); (826:) bile acid Coenzyme A:) amino acid N-acyltransferase [Homo sapiens]; (827:) Bile acid receptor (Farnesoid X-activated receptor) (Farnesol receptor HRR-1) (Retinoid X receptor-interacting protein 14) (RXR-interacting protein 14); (828:) Bile acyl-CoA synthetase (BACS) (Bile acid CoA ligase) (BA-CoA ligase) (BAL) (Cholate-CoA ligase) (Very long-chain acyl-CoA synthetase homolog 2) (VLCSH2) (VLCS-H2) (Very long chain acyl-CoA synthetase-related protein) (VLACS-related) (VLACSR) (Fatty-acid-coenzyme A ligase, very long-chain 3) (Fatty acid transport protein 5) (FATP-5) (Solute carrier family 27 member 5); (829:) Bile salt sulfotransferase (Hydroxysteroid Sulfotransferase) (HST) (Dehydroepiandrosterone sulfotransferase) (DHEA-ST) (ST2) (ST2A3); (830:) Bile salt-activated lipase precursor (BAL) (Bile salt-stimulated lipase) (BSSL) (Carboxyl ester lipase) (Sterol esterase) (Cholesterol esterase) (Pancreatic lysophospholipase); (831:) biliverdin reductase B (flavin reductase (NADPH)) [Homo sapiens]; (832:) biphenyl hydrolase-like [Homo sapiens]; (833:) Bis(5'-adenosyl)-triphosphatase (Diadenosine-5',5"-P1,P3-triphosphate hydrolase) (Dinucleosidetriphosphatase) (AP3A hydrolase) (AP3AASE) (Fragile histidine triad protein); (834:) BK158_1 (OTTHUMP00000040718) variant [Homo sapiens]; (835:) BK158_1 [Homo sapiens]; (836:) bleomycin hydrolase [Homo sapiens]; (837:) Blue-sensitive opsin (BOP) (Blue cone photoreceptor pigment); (838:) Bombesin receptor subtype-3 (BRS-3); (839:) bone morphogenetic protein 1 isoform 1, precursor [Homo sapiens]; (840:) bone morphogenetic protein 1 isoform 2, precursor [Homo sapiens]; (841:) bone morphogenetic protein 1 isoform 3, precursor [Homo sapiens]; (842:) Bone morphogenetic protein 1 precursor (BMP-1) (Procollagen C-proteinase) (PCP) (Mammalian tolloid protein) (mTld); (843:) Bone morphogenetic protein receptor type IA precursor (Serine/threonine-protein kinase receptor R5) (SKR5) (Activin receptor-like kinase 3) (ALK-3) (CD292 antigen); (844:) Bone morphogenetic protein receptor type IB precursor (CDw293antigen); (845:) Bone morphogenetic protein receptor type-2 precursor (Bone morphogenetic protein receptor type II) (BMP type II receptor) (BMPR-II); (846:) bradykinin receptor B1 [Homo sapiens]; (847:) bradykinin receptor B2 [Homo sapiens]; (848:) brain creatine kinase [Homo sapiens]; (849:) brain glycogen phosphorylase [Homo sapiens]; (850:) brain-derived neurotrophic factor isoform a preproprotein [Homo sapiens]; (851:) brain-derived neurotrophic factor isoform b preproprotein [Homo sapiens]; (852:) brain-derived neurotrophic factor isoform c preproprotein [Homo sapiens]; (853:) Brain-specific angiogenesis inhibitor 1 precursor; (854:) Brain-specific angiogenesis inhibitor 2 precursor; (855:) Brain-specific angiogenesis inhibitor 3 precursor; (856:) branched chain acyltransferase precursor; (857:) branched chain aminotransferase 1, cytosolic [Homo sapiens]; (858:) branched chain aminotransferase 2, mitochondrial [Homo sapiens]; (859:) branched chain keto acid dehydrogenase E1, alpha polypeptide [Homo sapiens]; (860:) branching-enzyme interacting dual-specificity protein phosphatase BEDP [Homo sapiens]; (861:) Breast cancer type 1 susceptibility protein (RING finger protein53); (862:) Brefeldin A-inhibited guanine nucleotide-exchange protein 1(Brefeldin A-inhibited GEP 1) (p200 ARF-GEP1) (p200 ARF guanine nucleotide exchange factor); (863:) Brefeldin A-inhibited guanine nucleotide-exchange protein 2(Brefeldin A-inhibited GEP 2); (864:) bubblegum related protein [Homo sapiens]; (865:) butyrylcholinesterase precursor [Homo sapiens]; (866:) C→U-editing enzyme APOBEC-1 (Apolipoprotein B mRNA-editing enzyme1) (HEPR); (867:) C1 esterase inhibitor [Homo sapiens]; (868:) C10orf129 protein [Homo sapiens]; (869:) C1GALT1-specific chaperone 1 [Homo sapiens]; (870:) C1-tetrahydrofolate synthase [Homo sapiens]; (871:) "C-1-tetrahydrofolate synthase, cytoplasmic (C1-THF synthase)[Includes:) Methylenetetrahydrofolate dehydrogenase; Methenyltetrahydrofolate cyclohydrolase; Formyltetrahydrofolatesynthetase]."; (872:) C3a anaphylatoxin chemotactic receptor (C3a-R) (C3AR); (873:) C5a anaphylatoxin chemotactic receptor (C5a-R) (C5aR) (CD88antigen); (874:) C5a anaphylatoxin chemotactic receptor C5L2 (G-protein coupled receptor 77); (875:) C9orf3 protein [Homo sapiens]; (876:) C9orf95 protein [Homo sapiens]; (877:) Ca2+/calmodulin-dependent protein kinase (EC 2.7.1.123) II gamma chain, splice form B—human; (878:) Ca2+/calmodulin-dependent protein kinase kinase beta-3 [Homo sapiens]; (879:) CAD protein [Homo sapiens]; (880:) cadherin 1, type 1 preproprotein [Homo sapiens]; (881:) Cadherin EGF LAG seven-pass G-type receptor 1 precursor (Flamingo homolog 2) (hFmi2); (882:) Cadherin EGF LAG seven-pass G-type receptor 2 precursor (Epidermal growth factor-like 2) (Multiple epidermal growth factor-like domains 3) (Flamingo 1); (883:) Cadherin EGF LAG seven-pass G-type receptor 3 precursor (Flamingo homolog 1) (hFmi1) (Multiple epidermal growth factor-like domains2) (Epidermal growth factor-like 1); (884:) Calcitonin gene-related peptide type 1 receptor precursor (CGRP type 1 receptor) (Calcitonin receptor-like receptor); (885:) calcitonin gene-related peptide-receptor component protein isoform a [Homo sapiens]; (886:) calcitonin gene-related peptide-receptor component protein isoform b [Homo sapiens]; (887:) calcitonin gene-related peptide-receptor component protein isoform c [Homo sapiens]; (888:) Calcitonin receptor precursor (CT-R); (889:) calcium activated nucleotidase 1 [Homo sapiens]; (890:) calcium receptor (clone phPCaR-4.0)—human; (891:) calcium receptor (clone phPCaR-5.2)—human; (892:) Calcium/calmodulin-dependent 3',5'-cyclic nucleotide phosphodiesterase 1A (Cam-PDE1A) (61 kDa Cam-PDE) (hCam-1); (893:) Calcium/calmodulin-dependent 3',5'-cyclic nucleotide phosphodiesterase 1B (Cam-PDE 1B) (63 kDa Cam-PDE); (894:) Calcium/calmodulin-dependent 3',5'-cyclic nucleotide phosphodiesterase 1C (Cam-PDE 1C) (hCam-3); (895:) calcium/calmodulin-dependent protein kinase I [Homo sapiens]; (896:) calcium/calmodulin-dependent protein kinase II delta isoform 1 [Homo sapiens]; (897:) calcium/calmodulin-dependent protein kinase II delta isoform 2 [Homo sapiens]; (898:) calcium/calmodulin-dependent protein kinase II delta isoform 3 [Homo sapiens]; (899:)

calcium/calmodulin-dependent protein kinase II gamma isoform 1 [*Homo sapiens*]; (900:) calcium/calmodulin-dependent protein kinase II gamma isoform 2 [*Homo sapiens*]; (901:) calcium/calmodulin-dependent protein kinase II gamma isoform 3 [*Homo sapiens*]; (902:) calcium/calmodulin-dependent protein kinase II gamma isoform 4 [*Homo sapiens*]; (903:) calcium/calmodulin-dependent protein kinase II gamma isoform 5 [*Homo sapiens*]; (904:) calcium/calmodulin-dependent protein kinase II gamma isoform 6 [*Homo sapiens*]; (905:) calcium/calmodulin-dependent protein kinase IIA isoform 1 [*Homo sapiens*]; (906:) calcium/calmodulin-dependent protein kinase IIA isoform 2 [*Homo sapiens*]; (907:) calcium/calmodulin-dependent protein kinase IIB isoform 1 [*Homo sapiens*]; (908:) calcium/calmodulin-dependent protein kinase IIB isoform 2 [*Homo sapiens*]; (909:) calcium/calmodulin-dependent protein kinase IIB isoform 3 [*Homo sapiens*]; (910:) calcium/calmodulin-dependent protein kinase IIB isoform 4 [*Homo sapiens*]; (911:) calcium/calmodulin-dependent protein kinase IIB isoform 5 [*Homo sapiens*]; (912:) calcium/calmodulin-dependent protein kinase IIB isoform 6 [*Homo sapiens*]; (913:) calcium/calmodulin-dependent protein kinase IIB isoform 7 [*Homo sapiens*]; (914:) calcium/calmodulin-dependent protein kinase IIB isoform 8 [*Homo sapiens*]; (915:) calcium/calmodulin-dependent protein kinase IV [*Homo sapiens*]; (916:) Calcium/calmodulin-dependent protein kinase kinase 1(Calcium/calmodulin-dependent protein kinase kinase alpha) (CaM-kinase kinase alpha) (CaM-KK alpha) (CaMKK alpha) (CaMKK 1) (CaM-kinase IV kinase); (917:) Calcium/calmodulin-dependent protein kinase kinase 2(Calcium/calmodulin-dependent protein kinase kinase beta) (CaM-kinase kinase beta) (CaM-KK beta) (CaMKK beta); (918:) Calcium/calmodulin-dependent protein kinase type 1 (CaM kinase I) (CaM-KI) (CaM kinase 1 alpha) (CaMKI-alpha); (919:) Calcium/calmodulin-dependent protein kinase type 1B (CaM kinase IB) (CaM kinase 1 beta) (CaMKI-beta) (CaM-KI beta) (Pregnancyup-regulated nonubiquitously expressed CaM kinase); (920:) Calcium/calmodulin-dependent protein kinase type 1D (CaM kinase ID) (CaM kinase I delta) (CaMKI-delta) (CaM-KI delta) (CaMKI delta) (Camk1D) (CamKI-like protein kinase) (CKLiK); (921:) Calcium/calmodulin-dependent protein kinase type 1G (CaM kinase IG) (CaM kinase I gamma) (CaMKI gamma) (CaMKI-gamma) (CaM-KI gamma) (CaMKIG) (CaMK-like CREB kinase III) (CLICK III); (922:) Calcium/calmodulin-dependent protein kinase type II alpha chain (CaM-kinase II alpha chain) (CaM kinase II alpha subunit) (CaMK-II subunit alpha); (923:) Calcium/calmodulin-dependent protein kinase type II beta chain (CaM-kinase II beta chain) (CaM kinase II subunit beta) (CaMK-II subunit beta); (924:) Calcium/calmodulin-dependent protein kinase type II delta chain (CaM-kinase II delta chain) (CaM kinase II subunit delta) (CaMK-II subunit delta); (925:) Calcium/calmodulin-dependent protein kinase type II gamma chain (CaM-kinase II gamma chain) (CaM kinase II gamma subunit) (CaMK-II subunit gamma); (926:) Calcium/calmodulin-dependent protein kinase type IV (CAM kinase-GR) (CaMK IV); (927:) Calcium-dependent phospholipase A2 precursor (Phosphatidylcholine-2-acylhydrolase) (PLA2-10) (Group V phospholipase A2); (928:) calcium-independent phospholipase A2 [*Homo sapiens*]; (929:) calcium-sensing receptor [*Homo sapiens*]; (930:) calcium-transporting ATPase 2C1 isoform 1a [*Homo sapiens*]; (931:) calcium-transporting ATPase 2C1 isoform 1b [*Homo sapiens*]; (932:) calcium-transporting ATPase 2C1 isoform 1c [*Homo sapiens*]; (933:) calcium-transporting ATPase 2C1 isoform 1d [*Homo sapiens*]; (934:) Calcium-transporting ATPase type 2C member I (ATPase 2C1) (ATP-dependent Ca(2+) pump PMR1); (935:) Calmodulin (Vertebrate); (936:) calmodulin-like skin protein [*Homo sapiens*]; (937:) calnexin precursor [*Homo sapiens*]; (938:) calpain [*Homo sapiens*]; (939:) calpain 1, large subunit [*Homo sapiens*]; (940:) calpain 2, large subunit [*Homo sapiens*]; (941:) calpain 3 isoform a [*Homo sapiens*]; (942:) calpain 3 isoform b [*Homo sapiens*]; (943:) calpain 3 isoform c [*Homo sapiens*]; (944:) calpain 3 isoform d [*Homo sapiens*]; (945:) calpain 3 isoform e [*Homo sapiens*]; (946:) calpain 3 isoform f [*Homo sapiens*]; (947:) calpain 3 isoform g [*Homo sapiens*]; (948:) calpain 3 isoform h [*Homo sapiens*]; (949:) Calpain-1 catalytic subunit (Calpain-1 large subunit) (Calcium-activated neutral proteinase 1) (CANP1) (Calpain mu-type) (muCANP) (Micromolar-calpain); (950:) Calpain-2 catalytic subunit precursor (Calpain-2 large subunit) (Calcium-activated neutral proteinase 2) (CANP 2) (Calpain M-type) (M-calpain) (Millimolar-calpain) (Calpain large polypeptide L2); (951:) Calpain-3 (Calpain L3) (Calpain p94) (Calcium-activated neutral proteinase 3) (CANP 3) (Muscle-specific calcium-activated neutral protease 3) (nCL-1); (952:) C-alpha-formyglycine-generating enzyme [*Homo sapiens*]; (953:) cAMP and cAMP-inhibited cGMP 3',5'-cyclic phosphodiesterase 10A; (954:) cAMP responsive element binding protein 3 [*Homo sapiens*]; (955:) cAMP-dependent protein kinase catalytic subunit alpha isoform 1 [*Homo sapiens*]; (956:) cAMP-dependent protein kinase catalytic subunit alpha isoform 2 [*Homo sapiens*]; (957:) cAMP-dependent protein kinase inhibitor alpha (PKI-alpha) (cAMP-dependent protein kinase inhibitor, muscle/brain isoform); (958:) cAMP-dependent protein kinase inhibitor beta (PKI-beta); (959:) cAMP-dependent protein kinase inhibitor gamma (PKI-gamma); (960:) cAMP-dependent protein kinase type I-alpha regulatory subunit (Tissue-specific extinguisher 1) (TSE1); (961:) cAMP-dependent protein kinase type 1-beta regulatory subunit; (962:) cAMP-dependent protein kinase type 11-alpha regulatory subunit; (963:) cAMP-dependent protein kinase type II-beta regulatory subunit; (964:) cAMP-dependent protein kinase, alpha-catalytic subunit (PKAC-alpha); (965:) cAMP-dependent protein kinase, beta-catalytic subunit (PKA C-beta); (966:) cAMP-dependent protein kinase, gamma-catalytic subunit (PKAC-gamma); (967:) cAMP-specific 3',5'-cyclic phosphodiesterase 4A (DPDE2) (PDE46); (968:) cAMP-specific 3',5'-cyclic phosphodiesterase 4B (DPDE4) (PDE32); (969:) cAMP-specific 3',5'-cyclic phosphodiesterase 4C (DPDE1) (PDE21); (970:) cAMP-specific 3',5'-cyclic phosphodiesterase 4D (DPDE3) (PDE43); (971:) cAMP-specific 3',5'-cyclic phosphodiesterase 7B; (972:) cAMP-specific phosphodiesterase 4D [*Homo sapiens*]; (973:) Cannabinoid receptor 1 (CB1) (CB-R) (CANN6); (974:) Cannabinoid receptor 2 (CB2) (CB-2) (CX5); (975:) CAP10-like 46 kDa protein precursor (Myelodysplastic syndromes relative protein); (976:) capping enzyme 1 [*Homo sapiens*]; (977:) capping enzyme IA [*Homo sapiens*]; (978:) capping enzyme 1B [*Homo sapiens*]; (979:) Carbamoyl-phosphate synthase [ammonia], mitochondrial precursor (Carbamoyl-phosphate synthetase 1) (CPSase I); (980:) carbamoyl-phosphate synthetase 1, mitochondrial [*Homo sapiens*]; (981:) Carbamoyl-phosphate synthetase 2, aspartate transcarbamylase, and dihydroorotase [*Homo sapiens*]; (982:) carbamoylphosphate synthetase 2/aspartate transcarbamylase/dihydroorotase [*Homo sapiens*]; (983:) carbohydrate (N-acetylglucosamine 6-O) sulfotransferase 6 [*Homo sapiens*]; (984:) carbohydrate (N-acetylglucosamine 6-O) sulfotransferase 7 [*Homo sapiens*]; (985:) carbohydrate (N-acetylglucosamine-6-O) sulfotransferase 2 [*Homo sapiens*]; (986:) Carbohydrate sulfotransferase 10 (HNK-1 sulfotransferase) (HNK1ST) (HNK-1ST) (huHNK-1ST); (987:) Carbohydrate sulfotransferase 11 (Chondroitin 4-O-sulfotransferase 1) (Chondroitin 4-sulfotransferase 1) (C4ST) (C4ST-1) (C4ST); (988:) Carbohydrate sulfotransferase 12 (Chondroitin 4-O-sulfotransferase 2) (Chondroitin 4-sulfotransferase 2) (C4ST2) (C4ST-2) (Sulfotransferase Hlo); (989:) Carbohydrate sulfotransferase 13 (Chondroitin 4-O-sulfotransferase 3) (Chondroitin 4-sulfotransferase 3) (C4ST3) (C4ST-3); (990:) Carbohydrate sulfotransferase 2 (N-acetylglucosamine-6-O-sulfotransferase 1) (GlcNAc6ST-1) (Gn6ST) (Galactose/N-acetylglucosamine/N-acetylglucosamine-6-O-sulfotransferase 2) (GST-2); (991:) Carbohydrate sulfotransferase 3 (Chondroitin 6-sulfotransferase) (Chondroitin 6-O-sulfotransferase 1) (C6ST-1) (C6ST) (Galactose/N-acetylglucosamine/N-acetylglucosamine-6-O-sulfotransferase 0) (GST-0); (992:) Carbohydrate sulfotransferase 4 (N-acetylglucosamine-6-O-sulfotransferase 2) (GlcNAc6ST-2) (High endothelial cells N-acetylglucosamine 6-O-sulfotransferase) (HEC-GlcNAc6ST) (L-selectin ligand sulfotransferase) (LSST) (Galactose/N-acetylglucosamine/N-acetylglucosamine-6-O-sulfotransferase 3) (GST-3); (993:) Carbohydrate sulfotransferase 7 (Chondroitin 6-sulfotransferase 2) (C6ST-2) (N-acetylglucosamine 6-O-sulfotransferase 1) (GlcNAc6ST-4) (Galactose/N-acetylglucosamine/N-acetylglucosamine-6-O-sulfotransferase 5) (GST-5); (994:) Carbohydrate sulfotransferase 8(N-acetylgalactosamine-4-O-sulfotransferase 1) (GalNAc-4-O-sulfotransferase 1) (GalNAc-4-ST1) (GalNAc4ST-1); (995:) Carbohydrate sulfotransferase 9(N-acetylgalactosamine-4-O-sulfotransferase 2) (GalNAc-4-O-sulfotransferase 2) (GalNAc-4-ST2); (996:) Carbohydrate sulfotransferase D4ST1 (Dermatan 4-sulfotransferase 1) (D4ST-1) (hD4ST); (997:) Carbonic anhydrase 12 precursor (Carbonic anhydrase XII) (Carbonate dehydratase XII) (CA-XII) (Tumor antigen HOM-RCC-3.1.3); (998:) Carbonic anhydrase 4 precursor (Carbonic anhydrase IV) (Carbonate dehydratase IV) (CA-IV); (999:) Carbonic Anhydrase I (E.C.4.2.1.1) Complexed With Bicarbonate; (1000:) carbonic anhydrase I [Homo sapiens]; (1001:) carbonic anhydrase 11 [Homo sapiens]; (1002:) carbonic anhydrase IV precursor [Homo sapiens]; (1003:) carbonic anhydrase IX precursor [Homo sapiens]; (1004:) carbonic anhydrase VIII [Homo sapiens]; (1005:) carbonyl reductase 1 [Homo sapiens]; (1006:) carbonyl reductase 3 [Homo sapiens]; (1007:) carboxyl ester lipase precursor [Homo sapiens]; (1008:) carboxylesterase 1 isoform a precursor [Homo sapiens]; (1009:) carboxylesterase 1 isoform b precursor [Homo sapiens]; (1010:) carboxylesterase 1 isoform c precursor [Homo sapiens]; (1011:) carboxylesterase 2 isoform 1 [Homo sapiens]; (1012:) carboxylesterase 2 isoform 2 [Homo sapiens]; (1013:) carboxylesterase; (1014:) carboxypeptidase A2 (pancreatic) [Homo sapiens]; (1015:) carboxypeptidase A4 preproprotein [Homo sapiens]; (1016:) carboxypeptidase A5 [Homo sapiens]; (1017:) carboxypeptidase B precursor [Homo sapiens]; (1018:) Carboxypeptidase D precursor (Metallocarboxypeptidase D) (gp180); (1019:) carboxypeptidase E precursor [Homo sapiens]; (1020:) Carboxypeptidase M precursor (CPM); (1021:) carboxypeptidase N, polypeptide 1, 50 kD precursor [Homo sapiens]; (1022:) carboxypeptidase Z isoform 1 [Homo sapiens]; (1023:) carboxypeptidase Z isoform 2 precursor [Homo sapiens]; (1024:) carboxypeptidase Z isoform 3 [Homo sapiens]; (1025:) Carboxypeptidase Z precursor (CPZ); (1026:) carnitine acetyltransferase isoform 1 precursor [Homo sapiens]; (1027:) carnitine acetyltransferase isoform 2 [Homo sapiens]; (1028:) carnitine acetyltransferase isoform 3 precursor [Homo sapiens]; (1029:) Carnitine O-acetyltransferase (Carnitine acetylase) (CAT) (Carnitine acetyltransferase) (CrAT); (1030:) carnitine O-octanoyltransferase [Homo sapiens]; (1031:) Carnitine O-palmitoyltransferase I, liver isoform (CPT I) (CPTI-L) (Carnitine palmitoyltransferase 1A); (1032:) carnitine palmitoyltransferase 1A isoform 1 [Homo sapiens]; (1033:) carnitine palmitoyltransferase 1A isoform 2 [Homo sapiens]; (1034:) carnitine palmitoyltransferase 1β isoform a [Homo sapiens]; (1035:) carnitine palmitoyltransferase 1β isoform b [Homo sapiens]; (1036:) "Cartilage intermediate layer protein 1 precursor (CILP-1) (Cartilage intermediate-layer protein) [Contains:] Cartilage intermediate layer protein 1 C1; Cartilage intermediate layer protein 1 C2]."; (1037:) Cas-Br-M (murine) ecotropic retroviral transforming sequence [Homo sapiens]; (1038:) casein alpha s1 isoform 1 [Homo sapiens]; (1039:) casein alpha s1 isoform 2 [Homo sapiens]; (1040:) casein beta [Homo sapiens]; (1041:) casein kinase 1, gamma 1 [Homo sapiens]; (1042:) casein kinase 1, gamma 1 isoform L [Homo sapiens]; (1043:) casein kinase 2, alpha prime polypeptide [Homo sapiens]; (1044:) casein kinase 2, beta polypeptide [Homo sapiens]; (1045:) Casein kinase I isoform delta (CKI-delta) (CKId); (1046:) casein kinase II alpha 1 subunit isoform a [Homo sapiens]; (1047:) casein kinase II alpha 1 subunit isoform b [Homo sapiens]; (1048:) CASH alpha protein [Homo sapiens]; (1049:) CASP1 protein [Homo sapiens]; (1050:) CASP10 protein [Homo sapiens]; (1051:) CASP12P1 [Homo sapiens]; (1052:) CASP2 [Homo sapiens]; (1053:) CASP8 and FADD-like apoptosis regulator [Homo sapiens]; (1054:) "CASP8 and FADD-like apoptosis regulator precursor (Cellular FLICE-like inhibitory protein) (c-FLIP) (Caspase-eight-related protein) (Casper) (Caspase-like apoptosis regulatory protein) (CLARP) (MACH-related inducer of toxicity) (MRIT) (Caspase homolog) (CASH) (Inhibitor of FLICE) (I-FLICE) (FADD-like antiapoptotic molecule 1) (FLAME-1) (Usurpin) [Contains:) CASP8 and FADD-like apoptosis regulator subunit p43; CASP8 and FADD-like apoptosis regulator subunit p12]."; (1055:) CASP8 protein [Homo sapiens]; (1056:) caspase 1 isoform alpha precursor [Homo sapiens]; (1057:) caspase 1 isoform alpha precursor variant [Homo sapiens]; (1058:) caspase 1 isoform beta precursor [Homo sapiens]; (1059:) caspase 1 isoform delta [Homo sapiens]; (1060:) caspase 1 isoform epsilon [Homo sapiens]; (1061:) caspase 1 isoform gamma precursor [Homo sapiens]; (1062:) Caspase 1, apoptosis-related cysteine peptidase (interleukin 1,beta, convertase) [Homo sapiens]; (1063:) caspase 10 [Homo sapiens]; (1064:) caspase 10 isoform a preproprotein [Homo sapiens]; (1065:) caspase 10 isoform b preproprotein [Homo sapiens]; (1066:) caspase 10 isoform d preproprotein [Homo sapiens]; (1067:) caspase 10, apoptosis-related cysteine peptidase [Homo sapiens]; (1068:) caspase 14 precursor [Homo sapiens]; (1069:) Caspase 14, apoptosis-related cysteine peptidase [Homo sapiens]; (1070:) caspase 2 isoform 1 preproprotein [Homo sapiens]; (1071:) caspase 2 isoform 2 precursor variant [Homo sapiens]; (1072:) caspase 2 isoform 3 [Homo sapiens]; (1073:) Caspase 2, apoptosis-related cysteine peptidase (neural precursor cell expressed, developmentally down-regulated 2) [Homo sapiens]; (1074:) caspase 2, apoptosis-related cysteine protease (neural precursor cell expressed, developmentally down-regulated 2) [Homo sapiens]; (1075:) caspase 3 preproprotein [Homo sapiens]; (1076:) Caspase 3, apoptosis-related cysteine peptidase [Homo sapiens]; (1077:) caspase 3, apoptosis-related cysteine protease [Homo sapiens]; (1078:) caspase 4 isoform alpha precursor [Homo sapiens]; (1079:) caspase 4 isoform delta [Homo sapiens]; (1080:) caspase 4 isoform gamma precursor [Homo sapiens]; (1081:) Caspase 4, apoptosis-related cysteine peptidase [Homo sapiens]; (1082:) caspase 5 precursor [Homo sapiens]; (1083:) Caspase 5, apoptosis-related cysteine peptidase [Homo sapiens]; (1084:) caspase 6 isoform alpha preproprotein [Homo sapiens]; (1085:) caspase 6 isoform beta [Homo sapiens]; (1086:) Caspase 6, apoptosis-related cysteine peptidase [Homo sapiens]; (1087:) caspase 6, apoptosis-related cysteine protease [Homo sapiens]; (1088:) caspase 7 isoform alpha [Homo sapiens]; (1089:) caspase 7 isoform alpha precursor [Homo sapiens]; (1090:) caspase 7 isoform beta [Homo sapiens]; (1091:) caspase 7 isoform delta [Homo sapiens]; (1092:) Caspase 7, apoptosis-related cysteine peptidase [Homo sapiens]; (1093:) caspase 7, apoptosis-related cysteine protease [Homo sapiens]; (1094:) caspase 8 isoform A [Homo sapiens]; (1095:) caspase 8 isoform B precursor [Homo sapiens]; (1096:) caspase 8 isoform C [Homo sapiens]; (1097:) caspase 8 isoform E [Homo sapiens]; (1098:) caspase 8, apoptosis-related cysteine peptidase [Homo sapiens]; (1099:j caspase 9 isoform alpha preproprotein [Homo sapiens]; (1100:) caspase 9 isoform alpha preproprotein variant [Homo sapiens]; (1101:) caspase 9 isoform beta preproprotein [Homo sapiens]; (1102:) caspase 9 short isoform [Homo sapiens]; (1103:) Caspase 9, apoptosis-related cysteine peptidase [Homo sapiens]; (1104:) caspase 9, apoptosis-related cysteine protease [Homo sapiens]; (1105:) caspase-1 dominant-negative inhibitor pseudo-ICE isoform 1 [Homo sapiens]; (1106:) caspase-1 dominant-negative inhibitor pseudo-ICE isoform 2 [Homo sapiens]; (1107:) caspase-1 isoform zeta precursor [Homo sapiens]; (1108:) "Caspase-1 precursor (CASP-1) (Interleukin-1 beta convertase) (IL-1BC) (IL-1 beta-converting enzyme) (ICE) (Interleukin-1 beta-converting enzyme) (p45) [Contains:) Caspase-1 p20 subunit; Caspase-1 p10 subunit]."; (1109:) "Caspase-10 precursor (CASP-10) (ICE-like apoptotic protease 4) (Apoptotic protease Mch-4) (FAS-associated death domain protein interleukin-1B-converting enzyme 2) (FLICE2) [Contains:) Caspase-10 subunit p23/17; Caspase-10 subunit p12]."; (1110:) caspase-10/d [Homo sapiens]; (1111:) caspase-10a [Homo sapiens]; (1112:) caspase-10b [Homo sapiens]; (1113:) "Caspase-14 precursor (CASP-14) [Contains:) Caspase-14 subunit 1; Caspase-14 subunit 2]."; (1114:) "Caspase-2 precursor (CASP-2) (ICH-1 protease) (ICH-1 L/1S)[Contains:) Caspase-2 subunit p18; Caspase-2 subunit p13; Caspase-2subunit p12]."; (1115:) caspase-3 [Homo sapiens]; (1116:) "Caspase-3 precursor (CASP-3) (Apopain) (Cysteine protease CPP32) (Yama protein) (CPP-32) (SREBP cleavage activity 1) (SCA-1)[Contains:) Caspase-3 p17 subunit; Caspase-3 p12 subunit]."; (1117:) "Caspase-4 precursor (CASP-4) (ICH-2 protease) (TX protease) (ICE(rel)-II) [Contains:) Caspase-4 subunit 1; Caspase-4 subunit 2]."; (1118:) "Caspase-5 precursor (CASP-5) (ICH-3 protease) (TY protease) (ICE(rel)-III) [Contains:) Caspase-5 subunit p20; Caspase-5 subunit p10]."; (1119:) caspase-5/b [Homo sapiens]; (1120:) caspase-5/f [Homo sapiens]; (1121:) "Caspase-6 precursor (CASP-6) (Apoptotic protease Mch-2) [Contains:Caspase-6 subunit p18; Caspase-6 subunit p11]."; (1122:) "Caspase-7 precursor (CASP-7) (ICE-like apoptotic protease 3) (ICE-LAP3) (Apoptotic protease Mch-3) (CMH-1) [Contains:) Caspase-7 subunit p20; Caspase-7 subunit p11]."; (1123:) caspase-8 [Homo sapiens]; (1124:) "Caspase-8 precursor (CASP-8) (ICE-like apoptotic protease 5) (MORT1-associated CED-3 homolog) (MACH) (FADD-homologous ICE/CED-3-like protease) (FADD-like ICE) (FLICE) (Apoptotic cysteine protease) (Apoptotic protease Mch-5) (CAP4) [Contains:Caspase-8 subunit p18; Caspase-8 subunit p10]."; (1125:) caspase-8L [Homo sapiens]; (1126:) Caspase-9 [Homo sapiens]; (1127:) caspase-9 beta [Homo sapiens]; (1128:) "Caspase-9 precursor (CASP-9) (ICE-like apoptotic protease 6) (ICE-LAP6) (Apoptotic protease Mch-6) (Apoptotic protease-activating factor 3) (APAF-3) [Contains:) Caspase-9 subunit p35; Caspase-9 subunit p10]."; (1129:) caspase-9S precursor [Homo sapiens]; (1130:) caspase-like apoptosis regulatory protein [Homo sapiens]; (1131:) Casper [Homo sapiens]; (1132:) catalase [Homo sapiens]; (1133:) Catechol O-methyltransferase; (1134:) catechol-O-methyltransferase isoform MB-COMT [Homo sapiens]; (1135:) catechol-O-methyltransferase isoform S-COMT [Homo sapiens]; (1136:) catenin (cadherin-associated protein), beta 1, 88 kDa [Homo sapiens]; (1137:) cathepsin B preproprotein [Homo sapiens]; (1138:) cathepsin C isoform a preproprotein [Homo sapiens]; (1139:) cathepsin C isoform b precursor [Homo sapiens]; (1140:) cathepsin D preproprotein [Homo sapiens]; (1141:) Cathepsin E precursor; (1142:) Cathepsin F precursor (CATSF); (1143:) cathepsin G preproprotein [Homo sapiens]; (1144:) cathepsin H isoform a preproprotein [Homo sapiens]; (1145:) cathepsin H isoform b precursor [Homo sapiens]; (1146:) cathepsin K preproprotein [Homo sapiens]; (1147:) cathepsin L preproprotein [Homo sapiens]; (1148:) Cathepsin L2 precursor (Cathepsin V) (Cathepsin U); (1149:) cathepsin O [Homo sapiens]; (1150:) Cathepsin O precursor; (1151:) cathepsin O preproprotein [Homo sapiens]; (1152:) cathepsin S [Homo sapiens]; (1153:) cathepsin S preproprotein [Homo sapiens]; (1154:) Cation-dependent mannose-6-phosphate receptor precursor (CD Man-6-Preceptor) (CD-MPR) (46 kDa mannose 6-phosphate receptor) (MPR 46); (1155:) cation-dependent mannose-6-phosphate receptor precursor [Homo sapiens]; (1156:) Cation-independent mannose-6-phosphate receptor precursor (CIMan-6-P receptor) (CI-MPR) (M6PR) (Insulin-like growth factor 2receptor) (Insulin-like growth factor II receptor) (IGF-II receptor) (M6P/IGF2 receptor) (M6P/IGF2R) (300 kDa mannose6-phosphate receptor) (MPR 300) (MPR300) (CD222 antigen); (1157:) caveolin 1 [Homo sapiens]; (1158:) CBS protein [Homo sapiens]; (1159:) C-C chemokine receptor type 11 (C-C CKR-1) (CC-CKR-1) (CCR-1) (CCR1) (Macrophage inflammatory protein 1-alpha receptor) (MIP-1alpha-R) (RANTES-R) (HM145) (LD78 receptor) (CD191 antigen); (1160:) C-C chemokine receptor type 10 (C-C CKR-10) (CC-CKR-10) (CCR-10) (G-protein coupled receptor 2); (1161:) C-C chemokine receptor type II (C-C CKR-1) (CC-CKR-11) (CCR-11) (CC chemokine receptor-like 1) (CCRL1) (CCX CKR); (1162:) C-C chemokine receptor type 2 (C-C CKR-2) (CC-CKR-2) (CCR-2) (CCR2) (Monocyte chemoattractant protein 1 receptor) (MCP-1-R) (CD192antigen); (1163:) C-C chemokine receptor type 3 (C-C CKR-3) (CC-CKR-3) (CCR-3) (CCR3) (CKR3) (Eosinophil eotaxin receptor) (CD193 antigen); (1164:) C-C chemokine receptor type 4 (C-C CKR-4) (CC-CKR-4) (CCR-4) (CCR4) (K5-5); (1165:) C-C chemokine receptor type 5 (C-C CKR-5) (CC-CKR-5) (CCR-5) (CCR5) (HIV-1 fusion coreceptor) (CHEMR13) (CD195 antigen); (1166:) C-C chemokine receptor type 6 (C-C CKR-6) (CC-CKR-6) (CCR-6) (LAR-Creceptor) (GPR-CY4) (GPRCY4) (Chemokine receptor-like 3) (CKR-L3) (DRY6) (G-protein coupled receptor 29) (CD196 antigen); (1167:) C-C chemokine receptor type 7 precursor (C-C CKR-7) (CC-CKR-7) (CCR-7) (MIP-3 beta receptor) (EBV-induced G-protein coupled receptor 1) (EBI1) (BLR2) (CD197 antigen) (CDw197); (1168:) C-C chemokine receptor type 8 (C-C CKR-8) (CC-CKR-8) (CCR-8) (GPR-CY6) (GPRCY6) (Chemokine receptor-like 1) (CKR-L1) (TER1) (CMKBRL2) (CC-chemokine receptor CHEMR1) (CDw198 antigen); (1169:) C-C chemokine receptor type 9 (C-C CKR-9) (CC-CKR-9) (CCR-9) (GPR-9-6) (G-protein coupled receptor 28) (CDw199 antigen); (1170:) C-C chemokine receptor-like 2 (Putative MCP-1 chemokine receptor) (Chemokine receptor CCR11) (Chemokine receptor X); (1171:) CCR4-NOT transcription complex, subunit 4 isoform a [Homo sapiens]; (1172:) CCR4-NOT transcription complex, subunit 4 isoform b [Homo sapiens]; (1173:) CD160 antigen precursor (Natural killer cell receptor BY55); (1174:) CD180 antigen precursor (Lymphocyte antigen 64) (Radio protective 106 kDa protein); (1175:) CD200 antigen isoform a precursor [Homo sapiens]; (1176:) CD200 antigen isoform b [Homo sapiens]; (1177:) CD209 antigen (Dendritic cell-specific ICAM-3-grabbing nonintegrin1) (DC-SIGN1) (DC-SIGN) (C-type lectin domain family 4 member L); (1178:) CD226 antigen precursor (DNAX accessory molecule 1) (DNAM-1); (1179:) CD2-associated protein (Cas ligand with multiple SH3 domains) (Adapter protein CMS); (1180:) CD38 antigen [Homo sapiens]; (1181:) CD40 antigen isoform 1 precursor [Homo sapiens]; (1182:) CD40 antigen isoform 2 precursor [Homo sapiens]; (1183:) CD44 antigen precursor (Phagocytic glycoprotein 1) (PGP-1) (HUTCH-I) (Extracellular matrix receptor-III) (ECMR-III) (GP90lymphocyte homing/adhesion receptor) (Hermes antigen) (Hyaluronate receptor) (Heparan sulfate proteoglycan) (Epican) (CDw44); (1184:) CD53 antigen [Homo sapiens]; (1185:) CD63 antigen isoform A [Homo sapiens]; (1186:) CD63 antigen isoform B [Homo sapiens]; (1187:) CD97 antigen precursor (Leukocyte antigen CD97); (1188:) CDC16 homolog [Homo sapiens]; (1189:) CDC26 subunit of anaphase promoting complex [Homo sapiens]; (1190:) Cdc34 [Homo sapiens]; (1191:) Cdk5 and Abl enzyme substrate 1 [Homo sapiens]; (1192:) Cdk5 and Abl enzyme substrate 2 [Homo sapiens]; (1193:) CDK5 and ABL1 enzyme substrate 1 (Interactor with CDK3 1) (Ik3-1); (1194:) CDK5 and ABL1 enzyme substrate 2 (Interactor with CDK32) (Ik3-2); (1195:) CDP-diacylglycerol-inositol 3-phosphatidyltransferase (Phosphatidylinositol synthase) (PtdIns synthase) (PI synthase); (1196:) Cell division control protein 2 homolog (p34 protein kinase) (Cyclin-dependent kinase 1) (CDK1); (1197:) Cell division control protein 42 homolog precursor (G25KGTP-binding protein); (1198:) cell division cycle 2 protein isoform 1 [Homo sapiens]; (1199:) cell division cycle 2 protein isoform 2 [Homo sapiens]; (1200:) cell division cycle 2-like 1 (PITSLRE proteins) isoform 1 [Homo sapiens]; (1201:) cell division cycle 2-like 1 (PITSLRE proteins) isoform 2 [Homo sapiens]; (1202:) cell division cycle 2-like 1 (PITSLRE proteins) isoform 3 [Homo sapiens]; (1203:) cell division cycle 2-like 1 (PITSLRE proteins) isoform 4 [Homo sapiens]; (1204:) cell division cycle 2-like 1 (PITSLRE proteins) isoform 5 [Homo sapiens]; (1205:) cell division cycle 2-like 1 (PITSLRE proteins) isoform 6 [Homo sapiens]; (1206:) cell division cycle 2-like 1 (PITSLRE proteins) isoform 8 [Homo sapiens]; (1207:) cell division cycle 2-like 1 (PITSLRE proteins) isoform 9 [Homo sapiens]; (1208:) Cell division cycle 34 [Homo sapiens]; (1209:) Cell division cycle 34 homolog (S. cerevisiae) [Homo sapiens]; (1210:) cell division cycle protein 23 [Homo sapiens]; (1211:) cell division cycle protein 27 [Homo sapiens]; (1212:) Cell division protein kinase 2 (p33 protein kinase); (1213:) Cell division protein kinase 4 (Cyclin-dependent kinase 4) (PSK-J3); (1214:) Cell division protein kinase 7 (CDK-activating kinase) (CAK) (TFIIH-basal transcription factor complex kinase subunit) (39 kDa protein kinase) (P39 Mo15) (STK1) (CAK1); (1215:) Cell surface glycoprotein OX2 receptor precursor (CD200 cell surface glycoprotein receptor); (1216:) Centaurin-gamma 1 (ARF-GAP with GTP-binding protein-like, ankyrin repeat and pleckstrin homology domains 2) (AGAP-2) (Phosphatidylinositol-3-kinase enhancer) (PIKE) (GTP-binding and GTPase-activating protein 2) (GGAP2); (1217:) Centaurin-gamma 2 (ARF-GAP with GTP-binding protein-like, ankyrin repeat and pleckstrin homology domains 1) (AGAP-1) (GTP-binding and GTPase-activating protein 1) (GGAP1); (1218:) Centaurin-gamma 3 (ARF-GAP with GTP-binding protein-like, ankyrin repeat and pleckstrin homology domains 3) (AGAP-3) (MR1-interacting protein) (MRIP-1) (CRAM-associated GTPase) (CRAG); (1219:) CGI-02 protein [Homo sapiens]; (1220:) CGI-11 protein [Homo sapiens]; (1221:) CGI-76 protein [Homo sapiens]; (1222:) cGMP-dependent protein kinase 1, alpha isozyme (CGK 1 alpha) (cGKI-alpha); (1223:) cGMP-dependent protein kinase 1, beta isozyme (cGK 1 beta) (cGKI-beta); (1224:) cGMP-dependent protein kinase 2 (CGK 2) (cGKII) (Type II cGMP-dependent protein kinase); (1225:) cGMP-inhibited 3',5'-cyclic phosphodiesterase A (Cyclic GMP-inhibited phosphodiesterase A) (CGI-PDE A); (1226:) cGMP-inhibited 3',5'-cyclic phosphodiesterase B (Cyclic GMP-inhibited phosphodiesterase B) (CGI-PDE B) (CGIPDE1) (CGIP1); (1227:) cGMP-specific 3',5'-cyclic phosphodiesterase (CGB-PDE) (cGMP-binding cGMP-specific phosphodiesterase); (1228:) CHCHD2 protein [Homo sapiens]; (1229:) CHCHD4 protein [Homo sapiens]; (1230:) chemokine (C-C motif) ligand 14 isoform 1 precursor [Homo sapiens]; (1231:) chemokine (C-C motif) ligand 14 isoform 2 precursor [Homo sapiens]; (1232:) chemokine (C-C motif) ligand 7 precursor [Homo sapiens]; (1233:) chemokine (C-C motif) receptor 2 isoform A [Homo sapiens]; (1234:) chemokine (C-C motif) receptor 2 isoform B [Homo sapiens]; (1235:) chemokine (C-X3-C motif) ligand 1 [Homo sapiens]; (1236:) chemokine (C-X-C motif) ligand 12 (stromal cell-derived factor 1)isoform alpha [Homo sapiens]; (1237:) chemokine (C-X-C motif) ligand 12 (stromal cell-derived factor 1)isoform beta [Homo sapiens]; (1238:) chemokine (C-X-C motif) ligand 12 (stromal cell-derived factor 1)isoform gamma [Homo sapiens]; (1239:) Chemokine receptor-like 1 (G-protein coupled receptor DEZ) (G-protein coupled receptor ChemR23); (1240:) Chemokine receptor-like 2 (G-protein coupled receptor 30) (IL8-related receptor DRY12) (Flow-induced endothelial G-protein coupled receptor) (FEG-1) (GPCR-BR); (1241:) Chemokine XC receptor 1 (XC chemokine receptor 1) (Lymphotactin receptor) (G-protein coupled receptor 5); (1242:) Chemokine-binding protein 2 (Chemokine-binding protein D6) (C-C chemokine receptor D6) (Chemokine receptor CCR-9) (Chemokine receptor CCR-10); (1243:) chitotriosidase [Homo sapiens]; (1244:) chitotriosidase precursor [Homo sapiens]; (1245:) Chitotriosidase-1 precursor (Chitinase-1); (1246:) chloride channel 6 isoform CIC-6a [Homo sapiens]; (1247:) chloride channel 6 isoform CIC-6b [Homo sapiens]; (1248:) chloride channel 6 isoform CIC-6c [Homo sapiens]; (1249:) chloride channel 6 isoform CIC-6d [Homo sapiens]; (1250:) cholecystokinin A receptor [Homo sapiens]; (1251:) cholecystokinin preproprotein [Homo sapiens]; (1252:) Cholecystokinin type A receptor (CCK-A receptor) (CCK-AR) (Cholecystokinin-1 receptor) (CCK1-R); (1253:) cholesterol 25-hydroxylase [Homo sapiens]; (1254:) cholesterol side-chain cleavage enzyme P450scc (EC 1.14.15.67); (1255:) choline acetyltransferase [Homo sapiens]; (1256:) choline acetyltransferase isoform 1 [Homo sapiens]; (1257:) choline acetyltransferase isoform 2 [Homo sapiens]; (1258:) choline kinase alpha isoform a [Homo sapiens]; (1259:) choline kinase alpha isoform b [Homo sapiens]; (1260:) Choline O-acetyltransferase (CHO-ACTase) (Choline acetylase) (ChAT); (1261:) choline phosphotransferase 1 [Homo sapiens]; (1262:) choline/ethanolamine kinase isoform a [Homo sapiens]; (1263:) choline/ethanolamine kinase isoform b [Homo sapiens]; (1264:) Choline-phosphate cytidylyltransferase A (Phosphorylcholine transferase A) (CTP:phosphocholine cytidylyltransferase A) (CT A) (CCT A) (CCT-alpha); (1265:) choline phosphotransferase [Homo sapiens]; (1266:) cholinergic receptor, nicotinic, alpha 4 subunit precursor [Homo sapiens]; (1267:) Cholinesterase precursor (Acylcholine acylhydrolase) (Cholineesterase II) (Butyrylcholine esterase) (Pseudocholinesterase); (1268:) chondroitin beta-1,4 N-acetylgalactosaminyltransferase [Homo sapiens]; (1269:) chondroitin beta-1,4 N-acetylgalactosaminyltransferase 2 [Homo sapiens]; (1270:) Chondroitin beta-1,4-N-acetylgalactosaminyltransferase 1(beta4GalNAcT-1); (1271:) Chondroitin beta-1,4-N-acetylgalactosaminyltransferase 2(GalNAcT-2) (beta4GalNAcT-2); (1272:) chondroitin sulfate proteoglycan 2 (versican) [Homo sapiens]; (1273:) chondroitin sulfate synthase 3 [Homo sapiens]; (1274:) chromatin-specific transcription elongation factor large subunit [Homo sapiens]; (1275:) chymase 1, mast cell preproprotein [Homo sapiens]; (1276:) Chymase precursor (Mast cell protease I); (1277:) chymotrypsin-like [Homo sapiens]; (1278:) Chymotrypsin-like serine proteinase (LCLP); (1279:) Ciliary neurotrophic factor receptor alpha precursor (CNTFR alpha); (1280:) citrate synthase precursor, isoform a [Homo sapiens]; (1281:) citrate synthase precursor, isoform b [Homo sapiens]; (1282:) Class B basic helix-loop-helix protein 2 (bHLHB2) (Differentially expressed in chondrocytes protein 1) (DEC1) (Enhancer-of-split and hairy-related protein 2) (SHARP-2) (Stimulated with retinoic acid 13); (1283:) class I alcohol dehydrogenase, alpha subunit [Homo sapiens]; (1284:) class I alcohol dehydrogenase, gamma subunit [Homo sapiens]; (1285:) class II alcohol dehydrogenase 4 pi subunit [Homo sapiens]; (1286:) class III alcohol dehydrogenase 5 chi subunit [Homo sapiens]; (1287:) class IV alcohol dehydrogenase 7 mu or sigma subunit [Homo sapiens]; (1288:) class IV alcohol dehydrogenase, sigma sigma-ADH; (1289:) clathrin heavy chain 1 [Homo sapiens]; (1290:) CLCN6 [Homo sapiens]; (1291:) CMH-1; (1292:) CMP-N-acetylneuraminate-beta-galactosamide-alpha-2,6-sialyltransferase (Beta-galactoside alpha-2,6-sialyltransferase) (Alpha 2,6-ST) (Sialyltransferase 1) (ST6Gal I) (B-cell antigen CD75); (1293:) CMRF35-H antigen precursor (CMRF35-H9) (CMRF-35-H9) (CD300a antigen) (Inhibitory receptor protein 60) (IRp60) (IRC1/IRC2) (NK inhibitory receptor); (1294:) CMRF35-like-molecule 1 precursor (CLM-1) (Immune receptor expressed on myeloid cells protein 1) (IREM-1) (Immunoglobulin superfamily member 13) (NK inhibitory receptor) (CD300 antigen like family member F) (IgSF13); (1295:) c-myc binding protein [Homo sapiens]; (1296:) coactivator-associated arginine methyltransferase 1 [Homo sapiens]; (1297:) coactosin-like 1 [Homo sapiens]; (1298:) coagulation factor 11 (thrombin) receptor-like 1 precursor [Homo sapiens]; (1299:) coagulation factor 11 precursor [Homo sapiens]; (1300:) coagulation factor III precursor [Homo sapiens]; (1301:) coagulation factor IX [Homo sapiens]; (1302:) coagulation factor V precursor [Homo sapiens]; (1303:) coagulation factor VII isoform a precursor [Homo sapiens]; (1304:) coagulation factor VII isoform b precursor [Homo sapiens]; (1305:) coagulation factor VIII isoform a precursor [Homo sapiens]; (1306:) coagulation factor VIII isoform b precursor [Homo sapiens]; (1307:) coagulation factor X preproprotein [Homo sapiens]; (1308:) coagulation factor XIII A1 subunit precursor [Homo sapiens]; (1309:) coagulation factor XIII B subunit precursor [Homo sapiens]; (1310:) COASY protein [Homo sapiens]; (1311:) Coenzyme A synthase [Homo sapiens]; (1312:) coenzyme A synthase isoform a [Homo sapiens]; (1313:) coenzyme A synthase isoform b [Homo sapiens]; (1314:) Cofactor required for Sp1 transcriptional activation subunit 9(Transcriptional coactivator CRSP33) (RNA polymerase transcriptional regulation mediator subunit 7 homolog) (hMED7) (Activator-recruited cofactor 34 kDa component) (ARC34); (1315:) coilin-interacting nuclear ATPase protein [Homo sapiens]; (1316:) coilin-interacting nuclear ATPase protein [Homo sapiens]; (1317:) Colipase precursor; (1318:) colony stimulating factor 3 isoform a precursor [Homo sapiens]; (1319:) colony stimulating factor 3 isoform b precursor [Homo sapiens]; (1320:) colony stimulating factor 3 isoform c [Homo sapiens]; (1321:) colony-stimulating factor; (1322:) complement C1r activated form; (1323:) "Complement C1r subcomponent precursor (Complement component 1, r subcomponent) [Contains:] Complement C1r subcomponent heavy chain; Complement C1r subcomponent light chain]."; (1324:) complement component 1, s subcomponent [Homo sapiens]; (1325:) complement component 3 precursor [Homo sapiens]; (1326:) Complement component 6 precursor [Homo sapiens]; (1327:) Complement component C1q receptor precursor (Complement component 1q subcomponent receptor 1) (C1qR) (C1qRp) (C1qR(p)) (C1q/MBL/SPA receptor) (CD93 antigen) (CDw93); (1328:) complement factor D preproprotein [Homo sapiens]; (1329:) Complement receptor type 1 precursor (C3b/C4b receptor) (CD35antigen); (1330:) Complement receptor type 2 precursor (Cr2) (Complement C3d receptor) (Epstein-Barr virus receptor) (EBV receptor) (CD21 antigen); (1331:) copper monamine oxidase; (1332:) coproporphyrinogen oxidase [Homo sapiens]; (1333:) core 2 beta-1,6-N-acetylglucosaminyltransferase 3 [Homo sapiens]; (1334:) corin [Homo sapiens]; (1335:) Corticosteroid 11-beta-dehydrogenase isozyme 1 (11-DH) (11-beta-hydroxysteroid dehydrogenase 1) (11-beta-HSD1); (1336:) Corticosteroid 11-beta-dehydrogenase isozyme 2 (11-DH2) (11-beta-hydroxysteroid dehydrogenase type 2) (11-beta-HSD2) (NAD-dependent 11-beta-hydroxysteroid dehydrogenase); (1337:) Corticotropin-releasing factor receptor 1 precursor (CRF-R) (CRF1) (Corticotropin-releasing hormone receptor 1) (CRH-R 1); (1338:) Corticotropin-releasing factor receptor 2 precursor (CRF-R 2) (CRF2) (Corticotropin-releasing hormone receptor 2) (CRH-R 2); (1339:) COUP transcription factor 1 (COUP-TF1) (COUP-TF I) (V-ERBA-related protein EAR-3); (1340:) COUP transcription factor 2 (COUP-TF2) (COUP-TF II) (Apolipoprotein AI regulatory protein 1) (ARP-1); (1341:) COX11 homolog [Homo sapiens]; (1342:) Coxsackievirus and adenovirus receptor precursor (Coxsackievirus B-adenovirus receptor) (hCAR) (CVB3-binding protein) (HCVADR); (1343:) CPA4 protein [Homo sapiens]; (1344:) C-reactive protein, pentraxin-related [Homo sapiens]; (1345:) CREB binding protein [Homo sapiens]; (1346:) CRSP complex subunit 2 (Cofactor required for Sp1 transcriptional activation subunit 2) (Transcriptional coactivator CRSP150) (Vitamin D3 receptor-interacting protein complex 150 kDa component) (DRIP150) (Thyroid hormone receptor-associated protein complex 170 kDa component) (Trap170) (Activator-recruited cofactor 150 kDa component) (ARC150); (1347:) CRSP complex subunit 3 (Cofactor required for Sp1 transcriptional activation subunit 3) (Transcriptional coactivator CRSP130) (Vitamin D3 receptor-interacting protein complex 130 kDa component) (DRIP130) (Activator-recruited cofactor 130 kDa component) (ARC130); (1348:) CRSP complex subunit 6 (Cofactor required for Sp1 transcriptional activation subunit 6) (Transcriptional coactivator CRSP77) (Vitamin D3 receptor-interacting protein complex 80 kDa component) (DRIP80) (Thyroid hormone receptor-associated protein complex 80 kDa component) (Trap80) (Activator-recruited cofactor 77 kDa component) (ARC77); (1349:) CRSP complex subunit 7 (Cofactor required for Sp1 transcriptional activation subunit 7) (Transcriptional coactivator CRSP70) (Activator-recruited cofactor 70 kDa component) (ARC70); (1350:) crystallin, alpha A [Homo sapiens]; (1351:) crystallin, alpha B [Homo sapiens]; (1352:) crystallin, beta A2 [Homo sapiens]; (1353:) crystallin, beta A3 [Homo sapiens]; (1354:) crystallin, beta A4 [Homo sapiens]; (1355:) crystallin, beta B1 [Homo sapiens]; (1356:) crystallin, beta B2 [Homo sapiens]; (1357:) crystallin, beta B3 [Homo sapiens]; (1358:) crystallin, gamma A [Homo sapiens]; (1359:) crystallin, gamma B [Homo sapiens]; (1360:) crystallin, gamma C [Homo sapiens]; (1361:) crystallin, gamma D [Homo sapiens]; (1362:) crystallin, gamma S [Homo sapiens]; (1363:) crystallin, mu isoform 1 [Homo sapiens]; (1364:) crystallin, mu isoform 2 [Homo sapiens]; (1365:) crystallin, zeta [Homo sapiens]; (1366:) c-src tyrosine kinase [Homo sapiens]; (1367:) CTP synthase [Homo sapiens]; (1368:) CTP synthase 1 (UTP—ammonia ligase 1) (CTP synthetase 1); (1369:) CTP synthase 2 (UTP—ammonia ligase 2) (CTP synthetase 2); (1370:) C-type lectin domain family 4 member F (C-type lectin superfamily member 13) (C-type lectin 13); (1371:) C-type lectin domain family 4 member M (CD209 antigen-like protein1) (Dendritic cell-specific ICAM-3-grabbing nonintegrin 2) (DC-SIGN2) (DC-SIGN-related protein) (DC-SIGNR) (Liver/lymphnode-specific ICAM-3-grabbing non-integrin) (L-SIGN) (CD299antigen); (1372:) C-type lectin domain family 9 member A; (1373:) Cubilin precursor (Intrinsic factor-cobalamin receptor) (Intrinsic factor-vitamin B12 receptor) (460 kDa receptor) (Intestinal intrinsic factor receptor); (1374:) Cullin-1 (CUL-1); (1375:) Cullin-2 (CUL-2); (1376:) Cullin-5 (CUL-5) (Vasopressin-activated calcium-mobilizing receptor) (VACM-1); (1377:) CX3C chemokine receptor 1 (C-X3-C CKR-1) (CX3CR1) (Fractalkine receptor) (G-protein coupled receptor 13) (V28) (Beta chemokine receptor-like 1) (CMK-BRL-1) (CMK-BLR1); (1378:) C-X-C chemokine receptor type 3 (CXC-R3) (CXCR-3) (Interferon-inducible protein 10 receptor) (IP-10 receptor) (CKR-L2) (CD183 antigen) (G protein-coupled receptor 9); (1379:) C-X-C chemokine receptor type 4 (CXC-R4) (CXCR-4) (Stromal cell-derived factor 1 receptor) (SDF-1 receptor) (Fusin) (Leukocyte-derived seven transmembrane domain receptor) (LESTR) (LCR1) (FB22) (NPYRL) (HM89) (CD184 antigen); (1380:) C-X-C chemokine receptor type 5 (CXC-R5) (CXCR-5) (Burkitt lymphoma receptor 1) (Monocyte-derived receptor 15) (MDR-15) (CD185antigen); (1381:) C-X-C chemokine receptor type 6 (CXC-R6) (CXCR-6) (G-protein coupled receptor bonzo) (G-protein coupled receptor STRL33) (CD186antigen) (CDw186); (1382:) C-X-C chemokine receptor type 7 (CXC-R7) (CXCR-7) (G-protein coupled receptor RDC1 homolog) (RDC-1) (Chemokine orphan receptor1) (G-protein coupled receptor 159); (1383:) cyclin D1 [Homo sapiens]; (1384:) cyclin-dependent kinase 2 isoform 1 [Homo sapiens]; (1385:) cyclin-dependent kinase 2 isoform 2 [Homo sapiens]; (1386:) cyclin-dependent kinase inhibitor 1B [Homo sapiens]; (1387:) cyclin-dependent kinase inhibitor 2A isoform 1 [Homo sapiens]; (1388:) cyclin-dependent kinase inhibitor 2A isoform 3 [Homo sapiens]; (1389:) cyclin-dependent kinase inhibitor 2A isoform 4 [Homo sapiens]; (1390:) Cyclin-dependent kinase inhibitor 2A, isoform 4 (p14ARF) (p19ARF); (1391:) Cyclin-dependent kinase-like 5 (Serine/threonine-protein kinase 9); (1392:) cyclin-selective ubiquitin carrier protein [Homo sapiens]; (1393:) Cystathionase (cystathionine gamma-lyase) [Homo sapiens]; (1394:) cystathionase isoform 1 [Homo sapiens]; (1395:) cystathionase isoform 1 variant [Homo sapiens]; (1396:) cystathionase isoform 2 [Homo sapiens]; (1397:) cystathionine B synthase [Homo sapiens]; (1398:) Cystathionine beta-synthase (Serine sulfhydrase) (Beta-thionase); (1399:) cystathionine beta-synthase major isoform [Homo sapiens]; (1400:) cystathionine beta-synthase; (1401:) Cystathionine gamma-lyase (Gamma-cystathionase); (1402:) "cystathionine gamma-lyase; cystathionase [Homo sapiens]."; (1403:) cystathionine-beta-synthase [Homo sapiens]; (1404:) Cystatin C precursor (Neuroendocrine basic polypeptide) (Gamma-trace) (Post-gamma-globulin); (1405:) "cysteine conjugate-beta lyase; cytoplasmic (glutamine transaminase k, kyneurenine aminotransferase) [Homo sapiens]."; (1406:) cysteine desulfurase [Homo sapiens]; (1407:) Cysteine desulfurase, mitochondrial precursor; (1408:) cysteine dioxygenase [Homo sapiens]; (1409:) Cysteine protease ATG4A (Autophagy-related protein 4 homolog A) (hAPG4A) (Autophagin-2) (Autophagy-related cysteine endopeptidase 2) (AUT-like 2 cysteine endopeptidase); (1410:) Cysteine protease ATG4B (Autophagy-related protein 4 homolog B) (hAPG4B) (Autophagin-1) (Autophagy-related cysteine endopeptidase 1) (AUT-like 1 cysteine endopeptidase); (1411:) Cysteine protease ATG4C (Autophagy-related protein 4 homolog C) (Autophagin-3) (Autophagy-related cysteine endopeptidase 3) (AUT-like 3 cysteine endopeptidase); (1412:) Cysteine protease ATG4D (Autophagy-related protein 4 homolog D) (Autophagin-4) (Autophagy-related cysteine endopeptidase 4) (AUT-like 4 cysteine endopeptidase); (1413:) cysteine protease CPP32 isoform alpha; (1414:) cysteine protease CPP32 isoform beta; (1415:) cysteine protease Mch2 isoform alpha; (1416:) cysteine protease Mch2 isoform beta; (1417:) cysteine protease; (1418:) cysteine-rich, angiogenic inducer, 61 [Homo sapiens]; (1419:) Cysteinyl leukotriene receptor 1 (CysLTR1) (Cysteinyl leukotriene D4 receptor) (LTD4 receptor) (HG55) (HMTMF81); (1420:) Cysteinyl leukotriene receptor 2 (CysLTR2) (HG57) (HPN321) (hGPCR21); (1421:) cytidine 5'-monophosphate N-acetylneuraminic acid synthetase [Homo sapiens]; (1422:) Cytidine deaminase (Cytidine aminohydrolase); (1423:) cytidine deaminase [Homo sapiens]; (1424:) Cytidine monophosphate-N-acetylneuraminic acid hydroxylase-like protein (CMP-NeuAc hydroxylase-like protein); (1425:) cytidine triphosphate synthase 11 [Homo sapiens]; (1426:) cytidylate kinase [Homo sapiens]; (1427:) cytochrome b [Homo sapiens]; (1428:) cytochrome b, alpha polypeptide [Homo sapiens]; (1429:) Cytochrome b; (1430:) cytochrome b5 reductase b5R.2 [Homo sapiens]; (1431:) cytochrome b5 reductase isoform 1 [Homo sapiens]; (1432:) cytochrome b5 reductase isoform 2 [Homo sapiens]; (1433:) cytochrome c [Homo sapiens]; (1434:) Cytochrome c oxidase subunit 1 (Cytochrome c oxidase polypeptideI); (1435:) Cytochrome c oxidase subunit 2 (Cytochrome c oxidase polypeptideII); (1436:) Cytochrome c oxidase subunit 3 (Cytochrome c oxidase polypeptideIII); (1437:) cytochrome c oxidase subunit 8A [Homo sapiens]; (1438:) cytochrome c oxidase subunit IV isoform 1 precursor [Homo sapiens]; (1439:) cytochrome c oxidase subunit IV isoform 2 [Homo sapiens]; (1440:) cytochrome c oxidase subunit IV precursor [Homo sapiens]; (1441:) cytochrome c oxidase subunit Va precursor [Homo sapiens]; (1442:) cytochrome c oxidase subunit Vb precursor [*Homo sapiens*]; (1443:) cytochrome c oxidase subunit VIa polypeptide 1 precursor [*Homo sapiens*]; (1444:) cytochrome c oxidase subunit Via polypeptide 2 precursor [*Homo sapiens*]; (1445:) cytochrome c oxidase subunit VIb [*Homo sapiens*]; (1446:) cytochrome c oxidase subunit VIc proprotein [*Homo sapiens*]; (1447:) cytochrome c-1 [*Homo sapiens*]; (1448:) cytochrome P450 [*Homo sapiens*]; (1449:) Cytochrome P450 11A1, mitochondrial precursor (CYPXIA1) (P450 (scc)) (Cholesterol side-chain cleavage enzyme) (Cholesterol desmolase); (1450:) Cytochrome P450 11B2, mitochondrial precursor (CYPXIB2) (P-450Aldo) (Aldosterone synthase) (ALDOS) (Aldosterone-synthesizing enzyme) (Steroid 18-hydroxylase) (P-450C18); (1451:) Cytochrome P450 17A1 (CYPXVII) (P450-C17) (P450c17) (Steroid 17-alpha-monooxygenase) (Steroid 17-alpha-hydroxylase/17,20 lyase); (1452:) Cytochrome P450 19A1 (Aromatase) (CYPXIX) (Estrogen synthetase) (P-450AROM); (1453:) Cytochrome P450 1A1 (CYPIA1) (P450-P1) (P450 form 6) (P450-C); (1454:) cytochrome P450 1A1 variant [*Homo sapiens*]; (1455:) Cytochrome P450 1A2 (CYPIA2) (P450-P3) (P(3)-450) (P450 4); (1456:) Cytochrome P450 1B1 (CYPIB1); (1457:) Cytochrome P450 21 (Cytochrome P450 XXI) (Steroid 21-hydroxylase) (21-OHase) (P450-C21) (P-450c21) (P450-C21B); (1458:) Cytochrome P450 26A1 (Retinoic acid-metabolizing cytochrome) (P450 retinoic acid-inactivating 1) (P450RAI) (hP450RAI) (Retinoic acid-4-hydroxylase); (1459:) Cytochrome P450 26B1 (P450 26A2) (P450 retinoic acid-inactivating 2) (P450RAI-2) (Retinoic acid-metabolizing cytochrome); (1460:) Cytochrome P450 27, mitochondrial precursor (Cytochrome P-450C27/25) (Sterol 26-hydroxylase) (Sterol 27-hydroxylase) (Vitamin D(3) 25-hydroxylase) (5-beta-cholestane-3-alpha,7-alpha,12-alpha-triol 27-hydroxylase); (1461:) cytochrome P450 2A3, hepatic—human (fragment); (1462:) Cytochrome P450 2A7 (CYPIIA7) (P450-11A4); (1463:) Cytochrome P450 2B6 (CYPIIB6) (P450 IIB1); (1464:) Cytochrome P450 2C18 (CYPIIC18) (P450-6B/29C); (1465:) Cytochrome P450 2C8 (CYPIIC8) (P450 form 1) (P450MP-12/MP-20) (P450 IIC2) (S-mephenyloin 4-hydroxylase); (1466:) Cytochrome P450 2C9 ((R)-limonene 6-monooxygenase) ((S)-limonene 6-monooxygenase) ((S)-limonene 7-monooxygenase) (CYPIIC9) (P450PB-1) (P450MP-4/MP-8) (S-mephenyloin 4-hydroxylase) (P-450 MP); (1467:) Cytochrome P450 2E1 (CYPIIE1) (P450-J); (1468:) Cytochrome P450 2J2 (CYPIIJ2) (Arachidonic acid epoxygenase); (1469:) Cytochrome P450 2R1 (Vitamin D 25-hydroxylase); (1470:) Cytochrome P450 3A3 (CYPIIIA3) (HLp); (1471:) Cytochrome P450 3A4 (Quinine 3-monooxygenase) (CYPIIIA4) (Nifedipine oxidase) (Taurochenodeoxycholate 6-alpha-hydroxylase) (NF-25) (P450-PCN1); (1472:) Cytochrome P450 3A5 (CYPIIIA5) (P450-PCN3) (HLp2); (1473:) Cytochrome P450 3A7 (CYPIIIA7) (P450-HFLA); (1474:) Cytochrome P450 4A11 precursor (CYPIVA11) (Fatty acid omega-hydroxylase) (P-450 HK omega) (Lauric acid omega-hydroxylase) (CYP4AII) (P450-HL-omega); (1475:) Cytochrome P450 4B1 (CYPIVB1) (P450-HP); (1476:) Cytochrome P450 4F2 (CYPIVF2) (Leukotriene-B(4) omega-hydroxylase) (Leukotriene-B(4) 20-monooxygenase) (Cytochrome P450-LTB-omega); (1477:) Cytochrome P450 4F3 (CYPIVF3) (Leukotriene-B(4) omega-hydroxylase) (Leukotriene-B(4) 20-monooxygenase) (Cytochrome P450-LTB-omega); (1478:) cytochrome P450 family 1 subfamily A polypeptide 1 [*Homo sapiens*]; (1479:) cytochrome P450 family 3 subfamily A polypeptide 4 [*Homo sapiens*]; (1480:) cytochrome P450 reductase [*Homo sapiens*]; (1481:) cytochrome P450, family 1, subfamily A, polypeptide 1 [*Homo sapiens*]; (1482:) cytochrome P450, family 1, subfamily A, polypeptide 2 [*Homo sapiens*]; (1483:) cytochrome P450, family 1, subfamily B, polypeptide 1 [*Homo sapiens*]; (1484:) cytochrome P450, family 11, subfamily B, polypeptide 1 isoform 1 precursor [*Homo sapiens*]; (1485:) cytochrome P450, family 11, subfamily B, polypeptide 1 isoform 2precursor [*Homo sapiens*]; (1486:) cytochrome P450, family 17 [*Homo sapiens*]; (1487:) cytochrome P450, family 19 [*Homo sapiens*]; (1488:) cytochrome P450, family 2, subfamily A, polypeptide 6 [*Homo sapiens*]; (1489:) cytochrome P450, family 2, subfamily B, polypeptide 6 [*Homo sapiens*]; (1490:) cytochrome P450, family 2, subfamily C, polypeptide 18 [*Homo sapiens*]; (1491:) cytochrome P450, family 2, subfamily C, polypeptide 19 [*Homo sapiens*]; (1492:) cytochrome P450, family 2, subfamily C, polypeptide 8 [*Homo sapiens*]; (1493:) cytochrome P450, family 2, subfamily C, polypeptide 9 [*Homo sapiens*]; (1494:) cytochrome P450, family 2, subfamily D, polypeptide 6 isoform 1 [*Homo sapiens*]; (1495:) cytochrome P450, family 2, subfamily D, polypeptide 6 isoform 2 [*Homo sapiens*]; (1496:) cytochrome P450, family 2, subfamily E, polypeptide 1 [*Homo sapiens*]; (1497:) cytochrome P450, family 2, subfamily J, polypeptide 2 [*Homo sapiens*]; (1498:) cytochrome P450, family 2, subfamily R, polypeptide 1 [*Homo sapiens*]; (1499:) cytochrome P450, family 2, subfamily U, polypeptide 1 [*Homo sapiens*]; (1500:) cytochrome P450, family 2, subfamily W, polypeptide 1 [*Homo sapiens*]; (1501:) cytochrome P450, family 21, subfamily A, polypeptide 2 [*Homo sapiens*]; (1502:) cytochrome P450, family 24 precursor [*Homo sapiens*]; (1503:) cytochrome P450, family 26, subfamily A, polypeptide 1 isoform 1 [*Homo sapiens*]; (1504:) cytochrome P450, family 26, subfamily A, polypeptide 1 isoform 2 [*Homo sapiens*]; (1505:) cytochrome P450, family 26, subfamily b, polypeptide 1 [*Homo sapiens*]; (1506:) cytochrome P450, family 26, subfamily C, polypeptide 1 [*Homo sapiens*]; (1507:) cytochrome P450, family 27, subfamily A, polypeptide 1 precursor[*Homo sapiens*]; (1508:) cytochrome P450, family 27, subfamily B, polypeptide 1 [*Homo sapiens*]; (1509:) cytochrome P450, family 3, subfamily A, polypeptide 43 isoform 1 [*Homo sapiens*]; (1510:) cytochrome P450, family 3, subfamily A, polypeptide 43 isoform 2 [*Homo sapiens*]; (1511:) cytochrome P450, family 3, subfamily A, polypeptide 43 isoform 3 [*Homo sapiens*]; (1512:) cytochrome P450, family 3, subfamily A, polypeptide 5 [*Homo sapiens*]; (1513:) cytochrome P450, family 3, subfamily A, polypeptide 7 [*Homo sapiens*]; (1514:) cytochrome P450, family 4, subfamily A, polypeptide 11 [*Homo sapiens*]; (1515:) cytochrome P450, family 4, subfamily F, polypeptide 12 [*Homo sapiens*]; (1516:) cytochrome P450, family 4, subfamily F, polypeptide 2 [*Homo sapiens*]; (1517:) cytochrome P450, family 4, subfamily F, polypeptide 3 [*Homo sapiens*]; (1518:) cytochrome P450, family 46 [*Homo sapiens*]; (1519:) cytochrome P450, family 7, subfamily A, polypeptide 1 [*Homo sapiens*]; (1520:) cytochrome P450, family 7, subfamily B, polypeptide 1 [*Homo sapiens*]; (1521:) cytochrome P450, subfamily IIIA, polypeptide 4 [*Homo sapiens*]; (1522:) cytochrome P450, subfamily XIA precursor [*Homo sapiens*]; (1523:) cytochrome P450, subfamily XIB polypeptide 2 precursor [*Homo sapiens*]; (1524:) cytochrome P450; (1525:) cytochrome P450j; (1526:) Cytokine receptor common beta chain precursor (GM-CSF/IL-3/1L-5receptor common beta-chain) (CD131 antigen) (CDw131); (1527:) Cytokine receptor common gamma chain precursor (Gamma-C) (Interleukin-2 receptor gamma chain) (IL-2R gamma chain) (p64) (CD132 antigen); (1528:) Cytokine receptor-like factor 1 precursor (Cytokine-like factor 1) (CLF-1) (ZcytoR5); (1529:) Cytokine receptor-like factor 2 precursor (Cytokine receptor-like2) (CRL2) (IL-XR) (Thymic stromal lymphopoietin protein receptor) (TSLPR); (1530:) cytoplasmic cysteine conjugate-beta lyase [Homo sapiens]; (1531:) Cytoplasmic dynein 1 light intermediate chain 1 (Dynein light intermediate chain 1, cytosolic) (Dynein light chain A) (DLC-A); (1532:) Cytosol aminopeptidase (Leucine aminopeptidase) (LAP) (Leucyl aminopeptidase) (Proline aminopeptidase) (Prolyl aminopeptidase) (Peptidase S); (1533:) Cytosolic 5'-nucleotidase 1A (Cytosolic 5'-nucleotidase IA) (cN1A) (cN-IA) (cN-1); (1534:) Cytosolic 5'-nucleotidase 1B (Cytosolic 5'-nucleotidase IB) (cN1B) (cN-IB) (Autoimmune infertility-related protein); (1535:) cytosolic acetyl-CoA hydrolase [Homo sapiens]; (1536:) cytosolic aminopeptidase P [Homo sapiens]; (1537:) Cytosolic beta-glucosidase (Cytosolic beta-glucosidase-like protein1); (1538:) cytosolic beta-glucosidase [Homo sapiens]; (1539:) cytosolic inhibitor of NRF2 [Homo sapiens]; (1540:) cytosolic leucyl-tRNA synthetase [Homo sapiens]; (1541:) cytosolic malic enzyme 1 [Homo sapiens]; (1542:) cytosolic malic enzyme 1 variant [Homo sapiens]; (1543:) cytosolic malic enzyme; (1544:) cytosolic NADP(+)-dependent malic enzyme; (1545:) cytosolic ovarian carcinoma antigen 1 isoform a [Homo sapiens]; (1546:) cytosolic ovarian carcinoma antigen 1 isoform b [Homo sapiens]; (1547:) cytosolic phosphoenolpyruvate carboxykinase 1 [Homo sapiens]; (1548:) "Cytosolic phospholipase A2 (cPLA2) (Phospholipase A2 group IVA)[Includes:) Phospholipase A2 (Phosphatidylcholine 2-acylhydrolase); Lysophospholipase]."; (1549:) Cytosolic phospholipase A2 beta (cPLA2-beta) (Phospholipase A2 group IVB); (1550:) Cytosolic phospholipase A2 delta (cPLA2-delta) (Phospholipase A2 group IVD); (1551:) Cytosolic phospholipase A2 epsilon (cPLA2-epsilon) (Phospholipase A2 group IVE); (1552:) Cytosolic phospholipase A2 gamma precursor (cPLA2-gamma) (Phospholipase A2 group IVC); (1553:) Cytosolic phospholipase A2 zeta (cPLA2-zeta) (Phospholipase A2 group IVF); (1554:) cytosolic phospholipase A2, group IVA [Homo sapiens]; (1555:) Cytosolic purine 5'-nucleotidase (5'-nucleotidase cytosolic 11); (1556:) cytosolic thyroid hormone-binding protein (EC 2.7.1.40); (1557:) CAAX prenyl protease 1 homolog (Prenyl protein-specific endoprotease 1) (Farnesylated proteins-converting enzyme 1) (FACE-1) (Zinc metalloproteinase Step 24 homolog); (1558:) CAAX prenyl protease 2 (Prenyl protein-specific endoprotease 2) (Farnesylated proteins-converting enzyme 2) (FACE-2) (hRCE1); (1559:) D(1A) dopamine receptor; (1560:) D(1B) dopamine receptor (D(5) dopamine receptor) (D1beta dopamine receptor); (1561:) D(2) dopamine receptor (Dopamine D2 receptor); (1562:) D(3) dopamine receptor; (1563:) D(4) dopamine receptor (Dopamine D4 receptor) (D(2C) dopamine receptor); (1564:) D-2-hydroxyglutarate dehydrogenase, mitochondrial precursor; (1565:) dachshund homolog 1 isoform a [Homo sapiens]; (1566:) dachshund homolog 1 isoform b [Homo sapiens]; (1567:) dachshund homolog 1 isoform c [Homo sapiens]; (1568:) D-amino-acid oxidase [Homo sapiens]; (1569:) D-aspartate oxidase isoform a [Homo sapiens]; (1570:) D-aspartate oxidase isoform b [Homo sapiens]; (1571:) D-beta-hydroxybutyrate dehydrogenase, mitochondrial precursor (BDH) (3-hydroxybutyrate dehydrogenase); (1572:) DCP1 decapping enzyme homolog A [Homo sapiens]; (1573:) DCP1 decapping enzyme homolog B (S. cerevisiae) [Homo sapiens]; (1574:) DCP2 decapping enzyme [Homo sapiens]; (1575:) D-dopachrome decarboxylase (D-dopachrome tautomerase) (Phenylpyruvate tautomerase II); (1576:) D-dopachrome tautomerase [Homo sapiens]; (1577:) DEAD/H (Asp-Glu-Ala-Asp/His) box polypeptide 11 isoform 1 [Homo sapiens]; (1578:) DEAD/H (Asp-Glu-Ala-Asp/His) box polypeptide 11 isoform 2 [Homo sapiens]; (1579:) deaminase, adenosine; (1580:) Death-associated protein kinase 1 (DAP kinase 1); (1581:) Death-associated protein kinase 2 (DAP kinase 2) (DAP-kinase-related protein 1) (DRP-1); (1582:) Debranching enzyme homolog 1 (S. cerevisiae) [Homo sapiens]; (1583:) debranching enzyme homolog 1 [Homo sapiens]; (1584:) decapping enzyme Dcp1b [Homo sapiens]; (1585:) decapping enzyme hDcp1a [Homo sapiens]; (1586:) decapping enzyme hDcp1b [Homo sapiens]; (1587:) decapping enzyme hDcp2 [Homo sapiens]; (1588:) Decapping enzyme, scavenger [Homo sapiens]; (1589:) defender against cell death 1 [Homo sapiens]; (1590:) defensin, alpha 5 preproprotein [Homo sapiens]; (1591:) Dehydrogenase/reductase SDR family member 8 precursor (17-beta-hydroxysteroid dehydrogenase 11) (17-beta-HSD 11) (17-beta-HSDXI) (17betaHSDXI) (17bHSD11) (17betaHSD11) (Retinal short-chain dehydrogenase/reductase 2) (retSDR2) (Cutaneous T-cell lymphoma-associated antigen HD-CL-03) (CTCL tumor antigen HD-CL-03); (1592:) deiodinase, iodothyronine, type I isoform a [Homo sapiens]; (1593:) deiodinase, iodothyronine, type I isoform b [Homo sapiens]; (1594:) deiodinase, iodothyronine, type I isoform c [Homo sapiens]; (1595:) deiodinase, iodothyronine, type I isoform d [Homo sapiens]; (1596:) deiodinase, iodothyronine, type II isoform a [Homo sapiens]; (1597:) deiodinase, iodothyronine, type II isoform b [Homo sapiens]; (1598:) deiodinase, iodothyronine, type III [Homo sapiens]; (1599:) "Delta 1-pyrroline-5-carboxylate synthetase (P5CS) (Aldehydedehydrogenase 18 family member A1) [Includes:) Glutamate 5-kinase (Gamma-glutamyl kinase) (GK); Gamma-glutamyl phosphate reductase (GPR) (Glutamate-5-semialdehyde dehydrogenase) (Glutamyl-gamma-semialdehyde dehydrogenase)]."; (1600:) delta 4-3-oxosteroid 5 beta-reductase [Homo sapiens]; (1601:) delta-aminolevulinate synthase (housekeeping) [Homo sapiens]; (1602:) Delta and Notch-like epidermal growth factor-related receptor precursor; (1603:) delta isoform of regulatory subunit B56, protein phosphatase 2A isoform 1 [Homo sapiens]; (1604:) delta isoform of regulatory subunit B56, protein phosphatase 2A isoform 2 [Homo sapiens]; (1605:) delta isoform of regulatory subunit B56, protein phosphatase 2A isoform 3 [Homo sapiens]; (1606:) Delta-1-pyrroline-5-carboxylate dehydrogenase, mitochondrial precursor (P5C dehydrogenase) (Aldehyde dehydrogenase 4A1); (1607:) delta3, delta2-enoyl-CoA isomerase; (1608:) Delta-4-3-oxosteroid 5beta reductase; (1609:) Delta-aminolevulinic acid dehydratase (Porphobilinogen synthase) (ALADH); (1610:) delta-aminolevulinic acid dehydratase isoform a [Homo sapiens]; (1611:) delta-amino; evulinic acid dehydratase isoform b [Homo sapiens]; (1612:) Delta-type opioid receptor (DOR-1); (1613:) deoxy-5'-nucleotidase [Homo sapiens]; (1614:) deoxycytidine kinase [Homo sapiens]; (1615:) Deoxycytidylate deaminase (dCMP deaminase); (1616:) deoxycytidylate deaminase; (1617:) deoxyguanosine kinase isoform a precursor [Homo sapiens]; (1618:) deoxyguanosine kinase isoform b precursor [Homo sapiens]; (1619:) Deoxyhypusine hydroxylase (Deoxyhypusine monooxygenase) (hDOHH) (HEAT-like repeat-containing protein 1); (1620:) Deoxyhypusine synthase (DHS); (1621:) deoxyhypusine synthase isoform a [Homo sapiens]; (1622:) deoxyhypusine synthase isoform b [Homo sapiens]; (1623:) deoxyhypusine synthase isoform c [Homo sapiens]; (1624:) deoxyhypusine synthase; (1625:) Deoxyribonuclease gamma precursor (DNase gamma) (DeoxyribonucleaseI-like 3) (DNase I homolog protein DHP2) (Liver and spleen DNase) (LS-DNase) (LSD); (1626:) deoxyribonuclease I precursor [Homo sapiens]; (1627:) deoxyribonuclease II, lysosomal precursor [Homo sapiens]; (1628:) deoxyribonuclease III (DNase III) [Homo sapiens]; (1629:) Deoxyribonuclease-2-alpha precursor (Deoxyribonuclease II alpha) (DNase II alpha) (Acid DNase) (Lysosomal DNase II) (R31240_2); (1630:) Deoxyuridine 5'-triphosphate nucleotidohydrolase, mitochondrial precursor (dUTPase) (dUTP pyrophosphatase); (1631:) de-ubiquitinase [Homo sapiens]; (1632:) deubiquitinating enzyme [Homo sapiens]; (1633:) deubiquitinating enzyme 1 [Homo sapiens]; (1634:) deubiquitinating enzyme 3 [Homo sapiens]; (1635:) deubiquitinating enzyme DUB1 [Homo sapiens]; (1636:) deubiquitinating enzyme DUB2 [Homo sapiens]; (1637:) deubiquitinating enzyme DUB4 [Homo sapiens]; (1638:) Deubiquitinating Enzyme Uch-L3 (Human) At 1.8 Angstrom Resolution; (1639:) Deubiquitinating protein VCIP135 (Valosin-containing protein p97/p47 complex-interacting protein p135) (Valosin-containing protein p97/p47 complex-interacting protein 1); (1640:) D-glucuronyl C5-epimerase [Homo sapiens]; (1641:) Diacylglycerol kinase alpha (Diglyceride kinase alpha) (DGK-alpha) (DAG kinase alpha) (80 kDa diacylglycerol kinase); (1642:) Diacylglycerol kinase beta (Diglyceride kinase beta) (DGK-beta) (DAG kinase beta) (90 kDa diacylglycerol kinase); (1643:) Diacylglycerol kinase delta (Diglyceride kinase delta) (DGK-delta) (DAG kinase delta) (130 kDa diacylglycerol kinase); (1644:) Diacylglycerol kinase gamma (Diglyceride kinase gamma) (DGK-gamma) (DAG kinase gamma); (1645:) diacylglycerol kinase gamma [Homo sapiens]; (1646:) Diacylglycerol kinase kappa (Diglyceride kinase kappa) (DGK-kappa) (DAG kinase kappa) (142 kDa diacylglycerol kinase); (1647:) diacylglycerol kinase, beta isoform 1 [Homo sapiens]; (1648:) diacylglycerol kinase, beta isoform 2 [Homo sapiens]; (1649:) diacylglycerol kinase, delta 130 kDa isoform 1 [Homo sapiens]; (1650:) diacylglycerol kinase, delta 130 kDa isoform 2 [Homo sapiens]; (1651:) diacylglycerol kinase, eta isoform 1 [Homo sapiens]; (1652:) diacylglycerol kinase, eta isoform 2 [Homo sapiens]; (1653:) diacylglycerol kinase, gamma 90 kDa [Homo sapiens]; (1654:) diacylglycerol kinase, iota [Homo sapiens]; (1655:) diacylglycerol O-acyltransferase 1 [Homo sapiens]; (1656:) Diacylglycerol O-acyltransferase 2 (Diglyceride acyltransferase 2); (1657:) diacylglycerol O-acyltransferase 2-like 4 [Homo sapiens]; (1658:) Diamine acetyltransferase 1 (Spermidine/spermine N(1)-acetyltransferase 1) (SSAT) (SSAT-1) (Putrescine acetyltransferase) (Polyamine N-acetyltransferase 1); (1659:) Diamine acetyltransferase 2 (Spermidine/spermine N(1)-acetyltransferase 2) (Polyamine N-acetyltransferase 2); (1660:) diamine oxidase, copper/topa quinone containing; (1661:) diamine oxidase; (1662:) dicarbonyl/L-xylulose reductase [Homo sapiens]; (1663:) dicer 1 [Homo sapiens]; (1664:) dihydrofolate reductase [Homo sapiens]; (1665:) Dihydrofolate reductase; (1666:) dihydrolipoamide acetyltransferase; (1667:) "dihydrolipoamide branched chain transacylase (E2 component of branched chain keto acid dehydrogenase complex; maple syrup urine disease) [Homo sapiens]."; (1668:) Dihydrolipoamide branched chain transacylase E2 [Homo sapiens]; (1669:) dihydrolipoamide branched chain transacylase precursor [Homo sapiens]; (1670:) dihydrolipoamide dehydrogenase precursor [Homo sapiens]; (1671:) dihydrolipoamide dehydrogenase-binding protein [Homo sapiens]; (1672:) dihydrolipoamide S-acetyltransferase (E2 component of pyruvate dehydrogenase complex) [Homo sapiens]; (1673:) dihydrolipoamide S-acetyltransferase (E2 component of pyruvate dehydrogenase complex) variant [Homo sapiens]; (1674:) dihydrolipoamide S-succinyltransferase (E2 component of 2-oxoglutarate complex) [Homo sapiens]; (1675:) dihydrolipoamide S-succinyltransferase (EC 2.3.1.61)-human; (1676:) dihydrolipoamide succinyltransferase [Homo sapiens]; (1677:) dihydrolipoamide succinyltransferase; (1678:) Dihydrolipoyl dehydrogenase, mitochondrial precursor (Dihydrolipoamide dehydrogenase) (Glycine cleavage system L protein); (1679:) dihydrolipoyl transacylase; (1680:) Dihydrolipoyllysine-residue acetyltransferase component of pyruvate dehydrogenase complex, mitochondrial precursor (Pyruvate dehydrogenase complex E2 subunit) (PDCE2) (E2) (Dihydrolipoamide S-acetyltransferase component of pyruvate dehydrogenase complex) (PDC-E2) (70 kDa mitochondrial autoantigen of primary biliary cirrhosis) (PBC) (M2 antigen complex 70 kDa subunit); (1681:) Dihydrolipoyllysine-residue succinyltransferase component of 2-oxoglutarate dehydrogenase complex, mitochondrial precursor (Dihydrolipoamide succinyltransferase component of 2-oxoglutarate dehydrogenase complex) (E2) (E2K); (1682:) dihydroorotate dehydrogenase isoform 1 precursor [Homo sapiens]; (1683:) dihydroorotate dehydrogenase isoform 2 precursor [Homo sapiens]; (1684:) Dihydroorotate dehydrogenase, mitochondrial precursor (Dihydroorotate oxidase) (DHOdehase); (1685:) Dihydropteridine reductase (HDHPR) (Quinoid dihydropteridine reductase); (1686:) dihydropyrimidine dehydrogenase [Homo sapiens]; (1687:) Dihydropyrimidine dehydrogenase [NADP+] precursor (DPD) (DHPDHase) (Dihydrouracil dehydrogenase) (Dihydrothymine dehydrogenase); (1688:) dihydropyrimidine dehydrogenase; (1689:) dimerization cofactor of hepatocyte nuclear factor 1 (HNF1) from muscle [Homo sapiens]; (1690:) dimethylaniline monooxygenase (N-oxide-forming) (EC 1.14.13.8), hepatic 2-human; (1691:) Dimethylaniline monooxygenase [N-oxide-forming] 5 (Hepaticflavin-containing monooxygenase 5) (FMO 5) (Dimethylaniline oxidase 5); (1692:) dimethylarginine dimethylaminohydrolase 1 [Homo sapiens]; (1693:) dimethylarginine dimethylaminohydrolase 2 [Homo sapiens]; (1694:) dimethylglycine dehydrogenase precursor [Homo sapiens]; (1695:) DIP2 disco-interacting protein 2 homolog B [Homo sapiens]; (1696:) DIP2 disco-interacting protein 2 homolog C (Drosophila) [Homo sapiens]; (1697:) DIP2 disco-interacting protein 2 homolog C [Homo sapiens]; (1698:) DIP2B protein [Homo sapiens]; (1699:) DIP2C protein [Homo sapiens]; (1700:) DIP2-like protein isoform a [Homo sapiens]; (1701:) dipeptidase 1 (renal) [Homo sapiens]; (1702:) Dipeptidase 1 precursor (Microsomal dipeptidase) (Renal dipeptidase) (hRDP) (Dehydropeptidase-1); (1703:) Dipeptidase 2 precursor; (1704:) Dipeptidase 3 precursor; (1705:) dipeptidyl peptidase 7 preproprotein [Homo sapiens]; (1706:) Dipeptidyl peptidase 8 (Dipeptidyl peptidase VIII) (DP8) (Prolyl dipeptidase DPP8) (Dipeptidyl peptidase IV-related protein 1) (DPRP-1); (1707:) dipeptidyl peptidase 8 [Homo sapiens]; (1708:) dipeptidyl peptidase 8 isoform 1 [Homo sapiens]; (1709:) dipeptidyl peptidase 8 isoform 2 [Homo sapiens]; (1710:) dipeptidyl peptidase 8 isoform 3 [Homo sapiens]; (1711:) dipeptidyl peptidase 8 isoform 4 [Homo sapiens]; (1712:) Dipeptidyl peptidase 9 (Dipeptidyl peptidase IX) (DP9) (Dipeptidylpeptidase-like protein 9) (DPLP9) (Dipeptidyl peptidase IV-related protein 2) (DPRP-2); (1713:) dipeptidyl peptidase III [Homo sapiens]; (1714:) dipeptidylpeptidase 9 [Homo sapiens]; (1715:) dipeptidylpeptidase IV [Homo sapiens]; (1716:) Diphosphoinositol polyphosphate phosphohydrolase 1 (DIPP-1) (Diadenosine 5',5'''-P1,P6-hexaphosphate hydrolase 1) (Nucleosidediphosphate-linked moiety X motif 3) (Nudix motif 3); (1717:) Diphosphoinositol polyphosphate phosphohydrolase 2 (DIPP-2) (Diadenosine 5',5'''-P1,P6-hexaphosphate hydrolase 2) (Nucleosidediphosphate-linked moiety X motif 4) (Nudix motif 4); (1718:) Diphosphoinositol polyphosphate phosphohydrolase 3 alpha (DIPP-3alpha) (DIPP3 alpha) (hDIPP3alpha) (Diadenosine-5',5'''-P1,P6-hexaphosphate hydrolase 3 alpha) (Nucleosidediphosphate-linked moiety X motif 10) (Nudix motif 10) (hAps2); (1719:) Diphosphoinositol polyphosphate phosphohydrolase 3 beta (DIPP-3beta) (DIPP3 beta) (hDIPP3beta) (Diadenosine-5', 5'''-P1,P6-hexaphosphate hydrolase 3 beta) (Nucleosidediphosphate-linked moiety X motif 11) (Nudix motif 11) (hAps1); (1720:) diphosphomevalonate decarboxylase [*Homo sapiens*]; (1721:) Discoidin domain-containing receptor 2 precursor (Discoidin domain receptor 2) (Receptor protein-tyrosine kinase TKT) (Tyrosine-protein kinase TYRO 10) (Neurotrophic tyrosine kinase, receptor-related 3) (CD167b antigen); (1722:) Disco-interacting protein 2 homolog A; (1723:) Disco-interacting protein 2 homolog C; (1724:) DLST [*Homo sapiens*]; (1725:) DNA (cytosine-5-)-methyltransferase 1 [*Homo sapiens*]; (1726:) DNA cytosine methyltransferase 3 alpha isoform a [*Homo sapiens*]; (1727:) DNA cytosine methyltransferase 3 alpha isoform b [*Homo sapiens*]; (1728:) DNA cytosine methyltransferase 3 alpha isoform c [*Homo sapiens*]; (1729:) DNA cytosine-5 methyltransferase 3 beta isoform 1 [*Homo sapiens*]; (1730:) DNA cytosine-5 methyltransferase 3 beta isoform 2 [*Homo sapiens*]; (1731:) DNA cytosine-5 methyltransferase 3 beta isoform 3 [*Homo sapiens*]; (1732:) DNA cytosine-5 methyltransferase 3 beta isoform 6 [*Homo sapiens*]; (1733:) DNA dC→dU-editing enzyme APOBEC-3F (Apolipoprotein B mRNA-editing enzyme catalytic polypeptide-like 3F); (1734:) DNA dC→dU-editing enzyme APOBEC-3G (APOBEC-related cytidine deaminase) (ARCD) (APOBEC-related protein) (ARP-9) (CEM15) (CEM-15); (1735:) DNA directed RNA polymerase II polypeptide A [*Homo sapiens*]; (1736:) DNA directed RNA polymerase II polypeptide B [*Homo sapiens*]; (1737:) DNA fragmentation factor subunit beta (DNA fragmentation factor 40 kDa subunit) (DFF-40) (Caspase-activated deoxyribonuclease) (Caspase-activated DNase) (CAD) (Caspase-activated nuclease) (CPAN); (1738:) DNA helicase II, HDH II=ATP-dependent DNA unwinding enzyme/Ku autoantigen large subunit {N-terminal} [human, HeLa cells, Peptide Partial, 19 aa]; (1739:) DNA ligase 3 (DNA ligase III) (Polydeoxyribonucleotide synthase [ATP] 3); (1740:) DNA ligase 4 (DNA ligase IV) (Polydeoxyribonucleotide synthase [ATP]-4); (1741:) DNA ligase I [*Homo sapiens*]; (1742:) DNA ligase III [*Homo sapiens*]; (1743:) DNA ligase IV [*Homo sapiens*]; (1744:) DNA mismatch repair protein [*Homo sapiens*]; (1745:) DNA mismatch repair protein homolog [*Homo sapiens*]; (1746:) DNA mismatch repair protein Mlh1 (MutL protein homolog 1); (1747:) DNA mismatch repair protein Mlh3 (MutL protein homolog 3); (1748:) DNA mismatch repair protein MLH3 [*Homo sapiens*]; (1749:) DNA mismatch repair protein; (1750:) DNA nucleotidylexotransferase (Terminal addition enzyme) (Terminal deoxynucleotidyl transferase) (Terminal transferase); (1751:) DNA polymerase beta; (1752:) DNA polymerase beta2 [*Homo sapiens*]; (1753:) DNA polymerase epsilon, catalytic subunit A (DNA polymerase II subunit A); (1754:) DNA polymerase lambda (Pol Lambda) (DNA polymerase kappa) (DNA polymerase beta-2) (Pol beta2); (1755:) DNA polymerase subunit alpha B (DNA polymerase alpha 70 kDa subunit); (1756:) DNA polymerase subunit gamma 2, mitochondrial precursor (Mitochondrial DNA polymerase accessory subunit) (PoIGbeta) (MtPoIB) (DNA polymerase gamma accessory 55 kDa subunit) (p55); (1757:) DNA polymerase theta [*Homo sapiens*]; (1758:) DNA primase large subunit, 58 kDa [*Homo sapiens*]; (1759:) DNA primase small subunit, 49 kDa [*Homo sapiens*]; (1760:) DNA repair enzyme; (1761:) DNA replication licensing factor MCM6 (p105MCM); (1762:) DNA topoisomerase 1 (DNA topoisomerase I); (1763:) DNA topoisomerase 2-alpha (DNA topoisomerase II, alpha isozyme); (1764:) DNA topoisomerase I [*Homo sapiens*]; (1765:) DNA topoisomerase 1, mitochondrial precursor (TOP1mt); (1766:) DNA topoisomerase II [*Homo sapiens*]; (1767:) DNA topoisomerase II, alpha isozyme [*Homo sapiens*]; (1768:) DNA topoisomerase II, beta isozyme [*Homo sapiens*]; (1769:) DNA-(apurinic or apyrimidinic site) lyase (AP endonuclease 1) (APEX nuclease) (APEN) (REF-1 protein); (1770:) DNA-3-methyladenine glycosylase (3-methyladenine DNA glycosidase) (ADPG) (3-alkyladenine DNA glycosylase) (N-methyl purine-DNA glycosylase); (1771:) DNA-binding protein [*Homo sapiens*]; (1772:) DNA-dependent protein kinase catalytic subunit (DNA-PK catalytic subunit) (DNA-PKcs) (DNPK1) (p460); (1773:) DNA-directed RNA polymerase II 19 kDa polypeptide (RPB7); (1774:) DNA-directed RNA polymerase III largest subunit (RPC155) (RPC1); (1775:) DNA-directed RNA polymerase III subunit C (DNA-directed III 62 kDa polypeptide) (RNA polymerase III C62 subunit) (RPC3); (1776:) DnaJ (Hsp40) homolog, subfamily B, member 6 isoform a [*Homo sapiens*]; (1777:) DnaJ (Hsp40) homolog, subfamily B, member 6 isoform b [*Homo sapiens*]; (1778:) docking protein 1 [*Homo sapiens*]; (1779:) dodecenoyl-CoA delta-isomerase [*Homo sapiens*]; (1780:) dodecenoyl-Coenzyme A delta isomerase precursor [*Homo sapiens*]; (1781:) dolichol monophosphate mannose synthase [*Homo sapiens*]; (1782:) Dolichol-phosphate mannosyltransferase (Dolichol-phosphate mannosesynthase) (Dolichyl-phosphate beta-D-mannosyltransferase) (Mannose-P-dolichol synthase) (MPD synthase) (DPM synthase); (1783:) Dolichyl-diphosphooligosaccharide—protein glycosyltransferase 48 kDa subunit precursor (Oligosaccharyl transferase 48 kDa subunit) (DDOST 48 kDa subunit); (1784:) Dolichyl-diphosphooligosaccharide—protein glycosyltransferase 63 kDa subunit precursor (Ribophorin II) (RPN-II) (RIBIIR); (1785:) Dolichyl-diphosphooligosaccharide—protein glycosyltransferase 67 kDa subunit precursor (Ribophorin I) (RPN-I); (1786:) Dolichyl-diphosphooligosaccharide—protein glycosyltransferase subunit DAD1 (Oligosaccharyl transferase subunit DAD1) (Defender against cell death 1) (DAD-1); (1787:) Dolichyl-diphosphooligosaccharide—protein glycosyltransferase subunit STT3A (Oligosaccharyl transferase subunit STT3A) (STT3-A) (B5) (Integral membrane protein 1) (TMC); (1788:) Dolichyl-diphosphooligosaccharide—protein glycosyltransferase subunit STT3B (Oligosaccharyl transferase subunit STT3B) (STT3-B) (Source of immunodominant MHC-associated peptides homolog); (1789:) dolichyl-phosphate mannosyltransferase polypeptide 1 [*Homo sapiens*]; (1790:) dolichyl-phosphate mannosyltransferase polypeptide 2, regulatory subunit [*Homo sapiens*]; (1791:) dolichyl-phosphate mannosyltransferase polypeptide 3 isoform 1 [*Homo sapiens*]; (1792:) dolichyl-phosphate mannosyltransferase polypeptide 3 isoform 2 [*Homo sapiens*]; (1793:) DOLPP1 protein [*Homo sapiens*]; (1794:) dopa decarboxylase (aromatic L-amino acid decarboxylase) [*Homo sapiens*]; (1795:) dopachrome tautomerase (dopachrome delta-isomerase, tyrosine-related protein 2) [*Homo sapiens*]; (1796:) Dopamine beta-hydroxylase precursor (Dopamine beta-monooxygenase); (1797:) dopamine beta-hydroxylase precursor [*Homo sapiens*]; (1798:) double-stranded RNA adenosine deaminase; (1799:) Double-stranded RNA-specific adenosine deaminase (DRADA) (136 kDa double-stranded RNA-binding protein) (P136) (K88DSRBP) (Interferon-inducible protein 4) (IFI-4 protein); (1800:) Double-stranded RNA-specific editase 1 (dsRNA adenosine deaminase) (RNA-editing deaminase 1) (RNA-editing enzyme 1); (1801:) Double-stranded RNA-specific editase B2 (dsRNA adenosine deaminase B2) (RNA-dependent adenosine deaminase 3) (RNA-editing deaminase 2) (RNA-editing enzyme 2); (1802:) Drug-Protein Interactions:) Structure Of Sulfonamide Drug Complexed With Human Carbonic Anhydrase I; (1803:) dsRNA adenosine deaminase DRADA2a [*Homo sapiens*]; (1804:) dsRNA adenosine deaminase DRADA2b [*Homo sapiens*]; (1805:) dsRNA adenosine deaminase DRADA2c [*Homo sapiens*]; (1806:) Dual 3',5'-cyclic-AMP and -GMP phosphodiesterase 11A (cAMP and cGMP phosphodiesterase 11A); (1807:) Dual oxidase 1 precursor (NADPH thyroid oxidase 1) (Thyroid oxidase 1) (Large NOX 1) (Long NOX 1); (1808:) Dual oxidase 2 precursor (NADPH oxidase/peroxidase DUOX2) (NADPH thyroid oxidase 2) (Thyroid oxidase 2) (NADH/NADPH thyroid oxidase p138-tox) (p138 thyroid oxidase) (Large NOX 2) (Long NOX 2); (1809:) Dual specificity mitogen-activated protein kinase kinase 1 (MAPkinase kinase 1) (MAPKK 1) (ERK activator kinase 1) (MAPK/ERK kinase 1) (MEK1); (1810:) Dual specificity mitogen-activated protein kinase kinase 3 (MAPkinase kinase 3) (MAPKK 3) (MAPK/ERK kinase 3); (1811:) Dual specificity mitogen-activated protein kinase kinase 6 (MAPkinase kinase 6) (MAPKK 6) (MAPK/ERK kinase 6) (SAPKK3); (1812:) Dual specificity protein phosphatase 18 (Low molecular weight dual specificity phosphatase 20); (1813:) Dual specificity protein phosphatase 23 (Low molecular mass dual specificity phosphatase 3) (LDP-3) (VH1-like phosphatase Z); (1814:) Dual specificity testis-specific protein kinase 1 (Testicular protein kinase 1); (1815:) Dual specificity testis-specific protein kinase 2 (Testicular protein kinase 2); (1816:) Dual specificity tyrosine-phosphorylation-regulated kinase 1A (Protein kinase minibrain homolog) (MNBH) (HP86) (Dual specificity YAK1-related kinase); (1817:) Dual specificity tyrosine-phosphorylation-regulated kinase 1B (Mirk protein kinase) (Minibrain-related kinase); (1818:) Dual specificity tyrosine-phosphorylation-regulated kinase 2; (1819:) Duffy antigen/chemokine receptor (Fy glycoprotein) (GpFy) (Glycoprotein D) (*Plasmodium vivax* receptor) (CD234 antigen); (1820:) dUTP pyrophosphatase isoform 1 precursor [*Homo sapiens*]; (1821:) dUTP pyrophosphatase isoform 2 [*Homo sapiens*]; (1822:) dUTP pyrophosphatase isoform 3 [*Homo sapiens*]; (1823:) dUTP pyrophosphatase; (1824:) dynamin 1 isoform 1 [*Homo sapiens*]; (1825:) dynamin 1 isoform 2 [*Homo sapiens*]; (1826:) Dynamin-1-like protein (Dynamin-like protein) (Dnm1p/Vps1p-like protein) (DVLP) (Dynamin family member proline-rich carboxyl-terminal domain less) (Dymple) (Dynamin-related protein 1) (Dynamin-like protein 4) (Dynamin-like protein IV) (HdynIV); (1827:) dynein light chain 1 [*Homo sapiens*]; (1828:) dystonin isoform 1 [*Homo sapiens*]; (1829:) dystonin isoform 1e precursor [*Homo sapiens*]; (1830:) dystonin isoform 1eA precursor [*Homo sapiens*]; (1831:) dystonin isoform 1eB precursor [*Homo sapiens*]; (1832:) E-1 enzyme [*Homo sapiens*]; (1833:) E1A binding protein p300 [*Homo sapiens*]; (1834:) E1A-associated protein p300; (1835:) E2 protein [*Homo sapiens*]; (1836:) E2 ubiquitin-conjugating enzyme [*Homo sapiens*]; (1837:) E2F transcription factor 2 [*Homo sapiens*]; (1838:) E3 ubiquitin ligase IBRDC2 (IBR domain-containing protein 2) (p53-inducible RING finger protein); (1839:) E3 ubiquitin ligase TRIAD3 (Ubiquitin-conjugating enzyme7-interacting protein 1) (Zinc finger protein inhibiting NF-kappa-B) (Triad domain-containing protein 3); (1840:) E3 ubiquitin protein ligase TRAF7 (TNF receptor-associated factor 7) (RING finger and WD repeat domain protein 1) (RING finger protein 119); (1841:) E3 ubiquitin-protein ligase CBL (Signal transduction protein CBL) (Proto-oncogene c-CBL) (Casitas B-lineage lymphoma proto-oncogene) (RING finger protein 55); (1842:) E3 ubiquitin-protein ligase CBL-B (Signal transduction protein CBL-B) (SH3-binding protein CBL-B) (Casitas B-lineage lymphoma proto-oncogene b) (RING finger protein 56); (1843:) E3 ubiquitin-protein ligase HECTD1 (HECT domain-containing protein1) (E3 ligase for inhibin receptor) (EULIR); (1844:) E3 ubiquitin-protein ligase NEDD4; (1845:) E3 ubiquitin-protein ligase NEDD4-like protein (Nedd-4-2) (NEDD4.2); (1846:) early growth response 1 [*Homo sapiens*]; (1847:) EBV-induced G-protein coupled receptor 2 (EBI2); (1848:) ECE-1 [*Homo sapiens*]; (1849:) ectonucleoside triphosphate diphosphohydrolase 2 isoform 1 [*Homo sapiens*]; (1850:) ectonucleoside triphosphate diphosphohydrolase 2 isoform 2 [*Homo sapiens*]; (1851:) "Ectonucleotide pyrophosphatase/phosphodiesterase 1 (E-NPP 1) (Phosphodiesterase I/nucleotide pyrophosphatase 1) (Plasma-cell membrane glycoprotein PC-1) [Includes:) Alkaline phosphodiesterase I; Nucleotide pyrophosphatase (NPPase)]."; (1852:) Ectonucleotide pyrophosphatase/phosphodiesterase 6 precursor (E-NPP6) (NPP-6) [Contains:) Ectonucleotide pyrophosphatase/phosphodiesterase 6 soluble form]; (1853:) ectonucleotide pyrophosphatase/phosphodiesterase 7 [*Homo sapiens*]; (1854:) Ectonucleotide pyrophosphatase/phosphodiesterase 7 precursor (E-NPP7) (NPP-7) (Alkaline sphingomyelin phosphodiesterase) (Intestinal alkaline sphingomyelinase) (Alk-SMase); (1855:) EGF, latrophilin and seven transmembrane domain-containing protein1 precursor (EGF-TM7-latrophilin-related protein) (ETL protein); (1856:) EGF-like module-containing mucin-like hormone receptor-like 1 precursor (Cell surface glycoprotein EMR1) (EMR1 hormone receptor); (1857:) EGF-like module-containing mucin-like hormone receptor-like 2precursor (EGF-like module EMR2) (CD312 antigen); (1858:) EGF-like module-containing mucin-like hormone receptor-like 3precursor (EGF-like module-containing mucin-like receptor EMR3); (1859:) EGF-like module-containing mucin-like hormone receptor-like 4precursor (G-protein coupled receptor 127); (1860:) EGL nine (*C. elegans*) homolog 2 isoform 1 [*Homo sapiens*]; (1861:) EGL nine (*C. elegans*) homolog 2 isoform 2 [*Homo sapiens*]; (1862:) EGL nine (*C. elegans*) homolog 2 isoform 3 [*Homo sapiens*]; (1863:) Egl nine homolog 1 (Hypoxia-inducible factor prolyl hydroxylase 2) (HIF-prolyl hydroxylase 2) (HIF-PH2) (HPH-2) (Prolyl hydroxylase domain-containing protein 2) (PHD2) (SM-20); (1864:) Egl nine homolog 3 (Hypoxia-inducible factor prolyl hydroxylase 3) (HIF-prolyl hydroxylase 3) (HIF-PH3) (HPH-1) (Prolyl hydroxylase domain-containing protein 3) (PHD3); (1865:) elastase 1, pancreatic [*Homo sapiens*]; (1866:) elastase 2, neutrophil preproprotein [*Homo sapiens*]; (1867:) elastase isozyme 4, HSE I-4 [human, sputum, Peptide Partial, 21aa]; (1868:) ELAV-like 1 [*Homo sapiens*]; (1869:) Electrogenic sodium bicarbonate cotransporter 1 (Sodium bicarbonate cotransporter) (Na(+)/HCO3(−) cotransporter) (Solute carrier family 4 member 4) (kNBC1); (1870:) Elongation factor 2 kinase (eEF-2 kinase) (eEF-2K) (Calcium/calmodulin-dependent eukaryotic elongation factor 2kinase); (1871:) elongin B [*Homo sapiens*]; (1872:) elongin B isoform a [Homo sapiens]; (1873:) elongin B isoform b [Homo sapiens]; (1874:) elongin C [Homo sapiens]; (1875:) endo-beta-N-acetylglucosaminidase [Homo sapiens]; (1876:) endonuclease III [Homo sapiens]; (1877:) Endonuclease III-like protein 1; (1878:) Endonuclease VIII-like 2 (Nei-like 2) (DNA glycosylase/AP lyase Neil2) (DNA-(apurinic or apyrimidinic site) lyase Neil2) (NEH2); (1879:) endopeptidase La homolog (EC 3.4.21.-) precursor, mitochondrial (version 2)-human; (1880:) endoplasmic reticulum alpha-mannosidase I [Homo sapiens]; (1881:) Endoplasmic reticulum mannosyl-oligosaccharide 1,2-alpha-mannosidase (ER alpha-1,2-mannosidase) (Mannosidase alpha class 1B member 1) (Man9GlcNAc2-specific-processing alpha-mannosidase); (1882:) endothelial cell growth factor 1 (platelet-derived) [Homo sapiens]; (1883:) Endothelial cells scavenger receptor precursor (Acetyl LDL receptor) (Scavenger receptor class F member 1); (1884:) Endothelial lipase precursor (Endothelial cell-derived lipase) (EDL) (EL); (1885:) Endothelial protein C receptor precursor (Endothelial cell protein C receptor) (Activated protein C receptor) (APC receptor) (CD201 antigen); (1886:) endothelin 1 [Homo sapiens]; (1887:) endothelin 3 isoform 1 preproprotein [Homo sapiens]; (1888:) endothelin 3 isoform 2 preproprotein [Homo sapiens]; (1889:) endothelin 3 isoform 3 preproprotein [Homo sapiens]; (1890:) Endothelin B receptor precursor (ET-B) (Endothelin receptor Non-selective type); (1891:) Endothelin B receptor-like protein 2 precursor (ETBR-LP-2) (G-protein coupled receptor 37-like 1); (1892:) endothelin converting enzyme [Homo sapiens]; (1893:) endothelin converting enzyme 1 [Homo sapiens]; (1894:) endothelin converting enzyme 1 isoform 1c [Homo sapiens]; (1895:) endothelin converting enzyme 2 isoform A [Homo sapiens]; (1896:) endothelin converting enzyme 2 isoform B [Homo sapiens]; (1897:) endothelin converting enzyme-1 [Homo sapiens]; (1898:) endothelin converting enzyme-2A [Homo sapiens]; (1899:) endothelin converting enzyme-2B [Homo sapiens]; (1900:) endothelin converting enzyme-like 1 [Homo sapiens]; (1901:) endothelin receptor type A [Homo sapiens]; (1902:) endothelin receptor type β isoform 1 [Homo sapiens]; (1903:) endothelin receptor type β isoform 2 [Homo sapiens]; (1904:) Endothelin-1 receptor precursor (Endothelin A receptor) (ET-A) (hET-AR) (ETA-R); (1905:) endothelin-converting enzyme [Homo sapiens]; (1906:) Endothelin-converting enzyme 1 (ECE-1); (1907:) Endothelin-converting enzyme 2 (ECE-2); (1908:) endothelin-converting enzyme 2B [Homo sapiens]; (1909:) endothelin-converting enzyme, isoform ECE-1a [Homo sapiens]; (1910:) endothelin-converting enzyme, isoform ECE-1b [Homo sapiens]; (1911:) endothelin-converting enzyme; (1912:) endothelin-converting enzyme-1c [Homo sapiens]; (1913:) endothelin-converting enzyme-2C [Homo sapiens]; (1914:) Endothelin-converting enzyme-like 1 (Xce protein); (1915:) endothelin-converting-enzyme 1 [Homo sapiens]; (1916:) endotheline-converting enzyme ECEL1 [Homo sapiens]; (1917:) enolase 1 [Homo sapiens]; (1918:) enolase 2 [Homo sapiens]; (1919:) enolase 3 [Homo sapiens]; (1920:) enoyl-CoA hydratase:) 3-hydroxyacyl-CoA dehydrogenase; (1921:) enoyl-Coenzyme A, hydratase/3-hydroxyacyl Coenzyme A dehydrogenase[Homo sapiens]; (1922:) enterocyte differentiation associated factor EDAF-1 [Homo sapiens]; (1923:) enterokinase precursor [Homo sapiens]; (1924:) enyol-CoA:) hydratase/3-hydroxyacyl-CoA dehydrogenase; (1925:) eosinophil serine protease [Homo sapiens]; (1926:) eosinophil serine protease 1 splicing variant [Homo sapiens]; (1927:) ephrin receptor EphB2 isoform 1 precursor [Homo sapiens]; (1928:) ephrin receptor EphB2 isoform 2 precursor [Homo sapiens]; (1929:) Ephrin type-A receptor 1 precursor (Tyrosine-protein kinase receptor EPH); (1930:) Ephrin type-A receptor 10 precursor; (1931:) Ephrin type-A receptor 2 precursor (Tyrosine-protein kinase receptor ECK) (Epithelial cell kinase); (1932:) Ephrin type-A receptor 3 precursor (Tyrosine-protein kinase receptor ETK1) (HEK) (HEK4); (1933:) Ephrin type-A receptor 4 precursor (Tyrosine-protein kinase receptor SEK) (Receptor protein-tyrosine kinase HEK8); (1934:) Ephrin type-A receptor 5 precursor (Tyrosine-protein kinase receptor EHK-1) (EPH homology kinase 1) (Receptor protein-tyrosine kinase HEK7); (1935:) Ephrin type-A receptor 6 precursor (Tyrosine-protein kinase receptor EHK-2) (EPH homology kinase 2); (1936:) Ephrin type-A receptor 7 precursor (Tyrosine-protein kinase receptor EHK-3) (EPH homology kinase 3) (Receptor protein-tyrosine kinase HEK11); (1937:) Ephrin type-A receptor 8 precursor (Tyrosine-protein kinase receptor EEK) (EPH- and ELK-related kinase) (HEK3); (1938:) Ephrin type-B receptor 1 precursor (Tyrosine-protein kinase receptor EPH-2) (NET) (HEK6) (ELK); (1939:) Ephrin type-B receptor 2 precursor (Tyrosine-protein kinase receptor EPH-3) (DRT) (Receptor protein-tyrosine kinase HEK5) (ERK) (NY-REN-47 antigen); (1940:) Ephrin type-B receptor 3 precursor (Tyrosine-protein kinase receptor HEK-2); (1941:) Ephrin type-B receptor 4 precursor (Tyrosine-protein kinase receptor HTK); (1942:) Ephrin type-B receptor 6 precursor (Tyrosine-protein kinase-defective receptor EPH-6) (HEP); (1943:) epidermal growth factor (beta-urogastrone) [Homo sapiens]; (1944:) epidermal growth factor receptor isoform a [Homo sapiens]; (1945:) epidermal growth factor receptor isoform b [Homo sapiens]; (1946:) epidermal growth factor receptor isoform c [Homo sapiens]; (1947:) epidermal growth factor receptor isoform d [Homo sapiens]; (1948:) epidermal growth factor receptor pathway substrate 15 [Homo sapiens]; (1949:) Epidermal growth factor receptor precursor (Receptor tyrosine-protein kinase ErbB-1); (1950:) Epithelial discoidin domain-containing receptor 1 precursor (Epithelial discoidin domain receptor 1) (Tyrosine kinase DDR) (Discoidin receptor tyrosine kinase) (Tyrosine-protein kinase CAK) (Cell adhesion kinase) (TRK E) (Protein-tyrosine kinase RTK 6) (HGK2) (CD167a antigen); (1951:) Epoxide hydrolase 1 (Microsomal epoxide hydrolase) (Epoxidehydratase); (1952:) Epoxide hydrolase 2 (Soluble epoxide hydrolase) (SEH) (Epoxidehydratase) (Cytosolic epoxide hydrolase) (CEH); (1953:) epoxide hydrolase 2, cytoplasmic [Homo sapiens]; (1954:) epsilon isoform of regulatory subunit B56, protein phosphatase 2A[Homo sapiens]; (1955:) epsilon-trimethyllysine 2-oxoglutarate dioxygenase [Homo sapiens]; (1956:) ER lumen protein retaining receptor 1 (KDEL receptor 1) (KDEL endoplasmic reticulum protein retention receptor 1) (Putative MAPK-activating protein PM23); (1957:) ER lumen protein retaining receptor 2 (KDEL receptor 2) (KDEL endoplasmic reticulum protein retention receptor 2) (ERD2-like protein 1) (ELP-1); (1958:) ER lumen protein retaining receptor 3 (KDEL receptor 3) (KDEL endoplasmic reticulum protein retention receptor 3); (1959:) ERO1-like protein alpha precursor (ERO1-L alpha) (Oxidoreductin-1-L alpha) (Endoplasmic oxidoreductin-1-like protein) (ERO1-L); (1960:) ERO1-like protein beta precursor (ERO1-L beta) (Oxidoreductin-1-L beta) (Endoplasmic oxidoreductin-1-like protein B); (1961:) erythrocyte acylphosphatase 1 isoform a [Homo sapiens]; (1962:) erythrocyte acylphosphatase 1 isoform b [Homo sapiens]; (1963:) erythrocyte adenosine monophosphate deaminase isoform 1A [Homo sapiens]; (1964:) erythrocyte adenosine monophosphate deaminase isoform 1B [Homo sapiens]; (1965:) erythrocyte adenosine monophosphate deaminase isoform 1C [Homo sapiens]; (1966:) Erythropoietin receptor precursor (EPO-R); (1967:) estradiol 17 beta-dehydrogenase 8 [Homo sapiens]; (1968:) Estradiol 17-beta-dehydrogenase 1 (17-beta-hydroxysteroid dehydrogenase type 1) (17-beta-HSD1) (Placental 17-beta-hydroxysteroid dehydrogenase) (20 alpha-hydroxysteroid dehydrogenase) (20-alpha-HSD) (E2DH); (1969:) Estradiol 17-beta-dehydrogenase 12 (17-beta-HSD 12) (17-beta-hydroxysteroid dehydrogenase 12) (3-ketoacyl-CoA reductase) (KAR); (1970:) Estradiol 17-beta-dehydrogenase 2 (17-beta-HSD 2) (Microsomal 17-beta-hydroxysteroid dehydrogenase) (20 alpha-hydroxysteroid dehydrogenase) (20-alpha-HSD) (E2DH); (1971:) Estrogen receptor (ER) (Estradiol receptor) (ER-alpha); (1972:) Estrogen receptor beta (ER-beta); (1973:) estrogen-related receptor alpha [Homo sapiens]; (1974:) Estrogen-related receptor gamma (Estrogen receptor-related protein3) (ERR gamma-2); (1975:) ethanolamine kinase 1 isoform A [Homo sapiens]; (1976:) ethanolamine kinase 1 isoform B [Homo sapiens]; (1977:) ets variant gene 6 [Homo sapiens]; (1978:) Eukaryotic translation initiation factor 2-alpha kinase 1 (Heme-regulated eukaryotic initiation factor eIF-2-alpha kinase) (Heme-regulated inhibitor) (Heme-controlled repressor) (HCR) (Hemin-sensitive initiation factor 2-alpha kinase); (1979:) eukaryotic translation initiation factor 2-alpha kinase 2 [Homo sapiens]; (1980:) Eukaryotic translation initiation factor 2-alpha kinase 3 precursor (PRKR-like endoplasmic reticulum kinase) (Pancreatic eIF2-alpha kinase) (HsPEK); (1981:) Eukaryotic translation initiation factor 4 gamma 2 (eIF-4-gamma 2) (eIF-4G 2) (eIF4G 2) (p97) (Death-associated protein 5) (DAP-5); (1982:) evolutionarily related interleukin-1 beta converting enzyme [Homo sapiens]; (1983:) Exostosin-like 2 (Glucuronyl-galactosyl-proteoglycan-4-alpha-N-acetylglucosaminyltransferase) (Alpha-1,4-N-acetylhexosaminyltransferase EXTL2) (Alpha-GalNAcTEXTL2) (EXT-related protein 2); (1984:) Extracellular calcium-sensing receptor precursor (CaSR) (Parathyroid Cell calcium-sensing receptor); (1985:) FAD synthetase isoform 1 [Homo sapiens]; (1986:) FAD1 flavin adenine dinucleotide synthetase homolog (S. cerevisiae)[Homo sapiens]; (1987:) FADD-homologous ICE/CED-3-like protease [Homo sapiens]; (1988:) FAD-synthetase (PP591) [Homo sapiens]; (1989:) FAD-synthetase [Homo sapiens]; (1990:) FAM80B protein [Homo sapiens]; (1991:) Family with sequence similarity 80, member A [Homo sapiens]; (1992:) Family with sequence similarity 80, member B [Homo sapiens]; (1993:) Fanconi anemia complementation group D2 isoform a [Homo sapiens]; (1994:) Fanconi anemia complementation group D2 isoform b [Homo sapiens]; (1995:) Fanconi anemia group D2 protein (Protein FACD2); (1996:) Fanconi anemia, complementation group G [Homo sapiens]; (1997:) Far upstream element-binding protein 2 (FUSE-binding protein 2) (KH type-splicing regulatory protein) (KSRP) (p75); (1998:) farnesyl diphosphate synthase [Homo sapiens]; (1999:) farnesylated-proteins converting enzyme 1 [Homo sapiens]; (2000:) farnesylated-proteins converting enzyme 2 [Homo sapiens]; (2001:) farnesyl-diphosphate farnesyltransferase 1 [Homo sapiens]; (2002:) Fas-associated death domain protein interleukin-1b-converting enzyme 2 [Homo sapiens]; (2003:) Fas-associated via death domain [Homo sapiens]; (2004:) fatty acid amide hydrolase [Homo sapiens]; (2005:) fatty acid CoA ligase-like AMP-binding enzyme [Homo sapiens]; (2006:) fatty acid coenzyme A ligase 5 [Homo sapiens]; (2007:) fatty acid desaturase 2 [Homo sapiens]; (2008:) fatty acid omega-hydroxylase (cytochrome P450 4A); (2009:) fatty acid synthase [Homo sapiens]; (2010:) fatty-acid-Coenzyme A ligase, long-chain 5 [Homo sapiens]; (2011:) FBP2 [Homo sapiens]; (2012:) Fc receptor-like protein 2 precursor (SH2 domain-containing phosphatase anchor protein 1) (Fc receptor homolog 2) (FcRH2) (Immunoglobulin receptor translocation-associated 4 protein); (2013:) Fc receptor-like protein 5 precursor (Immunoglobulin receptor translocation-associated gene 2 protein) (BXMAS1) (CD307 antigen); (2014:) Feline leukemia virus subgroup C receptor-related protein 1 (Feline leukemia virus subgroup C receptor) (hFLVCR); (2015:) ferredoxin 1 precursor [Homo sapiens]; (2016:) ferredoxin reductase isoform 1 precursor [Homo sapiens]; (2017:) ferredoxin reductase isoform 2 precursor [Homo sapiens]; (2018:) Ferrochelatase (protoporphyria) [Homo sapiens]; (2019:) ferrochelatase [Homo sapiens]; (2020:) ferrochelatase isoform a precursor [Homo sapiens]; (2021:) ferrochelatase isoform b precursor [Homo sapiens]; (2022:) ferrochelatase precursor [Homo sapiens]; (2023:) Ferrochelatase, mitochondrial precursor (Protoheme ferro-lyase) (Heme synthetase); (2024:) fibrinogen, alpha polypeptide isoform alpha preproprotein [Homo sapiens]; (2025:) fibrinogen, alpha polypeptide isoform alpha-E preproprotein [Homo sapiens]; (2026:) fibroblast activation protein, alpha subunit [Homo sapiens]; (2027:) fibroblast growth factor 23 precursor [Homo sapiens]; (2028:) Fibroblast growth factor receptor 2 precursor (FGFR-2) (Keratinocyte growth factor receptor 2) (CD332 antigen); (2029:) Fibroblast growth factor receptor 3 precursor (FGFR-3) (CD333antigen); (2030:) Fibroblast growth factor receptor 4 precursor (FGFR-4) (CD334antigen); (2031:) Fibroblast growth factor receptor-like 1 precursor (FGF receptor-like protein 1) (Fibroblast growth factor receptor 5) (FGFR-like protein) (FGF homologous factor receptor); (2032:) fibronectin 1 isoform 1 preproprotein [Homo sapiens]; (2033:) fibronectin 1 isoform 2 preproprotein [Homo sapiens]; (2034:) fibronectin 1 isoform 3 preproprotein [Homo sapiens]; (2035:) fibronectin 1 isoform 4 preproprotein [Homo sapiens]; (2036:) fibronectin 1 isoform 5 preproprotein [Homo sapiens]; (2037:) fibronectin 1 isoform 6 preproprotein [Homo sapiens]; (2038:) fibronectin 1 isoform 7 preproprotein [Homo sapiens]; (2039:) Fk506 And Rapamycin-Binding Protein (Fkbp12) (Nmr, 20 Structures); (2040:) Fk506 And Rapamycin-Binding Protein (Fkbp12) (Nmr, Minimized Average Structure Excluding Electrostatic Interactions); (2041:) Fk506 And Rapamycin-Binding Protein (Fkbp12) (Nmr, Minimized Average Structure); (2042:) FK506 binding protein 12-rapamycin associated protein 1 [Homo sapiens]; (2043:) FK506 binding protein 5 [Homo sapiens]; (2044:) FK506-binding protein 10 precursor (Peptidyl-prolyl cis-transisomerase) (PPIase) (Rotamase) (65 kDa FK506-binding protein) (FKBP65) (Immunophilin FKBP65); (2045:) FK506-binding protein 1A (Peptidyl-prolyl cis-trans isomerase) (PPIase) (Rotamase) (12 kDa FKBP) (FKBP-12) (Immunophilin FKBP12); (2046:) FK506-binding protein 1A [Homo sapiens]; (2047:) FK506-binding protein 1B (Peptidyl-prolyl cis-trans isomerase 1B) (PPIase 1B) (Rotamase 1B) (12.6 kDa FKBP) (FKBP-12.6) (Immunophilin FKBP12.6) (h-FKBP-12); (2048:) FK506-binding protein 1B isoform a [Homo sapiens]; (2049:) FK506-binding protein 1B isoform b [Homo sapiens]; (2050:) FK506-binding protein 2 precursor (Peptidyl-prolyl cis-transisomerase) (PPIase) (Rotamase) (13 kDa FKBP) (FKBP-13); (2051:) FK506-binding protein 3 (Peptidyl-prolyl cis-trans isomerase) (PPIase) (Rotamase) (25 kDa FKBP) (FKBP-25) (Rapamycin-selective 25 kDa immunophilin); (2052:) FK506-binding protein 4 [Homo sapiens]; (2053:) FK506-binding protein 5 (Peptidyl-prolyl cis-trans isomerase) (PPIase) (Rotamase) (51 kDa FK506-binding protein) (FKBP-51) (54 kDa progesterone receptor-associated immunophilin) (FKBP54) (P54) (FF1 antigen) (HSP90-binding immunophilin) (Androgen-regulated protein 6); (2054:) FK506-binding protein 6 [Homo sapiens]; (2055:) FK506-binding protein 9 precursor (Peptidyl-prolyl cis-transisomerase) (PPIase) (Rotamase); (2056:) FL cytokine receptor precursor (Tyrosine-protein kinase receptor FLT3) (Stem cell tyrosine kinase 1) (STK-1) (CD135 antigen); (2057:) FLAD1 protein [Homo sapiens]; (2058:) FLAME-1 [Homo sapiens]; (2059:) FLAME-1-beta [Homo sapiens]; (2060:) FLAME-1-delta [Homo sapiens]; (2061:) FLAME-1-gamma [Homo sapiens]; (2062:) flap structure-specific endonuclease 1 [Homo sapiens]; (2063:) flavin adenine dinucleotide synthetase isoform 1 [Homo sapiens]; (2064:) flavin adenine dinucleotide synthetase isoform 2 [Homo sapiens]; (2065:) flavin containing monooxygenase 1 [Homo sapiens]; (2066:) flavin containing monooxygenase 2 (non-functional) [Homo sapiens]; (2067:) flavin containing monooxygenase 4 [Homo sapiens]; (2068:) flavin containing monooxygenase 5 [Homo sapiens]; (2069:) Flavin reductase (FR) (NADPH-dependent diaphorase) (NADPH-flavin reductase) (FLR) (Biliverdin reductase B) (BVR-B) (Biliverdin-IX beta-reductase) (Green heme-binding protein) (GHBP); (2070:) FLICE-like inhibitory protein long form [Homo sapiens]; (2071:) FLJ00013 protein [Homo sapiens]; (2072:) FLJ00207 protein [Homo sapiens]; (2073:) FLJ00405 protein [Homo sapiens]; (2074:) FLJ11011 [Homo sapiens]; (2075:) FLJ12389 protein [Homo sapiens]; (2076:) FLJ13855 [Homo sapiens]; (2077:) FLJ20581 protein [Homo sapiens]; (2078:) FLJ21963 protein [Homo sapiens]; (2079:) fMet-Leu-Phe receptor (fMLP receptor) (N-formyl peptide receptor) (FPR) (N-formyl peptide chemoattractant receptor); (2080:) FMLP-related receptor I (FMLP-R-I) (Lipoxin A4 receptor) (LXA4receptor) (Formyl peptide receptor-like 1) (RFP) (HM63); (2081:) FMLP-related receptor 11 (FMLP-R-II) (Formylpeptide receptor-like2); (2082:) fms-related tyrosine kinase 1 (vascular endothelial growth factor/vascular permeability factor receptor) [Homo sapiens]; (2083:) folate hydrolase 1 isoform 1 [Homo sapiens]; (2084:) folate hydrolase 1 isoform 2 [Homo sapiens]; (2085:) Folate receptor alpha precursor (FR-alpha) (Folate receptor 1) (Folate receptor, adult) (Adult folate-binding protein) (FBP) (Ovarian tumor-associated antigen MOv18) (KB cells FBP); (2086:) Folate receptor beta precursor (FR-beta) (Folate receptor 2) (Folate receptor, fetal/placental) (Placental folate-binding protein) (FBP); (2087:) Folate receptor gamma precursor (FR-gamma) (Folate receptor 3); (2088:) Follicle-stimulating hormone receptor precursor (FSH-R) (Follitropin receptor); (2089:) folylpolyglutamate synthase isoform a precursor [Homo sapiens]; (2090:) folylpolyglutamate synthase isoform b [Homo sapiens]; (2091:) Folylpolyglutamate synthase, mitochondrial precursor (Folylpoly-gamma-glutamate synthetase) (FPGS) (Tetrahydrofolatesynthase) (Tetrahydrofolylpolyglutamate synthase); (2092:) "Formimidoyltransferase-cyclodeaminase (Formiminotransferase-cyclodeaminase) (FTCD) (LCHC1) [Includes:Glutamate formimidoyltransferase (Glutamate formiminotransferase) (Glutamate formyltransferase); Formimidoyltetrahydrofolatecyclodeaminase (Formiminotetrahydrofolate cyclodeaminase)]."; (2093:) formiminotransferase cyclodeaminase [Homo sapiens]; (2094:) fragile histidine triad gene [Homo sapiens]; (2095:) frataxin isoform 1 preproprotein [Homo sapiens]; (2096:) frataxin isoform 2 preproprotein [Homo sapiens]; (2097:) Free fatty acid receptor 1 (G-protein coupled receptor 40); (2098:) Free fatty acid receptor 2 (G-protein coupled receptor 43); (2099:) Free fatty acid receptor 3 (G-protein coupled receptor 41); (2100:) Frizzled-1 precursor (Fz-1) (hFz1) (FzE1); (2101:) Frizzled-10 precursor (Fz-10) (hFz10) (FzE7); (2102:) Frizzled-2 precursor (Fz-2) (hFz2) (FzE2); (2103:) Frizzled-3 precursor (Fz-3) (hFz3); (2104:) Frizzled-4 precursor (Fz-4) (hFz4) (FzE4); (2105:) Frizzled-5 precursor (Fz-5) (hFz5) (FzE5); (2106:) Frizzled-6 precursor (Fz-6) (hFz6); (2107:) Frizzled-7 precursor (Fz-7) (hFz7) (FzE3); (2108:) Frizzled-8 precursor (Fz-8) (hFz8); (2109:) Frizzled-9 precursor (Fz-9) (hFz9) (FzE6) (CD349 antigen); (2110:) fructosamine 3 kinase [Homo sapiens]; (2111:) fructosamine-3-kinase-related protein [Homo sapiens]; (2112:) fructose-1,6-bisphosphatase [Homo sapiens]; (2113:) Fructose-1,6-bisphosphatase 1 (D-fructose-1,6-bisphosphate1-phosphohydrolase 1) (FBPase 1); (2114:) fructose-1,6-bisphosphatase 1 [Homo sapiens]; (2115:) fructose-1,6-bisphosphatase 1 variant [Homo sapiens]; (2116:) fructose-1,6-bisphosphatase 2 [Homo sapiens]; (2117:) Fructose-1,6-bisphosphatase isozyme 2 (D-fructose-1,6-bisphosphate1-phosphohydrolase 2) (FBPase 2); (2118:) fructose-1,6-bisphosphatase; (2119:) fructose-6-phosphate, 2-kinase/fructose-2,6-bisphosphatase [Homo sapiens]; (2120:) Fructose-bisphosphate aldolase A (Muscle-type aldolase) (Lung cancer antigen NY-LU-1); (2121:) Fructose-bisphosphate aldolase B (Liver-type aldolase); (2122:) Fructose-bisphosphate aldolase C (Brain-type aldolase); (2123:) fructose-bisphosphate aldolase C [Homo sapiens]; (2124:) fucokinase [Homo sapiens]; (2125:) fucose-1-phosphate guanyltransferase [Homo sapiens]; (2126:) Fucose-1-phosphate guanylyltransferase (GDP-L-fucosepyrophosphorylase) (GDP-L-fucose diphosphorylase); (2127:) fucosidase, alpha-L-1, tissue [Homo sapiens]; (2128:) fucosidase, alpha-L-2, plasma [Homo sapiens]; (2129:) fucosyltransferase 1 [Homo sapiens]; (2130:) fucosyltransferase 2 (secretor status included) [Homo sapiens]; (2131:) fucosyltransferase 3 (galactoside 3(4)-L-fucosyltransferase, Lewis blood group included) [Homo sapiens]; (2132:) fucosyltransferase 5 [Homo sapiens]; (2133:) fucosyltransferase 8 isoform a [Homo sapiens]; (2134:) fucosyltransferase 8 isoform b [Homo sapiens]; (2135:) fucosyltransferase 8 isoform c [Homo sapiens]; (2136:) fukutin-related protein [Homo sapiens]; (2137:) fumarate hydratase precursor [Homo sapiens]; (2138:) Fumarylacetoacetase (Fumarylacetoacetate hydrolase) (Beta-diketonase) (FM); (2139:) fumarylacetoacetate hydrolase (fumarylacetoacetase) [Homo sapiens]; (2140:) Furin (paired basic amino acid cleaving enzyme) [Homo sapiens]; (2141:) Furin precursor (Paired basic amino acid residue cleaving enzyme) (PACE) (Dibasic-processing enzyme); (2142:) furin preproprotein [Homo sapiens]; (2143:) Fused toes protein homolog (Ft1); (2144:) FXYD domain containing ion transport regulator 3 isoform 1precursor [Homo sapiens]; (2145:) FXYD domain containing ion transport regulator 3 isoform 2precursor [Homo sapiens]; (2146:) FXYD domain-containing ion transport regulator 2 isoform 1 [Homo sapiens]; (2147:) FXYD domain-containing ion transport regulator 2 isoform 2 [Homo sapiens]; (2148:) FXYD domain-containing ion transport regulator 5 [Homo sapiens]; (2149:) FXYD domain-containing ion transport regulator 6 [Homo sapiens]; (2150:) FXYD domain-containing ion transport regulator 7 [Homo sapiens]; (2151:) G protein-coupled bile acid receptor 1 [Homo sapiens]; (2152:) G protein-coupled receptor kinase-interactor 2 isoform 1 [Homo sapiens]; (2153:) G protein-coupled receptor kinase-interactor 2 isoform 2 [Homo sapiens]; (2154:) G protein-coupled receptor kinase-interactor 2 isoform 3 [Homo sapiens]; (2155:) G protein-coupled receptor kinase-interactor 2 isoform 4

[*Homo sapiens*]; (2156:) G/T mismatch-specific thymine DNA glycosylase; (2157:) G6b protein precursor; (2158:) GA binding protein transcription factor, alpha subunit (60 kD) [*Homo sapiens*]; (2159:) GABA(A) receptor-associated protein [*Homo sapiens*]; (2160:) Galactocerebrosidase precursor (GALCERase) (Galactosylceramidase) (Galactosylceramide beta-galactosidase) (Galactocerebroside beta-galactosidase); (2161:) Galactokinase (Galactose kinase); (2162:) galactokinase 1 [*Homo sapiens*]; (2163:) galactose mutarotase (aldose 1-epimerase) [*Homo sapiens*]; (2164:) galactose-1-phosphate uridyl transferase [*Homo sapiens*]; (2165:) galactose-1-phosphate uridyl transferase; (2166:) Galactose-1-phosphate uridylyltransferase (Gal-1-Puridylyltransferase) (UDP-glucose—hexose-1-phosphateuridylyltransferase); (2167:) galactose-1-phosphate uridylyltransferase [*Homo sapiens*]; (2168:) galactose-3-O-sulfotransferase [*Homo sapiens*]; (2169:) Galactose-3-O-sulfotransferase 2 (Gal3ST-2) (Galbeta1-3GalNAc3'-sulfotransferase 2) (Beta-galactose-3-O-sulfotransferase 2) (Glycoprotein beta-Gal 3'-sulfotransferase 2); (2170:) galactose-3-O-sulfotransferase 2 [*Homo sapiens*]; (2171:) galactosidase, alpha [*Homo sapiens*]; (2172:) galactosidase, beta 1 [*Homo sapiens*]; (2173:) Galactoside 2-alpha-L-fucosyltransferase 1(GDP-L-fucose:beta-D-galactoside 2-alpha-L-fucosyltransferase 1) (Alpha(1,2)FT 1) (Fucosyltransferase 1) (Blood group H alpha2-fucosyltransferase); (2174:) Galactoside 2-alpha-L-fucosyltransferase 2(GDP-L-fucose:beta-D-galactoside 2-alpha-L-fucosyltransferase 2) (Alpha (1,2)FT 2) (Fucosyltransferase 2) (Secretor blood group alpha-2-fucosyltransferase) (Secretor factor) (Se) (SE2); (2175:) Galactoside 3(4)-L-fucosyltransferase (Blood group Lewis alpha-4-fucosyltransferase) (Lewis FT) (Fucosyltransferase 3) (FUCT-III); (2176:) galactosyl transferase-associated protein [*Homo sapiens*]; (2177:) galactosylceramidase (EC 3.2.1.46) precursor-human; (2178:) galactosylceramidase isoform a precursor [*Homo sapiens*]; (2179:) galactosylceramidase isoform b precursor [*Homo sapiens*]; (2180:) Galactosylgalactosylxylosyl protein 3-beta-glucuronosyltransferase 1 (Beta-1,3-glucuronyltransferase 1) (Glucuronosyltransferase-P) (GlcAT-P) (UDP-GlcUA:glycoprotein beta-1,3-glucuronyltransferase) (GlcUAT-P); (2181:) Galactosylgalactosylxylosyl protein 3-beta-glucuronosyltransferase 2(Beta-1,3-glucuronyltransferase 2) (Glucuronosyltransferase-S) (GlcAT-S) (UDP-glucuronosyltransferase-S) (GlcAT-D); (2182:) galactosylgalactosylxylosyl protein 3-beta-glucuronosyltransferase 2 [*Homo sapiens*]; (2183:) Galactosylgalactosylxylosyl protein 3-beta-glucuronosyltransferase 3(Beta-1,3-glucuronyltransferase 3) (Glucuronosyltransferase-1) (GlcAT-1) (UDP-GlcUA:Gal beta-1,3-Gal-R glucuronyltransferase) (GlcUAT-1); (2184:) Galanin receptor type 1 (GAL1-R) (GALR1); (2185:) Galanin receptor type 2 (GAL2-R) (GALR2); (2186:) Galanin receptor type 3 (GAL3-R) (GALR3); (2187:) galctocerebrosidase; (2188:) galectin 3 [*Homo sapiens*]; (2189:) GalNAc 4-sulfotransferase [*Homo sapiens*]; (2190:) gamma isoform of regulatory subunit B55, protein phosphatase 2 isoform a [*Homo sapiens*]; (2191:) gamma isoform of regulatory subunit B55, protein phosphatase 2 isoform b [*Homo sapiens*]; (2192:) gamma isoform of regulatory subunit B56, protein phosphatase 2A isoform a [*Homo sapiens*]; (2193:) gamma isoform of regulatory subunit B56, protein phosphatase 2A isoform b [*Homo sapiens*]; (2194:) gamma isoform of regulatory subunit B56, protein phosphatase 2A isoform c [*Homo sapiens*]; (2195:) gamma isoform of regulatory subunit B56, protein phosphatase 2A isoform d [*Homo sapiens*]; (2196:) Gamma-aminobutyric acid type B receptor, subunit 1 precursor (GABA-B receptor 1) (GABA-B-R1) (Gb1); (2197:) Gamma-aminobutyric acid type B receptor, subunit 2 precursor (GABA-B receptor 2) (GABA-B-R2) (Gb2) (GABABR2) (G-protein coupled receptor 51) (HG20); (2198:) gamma-butyrobetaine dioxygenase [*Homo sapiens*]; (2199:) gamma-catenin [*Homo sapiens*]; (2200:) gamma-glutamyl carboxylase [*Homo sapiens*]; (2201:) gamma-glutamyl hydrolase (EC 3.4.19.9)—human; (2202:) Gamma-glutamyl hydrolase precursor (Gamma-Glu-X carboxypeptidase) (Conjugase) (GH); (2203:) gamma-glutamyl hydrolase precursor [*Homo sapiens*]; (2204:) gamma-glutamyltransferase 1 precursor [*Homo sapiens*]; (2205:) "Gamma-glutamyltransferase 5 precursor (Gamma-glutamyltranspeptidase 5) (Gamma-glutamyltransferase-like activity 1) (GGT-rel) [Contains:Gamma-glutamyltransferase 5 heavy chain; Gamma-glutamyltransferase 5 light chain]."; (2206:) gamma-glutamyltransferase-like activity 1 [*Homo sapiens*]; (2207:) gamma-glutamyltransferase-like activity 4 [*Homo sapiens*]; (2208:) "Gamma-glutamyltranspeptidase 1 precursor (Gamma-glutamyltransferase 1) (GGT 1) (CD224 antigen) [Contains:) Gamma-glutamyltranspeptidase 1 heavy chain; Gamma-glutamyltranspeptidase 1 light chain] ."; (2209:) gamma-glutmyl transpeptidase-related protein; (2210:) Gamma-secretase subunit APH-1A (APH-1a) (Aph-1 alpha) (Presenilin-stabilization factor); (2211:) Gamma-secretase subunit PEN-2 (Presenilin enhancer protein 2); (2212:) ganglioside-specific alpha-2,8-polysialyltransferase; (2213:) gastric inhibitory polypeptide preproprotein [*Homo sapiens*]; (2214:) Gastric inhibitory polypeptide receptor precursor (GIP-R) (Glucose-dependent insulinotropic polypeptide receptor); (2215:) gastric lipase precursor [*Homo sapiens*]; (2216:) Gastric triacylglycerol lipase precursor (Gastric lipase) (GL); (2217:) Gastrin/cholecystokinin type B receptor (CCK-B receptor) (CCK-BR) (Cholecystokinin-2 receptor) (CCK2-R); (2218:) gastrin-releasing peptide isoform 1 preproprotein [*Homo sapiens*]; (2219:) gastrin-releasing peptide isoform 2 preproprotein [*Homo sapiens*]; (2220:) gastrin-releasing peptide isoform 3 preproprotein [*Homo sapiens*]; (2221:) Gastrin-releasing peptide receptor (GRP-R) (GRP-preferring bombesin receptor); (2222:) GCNT2 [*Homo sapiens*]; (2223:) GCNT3 protein [*Homo sapiens*]; (2224:) GDNF family receptor alpha-1 precursor (GFR-alpha-1) (GDNF receptor alpha) (GDNFR-alpha) (TGF-beta-related neurotrophic factor receptor1) (RET ligand 1); (2225:) GDNF family receptor alpha-2 precursor (GFR-alpha-2) (Neurturin receptor alpha) (NTNR-alpha) (NRTNR-alpha) (TGF-beta-related neurotrophic factor receptor 2) (GDNF receptor beta) (GDNFR-beta) (RET ligand 2); (2226:) GDNF family receptor alpha-3 precursor (GFR-alpha-3); (2227:) GDNF family receptor alpha-4 precursor (GFR-alpha-4) (Persephin receptor); (2228:) GDNF family receptor alpha-like precursor; (2229:) GDP-D-mannose-4,6-dehydratase [*Homo sapiens*]; (2230:) GDP-L-fucose pyrophosphorylase [*Homo sapiens*]; (2231:) GDP-mannose 4,6-dehydratase [*Homo sapiens*]; (2232:) GDP-mannose pyrophosphorylase A [*Homo sapiens*]; (2233:) GDP-mannose pyrophosphorylase β isoform 1 [*Homo sapiens*]; (2234:) GDP-mannose pyrophosphorylase β isoform 2 [*Homo sapiens*]; (2235:) gelatinase, type IV collagenase {N-terminal} [human, neutrophils, Peptide Partial, 19 aa]; (2236:) Gephyrin [*Homo sapiens*]; (2237:) gephyrin isoform 1 [*Homo sapiens*]; (2238:) gephyrin isoform 2 [*Homo sapiens*]; (2239:) geranylgeranyl diphosphate synthase 1 isoform A [*Homo sapiens*]; (2240:) geranylgeranyl diphosphate synthase 1 isoform B [*Homo sapiens*]; (2241:) geranylgeranyl transferase 11 [*Homo sapiens*]; (2242:) Geranylgeranyl transferase type-2 alpha subunit (Geranylgeranyl transferase type 11 alpha subunit) (Rab geranylgeranyl transferase alpha subunit) (Rab geranyl-geranyl transferase alpha subunit) (RabGG transferase alpha) (Rab GGTase alpha); (2243:) Geranylgeranyl transferase type-2 subunit beta (Geranylgeranyl transferase type II subunit beta) (Rab geranylgeranyl transferase subunit beta) (Rab geranyl-geranyl transferase subunit beta) (Rab GG transferase beta) (Rab GGTase beta); (2244:) ghrelin precursor [Homo sapiens]; (2245:) GlcNac-1-P transferase [Homo sapiens]; (2246:) GlcNAc-phosphotransferase precursor [Homo sapiens]; (2247:) Globoside alpha-1,3-N-acetylgalactosaminyltransferase 1 (Forssmanglycolipid synthetase-like protein); (2248:) glomulin [Homo sapiens]; (2249:) Glucagon receptor precursor (GL-R); (2250:) Glucagon-like peptide 1 receptor precursor (GLP-1 receptor) (GLP-1-R) (GLP-1R); (2251:) Glucagon-like peptide 2 receptor precursor (GLP-2 receptor) (GLP-2-R) (GLP-2R); (2252:) glucan (1,4-alpha-, branching enzyme 1 (glycogen branching enzyme)[Homo sapiens]; (2253:) Glucan, branching enzyme 1 variant [Homo sapiens]; (2254:) glucocerebrosidase precursor [Homo sapiens]; (2255:) Glucocorticoid receptor (GR); (2256:) Glucokinase (Hexokinase-4) (Hexokinase type IV) (HK IV) (HK4) (Hexokinase-D); (2257:) glucokinase isoform 1 [Homo sapiens]; (2258:) glucokinase isoform 2 [Homo sapiens]; (2259:) glucokinase isoform 3 [Homo sapiens]; (2260:) Glucokinase regulatory protein (Glucokinase regulator); (2261:) glucokinase regulatory protein [Homo sapiens]; (2262:) glucosamine (N-acetyl)-6-sulfatase precursor [Homo sapiens]; (2263:) glucosamine-fructose-6-phosphate aminotransferase [Homo sapiens]; (2264:) Glucosaminyl (N-acetyl) transferase 1, core 2(beta-1,6-N-acetylglucosaminyltransferase) [Homo sapiens]; (2265:) Glucosaminyl (N-acetyl) transferase 2,1-branching enzyme (I blood group) [Homo sapiens]; (2266:) glucosaminyl (N-acetyl) transferase 2,1-branching enzyme isoform A[Homo sapiens]; (2267:) glucosaminyl (N-acetyl) transferase 2,1-branching enzyme isoform B [Homo sapiens]; (2268:) glucosaminyl (N-acetyl) transferase 2,1-branching enzyme isoform C[Homo sapiens]; (2269:) Glucosaminyl (N-acetyl) transferase 2, I-branching enzyme, isoform B [Homo sapiens]; (2270:) glucosaminyl (N-acetyl) transferase 3, mucin type [Homo sapiens]; (2271:) glucose phosphate isomerase [Homo sapiens]; (2272:) glucose transporter 4 [Homo sapiens]; (2273:) Glucose-6-phosphatase (G6 Pase) (G-6-Pase); (2274:) glucose-6-phosphatase, catalytic subunit [Homo sapiens]; (2275:) Glucose-6-phosphate 1-dehydrogenase (G6PD); (2276:) glucose-6-phosphate dehydrogenase isoform a [Homo sapiens]; (2277:) glucose-6-phosphate dehydrogenase isoform b [Homo sapiens]; (2278:) "glucosidase, alpha; neutral C [Homo sapiens]."; (2279:) glucuronidase, beta [Homo sapiens]; (2280:) glucuronyltransferase [Homo sapiens]; (2281:) glucuronyltransferase I [Homo sapiens]; (2282:) Glutamate [NMDA] receptor subunit 3A precursor (N-methyl-D-aspartate receptor subtype NR3A) (NMDAR-L); (2283:) Glutamate [NMDA] receptor subunit 3B precursor (N-methyl-D-aspartate receptor subtype NR3B) (NR3B) (NMDAR3B); (2284:) Glutamate [NMDA] receptor subunit epsilon 1 precursor (N-methyl D-aspartate receptor subtype 2A) (NR2A) (NMDAR2A) (hNR2A); (2285:) Glutamate [NMDA] receptor subunit epsilon 2 precursor (N-methyl D-aspartate receptor subtype 2B) (NR2B) (NMDAR2B) (N-methyl-D-aspartate receptor subunit 3) (NR3) (hNR3); (2286:) Glutamate [NMDA] receptor subunit epsilon 3 precursor (N-methyl D-aspartate receptor subtype 2C) (NR2C) (NMDAR2C); (2287:) Glutamate [NMDA] receptor subunit epsilon 4 precursor (N-methyl D-aspartate receptor subtype 2D) (NR2D) (NMDAR2D) (EB11); (2288:) Glutamate [NMDA] receptor subunit zeta 1 precursor (N-methyl-D-aspartate receptor subunit NR1); (2289:) Glutamate carboxypeptidase 2 (Glutamate carboxypeptidase II) (Membrane glutamate carboxypeptidase) (mGCP) (N-acetylated-alpha-linked acidic dipeptidase 1) (NAALADase I) (Pteroylpoly-gamma-glutamate carboxypeptidase) (Folylpoly-gamma-glutamate carboxypeptidase) (FGCP) (Folatehydrolase 1) (Prostate-specific membrane antigen) (PSMA) (PSM); (2290:) Glutamate decarboxylase 1 (Glutamate decarboxylase 67 kDa isoform) (GAD-67) (67 kDa glutamic acid decarboxylase); (2291:) glutamate decarboxylase 1 isoform GAD25 [Homo sapiens]; (2292:) glutamate decarboxylase 1 isoform GAD67 [Homo sapiens]; (2293:) glutamate decarboxylase 2 [Homo sapiens]; (2294:) glutamate dehydrogenase 1 [Homo sapiens]; (2295:) Glutamate dehydrogenase 1, mitochondrial precursor (GDH); (2296:) glutamate dehydrogenase 2 [Homo sapiens]; (2297:) Glutamate receptor 1 precursor (GluR-1) (GluR-A) (GluR-K1) (Glutamate receptor ionotropic, AMPA 1) (AMPA-selective glutamate receptor 1); (2298:) Glutamate receptor 2 precursor (GluR-2) (GluR-B) (GluR-K2) (Glutamate receptor ionotropic, AMPA 2) (AMPA-selective glutamate receptor 2); (2299:) Glutamate receptor 3 precursor (GluR-3) (GluR-C) (GluR-K3) (Glutamate receptor ionotropic, AMPA 3) (AMPA-selective glutamate receptor 3); (2300:) Glutamate receptor 4 precursor (GluR-4) (GluR4) (GluR-D) (Glutamate receptor ionotropic, AMPA 4) (AMPA-selective glutamate receptor 4); (2301:) Glutamate receptor delta-1 subunit precursor (GluR delta-1); (2302:) Glutamate receptor delta-2 subunit precursor (GluR delta-2); (2303:) Glutamate receptor, ionotropic kainate 1 precursor (Glutamate receptor 5) (GluR-5) (GluR5) (Excitatory amino acid receptor 3) (EM3); (2304:) Glutamate receptor, ionotropic kainate 2 precursor (Glutamate receptor 6) (GluR-6) (GluR6) (Excitatory amino acid receptor 4) (EAA4); (2305:) Glutamate receptor, ionotropic kainate 3 precursor (Glutamate receptor 7) (GluR-7) (GluR7) (Excitatory amino acid receptor 5) (EAA5); (2306:) Glutamate receptor, ionotropic kainate 4 precursor (Glutamate receptor KA-1) (KA1) (Excitatory amino acid receptor 1) (EAA1); (2307:) Glutamate receptor, ionotropic kainate 5 precursor (Glutamate receptor KA-2) (KA2) (Excitatory amino acid receptor 2) (EAA2); (2308:) glutamate-5-semialdehyde dehydrogenase (EC 1.2.1.41)—human (fragments); (2309:) Glutamate—cysteine ligase catalytic subunit (Gamma-glutamyl cysteine synthetase) (Gamma-ECS) (GCS heavy chain); (2310:) glutamate-cysteine ligase regulatory protein [Homo sapiens]; (2311:) glutamate-cysteine ligase, catalytic subunit [Homo sapiens]; (2312:) glutamic gamma-semialdehyde dehydrogenase; (2313:) glutaminase 2 [Homo sapiens]; (2314:) glutaminase C [Homo sapiens]; (2315:) glutamine synthetase [Homo sapiens]; (2316:) glutaminyl-peptide cyclotransferase precursor [Homo sapiens]; (2317:) Glutaminyl-tRNA synthetase (Glutamine—tRNA ligase) (GlnRS); (2318:) glutaminyl-tRNA synthetase [Homo sapiens]; (2319:) Glutaredoxin-2, mitochondrial precursor; (2320:) glutaryl-CoA dehydrogenase [Homo sapiens]; (2321:) Glutaryl-CoA dehydrogenase, mitochondrial precursor (GCD); (2322:) glutaryl-Coenzyme A dehydrogenase isoform a precursor [Homo sapiens]; (2323:) glutaryl-Coenzyme A dehydrogenase isoform b precursor [Homo sapiens]; (2324:) glutathione peroxidase [Homo sapiens]; (2325:) glutathione peroxidase 1 isoform 1 [Homo sapiens]; (2326:) glutathione peroxidase 1 isoform 2 [Homo sapiens]; (2327:) glutathione peroxidase 4 isoform A precursor [Homo sapiens]; (2328:) glutathione peroxidase 4 isoform B precursor [Homo sapiens]; (2329:) glutathione peroxidase 4 isoform C precursor [*Homo sapiens*]; (2330:) Glutathione Reductase (E.C.1.6.4.2) (Oxidized) Complex With Glutathione Disulfide And Nadp+; (2331:) Glutathione Reductase (E.C.1.6.4.2) Carboxymethylated At Cys 58 Complex With Phosphate; (2332:) Glutathione Reductase (E.C.1.6.4.2) Complex With Covalently Bound Glutathione And Phosphate; (2333:) Glutathione Reductase (E.C.1.6.4.2) Modified By Bcnu(1,3-Bis(2-Chloroethyl)-1-Nitrosourea) At Cys 58 Complexed With Phosphate; (2334:) Glutathione Reductase (E.C.1.6.4.2) Modified By Hecnu(1-(2-Chloroethyl)-3-(2-Hydroxyethyl)-1-Nitrosourea) At Cys 58Complexed With Phosphate; (2335:) glutathione reductase [*Homo sapiens*]; (2336:) Glutathione reductase, mitochondrial precursor (GR) (GRase); (2337:) glutathione S-transferase A1 [*Homo sapiens*]; (2338:) glutathione S-transferase A3 [*Homo sapiens*]; (2339:) Glutathione S-transferase A4 (Glutathione S-transferase A4-4) (GST class-alpha member 4); (2340:) glutathione S-transferase A4 [*Homo sapiens*]; (2341:) glutathione S-transferase M1 isoform 1 [*Homo sapiens*]; (2342:) glutathione S-transferase M1 isoform 2 [*Homo sapiens*]; (2343:) glutathione S-transferase M3 [*Homo sapiens*]; (2344:) Glutathione S-transferase Mu 1 (GSTM1-1) (GST class-mu 1) (GSTM1a-1a) (GSTM1b-1b) (HB subunit 4) (GTH4); (2345:) glutathione S-transferase theta 1 [*Homo sapiens*]; (2346:) Glutathione S-transferase theta-1 (GST class-theta-1) (Glutathione transferase T1-1); (2347:) glutathione transferase [*Homo sapiens*]; (2348:) glutathione transferase A4-4 [*Homo sapiens*]; (2349:) glutathione transferase kappa 1 [*Homo sapiens*]; (2350:) glutathione transferase T1-1 [*Homo sapiens*]; (2351:) glutathione transferase zeta 1 isoform 1 [*Homo sapiens*]; (2352:) glutathione transferase zeta 1 isoform 2 [*Homo sapiens*]; (2353:) glutathione transferase zeta 1 isoform 3 [*Homo sapiens*]; (2354:) glutathione transferase; (2355:) glyceraldehyde-3-phosphate dehydrogenase [*Homo sapiens*]; (2356:) Glycerol kinase (ATP:glycerol 3-phosphotransferase) (Glycerokinase) (GK); (2357:) Glycerol kinase, testis specific 1 (ATP:glycerol3-phosphotransferase) (Glycerokinase) (GK); (2358:) Glycerol kinase, testis specific 2 (ATP:glycerol3-phosphotransferase) (Glycerokinase) (GK); (2359:) glycerol-3-phosphate dehydrogenase 2 (mitochondrial) [*Homo sapiens*]; (2360:) Glycerol-3-phosphate dehydrogenase, mitochondrial precursor (GPD-M) (GPDH-M) (mtGPD); (2361:) glycine amidino transferase (L-arginine:glycine amidino transferase)[*Homo sapiens*]; (2362:) Glycine amidino transferase, mitochondrial precursor (L-arginine:glycine amidino transferase) (Transamidinase) (AT); (2363:) Glycine C-acetyltransferase (2-amino-3-ketobutyrate coenzyme Aligase) [*Homo sapiens*]; (2364:) glycine C-acetyltransferase precursor [*Homo sapiens*]; (2365:) Glycine cleavage system H protein, mitochondrial precursor; (2366:) glycine cleavage system protein H (aminomethyl carrier) [*Homo sapiens*]; (2367:) glycine dehydrogenase (decarboxylating) [*Homo sapiens*]; (2368:) glycine N-methyltransferase [*Homo sapiens*]; (2369:) Glycine receptor subunit alpha-1 precursor (Glycine receptor 48 kDa subunit) (Glycine receptor strychnine-binding subunit); (2370:) Glycine receptor subunit alpha-2 precursor; (2371:) Glycine receptor subunit alpha-3 precursor; (2372:) Glycine receptor subunit beta precursor (Glycine receptor 58 kDa subunit); (2373:) glycine-N-acyltransferase isoform a [*Homo sapiens*]; (2374:) glycine-N-acyltransferase isoform b [*Homo sapiens*]; (2375:) glycoasparaginase; (2376:) Glycogen [starch] synthase, liver; (2377:) Glycogen [starch] synthase, muscle; (2378:) "Glycogen debranching enzyme (Glycogen debrancher) [Includes: 4-alpha-glucanotransferase (Oligo-1, 4-1,4-glucantransferase); Amylo-alpha-1,6-glucosidase (Amylo-1,6-glucosidase) (Dextrin6-alpha-D-glucosidase)] ."; (2379:) glycogen debranching enzyme [*Homo sapiens*]; (2380:) glycogen debranching enzyme isoform 1 [*Homo sapiens*]; (2381:) glycogen debranching enzyme isoform 2 [*Homo sapiens*]; (2382:) glycogen debranching enzyme isoform 3 [*Homo sapiens*]; (2383:) glycogen debranching enzyme isoform 4 [*Homo sapiens*]; (2384:) glycogen debranching enzyme isoform 6 [*Homo sapiens*]; (2385:) glycogen phosphorylase [*Homo sapiens*]; (2386:) Glycogen phosphorylase, brain form; (2387:) Glycogen phosphorylase, liver form; (2388:) Glycogen phosphorylase, muscle form (Myophosphorylase); (2389:) glycogen synthase kinase 3 beta [*Homo sapiens*]; (2390:) Glycogen synthase kinase-3 beta (GSK-3 beta); (2391:) glycogen-debranching enzyme [*Homo sapiens*]; (2392:) glycophorin A precursor [*Homo sapiens*]; (2393:) glycoprotein V (platelet) [*Homo sapiens*]; (2394:) glycoprotein-fucosylgalactosidealpha-N-acetylgalactosaminyltransferase (EC 2.4.1.40) A1 allele [validated]—human; (2395:) glycosylphosphatidylinositol specific phospholipase D1 isoform 1 precursor [*Homo sapiens*]; (2396:) glycosylphosphatidylinositol specific phospholipase D1 isoform 2precursor [*Homo sapiens*]; (2397:) Glycyl peptide N-tetradecanoyltransferase 1 (Peptide N-myristoyltransferase 1) (Myristoyl-CoA:protein N-myristoyltransferase 1) (NMT 1) (Type I N-myristoyltransferase); (2398:) glycyl-tRNA synthetase [*Homo sapiens*]; (2399:) glyoxalase I [*Homo sapiens*]; (2400:) glyoxylate reductase/hydroxypyruvate reductase [*Homo sapiens*]; (2401:) Glyoxylate reductase/hydroxypyruvate reductase; (2402:) GM2 ganglioside activator precursor [*Homo sapiens*]; (2403:) Golgi autoantigen, golgin subfamily a, 2 [*Homo sapiens*]; (2404:) golgi autoantigen, golgin subfamily b, macrogolgin (with transmembrane signal), 1 [*Homo sapiens*]; (2405:) Golgi reassembly stacking protein 1 [*Homo sapiens*]; (2406:) Golgi-specific brefeldin A-resistance guanine nucleotide exchange factor 1 (BFA-resistant GEF 1); (2407:) Golli-mbp isoform 1 [*Homo sapiens*]; (2408:) Golli-mbp isoform 2 [*Homo sapiens*]; (2409:) Gonadotropin-releasing hormone 11 receptor (Type II GnRH receptor) (GnRH-II-R); (2410:) Gonadotropin-releasing hormone receptor (GnRH receptor) (GnRH-R); (2411:) gp180-carboxypeptidase D-like enzyme [*Homo sapiens*]; (2412:) GPI mannosyltransferase 1 (GPI mannosyltransferase 1) (GPI-MT-I) (Phosphatidylinositol-glycan biosynthesis class M protein) (PIG-M); (2413:) GPI mannosyltransferase 2 (GPI mannosyltransferase II) (GPI-MT-II) (Phosphatidylinositol-glycan biosynthesis class V protein) (PIG-V); (2414:) GPI transamidase component PIG-T precursor (Phosphatidylinositol-glycan biosynthesis class T protein); (2415:) GPI-anchor transamidase precursor (GPI transamidase) (Phosphatidylinositol-glycan biosynthesis class K protein) (PIG-K) (hGPI8); (2416:) G-protein coupled bile acid receptor 1 (Membrane-type receptor for-bile acids) (M-BAR) (hGPCR19) (BG37) (hBG37); (2417:) G-protein coupled receptor 120 (G-protein coupled receptor PGR4) (G-protein coupled receptor GTO01) (G-protein coupled receptor 129); (2418:) G-protein coupled receptor 143 (Ocular albinism type 1 protein); (2419:) G-protein coupled receptor 15 (BOB); (2420:) G-protein coupled receptor 56 precursor (TM7XN1 protein); (2421:) G-protein coupled receptor 64 precursor (Epididymis-specific protein 6) (He6 receptor); (2422:) G-protein coupled receptor 98 precursor (Monogenic audiogenic seizure susceptibility protein 1 homolog) (Very large G-protein coupled receptor 1) (Usher syndrome type-2C protein); (2423:) G-protein coupled receptor family C group 5 member B precursor (Retinoic acid-induced gene 2 protein) (RAIG-2) (A-69G12.1); (2424:) G-protein coupled receptor family C group 5 member C precursor (Retinoic acid-induced gene 3 protein) (RAIG-3); (2425:) G-protein coupled receptor family C group 5 member D; (2426:) G-protein coupled receptor family C group 6 member A precursor (hGPRC6A) (G-protein coupled receptor 33) (hGPCR33); (2427:) Grainy head-like protein 1 homolog (Transcription factor CP2-like 2) (Transcription factor LBP-32) (NH32) (Mammalian grainy head); (2428:) Granulocyte colony-stimulating factor receptor precursor (G-CSF-R) (CD114 antigen); (2429:) Granulocyte-macrophage colony-stimulating factor receptor alpha chain precursor (GM-CSF-R-alpha) (GMR) (CD116 antigen) (CDw116); (2430:) Granzyme A precursor (Cytotoxic T-lymphocyte proteinase 1) (Hanukkah factor) (H factor) (HF) (Granzyme-1) (CTL tryptase); (2431:) Granzyme B precursor (T-cell serine protease 1-3E) (Cytotoxic T-lymphocyte proteinase 2) (Lymphocyte protease) (SECT) (Granzyme-2) (Cathepsin G-like 1) (CTSGL1) (CTLA-1) (Human lymphocyte protein) (HLP) (C11); (2432:) granzyme B precursor [Homo sapiens]; (2433:) Granzyme H precursor (Cytotoxic T-lymphocyte proteinase) (Cathepsin G-like 2) (CTSGL2) (CCP-X) (Cytotoxic serine protease C) (CSP-C); (2434:) granzyme M precursor [Homo sapiens]; (2435:) Green-sensitive opsin (Green cone photoreceptor pigment); (2436:) Group 3 secretory phospholipase A2 precursor (Group III secretory phospholipase A2) (Phosphatidylcholine 2-acylhydrolase GIII) (GIIIsPLA2); (2437:) group III secreted phospholipase A2 [Homo sapiens]; (2438:) growth factor receptor-bound protein 2 isoform 1 [Homo sapiens]; (2439:) growth factor receptor-bound protein 2 isoform 2 [Homo sapiens]; (2440:) growth hormone 1 isoform 1 [Homo sapiens]; (2441:) growth hormone 1 isoform 2 [Homo sapiens]; (2442:) growth hormone 1 isoform 3 [Homo sapiens]; (2443:) growth hormone 1 isoform 4 [Homo sapiens]; (2444:) growth hormone 1 isoform 5 [Homo sapiens]; (2445:) Growth hormone receptor precursor (GH receptor) (Somatotropin receptor) [Contains:) Growth hormone-binding protein (GH-binding protein) (GHBP) (Serum-binding protein)]; (2446:) Growth hormone secretagogue receptor type 1 (GHS-R) (GH-releasing peptide receptor) (GHRP) (Ghrelin receptor); (2447:) Growth hormone-releasing hormone receptor precursor (GHRH receptor) (GRF receptor) (GRFR); (2448:) growth-inhibiting protein 17 [Homo sapiens]; (2449:) G-T3 synthase; (2450:) GTP cyclohydrase I [Homo sapiens]; (2451:) GTP cyclohydrolase 1 isoform 1 [Homo sapiens]; (2452:) GTP cyclohydrolase 1 isoform 2 [Homo sapiens]; (2453:) GTP cyclohydrolase 1 isoform 3 [Homo sapiens]; (2454:) GTP cyclohydrolase I (GTP-CH-1); (2455:) GTP cyclohydrolase I [Homo sapiens]; (2456:) GTPase activating Rap/RanGAP domain-like 1 isoform 1 [Homo sapiens]; (2457:) GTPase activating Rap/RanGAP domain-like 1 isoform 2 [Homo sapiens]; (2458:) GTPase ERas precursor (E-Ras) (Embryonic stem cell-expressed Ras); (2459:) GTPase HRas precursor (Transforming protein p21) (p21 ras) (H-Ras-1) (c-H-ras); (2460:) GTPase KRas (K-Ras 2) (Ki-Ras) (c-K-ras) (c-Ki-ras); (2461:) GTPase NRas precursor (Transforming protein N-Ras); (2462:) GTP-binding protein Rit1 (Ras-like protein expressed in many tissues) (Ras-like without CAAX protein 1); (2463:) guanine deaminase [Homo sapiens]; (2464:) guanine nucleotide exchange factor p532 [Homo sapiens]; (2465:) guanosine monophosphate reductase [Homo sapiens]; (2466:) guanylate cyclase 1, soluble, alpha 2 [Homo sapiens]; (2467:) guanylate cyclase activator 1A (retina) [Homo sapiens]; (2468:) "Guanylate cyclase activator 2B precursor [Contains:) Guanylatecyclase C-activating peptide 2 (Guanylate cyclase C-activating peptide II) (GCAP-II); Uroguanylin (UGN)]."; (2469:) Guanylate cyclase soluble subunit alpha-2 (GCS-alpha-2); (2470:) Guanylate cyclase soluble subunit alpha-3 (GCS-alpha-3) (Soluble guanylate cyclase large subunit) (GCS-alpha-1); (2471:) Guanylate cyclase soluble subunit beta-1 (GCS-beta-1) (Soluble guanylate cyclase small subunit) (GCS-beta-3); (2472:) Guanylate cyclase soluble subunit beta-2 (GCS-beta-2); (2473:) guanylate cyclase: SUBUNIT=alpha2; (2474:) "Guanylin precursor (Guanylate cyclase activator 2A) (Guanylatecyclase-activating protein 1) (Gap-1) [Contains:) HMW-guanylin; Guanylin]."; (2475:) H(+)-transporting two-sector ATPase [Homo sapiens]; (2476:) H+-exporting ATPase (EC 3.6.3.6) chain D, vacuolar—human; (2477:) H2A histone family, member O [Homo sapiens]; (2478:) HACL1 protein [Homo sapiens]; (2479:) head and neck tumor and metastasis related protein [Homo sapiens]; (2480:) heat shock 27 kDa protein 1 [Homo sapiens]; (2481:) heat shock 27 kDa protein 2 [Homo sapiens]; (2482:) heat shock 70 kDa protein 5 [Homo sapiens]; (2483:) heat shock-like protein 1 [Homo sapiens]; (2484:) HEAT-like (PBS lyase) repeat containing 1 [Homo sapiens]; (2485:) Heat-stable enterotoxin receptor precursor (GC-C) (Intestinal guanylate cyclase) (STA receptor) (hSTAR); (2486:) hect domain and RLD 5 [Homo sapiens]; (2487:) hedgehog acyltransferase [Homo sapiens]; (2488:) heme oxygenase (decyclizing) 1 [Homo sapiens]; (2489:) heme oxygenase (decyclizing) 2 [Homo sapiens]; (2490:) heparan sulfate (glucosamine) 3-O-sulfotransferase 5 [Homo sapiens]; (2491:) heparan sulfate (glucosamine) 3-O-sulfotransferase 6 [Homo sapiens]; (2492:) heparan sulfate 2-O-sulfotransferase 1 [Homo sapiens]; (2493:) heparan sulfate 3-O-sulfotransferase-1 precursor [Homo sapiens]; (2494:) heparan sulfate 6-O-sulfotransferase [Homo sapiens]; (2495:) heparan sulfate 6-O-sulfotransferase 3 [Homo sapiens]; (2496:) heparan sulfate D-glucosaminyl 3-O-sulfotransferase 2 [Homo sapiens]; (2497:) heparan sulfate D-glucosaminyl 3-O-sulfotransferase 1 precursor[Homo sapiens]; (2498:) heparan sulfate D-glucosaminyl 3-O-sulfotransferase 3A1 [Homo sapiens]; (2499:) heparan sulfate D-glucosaminyl 3-O-sulfotransferase 3B1 [Homo sapiens]; (2500:) heparan sulfate D-glucosaminyl 3-O-sulfotransferase 4 [Homo sapiens]; (2501:) Heparan sulfate glucosamine 3-O-sulfotransferase 1 precursor (Heparan sulfate D-glucosaminyl 3-O-sulfotransferase 1) (Heparansulfate 3-O-sulfotransferase 1) (h3-OST-1); (2502:) Heparan sulfate glucosamine 3-O-sulfotransferase 3A1 (Heparansulfate D-glucosaminyl 3-O-sulfotransferase 3A1) (Heparan sulfate3-O-sulfotransferase 3A1) (h3-OST-3A); (2503:) Heparan sulfate glucosamine 3-O-sulfotransferase 3B1 (Heparansulfate D-glucosaminyl 3-O-sulfotransferase 3B1) (Heparan sulfate3-O-sulfotransferase 3B1) (h3-OST-3B); (2504:) Heparan sulfate glucosamine 3-O-sulfotransferase 5 (Heparan sulfate D-glucosaminyl 3-O-sulfotransferase 5) (Heparan sulfate3-O-sulfotransferase 5) (h3-OST-5); (2505:) Heparan sulfate glucosamine 3-O-sulfotransferase 6 (Heparan sulfate D-glucosaminyl 3-O-sulfotransferase 6) (Heparan sulfate3-O-sulfotransferase 6) (h3-OST-6); (2506:) heparanase [Homo sapiens]; (2507:) "Heparanase precursor (Heparanase-1) (Hpa1) (Endo-glucoronidase)[Contains:) Heparanase 8 kDa subunit; Heparanase 50 kDa subunit]."; (2508:) heparanase precursor [Homo sapiens]; (2509:) Heparanase-2 (Hpa2); (2510:) Heparan-sulfate 6-O-sulfotransferase 1 (HS6ST-1); (2511:) Heparan-sulfate 6-O-sulfotransferase 2 (HS6ST-2); (2512:) Heparan-sulfate 6-O-sulfotransferase 3 (HS6ST-3); (2513:) Heparin-binding EGF-like growth factor precursor (HB-EGF) (HBEGF) (Diphtheria toxin receptor) (DT-R); (2514:) Hepatic triacylglycerol lipase precursor (Hepatic lipase) (HL); (2515:)

Hepatitis A virus cellular receptor 1 precursor (HAVcr-1) (T cell immunoglobulin and mucin domain-containing protein 1) (TIMD-1) (Tcell membrane protein 1) (TIM-1) (TIM); (2516:) Hepatocyte growth factor receptor precursor (HGF receptor) (Scatter factor receptor) (SF receptor) (HGF/SF receptor) (Met proto-oncogene tyrosine kinase) (c-Met); (2517:) Hepatocyte nuclear factor 4-alpha (HNF-4-alpha) (Transcription factor HNF-4) (Transcription factor 14); (2518:) Hepatocyte nuclear factor 4-gamma (HNF-4-gamma); (2519:) herpesvirus associated ubiquitin-specific protease (HAUSP) [Homo sapiens]; (2520:) "HERV-K_3q27.3 provirus ancestral Pol protein [Includes:) Reverse transcriptase (RT); Ribonuclease H(RNase H); Integrase (IN)]."; (2521:) HERV-K_5q33.3 provirus ancestral Pro protein (HERV-K10 Pro protein) (HERV-K107 Pro protein) (Protease) (Proteinase) (PR); (2522:) "HERV-K_7p22.1 provirus ancestral Pol protein (HERV-K(HML-2.HOM) Polprotein) (HERV-K$_{108}$ Pol protein) (HERV-K(C7) Pol protein) [Includes:) Reverse transcriptase (RT); Ribonuclease H(RNase H); Integrase (IN)]."; (2523:) heterogeneous nuclear ribonucleoprotein AB isoform a [Homo sapiens]; (2524:) heterogeneous nuclear ribonucleoprotein AB isoform b [Homo sapiens]; (2525:) hexokinase 1 [Homo sapiens]; (2526:) hexokinase 1 isoform HKI [Homo sapiens]; (2527:) hexokinase 1 isoform HKI-R [Homo sapiens]; (2528:) hexokinase 1 isoform HKI-ta/tb [Homo sapiens]; (2529:) hexokinase 1 isoform HKI-td [Homo sapiens]; (2530:) hexokinase 2 [Homo sapiens]; (2531:) hexokinase 3 [Homo sapiens]; (2532:) Hexokinase-1 (Hexokinase type 1) (HK I) (Brain form hexokinase); (2533:) Hexokinase-2 (Hexokinase type II) (HK II) (Muscle form hexokinase); (2534:) Hexokinase-3 (Hexokinase type II) (HK III); (2535:) hexosaminidase A preproprotein [Homo sapiens]; (2536:) hexosaminidase B preproprotein [Homo sapiens]; (2537:) hexose-6-phosphate dehydrogenase precursor [Homo sapiens]; (2538:) HGD protein [Homo sapiens]; (2539:) "HHR6A (Human homologue of yeast RAD 6); putative."; (2540:) "HHR6B (Human homologue of yeast RAD 6); putative."; (2541:) High affinity immunoglobulin epsilon receptor alpha-subunit precursor (FcER1) (IgE Fc receptor, alpha-subunit) (Fc-epsilon RI-alpha); (2542:) High affinity immunoglobulin epsilon receptor gamma-subunit precursor (FceRI gamma) (IgE Fc receptor gamma-subunit) (Fc-epsilon RI-gamma); (2543:) High affinity immunoglobulin epsilon receptor subunit beta (FcER1) (IgE Fc receptor, subunit beta) (Fc epsilon receptor 1 beta-chain); (2544:) High affinity immunoglobulin gamma Fc receptor I precursor (Fc-gamma RI) (FcRI) (IgG Fc receptor 1) (CD64 antigen); (2545:) High affinity interleukin-8 receptor A (IL-8R A) (IL-8 receptor type 1) (CXCR-1) (CD181 antigen) (CDw128a); (2546:) High affinity interleukin-8 receptor B (IL-8R B) (CXCR-2) (GRO/MGSA receptor) (IL-8 receptor type 2) (CD182 antigen) (CDw128b); (2547:) High affinity nerve growth factor receptor precursor (Neurotrophictyrosine kinase receptor type 1) (TRK1 transforming tyrosine kinase protein) (p140-TrkA) (Trk-A); (2548:) High-affinity cAMP-specific 3',5'-cyclic phosphodiesterase 7A (HCP1) (TM22); (2549:) High-affinity cAMP-specific and IBMX-insensitive 3',5'-cyclic phosphodiesterase 8A; (2550:) High-affinity cAMP-specific and IBMX-insensitive 3',5'-cyclic phosphodiesterase 8B (HSPDE8B); (2551:) High-affinity cationic amino acid transporter 1 (CAT-1) (CAT1) (System Y+ basic amino acid transporter) (Ecotropic retroviral leukemia receptor homolog) (ERR) (Ecotropic retrovirus receptor homolog); (2552:) High-affinity cGMP-specific 3',5'-cyclic phosphodiesterase 9A; (2553:) Histamine H1 receptor; (2554:) Histamine H2 receptor (H2R) (Gastric receptor I); (2555:) Histamine H3 receptor (HH3R) (G-protein coupled receptor 97); (2556:) Histamine H4 receptor (HH4R) (GPRv53) (G-protein coupled receptor105) (GPCR105) (SP9144) (AXOR35); (2557:) Histamine N-methyltransferase (HMT); (2558:) histamine N-methyltransferase [Homo sapiens]; (2559:) histamine N-methyltransferase isoform 1 [Homo sapiens]; (2560:) histamine N-methyltransferase isoform 2 [Homo sapiens]; (2561:) histamine N-methyltransferase isoform 3 [Homo sapiens]; (2562:) histamine N-methyltransferase variant 1 [Homo sapiens]; (2563:) histamine N-methyltransferase variant 2 [Homo sapiens]; (2564:) histamine N-methyltransferase variant 3 [Homo sapiens]; (2565:) histamine N-methyltransferase; (2566:) Histidine acid phosphatase domain containing 1 [Homo sapiens]; (2567:) Histidine acid phosphatase domain containing 2A isoform 4 [Homo sapiens]; (2568:) histidine ammonia-lyase [Homo sapiens]; (2569:) histidine decarboxylase [Homo sapiens]; (2570:) histidine triad nucleotide binding protein 1 [Homo sapiens]; (2571:) histidine triad protein member 5 [Homo sapiens]; (2572:) histidyl-tRNA synthetase [Homo sapiens]; (2573:) histidyl-tRNA synthetase-like [Homo sapiens]; (2574:) Histone acetyltransferase HTATIP (60 kDa Tat interactive protein) (Tip60) (HIV-1 Tat interactive protein) (cPLA(2)-interacting protein); (2575:) Histone acetyltransferase MYST3 (MYST protein 3) (MOZ, YBF2/SAS3, SAS2 and TIP60 protein 3) (Runt-related transcription factor-binding protein 2) (Monocytic leukemia zinc finger protein) (Zinc finger protein 220); (2576:) Histone acetyltransferase MYST4 (MYST protein 4) (MOZ, YBF2/SAS3, SAS2 and TIP60 protein 4) (Histone acetyltransferase MOZ2) (Monocytic leukemia zinc finger protein-related factor) (Histoneacetyltransferase MORF); (2577:) Histone acetyltransferase PCAF (P300/CBP-associated factor) (P/CAF) (Histone acetylase PCAF); (2578:) histone deacetylase 2 [Homo sapiens]; (2579:) histone stem-loop binding protein [Homo sapiens]; (2580:) Histone-lysine N-methyltransferase, H3 lysine-79 specific (Histone H3-K79 methyltransferase) (H3-K79-HMTase) (DOT1-like protein); (2581:) Histone-lysine N-methyltransferase, H3 lysine-9 specific 1 (Histone H3-K9 methyltransferase 1) (H3-K9-HMTase 1) (Suppressor of variegation 3-9 homolog 1) (Su(var)3-9 homolog 1); (2582:) Histone-lysine N-methyltransferase, H3 lysine-9 specific 3 (Histone H3-K9 methyltransferase 3) (H3-K9-HMTase 3) (Euchromatichistone-lysine N-methyltransferase 2) (HLA-B-associated transcript 8) (Protein G9a); (2583:) Histone-lysine N-methyltransferase, H3 lysine-9 specific 5 (Histone H3-K9 methyltransferase 5) (H3-K9-HMTase 5) (Euchromatichistone-lysine N-methyltransferase 1) (Eu-HMTase 1) (G9a-like protein 1) (GLP1); (2584:) HIV-1 Tat interactive protein, 60 kDa isoform 1 [Homo sapiens]; (2585:) HIV-1 Tat interactive protein, 60 kDa isoform 2 [Homo sapiens]; (2586:) HIV-1 Tat interactive protein, 60 kDa isoform 3 [Homo sapiens]; (2587:) HLA class II histocompatibility antigen, DP alpha chain precursor (HLA-SB alpha chain) (MHC class II DP3-alpha) (DP(W3)) (DP(W4)); (2588:) HLA-B associated transcript 8 isoform a [Homo sapiens]; (2589:) HLA-B associated transcript 8 isoform b [Homo sapiens]; (2590:) hla-dcalpha alpha 2 domain (partial) [Homo sapiens]; (2591:) hla-dralpha related alpha 2 domain [Homo sapiens]; (2592:) HMC chymase I [Homo sapiens]; (2593:) HMGCR protein [Homo sapiens]; (2594:) hMLH1 gene product; (2595:) HMT1 hnRNP methyltransferase-like 6 [Homo sapiens]; (2596:) hMYHalpha1 [Homo sapiens]; (2597:) hMY-Halpha2 [Homo sapiens]; (2598:) hMYHalpha3 [Homo sapiens]; (2599:) hMYHalpha4 [Homo sapiens]; (2600:) hMYHbeta1 [Homo sapiens]; (2601:) hMYHbeta3 [Homo

*sapiens*]; (2602:) hMYHbeta5 [*Homo sapiens*]; (2603:) hMYHgamma2 [*Homo sapiens*]; (2604:) hMYHgamma3 [*Homo sapiens*]; (2605:) hMYHgamma4 [*Homo sapiens*]; (2606:) HNF1-alpha dimerization cofactor [*Homo sapiens*]; (2607:) homogentisate 1,2-dioxygenase [*Homo sapiens*]; (2608:) "homogentisate 1,2-dioxygenase; HGO [*Homo sapiens*]."; (2609:) homogentisate dioxygenase [*Homo sapiens*]; (2610:) homolgue of yeast DNA repair and recombination enzyme (RAD52)gene; (2611:) homolog of yeast long chain polyunsaturated fatty acid elongatio [*Homo sapiens*]; (2612:) homolog of yeast mutL gene; (2613:) Hormone-sensitive lipase (HSL); (2614:) hormone-sensitive lipase [*Homo sapiens*]; (2615:) HOYS7 [*Homo sapiens*]; (2616:) hPMS7 [*Homo sapiens*]; (2617:) H-protein; (2618:) HSPC015 [*Homo sapiens*]; (2619:) HSPC140 [*Homo sapiens*]; (2620:) HSPC150 [*Homo sapiens*]; (2621:) HSPC153 [*Homo sapiens*]; (2622:) HSPC279 [*Homo sapiens*]; (2623:) HtrA serine peptidase 1 [*Homo sapiens*]; (2624:) human 26S proteasome subunit p97 [*Homo sapiens*]; (2625:) Human Arylsulfatase A; (2626:) human endothelin-converting enzyme-1d isoform [*Homo sapiens*]; (2627:) human gamma-glutamyl hydrolase [*Homo sapiens*]; (2628:) Human Glutathione Reductase A34e, R37w Mutant, Mixed Disulfide Between Trypanothione And The Enzyme; (2629:) Human Glutathione Reductase A34e, R37w Mutant, Oxidized Glutathione Complex; (2630:) Human Glutathione Reductase A34e, R37w Mutant, Oxidized Trypanothione Complex; (2631:) Human Glutathione Reductase A34e, R37w Mutant, Glutathionylspermidine Complex; (2632:) Human Glutathione Reductase A34eR37W MUTANT; (2633:) Human Glutathione Reductase Modified By Dinitrosoglutathione; (2634:) Human Glutathione Reductase Modified By Diglutathione-Dinitroso-Iron; (2635:) human homolog of *E. coli* mutL gene product, Swiss-Prot Accession Number P23367; (2636:) human mammary dihydrolipoamide acetyltransferase, mature sequence[*Homo sapiens*]; (2637:) Human Ubc9; (2638:) human ubiquitin conjugating enzyme G2 EC 6.3.2.19. [*Homo sapiens*]; (2639:) huntingtin [*Homo sapiens*]; (2640:) huntingtin interacting protein 2 [*Homo sapiens*]; (2641:) huntingtin interacting protein; (2642:) hyaluronan synthase (EC 2.4.1.-)—human; (2643:) hyaluronan synthase 3 [*Homo sapiens*]; (2644:) Hyaluronidase-2 precursor (Hyal-2) (Hyaluronoglucosaminidase-2) (LUCA-2); (2645:) hyaluronoglucosaminidase 1 isoform 1 [*Homo sapiens*]; (2646:) hyaluronoglucosaminidase 1 isoform 2 [*Homo sapiens*]; (2647:) hyaluronoglucosaminidase 1 isoform 3 [*Homo sapiens*]; (2648:) hyaluronoglucosaminidase 1 isoform 4 [*Homo sapiens*]; (2649:) hyaluronoglucosaminidase 1 isoform 5 [*Homo sapiens*]; (2650:) hyaluronoglucosaminidase 1 isoform 6 [*Homo sapiens*]; (2651:) hydroxyacyl glutathione hydrolase isoform 1 [*Homo sapiens*]; (2652:) hydroxyacyl glutathione hydrolase isoform 2 [*Homo sapiens*]; (2653:) hydroxyacyl-Coenzyme A dehydrogenase, type II isoform 1 [*Homo sapiens*]; (2654:) hydroxyacyl-Coenzyme A dehydrogenase, type II isoform 2 [*Homo sapiens*]; (2655:) hydroxy-delta-5-steroid dehydrogenase, 3 beta- and steroid delta-isomerase 1 [*Homo sapiens*]; (2656:) hydroxy-delta-5-steroid dehydrogenase, 3 beta- and steroid delta-isomerase 2 [*Homo sapiens*]; (2657:) Hydroxymethylbilane synthase [*Homo sapiens*]; (2658:) hydroxymethylbilane synthase isoform 1 [*Homo sapiens*]; (2659:) hydroxymethylbilane synthase isoform 2 [*Homo sapiens*]; (2660:) hydroxymethylbilane synthase) (3-hydroxy-3-methylglutaryl coenzyme A synthase); (2663:) hydroxyprostaglandin dehydrogenase 15-(NAD) [*Homo sapiens*]; (2664:) hydroxysteroid (11-beta) dehydrogenase 2 [*Homo sapiens*]; (2665:) hydroxysteroid (17-beta) dehydrogenase 1 [*Homo sapiens*]; (2666:) hydroxysteroid (17-beta) dehydrogenase 2 [*Homo sapiens*]; (2667:) hydroxysteroid (17-beta) dehydrogenase 4 [*Homo sapiens*]; (2668:) hydroxysteroid (17-beta) dehydrogenase 7 [*Homo sapiens*]; (2669:) hypoxanthine phosphoribosyltransferase [*Homo sapiens*]; (2670:) hypoxanthine phosphoribosyltransferase 1 [*Homo sapiens*]; (2671:) Hypoxanthine-guanine phosphoribosyltransferase (HGPRT) (HGPRTase); (2672:) Hypoxia-inducible factor 1 alpha (HIF-1 alpha) (HIF1 alpha) (ARNT-interacting protein) (Member of PAS protein 1) (MOP1); (2673:) Hypoxia-inducible factor 1 alpha inhibitor (Hypoxia-inducible factor asparagine hydroxylase) (Factor inhibiting HIF-1) (FIH-1); (2674:) hypoxia-inducible factor 1, alpha subunit inhibitor [*Homo sapiens*]; (2675:) hypoxia-inducible factor 1, alpha subunit isoform 1 [*Homo sapiens*]; (2676:) hypoxia-inducible factor 1, alpha subunit isoform 2 [*Homo sapiens*]; (2677:) 1 beta 1-6 N-acetylglucosaminyltransferase; (2678:) 1 beta-1,6-N-acetylglucosaminyltransferase A form [*Homo sapiens*]; (2679:) 1 beta-1,6-N-acetylglucosaminyltransferase B form [*Homo sapiens*]; (2680:) 1 beta-1,6-N-acetylglucosaminyltransferase C form [*Homo sapiens*]; (2681:) IARS2 protein [*Homo sapiens*]; (2682:) "i-beta-1,3-N-acetylglucosaminyltransferase; poly-N-acetyllactosamine extension enzyme i-antigen; iGnT [*Homo sapiens*]."; (2683:) 1-branching beta-1,6-acetylglucosaminyltransferase family polypeptide 1 [*Homo sapiens*]; (2684:) I-branching beta-1,6-acetylglucosaminyltransferase family polypeptide 2 [*Homo sapiens*]; (2685:) I-branching beta-1,6-acetylglucosaminyltransferase family polypeptide 3 [*Homo sapiens*]; (2686:) 1-branching enzyme [*Homo sapiens*]; (2687:) ICE-LAP6—human; (2688:) ICE-LAP6; (2689:) ICH-1L; (2690:) ICH-1S; (2691:) lch-2; (2692:) "Iduronate 2-sulfatase precursor (Alpha-L-iduronate sulfatesulfatase) (Idursulfase) [Contains:) Iduronate 2-sulfatase 42 kDa chain; Iduronate 2-sulfatase 14 kDa chain]."; (2693:) iduronate 2-sulfatase; (2694:) I-FLICE [*Homo sapiens*]; (2695:) I-FLICE isoform 2 [*Homo sapiens*]; (2696:) I-FLICE isoform 3 [*Homo sapiens*]; (2697:) I-FLICE isoform 4 [*Homo sapiens*]; (2698:) I-FLICE isoform 5 [*Homo sapiens*]; (2699:) IgG receptor FcRn large subunit p51 precursor (FcRn) (Neonatal Fc receptor) (IgG Fc fragment receptor transporter, alpha chain); (2700:) IKK-related kinase epsilon [*Homo sapiens*]; (2701:) IlvB (bacterial acetolactate synthase)-like [*Homo sapiens*]; (2702:) ilvB (bacterial acetolactate synthase)-like isoform 1 [*Homo sapiens*]; (2703:) ilvB (bacterial acetolactate synthase)-like isoform 1 variant [*Homo sapiens*]; (2704:) ilvB (bacterial acetolactate synthase)-like isoform 2 [*Homo sapiens*]; (2705:) immunodeficiency virus type 1, HIV-1 gp120—human (fragments); (2706:) Immunoglobulin alpha Fc receptor precursor (IgA Fc receptor) (CD89antigen); (2707:) Immunoglobulin-like domain-containing receptor 1 precursor; (2708:) Importin-11 (Imp 11) (Ran-binding protein 11) (RanBP11); (2709:) Inactive ubiquitin carboxyl-terminal hydrolase 50 (Inactive ubiquitin-specific peptidase 50); (2710:) indoleamine-pyrrole 2,3 dioxygenase [*Homo sapiens*]; (2711:) indolethylamine N-methyltransferase [*Homo sapiens*]; (2712:) inducible nitric oxide synthase; (2713:) inhibin alpha subunit precursor [*Homo sapiens*]; (2714:) inhibin beta A precursor [*Homo sapiens*]; (2715:) inhibin beta B subunit precursor [*Homo sapiens*]; (2716:) inhibitor of kappa light polypeptide gene enhancer in B-cells, kinase beta [*Homo sapiens*]; (2717:) inhibitor of kappa light polypeptide gene enhancer in B-cells, kinase gamma [*Homo sapiens*]; (2718:) Inhibitor of nuclear factor kappa-B kinase alpha subunit (I kappa-B kinase alpha) (IkBKA) (IKK-alpha) (IKK-A) (IkappaB kinase) (1-kappa-B kinase 1) (IKK1) (Conserved helix-loop-helix ubiquitous kinase) (Nuclear factor NF-kappa-B inhibitor kinase alpha) (NFK-BIKA); (2719:) Inner Lipoyl Domain From Human Pyruvate Dehydrogenase (Pdh) Complex, Nmr, 1 Structure; (2720:) Inorganic pyrophosphatase (Pyrophosphate phospho-hydrolase) (PPase); (2721:) Inorganic pyrophosphatase 2, mitochondrial precursor (PPase 2) (Pyrophosphatase SID6-306); (2722:) inosine monophosphate dehydrogenase 2 [*Homo sapiens*]; (2723:) Inosine triphosphate pyrophosphatase (ITPase) (Inosine triphosphatase) (Putative oncogene protein hlc14-06-p); (2724:) Inosine-5'-monophosphate dehydrogenase 1 (IMP dehydrogenase 1) (IMPDH-I) (IMPD 1); (2725:) Inosine-5'-monophosphate dehydrogenase 2 (IMP dehydrogenase 2) (IMPDH-II) (IMPD 2); (2726:) inositol 1,3,4,5,6-pentakisphosphate 2-kinase [*Homo sapiens*]; (2727:) inositol 1,3,4-triphosphate 5/6 kinase [*Homo sapiens*]; (2728:) inositol 1,3,4-trisphosphate 5/6-kinase; (2729:) inositol 1,4,5-triphosphate receptor, type 3 [*Homo sapiens*]; (2730:) inositol 1,4,5-trisphosphate 3-kinase B—human; (2731:) Inositol 1,4,5-trisphosphate receptor type 1 (Type 1 inositol 1,4,5-trisphosphate receptor) (Type 1 InsP3 receptor) (IP3 receptor isoform 1) (InsP3R1) (IP3R); (2732:) Inositol 1,4,5-trisphosphate receptor type 2 (Type 2 inositol 1,4,5-trisphosphate receptor) (Type 2 InsP3 receptor) (IP3 receptor isoform 2) (InsP3R2); (2733:) Inositol 1,4,5-trisphosphate receptor type 3 (Type 3 inositol 1,4,5-trisphosphate receptor) (Type 3 InsP3 receptor) (IP3 receptor isoform 3) (InsP3R3); (2734:) Inositol Monophosphatase (E.C.3.1.3.25) (Apoenzyme); (2735:) Inositol monophosphatase (IMPase) (IMP) (Inositol-1(or 4)-monophosphatase) (Lithium-sensitive myo-inositol monophosphatase A1); (2736:) Inositol monophosphatase 2 (IMPase 2) (IMP 2) (Inositol-1(or 4)-monophosphatase 2) (Myo-inositol monophosphatase A2); (2737:) Inositol polyphosphate 1-phosphatase (IPPase) (IPP); (2738:) inositol polyphosphate-1-phosphatase [*Homo sapiens*]; (2739:) inositol polyphosphate-4-phosphatase, type 1 isoform a [*Homo sapiens*]; (2740:) inositol polyphosphate-4-phosphatase, type 1 isoform b [*Homo sapiens*]; (2741:) inositol polyphosphate-4-phosphatase, type II, 105 kD [*Homo sapiens*]; (2742:) inositol(myo)-1(or 4)-monophosphatase 1 [*Homo sapiens*]; (2743:) Inositol-pentakisphosphate 2-kinase (Inositol-1,3,4,5,6-pentakisphosphate 2-kinase) (Ins(1,3,4,5,6)P52-kinase) (InsP5 2-kinase) (IPK1 homolog); (2744:) Inositol-tetrakisphosphate 1-kinase (Inositol-triphosphate 5/6-kinase) (Inositol 1,3,4-trisphosphate 5/6-kinase); (2745:) Inositol-trisphosphate 3-kinase A (Inositol 1,4,5-trisphosphate 3-kinase A) (IP3K A) (IP3 3-kinase A); (2746:) Inositol-trisphosphate 3-kinase B (Inositol 1,4,5-trisphosphate 3-kinase B) (IP3K B) (IP3 3-kinase B) (IP3K-B); (2747:) Inositol-trisphosphate 3-kinase C (Inositol 1,4,5-trisphosphate 3-kinase C) (InsP 3-kinase C) (IP3K-C); (2748:) insulin receptor [*Homo sapiens*]; (2749:) "Insulin receptor precursor (1R) (CD220 antigen) [Contains:) Insulin receptor subunit alpha; Insulin receptor subunit beta]."; (2750:) insulin receptor substrate 1 [*Homo sapiens*]; (2751:) "Insulin receptor-related protein precursor (IRR) (IR-related receptor) [Contains:) Insulin receptor-related protein alpha chain; Insulin receptor-related protein beta chain]."; (2752:) insulin receptor-related receptor—human (fragment); (2753:) Insulin-degrading enzyme (Insulysin) (Insulinase) (Insulin protease); (2754:) Insulin-degrading enzyme [*Homo sapiens*]; (2755:) insulin-like growth factor 1 (somatomedin C) [*Homo sapiens*]; (2756:) "Insulin-like growth factor 1 receptor precursor (Insulin-like growth factor I receptor) (IGF-I receptor) (CD221 antigen) [Contains:) Insulin-like growth factor 1 receptor alpha chain; Insulin-like growth factor 1 receptor beta chain]."; (2757:) insulin-like growth factor 2 [*Homo sapiens*]; (2758:) insulin-like growth factor 2 receptor [*Homo sapiens*]; (2759:) insulysin [*Homo sapiens*]; (2760:) Integral membrane protein 2B (Transmembrane protein BRI) [Contains: ABri/ADan amyloid peptide]; (2761:) Integral membrane protein 2C (Transmembrane protein BRI3) (Cerebral protein 14) [Contains:) CT-BRI3]; (2762:) integral membrane protein 2C isoform 1 [*Homo sapiens*]; (2763:) integral membrane protein 2C isoform 2 [*Homo sapiens*]; (2764:) integral membrane protein 2C isoform 3 [*Homo sapiens*]; (2765:) Integral membrane protein DGCR2/IDD precursor; (2766:) integrin alpha chain, alpha 6 [*Homo sapiens*]; (2767:) Integrin alpha-1 (Laminin and collagen receptor) (VLA-1) (CD49a antigen); (2768:) Integrin alpha-10 precursor; (2769:) Integrin alpha-11 precursor; (2770:) Integrin alpha-2 precursor (Platelet membrane glycoprotein Ia) (GPIa) (Collagen receptor) (VLA-2 alpha chain) (CD49b antigen); (2771:) "Integrin alpha-3 precursor (Galactoprotein B3) (GAPB3) (VLA-3 alpha chain) (FRP-2) (CD49c antigen) [Contains:) Integrin alpha-3 heavy chain; Integrin alpha-3 light chain]."; (2772:) Integrin alpha-4 precursor (Integrin alpha-IV) (VLA-4) (CD49d antigen); (2773:) "Integrin alpha-5 precursor (Fibronectin receptor subunit alpha) (Integrin alpha-F) (VLA-5) (CD49e antigen) [Contains:) Integrin alpha-5 heavy chain; Integrin alpha-5 light chain]."; (2774:) "Integrin alpha-6 precursor (VLA-6) (CD49f antigen) [Contains:Integrin alpha-6 heavy chain; Integrin alpha-6 light chain]."; (2775:) "Integrin alpha-7 precursor [Contains:) Integrin alpha-7 heavy chain; Integrin alpha-7 light chain]."; (2776:) "Integrin alpha-8 precursor [Contains:) Integrin alpha-8 heavy chain; Integrin alpha-8 light chain]."; (2777:) Integrin alpha-9 precursor (Integrin alpha-RLC); (2778:) Integrin alpha-D precursor (Leukointegrin alpha D) (ADB2) (CD11d antigen); (2779:) "Integrin alpha-E precursor (Mucosal lymphocyte 1 antigen) (HML-1 antigen) (Integrin alpha-IEL) (CD103 antigen) [Contains:) Integrin alpha-E light chain; Integrin alpha-E heavy chain]."; (2780:) "Integrin alpha-11b precursor (Platelet membrane glycoprotein IIb) (GPalpha IIb) (GPIIb) (CD41 antigen) [Contains:) Integrin alpha-IIb heavy chain; Integrin alpha-IIb light chain]."; (2781:) Integrin alpha-L precursor (Leukocyte adhesion glycoprotein LFA-1 alpha chain) (LFA-1A) (Leukocyte function-associated molecule 1alpha chain) (CD1a antigen); (2782:) Integrin alpha-M precursor (Cell surface glycoprotein MAC-1 alpha subunit) (CR-3 alpha chain) (Leukocyte adhesion receptor MO) (Neutrophil adherence receptor) (CD11b antigen); (2783:) "Integrin alpha-V precursor (Vitronectin receptor subunit alpha) (CD51 antigen) [Contains:) Integrin alpha-V heavy chain; Integrin alpha-V light chain]."; (2784:) Integrin alpha-X precursor (Leukocyte adhesion glycoprotein p150,95alpha chain) (Leukocyte adhesion receptor p150,95) (Leu M5) (CD11c antigen); (2785:) Integrin beta 1 binding protein 3 [*Homo sapiens*]; (2786:) integrin beta 1 binding protein 3 isoform 2 [*Homo sapiens*]; (2787:) Integrin beta-1 precursor (Fibronectin receptor subunit beta) (Integrin VLA-4 subunit beta) (CD29 antigen); (2788:) Integrin beta-2 precursor (Cell surface adhesion glycoproteins LFA-1/CR3/p150,95 subunit beta) (Complement receptor C3 subunit beta) (CD18 antigen); (2789:) Integrin beta-3 precursor (Platelet membrane glycoprotein IIIa) (GPIIIa) (CD61 antigen); (2790:) Integrin beta-4 precursor (GP150) (CD104 antigen); (2791:) Integrin beta-5 precursor; (2792:) Integrin beta-6 precursor; (2793:)

Integrin beta-7 precursor; (2794:) integrin beta-8 precursor; (2795:) integrin-linked kinase [*Homo sapiens*]; (2796:) Integrin-linked protein kinase 1 (ILK-1) (59 kDa serine/threonine-protein kinase) (p591LK); (2797:) inter-alpha globulin inhibitor H2 polypeptide [*Homo sapiens*]; (2798:) intercellular adhesion molecule 1 precursor [*Homo sapiens*]; (2799:) interferon, gamma [*Homo sapiens*]; (2800:) interferon, gamma-inducible protein 30 preproprotein [*Homo sapiens*]; (2801:) Interferon-alpha/beta receptor alpha chain precursor (IFN-alpha-REC); (2802:) Interferon-alpha/beta receptor beta chain precursor (IFN-alpha-REC) (Type I interferon receptor) (IFN-R) (Interferon alpha/beta receptor 2); (2803:) Interferon-gamma receptor alpha chain precursor (IFN-gamma-R1) (CD119 antigen) (CDw119); (2804:) Interferon-gamma receptor beta chain precursor (Interferon-gamma receptor accessory factor 1) (AF-1) (Interferon-gamma transducer 1); (2805:) Interferon-induced 17 kDa protein precursor [Contains:] Ubiquitin cross-reactive protein (hUCRP) (Interferon-induced 15 kDa protein)]; (2806:) Interferon-induced, double-stranded RNA-activated protein kinase (Interferon-inducible RNA-dependent protein kinase) (Protein kinase RNA-activated) (PKR) (p68 kinase) (P1/eIF-2A protein kinase); (2807:) Interferon-stimulated gene 20 kDa protein (Promyelocytic leukemia nuclear body-associated protein ISG20) (Estrogen-regulated transcript 45 protein); (2808:) interleukin 1 receptor antagonist isoform 1 precursor [*Homo sapiens*]; (2809:) interleukin 1 receptor antagonist isoform 2 [*Homo sapiens*]; (2810:) interleukin 1 receptor antagonist isoform 3 [*Homo sapiens*]; (2811:) interleukin 1 receptor antagonist isoform 4 [*Homo sapiens*]; (2812:) interleukin 1, beta proprotein [*Homo sapiens*]; (2813:) interleukin 18 proprotein [*Homo sapiens*]; (2814:) interleukin 1-beta convertase [*Homo sapiens*]; (2815:) interleukin 1-beta convertase; (2816:) Interleukin 1-beta converting enzyme isoform beta; (2817:) Interleukin 1-beta converting enzyme isoform delta; (2818:) Interleukin 1-beta converting enzyme isoform epsilon; (2819:) interleukin 1-beta converting enzyme isoform gamma; (2820:) interleukin 1 beta-converting enzyme; (2821:) interleukin 6 receptor isoform 1 precursor [*Homo sapiens*]; (2822:) interleukin 6 receptor isoform 2 precursor [*Homo sapiens*]; (2823:) interleukin 8 precursor [*Homo sapiens*]; (2824:) interleukin 8 receptor beta [*Homo sapiens*]; (2825:) interleukin-1 beta converting enzyme {N-terminal} [human, Peptide Partial, 23 aa]; (2826:) Interleukin-1 receptor accessory protein precursor (IL-1 receptor accessory protein) (IL-1 RAcP); (2827:) Interleukin-1 receptor type I precursor (IL-1R-1) (IL-1RT1) (IL-1R-alpha) (p80) (CD121a antigen); (2828:) Interleukin-1 receptor type II precursor (IL-1R-2) (IL-1R-beta) (CD121b antigen) (CDw121b); (2829:) Interleukin-1 receptor-associated kinase 1 (IRAK-1); (2830:) Interleukin-1 receptor-associated kinase-like 2 (IRAK-2); (2831:) Interleukin-1 receptor-like 1 precursor (ST2 protein); (2832:) Interleukin-1 receptor-like 2 precursor (IL-1Rrp2) (Interleukin-1 receptor-related protein 2) (IL1R-rp2); (2833:) Interleukin-10 receptor alpha chain precursor (IL-10R-A) (IL-10R1) (CDw210a antigen); (2834:) Interleukin-10 receptor beta chain precursor (IL-10R-B) (IL-10R2) (Cytokine receptor family 2 member 4) (Cytokine receptor class-II member 4) (CRF2-4) (CDw210b antigen); (2835:) Interleukin-11 receptor alpha chain precursor (IL-11R-alpha) (IL-11RA); (2836:) Interleukin-12 receptor beta-1 chain precursor (IL-12R-beta1) (Interleukin-12 receptor beta) (IL-12 receptor beta component) (IL-12RB1) (CD212 antigen); (2837:) Interleukin-12 receptor beta-2 chain precursor (IL-12 receptor beta-2) (IL-12R-beta2); (2838:) Interleukin-13 receptor alpha-1 chain precursor (IL-13R-alpha-1) (IL-13RA-1) (CD213a1 antigen); (2839:) Interleukin-13 receptor alpha-2 chain precursor (Interleukin-1,3-binding protein) (CD213a2 antigen); (2840:) Interleukin-15 receptor alpha chain precursor (IL-15R-alpha) (IL-15RA); (2841:) Interleukin-17 receptor A precursor (IL-17 receptor) (CD217antigen) (CDw217); (2842:) Interleukin-17 receptor B precursor (IL-17 receptor B) (IL-17RB) (Interleukin-17B receptor) (IL-17B receptor) (IL-17 receptor homolog 1) (IL-17Rh1) (IL17Rh1) (Cytokine receptor CRL4); (2843:) Interleukin-17 receptor C precursor (IL-17 receptor C) (IL-17RC) (Interleukin-17 receptor-like protein) (IL-17RL) (Interleukin-17receptor homolog) (IL17Rhom); (2844:) Interleukin-17 receptor D precursor (IL-17 receptor D) (IL-17RD) (Interleukin-17D receptor) (IL-17D receptor) (IL17Rhom) (Interleukin-17 receptor-like protein) (Sef homolog) (hSef); (2845:) Interleukin-18 receptor 1 precursor (IL1 receptor-related protein) (IL-1Rrp) (CDw218a antigen); (2846:) Interleukin-18 receptor accessory protein precursor (IL-18 receptor accessory protein) (IL-18RAcP) (Interleukin-18 receptor accessory protein-like) (IL-18Rbeta) (IL-1R accessory protein-like) (IL-1RAcPL) (Accessory protein-like) (AcPL) (IL-1R7) (CDw218b antigen); (2847:) interleukin-1B converting enzyme [*Homo sapiens*]; (2848:) Interleukin-2 receptor alpha chain precursor (IL-2 receptor alpha subunit) (IL-2-RA) (IL2-RA) (p55) (TAC antigen) (CD25 antigen); (2849:) Interleukin-2 receptor subunit beta precursor (IL-2 receptor) (P70-75) (p75) (High affinity IL-2 receptor subunit beta) (CD122antigen); (2850:) Interleukin-20 receptor alpha chain precursor (IL-20R-alpha) (IL-20R1) (Cytokine receptor family 2 member 8) (Cytokine receptor class-II member 8) (CRF2-8) (ZcytoR7); (2851:) Interleukin-20 receptor beta chain precursor (IL-20R-beta) (IL-20R2); (2852:) Interleukin-21 receptor precursor (IL-21R) (Novel interleukin receptor); (2853:) Interleukin-22 receptor alpha-2 chain precursor (IL-22R-alpha-2) (Interleukin 22-binding protein) (IL22BP) (Cytokine receptor family class II member 10) (CRF2-10) (Cytokine receptor family type 2, soluble 1) (CRF2-S1); (2854:) Interleukin-27 receptor alpha chain precursor (IL-27R-alpha) (WSX-1) (Type I T-cell cytokine receptor) (TCCR) (Protein CRL1); (2855:) Interleukin-28 receptor alpha chain precursor (IL-28R-alpha) (IL-28RA) (Cytokine receptor family 2 member 12) (Cytokine receptor class-II member 12) (CRF2-12) (Interferon lambda receptor 1) (IFN-lambda R1) (Likely interleukin or cytokine receptor 2); (2856:) Interleukin-3 receptor alpha chain precursor (IL-3R-alpha) (CD123antigen); (2857:) Interleukin-4 receptor alpha chain precursor (IL-4R-alpha) (CD124antigen) [Contains:] Soluble interleukin-4 receptor alpha chain (sIL4R alpha/prot) (IL-4-binding protein) (IL4-BP)]; (2858:) Interleukin-5 receptor alpha chain precursor (IL-5R-alpha) (CD125antigen) (CDw125); (2859:) Interleukin-6 receptor alpha chain precursor (IL-6R-alpha) (IL-6R1) (Membrane glycoprotein 80) (gp80) (CD126 antigen); (2860:) Interleukin-6 receptor subunit beta precursor (IL-6R-beta) (Interleukin-6 signal transducer) (Membrane glycoprotein 130) (gp130) (Oncostatin-M receptor alpha subunit) (CD130 antigen) (CDw130); (2861:) Interleukin-7 receptor alpha chain precursor (IL-7R-alpha) (CD127antigen) (CDw127); (2862:) Interleukin-9 receptor precursor (IL-9R) (CD129 antigen); (2863:) Interphotoreceptor matrix proteoglycan 1 precursor (Interphotoreceptor matrix proteoglycan of 150 kDa) (IPM-150) (Sialoprotein associated with cones and rods); (2864:) "Interstitial collagenase precursor (Matrix metalloproteinase-1) (MMP-1) (Fibroblast collagenase) [Contains:] 22 kDa interstitial collagenase; 27 kDa interstitial collagenase]."; (2865:) intestinal alkaline phosphatase precursor [*Homo sapiens*]; (2866:) intestinal alkaline sphingomyelinase [*Homo sapiens*]; (2867:) iron-sulfur cluster assembly enzyme isoform ISCU1 [*Homo sapiens*]; (2868:) iron-sulfur cluster assembly enzyme isoform ISCU2 precursor [*Homo sapiens*]; (2869:) islet amyloid polypeptide precursor [*Homo sapiens*]; (2870:) Isocitrate dehydrogenase [NAD] subunit gamma, mitochondrial precursor (Isocitric dehydrogenase) (NAD(+)-specific ICDH); (2871:) Isocitrate dehydrogenase [NADP] cytoplasmic (Cytosolic NADP-isocitrate dehydrogenase) (Oxalosuccinate decarboxylase) (IDH) (NADP(+)-specific ICDH) (IDP); (2872:) isocitrate dehydrogenase 1 (NADP+), soluble [*Homo sapiens*]; (2873:) isocitrate dehydrogenase 3 (NAD+) alpha precursor [*Homo sapiens*]; (2874:) isopentenyl-diphosphate delta isomerase [*Homo sapiens*]; (2875:) isopeptidase T; (2876:) isopeptidase T-3 [*Homo sapiens*]; (2877:) isoprenylcysteine carboxyl methyltransferase [*Homo sapiens*]; (2878:) isovaleryl Coenzyme A dehydrogenase [*Homo sapiens*]; (2879:) Itchy homolog E3 ubiquitin protein ligase (Itch) (Atrophin-1-interacting protein 4) (AIP4) (NFE2-associated polypeptide 1) (NAPP1); (2880:) Janus kinase 3 [*Homo sapiens*]; (2881:) JmjC domain-containing histone demethylation protein 1B([Histone-H3]-lysine-36 demethylase 1B) (F-box/LRR-repeat protein10) (F-box and leucine-rich repeat protein 10) (F-box protein FBL10) (Protein JEMMA) (Jumonji domain-containing EMSY-interactormethyltransferase motif protein) (CXXC-type zinc finger protein 2) (Protein-containing CXXC domain 2); (2882:) JmjC domain-containing histone demethylation protein 2B (Jumonji domain-containing protein 1B) (Nuclear protein 5qNCA); (2883:) JmjC domain-containing histone demethylation protein 3B (Jumonji domain-containing protein 2B); (2884:) JmjC domain-containing histone demethylation protein 3C (Jumonji domain-containing protein 2C) (Gene amplified in squamous cell carcinoma 1 protein) (GASC-1 protein); (2885:) JmjC domain-containing histone demethylation protein 3D (Jumonji domain-containing protein 2D); (2886:) JRK protein [*Homo sapiens*]; (2887:) jub, ajuba homolog isoform 1 [*Homo sapiens*]; (2888:) jub, ajuba homolog isoform 2 [*Homo sapiens*]; (2889:) jun oncogene [*Homo sapiens*]; (2890:) junction plakoglobin [*Homo sapiens*]; (2891:) JUP protein [*Homo sapiens*]; (2892:) kalirin, RhoGEF kinase isoform 1 [*Homo sapiens*]; (2893:) kalirin, RhoGEF kinase isoform 2 [*Homo sapiens*]; (2894:) kalirin, RhoGEF kinase isoform 3 [*Homo sapiens*]; (2895:) kallikrein 8 isoform 1 preproprotein [*Homo sapiens*]; (2896:) kallikrein 8 isoform 2 [*Homo sapiens*]; (2897:) kallikrein 8 isoform 3 [*Homo sapiens*]; (2898:) kallikrein 8 isoform 4 [*Homo sapiens*]; (2899:) Kallikrein-5 precursor (Stratum corneum tryptic enzyme) (Kallikrein-like protein 2) (KLK-L2); (2900:) Kallikrein-6 precursor (Protease M) (Neurosin) (Zyme) (SP59); (2901:) Kallikrein-7 precursor (hK7) (Stratum corneum chymotryptic enzyme) (hSCCE); (2902:) kallikrein-related peptidase 4 preproprotein [*Homo sapiens*]; (2903:) kallikrein-related peptidase 5 preproprotein [*Homo sapiens*]; (2904:) kallikrein-related peptidase 6 isoform A preproprotein [*Homo sapiens*]; (2905:) kallikrein-related peptidase 6 isoform B [*Homo sapiens*]; (2906:) Kallistatin precursor (Serpin A4) (Kallikrein inhibitor) (Protease inhibitor 4); (2907:) Kappa-type opioid receptor (KOR-1); (2908:) KAT3 protein [*Homo sapiens*]; (2909:) Katanin p60 ATPase-containing subunit A1 (Katanin p60 subunit A1) (p60 katanin); (2910:) katanin p60 subunit A 1 [*Homo sapiens*]; (2911:) katanin p80 subunit B1 [*Homo sapiens*]; (2912:) KDEL (Lys-Asp-Glu-Leu) containing 1 [*Homo sapiens*]; (2913:) KDEL (Lys-Asp-Glu-Leu) containing 2 [*Homo sapiens*]; (2914:) KDEL motif-containing protein 1 precursor; (2915:) KDEL motif-containing protein 2 precursor; (2916:) Kelch-like ECH-associated protein 1 (Cytosolic inhibitor of Nrf2) (Kelch-like protein 19); (2917:) Kell blood group, metallo-endopeptidase [*Homo sapiens*]; (2918:) keratan sulfate Gal-6-sulfotransferase [*Homo sapiens*]; (2919:) Ketohexokinase (Hepatic fructokinase); (2920:) Ketosamine-3-kinase (Fructosamine-3-kinase-related protein); (2921:) KH-type splicing regulatory protein (FUSE binding protein 2) [*Homo sapiens*]; (2922:) kidney and liver proline oxidase 1 [*Homo sapiens*]; (2923:) Killer cell immunoglobulin-like receptor 2DL1 precursor (MHC classI NK cell receptor) (Natural killer-associated transcript 1) (NKAT-1) (p58 natural killer cell receptor clones CL-42/47.11) (p58NK receptor) (p58.1 MHC class-I-specific NK receptor) (CD158a antigen); (2924:) Killer cell immunoglobulin-like receptor 2DL2 precursor (MHC classI NK cell receptor) (Natural killer-associated transcript 6) (NKAT-6) (p58 natural killer cell receptor clone CL-43) (p58 NK receptor); (2925:) Killer cell immunoglobulin-like receptor 2DL3 precursor (MHC classI NK cell receptor) (Natural killer-associated transcript 2) (NKAT-2) (NKAT2a) (NKAT2b) (p58 natural killer cell receptor clone CL-6) (p58 NK receptor) (p58.2 MHC class-1-specific NK receptor) (Killer inhibitory receptor cl 2-3) (KIR-023 GB) (CD158b antigen); (2926:) Killer cell immunoglobulin-like receptor 2DL4 precursor (MHC classI NK cell receptor KIR103AS) (Killer cell inhibitory receptor103AS) (KIR-103AS) (G9P) (CD158d antigen); (2927:) Killer cell immunoglobulin-like receptor 2DS1 precursor (MHC classI NK cell receptor Eb6 ActI) (CD158h antigen); (2928:) Killer cell immunoglobulin-like receptor 2DS2 precursor (MHC classI NK cell receptor) (Natural killer-associated transcript 5) (NKAT-5) (p58 natural killer cell receptor clone CL-49) (p58 NK receptor) (NK receptor 183 ActI) (CD158j antigen); (2929:) Killer cell immunoglobulin-like receptor 2DS3 precursor (MHC classI NK cell receptor) (Natural killer-associated transcript 7) (NKAT-7); (2930:) Killer cell immunoglobulin-like receptor 2DS4 precursor (MHC classI NK cell receptor) (Natural killer-associated transcript 8) (NKAT-8) (P58 natural killer cell receptor clone CL-39) (p58 NK receptor) (CL-17) (CD158i antigen); (2931:) Killer cell immunoglobulin-like receptor 2DS5 precursor (MHC classI NK cell receptor) (Natural killer-associated transcript 9) (NKAT-9) (CD158g antigen); (2932:) Killer cell immunoglobulin-like receptor 3DL1 precursor (MHC classI NK cell receptor) (Natural killer-associated transcript 3) (NKAT-3) (p70 natural killer cell receptor clones CL-2/CL-11) (HLA-BW4-specific inhibitory NK cell receptor); (2933:) Killer cell immunoglobulin-like receptor 3DL2 precursor (MHC classI NK cell receptor) (Natural killer-associated transcript 4) (NKAT-4) (p70 natural killer cell receptor clone CL-5) (CD158k antigen); (2934:) Killer cell immunoglobulin-like receptor 3DL3 precursor (Killer cell inhibitory receptor 1) (CD158z antigen); (2935:) Killer cell immunoglobulin-like receptor 3DS1 precursor (MHC classI NK cell receptor) (Natural killer-associated transcript 10) (NKAT-10); (2936:) Killer cell lectin-like receptor subfamily F member 1 (Lectin-like receptor F1) (Activating coreceptor NKp80); (2937:) kinase insert domain receptor (a type III receptor tyrosine kinase)[*Homo sapiens*]; (2938:) kinase interacting stathmin [*Homo sapiens*]; (2939:) kinase related protein, telokin isoform 7 [*Homo sapiens*]; (2940:) kinase related protein, telokin isoform 8 [*Homo sapiens*]; (2941:) kinase, phosphoglycerate; (2942:) kinesin family member 23 isoform 1 [*Homo sapiens*]; (2943:) kinesin family member 23 isoform 2 [*Homo sapiens*]; (2944:) Kinesin-like protein KIF23 (Mitotic kinesin-like protein 1) (Kinesin-like protein 5); (2945:) Kinesin-like protein KIFC1 (Kinesin-like protein 2) (Kinesin-related protein HSET); (2946:) KiSS-1 receptor (KiSS-1R) (Kisspeptins receptor) (Metastin receptor) (G-protein coupled receptor 54) (Hypogonadotropin-1) (hOT7T175); (2947:) KIAA0184 [Homo sapiens]; (2948:) KIAA0184 protein [Homo sapiens]; (2949:) KIAA0377 splice variant 4 [Homo sapiens]; (2950:) KIAA0398 [Homo sapiens]; (2951:) KIAA0433 [Homo sapiens]; (2952:) KIAA0837 protein [Homo sapiens]; (2953:) KIAA0934 protein [Homo sapiens]; (2954:) KIAA1238 protein [Homo sapiens]; (2955:) KIAA1289 protein [Homo sapiens]; (2956:) KIAA1385 protein [Homo sapiens]; (2957:) KIAA1463 protein [Homo sapiens]; (2958:) KIAA1516 protein [Homo sapiens]; (2959:) KIAA1734 protein [Homo sapiens]; (2960:) KIAA1846 protein [Homo sapiens]; (2961:) KIAA1963 protein [Homo sapiens]; (2962:) KIAA1992 protein [Homo sapiens]; (2963:) Kruppel-like factor 4 (gut) [Homo sapiens]; (2964:) kynureninase (L-kynurenine hydrolase) isoform a [Homo sapiens]; (2965:) kynureninase (L-kynurenine hydrolase) isoform b [Homo sapiens]; (2966:) Kynureninase (L-kynurenine hydrolase); (2967:) Kynurenine 3-monooxygenase (Kynurenine 3-hydroxylase); (2968:) kynurenine aminotransferase III [Homo sapiens]; (2969:) kynurenine aminotransferase III isoform 1 [Homo sapiens]; (2970:) kynurenine aminotransferase III isoform 2 [Homo sapiens]; (2971:) L-3-hydroxyacyl-Coenzyme A dehydrogenase precursor [Homo sapiens]; (2972:) "Lactase-phlorizin hydrolase precursor (Lactase-glycosylceramidase)[Includes:) Lactase; Phlorizin hydrolase]."; (2973:) lactase-phlorizin hydrolase preproprotein [Homo sapiens]; (2974:) lactate dehydrogenase A [Homo sapiens]; (2975:) Lactosylceramide 4-alpha-galactosyltransferase (Alpha-1,4-galactosyltransferase) (UDP-galactose:beta-D-galactosyl-beta1-R4-alpha-D-galactosyltransferase) (Alpha-1,4-N-acetylglucosaminyltransferase) (Alpha4Gal-T1) (Globotriaosylceramide synthase) (Gb3 synthase) (CD77 synthase) (P1/Pk synthase); (2976:) Lactoylglutathione lyase (Methylglyoxalase) (Aldoketomutase) (Glyoxalase I) (Glx I) (Ketone-aldehyde mutase) (S-D-lactoylglutathione methylglyoxal lyase); (2977:) laeverin [Homo sapiens]; (2978:) lambda-crystallin [Homo sapiens]; (2979:) Lambda-crystallin homolog; (2980:) Lamin-B receptor (Integral nuclear envelope inner membrane protein) (LMN2R); (2981:) laminin alpha 3 subunit isoform 1 [Homo sapiens]; (2982:) laminin alpha 3 subunit isoform 2 [Homo sapiens]; (2983:) laminin subunit beta 3 precursor [Homo sapiens]; (2984:) laminin, gamma 2 isoform a precursor [Homo sapiens]; (2985:) laminin, gamma 2 isoform b precursor [Homo sapiens]; (2986:) LANCL2 protein [Homo sapiens]; (2987:) lanthionine synthetase C-like protein 1 [Homo sapiens]; (2988:) Lariat debranching enzyme; (2989:) Latrophilin-1 precursor (Calcium-independent alpha-latrotoxin receptor 1) (Lectomedin-2); (2990:) Latrophilin-2 precursor (Calcium-independent alpha-latrotoxin receptor 2) (Latrophilin homolog 1) (Lectomedin-1); (2991:) Latrophilin-3 precursor (Calcium-independent alpha-latrotoxin receptor 3) (Lectomedin-3); (2992:) LBP-32 [Homo sapiens]; (2993:) LBP-9 [Homo sapiens]; (2994:) LCFA CoA ligase [Homo sapiens]; (2995:) leader-binding protein 32 isoform 1 [Homo sapiens]; (2996:) leader-binding protein 32 isoform 2 [Homo sapiens]; (2997:) Lecithin retinol acyltransferase (Phosphatidylcholine—retinolO-acyltransferase); (2998:) lecithin retinol acyltransferase [Homo sapiens]; (2999:) lecithin-cholesterol acyltransferase precursor [Homo sapiens]; (3000:) legumain preproprotein [Homo sapiens]; (3001:) legumaturain [Homo sapiens]; (3002:) leprecan-like 1 [Homo sapiens]; (3003:) leprecan-like 2 [Homo sapiens]; (3004:) Leptin receptor precursor (LEP-R) (OB receptor) (OB-R) (HuB219) (CD295 antigen); (3005:) leucine aminopeptidase 3 [Homo sapiens]; (3006:) leucine proline-enriched proteoglycan (leprecan) 1 [Homo sapiens]; (3007:) leucine-rich alpha-2-glycoprotein 1 [Homo sapiens]; (3008:) Leucine-rich repeat serine/threonine-protein kinase 1; (3009:) Leucine-rich repeat-containing G-protein coupled receptor 4precursor (G-protein coupled receptor 48); (3010:) Leucine-rich repeat-containing G-protein coupled receptor 5precursor (Orphan G-protein coupled receptor HG38) (G-protein coupled receptor 49) (G-protein coupled receptor 67); (3011:) Leucine-rich repeat-containing G-protein coupled receptor 6(VTS20631); (3012:) leucyl aminopeptidase (EC 3.4.11.1)/prolyl aminopeptidase (EC3.4.11.5)—human (fragment); (3013:) Leucyl-cystinyl aminopeptidase (Cystinyl aminopeptidase) (Oxytocinase) (OTase) (Insulin-regulated membrane aminopeptidase) (Insulin-responsive aminopeptidase) (IRAP) (Placental leucineaminopeptidase) (P-LAP); (3014:) Leukemia inhibitory factor receptor precursor (LIF receptor) (LIF-R) (CD118 antigen); (3015:) Leukocyte elastase precursor (Elastase-2) (Neutrophil elastase) (PMN elastase) (Bone marrow serine protease) (Medullasin) (Human leukocyte elastase) (HLE); (3016:) Leukocyte immunoglobulin-like receptor subfamily A member 1 precursor (Leukocyte immunoglobulin-like receptor 6) (LIR-6) (CD85i antigen); (3017:) Leukocyte immunoglobulin-like receptor subfamily A member 2precursor (Leukocyte immunoglobulin-like receptor 7) (LIR-7) (Immunoglobulin-like transcript 1) (ILT-1) (CD85h antigen); (3018:) Leukocyte immunoglobulin-like receptor subfamily A member 3precursor (Leukocyte immunoglobulin-like receptor 4) (LIR-4) (Immunoglobulin-like transcript 6) (ILT-6) (Monocyte inhibitory receptor HM43/HM31) (CD85e antigen); (3019:) Leukocyte immunoglobulin-like receptor subfamily A member 4precursor (Immunoglobulin-like transcript 7) (ILT-7) (CD85g antigen); (3020:) Leukocyte immunoglobulin-like receptor subfamily B member 1 precursor (Leukocyte immunoglobulin-like receptor 1) (LIR-1) (Immunoglobulin-like transcript 2) (ILT-2) (Monocyte/macrophage immunoglobulin-like receptor 7) (MIR-7) (CD85j antigen); (3021:) Leukocyte immunoglobulin-like receptor subfamily B member 2precursor (Leukocyte immunoglobulin-like receptor 2) (LIR-2) (Immunoglobulin-like transcript 4) (ILT-4) (Monocyte/macrophage immunoglobulin-like receptor 10) (MIR-10) (CD85d antigen); (3022:) Leukocyte immunoglobulin-like receptor subfamily B member 3precursor (Leukocyte immunoglobulin-like receptor 3) (LIR-3) (Immunoglobulin-like transcript 5) (ILT-5) (Monocyte inhibitory receptor HL9) (CD85a antigen); (3023:) Leukocyte immunoglobulin-like receptor subfamily B member 4precursor (Leukocyte immunoglobulin-like receptor 5) (LIR-5) (Immunoglobulin-like transcript 3) (ILT-3) (Monocyte inhibitory receptor HM18) (CD85k antigen); (3024:) Leukocyte immunoglobulin-like receptor subfamily B member 5precursor (Leukocyte immunoglobulin-like receptor 8) (LIR-8) (CD85c antigen); (3025:) Leukocyte tyrosine kinase receptor precursor (Protein tyrosine kinase 1); (3026:) Leukocyte-associated immunoglobulin-like receptor 1 precursor (LAIR-1) (hLAIR1) (CD305 antigen); (3027:) Leukocyte-associated immunoglobulin-like receptor 2 precursor (LAIR-2) (CD306 antigen); (3028:) Leukotriene A-4 hydrolase (LTA-4 hydrolase) (Leukotriene A(4)hydrolase); (3029:) leukotriene A4 hydrolase [Homo sapiens]; (3030:) leukotriene A-4 hydrolase precursor; (3031:) Leukotriene A4 hydrolase, LTA4 hydrolase [human, B-lymphocytic cell line Raji, Peptide Partial, 21 aa]; (3032:) leukotriene A4 hydrolase; (3033:) leukotriene B4 receptor [Homo sapiens];

(3034:) Leukotriene B4 receptor 1 (LTB4-R1) (P2Y purinoceptor 7) (P2Y7) (Chemoattractant receptor-like 1) (G-protein coupled receptor 16); (3035:) Leukotriene B4 receptor 2 (LTB4-R2) (Seven transmembrane receptor BLTR2) (Leukotriene B4 receptor BLT2) (LTB4 receptor JULF2); (3036:) leukotriene C4 synthase (EC 6.-.-.-)—human; (3037:) leukotriene C4 synthase [Homo sapiens]; (3038:) Lice2 alpha [Homo sapiens]; (3039:) Lice2 beta cysteine protease [Homo sapiens]; (3040:) Lice2 gamma cysteine protease [Homo sapiens]; (3041:) ligase III, DNA, ATP-dependent isoform alpha precursor [Homo sapiens]; (3042:) ligase III, DNA, ATP-dependent isoform beta precursor [Homo sapiens]; (3043:) Limb region 1 protein homolog (Differentiation-related gene 14protein); (3044:) lipase A precursor [Homo sapiens]; (3045:) lipase C precursor [Homo sapiens]; (3046:) Lipase member I precursor (Membrane-associated phosphatidic acid-selective phospholipase A1-beta) (mPA-PLA1 beta) (LPD lipase); (3047:) lipase, gastric [Homo sapiens]; (3048:) Lipid phosphate phosphohydrolase 1 (Phosphatidic acid phosphatase 2a) (Phosphatidate phosphohydrolase type 2a) (PAP2a) (PAP-2a) (PAP2-alpha); (3049:) Lipid phosphate phosphohydrolase 2 (Phosphatidic acid phosphatase 2c) (Phosphatidate phosphohydrolase type 2c) (PAP2c) (PAP-2c) (PAP2-gamma) (PAP2-G); (3050:) Lipid phosphate phosphohydrolase 3 (Phosphatidic acid phosphatase 2b) (Phosphatidate phosphohydrolase type 2b) (PAP2b) (PAP-2b) (PAP2-beta) (Vascular endothelial growth factor and type I collagen-inducible protein) (VCIP); (3051:) lipin 1 [Homo sapiens]; (3052:) Lipoamide acyltransferase component of branched-chain alpha-ketoacid dehydrogenase complex, mitochondrial precursor (Dihydrolipoyllysine-residue (2-methylpropanoyl)transferase) (E2) (Dihydrolipoamide branched chain transacylase) (BCKAD E2 subunit); (3053:) lipocalin 2 [Homo sapiens]; (3054:) Lipolysis-stimulated lipoprotein receptor; (3055:) Lipoprotein lipase precursor (LPL); (3056:) lipoprotein lipase precursor [Homo sapiens]; (3057:) lipoprotein Lp(a) precursor [Homo sapiens]; (3058:) lipoyl-containing component X [Homo sapiens]; (3059:) lipoyl-transferase [Homo sapiens]; (3060:) lipoyltransferase 1 [Homo sapiens]; (3061:) Lipoyltransferase 1, mitochondrial precursor (Lipoate-protein ligase) (Lipoate biosynthesis protein) (Lipoyl ligase); (3062:) Liver carboxylesterase 1 precursor (Acyl coenzyme A:cholesterolacyltransferase) (ACAT) (Monocyte/macrophage serine esterase) (HMSE) (Serine esterase 1) (Brain carboxylesterase hBr1) (Triacylglycerol hydrolase) (TGH) (Egasyn); (3063:) liver phosphofructokinase isoform a [Homo sapiens]; (3064:) liver phosphofructokinase isoform a variant [Homo sapiens]; (3065:) liver phosphofructokinase isoform b [Homo sapiens]; (3066:) liver-type 1-phosphofructokinase [Homo sapiens]; (3067:) long chain fatty acyl CoA synthetase 2 [Homo sapiens]; (3068:) long chain polyunsaturated fatty acid elongation enzyme [Homo sapiens]; (3069:) long-chain acyl-CoA synthetase [Homo sapiens]; (3070:) long-chain acyl-CoA synthetase 5 [Homo sapiens]; (3071:) long-chain acyl-CoA synthetase; (3072:) Long-chain fatty acid transport protein 1 (Fatty acid transport protein 1) (FATP-1) (Solute carrier family 27 member 1); (3073:) Long-chain fatty acid transport protein 3 (Fatty acid transport protein 3) (FATP-3) (Very long-chain acyl-CoA synthetase homolog 3) (VLCS-3) (Solute carrier family 27 member 3); (3074:) Long-chain fatty acid transport protein 4 (Fatty acid transport protein 4) (FATP-4) (Solute carrier family 27 member 4); (3075:) Long-chain fatty acid transport protein 6 (Fatty acid transport protein 6) (FATP-6) (Very long-chain acyl-CoA synthetase homolog 1) (VLCSH1) (hVLCS-H1) (Fatty-acid-coenzyme A ligase, very long-chain 2) (Solute carrier family 27 member 6); (3076:) Long-chain-fatty-acid—CoA ligase 1 (Long-chain acyl-CoA synthetase 1) (LACS1) (Palmitoyl-CoA ligase 1) (Long-chain fatty acid CoA ligase 2) (Long-chain acyl-CoA synthetase 2) (LACS 2) (Acyl-CoA synthetase 1) (ACS1) (Palmitoyl-CoA ligase 2); (3077:) Long-chain-fatty-acid—CoA ligase 3 (Long-chain acyl-CoA synthetase 3) (LACS 3); (3078:) Long-chain-fatty-acid—CoA ligase 4 (Long-chain acyl-CoA synthetase 4) (LACS 4); (3079:) Long-chain-fatty-acid—CoA ligase 5 (Long-chain acyl-CoA synthetase 5) (LACS 5); (3080:) Long-chain-fatty-acid—CoA ligase 6 (Long-chain acyl-CoA synthetase 6) (LACS 6); (3081:) "Low affinity immunoglobulin epsilon Fc receptor (Lymphocyte IgE receptor) (Fc-epsilon-RII) (BLAST-2) (Immunoglobulin E-binding factor) (CD23 antigen) [Contains:) Low affinity immunoglobulin epsilon Fc receptor membrane-bound form; Low affinity immunoglobulin epsilon Fc receptor soluble form]."; (3082:) Low affinity immunoglobulin gamma Fc region receptor II-a precursor (Fc-gamma RII-a) (FcRII-a) (IgG Fc receptor II-a) (Fc-gamma-RIIa) (CD32 antigen) (CDw32); (3083:) Low affinity immunoglobulin gamma Fc region receptor II-b precursor (Fc-gamma RII-b) (FcRII-b) (IgG Fc receptor II-b) (Fc-gamma-RIIb) (CD32 antigen) (CDw32); (3084:) Low affinity immunoglobulin gamma Fc region receptor II-c precursor (Fc-gamma RII-c) (FcRII-c) (IgG Fc receptor II-c) (Fc-gamma-RIIc) (CD32 antigen) (CDw32); (3085:) Low affinity immunoglobulin gamma Fc region receptor III-A precursor (IgG Fc receptor III-2) (Fc-gamma RIII-alpha) (Fc-gamma RIIIa) (FcRIIIa) (Fc-gamma RIII) (FcRIII) (FcR-10) (CD16a antigen); (3086:) Low affinity immunoglobulin gamma Fc region receptor III-B precursor (IgG Fc receptor III-1) (Fc-gamma RIII-beta) (Fc-gamma RIIIb) (FcRIIIb) (Fc-gamma RIII) (FcRIII) (FcR-10) (CD16b antigen); (3087:) low density lipoprotein receptor precursor [Homo sapiens]; (3088:) low density lipoprotein-related protein 1 [Homo sapiens]; (3089:) Low molecular weight phosphotyrosine protein phosphatase (LMW-PTP) (Low molecular weight cytosolic acid phosphatase) (Red cell acid phosphatase 1) (PTPase) (Adipocyte acid phosphatase); (3090:) Low-density lipoprotein receptor precursor (LDL receptor); (3091:) Low-density lipoprotein receptor-related protein 1 precursor (LRP) (Alpha-2-macroglobulin receptor) (A2MR) (Apolipoprotein E receptor) (APOER) (CD91 antigen); (3092:) Low-density lipoprotein receptor-related protein 10 precursor; (3093:) Low-density lipoprotein receptor-related protein 11 precursor; (3094:) Low-density lipoprotein receptor-related protein 12 precursor (Suppressor of tumorigenicity protein 7); (3095:) Low-density lipoprotein receptor-related protein 1B precursor (Low-density lipoprotein receptor-related protein-deleted in tumor) (LRP-DIT); (3096:) Low-density lipoprotein receptor-related protein 2 precursor (Megalin) (Glycoprotein 330) (gp330); (3097:) Low-density lipoprotein receptor-related protein 3 precursor (hLRp105); (3098:) Low-density lipoprotein receptor-related protein 4 precursor (Multiple epidermal growth factor-like domains 7); (3099:) Low-density lipoprotein receptor-related protein 5 precursor; (3100:) Low-density lipoprotein receptor-related protein 6 precursor; (3101:) Low-density lipoprotein receptor-related protein 8 precursor (Apolipoprotein E receptor 2); (3102:) L-pipecolic acid oxidase [Homo sapiens]; (3103:) LRAP protein [Homo sapiens]; (3104:) L-serine dehydratase (L-serine deaminase); (3105:) L-UBC [Homo sapiens]; (3106:) luteinizing hormone/choriogonadotropin receptor precursor [Homo sapiens]; (3107:) Lutheran blood group glycoprotein precursor (B-CAM cell surface glycoprotein) (Auberger B antigen) (F8/G253 antigen) (CD239antigen); (3108:) Lutropin-choriogonadotropic hormone receptor precursor (LH/CG-R) (LSH-R) (Luteinizing hormone receptor) (LHR); (3109:) L-xylulose reductase (XR) (Dicarbonyl/L-xylulose reductase) (Kidney dicarbonyl reductase) (kiDCR) (Carbonyl reductase II) (Sperm surface protein P34H); (3110:) Lymphatic vessel endothelial hyaluronic acid receptor 1 precursor (LYVE-1) (Cell surface retention sequence-binding protein 1) (CRSBP-1) (Hyaluronic acid receptor) (Extracellular link domain-containing protein 1); (3111:) Lymphocyte antigen 75 precursor (DEC-205) (gp200-MR6) (CD205antigen); (3112:) Lysine-specific histone demethylase 1 (Flavin-containing amineoxidase domain-containing protein 2) (BRAF35-HDAC complex protein BHC110); (3113:) Lysophosphatidic acid receptor 4 (LPA receptor 4) (LPA-4) (P2Y purinoceptor 9) (P2Y9) (Purinergic receptor 9) (G-protein coupled receptor 23) (P2Y5-like receptor); (3114:) Lysophosphatidic acid receptor Edg-2 (LPA receptor 1) (LPA-1); (3115:) Lysophosphatidic acid receptor Edg-4 (LPA receptor 2) (LPA-2); (3116:) Lysophosphatidic acid receptor Edg-7 (LPA receptor 3) (LPA-3); (3117:) lysophospholipase 3 (lysosomal phospholipase A2) [Homo sapiens]; (3118:) "Lysosomal alpha-glucosidase precursor (Acid maltase) (Aglucosidasealfa) [Contains:) 76 kDa lysosomal alpha-glucosidase; 70 kDa lysosomal alpha-glucosidase]."; (3119:) "Lysosomal alpha-mannosidase precursor (Mannosidase, alpha B) (Lysosomal acid alpha-mannosidase) (Laman) (Mannosidase alpha class 2B member 1) [Contains:) Lysosomal alpha-mannosidase A peptide; Lysosomal alpha-mannosidase B peptide; Lysosomal alpha-mannosidase C peptide; Lysosomal alpha-mannosidase D peptide; Lysosomal alpha-mannosidase E peptide]."; (3120:) lysosomal enzyme beta-N-acetylhexosaminidase A [Homo sapiens]; (3121:) lysosomal glucocerebrosidase precursor [Homo sapiens]; (3122:) lysosomal neuraminidase precursor [Homo sapiens]; (3123:) "Lysosomal protective protein precursor (Cathepsin A) (Carboxypeptidase C) (Protective protein for beta-galactosidase)[Contains:) Lysosomal protective protein 32 kDa chain; Lysosomal protective protein 20 kDa chain]."; (3124:) Lysosomal thioesterase PPT2 precursor (PPT-2) (S-thioesterase G14); (3125:) Lysosome membrane protein 2 (Lysosome membrane protein II) (LIMPII) (Scavenger receptor class B member 2) (85 kDa lysosomal membrane sialo glycoprotein) (LGP85) (CD36 antigen-like 2); (3126:) Lysozyme-like protein 4 precursor; (3127:) lysyl hydroxylase precursor [Homo sapiens]; (3128:) lysyl oxidase preproprotein [Homo sapiens]; (3129:) lysyl oxidase-like 2 precursor [Homo sapiens]; (3130:) lysyl oxidase-like 3 precursor [Homo sapiens]; (3131:) lysyl-tRNA synthetase [Homo sapiens]; (3132:) M2-type pyruvate kinase; (3133:) MACH-alpha-1 [Homo sapiens]; (3134:) MACH-alpha-2 [Homo sapiens]; (3135:) MACH-alpha-3 [Homo sapiens]; (3136:) MACH-beta-3 [Homo sapiens]; (3137:) MACH-beta-4 [Homo sapiens]; (3138:) Macrophage colony-stimulating factor 1 receptor precursor (CSF-1-R) (Fms proto-oncogene) (c-fms) (CD115 antigen); (3139:) Macrophage mannose receptor 1 precursor (MMR) (CD206 antigen); (3140:) Macrophage mannose receptor 2 precursor (Urokinase receptor-associated protein) (Endocytic receptor 180) (CD280antigen); (3141:) Macrophage receptor MARCO (Macrophage receptor with collagenous structure) (Scavenger receptor class A member 2); (3142:) Macrophage scavenger receptor types I and II (Macrophage acetylated LDL receptor I and II) (Scavenger receptor class A member 1) (CD204antigen); (3143:) "Macrophage-stimulating protein receptor precursor (MSP receptor) (p185-Ron) (CD136 antigen) (CDw136) [Contains: Macrophage-stimulating protein receptor alpha chain; Macrophage-stimulating protein receptor beta chain]."; (3144:) Magnesium-dependent phosphatase 1 (MDP-1); (3145:) major histocompatibility complex, class II, DP alpha 1 precursor[Homo sapiens]; (3146:) major histocompatibility complex, class II, DQ alpha 2 [Homo sapiens]; (3147:) malate dehydrogenase (oxaloacetate decarboxylating) (NADP+) [Homo sapiens]; (3148:) male sterility domain containing 1 [Homo sapiens]; (3149:) male sterility domain containing 2 [Homo sapiens]; (3150:) Maleylacetoacetate isomerase (MAAI) (Glutathione S-transferase zeta1) (GSTZ1-1); (3151:) Malic enzyme 1, NADP(+)-dependent, cytosolic [Homo sapiens]; (3152:) malic enzyme 2 [Homo sapiens]; (3153:) malic enzyme 2, NAD(+)-dependent, mitochondrial [Homo sapiens]; (3154:) malic enzyme 3, NADP(+)-dependent, mitochondrial [Homo sapiens]; (3155:) Malonyl CoA-acyl carrier protein transacylase, mitochondrial precursor (MCT) (Mitochondrial malonyltransferase); (3156:) maltase-glucoamylase [Homo sapiens]; (3157:) manganese superoxide dismutase isoform A precursor [Homo sapiens]; (3158:) manganese superoxide dismutase isoform B precursor [Homo sapiens]; (3159:) mannan-binding lectin serine protease 2 isoform 1 precursor [Homo sapiens]; (3160:) mannan-binding lectin serine protease 2 isoform 2 precursor [Homo sapiens]; (3161:) "Mannan-binding lectin serine protease 2 precursor (Mannose-binding protein-associated serine protease 2) (MASP-2) (MBL-associated serine protease 2) [Contains:) Mannan-binding lectin serine protease 2 A chain; Mannan-binding lectin serine protease 2 B chain]."; (3162:) mannosidase, alpha, class 1A, member 1 [Homo sapiens]; (3163:) mannosidase, alpha, class 2A, member 1 [Homo sapiens]; (3164:) mannosidase, alpha, class 2B, member 1 precursor [Homo sapiens]; (3165:) mannosidase, alpha, class 2C, member 1 [Homo sapiens]; (3166:) mannosidase, endo-alpha [Homo sapiens]; (3167:) mannosyl (alpha-1,3-)-glycoprotein beta-1,2-N-acetylglucosaminyltransferase [Homo sapiens]; (3168:) mannosyl (alpha-1,6-)-glycoprotein beta-1,2-N-acetylglucosaminyltransferase [Homo sapiens]; (3169:) mannosyl (beta-1,4-)-glycoprotein beta-1,4-N-acetylglucosaminyltransferase [Homo sapiens]; (3170:) Mannosyl-oligosaccharide 1,2-alpha-mannosidase IA (Processing alpha-1,2-mannosidase IA) (Alpha-1,2-mannosidase IA) (Mannosidase alpha class IA member 1) (Man(9)-alpha-mannosidase) (Man9-mannosidase); (3171:) Mannosyl-oligosaccharide 1,2-alpha-mannosidase IB (Processing alpha-1,2-mannosidase IB) (Alpha-1,2-mannosidase IB) (Mannosidase alpha class 1A member 2); (3172:) Mannosyl-oligosaccharide 1,2-alpha-mannosidase IC (Processing alpha-1,2-mannosidase IC) (Alpha-1,2-mannosidase IC) (Mannosidase alpha class IC member 1) (HMIC); (3173:) mannosyl-oligosaccharide glucosidase [Homo sapiens]; (3174:) MAP kinase-activated protein kinase 2 (MAPK-activated protein kinase 2) (MAPKAP kinase 2) (MAPKAPK-2) (MK2); (3175:) MAP kinase-activated protein kinase 5 (MAPK-activated protein kinase 5) (MAPKAP kinase 5) (p38-regulated/activated protein kinase); (3176:) MAP kinase-interacting serine/threonine-protein kinase 1 (MAP kinase signal-integrating kinase 1) (Mnk1); (3177:) MAPK/MAK/MRK overlapping kinase (MOK protein kinase) (Renal tumor antigen 1) (RAGE-1); (3178:) marapsin [Homo sapiens]; (3179:) MAS proto-oncogene; (3180:) masA [Homo sapiens]; (3181:) Mas-related G-protein coupled receptor member D (Beta-alanine receptor) (G-protein coupled receptor TGR7); (3182:) Mas-related G-protein coupled receptor member E (G-protein coupled receptor 167); (3183:) Mas-related G-protein coupled receptor member F (Mas-related gene F protein) (G-protein coupled receptor 168); (3184:) Mas-related G-protein coupled receptor member G (G-protein coupled receptor 169); (3185:) Mas-related G-protein coupled receptor member XI (Sensory neuron-specific G-protein coupled receptor 3/4); (3186:) Mas-related G-protein coupled receptor member X2; (3187:) Mas-related G-protein coupled receptor member X3 (Sensory neuron-specific G-protein coupled receptor 1/2); (3188:) Mas-related G-protein coupled receptor member X4 (Sensory neuron-specific G-protein coupled receptor 5/6); (3189:) Mas-related G-protein coupled receptor MRG (MAS-R) (MAS1-like); (3190:) mast cell function-associated antigen [Homo sapiens]; (3191:) Mast/stem cell growth factor receptor precursor (SCFR) (Proto-oncogene tyrosine-protein kinase Kit) (c-kit) (CD117antigen); (3192:) matrix metalloproteinase 1 preproprotein [Homo sapiens]; (3193:) matrix metalloproteinase 10 preproprotein [Homo sapiens]; (3194:) matrix metalloproteinase 11 preproprotein [Homo sapiens]; (3195:) matrix metalloproteinase 12 preproprotein [Homo sapiens]; (3196:) matrix metalloproteinase 13 preproprotein [Homo sapiens]; (3197:) matrix metalloproteinase 14 preproprotein [Homo sapiens]; (3198:) matrix metalloproteinase 15 preproprotein [Homo sapiens]; (3199:) matrix metalloproteinase 16 isoform 1 preproprotein [Homo sapiens]; (3200:) matrix metalloproteinase 16 isoform 2 preproprotein [Homo sapiens]; (3201:) matrix metalloproteinase 17 preproprotein [Homo sapiens]; (3202:) matrix metalloproteinase 19 isoform 2 precursor [Homo sapiens]; (3203:) matrix metalloproteinase 19 isoform rasi-1 preproprotein [Homo sapiens]; (3204:) matrix metalloproteinase 2 preproprotein [Homo sapiens]; (3205:) matrix metalloproteinase 20 preproprotein [Homo sapiens]; (3206:) matrix metalloproteinase 23B precursor [Homo sapiens]; (3207:) matrix metalloproteinase 26 preproprotein [Homo sapiens]; (3208:) matrix metalloproteinase 28 isoform 1 preproprotein [Homo sapiens]; (3209:) matrix metalloproteinase 28 isoform 3 [Homo sapiens]; (3210:) matrix metalloproteinase 3 preproprotein [Homo sapiens]; (3211:) matrix metalloproteinase 7 preproprotein [Homo sapiens]; (3212:) matrix metalloproteinase 8 preproprotein [Homo sapiens]; (3213:) matrix metalloproteinase 9 preproprotein [Homo sapiens]; (3214:) Matrix metalloproteinase-16 precursor (MMP-16) (Membrane-type matrix metalloproteinase 3) (MT-MMP 3) (MTMMP3) (Membrane-type-3matrix metalloproteinase) (MT3-MMP) (MT3MMP) (MMP-X2); (3215:) Matrix metalloproteinase-19 precursor (MMP-19) (Matrixmetalloproteinase RASI) (MMP-18); (3216:) "Matrix metalloproteinase-9 precursor (MMP-9) (92 kDa type IV collagenase) (92 kDa gelatinase) (Gelatinase B) (GELB) [Contains:67 kDa matrix metalloproteinase-9; 82 kDa matrix metalloproteinase-9]."; (3217:) matrix, extracellular phosphoglycoprotein with ASARM motif (bone) [Homo sapiens]; (3218:) Mch3 isoform alpha; (3219:) Mch3 isoform beta; (3220:) "MDMCSF (EC 1.5.1.5; EC 3.5.4.9; EC 6.3.4.3)."; (3221:) MDS010 [Homo sapiens]; (3222:) ME2 protein [Homo sapiens]; (3223:) Mediator complex subunit 4 (Mediator of RNA polymerase II transcription subunit 4) (Vitamin D3 receptor-interacting protein complex 36 kDa component) (DRIP36) (Activator-recruited cofactor 36 kDa component) (ARC36) (TRAP/SMCC/PC2 subunit p36 subunit); (3224:) Mediator of RNA polymerase II transcription subunit 12 (Thyroid hormone receptor-associated protein complex 230 kDa component) (Trap230) (Activator-recruited cofactor 240 kDa component) (ARC240) (CAG repeat protein 45) (OPA-containing protein) (Trinucleotide repeat-containing gene 11 protein); (3225:) Mediator of RNA polymerase II transcription subunit 8 homolog (Activator-recruited cofactor 32 kDa component) (ARC32); (3226:) mediator of RNA polymerase II transcription subunit MED8 isoform 1 [Homo sapiens]; (3227:) mediator of RNA polymerase II transcription subunit MED8 isoform 2 [Homo sapiens]; (3228:) mediator of RNA polymerase II transcription subunit MED8 isoform 3 [Homo sapiens]; (3229:) mediator of RNA polymerase II transcription subunit MED8 isoform 4 [Homo sapiens]; (3230:) medium-chain acyl-CoA dehydrogenase (EC 1.3.99.3); (3231:) medium-chain acyl-CoA dehydrogenase; (3232:) Medium-chain specific acyl-CoA dehydrogenase, mitochondrial precursor (MCAD); (3233:) Meis1 homolog [Homo sapiens]; (3234:) Melanin-concentrating hormone receptor 1 (MCH receptor 1) (MCHR-1) (MCH-R1) (MCHIR) (MCH-1R) (MCHR) (G-protein coupled receptor 24) (Somatostatin receptor-like protein) (SLC-1); (3235:) Melanin-concentrating hormone receptor 2 (MCH receptor 2) (MCHR-2) (MCH-R2) (MCH2R) (MCH-2R) (MCH2) (G-protein coupled receptor 145) (GPRv17); (3236:) Melanocortin receptor 3 (MC3-R); (3237:) Melanocortin receptor 4 (MC4-R); (3238:) Melanocortin receptor 5 (MC5-R) (MC-2); (3239:) Melanocyte protein PmeI 17 precursor (Melanocyte lineage-specific antigen GP100) (Melanoma-associated ME20 antigen) (ME20M/ME20S) (ME20-M/ME20-S) (95 kDa melanocyte-specific secreted glycoprotein); (3240:) Melanocyte-stimulating hormone receptor (MSH-R) (Melanotropin receptor) (Melanocortin receptor 1) (MC1-R); (3241:) Melanopsin (Opsin-4); (3242:) Melatonin receptor type 1A (MeI-1A-R) (MeI1a melatonin receptor); (3243:) Melatonin receptor type 1B (MeI-1B-R) (MeI1b melatonin receptor); (3244:) Melatonin-related receptor (G protein-coupled receptor 50) (H9); (3245:) membrane alanine aminopeptidase precursor [Homo sapiens]; (3246:) membrane associated guanylate kinase, WW and PDZ domain containing 2 [Homo sapiens]; (3247:) Membrane copper amine oxidase (Semicarbazide-sensitive amineoxidase) (SSAO) (Vascular adhesion protein 1) (VAP-1) (HPAO); (3248:) membrane metallo-endopeptidase [Homo sapiens]; (3249:) Membrane metallo-endopeptidase-like 1 (Membrane metallo-endopeptidase-like 2) (Neprilysin-2) (Neprilysin II) (NL2) (NEPII) (NEP2(m)) [Contains:) Membrane metallo-endopeptidase-like 1, soluble form (Neprilysin-2 secreted) (NEP2(s))]; (3250:) Membrane progestin receptor alpha (mPR alpha) (Progestin and adipoQ receptor family member VII); (3251:) Membrane progestin receptor beta (mPR beta) (Progestin and adipoQ receptor family member VIII) (Lysosomal membrane protein in brain-1); (3252:) Membrane progestin receptor gamma (mPR gamma) (Progestin and adipoQ receptor family member V); (3253:) Membrane-associated progesterone receptor component 1 (mPR); (3254:) Membrane-associated progesterone receptor component 2 (Progesterone membrane-binding protein) (Steroid receptor protein DG6); (3255:) membrane-associated prostaglandin E synthase (EC 5.3.99.3)-2-human; (3256:) Membrane-associated tyrosine- and threonine-specific cdc2-inhibitory kinase (Myt1 kinase); (3257:) Membrane-bound transcription factor site 1 protease precursor (S1 Pendopeptidase) (Site-1 protease) (Subtilisin/kexin-isozyme 1) (SKI-1); (3258:) Membrane-spanning 4-domains subfamily A member 10; (3259:) Membrane-spanning 4-domains subfamily A member 12; (3260:) Membrane-spanning 4-domains subfamily A member 3(Hematopoietic-specific transmembrane 4 protein) (HTm4) (CD20 antigen-like protein); (3261:) Membrane-spanning 4-domains subfamily A member 4A (Four-span transmembrane protein 1) (CD20 antigen-like 1); (3262:) Membrane-spanning 4-domains subfamily A member 4E; (3263:) Membrane-spanning 4-domains subfamily A member 5 (Testis-expressed transmembrane 4 protein) (CD20 antigen-like 2); (3264:) Membrane-spanning 4-domains subfamily A member 6A (Four-span transmembrane protein 3) (CD20 antigen-like 3); (3265:) Membrane-spanning 4-domains subfamily A member 6E; (3266:) Membrane-spanning 4-domains subfamily A member 7(CD20/FC-epsilon-RI-beta family member 4) (Four-span transmembrane protein 2) (CD20 antigen-like 4); (3267:) Membrane-spanning 4-domains subfamily A member 8B (Four-span transmembrane protein 4); (3268:) membrane-type mosaic serine protease [*Homo sapiens*]; (3269:) menage a trois 1 (CAK assembly factor) [*Homo sapiens*]; (3270:) meningioma expressed antigen 5 (hyaluronidase) [*Homo sapiens*]; (3271:) meprin A, alpha (PABA peptide hydrolase) [*Homo sapiens*]; (3272:) meprin A, beta [*Homo sapiens*]; (3273:) mercaptopyruvate sulfur transferase variant [*Homo sapiens*]; (3274:) mesotrypsin preproprotein [*Homo sapiens*]; (3275:) mesotrypsinogen [*Homo sapiens*]; (3276:) Metabotropic glutamate receptor 1 precursor (mGluR1); (3277:) Metabotropic glutamate receptor 2 precursor (mGluR2); (3278:) Metabotropic glutamate receptor 3 precursor (mGluR3); (3279:) Metabotropic glutamate receptor 4 precursor (mGluR4); (3280:) metabotropic glutamate receptor 5 A—human; (3281:) metabotropic glutamate receptor 5 B—human; (3282:) Metabotropic glutamate receptor 5 precursor (mGluR5); (3283:) Metabotropic glutamate receptor 6 precursor (mGluR6); (3284:) Metabotropic glutamate receptor 7 precursor (mGluR7); (3285:) Metabotropic glutamate receptor 8 precursor (mGluR8); (3286:) metallopeptidase [*Homo sapiens*]; (3287:) metallothionein 1A [*Homo sapiens*]; (3288:) methionine sulfoxide reductase A [*Homo sapiens*]; (3289:) methionine synthase reductase isoform 1 [*Homo sapiens*]; (3290:) methionine synthase reductase isoform 2 [*Homo sapiens*]; (3291:) methionyl aminopeptidase 2 [*Homo sapiens*]; (3292:) Methionyl-tRNA synthetase, mitochondrial precursor (Methionine—tRNA ligase 2) (Mitochondrial methionine—tRNA ligase) (MtMetRS); (3293:) methyl sterol oxidase; (3294:) Methylated-DNA—protein-cysteine methyltransferase (6-O-methylguanine-DNA methyltransferase) (MGMT) (O-6-methylguanine-DNA-alkyltransferase); (3295:) Methylcrotonoyl-CoA carboxylase subunit alpha, mitochondrial precursor (3-methylcrotonyl-CoA carboxylase 1) (MCCase subunit alpha) (3-methylcrotonyl-CoA: carbon dioxide ligase subunit alpha) (3-methylcrotonyl-CoA carboxylase biotin-containing subunit); (3296:) methylcrotonoyl-Coenzyme A carboxylase 1 (alpha) [*Homo sapiens*]; (3297:) methylcrotonoyl-Coenzyme A carboxylase 1 (alpha) variant [*Homo sapiens*]; (3298:) methylcrotonoyl-Coenzyme A carboxylase 2 (beta) [*Homo sapiens*]; (3299:) methylene tetrahydrofolate dehydrogenase 2 isoform A precursor [*Homo sapiens*]; (3300:) methylene tetrahydrofolate dehydrogenase 2 isoform B [*Homo sapiens*]; (3301:) methylenetetrahydrofolate dehydrogenase (NADP+ dependent) 1-like [*Homo sapiens*]; (3302:) methylenetetrahydrofolate dehydrogenase 1 [*Homo sapiens*]; (3303:) methylenetetrahydrofolate reductase [*Homo sapiens*]; (3304:) methylenetetrahydrofolate reductase intermediate form [*Homo sapiens*]; (3305:) methylenetetrahydrofolate reductase long isoform [*Homo sapiens*]; (3306:) methylenetetrahydrofolate reductase short isoform [*Homo sapiens*]; (3307:) Methylenetetrahydrofolate reductase; (3308:) methylmalonyl Coenzyme A mutase precursor [*Homo sapiens*]; (3309:) Methylmalonyl-CoA mutase, mitochondrial precursor (MCM) (Methylmalonyl-CoA isomerase); (3310:) methylthioadenosine phosphorylase [*Homo sapiens*]; (3311:) methyltransferase like 3 [*Homo sapiens*]; (3312:) Mevalonate kinase (MK); (3313:) mevalonate kinase [*Homo sapiens*]; (3314:) mevalonate pyrophosphate decarboxylase; (3315:) MGC42638 protein [*Homo sapiens*]; (3316:) microphthalmia-associated transcription factor isoform 1 [*Homo sapiens*]; (3317:) microphthalmia-associated transcription factor isoform 2 [*Homo sapiens*]; (3318:) microphthalmia-associated transcription factor isoform 3 [*Homo sapiens*]; (3319:) microphthalmia-associated transcription factor isoform 4 [*Homo sapiens*]; (3320:) microphthalmia-associated transcription factor isoform 5 [*Homo sapiens*]; (3321:) microphthalmia-associated transcription factor isoform 6 [*Homo sapiens*]; (3322:) Microsomal glutathione S-transferase 1 (Microsomal GST-1) (Microsomal GST-1); (3323:) microsomal glutathione S-transferase 2 [*Homo sapiens*]; (3324:) Microsomal glutathione S-transferase 3 (Microsomal GST-3) (Microsomal GST-III); (3325:) microsomal glutathione S-transferase 3 [*Homo sapiens*]; (3326:) microtubule-associated protein tau isoform 1 [*Homo sapiens*]; (3327:) microtubule-associated protein tau isoform 2 [*Homo sapiens*]; (3328:) microtubule-associated protein tau isoform 3 [*Homo sapiens*]; (3329:) microtubule-associated protein tau isoform 4 [*Homo sapiens*]; (3330:) microtubule-associated proteins 1A/1B light chain 3 [*Homo sapiens*]; (3331:) migration-inducing gene 10 protein [*Homo sapiens*]; (3332:) migration-inducing protein 4 [*Homo sapiens*]; (3333:) Mih1/TX isoform beta [*Homo sapiens*]; (3334:) Mih1/TX isoform delta [*Homo sapiens*]; (3335:) Mih1/TX isoform gamma [*Homo sapiens*]; (3336:) Mineralocorticoid receptor (MR); (3337:) minichromosome maintenance protein 4 [*Homo sapiens*]; (3338:) minichromosome maintenance protein 6 [*Homo sapiens*]; (3339:) minichromosome maintenance protein 7 isoform 1 [*Homo sapiens*]; (3340:) minichromosome maintenance protein 7 isoform 2 [*Homo sapiens*]; (3341:) mitochondrial aldehyde dehydrogenase 2 precursor [*Homo sapiens*]; (3342:) mitochondrial C1-tetrahydrofolate synthetase—human; (3343:) mitochondrial dihydrolipoamide succinyltransferase [*Homo sapiens*]; (3344:) mitochondrial DNA polymerase accessory subunit precursor [*Homo sapiens*]; (3345:) mitochondrial glycine cleavage system H-protein precursor [*Homo sapiens*]; (3346:) Mitochondrial import receptor subunit TOM22 homolog (Translocase of outer membrane 22 kDa subunit homolog) (hTom22) (1C9-2); (3347:) Mitochondrial intermediate peptidase, mitochondrial precursor (MIP); (3348:) mitochondrial malate dehydrogenase precursor [*Homo sapiens*]; (3349:) mitochondrial MTO1-3 [*Homo sapiens*]; (3350:) mitochondrial NAD(P)+-dependent malic enzyme; (3351:) mitochondrial NADP(+)-dependent malic enzyme 3 [*Homo sapiens*]; (3352:) mitochondrial phosphoenolpyruvate carboxykinase 2 isoform 1 precursor [*Homo sapiens*]; (3353:) mitochondrial phosphoenolpyruvate carboxykinase 2 isoform 2precursor [*Homo sapiens*]; (3354:) mitochondrial short-chain enoyl-coenzyme A hydratase 1 precursor [*Homo sapiens*]; (3355:) mitochondrial topoisomerase I [*Homo sapiens*]; (3356:) Mitochondrial translation optimization 1 homolog (*S. cerevisiae*)[*Homo sapiens*]; (3357:) mitochondrial translation optimization 1 homolog isoform a [*Homo sapiens*]; (3358:) mitochondrial translation optimization 1 homolog isoform b [*Homo sapiens*]; (3359:) mitochondrial trifunctional protein, alpha subunit precursor [*Homo sapiens*]; (3360:) mitochondrial trifunctional protein, beta subunit precursor [*Homo sapiens*]; (3361:) Mitogen-activated protein kinase 1 (Extracellular signal-regulated kinase 2) (ERK-2) (Mitogen-activated protein kinase 2) (MAP kinase 2) (MAPK 2) (p42-MAPK) (ERT1); (3362:) mitogen-activated protein kinase 1 [*Homo sapiens*]; (3363:) Mitogen-activated protein kinase 10 (Stress-activated protein kinase JNK3) (c-Jun N-terminal kinase 3) (MAP kinase p49 3F12); (3364:) Mitogen-activated protein kinase II (Mitogen-activated protein kinase p38 beta) (MAP kinase p38 beta) (p38b) (p38-2) (Stress-activated protein kinase 2); (3365:) Mitogen-activated protein kinase 12 (Extracellular signal-regulated kinase 6) (ERK-6) (ERK5) (Stress-activated protein kinase 3) (Mitogen-activated protein kinase p38 gamma) (MAP kinase p38gamma); (3366:) Mitogen-activated protein kinase 13 (Stress-activated protein kinase 4) (Mitogen-activated protein kinase p38 delta) (MAP kinase p38 delta); (3367:) Mitogen-activated protein kinase 14 (Mitogen-activated protein kinase p38 alpha) (MAP kinase p38 alpha) (Cytokine suppressive anti-inflammatory drug-binding protein) (CSAID-binding protein) (CSBP) (MAX-interacting protein 2) (MAP kinase MXI2) (SAPK2A); (3368:) Mitogen-activated protein kinase 15 (Extracellular signal-regulated kinase 8); (3369:) Mitogen-activated protein kinase 3 (Extracellular signal-regulated kinase 1) (ERK-1) (Insulin-stimulated MAP2 kinase) (MAP kinase 1) (MAPK 1) (p44-ERK1) (ERT2) (p44-MAPK) (Microtubule-associated protein 2 kinase); (3370:) mitogen-activated protein kinase 3 isoform 1 [*Homo sapiens*]; (3371:) mitogen-activated protein kinase 3 isoform 2 [*Homo sapiens*]; (3372:) Mitogen-activated protein kinase 7 (Extracellular signal-regulated kinase 5) (ERK-5) (ERK4) (BMK1 kinase); (3373:) Mitogen-activated protein kinase 8 (Stress-activated protein kinase JNK1) (c-Jun N-terminal kinase 1) (JNK-46); (3374:) mitogen-activated protein kinase 8 isoform JNK1 alpha1 [*Homo sapiens*]; (3375:) mitogen-activated protein kinase 8 isoform JNK1 alpha2 [*Homo sapiens*]; (3376:) mitogen-activated protein kinase 8 isoform JNK1 beta1 [*Homo sapiens*]; (3377:) mitogen-activated protein kinase 8 isoform JNK1 beta2 [*Homo sapiens*]; (3378:) Mitogen-activated protein kinase 9 (Stress-activated protein kinase JNK2) (c-Jun N-terminal kinase 2) (JNK-55); (3379:) mitogen-activated protein kinase kinase 1 [*Homo sapiens*]; (3380:) Mitogen-activated protein kinase kinase kinase (Mixed lineage kinase 4); (3381:) Mitogen-activated protein kinase kinase kinase 1 (MAPK/ERK kinase kinase 1) (MEK kinase 1) (MEKK1); (3382:) Mitogen-activated protein kinase kinase kinase 10 (Mixed lineage kinase 2) (Protein kinase MST); (3383:) Mitogen-activated protein kinase kinase kinase II (Mixed lineage kinase 3) (Src-homology 3 domain-containing proline-rich kinase); (3384:) mitogen-activated protein kinase kinase kinase 12 [*Homo sapiens*]; (3385:) Mitogen-activated protein kinase kinase kinase 13 (Mixed lineage kinase) (MLK) (Leucine zipper-bearing kinase); (3386:) Mitogen-activated protein kinase kinase kinase 15 (MAPK/ERK kinase kinase 15) (MEK kinase 15) (MEKK 15); (3387:) Mitogen-activated protein kinase kinase kinase 2 (MAPK/ERK kinase kinase 2) (MEK kinase 2) (MEKK 2); (3388:) Mitogen-activated protein kinase kinase kinase 3 (MAPK/ERK kinase kinase 3) (MEK kinase 3) (MEKK 3); (3389:) Mitogen-activated protein kinase kinase kinase 4 (MAPK/ERK kinase kinase 4) (MEK kinase 4) (MEKK 4) (MAP three kinase 1); (3390:) Mitogen-activated protein kinase kinase kinase 5 (MAPK/ERK kinase kinase 5) (MEK kinase 5) (MEKK 5) (Apoptosis signal-regulating kinase 1) (ASK-1); (3391:) mitogen-activated protein kinase kinase kinase 5 [*Homo sapiens*]; (3392:) Mitogen-activated protein kinase kinase kinase 6; (3393:) Mitogen-activated protein kinase kinase kinase 9 (Mixed lineage kinase 1); (3394:) Mitogen-activated protein kinase kinase kinase MLT (MLK-like mitogen-activated protein kinase triple kinase) (Leucine zipper- and sterile alpha motif-containing kinase) (Sterile alpha motif- and leucine zipper-containing kinase AZK) (Mixed lineage kinase-related kinase) (MLK-related kinase) (MRK) (Cervical cancer suppressor gene4 protein); (3395:) mitogen-activated protein kinase-activated protein kinase 2 isoform1 [*Homo sapiens*]; (3396:) mitogen-activated protein kinase-activated protein kinase 2 isoform2 [*Homo sapiens*]; (3397:) Mitotic checkpoint serine/threonine-protein kinase BUB1 (hBUB1) (BUB1A); (3398:) mitotic kinase-like protein-1 [*Homo sapiens*]; (3399:) Mitotic Kinesin Eg5; (3400:) MLH1+ ins1a isoform [*Homo sapiens*]; (3401:) MLH1-Ex6 isoform [*Homo sapiens*]; (3402:) MLH3 protein [*Homo sapiens*]; (3403:) MMS2 [*Homo sapiens*]; (3404:) MOCS1 [*Homo sapiens*]; (3405:) MOCS1 protein [*Homo sapiens*]; (3406:) MOCS1A enzyme [*Homo sapiens*]; (3407:) MOCS1A protein [*Homo sapiens*]; (3408:) Molybdenum cofactor biosynthesis protein 1 A (MOCS1A); (3409:) Molybdenum cofactor biosynthesis protein 1 B (MOCS1B) (Molybdenum cofactor synthesis-step 1 protein A-B) (Molybdenum cofactor biosynthesis protein C); (3410:) molybdenum cofactor biosynthesis protein A [*Homo sapiens*]; (3411:) molybdenum cofactor synthesis-step 1 protein isoform 1 [*Homo sapiens*]; (3412:) molybdenum cofactor synthesis-step 1 protein isoform 2 [*Homo sapiens*]; (3413:) molybdenum cofactor synthesis-step 1 protein isoform 3 [*Homo sapiens*]; (3414:) molybdenum cofactor synthesis-step 1 protein isoform 4 [*Homo sapiens*]; (3415:) molybdopterin synthase large subunit MOCS2B [*Homo sapiens*]; (3416:) molybdopterin synthase small subunit MOCS2A [*Homo sapiens*]; (3417:) monoacylglycerol O-acyltransferase 3 [*Homo sapiens*]; (3418:) Monoamine Oxidase A (MAO-A); (3419:) monoamine oxidase A [*Homo sapiens*]; (3420:) Monoamine Oxidase B (MAO-B); (3421:) Monocyte Chemoattractant Protein 1 (MCP-1) Receptor; (3422:) Monocyte to macrophage differentiation factor 2 (Progestin and adipoQ receptor family member X); (3423:) Monocyte to macrophage differentiation protein (Progestin and adipoQ receptor family member XI); (3424:) MOP-4 [*Homo sapiens*]; (3425:) mosaic serine protease [*Homo sapiens*]; (3426:) Motilin Receptor; (3427:) Motilin receptor (G-protein coupled receptor 38); (3428:) M-phase inducer phosphatase 1 (Dual specificity phosphatase Cdc25A); (3429:) M-phase inducer phosphatase 2 (Dual specificity phosphatase Cdc25B); (3430:) MRIT-alpha-1 [*Homo sapiens*]; (3431:) mRNA (guanine-7-)methyltransferase [*Homo sapiens*]; (3432:) mRNA 5' cap guanine-N-7 methyltransferase [*Homo sapiens*]; (3433:) mRNA cap guanine-N7 methyltransferase (mRNA(guanine-N(7)-)-methyltransferase) (RG7MT1) (mRNA capmethyltransferase) (hcm1p) (hCMT1) (hMet); (3434:) "mRNA capping enzyme (HCE) (HCAP1) [Includes:) Polynucleotide 5'-triphosphatase (mRNA 5'-triphosphatase) (TPase); mRNA guanylyltransferase (GTP-RNA guanylyltransferase) (GTase)]."; (3435:) mRNA capping enzyme [*Homo sapiens*]; (3436:) mRNA decapping enzyme [*Homo sapiens*]; (3437:) mRNA decapping enzyme 1A (Transcription factor SMIF) (Smad-4-interacting transcriptional co-activator); (3438:) mRNA decapping enzyme 1B; (3439:) mRNA decapping enzyme 2 (hDpc) (Nucleoside diphosphate-linked moiety X motif 20) (Nudix motif 20); (3440:) mRNA decapping enzyme variant [*Homo sapiens*]; (3441:) mRNA-decapping enzyme [*Homo sapiens*]; (3442:) MSTP042 [*Homo sapiens*]; (3443:) MTO1 isoform [*Homo sapiens*]; (3444:) MTO1 isoform 2 [*Homo sapiens*]; (3445:) MTO1 protein [*Homo sapiens*]; (3446:) MTO1 protein isoform III [*Homo sapiens*]; (3447:) MTO1 protein isoform IV [*Homo sapiens*]; (3448:) MTO1-like protein [*Homo sapiens*]; (3449:) mucin 1 isoform 1 precursor [*Homo sapiens*]; (3450:) mucin 1 isoform 2 precursor [*Homo sapiens*]; (3451:) mucin 1 isoform 3 precursor [*Homo sapiens*]; (3452:) mucin 1 isoform 5 precursor [*Homo sapiens*];

(3453:) mucin 1 isoform 6 precursor [*Homo sapiens*]; (3454:) mucin 1 isoform 7 precursor [*Homo sapiens*]; (3455:) mucin 1 isoform 8 precursor [*Homo sapiens*]; (3456:) Mucin-1 (MUC1) Glycoprotein; (3457:) mu-crystallin [*Homo sapiens*]; (3458:) Mu-crystallin homolog (NADP-regulated thyroid-hormone-binding protein); (3459:) Multidrug Resistance-Associated Protein 1 (MRP1); (3460:) Multidrug resistance-associated protein 7 (ATP-binding cassette sub-family C member 10); (3461:) multifunctional protein CAD [*Homo sapiens*]; (3462:) multiple exostoses-like 2 [*Homo sapiens*]; (3463:) Mu-Opioid Receptor; (3464:) Muscarinic acetylcholine receptor M1; (3465:) Muscarinic acetylcholine receptor M2; (3466:) Muscarinic acetylcholine receptor M3; (3467:) Muscarinic acetylcholine receptor M4; (3468:) Muscarinic acetylcholine receptor M5; (3469:) Muscarinic M1 Receptor; (3470:) Muscarinic M2 Receptor; (3471:) Muscarinic M3 Receptor; (3472:) Muscarinic M4 Receptor; (3473:) muscle beta 1 integrin cytoplasmic domain binding protein MIBP [*Homo sapiens*]; (3474:) muscle creatine kinase [*Homo sapiens*]; (3475:) Muscle, skeletal receptor tyrosine protein kinase precursor (Muscle-specific tyrosine protein kinase receptor) (Muscle-specific kinase receptor) (MuSK); (3476:) mutant arylamine N-acetyltransferase [*Homo sapiens*]; (3477:) mutant 1 beta-1,6-N-acetylglucosaminyltransferase C form [*Homo sapiens*]; (3478:) mutL 3 homolog (*E. coli*) [*Homo sapiens*]; (3479:) MutL homolog 1, colon cancer, nonpolyposis type 2 (*E. coli*) [*Homo sapiens*]; (3480:) MutL homolog 3 (*E. coli*) [*Homo sapiens*]; (3481:) mutL homolog 3 isoform 1 [*Homo sapiens*]; (3482:) mutL homolog 3 isoform 2 [*Homo sapiens*]; (3483:) MutL protein homolog 1 [*Homo sapiens*]; (3484:) MutL protein homolog 1 variant [*Homo sapiens*]; (3485:) mutS homolog 2 [*Homo sapiens*]; (3486:) mutS homolog 6 [*Homo sapiens*]; (3487:) mutY homolog isoform 1 [*Homo sapiens*]; (3488:) mutY homolog isoform 2 [*Homo sapiens*]; (3489:) mutY homolog isoform 3 [*Homo sapiens*]; (3490:) mutY homolog isoform 4 [*Homo sapiens*]; (3491:) Mu-type opioid receptor (MOR-1); (3492:) Mycobacterial Arabinosyltransferases; (3493:) Mycobacterial Fatty Acid Synthetase I (FAS-I); (3494:) Mycobacterial Translocase I; (3495:) *Mycobacterium Tuberculosis* Adenosine Triphosphate (ATP) Synthase; (3496:) *Mycobacterium Tuberculosis* Enoyl-Acyl Carrier Protein Reductase (InhA); (3497:) *Mycobacterium Tuberculosis* Isocitrate Lyase (Icl); (3498:) myelin basic protein isoform 1 [*Homo sapiens*]; (3499:) myelin basic protein isoform 2 [*Homo sapiens*]; (3500:) myelin basic protein isoform 3 [*Homo sapiens*]; (3501:) myelin basic protein isoform 4 [*Homo sapiens*]; (3502:) myelin basic protein isoform 5 [*Homo sapiens*]; (3503:) myelin basic protein isoform 6 [*Homo sapiens*]; (3504:) Myelin Basic Protein Stimulator; (3505:) Myeloblastin precursor (Leukocyte proteinase 3) (PR-3) (PR3) (AGP7) (Wegener autoantigen) (P29) (C-ANCA antigen) (Neutrophil proteinase 4) (NP-4); (3506:) myelodysplastic syndromes relative [*Homo sapiens*]; (3507:) myeloperoxidase [*Homo sapiens*]; (3508:) myofibrillogenesis regulator 1 isoform 1 [*Homo sapiens*]; (3509:) myofibrillogenesis regulator 1 isoform 2 [*Homo sapiens*]; (3510:) myofibrillogenesis regulator 1 isoform 3 [*Homo sapiens*]; (3511:) myo-inositol oxygenase [*Homo sapiens*]; (3512:) myo-inositol-1 (or 4)-monophosphatase [*Homo sapiens*]; (3513:) Myosin heavy chain, cardiac muscle beta isoform (MyHC-beta); (3514:) myosin light chain kinase isoform 1 [*Homo sapiens*]; (3515:) myosin light chain kinase isoform 2 [*Homo sapiens*]; (3516:) myosin light chain kinase isoform 3A [*Homo sapiens*]; (3517:) myosin light chain kinase isoform 3B [*Homo sapiens*]; (3518:) Myosin light chain kinase, smooth muscle (MLCK) (Telokin) (Kinase-related protein) (KRP); (3519:) Myosin regulatory light chain 2, nonsarcomeric (Myosin RLC); (3520:) Myosin regulatory light chain 2, smooth muscle isoform (Myosin RLC) (Myosin regulatory light chain 9) (LC20); (3521:) Myostatin; (3522:) myotonic dystrophy protein kinase [*Homo sapiens*]; (3523:) Myotonin-protein kinase (Myotonic dystrophy protein kinase) (MDPK) (DM-kinase) (DMK) (DMPK) (MT-PK); (3524:) myristoyl CoA: protein N-myristoyltransferase [*Homo sapiens*]; (3525:) Myristoylated Alanine-Rich C-Kinase Substrate (MARCKS); (3526:) myristoylated alanine-rich protein kinase C substrate [*Homo sapiens*]; (3527:) myristoyl-CoA: protein N-myristoyltransferase [*Homo sapiens*]; (3528:) Na+/K+-ATPase alpha 1 subunit isoform a proprotein [*Homo sapiens*]; (3529:) Na+/K+-ATPase alpha 1 subunit isoform b proprotein [*Homo sapiens*]; (3530:) Na+/K+-ATPase alpha 2 subunit proprotein [*Homo sapiens*]; (3531:) Na+/K+-ATPase alpha 3 subunit [*Homo sapiens*]; (3532:) Na+/K+-ATPase alpha 4 subunit isoform 1 [*Homo sapiens*]; (3533:) Na+/K+-ATPase alpha 4 subunit isoform 2 [*Homo sapiens*]; (3534:) Na+/K+-ATPase beta 1 subunit isoform a [*Homo sapiens*]; (3535:) Na+/K+-ATPase beta 1 subunit isoform b [*Homo sapiens*]; (3536:) Na+/K+-ATPase beta 2 subunit [*Homo sapiens*]; (3537:) Na+/K+-ATPase beta 3 subunit [*Homo sapiens*]; (3538:) N-acetylated-alpha-linked acidic dipeptidase 2(N-acetylated-alpha-linked acidic dipeptidase II) (NAALADase II); (3539:) N-acetylated-alpha-linked-acidic dipeptidase (NAALADase); (3540:) N-acetyl-galactosamine 4-sulfate 6-O-sulfotransferase (GalNAc4S-6ST) (B-cell RAG-associated gene protein) (hBRAG); (3541:) N-acetylgalactosamine 6-sulfate sulfatase [*Homo sapiens*]; (3542:) N-acetylgalactosamine-6-sulfatase precursor [*Homo sapiens*]; (3543:) N-acetylgalactosaminyltransferase 7 (Protein-UDPacetylgalactosaminyltransferase 7) (UDP-GalNAc:polypeptide N-acetylgalactosaminyltransferase 7) (Polypeptide GalNActransferase 7) (GalNAc-T7) (pp-GaNTase 7); (3544:) N-Acetylglucosamine kinase [*Homo sapiens*]; (3545:) N-acetylglucosamine-1-phosphate transferase [*Homo sapiens*]; (3546:) N-acetylglucosamine-1-phosphodiester alpha-N-acetylglucosaminidase precursor (Phosphodiester alpha-GlcNAcase) (Mannose6-phosphate-uncovering enzyme); (3547:) N-acetylglucosamine-1-phosphodiester alpha-N-acetylglucosaminidase precursor [*Homo sapiens*]; (3548:) N-acetylglucosamine-1-phosphotransferase subunit gamma precursor (GlcNAc-1-phosphotransferase subunit gamma) (UDP-N-acetylglucosamine-1-phosphotransferase, subunit gamma); (3549:) "N-acetylglucosamine-1-phosphotransferase subunits alpha/beta precursor (GlcNAc-1-phosphotransferase alpha/beta subunits) (UDP-N-acetylglucosamine-1-phosphotransferase alpha/beta subunits) (Stealth protein GNPTAB) [Contains: N-acetylglucosamine-1-phosphotransferase subunit alpha; N-acetylglucosamine-1-phosphotransferase subunit beta]."; (3550:) N-acetylglucosamine-1-phosphotransferase, gamma subunit [*Homo sapiens*]; (3551:) N-acetylglucosamine-6-O-sulfotransferase (GlcNAc6ST) [*Homo sapiens*]; (3552:) N-acetylglutamate synthase [*Homo sapiens*]; (3553:) "N-acetylglutamate synthase, mitochondrial precursor (Amino-acid acetyltransferase) [Contains:) N-acetylglutamate synthase long form; N-acetylglutamate synthase short form; N-acetylglutamate synthase conserved domain form]."; (3554:) N-acetyllactosaminide beta-1,3-N-acetylglucosaminyltransferase (Poly-N-acetyllactosamine extension enzyme) (1-beta-1,3-N-acetylglucosaminyltransferase) (iGnT) (UDP-GlcNAc:betaGal beta-1,3-N-acetylglucosaminyltransferase 6); (3555:) N-acetyllactosaminide beta-1,6-N-acetylglucosaminyl-transferase (N-acetylglucosaminyltransferase) (1-branching enzyme) (IGNT); (3556:) N-acetyllactosaminide beta-1,6-N-acetylglucosaminyltransferase [*Homo sapiens*]; (3557:) N-acetylneuraminate pyruvate lyase [*Homo sapiens*]; (3558:) N-acetylneuraminic acid phosphate synthase [*Homo sapiens*]; (3559:) N-acetyltransferase 1 [*Homo sapiens*]; (3560:) N-acetyltransferase 2 [*Homo sapiens*]; (3561:) N-acetyltransferase ESCO1 (Establishment of cohesion 1 homolog 1) (ECO1 homolog 1) (ESO1 homolog 1) (Establishment factor-like protein 1) (EFO1p) (hEFO1) (CTF7 homolog 1); (3562:) N-acylaminoacyl-peptide hydrolase [*Homo sapiens*]; (3563:) N-acylethanolamine-hydrolyzing acid amidase precursor (N-acylsphingosine amidohydrolase-like) (ASAH-like protein) (Acidceramidase-like protein); (3564:) N-acylglucosamine 2-epimerase (GlcNAc 2-epimerase) (N-acetyl-D-glucosamine 2-epimerase) (AGE) (Renin-binding protein) (RnBP); (3565:) N-acyineuraminate cytidylyltransferase (CMP-N-acetylneuraminic acid synthetase) (CMP-NeuNAc synthetase); (3566:) N-acylneuraminate-9-phosphatase (Neu5Ac-9-Pase) (Haloaciddehalogenase-like hydrolase domain-containing protein 4); (3567:) N-acylsphingosine amidohydrolase (acid ceramidase) 1 isoform b[*Homo sapiens*]; (3568:) N-acylsphingosine amidohydrolase (acid ceramidase) 1 preproprotein isoform a [*Homo sapiens*]; (3569:) N-acylsphingosine amidohydrolase 3 [*Homo sapiens*]; (3570:) N-acylsphingosine amidohydrolase-like protein isoform 1 precursor[*Homo sapiens*]; (3571:) N-acylsphingosine amidohydrolase-like protein isoform 2 precursor[*Homo sapiens*]; (3572:) NAD kinase (Poly (P)/ATP NAD kinase); (3573:) NAD(P) dependent steroid dehydrogenase-like [*Homo sapiens*]; (3574:) NAD(P)H dehydrogenase [quinone] 1 (Quinone reductase 1) (NAD(P) H:quinone oxidoreductase 1) (QR1) (DT-diaphorase) (DTD) (Azoreductase) (Phylloquinone reductase) (Menadione reductase); (3575:) NAD(P)H menadione oxidoreductase 1, dioxin-inducible isoform a[*Homo sapiens*]; (3576:) NAD (P)H menadione oxidoreductase 1, dioxin-inducible isoform b[*Homo sapiens*]; (3577:) NAD(P)H menadione oxidoreductase 1, dioxin-inducible isoform c[*Homo sapiens*]; (3578:) NAD+ADP-ribosyltransferase; (3579:) NAD-dependent deacetylase sirtuin-1 (hSIRT1) (hSIR2) (SIR2-like protein 1); (3580:) NAD-dependent deacetylase sirtuin-2 (SIR2-like) (SIR2-like protein2); (3581:) NAD-dependent deacetylase sirtuin-3, mitochondrial precursor (SIR2-like protein 3) (hSIRT3); (3582:) NAD-dependent malic enzyme, mitochondrial precursor (NAD-ME) (Malic enzyme 2); (3583:) NADH dehydrogenase (ubiquinone) 1 alpha subcomplex, 10, 42 kDa precursor [*Homo sapiens*]; (3584:) NADH dehydrogenase (ubiquinone) 1 alpha subcomplex, 4, 9 kDa [*Homo sapiens*]; (3585:) NADH dehydrogenase (ubiquinone) 1 alpha subcomplex, 5 [*Homo sapiens*]; (3586:) NADH dehydrogenase (ubiquinone) 1 alpha subcomplex, 8, 19 kDa [*Homo sapiens*]; (3587:) NADH dehydrogenase (ubiquinone) 1 beta subcomplex, 2, 8 kDa precursor [*Homo sapiens*]; (3588:) NADH dehydrogenase (ubiquinone) 1 beta subcomplex, 3, 12 kDa [*Homo sapiens*]; (3589:) NADH dehydrogenase (ubiquinone) 1 beta subcomplex, 4, 15 kDa [*Homo sapiens*]; (3590:) NADH dehydrogenase (ubiquinone) 1 beta subcomplex, 5, 16 kDa precursor [*Homo sapiens*]; (3591:) NADH dehydrogenase (ubiquinone) 1 beta subcomplex, 6,17 kDa isoform 1 [*Homo sapiens*]; (3592:) NADH dehydrogenase (ubiquinone) 1 beta subcomplex, 6, 17 kDa isoform2 [*Homo sapiens*]; (3593:) NADH dehydrogenase (ubiquinone) 1 beta subcomplex, 7, 18 kDa [*Homo sapiens*]; (3594:) NADH dehydrogenase (ubiquinone) Fe—S protein 1, 75 kDa precursor[*Homo sapiens*]; (3595:) NADH dehydrogenase (ubiquinone) Fe—S protein 3, 30 kDa (NADH-coenzyme Q reductase) [*Homo sapiens*]; (3596:) NADH dehydrogenase (ubiquinone) Fe—S protein 4, 18 kDa (NADH-coenzyme Q reductase) [*Homo sapiens*]; (3597:) NADH dehydrogenase (ubiquinone) Fe—S protein 6, 13 kDa (NADH-coenzyme Q reductase) [*Homo sapiens*]; (3598:) NADH dehydrogenase [ubiquinone] 1 alpha subcomplex subunit 1 (NADH-ubiquinone oxidoreductase MWFE subunit) (Complex I-MWFE) (CI-MWFE); (3599:) NADH dehydrogenase [ubiquinone] 1 alpha subcomplex subunit 10, mitochondrial precursor (NADH-ubiquinone oxidoreductase 42 kDa subunit) (Complex I-42 kD) (CI-42 kD); (3600:) NADH dehydrogenase [ubiquinone] 1 alpha subcomplex subunit 11 (NADH-ubiquinone oxidoreductase subunit B14.7) (Complex I-B14.7) (C1-B14.7); (3601:) NADH dehydrogenase [ubiquinone] 1 alpha subcomplex subunit 12(NADH-ubiquinone oxidoreductase subunit B17.2) (Complex I-B17.2) (C1-B17.2) (CIB17.2) (13 kDa differentiation-associated protein); (3602:) NADH dehydrogenase [ubiquinone] 1 alpha subcomplex subunit 13(NADH-ubiquinone oxidoreductase B16.6 subunit) (Complex I-B16.6) (CI-B16.6) (Gene associated with retinoic-interferon-induced mortality 19 protein) (GRIM-19) (Cell death-regulatory protein GRIM-19); (3603:) NADH dehydrogenase [ubiquinone] 1 alpha subcomplex subunit 2(NADH-ubiquinone oxidoreductase B8 subunit) (Complex I-B8) (C1-B8); (3604:) NADH dehydrogenase [ubiquinone] 1 alpha subcomplex subunit 3(NADH-ubiquinone oxidoreductase B9 subunit) (Complex I-B9) (C1-B9); (3605:) NADH dehydrogenase [ubiquinone] 1 alpha subcomplex subunit 4(NADH-ubiquinone oxidoreductase MLRQ subunit) (Complex I-MLRQ) (CI-MLRQ); (3606:) NADH dehydrogenase [ubiquinone] 1 alpha subcomplex subunit 5(NADH-ubiquinone oxidoreductase 13 kDa-B subunit) (ComplexI-13 kD-B) (CI-13 kD-B) (Complex I subunit B13); (3607:) NADH dehydrogenase [ubiquinone] 1 alpha subcomplex subunit 6(NADH-ubiquinone oxidoreductase B14 subunit) (Complex I-B14) (CI-B14); (3608:) NADH dehydrogenase [ubiquinone] 1 alpha subcomplex subunit 7(NADH-ubiquinone oxidoreductase subunit B14.5a) (Complex I-B14.5a) (CI-B14.5a); (3609:) NADH dehydrogenase [ubiquinone] 1 alpha subcomplex subunit 8(NADH-ubiquinone oxidoreductase 19 kDa subunit) (Complex I-19 kD) (CI-19 kD) (Complex I-PGIV) (CI-PGIV); (3610:) NADH dehydrogenase [ubiquinone] 1 alpha subcomplex subunit 9, mitochondrial precursor (NADH-ubiquinone oxidoreductase 39 kDa subunit) (Complex I-39 kD) (CI-39 kD); (3611:) NADH dehydrogenase [ubiquinone] 1 beta subcomplex subunit 1(NADH-ubiquinone oxidoreductase MNLL subunit) (Complex I-MNLL) (CI-MNLL); (3612:) NADH dehydrogenase [ubiquinone] 1 beta subcomplex subunit 10(NADH-ubiquinone oxidoreductase PDSW subunit) (Complex I-PDSW) (CI-PDSW); (3613:) NADH dehydrogenase [ubiquinone] 1 beta subcomplex subunit 11, mitochondrial precursor (NADH-ubiquinone oxidoreductase ESSS subunit) (Complex I-ESSS) (CI-ESSS) (Neuronal protein 17.3) (p17.3) (Np17.3); (3614:) NADH dehydrogenase [ubiquinone] 1 beta subcomplex subunit 2, mitochondrial precursor (NADH-ubiquinone oxidoreductase AGGG subunit) (Complex I-AGGG) (CI-AGGG); (3615:) NADH dehydrogenase [ubiquinone] 1 beta subcomplex subunit 3(NADH-ubiquinone oxidoreductase B12 subunit) (Complex I-B12) (CI-B12); (3616:) NADH dehydrogenase [ubiquinone] 1 beta subcomplex subunit 4(NADH-ubiquinone oxidoreductase B15 subunit) (Complex I-B15) (CI-B15); (3617:) NADH dehydrogenase [ubiquinone] 1 beta subcomplex subunit 5, mitochondrial precursor (NADH-ubiquinone oxidoreductase SGDH subunit) (Complex I-SGDH) (CI-SGDH); (3618:) NADH dehydrogenase [ubiquinone] 1 beta subcomplex subunit 6(NADH-ubiquinone oxidoreductase B17 subunit) (Complex I-B17) (CI-B17); (3619:) NADH dehydrogenase [ubiquinone] 1 beta subcomplex subunit 7(NADH-ubiquinone oxidoreductase B18 subunit) (Complex I-B18) (CI-B18) (Cell adhesion protein SQM1); (3620:) NADH dehydrogenase [ubiquinone] 1 beta subcomplex subunit 8, mitochondrial precursor (NADH-ubiquinone oxidoreductase ASHI subunit) (Complex I-ASHI) (CI-ASHI); (3621:) NADH dehydrogenase [ubiquinone] 1 beta subcomplex subunit 9(NADH-ubiquinone oxidoreductase B22 subunit) (Complex I-B22) (CI-B22); (3622:) NADH dehydrogenase [ubiquinone] 1 subunit C1, mitochondrial precursor (NADH-ubiquinone oxidoreductase KFYI subunit) (ComplexI-KFYI) (CI-KFYI); (3623:) NADH dehydrogenase [ubiquinone] 1 subunit C2 (NADH-ubiquinoneoxido reductase subunit B14.5b) (Complex I-BI4.5b) (CI-B14.5b); (3624:) NADH dehydrogenase [ubiquinone] flavoprotein 1, mitochondrial precursor (NADH-ubiquinone oxidoreductase 51 kDa subunit) (ComplexI-51 kD) (CI-51 kD) (NADH dehydrogenase flavoprotein 1); (3625:) NADH dehydrogenase [ubiquinone] flavoprotein 2, mitochondrial precursor (NADH-ubiquinone oxidoreductase 24 kDa subunit); (3626:) NADH dehydrogenase [ubiquinone] flavoprotein 3, mitochondrial precursor (NADH-ubiquinone oxidoreductase 9 kDa subunit) (ComplexI-9 kD) ($C_{1-9}$ kD) (NY-REN-4 antigen); (3627:) NADH dehydrogenase [ubiquinone] iron-sulfur protein 2, mitochondrial precursor (NADH-ubiquinone oxidoreductase 49 kDa subunit) (Complex I-49 kD) (CI-49 kD); (3628:) NADH dehydrogenase [ubiquinone] iron-sulfur protein 3, mitochondrial precursor (NADH-ubiquinone oxidoreductase 30 kDa subunit) (Complex I-30 kD) (CI-30 kD); (3629:) NADH dehydrogenase [ubiquinone] iron-sulfur protein 4, mitochondrial precursor (NADH-ubiquinone oxidoreductase 18 kDa subunit) (Complex I-18 kDa) (CI-18 kDa) (Complex I-AQDQ) (CI-AQDQ); (3630:) NADH dehydrogenase [ubiquinone] iron-sulfur protein 5(NADH-ubiquinone oxidoreductase 15 kDa subunit) (Complex I-15 kDa) (CI-15 kDa); (3631:) NADH dehydrogenase [ubiquinone] iron-sulfur protein 6, mitochondrial precursor (NADH-ubiquinone oxidoreductase 13 kDa-A subunit) (Complex I-13 kD-A) (CI-13 kD-A); (3632:) NADH dehydrogenase [ubiquinone] iron-sulfur protein 7, mitochondrial precursor (NADH-ubiquinone oxidoreductase 20 kDa subunit) (Complex I-20 kD) (CI-20 kD) (PSST subunit); (3633:) "NADH-cytochrome b5 reductase (B5R) (Diaphorase-1) (Cytochrome b5reductase 3) [Contains:) NADH-cytochrome b5 reductase membrane-bound form; NADH-cytochrome b5 reductase soluble form]."; (3634:) NADH-cytochrome b5 reductase [*Homo sapiens*]; (3635:) "NADH-cytochrome b5 reductase; b5R [*Homo sapiens*]."; (3636:) NADH-ubiquinone oxidoreductase 75 kDa subunit, mitochondrial precursor (Complex I-75 kD) (C1-75 kD); (3637:) NADP(+)-dependent malic enzyme—human (fragments); (3638:) "NADP+-dependent malic enzyme; malate dehydrogenase (oxaloacetate decarboxylating) (NADP+) [*Homo sapiens*]."; (3639:) NADP-dependent isocitrate dehydrogenase [*Homo sapiens*]; (3640:) NADP-dependent malic enzyme (NADP-ME) (Malic enzyme 1); (3641:) NADP-dependent malic enzyme, mitochondrial precursor (NADP-ME) (Malic enzyme 3); (3642:) NADP-dependent malic enzyme; (3643:) NADPH oxidase 1 isoform long [*Homo sapiens*]; (3644:) NADPH oxidase 1 isoform long variant [*Homo sapiens*]; (3645:) NADPH oxidase 1 isoform short [*Homo sapiens*]; (3646:) NADPH oxidase 3 (gp91phox homolog 3) (GP91-3) (Mitogenic oxidase 2); (3647:) NADPH oxidase 3 [*Homo sapiens*]; (3648:) NADPH oxidase 4 (Kidney superoxide-producing NADPH oxidase) (KOX-1) (Renal NAD(P)H-oxidase); (3649:) NADPH oxidase 5; (3650:) NADPH oxidase homolog 1 (NOX-1) (NOH-1) (NADH/NADPH mitogenic oxidase subunit P65-MOX) (Mitogenic oxidase 1) (MOX1); (3651:) NADPH oxidase, EF hand calcium-binding domain 5 [*Homo sapiens*]; (3652:) NADPH—cytochrome P450 reductase (CPR) (P450R); (3653:) nardilysin (N-arginine dibasic convertase) [*Homo sapiens*]; (3654:) Nardilysin precursor (N-arginine dibasic convertase) (NRD convertase) (NRD-C); (3655:) N-arginine dibasic convertase [*Homo sapiens*]; (3656:) natriuretic peptide precursor A [*Homo sapiens*]; (3657:) natriuretic peptide precursor B preproprotein [*Homo sapiens*]; (3658:) Natriuretic Peptide Receptor A (NPR-A); (3659:) natriuretic peptide receptor A/guanylate cyclase A (atrionatriuretic peptide receptor A) [*Homo sapiens*]; (3660:) natriuretic peptide receptor B precursor [*Homo sapiens*]; (3661:) Natural cytotoxicity triggering receptor 1 precursor (Natural killer cell p46-related protein) (NKp46) (hNKp46) (NK-p46) (NK cell-activating receptor) (Lymphocyte antigen 94 homolog) (CD335antigen); (3662:) Natural cytotoxicity triggering receptor 2 precursor (Natural killer cell p44-related protein) (NKp44) (NK-p44) (NK cell-activating receptor) (Lymphocyte antigen 95 homolog) (CD336antigen); (3663:) Natural cytotoxicity triggering receptor 3 precursor (Natural killer cell p30-related protein) (NKp30) (NK-p30) (CD337 antigen); (3664:) Natural killer cell receptor 2B4 precursor (NKR2B4) (NK cell type I receptor protein 2B4) (h2B4) (CD244 antigen) (NK cell activation-inducing ligand) (NAIL); (3665:) Natural killer cells antigen CD94 (NK cell receptor) (Killer cell lectin-like receptor subfamily D member 1) (KP43); (3666:) N-Cadherin; (3667:) NCUBE1 [*Homo sapiens*]; (3668:) N-deacetylase/N-sulfotransferase (heparan glucosaminyl)$_2$ [*Homo sapiens*]; (3669:) NDUFS1 protein [*Homo sapiens*]; (3670:) NEDD4-like E3 ubiquitin-protein ligase WWP1 (WW domain-containing protein 1) (Atropin-1-interacting protein 5) (AIP5); (3671:) NEDD4-like E3 ubiquitin-protein ligase WWP2 (WW domain-containing protein 2) (Atrophin-1-interacting protein 2) (AIP2); (3672:) NEDD8 precursor (Ubiquitin-like protein Nedd8) (Neddylin); (3673:) NEDD8-activating enzyme E1 catalytic subunit (Ubiquitin-activating enzyme 3) (NEDD8-activating enzyme E1C) (Ubiquitin-activating enzyme E1C); (3674:) NEDD8-activating enzyme E1 regulatory subunit (Amyloid protein-binding protein 1) (Amyloid beta precursor protein-binding protein 1, 59 kDa) (APP-BP1) (Protooncogene protein 1) (HPP1); (3675:) Nedd8-activating enzyme hUba3 [*Homo sapiens*]; (3676:) NEDD8-conjugating enzyme [*Homo sapiens*]; (3677:) Nedd8-conjugating enzyme hUbc12 [*Homo sapiens*]; (3678:) NEDD8-conjugating enzyme NCE2 [*Homo sapiens*]; (3679:) NEDD8-conjugating enzyme Ubc12 (Ubiquitin-conjugating enzyme E2 M) (NEDD8 protein ligase) (NEDD8 carrier protein); (3680:) Nef associated protein 1 [*Homo sapiens*]; (3681:) nei endonuclease VIII-like 1 [*Homo sapiens*]; (3682:) nei-like 2 [*Homo sapiens*]; (3683:) Nematode Nicotinic Acetylcholine Receptor (nAChR); (3684:) neo-poly(A) polymerase [*Homo sapiens*]; (3685:) nephrin [*Homo sapiens*]; (3686:) Nerve Growth Factor (NGF); (3687:) Netrin receptor DCC precursor (Tumor suppressor protein DCC) (Colorectal cancer suppressor); (3688:) Netrin receptor UNC5A precursor (Unc-5 homolog A) (Unc-5 homolog1); (3689:) Netrin receptor UNC5B precursor (Unc-5 homolog B) (Unc-5 homolog 2) (p53-regulated receptor for death and life protein 1); (3690:)

Netrin receptor UNC5C precursor (Unc-5 homolog C) (Unc-5 homolog3); (3691:) Netrin receptor UNC5D precursor (Unc-5 homolog D) (Unc-5 homolog4); (3692:) neural stem cell-derived dendrite regulator [Homo sapiens]; (3693:) Neural Thread Protein (NTP); (3694:) Neutralized-like protein 2; (3695:) Neuraminidase; (3696:) neuraminidase precursor [Homo sapiens]; (3697:) neuroblastoma apoptosis-related protease [Homo sapiens]; (3698:) Neuroendocrine convertase 1 precursor (NEC 1) (PC1) (Prohormone convertase 1) (Proprotein convertase 1); (3699:) Neuroendocrine convertase 2 precursor (NEC 2) (PC2) (Prohormone convertase 2) (Proprotein convertase 2) (KEX2-like endoprotease 2); (3700:) Neurofibromin (Neurofibromatosis-related protein NF-1) [Contains:Neurofibromin truncated]; (3701:) neurofibromin isoform 1 [Homo sapiens]; (3702:) neurofibromin isoform 2 [Homo sapiens]; (3703:) neurofilament, light polypeptide 68 kDa [Homo sapiens]; (3704:) "Neurogenic locus notch homolog protein 1 precursor (Notch 1) (hN1) (Translocation-associated notch protein TAN-1) [Contains:) Notch 1 extracellular truncation; Notch 1 intracellular domain]."; (3705:) "Neurogenic locus notch homolog protein 2 precursor (Notch 2) (hN2)[Contains:) Notch 2 extracellular truncation; Notch 2 intracellular domain]."; (3706:) "Neurogenic locus notch homolog protein 3 precursor (Notch 3)[Contains:) Notch 3 extracellular truncation; Notch 3 intracellular domain]."; (3707:) "Neurogenic locus notch homolog protein 4 precursor (Notch 4) (hNotch4) [Contains:) Notch 4 extracellular truncation; Notch 4 intracellular domain]."; (3708:) Neurokinin NK1 Receptor; (3709:) Neurokinin NK2 Receptor; (3710:) Neurokinin NK3 Receptor; (3711:) Neuromedin K receptor (NKR) (Neurokinin B receptor) (NK-3 receptor) (NK-3R) (Tachykinin receptor 3); (3712:) Neuromedin U receptor 1 (NMU-R1) (G-protein coupled receptor 66) (G-protein coupled receptor FM-3); (3713:) Neuromedin U receptor 2 (NMU-R2) (G-protein coupled receptor TGR-1) (G-protein coupled receptor FM-4); (3714:) Neuromedin-B receptor (NMB-R) (Neuromedin-B-preferring bombesin receptor); (3715:) Neuronal acetylcholine receptor protein subunit alpha-10 precursor (Nicotinic acetylcholine receptor subunit alpha 10) (NACHR alpha10); (3716:) Neuronal acetylcholine receptor protein subunit alpha-3 precursor; (3717:) Neuronal acetylcholine receptor protein subunit alpha-5 precursor; (3718:) Neuronal acetylcholine receptor protein subunit alpha-6 precursor; (3719:) Neuronal acetylcholine receptor protein subunit alpha-9 precursor (Nicotinic acetylcholine receptor subunit alpha 9) (NACHR alpha 9); (3720:) Neuronal Nicotinic Acetylcholine Receptor (nAChR); (3721:) Neuronal pentraxin receptor; (3722:) neuronal tryptophan hydroxylase [Homo sapiens]; (3723:) neuron-derived receptor NOR-1—human; (3724:) Neuropeptide FF receptor 1 (G-protein coupled receptor 147) (RF amide-related peptide receptor OT7T022); (3725:) Neuropeptide FF receptor 2 (Neuropeptide G-protein coupled receptor) (G-protein coupled receptor 74) (G-protein coupled receptor HLWAR77); (3726:) Neuropeptide S receptor (G-protein coupled receptor 154) (G-protein coupled receptor for asthma susceptibility) (G-protein coupled receptor PGR14); (3727:) Neuropeptide Y receptor type 1 (NPY1-R); (3728:) Neuropeptide Y receptor type 2 (NPY2-R) (NPY-Y2 receptor); (3729:) Neuropeptide Y receptor type 4 (NPY4-R) (Pancreatic polypeptide receptor 1) (PP1); (3730:) Neuropeptide Y receptor type 5 (NPY5-R) (NPY-Y5 receptor) (Y5receptor) (NPYY5); (3731:) Neuropeptide Y Y1 Receptor (NPY Y1R); (3732:) Neuropeptide Y Y2 Receptor (NPY Y2R); (3733:) Neuropeptide Y Y4 Receptor (NPY Y4R); (3734:) Neuropeptide Y Y5 Receptor (NPY Y5R); (3735:) Neuropeptides B/W receptor type 1 (G-protein coupled receptor 7); (3736:) Neuropeptides B/W receptor type 2 (G-protein coupled receptor 8); (3737:) Neuropilin and tolloid-like protein 1 precursor (Brain-specific transmembrane protein containing 2 CUB and 1 LDL-receptor class A domains protein 1); (3738:) Neuropilin and tolloid-like protein 2 precursor (Brain-specific transmembrane protein containing 2 CUB and 1 LDL-receptor class A domains protein 2); (3739:) Neuropilin-1 precursor (Vascular endothelial cell growth factor 165receptor) (CD304 antigen); (3740:) Neuropilin-2 precursor (Vascular endothelial cell growth factor 165receptor 2); (3741:) Neurotensin Receptor; (3742:) Neurotensin receptor type 1 (NT-R-1) (High-affinity levocabastine-insensitive neurotensin receptor) (NTRH); (3743:) Neurotensin receptor type 2 (NT-R-2) (Levocabastine-sensitive neurotensin receptor) (NTR2 receptor); (3744:) neurotensin/neuromedin N preproprotein [Homo sapiens]; (3745:) Neurotrophic factor production accelerator; (3746:) Neurotrophic Tyrosine Kinase Receptor 1 (NTRK1); (3747:) Neurotrophic Tyrosine Kinase Receptor 2 (NTRK2); (3748:) neurotrophin 5 preproprotein [Homo sapiens]; (3749:) neurotrypsin precursor [Homo sapiens]; (3750:) Neutral alpha-glucosidase AB precursor (Glucosidase II subunit alpha); (3751:) Neutral amino acid transporter B(0) (ATB(0)) (Sodium-dependent neutral amino acid transporter type 2) (RD114/simian type Dretrovirus receptor) (Baboon M7 virus receptor); (3752:) Neutral ceramidase (NCDase) (N-CDase) (Acylsphingosine deacylase 2) (N-acylsphingosine amidohydrolase 2) (BCDase) (LCDase) (hCD)[Contains:) Neutral ceramidase soluble form]; (3753:) Neutral Endopeptidase (NEP); (3754:) Neutral Sphingomyelinase (nSMase); (3755:) Neutrophil Cathepsin G; (3756:) Neutrophil collagenase precursor (Matrix metalloproteinase-8) (MMP-8) (PMNL collagenase) (PMNL-CL); (3757:) Neutrophil cytosol factor 4 (NCF-4) (Neutrophil NADPH oxidase factor 4) (p40-phox) (p40phox); (3758:) neutrophil cytosolic factor 1 [Homo sapiens]; (3759:) neutrophil cytosolic factor 4 (40 kD) isoform 1 [Homo sapiens]; (3760:) neutrophil cytosolic factor 4 (40 kD) isoform 2 [Homo sapiens]; (3761:) Neutrophil Elastase; (3762:) NFS1 nitrogen fixation 1 [Homo sapiens]; (3763:) "N-glycosylase/DNA lyase [Includes:) 8-oxoguanine DNA glycosylase; DNA-(apurinic or apyrimidinic site) lyase (Alyase)]."; (3764:) Niacin Receptor; (3765:) Nicastrin precursor; (3766:) NICE-S protein [Homo sapiens]; (3767:) Nicotinamide Adenine Dinucleotide synthetase (NADs); (3768:) nicotinamide mononucleotide adenylyl transferase [Homo sapiens]; (3769:) Nicotinamide mononucleotide adenylyltransferase 1 (NMN adenylyltransferase 1); (3770:) nicotinamide mononucleotide adenylyltransferase 2 isoform 1 [Homo sapiens]; (3771:) nicotinamide mononucleotide adenylyltransferase 2 isoform 2 [Homo sapiens]; (3772:) nicotinamide nucleotide adenylyltransferase 1 [Homo sapiens]; (3773:) nicotinamide nucleotide adenylyltransferase 3 [Homo sapiens]; (3774:) nicotinamide riboside kinase 1 [Homo sapiens]; (3775:) Nicotinamide riboside kinase 2 (Integrin beta-1-binding protein 3) (Muscle integrin-binding protein) (MIBP); (3776:) nicotinamide riboside kinase 2 [Homo sapiens]; (3777:) Nicotinic acid receptor 1 (G-protein coupled receptor 109A) (G-protein coupled receptor HM74A); (3778:) Nicotinic acid receptor 2 (G-protein coupled receptor 109B) (G-protein coupled receptor HM74) (G-protein coupled receptor HM74B); (3779:) Nicotinic Receptor; (3780:) NifU-like N-terminal domain-containing protein, mitochondrial precursor (NifU-like protein) (Iron-sulfur cluster assembly enzyme ISCU); (3781:) Nitric Oxide Neutralizer; (3782:) Nitric Oxide Synthase (NOS); (3783:)

nitric oxide synthase 1 (neuronal) [*Homo sapiens*]; (3784:) nitric oxide synthase 2A isoform 1 [*Homo sapiens*]; (3785:) nitric oxide synthase 2A isoform 2 [*Homo sapiens*]; (3786:) nitric oxide synthase 3 (endothelial cell) [*Homo sapiens*]; (3787:) nitric oxide synthase trafficking isoform 1 [*Homo sapiens*]; (3788:) nitric oxide synthase trafficking isoform 2 [*Homo sapiens*]; (3789:) Nitric oxide synthase, inducible (NOS type 11) (Inducible NO synthase) (Inducible NOS) (iNOS) (Hepatocyte NOS) (HEP-NOS); (3790:) nitric oxide synthase; (3791:) Nitric-oxide synthase IIC (NOS type II C) (NOSIIc); (3792:) Nitric-oxide synthase, brain (NOS type 1) (Neuronal NOS) (N-NOS) (nNOS) (Constitutive NOS) (NC-NOS) (bNOS); (3793:) Nitric-oxide synthase, endothelial (EC-NOS) (NOS type II) (NOSII) (Endothelial NOS) (eNOS) (Constitutive NOS) (cNOS); (3794:) NKG2-A/NKG2-B type II integral membrane protein (NKG2-A/B-activating NK receptor) (NK cell receptor A) (CD159a antigen); (3795:) NKG2-C type II integral membrane protein (NKG2-C-activating NK receptor) (NK cell receptor C) (CD159c antigen); (3796:) NKG2-D type II integral membrane protein (NKG2-D-activating NK receptor) (NK cell receptor D) (Killer cell lectin-like receptor subfamily K member 1) (CD314 antigen); (3797:) NKG2-E type II integral membrane protein (NKG2-E-activating NK receptor) (NK cell receptor E); (3798:) NKG2-F type II integral membrane protein (NKG2-F-activating NK receptor) (NK cell receptor F); (3799:) N-kinase; (3800:) NME1-NME2 protein [*Homo sapiens*]; (3801:) N-methyl purine DNA-glycosylase [*Homo sapiens*]; (3802:) N-Methyl-D-Aspartate (NMDA) Receptor; (3803:) N-methylpurine-DNA glycosylase isoform a [*Homo sapiens*]; (3804:) N-methylpurine-DNA glycosylase isoform b [*Homo sapiens*]; (3805:) N-methylpurine-DNA glycosylase isoform c [*Homo sapiens*]; (3806:) N-myristoyltransferase 1 [*Homo sapiens*]; (3807:) Nociceptin receptor (Orphanin FQ receptor) (Kappa-type 3 opioid receptor) (KOR-3); (3808:) NOD2 (CARD15) Receptor; (3809:) Non-Canonical UBiquitin Conjugating Enzyme 1 (NCUBE1) [*Homo sapiens*]; (3810:) nonfunctional alpha(1,2)-fucosyltransferase [*Homo sapiens*]; (3811:) non-metastatic cells 1, protein (NM23A) expressed in isoform a[*Homo sapiens*]; (3812:) non-metastatic cells 1, protein (NM23A) expressed in isoform b[*Homo sapiens*]; (3813:) non-metastatic cells 2, protein (NM23B) expressed in [*Homo sapiens*]; (3814:) Norepinephrine Reuptake; (3815:) Notch-1 Protein; (3816:) nov precursor [*Homo sapiens*]; (3817:) novel AMP-binding enzyme [*Homo sapiens*]; (3818:) novel protein [*Homo sapiens*]; (3819:) N-sulfoglucosamine sulfohydrolase (sulfamidase) [*Homo sapiens*]; (3820:) N-sulphoglucosamine sulphohydrolase [*Homo sapiens*]; (3821:) N-sulphoglucosamine sulphohydrolase precursor (Sulfoglucosaminesulfamidase) (Sulphamidase); (3822:) NT-3 growth factor receptor precursor (Neurotrophic tyrosine kinase receptor type 3) (TrkC tyrosine kinase) (GP145-TrkC) (Trk-C); (3823:) N-terminal Asn amidase [*Homo sapiens*]; (3824:) nth endonuclease III-like 1 [*Homo sapiens*]; (3825:) N-Type Calcium Channel Blocker (NCCB); (3826:) NUAK family SNF1-like kinase 1 (AMPK-related protein kinase 5); (3827:) NUAK family SNF1-like kinase 2 (SNF1/AMP kinase-related kinase) (SNARK); (3828:) nuclear factor (erythroid-derived 2)-like 2 [*Homo sapiens*]; (3829:) nuclear factor kappa-B, subunit 1 [*Homo sapiens*]; (3830:) Nuclear Factor-Kappa B (NF-kB); (3831:) Nuclear receptor OB1 (Nuclear receptor DAX-1) (DSS-AHC critical region on the X chromosome protein 1); (3832:) Nuclear receptor OB2 (Orphan nuclear receptor SHP) (Small heterodimer partner); (3833:) Nuclear receptor coactivator 3 (NCoA-3) (Thyroid hormone receptor activator molecule 1) (TRAM-1) (ACTR) (Receptor-associated coactivator 3) (RAC-3) (Amplified in breast cancer-1 protein) (AIB-1) (Steroid receptor coactivator protein 3) (SRC-3) (CBP-interacting protein) (pCIP); (3834:) nuclear receptor interacting protein 1 [*Homo sapiens*]; (3835:) Nuclear receptor ROR-alpha (Nuclear receptor RZR-alpha); (3836:) Nuclear receptor ROR-beta (Nuclear receptor RZR-beta); (3837:) Nuclear receptor ROR-gamma (Nuclear receptor RZR-gamma); (3838:) nuclear receptor subfamily 1, group H, member 4 [*Homo sapiens*]; (3839:) nuclear receptor subfamily 3, group C, member 1 isoform alpha [*Homo sapiens*]; (3840:) nuclear receptor subfamily 3, group C, member 1 isoform beta [*Homo sapiens*]; (3841:) nuclear receptor subfamily 3, group C, member 1 isoform gamma [*Homo sapiens*]; (3842:) nuclear receptor subfamily 5, group A, member 1 [*Homo sapiens*]; (3843:) nuclear receptor subfamily 5, group A, member 2 isoform 1 [*Homo sapiens*]; (3844:) nuclear receptor subfamily 5, group A, member 2 isoform 2 [*Homo sapiens*]; (3845:) nucleolar protein GU2 [*Homo sapiens*]; (3846:) Nucleolin; (3847:) Nucleoside diphosphate kinase A (NDK A) (NDP kinase A) (Tumor metastatic process-associated protein) (Metastasis inhibition factor nm23) (nm23-H1) (Granzyme A-activated DNase) (GAAD); (3848:) Nucleoside diphosphate kinase B (NDK B) (NDP kinase B) (nm23-H2) (C-myc purine-binding transcription factor PUF); (3849:) Nucleoside Reverse Transcriptase (NRTI); (3850:) "nucleotide binding protein; NBP [*Homo sapiens*]."; (3851:) nudix-type motif 14 [*Homo sapiens*]; (3852:) nudix-type motif 1 isoform p18 [*Homo sapiens*]; (3853:) nudix-type motif 1 isoform p22 [*Homo sapiens*]; (3854:) nudix-type motif 2 [*Homo sapiens*]; (3855:) 06-Alkylguanine-DNA Alkyltransferase (AGT); (3856:) O-6-methylguanine-DNA methyltransferase; (3857:) OB-Cadherin; (3858:) Olfactory receptor 10A1 (Olfactory receptor 11-403) (OR11-403); (3859:) Olfactory receptor 10A3 (HTPCRX12); (3860:) Olfactory receptor 10A4 (HP2) (Olfactory receptor-like protein JCG5); (3861:) Olfactory receptor 10A5 (HP3) (Olfactory receptor-like protein JCG6); (3862:) Olfactory receptor 10A6; (3863:) Olfactory receptor 10A7; (3864:) Olfactory receptor 10AD1; (3865:) Olfactory receptor 10AG1 (Olfactory receptor OR11-160); (3866:) Olfactory receptor 10C1 (Hs6M1-17); (3867:) Olfactory receptor 10D4; (3868:) Olfactory receptor 10G2; (3869:) Olfactory receptor 10G3 (Olfactory receptor OR14-40); (3870:) Olfactory receptor 10G4 (Olfactory receptor OR11-278); (3871:) Olfactory receptor 10G6 (Olfactory receptor OR11-280); (3872:) Olfactory receptor 10G7; (3873:) Olfactory receptor 10G8 (Olfactory receptor OR11-282); (3874:) Olfactory receptor 10G9; (3875:) Olfactory receptor 10H1; (3876:) Olfactory receptor 10H2; (3877:) Olfactory receptor 10H3; (3878:) Olfactory receptor 10H4; (3879:) Olfactory receptor 10H5; (3880:) Olfactory receptor 10J1 (Olfactory receptor-like protein HGMP07J) (Olfactory receptor OR1-26); (3881:) Olfactory receptor 10J3; (3882:) Olfactory receptor 10J5; (3883:) Olfactory receptor 10J6; (3884:) Olfactory receptor 10K1; (3885:) Olfactory receptor 10K2 (Olfactory receptor OR1-4); (3886:) Olfactory receptor 10P1 (Olfactory receptor OR12-7); (3887:) Olfactory receptor 10Q1; (3888:) Olfactory receptor 10R2; (3889:) Olfactory receptor 10S1; (3890:) Olfactory receptor 10T2 (Olfactory receptor OR1-3); (3891:) Olfactory receptor 10V1; (3892:) Olfactory receptor 10W1 (Olfactory receptor OR11-236); (3893:) Olfactory receptor 10X1 (Olfactory receptor OR1-14); (3894:) Olfactory receptor 10Z1; (3895:) Olfactory receptor 11A1 (Hs6M1-18); (3896:) Olfactory receptor 11G2;

(3897:) Olfactory receptor 11H1 (Olfactory receptor 22-1) (OR22-1); (3898:) Olfactory receptor 11H4 (Olfactory receptor OR14-36); (3899:) Olfactory receptor 11H6 (Olfactory receptor OR14-35); (3900:) Olfactory receptor 11L1; (3901:) Olfactory receptor 12D2 (Hs6M1-20); (3902:) Olfactory receptor 12D3 (Hs6M1-27); (3903:) Olfactory receptor 13A1 (Olfactory receptor OR10-3); (3904:) Olfactory receptor 13C2; (3905:) Olfactory receptor 13C3; (3906:) Olfactory receptor 13C4; (3907:) Olfactory receptor 13C5; (3908:) Olfactory receptor 13C8; (3909:) Olfactory receptor 13C9; (3910:) Olfactory receptor 13D1; (3911:) Olfactory receptor 13F1; (3912:) Olfactory receptor 13G1; (3913:) Olfactory receptor 13H1; (3914:) Olfactory receptor 13J1; (3915:) Olfactory receptor 1A1 (Olfactory receptor 17-7) (OR17-7) (Olfactory receptor OR17-11); (3916:) Olfactory receptor 1A2 (Olfactory receptor 17-6) (OR17-6) (Olfactory receptor OR17-10); (3917:) Olfactory receptor 1 BI (Olfactory receptor 9-B) (OR9-B) (Olfactory receptor OR9-26); (3918:) Olfactory receptor 1C1 (Olfactory receptor TPCR27) (Olfactory receptor OR1-42); (3919:) Olfactory receptor 1 D2 (Olfactory receptor-like protein HGMP07E) (Olfactory receptor 17-4) (OR17-4); (3920:) Olfactory receptor 1 D4 (Olfactory receptor 17-30) (OR17-30); (3921:) Olfactory receptor 1D5 (Olfactory receptor 17-31) (OR17-31); (3922:) Olfactory receptor 1E1 (Olfactory receptor-like protein HGMP071) (Olfactory receptor 17-2/17-32) (OR17-2) (OR17-32) (Olfactory receptor 13-66) (OR13-66) (Olfactory receptor 5-85) (OR5-85); (3923:) Olfactory receptor 1E2 (Olfactory receptor 17-93/17-135/17-136) (OR17-93) (OR17-135) (OR17-136); (3924:) Olfactory receptor 1F1 (Olfactory receptor 16-35) (OR16-35) (Olfactory receptor OR16-4); (3925:) Olfactory receptor 1F10 (Olfactory receptor 3-145) (OR3-145); (3926:) Olfactory receptor 1F12 (Hs6M1-35P); (3927:) Olfactory receptor 1F2 (OLFmf2); (3928:) Olfactory receptor 1G1 (Olfactory receptor 17-209) (OR17-209); (3929:) Olfactory receptor 111 (Olfactory receptor 19-20) (OR19-20); (3930:) Olfactory receptor 1J1 (Olfactory receptor OR9-18); (3931:) Olfactory receptor 1J2 (OST044) (HSA5) (HTPCRX15) (Olfactory receptor OR9-19); (3932:) Olfactory receptor 1J4 (HTPCRX01) (Olfactory receptor OR9-21); (3933:) Olfactory receptor 1K1; (3934:) Olfactory receptor 1L1 (Olfactory receptor 9-C) (OR9-C); (3935:) Olfactory receptor 1L3 (Olfactory receptor 9-D) (OR9-D) (Olfactory receptor OR9-28); (3936:) Olfactory receptor 1L4 (Olfactory receptor 9-E) (OR9-E) (OST046); (3937:) Olfactory receptor 1L6; (3938:) Olfactory receptor 1L8 (Olfactory receptor OR9-24); (3939:) Olfactory receptor 1M1 (Olfactory receptor 19-6) (OR19-6); (3940:) Olfactory receptor 1N1 (Olfactory receptor 1-26) (OR1-26) (Olfactory receptor 1N3) (Olfactory receptor OR9-22); (3941:) Olfactory receptor 1N2; (3942:) Olfactory receptor 1Q1 (Olfactory receptor TPCR106) (Olfactory receptor 9-A) (OR9-A) (OST226) (Olfactory receptor OR9-25); (3943:) Olfactory receptor 1S1; (3944:) Olfactory receptor 1S2; (3945:) Olfactory receptor 2A12; (3946:) Olfactory receptor 2A14 (OST182); (3947:) Olfactory receptor 2A2 (Olfactory receptor OR7-11); (3948:) Olfactory receptor 2A4 (Olfactory receptor OR6-37); (3949:) Olfactory receptor 2A42; (3950:) Olfactory receptor 2A5 (Olfactory receptor 7-138/7-141) (OR7-138) (OR7-141); (3951:) Olfactory receptor 2A7; (3952:) Olfactory receptor 2AE1; (3953:) Olfactory receptor 2AG1 (HT3); (3954:) Olfactory receptor 2AJ1; (3955:) Olfactory receptor 2AK2 (Olfactory receptor OR1-47); (3956:) Olfactory receptor 2AP1 (Olfactory receptor OR12-9); (3957:) Olfactory receptor 2B11; (3958:) Olfactory receptor 2B2 (Olfactory receptor 6-1) (OR6-1) (Hs6M1-10); (3959:) Olfactory receptor 2B3 (Olfactory receptor 6-4) (OR6-4) (Olfactory receptor OR6-14) (Hs6M1-1); (3960:) Olfactory receptor 2B6 (Olfactory receptor 6-31) (OR6-31) (Olfactory receptor 5-40) (OR5-40) (Hs6M1-32); (3961:) Olfactory receptor 2B8 (Hs6M1-29P); (3962:) Olfactory receptor 2C1 (OLFmf3); (3963:) Olfactory receptor 2C3; (3964:) Olfactory receptor 2D2 (Olfactory receptor 11-610) (OR11-610) (HB2) (Olfactory receptor OR11-88); (3965:) Olfactory receptor 2D3; (3966:) Olfactory receptor 2F1 (Olfactory receptor-like protein OLF3); (3967:) Olfactory receptor 2F2 (Olfactory receptor 7-1) (OR7-1) (Olfactory receptor OR7-6); (3968:) Olfactory receptor 2G2 (Olfactory receptor OR1-32); (3969:) Olfactory receptor 2G3 (Olfactory receptor OR1-33); (3970:) Olfactory receptor 2G6; (3971:) Olfactory receptor 2H1 (Hs6M1-16) (Olfactory receptor 6-2) (OR6-2) (OLFR42A-9004.14/9026.2); (3972:) Olfactory receptor 2H2 (Hs6M1-12) (Olfactory receptor-like protein FAT11); (3973:) Olfactory receptor 2H7 (OLFR42B-9079.6); (3974:) Olfactory receptor 211; (3975:) Olfactory receptor 2J1 (Olfactory receptor 6-5) (OR6-5) (Hs6M1-4); (3976:) Olfactory receptor 2J2 (Olfactory receptor 6-8) (OR6-8) (Hs6M1-6); (3977:) Olfactory receptor 2J3 (Olfactory receptor 6-6) (OR6-6) (Hs6M1-3); (3978:) Olfactory receptor 2K2(HTPCRH06); (3979:) Olfactory receptor 2L13; (3980:) Olfactory receptor 2L2 (HTPCRH07); (3981:) Olfactory receptor 2L3; (3982:) Olfactory receptor 2L5 (Olfactory receptor OR1-53); (3983:) Olfactory receptor 2L8 (Olfactory receptor OR1-46); (3984:) Olfactory receptor 2M1 (Olfactory receptor-like protein JCG10) (OST037); (3985:) Olfactory receptor 2M2 (OST423); (3986:) Olfactory receptor 2M3 (Olfactory receptor OR1-54); (3987:) Olfactory receptor 2M4 (Olfactory receptor TPCR100) (OST710) (HTPCRX18) (Olfactory receptor OR1-55); (3988:) Olfactory receptor 2M7 (Olfactory receptor OR1-58); (3989:) Olfactory receptor 2S2 (Olfactory receptor OR9-3); (3990:) Olfactory receptor 2T1 (Olfactory receptor 1-25) (OR1-25) (Olfactory receptor OR1-61); (3991:) Olfactory receptor 2T10 (Olfactory receptor OR1-64); (3992:) Olfactory receptor 2T11 (Olfactory receptor OR1-65); (3993:) Olfactory receptor 2T12 (Olfactory receptor OR1-57); (3994:) Olfactory receptor 2T2 (Olfactory receptor OR1-43); (3995:) Olfactory receptor 2T27 (Olfactory receptor OR1-67); (3996:) Olfactory receptor 2T29; (3997:) Olfactory receptor 2T3; (3998:) Olfactory receptor 2T33 (Olfactory receptor OR1-56); (3999:) Olfactory receptor 2T34 (Olfactory receptor OR1-63); (4000:) Olfactory receptor 2T35 (Olfactory receptor OR1-66); (4001:) Olfactory receptor 2T4 (Olfactory receptor OR1-60); (4002:) Olfactory receptor 2T5 (Olfactory receptor OR1-62); (4003:) Olfactory receptor 2T6 (OST703); (4004:) Olfactory receptor 2V2 (Olfactory receptor OR5-3); (4005:) Olfactory receptor 2W1 (Hs6M1-15); (4006:) Olfactory receptor 2W3 (Olfactory receptor OR1-49); (4007:) Olfactory receptor 2Y1 (Olfactory receptor OR5-2); (4008:) Olfactory receptor 2Z1 (Olfactory receptor OR19-4); (4009:) Olfactory receptor 3A1 (Olfactory receptor 17-40) (OR17-40); (4010:) Olfactory receptor 3A2 (Olfactory receptor 17-228) (OR17-228); (4011:) Olfactory receptor 3A3 (Olfactory receptor 17-201) (OR17-201); (4012:) Olfactory receptor 3A4 (Olfactory receptor 17-24) (OR17-24); (4013:) Olfactory receptor 4A15 (Olfactory receptor OR11-118); (4014:) Olfactory receptor 4A16 (Olfactory receptor OR11-117); (4015:) Olfactory receptor 4A4 (Olfactory receptor OR11-107); (4016:) Olfactory receptor 4A47 (Olfactory receptor OR11-113); (4017:) Olfactory receptor 4A5 (Olfactory receptor OR11-111); (4018:) Olfactory receptor 4B1 (OST208) (Olfactory receptor OR11-106);

(4019:) Olfactory receptor 4C11 (Olfactory receptor OR11-136); (4020:) Olfactory receptor 4C12 (Olfactory receptor OR11-259); (4021:) Olfactory receptor 4C13 (Olfactory receptor OR11-260); (4022:) Olfactory receptor 4C15 (Olfactory receptor OR11-127) (Olfactory receptor OR11-134); (4023:) Olfactory receptor 4C16 (Olfactory receptor OR11-135); (4024:) Olfactory receptor 4C3 (Olfactory receptor OR11-98); (4025:) Olfactory receptor 4C5 (Olfactory receptor OR11-99); (4026:) Olfactory receptor 4C6 (Olfactory receptor OR11-138); (4027:) Olfactory receptor 4D1 (Olfactory receptor TPCR16); (4028:) Olfactory receptor 4D10 (Olfactory receptor OR11-251); (4029:) Olfactory receptor 4D11; (4030:) Olfactory receptor 4D2 (Olfactory receptor OR17-24) (B-lymphocyte membrane protein BC2009); (4031:) Olfactory receptor 4D5 (Olfactory receptor OR11-276); (4032:) Olfactory receptor 4D6 (Olfactory receptor OR11-250); (4033:) Olfactory receptor 4D9 (Olfactory receptor OR11-253); (4034:) Olfactory receptor 4E2 (Olfactory receptor OR14-42); (4035:) Olfactory receptor 4F14; (4036:) Olfactory receptor 4F15; (4037:) Olfactory receptor 4F17; (4038:) Olfactory receptor 4F29 (Olfactory receptor OR1-1); (4039:) Olfactory receptor 4F3; (4040:) Olfactory receptor 4F4 (HS14a-1-A) (Olfactory receptor OR19-3); (4041:) Olfactory receptor 4F5; (4042:) Olfactory receptor 4F6; (4043:) Olfactory receptor 4H12; (4044:) Olfactory receptor 4K1; (4045:) Olfactory receptor 4K13 (Olfactory receptor OR14-27); (4046:) Olfactory receptor 4K14 (Olfactory receptor OR14-22); (4047:) Olfactory receptor 4K15; (4048:) Olfactory receptor 4K17; (4049:) Olfactory receptor 4K2; (4050:) Olfactory receptor 4K3; (4051:) Olfactory receptor 4K5; (4052:) Olfactory receptor 4L1 (Olfactory receptor OR14-28); (4053:) Olfactory receptor 4M1; (4054:) Olfactory receptor 4M2; (4055:) Olfactory receptor 4N2 (Olfactory receptor OR14-8); (4056:) Olfactory receptor 4N4; (4057:) Olfactory receptor 4N5 (Olfactory receptor OR14-33); (4058:) Olfactory receptor 4P4; (4059:) Olfactory receptor 4Q3 (Olfactory receptor OR14-3); (4060:) Olfactory receptor 4S1; (4061:) Olfactory receptor 4S2; (4062:) Olfactory receptor 4×1; (4063:) Olfactory receptor 4X2; (4064:) Olfactory receptor 51A2; (4065:) Olfactory receptor 51A4; (4066:) Olfactory receptor 51A7; (4067:) Olfactory receptor 51B2 (Odorant receptor HOR5'beta3); (4068:) Olfactory receptor 51B4 (Odorant receptor HOR5'beta1); (4069:) Olfactory receptor 51B5 (Odorant receptor HOR5'beta5) (Olfactory receptor OR11-37); (4070:) Olfactory receptor 51B5 (Odorant receptor HOR5'beta6); (4071:) Olfactory receptor 51D1 (Olfactory receptor OR11-14); (4072:) Olfactory receptor 51E1; (4073:) Olfactory receptor 51E2 (Prostate-specific G-protein coupled receptor) (HPRAJ); (4074:) Olfactory receptor 51F2; (4075:) Olfactory receptor 51 G1; (4076:) Olfactory receptor 51G2; (4077:) Olfactory receptor 51H1; (4078:) Olfactory receptor 51I1 (Odorant receptor HOR5'beta11) (Olfactory receptor OR11-39); (4079:) Olfactory receptor 51I2 (Odorant receptor HOR5'beta12) (Olfactory receptor OR11-38); (4080:) Olfactory receptor 51L1; (4081:) Olfactory receptor 51M1 (Odorant receptor HOR5'beta7) (Olfactory receptor OR11-40); (4082:) Olfactory receptor 51Q1; (4083:) Olfactory receptor 51 S1; (4084:) Olfactory receptor 51T1; (4085:) Olfactory receptor 51V1 (Odorant receptor HOR3'beta1) (Olfactory receptor OR11-36); (4086:) Olfactory receptor 52A1 (HPFH1OR) (Odorant receptor HOR3'beta4); (4087:) Olfactory receptor 52A5 (Odorant receptor HOR3'beta5) (Olfactory receptor OR11-33); (4088:) Olfactory receptor 52B2; (4089:) Olfactory receptor 52B4 (Olfactory receptor OR11-3); (4090:) Olfactory receptor 52B6; (4091:) Olfactory receptor 52D1 (Odorant receptor HOR5'beta14) (Olfactory receptor OR11-43); (4092:) Olfactory receptor 52E1; (4093:) Olfactory receptor 52E2; (4094:) Olfactory receptor 52E4; (4095:) Olfactory receptor 52E5; (4096:) Olfactory receptor 52E6; (4097:) Olfactory receptor 52E8 (Olfactory receptor OR11-54); (4098:) Olfactory receptor 52H1; (4099:) Olfactory receptor 52I1; (4100:) Olfactory receptor 52I2; (4101:) Olfactory receptor 52J3; (4102:) Olfactory receptor 52K1; (4103:) Olfactory receptor 52K2; (4104:) Olfactory receptor 52L1; (4105:) Olfactory receptor 52L2; (4106:) Olfactory receptor 52M1 (Olfactory receptor OR11-11); (4107:) Olfactory receptor 52N1; (4108:) Olfactory receptor 52N2; (4109:) Olfactory receptor 52N4; (4110:) Olfactory receptor 52N5; (4111:) Olfactory receptor 52P1; (4112:) Olfactory receptor 52R1; (4113:) Olfactory receptor 52W1 (Olfactory receptor OR11-71); (4114:) Olfactory receptor 56A1; (4115:) Olfactory receptor 56A3; (4116:) Olfactory receptor 56A4; (4117:) Olfactory receptor 56B1 (Olfactory receptor OR11-65); (4118:) Olfactory receptor 56B2; (4119:) Olfactory receptor 56B4; (4120:) Olfactory receptor 5A1 (OST181); (4121:) Olfactory receptor 5A2; (4122:) Olfactory receptor 5AC2 (HSA1); (4123:) Olfactory receptor 5AK2; (4124:) Olfactory receptor 5AK3; (4125:) Olfactory receptor 5AN1 (Olfactory receptor OR11-244); (4126:) Olfactory receptor 5AP2; (4127:) Olfactory receptor 5AR1; (4128:) Olfactory receptor 5AS1; (4129:) Olfactory receptor 5AT1; (4130:) Olfactory receptor 5AU1; (4131:) Olfactory receptor 5AV1; (4132:) Olfactory receptor 5AY1; (4133:) Olfactory receptor 5B12 (Olfactory receptor OR11-241); (4134:) Olfactory receptor 5B117 (Olfactory receptor OR11-237); (4135:) Olfactory receptor 5B2 (OST073) (Olfactory receptor OR11-240); (4136:) Olfactory receptor 5B3 (Olfactory receptor OR11-239); (4137:) Olfactory receptor 5BF1; (4138:) Olfactory receptor 5C1 (Olfactory receptor 9-F) (OR9-F); (4139:) Olfactory receptor 5D13; (4140:) Olfactory receptor 5D14; (4141:) Olfactory receptor 5D16; (4142:) Olfactory receptor 5D18; (4143:) Olfactory receptor 5F1 (Olfactory receptor 11-10) (OR11-10); (4144:) Olfactory receptor 5H2; (4145:) Olfactory receptor 5H6; (4146:) Olfactory receptor 5I1 (Olfactory receptor-like protein OLF1) (Olfactory receptor OR11-159); (4147:) Olfactory receptor 5J2 (Olfactory receptor OR11-266); (4148:) Olfactory receptor 5K1 (HTPCRX10); (4149:) Olfactory receptor 5K2 (Olfactory receptor OR3-9); (4150:) Olfactory receptor 5L1 (OST262); (4151:) Olfactory receptor 5L2 (HTPCRX16); (4152:) Olfactory receptor 5M1 (OST050); (4153:) Olfactory receptor 5M10 (Olfactory receptor OR11-207); (4154:) Olfactory receptor 5M11; (4155:) Olfactory receptor 5M3 (Olfactory receptor OR1'-191); (4156:) Olfactory receptor 5M8 (Olfactory receptor OR11-194); (4157:) Olfactory receptor 5M9 (Olfactory receptor OR11-190); (4158:) Olfactory receptor 5P2 (Olfactory receptor-like protein JCG3); (4159:) Olfactory receptor 5P3 (Olfactory receptor-like protein JCG1); (4160:) Olfactory receptor 5R1 (Olfactory receptor OR11-185); (4161:) Olfactory receptor 5T1 (Olfactory receptor OR11-179); (4162:) Olfactory receptor 5T2; (4163:) Olfactory receptor 5T3; (4164:) Olfactory receptor 5U1 (Olfactory receptor OR6-25) (Hs6M1-28); (4165:) Olfactory receptor 5V1 (Hs6M1-21); (4166:) Olfactory receptor 5W2 (Olfactory receptor OR11-1S55); (4167:) Olfactory receptor 6A2 (Olfactory receptor 11-55) (OR11-55) (hP2olfactory receptor); (4168:) Olfactory receptor 6B1 (Olfactory receptor 7-3) (OR7-3); (4169:) Olfactory receptor 6B2 (Olfactory receptor OR2-1); (4170:) Olfactory receptor 6B3 (Olfactory receptor OR2-2); (4171:) Olfactory receptor 6C1 (OST267); (4172:) Olfactory receptor 6C2 (HSA3); (4173:) Olfactory receptor 6C3 (HSA8);

(4174:) Olfactory receptor 6C4; (4175:) Olfactory receptor 6F1 (Olfactory receptor OR1-38); (4176:) Olfactory receptor 6J1; (4177:) Olfactory receptor 6K2; (4178:) Olfactory receptor 6K3; (4179:) Olfactory receptor 6K6; (4180:) Olfactory receptor 6M1 (Olfactory receptor OR11-271); (4181:) Olfactory receptor 6N1; (4182:) Olfactory receptor 6N2; (4183:) Olfactory receptor 6P1 (Olfactory receptor OR1-12); (4184:) Olfactory receptor 6Q1; (4185:) Olfactory receptor 6S1; (4186:) Olfactory receptor 6T1; (4187:) Olfactory receptor 6V1; (4188:) Olfactory receptor 6W1 (Olfactory receptor sdolf); (4189:) Olfactory receptor 6×1 (Olfactory receptor OR11-270); (4190:) Olfactory receptor 6Y1 (Olfactory receptor OR-11); (4191:) Olfactory receptor 7A10 (OST027) (Olfactory receptor OR19-18); (4192:) Olfactory receptor 7A17; (4193:) Olfactory receptor 7A2; (4194:) Olfactory receptor 7A5 (Olfactory receptor TPCR92); (4195:) Olfactory receptor 7C1 (Olfactory receptor TPCR86); (4196:) Olfactory receptor 7C2 (Olfactory receptor 19-18) (OR19-18); (4197:) Olfactory receptor 7D2 (Olfactory receptor 19-4) (OR19-4) (HTPCRH03); (4198:) Olfactory receptor 7D4 (Olfactory receptor OR19-7); (4199:) Olfactory receptor 7G1 (Olfactory receptor 19-15) (OR19-15); (4200:) Olfactory receptor 7G2 (Olfactory receptor 19-13) (OR19-13) (OST260); (4201:) Olfactory receptor 7G3 (OST085); (4202:) Olfactory receptor 8A1 (OST025); (4203:) Olfactory receptor 8B12 (Olfactory receptor OR11-317); (4204:) Olfactory receptor 8B2; (4205:) Olfactory receptor 8B3; (4206:) Olfactory receptor 8B4; (4207:) Olfactory receptor 8B8 (Olfactory receptor TPCR85) (Olfactory-like receptor JCG8); (4208:) Olfactory receptor 8D1 (Olfactory receptor-like protein JCG9) (OST004) (Olfactory receptor OR11-301); (4209:) Olfactory receptor 8D2 (Olfactory receptor-like protein JCG2); (4210:) Olfactory receptor 8D4; (4211:) Olfactory receptor 8G1 (Olfactory receptor TPCR25) (Olfactory receptor OR11-281); (4212:) Olfactory receptor 8G2 (Olfactory receptor TPCR120) (Olfactory receptor OR11-297); (4213:) Olfactory receptor 8G5 (Olfactory receptor OR11-298); (4214:) Olfactory receptor 8H1; (4215:) Olfactory receptor 8H2; (4216:) Olfactory receptor 8H3; (4217:) Olfactory receptor 812; (4218:) Olfactory receptor 8J1; (4219:) Olfactory receptor 8J3; (4220:) Olfactory receptor 8K1; (4221:) Olfactory receptor 8K3; (4222:) Olfactory receptor 8K5; (4223:) Olfactory receptor 8S1; (4224:) Olfactory receptor 8U1; (4225:) Olfactory receptor 9A2; (4226:) Olfactory receptor 9A4; (4227:) Olfactory receptor 9G1; (4228:) Olfactory receptor 9G4; (4229:) Olfactory receptor 9G5 (Olfactory receptor OR11-114); (4230:) Olfactory receptor 911; (4231:) Olfactory receptor 9K2; (4232:) Olfactory receptor 9Q1; (4233:) Olfactory receptor 9Q2; (4234:) olfactory receptor, family 4, subfamily F, member 6 [*Homo sapiens*]; (4235:) oligoadenylate synthetase; (4236:) O-linked GlcNAc transferase isoform 1 [*Homo sapiens*]; (4237:) O-linked GlcNAc transferase isoform 2 [*Homo sapiens*]; (4238:) Oncomodulin (OM) (Parvalbumin beta); (4239:) Opa-interacting protein OIP3 [*Homo sapiens*]; (4240:) Opioid Growth Factor Receptor (OGFr); (4241:) Opioid growth factor receptor (OGFr) (Zeta-type opioid receptor) (7-60 protein); (4242:) Opioid Receptor; (4243:) opioid receptor, mu 1 isoform MOR-1 [*Homo sapiens*]; (4244:) opioid receptor, mu 1 isoform MOR-1A [*Homo sapiens*]; (4245:) opioid receptor, mu 1 isoform MOR-10 [*Homo sapiens*]; (4246:) opioid receptor, mu 1 isoform MOR-LX [*Homo sapiens*]; (4247:) Opioid Receptor-Like1 (ORL1) Receptor; (4248:) Opsin-3 (Encephalopsin) (Panopsin); (4249:) Opsin-5 (Neuropsin) (G-protein coupled receptor 136) (G-protein coupled receptor PGR12) (Transmembrane protein 13); (4250:) Orexigenic neuropeptide QRFP receptor (G-protein coupled receptor103) (SP9155) (AQ27); (4251:) Orexin Receptor; (4252:) Orexin receptor type 1 (Ox1r) (Hypocretin receptor type 1); (4253:) Orexin receptor type 2 (0x2r) (Hypocretin receptor type 2); (4254:) Organic Anion Transporter 3 (OAT3); (4255:) Organic cation/carnitine transporter 1 (Solute carrier family 22member 4) (Ergothioneine transporter) (ET transporter); (4256:) ornithine aminotransferase precursor [*Homo sapiens*]; (4257:) ornithine carbamoyltransferase precursor [*Homo sapiens*]; (4258:) Ornithine carbamoyltransferase, mitochondrial precursor (OTCase) (Ornithine transcarbamylase); (4259:) Ornithine Decarboxylase; (4260:) ornithine decarboxylase 1 [*Homo sapiens*]; (4261:) ornithine decarboxylase-like protein [*Homo sapiens*]; (4262:) Orphan nuclear receptor EAR-2 (V-erbA-related protein EAR-2); (4263:) Orphan nuclear receptor NR1D1 (V-erbA-related protein EAR-1) (Rev-erbA-alpha); (4264:) Orphan nuclear receptor NR1D2 (Rev-erb-beta) (EAR-1R) (Orphan nuclear hormone receptor BD73); (4265:) Orphan nuclear receptor NR1I3 (Constitutive androstane receptor) (CAR) (Constitutive activator of retinoid response) (Constitutive active response) (Orphan nuclear receptor MB67); (4266:) Orphan nuclear receptor NR2E1 (Nuclear receptor TLX) (Tailless homolog) (TII) (hTII); (4267:) Orphan nuclear receptor NR4A1 (Orphan nuclear receptor HMR) (Early response protein NAK1) (TR3 orphan receptor) (ST-59); (4268:) Orphan nuclear receptor NR4A2 (Orphan nuclear receptor NURR1) (Immediate-early response protein NOT) (Transcriptionally-inducible nuclear receptor); (4269:) Orphan nuclear receptor NR4A3 (Nuclear hormone receptor NOR-1) (Neuron-derived orphan receptor 1) (Mitogen-induced nuclear orphan receptor); (4270:) Orphan nuclear receptor NR5A2 (Alpha-1-fetoprotein transcription factor) (Hepatocytic transcription factor) (B1-binding factor) (hB1F) (CYP7A promoter-binding factor) (Liver receptor homolog 1) (LRH-1); (4271:) Orphan nuclear receptor NR6A1 (Germ cell nuclear factor) (GCNF) (Retinoid receptor-related testis-specific receptor) (RTR); (4272:) Orphan nuclear receptor PXR (Pregnane X receptor) (Orphan nuclear receptor PAR1) (Steroid and xenobiotic receptor) (SXR); (4273:) orphan nuclear receptor steroidogenic factor 1, SF-1 (long terminal repeat-binding protein, ELP) [human, Peptide, 205 aa]; (4274:) Orphan nuclear receptor TR2 (Testicular receptor 2); (4275:) Orphan nuclear receptor TR4 (Orphan nuclear receptor TAK1); (4276:) orphan UDP-glucuronosyltransferase (EC 2.4.-.-)—human; (4277:) OTU domain-containing protein 7B (Zinc finger protein Cezanne) (Zinc finger A20 domain-containing protein 1) (Cellular zinc finger anti-NF-kappa B protein); (4278:) oxidised low density lipoprotein (lectin-like) receptor 1 [*Homo sapiens*]; (4279:) Oxidized low-density lipoprotein receptor 1 (Ox-LDL receptor 1) (Lectin-type oxidized LDL receptor 1) (Lectin-like oxidized LDL receptor 1) (Lectin-like ox LDL receptor 1) (LOX-1) (hLOX-1)[Contains:) Oxidized low-density lipoprotein receptor 1, soluble form]; (4280:) Oxidosqualene Cyclase (OSC); (4281:) Oxoeicosanoid receptor 1 (G-protein coupled receptor TG1019) (5-oxo-ETE G-protein coupled receptor) (G-protein coupled receptor170) (G-protein coupled receptor R527); (4282:) Oxysterols receptor LXR-alpha (Liver X receptor alpha) (Nuclear orphan receptor LXR-alpha); (4283:) Oxysterols receptor LXR-beta (Liver X receptor beta) (Nuclear orphan receptor LXR-beta) (Ubiquitously-expressed nuclear receptor) (Nuclear receptor NER); (4284:) Oxytocin Receptor (OTR); (4285:) oxytocin-neurophysin I preproprotein [*Homo sapiens*]; (4286:) P/Q-Type Calcium Channel Blocker; (4287:)

p136 [Homo sapiens]; (4288:) P2 purinergic Receptor; (4289:) p21-activated kinase 2 [Homo sapiens]; (4290:) P2X purinoceptor 1 (ATP receptor) (P2X1) (Purinergic receptor); (4291:) P2X purinoceptor 2 (ATP receptor) (P2X2) (Purinergic receptor); (4292:) P2X purinoceptor 3 (ATP receptor) (P2X3) (Purinergic receptor); (4293:) P2X purinoceptor 4 (ATP receptor) (P2X4) (Purinergic receptor); (4294:) P2X purinoceptor 5 (ATP receptor) (P2X5) (Purinergic receptor); (4295:) P2X purinoceptor 6 (ATP receptor) (P2X6) (Purinergic receptor) (P2XM) (Purinergic receptor P2X-like 1); (4296:) P2X purinoceptor 7 (ATP receptor) (P2X7) (Purinergic receptor) (P2Z receptor); (4297:) P2X3 Purinergic Receptor; (4298:) P2X7 Purinergic Receptor; (4299:) P2Y purinoceptor 1 (ATP receptor) (P2Y1) (Purinergic receptor); (4300:) P2Y purinoceptor 11 (P2Y11); (4301:) P2Y purinoceptor 12 (P2Y12) (P2Y12 platelet ADP receptor) (P2Y (ADP)) (ADP-glucose receptor) (ADPG-R) (P2Y(AC)) (P2Y(cyc)) (P2T(AC)) (SP1999); (4302:) P2Y purinoceptor 13 (P2Y13) (G-protein coupled receptor 86) (G-protein coupled receptor 94); (4303:) P2Y purinoceptor 14 (P2Y14) (UDP-glucose receptor) (G-protein coupled receptor 105); (4304:) P2Y purinoceptor 2 (P2Y2) (P2U purinoceptor 1) (P2U1) (ATP receptor) (Purinergic receptor); (4305:) P2Y purinoceptor 4 (P2Y4) (Uridine nucleotide receptor) (UNR) (P2P); (4306:) P2Y purinoceptor 5 (P2Y5) (Purinergic receptor 5) (RB intron encoded G-protein coupled receptor); (4307:) P2Y purinoceptor 6 (P2Y6); (4308:) P2Y purinoceptor 8 (P2Y8); (4309:) P2Y12 Purinergic Receptor; (4310:) P2Y2 Purinergic Receptor; (4311:) p300/CBP-associated factor [Homo sapiens]; (4312:) p38 Mitogen-Activated Protein (MAP) Kinase; (4313:) p38 mitogen-activated protein (MAP) kinase activator; (4314:) p53 Activator; (4315:) p65 Protein; (4316:) p70 Ribosomal Protein S6 Kinase (S6K); (4317:) p85 beta subunit of phosphatidyl-inositol-3-kinase [Homo sapiens]; (4318:) Paired Box Gene 4 (Pax4) Functional; (4319:) Paired immunoglobulin-like type 2 receptor alpha precursor (Inhibitory receptor PILR-alpha) (Cell surface receptor FDF03); (4320:) Paired immunoglobulin-like type 2 receptor beta precursor (Activating receptor PILR-beta) (Cell surface receptor FDFACT); (4321:) palmitoyl-protein thioesterase [Homo sapiens]; (4322:) palmitoyl-protein thioesterase 1 (ceroid-lipofuscinosis, neuronal1, infantile) [Homo sapiens]; (4323:) Palmitoyl-protein thioesterase 1 precursor (PPT-1) (Palmitoyl-protein hydrolase 1); (4324:) PAN2 [Homo sapiens]; (4325:) pancreas-enriched phospholipase C [Homo sapiens]; (4326:) pancreatic ribonuclease precursor [Homo sapiens]; (4327:) Pantothenate kinase 1 (Pantothenic acid kinase 1) (hPanK1) (hPanK); (4328:) pantothenate kinase 1 isoform alpha [Homo sapiens]; (4329:) pantothenate kinase 1 isoform beta [Homo sapiens]; (4330:) pantothenate kinase 1 isoform gamma [Homo sapiens]; (4331:) pantothenate kinase 2 isoform 1 preproprotein [Homo sapiens]; (4332:) pantothenate kinase 2 isoform 2 [Homo sapiens]; (4333:) Pantothenate kinase 2, mitochondrial precursor (Pantothenic acid kinase 2) (hPANK2); (4334:) Pantothenate kinase 3 (Pantothenic acid kinase 3) (hPanK3); (4335:) pantothenate kinase 3 [Homo sapiens]; (4336:) Pantothenate kinase 4 (Pantothenic acid kinase 4) (hPanK4); (4337:) pantothenate kinase 4 [Homo sapiens]; (4338:) Pappalysin-1 precursor (Pregnancy-associated plasma protein-A) (PAPP-A) (Insulin-like growth factor-dependent IGF-binding protein4 protease) (IGF-dependent IGFBP-4 protease) (IGFBP-4-ase); (4339:) PAPSS1 protein [Homo sapiens]; (4340:) paraoxanase-3 [Homo sapiens]; (4341:) paraoxonase 1 [Homo sapiens]; (4342:) paraoxonase 1 isoform 1 [Homo sapiens]; (4343:) paraoxonase 2 isoform 2 [Homo sapiens]; (4344:) paraoxonase 3 [Homo sapiens]; (4345:) Parathyroid Hormone (PTH); (4346:) Parathyroid hormone receptor precursor (PTH2 receptor); (4347:) Parathyroid hormone/parathyroid hormone-related peptide receptor precursor (PTH/PTHr receptor) (PTH/PTHrP type I receptor); (4348:) parkin isoform 1 [Homo sapiens]; (4349:) parkin isoform 2 [Homo sapiens]; (4350:) parkin isoform 3 [Homo sapiens]; (4351:) PAS domain-containing serine/threonine-protein kinase (PAS-kinase) (PASKIN) (hPASK); (4352:) patatin-like phospholipase domain containing 1 isoform 2 [Homo sapiens]; (4353:) patatin-like phospholipase domain containing 1 [Homo sapiens]; (4354:) PC Cell-Derived Growth Factor (PCDGF); (4355:) PC1/PC3 [Homo sapiens]; (4356:) PC8 precursor; (4357:) PCBD [Homo sapiens]; (4358:) PCK1 [Homo sapiens]; (4359:) PCK2 [Homo sapiens]; (4360:) PCTAIRE protein kinase 1 [Homo sapiens]; (4361:) PDC-E2 precursor (AA-54 to 561) [Homo sapiens]; (4362:) Pepsin; (4363:) Peptide Deformylase (PDF); (4364:) Peptide methionine sulfoxide reductase (Protein-methionine-5-oxide reductase) (PMSR) (Peptide Met(O) reductase); (4365:) Peptide-N(4)-(N-acetyl-beta-glucosaminyl)asparagine amidase (PNGase) (hPNGase) (Peptide:N-glycanase) (N-glycanase 1); (4366:) peptidyl arginine deiminase, type IV [Homo sapiens]; (4367:) peptidyl dipeptidase I [Homo sapiens]; (4368:) peptidylarginine deiminase type III [Homo sapiens]; (4369:) peptidylglycine alpha-amidating monooxygenase COOH-terminal interactor [Homo sapiens]; (4370:) peptidylglycine alpha-amidating monooxygenase isoform a, preproprotein [Homo sapiens]; (4371:) peptidylglycine alpha-amidating monooxygenase isoform b, preproprotein [Homo sapiens]; (4372:) peptidylglycine alpha-amidating monooxygenase isoform c, preproprotein [Homo sapiens]; (4373:) peptidylglycine alpha-amidating monooxygenase isoform d, preproprotein [Homo sapiens]; (4374:) "Peptidyl-glycine alpha-amidating monooxygenase precursor (PAM) [Includes:) Peptidylglycine alpha-hydroxylating monooxygenase (PHM); Peptidyl-alpha-hydroxyglycine alpha-amidating lyase (Peptidylamidoglycolate lyase) (PAL)]."; (4375:) Peptidylprolyl Cis-Trans Isomerase (PPIase); (4376:) Peptidyl-prolyl cis-trans isomerase A (PPIase A) (Rotamase A) (Cyclophilin A) (Cyclosporin A-binding protein); (4377:) Peptidyl-prolyl cis-trans isomerase B precursor (PPIase) (Rotamase) (Cyclophilin B) (S-cyclophilin) (SCYLP) (CYP-S1); (4378:) Peptidyl-prolyl cis-trans isomerase C (PPIase) (Rotamase) (Cyclophilin C); (4379:) Peptidyl-prolyl cis-trans isomerase G (Peptidyl-prolyl isomerase G) (PPIase G) (Rotamase G) (Cyclophilin G) (Clk-associating RS-cyclophilin) (CARS-cyclophilin) (CARS-Cyp) (SR-cyclophilin) (SRcyp) (SR-cyp) (CASP10); (4380:) Peptidyl-prolyl cis-trans isomerase-like 1 (PPIase) (Rotamase); (4381:) peptidylprolyl isomerase A [Homo sapiens]; (4382:) Peptidyl-tRNA hydrolase 2, mitochondrial precursor (PTH 2) (Bcl-2 inhibitor of transcription 1); (4383:) Peripheral Chemoreceptor; (4384:) Peripheral-type benzodiazepine receptor (PBR) (PKBS) (Mitochondrial benzodiazepine receptor); (4385:) peroxiredoxin 2 isoform a [Homo sapiens]; (4386:) peroxiredoxin 2 isoform c [Homo sapiens]; (4387:) peroxiredoxin 5 precursor, isoform a [Homo sapiens]; (4388:) peroxiredoxin 5 precursor, isoform b [Homo sapiens]; (4389:) peroxiredoxin 5 precursor, isoform c [Homo sapiens]; (4390:) peroxiredoxin 6 [Homo sapiens]; (4391:) Peroxiredoxin-1 (Thioredoxin peroxidase 2) (Thioredoxin-dependent peroxide reductase 2) (Proliferation-associated protein PAG) (Natural killer cell-enhancing factor A) (NKEF-A); (4392:) Peroxiredoxin-2 (Thioredoxin peroxidase 1) (Thioredoxin-dependent peroxide reductase 1) (Thiol-specific antioxidant protein) (TSA) (PRP) (Natural killer cell-enhancing factor B) (NKEF-B); (4393:) Peroxiredoxin-4 (Prx-IV) (Thioredoxin peroxidase A0372) (Thioredoxin-dependent peroxide reductase A0372) (Antioxidant enzyme AOE372) (AOE37-2); (4394:) Peroxiredoxin-5, mitochondrial precursor (Prx-V) (Peroxisomal antioxidant enzyme) (PLP) (Thioredoxin reductase) (Thioredoxin peroxidase PMP20) (Antioxidant enzyme B166) (AOEB166) (TPx type VI) (Liver tissue 2D-page spot 71B) (Alu corepressor 1); (4395:) Peroxiredoxin-6 (Antioxidant protein 2) (1-Cys peroxiredoxin) (1-Cys PRX) (Acidic calcium-independent phospholipase A2) (aiPLA2) (Non-selenium glutathione peroxidase) (NSGPx) (24 kDa protein) (Liver 2D page spot 40) (Red blood cells page spot 12); (4396:) Peroxisomal 2,4-dienoyl-CoA reductase (2,4-dienoyl-CoA reductase 2) (pDCR); (4397:) peroxisomal acyl-CoA thioesterase 1 isoform a [Homo sapiens]; (4398:) peroxisomal acyl-CoA thioesterase 1 isoform c [Homo sapiens]; (4399:) "Peroxisomal bifunctional enzyme (PBE) (PBFE) [Includes:] Enoyl-CoA hydratase; 3,2-trans-enoyl-CoA isomerase; 3-hydroxyacyl-CoA dehydrogenase]."; (4400:) Peroxisomal coenzyme A diphosphatase NUDT7 (Nucleosidediphosphate-linked moiety X motif 7) (Nudix motif 7); (4401:) peroxisomal D3,D2-enoyl-CoA isomerase isoform 1 [Homo sapiens]; (4402:) peroxisomal D3,D2-enoyl-CoA isomerase isoform 2 [Homo sapiens]; (4403:) peroxisomal enoyl-coenzyme A hydratase-like protein [Homo sapiens]; (4404:) Peroxisomal multifunctional enzyme type 2 (MFE-2) (D-bifunctional protein) (DBP) (17-beta-hydroxysteroid dehydrogenase 4) (17-beta-HSD 4) (D-3-hydroxyacyl-CoA dehydratase) (3-alpha,7-alpha,12-alpha-trihydroxy-5-beta-cholest-24-enoyl-CoA hydratase) (3-hydroxyacyl-CoA dehydrogenase); (4405:) Peroxisomal NADH pyrophosphatase NUDT12 (Nucleosidediphosphate-linked moiety X motif 12) (Nudix motif 12); (4406:) Peroxisomal sarcosine oxidase (PSO) (L-pipecolate oxidase) (L-pipecolic acid oxidase); (4407:) Peroxisomal trans-2-enoyl-CoA reductase (TERP) (HPDHase) (pVi-ARL) (2,4-dienoyl-CoA reductase-related protein) (DCR-RP); (4408:) peroxisome proliferative activated receptor gamma isoform 1 [Homo sapiens]; (4409:) peroxisome proliferative activated receptor gamma isoform 2 [Homo sapiens]; (4410:) Peroxisome proliferator-activated receptor alpha (PPAR-alpha); (4411:) Peroxisome proliferator-activated receptor delta (PPAR-delta) (PPAR-beta) (Nuclear hormone receptor 1) (NUC1) (NUC1); (4412:) Peroxisome proliferator-activated receptor gamma (PPAR-gamma); (4413:) peroxisome proliferator-activated receptor gamma, coactivator 1 alpha [Homo sapiens]; (4414:) peroxisome proliferator-activated receptor gamma-2—human; (4415:) Peroxisome Proliferator-Activated Receptor-Alpha (PPAR-Alpha); (4416:) Peroxisome Proliferator-Activated Receptor-Delta (PPAR-Delta); (4417:) Peroxisome proliferator-activated receptor-gamma (PPAR-gamma) Partial; (4418:) PFKL protein [Homo sapiens]; (4419:) PFKM [Homo sapiens]; (4420:) PFKM protein [Homo sapiens]; (4421:) PFKP protein [Homo sapiens]; (4422:) PGK1 [Homo sapiens]; (4423:) P-Glycoprotein (P-gp); (4424:) PH domain leucine-rich repeat-containing protein phosphatase (PH domain leucine-rich repeat protein phosphatase) (Pleckstrin homology domain-containing family E protein 1) (Suprachiasmatic nucleus circadian oscillatory protein) (hSCOP); (4425:) phenylalanine hydroxylase [Homo sapiens]; (4426:) phenylalanine hydroxylase-stimulating protein, pterin-4-alpha-carbinolamine dehydratase, PHS, PCD [human, liver, Peptide, 103 aa]; (4427:) Phenylalanine-4-hydroxylase (PAH) (Phe-4-monooxygenase); (4428:) Phenylethanolamine N-methyltransferase (PNMTase) (Noradrenaline N-methyltransferase); (4429:) phenylethanolamine N-methyltransferase [Homo sapiens]; (4430:) phenylethanolamine N-methyltransferase; (4431:) phosphate cytidylyltransferase 1, choline, alpha isoform [Homo sapiens]; (4432:) phosphatidate cytidylyltransferase 1 [Homo sapiens]; (4433:) phosphatidate cytidylyltransferase 2 [Homo sapiens]; (4434:) phosphatidic acid phosphatase type 2 domain containing 2 [Homo sapiens]; (4435:) phosphatidic acid phosphatase type 2A isoform 1 [Homo sapiens]; (4436:) phosphatidic acid phosphatase type 2A isoform 2 [Homo sapiens]; (4437:) Phosphatidylcholine (PtdCho) Synthesis; (4438:) Phosphatidylcholine:ceramide choline phosphotransferase 1(Transmembrane protein 23) (Sphingomyelin synthase 1) (Mob protein); (4439:) Phosphatidylcholine:ceramide choline phosphotransferase 2(Sphingomyelin synthase 2); (4440:) Phosphatidylcholine-sterol acyltransferase precursor (Lecithin-cholesterol acyltransferase) (Phospholipid-cholesterol acyltransferase); (4441:) Phosphatidylethanolamine N-methyltransferase (PEAMT) (PEMT) (PEMT2); (4442:) phosphatidylethanolamine N-methyltransferase isoform 1 [Homo sapiens]; (4443:) phosphatidylethanolamine N-methyltransferase isoform 2 [Homo sapiens]; (4444:) Phosphatidylinositol 3-Kinase (PI3K); (4445:) Phosphatidylinositol 3-kinase catalytic subunit type 3(PtdIns-3-kinase type 3) (PI3-kinase type 3) (PI3K type 3) (Phosphoinositide-3-kinase class 3) (Phosphatidylinositol 3-kinase p100 subunit); (4446:) Phosphatidylinositol 3-kinase regulatory subunit beta (PI3-kinase p85-subunit beta) (PtdIns-3-kinase p85-beta); (4447:) Phosphatidylinositol 4-kinase alpha (PI4-kinase alpha) (PtdIns-4-kinase alpha) (PI4K-alpha); (4448:) Phosphatidylinositol 4-kinase beta (PtdIns 4-kinase beta) (PI4 Kbeta) (PI4K-beta) (NPIK) (PI4K92); (4449:) phosphatidylinositol 4-kinase type II [Homo sapiens]; (4450:) phosphatidylinositol 4-kinase type-II beta [Homo sapiens]; (4451:) phosphatidylinositol 4-kinase, catalytic, alpha polypeptide isoform1 [Homo sapiens]; (4452:) phosphatidylinositol 4-kinase, catalytic, alpha polypeptide isoform2 [Homo sapiens]; (4453:) phosphatidylinositol 4-kinase, catalytic, beta polypeptide [Homo sapiens]; (4454:) phosphatidylinositol glycan anchor biosynthesis, class K precursor[Homo sapiens]; (4455:) phosphatidylinositol glycan anchor biosynthesis, class L [Homo sapiens]; (4456:) phosphatidylinositol glycan anchor biosynthesis, class P isoform 1 [Homo sapiens]; (4457:) phosphatidylinositol glycan anchor biosynthesis, class P isoform 2 [Homo sapiens]; (4458:) phosphatidylinositol glycan anchor biosynthesis, class Q isoform 1 [Homo sapiens]; (4459:) phosphatidylinositol glycan anchor biosynthesis, class Q isoform 2 [Homo sapiens]; (4460:) phosphatidylinositol glycan anchor biosynthesis, class S [Homo sapiens]; (4461:) phosphatidylinositol glycan anchor biosynthesis, class T precursor[Homo sapiens]; (4462:) phosphatidylinositol glycan anchor biosynthesis, class Y isoform 1 [Homo sapiens]; (4463:) phosphatidylinositol glycan anchor biosynthesis, class Y isoform 2 [Homo sapiens]; (4464:) phosphatidylinositol glycan class Y [Homo sapiens]; (4465:) phosphatidylinositol glycan, class C [Homo sapiens]; (4466:) Phosphatidylinositol N-acetylglucosaminyltransferase subunit A (GlcNAc-PI synthesis protein) (Phosphatidylinositol-glycan biosynthesis class A protein) (PIG-A); (4467:) phosphatidylinositol N-acetylglucosaminyltransferase subunit A isoform 1 [Homo sapiens]; (4468:) phosphatidylinositol N-acetylglucosaminyltransferase subunit A isoform 3 [Homo sapiens]; (4469:) Phosphatidylinositol N-acetylglucosaminyltransferase subunit P (Phosphatidylinositol-glycan biosynthesis class P protein) (PIG-P) (Down syndrome critical region protein 5) (Down syndrome critical region protein C);

(4470:) Phosphatidylinositol N-acetylglucosaminyltransferase subunit Q (Phosphatidylinositol-glycan biosynthesis class Q protein) (PIG-Q) (N-acetylglucosamyl transferase component GPI1); (4471:) Phosphatidylinositol N-acetylglucosaminyltransferase subunit Y (Phosphatidylinositol-glycan biosynthesis class Y protein) (PIG-Y); (4472:) phosphatidylinositol polyphosphate 5-phosphatase isoform a [Homo sapiens]; (4473:) phosphatidylinositol polyphosphate 5-phosphatase isoform b [Homo sapiens]; (4474:) Phosphatidylinositol-4,5-bisphosphate 3-kinase catalytic subunit gamma isoform (PI3-kinase p110 subunit gamma) (PtdIns-3-kinase subunit p110) (PI3K) (PI3K gamma) (p120-PI3K); (4475:) Phosphatidylinositol-4-phosphate 3-kinase C2 domain-containing beta polypeptide (Phosphoinositide 3-Kinase-C2-beta) (PtdIns-3-kinase C2beta) (PI3K-C2beta) (C2-PI3K); (4476:) Phosphatidylinositol-4-phosphate 3-kinase C2 domain-containing alpha polypeptide (Phosphoinositide 3-Kinase-C2-alpha) (PtdIns-3-kinase C2 alpha) (PI3K-C2alpha); (4477:) phosphatidylinositol-4-phosphate 5-kinase type 11 alpha [Homo sapiens]; (4478:) Phosphatidylinositol-4-phosphate 5-kinase type-1 gamma(Phosphatidylinositol-4-phosphate 5-kinase type I gamma) (PtdIns(4) P-5-kinase gamma) (PtdIns PKI gamma) (PIP5KI gamma); (4479:) phosphatidylinositol-4-phosphate 5-kinase, type 1, alpha [Homo sapiens]; (4480:) phosphatidylinositol-4-phosphate 5-kinase, type 1, gamma [Homo sapiens]; (4481:) Phosphatidylserine Receptor (PTDSR); (4482:) Phosphatidylserine synthase 1 (PtdSer synthase 1) (PSS-1) (Serine-exchange enzyme I); (4483:) Phosphatidylserine synthase 2 (PtdSer synthase 2) (PSS-2) (Serine-exchange enzyme 11); (4484:) Phosphodiesterase (PDE); (4485:) phosphodiesterase 5A isoform 1 [Homo sapiens]; (4486:) phosphodiesterase 5A isoform 2 [Homo sapiens]; (4487:) phosphodiesterase 5A isoform 3 [Homo sapiens]; (4488:) phosphodiesterase 6B, cGMP-specific, rod, beta [Homo sapiens]; (4489:) phosphodiesterase 8A isoform 1 [Homo sapiens]; (4490:) phosphodiesterase 8A isoform 2 [Homo sapiens]; (4491:) phosphodiesterase 8A isoform 3 [Homo sapiens]; (4492:) phosphodiesterase 8A isoform 4 [Homo sapiens]; (4493:) phosphodiesterase II/nucleotide pyrophosphatase beta [Homo sapiens]; (4494:) Phosphodiesterase-1 (PDE-1); (4495:) Phosphodiesterase-10A (PDE-10A); (4496:) Phosphodiesterase-2 (PDE-2); (4497:) Phosphodiesterase-3 (PDE-3); (4498:) Phosphodiesterase-4 (PDE-4); (4499:) Phosphodiesterase-5 (PDE-5); (4500:) Phosphodiesterase-5 (PDE-5); (4501:) phosphoenolpyruvate carboxykinase (GTP) [Homo sapiens]; (4502:) Phosphoenolpyruvate carboxykinase [GTP], mitochondrial precursor (Phosphoenolpyruvate carboxylase) (PEPCK-M); (4503:) Phosphoenolpyruvate carboxykinase 1 (soluble) [Homo sapiens]; (4504:) Phosphoenolpyruvate carboxykinase 2 (mitochondrial) [Homo sapiens]; (4505:) Phosphoenolpyruvate carboxykinase, cytosolic [GTP](Phosphoenolpyruvate carboxylase) (PEPCK-C); (4506:) phosphoenolpyruvate carboxykinase; (4507:) Phosphoethanolamine/phosphocholine phosphatase; (4508:) phosphofructokinase [Homo sapiens]; (4509:) Phosphofructokinase, liver [Homo sapiens]; (4510:) phosphofructokinase, muscle [Homo sapiens]; (4511:) phosphofructokinase, platelet [Homo sapiens]; (4512:) phosphofructokinase; (4513:) phosphofructokinase-M; (4514:) phosphofructokinase-P [Homo sapiens]; (4515:) phosphoglucomutase 1 [Homo sapiens]; (4516:) Phosphoglucomutase-1 (Glucose phosphomutase 1) (PGM 1); (4517:) Phosphoglucomutase-2 (Glucose phosphomutase 2) (PGM 2); (4518:) phosphogluconate dehydrogenase [Homo sapiens]; (4519:) phosphoglycerate dehydrogenase [Homo sapiens]; (4520:) phosphoglycerate kinase [Homo sapiens]; (4521:) Phosphoglycerate kinase 1 (Primer recognition protein 2) (PRP 2); (4522:) phosphoglycerate kinase 1 [Homo sapiens]; (4523:) Phosphoglycerate kinase 2 [Homo sapiens]; (4524:) Phosphoglycerate kinase, testis specific; (4525:) phosphoglycerete kinase 1 [Homo sapiens]; (4526:) phosphoinositide 3-kinase (EC 2.7.-.-) T105—human (fragment); (4527:) phosphoinositide 3-kinase (EC 2.7.-.-) T14—human (fragment); (4528:) Phosphoinositide 3-kinase regulatory subunit 5 (PI3-kinase regulatory subunit 5) (PI3-kinase p101 subunit) (PtdIns-3-kinase p101) (p101-PI3K) (Phosphatidylinositol-4,5-bisphosphate 3-kinase regulatory subunit) (PtdIns-3-kinase regulatory subunit) (Protein FOAP-2); (4529:) phosphoinositide-3-kinase, catalytic, alpha polypeptide [Homo sapiens]; (4530:) phosphoinositide-3-kinase, catalytic, beta polypeptide [Homo sapiens]; (4531:) phosphoinositide-3-kinase, catalytic, gamma polypeptide [Homo sapiens]; (4532:) phosphoinositide-3-kinase, class 2, beta polypeptide [Homo sapiens]; (4533:) phosphoinositide-3-kinase, class 3 [Homo sapiens]; (4534:) phosphoinositide-3-kinase, regulatory subunit 2 (p85 beta) [Homo sapiens]; (4535:) phosphoinositide-3-kinase, regulatory subunit, polypeptide 1 isoform 1 [Homo sapiens]; (4536:) phosphoinositide-3-kinase, regulatory subunit, polypeptide 1 isoform 2 [Homo sapiens]; (4537:) phosphoinositide-3-kinase, regulatory subunit, polypeptide 1 isoform 3 [Homo sapiens]; (4538:) phosphoinositide-specific phospholipase C PLC-epsilon [Homo sapiens]; (4539:) phospholemman precursor [Homo sapiens]; (4540:) Phospholipase A2 (PLA2); (4541:) Phospholipase A2 precursor (Phosphatidylcholine 2-acylhydrolase) (Group IB phospholipase A2); (4542:) phospholipase A2, group IIA [Homo sapiens]; (4543:) phospholipase A2, group IIE [Homo sapiens]; (4544:) phospholipase A2, group III precursor [Homo sapiens]; (4545:) phospholipase A2, group V precursor [Homo sapiens]; (4546:) phospholipase A2, group VI isoform a [Homo sapiens]; (4547:) phospholipase A2, group VI isoform b [Homo sapiens]; (4548:) phospholipase A2, group VII [Homo sapiens]; (4549:) Phospholipase A2, membrane associated precursor (Phosphatidylcholine 2-acylhydrolase) (Group IIA phospholipase A2) (GIIC sPLA2) (Non-pancreatic secretory phospholipase A2) (NPS-PLA2); (4550:) phospholipase A2; (4551:) phospholipase C delta 3 [Homo sapiens]; (4552:) phospholipase C epsilon [Homo sapiens]; (4553:) phospholipase C epsilon 1 [Homo sapiens]; (4554:) phospholipase C gamma 1 isoform a [Homo sapiens]; (4555:) phospholipase C gamma 1 isoform b [Homo sapiens]; (4556:) phospholipase C, delta 1 [Homo sapiens]; (4557:) phospholipase C, delta 4 [Homo sapiens]; (4558:) phospholipase C, epsilon 1 [Homo sapiens]; (4559:) phospholipase C-eta2 [Homo sapiens]; (4560:) Phospholipase D1 (PLD 1) (Choline phosphatase 1) (Phosphatidylcholine-hydrolyzing phospholipase D1) (hPLD1); (4561:) Phospholipase D2 (PLD 2) (Choline phosphatase 2) (Phosphatidylcholine-hydrolyzing phospholipase D2) (PLD1C) (hPLD2); (4562:) phospholipid scramblase 1 [Homo sapiens]; (4563:) phospholipid transfer protein isoform a precursor [Homo sapiens]; (4564:) phospholipid transfer protein isoform b precursor [Homo sapiens]; (4565:) phospholysine phosphohistidine inorganic pyrophosphate phosphatase (EC 3.6.1.1)—Human; (4566:) phosphomevalonate kinase [Homo sapiens]; (4567:) phosphopantetheine adenylyltransferase/dephospho coenzyme A kinase [Homo sapiens]; (4568:) Phosphopantothenate—cysteine ligase (Phosphopantothenoyl cysteine synthetase) (PPC synthetase); (4569:) phosphoprotein phosphatase (EC 3.1.3.16) 2A BR gamma regulatory chain—human; (4570:) phosphoribosyl pyrophosphate amidotransferase proprotein [Homo sapiens];

(4571:) phosphoribosyl pyrophosphate synthetase-associated protein 2 [*Homo sapiens*]; (4572:) phosphoribosylformylglycinamidine synthase [*Homo sapiens*]; (4573:) phosphoribosylglycinamide formyltransferase, phosphoribosylglycinamide synthetase, phosphoribosylaminoimidazole synthetase isoform 1 [*Homo sapiens*]; (4574:) phosphoribosylglycinamide formyltransferase, phosphoribosylglycinamide synthetase, phosphoribosylaminoimidazole synthetase isoform 2 [*Homo sapiens*]; (4575:) phosphoribosylpyrophosphate synthetase subunit III; (4576:) Phosphorylase b kinase regulatory subunit alpha, liver isoform (Phosphorylase kinase alpha L subunit); (4577:) Phosphorylase b kinase regulatory subunit alpha, skeletal muscle isoform (Phosphorylase kinase alpha M subunit); (4578:) Phosphorylase b kinase regulatory subunit beta (Phosphorylase kinase subunit beta); (4579:) phosphorylase kinase gamma subunit 1 [*Homo sapiens*]; (4580:) phosphorylase kinase, alpha 1 (muscle) [*Homo sapiens*]; (4581:) phosphoserine aminotransferase isoform 1 [*Homo sapiens*]; (4582:) phosphoserine aminotransferase isoform 2 [*Homo sapiens*]; (4583:) Phosphoserine phosphatase (PSP) (O-phosphoserine phosphohydrolase) (PSPase) (L-3-phosphoserine phosphatase); (4584:) phosphoserine phosphatase [*Homo sapiens*]; (4585:) photoreceptor outer segment all-trans retinol dehydrogenase [*Homo sapiens*]; (4586:) Photoreceptor-specific nuclear receptor (Retina-specific nuclear receptor); (4587:) phytanoil-CoA alpha hydroxylase [*Homo sapiens*]; (4588:) phytanoyl-CoA 2-hydroxylase isoform a precursor [*Homo sapiens*]; (4589:) phytanoyl-CoA 2-hydroxylase isoform b precursor [*Homo sapiens*]; (4590:) Phytanoyl-CoA dioxygenase, peroxisomal precursor (Phytanoyl-CoA alpha-hydroxylase) (PhyH) (Phytanic acid oxidase); (4591:) phytoceramidase, alkaline [*Homo sapiens*]; (4592:) PI-3 kinase [*Homo sapiens*]; (4593:) PIG50 [*Homo sapiens*]; (4594:) pim-1 oncogene [*Homo sapiens*]; (4595:) Pim-1 Receptor Tyrosine Kinase; (4596:) PITSLRE serine/threonine-protein kinase CDC2L1(Galactosyltransferase-associated protein kinase p58/GTA) (Cell division cycle 2-like protein kinase 1) (CLK-1) (CDK11) (p58CLK-1); (4597:) PITSLRE serine/threonine-protein kinase CDC2L2(Galactosyltransferase-associated protein kinase p58/GTA) (Cell division cycle 2-like protein kinase 2) (CDK11); (4598:) Pituitary Adenylate Cyclase Activating Peptide Receptor 3 (PACAP R3); (4599:) pituitary adenylate cyclase activating peptide receptor type 1precursor—human; (4600:) Pituitary adenylate cyclase-activating polypeptide type I receptor precursor (PACAP type I receptor) (PACAP-R-1); (4601:) PKM2 protein [*Homo sapiens*]; (4602:) placenta copper monamine oxidase [*Homo sapiens*]; (4603:) Placental Alkaline Phosphatase (PALP); (4604:) placental alkaline phosphatase preproprotein [*Homo sapiens*]; (4605:) placental lactogen hormone precursor [*Homo sapiens*]; (4606:) placental lactogen; (4607:) placental-like alkaline phosphatase preproprotein [*Homo sapiens*]; (4608:) plakoglobin [*Homo sapiens*]; (4609:) plasma carboxypeptidase B2 isoform a preproprotein [*Homo sapiens*]; (4610:) plasma carboxypeptidase B2 isoform b [*Homo sapiens*]; (4611:) plasma glutathione peroxidase 3 precursor [*Homo sapiens*]; (4612:) plasma kallikrein B1 precursor [*Homo sapiens*]; (4613:) "Plasma kallikrein precursor (Plasma prekallikrein) (Kininogenin) (Fletcher factor) [Contains:) Plasma kallikrein heavy chain; Plasma kallikrein light chain]."; (4614:) Plasma membrane calcium-transporting ATPase 1 (PMCA1) (Plasma membrane calcium pump isoform 1) (Plasma membrane calcium ATPase isoform 1); (4615:) Plasma membrane calcium-transporting ATPase 2 (PMCA2) (Plasma membrane calcium pump isoform 2) (Plasma membrane calcium ATPase isoform 2); (4616:) Plasma membrane calcium-transporting ATPase 3 (PMCA3) (Plasma membrane calcium pump isoform 3) (Plasma membrane calcium ATPase isoform 3); (4617:) Plasma membrane calcium-transporting ATPase 4 (PMCA4) (Plasma membrane calcium pump isoform 4) (Plasma membrane calcium ATPase isoform 4); (4618:) plasminogen [*Homo sapiens*]; (4619:) Plasminogen activator (PAI); (4620:) Plasminogen activator-1 (PAI-1); (4621:) plasminogen activator, tissue type isoform 1 preproprotein [*Homo sapiens*]; (4622:) plasminogen activator, tissue type isoform 2 precursor [*Homo sapiens*]; (4623:) plasminogen activator, tissue type isoform 3 precursor [*Homo sapiens*]; (4624:) plasminogen activator, urokinase receptor isoform 1 precursor [*Homo sapiens*]; (4625:) plasminogen activator, urokinase receptor isoform 2 precursor [*Homo sapiens*]; (4626:) plasminogen activator, urokinase receptor isoform 3 precursor [*Homo sapiens*]; (4627:) "Plasminogen precursor [Contains:) Plasmin heavy chain A; Activation peptide; Angiostatin; Plasmin heavy chain A, short form; Plasmin light chain B]."; (4628:) *Plasmodium Falciparum* Calcium-Dependent ATPase (PfATP6); (4629:) platelet coagulation factor XI isoform b [*Homo sapiens*]; (4630:) platelet coagulation factor XI precursor [*Homo sapiens*]; (4631:) Platelet Derived Growth Factor Receptor-Alpha (PDGFR-Alpha); (4632:) Platelet Derived Growth Factor Receptor-Beta (PDGFR-Beta); (4633:) platelet factor 4 (chemokine (C-X-C motif) ligand 4) [*Homo sapiens*]; (4634:) Platelet glycoprotein 4 (Platelet glycoprotein IV) (GPIV) (Glycoprotein IIIb) (GPIIIB) (Leukocyte differentiation antigen CD36) (CD36 antigen) (PAS IV) (PAS-4 protein) (Platelet collagen receptor) (Fatty acid translocase) (FAT) (Thrombospondin receptor); (4635:) Platelet glycoprotein VI precursor; (4636:) Platelet receptor Gi24 precursor; (4637:) Platelet-Activating Factor (PAF); (4638:) platelet-activating factor acetylhydrolase 2 [*Homo sapiens*]; (4639:) Platelet-activating factor acetylhydrolase 2, cytoplasmic (Serine-dependent phospholipase A2) (HSD-PLA2); (4640:) Platelet-activating factor acetylhydrolase IB subunit alpha (PAF acetylhydrolase 45 kDa subunit) (PAF-AH 45 kDa subunit) (PAF-AH alpha) (PAFAH alpha) (Lissencephaly-1 protein) (LIS-1); (4641:) Platelet-activating factor acetylhydrolase 1B subunit beta (PAF acetylhydrolase 30 kDa subunit) (PAF-AH 30 kDa subunit) (PAF-AH subunit beta) (PAFAH subunit beta); (4642:) Platelet-activating factor acetylhydrolase IB subunit gamma (PAF acetylhydrolase 29 kDa subunit) (PAF-AH 29 kDa subunit) (PAF-AH subunit gamma) (PAFAH subunit gamma); (4643:) platelet-activating factor acetylhydrolase, isoform Ib, alpha subunit (45 kD) [*Homo sapiens*]; (4644:) Platelet-activating factor receptor (PAF-R); (4645:) Platelet-Derived Growth Factor Receptor (PDGFR); (4646:) platelet-derived growth factor receptor beta precursor [*Homo sapiens*]; (4647:) Platelet-derived growth factor-D (PDGF-D); (4648:) platelet-type phosphofructokinase [*Homo sapiens*]; (4649:) Plexin-A3 precursor (Plexin-4) (Semaphorin receptor SEX); (4650:) Plexin-A4 precursor; (4651:) Plexin-B1 precursor (Semaphorin receptor SEP); (4652:) Plexin-B2 precursor (MM1); (4653:) Plexin-B3 precursor; (4654:) Plexin-D1 precursor; (4655:) PMS1 nirs variant 1 [*Homo sapiens*]; (4656:) PMS1 nirs variant 2 [*Homo sapiens*]; (4657:) PMS1 nirs variant 3 [*Homo sapiens*]; (4658:) PMS1 nirs variant 5 [*Homo sapiens*]; (4659:) PMS1 nirs variant 6 [*Homo sapiens*]; (4660:) PMS1 nirs variant 7 [*Homo sapiens*]; (4661:) PMS1 nirs variant 8 [*Homo sapiens*]; (4662:) PMS1 nirs variant 9 [*Homo sapiens*]; (4663:) PMS1 postmeiotic segregation increased 1 (*S. cerevisiae*) [*Homo sapiens*]; (4664:) PMS1 protein [*Homo sapiens*]; (4665:) PMS1 protein homolog 1

(DNA mismatch repair protein PMS1); (4666:) PMS1 protein homolog 2 (DNA mismatch repair protein PMS2); (4667:) PMS2 gene; (4668:) PMS2 postmeiotic segregation increased 2 (*S. cerevisiae*) [*Homo sapiens*]; (4669:) PMS2 postmeiotic segregation increased 2 isoform a [*Homo sapiens*]; (4670:) PMS2 protein [*Homo sapiens*]; (4671:) PMS2-C terminal-like [*Homo sapiens*]; (4672:) PMS2CL protein [*Homo sapiens*]; (4673:) PMS2L14 [*Homo sapiens*]; (4674:) PMS2L15 [*Homo sapiens*]; (4675:) PMS2L16 [*Homo sapiens*]; (4676:) PMS2L5 protein [*Homo sapiens*]; (4677:) PMS7 [*Homo sapiens*]; (4678:) Poliovirus receptor precursor (Nectin-like protein 5) (Necl-5) (CD155 antigen); (4679:) poliovirus receptor-related 4 [*Homo sapiens*]; (4680:) Poliovirus receptor-related protein 1 precursor (Herpes virus entry mediator C) (HveC) (Nectin-1) (Herpesvirus Ig-like receptor) (HIgR) (CD111 antigen); (4681:) Poliovirus receptor-related protein 2 precursor (Herpes virus entry mediator B) (HveB) (Nectin-2) (CD112 antigen); (4682:) Polo-Like Kinase (Plk); (4683:) polo-like kinase [*Homo sapiens*]; (4684:) Polo-Like Kinase 1 (Plk1); (4685:) POLS protein [*Homo sapiens*]; (4686:) poly (ADP-ribose) glycohydrolase [*Homo sapiens*]; (4687:) poly (ADP-ribose) polymerase family, member 1 [*Homo sapiens*]; (4688:) poly (ADP-ribose) polymerase family, member 10 [*Homo sapiens*]; (4689:) Poly [ADP-ribose] polymerase 1 (PARP-1) (ADPRT) (NAD(+)ADP-ribosyltransferase 1) (Poly[ADP-ribose] synthetase 1); (4690:) Poly(A) polymerase gamma (PAP gamma) (Polynucleotide adenylyl transferase gamma) (SRP RNA 3' adenylating enzyme) (Neo-poly(A) polymerase) (Neo-PAP); (4691:) poly(A) polymerase gamma [*Homo sapiens*]; (4692:) Poly(A)-specific ribonuclease PARN (Polyadenylate-specific ribonuclease) (Deadenylating nuclease) (Deadenylation nuclease); (4693:) Poly(ADP-Ribose) Glycohydrolase (PARG); (4694:) Poly(ADP-ribose) polymerase (PARP); (4695:) Poly(ADP-ribose) polymerase-1 (PARP-1); (4696:) Poly(ADP-ribose) polymerase-2 (PARP-2); (4697:) poly(rC) binding protein 1 [*Homo sapiens*]; (4698:) polyamine oxidase isoform 1 [*Homo sapiens*]; (4699:) polyamine oxidase isoform 2 [*Homo sapiens*]; (4700:) polyamine oxidase isoform 3 [*Homo sapiens*]; (4701:) polyamine oxidase isoform 4 [*Homo sapiens*]; (4702:) Polycystic kidney and hepatic disease 1 precursor (Fibrocystin) (Polyductin) (Tigmin); (4703:) polymerase (DNA directed) kappa [*Homo sapiens*]; (4704:) polymerase (DNA directed), beta [*Homo sapiens*]; (4705:) polymerase (DNA directed), delta 2, regulatory subunit [*Homo sapiens*]; (4706:) polymerase (DNA directed), eta [*Homo sapiens*]; (4707:) polymerase (DNA directed), gamma 2, accessory subunit [*Homo sapiens*]; (4708:) polymerase (DNA directed), lambda [*Homo sapiens*]; (4709:) polymerase (DNA-directed), alpha [*Homo sapiens*]; (4710:) polymerase (RNA) III (DNA directed) polypeptide A, 155 kDa [*Homo sapiens*]; (4711:) polymerase (RNA) III (DNA directed) polypeptide C (62 kD) [*Homo sapiens*]; (4712:) polynucleotide kinase 3'-phosphatase [*Homo sapiens*]; (4713:) Polypeptide N-acetylgalactosaminyltransferase 1 (Protein-UDPacetylgalactosaminyltransferase 1) (UDP-GalNAc:polypeptide N-acetylgalactosaminyltransferase 1) (Polypeptide GalNActransferase 1) (GalNAc-T1) (pp-GaNTase 1) [Contains:) Polypeptide N-acetylgalactosaminyltransferase 1 soluble form]; (4714:) Polypeptide N-acetylgalactosaminyltransferase 10 (Protein-UDPacetylgalactosaminyltransferase 10) (UDP-GalNAc:polypeptide N-acetylgalactosaminyltransferase 10) (Polypeptide GalNActransferase 10) (GalNAc-T10) (pp-GaNTase 10); (4715:) Polypeptide N-acetylgalactosaminyltransferase 11 (Protein-UDPacetylgalactosaminyltransferase 11) (UDP-GalNAc:polypeptide N-acetylgalactosaminyltransferase 11) (Polypeptide GalNActransferase 11) (GalNAc-T11) (pp-GaNTase 11); (4716:) Polypeptide N-acetylgalactosaminyltransferase 12 (Protein-UDPacetylgalactosaminyltransferase 12) (UDP-GalNAc: polypeptide N-acetylgalactosaminyltransferase 12) (Polypeptide GalNActransferase 12) (GalNAc-T12) (pp-GaNTase 12); (4717:) Polypeptide N-acetylgalactosaminyltransferase 13 (Protein-UDPacetylgalactosaminyltransferase 13) (UDP-GalNAc:polypeptide N-acetylgalactosaminyltransferase 13) (Polypeptide GalNActransferase 13) (GalNAc-T13) (pp-GaNTase 13); (4718:) Polypeptide N-acetylgalactosaminyltransferase 14 (Protein-UDPacetylgalactosaminyltransferase 14) (UDP-GalNAc:polypeptide N-acetylgalactosaminyltransferase 14) (Polypeptide GalNActransferase 14) (GalNAc-T14) (pp-GaNTase 14); (4719:) Polypeptide N-acetylgalactosaminyltransferase 2 (Protein-UDPacetylgalactosaminyltransferase 2) (UDP-GalNAc:polypeptide N-acetylgalactosaminyltransferase 2) (Polypeptide GalNActransferase 2) (GalNAc-T2) (pp-GaNTase 2) [Contains:) Polypeptide N-acetylgalactosaminyltransferase 2 soluble form]; (4720:) polypeptide N-acetylgalactosaminyltransferase 2 [*Homo sapiens*]; (4721:) Polypeptide N-acetylgalactosaminyltransferase 3 (Protein-UDPacetylgalactosaminyltransferase 3) (UDP-GalNAc: polypeptide N-acetylgalactosaminyltransferase 3) (Polypeptide GalNActransferase 3) (GalNAc-T3) (pp-GaNTase 3); (4722:) Polypeptide N-acetylgalactosaminyltransferase 4 (Protein-UDPacetylgalactosaminyltransferase 4) (UDP-GalNAc:polypeptide N-acetylgalactosaminyltransferase 4) (Polypeptide GalNActransferase 4) (GalNAc-T4) (pp-GaNTase 4); (4723:) Polypeptide N-acetylgalactosaminyltransferase 6 (Protein-UDPacetylgalactosaminyltransferase 6) (UDP-GalNAc:polypeptide N-acetylgalactosaminyltransferase 6) (Polypeptide GalNActransferase 6) (GalNAc-T6) (pp-GaNTase 6); (4724:) polypeptide N-acetylgalactosaminyltransferase 7 [*Homo sapiens*]; (4725:) polypeptide N-acetylgalactosaminyltransferase 8 [*Homo sapiens*]; (4726:) Polypeptide N-acetylgalactosaminyltransferase 9 (Protein-UDPacetylgalactosaminyltransferase 9) (UDP-GalNAc:polypeptide N-acetylgalactosaminyltransferase 9) (Polypeptide GalNActransferase 9) (GalNAc-T9) (pp-GaNTase 9); (4727:) Polypeptide N-acetylgalactosaminyltransferase-like protein 2(Protein-UDP acetylgalactosaminyltransferase-like protein 2) (UDP-GalNAc:polypeptide N-acetylgalactosaminyltransferase-like protein 2) (Polypeptide GalNAc transferase-like protein 2) (GalNAc-T-like protein 2) (pp-GaNTase-like protein 2); (4728:) polyserase-2 [*Homo sapiens*]; (4729:) Polyserase-2 precursor (Polyserine protease 2) (Protease serine-36); (4730:) Porcine endogenous retrovirus A receptor 1 precursor (PERV-A receptor 1) (Protein GPR172A); (4731:) Porcine endogenous retrovirus A receptor 2 precursor (PERV-A receptor 2) (Protein GPR172B); (4732:) Porimin precursor (Transmembrane protein 123) (Pro-oncosis receptor inducing membrane injury) (Keratinocytes-associated transmembrane protein 3) (KCT-3); (4733:) Porphobilinogen deaminase (Hydroxymethylbilane synthase) (HMBS) (Pre-uroporphyrinogen synthase) (PBG-D); (4734:) "porphobilinogen deaminase; PBGD [*Homo sapiens*]."; (4735:) postmeiotic segregation 1 [*Homo sapiens*]; (4736:) postmeiotic segregation increased 2 nirs variant 2 [*Homo sapiens*]; (4737:) postmeiotic segregation increased 2 nirs variant 5 [*Homo sapiens*]; (4738:) postmeiotic segregation increased 2-like 5 [*Homo sapiens*]; (4739:) postreplication repair protein hRAD18p [*Homo sapiens*]; (4740:) PP3895 [*Homo sapiens*]; (4741:) PPP2R5E protein [*Homo sapiens*]; (4742:) prenyl diphosphate synthase, subunit 1 [*Homo sapiens*]; (4743:) prenyl protein peptidase RCE1 isoform 1 [*Homo sapiens*]; (4744:) prenyl protein peptidase RCE1 isoform 2 [*Homo sapiens*]; (4745:) prenylcysteine lyase [*Homo sapiens*]; (4746:) prenylcysteine oxidase 1 [*Homo sapiens*]; (4747:) presenilin 1 [*Homo sapiens*]; (4748:) presenilin 2 isoform 1 [*Homo sapiens*]; (4749:) presenilin 2 isoform 2 [*Homo sapiens*]; (4750:) "Presenilin-1 (PS-1) (Protein S182) [Contains:) Presenilin-1 NTF subunit; Presenilin-1 CTF subunit; Presenilin-1 CTF12 (PSI-CTF12)]."; (4751:) Presequence protease, mitochondrial precursor (hPreP) (Pitrilysinmetalloproteinase 1) (Metalloprotease 1) (hMP1); (4752:) Presqualene diphosphate phosphatase (Phosphatidic acid phosphatase type 2 domain-containing protein 2); (4753:) prion protein preproprotein [*Homo sapiens*]; (4754:) pristanoyl-CoA oxidase [*Homo sapiens*]; (4755:) Pro oligopeptidase; (4756:) Probable allantoicase (Allantoate amidinohydrolase); (4757:) Probable C→U-editing enzyme APOBEC-2; (4758:) Probable calcium-transporting ATPase KIAA0703; (4759:) Probable DNA dC→dU-editing enzyme APOBEC-3A (Phorbolin-1); (4760:) Probable DNA dC→dU-editing enzyme APOBEC-3B (Phorbolin-1-related protein) (Phorbolin-2/3); (4761:) Probable DNA dC→dU-editing enzyme APOBEC-3C (APOBEC1-like) (Phorbolin I protein); (4762:) Probable DNA dC→dU-editing enzyme APOBEC-3D; (4763:) Probable E3 ubiquitin-protein ligase HECTD2 (HECT domain-containing protein 2); (4764:) Probable E3 ubiquitin-protein ligase HECTD3 (HECT domain-containing protein 3); (4765:) Probable G-protein coupled receptor 1; (4766:) Probable G-protein coupled receptor 101; (4767:) Probable G-protein coupled receptor 110 precursor (G-protein coupled receptor PGR19) (G-protein coupled receptor KPG_012); (4768:) Probable G-protein coupled receptor 111 (G-protein coupled receptor PGR20); (4769:) Probable G-protein coupled receptor 112; (4770:) Probable G-protein coupled receptor 113 precursor (G-protein coupled receptor PGR23); (4771:) Probable G-protein coupled receptor 114 precursor (G-protein coupled receptor PGR27); (4772:) Probable G-protein coupled receptor 115 (G-protein coupled receptor PGR18); (4773:) Probable G-protein coupled receptor 116 precursor; (4774:) Probable G-protein coupled receptor 119; (4775:) Probable G-protein coupled receptor 12; (4776:) Probable G-protein coupled receptor 123; (4777:) Probable G-protein coupled receptor 124 precursor (Tumor endothelial marker 5); (4778:) Probable G-protein coupled receptor 125 precursor; (4779:) Probable G-protein coupled receptor 126 precursor; (4780:) Probable G-protein coupled receptor 128 precursor; (4781:) Probable G-protein coupled receptor 132 (G2 accumulation protein); (4782:) Probable G-protein coupled receptor 133 precursor (G-protein coupled receptor PGR25); (4783:) Probable G-protein coupled receptor 135; (4784:) Probable G-protein coupled receptor 139 (G(q)-coupled orphan receptor GPRg1) (G-protein-coupled receptor PGR3); (4785:) Probable G-protein coupled receptor 141 (G-protein coupled receptor PGR13); (4786:) Probable G-protein coupled receptor 142 (G-protein coupled receptor PGR2); (4787:) Probable G-protein coupled receptor 144 (G-protein coupled receptor PGR24); (4788:) Probable G-protein coupled receptor 148 (G-protein coupled receptor PGR6) (Brain and testis restricted GPCR); (4789:) Probable G-protein coupled receptor 149 (G-protein coupled receptor PGR10); (4790:) Probable G-protein coupled receptor 150; (4791:) Probable G-protein coupled receptor 151 (G-protein coupled receptor PGR7) (GPCR-2037); (4792:) Probable G-protein coupled receptor 152 (G-protein coupled receptor PGR5); (4793:) Probable G-protein coupled receptor 153 (G-protein coupled receptor PGR1); (4794:) Probable G-protein coupled receptor 156 (GABAB-related G-protein coupled receptor) (G-protein coupled receptor PGR28); (4795:) Probable G-protein coupled receptor 157; (4796:) Probable G-protein coupled receptor 158 precursor; (4797:) Probable G-protein coupled receptor 160; (4798:) Probable G-protein coupled receptor 161 (G-protein coupled receptor RE2); (4799:) Probable G-protein coupled receptor 162 (Gene-rich cluster gene Aprotein); (4800:) Probable G-protein coupled receptor 171 (G-protein coupled receptor H963); (4801:) Probable G-protein coupled receptor 173 (Super conserved receptor expressed in brain 3); (4802:) Probable G-protein coupled receptor 174; (4803:) Probable G-protein coupled receptor 176 (HB-954); (4804:) Probable G-protein coupled receptor 179 precursor (Probable G-protein coupled receptor 158-like 1); (4805:) Probable G-protein coupled receptor 18; (4806:) Probable G-protein coupled receptor 19 (GPR-NGA); (4807:) Probable G-protein coupled receptor 20; (4808:) Probable G-protein coupled receptor 21; (4809:) Probable G-protein coupled receptor 22; (4810:) Probable G-protein coupled receptor 25; (4811:) Probable G-protein coupled receptor 26; (4812:) Probable G-protein coupled receptor 27 (Super conserved receptor expressed in brain 1); (4813:) Probable G-protein coupled receptor 3 (ACCA orphan receptor); (4814:) Probable G-protein coupled receptor 31; (4815:) Probable G-protein coupled receptor 32; (4816:) Probable G-protein coupled receptor 33; (4817:) Probable G-protein coupled receptor 34; (4818:) Probable G-protein coupled receptor 35; (4819:) Probable G-protein coupled receptor 37 precursor (Endothelin B receptor-like protein 1) (ETBR-LP-1) (Parkin-associated endothelin receptor-like receptor) (PAELR); (4820:) Probable G-protein coupled receptor 39; (4821:) Probable G-protein coupled receptor 4 (G-protein coupled receptor 19); (4822:) Probable G-protein coupled receptor 45 (PSP24-alpha) (PSP24-1); (4823:) Probable G-protein coupled receptor 52; (4824:) Probable G-protein coupled receptor 55; (4825:) Probable G-protein coupled receptor 61 (Biogenic amine receptor-like G-protein coupled receptor); (4826:) Probable G-protein coupled receptor 62 (hGPCR8); (4827:) Probable G-protein coupled receptor 63 (PSP24-beta) (PSP24-2); (4828:) Probable G-protein coupled receptor 75; (4829:) Probable G-protein coupled receptor 78; (4830:) Probable G-protein coupled receptor 81 (G-protein coupled receptor104); (4831:) Probable G-protein coupled receptor 82; (4832:) Probable G-protein coupled receptor 83 precursor (G-protein coupled receptor 72); (4833:) Probable G-protein coupled receptor 84 (Inflammation-related G-protein coupled receptor EX33); (4834:) Probable G-protein coupled receptor 85 (Super conserved receptor expressed in brain 2); (4835:) Probable G-protein coupled receptor 87 (G-protein coupled receptor95); (4836:) Probable G-protein coupled receptor 88 (Striatum-specific G-protein coupled receptor); (4837:) Probable G-protein coupled receptor 92; (4838:) Probable G-protein coupled receptor 97 precursor (G-protein coupled receptor PGR26); (4839:) Probable G-protein-coupled receptor 146 (G-protein coupled receptor PGR8); (4840:) Probable P2Y purinoceptor GPR17 (G protein-coupled receptor 17) (P2Y-like receptor) (R12); (4841:) Probable ubiquitin carboxyl-terminal hydrolase CYLD (Ubiquitinthioesterase CYLD) (Ubiquitin-specific-processing protease CYLD) (Deubiquitinating enzyme CYLD); (4842:) Probable ubiquitin carboxyl-terminal hydrolase FAF-X (Ubiquitinthioesterase FAF-X) (Ubiquitin-specific-processing protease FAF-X) (Deubiquitinating enzyme FAF-X) (Fat facets protein-related, X-linked) (Ubiquitin-specific protease 9, X chromosome); (4843:) Probable ubiquitin carboxyl-terminal hydrolase FAF-Y (Ubiquitinthioesterase FAF-Y) (Ubiquitin-specific-processing protease FAF-Y) (Deubiquitinating enzyme FAF-Y) (Fat facets protein-related, Y-linked) (Ubiquitin-specific protease 9, Y chromosome); (4844:) Probable ubiquitin-conjugating enzyme E2 W (Ubiquitin-protein ligase W) (Ubiquitin carrier protein W); (4845:) procaspase-8 [Homo sapiens]; (4846:) procaspase-8L [Homo sapiens]; (4847:) procollagen-lysine, 2-oxoglutarate 5-dioxygenase 2 isoform a precursor [Homo sapiens]; (4848:) procollagen-lysine, 2-oxoglutarate 5-dioxygenase 2 isoform b precursor [Homo sapiens]; (4849:) procollagen-lysine, 2-oxoglutarate 5-dioxygenase 3 precursor [Homo sapiens]; (4850:) Procollagen-lysine, 2-oxoglutarate 5-dioxygenase 1 precursor (Lysylhydroxylase 1) (LH1); (4851:) Procollagen-lysine, 2-oxoglutarate 5-dioxygenase 2 precursor (Lysylhydroxylase 2) (LH2); (4852:) Progesterone Receptor (PR); (4853:) Progesterone-induced-blocking factor 1; (4854:) Progestin and adipoQ receptor family member 3 (Progestin and adipoQ receptor family member III); (4855:) Progestin and adipoQ receptor family member 4 (Progestin and adipoQ receptor family member IV); (4856:) Progestin and adipoQ receptor family member 6 (Progestin and adipoQ receptor family member VI); (4857:) Progestin and adipoQ receptor family member 9 (Progestin and adipoQ receptor family member IX); (4858:) Programmed Cell Death 1 (PDCD1) Receptor; (4859:) Programmed cell death 1 ligand 1 precursor (Programmed death ligand 1) (PD-L1) (PDCD1 ligand 1) (B7 homolog 1) (B7-H1) (CD274 antigen); (4860:) Programmed cell death 1 ligand 2 precursor (Programmed death ligand 2) (PD-L2) (PD-1-ligand 2) (PDCD1 ligand 2) (Butyrophilin B7-DC) (B7-DC) (CD273 antigen); (4861:) Prohibitin-2 (B-cell receptor-associated protein BAP37) (Repressor of estrogen receptor activity) (D-prohibitin); (4862:) prohormone convertase 2 [Homo sapiens]; (4863:) prohormone convertase 2, PC2 [human, Peptide, 638 aa]; (4864:) prohormone convertase; (4865:) proinsulin precursor [Homo sapiens]; (4866:) Prokineticin 2 (PK2) Receptor; (4867:) Prokineticin receptor 1 (PK-R1) (G-protein coupled receptor 73) (GPR73a) (G-protein coupled receptor ZAQ); (4868:) Prokineticin receptor 2 (PK-R2) (G-protein coupled receptor 73-like1) (GPR73b) (GPRg2); (4869:) Prolactin receptor precursor (PRL-R); (4870:) Prolactin-releasing peptide receptor (PrRP receptor) (PrRPR) (G-protein coupled receptor 10) (hGR3); (4871:) proliferating cell nuclear antigen [Homo sapiens]; (4872:) Prolyl 4-Hydroxylase; (4873:) prolyl 4-hydroxylase alpha (II) subunit [Homo sapiens]; (4874:) Prolyl 4-hydroxylase alpha-2 subunit precursor (4-PH alpha-2) (Procollagen-proline, 2-oxoglutarate-4-dioxygenase alpha-2 subunit); (4875:) prolyl 4-hydroxylase, alpha I subunit isoform 1 precursor [Homo sapiens]; (4876:) prolyl 4-hydroxylase, alpha I subunit isoform 2 precursor [Homo sapiens]; (4877:) prolyl 4-hydroxylase, alpha II subunit isoform 1 precursor [Homo sapiens]; (4878:) prolyl 4-hydroxylase, alpha II subunit isoform 2 precursor [Homo sapiens]; (4879:) prolyl 4-hydroxylase, alpha III subunit precursor [Homo sapiens]; (4880:) prolyl 4-hydroxylase, beta subunit [Homo sapiens]; (4881:) Prolyl Endopeptidase (PEP); (4882:) prolyl endopeptidase [Homo sapiens]; (4883:) prolylcarboxypeptidase isoform 1 preproprotein [Homo sapiens]; (4884:) prolylcarboxypeptidase isoform 2 preproprotein [Homo sapiens]; (4885:) prolylcarboxypeptidase; (4886:) pro-matrix metalloproteinase-3—human (fragment); (4887:) proMch6; (4888:) Promyelocytic Leukemia/Retinoic Acid Receptor Alpha (PML/RAR) Protein; (4889:) Properdin precursor (Factor P); (4890:) "propionyl CoA carboxylase alpha subunit; PCCA [Homo sapiens]."; (4891:) propionyl Coenzyme A carboxylase, alpha polypeptide [Homo sapiens]; (4892:) propionyl-CoA carboxylase [Homo sapiens]; (4893:) Propionyl-CoA carboxylase alpha chain, mitochondrial precursor (PCCase subunit alpha) (Propanoyl-CoA:carbon dioxide ligase subunit alpha); (4894:) propionyl-CoA carboxylase alpha polypeptide precursor [Homo sapiens]; (4895:) propionyl-CoA carboxylase alpha subunit [Homo sapiens]; (4896:) Propionyl-CoA carboxylase beta chain, mitochondrial precursor (PCCase subunit beta) (Propanoyl-CoA:carbon dioxide ligase subunit beta); (4897:) propionyl-CoA carboxylase; (4898:) propionyl-Coenzyme A carboxylase, alpha polypeptide precursor [Homo sapiens]; (4899:) proprotein convertase subtilisin/kexin type 1 preproprotein [Homo sapiens]; (4900:) proprotein convertase subtilisin/kexin type 2 [Homo sapiens]; (4901:) proprotein convertase subtilisin/kexin type 5 preproprotein [Homo sapiens]; (4902:) Proprotein convertase subtilisin/kexin type 6 precursor (Paired basic amino acid cleaving enzyme 4) (Subtilisin/kexin-like protease PACE4) (Subtilisin-like proprotein convertase 4) (SPC4); (4903:) Proprotein convertase subtilisin/kexin type 7 precursor (Proprotein convertase PC7) (Subtilisin/kexin-like protease PC7) (Prohormone convertase PC7) (PC8) (hPC8) (Lymphoma proprotein convertase); (4904:) proprotein convertase subtilisin/kexin type 7 preproprotein [Homo sapiens]; (4905:) Proprotein convertase subtilisin/kexin type 9 precursor (Proprotein convertase PC9) (Subtilisin/kexin-like protease PC9) (Neural apoptosis-regulated convertase 1) (NARC-1); (4906:) prosaposin isoform a preproprotein [Homo sapiens]; (4907:) prosaposin isoform b preproprotein [Homo sapiens]; (4908:) prosaposin isoform c preproprotein [Homo sapiens]; (4909:) Prostacyclin receptor (Prostanoid IP receptor) (PGI receptor) (Prostaglandin I2 receptor); (4910:) Prostaglandin D2 (PGD2) Receptor; (4911:) Prostaglandin D2 receptor (Prostanoid DP receptor) (PGD receptor); (4912:) Prostaglandin E synthase (Microsomal glutathione S-transferase 1-like 1) (MGST1-L1) (p53-induced apoptosis protein 12); (4913:) prostaglandin E synthase [Homo sapiens]; (4914:) Prostaglandin E synthase 2 (Microsomal prostaglandin E synthase 2) (mPGES-2) [Contains:) Prostaglandin E synthase 2 truncated form]; (4915:) Prostaglandin E1 (PGE1) Receptor; (4916:) prostaglandin E2 receptor EP3-chain—human; (4917:) Prostaglandin E2 receptor, EP1 subtype (Prostanoid EP1 receptor) (PGE receptor, EP1 subtype); (4918:) Prostaglandin E2 receptor, EP2 subtype (Prostanoid EP2 receptor) (PGE receptor, EP2 subtype); (4919:) Prostaglandin E2 receptor, EP3 subtype (Prostanoid EP3 receptor) (PGE receptor, EP3 subtype) (PGE2-R); (4920:) Prostaglandin E2 receptor, EP4 subtype (Prostanoid EP4 receptor) (PGE receptor, EP4 subtype); (4921:) Prostaglandin F2 alpha (PGF2 alpha) Receptor; (4922:) Prostaglandin F2-alpha receptor (Prostanoid FP receptor) (PGF receptor) (PGF2 alpha receptor); (4923:) Prostaglandin G/H synthase 1 precursor (Cyclooxygenase-1) (COX-1) (Prostaglandin-endoperoxide synthase 1) (Prostaglandin H2 synthase 1) (PGH synthase 1) (PGHS-1) (PHS1); (4924:) Prostaglandin G/H synthase 2 precursor (Cyclooxygenase-2) (COX-2) (Prostaglandin-endoperoxide synthase 2) (Prostaglandin H2 synthase 2) (PGH synthase 2) (PGHS-2) (PHS II); (4925:) Prostaglandin I2 (PGI2) Receptor; (4926:) prostaglandin I2 (prostacyclin) synthase [Homo sapiens]; (4927:) prostaglandin-D synthase [Homo sapiens]; (4928:) prostaglandin-endoperoxide synthase 1 isoform 1 precursor [Homo sapiens]; (4929:) prostaglandin-endoperoxide synthase 1 isoform 2 precursor [Homo sapiens]; (4930:) prostaglandin-endoperoxide synthase 2 precursor [Homo sapiens]; (4931:) prostaglandin-endoperoxide synthase-1 [*Homo sapiens*]; (4932:) Prostasin; (4933:) prostasin preproprotein [*Homo sapiens*]; (4934:) Prostate-Specific Membrane Antigen (PSMA); (4935:) prostatic acid phosphatase precursor [*Homo sapiens*]; (4936:) protease, serine, 1 preproprotein [*Homo sapiens*]; (4937:) protease, serine, 2 preproprotein [*Homo sapiens*]; (4938:) protease, serine, 22 [*Homo sapiens*]; (4939:) protease, serine, 36 [*Homo sapiens*]; (4940:) Protease-Activated Receptor 1 (PAR1); (4941:) Proteasome; (4942:) proteasome 26S ATPase subunit 1 [*Homo sapiens*]; (4943:) proteasome 26S ATPase subunit 2 [*Homo sapiens*]; (4944:) proteasome 26S ATPase subunit 3 [*Homo sapiens*]; (4945:) proteasome 26S ATPase subunit 4 isoform 1 [*Homo sapiens*]; (4946:) proteasome 26S ATPase subunit 4 isoform 2 [*Homo sapiens*]; (4947:) proteasome 26S ATPase subunit 5 [*Homo sapiens*]; (4948:) proteasome 26S ATPase subunit 6 [*Homo sapiens*]; (4949:) proteasome 26S non-ATPase subunit 1 [*Homo sapiens*]; (4950:) proteasome 26S non-ATPase subunit 10 isoform 2 [*Homo sapiens*]; (4951:) proteasome 26S non-ATPase subunit 10 isoform 1 [*Homo sapiens*]; (4952:) proteasome 26S non-ATPase subunit 11 [*Homo sapiens*]; (4953:) proteasome 26S non-ATPase subunit 12 [*Homo sapiens*]; (4954:) proteasome 26S non-ATPase subunit 13 isoform 1 [*Homo sapiens*]; (4955:) proteasome 26S non-ATPase subunit 13 isoform 2 [*Homo sapiens*]; (4956:) proteasome 26S non-ATPase subunit 2 [*Homo sapiens*]; (4957:) proteasome 26S non-ATPase subunit 3 [*Homo sapiens*]; (4958:) proteasome 26S non-ATPase subunit 4 isoform 1 [*Homo sapiens*]; (4959:) proteasome 26S non-ATPase subunit 4 isoform 2 [*Homo sapiens*]; (4960:) proteasome 26S non-ATPase subunit 5 [*Homo sapiens*]; (4961:) proteasome 26S non-ATPase subunit 7 [*Homo sapiens*]; (4962:) proteasome 26S non-ATPase subunit 8 [*Homo sapiens*]; (4963:) proteasome 26S non-ATPase subunit 9 [*Homo sapiens*]; (4964:) proteasome activator hPA28 subunit beta [*Homo sapiens*]; (4965:) proteasome activator subunit 1 isoform 1 [*Homo sapiens*]; (4966:) proteasome activator subunit 1 isoform 2 [*Homo sapiens*]; (4967:) proteasome activator subunit 2 [*Homo sapiens*]; (4968:) proteasome activator subunit 3 isoform 1 [*Homo sapiens*]; (4969:) proteasome activator subunit 3 isoform 2 [*Homo sapiens*]; (4970:) proteasome alpha 1 subunit isoform 1 [*Homo sapiens*]; (4971:) proteasome alpha 1 subunit isoform 2 [*Homo sapiens*]; (4972:) proteasome alpha 2 subunit [*Homo sapiens*]; (4973:) proteasome alpha 3 subunit isoform 1 [*Homo sapiens*]; (4974:) proteasome alpha 3 subunit isoform 2 [*Homo sapiens*]; (4975:) proteasome alpha 4 subunit [*Homo sapiens*]; (4976:) proteasome alpha 5 subunit [*Homo sapiens*]; (4977:) proteasome alpha 6 subunit [*Homo sapiens*]; (4978:) proteasome alpha 7 subunit [*Homo sapiens*]; (4979:) proteasome beta 1 subunit [*Homo sapiens*]; (4980:) proteasome beta 10 subunit proprotein [*Homo sapiens*]; (4981:) proteasome beta 2 subunit [*Homo sapiens*]; (4982:) proteasome beta 3 subunit [*Homo sapiens*]; (4983:) proteasome beta 4 subunit [*Homo sapiens*]; (4984:) proteasome beta 5 subunit [*Homo sapiens*]; (4985:) proteasome beta 6 subunit [*Homo sapiens*]; (4986:) proteasome beta 7 subunit proprotein [*Homo sapiens*]; (4987:) proteasome beta 8 subunit isoform E1 proprotein [*Homo sapiens*]; (4988:) proteasome beta 8 subunit isoform E2 proprotein [*Homo sapiens*]; (4989:) proteasome beta 9 subunit isoform 1 proprotein [*Homo sapiens*]; (4990:) proteasome beta 9 subunit isoform 2 proprotein [*Homo sapiens*]; (4991:) proteasome inhibitor subunit 1 isoform 1 [*Homo sapiens*]; (4992:) proteasome inhibitor subunit 1 isoform 2 [*Homo sapiens*]; (4993:) Proteasome subunit alpha type 1 (Proteasome component C2) (Macropain subunit C2) (Multicatalytic endopeptidase complex subunit C2) (Proteasome nu chain) (30 kDa prosomal protein) (PROS-30); (4994:) Proteasome subunit alpha type 2 (Proteasome component C3) (Macropain subunit C3) (Multicatalytic endopeptidase complex subunit C3); (4995:) Proteasome subunit alpha type 3 (Proteasome component C8) (Macropain subunit C8) (Multicatalytic endopeptidase complex subunit C8); (4996:) Proteasome subunit alpha type 4 (Proteasome component C9) (Macropain subunit C9) (Multicatalytic endopeptidase complex subunit C9) (Proteasome subunit L); (4997:) Proteasome subunit beta type 1 (Proteasome component C5) (Macropain subunit C5) (Multicatalytic endopeptidase complex subunit C5) (Proteasome gamma chain); (4998:) Proteasome subunit beta type 2 (Proteasome component C7-I) (Macropain subunit C7-I) (Multicatalytic endopeptidase complex subunit C7-I); (4999:) Proteasome subunit beta type 3 (Proteasome theta chain) (Proteasome chain 13) (Proteasome component C10-II); (5000:) Proteasome subunit beta type 4 precursor (Proteasome beta chain) (Macropain beta chain) (Multicatalytic endopeptidase complex beta chain) (Proteasome chain 3) (HSN3) (HsBPROS26); (5001:) proteasome subunit C2 [*Homo sapiens*]; (5002:) proteasome subunit C3 [*Homo sapiens*]; (5003:) proteasome subunit C5 [*Homo sapiens*]; (5004:) proteasome subunit C8 [*Homo sapiens*]; (5005:) proteasome subunit C9 [*Homo sapiens*]; (5006:) proteasome subunit HsC10-II [*Homo sapiens*]; (5007:) proteasome subunit HsC7-I [*Homo sapiens*]; (5008:) proteasome subunit HsN3 [*Homo sapiens*]; (5009:) proteasome subunit p40/Mov34 protein [*Homo sapiens*]; (5010:) proteasome subunit X [*Homo sapiens*]; (5011:) proteasome subunit Y [*Homo sapiens*]; (5012:) proteasome:SUBUNIT=HsC10-II; (5013:) proteasome:SUBUNIT=HsC7-I; (5014:) proteasome:SUBUNIT=HsN3; (5015:) protective protein for beta-galactosidase [*Homo sapiens*]; (5016:) Protein arginine N-methyltransferase 1 (Interferon receptor 1-bound protein 4); (5017:) Protein arginine N-methyltransferase 3 (Heterogeneous nuclear ribonucleoprotein methyltransferase-like protein 3); (5018:) Protein arginine N-methyltransferase 6 (Heterogeneous nuclear ribonucleoprotein methyltransferase-like protein 6); (5019:) Protein ariadne-1 homolog (ARI-1) (Ubiquitin-conjugating enzyme E2-binding protein 1) (UbCH7-binding protein) (UbcM4-interacting protein) (HHARI) (H7-AP2) (MOP-6); (5020:) protein disulfide isomerase-associated 3 precursor [*Homo sapiens*]; (5021:) protein disulfide isomerase-associated 4 [*Homo sapiens*]; (5022:) protein disulfide isomerase-related protein; (5023:) Protein disulfide-isomerase A4 precursor (Protein ERp-72) (ERp72); (5024:) Protein disulfide-isomerase TXNDC10 precursor (Thioredoxin domain-containing protein 10) (Thioredoxin-related transmembrane protein 3); (5025:) Protein FAM125A (CIN85/CD2AP family-binding protein); (5026:) protein kinase (EC 2.7.1.37), cAMP-dependent, type 1-beta regulatory chain—human; (5027:) Protein Kinase A (PKA); (5028:) Protein Kinase B (PKB); (5029:) Protein Kinase B (PKB); (5030:) protein kinase C (EC 2.7.1.-) beta-1—human; (5031:) Protein Kinase C (PKC); (5032:) Protein kinase C alpha type (PKC-alpha) (PKC-A); (5033:) Protein kinase C beta type (PKC-beta) (PKC-B); (5034:) Protein kinase C delta type (nPKC-delta); (5035:) Protein kinase C epsilon type (nPKC-epsilon); (5036:) Protein kinase C eta type (nPKC-eta) (PKC-L); (5037:) Protein kinase C gamma type (PKC-gamma); (5038:) Protein kinase C iota type (nPKC-iota) (Atypical protein kinase C-lambda/iota) (aPKC-lambda/iota) (PRKC-lambda/iota); (5039:) protein kinase C substrate 80K-H isoform 1 [*Homo sapiens*]; (5040:) protein kinase C substrate 80K-H isoform 2 [*Homo sapiens*]; (5041:) Protein kinase C theta type (nPKC-theta);

(5042:) Protein kinase C zeta type (nPKC-zeta); (5043:) protein kinase C, alpha [Homo sapiens]; (5044:) protein kinase C, delta [Homo sapiens]; (5045:) protein kinase C, epsilon [Homo sapiens]; (5046:) protein kinase C, gamma [Homo sapiens]; (5047:) Protein Kinase C-alpha (PKC-alpha); (5048:) Protein Kinase C-beta (PKC-beta); (5049:) Protein Kinase C-delta (PKC-delta); (5050:) protein kinase CHK2 isoform a [Homo sapiens]; (5051:) protein kinase CHK2 isoform b [Homo sapiens]; (5052:) protein kinase CHK2 isoform c [Homo sapiens]; (5053:) protein kinase, cGMP-dependent, type I [Homo sapiens]; (5054:) protein kinase, DNA-activated, catalytic polypeptide [Homo sapiens]; (5055:) Protein Kinase-C Like 2 (PRKCL2); (5056:) Protein LMBR1L (Lipocalin-1-interacting membrane receptor) (Lipocalin-interacting membrane receptor) (Limb region 1 protein homolog-like); (5057:) Protein MTO1 homolog, mitochondrial precursor; (5058:) Protein N-terminal asparagine amidohydrolase (Protein NH2-terminal asparagine deamidase) (N-terminal Asn amidase) (NTN-amidase) (PNAD) (Protein NH2-terminal asparagine amidohydrolase) (PNAA); (5059:) protein O-fucosyltransferase 1 isoform 1 precursor [Homo sapiens]; (5060:) protein O-fucosyltransferase 1 isoform 2 precursor [Homo sapiens]; (5061:) Protein O-mannosyl-transferase 1(Dolichyl-phosphate-mannose—protein mannosyltransferase 1); (5062:) Protein O-mannosyl-transferase 2(Dolichyl-phosphate-mannose—protein mannosyltransferase 2); (5063:) Protein patched homolog 1 (PTC1) (PTC); (5064:) Protein patched homolog 2 (PTC2); (5065:) protein phosphatase 1, catalytic subunit, alpha isoform 1 [Homo sapiens]; (5066:) protein phosphatase 1, catalytic subunit, alpha isoform 2 [Homo sapiens]; (5067:) protein phosphatase 1, catalytic subunit, alpha isoform 3 [Homo sapiens]; (5068:) protein phosphatase 1, catalytic subunit, gamma isoform [Homo sapiens]; (5069:) protein phosphatase 1G [Homo sapiens]; (5070:) protein phosphatase 1J (PP2C domain containing) [Homo sapiens]; (5071:) protein phosphatase 2, catalytic subunit, alpha isoform [Homo sapiens]; (5072:) protein phosphatase 2, catalytic subunit, beta isoform [Homo sapiens]; (5073:) protein phosphatase 2, regulatory subunit B (B56), alpha isoform [Homo sapiens]; (5074:) protein phosphatase 2, regulatory subunit B", alpha isoform 1 [Homo sapiens]; (5075:) protein phosphatase 2, regulatory subunit B", alpha isoform 2 [Homo sapiens]; (5076:) protein phosphatase 2, regulatory subunit B", beta isoform 1 [Homo sapiens]; (5077:) protein phosphatase 2, regulatory subunit B", beta isoform 2 [Homo sapiens]; (5078:) protein phosphatase 2A, regulatory subunit B' isoform a [Homo sapiens]; (5079:) protein phosphatase 2A, regulatory subunit B' isoform b [Homo sapiens]; (5080:) protein phosphatase 2A, regulatory subunit B' isoform d [Homo sapiens]; (5081:) Protein phosphatase 2C isoform alpha (PP2C-alpha) (IA) (Protein phosphatase 1A); (5082:) Protein phosphatase 2C isoform beta (PP2C-beta); (5083:) Protein preY, mitochondrial precursor; (5084:) Protein Tyrosine Phosphatase 1B (PTP1B); (5085:) Protein tyrosine phosphatase type IVA protein 1 (Protein-tyrosine phosphatase 4a1) (Protein-tyrosine phosphatase of regenerating liver 1) (PRL-1) (PTP (CAAXI)); (5086:) Protein tyrosine phosphatase type IVA protein 2 (Protein-tyrosine phosphatase 4a2) (Protein-tyrosine phosphatase of regenerating liver 2) (PRL-2) (PTP (CAAXII)) (HU-PP-1) (OV-1); (5087:) Protein tyrosine phosphatase type IVA protein 3 (Protein-tyrosine phosphatase 4a3) (Protein-tyrosine phosphatase of regenerating liver 3) (PRL-3) (PRL-R); (5088:) protein tyrosine phosphatase type IVA, member 1 [Homo sapiens]; (5089:) protein tyrosine phosphatase, non-receptor type 22 (lymphoid) isoform 1 [Homo sapiens]; (5090:) protein tyrosine phosphatase, non-receptor type 22 (lymphoid)isoform 2 [Homo sapiens]; (5091:) protein tyrosine phosphatase, receptor type, N precursor [Homo sapiens]; (5092:) protein X [Homo sapiens]; (5093:) protein Z; (5094:) Protein-arginine deiminase type-3 (Protein-arginine deiminase type III) (Peptidylarginine deiminase III); (5095:) Protein-arginine deiminase type-4 (Protein-arginine deiminase type IV) (Peptidylarginine deiminase IV) (HL-60 PAD); (5096:) proteinase 3 (serine proteinase, neutrophil, Wegener granulomatosis autoantigen) [Homo sapiens]; (5097:) Proteinase Activated Receptor-2 (PAR-2); (5098:) Proteinase-activated receptor 1 precursor (PAR-1) (Thrombin receptor) (Coagulation factor II receptor); (5099:) Proteinase-activated receptor 2 precursor (PAR-2) (Thrombin receptor-like 1) (Coagulation factor II receptor-like 1) (G-protein coupled receptor II); (5100:) Proteinase-activated receptor 3 precursor (PAR-3) (Thrombin receptor-like 2) (Coagulation factor II receptor-like 2); (5101:) Proteinase-activated receptor 4 precursor (PAR-4) (Thrombin receptor-like 3) (Coagulation factor II receptor-like 3); (5102:) Protein-glutamine gamma-glutamyltransferase 5 (Transglutaminase-5) (TGase 5) (Transglutaminase X) (TGase X) (TGX) (TG(X)); (5103:) "Protein-glutamine gamma-glutamyltransferase E precursor (TGase E) (TGE) (TG(E)) (Transglutaminase-3) [Contains:) Protein-glutamine gamma-glutamyltransferase E 50 kDa non-catalytic chain; Protein-glutamine gamma-glutamyltransferase E 27 kDa catalytic chain]."; (5104:) Protein-glutamine gamma-glutamyltransferase K (Transglutaminase K) (TGase K) (TGK) (TG(K)) (Transglutaminase-1) (Epidermal TGase); (5105:) protein-L-isoaspartate (D-aspartate) O-methyltransferase [Homo sapiens]; (5106:) protein-O-mannosyltransferase 1 isoform a [Homo sapiens]; (5107:) protein-O-mannosyltransferase 1 isoform b [Homo sapiens]; (5108:) protein-O-mannosyltransferase 1 isoform c [Homo sapiens]; (5109:) protein-tyrosine kinase (EC 2.7.1.112), receptor type tie precursor-human; (5110:) Protein-tyrosine sulfotransferase 1 (Tyrosyl protein sulfotransferase-1) (TPST-1); (5111:) protein-tyrosine-phosphatase (EC 3.1.3.48), receptor type Hp recursor—human; (5112:) protein-tyrosine-phosphatase (EC 3.1.3.48), receptor type Op recursor—human; (5113:) "Prothrombin precursor (Coagulation factor 11) [Contains:) Activation peptide fragment 1; Activation peptide fragment 2; Thrombin light chain; Thrombin heavy chain]."; (5114:) protooncogene protein 1 [Homo sapiens]; (5115:) Proto-oncogene tyrosine-protein kinase ABL1 (p150) (c-ABL) (Abelsonmurine leukemia viral oncogene homolog 1); (5116:) Proto-oncogene tyrosine-protein kinase MER precursor (C-mer) (Receptor tyrosine kinase MerTK); (5117:) Proto-oncogene tyrosine-protein kinase ROS precursor (c-ros-1); (5118:) Protoporphyrinogen oxidase (PPO); (5119:) PRTD-NY3 [Homo sapiens]; (5120:) P-Selectin Activator; (5121:) Psychosine receptor (G-protein coupled receptor 65) (T cell death-associated protein 8); (5122:) pterin carbinolamine dehydratase [Homo sapiens]; (5123:) pterin-4 alpha-carbinolamine dehydratase precursor [Homo sapiens]; (5124:) Pterin-4 alpha-carbinolamine dehydratase/dimerization cofactor of hepatocyte nuclear factor 1 alpha (TCF1) [Homo sapiens]; (5125:) Pterin-4 alpha-carbinolamine dehydratase/dimerization cofactor of hepatocyte nuclear factor 1 alpha (TCF1) 2 [Homo sapiens]; (5126:) pterin-4-a-carbinolamine dehydratase; (5127:) Pterin-4-alpha-carbinolamine dehydratase (PHS) (4-alpha-hydroxy-tetrahydropterin dehydratase) (Phenylalaninehydroxylase-stimulating protein) (Pterin carbinolamine dehydratase) (PCD) (Dimerization cofactor of hepatocyte nuclear factor 1-alpha) (Dimerization cofactor of HNF1) (DCoH); (5128:) Pterin-4-alpha-carbinolamine dehydratase 2 (PHS 2) (4-alpha-hydroxy-tetrahydropterin dehydratase 2) (DcoH-like protein DCoHm) (Dimerization cofactor of hepatocyte nuclear factor 1 from muscle) (HNF1-alpha dimerization cofactor); (5129:) PTK2 protein tyrosine kinase 2 isoform a [Homo sapiens]; (5130:) PTK2 protein tyrosine kinase 2 isoform b [Homo sapiens]; (5131:) P-Type Calcium Channel Blocker; (5132:) Purine Nucleoside Phosphorylase (PNP); (5133:) purine nucleoside phosphorylase [Homo sapiens]; (5134:) putative 1-aminocyclopropane-1-carboxylate synthase [Homo sapiens]; (5135:) putative acyl-CoA dehydrogenase [Homo sapiens]; (5136:) putative b,b-carotene-9',10'-dioxygenase [Homo sapiens]; (5137:) Putative C→U-editing enzyme APOBEC-4 (Apolipoprotein BmRNA-editing enzyme catalytic polypeptide-like 4); (5138:) putative carotene dioxygenase [Homo sapiens]; (5139:) putative deubiquitinazing enzyme [Homo sapiens]; (5140:) Putative G-protein coupled receptor 42; (5141:) Putative G-protein coupled receptor 44 (Chemoattractant receptor-homologous molecule expressed on Th2 cells) (CD294antigen); (5142:) "putative non-ribosomal peptide synthetase NRPS1098; hNRPS1098 [Homo sapiens]."; (5143:) putative non-ribosomal peptide synthetase NRPS998 [Homo sapiens]; (5144:) Putative P2Y purinoceptor 10 (P2Y10) (P2Y-like receptor); (5145:) putative peroxisomal antioxidant enzyme [Homo sapiens]; (5146:) putative protein O-mannosyltransferase [Homo sapiens]; (5147:) putative pyroglutamyl-peptidase I [Homo sapiens]; (5148:) Putative Taste receptor type 2 member 12 (T2R12) (Taste receptor type 2 member 26) (T2R26); (5149:) putative ubiquitin-conjugating enzyme E2 variant [Homo sapiens]; (5150:) pVHL-interacting deubiquitinating enzyme 1 type I [Homo sapiens]; (5151:) pVHL-interacting deubiquitinating enzyme 1 type II [Homo sapiens]; (5152:) pVHL-interacting deubiquitinating enzyme 2 [Homo sapiens]; (5153:) Pyridoxal kinase (Pyridoxine kinase); (5154:) pyridoxal kinase [Homo sapiens]; (5155:) Pyridoxal phosphate phosphatase (PLP phosphatase); (5156:) Pyridoxal phosphate phosphatase PHOSPHO2; (5157:) pyridoxine 5'-phosphate oxidase [Homo sapiens]; (5158:) pyroglutamyl-peptidase 1 [Homo sapiens]; (5159:) pyrophosphatase 1 [Homo sapiens]; (5160:) pyrroline 5-carboxylate synthetase [Homo sapiens]; (5161:) pyrroline-5-carboxylate reductase 1 isoform 1 [Homo sapiens]; (5162:) pyrroline-5-carboxylate reductase 1 isoform 2 [Homo sapiens]; (5163:) pyrroline-5-carboxylate synthase [Homo sapiens]; (5164:) pyrroline-5-carboxylate synthase long form [Homo sapiens]; (5165:) pyrroline-5-carboxylate synthetase isoform 1 [Homo sapiens]; (5166:) pyrroline-5-carboxylate synthetase isoform 2 [Homo sapiens]; (5167:) Pyruvate carboxylase [Homo sapiens]; (5168:) pyruvate carboxylase precursor [Homo sapiens]; (5169:) pyruvate carboxylase precursor; (5170:) Pyruvate carboxylase, mitochondrial precursor (Pyruvic carboxylase) (PCB); (5171:) pyruvate carboxylase; (5172:) "pyruvate carboxylase; pyruvate:carbon dioxide ligase [Homo sapiens]."; (5173:) pyruvate dehydrogenase (lipoamide) alpha 1 [Homo sapiens]; (5174:) Pyruvate Dehydrogenase (PDH) Kinase; (5175:) pyruvate dehydrogenase complex protein X subunit precursor [Homo sapiens]; (5176:) pyruvate dehydrogenase complex, component X [Homo sapiens]; (5177:) Pyruvate dehydrogenase E1 component alpha subunit, somatic form, mitochondrial precursor (PDHE1-A type I); (5178:) Pyruvate dehydrogenase E1 component alpha subunit, testis-specific form, mitochondrial precursor (PDHE1-A type II); (5179:) Pyruvate dehydrogenase E1 component subunit beta, mitochondrial precursor (PDHE1-B); (5180:) Pyruvate Dehydrogenase Kinase 2 (PDHK2); (5181:) Pyruvate dehydrogenase protein X component, mitochondrial precursor (Dihydrolipoamide dehydrogenase-binding protein of pyruvate dehydrogenase complex) (Lipoyl-containing pyruvate dehydrogenase complex component X) (E3-binding protein) (E3BP) (proX); (5182:) pyruvate kinase (EC 2.7.1.40), muscle splice form M1—human; (5183:) pyruvate kinase [Homo sapiens]; (5184:) pyruvate kinase 3 isoform 1 [Homo sapiens]; (5185:) pyruvate kinase 3 isoform 1 variant [Homo sapiens]; (5186:) pyruvate kinase 3 isoform 2 [Homo sapiens]; (5187:) Pyruvate kinase isozymes M1/M2 (Pyruvate kinase muscle isozyme) (Pyruvate kinase 2/3) (Cytosolic thyroid hormone-binding protein) (CTHBP) (THBP1); (5188:) Pyruvate kinase isozymes R/L (R-type/L-type pyruvate kinase) (Red cell/liver pyruvate kinase) (Pyruvate kinase 1); (5189:) pyruvate kinase L [Homo sapiens]; (5190:) pyruvate kinase M2 [Homo sapiens]; (5191:) pyruvate kinase PK-L isoenzyme [Homo sapiens]; (5192:) pyruvate kinase PK-R isoenzyme [Homo sapiens]; (5193:) Pyruvate kinase, liver and RBC [Homo sapiens]; (5194:) pyruvate kinase, liver and RBC isoform 1 [Homo sapiens]; (5195:) pyruvate kinase, liver and RBC isoform 2 [Homo sapiens]; (5196:) Pyruvate kinase, muscle [Homo sapiens]; (5197:) pyruvate kinase; (5198:) carbon-dioxide ligase (ADP-forming); (5199:) Pyruvate:Ferredoxin Oxidoreductase (PFOR); (5200:) QTRT1 protein [Homo sapiens]; (5201:) QTRTD1 protein [Homo sapiens]; (5202:) Queuine tRNA-ribosyltransferase (tRNA-guanine transglycosylase) (Guanine insertion enzyme); (5203:) quinoid dihydropteridine reductase [Homo sapiens]; (5204:) quinolinate phosphoribosyltransferase [Homo sapiens]; (5205:) rabaptin, RAB GTPase binding effector protein 1 [Homo sapiens]; (5206:) Rac GTPase activating protein 1 [Homo sapiens]; (5207:) RAD18 [Homo sapiens]; (5208:) RAD51 homolog protein isoform 1 [Homo sapiens]; (5209:) RAD51 homolog protein isoform 2 [Homo sapiens]; (5210:) RAD6 homolog; (5211:) Raf Kinase (RKI); (5212:) ralA binding protein 1 [Homo sapiens]; (5213:) RALBP1 associated Eps domain containing 2 [Homo sapiens]; (5214:) Ran binding protein 11 [Homo sapiens]; (5215:) RAN binding protein 2 [Homo sapiens]; (5216:) RAN binding protein 9 [Homo sapiens]; (5217:) Ran GTPase activating protein 1 [Homo sapiens]; (5218:) Ran GTPase-activating protein 1; (5219:) Ran-binding protein 2 (RanBP2) (Nuclear pore complex protein Nup358) (Nucleoporin Nup358) (358 kDa nucleoporin) (P270); (5220:) Ran-binding protein 9 (RanBP9) (RanBP7) (Ran-binding protein M) (RanBPM) (BPM90) (BPM-L); (5221:) RanBP-type and C3HC4-type zinc finger containing 1 isoform 1 [Homo sapiens]; (5222:) RanBP-type and C3HC4-type zinc finger containing 1 isoform 2 [Homo sapiens]; (5223:) RanBP-type and C3HC4-type zinc finger-containing protein 1(Ubiquitin-conjugating enzyme 7-interacting protein 3) (Hepatitis B virus X-associated protein 4) (HBV-associated factor 4) (RING finger protein 54); (5224:) Ras-GTPase-activating protein SH3-domain-binding protein [Homo sapiens]; (5225:) Ras-related C3 botulinum toxin substrate 1 precursor (p21-Rac1) (Ras-like protein TC25); (5226:) Ras-related C3 botulinum toxin substrate 2 precursor (p21-Rac2) (Small G protein) (GX); (5227:) Ras-related protein Rab-5A; (5228:) Ras-related protein Rab-5B; (5229:) Ras-related protein Rap-1A precursor (GTP-binding protein smg-p21A) (Ras-related protein Krev-1) (C21 KG) (G-22K); (5230:) Ras-related protein Rap-1b precursor (GTP-binding protein smgp21B); (5231:) Ras-related protein Rap-2a (RbBP-30); (5232:) rcUBE2S [Homo sapiens]; (5233:) Receptor activity-modifying protein 1 precursor (CRLR activity-modifying protein 1) (Calcitonin-receptor-like receptor activity-modifying protein 1); (5234:) Receptor activity-modifying protein 2 precursor (CRLR activity-modifying protein 2) (Calcitonin-receptor-like receptor activity-modifying protein 2); (5235:) Receptor activity-modifying protein 3 precursor (CRLR activity-modifying protein 3) (Calcitonin-receptor-like receptor activity-modifying protein 3); (5236:) Receptor Gamma (RXR Gamma); (5237:) Receptor tyrosine-protein kinase erbB-2 precursor (p185erbB2) (C-erbB-2) (NEU proto-oncogene) (Tyrosine kinase-type cell surface receptor HER2) (MLN 19) (CD340 antigen); (5238:) Receptor tyrosine-protein kinase erbB-3 precursor (c-erbB3) (Tyrosine kinase-type cell surface receptor HER3); (5239:) Receptor tyrosine-protein kinase erbB-4 precursor (p180erbB4) (Tyrosine kinase-type cell surface receptor HER4); (5240:) Receptor-binding cancer antigen expressed on SiSo cells (Cancer-associated surface antigen RCAS1) (Estrogen receptor-binding fragment-associated gene 9 protein); (5241:) receptor-interacting serine-threonine kinase 2 [*Homo sapiens*]; (5242:) Receptor-type tyrosine-protein phosphatase delta precursor (Protein-tyrosine phosphatase delta) (R-PTP-delta); (5243:) Receptor-type tyrosine-protein phosphatase F precursor (LAR protein) (Leukocyte antigen related); (5244:) Receptor-type tyrosine-protein phosphatase kappa precursor (Protein-tyrosine phosphatase kappa) (R-PTP-kappa); (5245:) Receptor-type tyrosine-protein phosphatase mu precursor (Protein-tyrosine phosphatase mu) (R-PTP-mu); (5246:) Receptor-type tyrosine-protein phosphatase N2 precursor (R-PTP-N2) (Islet cell autoantigen-related protein) (ICMR) (IAR) (Phogrin); (5247:) Receptor-type tyrosine-protein phosphatase O precursor (Glomerular epithelial protein 1) (Protein tyrosine phosphatase U2) (PTPase U2) (PTP-U2); (5248:) Receptor-type tyrosine-protein phosphatase R precursor (Protein-tyrosine phosphatase PCPTP1) (NC-PTPCOM1) (Ch-1 PTPase); (5249:) Receptor-type tyrosine-protein phosphatase S precursor (R-PTP-S) (Protein-tyrosine phosphatase sigma) (R-PTP-sigma); (5250:) Receptor-type tyrosine-protein phosphatase T precursor (R-PTP-T) (RPTP-rho); (5251:) Receptor-type tyrosine-protein phosphatase U precursor (R-PTP-U) (Protein-tyrosine phosphatase J) (PTP-J) (Pancreatic carcinoma phosphatase 2) (PCP-2); (5252:) Receptor-type tyrosine-protein phosphatase-like N precursor (R-PTP-N) (PTP IA-2) (Islet cell antigen 512) (ICA 512) (Islet cell autoantigen 3); (5253:) RECK protein precursor [*Homo sapiens*]; (5254:) RecQ protein-like isoform 1 [*Homo sapiens*]; (5255:) redox active peptide; (5256:) Red-sensitive opsin (Red cone photoreceptor pigment); (5257:) reductase, dihydrofolate; (5258:) Ref-1 [*Homo sapiens*]; (5259:) regenerating islet-derived 1 alpha precursor [*Homo sapiens*]; (5260:) Relaxin receptor 1 (Relaxin family peptide receptor 1) (Leucine-rich repeat-containing G-protein coupled receptor 7); (5261:) Relaxin receptor 2 (Relaxin family peptide receptor 2) (Leucine-rich repeat-containing G-protein coupled receptor 8) (G-protein coupled receptor affecting testicular descent) (G-protein coupled receptor 106); (5262:) Relaxin-3 receptor 1 (RLN3 receptor 1) (Relaxin family peptide receptor 3) (Somatostatin- and angiotensin-like peptide receptor) (G protein-coupled receptor SALPR) (GPCR135); (5263:) Relaxin-3 receptor 2 (Relaxin family peptide receptor 4) (G-protein coupled receptor 100) (GPCR142); (5264:) Renin; (5265:) renin binding protein [*Homo sapiens*]; (5266:) Renin precursor (Angiotensinogenase); (5267:) Renin receptor precursor (Renin/prorenin receptor) (ATPaseH(+)-transporting lysosomal accessory protein 2) (ATPaseH(+)-transporting lysosomal-interacting protein 2) (Vacuolar ATPsynthase membrane sector-associated protein M8-9) (V-ATPase M8.9subunit) (ATP6M8-9) (N14F) (ER-localized type I transmembrane adaptor) (Embryonic liver differentiation factor 10); (5268:) resistin [*Homo sapiens*]; (5269:) Ret Receptor Tyrosine Kinase Stimulator; (5270:) Reticulon-4 receptor precursor (Nogo receptor) (NgR) (Nogo-66receptor); (5271:) Reticulon-4 receptor-like 1 precursor (Nogo-66 receptor homolog 2) (Nogo-66 receptor-related protein 3) (NgR3) (Nogo receptor-like 2); (5272:) Reticulon-4 receptor-like 2 precursor (Nogo-66 receptor homolog 1) (Nogo-66 receptor-related protein 2) (NgR2) (Nogo receptor-like 3); (5273:) retina copper-containing monoamine oxidase [*Homo sapiens*]; (5274:) Retinal dehydrogenase 1 (RalDH1) (RALDH1) (Aldehyde dehydrogenase family 1 member A1) (Aldehyde dehydrogenase, cytosolic) (ALHDII) (ALDH-E1); (5275:) Retinal guanylyl cyclase 1 precursor (Guanylate cyclase 2D, retinal) (RETGC-1) (Rod outer segment membrane guanylate cyclase) (ROS-GC); (5276:) Retinal guanylyl cyclase 2 precursor (Guanylate cyclase 2F, retinal) (RETGC-2) (Rod outer segment membrane guanylate cyclase 2) (ROS-GC2) (Guanylate cyclase F) (GC-F); (5277:) retinal pigment epithelium-specific protein 65 kDa [*Homo sapiens*]; (5278:) retina-specific amine oxidase [*Homo sapiens*]; (5279:) Retina-specific copper amine oxidase precursor (RAO) (Amine oxidase [copper-containing]); (5280:) retinoblastoma 1 [*Homo sapiens*]; (5281:) retinoblastoma-like 2 (p130) [*Homo sapiens*]; (5282:) retinoic acid hydroxylase [*Homo sapiens*]; (5283:) Retinoic acid receptor alpha (RAR-alpha); (5284:) Retinoic acid receptor beta (RAR-beta) (RAR-epsilon) (HBV-activated protein); (5285:) Retinoic acid receptor gamma-1 (RAR-gamma-1); (5286:) Retinoic acid receptor gamma-2 (RAR-gamma-2); (5287:) Retinoic acid receptor RXR-alpha (Retinoid X receptor alpha); (5288:) Retinoic acid receptor RXR-beta (Retinoid X receptor beta); (5289:) Retinoic acid receptor RXR-gamma (Retinoid X receptor gamma); (5290:) Retinoic Acid Receptor-Alpha (RAR Alpha); (5291:) Retinoic Acid Receptor-Beta (RAR Beta); (5292:) Retinoic Acid Receptor-Gamma (RAR Gamma); (5293:) Retinoic acid-induced protein 3 (G-protein coupled receptor family C group 5 member A) (Retinoic acid-induced gene 1 protein) (RAIG-1) (Orphan G-protein coupling receptor PEIG-1); (5294:) Retinoic X Receptor Alpha (RXR Alpha); (5295:) Retinoic X Receptor Beta (RXR Beta); (5296:) retinoid X receptor, alpha [*Homo sapiens*]; (5297:) Retinol Dehydrogenase; (5298:) Retinol dehydrogenase 12 (All-trans and 9-cis retinol dehydrogenase); (5299:) retinol dehydrogenase 12 (all-trans and 9-cis) [*Homo sapiens*]; (5300:) Retinol dehydrogenase 13; (5301:) retinol dehydrogenase 16 [*Homo sapiens*]; (5302:) retinol dehydrogenase 5 (11-cis and 9-cis) [*Homo sapiens*]; (5303:) retinol dehydrogenase 8 (all-trans) [*Homo sapiens*]; (5304:) rhabdomyosarcoma antigen MU-RMS-40.10E [*Homo sapiens*]; (5305:) Rho GTPase Protein; (5306:) Rho-associated protein kinase 1 (Rho-associated, coiled-coil-containing protein kinase 1) (p160 ROCK-1) (p160ROCK) (NY-REN-35 antigen); (5307:) Rho-associated protein kinase 2 (Rho-associated, coiled-coil-containing protein kinase 2) (p164 ROCK-2) (Rho kinase 2); (5308:) Rho-associated, coiled-coil containing protein kinase 1 [*Homo sapiens*]; (5309:) Rhodopsin (Opsin-2); (5310:) Rho-Kinase; (5311:) Rho-related GTP-binding protein RhoQ (Ras-related GTP-binding protein TC10); (5312:) Ribonuclease 4 precursor (RNase 4); (5313:) Ribonuclease H1 (RNase H1) (Ribonuclease H type II); (5314:) ribonuclease H1 [*Homo sapiens*]; (5315:) Ribonuclease H2 subunit A (RNase H2 subunit A) (Ribonuclease HI subunit A) (Ribonuclease HI large subunit) (RNase HI large subunit) (RNase H(35)) (Aicardi-Goutieres syndrome 4 protein) (AGS4); (5316:) ribonuclease HI, large subunit [*Homo sapiens*]; (5317:) ribonuclease III, nuclear [*Homo sapiens*]; (5318:) ribonuclease, RNase A family, 4 precursor [*Homo sapiens*]; (5319:) Ribonucleoside-diphosphate reductase large subunit (Ribonucleoside-diphosphate reductase M1 subunit) (Ribonucleotide reductase large chain); (5320:) ribonucleoside-diphosphate reductase M1 chain [*Homo sapiens*]; (5321:) Ribonucleotide Reductase (RR); (5322:) Ribose-phosphate pyrophosphokinase I (Phosphoribosyl pyrophosphate synthetase I) (PRS-I) (PPRibP); (5323:) Ribose-phosphate pyrophosphokinase II (Phosphoribosyl pyrophosphate synthetase II) (PRS-II) (PPRibP); (5324:) Ribose-phosphate pyrophosphokinase III (Phosphoribosylpyrophosphate synthetase III) (PRS-III) (Phosphoribosylpyrophosphate synthetase 1-like 1); (5325:) Ribosomal protein S6 kinase alpha-1 (S6K-alpha 1) (90 kDa ribosomal protein S6 kinase 1) (p90-RSK1) (Ribosomal S6 kinase 1) (RSK-1) (pp 90RSK1) (p90S6K) (MAP kinase-activated protein kinase 1a) (MAPKAPK1A); (5326:) Ribosomal protein S6 kinase alpha-2 (S6K-alpha 2) (90 kDa ribosomal protein S6 kinase 2) (p90-RSK 2) (Ribosomal S6 kinase 3) (RSK-3) (pp 90RSK3) (MAP kinase-activated protein kinase 1c) (MAPKAPK1C); (5327:) Ribosomal protein S6 kinase alpha-3 (S6K-alpha 3) (90 kDa ribosomal protein S6 kinase 3) (p90-RSK 3) (Ribosomal S6 kinase 2) (RSK-2) (pp 90RSK2) (Insulin-stimulated protein kinase 1) (ISPK-1) (MAPkinase-activated protein kinase 1b) (MAPKAPK1B); (5328:) Ribosomal protein S6 kinase alpha-4 (Nuclear mitogen- and stress-activated protein kinase 2) (90 kDa ribosomal protein S6kinase 4) (Ribosomal protein kinase B) (RSKB); (5329:) Ribosomal protein S6 kinase alpha-5 (Nuclear mitogen- and stress-activated protein kinase 1) (90 kDa ribosomal protein S6kinase 5) (RSK-like protein kinase) (RSKL); (5330:) Ribosomal protein S6 kinase alpha-6 (S6K-alpha 6) (90 kDa ribosomal protein S6 kinase 6) (p90-RSK 6) (Ribosomal S6 kinase 4) (RSK-4) (pp 90RSK4); (5331:) Ribosomal protein S6 kinase beta-1 (Ribosomal protein S6 kinase 1) (S6K) (S6K1) (70 kDa ribosomal protein S6 kinase 1) (p70 S6 kinase alpha) (p70(S6K)-alpha) (p70-S6K) (P70S6K) (p70-alpha); (5332:) Ribosyldihydronicotinamide dehydrogenase [quinone] (NRH dehydrogenase [quinone] 2) (Quinone reductase 2) (QR2) (NRH:quinoneoxidoreductase 2); (5333:) RING finger and WD repeat domain protein 2 (Ubiquitin-protein ligase COP1) (Constitutive photomorphogenesis protein 1 homolog) (hCOP1); (5334:) RING finger protein 125 (T-cell RING activation protein 1) (TRAC-1); (5335:) RING finger protein 139 (Translocation in renal carcinoma onchromosome 8); (5336:) ring finger protein 139 [*Homo sapiens*]; (5337:) ring finger protein 144 [*Homo sapiens*]; (5338:) ring finger protein 2 [*Homo sapiens*]; (5339:) ring finger protein 25 [*Homo sapiens*]; (5340:) RING finger protein 25; (5341:) RING finger protein 37 (Ubiquitin-conjugating enzyme 7-interacting protein 5) (U-box domain-containing protein 5); (5342:) ring finger protein 41 isoform 1 [*Homo sapiens*]; (5343:) ring finger protein 41 isoform 2 [*Homo sapiens*]; (5344:) ring finger protein 7 isoform 1 [*Homo sapiens*]; (5345:) ring finger protein 7 isoform 3 [*Homo sapiens*]; (5346:) RING-box protein 1 (Rbx1) (Regulator of cullins 1) (RING finger protein 75) (Protein ZYP); (5347:) RING-box protein 2 (Rbx2) (RING finger protein 7) (Regulator of cullins 2) (CKII beta-binding protein 1) (CKBBP1) (Sensitive to apoptosis gene protein); (5348:) RNA (guanine-7-) methyltransferase [*Homo sapiens*]; (5349:) RNA (guanine-N-7-) methyltransferase [*Homo sapiens*]; (5350:) RNA 3'-terminal phosphate cyclase (RNA-3'-phosphate cyclase) (RNA cyclase); (5351:) RNA cyclase homolog [*Homo sapiens*]; (5352:) RNA guanylyltransferase and 5'-phosphatase [*Homo sapiens*]; (5353:) RNA lariat debranching enzyme [*Homo sapiens*]; (5354:) RNA polymerase I-associated factor PAF49 (Anti-sense to ERCC-1 protein) (ASE-1) (CD3-epsilon-associated protein) (CD3E-associated protein) (CAST); (5355:) RNA polymerase II transcription factor SIII p18 subunit; (5356:) RNA polymerase III subunit RPC155-A [*Homo sapiens*]; (5357:) RNA polymerase III subunit RPC155-B [*Homo sapiens*]; (5358:) RNA polymerase III subunit RPC155-C [*Homo sapiens*]; (5359:) RNA polymerase III subunit RPC155-D [*Homo sapiens*]; (5360:) RNA polymerase III subunit RPC62 [*Homo sapiens*]; (5361:) RNA polymerase transcriptional regulation mediator, subunit 6homolog (Activator-recruited cofactor 33 kDa component) (ARC33) (NY-REN-28 antigen); (5362:) RNA-specific adenosine deaminase B1 isoform 1 [*Homo sapiens*]; (5363:) RNA-specific adenosine deaminase B1 isoform 2 [*Homo sapiens*]; (5364:) RNA-specific adenosine deaminase B1 isoform 3 [*Homo sapiens*]; (5365:) RNA-specific adenosine deaminase B1 isoform 4 [*Homo sapiens*]; (5366:) RNPEPL1 protein [*Homo sapiens*]; (5367:) Roundabout homolog 1 precursor (H-Robo-1) (Deleted in U twentytwenty); (5368:) Roundabout homolog 3 precursor (Roundabout-like protein 3); (5369:) Roundabout homolog 4 precursor (Magic roundabout); (5370:) RP11-235014.2 [*Homo sapiens*]; (5371:) RPE-retinal G protein-coupled receptor; (5372:) "R-type pyruvate kinase; R-type PK [*Homo sapiens*]."; (5373:) Ryanodine Receptor 1 (RYR1); (5374:) Ryanodine receptor 1 (Skeletal muscle-type ryanodine receptor) (RYR1) (RYR-1) (Skeletal muscle calcium release channel); (5375:) Ryanodine receptor 2 (Cardiac muscle-type ryanodine receptor) (RYR2) (RYR-2) (Cardiac muscle ryanodine receptor-calcium release channel) (hRYR-2); (5376:) Ryanodine receptor 3 (Brain-type ryanodine receptor) (RYR3) (RYR-3) (Brain ryanodine receptor-calcium release channel); (5377:) S100 calcium-binding protein A8 [*Homo sapiens*]; (5378:) S100 calcium-binding protein A9 [*Homo sapiens*]; (5379:) SA [*Homo sapiens*]; (5380:) SA hypertension-associated homolog isoform 2 [*Homo sapiens*]; (5381:) S-adenosylhomocysteine hydrolase [*Homo sapiens*]; (5382:) S-adenosylmethionine decarboxylase (SAMDC); (5383:) S-adenosylmethionine decarboxylase 1 isoform 1 precursor [*Homo sapiens*]; (5384:) S-adenosylmethionine decarboxylase 1 isoform 2 [*Homo sapiens*]; (5385:) "S-adenosylmethionine decarboxylase proenzyme (AdoMetDC) (SamDC)[Contains: S-adenosylmethionine decarboxylase alpha chain; S-adenosylmethionine decarboxylase beta chain]."; (5386:) Salivary alpha-amylase precursor (1,4-alpha-D-glucanglucanohydrolase); (5387:) sarco/endoplasmic reticulum Ca2+-ATPase isoform a [*Homo sapiens*]; (5388:) sarco/endoplasmic reticulum Ca2+-ATPase isoform b [*Homo sapiens*]; (5389:) sarco/endoplasmic reticulum Ca2+-ATPase isoform c [*Homo sapiens*]; (5390:) sarco/endoplasmic reticulum Ca2+-ATPase isoform d [*Homo sapiens*]; (5391:) sarco/endoplasmic reticulum Ca2+-ATPase isoform e [*Homo sapiens*]; (5392:) sarco/endoplasmic reticulum Ca2+-ATPase isoform f [*Homo sapiens*]; (5393:) Sarcoplasmic/endoplasmic reticulum calcium ATPase 1 (Calcium pump 1) (SERCA1) (SR Ca(2+)-ATPase 1) (Calcium-transporting ATPasesarcoplasmic reticulum type, fast twitch skeletal muscle isoform) (Endoplasmic reticulum class 1/2 Ca(2+) ATPase); (5394:) Sarcoplasmic/endoplasmic reticulum calcium ATPase 2 (Calcium pump 2) (SERCA2) (SR Ca(2+)-ATPase 2) (Calcium-transporting ATPasesarcoplasmic reticulum type, slow twitch skeletal muscle isoform) (Endoplasmic reticulum class 1/2 Ca(2+) ATPase); (5395:) Sarcoplasmic/endoplasmic reticulum calcium ATPase 3 (Calcium pump 3) (SERCA3) (SR Ca(2+)-ATPase 3); (5396:) SARS Virus Protease; (5397:) scavenger mRNA decapping enzyme [*Homo sapiens*]; (5398:) Scavenger mRNA decapping enzyme DcpS (DCS-1) (Hint-related7meGMP-directed hydrolase) (Histidine triad protein member 5) (HINT-5); (5399:) Scavenger receptor class B member 1 (SRB1) (SR-BI) (CD36antigen-like 1) (CD36 and LIMPII analogous 1) (CLA-1) (Collagen type I receptor, thrombospondin receptor-like 1); (5400:) scavenger receptor class B, member 1 [*Homo sapiens*]; (5401:) Scavenger receptor class F member 2 precursor (Scavenger receptor expressed by endothelial cells 2 protein) (SREC-II) (SRECRP-1); (5402:) SDS protein [*Homo sapiens*]; (5403:) SDSL protein [*Homo sapiens*]; (5404:) SEC14-like 2 [*Homo sapiens*]; (5405:) SECIS binding protein 2 [*Homo sapiens*]; (5406:) Secreted Apoptosis-Related Protein 2 (SARP2); (5407:) Secretin Receptor (SCTR); (5408:) Secretin receptor precursor (SCT-R); (5409:) Secretory Leukocyte Protease (SLPI); (5410:) Secretory Phospholipase A2 (sPLA2); (5411:) Secretory Protein Clusterin (sCLU); (5412:) selectin E precursor [*Homo sapiens*]; (5413:) selectin L precursor [*Homo sapiens*]; (5414:) selectin P ligand [*Homo sapiens*]; (5415:) selectin P precursor [*Homo sapiens*]; (5416:) selenocysteine lyase [*Homo sapiens*]; (5417:) selenophosphate synthetase [*Homo sapiens*]; (5418:) selenophosphate synthetase 2 [*Homo sapiens*]; (5419:) Semaphorin-4D precursor (Leukocyte activation antigen CD100) (BB18) (A8) (GR3); (5420:) Semicarbazide-Sensitive Amine Oxidase (SSAO); (5421:) Sentrin-specific protease 8 (Sentrin/SUMO-specific protease SENP8) (Protease, cysteine 2) (NEDD8-specific protease 1) (Deneddylase-1); (5422:) Separin (Separase) (Caspase-like protein ESPL1) (Extra spindle poles-like 1 protein); (5423:) sepiapterin reductase (7,8-dihydrobiopterin:NADP+oxidoreductase)[*Homo sapiens*]; (5424:) Sepiapterin reductase (SPR); (5425:) sepiapterin reductase; (5426:) Serase-1B [*Homo sapiens*]; (5427:) serine (or cysteine) proteinase inhibitor, clade A (alpha-lantiproteinase, antitrypsin), member 1 [*Homo sapiens*]; (5428:) serine (or cysteine) proteinase inhibitor, clade B (ovalbumin), member 2 [*Homo sapiens*]; (5429:) serine (or cysteine) proteinase inhibitor, clade B (ovalbumin), member 9 [*Homo sapiens*]; (5430:) serine (or cysteine) proteinase inhibitor, clade I (neuroserpin), member 1 [*Homo sapiens*]; (5431:) serine dehydratase (EC 4.2.1.13); (5432:) serine dehydratase [*Homo sapiens*]; (5433:) serine dehydratase-2 [*Homo sapiens*]; (5434:) serine dehydratase-like [*Homo sapiens*]; (5435:) serine hydroxymethyltransferase 1 (soluble) isoform 1 [*Homo sapiens*]; (5436:) serine hydroxymethyltransferase 1 (soluble) isoform 2 [*Homo sapiens*]; (5437:) Serine hydroxymethyltransferase, cytosolic (Serine methylase) (Glycine hydroxymethyltransferase) (SHMT); (5438:) Serine hydroxymethyltransferase, mitochondrial precursor (Serine methylase) (Glycine hydroxymethyltransferase) (SHMT); (5439:) serine palmitoyltransferase (SPT); (5440:) Serine palmitoyltransferase 1 (Long chain base biosynthesis protein1) (LCB 1) (Serine-palmitoyl-CoA transferase 1) (SPT 1) (SPT1); (5441:) Serine palmitoyltransferase 2 (Long chain base biosynthesis protein2) (LCB 2) (Serine-palmitoyl-CoA transferase 2) (SPT 2); (5442:) serine palmitoyltransferase subunit 1 isoform a [*Homo sapiens*]; (5443:) serine palmitoyltransferase subunit 1 isoform b [*Homo sapiens*]; (5444:) serine palmitoyltransferase, long chain base subunit 2 [*Homo sapiens*]; (5445:) serine palmitoyltransferase, subunit I [*Homo sapiens*]; (5446:) serine palmitoyltransferase, subunit II [*Homo sapiens*]; (5447:) serine protease inhibitor, Kazal type 1 [*Homo sapiens*]; (5448:) serine racemase [*Homo sapiens*]; (5449:) Serine racemase; (5450:) serine/threonine kinase 16 [*Homo sapiens*]; (5451:) Serine/threonine kinase NLK (Nemo-like kinase) (Protein LAK1); (5452:) Serine/threonine-protein kinase 25 (Sterile 20/oxidant stress-response kinase 1) (Step 20/oxidant stress response kinase 1) (SOK-1) (Step 20-like kinase); (5453:) Serine/threonine-protein kinase 3 (STE20-like kinase MST2) (MST-2) (Mammalian STE20-like protein kinase 2) (Serine/threonine-protein kinase Krs-1); (5454:) Serine/threonine-protein kinase 36 (Fused homolog); (5455:) Serine/threonine-protein kinase 38 (NDR1 protein kinase) (Nuclear Dbf2-related kinase 1); (5456:) Serine/threonine-protein kinase 38-like (NDR2 protein kinase) (Nuclear Dbf2-related kinase 2); (5457:) Serine/threonine-protein kinase 4 (STE20-like kinase MST1) (MST-1) (Mammalian STE20-like protein kinase 1) (Serine/threonine-protein kinase Krs-2); (5458:) Serine/threonine-protein kinase ATR (Ataxia telangiectasia and Rad3-related protein) (FRAP-related protein 1); (5459:) Serine/threonine-protein kinase Chk2 (Cds1); (5460:) Serine/threonine-protein kinase D1 (nPKC-D1) (Protein kinase D) (Protein kinase C mu type) (nPKC-mu); (5461:) Serine/threonine-protein kinase D2 (nPKC-D2); (5462:) Serine/threonine-protein kinase D3 (Protein kinase C nu type) (nPKC-nu) (Protein kinase EPK2); (5463:) Serine/threonine-protein kinase H1 (PSK-H1); (5464:) Serine/threonine-protein kinase ICK (Intestinal cell kinase) (hICK) (MAK-related kinase) (MRK) (Laryngeal cancer kinase 2) (LCK2); (5465:) Serine/threonine-protein kinase MARK1 (MAP/microtubule affinity-regulating kinase 1); (5466:) Serine/threonine-protein kinase MARK2 (MAP/microtubule affinity-regulating kinase 2) (ELKL motif kinase) (EMK1) (PAR1 homolog); (5467:) Serine/threonine-protein kinase MRCK alpha (CDC42-binding protein kinase alpha) (Myotonic dystrophy kinase-related CDC42-binding kinase alpha) (Myotonic dystrophy protein kinase-like alpha) (MRCK alpha) (DMPK-like alpha); (5468:) Serine/threonine-protein kinase MRCK beta (CDC42-binding protein kinase beta) (Myotonic dystrophy kinase-related CDC42-binding kinase beta) (Myotonic dystrophy protein kinase-like beta) (MRCK beta) (DMPK-like beta); (5469:) Serine/threonine-protein kinase MRCK gamma (CDC42-binding protein kinase gamma) (Myotonic dystrophy kinase-related CDC42-binding kinase gamma) (Myotonic dystrophy protein kinase-like alpha) (MRCK gamma) (DMPK-like gamma); (5470:) Serine/threonine-protein kinase MST4 (STE20-like kinase MST4) (MST-4) (Mammalian STE20-like protein kinase 4) (Serine/threonine-protein kinase MASK) (Mst3 and SOK1-related kinase); (5471:) Serine/threonine-protein kinase N1 (Protein kinase C-like 1) (Protein-kinase C-related kinase 1) (Protein kinase C-like PKN) (Serine-threonine protein kinase N) (Protein kinase PKN-alpha); (5472:) Serine/threonine-protein kinase N2 (Protein kinase C-like 2) (Protein-kinase C-related kinase 2); (5473:) Serine/threonine-protein kinase Nek11 (NimA-related protein kinase 11) (Never in mitosis A-related kinase 11); (5474:) Serine/threonine-protein kinase Nek2 (NimA-related protein kinase 2) (NimA-like protein kinase 1) (HSPK 21); (5475:) Serine/threonine-protein kinase Nek9 (NimA-related protein kinase 9) (Never in mitosis A-related kinase 9) (Nercci kinase) (NIMA-related kinase 8) (Nek8); (5476:) Serine/threonine-protein kinase NIM1; (5477:) Serine/threonine-protein kinase OSR1 (Oxidative stress-responsive 1 protein); (5478:) Serine/threonine-protein kinase PAK 1 (p21-activated kinase 1) (PAK-1) (P65-PAK) (Alpha-PAK); (5479:) Serine/threonine-protein kinase PAK 2 (p21-activated kinase 2) (PAK-2) (PAK65) (Gamma-PAK) (S6/H4 kinase); (5480:) Serine/threonine-protein kinase PAK 3 (p21-activated kinase 3)

(PAK-3) (Beta-PAK) (Oligophrenin-3); (5481:) Serine/threonine-protein kinase receptor R3 precursor (SKR3) (Activin receptor-like kinase 1) (ALK-1) (TGF-B superfamily receptor type I) (TSR-I); (5482:) Serine/threonine-protein kinase SMG1 (SMG-1) (hSMG-1) (Lambda/iotaprotein kinase C-interacting protein) (Lambda-interacting protein) (61E3.4); (5483:) Serine/threonine-protein kinase SNF1-like kinase 1(Serine/threonine-protein kinase SNF1LK); (5484:) Serine/threonine-protein kinase SNF1-like kinase 2 (Qin-induced kinase); (5485:) Serine/threonine-protein kinase SRPK1 (Serine/arginine-rich protein-specific kinase 1) (SR-protein-specific kinase 1) (SFRSprotein kinase 1); (5486:) Serine/threonine-protein kinase SRPK2 (Serine/arginine-rich protein-specific kinase 2) (SR-protein-specific kinase 2) (SFRSprotein kinase 2); (5487:) Serine/threonine-protein kinase TBK1 (TANK-binding kinase 1) (T2K) (NF-kappa-B-activating kinase); (5488:) Serine/threonine-protein kinase tousled-like 1 (Tousled-like kinase 1) (PKU-beta); (5489:) Serine/threonine-protein kinase tousled-like 2 (Tousled-like kinase 2) (PKU-alpha); (5490:) Serine/threonine-protein kinase VRK1 (Vaccinia-related kinase 1); (5491:) Serine/threonine-protein kinase WNK1 (Protein kinase with no lysine 1) (Protein kinase, lysine-deficient 1) (Kinase deficient protein); (5492:) Serine/threonine-protein kinase WNK2 (Protein kinase with no lysine-2) (Protein kinase, lysine-deficient 2); (5493:) Serine/threonine-protein kinase WNK3 (Protein kinase with no lysine-3) (Protein kinase, lysine-deficient 3); (5494:) Serine/threonine-protein kinase WNK4 (Protein kinase with no lysine-4) (Protein kinase, lysine-deficient 4); (5495:) "Serine/threonine-protein kinase/endoribonuclease IRE1 precursor (Inositol-requiring protein 1) (hIRE1p) (IRE1a) (Ire1-alpha) (Endoplasmic reticulum-to-nucleus signaling 1) [Includes:Serine/threonine-protein kinase; Endoribonuclease]."; (5496:) "Serine/threonine-protein kinase/endoribonuclease IRE2 precursor (Inositol-requiring protein 2) (hIRE2p) (IRE1b) (Ire1-beta) (Endoplasmic reticulum-to-nucleus signaling 2) [Includes:Serine/threonine-protein kinase; Endoribonuclease]."; (5497:) Serine/threonine-protein phosphatase 2A 48 kDa regulatory subunit B(PP2A, subunit B, PR48 isoform); (5498:) Serine/threonine-protein phosphatase 2A 55 kDa regulatory subunit B alpha isoform (PP2A, subunit B, B-alpha isoform) (PP2A, subunit B, B55-alpha isoform) (PP2A, subunit B, PR55-alpha isoform) (PP2A, subunit B, R2-alpha isoform); (5499:) Serine/threonine-protein phosphatase 2A 55 kDa regulatory subunit B beta isoform (PP2A, subunit B, B-beta isoform) (PP2A, subunit B, B55-beta isoform) (PP2A, subunit B, PR55-beta isoform) (PP2A, subunit B, R2-beta isoform); (5500:) Serine/threonine-protein phosphatase 2A 55 kDa regulatory subunit B delta isoform (PP2A, subunit B, B-delta isoform) (PP2A, subunit B, B55-delta isoform) (PP2A, subunit B, PR55-delta isoform) (PP2A, subunit B, R2-delta isoform); (5501:) Serine/threonine-protein phosphatase 2A 55 kDa regulatory subunit B gamma isoform (PP2A, subunit B, B-gamma isoform) (PP2A, subunit B, B55-gamma isoform) (PP2A, subunit B, PR55-gamma isoform) (PP2A, subunit B, R2-gamma isoform) (IMYPNO1); (5502:) Serine/threonine-protein phosphatase 2A 56 kDa regulatory subunit alpha isoform (PP2A, B subunit, B' alpha isoform) (PP2A, B subunit, B56 alpha isoform) (PP2A, B subunit, PR61 alpha isoform) (PP2A, B subunit, R5 alpha isoform); (5503:) Serine/threonine-protein phosphatase 2A 56 kDa regulatory subunit beta isoform (PP2A, B subunit, B' beta isoform) (PP2A, B subunit, B56 beta isoform) (PP2A, B subunit, PR61 beta isoform) (PP2A, B subunit, R5 beta isoform); (5504:) Serine/threonine-protein phosphatase 2A 56 kDa regulatory subunit delta isoform (PP2A, B subunit, B' delta isoform) (PP2A, B subunit, B56 delta isoform) (PP2A, B subunit, PR61 delta isoform) (PP2A, B subunit, R5 delta isoform); (5505:) Serine/threonine-protein phosphatase 2A 56 kDa regulatory subunit epsilon isoform (PP2A, B subunit, B' epsilon isoform) (PP2A, B subunit, B56 epsilon isoform) (PP2A, B subunit, PR61 epsilon isoform) (PP2A, B subunit, R5 epsilon isoform); (5506:) Serine/threonine-protein phosphatase 2A 56 kDa regulatory subunit gamma isoform (PP2A, B subunit, B' gamma isoform) (PP2A, B subunit, B56 gamma isoform) (PP2A, B subunit, PR61 gamma isoform) (PP2A, B subunit, R5 gamma isoform) (NY-REN-29 antigen); (5507:) Serine/threonine-protein phosphatase 2A 65 kDa regulatory subunit A beta isoform (PP2A, subunit A, PR65-beta isoform) (PP2A, subunit A, R1-beta isoform); (5508:) Serine/threonine-protein phosphatase 2A 65 kDa regulatory subunit A alpha isoform (PP2A, subunit A, PR65-alpha isoform) (PP2A, subunit A, R1-alpha isoform) (Medium tumor antigen-associated 61 kDa protein); (5509:) Serine/threonine-protein phosphatase 2A 72/130 kDa regulatory subunit B (PP2A, subunit B, B"-PR72/PR130) (PP2A, subunit B, B72/B130 isoforms) (PP2A, subunit B, PR72/PR130 isoforms) (PP2A, subunit B, R3 isoform); (5510:) Serine/threonine-protein phosphatase 2A catalytic subunit alpha isoform (PP2A-alpha) (Replication protein C) (RP-C); (5511:) Serine/threonine-protein phosphatase 2A catalytic subunit beta isoform (PP2A-beta); (5512:) Serine/threonine-protein phosphatase 2A regulatory subunit B'(PP2A, subunit B', PR53 isoform) (Phosphotyrosyl phosphatase activator) (PTPA); (5513:) Serine/threonine-protein phosphatase with EF-hands 1 (PPEF-1) (Protein phosphatase with EF calcium-binding domain) (PPEF) (Serine/threonine-protein phosphatase 7) (PP7); (5514:) Serine/threonine-protein phosphatase with EF-hands 2 (PPEF-2); (5515:) Serine-protein kinase ATM (Ataxia telangiectasia mutated) (A-T, mutated); (5516:) serum albumin precursor [*Homo sapiens*]; (5517:) Serum paraoxonase/arylesterase 1 (PON 1) (Serumaryidialkylphosphatase 1) (A-esterase 1) (Aromatic esterase 1) (K-45); (5518:) serum/glucocorticoid regulated kinase [*Homo sapiens*]; (5519:) seryl-tRNA synthetase [*Homo sapiens*]; (5520:) SET and MYND domain-containing protein 3 (Zinc finger MYND domain-containing protein 1); (5521:) SET domain-containing protein 7 [*Homo sapiens*]; (5522:) SH3-containing GRB2-like protein 2 (Endophilin-1) (Endophilin-A1) (SH3 domain protein 2A) (EEN-B1); (5523:) SH3-domain kinase-binding protein 1 (Cbl-interacting protein of 85 kDa) (Human Src-family kinase-binding protein 1) (HSB-1) (CD2-binding protein 3) (CD2BP3); (5524:) short/branched chain acyl-CoA dehydrogenase [*Homo sapiens*]; (5525:) Short/branched chain specific acyl-CoA dehydrogenase, mitochondrial precursor (SBCAD) (2-methyl branched chain acyl-CoA dehydrogenase) (2-MEBCAD) (2-methylbutyryl-coenzyme A dehydrogenase) (2-methylbutyryl-CoA dehydrogenase); (5526:) sialidase 2 [*Homo sapiens*]; (5527:) sialidase 3 [*Homo sapiens*]; (5528:) sialidase 4 [*Homo sapiens*]; (5529:) Sialidase-1 precursor (Lysosomal sialidase) (N-acetyl-alpha-neuraminidase 1) (Acetylneuraminyl hydrolase) (G9sialidase); (5530:) sialyltransferase 1 isoform a [*Homo sapiens*]; (5531:) sialyltransferase 1 isoform b [*Homo sapiens*]; (5532:) sialyltransferase 6 isoform a [*Homo sapiens*]; (5533:) sialyltransferase 6 isoform b [*Homo sapiens*]; (5534:) sialyltransferase 6 isoform c [*Homo sapiens*]; (5535:) sialyltransferase 6 isoform d [*Homo sapiens*]; (5536:) sialyltransferase 6 isoform e [*Homo sapiens*]; (5537:) sialyltransferase 6 isoform f [*Homo sapiens*]; (5538:) sialyltransferase 6 isoform g [*Homo sapiens*];

(5539:) sialyltransferase 6 isoform h [*Homo sapiens*]; (5540:) sialyltransferase 6 isoform i [*Homo sapiens*]; (5541:) sialyltransferase 6 isoform j [*Homo sapiens*]; (5542:) Sigma Receptor; (5543:) Sigma1 Receptor; (5544:) Sigma2 Receptor; (5545:) signal peptide peptidase-like 2β isoform 2 [*Homo sapiens*]; (5546:) signal peptide peptidase-like 2β isoform 3 [*Homo sapiens*]; (5547:) Signal recognition particle receptor subunit alpha (SR-alpha) (Docking protein alpha) (DP-alpha); (5548:) Signal recognition particle receptor subunit beta (SR-beta) (Protein APMCF1); (5549:) Signal Transducer and Activator of Transcription 1 (STAT1); (5550:) Signal Transducer and Activator of Transcription 3 (STAT3); (5551:) Signal Transducer and Activator of Transcription 4 (STAT4); (5552:) Signal transducing adapter molecule 2 (STAM-2); (5553:) signal transducing adaptor molecule 1 [*Homo sapiens*]; (5554:) signal transducing adaptor molecule 2 [*Homo sapiens*]; (5555:) Signal transduction protein CBL-C(SH3-binding protein CBL-C) (CBL-3) (RING finger protein 57); (5556:) Signaling lymphocytic activation molecule precursor (IPO-3) (CD150antigen) (CDw150); (5557:) Single-strand selective monofunctional uracil DNA glycosylase; (5558:) Sirtunin 1 (SIRT1); (5559:) skeletal myosin light chain kinase [*Homo sapiens*]; (5560:) Skin Protease (SPI); (5561:) SLAM family member 5 precursor (Signaling lymphocytic activation molecule 5) (Leukocyte differentiation antigen CD84) (CD84 antigen) (Cell surface antigen MAX.3) (Hly9-beta); (5562:) SLAM family member 6 precursor (NK-T-B-antigen) (NTB-A) (Activating NK receptor); (5563:) SLAM family member 7 precursor (CD2-like receptor activating cytotoxic cells) (CRACC) (Protein 19A) (CD2 subset 1) (Novel Ly9) (Membrane protein FOAP-12) (CD319 antigen); (5564:) SLC27A1 protein [*Homo sapiens*]; (5565:) SLC27A3 protein [*Homo sapiens*]; (5566:) Smad ubiquitination regulatory factor 1 (Ubiquitin—protein ligase SMURF1) (Smad-specific E3 ubiquitin ligase 1) (hSMURF1); (5567:) Smad ubiquitination regulatory factor 2 (Ubiquitin—protein ligase SMURF2) (Smad-specific E3 ubiquitin ligase 2) (hSMURF2); (5568:) "Small inducible cytokine A14 precursor (CCL14) (Chemokine CC-1/CC-3) (HCC-1/HCC-3) (HCC-1(1-74)) (NCC-2) [Contains:HCC-1(3-74); HCC-1 (4-74); HCC-1(9-74)]."; (5569:) small inducible cytokine A2 precursor [*Homo sapiens*]; (5570:) "Small inducible cytokine A5 precursor (CCL5) (T-cell-specific RANTES protein) (SIS-delta) (T cell-specific protein P228) (TCP228) [Contains:) RANTES(3-68); RANTES(4-68)]."; (5571:) small inducible cytokine B10 precursor [*Homo sapiens*]; (5572:) Small ubiquitin-related modifier 4 precursor (SUMO-4) (Small ubiquitin-like protein 4); (5573:) S-methyl-5-thioadenosine phosphorylase (5'-methylthioadenosinephosphorylase) (MTA phosphorylase) (MTAPase); (5574:) Smoothened homolog precursor (SMO) (Gx protein); (5575:) SMT3 suppressor of mif two 3 homolog 1 isoform a precursor [*Homo sapiens*]; (5576:) SMT3 suppressor of mif two 3 homolog 1 isoform b precursor [*Homo sapiens*]; (5577:) Sn1-specific diacylglycerol lipase alpha (DGL-alpha) (Neural stem cell-derived dendrite regulator); (5578:) Sn1-specific diacylglycerol lipase beta (DGL-beta) (KCCR13L); (5579:) snake venom-like protease [*Homo sapiens*]; (5580:) SNF-related serine/threonine-protein kinase (SNF1-related kinase); (5581:) Sodium bicarbonate cotransporter 3 (Sodium bicarbonate cotransporter 2) (Sodium bicarbonate cotransporter 2b) (Bicarbonate transporter) (Solute carrier family 4 member 7); (5582:) Sodium Hydrogen Exchange (NHE); (5583:) Sodium Hydrogen Exchange Isoform-1 (NHE-1); (5584:) Sodium Hydrogen Exchange Isoform-3 (NHE-3); (5585:) Sodium/calcium exchanger 1 precursor (Na(+)/Ca(2+)-exchange protein1); (5586:) Sodium/calcium exchanger 2 precursor (Na(+)/Ca (2+)-exchange protein2); (5587:) Sodium/calcium exchanger 3 precursor (Na(+)/Ca(2+)-exchange protein3); (5588:) Sodium/nucleoside cotransporter 2 (Na(+)/nucleoside cotransporter 2) (Sodium-coupled nucleoside transporter 2) (Concentrative nucleoside transporter 2) (CNT 2) (hCNT2) (Sodium/purine nucleoside co-transporter) (SPNT); (5589:) Sodium/potassium-transporting ATPase alpha-1 chain precursor (Sodium pump 1) (Na+/K+ ATPase 1); (5590:) Sodium/potassium-transporting ATPase alpha-2 chain precursor (Sodium pump 2) (Na+/K+ ATPase 2); (5591:) Sodium/potassium-transporting ATPase alpha-3 chain (Sodium pump 3) (Na+/K+ ATPase 3) (Alpha(III)); (5592:) Sodium/potassium-transporting ATPase alpha-4 chain (Sodium pump 4) (Na+/K+ ATPase 4); (5593:) Sodium/potassium-transporting ATPase subunit beta-1 (Sodium/potassium-dependent ATPase beta-1 subunit); (5594:) Sodium/potassium-transporting ATPase subunit beta-2(Sodium/potassium-dependent ATPase beta-2 subunit); (5595:) Sodium/potassium-transporting ATPase subunit beta-3(Sodium/potassium-dependent ATPase beta-3 subunit) (ATPB-3) (CD298antigen); (5596:) Sodium-Chloride Cotransporter (NCC); (5597:) Sodium-dependent phosphate transporter 1 (Solute carrier family 20member 1) (Phosphate transporter 1) (PiT-1) (Gibbon ape leukemia virus receptor 1) (GLVR-1) (Leukemia virus receptor 1 homolog); (5598:) Sodium-Glucose Cotransporter (SGLT); (5599:) Sodium-Glucose Cotransporter Type 1 (SGLT1); (5600:) Sodium-Glucose Cotransporter Type 2 (SGLT2); (5601:) Sodium-Potassium ATPase; (5602:) Sodium-Potassium-Chloride Cotransporter; (5603:) Soluble calcium-activated nucleotidase 1 (SCAN-1) (Apyrase homolog) (Putative NF-kappa-B-activating protein 107) (Putative MAPK-activating protein PM09); (5604:) soluble calcium-activated nucleotidase 1 [*Homo sapiens*]; (5605:) solute carrier family 2 (facilitated glucose transporter), member 1 [*Homo sapiens*]; (5606:) solute carrier family 27 (fatty acid transporter), member 2 [*Homo sapiens*]; (5607:) solute carrier family 7 (cationic amino acid transporter, y+system), member 1 [*Homo sapiens*]; (5608:) solute carrier family 7, member 2 isoform 1 [*Homo sapiens*]; (5609:) solute carrier family 7, member 2 isoform 2 [*Homo sapiens*]; (5610:) Somatostatin Receptor (SSTR); (5611:) Somatostatin Receptor 1 (SSTR1); (5612:) Somatostatin Receptor 2 (SSTR2); (5613:) Somatostatin Receptor 3 (SSTR3); (5614:) Somatostatin Receptor 5 (SSTR5); (5615:) Somatostatin receptor type 1 (SS1R) (SRIF-2); (5616:) Somatostatin receptor type 2 (SS2R) (SRIF-1); (5617:) Somatostatin receptor type 3 (SS3R) (SSR-28); (5618:) Somatostatin receptor type 4 (SS4R); (5619:) Somatostatin receptor type 5 (SS5R); (5620:) Sorbitol dehydrogenase (L-iditol 2-dehydrogenase); (5621:) sorbitol dehydrogenase [*Homo sapiens*]; (5622:) Sortilin precursor (Neurotensin receptor 3) (NTR3) (NT3) (Glycoprotein 95) (Gp95) (100 kDa NT receptor); (5623:) sortilin-related receptor containing LDLR class A repeats preproprotein [*Homo sapiens*]; (5624:) Sortilin-related receptor precursor (Sorting protein-related receptor containing LDLR class A repeats) (SorLA) (SorLA-1) (Low-density lipoprotein receptor relative with 11 ligand-binding repeats) (LDLR relative with 11 ligand-binding repeats) (LR11); (5625:) Sorting nexin-1; (5626:) Sorting nexin-2 (Transformation-related gene 9 protein) (TRG-9); (5627:) Sp1 transcription factor [*Homo sapiens*]; (5628:) spectrin, alpha, erythrocytic 1 [*Homo sapiens*]; (5629:) spen homolog, transcriptional regulator [*Homo sapiens*]; (5630:) sperm adhesion molecule 1 isoform 1 [*Homo sapiens*]; (5631:) sperm adhesion molecule 1 isoform 2 [*Homo sapiens*]; (5632:) Spermidine synthase (Putrescine aminopropyl transferase) (SPDSY); (5633:) spermidine synthase [*Homo sapiens*]; (5634:) Spermidine/Spermine N1-Acetyltransferase (SSAT); (5635:) spermidine/spermine N1-acetyltransferase [*Homo sapiens*]; (5636:) Spermine oxidase (Polyamine oxidase 1) (PAO-1) (PAOh1); (5637:) spermine synthase [*Homo sapiens*]; (5638:) S-phase kinase-associated protein 1A isoform a [*Homo sapiens*]; (5639:) S-phase kinase-associated protein 1A isoform b [*Homo sapiens*]; (5640:) S-phase kinase-associated protein 2 isoform 1 [*Homo sapiens*]; (5641:) S-phase kinase-associated protein 2 isoform 2 [*Homo sapiens*]; (5642:) sphingomyelin phosphodiesterase (EC 3.1.4.12)—human (fragments); (5643:) sphingomyelin phosphodiesterase [*Homo sapiens*]; (5644:) sphingomyelin phosphodiesterase 1, acid lysosomal isoform 1precursor [*Homo sapiens*]; (5645:) sphingomyelin phosphodiesterase 1, acid lysosomal isoform 2precursor [*Homo sapiens*]; (5646:) Sphingomyelin phosphodiesterase 3 (Neutral sphingomyelinase 2) (Neutral sphingomyelinase 11) (nSMase 2) (nSMase-2); (5647:) Sphingomyelin phosphodiesterase precursor (Acid sphingomyelinase) (aSMase); (5648:) Sphingosine 1-Phosphate (SIP) Receptor; (5649:) Sphingosine 1-Phosphate Receptor 1 (S1P1); (5650:) Sphingosine 1-phosphate receptor Edg-1 (Sphingosine 1-phosphate receptor 1) (S1P1); (5651:) Sphingosine 1-phosphate receptor Edg-3 (S1P receptor Edg-3) (Endothelial differentiation G-protein coupled receptor 3) (Sphingosine 1-phosphate receptor 3) (S1P3); (5652:) Sphingosine 1-phosphate receptor Edg-5 (S1P receptor Edg-5) (Endothelial differentiation G-protein coupled receptor 5) (Sphingosine 1-phosphate receptor 2) (S1P2); (5653:) Sphingosine 1-phosphate receptor Edg-6 (SIP receptor Edg-6) (Endothelial differentiation G-protein coupled receptor 6) (Sphingosine 1-phosphate receptor 4) (S1P4); (5654:) Sphingosine 1-phosphate receptor Edg-8 (Endothelial differentiation sphingolipid G-protein-coupled receptor 8) (Sphingosine 1-phosphate receptor 5) (S1P5); (5655:) Sphingosine 1-phosphate receptor GPR6 (G-protein coupled receptor6); (5656:) sphingosine kinase 1 isoform 1 [*Homo sapiens*]; (5657:) sphingosine kinase 1 isoform 2 [*Homo sapiens*]; (5658:) Sphingosylphosphorylcholine receptor (Ovarian cancer G-protein coupled receptor 1) (OGR-1) (G-protein coupled receptor 68) (GPR12A); (5659:) Spleen Tyrosine Kinase (Syk); (5660:) Squalene Synthase; (5661:) Squalene synthetase (SQS) (SS) (Farnesyl-diphosphate farnesyltransferase) (FPP:FPP farnesyltransferase); (5662:) Sqv-8-like protein [*Homo sapiens*]; (5663:) Src Homology-2-Containing Protein Tyrosine Phosphatase-1 (SHP-1); (5664:) Src Tyrosine Kinase (STK); (5665:) SRC/ABL Kinase; (5666:) SRP RNA 3' adenylating enzyme/pap2 [*Homo sapiens*]; (5667:) SRR [*Homo sapiens*]; (5668:) ST3 beta-galactoside alpha-2,3-sialyltransferase 5 isoform 1 [*Homo sapiens*]; (5669:) ST3 beta-galactoside alpha-2,3-sialyltransferase 5 isoform 2 [*Homo sapiens*]; (5670:) ST8 alpha-N-acetyl-neuraminide alpha-2,8-sialyltransferase 1 [*Homo sapiens*]; (567-1:) Stabilin-1 precursor (FEEL-1 protein) (MS-1 antigen); (5672:) Stabilin-2 precursor (FEEL-2 protein) (Fasciclin EGF-like laminin-type EGF-like and link domain-containing scavenger receptor1) (FAS1 EGF-like and X-link domain-containing adhesion molecule 2) (Hyaluronan receptor for endocytosis) [Contains:) 190 kDa formstabilin-2 (190 kDa hyaluronan receptor for endocytosis)]; (5673:) STAM binding protein [*Homo sapiens*]; (5674:) STAM-binding protein (Associated molecule with the SH3 domain of STAM); (5675:) *Staphylococcus aureus* Methionyl-tRNA Synthetase (MetS); (5676:) steaoryl-CoA desaturase [*Homo sapiens*]; (5677:) stearoyl-CoA desaturase 4 isoform a [*Homo sapiens*]; (5678:) stearoyl-CoA desaturase 4 isoform b [*Homo sapiens*]; (5679:) steroid dehydrogenase homolog [*Homo sapiens*]; (5680:) Steroid hormone receptor ERR1 (Estrogen-related receptor, alpha) (ERR-alpha) (Estrogen receptor-like 1); (5681:) Steroid hormone receptor ERR2 (Estrogen-related receptor, beta) (ERR-beta) (Estrogen receptor-like 2) (ERR beta-2); (5682:) Steroid receptor RNA activator 1 (Steroid receptor RNA activator protein) (SRAP); (5683:) steroid sulfatase [*Homo sapiens*]; (5684:) Steroid X Receptor (SXR); (5685:) steroid-5-alpha-reductase 1 [*Homo sapiens*]; (5686:) Steroidogenic factor 1 (STF-1) (SF-1) (Adrenal 4-binding protein) (Steroid hormone receptor Ad4BP) (Fushi tarazu factor homolog 1); (5687:) sterol O-acyltransferase (acyl-Coenzyme A:) cholesterolacyltransferase) 1 [*Homo sapiens*]; (5688:) sterol-C5-desaturase-like [*Homo sapiens*]; (5689:) steryl-sulfatase precursor [*Homo sapiens*]; (5690:) Stomach Acid Neutralizer; (5691:) Stratum Corneum Chymotryptic Enzyme (SCCE); (5692:) stratum corneum chymotryptic enzyme [*Homo sapiens*]; (5693:) stratum corneum chymotryptic enzyme preproprotein [*Homo sapiens*]; (5694:) stratum corneum chymotryptic enzyme; (5695:) stratum corneum tryptic enzyme [*Homo sapiens*]; (5696:) Stress-Associated Endoplasmic Reticulum Protein 1 (SERP1); (5697:) Substance-K receptor (SKR) (Neurokinin A receptor) (NK-2 receptor) (NK-2R) (Tachykinin receptor 2); (5698:) Substance-P receptor (SPR) (NK-1 receptor) (NK-1R) (Tachykinin receptor 1); (5699:) Substrate Binding And Catalysis By Glutathione Reductase As Derived From Refined Enzyme:) Substrate Crystal Structures At 2 Angstroms Resolution; (5700:) subtilisin-like proprotein convertase (EC 3.4.21.-) homolog-human; (5701:) succinate dehydrogenase complex, subunit A, flavoprotein precursor[*Homo sapiens*]; (5702:) succinate dehydrogenase complex, subunit B, iron sulfur (Ip) [*Homo sapiens*]; (5703:) succinate dehydrogenase complex, subunit C isoform 1 precursor[*Homo sapiens*]; (5704:) succinate dehydrogenase complex, subunit C isoform 2 precursor[*Homo sapiens*]; (5705:) succinate dehydrogenase complex, subunit C isoform 3 precursor [*Homo sapiens*]; (5706:) succinate dehydrogenase complex, subunit C isoform 4 precursor[*Homo sapiens*]; (5707:) succinate dehydrogenase complex, subunit D precursor [*Homo sapiens*]; (5708:) succinate dehydrogenase flavoprotein subunit; (5709:) Succinate receptor 1 (G-protein coupled receptor 91) (P2Y purinoceptor 1-like); (5710:) Succinate semialdehyde dehydrogenase, mitochondrial precursor (NAD (+)-dependent succinic semialdehyde dehydrogenase); (5711:) succinate-CoA ligase, ADP-forming, beta subunit [*Homo sapiens*]; (5712:) succinyl CoA:3-oxoacid CoA transferase precursor; (5713:) Succinyl-CoA ligase [ADP-forming] beta-chain, mitochondrial precursor (Succinyl-CoA synthetase, betaA chain) (SCS-betaA) (ATP-specific succinyl-CoA synthetase subunit beta) (NY-REN-39antigen); (5714:) Succinyl-CoA:3-ketoacid-coenzyme A transferase 1, mitochondrial precursor (Somatic-type succinyl CoA:3-oxoacid CoA-transferase) (Scot-S); (5715:) Succinyl-CoA:3-ketoacid-coenzyme A transferase 2, mitochondrial precursor (Testis-specific succinyl CoA:3-oxoacid CoA-transferase) (SCOT-t); (5716:) "Sucrase-isomaltase, intestinal [Contains:) Sucrase; Isomaltase]."; (5717:) Sulfatase; (5718:) sulfatase modifying factor 1 [*Homo sapiens*]; (5719:) sulfatase modifying factor 2 isoform a precursor [*Homo sapiens*]; (5720:) sulfatase modifying factor 2 isoform b precursor [*Homo sapiens*]; (5721:) sulfatase modifying factor 2 isoform c precursor [*Homo sapiens*]; (5722:) sulfatase modifying factor 2 isoform d precursor [*Homo sapiens*]; (5723:) Sulfatase-modifying factor 1 precursor (C-alpha-formyglycine-generating enzyme 1); (5724:) Sulfatase-modifying factor 2 precursor (C-alpha-formyglycine-generating enzyme 2); (5725:) sulfite oxidase [*Homo sapiens*]; (5726:) Sulfite oxidase, mitochondrial precursor; (5727:) Sulfonylurea Receptor 1 (SUR1); (5728:) Sulfotransferase 1A1 (Aryl sulfotransferase 1) (Phenolsulfotransferase 1) (Phenol-sulfating phenol sulfotransferase 1) (P-PST 1) (Thermostable phenol sulfotransferase) (Ts-PST) (HAST1/HAST2) (ST1A3); (5729:) sulfotransferase family, cytosolic, 1A, phenol-preferring, member 1 isoform a [*Homo sapiens*]; (5730:) sulfotransferase family, cytosolic, 1A, phenol-preferring, member 1 isoform b [*Homo sapiens*]; (5731:) sulfotransferase family, cytosolic, 1A, phenol-preferring, member 2 [*Homo sapiens*]; (5732:) sulfotransferase family, cytosolic, 1A, phenol-preferring, member 3 [*Homo sapiens*]; (5733:) sulfotransferase family, cytosolic, 1A, phenol-preferring, member 4 [*Homo sapiens*]; (5734:) sulfotransferase family, cytosolic, 2A, dehydroepiandrosterone-preferring, member 1 [*Homo sapiens*]; (5735:) sulfotransferase family, cytosolic, 2B, member 1 isoform a [*Homo sapiens*]; (5736:) sulfotransferase family, cytosolic, 2B, member 1 isoform b [*Homo sapiens*]; (5737:) SUMO1 activating enzyme subunit 1 [*Homo sapiens*]; (5738:) SUMO-1 activating enzyme subunit 1 [*Homo sapiens*]; (5739:) SUMO1 activating enzyme subunit 2 [*Homo sapiens*]; (5740:) SUMO-1 activating enzyme subunit 2 [*Homo sapiens*]; (5741:) SUMO-1 activating enzyme subunit 2 variant [*Homo sapiens*]; (5742:) SUMO-1-activating enzyme E1 C subunit [*Homo sapiens*]; (5743:) SUMO-1-activating enzyme E1 N subunit [*Homo sapiens*]; (5744:) SUMO-1-conjugating enzyme UBC9 (SUMO-1-protein ligase) (Ubiquitin-conjugating enzyme E2 I) (Ubiquitin-protein ligase I) (Ubiquitin carrier protein 1) (Ubiquitin carrier protein 9) (p18); (5745:) Superoxide Dismutase (SOD) Mimetic; (5746:) Superoxide dismutase [Cu—Zn]; (5747:) Superoxide Dismutase 1 (SOD1); (5748:) superoxide dismutase 1, soluble [*Homo sapiens*]; (5749:) suppressor of variegation 3-9 homolog 1 [*Homo sapiens*]; (5750:) SUR5 [*Homo sapiens*]; (5751:) Survivin; (5752:) SWI/SNF related, matrix associated, actin dependent regulator of chromatin, subfamily b, member 1 isoform a [*Homo sapiens*]; (5753:) SWI/SNF related, matrix associated, actin dependent regulator of chromatin, subfamily b, member 1 isoform b [*Homo sapiens*]; (5754:) SWI/SNF-related matrix-associated actin-dependent regulator of chromatin a4 [*Homo sapiens*]; (5755:) SWI/SNF-related matrix-associated actin-dependent regulator of chromatin a5 [*Homo sapiens*]; (5756:) synapsin I [*Homo sapiens*]; (5757:) synapsin I isoform Ia [*Homo sapiens*]; (5758:) synapsin I isoform Ib [*Homo sapiens*]; (5759:) Synapsin-1 (Synapsin I) (Brain protein 4.1); (5760:) synaptojanin 2 binding protein [*Homo sapiens*]; (5761:) synuclein alpha interacting protein [*Homo sapiens*]; (5762:) synuclein, gamma (breast cancer-specific protein 1) [*Homo sapiens*]; (5763:) T cell receptor delta chain [*Homo sapiens*]; (5764:) tachykinin receptor 1 isoform long [*Homo sapiens*]; (5765:) tachykinin receptor 1 isoform short [*Homo sapiens*]; (5766:) TAF2 protein [*Homo sapiens*]; (5767:) TAF9 RNA polymerase II isoform b [*Homo sapiens*]; (5768:) TAF9 RNA polymerase II isoform c [*Homo sapiens*]; (5769:) TAF9 RNA polymerase II, TATA box binding protein (TBP)-associated factor, 32 kDa [*Homo sapiens*]; (5770:) talin 1 [*Homo sapiens*]; (5771:) TANK-binding kinase 1 [*Homo sapiens*]; (5772:) tartrate resistant acid phosphatase 5 precursor [*Homo sapiens*]; (5773:) Taste receptor type 1 member 1 precursor (G-protein coupled receptor 70); (5774:) Taste receptor type 1 member 2 precursor (G-protein coupled receptor 71) (Sweet taste receptor T1R2); (5775:) Taste receptor type 1 member 3 precursor (Sweet taste receptor T1 R3); (5776:) Taste receptor type 2 member 1 (T2R1) (Taste receptor family B member 7) (TRB7); (5777:) Taste receptor type 2 member 10 (T2R10) (Taste receptor family B member 2) (TRB2); (5778:) Taste receptor type 2 member 13 (T2R13) (Taste receptor family B member 3) (TRB3); (5779:) Taste receptor type 2 member 14 (T2R14) (Taste receptor family B member 1) (TRB1); (5780:) Taste receptor type 2 member 16 (T2R16); (5781:) Taste receptor type 2 member 3 (T2R3); (5782:) Taste receptor type 2 member 38 (T2R38) (T2R61) (PTC bitter taste receptor); (5783:) Taste receptor type 2 member 39 (T2R39) (T2R57); (5784:) Taste receptor type 2 member 4 (T2R4); (5785:) Taste receptor type 2 member 40 (T2R40) (T2R58) (G-protein coupled receptor 60); (5786:) Taste receptor type 2 member 41 (T2R41) (T2R59); (5787:) Taste receptor type 2 member 42 (T2R42) (T2R55); (5788:) Taste receptor type 2 member 43 (T2R43) (T2R52); (5789:) Taste receptor type 2 member 44 (T2R44) (T2R53); (5790:) Taste receptor type 2 member 45 (T2R45) (G-protein coupled receptor59); (5791:) Taste receptor type 2 member 46 (T2R46) (T2R54); (5792:) Taste receptor type 2 member 47 (T2R47); (5793:) Taste receptor type 2 member 48 (T2R48); (5794:) Taste receptor type 2 member 49 (T2R49) (T2R56); (5795:) Taste receptor type 2 member 5 (T2R5); (5796:) Taste receptor type 2 member 50 (T2R50) (T2R51); (5797:) Taste receptor type 2 member 60 (T2R60) (T2R56); (5798:) Taste receptor type 2 member 7 (T2R7) (Taste receptor family B member 4) (TRB4); (5799:) Taste receptor type 2 member 8 (T2R8) (Taste receptor family B member 5) (TRB5); (5800:) Taste receptor type 2 member 9 (T2R9) (Taste receptor family B member 6) (TRB6); (5801:) TBP-associated factor 1 isoform 1 [*Homo sapiens*]; (5802:) TBP-associated factor 1 isoform 2 [*Homo sapiens*]; (5803:) T-cell antigen CD7 precursor (GP40) (T-cell leukemia antigen) (TP41) (Leu-9); (5804:) T-cell receptor alpha chain (clone A21)—human (fragment); (5805:) T-cell receptor alpha chain (Mb11a) precursor—human (fragment); (5806:) T-cell receptor alpha chain C region; (5807:) T-cell receptor alpha chain V region CTL-L17 precursor; (5808:) T-cell receptor alpha chain V region HPB-MLT precursor; (5809:) T-cell receptor alpha chain V region PY14 precursor; (5810:) T-cell receptor beta chain C region; (5811:) T-cell receptor beta chain V region—human (fragment); (5812:) T-cell receptor beta chain V region CTL-L17 precursor; (5813:) T-cell receptor beta chain V region YT35 precursor; (5814:) T-cell receptor gamma chain C region PT-gamma-1/2; (5815:) T-cell receptor gamma chain V region PT-gamma-1/2 precursor; (5816:) T-cell receptor Vb CDR3, carrier PBL Vb 12a.sbt—human (fragment); (5817:) T-cell receptor Vb CDR3, carrier PBL Vb 12b.sbt—human (fragment); (5818:) T-cell receptor Vb CDR3, carrier PBL Vb 2.sbt—human (fragment); (5819:) T-cell receptor Vb CDR3, carrier PBL Vb 6.sbt—human (fragment); (5820:) T-cell receptor Vb CDR3, carrier PBL Vb 7.sbt—human (fragment); (5821:) T-cell receptor Vb CDR3, carrier Vb 17.sbt—human (fragment); (5822:) T-cell receptor Vb CDR3, Ctrl TCR Vb 12 CDR3aa.sbt—human (fragment); (5823:) T-cell receptor Vb CDR3, Ctrl TCR Vb 7CDR3aas.sbt—human (fragment); (5824:) T-cell receptor Vb CDR3, Ctrl TCR Vb8 CDR3aas.sbt—human (fragment); (5825:) T-cell receptor Vb CDR3, Ctr2 TCR Vb12 CDR3aa.sbt—human (fragment); (5826:) T-cell receptor Vb CDR3, HAM1TCR Vb12b CDR3a.sbt—human (fragment); (5827:) T-cell receptor Vb CDR3, HAM1TCR Vb14 CDR3a.sbt—human (fragment); (5828:) T-cell receptor Vb CDR3, HAM1TCR Vb5a CDR3a.sbt—human (fragment); (5829:) T-cell receptor Vb CDR3, HAM1TCR Vb5b CDR3a.sbt—human (fragment); (5830:) T-cell receptor Vb CDR3, HAM1TCR Vb5C CDR3aa.sbt—human (fragment); (5831:) T-cell receptor Vb CDR3, HAM1TCR Vb5d CDR3a.sbt—human (fragment); (5832:) T-cell receptor Vb CDR3, HAM1TCR Vb6b CDR3a.sbt—human (fragment); (5833:) T-cell receptor Vb CDR3, HAM1TCR Vb7a CDR3a.sbt—human (fragment); (5834:) T-cell receptor Vb CDR3, HAM1TCR Vb7b CDR3a.sbt—human (fragment); (5835:) T-cell receptor Vb CDR3, HAM1TCR Vb8a CDR3a.sbt—human (fragment); (5836:) T-cell receptor Vb CDR3, HAM1TCR Vb8b CDR3a.sbt—human (fragment); (5837:) T-cell receptor Vb CDR3, HAM2TCR Vb 19a.sbt—human (fragment); (5838:) T-cell receptor Vb CDR3, HAM2TCR Vb17 CDR3a.sbt—human (fragment); (5839:) T-cell receptor Vb CDR3, HAM2TCR Vb19b CDR3a.sbt—human (fragment); (5840:) T-cell receptor Vb CDR3, HAM2TCR Vb6a CDR3a.sbt—human (fragment); (5841:) T-cell receptor Vb CDR3, HAM2TCR Vb6b CDR3a.sbt—human (fragment); (5842:) T-cell receptor Vb CDR3, HAM2TCR Vb8a CDR3a.sbt—human (fragment); (5843:) T-cell receptor Vb CDR3, HAM2TCR Vb8c CDR3a.sbt—human (fragment); (5844:) T-cell receptor zeta chain isoform 1 precursor [*Homo sapiens*]; (5845:) T-cell receptor zeta chain isoform 2 precursor [*Homo sapiens*]; (5846:) T-cell surface glycoprotein CD3 delta chain precursor (T-cell receptor T3 delta chain); (5847:) T-cell surface glycoprotein CD3 epsilon chain precursor (T-cell surface antigen T3/Leu-4 epsilon chain); (5848:) T-cell surface glycoprotein CD3 gamma chain precursor (T-cell receptor T3 gamma chain); (5849:) T-cell surface glycoprotein CD3 zeta chain precursor (T-cell receptor T3 zeta chain) (CD237 antigen); (5850:) T-cell, immune regulator 1 isoform a [*Homo sapiens*]; (5851:) T-cell, immune regulator 1 isoform b [*Homo sapiens*]; (5852:) TEA domain family member 3 [*Homo sapiens*]; (5853:) TEK Receptor Tyrosine Kinase Activator; (5854:) Telomerase; (5855:) Telomerase Activator; (5856:) Telomerase reverse transcriptase (Telomerase catalytic subunit) (HEST2) (Telomerase-associated protein 2) (TP2); (5857:) telomerase reverse transcriptase isoform 1 [*Homo sapiens*]; (5858:) telomerase reverse transcriptase isoform 2 [*Homo sapiens*]; (5859:) terminal deoxynucleotidyltransferase isoform 1 [*Homo sapiens*]; (5860:) terminal deoxynucleotidyltransferase isoform 2 [*Homo sapiens*]; (5861:) testicular ECA [*Homo sapiens*]; (5862:) testisin isoform 1 [*Homo sapiens*]; (5863:) testisin isoform 2 [*Homo sapiens*]; (5864:) testisin isoform 3 [*Homo sapiens*]; (5865:) Testisin precursor (Eosinophil serine protease 1) (ESP-1); (5866:) Testis-specific serine/threonine-protein kinase 1 (TSSK-1) (Testis-specific kinase 1) (TSK-1) (Serine/threonine-protein kinase 22A); (5867:) Testis-specific serine/threonine-protein kinase 2 (TSSK-2) (Testis-specific kinase 2) (TSK-2) (Serine/threonine-protein kinase 22B) (DiGeorge syndrome protein G); (5868:) Testis-specific serine/threonine-protein kinase 3 (TSSK-3) (Testis-specific kinase 3) (TSK-3) (Serine/threonine-protein kinase 22C); (5869:) Testis-specific serine/threonine-protein kinase 4 (TSSK-4) (Testis-specific kinase 4) (TSK-4) (Serine/threonine-protein kinase 22E); (5870:) TGF-beta receptor type III precursor (TGFR-3) (Transforming growth factor beta receptor III) (Betaglycan); (5871:) TGF-beta receptor type-1 precursor (TGF-beta receptor type I) (TGFR-1) (TGF-beta type I receptor) (Serine/threonine-protein kinase receptor R4) (SKR4) (Activin receptor-like kinase 5) (ALK-5); (5872:) TGF-beta receptor type-2 precursor (TGF-beta receptor type II) (TGFR-2) (TGF-beta type II receptor) (Transforming growth factor-beta receptor type II) (TbetaR-II); (5873:) The Solution Structure Of Reduced Monomeric Superoxide Dismutase, Nmr, 36 Structures; (5874:) thimet oligopeptidase 1 [*Homo sapiens*]; (5875:) thioesterase 11 [*Homo sapiens*]; (5876:) Thiopurine S-methyltransferase (Thiopurine methyltransferase); (5877:) thiopurine S-methyltransferase [*Homo sapiens*]; (5878:) thioredoxin [*Homo sapiens*]; (5879:) Thioredoxin domain-containing protein 2 (Spermatid-specific thioredoxin-1) (Sptrx-1); (5880:) Thioredoxin domain-containing protein 6 (Thioredoxin-like protein2) (Txl-2); (5881:) thioredoxin peroxidase [*Homo sapiens*]; (5882:) Thioredoxin Reductase (TrxR); (5883:) thioredoxin reductase [*Homo sapiens*]; (5884:) thioredoxin reductase 1 [*Homo sapiens*]; (5885:) thioredoxin reductase 2 precursor [*Homo sapiens*]; (5886:) Thioredoxin-1 (Trx-1); (5887:) Thioredoxin-dependent peroxide reductase, mitochondrial precursor (Peroxiredoxin-3) (PRX III) (Antioxidant protein 1) (AOP-1) (Protein MER5 homolog) (HBC189); (5888:) thiosulfate sulfurtransferase [*Homo sapiens*]; (5889:) Three prime repair exonuclease 1 (3'-5' exonuclease TREX1) (DNaseIII); (5890:) three prime repair exonuclease 1 isoform a [*Homo sapiens*]; (5891:) three prime repair exonuclease 1 isoform b [*Homo sapiens*]; (5892:) three prime repair exonuclease 1 isoform c [*Homo sapiens*]; (5893:) three prime repair exonuclease 1 isoform d [*Homo sapiens*]; (5894:) three prime repair exonuclease 2 [*Homo sapiens*]; (5895:) "Threonine aspartase 1 (Taspase-1) [Contains:) Threonine aspartase subunit alpha; Threonine aspartase subunit beta]."; (5896:) Threonine synthase-like 1 (bacterial) [*Homo sapiens*]; (5897:) threonine synthase-like 1 [*Homo sapiens*]; (5898:) Threonine synthase-like 1; (5899:) Thrombin; (5900:) Thrombin Receptor; (5901:) Thrombomodulin precursor (TM) (Fetomodulin) (CD141 antigen); (5902:) Thrombomodulin Receptor; (5903:) Thrombopoietin (TPO) Receptor; (5904:) Thrombopoietin receptor precursor (TPO-R) (Myeloproliferative leukemia protein) (C-mpl) (CD110 antigen); (5905:) Thrombospondin-1 (TSP-1); (5906:) Thromboxane (TX) Synthesis; (5907:) thromboxane A synthase 1 (platelet, cytochrome P450, family 5, subfamily A) isoform TXS-I [*Homo sapiens*]; (5908:) thromboxane A synthase 1 (platelet, cytochrome P450, family 5, subfamily A) isoform TXS-11 [*Homo sapiens*]; (5909:) Thromboxane A2 (TXA2) Receptor; (5910:) Thromboxane A2 receptor (TXA2-R) (Prostanoid TP receptor); (5911:) thymidine kinase 1, soluble [*Homo sapiens*]; (5912:) thymidine kinase 2 [*Homo sapiens*]; (5913:) thymidine kinase 2, mitochondrial [*Homo sapiens*]; (5914:) Thymidine kinase 2, mitochondrial precursor (Mt-TK); (5915:) Thymidine kinase, cytosolic; (5916:) Thymidine Phosphorylase (TP); (5917:) Thymidylate Synthase (TS); (5918:) thymidylate synthetase [*Homo sapiens*]; (5919:) thymine-DNA glycosylase [*Homo sapiens*]; (5920:) Thyroid Hormone Receptor (TR); (5921:) Thyroid hormone receptor alpha (C-erbA-alpha) (c-erbA-1) (EAR-7) (EAR7); (5922:) Thyroid hormone receptor beta-1; (5923:) Thyroid hormone receptor beta-2; (5924:) Thyroid hormone receptor-associated protein 2 (Thyroid hormone receptor-associated protein complex 240 kDa component-like); (5925:) Thyroid hormone receptor-associated protein 3 (Thyroid hormone receptor-associated protein complex 150 kDa component) (Trap150); (5926:) Thyroid hormone receptor-associated protein complex 240 kDa component (Trap240) (Thyroid hormone receptor-associated protein 1) (Vitamin D3 receptor-interacting protein complex component DRIP250) (DRIP 250) (Activator-recruited cofactor 250 kDa component) (ARC250); (5927:) Thyroid Hormone Receptor-Beta (TR Beta); (5928:) Thyroid Peroxidase; (5929:) thyroid peroxidase [*Homo sapiens*]; (5930:) thyroid peroxidase isoform a [*Homo sapiens*]; (5931:) thyroid peroxidase isoform b [Homo sapiens]; (5932:) thyroid peroxidase isoform c [Homo sapiens]; (5933:) thyroid peroxidase isoform d [Homo sapiens]; (5934:) thyroid peroxidase isoform e [Homo sapiens]; (5935:) Thyroid peroxidase precursor (TPO); (5936:) Thyroid receptor-interacting protein 12 (TRIP12); (5937:) Thyrotropin receptor precursor (TSH-R) (Thyroid-stimulating hormone receptor); (5938:) Thyrotropin-Releasing Hormone (TRH) Receptor; (5939:) thyrotropin-releasing hormone degrading enzyme [Homo sapiens]; (5940:) Thyrotropin-releasing hormone receptor (TRH-R) (Thyroliberin receptor); (5941:) Tie-1 Receptor Tyrosine Kinase; (5942:) TIGD5 protein [Homo sapiens]; (5943:) Tissue alpha-L-fucosidase precursor (Alpha-L-fucosidase I) (Alpha-L-fucoside fucohydrolase); (5944:) Tissue Factor; (5945:) tissue inhibitor of metalloproteinase 1 precursor [Homo sapiens]; (5946:) tissue inhibitor of metalloproteinase 2 precursor [Homo sapiens]; (5947:) tissue inhibitor of metalloproteinase 3 precursor [Homo sapiens]; (5948:) tissue inhibitor of metalloproteinase 4 precursor [Homo sapiens]; (5949:) tissue non-specific alkaline phosphatase precursor [Homo sapiens]; (5950:) Tissue Plasminogen Activator (tPA); (5951:) tissue plasminogen activator (t-PA) [Homo sapiens]; (5952:) "Tissue-type plasminogen activator precursor (tPA) (t-PA) (t-plasminogen activator) (Alteplase) (Reteplase) [Contains:Tissue-type plasminogen activator chain A; Tissue-type plasminogen activator chain B]."; (5953:) Titin (Connectin) (Rhabdomyosarcoma antigen MU-RMS-40.14); (5954:) TLL1 protein [Homo sapiens]; (5955:) TLL2 protein [Homo sapiens]; (5956:) T-lymphocyte activation antigen CD80 precursor (Activation B7-1 antigen) (CTLA-4 counter-receptor B7.1) (B7) (BB1); (5957:) T-lymphocyte activation antigen CD86 precursor (Activation B7-2antigen) (CTLA-4 counter-receptor B7.2) (B70) (FUN-1) (BU63); (5958:) T-lymphokine-activated killer cell-originated protein kinase (T-LAK cell-originated protein kinase) (PDZ-binding kinase) (Spermatogenesis-related protein kinase) (SPK) (MAPKK-like protein kinase) (Nori-3); (5959:) TNF receptor-associated factor 2 (Tumor necrosis factor type 2receptor-associated protein 3); (5960:) TNF receptor-associated factor 6 (Interleukin 1 signal transducer) (RING finger protein 85); (5961:) TNF receptor-associated factor 6 [Homo sapiens]; (5962:) TNF-alpha converting enzyme [Homo sapiens]; (5963:) TNF-alpha converting enzyme precursor [Homo sapiens]; (5964:) Toll-Like Receptor (TLR); (5965:) Toll-like receptor 1 precursor (Toll/interleukin-1 receptor-like protein) (TIL) (CD281 antigen); (5966:) Toll-like receptor 10 precursor (CD290 antigen); (5967:) Toll-like receptor 2 precursor (Toll/interleukin 1 receptor-like protein 4) (CD282 antigen); (5968:) Toll-Like Receptor 3 (TLR3); (5969:) Toll-like receptor 3 precursor (CD283 antigen); (5970:) Toll-Like Receptor 4 (TLR4); (5971:) Toll-like receptor 4 precursor (hToll) (CD284 antigen); (5972:) toll-like receptor 4 precursor [Homo sapiens]; (5973:) Toll-like receptor 5 precursor (Toll/interleukin-1 receptor-like protein 3); (5974:) Toll-like receptor 6 precursor; (5975:) Toll-Like Receptor 7 (TLR7); (5976:) Toll-like receptor 7 precursor; (5977:) Toll-like receptor 8 precursor (CD288 antigen); (5978:) Toll-Like Receptor 9 (TLR9); (5979:) Toll-like receptor 9 precursor (CD289 antigen); (5980:) topoisomerase (DNA) III alpha [Homo sapiens]; (5981:) topoisomerase (DNA) III beta [Homo sapiens]; (5982:) Topoisomerase I; (5983:) Topoisomerase II; (5984:) Topoisomerase IV; (5985:) topoisomerase-related function protein [Homo sapiens]; (5986:) TP53-induced glycolysis and apoptosis regulator [Homo sapiens]; (5987:) TPA:) ubiquitin-specific protease 17-like protein [Homo sapiens]; (5988:) TPA-exp:) cytosolic 5'(3')-deoxyribonucleotidase [Homo sapiens]; (5989:) TPK1 protein [Homo sapiens]; (5990:) Trace amine-associated receptor 1 (Trace amine receptor 1) (TaR-1); (5991:) Trace amine-associated receptor 2 (G-protein coupled receptor 58); (5992:) Trace amine-associated receptor 3 (G-protein coupled receptor 57); (5993:) Trace amine-associated receptor 5 (Putative neurotransmitter receptor); (5994:) Trace amine-associated receptor 6 (Trace amine receptor 4) (TaR-4); (5995:) Trace amine-associated receptor 8 (Trace amine receptor 5) (TaR-5) (G-protein coupled receptor 102); (5996:) Trace amine-associated receptor 9 (Trace amine receptor 3) (TaR-3); (5997:) TRAF6-regulated IKK activator 1 beta Uev1A [Homo sapiens]; (5998:) Trans-2-enoyl-CoA reductase, mitochondrial precursor (HsNrbf-1) (NRBF-1); (5999:) transacylase [Homo sapiens]; (6000:) transaldolase 1 [Homo sapiens]; (6001:) Transcription elongation factor B (SIII), polypeptide 2 (18 kDa, elongin B) [Homo sapiens]; (6002:) Transcription elongation factor B polypeptide 2 (RNA polymerase II transcription factor SIII subunit B) (SIII p18) (Elongin B) (EloB) (Elongin 18 kDa subunit); (6003:) Transcription elongation factor SPT4 (hSPT4) (DRB sensitivity-inducing factor small subunit) (DSIF small subunit) (DSIF p14); (6004:) Transcription elongation factor SPT5 (hSPT5) (DRB sensitivity-inducing factor large subunit) (DSIF large subunit) (DSIF p160) (Tat-cotransactivator 1 protein) (Tat-CT1 protein); (6005:) transcription factor 1, hepatic [Homo sapiens]; (6006:) transcription factor AP-2 alpha isoform a [Homo sapiens]; (6007:) transcription factor AP-2 alpha isoform b [Homo sapiens]; (6008:) transcription factor AP-2 alpha isoform c [Homo sapiens]; (6009:) transcription factor AP-2 beta (activating enhancer binding protein2 beta) [Homo sapiens]; (6010:) transcription factor AP-2 gamma [Homo sapiens]; (6011:) Transcription factor CP2-like protein 1 (CP2-related transcriptional repressor 1) (CRTR-1) (Transcription factor LBP-9); (6012:) transcription factor LBP-1b [Homo sapiens]; (6013:) transcription factor LBP-9 [Homo sapiens]; (6014:) Transcription factor p65 (Nuclear factor NF-kappa-B p65 subunit); (6015:) transcription factor-like protein 4 isoform alpha [Homo sapiens]; (6016:) transcription factor-like protein 4 isoform beta [Homo sapiens]; (6017:) transcription factor-like protein 4 isoform gamma [Homo sapiens]; (6018:) Transcription initiation factor IIF alpha subunit (TFIIF-alpha) (Transcription initiation factor RAP74) (General transcription factor IIF polypeptide 174 kDa subunit protein); (6019:) Transcription initiation factor TFIID subunit 1 (Transcription initiation factor TFIID 250 kDa subunit) (TAF(II)250) (TAFII-250) (TAFII250) (TBP-associated factor 250 kDa) (p250) (Cell cycle gene 1 protein); (6020:) Transcriptional repressor NF-X1 (Nuclear transcription factor, Xbox-binding, 1); (6021:) transferrin [Homo sapiens]; (6022:) Transferrin Receptor (Tf-R); (6023:) Transferrin receptor protein 1 (TfR1) (TR) (TfR) (Trfr) (CD71 antigen) (T9) (p90); (6024:) Transferrin receptor protein 2 (TfR2); (6025:) Transforming growth factor-beta (TGF-beta); (6026:) Transforming growth factor-beta 1 (TGF-beta 1); (6027:) Transforming growth factor-beta 2 (TGF-beta 2); (6028:) Transforming growth factor alpha (TGF-alpha); (6029:) transforming growth factor, alpha [Homo sapiens]; (6030:) transforming growth factor, beta 1 [Homo sapiens]; (6031:) transforming growth factor, beta receptor 11 isoform A precursor[Homo sapiens]; (6032:) transforming growth factor, beta receptor 11 isoform B precursor[Homo sapiens]; (6033:) Transforming Growth Factor-Beta3 (TGF-Beta3) Receptor; (6034:) Transglutaminase (TGase); (6035:) transglutaminase 1 [Homo sapiens]; (6036:) transglutaminase 2 isoform a [Homo sapiens];

(6037:) transglutaminase 2 isoform b [Homo sapiens]; (6038:) transglutaminase 3 precursor [Homo sapiens]; (6039:) transglutaminase K enzyme; (6040:) Transient receptor potential cation channel subfamily M member 2(Long transient receptor potential channel 2) (LTrpC2) (LTrpC-2) (Transient receptor potential channel 7) (TrpC7) (Estrogen-responsive element-associated gene 1 protein); (6041:) Transketolase (TK); (6042:) transketolase-like 1 [Homo sapiens]; (6043:) translation repressor NAT1 [Homo sapiens]; (6044:) transmembrane 4 superfamily member 15 [Homo sapiens]; (6045:) transmembrane aspartic proteinase Asp 1 [Homo sapiens]; (6046:) transmembrane aspartic proteinase Asp 2 [Homo sapiens]; (6047:) Transmembrane glycoprotein NMB precursor (Transmembrane glycoprotein HGFIN); (6048:) transmembrane protease, serine 11 D [Homo sapiens]; (6049:) "Transmembrane protease, serine 11 D precursor (Airway trypsin-like protease) [Contains:) Transmembrane protease, serine 11 D non-catalytic chain; Transmembrane protease, serine 11D catalytic chain]."; (6050:) Transmembrane protease, serine 13 (Mosaic serine protease) (Membrane-type mosaic serine protease); (6051:) transmembrane protease, serine 13 [Homo sapiens]; (6052:) "Transmembrane protease, serine 9 (Polyserase-1) (Polyserase-1) (Polyserine protease 1) [Contains:) Serase-1; Serase-2; Serase-3]."; (6053:) trehalase [Homo sapiens]; (6054:) Trem-like transcript 1 protein precursor (TLT-1) (Triggering receptor expressed on myeloid cells-like protein 1); (6055:) Trem-like transcript 2 protein precursor (TLT-2) (Triggering receptor expressed on myeloid cells-like protein 2); (6056:) TRIAD3 protein isoform a [Homo sapiens]; (6057:) TRIAD3 protein isoform b [Homo sapiens]; (6058:) "Trifunctional enzyme subunit alpha, mitochondrial precursor (TP-alpha) (78 kDa gastrin-binding protein) [Includes:) Long-chain enoyl-CoA hydratase; Long chain 3-hydroxyacyl-CoA dehydrogenase]."; (6059:) Trifunctional enzyme subunit beta, mitochondrial precursor (TP-beta) [Includes:) 3-ketoacyl-CoA thiolase (Acetyl-CoA acyltransferase) (Beta-ketothiolase)]; (6060:) Triggering receptor expressed on myeloid cells 1 precursor (TREM-1) (Triggering receptor expressed on monocytes 1); (6061:) Triggering receptor expressed on myeloid cells 2 precursor (Triggering receptor expressed on monocytes 2) (TREM-2); (6062:) Triggering Receptor Expressed on Myeloid Cells-1 (TREM-1) Receptor; (6063:) Trimethyllysine dioxygenase, mitochondrial precursor (Epsilon-trimethyllysine 2-oxoglutarate dioxygenase) (TML-alpha-ketoglutarate dioxygenase) (TML hydroxylase) (TML dioxygenase) (TMLD); (6064:) trimethyllysine hydroxylase, epsilon [Homo sapiens]; (6065:) Triosephosphate isomerase (TIM) (Triose-phosphate isomerase); (6066:) triosephosphate isomerase 1 [Homo sapiens]; (6067:) tripeptidyl peptidase 11 [Homo sapiens]; (6068:) tripeptidyl peptidase II; (6069:) Tripeptidyl-peptidase 2 (Tripeptidyl-peptidase II) (TPP-II) (Tripeptidyl aminopeptidase); (6070:) tripeptidyl-peptidase I precursor [Homo sapiens]; (6071:) tRNA 5-methylaminomethyl-2-thiouridylate methyltransferase 1 [Homo sapiens]; (6072:) tRNA isopentenyl transferase [Homo sapiens]; (6073:) tRNA isopentenyltransferase 1 [Homo sapiens]; (6074:) tRNA isopentenyltransferase, mitochondrial precursor (Isopentenyl-diphosphate:tRNA isopentenyltransferase) (IPP transferase) (IPTase) (IPPT) (hGRO1); (6075:) tRNA nucleotidyl transferase, CCA-adding, 1 isoform 1 [Homo sapiens]; (6076:) tRNA nucleotidyl transferase, CCA-adding, 1 isoform 2 [Homo sapiens]; (6077:) tRNA-guanine transglycosylase [Homo sapiens]; (6078:) tRNA-nucleotidyltransferase [Homo sapiens]; (6079:) tRNA-nucleotidyltransferase 1, mitochondrial precursor (Mitochondrial tRNA nucleotidyl transferase, CCA-adding) (mt tRNA adenylyltransferase) (mt tRNA CCA-pyrophosphorylase) (mt tRNACCA-diphosphorylase) (mt CCA-adding enzyme); (6080:) truncated mercaptopyruvate sulfurtransferase variant [Homo sapiens]; (6081:) Trypanosoma Cruzi Trypanothione Reductase; (6082:) Trypsin; (6083:) Tryptase; (6084:) Tryptase Beta; (6085:) Tryptase delta precursor (Delta tryptase) (Mast cell mMCP-7-like) (Tryptase-3) (HmMCP-3-like tryptase I11); (6086:) tryptophan hydroxylase 1 [Homo sapiens]; (6087:) tryptophanyl-tRNA synthetase isoform a [Homo sapiens]; (6088:) tryptophanyl-tRNA synthetase isoform b [Homo sapiens]; (6089:) TTLL3 protein [Homo sapiens]; (6090:) T-Type Calcium Channel (CaV3.1d) Blocker; (6091:) Tubulin; (6092:) Tubulin Polymerase; (6093:) tubulin tyrosine ligase [Homo sapiens]; (6094:) Tumor Necrosis Apoptosis Inducing Ligand Receptor 1 (TRAIL-R1); (6095:) Tumor Necrosis Apoptosis Inducing Ligand Receptor 2 (TRAIL-R2); (6096:) Tumor Necrosis Factor (TNF) Release; (6097:) tumor necrosis factor alpha [Homo sapiens]; (6098:) "Tumor necrosis factor ligand superfamily member 11 (Receptor activator of nuclear factor kappa B ligand) (RANKL) (TNF-related activation-induced cytokine) (TRANCE) (Osteoprotegerin ligand) (OPGL) (Osteoclast differentiation factor) (ODF) (CD254 antigen)[Contains:) Tumor necrosis factor ligand superfamily member 11, membrane form; Tumor necrosis factor ligand superfamily member 11, soluble form]."; (6099:) tumor necrosis factor ligand superfamily, member 11 isoform 1 [Homo sapiens]; (6100:) tumor necrosis factor ligand superfamily, member 11 isoform 2 [Homo sapiens]; (6101:) Tumor Necrosis Factor Receptor 1 (TNFR1); (6102:) tumor necrosis factor receptor 1 precursor [Homo sapiens]; (6103:) Tumor necrosis factor receptor superfamily member 10A precursor (Death receptor 4) (TNF-related apoptosis-inducing ligand receptors) (TRAIL receptor 1) (TRAIL-R1) (CD261 antigen); (6104:) Tumor necrosis factor receptor superfamily member 10B precursor (Death receptor 5) (TNF-related apoptosis-inducing ligand receptor2) (TRAIL receptor 2) (TRAIL-R2) (CD262 antigen); (6105:) Tumor necrosis factor receptor superfamily member 10C precursor (Decoy receptor 1) (DcR1) (Decoy TRAIL receptor without death domain) (TNF-related apoptosis-inducing ligand receptor 3) (TRAIL receptor 3) (TRAIL-R3) (Trail receptor without an intracellular domain) (Lymphocyte inhibitor of TRAIL) (Antagonist decoy receptor for TRAIL/Apo-2L) (CD263 antigen); (6106:) Tumor necrosis factor receptor superfamily member 10D precursor (Decoy receptor 2) (DcR2) (TNF-related apoptosis-inducing ligand receptor 4) (TRAIL receptor 4) (TRAIL-R4) (TRAIL receptor with a truncated death domain) (CD264 antigen); (6107:) Tumor necrosis factor receptor superfamily member 11A precursor (Receptor activator of NF-KB) (Osteoclast differentiation factor receptor) (ODFR) (CD265 antigen); (6108:) Tumor necrosis factor receptor superfamily member 11B precursor (Osteoprotegerin) (Osteoclastogenesis inhibitory factor); (6109:) Tumor necrosis factor receptor superfamily member 12A precursor (Fibroblast growth factor-inducible immediate-early response protein 14) (FGF-inducible 14) (Tweak-receptor) (TweakR) (CD266antigen); (6110:) Tumor necrosis factor receptor superfamily member 13B (Transmembrane activator and CAML interactor) (CD267 antigen); (6111:) Tumor necrosis factor receptor superfamily member 13C (B cell-activating factor receptor) (BAFF receptor) (BAFF-R) (BLyS receptor 3) (CD268 antigen); (6112:) Tumor necrosis factor receptor superfamily member 14 precursor (Herpesvirus entry mediator A) (Tumor necrosis factor receptor-like2) (TR2); (6113:) Tumor necrosis factor receptor superfamily member 16 precursor (Low-affinity nerve growth factor receptor) (NGF receptor) (Gp80-LNGFR) (p75 ICD) (Low affinity neurotrophin receptor p75NTR) (CD271 antigen); (6114:) Tumor necrosis factor receptor superfamily member 17 (B-cell maturation protein) (CD269 antigen); (6115:) Tumor necrosis factor receptor superfamily member 18 precursor (Glucocorticoid-induced TNFR-related protein) (Activation-inducible TN FR family receptor); (6116:) Tumor necrosis factor receptor superfamily member 19 precursor (Toxicity and JNK inducer) (TRADE); (6117:) Tumor necrosis factor receptor superfamily member 19L precursor (Receptor expressed in lymphoid tissues); (6118:) "Tumor necrosis factor receptor superfamily member 1A precursor (p60) (TNF-R1) (TNF-R1) (TNFR-1) (p55) (CD120a antigen) [Contains:Tumor necrosis factor receptor superfamily member 1A, membrane form; Tumor necrosis factor-binding protein 1 (TBPI)]."; (6119:) "Tumor necrosis factor receptor superfamily member 1B precursor (Tumor necrosis factor receptor 2) (TNF-R2) (Tumor necrosis factor receptor type II) (p75) (p80 TNF-alpha receptor) (CD120b antigen) (Etanercept) [Contains:) Tumor necrosis factor receptor superfamily member 1b, membrane form; Tumor necrosis factor-binding protein 2(TBPII) (TBP-2)]."; (6120:) Tumor necrosis factor receptor superfamily member 21 precursor (TNFR-related death receptor 6) (Death receptor 6); (6121:) Tumor necrosis factor receptor superfamily member 25 precursor (WSL-1 protein) (Apoptosis-mediating receptor DR3) (Apoptosis-mediating receptor TRAMP) (Death domain receptor 3) (WSL protein) (Apoptosis-inducing receptor AIR) (Apo-3) (Lymphocyte-associated receptor of death) (LARD); (6122:) Tumor necrosis factor receptor superfamily member 27 (X-linked ectodysplasin-A2 receptor) (EDA-A2 receptor); (6123:) Tumor necrosis factor receptor superfamily member 3 precursor (Lymphotoxin-beta receptor) (Tumor necrosis factor receptor2-related protein) (Tumor necrosis factor C receptor); (6124:) Tumor necrosis factor receptor superfamily member 4 precursor (OX40L receptor) (ACT35 antigen) (TAX transcriptionally-activated glycoprotein 1 receptor) (CD134 antigen); (6125:) Tumor necrosis factor receptor superfamily member 5 precursor (CD40L receptor) (B-cell surface antigen CD40) (CDw40) (Bp50); (6126:) Tumor necrosis factor receptor superfamily member 6 precursor (FASLG receptor) (Apoptosis-mediating surface antigen FAS) (Apo-1 antigen) (CD95 antigen); (6127:) Tumor necrosis factor receptor superfamily member 6B precursor (Decoy receptor for Fas ligand) (Decoy receptor 3) (DcR3) (M68); (6128:) Tumor necrosis factor receptor superfamily member 7 precursor (CD27L receptor) (T-cell activation antigen CD27) (T14); (6129:) Tumor necrosis factor receptor superfamily member 8 precursor (CD30L receptor) (Lymphocyte activation antigen CD30) (KI-1 antigen); (6130:) Tumor necrosis factor receptor superfamily member 9 precursor (4-1BB ligand receptor) (T-cell antigen 4-1BB homolog) (T-cell antigen ILA) (CD137 antigen) (CDw137); (6131:) Tumor necrosis factor receptor superfamily member EDAR precursor (Anhidrotic ectodysplasin receptor 1) (Ectodysplasin-A receptor) (EDA-A1 receptor) (Ectodermal dysplasia receptor) (Downless homolog); (6132:) tumor necrosis factor receptor superfamily, member 6 isoform 1precursor [Homo sapiens]; (6133:) tumor necrosis factor receptor superfamily, member 6 isoform 2precursor [Homo sapiens]; (6134:) tumor necrosis factor receptor superfamily, member 6 isoform 3precursor [Homo sapiens]; (6135:) tumor necrosis factor receptor superfamily, member 6 isoform 4precursor [Homo sapiens]; (6136:) tumor necrosis factor receptor superfamily, member 6 isoform 5precursor [Homo sapiens]; (6137:) tumor necrosis factor receptor superfamily, member 6 isoform 6precursor [Homo sapiens]; (6138:) tumor necrosis factor receptor superfamily, member 6 isoform 7precursor [Homo sapiens]; (6139:) tumor necrosis factor receptor superfamily, member 8 isoform 1 precursor [Homo sapiens]; (6140:) tumor necrosis factor receptor superfamily, member 8 isoform 2 [Homo sapiens]; (6141:) tumor necrosis factor, alpha-induced protein 8 isoform a [Homo sapiens]; (6142:) tumor necrosis factor, alpha-induced protein 8 isoform b [Homo sapiens]; (6143:) Tumor Necrosis Factor-Alpha (TNF-Alpha) Synthesis; (6144:) Tumor Necrosis Factor-Alpha Converting Enzyme (TACE); (6145:) tumor protein p53 [Homo sapiens]; (6146:) tumor stroma and activated macrophage protein DLM-1 [Homo sapiens]; (6147:) Tumor susceptibility gene 101 protein; (6148:) "Tumor-associated hydroquinone oxidase (tNOX) (Cytosolic ovarian carcinoma antigen 1) (APK1 antigen) [Includes:) Hydroquinone [NADH]oxidase; Protein disulfide-thiol oxidoreductase]."; (6149:) Tumour Cell Survival Phosphatase-1 (TCSP-1); (6150:) TX protease precursor [Homo sapiens]; (6151:) TY protease [Homo sapiens]; (6152:) Type II inositol-3,4-bisphosphate 4-phosphatase (Inositol polyphosphate 4-phosphatase type II); (6153:) Type-1 angiotensin II receptor (AT1) (AT1AR) (AT1 BR); (6154:) Type-2 angiotensin II receptor (AT2); (6155:) Tyrosinase; (6156:) Tyrosinase precursor (Monophenol monooxygenase) (Tumor rejection antigen AB) (SK29-AB) (LB24-AB); (6157:) tyrosinase precursor [Homo sapiens]; (6158:) tyrosine 3/tryptophan 5-monooxygenase activation protein, thetapolypeptide [Homo sapiens]; (6159:) tyrosine 3/tryptophan 5-monooxygenase activation protein, zetapolypeptide [Homo sapiens]; (6160:) Tyrosine 3-monooxygenase (Tyrosine 3-hydroxylase) (TH); (6161:) tyrosine hydroxylase isoform a [Homo sapiens]; (6162:) tyrosine hydroxylase isoform b [Homo sapiens]; (6163:) tyrosine hydroxylase isoform c [Homo sapiens]; (6164:) Tyrosine Kinase; (6165:) Tyrosine-protein kinase 6 (Breast tumor kinase) (Tyrosine-protein kinase BRK); (6166:) Tyrosine-protein kinase receptor Tie-1 precursor; (6167:) Tyrosine-protein kinase receptor TYRO3 precursor (Tyrosine-protein kinase RSE) (Tyrosine-protein kinase SKY) (Tyrosine-protein kinase DTK) (Protein-tyrosine kinase byk); (6168:) Tyrosine-protein kinase receptor UFO precursor (AXL oncogene); (6169:) Tyrosine-protein kinase RYK precursor; (6170:) Tyrosine-protein kinase transmembrane receptor ROR1 precursor (Neurotrophic tyrosine kinase, receptor-related 1); (6171:) Tyrosine-protein kinase transmembrane receptor ROR2 precursor (Neurotrophic tyrosine kinase, receptor-related 2); (6172:) Tyrosine-protein kinase-like 7 precursor (Colon carcinoma kinase 4) (CCK-4); (6173:) Tyrosine-protein phosphatase non-receptor type II (Protein-tyrosine phosphatase 2C) (PTP-2C) (PTP-1 D) (SH-PTP3) (SH-PTP2) (SHP-2) (Shp2); (6174:) Tyrosyl-DNA phosphodiesterase 1 (Tyr-DNA phosphodiesterase 1); (6175:) tyrosyl-DNA phosphodiesterase 1 [Homo sapiens]; (6176:) tyrosyl protein sulfotransferase 1 [Homo sapiens]; (6177:) tyrosyl protein sulfotransferase-1 [Homo sapiens]; (6178:) tyrosyl protein sulfotransferase-2 [Homo sapiens]; (6179:) "tyrosyl protein sulfotransferase-2; TPST-2 [Homo sapiens]."; (6180:) tyrosyl-tRNA synthetase [Homo sapiens]; (6181:) UBA2 [Homo sapiens]; (6182:) UBA3 [Homo sapiens]; (6183:) UBC13/UEV-interacting ring finger protein [Homo sapiens]; (6184:) Ubc6p homolog [Homo sapiens]; (6185:) UbCH5B; (6186:) UbCH5C; (6187:) UbcM2 [Homo sapiens]; (6188:) UBE1C [Homo sapiens]; (6189:) UBE1L protein [Homo sapiens]; (6190:) UBE1L2 protein [Homo sapiens]; (6191:) UBE21 [Homo sapiens]; (6192:) UBE2B

[*Homo sapiens*]; (6193:) UBE2C [*Homo sapiens*]; (6194:) UBE2D3 [*Homo sapiens*]; (6195:) UBE2G1 protein [*Homo sapiens*]; (6196:) UBE2H protein [*Homo sapiens*]; (6197:) UBE21 protein [*Homo sapiens*]; (6198:) UBE2L3 [*Homo sapiens*]; (6199:) UBE2L6 [*Homo sapiens*]; (6200:) UBE20 protein [*Homo sapiens*]; (6201:) UBE2Q [*Homo sapiens*]; (6202:) UBE2Q1 protein [*Homo sapiens*]; (6203:) UBE2Q2 protein [*Homo sapiens*]; (6204:) UBE2R2 [*Homo sapiens*]; (6205:) UBE2S protein [*Homo sapiens*]; (6206:) UBE2V1 protein [*Homo sapiens*]; (6207:) UBE2V2 [*Homo sapiens*]; (6208:) UBE2W protein [*Homo sapiens*]; (6209:) UBE2Z protein [*Homo sapiens*]; (6210:) ubenimex (Bestatin)-sensitive aminopeptidase B-like enzyme (EC3.4.11.-)—human (fragments); (6211:) ubiquinol-cytochrome-c reductase (EC 1.10.2.2) cytochrome b—human mitochondrion; (6212:) Ubiquitin activating enzyme [*Homo sapiens*]; (6213:) ubiquitin activating enzyme E1 [*Homo sapiens*]; (6214:) ubiquitin associated protein 2 [*Homo sapiens*]; (6215:) ubiquitin B precursor [*Homo sapiens*]; (6216:) ubiquitin carboxyl-terminal esterase L1 (ubiquitin thiolesterase) [*Homo sapiens*]; (6217:) ubiquitin carboxyl-terminal esterase L3 [*Homo sapiens*]; (6218:) Ubiquitin carboxyl-terminal hydrolase 1 (Ubiquitin thioesterase 1) (Ubiquitin-specific-processing protease 1) (Deubiquitinating enzyme 1) (hUBP); (6219:) Ubiquitin carboxyl-terminal hydrolase 10 (Ubiquitin thioesterase 10) (Ubiquitin-specific-processing protease 10) (Deubiquitinating enzyme 10); (6220:) Ubiquitin carboxyl-terminal hydrolase 11 (Ubiquitin thioesterase 11) (Ubiquitin-specific-processing protease 11) (Deubiquitinating enzyme 11); (6221:) Ubiquitin carboxyl-terminal hydrolase 12 (Ubiquitin thioesterase 12) (Ubiquitin-specific-processing protease 12) (Deubiquitinating enzyme 12) (Ubiquitin-hydrolyzing enzyme 1); (6222:) Ubiquitin carboxyl-terminal hydrolase 13 (Ubiquitin thioesterase 13) (Ubiquitin-specific-processing protease 13) (Deubiquitinating enzyme 13) (Isopeptidase T-3) (ISOT-3); (6223:) Ubiquitin carboxyl-terminal hydrolase 14 (Ubiquitin thioesterase 14) (Ubiquitin-specific-processing protease 14) (Deubiquitinating enzyme 14); (6224:) Ubiquitin carboxyl-terminal hydrolase 15 (Ubiquitin thioesterase 15) (Ubiquitin-specific-processing protease 15) (Deubiquitinating enzyme 15) (Unph-2) (Unph4); (6225:) Ubiquitin carboxyl-terminal hydrolase 16 (Ubiquitin thioesterase 16) (Ubiquitin-specific-processing protease 16) (Deubiquitinating enzyme 16) (Ubiquitin-processing protease UBP-M); (6226:) Ubiquitin carboxyl-terminal hydrolase 17-like protein (Ubiquitinthioesterase 17-like) (Ubiquitin-specific-processing protease 17-like) (Deubiquitinating enzyme 17-like); (6227:) Ubiquitin carboxyl-terminal hydrolase 19 (Ubiquitin thioesterase 19) (Ubiquitin-specific-processing protease 19) (Deubiquitinating enzyme 19) (Zinc finger MYND domain-containing protein 9); (6228:) Ubiquitin carboxyl-terminal hydrolase 2 (Ubiquitin thioesterase 2) (Ubiquitin-specific-processing protease 2) (Deubiquitinating enzyme2) (41 kDa ubiquitin-specific protease); (6229:) Ubiquitin carboxyl-terminal hydrolase 20 (Ubiquitin thioesterase 20) (Ubiquitin-specific-processing protease 20) (Deubiquitinating enzyme 20); (6230:) Ubiquitin carboxyl-terminal hydrolase 21 (Ubiquitin thioesterase 21) (Ubiquitin-specific-processing protease 21) (Deubiquitinating enzyme 21) (NEDD8-specific protease); (6231:) Ubiquitin carboxyl-terminal hydrolase 22 (Ubiquitin thioesterase 22) (Ubiquitin-specific-processing protease 22) (Deubiquitinating enzyme 22); (6232:) Ubiquitin carboxyl-terminal hydrolase 24 (Ubiquitin thioesterase 24) (Ubiquitin-specific-processing protease 24) (Deubiquitinating enzyme 24); (6233:) Ubiquitin carboxyl-terminal hydrolase 25 (Ubiquitin thioesterase 25) (Ubiquitin-specific-processing protease 25) (Deubiquitinating enzyme 25) (USP on chromosome 21); (6234:) Ubiquitin carboxyl-terminal hydrolase 26 (Ubiquitin thioesterase 26) (Ubiquitin-specific-processing protease 26) (Deubiquitinating enzyme 26); (6235:) Ubiquitin carboxyl-terminal hydrolase 28 (Ubiquitin thioesterase 28) (Ubiquitin-specific-processing protease 28) (Deubiquitinating enzyme 28); (6236:) Ubiquitin carboxyl-terminal hydrolase 29 (Ubiquitin thioesterase 29) (Ubiquitin-specific-processing protease 29) (Deubiquitinating enzyme 29); (6237:) Ubiquitin carboxyl-terminal hydrolase 3 (Ubiquitin thioesterase 3) (Ubiquitin-specific-processing protease 3) (Deubiquitinating enzyme3); (6238:) Ubiquitin carboxyl-terminal hydrolase 30 (Ubiquitin thioesterase 30) (Ubiquitin-specific-processing protease 30) (Deubiquitinating enzyme 30); (6239:) Ubiquitin carboxyl-terminal hydrolase 31 (Ubiquitin thioesterase 31) (Ubiquitin-specific-processing protease 31) (Deubiquitinating enzyme 31); (6240:) Ubiquitin carboxyl-terminal hydrolase 32 (Ubiquitin thioesterase 32) (Ubiquitin-specific-processing protease 32) (Deubiquitinating enzyme 32) (NY-REN-60 antigen); (6241:) Ubiquitin carboxyl-terminal hydrolase 33 (Ubiquitin thioesterase 33) (Ubiquitin-specific-processing protease 33) (Deubiquitinating enzyme 33) (VHL-interacting deubiquitinating enzyme 1); (6242:) Ubiquitin carboxyl-terminal hydrolase 34 (Ubiquitin thioesterase 34) (Ubiquitin-specific-processing protease 34) (Deubiquitinating enzyme 34); (6243:) Ubiquitin carboxyl-terminal hydrolase 35 (Ubiquitin thioesterase 35) (Ubiquitin-specific-processing protease 35) (Deubiquitinating enzyme 35); (6244:) Ubiquitin carboxyl-terminal hydrolase 36 (Ubiquitin thioesterase 36) (Ubiquitin-specific-processing protease 36) (Deubiquitinating enzyme 36); (6245:) Ubiquitin carboxyl-terminal hydrolase 37 (Ubiquitin thioesterase 37) (Ubiquitin-specific-processing protease 37) (Deubiquitinating enzyme 37); (6246:) Ubiquitin carboxyl-terminal hydrolase 38 (Ubiquitin thioesterase 38) (Ubiquitin-specific-processing protease 38) (Deubiquitinating enzyme 38) (HP43.8 KD); (6247:) Ubiquitin carboxyl-terminal hydrolase 4 (Ubiquitin thioesterase 4) (Ubiquitin-specific-processing protease 4) (Deubiquitinating enzyme4) (Ubiquitous nuclear protein homolog); (6248:) Ubiquitin carboxyl-terminal hydrolase 40 (Ubiquitin thioesterase 40) (Ubiquitin-specific-processing protease 40) (Deubiquitinating enzyme 40); (6249:) Ubiquitin carboxyl-terminal hydrolase 42 (Ubiquitin thioesterase 42) (Ubiquitin-specific-processing protease 42) (Deubiquitinating enzyme 42); (6250:) Ubiquitin carboxyl-terminal hydrolase 43 (Ubiquitin thioesterase 43) (Ubiquitin-specific-processing protease 43) (Deubiquitinating enzyme 43); (6251:) Ubiquitin carboxyl-terminal hydrolase 44 (Ubiquitin thioesterase 44) (Ubiquitin-specific-processing protease 44) (Deubiquitinating enzyme 44); (6252:) Ubiquitin carboxyl-terminal hydrolase 46 (Ubiquitin thioesterase 46) (Ubiquitin-specific-processing protease 46) (Deubiquitinating enzyme 46); (6253:) Ubiquitin carboxyl-terminal hydrolase 47 (Ubiquitin thioesterase 47) (Ubiquitin-specific-processing protease 47) (Deubiquitinating enzyme 47); (6254:) Ubiquitin carboxyl-terminal hydrolase 48 (Ubiquitin thioesterase 48) (Ubiquitin-specific-processing protease 48) (Deubiquitinating enzyme 48); (6255:) Ubiquitin carboxyl-terminal hydrolase 49 (Ubiquitin thioesterase 49) (Ubiquitin-specific-processing protease 49) (Deubiquitinating enzyme 49); (6256:) Ubiquitin carboxyl-terminal hydrolase 5 (Ubiquitin thioesterase 5) (Ubiquitin-specific-processing protease 5) (Deubiquitinating enzyme5) (Isopeptidase T); (6257:) Ubiquitin carboxyl-terminal hydrolase 51 (Ubiquitin thioesterase 51) (Ubiquitin-specific-processing protease 51) (Deubiquitinating enzyme 51); (6258:) Ubiquitin carboxyl-terminal hydrolase 6 (Ubiquitin thioesterase 6) (Ubiquitin-specific-processing protease 6) (Deubiquitinating enzyme6) (Proto-oncogene TRE-2); (6259:) Ubiquitin carboxyl-terminal hydrolase 7 (Ubiquitin thioesterase 7) (Ubiquitin-specific-processing protease 7) (Deubiquitinating enzyme7) (Herpesvirus-associated ubiquitin-specific protease); (6260:) Ubiquitin carboxyl-terminal hydrolase 8 (Ubiquitin thioesterase 8) (Ubiquitin-specific-processing protease 8) (Deubiquitinating enzyme8) (hUBPy); (6261:) Ubiquitin carboxyl-terminal hydrolase BAP1 (BRCA1-associated protein 1) (Cerebral protein 6); (6262:) ubiquitin carboxyl-terminal hydrolase CYLD isoform 1 [Homo sapiens]; (6263:) ubiquitin carboxyl-terminal hydrolase CYLD isoform 2 [Homo sapiens]; (6264:) Ubiquitin carboxyl-terminal hydrolase isozyme L1 (UCH-L1) (Ubiquitin thioesterase L1) (Neuron cytoplasmic protein 9.5) (PGP9.5) (PGP9.5); (6265:) Ubiquitin carboxyl-terminal hydrolase isozyme L3 (UCH-L3) (Ubiquitin thioesterase L3); (6266:) Ubiquitin carboxyl-terminal hydrolase isozyme L5 (UCH-L5) (Ubiquitin thioesterase L5) (Ubiquitin C-terminal hydrolase UCH37); (6267:) ubiquitin carrier protein [Homo sapiens]; (6268:) ubiquitin carrier protein E2—human; (6269:) ubiquitin carrier protein; (6270:) ubiquitin conjugating enzyme—human (fragment); (6271:) ubiquitin conjugating enzyme [Homo sapiens]; (6272:) ubiquitin conjugating enzyme 12 [Homo sapiens]; (6273:) ubiquitin conjugating enzyme 6 [Homo sapiens]; (6274:) ubiquitin conjugating enzyme 7 interacting protein 5 isoform a variant [Homo sapiens]; (6275:) ubiquitin conjugating enzyme 7 interacting protein 5 isoform b variant [Homo sapiens]; (6276:) ubiquitin conjugating enzyme 9 [Homo sapiens]; (6277:) ubiquitin conjugating enzyme 9; (6278:) ubiquitin conjugating enzyme E2 [Homo sapiens]; (6279:) ubiquitin conjugating enzyme E2, J2 isoform 1 [Homo sapiens]; (6280:) ubiquitin conjugating enzyme E2, J2 isoform 2 [Homo sapiens]; (6281:) ubiquitin conjugating enzyme E2, J2 isoform 3 [Homo sapiens]; (6282:) ubiquitin conjugating enzyme G2 [Homo sapiens]; (6283:) ubiquitin conjugating enzyme homolog; (6284:) ubiquitin conjugating enzyme; (6285:) ubiquitin C-terminal hydrolase UCH37 [Homo sapiens]; (6286:) ubiquitin hydrolyzing enzyme 1 [Homo sapiens]; (6287:) ubiquitin hydrolyzing enzyme I [Homo sapiens]; (6288:) Ubiquitin isopeptidase T [Homo sapiens]; (6289:) Ubiquitin Ligase; (6290:) ubiquitin ligase E3A isoform 1 [Homo sapiens]; (6291:) Ubiquitin ligase LNX (Numb-binding protein 1) (Ligand of Numb-protein X1); (6292:) Ubiquitin ligase protein DZIP3 (DAZ-interacting protein 3) (RNA-binding ubiquitin ligase of 138 kDa) (hRUL138); (6293:) Ubiquitin ligase protein RING2 (RING finger protein 2) (RING finger protein 1B) (RING1b) (RING finger protein BAP-1) (DinG protein) (Huntingtin-interacting protein 2-interacting protein 3) (HIP2-interacting protein 3); (6294:) Ubiquitin ligase SIAH1 (Seven in absentia homolog 1) (Siah-1) (Siah-1a); (6295:) Ubiquitin ligase SIAH2 (Seven in absentia homolog 2) (Siah-2) (hSiah2); (6296:) ubiquitin processing protease [Homo sapiens]; (6297:) ubiquitin protein ligase E3A isoform 1 [Homo sapiens]; (6298:) ubiquitin protein ligase E3A isoform 2 [Homo sapiens]; (6299:) ubiquitin protein ligase E3A isoform 3 [Homo sapiens]; (6300:) ubiquitin protein ligase E3B [Homo sapiens]; (6301:) ubiquitin protein ligase E3C [Homo sapiens]; (6302:) Ubiquitin protein ligase Praja1 (RING finger protein 70); (6303:) ubiquitin specific protease 1 [Homo sapiens]; (6304:) ubiquitin specific protease 11 [Homo sapiens]; (6305:) ubiquitin specific protease 14 isoform a [Homo sapiens]; (6306:) ubiquitin specific protease 14 isoform b [Homo sapiens]; (6307:) ubiquitin specific protease 15 [Homo sapiens]; (6308:) ubiquitin specific protease 16 isoform a [Homo sapiens]; (6309:) ubiquitin specific protease 16 isoform b [Homo sapiens]; (6310:) ubiquitin specific protease 2 isoform b [Homo sapiens]; (6311:) ubiquitin specific protease 20 [Homo sapiens]; (6312:) ubiquitin specific protease 25 [Homo sapiens]; (6313:) ubiquitin specific protease 28 [Homo sapiens]; (6314:) ubiquitin specific protease 29 [Homo sapiens]; (6315:) ubiquitin specific protease 2b [Homo sapiens]; (6316:) ubiquitin specific protease 31 [Homo sapiens]; (6317:) ubiquitin specific protease 33 isoform 1 [Homo sapiens]; (6318:) ubiquitin specific protease 33 isoform 2 [Homo sapiens]; (6319:) ubiquitin specific protease 33 isoform 3 [Homo sapiens]; (6320:) ubiquitin specific protease 36 [Homo sapiens]; (6321:) ubiquitin specific protease 42 [Homo sapiens]; (6322:) ubiquitin specific protease 48 [Homo sapiens]; (6323:) ubiquitin specific protease 48 isoform a [Homo sapiens]; (6324:) ubiquitin specific protease 51 [Homo sapiens]; (6325:) ubiquitin specific protease 7 (herpes virus-associated) [Homo sapiens]; (6326:) ubiquitin specific protease 8 [Homo sapiens]; (6327:) ubiquitin specific protease 9, X-linked isoform 3 [Homo sapiens]; (6328:) ubiquitin specific protease 9, X-linked isoform 4 [Homo sapiens]; (6329:) ubiquitin specific protease 9, Y-linked [Homo sapiens]; (6330:) ubiquitin specific protease, proto-oncogene isoform a [Homo sapiens]; (6331:) ubiquitin specific protease, proto-oncogene isoform b [Homo sapiens]; (6332:) Ubiquitin thioesterase protein OTUB1 (Otubain-1) (OTU domain-containing ubiquitin aldehyde-binding protein 1) (Ubiquitin-specific-processing protease OTUB1) (Deubiquitinating enzyme OTUB1); (6333:) Ubiquitin thioesterase protein OTUB2 (Otubain-2) (OTU domain-containing ubiquitin aldehyde-binding protein 2) (Ubiquitin-specific-processing protease OTUB2) (Deubiquitinating enzyme OTUB2); (6334:) Ubiquitin; (6335:) Ubiquitin-activating enzyme E1 (A1S9 protein); (6336:) Ubiquitin-activating enzyme E1 (A1S9T and BN75 temperature sensitivity complementing) [Homo sapiens]; (6337:) ubiquitin-activating enzyme E1 [Homo sapiens]; (6338:) Ubiquitin-activating enzyme E1 domain-containing protein 1(UFM1-activating enzyme) (Ubiquitin-activating enzyme 5) (ThiFP1); (6339:) Ubiquitin-activating enzyme E1 homolog (D8); (6340:) Ubiquitin-activating enzyme E1C (UBA3 homolog, yeast) [Homo sapiens]; (6341:) ubiquitin-activating enzyme E1C isoform 1 [Homo sapiens]; (6342:) ubiquitin-activating enzyme E1C isoform 2 [Homo sapiens]; (6343:) ubiquitin-activating enzyme E1C isoform 3 [Homo sapiens]; (6344:) Ubiquitin-activating enzyme E1-domain containing 1 [Homo sapiens]; (6345:) ubiquitin-activating enzyme E1-domain containing 1 isoform 1 [Homo sapiens]; (6346:) ubiquitin-activating enzyme E1-domain containing 1 isoform 2 [Homo sapiens]; (6347:) ubiquitin-activating enzyme E1-like [Homo sapiens]; (6348:) Ubiquitin-activating enzyme E1-like 2 [Homo sapiens]; (6349:) ubiquitin-activating enzyme E1-related protein; (6350:) ubiquitination factor E4A [Homo sapiens]; (6351:) ubiquitin-conjugating enzyme [Homo sapiens]; (6352:) ubiquitin-conjugating BIR-domain enzyme APOLLON [Homo sapiens]; (6353:) ubiquitin-conjugating enzyme [Homo sapiens]; (6354:) ubiquitin-conjugating enzyme 1 isoform [Homo sapiens]; (6355:) ubiquitin-conjugating enzyme 16 [Homo sapiens]; (6356:) Ubiquitin-conjugating enzyme 7-interacting protein 4(UbcM4-interacting protein 4) (RING finger protein 144); (6357:) ubiquitin-conjugating enzyme 9 (UBC9); (6358:) ubiquitin-conjugating enzyme E2 [Homo sapiens]; (6359:) Ubiquitin-conjugating enzyme E2 A (Ubiquitin-protein ligase A) (Ubiquitin carrier protein A) (HR6A) (hHR6A); (6360:)

Ubiquitin-conjugating enzyme E2 B (Ubiquitin-protein ligase B) (Ubiquitin carrier protein B) (HR6B) (hHR6B) (E2-17 kDa); (6361:) Ubiquitin-conjugating enzyme E2 C (Ubiquitin-protein ligase C) (Ubiquitin carrier protein C) (UbcH10); (6362:) Ubiquitin-conjugating enzyme E2 D1 (Ubiquitin-protein ligase D1) (Ubiquitin carrier protein D1) (UbCH5) (Ubiquitin-conjugating enzyme E2-17 kDa 1) (E2(17)KB 1); (6363:) Ubiquitin-conjugating enzyme E2 D2 (Ubiquitin-protein ligase D2) (Ubiquitin carrier protein D2) (Ubiquitin-conjugating enzyme E2-17 kDa 2) (E2(17) KB 2); (6364:) ubiquitin-conjugating enzyme E2 D2 transcript variant 1 [Homo sapiens]; (6365:) Ubiquitin-conjugating enzyme E2 D3 (Ubiquitin-protein ligase D3) (Ubiquitin carrier protein D3) (Ubiquitin-conjugating enzyme E2-17 kDa 3) (E2(17)KB 3); (6366:) Ubiquitin-conjugating enzyme E2 E1 (Ubiquitin-protein ligase E1) (Ubiquitin carrier protein E1) (UbCH6); (6367:) Ubiquitin-conjugating enzyme E2 E2 (Ubiquitin-protein ligase E2) (Ubiquitin carrier protein E2) (UbCH8); (6368:) Ubiquitin-conjugating enzyme E2 E3 (Ubiquitin-protein ligase E3) (Ubiquitin carrier protein E3) (Ubiquitin-conjugating enzyme E2-23 kDa) (UbCH9) (UbcM2); (6369:) Ubiquitin-conjugating enzyme E2 G1 (Ubiquitin-protein ligase G1) (Ubiquitin carrier protein G1) (E217K) (UBC7); (6370:) Ubiquitin-conjugating enzyme E2 G2 (Ubiquitin-protein ligase G2) (Ubiquitin carrier protein G2); (6371:) Ubiquitin-conjugating enzyme E2H (Ubiquitin-protein ligase H) (Ubiquitin carrier protein H) (UbCH2) (E2-20K); (6372:) Ubiquitin-conjugating enzyme E2 J1 (Non-canonical ubiquitin-conjugating enzyme 1) (NCUBE1) (Yeast ubiquitin-conjugating enzyme UBC6 homolog E) (HSUBC6e); (6373:) Ubiquitin-conjugating enzyme E2 J2 (Non-canonical ubiquitin-conjugating enzyme 2) (NCUBE2); (6374:) ubiquitin-conjugating enzyme E2 Kua-UEV isoform 1 [Homo sapiens]; (6375:) ubiquitin-conjugating enzyme E2 Kua-UEV isoform 2 [Homo sapiens]; (6376:) Ubiquitin-conjugating enzyme E2 L3 (Ubiquitin-protein ligase L3) (Ubiquitin carrier protein L3) (UbCH7) (E2-F1) (L-UBC); (6377:) Ubiquitin-conjugating enzyme E2 L6 (Ubiquitin-protein ligase L6) (Ubiquitin carrier protein L6) (UbCH8) (Retinoic acid-induced gene B protein) (RIG-B); (6378:) Ubiquitin-conjugating enzyme E2 N (Ubiquitin-protein ligase N) (Ubiquitin carrier protein N) (Ubc13) (Bendless-like ubiquitin-conjugating enzyme); (6379:) Ubiquitin-conjugating enzyme E2Q1 (Ubiquitin-protein ligase Q1) (Ubiquitin carrier protein Q1) (Protein NICE-5); (6380:) Ubiquitin-conjugating enzyme E2Q2 (Ubiquitin-protein ligase Q2) (Ubiquitin carrier protein Q2); (6381:) Ubiquitin-conjugating enzyme E2 S (Ubiquitin-protein ligase S) (Ubiquitin carrier protein S) (Ubiquitin-conjugating enzyme E2-24 kDa) (E2-EPF5); (6382:) Ubiquitin-conjugating enzyme E2 T (Ubiquitin-protein ligase T) (Ubiquitin carrier protein T); (6383:) Ubiquitin-conjugating enzyme E2 U (Ubiquitin-protein ligase U) (Ubiquitin carrier protein U); (6384:) ubiquitin-conjugating enzyme E2 UbcH-ben [Homo sapiens]; (6385:) Ubiquitin-conjugating enzyme E2 variant 1 (UEV-1) (CROC-1) (Ubiquitin-conjugating enzyme variant Kua) (TRAF6-regulated IKK activator 1 beta Uev1A); (6386:) Ubiquitin-conjugating enzyme E2 variant 1 [Homo sapiens]; (6387:) ubiquitin-conjugating enzyme E2 variant 1 isoform a [Homo sapiens]; (6388:) ubiquitin-conjugating enzyme E2 variant 1 isoform c [Homo sapiens]; (6389:) ubiquitin-conjugating enzyme E2 variant 1 isoform d [Homo sapiens]; (6390:) Ubiquitin-conjugating enzyme E2 variant 2 (MMS2) (Enterocyte differentiation-associated factor EDAF-1) (Enterocyte differentiation-promoting factor) (EDPF-1) (Vitamin D3-inducible protein) (DDVit 1); (6391:) ubiquitin-conjugating enzyme E2 variant 2 [Homo sapiens]; (6392:) Ubiquitin-conjugating enzyme E2, J1 (UBC6 homolog, yeast) [Homo sapiens]; (6393:) ubiquitin-conjugating enzyme E2, J1 [Homo sapiens]; (6394:) ubiquitin-conjugating enzyme E2, J1 variant [Homo sapiens]; (6395:) Ubiquitin-conjugating enzyme E2, J2 (UBC6 homolog, yeast) [Homo sapiens]; (6396:) ubiquitin-conjugating enzyme E2-17 kDa [Homo sapiens]; (6397:) Ubiquitin-conjugating enzyme E2-25 kDa (Ubiquitin-protein ligase) (Ubiquitin carrier protein) (E2(25K)) (Huntingtin-interacting protein 2) (HIP-2); (6398:) Ubiquitin-conjugating enzyme E2-32 kDa complementing (Ubiquitin-protein ligase) (Ubiquitin carrier protein) (E2-CDC34); (6399:) Ubiquitin-conjugating enzyme E2A (RAD6 homolog) [Homo sapiens]; (6400:) ubiquitin-conjugating enzyme E2A isoform 1 [Homo sapiens]; (6401:) ubiquitin-conjugating enzyme E2A isoform 1 variant [Homo sapiens]; (6402:) ubiquitin-conjugating enzyme E2A isoform 2 [Homo sapiens]; (6403:) ubiquitin-conjugating enzyme E2A isoform 3 [Homo sapiens]; (6404:) Ubiquitin-conjugating enzyme E2B (RAD6 homolog) [Homo sapiens]; (6405:) ubiquitin-conjugating enzyme E2B [Homo sapiens]; (6406:) Ubiquitin-conjugating enzyme E2C [Homo sapiens]; (6407:) ubiquitin-conjugating enzyme E2C isoform 1 [Homo sapiens]; (6408:) ubiquitin-conjugating enzyme E2C isoform 2 [Homo sapiens]; (6409:) ubiquitin-conjugating enzyme E2C isoform 3 [Homo sapiens]; (6410:) ubiquitin-conjugating enzyme E2C isoform 4 [Homo sapiens]; (6411:) ubiquitin-conjugating enzyme E2C isoform 5 [Homo sapiens]; (6412:) Ubiquitin-conjugating enzyme E2D1 (UBC4/5 homolog, yeast) [Homo sapiens]; (6413:) ubiquitin-conjugating enzyme E2D1 [Homo sapiens]; (6414:) Ubiquitin-conjugating enzyme E2D 2 (UBC4/5 homolog, yeast) [Homo sapiens]; (6415:) ubiquitin-conjugating enzyme E2D 2 isoform 1 [Homo sapiens]; (6416:) ubiquitin-conjugating enzyme E2D 2 isoform 2 [Homo sapiens]; (6417:) Ubiquitin-conjugating enzyme E2D 3 (UBC4/5 homolog, yeast) [Homo sapiens]; (6418:) ubiquitin-conjugating enzyme E2D 3 [Homo sapiens]; (6419:) ubiquitin-conjugating enzyme E2D 3 isoform 1 [Homo sapiens]; (6420:) ubiquitin-conjugating enzyme E2D 3 isoform 2 [Homo sapiens]; (6421:) ubiquitin-conjugating enzyme E2D 3 isoform 3 [Homo sapiens]; (6422:) ubiquitin-conjugating enzyme E2D 4 (putative) [Homo sapiens]; (6423:) Ubiquitin-conjugating enzyme E2E1 (UBC4/5 homolog, yeast) [Homo sapiens]; (6424:) ubiquitin-conjugating enzyme E2E1 isoform 1 [Homo sapiens]; (6425:) ubiquitin-conjugating enzyme E2E 1 isoform 2 [Homo sapiens]; (6426:) ubiquitin-conjugating enzyme E2E 2 (UBC4/5 homolog, yeast) [Homo sapiens]; (6427:) Ubiquitin-conjugating enzyme E2E 3 (UBC4/5 homolog, yeast) [Homo sapiens]; (6428:) ubiquitin-conjugating enzyme E2E 3 [Homo sapiens]; (6429:) Ubiquitin-conjugating enzyme E2F (putative) [Homo sapiens]; (6430:) ubiquitin-conjugating enzyme E2G1 (UBC7 homolog, C. elegans) [Homo sapiens]; (6431:) Ubiquitin-conjugating enzyme E2G 1 (UBC7 homolog, yeast) [Homo sapiens]; (6432:) ubiquitin-conjugating enzyme E2G1 [Homo sapiens]; (6433:) Ubiquitin-conjugating enzyme E2G 2 (UBC7 homolog, yeast) [Homo sapiens]; (6434:) ubiquitin-conjugating enzyme E2G 2 isoform 1 [Homo sapiens]; (6435:) ubiquitin-conjugating enzyme E2G 2 isoform 2 [Homo sapiens]; (6436:) ubiquitin-conjugating enzyme E2H (UBC8 homolog, yeast) [Homo sapiens]; (6437:) ubiquitin-conjugating enzyme E2H isoform 1 [Homo sapiens]; (6438:) ubiquitin-conjugating enzyme E2H isoform 2 [Homo sapiens]; (6439:) Ubiquitin-conjugating enzyme E2I (UBC9 homolog, yeast) [Homo sapiens]; (6440:) ubiquitin-conjugating enzyme E2I [Homo

*sapiens*]; (6441:) ubiquitin-conjugating enzyme E2I variant [*Homo sapiens*]; (6442:) Ubiquitin-conjugating enzyme E2L 3 [*Homo sapiens*]; (6443:) ubiquitin-conjugating enzyme E2L 3 isoform 1 [*Homo sapiens*]; (6444:) ubiquitin-conjugating enzyme E2L 3 isoform 2 [*Homo sapiens*]; (6445:) Ubiquitin-conjugating enzyme E2L 6 [*Homo sapiens*]; (6446:) ubiquitin-conjugating enzyme E2L 6 isoform 1 [*Homo sapiens*]; (6447:) ubiquitin-conjugating enzyme E2L 6 isoform 2 [*Homo sapiens*]; (6448:) ubiquitin-conjugating enzyme E2-like isoform a [*Homo sapiens*]; (6449:) ubiquitin-conjugating enzyme E2-like isoform b [*Homo sapiens*]; (6450:) Ubiquitin-conjugating enzyme E2M (UBC12 homolog, yeast) [*Homo sapiens*]; (6451:) ubiquitin-conjugating enzyme E2M [*Homo sapiens*]; (6452:) Ubiquitin-conjugating enzyme E2N (UBC13 homolog, yeast) [*Homo sapiens*]; (6453:) ubiquitin-conjugating enzyme E2N [*Homo sapiens*]; (6454:) ubiquitin-conjugating enzyme E2N-like [*Homo sapiens*]; (6455:) ubiquitin-conjugating enzyme E2O [*Homo sapiens*]; (6456:) ubiquitin-conjugating enzyme E2Q (putative) [*Homo sapiens*]; (6457:) ubiquitin-conjugating enzyme E2Q (putative) 2 [*Homo sapiens*]; (6458:) ubiquitin-conjugating enzyme E2Q [*Homo sapiens*]; (6459:) Ubiquitin-conjugating enzyme E2R 2 [*Homo sapiens*]; (6460:) ubiquitin-conjugating enzyme E2S [*Homo sapiens*]; (6461:) ubiquitin-conjugating enzyme E2T (putative) [*Homo sapiens*]; (6462:) ubiquitin-conjugating enzyme E2U (putative) [*Homo sapiens*]; (6463:) Ubiquitin-conjugating enzyme E2W (putative) [*Homo sapiens*]; (6464:) ubiquitin-conjugating enzyme E2W (putative) isoform 1 [*Homo sapiens*]; (6465:) ubiquitin-conjugating enzyme E2W (putative) isoform 2 [*Homo sapiens*]; (6466:) ubiquitin-conjugating enzyme E2W (putative) isoform 3 [*Homo sapiens*]; (6467:) ubiquitin-conjugating enzyme E2Z (putative) [*Homo sapiens*]; (6468:) ubiquitin-conjugating enzyme HBUCE1 [*Homo sapiens*]; (6469:) ubiquitin-conjugating enzyme isolog [*Homo sapiens*]; (6470:) ubiquitin-conjugating enzyme RIG-B [*Homo sapiens*]; (6471:) ubiquitin-conjugating enzyme UBC3B [*Homo sapiens*]; (6472:) ubiquitin-conjugating enzyme UbCH2 [*Homo sapiens*]; (6473:) ubiquitin-conjugating enzyme UbCH6 [*Homo sapiens*]; (6474:) ubiquitin-conjugating enzyme UbCH7 [*Homo sapiens*]; (6475:) ubiquitin-conjugating enzyme UbcM2 [*Homo sapiens*]; (6476:) ubiquitin-conjugating enzyme variant Kua [*Homo sapiens*]; (6477:) ubiquitin-conjugating enzyme, UBC9 [*Homo sapiens*]; (6478:) ubiquitin-conjugating enzyme; [*Homo sapiens*]; (6479:) ubiquitin-conjugating enzyme E2 [*Homo sapiens*]; (6480:) Ubiquitin-fold modifier conjugating enzyme 1 [*Homo sapiens*]; (6481:) Ubiquitin-like 1-activating enzyme E1A (SUMO-1-activating enzyme subunit 1); (6482:) Ubiquitin-like 1-activating enzyme E1B (SUMO-1-activating enzyme subunit 2) (Anthracycline-associated resistance ARX); (6483:) Ubiquitin-like PHD and RING finger domain-containing protein 2(Ubiquitin-like-containing PHD and RING finger domains protein 2) (Np95/ICBP90-like RING finger protein) (Np95-like RING finger protein) (Nuclear zinc finger protein Np97) (RING finger protein107); (6484:) "ubiquitin-like protein activating enzyme; sentrin activating enzyme [*Homo sapiens*]."; (6485:) Ubiquitin-protein E3 ligase Topors (SUMO1-protein E3 ligase Topors) (Topoisomerase I-binding RING finger protein) (Topoisomerase I-binding arginine/serine-rich protein) (Tumor suppressor p53-binding protein 3) (p53-binding protein 3) (p53BP3); (6486:) Ubiquitin-protein ligase BRE1A (BRE1-A) (hBRE1) (RING finger protein 20); (6487:) Ubiquitin-protein ligase BRE1B (BRE1-B) (RING finger protein 40) (95 kDa retinoblastoma-associated protein) (RBP95); (6488:) ubiquitin-protein ligase E1 homolog—human; (6489:) Ubiquitin-protein ligase E3A (E6AP ubiquitin-protein ligase) (Oncogenic protein-associated protein E6-AP) (Human papillomavirus E6-associated protein) (NY-REN-54 antigen); (6490:) Ubiquitin-protein ligase E3C; (6491:) Ubiquitin-protein ligase EDD1 (Hyperplastic discs protein homolog) (hHYD) (Progestin-induced protein); (6492:) ubiquitin-specific processing protease [*Homo sapiens*]; (6493:) ubiquitin-specific protease 12-like 1 [*Homo sapiens*]; (6494:) ubiquitin-specific protease 21 [*Homo sapiens*]; (6495:) ubiquitin-specific protease 26 [*Homo sapiens*]; (6496:) ubiquitin-specific protease 3 [*Homo sapiens*]; (6497:) ubiquitin-specific protease 31 [*Homo sapiens*]; (6498:) ubiquitin-specific protease 7 isoform [*Homo sapiens*]; (6499:) U-box domain containing 5 isoform a [*Homo sapiens*]; (6500:) U-box domain containing 5 isoform b [*Homo sapiens*]; (6501:) UDP glucuronosyltransferase (EC 2.4.1.-) 1A10 precursor—human; (6502:) UDP glycosyltransferase 1 family, polypeptide A1 precursor [*Homo sapiens*]; (6503:) UDP glycosyltransferase 1 family, polypeptide A10 precursor [*Homo sapiens*]; (6504:) UDP glycosyltransferase 1 family, polypeptide A3 precursor [*Homo sapiens*]; (6505:) UDP glycosyltransferase 1 family, polypeptide A4 precursor [*Homo sapiens*]; (6506:) UDP glycosyltransferase 1 family, polypeptide A5 precursor [*Homo sapiens*]; (6507:) UDP glycosyltransferase 1 family, polypeptide A6 isoform 1 precursor [*Homo sapiens*]; (6508:) UDP glycosyltransferase 1 family, polypeptide A6 isoform 2 [*Homo sapiens*]; (6509:) UDP glycosyltransferase 1 family, polypeptide A7 precursor [*Homo sapiens*]; (6510:) UDP glycosyltransferase 1 family, polypeptide A8 precursor [*Homo sapiens*]; (6511:) UDP glycosyltransferase 1 family, polypeptide A9 precursor [*Homo sapiens*]; (6512:) UDP glycosyltransferase 2 family, polypeptide B15 [*Homo sapiens*]; (6513:) UDP glycosyltransferase 2 family, polypeptide B4 [*Homo sapiens*]; (6514:) UDP glycosyltransferase 8 (UDP-galactose ceramidegalactosyltransferase) [*Homo sapiens*]; (6515:) UDP-Gal:betaGlcNAc beta 1,3-galactosyltransferase 5 [*Homo sapiens*]; (6516:) UDP-Gal:betaGlcNAc beta 1,4-galactosyltransferase 1, membrane-bound form [*Homo sapiens*]; (6517:) UDP-Gal:betaGlcNAc beta 1,4-galactosyltransferase 2 [*Homo sapiens*]; (6518:) UDP-Gal:betaGlcNAc beta 1,4-galactosyltransferase 3 [*Homo sapiens*]; (6519:) UDP-Gal:betaGlcNAc beta 1,4-galactosyltransferase 4 [*Homo sapiens*]; (6520:) UDP-Gal:betaGlcNAc beta 1,4-galactosyltransferase 5 [*Homo sapiens*]; (6521:) UDP-Gal:betaGlcNAc beta 1,4-galactosyltransferase 6 [*Homo sapiens*]; (6522:) UDP-galactose-4-epimerase [*Homo sapiens*]; (6523:) UDP-GlcNAc:betaGal beta-1,3-N-acetylglucosaminyltransferase 1 [*Homo sapiens*]; (6524:) UDP-GlcNAc:betaGal beta-1,3-N-acetylglucosaminyltransferase 2 [*Homo sapiens*]; (6525:) UDP-GlcNAc:betaGal beta-1,3-N-acetylglucosaminyltransferase 3 [*Homo sapiens*]; (6526:) UDP-GlcNAc:betaGal beta-1,3-N-acetylglucosaminyltransferase 4 [*Homo sapiens*]; (6527:) UDP-GlcNAc:betaGal beta-1,3-N-1-acetylglucosaminyltransferase 5 [*Homo sapiens*]; (6528:) UDP-GlcNAc:betaGal beta-1,3-N-acetylglucosaminyltransferase 6 [*Homo sapiens*]; (6529:) UDP-glucose 4-epimerase (Galactowaldenase) (UDP-galactose-4-epimerase); (6530:) UDP-glucose pyrophosphorylase 2 isoform a [*Homo sapiens*]; (6531:) UDP-glucose pyrophosphorylase 2 isoform b [*Homo sapiens*]; (6532:) UDP-glucuronate decarboxylase 1 [*Homo sapiens*]; (6533:) UDP-glucuronosyltransferase 1-1 precursor (UDP-glucuronosyltransferase 1A1) (UDPGT) (UGT1*1) (UGT1-01) (UGT1.1) (UGT-1A) (UGT1A) (Bilirubin-specific UDPGT isozyme 1) (HUG-BR1); (6534:) UDP-glucuronosyltransferase 1-6 precursor (UDP-glucuronosyltransferase 1A6) (UDPGT) (UGT1*6)

(UGT1-06) (UGT1.6) (UGT-1F) (UGT1F) (Phenol-metabolizing UDP-glucuronosyltransferase); (6535:) UDP-glucuronosyltransferase 2B15 precursor (UDPGT) (UDPGTh-3) (HLUG4); (6536:) UDP-glucuronosyltransferase 2B17 precursor (UDPGT) (C19-steroid-specific UDP-glucuronosyltransferase); (6537:) UDP-glucuronosyltransferase 2B4 precursor (UDPGT) (Hyodeoxycholic acid) (HLUG25) (UDPGTh-1); (6538:) UDP-glucuronyltransferase-S [Homo sapiens]; (6539:) UDP-N-acetylglucosamine-2-epimerase/N-acetylmannosamine kinase [Homo sapiens]; (6540:) UDP-N-acetylglucosamine-2-epimerase [Homo sapiens]; (6541:) UDP-N-acetylglucosamine-2-epimerase/N-acetylmannosamine kinase [Homo sapiens]; (6542:) UDP-N-acetylglucosamine—dolichyl-phosphate N-acetylglucosamine phosphotransferase (GPT) (G1PT) (N-acetylglucosamine-1-phosphate transferase) (GlcNAc-1-P transferase); (6543:) UDP-N-acetylglucosamine-dolichyl-phosphateN-acetylglucosaminephosphotransferase isoform a [Homo sapiens]; (6544:) UDP-N-acetylglucosamine-dolichyl-phosphateN-acetylglucosaminephosphotransferase isoform b [Homo sapiens]; (6545:) "UDP-N-acetylhexosamine pyrophosphorylase (Antigen X) (AGX) (Sperm-associated antigen 2) [Includes:) UDP-N-acetylgalactosamine pyrophosphorylase (AGX-1); UDP-N-acetylglucosamine pyrophosphorylase (AGX-2)]."; (6546:) UDP-N-acteylglucosamine pyrophosphorylase 1 [Homo sapiens]; (6547:) UEV-1 [Homo sapiens]; (6548:) UEV1As [Homo sapiens]; (6549:) UEV1 Bs [Homo sapiens]; (6550:) Ufm1-conjugating enzyme 1 (Ubiquitin-fold modifier-conjugating enzyme 1); (6551:) Ufm1-conjugating enzyme 1 [Homo sapiens]; (6552:) UGA suppressor tRNA-associated protein (tRNA(Ser/Sec)-associated antigenic protein) (SLA/LP autoantigen) (Soluble liver antigen) (SLA) (Liver-pancreas antigen) (LP) (SLA-p35); (6553:) UMP synthase [Homo sapiens]; (6554:) UMP-CMP kinase (Cytidylate kinase) (Deoxycytidylate kinase) (Cytidine monophosphate kinase) (Uridine monophosphate/cytidine monophosphate kinase) (UMP/CMP kinase) (UMP/CMPK) (Uridinemonophosphate kinase); (6555:) UMP-CMP kinase [Homo sapiens]; (6556:) UnpEL [Homo sapiens]; (6557:) UnpES [Homo sapiens]; (6558:) u-plasminogen activator receptor form 1 precursor—human; (6559:) upstream binding protein 1 (LBP-1a) [Homo sapiens]; (6560:) Upstream-binding protein 1 (LBP-1); (6561:) Uracil-DNA glycosylase (UDG); (6562:) uracil-DNA glycosylase isoform UNG1 precursor [Homo sapiens]; (6563:) uracil-DNA glycosylase isoform UNG2 [Homo sapiens]; (6564:) Urate Transporter 1 (URAT1); (6565:) Urease; (6566:) Uridine diphosphate glucose pyrophosphatase (UDPG pyrophosphatase) (UGPPase) (Nucleoside diphosphate-linked moiety X motif 14) (Nudix motif 14); (6567:) uridine diphosphate glucose pyrophosphatase [Homo sapiens]; (6568:) uridine phosphorylase (EC 2.4.2.3)-2—human; (6569:) Uridine Phosphorylase (UrdPase); (6570:) uridine-cytidine kinase 2 [Homo sapiens]; (6571:) UROD [Homo sapiens]; (6572:) urokinase plasminogen activator preproprotein [Homo sapiens]; (6573:) Urokinase plasminogen activator surface receptor precursor (uPAR) (U-PAR) (Monocyte activation antigen Mo3) (CD87 antigen); (6574:) Urokinase-type plasminogen activator (uPA); (6575:) Urokinase-type plasminogen activator receptor (uPAR); (6576:) Uronyl 2-sulfotransferase; (6577:) uroporphyrinogen decarboxylase (EC 4.1.1.37); (6578:) Uroporphyrinogen decarboxylase (URO-D) (UPD); (6579:) uroporphyrinogen decarboxylase [Homo sapiens]; (6580:) uroporphyrinogen decarboxylase; (6581:) Urotensin II (UT-II) Receptor; (6582:) Urotensin II receptor (UR-II-R) (G-protein coupled receptor 14); (6583:) USP48 protein [Homo sapiens]; (6584:) usurpin beta [Homo sapiens]; (6585:) Usurpin-alpha [Homo sapiens]; (6586:) Usurpin-beta [Homo sapiens]; (6587:) Usurpin-gamma [Homo sapiens]; (6588:) UTP-hexose-1-phosphate uridylyltransferase (EC 2.7.7.10)—human; (6589:) UURF2 ubiquitin ligase [Homo sapiens]; (6590:) Vacuolar ATP synthase 16 kDa proteolipid subunit; (6591:) Vacuolar ATP synthase catalytic subunit A, osteoclast isoform (V-ATPase subunit A 2) (Vacuolar proton pump alpha subunit 2) (V-ATPase 69 kDa subunit 2) (Isoform H068); (6592:) Vacuolar ATP synthase catalytic subunit A, ubiquitous isoform (V-ATPase subunit A 1) (Vacuolar proton pump alpha subunit 1) (V-ATPase 69 kDa subunit 1) (Isoform VA68); (6593:) Vacuolar ATP synthase subunit B, brain isoform (V-ATPase B2subunit) (Vacuolar proton pump β isoform 2) (Endomembrane proton pump 58 kDa subunit) (H057); (6594:) Vacuolar ATP synthase subunit B, kidney isoform (V-ATPase B1 subunit) (Vacuolar proton pump β isoform 1) (Endomembrane proton pump 58 kDa subunit); (6595:) Vacuolar ATP synthase subunit C (V-ATPase C subunit) (Vacuolar proton pump C subunit); (6596:) Vacuolar ATP synthase subunit D (V-ATPase D subunit) (Vacuolar proton pump D subunit) (V-ATPase 28 kDa accessory protein); (6597:) Vacuolar ATP synthase subunit d (V-ATPase d subunit) (Vacuolar proton pump subunit d) (V-ATPase AC39 subunit) (V-ATPase 40 kDa accessory protein) (P39) (32 kDa accessory protein); (6598:) Vacuolar ATP synthase subunit E (V-ATPase E subunit) (Vacuolar proton pump E subunit) (V-ATPase 31 kDa subunit) (P31); (6599:) Vacuolar ATP synthase subunit F (V-ATPase F subunit) (Vacuolar proton pump F subunit) (V-ATPase 14 kDa subunit); (6600:) Vacuolar ATP synthase subunit G1 (V-ATPase G subunit 1) (Vacuolar proton pump G subunit 1) (V-ATPase 13 kDa subunit 1) (Vacuolar ATPsynthase subunit M16); (6601:) Vacuolar ATP synthase subunit G 2 (V-ATPase G subunit 2) (Vacuolar proton pump G subunit 2) (V-ATPase 13 kDa subunit 2); (6602:) Vacuolar ATP synthase subunit G 3 (V-ATPase G subunit 3) (Vacuolar proton pump G subunit 3) (V-ATPase 13 kDa subunit 3); (6603:) Vacuolar ATP synthase subunit H (V-ATPase H subunit) (Vacuolar proton pump subunit H) (V-ATPase 50/57 kDa subunits) (Vacuolar proton pump subunit SFD) (VMA13) (Nef-binding protein 1) (NBP1); (6604:) vacuolar ATPase subunit H [Homo sapiens]; (6605:) vacuolar H+ ATPase C2 isoform a [Homo sapiens]; (6606:) vacuolar H+ ATPase C2 isoform b [Homo sapiens]; (6607:) vacuolar H+ ATPase E1 isoform a [Homo sapiens]; (6608:) vacuolar H+ ATPase E1 isoform b [Homo sapiens]; (6609:) vacuolar H+ ATPase E1 isoform c [Homo sapiens]; (6610:) vacuolar H+ ATPase G1 [Homo sapiens]; (6611:) vacuolar H+ ATPase B2 [Homo sapiens]; (6612:) Vacuolar Hydrogen Transporting ATPase (V-ATPase); (6613:) Vacuolar protein sorting-associated protein 26A (Vesicle protein sorting 26A) (hVPS26); (6614:) Vacuolar protein sorting-associated protein 26B (Vesicle protein sorting 26B); (6615:) Vacuolar protein sorting-associated protein 29 (Vesicle protein sorting 29) (hVPS29) (PEP11); (6616:) Vacuolar protein sorting-associated protein 35 (Vesicle protein sorting 35) (hVPS35) (Maternal-embryonic 3); (6617:) vacuolar proton pump subunit SFD alpha isoform [Homo sapiens]; (6618:) Vacuolar proton translocating ATPase 116 kDa subunit a isoform 1 (V-ATPase 116 kDa isoform a1) (Clathrin-coated vesicle/synaptic vesicle proton pump 116 kDa subunit) (Vacuolar proton pump subunit 1) (Vacuolar adenosine triphosphatase subunit Ac 16); (6619:) Vacuolar proton translocating ATPase 116 kDa subunit a isoform 2(V-ATPase 116 kDa isoform a2) (TJ6); (6620:) Vacuolar proton translocating ATPase 116 kDa subunit a isoform 3(V-ATPase 116 kDa isoform a3) (Osteoclastic proton pump 116 kDa subunit) (OC-116 kDa) (OC116) (T-cell immune regulator 1) (T cell immune response cDNA7 protein) (TIRC7); (6621:) Vacuolar proton translocating ATPase 116 kDa subunit a isoform 4(V-ATPase 116 kDa isoform a4) (Vacuolar proton translocating ATPase 116 kDa subunit a kidney isoform); (6622:) v-akt murine thymoma viral oncogene homolog 1 [*Homo sapiens*]; (6623:) v-akt murine thymoma viral oncogene homolog 2 [*Homo sapiens*]; (6624:) Valacyclovir hydrolase precursor (VACVase) (Biphenyl hydrolase-like protein) (Biphenyl hydrolase-related protein) (Bph-rp) (Breast epithelial mucin-associated antigen) (MCNAA); (6625:) valosin containing protein (p97)/p47 complex interacting protein 1 [*Homo sapiens*]; (6626:) Valyl-tRNA synthetase (Valine—tRNA ligase) (ValRS) (Protein G7a); (6627:) Vanilloid Receptor 1 (VR1); (6628:) Vascular Adhesion Protein-1 (VAP-1) Receptor; (6629:) vascular adhesion protein-1 [*Homo sapiens*]; (6630:) Vascular Adhesion Protein-1/Semicarbazide-Sensitive Amine Oxidase (VAP-1/SSAO); (6631:) "vascular adhesion protein-1; semicarbazide sensitive amine oxidase; copper-containing amine oxidase homolog [*Homo sapiens*]."; (6632:) Vascular Cell Adhesion Molecule-1 (VCAM-1) Expression; (6633:) Vascular Endothelial Growth Factor (VEGF); (6634:) Vascular Endothelial Growth Factor (VEGF) Receptor; (6635:) Vascular Endothelial Growth Factor 121 (VEGF121); (6636:) Vascular Endothelial Growth Factor 145 (VEGF145); (6637:) Vascular Endothelial Growth Factor 165 (VEGF165); (6638:) Vascular Endothelial Growth Factor 165 (VEGF165) Receptor; (6639:) vascular endothelial growth factor A isoform a precursor [*Homo sapiens*]; (6640:) vascular endothelial growth factor A isoform b precursor [*Homo sapiens*]; (6641:) vascular endothelial growth factor A isoform c precursor [*Homo sapiens*]; (6642:) vascular endothelial growth factor A isoform d precursor [*Homo sapiens*]; (6643:) vascular endothelial growth factor A isoform e precursor [*Homo sapiens*]; (6644:) vascular endothelial growth factor A isoform f precursor [*Homo sapiens*]; (6645:) vascular endothelial growth factor A isoform g precursor [*Homo sapiens*]; (6646:) Vascular Endothelial Growth Factor Receptor 1 (VEGFR-1); (6647:) Vascular endothelial growth factor receptor 1 precursor (VEGFR-1) (Vascular permeability factor receptor) (Tyrosine-protein kinase receptor FLT) (Flt-1) (Tyrosine-protein kinase FRT) (Fms-like tyrosine kinase 1); (6648:) Vascular Endothelial Growth Factor Receptor 2 (VEGFR-2); (6649:) Vascular endothelial growth factor receptor 2 precursor (VEGFR-2) (Kinase insert domain receptor) (Protein-tyrosine kinase receptor Flk-1) (CD309 antigen); (6650:) Vascular endothelial growth factor receptor 3 precursor (VEGFR-3) (Tyrosine-protein kinase receptor FLT4); (6651:) Vascular Endothelial Growth Factor Receptor 1-Tyrosine Kinase (VEGFR1-TK); (6652:) Vascular Endothelial Growth Factor Receptor2-Tyrosine Kinase (VEGFR2-TK); (6653:) Vascular Endothelial Growth Factor Receptor-Tyrosine Kinase (VEGFR-TK); (6654:) Vascular Endothelial-Cadherin (VE-Cadherin); (6655:) Vasoactive Intestinal Peptide Receptor 1 (VPAC1); (6656:) vasoactive intestinal peptide receptor-related protein precursor (clone hIVR5)—human; (6657:) Vasoactive intestinal polypeptide receptor 1 precursor (VIP-R-1) (Pituitary adenylate cyclase-activating polypeptide type II receptor) (PACAP type II receptor) (PACAP-R-2); (6658:) Vasoactive intestinal polypeptide receptor 2 precursor (VIP-R-2) (Pituitary adenylate cyclase-activating polypeptide type III receptor) (PACAP type III receptor) (PACAP-R-3) (Helodermin-preferring VIP receptor); (6659:) Vasopressin V1a receptor (V1aR) (Vascular/hepatic-type arginine vasopressin receptor) (Antidiuretic hormone receptor 1a) (AVPRV1a); (6660:) Vasopressin V1 b receptor (V1bR) (AVPR V1b) (Vasopressin V3receptor) (AVPR V3) (Antidiuretic hormone receptor 1b); (6661:) Vasopressin V2 receptor (Renal-type arginine vasopressin receptor) (Antidiuretic hormone receptor) (AVPR V2); (6662:) VELF1904 [*Homo sapiens*]; (6663:) Very low-density lipoprotein receptor precursor (VLDL receptor) (VLDL-R); (6664:) Very-long-chain acyl-CoA synthetase (VLCS) (Very-long-chain-fatty-acid-CoA ligase) (VLACS) (THCA-CoA ligase) (Fatty-acid-coenzyme A ligase, very long-chain 1) (Long-chain-fatty-acid—CoA ligase) (Fatty acid transport protein2) (FATP-2) (Solute carrier family 27 member 2); (6665:) vesicle docking protein p115 [*Homo sapiens*]; (6666:) Vesicle-associated membrane protein 8 (VAMP-8) (Endobrevin) (EDB); (6667:) v-ets erythroblastosis virus E26 oncogene homolog 1 [*Homo sapiens*]; (6668:) visfatin precursor [*Homo sapiens*]; (6669:) Visual pigment-like receptor peropsin; (6670:) vitamin D (1,25-dihydroxy vitamin D3) receptor [*Homo sapiens*]; (6671:) vitamin D inducible protein [*Homo sapiens*]; (6672:) Vitamin D Receptor (VDR); (6673:) Vitamin D3 receptor (VDR) (1,25-dihydroxy vitamin D3 receptor); (6674:) Vitamin K; (6675:) Vitamin K epoxide reductase complex subunit 1 (Vitamin K12,3-epoxide reductase subunit 1); (6676:) vitamin K epoxide reductase complex, subunit 1 isoform 1 [*Homo sapiens*]; (6677:) vitamin K epoxide reductase complex, subunit 1 isoform 2 [*Homo sapiens*]; (6678:) "Vitamin K-dependent protein C precursor (Autoprothrombin IIA) (Anticoagulant protein C) (Blood coagulation factor XIV) [Contains:Vitamin K-dependent protein C light chain; Vitamin K-dependent protein C heavy chain; Activation peptide]."; (6679:) Vitamin K-dependent protein Z precursor; (6680:) v-kit Hardy-Zuckerman 4 feline sarcoma viral oncogene homolog precursor [*Homo sapiens*]; (6681:) v-maf musculoaponeurotic fibrosarcoma oncogene homolog G [*Homo sapiens*]; (6682:) v-maf musculoaponeurotic fibrosarcoma oncogene homolog isoform a [*Homo sapiens*]; (6683:) v-maf musculoaponeurotic fibrosarcoma oncogene homolog isoform b[*Homo sapiens*]; (6684:) Vomeronasal type-1 receptor 1 (V1 r-like receptor 1) (Vomeronasalol factory receptor chromosome 19 subtype I member 1) (V3r-related gene) (hGPCR24); (6685:) Vomeronasal type-1 receptor 2 (V1r-like receptor 2) (hGPCR25); (6686:) Vomeronasal type-1 receptor 3 (V1r-like receptor 3); (6687:) Vomeronasal type-1 receptor 4 (V1r-like receptor 4) (hGPCR27); (6688:) Vomeronasal type-1 receptor 5 (V1r-like receptor 5) (hGPCR26); (6689:) Von Hippel-Lindau disease tumor suppressor (PVHL) (G7 protein); (6690:) von Hippel-Lindau tumor suppressor isoform 1 [*Homo sapiens*]; (6691:) von Hippel-Lindau tumor suppressor isoform 2 [*Homo sapiens*]; (6692:) von Willebrand Factor (vWF) Receptor; (6693:) von Willebrand factor preproprotein [*Homo sapiens*]; (6694:) v-raf murine sarcoma 3611 viral oncogene homolog [*Homo sapiens*]; (6695:) v-raf murine sarcoma viral oncogene homolog B1 [*Homo sapiens*]; (6696:) v-raf-1 murine leukemia viral oncogene homolog 1 [*Homo sapiens*]; (6697:) v-rel reticuloendotheliosis viral oncogene homolog A, nuclear factor of kappa light polypeptide gene enhancer in B-cells 3, p65 [*Homo sapiens*]; (6698:) wax synthase [*Homo sapiens*]; (6699:) Weel-like protein kinase (Weel A kinase) (WEE1hu); (6700:) Werner syndrome protein [*Homo sapiens*]; (6701:) Wiskott-Aldrich syndrome protein [*Homo sapiens*]; (6702:) Wnt; (6703:) WW, C2 and coiled-coil domain containing 1 [*Homo sapiens*]; (6704:) xanthine dehydrogenase [*Homo sapiens*]; (6705:) "Xanthine dehydrogenase/oxidase [Includes:) Xanthine dehydrogenase (XD); Xanthine oxidase (XO) (Xanthine oxidoreductase)].";

(6706:) Xanthine Oxidase (XO); (6707:) X-Linked inhibitor of Apoptosis Protein (XIAP); (6708:) X-linked interleukin-1 receptor accessory protein-like 1 precursor (IL1 RAPL-1) (Oligophrenin-4) (Three immunoglobulin domain-containing IL-1 receptor-related 2) (TIGIRR-2); (6709:) X-linked interleukin-1 receptor accessory protein-like 2 precursor (ILL RAPL-2-related protein) (Interleukin-1 receptor 9) (IL-1 R9) (IL-1 receptor accessory protein-like 2) (Three immunoglobulin domain-containing IL-1 receptor-related 1) (TIGIRR-1); (6710:) X-linked phosphate regulating endopeptidase homolog [*Homo sapiens*]; (6711:) X-prolyl aminopeptidase (aminopeptidase P)$_1$, soluble [*Homo sapiens*]; (6712:) X-prolyl aminopeptidase 2, membrane-bound [*Homo sapiens*]; (6713:) xylosyl protein beta 1,4-galactosyltransferase 7 [*Homo sapiens*]; (6714:) Xylosyltransferase 1 (Xylosyltransferase I) (XyIT-I) (XT-I) (Peptide O-xylosyltransferase 1); (6715:) Xylosyltransferase 2 (Xylosyltransferase II) (xyIT-II) (XT-II) (Peptide O-xylosyltransferase 1); (6716:) xylosyltransferase I [*Homo sapiens*]; (6717:) xylosyltransferase II [*Homo sapiens*]; (6718:) Xaa-Pro aminopeptidase 1 (X-Pro aminopeptidase 1) (X-prolylaminopeptidase 1, soluble) (Cytosolic aminopeptidase P) (Soluble aminopeptidase P) (sAmp) (Aminoacylproline aminopeptidase); (6719:) Xaa-Pro dipeptidase (X-Pro dipeptidase) (Proline dipeptidase) (Prolidase) (Imidodipeptidase); (6720:) Xaa-Pro dipeptidase [*Homo sapiens*]; (6721:) Yama protein; (6722:) Ymer protein long isoform [*Homo sapiens*]; (6723:) Ymer protein short isoform [*Homo sapiens*]; (6724:) YOD1 OTU deubiquinating enzyme 1 homolog [*Homo sapiens*]; (6725:) Zinc finger FYVE domain-containing protein 9 (Mothers against decapentaplegic homolog-interacting protein) (Madh-interacting protein) (Smad anchor for receptor activation) (Receptor activation anchor) (hSARA) (Novel serine protease) (NSP); (6726:) zinc finger protein 146 [*Homo sapiens*]; (6727:) zinc finger protein Cezanne [*Homo sapiens*]; (6728:) Zinc finger protein OZF (Only zinc finger protein) (Zinc finger protein 146); (6729:) zinc metalloproteinase STE24 homolog [*Homo sapiens*]; (6730:) Zinc phosphodiesterase ELAC protein 1 (Ribonuclease Z1) (RNase Z1) (tRNase Z1) (tRNA 3 endonuclease 1) (ElaC homolog protein 1) (Deleted in Ma29); (6731:) Zinc phosphodiesterase ELAC protein 2 (Ribonuclease Z 2) (RNase Z2) (tRNase Z 2) (tRNA 3 endonuclease 2) (ElaC homolog protein 2) (Heredity prostate cancer protein 2); (6732:) Zona pellucida sperm-binding protein 2 precursor (Zona pellucida glycoprotein ZP2) (Zona pellucida protein A)

Methods for Isolating "Lead Compounds"

The present invention in one embodiment is also directed to a method for isolating novel "drug leads" or "lead compounds" from libraries of different molecules synthesised by the methods of the invention. A "drug lead" or "lead compound" is a compound which may not in itself be suitable as a drug, but which exhibits a number of characteristics which are interesting when viewed from the point of view of medical therapy.

The reasons why such "lead compounds" are often unsuitable could be toxicity, unsuitable pharmacokinetic or pharmacodynamic properties, difficulties relating to preparation and purification etc. In such cases, the "lead compound" is used as a model for de novo synthesis of other chemical compounds which are designed so as to be related to the active part of the lead compound in 3D structure and distribution of charged, polar and non-polar groups.

This approach can be refined by initially identifying the members of the library by methods of structure-based or nonstructure based computer drug-modelling. Suitable nonstructure based methods are disclosed in e.g. U.S. Pat. No. 5,307,287 and U.S. Pat. No. 5,025,388 (a method known as COMFA). An alternative is HASL (Hypothetical Active Site Lattice; Hypothesis Software). Both these methods are based on 3D-QSAR. A feasible structure-based approach is e.g. disclosed in WO 95/06293.

In view of the above, the present invention also pertains to a method for the preparation of a medicinal product, the method comprising the steps of a) selecting a chemical compound by the methods of the invention described above, b) performing pre-clinical tests with the chemical compound in order to assess the suitability thereof as a medicinal product, c) entering, if the chemical compound is deemed suitable in step (b), clinical trials using the chemical compound in order to obtain market authorization for a medicinal product including the chemical compound as a pharmaceutically active substance, and d) upon grant of a market authorization, admixing the chemical compound with a pharmaceutically acceptable carrier excipient or diluent and marketing the thus obtained medicinal product.

The above-outlined methods should take into consideration all necessary requirements in order to meet GCP and GMP standards.

Additional preferred uses and embodiments of the present invention is disclosed herein below. A number of assays which can be used to verify or identify an effect or property of a molecule identified by one or more methods of the present invention can be performed by a person skilled in the art.

In embodiments of the present invention, the bioactive species encoding it is used to identify pharmaceutically relevant target molecules, i.e. the molecules with which the bioactive species can form an interaction. As will be appreciated by those in the art, there can be primary target molecules to which the bioactive species binds or acts upon directly and there can be secondary target molecules, which are part of a signalling pathway affected by the bioactive species; the latter might be termed "validated targets".

In one embodiment, the present methods are useful in cancer applications. The ability to rapidly and specifically kill tumor cells is a cornerstone of cancer chemotherapy. In general, using the methods of the present invention, bioactive species can be identified which, when introduced into any tumor cell (primary or cultured), induce apoptosis, cell death loss of cell division or decreased cell growth. This can be done de novo, or by biased randomization toward known cancer agents, such as angiostatin, which inhibits blood vessel wall growth. According to one embodiment of the present invention, the methods for synthesising a molecule linked to a single stranded identifier oligonucleotide is targeted to a target compound known to be involved in induction of apoptosis, cell death loss of cell division or decreased cell growth.

Targets can include e.g. known proteins such as Abl, Src, Ras, and others, which lead to abnormal cell growth in certain cells or the development of micro-metastases. Thus, in one embodiment, bioactive species obtainable by the methods of the invention are introduced into cancer cells to select for bioactive species which reverse or correct a cancer condition. One of the signal features of oncogene activity in cells is the loss of contact inhibition and the ability to grow in soft-agar. When e.g. Abl, Src, or Ras are expressed 3T3 cells and subjected to puromycin selection, all of the 3T3 cells hyper-transform and detach from the plate. The cells can be removed by washing with fresh medium. This can serve as the basis of a screen, since cells which express a bioactive species having anti-cancer activity will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In one embodiment, the bioactive species obtainable by the methods of the invention are used to inhibit or stop tumor growth and/or spread selecting bioactive species capable of blocking the ability of the growth factor or cytokine to stimulate the tumor cell. The introduction of bioactive species obtainable by the methods of the present invention into specific tumor cells with the addition of the growth factor or cytokine, followed by selection of bioactive species which block the binding, signaling, phenotypic and/or functional responses of these tumor cells to the growth factor or cytokine in question, represent one embodiment of the present invention.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have bioactive species obtainable by the methods of the present invention introduced into them, and bioactive species selected which in a migration or invasion assay, inhibit the migration and/or invasion of specific tumor cells. Particular applications for inhibition of the metastatic phenotype, which could allow a more specific inhibition of metastasis, include the polypeptide encoded by the metastasis suppressor gene NM23, which codes for a dinucleoside diphosphate kinase. Thus, bioactive species acting as activators of this gene could block metastasis. Many oncogene products also enhance metastasis.

Bioactive species which inactivate or counteract gene products encoded by mutated RAS oncogenes, v-MOS, v-RAF, A-RAF, v-SRC, v-FES, and v-FMS would also act as anti-metastatics. Bioactive species obtainable by the invention which act intracellularly to block the release of combinations of proteases required for invasion, such as the matrix metalloproteases and urokinase, could also be effective antimetastatics.

In one embodiment, the bioactive species obtainable by the methods of the present invention are introduced into tumor cells known to have inactivated tumor suppressors, and successful reversal e.g. by compensation of suppression of the suppressor can be screened for e.g. by restoration of a normal phenotype. A major example is the reversal of p53-inactivating mutations, which are present in 50% or more of all cancers. Since p53's actions are complex and involve its action as a transcription factor, there are probably numerous potential ways a small molecule bioactive species could reverse the mutation. One example could be e.g. to increase the activity of the cyclin-dependent kinase p21CIP1NVAF1. To be useful such reversal would have to work for many of the different known p53 mutations. It is possible to screen for one or more small molecules possessing the above-cited activities.

In another embodiment, the methods of the present invention for synthesising and selecting small molecule bioactive species are useful in various cardiovascular applications. In one embodiment, cardiomyocytes can be screened for the prevention of cell damage or death in the presence of normally injurious conditions, including, but not limited to, the presence of toxic drugs (particularly chemo-therapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive species are inserted into cardiomyocytes, the cells are subjected to the insult. It is possible to screen for bioactive species are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In yet another embodiment, the bioactive species obtainable by the methods of the present invention are used to screen for diminished arrhythmia potential in cardiomyocytes. The screens comprise the introduction of the candidate bioactive species, followed by the application of arrythmogenic insults, with screening for bioactive species that block specific depolarization of cell membrane. This can be detected using patch clamps, or via fluorescence techniques). Similarly, channel activity (for example, potassium and chloride channels) in cardiomyocytes could be regulated using the bioactive species obtainable by the methods of the present invention in order to enhance contractility and prevent or diminish arrhythmias.

In yet another embodiment, the bioactive species obtainable by the methods of the present invention are used to screen for enhanced contractile properties of cardiomyocytes and diminish heart failure potential. The introduction of the bioactive species obtainable by the methods of the present invention followed by measuring the rate of change of myosin polymerization/depolymerization using fluorescent techniques can be done. It is possible to screen for bioactive species which increase the rate of change of this phenomenon can result in a greater contractile response of the entire myocardium, similar to the effect seen with digitalis.

In a still further embodiment, selected bioactive species obtainable by the methods of the present invention can be useful for identifying agents involved in the regulation of intracellular and sarcolemmal calcium cycling in cardiomyocytes in order to prevent arrhythmias. It is possible to screen for bioactive species which regulate sodium-calcium exchange, sodium proton pump function, and regulation of calcium-ATPase activity in human or animal cells.

In one embodiment, the bioactive species obtainable by the methods of the present invention are useful for identifying agents that diminish embolic phenomena in arteries and arterioles leading to strokes (and other occlusive events leading to kidney failure and limb ischemia) and angina precipitating a myocardial infarct are selected. For example, it is possible to screen for bioactive species which will diminish the adhesion of platelets and leukocytes, and thus diminish the occlusion events.

Adhesion in this setting can be inhibited by the bioactive species obtainable by the methods of the present invention once such bioactive species are inserted into endothelial cells (quiescent cells, or activated by cytokines, i.e. IL-1, and growth factors, i.e. PDGF I EGF) and then screened for either: 1) downregulation of adhesion molecule expression on the surface of the endothelial cells (binding assay); 2) blocking of adhesion molecule activation on the surface of these cells (signaling assay); or 3) releasing in an autocrine manner biological molecules including peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, the bioactive species obtainable by the methods of the present invention can be introduced into endothelial cells, followed by standard fluorogenic assays, which will allow monitoring of proteolytic activity on the cell surface towards a known substrate. Bioactive species can then be selected which activate specific enzymes towards specific substrates.

In one embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive species can thus be inserted into these cells, and one can screen for inhibition of the chemotactic response to diverse chemokines (for example, to the IL-8 family of chemokines, RANTES) in cell migration assays.

In yet another embodiment, arterial restenosis following coronary angioplasty can be controlled by regulating the proliferation of vascular intimal cells and capillary and/or arterial endothelial cells. Candidate bioactive species can be inserted into these cell types and their proliferation in response to specific stimuli can be monitored. It is possible to screen for bioactive species which are capable of blocking the expression or function of c-myc and other oncogene products in smooth muscle cells to stop their proliferation. It would also be possible to introduce the bioactive species obtainable by the methods of the present invention into vascular smooth muscle cells and to screen for bioactive species which can selectively induce apoptosis.

Application of small molecule bioactive species may require targeted drug delivery; this is available e.g. with stents, hydrogel coatings, and infusion-based catheter systems. Bioactive species which down regulate endothelin-1A receptors or which block the release of the potent vasoconstrictor and vascular smooth muscle cell mitogen endothelin-1 may also be candidates for therapeutics. Accordingly, it is possible to screen for bioactive species which can inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive species can be inserted into capillary endothelial cells and the growth of such cells can be monitored. Stimuli such as low oxygen tension and varying degrees of angiogenic factors can regulate the responses, and one can screen for bioactive species which can produce the appropriate phenotype. Screening for bioactive species capable of acting as antagonisms of vascular endothelial cell growth factor, important in angiogenesis, would also be useful.

In one embodiment, the bioactive species obtainable by the methods of the present invention are useful in screening for decreases in atherosclerosis producing mechanisms to find biological molecules that regulate LDL and HDL metabolism. Candidate bioactive species can be inserted into the appropriate cells (including hepatocytes, mononuclear leukocytes, endothelial cells) and one can screen for bioactive species which lead to a decreased release of LDL or diminished synthesis of LDL, or conversely to an increased release of HDL or enhanced synthesis of HDL. It is also possible to screen for bioactive species which decreases the production of oxidized LDL, which has been implicated in atherosclerosis and isolated from atherosclerotic lesions. This could occur e.g. by activating reducing systems or enzymes, or blocking the activity or production of enzymes implicated in production of oxidized LDL, such as 15-lipoxygenase in macrophages.

In one embodiment, the bioactive species obtainable by the methods of the present invention are used in screens to regulate obesity via the control of food intake mechanisms or diminishing the responses of receptor signaling pathways that regulate metabolism. One can screen for bioactive species that regulate or inhibit the responses of neuropeptide Y (NPY), cholecystokinin and galanin receptors. Candidate bioactive species can be inserted into cells that have these receptors cloned into them, and one can screen for bioactive species which block the signaling responses to galanin and NPY. In a similar manner, one can screen for bioactive species which regulate the leptin receptor.

In a still further embodiment, bioactive species obtainable by the methods of the present invention can be used in screens in neurobiology applications. Candidate bioactive species can be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory polypeptide (NAIP); screens for its upregulation, or effecting any coupled step could yield bioactive species which selectively block neuronal apoptosis. Other applications include neurodegenerative diseases such as Alzheimer's disease and Huntington's disease.

In another embodiment, bioactive species obtainable by the methods of the present invention can be used in screens in bone biology applications. Osteoclasts are known to play a key role in bone remodeling by breaking down "old" bone, so that osteoblasts can lay down "new" bone. In osteoporosis one has an imbalance of this process. A screen for osteoclast overactivity can be set up by introducing candidate bioactive species to these cells, and then screening for bioactive species that produce: 1) a diminished processing of collagen by these cells; 2) decreased pit formation on bone chips; and 3) decreased released of calcium from bone fragments.

The bioactive species obtainable by the methods of the present invention can also be used in screens for agonists of bone morphogenic biological molecules and hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate bioactive species and screened for their growth, proliferation, collagen stimulating activity, and/or proline incorporating ability on the target osteoblasts. Alternatively, candidate bioactive species can be screened for their ability to increase production of collagen or bone.

In one embodiment, bioactive species obtainable by the methods of the present invention can be screened for activities which are useful in various skin biology applications. Keratinocyte responses to a variety of stimuli may result in psoriasis, a proliferative change in these cells. Candidate bioactive species can be inserted into cells removed from active psoriatic plaques, and one can screen for bioactive species which decrease the rate of growth of these cells.

In one embodiment, the bioactive species obtainable by the methods of the present invention can be screened for activities which are useful in the regulation or inhibition of keloid formation (i.e. excessive scarring). Candidate bioactive species can be introduced into skin connective tissue cells isolated from individuals with this condition, and one can screen for bioactive species that decrease proliferation, collagen formation, or proline incorporation. Results from this work can be extended to treat the excessive scarring that also occurs in burn patients. If a common bioactive species motif is found in the context of the keloid work, then it can be tested if this motif can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Candidate bioactive species can be inserted into skin connective tissue cells, and one can screen for bioactive species which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Candidate bioactive species can be introduced into melanocytes and known stimuli that increase the synthesis of melanin applied to the cells. One can screen for bioactive species which inhibit the synthesis of melanin under these conditions.

In one embodiment, one can screen for activities of bioactive species obtainable by the methods of the present invention which are useful in endocrinology applications. The methods of the present invention and the bioactive species thus obtained can be applied broadly to any endocrine, growth factor, cytokine or chemokine network which involves a signaling peptide or polypeptide that acts in either an endocrine, paracrine or autocrine manner that binds or dimerizes a receptor and activates a signaling cascade that results in a known phenotypic or functional outcome. One can screen for bioactive species which either mimics a desired hormone (i.e., insulin, leptin, calcitonin, PDGF, EGF, EPO, GMCSF, IL1-17, mimetics) or inhibits its action by either blocking the release of the hormone, blocking its binding to a specific receptor or carrier polypeptide (for example, CRF binding polypeptide), or inhibiting the intracellular responses of the specific target cells to that hormone. It is also possible to screen for bioactive species which increase the expression or release of hormones from cells which normally produce them. This would have broad applications in conditions of hormonal deficiency.

In one embodiment, one can screen for activities of bioactive species obtainable by the methods of the present invention which are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate bioactive species can then be introduced into these cells under the above conditions, and one can screen for bioactive species which block or diminish the growth and/or release of the virus. As with chemotherapeutics, these experiments can also be done in combination with drugs which are only partially effective towards this outcome, and one can screen for bioactive species which enhance the virucidal effect of these drugs.

One example of many is the ability to block HIV-1 infection. HIV-1 requires CD4 and a co-receptor which can be one of several seven transmembrane G-polypeptide coupled receptors. In the case of the infection of macrophages, CCR-5 is the required coreceptor, and there is strong evidence that a block on CCR-5 will result in resistance to HIV-1 infection. There are two lines of evidence for this statement.

First, it is known that the natural ligands for CCR-5, the CC chemokines RANTES, MIPIa and MIPIb are responsible for CD8+ mediated resistance to HIV. Second, individuals homozygous for a mutant allele of CCR-5 are completely resistant to HIV infection. Accordingly, one can screen for activities of bioactive species obtainable by the methods of the present invention which are inhibitory for CCR-5/HIV interaction.

Viruses are known to enter cells using specific receptors to bind to cells (for example, HIV uses CD4, coronavirus uses CD13, murine leukemia virus uses transport polypeptide, and measles virus uses CD44) and to fuse with cells (HIV uses chemokine receptor). Candidate bioactive species can be introduced into target cells known to be permissive to these viruses, and one can screen for bioactive species which block the ability of these viruses to bind to and fuse with specific target cells.

In one embodiment, one can screen for activities of bioactive species obtainable by the methods of the present invention which have applications in the area of infectious organisms. Intracellular organisms such as mycobacteria, *listeria, salmonella, pneumocystis, yersinia, leishmania, T. cruzi*, can persist and replicate within cells, and become active in immunosuppressed patients. There are currently drugs on the market and in development which are either only partially effective or ineffective against these organisms. Candidate bioactive species can be inserted into specific cells infected with these organisms (pre- or post-infection), and one can screen for bioactive species which promote the intracellular destruction of these organisms in a manner analogous to intracellular "antibiotic bioactive species" similar to magainins. In addition, one can screen for bioactive species which enhance the cidal properties of drugs already under investigation which have insufficient potency by themselves, but, when combined with one or more bioactive species obtainable by the methods of the present invention, are dramatically more potent through a synergistic mechanism or otherwise. One can screen for bioactive species which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. One can introduce candidate bioactive species into the specific cell types where specific changes leading to cellular damage or apoptosis by the antibiotics are produced, and one can screen for bioactive species which confer protection, when these cells are treated with these specific antibiotics.

Furthermore, the present invention finds use in screening for bioactive species that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be introduced into specific cells derived from kidney cells and cells of the choroid plexus known to have active transport mechanisms for antibiotics. One can then screen for bioactive species which block the active transport of specific antibiotics and thus extend the serum halflife of these drugs.

In one embodiment bioactive species obtainable by the methods of the present invention are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss.

Specific examples include adriamycin induced cardiomyocyte death, cisplatinin-induced kidney toxicity, vincristine-induced gut motility disorders, and cyclosporin-induced kidney damage. Candidate bioactive species can be introduced into specific cell types with characteristic drug-induced phenotypic or functional responses, in the presence of the drugs, and one can screen for bioactive agents which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity can be due to a specific metabolite produced in the liver or kidney which is highly toxic to specific cells, or due to drug interactions in the liver which block or enhance the metabolism of an administered drug. Candidate bioactive species can be introduced into liver or kidney cells following the exposure of these cells to the drug known to produce the toxic metabolite. One can screen for bioactive species which alter how the liver or kidney cells metabolize the drug, and for bioactive species which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Candidate bioactive species can be introduced into tumor cell lines (primary and cultured) that have demonstrated specific or multiple drug resistance. One can then screen for bioactive species which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for bioactive species which block the normal efflux of fluorescent drug from these cells. Candidate bioactive species are particularly suited to screening for bioactive species which reverse poorly characterized or recently discovered intracellular mechanisms of resistance or mechanisms for which few or no chemosensitizers currently exist, such as mechanisms involving LRP (lung resistance polypeptide). This polypeptide has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for inhibitors of both MRP (multidrug resistance related polypeptide) and LRP for treatment of resistant cells in metastatic melanoma, for inhibitors of both p-glycopolypeptide and LRP in acute myeloid leukemia, and for inhibition (by any mechanism) of all three polybioactive species for treating pan-resistant cells.

In one embodiment, the bioactive species obtainable by the methods of the present invention are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs.

Reversible inhibitors would be delivered at the same time as, or slightly before, the drug of interest. Screening of candidate bioactive species in hepatocytes for inhibitors (by any mechanism, such as polypeptide down regulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione 5-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug.

The enzymes modifying the drug would not necessarily have to be known, if screening was for lack of alteration of the drug.

In one embodiment, the bioactive species obtainable by the methods of the present invention are useful in immunobiology, inflammation, and allergic response applications. Selective regulation of T lymphocyte responses is a desired goal in order to modulate immune-mediated diseases in a specific manner. Candidate bioactive species can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. One can screen for activities of bioactive species obtainable by the methods of the present invention which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific Cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate bioactive species can be introduced into B cells and one can screen for activities of bioactive species which inhibit the release and synthesis of a specific immunoglobulin. This can be useful in autoimmune diseases characterized by the overproduction of auto antibodies and the production of allergy causing antibodies, such as IgE. One can also screen for bioactive species which inhibit or enhance the binding of a specific immunoglobulin subclass to a specific antigen either foreign of self. Finally, one can screen for bioactive species which inhibit the binding of a specific immunoglobulin subclass to its receptor on specific cell types.

Similarly, one can screen for bioactive agents which affect cytokine production, generally by using two cell systems. For example, cytokine production from macrophages, monocytes, etc. can be evaluated. Similarly, one can screen for bioactive species which mimic cytokines, for example erythropoetin and IL1-17, or for bioactive species that bind cytokines such as TNF-alpha, before they bind their receptor.

Antigen processing by mononuclear leukocytes (ML) is an important early step in the immune system's ability to recognize and eliminate foreign polybioactive species. Candidate bioactive species can be introduced into ML cell lines and one can screen for bioactive species which alter the intracellular processing of foreign bioactive species and sequence of the foreign peptide that is presented to T cells by MLs on their cell surface in the context of Class II MHC. One can look for members of a library of bioactive species which enhance immune responses of a particular T cell subset (for example, the peptide would in fact work as a vaccine), or look for a bioactive species library member that binds more tightly to MHC, thus displacing naturally occurring bioactive species, but nonetheless the bioactive species would be less immunogenic (less stimulatory to a specific T cell clone). Such bioactive species would in fact induce immune tolerance and/or diminish immune responses to foreign agents, such as polypeptides. This approach could be used in transplantation, autoimmune diseases, and allergic diseases.

The release of inflammatory mediators (cytokines, leukotrienes, prostaglandins, platelet activating factor, histamine, neurobioactive species, and other peptide and lipid mediators) is a key element in maintaining and amplifying aberrant immune responses. Candidate bioactive species can be introduced into MLs, mast cells, eosinophils, and other cells participating in a specific inflammatory response, and one can screen for bioactive species which inhibit the synthesis, release and binding to the cognate receptor of each of these types of mediators.

In one embodiment, the bioactive species obtainable by the methods of the present invention are useful in biotechnology applications. Random bioactive species displayed on the surface of circulating cells can be used as tools to identify organ, tissue, and cell specific targeting sequences. Any cell introduced into the bloodstream of an animal expressing a library targeted to the cell surface can be selected for specific organ and tissue targeting. The bioactive species identified in this way can then be coupled to an antibody, enzyme, drug, imaging agent or substance for which organ targeting is desired.

Other bioactive species for which screens can be set up include: 1) bioactive species which block e.g. the activity of transcription factors, using cell lines with reporter genes; 2) bioactive species which block the interaction of two known biological molecules in cells, using the absence of normal cellular functions, the mammalian two-hybrid system or fluorescence resonance energy transfer mechanisms for detection.

Enrichment

The present invention also relates to a method for determining the identity of a chemical entity having a preselected property, comprising the steps of:
i) generating a tagged library of chemical entities by appending unique identifier tags to chemical entities,
ii) subjecting the library to a condition, wherein a chemical entity or a subset of chemical entities having a predetermined property is partitioned from the remainder of the library,
iii) recovering an anti-tag from the partitioned library, said anti-tag being capable of interacting with the unique identifier tag in a specific manner, and
iv) identifying the chemical entity/ies having a preselected function by decoding the anti-tag.

The tag is appended the chemical entity by a suitable process. Notably, each chemical entity is appended a tag by a reaction involving a chemical reaction between a reactive group of the chemical entity and a reactive group of the tag, such as method A and B of the selection section. The attachment of the chemical entity can be directly or through a bridging molecule part. The molecule part can be any suitable chemical structure able to connect the chemical entity to the tag.

The anti-tag has the ability to interact with the unique identifier tag in a specific manner. The chemical structure of the anti-tag is to a large extent dependant on the choice of unique tag. As an example, if the unique tag is chosen as an antibody, the anti-tag is selected as the epitope able to associate with the antibody. In general, it is preferred to use an anti-tag comprising a sequence of nucleotides complementary to a unique identifier tag.

The method can be performed without amplification in certain embodiments. However, when larger bioactive species are intended, it is in general preferred to use an anti-tag which is amplifiable. Anti-tags comprising a sequence of nucleotides can be amplified using standard techniques like PCR.

In the event the tag as well as the anti-tag is a sequence of nucleic acids, a tag:anti-tag hybrid can be formed prior to the subjecting the library to partitioning conditions or subsequent to the partitioning step. In some embodiments of the invention it is preferred to form the tag:anti-tag hybrid prior to the partition step in order to make the appended nucleotide sequence inert relative to the system as it is well known that certain sequences of nucleotides can bind to a target or catalyse a chemical reaction.

The oligonucleotide anti-tag can be formed in a variety of ways. In one embodiment of the invention, the anti-tag is formed as an enzymatic extension reaction. The extension comprises the initial annealing of a primer to the unique identifier tag and subsequent extension of the primer using a polymerase and dNTPs. Other types of extension reactions may also be contemplated. As an example ligases can be used to create the primer starting from di- or trinucleotide substrates and the extension can be performed using a suitable polymerase.

It can be desirable to recover the anti-tag at various steps during the process. To this end it is preferred in some aspects of the invention to provide the primer provided with a chemical entity capable of binding to a suitable affinity partner. An arsenal of different chemical entities and affinity partners are available to the skilled person in the art. The most widely used chemical entity is biotin, which in general are also preferred according to the present invention. Biotin binds to the affinity partner streptavidin or avidin. A standard technique in the laboratory is to recover a biochemical entity having attached a biotin using a solid phase covered with streptavidin. Suitably, the solid phase is a bead which can be separated from the liquid after the binding action by rotation or a magnetic field in case the solid bead comprises magnetic particles.

In other aspects of the present invention, the anti-tag is provided as a separate oligonucleotide. The separate oligonucleotide can be produced using standard amidite synthesis strategies or can be provided using other useful methods. It is in general preferred to provide the oligonucleotide by synthesis, at least in part, because the biotin amidite is easily incorporated in a nascent oligonucleotide strand. Following the addition of an oligonucleotide anti-tag to a liquid comprising chemical entities tagged with complementing oligonucleotide tags a double stranded library is formed as a hybridisation product between the unique identifier tag and the anti-tag oligonucleotide.

As mentioned above, the anti-tag oligonucleotide can be provided with a chemical entity, such as biotin, capable of binding to an affinity partner, such as streptavidin or avidin.

Following the addition of the anti-tag oligonucleotides to the tagged chemical entities, some of the oligonucleotides present in the media may not find a partner. In one embodiment of the invention it is preferred that oligonucleotides not hybridised to a cognate unique identifier and/or anti-tag are transformed into a double helix. In other aspects of the invention single stranded oligonucleotides are degraded prior to step ii) to avoid unintended interference.

The chemical entity can be used to purify the library prior to or subsequent to the partitioning step. In some embodiments of the invention, the purification step is performed prior to the partitioning step to reduce the noise of the system. In another aspect the chemical entity is used to purify the partitioned library subsequent to step ii) in order to recover a double stranded product which can be amplified.

The library is subjected to a condition in order to select chemical entities having a property which is responsive to this condition. The condition may involve the exposure of the library to a target and partitioning the chemical entities having an affinity towards this target. Another condition could be subjecting the library to a substrate and partitioning chemical entities having a catalytical activity relative to this substrate.

The anti-tag can be formed subsequent to the partitioning step. In an aspect of the invention, the single stranded nucleotide serving as a tag is made double stranded while the chemical entity is attached to the target of an affinity partitioning. Optionally, in a repeated temperature cycle, a plurality of anti-tags can be formed as extension products using the tag as template. In another aspect of the invention, the chemical entity bearing the single stranded oligonucleotide is detached from the target and a complementing anti-tag is subsequently prepared.

In the event the anti-tag comprises a chemical entity, this chemical entity can be used to purify the partitioned library. The recovery of the anti-tag is then performed by melting off said anti-tag from a partitioned double stranded library. Optionally, the amount of anti-tags can be multiplied by conventional amplification techniques, such as PCR.

The method according to the invention can be performed using a single partitioning step. Usually, it is preferred, however, to use more than one partitioning step in order to select the candidate having the desired properties from a large library. Thus, the recovered anti-tags can be mixed with the initial library or a subset thereof and the steps of partitioning (step ii)) and recovery (step iii)) may is repeated a desired number of times. Optionally, single stranded moieties in the mixture can be degraded or removed or made inert as described above.

Generally, the partitioned library obtained in step ii) is subjected to one or more further contacting steps using increasing stringency conditions. The stringency conditions can be increased by increasing the temperature, salt concentration, acidity, alkalinity, etc.

In one embodiment of the invention, the partitioned library is not subjected to intermediate process steps prior to a repeated contacting step. Especially, the partitioned library is not subjected to intermediate amplification of the anti-tag. This embodiment can be of advantage when relatively small bioactive species are used.

The method of the invention terminates with a decoding step, that is a step in which the identity of the chemical entity or entities are deciphered by an analysis of the anti-tag. When the anti-tag is an oligonucleotide, the decoding step iv) can be performed by sequencing an anti-tag nucleotide. Various methods for sequencing are apparent for the skilled person, including the use of cloning and exposure to a microarray.

The tags contain recognizing groups such as e.g. nucleotide sequence(s), epitope(s) a.o. The tags carries information of the entity to which it is attached, such as e.g. entity structure, mass, spatial position (plate information) etc. The tags can be composed of monoclonal antibodies, bioactive species, proteins, oligonucleotides, DNA, RNA, LNA, PNA, natural bioactive species, unnatural bioactive species, polymeric or oligomeric hydrazino aryl and alkyl carboxylic acids, polymeric or oligomeric aminoxy aryl and alkyl carboxylic acids, peptoids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da).

In one embodiment, entities consist of small non-polymeric molecules (molecular weight <1000 Da). Small molecules are generally the compounds of interest in the quest for drug oral candidates. Especially, small molecules not occurring in Nature are of interest in the drug discovery process and in one embodiment of the present invention the method are designed to select a oral drug candidate. A variety of drug candidate bioactive species are available on the market. The drug candidates of the library usually comprise a reactive group or a group which can be altered into a reactive group. In one preferred aspect of the present invention each of the members of the drug candidate library is appended a nucleic acid tag via said reactive group of the library member and a reactive group on the nucleic acid. Preferably, the nucleic acid is an oligonucleotide.

In another aspect of the invention, entities consist of large non-polymeric molecules (molecular weight >1000 Da). In still another embodiment, entities consist of polymeric molecules.

The tags and anti-tags can be composed of RNA linked to monoclonal antibodies, proteins, LNA, PNA, natural polybioactive species, unnatural polybioactive species, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da).

Alternatively, anti-tags can be composed of DNA linked to monoclonal antibodies, proteins, LNA, PNA, natural polybioactive species, unnatural polybioactive species, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Alternatively, anti-tags are just composed of oligonucleotides, DNA or RNA. In a embodiment, anti-tags are composed of DNA. In another embodiment anti-tags are composed of RNA.

Anti-tags which are linked to DNA or RNA are also encoded by the DNA/RNA linked to them, e.g. phage displayed or polysome displayed antibodies, bioactive species or proteins, and via DNA-templated synthesis of anti-tags, where the DNA encode the synthesis of the anti-tag, which is linked to its DNA during its synthesis.

Each chemical compound or group of compounds can be associated with a tag through formation of a covalent or non-covalent bond. For covalent bond formation, tagging may involve, but is not limited to, the formation of a cycloaddition product, an alkylation product, an arylation product, an acylation product, an amide bond, a carboxylic ester bond, a sulfonamide bond, a disulfide bond, an S-alkyl bond, an NR-alkyl bond, an O-alkyl bond, an aryl-vinyl bond, an alkyne-vinyl bond, an oxime bond, an imine bond, a bicyclic product, a trizole, a hexene, a 7-Oxa-bicyclo[2.2.1]hept-2-ene derivative, a 7-Aza-bicyclo[2.2.1]hept-2-ene derivative or a 7-Methyl-7-aza-bicyclo[2.2.1]hept-2-ene. Non-covalent bonds may involve, but are not limited to, attachment via e.g. hydrogen bonding, van der Waals interactions, pi-stacking or through hybridization. Hybridization can be between complementary strands of DNA, RNA, PNA or LNA or mixtures thereof. In such case both the tag and the chemical compound carries such a strand complementary to each other. The tagged entity, compound or mixture of compounds can be transformed into a new tagged entity, e.g. by transformation of the entity or by transformation of the tag. The transformation can be caused by either chemical or physical transformations such e.g. addition of reagents (e.g. oxidizing or reducing agents, pH adjustment a.o.) or subjection to UV-irradiation or heat.

The complex between tags and anti-tags can be formed on individually tagged entities immediately after tagging. Alternatively, after mixing individually tagged entities, either before or after the optionally use of library purification, or either before or after library enrichment for specific properties.

When tags and anti-tags are composed of nucleotides the complex consists of a double stranded nucleotide, e.g. duplex DNA or hybrids DNA/RNA.

The purification chemical entity (denoted "@") can be connected to the anti-tag. The purification chemical entity contains a recognizing group(s) such as e.g. nucleotide sequence(s), epitopes, reactive groups, high affine ligands a.o. The purification chemical entities can be composed of monoclonal antibodies, bioactive species, proteins, DNA, RNA, LNA, PNA, natural bioactive species, unnatural bioactive species, polymeric or oligomeric hydrazine aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Purification chemical entities may e.g. be a nucleotide sequence, biotin, streptavidin, avidin, "his-tags", mercapto groups or disulfide/activated disulfide groups. The purification chemical entity can be part of the anti-tag, e.g. in the case the anti-tag is nucleotide based or e.g. antibodies where part of the antibody may serve as epitop for another antibody (e.g. immobilized antibody which serve as purification filter).

Purification filters contains components which associate, interact or react with purification chemical entities whereby a complex is formed. This complex allows separation of non-complexed tagged entities and complexed tagged entities. The purification filter contains a recognizing group(s) such as e.g. nucleotide sequence(s), epitopes, reactive groups, high affine ligands a.o. The purification filter can be composed of monoclonal antibodies, bioactive species, proteins, DNA, RNA, LNA, PNA, natural bioactive species, unnatural bioactive species, polymeric or oligomeric hydrazino aryl or alkyl carboxylic acids, polymeric or oligomeric aminoxy aryl or alkyl carboxylic acids, other natural polymers or oligomers, unnatural polymers (molecular weight >1000 Da) or oligomers (molecular weight <1000 Da), small non-polymeric molecules (molecular weight <1000 Da) or large non-polymeric molecules (molecular weight >1000 Da). Purification filters may e.g. be a nucleotide sequence, biotin, strepdavidin, avidin, "his-tags", mercapto groups or disulfide/activated disulfide groups.

The library is probed and enriched for properties. Properties can be affinity, catalytic activity or membrane penetrating capability a.o.

Amplification may use PCR or RTPCR techniques. Anti-tags are amplifiable in some aspects of the invention. Anti-tags can be separated from tags by use of physical or chemical means, such as e.g. UV-irradiation, heat, pH-adjustment, use of salt solutions a.o.

Isolated tagged entities can be identified either trough their tag or anti-tag. Identification can be accomplished by cloning of anti-tags and sequencing their DNA/RNA or through mass analysis of either tagged entities or anti-tags or complexes of anti-tags/tagged entities.

The library of tagged entities may involve $10\text{-}10^{20}$ or $10\text{-}10^{14}$ or $10\text{-}10^2$ or $10\text{-}10^3$ or $10^2\text{-}10^3$ or $10^2\text{-}10^4$ or $10^3\text{-}10^6$ or $10^3\text{-}10^8$ or $10^3\text{-}10^{10}$ or $10^3\text{-}10^{14}$ or $10^5\text{-}10^6$ or $10^5\text{-}10^8$ or $10^5\text{-}10^{10}$ or $10^5\text{-}10^{14}$ or $10^8\text{-}10^{14}$ or $10^{14}\text{-}10^{20}$ entities.

Library complexes of tagged entities and anti-tags can be enriched for properties prior to purification by use of purification chemical entity and purification filter or after purification.

The term unique, when used together with sequences of nucleotides, implies that at least one of the nucleobases and/or backbone entities of the sequence does not appear together with different chemical entities. Preferably, a specific sequence is unique due to fact that no other chemical entities are associated with the same sequence of nucleobases.

Once the library has been formed, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-10 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selecting, cytokines, ICP4, complement proteins, etc.

The stringency conditions under which the library are screened are normally limited to such condition that maintain the hybridisation between the identifier tag and the anti-tag. High stringency conditions can be applied, however, followed by a renewed synthesis or attachment of the anti-tag. Screening conditions are known to one of ordinary skill in the art.

Chemical compounds having predetermined desirable characteristics can be partitioned away from the rest of the library while still attached to a nucleic acid identifier tag by various methods known to one of ordinary skill in the art. In one embodiment of the invention the desirable products are partitioned away from the entire library without chemical degradation of the attached nucleic acid such that the identifier nucleic acids are amplifiable. The identifier tag may then be amplified, either still attached to the desirable chemical compound or after separation from the desirable chemical compound.

In the most embodiment, the desirable chemical compound acts on the target without any interaction between the tag attached to the desirable chemical compound and the target. In one embodiment, the desirable chemical compounds bind to the target and the bound tag-desirable chemical compound-target complex can be partitioned from unbound products by a number of methods. The methods include nitrocellulose filter binding, column chromatography, filtration, affinity chromatography, centrifugation, and other well known methods.

Briefly, the library is subjected to the partitioning step, which may include contact between the library and a column onto which the target is bound. All tags which have not formed hybridisation products with a chemical entity-tag aggregate or those tags associated with undesirable chemical entities will pass through the column. Additional undesirable chemical entities (e.g., entities which cross-react with other targets) can be removed by counter-selection methods. Desirable complexes are bound to the column and can be eluted by changing the conditions of the column (e.g., salt, etc.) or the tag associated with the desirable chemical compound can be cleaved off and eluted directly.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of chemical entities on the basis of a desired function; this can be extended to the selection of small molecules with a desired function and specificity. Specificity can be required during the selection process by first extracting identifier sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Following the selection procedure, anti-tags are recovered. The recovery can be performed by subjecting the selected complexes to stringency conditions which will detach the anti-tag sequences from the identifier tag. In the event the tag and the anti-tag are nucleic acids, the stringency conditions can be increased by increasing the temperature gradually until the two strands of the double helix are melted apart. Further copies of anti-tag sequences can be provided by extension of the identifier sequences using a suitable primer and a polymerase. In the alternative, the recovered anti-tag sequence and/or the identifier sequence tag can be subjected to PCR to form a double stranded product. The strands comprising the sequence that complements at least a part of a unique identifier sequence are subsequently isolated.

The selected chemical entity can be attached to the target during the extension or amplification or can be detached from the target. In one embodiment of the invention, it is preferred that the target is immobilised and the chemical compound remain attached to the target during the extension or amplification, to allow for easy recovery of the extension or amplification product by simple elution. In another aspect the selected chemical entities are separated from the unique identifier sequences, prior to, simultaneous with or subsequent to the recovery of the enrichment sequences.

In order to recover the desired anti-tag sequences, it can be appropriate to provide the native as well as the amplified, if present, anti-tag sequences with one part of a molecular affinity pair. The one part of a molecular affinity pair is also referred to herein as a chemical entity. The anti-tags may then be recovered by using the other part of the molecular affinity pair attached to a solid phase, which is possible to isolate. The essential property of the molecular affinity pair is that the two parts are capable of interacting in order to assemble the molecular affinity pair. In the biotechnological field a variety of interacting molecular parts are known which can be used as the molecular affinity pair. Examples include, but are not restricted to protein-protein interactions, protein-polysaccharide interactions, RNA-protein interactions, DNA-DNA interactions, DNA-RNA interactions, RNA-RNA interactions, biotin-streptavidin interactions, enzyme-ligand interactions, antibody-ligand interaction, protein-ligand interaction, etc.

A suitable molecular affinity pair is biotin-streptavidin. The anti-tag sequences can be provided with biotin, e.g. by using a primer attached to a biotin moiety in the amplification or extension step and contacting the biotin tagged anti-tag sequence with beads coated with streptavidin.

After the recovery of the anti-tag sequences, these are contacted with the initial library or a fraction thereof and an enriched library is allowed to be formed by the hybridisation of the anti-tag sequences to the cognate sequence of the unique identifier tag.

The method according to the invention can be repeated one or more times. In a second round of the method, the part of the single stranded library not recognized by an anti-tag sequence can be cleared from the reaction media or the remaining part of the single stranded library may remain in admixture with the enrich library. In general, it is not necessary to separate the remaining part of the single stranded library from the media before the enriched double stranded library is subjected to a second contact with the target because conditions for the preselected function usually are more stringent than the first round, wherefore the members of the single stranded library presumably will not bind to the target. However, to reduce the noise of the system, it can be useful at some events to withdraw from the media the members of the single stranded initial library not mated with an anti-tag sequence. If the anti-tag sequences are provided with one part of a molecular affinity pair, like biotin, the chemical compounds of interest can be extracted from the media by treatment with immobilized streptavidin, e.g beads coated with streptavidin.

As mentioned above, the conditions for performing the second or further selection step is generally more stringent than in the first or preceding step. The increasing stringency conditions in sequential selection rounds provide for the formation of a sub-library of chemical compounds which is narrowed with respect to the number but enriched with respect to the desired property.

In the present description with claims, the terms nucleic acid, oligonucleotide, oligo, and nucleotides are used frequently. The terms nucleotide, nucleotide monomer, or mononucleotides are used to denote a compound normally composed of two parts, namely a nucleobase moiety, and a backbone. The back bone may in some cases be subdivided into a sugar moiety and an internucleoside linker. Mononucleotides can be linked to each other to form a oligonucleotide. Usually, the mononucleotides are linked through an internucleoside linkage. The term nucleic acid covers mononucleotides as well as oligonucleotides. Usually, however, the term denotes an oligonucleotide having from 2 to 30 mononucleotides linked together through internucleoside linkers.

Determining the Identifier Oligonucleotide of the Bifunctional Complex

The identifier oligonucleotide of the identifier sequence present in the isolated bifunctional molecules or the separated identifier oligonucleotides is determined to identify the chemical entities that participated in the formation of the molecule. The synthesis method of the molecule can be established if information on the functional entities as well as the point in time they have been incorporated in the molecule can be deduced from the identifier oligonucleotide. It can be sufficient to get information on the chemical structure of the various chemical entities that have participated in the molecule to deduce the full molecule due to structural constraints during the formation. As an example, the use of different kinds of attachment chemistries may ensure that a chemical entity on a reactant can only be transferred to a single position on a scaffold. Another kind of chemical constrains can be present due to steric hindrance on the scaffold molecule or the functional entity to be transferred. In general however, it is preferred that information can be inferred from the identifier sequence that enable the identification of each of the chemical entities that have participated in the formation of the molecule along with the point in time in the synthesis history the chemical entities have been incorporated in the (nascent) molecule.

Although conventional DNA sequencing methods are readily available and useful for this determination, the amount and quality of isolated bifunctional molecule may require additional manipulations prior to a sequencing reaction.

Where the amount is low, it is preferred to increase the amount of the identifier sequence by polymerase chain reaction (PCR) using PCR primers directed to primer binding sites present in the identifier sequence.

In addition, the quality of the isolated bifunctional molecule can be such that multiple species of bifunctional molecules are co-isolated by virtue of similar capacities for binding to the target. In cases where more than one species of bifunctional molecule are isolated, the different isolated species must be separated prior to sequencing of the identifier oligonucleotide.

Thus in one embodiment, the different identifier sequences of the isolated bifunctional complexes are cloned into separate sequencing vectors prior to determining their sequence by DNA sequencing methods. This is typically accomplished by amplifying all of the different identifier sequences by PCR as described herein, and then using a unique restriction endonuclease sites on the amplified product to directionally clone the amplified fragments into sequencing vectors. The cloning and sequencing of the amplified fragments then is a routine procedure that can be carried out by any of a number of molecular biological methods known in the art.

Alternatively, the bifunctional complex or the PCR amplified identifier sequence can be analysed in a microarray. The array can be designed to analyse the presence of a single tag or multiple tags in an identifier sequence.

EXAMPLES

General Procedures

The following general procedures were used to synthesize libraries. For example one general procedure used is the reaction of a reactant with a reactive site. Another general procedure used is the attachment of a tag to a nascent bifunctional complex. Yet another general procedure used is a purification of a nascent bifunctional complex or a quenching of a reactive site, e.g. by reaction with a reactant such that the reactive site was rendered unreactive. It is to be understood that any variable such as volume, amount, temperature, pressure, number, concentration, solvent type, reactant type, and composition described in the following general procedures can be varied according to specific needs. It is to be understood that the results obtained by these general procedures can be achieved with a vast number of other variant procedures.

General Procedures Containing a Volume Reduction Step:
V1) Volume Reduction by Lyophilization
The contents of wells were lyophilized in a speed vac
V2) Volume Reduction by Precipitation
The sample was precipitated using 0.1 volumes of 5 M NaCl and 0.5 volumes of isopropanol or 1.5 volumes of ethanol and washed with cold 70% ethanol. A sample of the material was analysed by polyacrylamide gel electrophoresis and autoradiography to verify the efficiency of dephosphorylation.

General Procedures Containing a Splitting Step:
S1) The total pool or a part of the pool the total pool was split equally in 1-10.000 wells, e.g. 8, 16, 24, 32, 40, 48, 56, 64, 72, 80, 88, 96, 192, 384, or 1536 wells.

General Procedures Containing a Mixing Step Include:
M1) the Contents of all Wells were Mixed to Form One Pool
M2) Different Pools were Formed by Mixing the Contents of Different Wells General Procedures Modifying a Reactant
B1) Method for Generating an Aliphatic Aldehyde
The material was redissolved in 25 µl NaIO4 (50 mM in Sodium Acetate Buffer pH 4 and shaken at 25° C. for 30 min. 25 µl 700 mM Phosphate buffer pH 6.7 was added.

General Procedures Containing a Reaction of a Reactant with a Reactive Site:
R1) Reactants Containing an Acid which Reacts with an Amine Forming an Amide Bond:
Bifunctional complexes were distributed to wells. Samples to undergo acylation were dissolved in 5 µl 200 mM Na-phosphate buffer pH 8.0 or 100 mM Na-Borate pH 9.0 or 100 mM Na-Borate pH 10.0. Then, 4 µl specific reactant (100 mM in dimethylsulfoxide) was added to each well. Then 1 µl DMT-MM mix (0.36 M DMT-MM in water and 56 mM Na-phosphate buffer pH 8) was mixed in each well and the sample was incubate at 30° C. for 16 hours.

R2) Reactants Containing an Isocyanate which can React with an Amine Forming an Urea Bond:
Lyophilize the contents of all wells. Mix 2 ml 100 mM Na-Borate buffer pH 8, with 2 ml 100 mM Na-phosphate buffer, pH 8. Add 8 µl buffer mix to each well. Add 1 µL specific BB in 300 mM CH3CN to each well. Mix contents of each well. Incubate at 50 degrees celcius for 16 hours.

R3) Reactants Containing a Sulfonyl Group which can React with an Amine Forming a Sulphonamide Bond:
Samples to undergo sulfonylation were dissolved in 8 µl 100 mM Sodium Borate buffer pH 9. 2 µl specific reactant (100 mM in tetrahydrofuran) was then to each well and incubated at 30° C. for 16 hours.

R4) Reactants Containing an Aldehyde Group which can React with a Primary Amine Forming a Secondary Amine or with a Secondary Amine Forming a Tertiary Amine:
Samples to undergo reductive amination were dissolved in 15 µl 200 mM NaOAc buffer pH 5.0 5 ul specific BB was added to each well (200 mM in DMSO) and incubate at 30° C. for 1 h. Then 5 µl of freshly prepared 140 mM NaCNBH3 (REA000025; 8.8 mg/ml) in NaOAc buffer pH 5.0 to was added each well and the samples were incubated at 30° C. for 16 hours in a PCR-machine. Then 25 µl water was added to each sample.

R5) Reactants Containing a Halogenated Heteroaromatic Moiety which can React with an Amine Forming a C—N Bond.
Samples to undergo nucleophilic aromatic substitution were dissolved in 12 µl 100 mM Borate Buffer pH 9. Then 12 µl specific BB was added to each well (100 mM in DMSO) and all wells were incubated for 16 hours at 90° C. Then, 40 µl water was added to each sample.

R6) Reactants Containing an Amine which can React with an Acid Forming an Amide Bond.
The material was redissolved in 10 µl H2O. 15 µl 100 mM Sulfo-NHS in water and 1 µl 100 mM EDC in water was added. The mixture was shaken at 25° C. for 15 min. The material was purified in a spin column equilibrated water directly into 1 µl 100 mM BB/RE in 100 mM sodium phosphate buffer pH 8.0. The mixture was shaken for 45 min at 50° C. or 16 hours at 37° C.

R7) Reactants Containing an Amine which can React with an Acid Forming an Amide Bond.
The material was redissolved in 35 µl 100 mM sodium phosphate buffer pH 8.0. 10 µl 100 mM building block solution in water or DMSO was added. 5.0 µl 500 mM DMT-MM in water was added. The mixture was incubated at 30° C. for 2-24 hours.

R8) Reactants containing an aldehyde group which can react with a primary amine forming a secondary amine or with a secondary amine forming a tertiary amine. The reaction being performed in organic solvent (MeOH).
The material was applied to a DEAE (Diethyl aminoethyl) column which had been washed 2 times with 10 mM Aq. AcOH. The material on DEAE was washed with water followed by washing with MeOH. 10 µL 100 mM BB in DMSO and 40 µL MeOH (dry) was added and the mixture was shaken at 600 rpm for 1 h at 30° C. 10 µl NaCNBH$_3$ solution (140 mM in MeOH, freshly prepared) was added and the mixture was shaken overnight at 30° C. The material was then released from DEAE by adding 70 µl Release solution (1.5 M NaCl) and incubating at 25° C. for 10 minutes in an eppendorph thermoshaker at 600 rpm. Water was added to the material to a final NaCl concentration of 0.5 M. Then the material was precipitated by adding one volume of isopropanol as described.

General Procedures Including Enabling or Including a Quality Control Step:

QC1) Quality Control of Reactant Reaction, e.g. Reaction with an Identifier Oligo Before a reactant reaction step, 10 μL of spike1 oligo [6TCAAGGAAGTAGGTCACGTA, where 6 is 6=5'C2OC2 aminomodifier, Glen research 10-1905] was added to specific wells. After a reactant reaction step 2 μL sample was taken from specific wells and transferred to a 96-well plate. 50 μL buffer which is compatible with mass spectrometry analysis was added. A Mass spectrometry analysis was performed of the sample(s). The yield of a reaction of a reactant with a reactive site was thus evaluated.

QC2) Quality Control of Tag Addition

At some point during library synthesis tags labelled with a 5' phosphorus-32 was added to specific wells. Then, prior to performing a tag addition step samples were taken from a number of wells. These samples were pooled to serve as a marker before tag addition. Following a tag addition, a 0.2 mm 10% PAGE gel was prepared and 0.5 μL samples were taken from a number of wells. PAGE loading buffer was added to the samples. The samples were processed by PAGE including a molecular weight marker suitably labelled. The gel was transferred to a support, wrapped in plastic, placed on film, exposed and developed. The efficiency of the tag addition (ligation) step was evaluated by comparing samples taken before and after tag addition.

QC3) Quality Control of Reactant Reaction

Before a reactant reaction step, 10 μL of spike1 oligo [6TCAAGGAAGTAGGTCACGTA, where 6 is 6=5'C2OC2 amino modifier, Glen research 10-1905] was added to specific wells. After a reactant reaction step. Contents of selected wells were added to 50 μL prewashed streptavidin sepharose. The spike1 oligo was captured by adding 500 pmol antispike1. (5TACGTGACCTACTTCCTTGA, where 5 is 5=5' Biotin-c6-) and incubating for 5 minutes at 30 degrees celcius. The sample was centrifuged for 1 minute. The flowthrough was removed and added back it to its well of origin. The streptavidin sepharose was washed 1× with 500 μL 25 mM NH4Ac pH7.5 and 2 times with 500 μL dH2O. The spike 1 oligo was eluted from the streptavidin sepharose (elution repeated 2 times) with 40 μL dH2O heated to 80 degrees celcius. The samples were purified e.g. using P6 [Biorad] and 10-20 μl was used for mass spectrometry analyses as described in general procedure QC2. The efficiency of reactant reactions could thus be determined.

QC4) Quality Control of a Step which Removes Tag or Renders them Unfunctional

Following the termination of a tag addition step, a specific tag (optionally with its anti-tag) was added. After library synthesis, library screening, tags were investigated for the presence of the specific tag which would indicate that a purification following the addition of that specific tag was not efficient.

General Procedures Containing a Purification Step:

P1) Purification by Size-Exclusion Chromatography 1 mL of washed P6 slurry was added to the wells of a filter plate (Whatman Unifilter 96 well plates). The filter was placed on a 2 mL collection plate and centrifuged for 4 minutes. The filterplate was placed on a collection plate (Eppendorff). The volume of samples to be purified was adjusted to 20-70 μl. The SEC plate on top of the collection plate was centrifuged 4 minutes at 900×RCF.

P2) Purification by Precipitation

The sample was precipitated using 0.1 volumes of 5 M NaCl and 0.5 volumes of isopropanol or 1.5 volumes of ethanol and washed with cold 70% ethanol. A sample of the material was analysed by polyacrylamide gel electrophoresis and autoradiography to verify the efficiency of dephosphorylation.

P3) PAGE Gel Purification

A 0.2, 1, or 2 mm thickness 6% or 10% acrylamide PAGE gel was prepared. A gel prerun was performed for 1 h at 60w. PAGE Loading buffer was added to the material to be purified and denatured by incubation for 10 min. @ 80 C. The material was loaded on the gel and run for 1 h @ 60 w. The gel was transferred to a plastic support, wrapped, placed on film, exosed, and developed. The gel was placed on the developed film. A gel slice corresponding to the material of interest were cut from the gel by comparing with the film. The exercised gel was distributed in aliquots to filter columns. 500 μL 500 mM NH4Ac+1 mM EDTA pH 7.4 was added to each tube, incubate on heated shaker @ 65° C. for 16 h. The material was recovered by centrifugation for 2 min @1000×RCF.

P4) Purification Using HPLC

Purification was done using a Reverse Phase HPLC with a Waters XterraRP 8 column. A binary mobile phase gradient profile was used to elute the product using a 50 mM aqueous triethylammonium acetate buffer at pH 7.5 and 99% acetonitrile/1% water solution. The purified material was concentrated by lyophilization and the resulting residue was dissolved in 5 mL of water.

P5) Purification by Ion-Exchange Chromatography

The material was applied to a DEAE (Diethyl aminoethyl) column which had been washed 2 times with 10 mM Aq. AcOH. The material on DEAE was washed extensively with water. The material was then released from DEAE by adding 200 μl Release solution (1.5 M NaCl) and incubating at 25° C. for 10 minutes in an eppendorph thermoshaker at 600 rpm. Water was added to the material to a final NaCl concentration of 0.5 M.

General Procedures Containing a Quenching Step:

Q1) Desphosphorylation to Remove 5' Phosphates from Tags Rendering them Unable to Participate in a Tagging Step, e.g. a Ligation The sample was dephosphorylated by first adding 80 μl SAP buffer (200 mM Hepes pH 7.8, 100 mM MgCl$_2$) and 2 μl Shrimp Alkaline Phosphatase (USB, 40 U/μl) to the sample followed by incubation of the sample at 37° C. for 1 hour. The phosphatase was inactivated by incubation at 68° C. for 10 minutes. The sample was precipitated using 0.05 volumes of 5 M NaCl and 50% isopropanol and washed with cold 70% ethanol. A sample of the material was analysed by polyacrylamide gel electrophoresis and autoradiography to verify the efficiency of dephosphorylation.

General Procedures Containing a Tagging Step:

T1) 10 μl buffer containing 120 mM HEPES (2-[4-(2-Hydroxy-ethyl)-piperazin-1-yl]-ethanesulfonic acid) pH 7.8, 40 mM MgCl$_2$, 40 mM DTT (dithiothretiol) and 4 mM ATP was added to each well. 500 μmol double-stranded tags (e.g., the combination A-0001 and Ax-0001) was also added. Annealing was then performed by a 80° C. to 200 ramp in a thermocycler (Eppendorf Mastercycler Gradient). 1 μl of T4 DNA ligase (20 U/μl) was added to each well. Samples were then incubated in a PCR-machine with the following temperature profile: 25° C. for 10 min, 45° C. for 10 min, and 25° C. for 10 min. The ligase was inactivated by incubating samples at 68° C. for 10 min.

General Procedures Containing a Deprotection Step:
D1) Remove Fmoc Protection Groups on a DEAE Ion Exchange Column Releasing an Amine
This procedure can also be used for removal of msec protection groups
Fmoc (fluorenylmethoxycarbonyl) Protection Group:

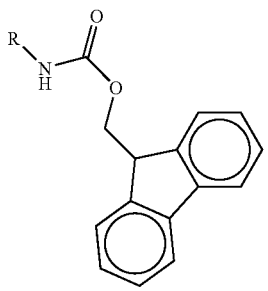

To remove the Fmoc protection group, the material was applied to a DEAE (Diethyl aminoethyl) column which had been washed 2 times with 10 mM Aq. AcOH. The material on DEAE was washed with water and 2 mL 10% Piperidine in dH2O was added folling by incubation for 10 min at RT. A further 2 mL 10% Piperidine in dH2O was added and incubated for 10 min @ RT. The column was drained and washed with 4×10 ml dH2O. The material was eluted by adding 750 μL Release Solution (1.5M NaCl). Incubate @ 60 C on shaker. Optionally repeat elution/release step.
D2) Remove Ns Protection Groups in Organic Solvent on a DEAE Ion Exchange Column
Ns (2-Nitro-benzenesulfonyl) Protection Group:

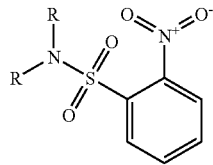

To remove the Ns protection group, the material was applied to a DEAE (Diethyl aminoethyl) column which had been washed 2 times with 10 mM Aq. AcOH. The material on DEAE was washed with water followed by washing with DMF (dimethyl formamide). Then the material on DEAE was incubated in a solution of 0.5M mercaptoethanol and 0.25 M DIPEA (N,N'-Diisopropylethylamine) in dimethyl formamide and incubated for 24 hours at 25° C. in an eppendorph thermoshaker at 600 rpm. Then the material on DEAE was washed with 0.3M AcOH in DMF, then twice with DMF and then with water. The Ns-deprotected material was then released from DEAE by adding 70 μl Release solution (1.5 M NaCl) and incubating at 25° C. for 10 minutes in an eppendorph thermoshaker at 600 rpm. Water was added to the material to a final NaCl concentration of 0.5 M. Then the material was precipitated by adding one volume of isopropanol as described.
D3) Remove Fmoc Protection Groups in Aqueous Solution
This procedure can also be used for removal of msec protection groups in aqueous solution
Samples were redissolved in water and adjusted to 6% piperidine. Samples were then incubated at 25° C. for 30 minutes to remove Fmoc protection groups.

D4) Remove Msec Protection Groups in Aqueous Solution
Msec (2-(methyl sulfonyl)ethyl carbamate) protection group used for protection of primary amines:

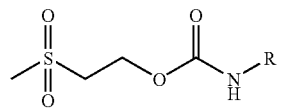

Msec protection groups were removed by dissolving the material in 25 μl 0.1 M Sodium Borate Buffer pH 10 and incubating at 40° C. for 3 hours. Then the material was lyophilized and dissolved in 85 μl H$_2$O.
D5) Remove tBu, Me, and Et Protection Groups Releasing the Carboxylic Acid in Aqueous Solution
The lyophilized material was dissolved in 20 μL 100 mM LiOH and incubated at 80° C. in PCR machine for 30 minutes. 40 μL 100 mM NaOAc buffer pH 5 was added tBu protection group:

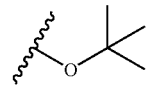 [SMILES: *OC(C)(C)C]

D6) Remove Boc Protection Group Releasing the Amine in Aqueous Solution
The lyophilized material was dissolved in 20 μL 37.5 mM NaOAc and 5 μL1 M MgCl2
and incubated at 70° C. ON (Lid 100° C.) in PCR-machine Boc Protection Group:

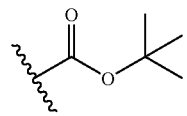

D6) Remove TFAc Protection Group Releasing the Amine in Aqueous Solution
The lyophilized material was dissolved in 20 μl and incubated at 45° C. ON (Lid 50° C.) in PCR-machine for 18 hours.
TFAc Protection Group:

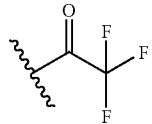 [SMILES: *C(=O)C(F)(F)F]

Example 1

Synthesis and Affinity Selection of a Library Encoding on the Order of 65.000 Scaffolded Compounds This example illustrates the use of general procedures in the following order:
Position A building blocks (reactants) and tags: R1-P1-T1-P1-Q1-V2,
Position B building blocks (reactants) and tags: T1-P1-R1-P1-Q1-D4-V1, Position C building blocks (reactants) and tags: T1-P1-(R1/R3/R2)-P1-Q1-V2-D2-V2,
Position D building blocks (reactants) and tags: T1-P1-(R1/R2/R3/R4/R5)-P1-D3-V2-P3

A library on the order of 65.000 DNA-tagged small molecules was synthesized. The synthesized small molecules were scaffolded (branched).

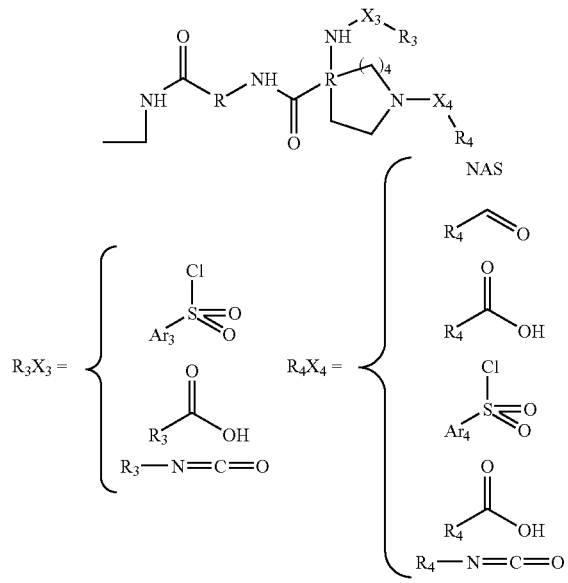

Scheme 1.1.

Layout of the synthesized display molecules. $R_3X_3$ building blocks (reactants) included sulfonyl chlorides ($Ar_3$—$SO_2$—Cl), acids ($R_3$—COOH), and isocyanates ($R_3$—N=C=O). $R_4X_4$ building blocks (reactants) included chloro- and fluoro-substituted heteroaromates (HetAr—Cl/F), aldehydes ($R_4$—C=O), acids ($R_4$—COOH), sulfonyl chlorides ($Ar_3$—$SO_2$—Cl), and isocyanates ($R_3$—N=C=O)

The first set of building blocks (reactants) (see table 1.5A) were loaded onto a display oligo:

Scheme 1.2. The display oligo containing a chemical reaction site ($H_2N$), a polyethylenglycol linker, and an oligonucleotide tag.

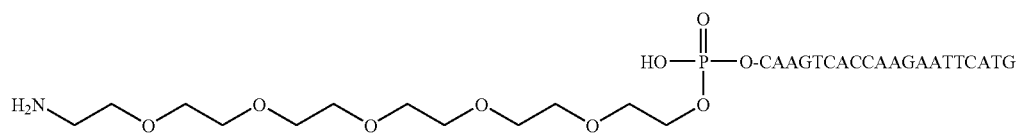

Subsequently, Fmoc protection groups present on the loaded building blocks (reactants) was removed by incubating them in a solution of 6% piperidine in water at 25° C. for 30 minutes. Samples were then purified using P-6 gel filtration spin columns (Biorad).

900 µmol Display oligo was added to each of 16 wells. In each well the display oligo carried a specific building block (position A building block).
Ligation of A-Tags 10 µl buffer containing 120 mM HEPES (2-[4-(2-Hydroxy-ethyl)-piperazin-1-yl]-ethanesulfonic acid) pH 7.8, 40 mM MgCl$_2$, 40 mM DTT (dithiothretiol) and 4 mM ATP was added to each well. 500 µmol double-stranded A-codons (e.g., the combination A-0001 and Ax-0001) was also added (See table 1.4A for tags and corresponding building blocks (reactants)). Annealing was then performed by a 80° C. to 200 ramp in a thermocycler (Eppendorf Mastercycler Gradient) In one well 50 µmol double-stranded 5' phosphate 32-labeled A-codon was added. 1 µl of T4 DNA ligase (20 U/µl) was added to each well. Samples were then incubated in a PCR-machine with the following temperature profile: 25° C. for 10 min, 45° C. for 10 min, and 25° C. for 10 min. The ligase was inactivated by incubating samples at 68° C. for 10 min. 25 ul of water was then added to each sample. To allow verification of the efficiency of the following dephosphorylation step, a "Dummy A" codon labelled with 5' phosphorus-32 was added to a sample. Bifunctional complexes were purified using gel-filtration with Bio-Gel P-6, (Bio-Rad) and the contents of the wells were pooled.
Desphosphorylation The pooled sample was dephosphorylated by first adding 80 µl SAP buffer (200 mM Hepes pH 7.8, 100 mM MgCl2) and 2 µl Shrimp Alkaline Phosphatase (USB, 40 U/µl) to the pooled sample followed by incubation of the sample at 37° C. for 1 hour. The phosphatase was inactivated by incubation at 68° C. for 10 minutes. The sample was precipitated using 0.05 volumes of 5 M NaCl and 50% isopropanol and washed with cold 70% ethanol. A sample of the material was analysed by polyacrylamide gel electrophoresis and autoradiography to verify the efficiency of dephosphorylation.
Ligation of B-Tags The sample was dissolved in water and distributed equally to 16 wells. To each well 750 µmol double-stranded B-codon was added and ligation and dephosphorylation was performed as described for the ligation of A-codons. After ligation and inactivation of the enzyme, the samples were lyophilized.
Load of Position B Building Blocks (Reactants)

Each sample was dissolved 5 µl 200 mM Na-phosphate buffer pH 8.0 or 100 mM Na-Borate pH 9.0 or 100 mM Na-Borate pH 10.0 according to previously identified reaction conditions. To each well was added add 4 µl solution of a building block (100 mM in dimethyl sulfoxide). For each well 0.72 µl 0.5M DMT-MM solution in water was mixed with 0.28 µl 200 mM Na-phosphate buffer pH 8 and added to the well. The wells were then incubated at 30° C. for 16 hours in a PCR-machine (Eppendorf Mastercycler Gradient). Then, 40 µl of water was added to each sample. Samples were purified using gel-filtration with Bio-Gel P-6, (Bio-Rad). The samples were pooled and purified by isopropanol precipitation as described.
Desphosphorylation The pooled sample was dephosphorylated by first adding 80 µl buffer containing 200 mM HEPES pH 7.8 and 100 mM MgCl$_2$ and 2 µl Shrimp Alkaline Phosphatase (USB, 40 U/µl) to the pooled sample followed by incubation of the sample at 37° C. for 1 hour. The phosphatase was inactivated by incubation at 68° C. for 10 minutes. The sample was precipitated using 0.05 volumes of 5 M NaCl and 50% isopropanol and washed with cold 70% ethanol. A sample of the material was analysed by polyacrylamide gel electrophoresis and autoradiography to verify the efficiency of dephosphorylation.

Msec Deprotection

Primary amines of position B building blocks (reactants) were protected by Msec groups:

Scheme 1.3 Msec (2-(methyl sulfonyl) ethyl carbamate) protection group used for protection of primary amines.

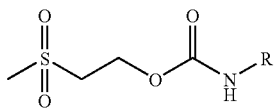

Msec protection groups were removed by dissolving the material in 25 µl 0.1 M Sodium Borate Buffer pH 10 and incubating at 40° C. for 3 hours. Then the material was lyophilized and dissolved in 85 µl $H_2O$.

Ligation of C-Tags

In each well ligation of double-stranded C-codons were performed as described for A- and B-codons.

Load of Position C Building Blocks (Reactants)

Samples to undergo isocyanate addition were redissolved in 8 µl buffer (100 mM sodium borate and 100 mM sodium phosphate pH 8.0). 1 µl of a specific building block (300 mM in $CH_3CN$) was added to each well and incubated at 50° C. for 16 hours. Then, 40 µL of water was added to each sample.

Samples to undergo sulfonylation were dissolved in 8 µl 100 mM Sodium Borate buffer pH 9. Then 2 µl specific building block (100 mM in tetrahydrofuran) was then to each well and incubated at 30° C. for 16 hours. Then, 40 µl of water was added to each sample.

Samples to undergo acylation were dissolved in 5 µl 200 mM Na-phosphate buffer pH 8.0 or 100 mM Na-Borate pH 9.0 or 100 mM Na-Borate pH 10.0. Then, 4 µl specific building block (100 mM in dimethylsulfoxide) was added to each well. Then 1 µl DMT-MM mix (0.36 M DMT-MM in water and 56 mM Na-phosphate buffer pH 8) was mixed in each well and the sample was incubate at 30° C. for 16 hours. Then, 40 µl water was added to each sample.

Samples were purified by gel-filtration as described.

Desphosphorylation

The pooled sample was dephosphorylated by first adding 80 µl buffer (200 mM Hepes pH 7.8, 100 mM MgCl2) and 2 µl Shrimp Alkaline Phosphatase (USB, 40 U/µl) to the pooled sample followed by incubation of the sample at 37° C. for 1 hour. The phosphatase was inactivated by incubation at 68° C. for 10 minutes. The sample was precipitated using 0.05 volumes of 5 M NaCl and 50% isopropanol and washed with cold 70% ethanol. A sample of the material was analysed by polyacrylamide gel electrophoresis and autoradiography to verify the efficiency of dephosphorylation.

Ns Protection Group Removal

Secondary amines of position B building blocks (reactants) were protected using Ns:

Scheme 1.4 Ns (2-Nitro-benzenesulfonyl) protection group used for protection of seconday amines.

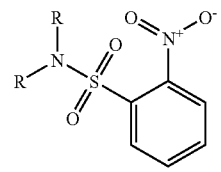

To remove the Ns protection group, the material was applied to a DEAE (Diethyl aminoethyl) column which had been washed 2 times with 10 mM Aq. AcOH. The material on DEAE was washed with water followed by washing with DMF (dimethyl formamide). Then the material on DEAE was incubated in a solution of 0.5M mercaptoethanol and 0.25 M DIPEA (N,N'-Diisopropylethylamine) in dimethyl formamide and incubated for 24 hours at 25° C. in an eppendorph thermoshaker at 600 rpm. Then the material on DEAE was washed with 0.3M AcOH in DMF, then twice with DMF and then with water. The Ns-deprotected material was then released from DEAE by adding 70 µl Release solution (1.5 M NaCl) and incubating at 25° C. for 10 minutes in an eppendorph thermoshaker at 600 rpm. Water was added to the material to a final NaCl concentration of 0.5 M. Then the material was precipitated by adding one volume of isopropanol as described.

Ligation of D-Tags

D-tags were ligated as described. Then samples were purified using gel-filtration as described and lyophilized.

Load of Position D Building Blocks (Reactants)

Samples to undergo isocyanate addition were redissolved in 8 µl buffer (100 mM sodium borate and 100 mM sodium phosphate pH 8.0) 1 µl of a specific building block (300 mM in $CH_3CN$) was added to each well and incubated at 50° C. for 16 hours. Then, 40 µL of water was added to each sample.

Samples to undergo sulfonylation were dissolved in 8 µl 100 mM Sodium Borate buffer pH 9. 2 µl specific building block (100 mM in tetrahydrofuran) was then to each well and incubated at 30° C. for 16 hours. Then, 40 µl of water was added to each sample.

Samples to undergo acylation were dissolved in 5 µl 200 mM Na-phosphate buffer pH 8.0 or 100 mM Na-Borate pH 9.0 or 100 mM Na-Borate pH 10.0. Then, 4 µl specific building block (100 mM in dimethylsulfoxide) was added to each well. Then 1 µl DMT-MM mix (0.36 M DMT-MM in water and 56 mM Na-phosphate buffer pH 8) was mixed in each well and the sample was incubate at 30° C. for 16 hours. Then, 40 µl water was added to each sample.

Samples to undergo reductive amination were dissolved in 15 µl 200 mM NaOAc buffer pH 5.0 5 ul specific BB was added to each well (200 mM in DMSO) and incubate at 30° C. for 1 h. Then 5 µl of freshly prepared 140 mM NaCNBH3 (REA000025; 8.8 mg/ml) in NaOAc buffer pH 5.0 to was added each well and the samples were incubated at 30° C. for 16 hours in a PCR-machine. Then 25 µl water was added to each sample.

Samples to undergo nucleophilic aromatic substitution were dissolved in 12 µl 100 mM Borate Buffer pH 9. Then 12 µl specific BB was added to each well (100 mM in DMSO) and all wells were incubated for 16 hours at 90° C. Then, 40 µl water was added to each sample.

Samples were then purified by gel-filtration as described.
Fmoc Deprotection

Samples were redissolved in water and adjusted to 6% piperidine. Samples were then incubated at 25° C. for 30 minutes to remove Fmoc protection groups. Samples were then again precipitated using isopropanol.

The combined material was redissolved in water and adjusted with polyacrylamide gel electrophoresis loading buffer. The material was electrophoresed and purified by isolating the material corresponding to bifunctional complexes with 4 tags. The single stranded bifunctional complexes were eluted from the gel, precipitated using isopropanol as described, and purified by gel-filtration as described.

Affinity Selection

Prior to selection the single stranded bifunctional complexes were converted to double-stranded for by extending a primer containing a sequence informative of the selection using the single-stranded tag of the bifunctional comples as a template. 200 μmol primer (5'-AAGGAACATCATCATGGAT) was mixed with 20 μmol bifunctional complexes and lyophilized. The sample was redissolved in 2.5 reaction buffer and 5 μl each dNTP (25 mM stock concentration) was added. The mixture was heated to 80° C. and slowly cooled to 55° C. Then 2.5 μl Taq Polymerase (5 units/μl) was added and the extension reaction was allowed to proceed for 1 hour. Then 25 μl water was added and the sample was purified using gel-filtration and used for affinity selection.

A fraction of the obtained bifunctional complexes was lyophilized and dissolved in 5 μl thrombin buffer (137 mM NaCl, 2.7 mM KCl, 10 mM sodium phosphate, 0.1% PEG8000). 50 μl streptavidin sepharose (Amersham Biosciences) slurry was washed in 4×100 μl thrombin buffer and resuspended in 50 μl thrombin buffer. Then 2 units biotinylated thrombin (Novagen) was added to the streptavidin sepharose slurry and the slurry was incubated at 15° C. with agitation (1400 rpm) for 30 minutes and subsequently washed 4 times with 100 μl thrombin buffer. A 10 μl Eppendorf tip was packed with glass wool up to the 2.5 μl mark. The streptavidin sepharose was applied to the tip and washed 3 times with 100 μl thrombin buffer by applying vacuum to the bottom end of the tip. The library was applied to the column and allowed to soak in. Then the column was washed 5 times with 100 μl thrombin buffer. Bifunctional complexes were eluted by applying 25 μl of a nanomolar ligand (100 μM in PBS) to the column for 10 min followed by centrifugation of the column (1000 rcf for 30 seconds). An additional 25 μl PBS was applied to the column and spun through. The eluted material was re-applied to a fresh column. This cycle was repeated 4 times. A 10 μl sample of eluted material was used PCR using the forward and reverse primers 5'-CAAGTCACCAAGAATTCATG and 5'-AAGGAACATCATCATGGAT. The PCR product was cloned and sequenced using standard methods.

TABLE 1.1

Layout of tags (A, B, C, and D) and anti-tags (Ax, Bx, Cx, Dx) showing codons (XXXXXXXXXXXXXXXXXXXX).
The specific nucleotide sequences of overhang sequences are shown.

| | |
|---|---|
| A | XXXXXXXXXXXXXXXXXXXXCCTAGGACCA |
| B | XXXXXXXXXXXXXXXXXXXXGTGTCACTTA |
| C | XXXXXXXXXXXXXXXXXXXXGTGCACGTGT |

TABLE 1.1-continued

Layout of tags (A, B, C, and D) and anti-tags (Ax, Bx, Cx, Dx) showing codons (XXXXXXXXXXXXXXXXXXXX).
The specific nucleotide sequences of overhang sequences are shown.

| | |
|---|---|
| D | XXXXXXXXXXXXXXXXXXXXGAATTCTACTCTCCTCAAGGTGATCCATGATGATGTTCCTT |
| Ax | XXXXXXXXXXXXXXXXXXXXCATGAATTCTTGGTGACTTG |
| Bx | XXXXXXXXXXXXXXXXXXXXTGGTCCTAGG |
| Cx | XXXXXXXXXXXXXXXXXXXXTAAGTGACAC |
| Dx | XXXXXXXXXXXXXXXXXXXXACACGTGCAC |

TABLE 1.2

Examples of specific tags and antitags. Both codon and overhang sequences are shown.

| Tag | Sequence |
|---|---|
| A-0001 | pTGTTGTCCATGATGCTTCCTCCTAGGACCA |
| A-0002 | pCAACTTGATCTCCAGTCGTCCCTAGGACCA |
| B-0001 | pCTAGTGGTCGAAGTTGCACAGTGTCACTTA |
| B-0002 | pCCTACGTCTTCATGGACCTTGTGTCACTTA |
| C-0001 | pTTCGTCCATGCACATGATCTGTGCACGTGT |
| C-0002 | pCAGTTCCTCCAAGCAGTAGGGTGCACGTGT |
| D0001 | pGTTCATCGTCTTCTAGGTGCGAATTCTACTCTCCTCAAGGTGATCCATGATGATGTTCCTT |
| D0002 | pTGAGGTTCGAGGTTGACGATGAATTCTACTCTCCTCAAGGTGATCCATGATGATGTTCCTT |
| Ax-0001 | AGGAAGCATCATGGACAACACATGAATTCTTGGTGACTTG |
| Ax-0002 | GACGACTGGAGATCAAGTTGCATGAATTCTTGGTGACTTG |
| Bx-0001 | TGTGCAACTTCGACCACTAGTGGTCCTAGG |
| Bx-0002 | AAGGTCCATGAAGACGTAGGTGGTCCTAGG |
| Cx-0001 | AGATCATGTGCATGGACGAATAAGTGACAC |
| Cx-0002 | CCTACTGCTTGGAGGAACTGTAAGTGACAC |
| Dx-0001 | GCACCTAGAAGACGATGAACACACGTGCAC |
| Dx-0002 | ATCGTCAACCTCGAACCTCAACACGTGCAC |

"p" denotes a 5' phosphate

TABLE 1.4A

Building blocks (reactants) used in synthesis position A and codons of the corresponding A-tags

| BB A | Tag A codon |
|---|---|
| Blank | AGTGCTCACACGACTGCTCG |
| BBA000008 | AGCTACGACAAGACTAGGAT |
| BBA000890 | CGTCCACTACCATCGACGAC |
| BBA001092 | CCAACTTGTAGGTGAGGACT |

TABLE 1.4A-continued

Building blocks (reactants) used in synthesis position A and codons of the corresponding A-tags

| BB A | Tag A codon |
| --- | --- |
| REA000251 | CTGCTGTTGGACTGCTTGTA |
| REA000252 | CTTCCAGGTCCTCGTAGTTC |
| REA000778 | AACATGCTCTAGGTGTCGTC |
| REA001185 | ACCTGCACCTGGATGGATCG |
| REA001315 | AACGAGGTCAGACGAAGCAC |
| REA001763 | CTCTCTAGTCCACAAGATGC |
| REA001764 | ATCTCAAGTACGACACATCC |
| REA001766 | CCATCACATCAGCAGGTAGA |
| REA001774 | TGTGTTGTGCTTGACCATCC |
| REA001775 | CAGACCTGTCTCCACGTAGC |
| REA001776 | GCACTTGTCGATCAAGCAGA |
| REA001779 | TGGTCCTTGCTTGATGGAGT |
| Dummy A | ATCGTACAGACTCCTCACAG |

TABLE 1.4

Building blocks (reactants) used in synthesis position B and codons of the corresponding B-tags

| BB B | Tag B codon |
| --- | --- |
| Blank | TCCAAGCACGTCTCGTACTC |
| REA001706 | GGTCGACCAGATGGACACTT |
| REA001710 | CATCATCTGTACAGGATGGT |
| REA001711 | TTCCAACTGCAAGGTACAGG |
| REA001713 | TAGCACCTACAAGATGGAGT |
| REA001714 | CTCGACACCAGGTCCAGAAG |
| REA001720 | GGTCATCTGAGCAACGTTGT |
| REA001732 | CACAAGCTAGGTACATGGAC |
| REA001737 | TGCAGCAGCTTGCTCGTACT |
| REA001738 | GTCCATGTCCAAGCATGAAG |
| REA001739 | TCCATCTCTAGGTTGCACAC |
| REA001740 | ATGCTACACCACTGCTGTGC |
| REA001741 | CAACATGGAGAGTGGAACAT |
| REA001742 | ACTCCATCCACTTCACAGAG |
| REA001743 | CTCCAGACTACCTGTGGACG |
| REA001744 | CGAGCAAGACATGAGCACTC |
| Dummy B | CCTCGTCCTGATGTTGCATC |

TABLE 1.4C

Building blocks (reactants) used in synthesis position C and codons of the corresponding C-tags

| BB C | Tag C codon |
| --- | --- |
| Blank | TCAGAACCATGCACTTGACG |
| REA001526 | GGAACATGCTGGAAGACCAG |
| REA001527 | TACAGACTGAGCTTCACTTG |
| REA001534 | TCCTGATGGTGTACCACCTT |
| REA001535 | AAGCAGCTCTGTCGAGCAAT |
| REA001537 | ATCAACCAAGGACATCTCTG |
| REA000032 | CCTTGTAGGTCGTAGTGCAT |
| REA001467 | ACCTTCACGATCAGAGCTAT |
| REA001469 | GATGTTGAGGACGTAGTGTG |
| REA001471 | CTTCGTCGAAGACTGAGTCA |
| REA001475 | ACGACTGTCGTACGAGACGT |
| BBA000820 | CGATCTGGTTGACGAACAGC |
| BBA000828 | CCACGATCTTGAGTGTACGG |
| BBA000836 | CACTGAGCAGCTTCTTCCAT |
| REA000736 | CTCTTGGTTCCTAGGAGACA |
| REA001712 | GTCAGGACAACTCAGTGCAG |
| Dummy C | CGTGCTACCACACTCACAAT |

TABLE 1.4D

Building blocks (reactants) used in synthesis position D and codons of the corresponding D-tags

| BB D | Tag D codon |
| --- | --- |
| Blank | TCACATGACCAGCACGTGCG |
| REA001526 | CGATCAAGCTACAGAAGAAG |
| REA001527 | TGGACTCTGTCGAAGGTACA |
| REA001535 | CTGTAGCATCCACTCCATCC |
| REA000032 | GACTGTGGTGACACCTGACT |
| REA001467 | GCTTCGACAGACATCACTCG |
| REA001469 | ATGGACAGTGGACACTCATT |
| BBA000031 | GCTTCTCCTGGTTGATGGTC |
| REA000736 | CGTCGATGGACGTGTCGATT |
| REA002313 | CGTTCCAACCAACCTTGGAG |
| REA000457 | CGAACAGAACTAGCACGTCA |
| REA001223 | GAAGTTCCTCTGGTCTAGGG |
| REA001366 | GGTCTAGTAGCATGATCGAA |

TABLE 1.4D-continued

Building blocks (reactants) used in synthesis position D and codons of the corresponding D-tags

| BB D | Tag D codon |
|---|---|
| REA001263 | CTTCTTGGAACCTGAGCTTA |
| REA001516 | TTGCTCAGCATCCTTGAACT |
| REA001754 | TGTTCCTGGTACACGAGGAG |

TABLE 1.5A

Position A building blocks (reactants). The unprotected structures are shown. The primary amines were protected by Fmoc groups during loading. After loading the Fmoc groups were removed.

BBA000008

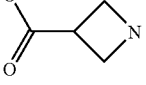

BBA000890

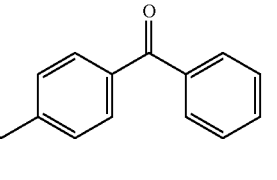

BBA001092

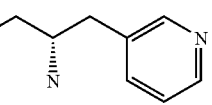

REA000251

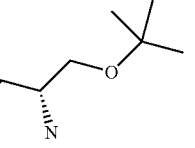

REA000252

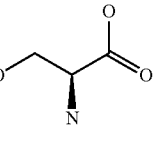

REA000778

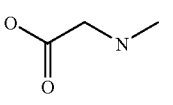

TABLE 1.5A-continued

Position A building blocks (reactants). The unprotected structures are shown. The primary amines were protected by Fmoc groups during loading. After loading the Fmoc groups were removed.

REA001185

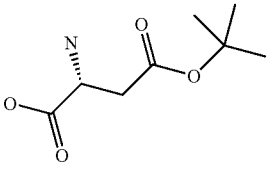

REA001315

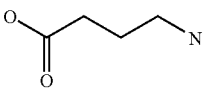

REA001763

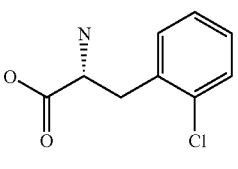

REA001764

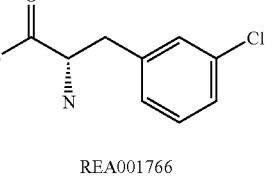

REA001766

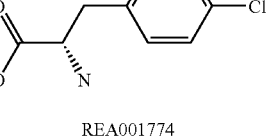

REA001774

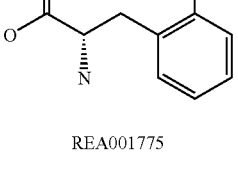

REA001775

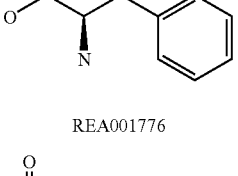

REA001776

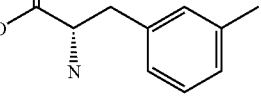

TABLE 1.5A-continued

Position A building blocks (reactants). The unprotected structures are shown. The primary amines were protected by Fmoc groups during loading. After loading the Fmoc groups were removed.

REA001779

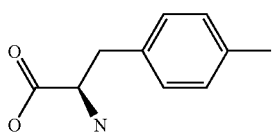

TABLE 1.5B

Position B building blocks (reactants). The unprotected structures are shown. The primary amines were protected by Msec groups and secondary amines were protected by Ns during loading. After loading the protection groups were removed sequentially.

REA001710

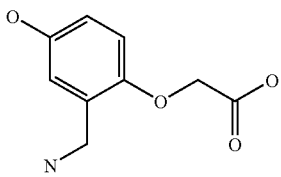

REA001706

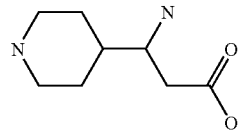

REA001711

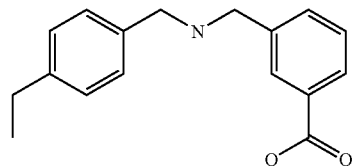

REA001713

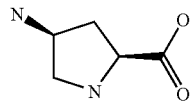

REA001714

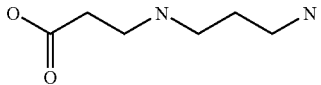

REA001720

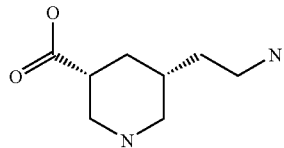

TABLE 1.5B-continued

Position B building blocks (reactants). The unprotected structures are shown. The primary amines were protected by Msec groups and secondary amines were protected by Ns during loading. After loading the protection groups were removed sequentially.

REA001732

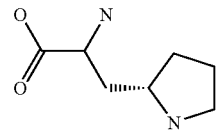

REA001737

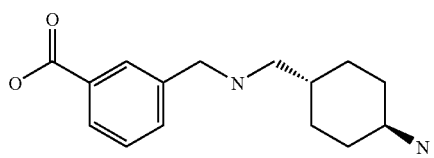

REA001738

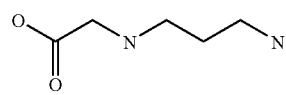

REA001739

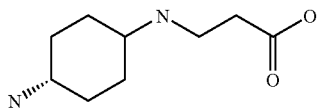

REA001740

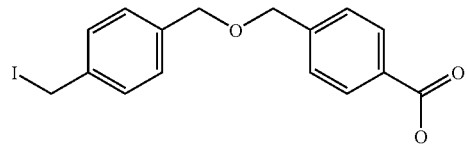

REA001741

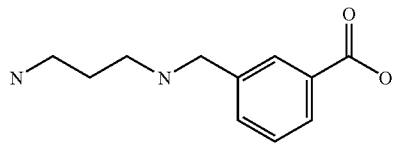

REA001742

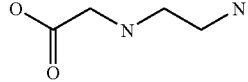

REA001743

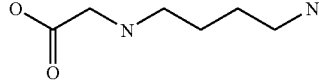

TABLE 1.5B-continued

Position B building blocks (reactants). The unprotected structures are shown. The primary amines were protected by Msec groups and secondary amines were protected by Ns during loading. After loading the protection groups were removed sequentially.

REA001744

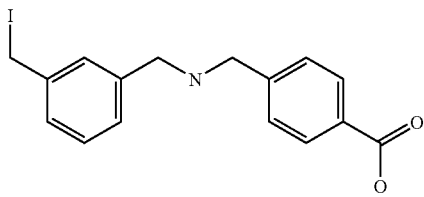

TABLE 1.5C

Position C building blocks (reactants).

REA001526

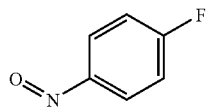

REA001526

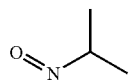

REA001534

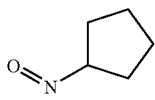

REA001555

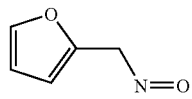

REA001537

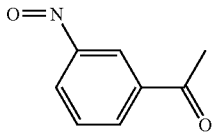

REA000032

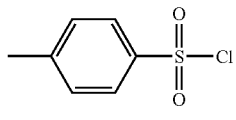

TABLE 1.5C-continued

Position C building blocks (reactants).

REA001467

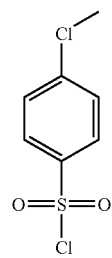

REA001469

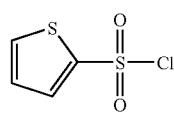

REA001471

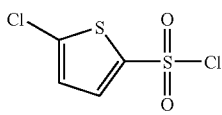

REA001475

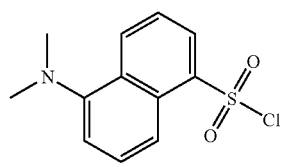

REA000320

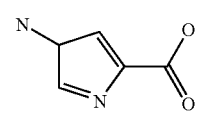

BBA000828

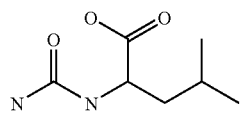

BBA000836

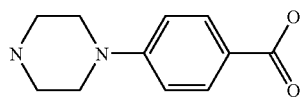

REA000736

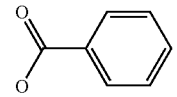

REA001712

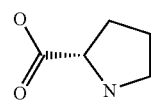

TABLE 1.5D

Position D building blocks (reactants).

REA001526

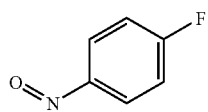

REA001526

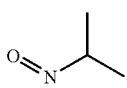

REA001555

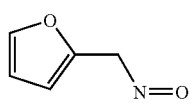

REA000032

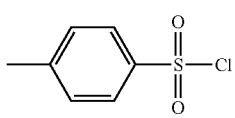

REA001467

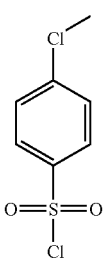

REA001469

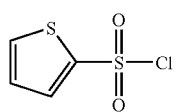

BBA000091

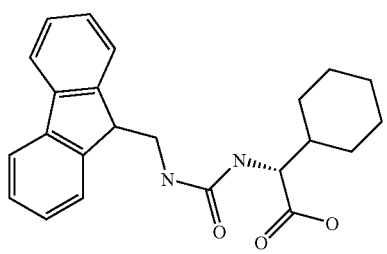

REA000736

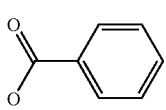

TABLE 1.5D-continued

Position D building blocks (reactants).

REA002313

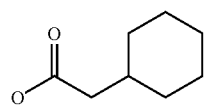

REA000457

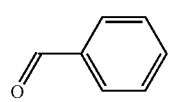

REA001223

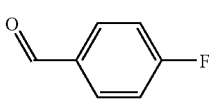

REA001366

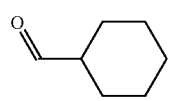

REA001263

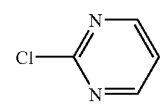

REA001516

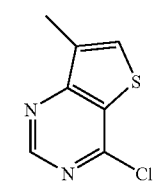

REA001754

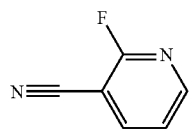

Selection Results

TABLE 1.6

Selection output sample showing the number of observations (n) of each combination of codons A, B, C, and D.

| | Position | | | |
|---|---|---|---|---|
| n | A | B | C | D |
| 2 | BBA001092 | REA001710 | BBA000820 | BBA000031 |
| 3 | REA001764 | REA001710 | REA001526 | BBA000031 |
| 1 | REA001315 | REA001710 | REA001537 | BBA000031 |
| 6 | BBA000890 | REA001710 | REA001712 | BBA000031 |
| 4 | REA001774 | REA001710 | REA001712 | BBA000031 |

TABLE 1.6-continued

Selection output sample showing the number of observations (n) of each combination of codons A, B, C, and D.

| n | Position | | | |
|---|---|---|---|---|
| | A | B | C | D |
| 3 | REA000252 | REA001710 | REA001712 | BBA000031 |
| 2 | REA000251 | REA001710 | REA001712 | BBA000031 |
| 1 | REA001775 | REA001710 | REA001712 | BBA000031 |
| 1 | REA001764 | REA001710 | REA001712 | BBA000031 |
| 2 | BBA000890 | REA001710 | REA001712 | REA001535 |
| 4 | REA001185 | REA001720 | REA001471 | BBA000031 |
| 3 | REA001766 | REA001732 | REA001526 | REA001535 |
| 1 | REA001766 | REA001732 | REA001527 | REA001527 |
| 1 | REA001766 | REA001732 | REA001527 | REA001535 |

The building block combination X-REA001710-REA001712-BBA000031 (X can be different position A building blocks (reactants)) corresponds to ligands with Ki values against human thrombin in the low nanomolar to subnanomolar range (Tucker T J et al. *J. Med. Chem.* 1998, 41, 3210-3219):

Scheme 1.5 Chemical structure corresponding to the building block combination X-REA001710-REA001712-BBA000031

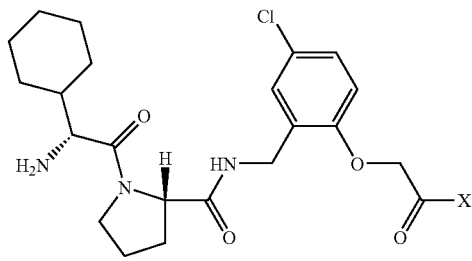

Example 2

Synthesis and Affinity Selection of a Library Encoding on the Order of 85.000.000 Compounds A library encoding approximately 85.000.000 compounds was generated using 4 rounds of building block addition.

Scheme 2.1 (a) Synthesis of small molecules composed of 4 building blocks (reactants) and encoded by 4 tags. The process is detailed in the text.

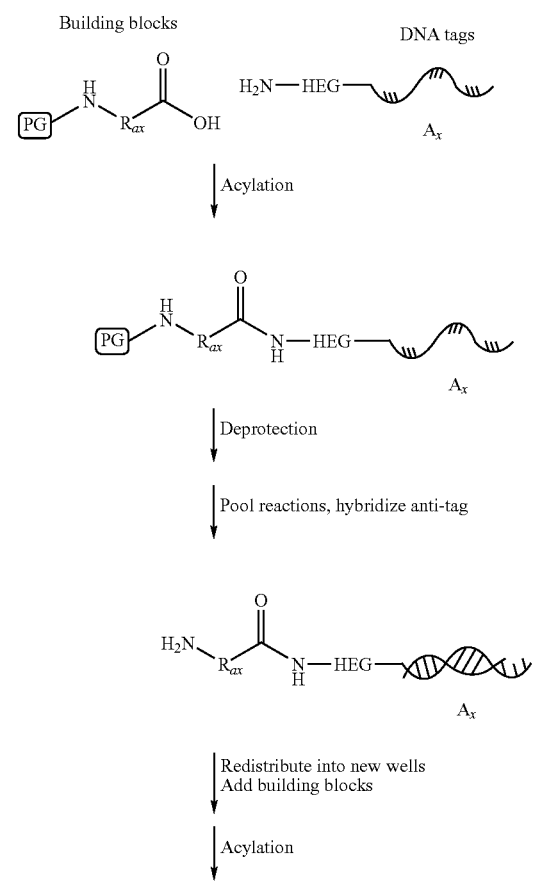

-continued

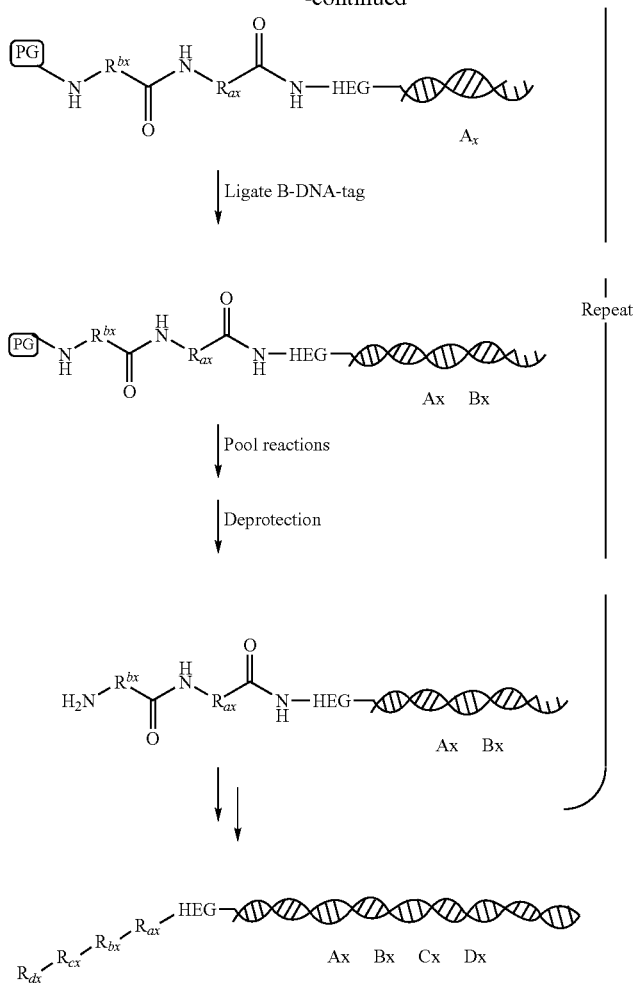

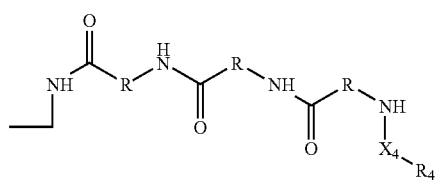

Scheme 2.2 Layout of the synthesized display molecules. $R_4X_4$ building blocks (reactants) included acids ($R_4$—COOH), sulfonyl chlorides ($Ar_4$—$SO_2$—Cl), and isocyanates ($R_4$—N=C=O)

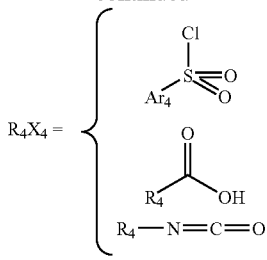

$R_4X_4 =$

The first set of building blocks (reactants) were loaded onto a display oligo:
Display Oligo Scheme 2.3 The display oligo containing a chemical reaction site ($H_2N$), a polyethylenglycol linker, and an oligonucleotide tag.

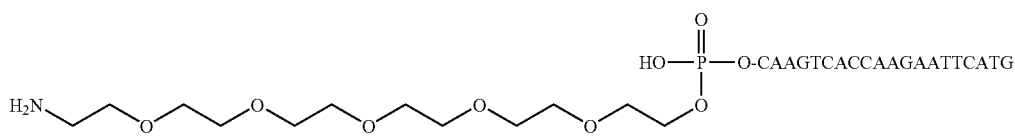

Subsequently, Fmoc protection groups present on the loaded building blocks (reactants) was removed by incubating them in a solution of 6% piperidine in water at 25° C. for 30 minutes. Samples were then purified using P-6 gel filtration spin columns (Biorad).

900 µmol Display oligo was added to each of 96 wells. In each well the display oligo carried a specific building block (position A building block).

Ligation of A-Tags 10 ul buffer (120 mM Hepes pH 7.8, 40 mM MgCl2, 40 mM DTT and 4 mM ATP) was added to each well. 500 µmol double-stranded A-codons (e.g., the combination A-0001 and Ax-0001) was also added. Annealing was then performed by a 80° C. to 20° ramp in a PCR machine (Eppendorf Mastercycler Gradient) In one well 50 µmol double-stranded 5' phosphate 32-labeled A-codon was added. 1 µl of T4 DNA ligase (20 U/µl) was added to each well. Samples were then incubated in a PCR-machine with the following temperature profile: 25° C. for 10 min, 45° C. for 10 min, and 25° C. for 10 min. The ligase was inactivated by incubating samples at 68° C. for 10 min. 25 ul of water was then added to each sample. To allow verification of the efficiency of the following dephosphorylation step, a "Dummy A" codon labelled with 5' phosphor-32 was added to a sample. Bifunctional complexes were purified using gel-filtration with Bio-Gel P-6, (Bio-Rad) and pooled.

Desphosphorylation

The pooled sample was dephosphorylated by first adding 92 µl SAP buffer (200 mM Hepes pH 7.8, 100 mM MgCl2) and 4 µl Shrimp Alkaline Phosphatase (USB, 40 U/µl) to the pooled sample followed by incubation of the sample at 37° C. for 1 hour. The phosphatase was inactivated by incubation at 68° C. for 10 minutes. The sample was precipitated using 0.05 volumes of 5 M NaCl and 50% isopropanol and washed with cold 70% ethanol. A sample of the material was analysed by polyacrylamide gel electrophoresis and autoradiography to verify the efficiency of dephosphorylation.

Ligation of B-Tags

The sample was dissolved in water and distributed equally to 96 wells. To each well 750 µmol double-stranded B-codon was added and ligation and dephosphorylation was performed as described for the ligation of A-codons. After ligation and inactivation of the enzyme, the samples were lyophilized.

Load of Position B Building Blocks (Reactants)

Each sample was dissolved 5 µl 200 mM Na-phosphate buffer pH 8.0 or 100 mM Na-Borate pH 9.0 or 100 mM Na-Borate pH 10.0 according to previously identified reaction conditions. To each well was added add 4 µl solution of a building block (100 mM in dimethyl sulfoxide). For each well 0.72 µl 0.5M DMT-MM solution in water was mixed with 0.28 µl 200 mM Na-phosphate buffer pH 8 and added to the well. The wells were then incubated at 30° C. for 16 hours in a PCR-machine (Eppendorf Mastercycler Gradient). Then, 40 µl of water was added to each sample. Samples were purified using gel-filtration with Bio-Gel P-6, (Bio-Rad). The samples were pooled and purified by isopropanol precipitation as described.

Fmoc Deprotection

Samples were redissolved in water and adjusted to 6% piperidine. Samples were then incubated at 25° C. for 30 minutes to remove Fmoc protection groups. Samples were then again precipitated using isopropanol. The samples were redissolved in water and distributed equally to 96 wells.

Ligation of C-Tags

In each well ligation of double-stranded C-codons were performed as described for A- and B-codons.

Load of Position C Building Blocks (Reactants)

Position C building blocks (reactants) were loaded as described for position B building blocks (reactants). Following loading, the samples were gel-filtration purified, desphosphorylated, precipitated using isopropanol and Fmoc protection groups were removed as described.

Ligation of D-Tags

D-codons were ligated as described. Then samples were purified using gel-filtration as described and lyophilized.

Load of Position D Building Blocks (Reactants)

Samples to undergo isocyanate addition were redissolved in 8 µl buffer (100 mM sodium borate and 100 mM sodium phosphate pH 8.0) 1 µl of a specific building block (300 mM in $CH_3CN$) was added to each well and incubated at 50° C. for 16 hours in a in PCR-machine (Eppendorf Mastercycler Gradient). Then, 40 µL of water was added to each sample.

Samples to undergo sulfonylation were dissolved in 8 µl 100 mM Sodium Borate buffer pH 9. 2 µl specific building block (100 mM in tetrahydrofuran) was then to each well and incubated at 30° C. for 16 hours in a PCR-machine. Then, 40 µl of water was added to each sample.

Samples to undergo acylation were dissolved in 5 µl 200 mM Na-phosphate buffer pH 8.0 or 100 mM Na-Borate pH 9.0 or 100 mM Na-Borate pH 10.0. Then, 4 µl specific building block (100 mM in dimethylsulfoxide) was added to each well. Then 1 µl DMT-MM mix (0.36 M DMT-MM in water and 56 mM Na-phosphate buffer pH 8) was mixed in each well and the sample was incubate at 30° C. for 16 hours in a PCR-machine. Then, 40 µl water was added to each sample.

Samples were purified by gel-filtration as described.

Fmoc Deprotection

Samples were redissolved in water and adjusted to 6% piperidine. Samples were then incubated at 25° C. for 30 minutes to remove Fmoc protection groups. Samples were then again precipitated using isopropanol.

The combined material was redissolved in water and adjusted with polyacrylamide gel electrophoresis loading buffer. The material was electrophoresed and purified by isolating the material corresponding to bifunctional complexes with 4 tags. The single stranded bifunctional complexes were eluted from the gel, precipitated using isopropanol as described, and purified by gel-filtration as described.

Prior to selection the single stranded bifunctional complexes were converted to double-stranded for by extending a primer containing a sequence informative of the selection using the single-stranded tag of the bifunctional complexes as a template. 200 µmol primer (5'-TCTGGTGGTCTACGT-GCTCTAAGGAACATCATCATGGATC) was mixed with 20 µmol bifunctional complexes and lyophilized. The sample was redissolved in 2.5 reaction buffer and 5 µl each dNTP (25 mM stock concentration) was added. The mixture was heated to 80° C. and slowly cooled to 55° C. Then 2.5 µl Taq Polymerase (5 units/µl) was added and the extension reaction was allowed to proceed for 1 hour. Then 25 µl of water was added and the sample was purified using gel-filtration and used for affinity selection.

Selection

A fraction of the obtained bifunctional complexes was lyophilized and dissolved in 5 µl thrombin buffer (137 mM NaCl, 2.7 mM KCl, 10 mM sodium phosphate, 0.1% PEG8000). 50 µl streptavidin sepharose (Amersham Biosciences) slurry was washed in 4×100 µl thrombin buffer and resuspended in 50 µl thrombin buffer. Then biotinylated thrombin (Novagen—2 units) was added to the streptavidin sepharose slurry and the slurry was incubated at 15° C. with agitation (1400 rpm) for 30 minutes and subsequently washed 4 times with 100 μl thrombin buffer. A 10 μl Eppendorf tip was packed with glass wool up to the 2.5 μl mark. The streptavidin sepharose was applied to the tip and washed 3 times with 100 μl thrombin buffer by applying vacuum to the bottom end of the tip. The library was applied to the column and allowed to soak in. Then the column was washed 5 times with 100 μl thrombin buffer. Bifunctional complexes were eluted by applying 25 μl of a nanomolar ligand (100 μM in PBS) to the column for 10 min followed by centrifugation of the column (1000 rcf for 30 seconds). An additional 25 μl PBS was applied to the column and spun through. The eluted material was re-applied to a fresh column. This cycle was repeated 4 times. A 10 μl sample of eluted material was used PCR using the forward and reverse primers 5'-CAAGTCACCAAGAATTCATG and 5'-TCTG-GTGGTCTACGTGCTCT. The PCR product was clones and sequenced using standard methods.
Selection Results

TABLE 2.1

Selection output sample showing the number of observations (n) of each combination of codons A, B, C, and D.

| n | Position | | | |
|---|---|---|---|---|
| | A | B | C | D |
| 1 | REA002420 | REA001464 | REA001829 | REA002088 |
| 1 | REA001821 | REA001710 | BBA001023 | BBA000031 |
| 1 | REA002407 | REA001710 | BBA001023 | BBA000031 |
| 1 | REA001423 | REA001710 | BBA001023 | BBA000031 |
| 1 | REA001828 | REA001906 | REA002449 | REA002036 |
| 1 | REA001416 | REA001917 | REA001557 | REA000798 |
| 2 | BBA000029 | REA001936 | REA002446 | REA002067 |
| 1 | REA002420 | REA002411 | REA001829 | REA002088 |
| 1 | REA001329 | REA002438 | BBA000029 | REA002042 |

The building block combination X-REA001710-BBA001023-BBA000031 (X can be different position A building blocks (reactants)) corresponds to ligands with Ki values against human thrombin in the low nanomolar to subnanomolar range (Tucker T J et al. *J. Med. Chem.* 1998, 41, 3210-3219):

Scheme 2.4 Chemical structure corresponding to the building block combination X-REA001710-BBA001023-BBA000031

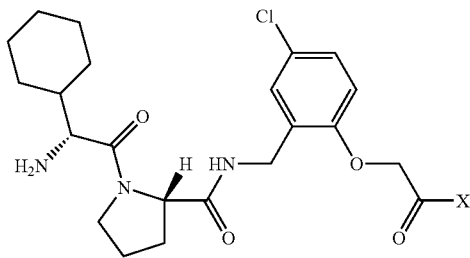

TABLE 2.2

Layout of tags (A, B, C, and D) and anti-tags (Ax, Bx, Cx, Dx) showing codons (XXXXXXXXXXXXXXXXXXXX). The specific nucleotide sequences of overhang sequences are shown.

| | |
|---|---|
| A | XXXXXXXXXXXXXXXXXXXXCCTAGGACCA |
| B | XXXXXXXXXXXXXXXXXXXXGTGTCACTTA |

TABLE 2.2-continued

Layout of tags (A, B, C, and D) and anti-tags (Ax, Bx, Cx, Dx) showing codons (XXXXXXXXXXXXXXXXXXXX). The specific nucleotide sequences of overhang sequences are shown.

| | |
|---|---|
| C | XXXXXXXXXXXXXXXXXXXXGTGCACGTGT |
| D | XXXXXXXXXXXXXXXXXXXXGAATTCTACTCTCCTCAAGGTGATCCATGATGATGTTCCTT |
| Ax | XXXXXXXXXXXXXXXXXXXXCATGAATTCTTGGTGACTTG |
| Bx | XXXXXXXXXXXXXXXXXXXXTGGTCCTAGG |
| Cx | XXXXXXXXXXXXXXXXXXXXTAAGTGACAC |
| Dx | XXXXXXXXXXXXXXXXXXXXACACGTGCAC |

TABLE 2.3

Examples of specific tags and antitags. Both codon and overhang sequences are shown.

| Tag | Sequence |
|---|---|
| A-0001 | pTGTTGTCCATGATGCTTCCTCCTAGGACCA |
| A-0002 | pCAACTTGATCTCCAGTCGTCCCTAGGACCA |
| B-0001 | pCTAGTGGTCGAAGTTGCACAGTGTCACTTA |
| B-0002 | pCCTACGTCTTCATGGACCTTGTGTCACTTA |
| C-0001 | pTTCGTCCATGCACATGATCTGTGCACGTGT |
| C-0002 | pCAGTTCCTCCAAGCAGTAGGGTGCACGTGT |
| D-0001 | pGTTCATCGTCTTCTAGGTGCGAATTCTACTCTCCTCAAGGTGATCCATGATGATGTTCCTT |
| D-0002 | pTGAGGTTCGAGGTTGACGATGAATTCTACTCTCCTCAAGGTGATCCATGATGATGTTCCTT |
| Ax-0001 | AGGAAGCATCATGGACAACACATGAATTCTTGGTGACTTG |
| Ax-0002 | GACGACTGGAGATCAAGTTGCATGAATTCTTGGTGACTTG |
| Bx-0001 | TGTGCAACTTCGACCACTAGTGGTCCTAGG |
| Bx-0002 | AAGGTCCATGAAGACGTAGGTGGTCCTAGG |
| Cx-0001 | AGATCATGTGCATGGACGAATAAGTGACAC |
| Cx-0002 | CCTACTGCTTGGAGGAACTGTAAGTGACAC |
| Dx-0001 | GCACCTAGAAGACGATGAACACACGTGCAC |
| Dx-0002 | ATCGTCAACCTCGAACCTCAACACGTGCAC |

"p" denotes a 5' phosphate

TABLE 2.4

Building blocks (reactants) and their corresponding tag codons used in the library synthesis.

| BB A | Tag A codon |
|---|---|
| BBA000029 | GTGCTACTGAGATGTTGCAG |
| BBA000890 | GCTGATGAGTTCGAGTTCTA |
| REA000250 | GGTAGCAAGATGGTACTACG |
| REA000778 | CCACGACATCAACCATGGTG |
| REA001143 | GATCACCTGTCGATGAACGA |
| REA001329 | TCTACGTTCACAGATGCTCG |
| REA001398 | TCATGGTCTGCACTCAGGAT |

TABLE 2.4-continued

Building blocks (reactants) and their corresponding tag codons used in the library synthesis.

| | |
|---|---|
| REA001399 | CCTGTACCAACTGGACATCG |
| REA001403 | TGCACTGTACGAGCAGGTCT |
| REA001405 | TAGGTCAGGAGTACAACACT |
| REA001410 | CTCGTTGTCCAACATCACAT |
| REA001411 | CACACGATGCTGTAGCTCTA |
| REA001415 | GAACTCTAGGTGGAAGGAAA |
| REA001416 | TACTGCATGTACCACCATGA |
| REA001419 | ACAGGAAGACGTGCATGTAC |
| Blank | TGGTCTCGTTCTCGTCACAG |
| REA001422 | TACAGAAGCATCGAGTAGCT |
| REA001423 | GGTCCTCTCAAGATGTGGAA |
| REA001424 | GTGGTGAGCTTGTGGTCGAA |
| REA001425 | CGAACCTCCAGTAGCATGGT |
| REA001426 | CCGATCCACGAGGAGCAAGT |
| REA001446 | ATCATGCAACCTACGAGCTT |
| REA001464 | TTGGAGGTACGATCCACACA |
| REA001767 | CTGCTTCGTACCACAAGCTC |
| REA001769 | TCACCACTTCCAGATCGTTC |
| REA001773 | CTCTTCAACCTGAGAACAAC |
| REA001774 | TGTGGTGGTGCTCGTACTGC |
| REA001775 | CGTTCCTCTCAGAACCAGAG |
| REA001780 | TGGAAGCTACCATCTCGTGC |
| REA001781 | GTGGATCGACCTCTAGCAAA |
| REA001782 | CCAGTGCTAGGTTGCTCGAC |
| REA001785 | CAAGTTCTTGCACTCGATCT |
| REA001792 | TACTGGACGACGTACTAGGC |
| REA001793 | CCTAGACGAGCTTCTGGTTG |
| REA001798 | ACAGTCTCATGGTCCAAGTC |
| REA001799 | ACAGCACCTCGTGTAGGACT |
| REA001800 | ACTGCAAGGATGCATCTGGC |
| REA001801 | CCTTGACACCAACGTGAAGT |
| REA001803 | AGGAACCAGCAACGAGGTTA |
| REA001805 | TACTCCTCAGATCGTACGAA |
| REA001806 | TTGTCTGAGGAGCTTCAGGA |
| REA001807 | CGTCGTCGACGATCCTCCAA |
| REA001808 | CACCTTGTCAGGAGTACGTT |
| REA001809 | CAGTTGTACGAGGTTGCAGC |
| REA001810 | CGTACCTTCTTCTAGCAACA |
| REA001811 | AGCTCCAGCTTCGAAGTTGA |
| REA001813 | CTCATCCACTTGTGTGACGC |
| REA001817 | ATGGATGGTCCTACCTTCTC |
| REA001818 | TGTTCCAGGACGTCCTGCAC |
| REA001821 | TACCTCGAAGGTCTGGATCG |
| REA001823 | TGTTCTAGTGGAACTCAACG |
| REA001824 | AGTTGAACCATGCACTCTCT |
| REA001827 | GAACTGATGTGCAAGAGTCT |
| REA001828 | GATGGTACCAACGACCTACA |
| REA001830 | CAACACGACACATCCAACCT |
| REA001833 | GATGTGCTCTGCACACCAGC |
| REA001834 | CCAGTAGAACACTAGAAGCG |
| REA001836 | AGATCGAAGACGAGTGAGTG |
| REA001837 | GTAGGAGAGGTTCGATGGTG |
| REA001838 | ATCCATGTCTGGATCAGCAA |
| REA001839 | GGTGCTCCAGAACGTACTTT |
| REA001840 | GGTAGGTACGTTGTTCTCCT |
| REA001891 | GTAGCTTGCACTGGACGTCC |
| REA001892 | CCACTTGTGTTCCACTGATT |
| REA001893 | CGAAGAGGTGGAACGACCAA |
| REA001894 | GTTGGTCGATCGAGTCCAAG |
| REA001895 | TGTCCTTGTTGCACTCCTTA |
| REA001897 | CACATGATGTTCTCCTTGGT |
| REA001899 | AAGTCTAGTCACACGACACC |
| REA001902 | GACCTAGCATGCTTCCTAGT |
| REA001903 | AGACACGTTCGTGGTCGAGA |
| REA001907 | CATCCAAGGTCTGGTCTCTT |
| REA001909 | AGGTTGAAGGTGCAACATGC |
| REA001910 | CCTGAGTGGTCCTTCTTGAA |
| REA001911 | ACCTAGATGCTAGGAAGCAG |
| REA001913 | GTAGACAAGTACCACTGGTC |
| REA001914 | GCATGGAACTTCCTGCAGGG |
| REA001916 | GATCAGGACTGGTTGGAAGG |
| REA001919 | GGACAGAAGGATCTTCAGCC |
| REA001924 | ATCTGAGTTCCTTGGTTCTC |
| REA001930 | AACTCGTGTCGTCTCCTTCT |
| REA001933 | TCTGTGAACATCCACCTTCG |
| REA001934 | ATGTCGATGTAGTGGTCCTC |
| REA001935 | GCAGTTGAACTCCACGTTGC |

TABLE 2.4-continued

Building blocks (reactants) and their corresponding tag codons used in the library synthesis.

| | |
|---|---|
| REA001937 | ATGTAGAGTGATGAGCTTCG |
| REA001942 | ACCAACGTCATCGTTGCTGA |
| REA002406 | GACGTACAAGTTCTTGGACC |
| REA002407 | GTTGTAGGACCAAGCAAGCG |
| REA002409 | TCGAAGTTCAGATCGTGATC |
| REA002411 | CTAGTGTGAAGTGGTCCATG |
| REA002413 | GCAACAGCATCACAGATGTT |
| REA002415 | CGTTCTTGAAGCTACGACAG |
| REA002419 | GTACCTGATCTGGATCTTGC |
| REA002420 | GGACTCTTCTCAACTGTTGT |
| REA002422 | GAAGTGCTCGACATGGTCAC |
| REA002423 | GTACTAGGACCTTCGTTGCC |
| Dummy A | ATCGTACAGACTCCTCACAG |

| BB B | Tag B codon |
|---|---|
| Blank | TTCGAGCTACACCTGCTGAC |
| REA001290 | GGTCCAGCAAGAGCACCATA |
| BBA001092 | CTGGTCCTTCAGGAACGTAA |
| REA001291 | TAGGTACCTGGTAGTGAAGT |
| REA001464 | GGTTGTTCCTGCTTGCTCAG |
| REA001806 | CCAGTGGACTGACCTTGTGC |
| REA002437 | CGTGGTTCATGGAAGCAACG |
| REA002438 | TCCTAGAGACATGCATGCAA |
| BBA000008 | CGAGCTGGATGCTACACTCA |
| BBA001023 | GGTTCTCTACCTGAAGCTTC |
| BBA001024 | CCACTTGCAGTCTGTGGAAT |
| BBA001025 | TGAACCAGGACACTGCTTGT |
| BBA001091 | AAGTGGAACTGGAGCACTAG |
| BBA001093 | ATCCTCCTACTCCAGCTTCA |
| REA000250 | ACCACGTACTACCTAGTCTC |
| REA000778 | GGTACTTGGATGGTGTTCGT |
| REA001143 | GGAACTTGAGTCCTTGATGA |
| REA001280 | GAAGAGGTCGTAGGAAGGAA |
| REA001281 | GAGGTGCTTCGTCGTTGGTA |
| REA001282 | GGAAGGATCTGGTACGTCCA |
| REA001284 | GCAAGTTGTAGCATCAAGGA |
| REA001285 | CAAGCAGACGATCAAGGATT |
| REA001286 | CCTCATCTCTCTCTGGTCAC |
| REA001313 | TCGTAGCATCCAGCAACAGT |
| REA001315 | TCGAAGGTCGTTCACCAGTG |
| REA001334 | AACGATCACAAGGAGCAGTC |
| REA001335 | CACGACTAGCAACTCATGGC |
| REA001336 | CTTGTGTCCACGAAGAACAT |
| REA001337 | CTAGAGGTGGTCCTCCTGTA |
| REA001398 | GAAGTAGAACGATGCAACGG |
| REA001399 | TACGATGCACACTTGGTTGC |
| REA001403 | GATCACAGGATCATGTTGGC |
| REA001405 | TGCATGAGAGACATGGAGAT |
| REA001414 | CGTTGTGCATGTACCAAGTG |
| REA001417 | TGTGTACCTAGCTGCTTGGG |
| REA001419 | TCTCCTGTGGAAGCAGCAGT |
| REA001557 | TAGCACTACGTGATCTGAGA |
| REA001558 | GTCTTGAACTGATCCTACAG |
| REA001710 | GCAGCTGCAGCAGTCGTAGT |
| REA001771 | TTGCTTGGAGAGTGTCACTG |
| REA001785 | GGAGTGGTTGGTGAGAGAGA |
| REA001790 | AACGAAGGTTCTGCTCTGGT |
| REA001801 | AGTCCATCTGCTCGTAGCAT |
| REA001804 | CGTGCTCCAAGCAGTAGCTG |
| REA001824 | GTCTGATCCTACCTTCCATA |
| REA001828 | AAGTTCTCCTGATGCTCATC |
| REA001833 | CTGATCCACTGAGCACTTCA |
| REA001840 | ACGTTCCAAGTCGTCATCGG |
| REA001841 | GGTCACGATGCATCCTGACA |
| REA001842 | TCGTAGCAAGTGAGGAACAG |
| REA001845 | GGTGCTTGGTACGAACGTCG |
| REA001846 | CTCGACCAACCTGACCTGAA |
| REA001847 | TTGGATCGACAGGACCTTCT |
| REA001848 | TACTTCGTCCAGTTCCTTGC |
| REA001849 | ATCCTCTTGCTGTCAGTCGC |
| REA001850 | GGTGAAGTACGACAACTACT |
| REA001853 | TCGTACCTGTCTTGTGTACC |
| REA001855 | CTGGATGACCAGAACTTCAT |
| REA001860 | GATCGACTTGCAGACGTGCA |
| REA001861 | AGCTACGTGAGAGAAGACAC |
| REA001865 | AGTCTGGTGGTGACGACTTT |
| REA001891 | GCTAGGAGCACCATCACGAT |
| REA001895 | TGAGAAGGATCTCGTACCTC |

TABLE 2.4-continued

Building blocks (reactants) and their corresponding tag codons used in the library synthesis.

| | |
|---|---|
| REA001901 | TAGCATCGTTGCTCCAGACA |
| REA001903 | AAGAACTCTTCGACTCCAAG |
| REA001906 | ACGTAGTAGAGCTACAAGTC |
| REA001910 | CGTCCTACCAACCAAGCTAT |
| REA001911 | GTTGCTCCTCCTTCTCGATT |
| REA001912 | GACAACTGTCCTCGTACACT |
| REA001916 | GCATGAGAACTCTTGATCCA |
| REA001917 | CCTCCATGCTGAAGTGGAAA |
| REA001918 | GGTACGACCATCAGTCCACC |
| REA001920 | TACAGTTGTCTCTGGTCTTG |
| REA001931 | ACCTTGAACAACGACTCCTG |
| REA001932 | GACCAAGTCAGTGCAAGAGC |
| REA001933 | CTACACAAGTGCTAGTCTTG |
| REA001936 | GTCTGCTGTAGCAACTCATC |
| REA001937 | ACTGCTCAAGAGATCACTCA |
| REA001940 | GATCCACACGTTGCACGTTC |
| REA001942 | AGACCTCCATCGATGGTAGG |
| REA002341 | TGTTCTCACAGCTTCCTACA |
| REA002342 | ATCACAAGGAGATGGTTCTC |
| REA002343 | CACCTTGCACCTTGCATCAC |
| REA002344 | TGTTGTCGAGTCCTCCAACT |
| REA002345 | ATCCACACCACGACATCTAA |
| REA002346 | CATGTGAAGAACCTCGTCCC |
| REA002347 | TCTCCTGTCCAACAGTCCTT |
| REA002348 | GTTGGACAGCAACCAGTGGT |
| REA002349 | GTAGGTACAGGTGAGGTACT |
| REA002350 | AAGATGAGGAGTGCAGTACA |
| REA002351 | TACCTTGAAGCACGATGGAA |
| REA002362 | ATCATGTCCTTGGATGGACT |
| REA002363 | GATGCTGATGAGTGCAACTA |
| REA002408 | TACGTCAACGTAGATGGTGA |
| REA002410 | CGATCTGACAGTCCAAGGTA |
| REA002411 | CCACGATCTCCTACGACTT |
| Dummy B | CCTCGTCCTGATGTTGCATC |

| BB C | Tag C codon |
|---|---|
| Blank | CCAACTTGGAGGTTCATGCG |
| REA001415 | TTGGTTCTGACACTGTAGAC |
| BBA001092 | ATCAACCTAGCACCAGGAAA |
| REA001332 | TTCTCACGACAGCAACCTTG |
| REA001938 | CTCTCTTGCAGCTACTGAAT |
| REA001939 | AGTCAAGTCAGAGTTCGTAC |
| REA001944 | TAGATCGTCACTGACGATCC |
| BBA000008 | GGACGTGAAGGACATCACAG |
| BBA000029 | CACTACTTGTTCTACGTGCC |
| BBA001023 | ATCGTTCCAGTCGAGTTGAT |
| BBA001024 | ATCAACCACCTCTACCACCG |
| BBA001035 | AAGCTACAACAGCAGCTACG |
| REA000250 | CCAGTAGGTGATGCAACGTA |
| REA000772 | AACAGGTCCACAACAGATGG |
| REA000778 | CCATGTCGTAGATCGTTCAC |
| REA001143 | TCATGTCTCGTAGACACTGC |
| REA001281 | GAGGAAGCACAGCATCCATA |
| REA001282 | GCTGCTTCTGAGGAGGATCC |
| REA001284 | GCAACAGAACTACATGACCG |
| REA001315 | GGACAGCTTGGATGCTTCAT |
| REA001331 | ACCTAGTGGTACATCTTCCT |
| REA001334 | CGTGTAGAACCACGTTCGAC |
| REA001337 | GTGCTACCAGAAGGATGCAA |
| REA001407 | CCACACAGGTCTCCTACATG |
| REA001414 | GTTGAGTCGATCCAGAGTAG |
| REA001421 | GGTTCCTTCCTGAGGTTCGA |
| REA001552 | ATCGTCCAACGAAGCAAGTT |
| REA001557 | AGTACGTTGCTAGTTGACGC |
| REA001558 | GGACCTACCTTGCATGAGGA |
| REA001768 | GATCGACTTGAACTTCACCC |
| REA001779 | TCAACGAACCTGTCCACG |
| REA001780 | GGTGAAGCAAGTGTTCAACT |
| REA001785 | GCTAGATGTGAAGGTCCTAA |
| REA001790 | AAGACAGTACCACGATGCTA |
| REA001793 | GTTCGTACCACCTTCAAGAC |
| REA001801 | TGGAGTCGTACAGAAGCATG |
| REA001815 | ACCTACAGTACCAGGTGGTG |
| REA001824 | CGAGACTGTTCCTGCACTCC |
| REA001828 | TACTCTGCACGTCAGTTGTA |
| REA001829 | GCTCCTGATGTCCTGGTTGC |
| REA001833 | TCCACATCCAGCTCGTGGTT |
| REA001838 | CGAGCACCAAGCACTGTTGT |

TABLE 2.4-continued

Building blocks (reactants) and their corresponding tag codons used in the library synthesis.

| | |
|---|---|
| REA001840 | AAGGAACCACAACCAACCTG |
| REA001841 | GGATCCATCGTCTACCTCTA |
| REA001845 | AAGATGGACTCTGCAACGTT |
| REA001851 | TACTGACACTCGTTGCTAGA |
| REA001852 | ATCTGATGGATCTGTGCTCC |
| REA001853 | ACGAGTCTCTCCTAGGACAA |
| REA001854 | TCGTTCTCGTACTTGTTGGA |
| REA001855 | GCTTGTCTAGACGTTCTCTG |
| REA001856 | TCCTGCTTCAACCTAGATGG |
| REA001857 | GACTACCTGGATCGTACATA |
| REA001858 | AAGCAAGGAGGTGTACGTTT |
| REA001859 | CCTGAGCTCAGAGTGTAGCC |
| REA001860 | AGTGAGTCCTACCAAGCATG |
| REA001861 | TACGAGTGTGCAAGCATGTA |
| REA001863 | CTCTTGACGTGTTGTGCTAG |
| REA001864 | AGGAGCAAGCAAGGTACCTT |
| REA001865 | CGTGTGCAGAGGTTGCTGAA |
| REA001892 | CCTACTAGCAACCATGGTCG |
| REA001893 | CTCACATGGTAGCACGATGC |
| REA001896 | CACTTGTACGAGAAGATCAG |
| REA001901 | CGTTCCACTCATCTGTGCTT |
| REA001902 | CCTTCACGATCCTACAGTCA |
| REA001905 | ATCTCAGACACCTTGATGTG |
| REA001906 | TCAGGTCTTGGTAGGATCCT |
| REA001907 | TACGTCCTACCAGTCCACGA |
| REA001909 | CCATGCTACCAGTACCACTG |
| REA001916 | GGACCTTGCTTCCACACGTC |
| REA001917 | CACCTGACTAGACAACAACT |
| REA001918 | TTGGTCGAAGGAGTCGTGAC |
| REA001920 | TGCACCTGCACTCACGTCCT |
| REA001923 | ACAGGAGCAAGGAAGCAACT |
| REA001931 | AACTGGAACTCAAGACAGAC |
| REA001932 | GAAGCTGAGACCATGAGAAT |
| REA001933 | CTCGAAGTAGTGTTGATGGC |
| REA001934 | CCATCCTCGATCTCGTGTTA |
| REA001935 | AGTCCATCTCGTGGAACTTC |
| REA001937 | TGCATCCATCATCACTAGGC |
| REA001940 | TAGATCCTGTCAAGGTTGCC |
| REA001945 | GCTTGGACTGTGCTGATGCG |
| REA001946 | CGTAGTAGACATCTCTAGCA |
| REA001961 | ACTGTTCTCGATGCTAGTAC |
| REA002341 | CTCTTGTCAGACGTGCTTCG |
| REA002344 | GCAGAAGTAGACTGTCCACG |
| REA002345 | TCGAGTGTGTGTACCAAGAC |
| REA002351 | TTGGATGCAGTCCAGGAGAA |
| REA002407 | CATCTCCAGTGTCGAGCATG |
| REA002409 | TACGTGACAAGGATCTTCGC |
| REA002411 | TGACCATCACCTTCTGCATT |
| REA002416 | AAGCACAAGCACTGAGTCGG |
| REA002444 | TCCTGTCACTCCAACCTCGG |
| REA002446 | ATGGAGAGTAGTCTCCTGGT |
| REA002447 | AAGAGATGCTGACTGGTAGG |
| REA002448 | TCTCTCAAGCTACGTTGGAC |
| REA002449 | ACCTTGGAAGTACCAAGTTG |
| Dummy C | CGTGCTACCACACTCACAAT |

| BB D | Tag D codon |
|---|---|
| BBA000895 | TAGTGGTTCACGTGACCTAT |
| BBA001041 | ATGTAGTCATGCTGTCCACT |
| REA000894 | CCTTCCAGTACATGCACTAT |
| BBA000100 | GATCCTCCTTGTACCTAGTG |
| BBA000139 | TGAGGTACCTTGTACTCTCA |
| BBA000837 | ATGGACGAGTCTGACGTAGC |
| BBA000849 | TTCGTTGAGGAACCTCACGG |
| BBA000893 | CTCATGGTTCCTCCTACTGT |
| BBA000894 | GTGTTCGTTGGTGACTCGTG |
| BBA000903 | CTGTGGAACGATGGAGGAGG |
| REA000194 | GCTCTTCCTTCGTCCTTGAT |
| REA000892 | CCTACGATCCACGAAGCTTC |
| REA001101 | GGATCTACCAGCTTGTCTTA |
| REA002259 | ATGCAAGTTGGTGCTGACTC |
| BBA000031 | TACAACGTCGTGTAGTCTCC |
| BBA000820 | GCAACTACCTGACCAACCAT |
| BBA000828 | GCACGAAGATGTCACTGGTT |
| BBA000829 | GGTTCCAAGTGTAGGAACGC |
| BBA000830 | TCCAACCAGCTCCTGGTACA |
| BBA000836 | ACCTAGCTCACAAGGTGGAT |
| BBA000843 | AACTTGTCCTAGACTACGAG |

TABLE 2.4-continued

Building blocks (reactants) and their corresponding tag codons used in the library synthesis.

| | |
|---|---|
| BBA000845 | ATCAGGTGTACGACTCAGTG |
| BBA000846 | CAGAAGCAACCAGTGGTCAC |
| BBA000847 | TGACCACGTGGTAGGTCAGA |
| BBA000851 | CGTCGTACTTGTTGCACGTT |
| BBA000852 | AGTGACACGACATGCACGAA |
| BBA000853 | CGACACTCTTGTAGTCGTGC |
| BBA000862 | GGTTGGATCTCTCTGCTCTC |
| BBA000886 | TAGGTAGCAACCAACGACGT |
| BBA000891 | ACCATGGTCCTCCTGGAGAT |
| BBA000892 | AGGATCCTCTTCAGCACTGT |
| BBA000896 | GCAACTGGAGTGTGATCCAC |
| BBA001038 | GACAGGTCATCAGTCGTTGC |
| BBA001039 | GGACTGTGAACGTACACCTC |
| BBA001042 | ATCCTTCAGTACGATCCATC |
| REA001095 | TGATGATCTGTGGACGATCT |
| REA000068 | ACGACTCCAACTGTCCTGGC |
| REA000402 | CCTTCATCTGGAGATGTCGA |
| REA000556 | TGGTAGTTCCTTCAGGAGTC |
| REA000736 | AAGAAGCAGTCCTAGCACGG |
| REA000749 | TGCTGGTAGACAAGACGATT |
| REA000893 | AACTCTTCGACGTGACACTC |
| REA000898 | AACAAGACGTGACGTTGCTG |
| REA000901 | GATCTCTTGAGTGGAGTCCC |
| REA001004 | CACCAACCTCAGACCTGAGA |
| REA001015 | GGATGCACAGGTACAGGAAT |
| REA001022 | TACCACAACCAGTCCTTCCT |
| REA001023 | ATGCTGTCAAGCTTGTAGGG |
| REA001028 | CTTGCATCAAGCATCGAGCG |
| REA001029 | AGGATCCTGTCACTAGTGGA |
| REA001031 | CTGCAAGCTAGACAACAGTG |
| REA001038 | CGACCTCCACTGGTAGACCT |
| REA001044 | TCCAAGACTACGATGTTGAG |
| REA001045 | CCTCTGATGGTTCATCCAGT |
| REA001055 | GATGAGACATGCTACAAGAG |
| REA001056 | GCTGGAGGTGTTCATCAACA |
| REA001058 | TGGAGTTCGAGTACGAGTCA |
| REA001061 | AGTTCAGACAGGATGAACG |
| REA001062 | GTAGTGAACGACCACGAGTG |
| REA001069 | TACGTCGTCCTTGCAGACAA |
| REA001070 | GTACAGGATCTACGTTGAGC |
| REA001071 | GTGCTCAACAGTCAGGTGCC |
| REA001072 | GCTTCGTACGATCATGTACC |
| REA001085 | GGTGTGTTCAGAACAAGCAC |
| REA001090 | CTCGATGGAGGTTGTAGCAC |
| REA001093 | TAGCACGTTGAGCTACGATC |
| REA001094 | ACAGCAAGTTCGTTCCTCTA |
| REA001097 | TGTTCGTTGTCAGCAGTTCG |
| REA001100 | TCATCGAGCAAGGTGTTCGC |
| REA002260 | CGAGTCTTCAACTTCCAAGC |
| REA002262 | TCCATGTTCGTACGACGATG |
| REA002264 | GTGTACTCCAGACTTCCTTT |
| REA002275 | TACTTGCACCAGACTTGTAC |
| REA002276 | AGTACAGGACAAGACACGTT |
| REA002279 | CGATGAGAGTAGTGTCTACG |
| REA002284 | GCAAGCTCAGAGCAGAAGTG |
| REA002292 | CGTGACACGTGTTCAGCACG |
| REA002298 | GTACGTGTTGCACAAGAGCA |
| REA002299 | ACGATCACTACGATGAAGGT |
| REA002301 | TAGGACGTAGCAGACAACTA |
| REA002303 | TCTCAGTACGTTCGTAGTCT |
| REA002305 | GCAAGCAACTTCGTTGGTAC |
| REA002307 | GTAGAGAGACATCCAACCAA |
| REA002310 | CCTGCTAGTGCTTCCTTGGG |
| REA002312 | CACACGATCTGTAGTCCTGA |
| REA002313 | ACACCAAGGTTCAGATGTGT |
| REA002323 | TTCTACTGCTGTTGACCTTG |
| Blank | CCTGTCATCCTTCGTACTAT |
| REA001966 | GTTCGAACAAGTCTCCAGAG |
| REA001969 | GGAAGGACCAGACTGTCACG |
| REA001970 | ACCTACAGACACACAGATGC |
| REA001973 | TTCTGTAGGACCTTGGAACT |
| REA001978 | GCTCCATGGATGTACCTTCA |
| REA001986 | ATCCTCTCCATGCTAGAGGT |
| REA001989 | GAGAAGGAGAAGGTCGTTGC |
| REA002000 | TACGTGAGTAGCTACTGGAA |
| REA002003 | TAGGAGTACTCCAGGATCGC |
| REA002004 | TCAAGTGTCTGACGAAGCTA |

TABLE 2.4-continued

Building blocks (reactants) and their corresponding tag codons used in the library synthesis.

| | |
|---|---|
| REA002009 | GTGATGGTAGACAGCTGTAA |
| REA002016 | AAGTGGAGTTGGATGCACCT |
| REA002019 | TTCCTGGTTGGACTCGTCGG |
| REA002020 | CCTGCACGAACACTTGCACA |
| REA002027 | TGAGTTGCTGCACTGTTGCT |
| REA002036 | CTTGTCAAGCAGTCACTAGA |
| REA000798 | TCACATGACCAGCACGTGCG |
| REA001466 | CGATCAAGCTACAGAAGAAG |
| REA001475 | TGGACTCTGTCGAAGGTACA |
| REA001508 | CTGTAGCATCCACTCCATCC |
| REA001646 | GACTGTGGTGACACCTGACT |
| REA002038 | GCTTCGACAGACATCACTCG |
| REA002042 | ATGGACAGTGGACACTCATT |
| REA002046 | GCTTCTCCTGGTTGATGGTC |
| REA002050 | CGTGGAAGGTTGAGCTCAAC |
| REA002065 | ACATCTAGTCCAGGTGGTTT |
| REA002067 | CCTCGAACCTTGCTACAGCG |
| REA002075 | CGACGAGCACACTCTCTCAG |
| REA002076 | ATGCTTGCACTGTGATGACA |
| REA002077 | GTGTACTGAGTGCAGCATGG |
| REA002086 | TACGAGCAAGGTAGCTGGTG |
| REA002088 | CGTTCTAGGAAGTGAAGCTG |

TABLE 2.5A

Position A building blocks (reactants). The unprotected structures are shown. The amines were protected by Fmoc groups during loading. After loading Fmoc groups were removed.

BBA000029

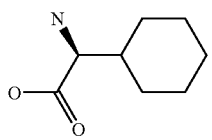

BBA000890

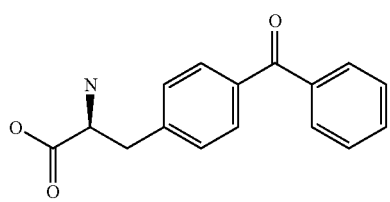

TABLE 2.5A-continued

Position A building blocks (reactants). The unprotected structures are shown. The amines were protected by Fmoc groups during loading. After loading Fmoc groups were removed.

REA000250

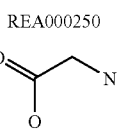

REA000778

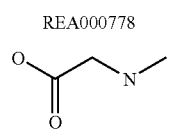

REA001143

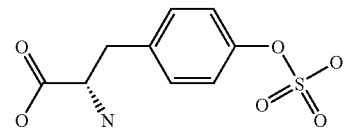

REA001329

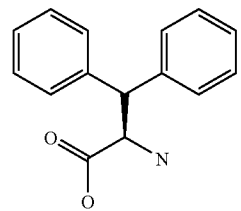

REA001398

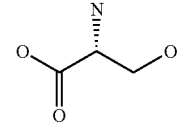

REA001399

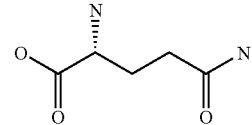

REA001403

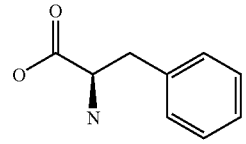

REA001405

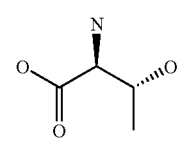

TABLE 2.5A-continued

Position A building blocks (reactants). The unprotected structures are shown. The amines were protected by Fmoc groups during loading. After loading Fmoc groups were removed.

REA001410

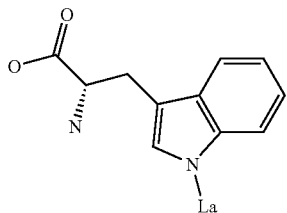

REA001411

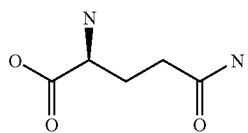

REA001415

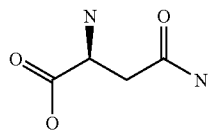

REA001416

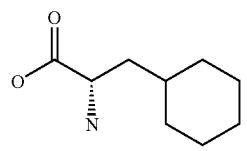

REA001419

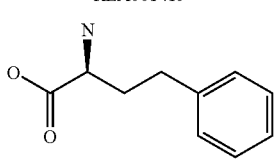

REA001422

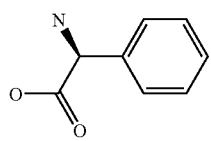

REA001423

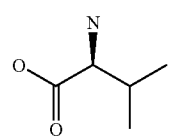

REA001424

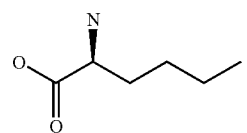

TABLE 2.5A-continued

Position A building blocks (reactants). The unprotected structures are shown. The amines were protected by Fmoc groups during loading. After loading Fmoc groups were removed.

REA001425

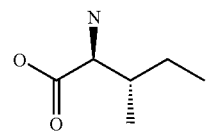

REA001426

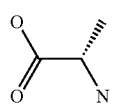

REA001446

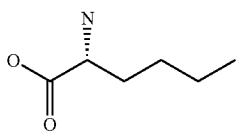

REA001464

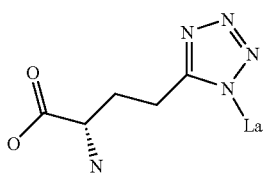

REA001767

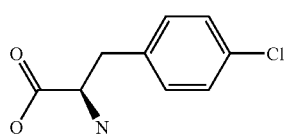

REA001769

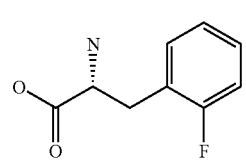

REA001773

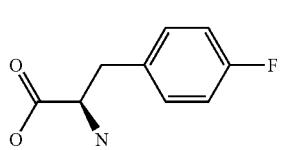

REA001774

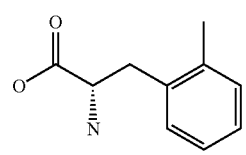

TABLE 2.5A-continued

Position A building blocks (reactants). The unprotected structures are shown. The amines were protected by Fmoc groups during loading. After loading Fmoc groups were removed.

REA001775

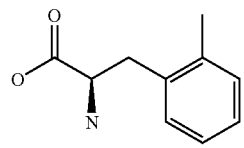

REA001780

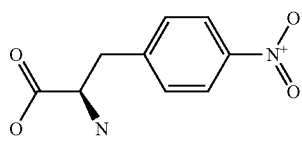

REA001781

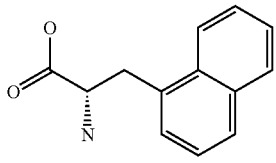

REA001782

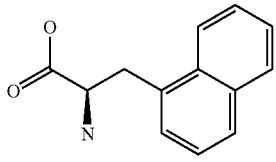

REA001785

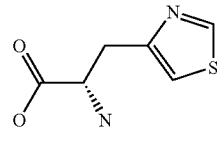

REA001792

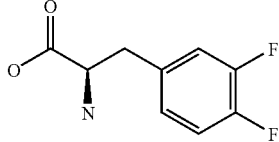

REA001793

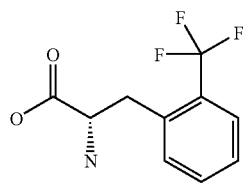

TABLE 2.5A-continued

Position A building blocks (reactants). The unprotected structures are shown. The amines were protected by Fmoc groups during loading. After loading Fmoc groups were removed.

REA001798

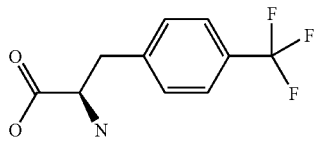

REA001799

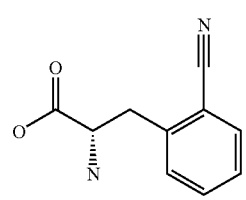

REA001800

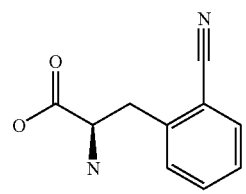

REA001801

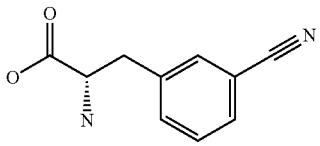

REA001803

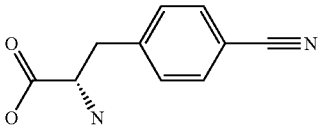

REA001805

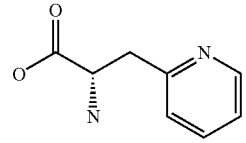

REA001806

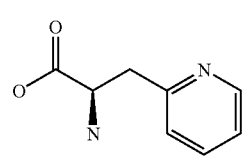

TABLE 2.5A-continued
Position A building blocks (reactants). The unprotected structures are shown. The amines were protected by Fmoc groups during loading. After loading Fmoc groups were removed.
REA001807
REA001808
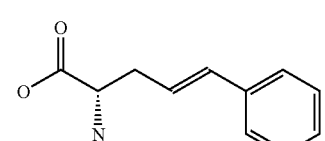
REA001809
REA001810
REA001811
REA001813
REA001817
REA001818
REA001821
REA001823
REA001824
REA001827
REA001828
REA001830
REA001833
REA001834

TABLE 2.5A-continued
Position A building blocks (reactants). The unprotected structures are shown. The amines were protected by Fmoc groups during loading. After loading Fmoc groups were removed.
REA001836
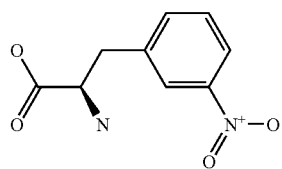
REA001837
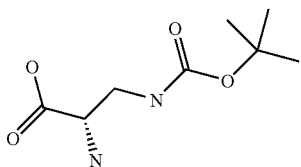
REA001838
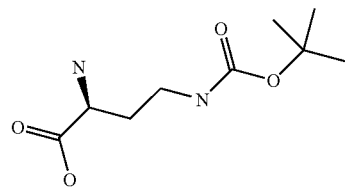
REA001839
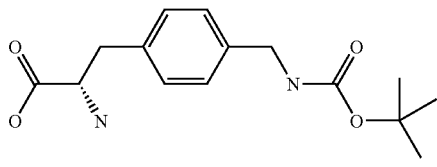
REA001840
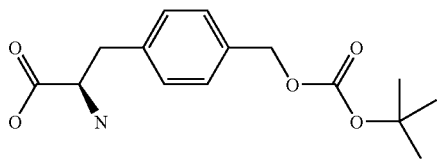
REA001891
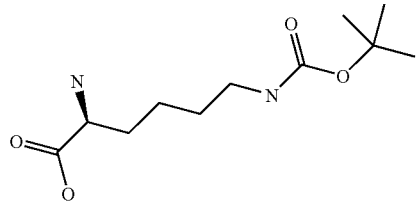
REA001892
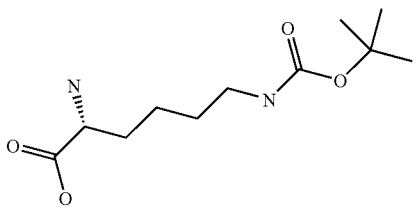
REA001893
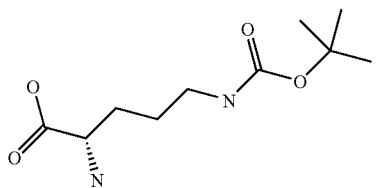
REA001894
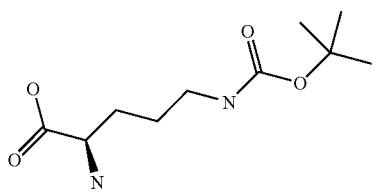
REA001895
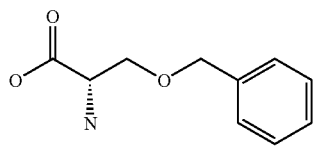
REA001897
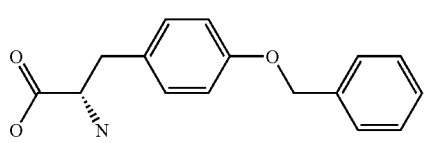
REA001899
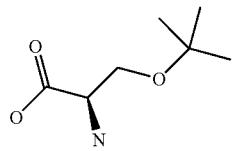
REA001902
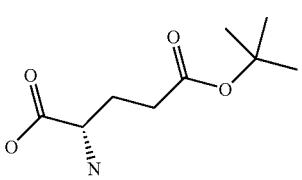

TABLE 2.5A-continued

Position A building blocks (reactants). The unprotected structures are shown. The amines were protected by Fmoc groups during loading. After loading Fmoc groups were removed.

REA001903

REA001907

REA001909

REA001910

REA001911

REA001913

REA001914

REA001916

REA001919

REA001924

REA001930

REA001933

REA001934

REA001935

REA001937

REA001942

TABLE 2.5A-continued

Position A building blocks (reactants). The unprotected structures are shown. The amines were protected by Fmoc groups during loading. After loading Fmoc groups were removed.

REA002406

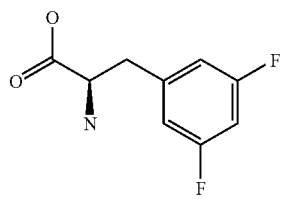

REA002407

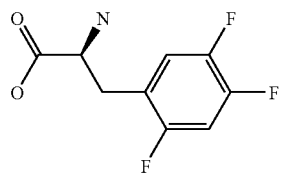

REA002409

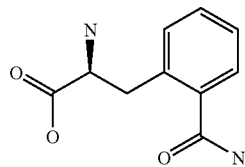

REA002411

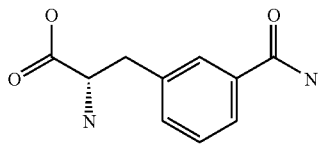

REA002413

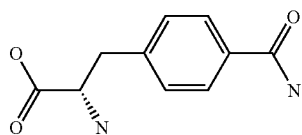

REA002415

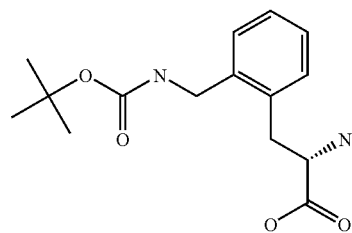

REA002419

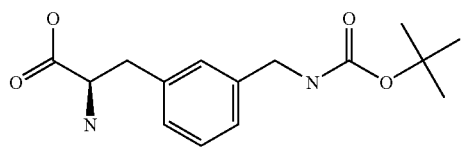

TABLE 2.5A-continued

Position A building blocks (reactants). The unprotected structures are shown. The amines were protected by Fmoc groups during loading. After loading Fmoc groups were removed.

REA002420

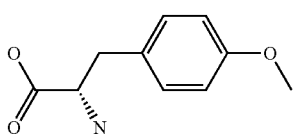

REA002422

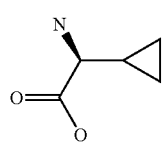

REA002423

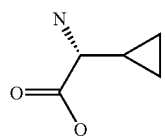

TABLE 2.5 B

REA001710

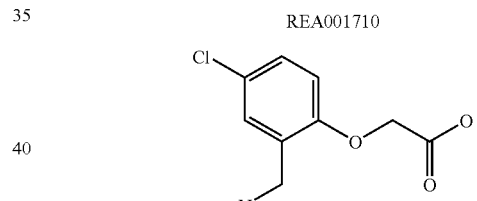

BBA000008

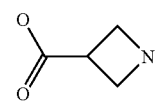

BBA001023

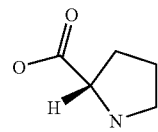

BBA001024

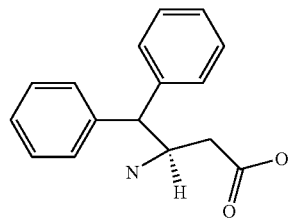

TABLE 2.5 B-continued
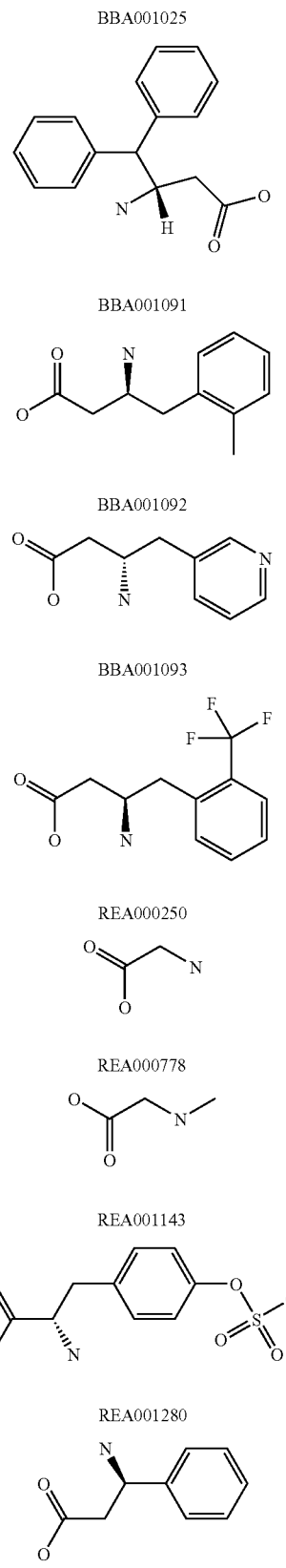
TABLE 2.5 B-continued
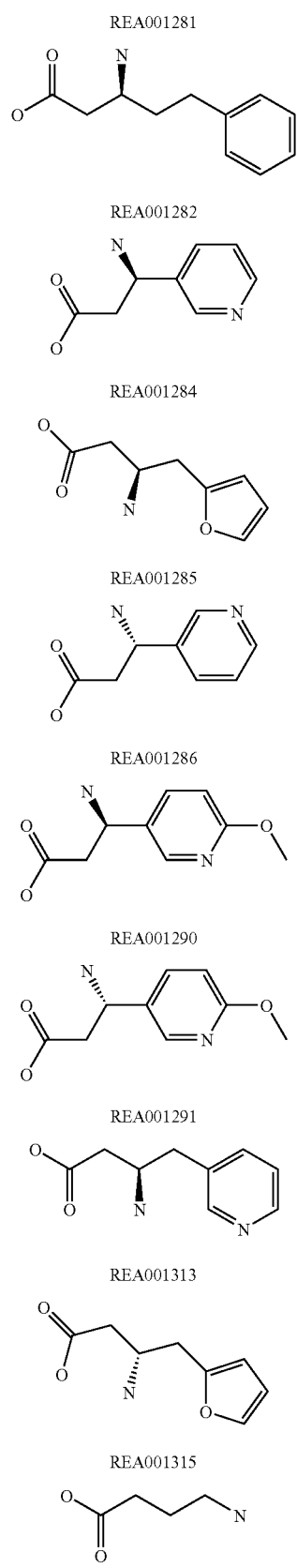

TABLE 2.5 B-continued
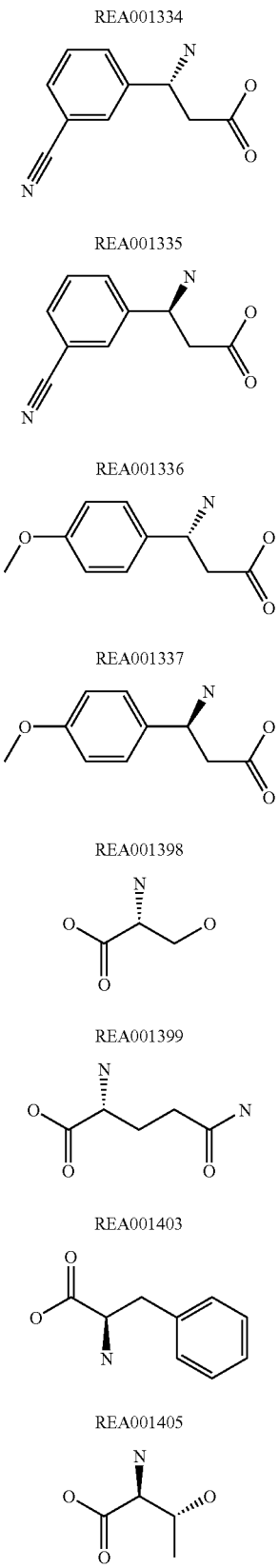
TABLE 2.5 B-continued
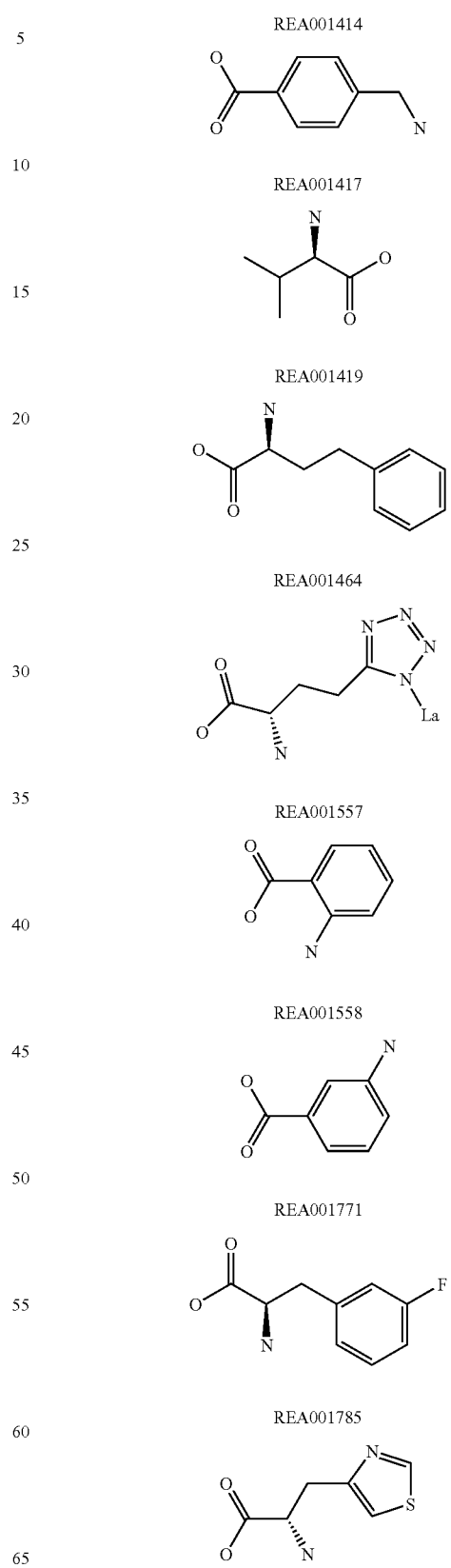

TABLE 2.5 B-continued
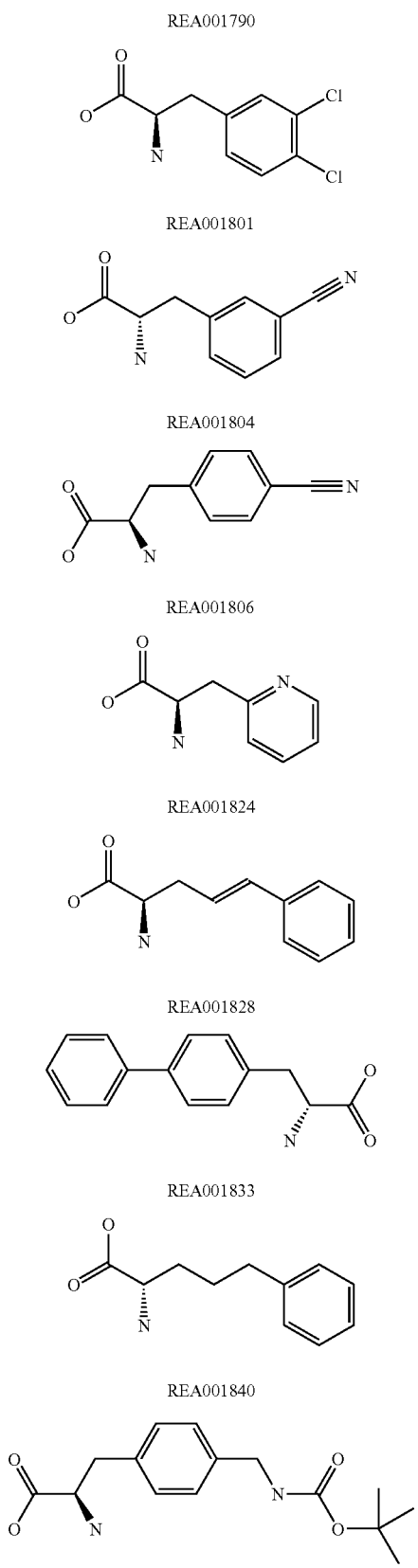
TABLE 2.5 B-continued
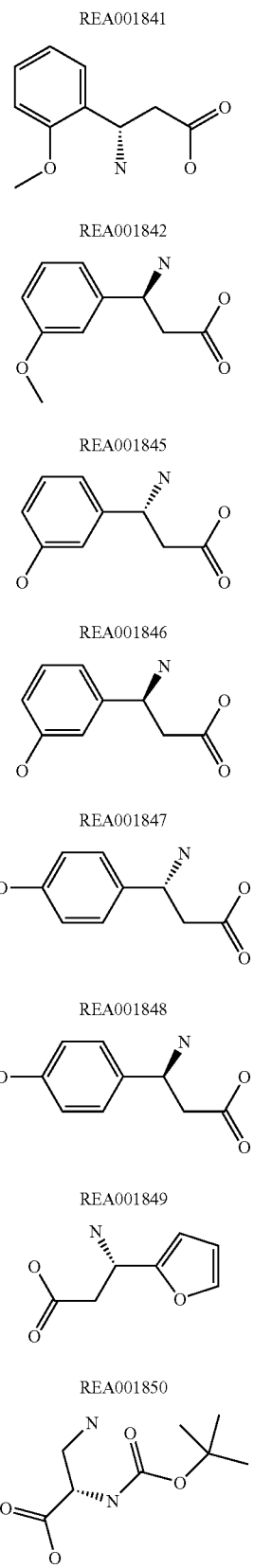

TABLE 2.5 B-continued
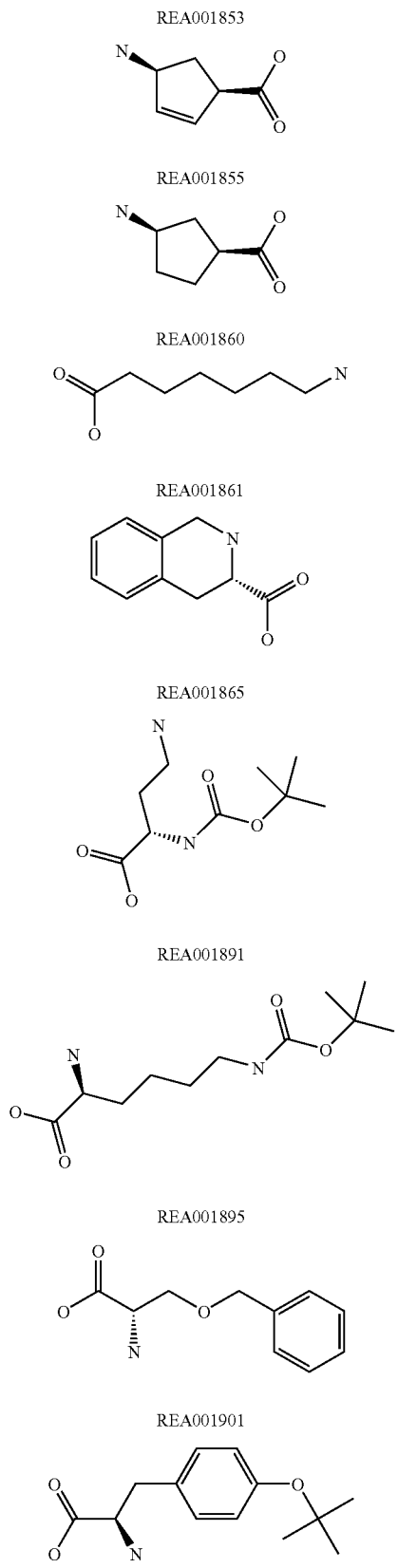
TABLE 2.5 B-continued
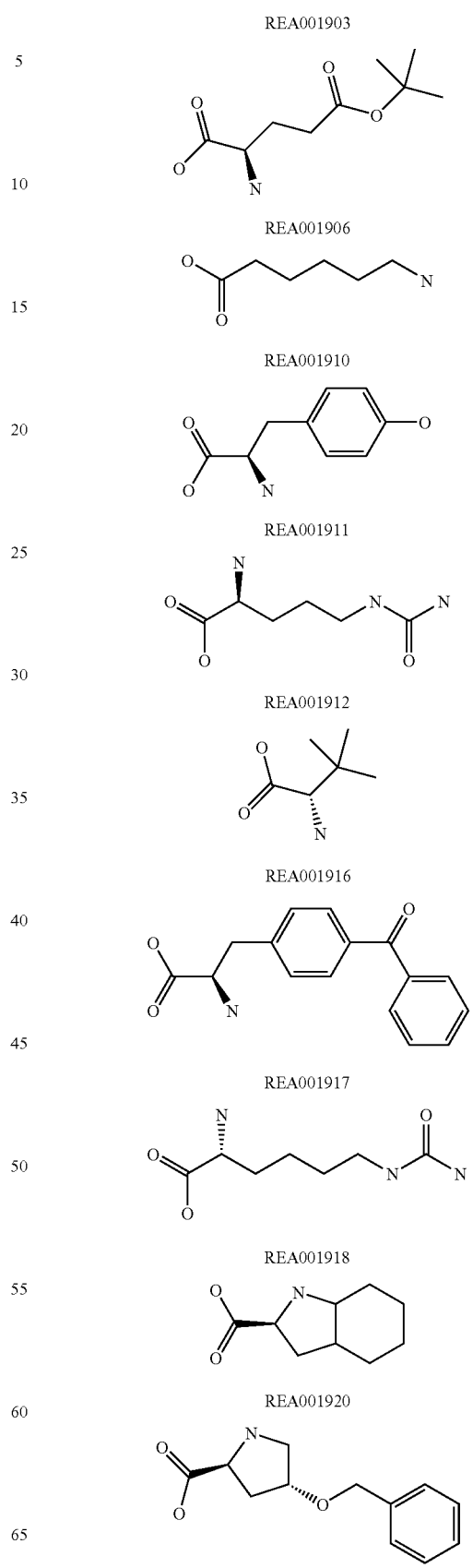

TABLE 2.5 B-continued
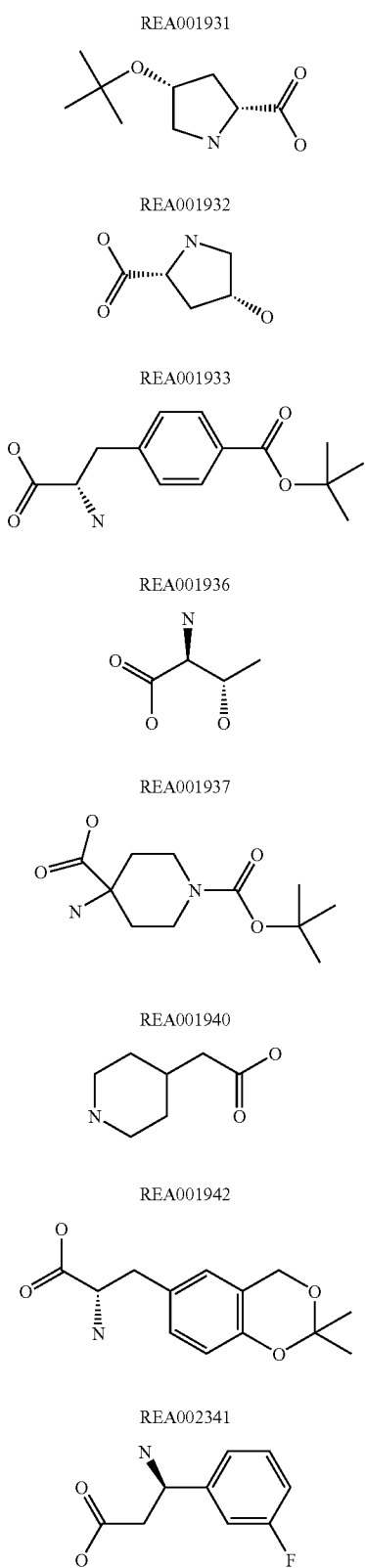
TABLE 2.5 B-continued
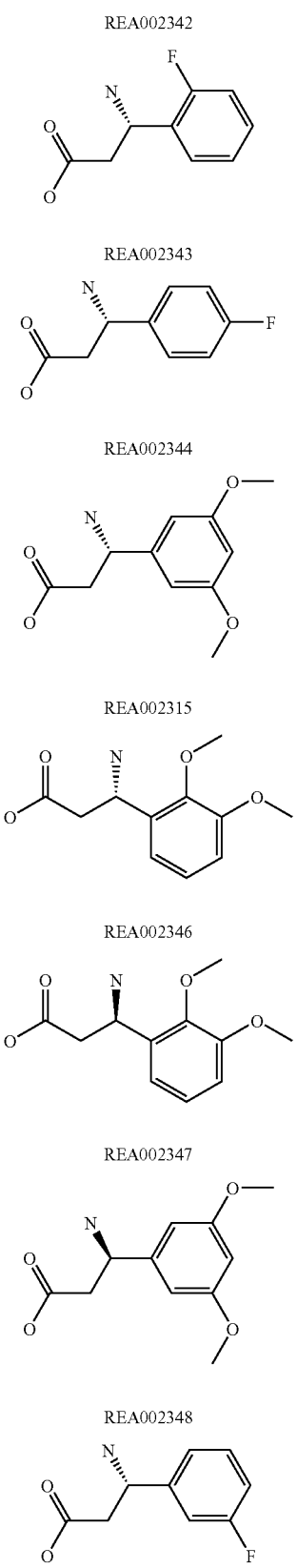

TABLE 2.5 B-continued
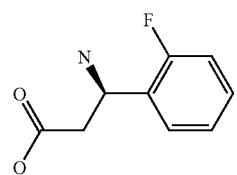
REA002349
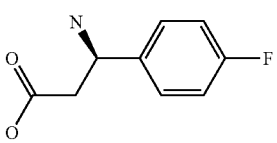
REA002350
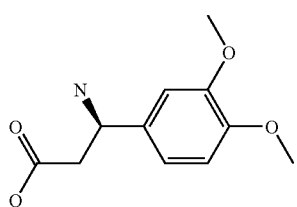
REA002351
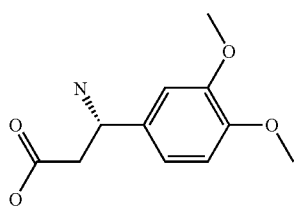
REA002362
TABLE 2.5C
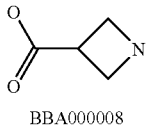
BBA000008
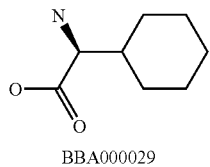 [SMILES: N[C@H](C(=O)O)C1CCCCC1]
BBA000029
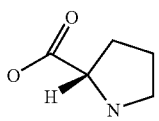
BBA001023
TABLE 2.5C-continued
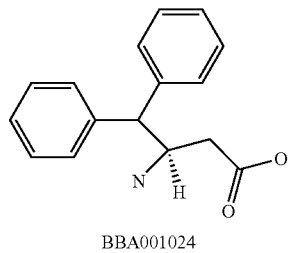 [SMILES: N[C@H](CC(=O)O)C(c1ccccc1)c1ccccc1]
BBA001024
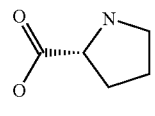
BBA001035
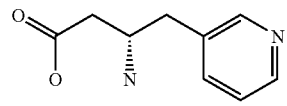
BBA001092
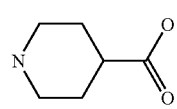
REA000250
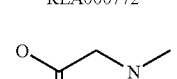
REA000772
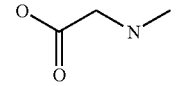
REA000778
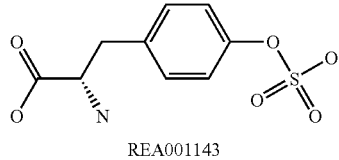 [SMILES: N[C@@H](Cc1ccc(OS(=O)(=O)O)cc1)C(=O)O]
REA001143
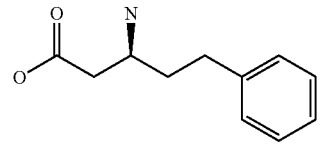
REA001281
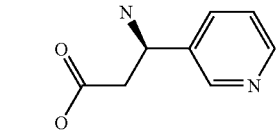
REA001282

TABLE 2.5C-continued
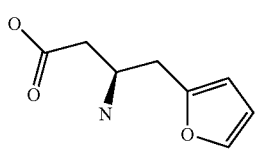
REA001284
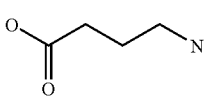
REA001315
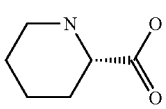
REA001331
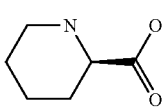
REA001332
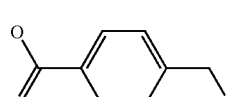
REA001414
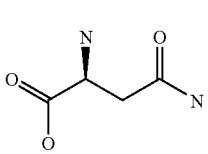
REA001415
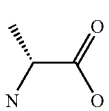
REA001421
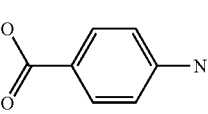
REA001552
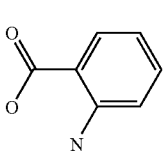
REA001557
TABLE 2.5C-continued
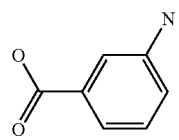
REA001558
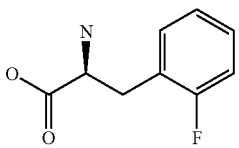
REA001768
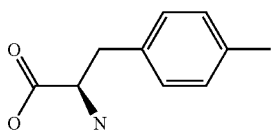
REA001779
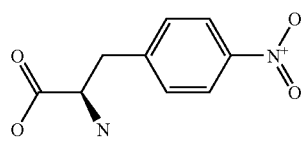
REA001780
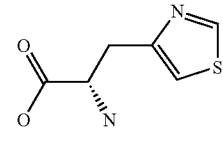
REA001785
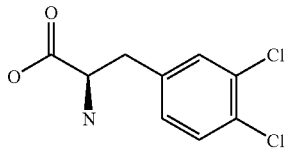
REA001790
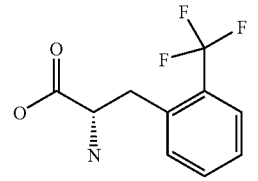
REA001793
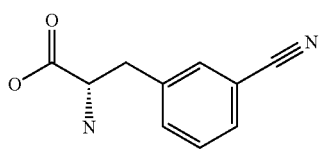
REA001801

TABLE 2.5C-continued
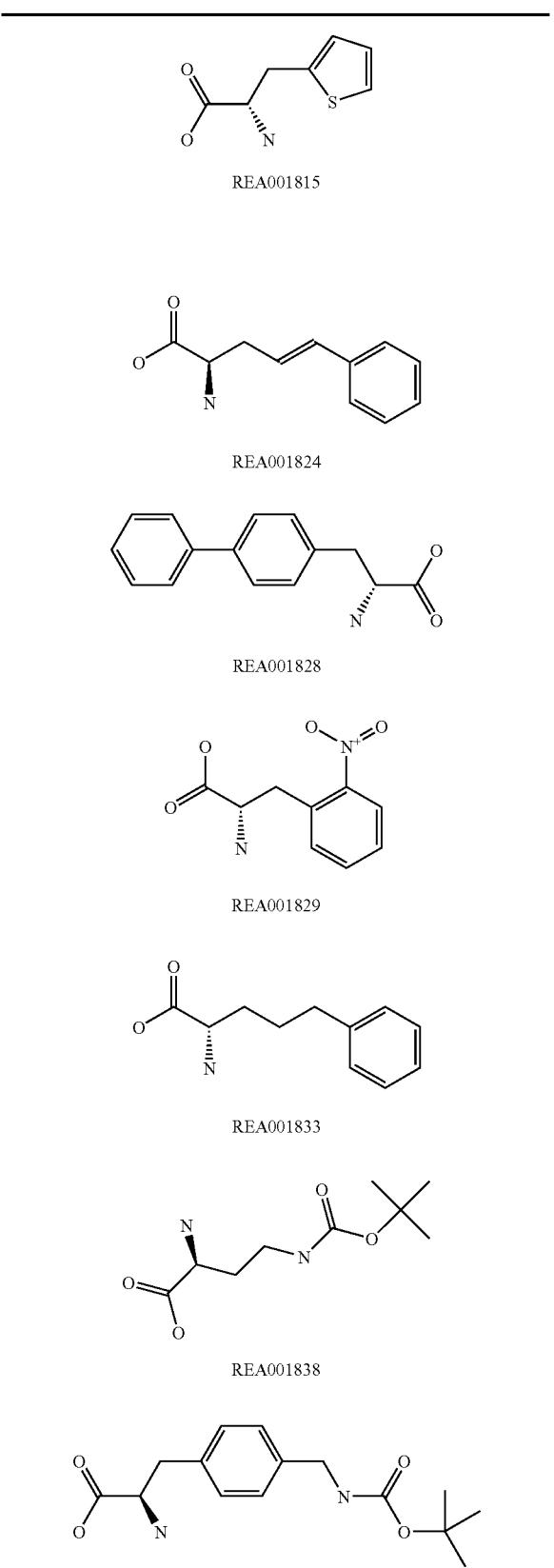
TABLE 2.5C-continued
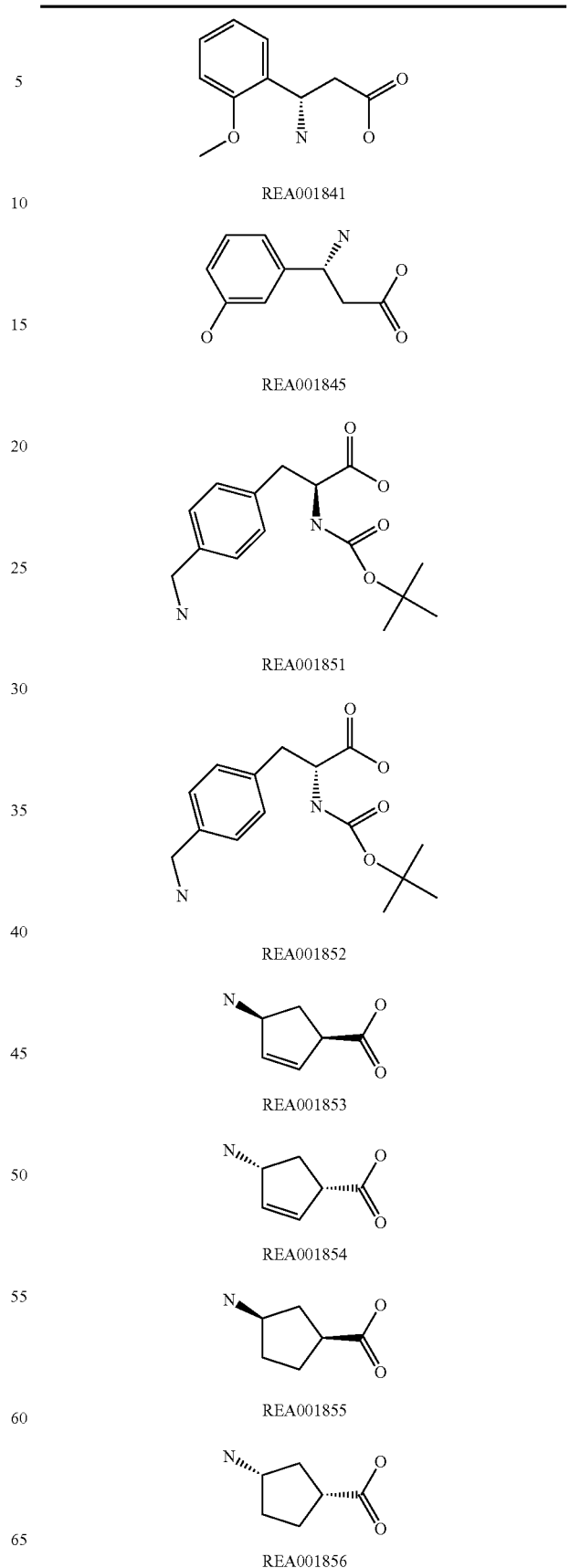

TABLE 2.5C-continued
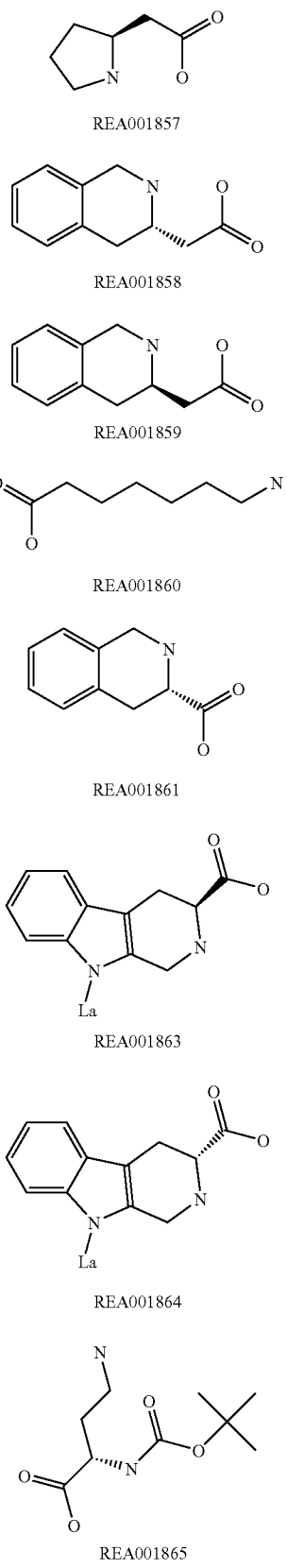
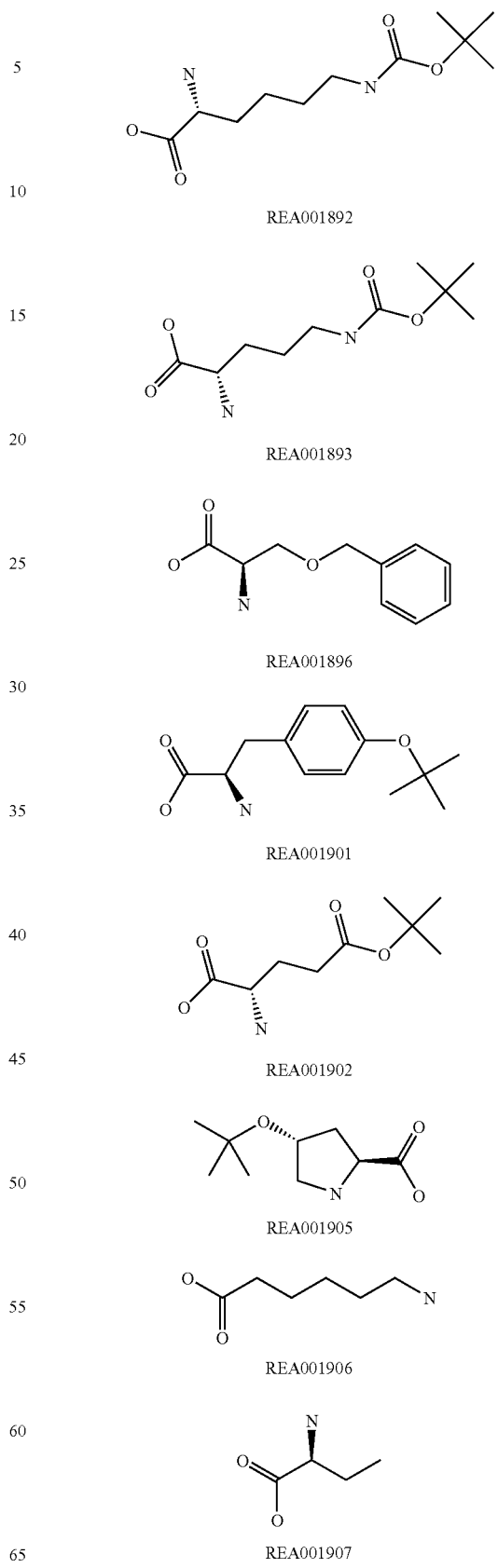

TABLE 2.5C-continued

REA001909

REA001916

REA001917

REA001918

REA001920

REA001923

REA001931

REA001932

REA001933

TABLE 2.5C-continued

REA001934

REA001935

REA001937

REA001938

REA001939

REA001940

REA001944

REA001945

TABLE 2.5C-continued
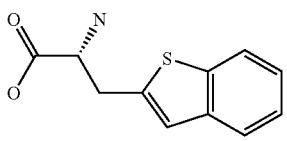
REA001946
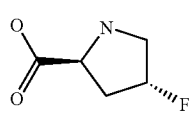
REA001961
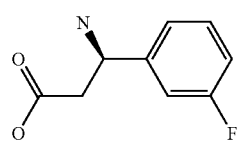
REA002341
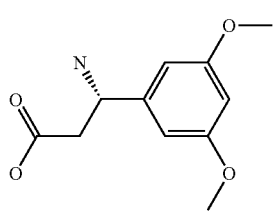
REA002344
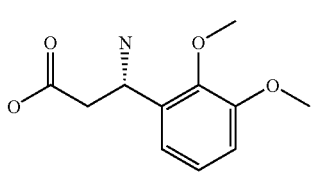
REA002345
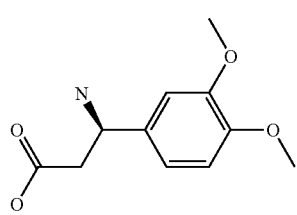
REA002351
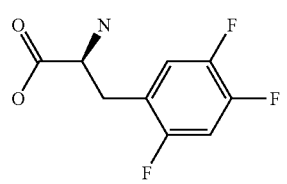
REA002407
TABLE 2.5C-continued
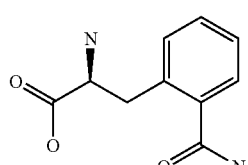
REA002409
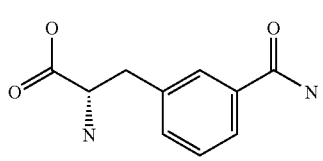
REA002411
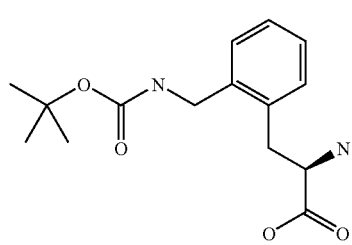
REA002416
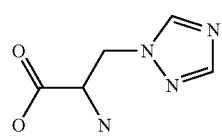
REA002444
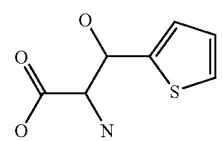
REA002446
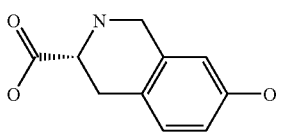
REA002447
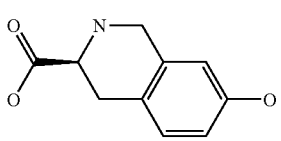
REA002448

TABLE 2.5C-continued
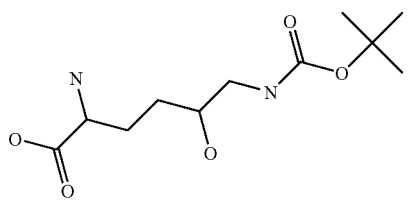
REA002449
TABLE 2.5D
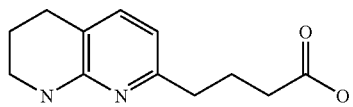
BBA000100
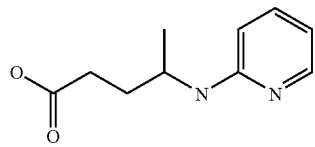
BBA000139
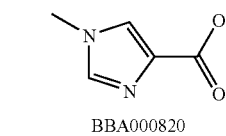
BBA000820
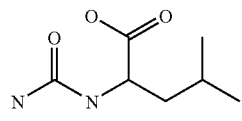
BBA000828
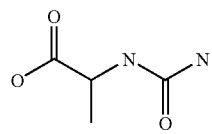
BBA000829
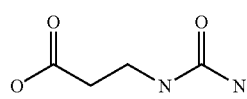
BBA000830
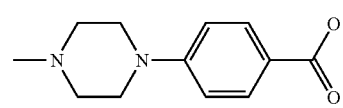
BBA000836
TABLE 2.5D-continued
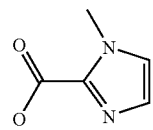
BBA000837
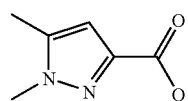
BBA000843
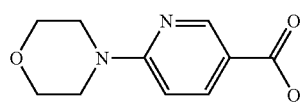
BBA000845
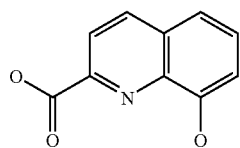
BBA000846
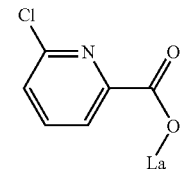
BBA000847
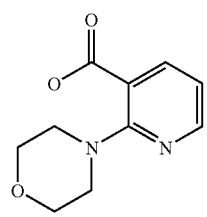
BBA000849
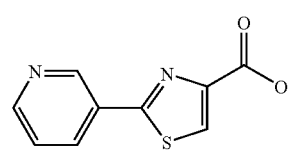
BBA000851
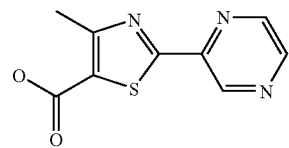
BBA000852

TABLE 2.5D-continued
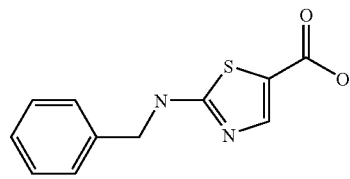
BBA000853
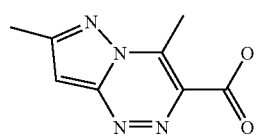
BBA000862
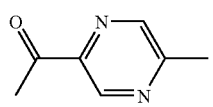
BBA000886
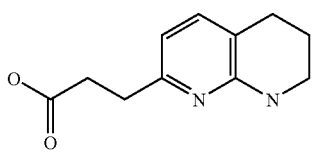
BBA000891
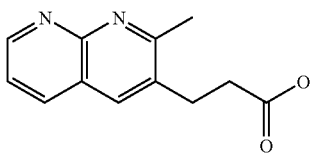
BBA000892
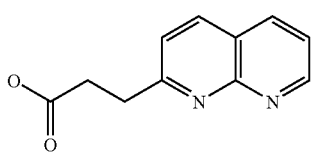
BBA000893
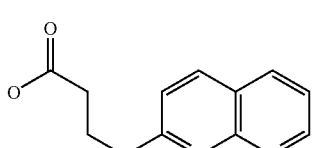
BBA000894
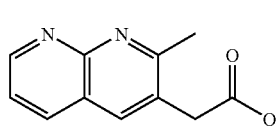
BBA000895
TABLE 2.5D-continued
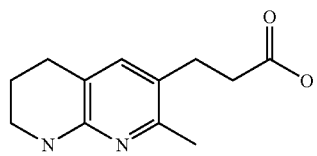
BBA000896
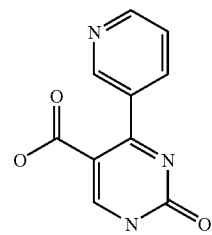
BBA000903
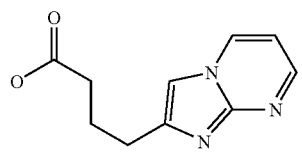
BBA001038
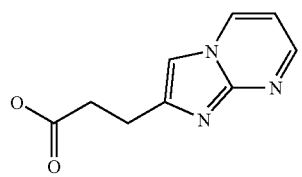
BBA001039
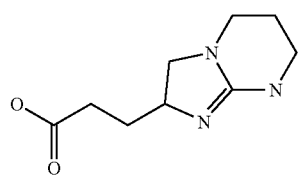
BBA001041
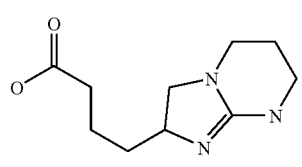
BBA001042
REA000068
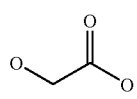
REA000194

TABLE 2.5D-continued
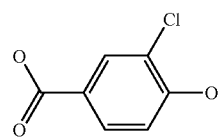
REA000402
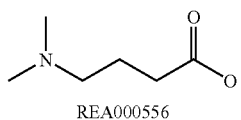
REA000556
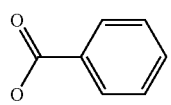
REA000736
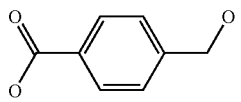
REA000749
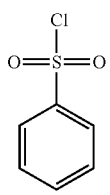
REA000798
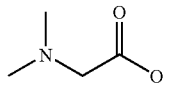
REA000892
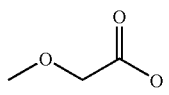
REA000893
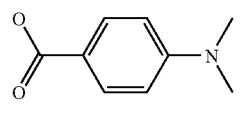
REA000894
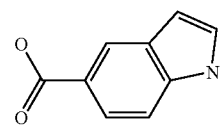
REA000898
TABLE 2.5D-continued
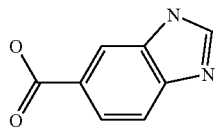
REA000901
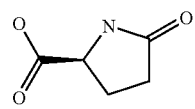
REA001004
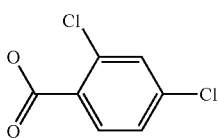
REA001015
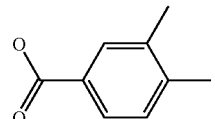
REA001022
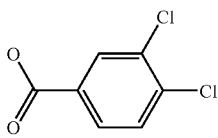
REA001023
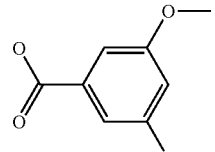
REA001028
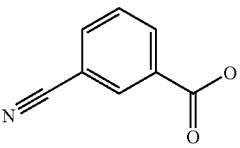
REA001029
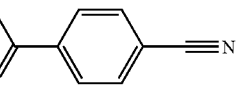
REA001031

TABLE 2.5D-continued
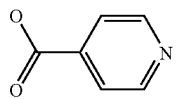
REA001038
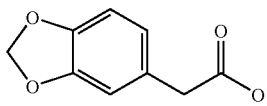
REA001044
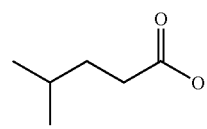
REA001045
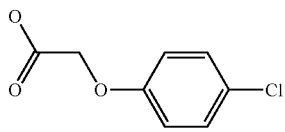
REA001055
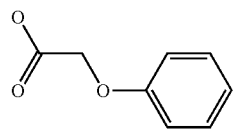
REA001056
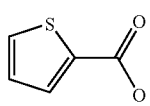
REA001058
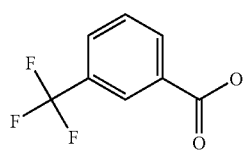
REA001061
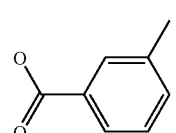
REA001062
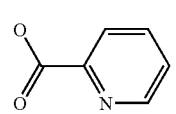
REA001069
TABLE 2.5D-continued
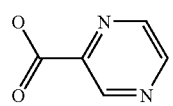
REA001070
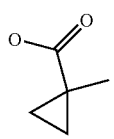
REA001071
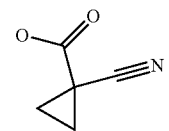
REA001072
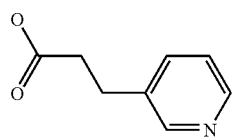
REA001085
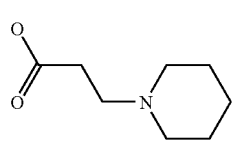
REA001090
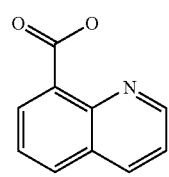
REA001093
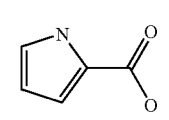
REA001094
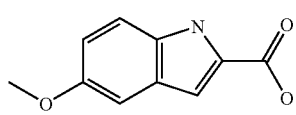
REA001095

TABLE 2.5D-continued
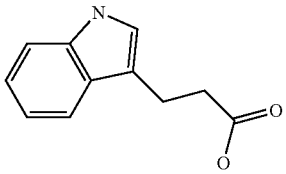
REA001097
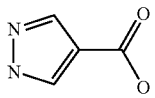
REA001100
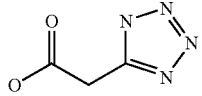
REA001101
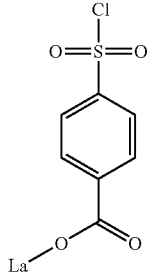
REA001466
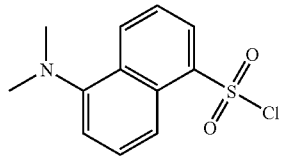
REA001475
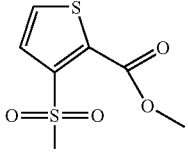
REA001508
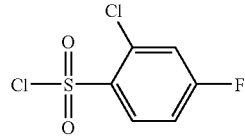
REA001646
TABLE 2.5D-continued
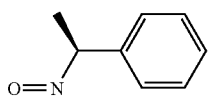
REA001966
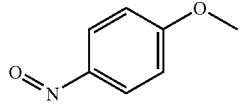
REA001969
REA001970
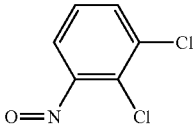
REA001973
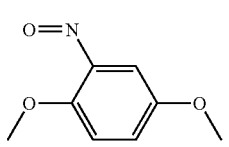
REA001978
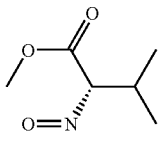
REA001986
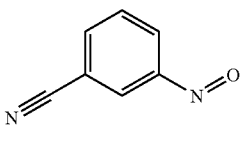
REA001989
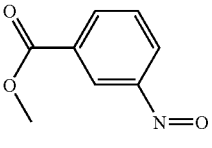
REA002000
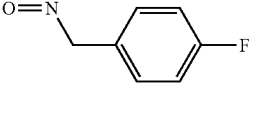
REA002003

TABLE 2.5D-continued

REA002004

REA002009

REA002016

REA002019

REA002020

REA002027

REA002036

REA002038

TABLE 2.5D-continued

REA002042

REA002046

REA002050

REA002065

REA002067

REA002075

TABLE 2.5D-continued
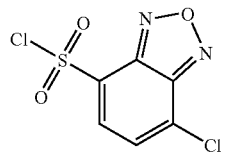
REA002076
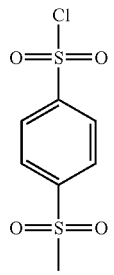
REA002077
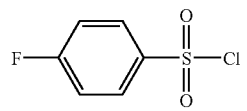
REA002086
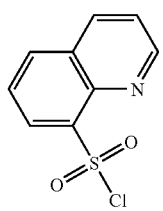
REA002088
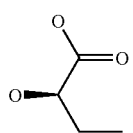
REA002259
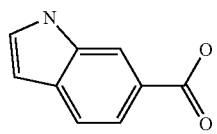
REA002260
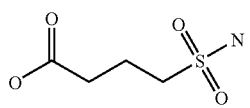
REA002262
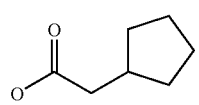
REA002264
TABLE 2.5D-continued
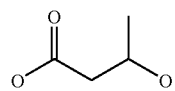
REA002275
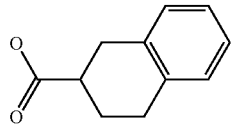
REA002276
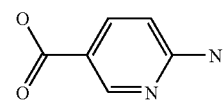
REA002279
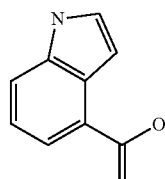
REA002284
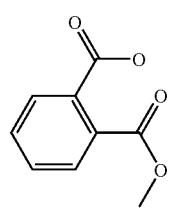
REA002292
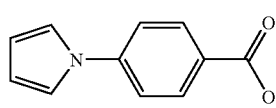
REA00298
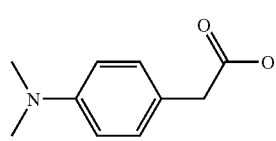
REA002299
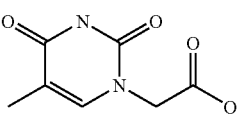
REA002301

TABLE 2.5D-continued

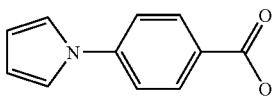
REA002298

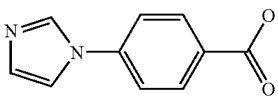
REA002305

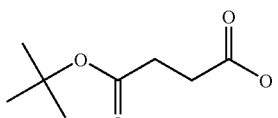
REA002307

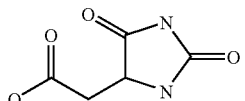
REA002310

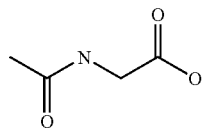
REA002312

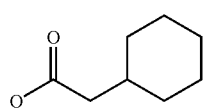
REA002313

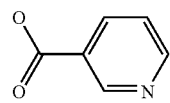
REA002323

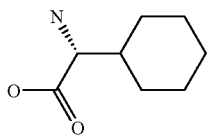
BBA000031

Example 3

Bifunctional Complexes Containing One or More Display Molecule(s) and One or More Identifier (s)

A library is synthesized as described in example 2. At a stage where the bifunctional complexes containing a display molecule (D) are purified and have single stranded identifier oligos, an anchor oligo containing a display molecule (R) is annealed to the single stranded identifier oligos:

a)
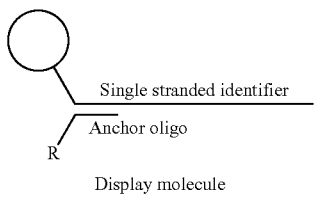

b)
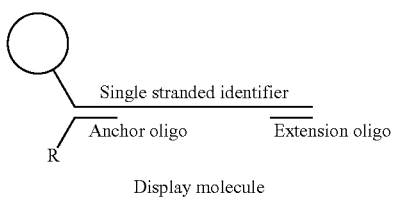

c)
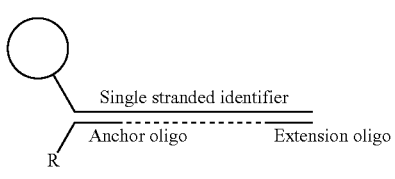

Then an extension oligo (b) is annealed to the single stranded identifier oligo of the bifunctional complexes. The extension oligo is then extended with an enzyme that does not displace or degrade the anchor oligo. The library is then used for selection. Using anchor oligos with different display molecules (R) it is possible to modulate the average affinity of the library.

Alternatively the following display oligo is used during library synthesis:

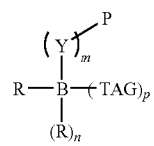

The display oligo contains one or more (n) of chemical reaction sites (R), one or more branching linkers (B), one or more (m) chemical reaction site(s) (Y) protected by a protection group (P). Using this display oligo a library of bifunctional complexes is synthesized as describe in example 2. The resulting bifunctional complexes contain one or more display molecules (D) and one or more (p) identifiers (i):

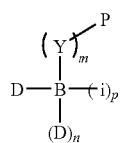

The protection group (P) is then removed allowing a molecule (M) to be linked to Y:

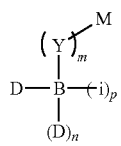

Thus, properties of the bifunctional complexes, such as affinity for a target or target site, solubility etc. can be modulated by attaching to the chemical reaction site (Y) one or more molecules (M) which confer the desired property onto the bifunctional complex.

Example 4

Synthesis and Affinity Selection of a Library Encoding on the Order of 65.000 Scaffolded Compounds Employing Quenching of Reactants A library on the order of 65.000 DNA-tagged small molecules is synthesized using the building blocks (reactants) and tags described in example 2.

900 pmol Display oligo is added to each of 16 wells. In each well the display oligo carries a specific building block (position A building block).

Ligation of A-Tags

10 µl buffer (120 mM HEPES pH 7.8, 40 mM MgCl2, 40 mM DTT and 4 mM ATP) is added to each well. 500 µmol double-stranded A-codons (e.g., the combination A-0001 and Ax-0001) is also added (See table 4.4A for tags and corresponding building blocks (reactants)). Annealing was then performed by a 80° C. to 20° ramp in a PCR machine (Eppendorf Mastercycler Gradient). In one well 50 pmol double-stranded 5' phosphate 32-labeled A-codon is added. 1 µl of T4 DNA ligase (20 U/µl) is added to each well. Samples are then incubated in a PCR-machine with the following temperature profile: 25° C. for 10 min, 45° C. for 10 min, and 25° C. for 10 min. The ligase is inactivated by incubating samples at 68° C. for 10 min. 25 µl of water is then added to each sample. To allow verification of the efficiency of the following dephosphorylation step, a "Dummy A" codon labelled with 5' phosphor-32 is added to a sample. A thermostable phosphatase is then added to each sample and samples are incubated to remove free 5' phosphate groups. The samples are then pooled and precipitated using 0.05 volumes of 5 M NaCl and 50% isopropanol as described in example 2.

Ligation of B-Tags

The sample is dissolved in water and distributed equally to 16 wells. To each well 750 pmol double-stranded B-tags is added and ligation and dephosphorylation is performed as described for the ligation of A-tags. After ligation and inactivation of the enzyme, the samples are lyophilized.

Load of Position B Building Blocks (Reactants)

Each sample is dissolved 5 µl 200 mM Na-phosphate buffer pH 8.0 or 100 mM Na-Borate pH 9.0 or 100 mM Na-Borate pH 10.0 according to previously identified reaction conditions. To each well is added add 4 µl solution of a building block (100 mM in dimethyl sulfoxide). For each well 0.72 µl 0.5M DMT-MM solution in water is mixed with 0.28 µl 200 mM Na-phosphate buffer pH 8 and added to the well. The wells are then incubated at 30° C. for 16 hours in a PCR-machine (Eppendorf Mastercycler Gradient). Then an appropriate quenching reagent, e.g. piperidine, is added to each sample to ensure that all reactive species are rendered unreactive. The samples are then pooled and precipitated using 0.05 volumes of 5 M NaCl and 50% isopropanol and washed with cold 70% ethanol.

Msec Deprotection

Primary amines of position B building blocks (reactants) are protected by Msec groups:

Scheme 4.1 Msec (2-(methyl sulfonyl) ethyl carbamate) protection group used for protection of primary amines.

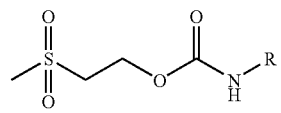

Msec protection groups are removed by dissolving the material in 25 µl 0.1 M Sodium Borate Buffer pH=10 and incubating at 40° C. for 3 hours. Then the material is lyophilized and dissolved in 85 µl H₂O.

Ligation of C-Tags

In each well ligation of double-stranded C-tags were performed as described for A- and B-tags.

Load of Position C Building Blocks (Reactants)

Samples to undergo isocyanate addition are redissolved in 8 µl buffer (100 mM sodium borate and 100 mM sodium phosphate pH 8.0) 1 µl of a specific building block (300 mM in CH₃CN) are added to each well and incubated at 50° C. for 16 hours in a in PCR-machine (Eppendorf Mastercycler Gradient).

Samples to undergo sulfonylation were dissolved in 8 µl 100 mM Sodium Borate buffer pH 9. Then, 2 µl specific building block (100 mM in tetrahydrofuran) was then to each well and incubated at 30° C. for 16 hours in a PCR-machine.

Samples to undergo acylation were dissolved in 5 µl 200 mM Na-phosphate buffer pH 8.0 or 100 mM Na-Borate pH 9.0 or 100 mM Na-Borate pH 10.0. Then, 4 µl specific building block (100 mM in dimethylsulfoxide) was added to each well. Then 1 µl DMT-MM mix (0.36 M DMT-MM in water and 56 mM Na-phosphate buffer pH 8) was mixed in each well and the sample was incubate at 30° C. for 16 hours in a PCR-machine.

Then an appropriate quenching reagent, e.g. piperidine, is added to each sample to ensure that all reactive species are rendered unreactive. The samples are then pooled and precipitated using 0.05 volumes of 5 M NaCl and 50% isopropanol and washed with cold 70% ethanol Desphosphorylation Dephosphorylation is performed as described for A-tags. The sample is then precipitated using 0.05 volumes of 5 M NaCl and 50% isopropanol and washed with cold 70% ethanol.

Ns Protection Group Removal

Secondary amines of position B building blocks (reactants) are protected using Ns:

Scheme 1.4 Ns (2-Nitro-benzenesulfonyl) protection group used for protection of secondary amines.

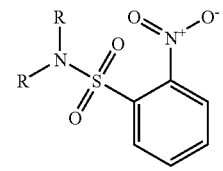

To remove the Ns protection group, the material is applied to DEAE (which had been washed 2 times with 10 mM Aq. AcOH), then the material on DEAE is washed with water followed by washing with dimethyl formamide. Then the material on DEAE is incubated in a solution of 0.5M mercaptoethanol and 0.25 M DIPEA in dimethyl formamide and incubated for 24 hours at 25° C. in an eppendorph thermoshaker at 600 rpm. Then the material on DEAE is washed with 0.3M AcOH in DMF, then twice with DMF and then with water. The Ns-deprotected material is then released from DEAE by adding 70 μl release solution (1.5 M NaCl) and incubating at 25° C. for 10 minutes in an eppendorph thermoshaker at 600 rpm. Water is added to the material to a final NaCl concentration of 0.5 M. Then the material is precipitated by adding one volume of isopropanol as described.

Ligation of D-Tags

D-tags are ligated as described for A-B-, and C-tags. Then samples were purified using gel-filtration as described and lyophilized.

Load of Position D Building Blocks (Reactants)

Samples to undergo isocyanate addition were redissolved in 8 μl buffer (100 mM sodium borate and 100 mM sodium phosphate pH 8.0) 1 μl of a specific building block (300 mM in $CH_3CN$) was added to each well and incubated at 50° C. for 16 hours in a in PCR-machine (Eppendorf Mastercycler Gradient). Then, 40 μL of water was added to each sample.

Samples to undergo sulfonylation were dissolved in 8 μl 100 mM Sodium Borate buffer pH 9. 2 μl specific building block (100 mM in tetrahydrofuran) was then to each well and incubated at 30° C. for 16 hours in a PCR-machine. Then, 40 μl of water was added to each sample.

Samples to undergo acylation were dissolved in 5 μl 200 mM Na-phosphate buffer pH 8.0 or 100 mM Na-Borate pH 9.0 or 100 mM Na-Borate pH 10.0. Then, 4 μl specific building block (100 mM in dimethylsulfoxide) was added to each well. Then 1 μl DMT-MM mix (0.36 M DMT-MM in water and 56 mM Na-phosphate buffer pH 8) was mixed in each well and the sample was incubate at 30° C. for 16 hours in a PCR-machine. Then, 40 μl of water was added to each sample.

Samples to undergo reductive amination were dissolved in 15 μl 200 mM NaOAc buffer pH 5.0 5 ul specific BB was added to each well (200 mM in DMSO) and incubate at 30° C. for 1 h. Then 5 μl of freshly prepared 140 mM NaCNBH3 (REA000025; 8.8 mg/ml) in NaOAc buffer pH 5.0 to was added each well and the samples were incubated at 30° C. for 16 hours in a PCR-machine (Eppendorf Mastercycler Gradient). Then 25 μl of water was added to each sample.

Samples to undergo nucleophilic aromatic substitution were dissolved in 12 μl 100 mM Borate Buffer pH 9. Then 12 μl specific BB was added to each well (100 mM in DMSO) and all wells were incubated for 16 hours at 90° C. in a PCR-machine (Eppendorf Mastercycler Gradient). Then 40 μl of water was added to each sample.

Then an appropriate quenching reagent, e.g. piperidine, is added to each sample to ensure that all reactive species are rendered unreactive. The samples are then pooled and precipitated using 0.05 volumes of 5 M NaCl and 50% isopropanol and washed with cold 70% ethanol Fmoc Deprotection Samples are redissolved in water and adjusted to 6% piperidine. Samples are then incubated at 25° C. for 30 minutes to remove Fmoc protection groups. Samples are then again precipitated using isopropanol.

The combined material is redissolved in water and adjusted with polyacrylamide gel electrophoresis loading buffer. The material is electrophoresed and purified by isolating the material corresponding to bifunctional complexes with 4 tags. The single stranded bifunctional complexes are eluted from the gel, precipitated using isopropanol as described, and purified by gel-filtration as described.

Primer extension and affinity selection is the performed as described for examples 1 and 2.

Example 5

Synthesis of Bifunctional Complexes Containing a Cleavable Linker and Release of Display Molecules Bifunctional complexes are synthesized from an initial bifunctional complex which contains a chemical reaction site linked with a cleavable linker to a tag. If bifunctional complexes are synthesized in a parallel synthesis fashion it is not necessary to add tags which encode the building blocks (reactants) that are added at the chemical reaction site(s). If bifunctional complexes are synthesized by a split-pool method, tags which encode the different building blocks (reactants) can be added during synthesis as described in examples 1 and 2. Following a split-pool synthesis the bifunctional complexes can then be sorted by employing capture oligos which hybridize to specific codons in the identifier oligonucleotides of the bifunctional complexes.

After synthesis and purification, the cleavable linker is cleaved using appropriate conditions such as electromagnetic radiation, enzymes etc. For example, a cleavable linker such as:

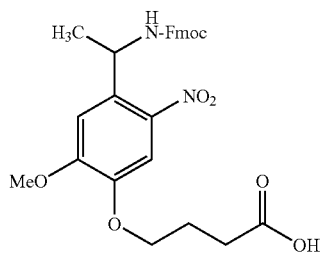

can be cleaved using ultraviolet radiation. The released small molecule can then be used in an assay to determine a property of the display molecule.

The bifunctional complex containing a DNA tag (T):

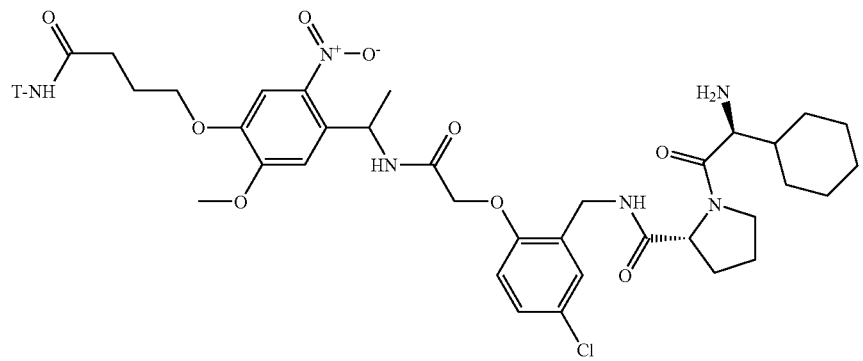

was synthesized employing the chemical reactions (acylation and Fmoc deprotection) as described in example 2. The bifunctional complex was exposed to ultraviolet radiation (omnilux lamp E40, Steinigke Showtechnic Germany) for 120 seconds to release the display molecule:

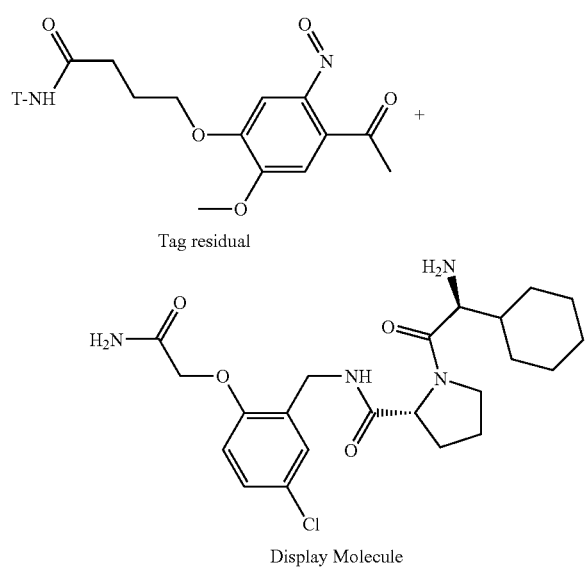

To determine the Ki of the released display molecule against the protease thrombin, human alpha-thrombin (Heamatologic Technologies Inc.) was diluted in buffer (0.015 units/µl) and the released display molecule was added. Following 5 minutes of incubation at 22° C. a chromogenic substrate (Chromogenix catalogue number S-2238) was added and the maximum turnover (Vmax) of the enzyme was determined in a by measuring the change in absorbance at 405 nm using a Versamax reader (Molecular Devices). This was repeated for different concentrations of the released display molecule and different concentrations of substrate. The Vmax values obtained were then fitted using nonlinear regression implemented in the Prism software (Graphpad) to obtain the Ki of the display molecule. A Ki value of 5.2 nM was obtained (95% confidence interval: 0-13 nM).

Example 6

Synthesis and Affinity Selection of a Library Encoding on the Order of 1.100.000.000 Compounds The first set of building blocks (reactants) were loaded onto a display oligo (see FIG. 1.2).

The described general procedures were used in the following order:

Position A building blocks (reactants) and A-tags: R1-P1-QC1-V1-T1-QC3-M1-V2-D1-V2-P3-V2-S1-V1
  80 position A building blocks (reactants) were used. The building block were trifunctional with one free —COOH reactive group, one Ns-protected amine and one Msec-protected amine.

Position B building blocks (reactants) and B-tags: R1-P1-QC1-V1-T1-QC3-M1-V2-D1-V2-P3-V2-S1-V1
  192 position B building blocks (reactants) were used Position C building blocks (reactants) and C-tags: (R1/R2/R3)-P1-QC1-V1-T1-QC3-M1-V2-D2-V2-P3-V2-S1-VI
  88 isocyanate building blocks (reactants) were used
  96 sulfonoyl building blocks (reactants) were used
  200 acylation building blocks (reactants) were used Position D building blocks (reactants) and D-tags: (R1/R3/R4/R5)-P1-QC1-V1-T1-QC3-M1-V2-P3-V2-D1-V2
  88 aldehyde building blocks (reactants) were used
  16 sulfonoyl building blocks (reactants) were used
  24 halogenated heteroaromatic building blocks (reactants) were used
  64 acylation building blocks (reactants) were used Example 7

Screening of a Library Using Unspecific Elution

Biotinylated Renin was used as the target.

A fraction of the obtained bifunctional complexes was lyophilized and dissolved in 5 µl target buffer (137 mM NaCl, 2.7 mM KCl, 10 mM sodium phosphate, 0.1% Tween-20, 0.1% BSA). 50 µl streptavidin sepharose (Amersham Biosciences) slurry was washed in 4×100 µl target buffer and resuspended in 50 µl target buffer. Then biotinylated target was added to the streptavidin sepharose slurry and the slurry was incubated at 15° C. with agitation (1400 rpm) for 30 minutes and subsequently washed 4 times with 100 µl target buffer. A 10XL barrier tip (AH diagnostics, Denmark) were prepared by pushing the tip filter approx. 5 mm towards the end of the tip. The tip was placed in a 1 mL pipette tip. The target-loaded streptavidin sepharose was applied to the tip and washed 3 times with 100 µl target buffer by applying vacuum to the bottom end of the tip. The library was applied to the column and allowed to soak in. Then the column was washed 5 times with 100 µl target buffer. Bifunctional complexes were eluted by applying 50 µl 1% SDS in H2O preheated to 60° C. for 10 min followed by centrifugation of the column (1000 rcf for 30 seconds). An additional 25 µl PBS was applied to the column and spun through. The eluted material was re-applied to a fresh column. This cycle was repeated 4 times. A 10 µl sample of eluted material was used PCR using the forward and reverse primers 5'-CAAGT-CACCAAGAATTCATG and 5'-TCTGGTGGTCTACGT-GCTCT. The PCR product was cloned and sequenced using standard methods.

Example 8

Synthesis and Affinity Selection of a Library Encoding on the Order of 3.5e6 Compounds Based on a Triazine Scaffold The described general procedures were used in the following order:
Position A building blocks (reactants) and A-tags: R1-P1-QC1-V1-T1-QC3-M1-V2-D1-V2-P3-V2-S1-V1
  96 position A building blocks (reactants) were used. The building blocks (reactants) were bifunctional with one free —COOH reactive group, one Fmoc-protected amine
  The material in all wells were redissolved in 10 µl buffer (100 mM Na-carbonate pH 9.3). 10 µl 1,3,5-trichloro-2,4,6-triazine dissolved to 200 mM in acetone was added to each well and incubated for at 4° C. for 1 hour
  Position B building blocks (reactants) and B-tags: P1-R5-P1-QC1-V1-T1-QC3-M1-V2-D1-V2-P3-V2-S1-V1
    192 position B building blocks (reactants) (amines) were used. At the R5 step the material in each well was redissolved in 10 µl 100 mM Na-carbonate pH 9.3 or 10 µl 100 mM Na-phosphate pH 8 and 10 µl building block solution (200 mM in acetone) was added and incubated at 4° C. or 25° C. for 1 hour or at 30° C. for 16 hours.
Position C building blocks (reactants) and C-tags: R5-P1-QC1-V1-T1-QC3-M1-V2-D2-V2-P3-V2
  192 position C building blocks (reactants) (amines) were used. At the R5 step the material in each well was redissolved in 10 µl 100 mM Na-borate pH 9.5 and 10 µl building blocks (reactants) (200 mM in DMSO) were added and incubated at 90° C. for 16 hours.

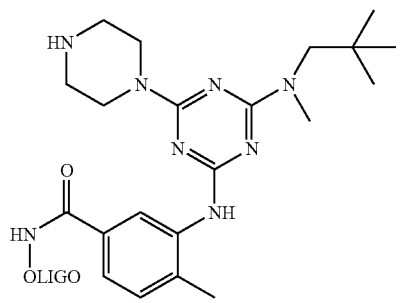

Example of a structure generated by this method.
Position D tags: P1-QC1-V1-T1-QC3-M1-V2-P3-V2
  No building blocks (reactants) were added at this step. The D-tags were ligated to diversify the bifunctional complexes such that several codon combinations corresponds to the same molecule. 192 different D-tags were used.

The library was screened on kinase p38 using unspecific elution and specific elution using a p38 ligand. The identifiers were amplified and subjected to ultra high-throughput sequencing. Ligands based on information deduced from the identifier sequences were resynthesized and tested in a p38 kinase assay. 15 ligands with nanomolar IC50 values were identified.

Example 9

Synthesis and Affinity Selection of a Second Library Designed Based on Results Obtained by Synthesis and Affinity Selection of a First Library A library encoding on the order of 110.000.000.000 molecules was synthesized using the method described in example 6. Briefly,
  The first set of building blocks (reactants) were loaded onto a display oligo (see FIG. 1.2).
  The described general procedures were used in the following order:
Position A building blocks (reactants) and A-tags: R1-P1-QC1-V1-T1-QC3-M1-V2-D1-V2-P3-V2-S1-V1
  576 position A building blocks (reactants) were used. The building block were trifunctional with one free —COOH reactive group, one Ns-protected amine and one Msec-protected amine.
Position B building blocks (reactants) and B-tags: R1-P1-QC1-V1-T1-QC3-M1-V2-D1-V2-P3-V2-S1-V1
  576 position B building blocks (reactants) were used
Position C building blocks (reactants) and C-tags: (R1/R2/R3)-P1-QC1-V1-T1-QC3-M1-V2-D2-V2-P3-V2-S1-V1
  96 isocyanate building blocks (reactants) were used
  96 sulfonoyl building blocks (reactants) were used
  384 acylation building blocks (reactants) were used
Position D building blocks (reactants) and D-tags: (R1/R3/R4/R5)-P1-QC1-V1-T1-QC3-M1-V2-P3-V2-D1-V2
  96 aldehyde building blocks (reactants) were used
  96 sulfonoyl building blocks (reactants) were used
  96 halogenated heteroaromatic building blocks (reactants) were used
  96 acylation building blocks (reactants) were used
  96 isocyanate building blocks (reactants) were used
  The library was screened using unspecific elution (example 7), identifiers were amplified and analyzed by ultra high-throughput sequencing. The sequencing revealed that identifiers containing the following tag combinations had been enriched:
  A523-B201-C341-D234
  A523-B201-C341-D234
  A523-B156-C341-D234
  A523-B156-C341-D142
  A523-B201-C341-D142
  (Tags A001-A576, B001-B576, C001-C576, and D001-576 were used for library synthesis at positions A, B, C, and D, respectively).
  Ligands corresponding to said enriched identifiers were synthesized according to the method described in example 5.

The affinity could not be determined in an affinity assay indicating that the ligands had affinities lower than 10 µM in the assay.

However, a second library was synthesized including the reactants corresponding to the tags in the enriched identifiers. Furthermore, reactants that were analogous in structure or function to said reactants were also used for synthesize of the second library.

The second library encoded on the order of 110.000.000.000 molecules and was synthesized using the method described in example 6. Briefly, The first set of building blocks (reactants) were loaded onto a display oligo (see FIG. 1.2).

The described general procedures were used in the following order:

Position A building blocks (reactants) and A-tags: R1-P1-QC1-V1-T1-QC3-M1-V2-D1-V2-P3-V2-S1-V1
  576 position A building blocks (reactants) were used. The building block were trifunctional with one free —COOH reactive group, one Ns-protected amine and one Msec-protected amine.

Position B building blocks (reactants) and B-tags: R1-P1-QC1-V1-T1-QC3-M1-V2-D1-V2-P3-V2-S1-V1
  576 position B building blocks (reactants) were used Position C building blocks (reactants) and C-tags: (R1/R2/R3)-P1-QC1-VI-T1-QC3-M1-V2-D2-V2-P3-V2-S1-V1
  96 isocyanate building blocks (reactants) were used
  192 sulfonoyl building blocks (reactants) were used
  192 acylation building blocks (reactants) were used Position D building blocks (reactants) and D-tags: (R1/R3/R4/R5)-P1-QC1-V1-T1-QC3-M1-V2-P3-V2-D1-V2
  96 aldehyde building blocks (reactants) were used
  96 sulfonoyl building blocks (reactants) were used
  192 halogenated heteroaromatic building blocks (reactants) were used
  96 acylation building blocks (reactants) were used The library was screened using unspecific elution (example 7), identifiers were amplified and analyzed by ultra high-throughput sequencing. The sequencing revealed that identifiers containing the following tag combinations had been enriched:

A543-B203-C131-D236
A543-B203-C131-D236
A543-B158-C131-D236
A543-B158-C131-D122
A543-B203-C131-D122

Ligands corresponding to said enriched identifiers were synthesized according to the method described in example 5. The affinity of the ligands were determined to be in the 1 nM to 10 µM range.

The invention claimed is:

1. A method for the synthesis of a bifunctional complex comprising a molecule and a single stranded oligonucleotide identifier attached to the molecule, said method comprising the steps of
  i) providing a display oligonucleotide attached to
    a) one or more chemical reaction site(s) comprising one or more reactive groups and
    b) one or more priming site(s) for enzymatic addition of a tag,
  ii) providing a first reactant comprising one or more chemical entities and one or more reactive groups capable of reacting with
    c) the chemical reaction site(s) of the display oligonucleotide, and/or
    d) one or more reactive groups of at least a first further reactant comprising one or more chemical entities, wherein said first further reactant is provided simultaneously or sequentially in any order with the first reactant,
  iii) providing a first oligonucleotide tag capable of hybridising to part of a first oligonucleotide anti-tag, wherein the first oligonucleotide tag identifies the first reactant and, optionally, the further first reactant,
  iv) providing a first oligonucleotide anti-tag capable of hybridising to at least part of the first oligonucleotide tag provided in step iii) and to at least part of the display oligonucleotide provided in step i),
  v) reacting the first reactant provided in step ii) with c) the one or more chemical reaction site(s) of the display oligonucleotide and/or with d) the one or more reactive groups of the first further reactant comprising one or more chemical entities,
    wherein the reaction of complementary reactive groups result in the formation of a covalent bond, and
    wherein one or more reactive group reactions of step v) result in the formation of one or more covalent bond(s) between the chemical reaction site(s) of the display oligonucleotide and at least one chemical entity of at least one reactant selected from the group consisting of the first reactant and the further first reactant,
  vi) hybridising the first anti-tag to the display oligonucleotide and to the first oligonucleotide tag,
    wherein method steps v) and vi) are simultaneous or sequential in any order,
  vii) enzymatically ligating the display oligonucleotide and the first oligonucleotide tag to form a nascent bifunctional complex,
  viii) providing a second reactant comprising one or more chemical entities and one or more reactive groups capable of reacting with
    c) the chemical reaction site(s) of the display oligonucleotide, and/or
    d) one or more reactive groups of one or more reactant(s) having reacted in a previous synthesis round, and/or
    e) one or more reactive groups of at least a second further reactant comprising one or more chemical entities, wherein said second further reactant is provided simultaneously or sequentially in any order with the second reactant,
  ix) providing a second oligonucleotide tag capable of hybridising to part of a second oligonucleotide anti-tag, wherein the second oligonucleotide tag identifies the second reactant and, optionally, the further second reactant,
  x) providing a second oligonucleotide anti-tag capable of hybridising to part of the first oligonucleotide tag provided in step iii) and to part of the second oligonucleotide tag provided in step ix),
  xi) reacting the second reactant provided in step viii) with
    c) the chemical reaction site(s) of the display oligonucleotide and/or d) one or more reactive groups of one or more reactant(s) having reacted in a previous synthesis round and/or e) one or more reactive groups of a further second reactant comprising one or more chemical entities,
    wherein the reaction of complementary reactive groups result in the formation of a covalent bond, and
    wherein one or more reactive group reactions of step xi) result in
    f) the formation of one or more covalent bond(s) between the one or more chemical reaction site(s) and at least one chemical entity of at least one reactant selected from the group consisting of the second reactant and the further second reactant, and/or
    g) the formation of one or more covalent bond(s) between a reactant having reacted in a previous synthesis round and at least one chemical entity of at least one reactant selected from the group consisting of the second reactant and the further second reactant,
  xii) hybridising the second anti-tag to the first oligonucleotide tag and the second oligonucleotide tag,
    wherein method steps xi) and xii) are simultaneous or sequential in any order,
  xiii) enzymatically ligating the first and second oligonucleotide tags in the absence of ligation the first and second anti-tag oligonucleotides to provide a bifunctional complex comprising an oligonucleotide identifier having ligated first and second oligonucleotide tags hybridized with unligated first and second anti-tag oligonucleotides
  xiv) displacing the unligated anti-tags from the bifunctional complex of step (xii) to provide a bifunctional complex comprising a molecule and a single stranded oligonucleotide identifier comprising tags identifying the reactants which participated in the synthesis of the molecule,
  xv) hybridising a primer to the 3'-end of the single stranded oligonucleotide identifier comprising tags identifying the reactants which participated in the synthesis of the molecule, and
  xvi) extending the primer by a polymerase extension reaction to generate a double stranded identifier oligonucleotide.

2. The method of claim 1, wherein the method of claim 1 is performed in parallel in different reaction compartments, wherein the display oligonucleotide of step i) is provided in each of a plurality of separate reaction compartments and subsequently, wherein, in each of said reaction compartments, the first reactant and optionally also the further first reactant is/are reacted with the one or more chemical reaction site(s), and wherein, in each of said compartments, a first oligonucleotide tag identifying said one or more reactant(s) is added enzymatically to the one or more priming site(s), said reaction(s) of said reactant(s) and said addition(s) of said tag resulting in the formation, in each of said reaction compartments, of different nascent bifunctional complexes.

3. The method of claim 2, wherein said different nascent bifunctional complexes are mixed, and wherein said mixture of different nascent bifunctional complexes is subsequently divided into a plurality of different reaction compartments.

4. The method of claim 3, wherein a different nascent bifunctional complex is provided in each of said plurality of separate reaction compartments and subsequently, in each of said reaction compartments, the second reactant and optionally also the further second reactant is/are reacted with one or more of a chemical reaction site and one or more reactive group(s) of a first reactant and/or further first reactant, and wherein, in each of said compartments, a second oligonucleotide tag identifying said one or more reactant(s) is added enzymatically to the first oligonucleotide tag, said reaction(s) of said reactant(s) and said addition(s) of said tag resulting in the formation, in each of said compartments, of further different nascent bifunctional complexes.

5. The method of claim 4, wherein, in each subsequent round of parallel synthesis, the reactant reaction product of a previous synthesis round reacts with the reactant in a subsequent synthesis round, and wherein a tag added in a previous synthesis round acts as a substrate for the enzyme which adds a tag in a subsequent synthesis round.

6. The method of claim 1, wherein the identifier oligonucleotide is amplifiable.

7. The method claim 1, wherein the display oligonucleotide has a length of from about 3 consecutive nucleotides to about 25 consecutive nucleotides.

8. The method claim 7, wherein tag(s) have from about 3 consecutive nucleotides to about 25 consecutive nucleotides.

9. The method of claim 7, wherein anti-tag(s) have from about 3 consecutive nucleotides to about 25 consecutive nucleotides.

10. The method of claim 7, wherein single-stranded over-hangs resulting from hybridisation of tags and anti-tags have a length of from about 3 consecutive nucleotides to about 25 consecutive nucleotides.

11. The method of claim 1, wherein the identifier oligonucleotide resulting from tag ligation(s) has a length of from 6 to about 200 consecutive nucleotides.

12. The method of claim 1, wherein the identifier oligonucleotide comprises a string of consecutive nucleotides comprising from 2 to 10 tags.

13. The method of claim 1, wherein end-positioned nucleotides of anti-tags comprises no reactive group(s) capable of being linked by an enzyme comprising ligase activity.

14. The method of any claim 1, wherein the one or more priming site(s) of the display oligonucleotide comprises a 3'-OH or 5'-phosphate group, or a functional derivative of such a group, capable of being linked by an enzyme comprising ligase activity.

15. The method of claim 1, wherein molecule decoding or reactant identification is performed by sequencing all or some of the nucleotides of each tag of the identifier oligonucleotide.

16. The method of claim 1, wherein the one or more chemical reaction site(s) of the display oligonucleotide each comprising one or more reactive groups react with one or more reactants each comprising one or more reactive groups, wherein the chemical reaction sites can be the same or different chemical reaction sites, wherein the reactive groups can be the same or different reactive groups, and wherein the reactants can be the same or different reactants.

17. The method of claim 1, wherein the reactive groups involved in the synthesis of a molecule are selected from the group consisting of carboxylic acids, alcohols, thiols, aldehydes, ketones, amides, imides, amines, azo, diazo, azido, hydrazines, carbamates, esters, thioesters, cyanides, ethers, isocyanates, isothiocyanates, sulfides, nitriles, nitrites, nitrates, nitro, peroxides, phosphates, thiophosphates, sulfides, epoxides, anhydrides, halides, acid halides, organometallics, nitrides, phosphides, carbides, and silicides.

18. The method of claim 1, wherein the reaction of the chemical reaction site and a reactant, or the reaction of different reactants, results in the formation of at least one bond selected from the group consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, and any combination thereof.

19. The method of claim 1, wherein the reaction of the chemical reaction site and a reactant, or the reaction of different reactants, results in the formation of at least one bond selected from the group consisting of $-NHN(R)CO-$; $-NHB(R)CO-$; $-NHC(RR')CO-$; $-NHC(=CHR)CO-$; $-NHC_6H_4CO-$; $-NHCH_2CHRCO-$; $-NHCHRCH_2CO-$; $-COCH_2-$; $-COS-$; $-CONR-$; $-COO-$; $-CSNH-$; $-CH_2NH-$; $-CH_2CH_2-$; $-CH_2S-$; $-CH_2SO-$; $-CH_2SO_2-$; $-CH(CH_3)S-$; $-CH=CH-$; $-NHCO-$; $-NHCONH-$; $-CONHO-$; $-C(=CH_2)CH_2-$; $-PO_2^-NH-$; $-PO_2^-CH_2-$; $-PO_2-CH_2N^+-$; $-SO_2NH^--$; and lactams.

20. The method of claim 1, wherein complementary reactive groups of the chemical reaction site and/or the reactive group(s) of one or more reactants reacting with each other and/or with the chemical reaction site are selected from the group consisting of
 a) activated carboxyl groups, reactive sulfonyl groups and reactive phosphonyl groups, or a combination thereof, and complementary primary or secondary amino groups; wherein the complementary reactive groups react under suitable conditions to form amide, sulfonamide and/or phosphonamidate bonds;
 b) epoxide groups and complementary primary and/or secondary amino groups; wherein a reactant comprising one or more epoxide reactive group(s) reacts with one or more amine-group(s) of a complementary reactant under suitable conditions to form one or more carbon-nitrogen bond(s);
 c) aziridine groups and complementary primary or secondary amino groups; wherein under suitable conditions, a reactant comprising one or more aziridine-group(s) reacts with one or more amine-group(s) of a complementary reactant to form one or more carbon-nitrogen bond(s);

d) isocyanate groups and complementary primary or secondary amino groups, wherein a reactant comprising one or more isocyanate-group(s) reacts with one or more amino-group(s) of a complementary reactant under suitable conditions to form one or more carbon-nitrogen bond(s);

e) isocyanate groups and complementary hydroxyl groups; wherein a reactant comprising one or more isocyanate-group(s) reacts with a complementary reactant comprising one or more hydroxyl-groups under suitable conditions to form one or more carbon-oxygen bond(s);

f) amino groups and complementary carbonyl groups; wherein a reactant comprising one or more amino groups reacts with a complementary reactant comprising one or more carbonyl-group(s); wherein the amines react with such groups via reductive animation to form a carbon-nitrogen bond;

g) phosphorous ylide groups and complementary aldehyde and/or ketone groups; wherein a reactant comprising a phosphorus-ylide-group reacts with an aldehyde and/or a ketone-group of a complementary reactant under suitable conditions to form a carbon-carbon double bond;

h) complementary reactive groups reacting via cycloaddition to form a cyclic structure; such as the reaction of alkynes and organic azides, which react under suitable conditions to form a triazole ring structure;

i) alkyl halide groups and one or more nucleophile group(s), such as amino groups, hydroxyl groups and carboxyl group; wherein such groups react under suitable conditions to form a carbon-nitrogen bond (alkyl halide plus amine) or carbon oxygen bond (alkyl halide plus hydroxyl or carboxyl group); and j) halogenated heteroaromatic groups and one or more nucleophile group(s), wherein the reactants react under suitable conditions via aromatic nucleophilic substitution; wherein halogenated heteroaromatic groups are optionally selected from chlorinated pyrimidines, triazines and purines, which react with nucleophiles under mild conditions in aqueous solution.

21. The method of claim 1, wherein the chemical reaction site comprises a scaffold comprising one or more reactive groups.

22. The method of claim 21, wherein the scaffold reactive groups are selected from the group consisting of carboxylic acids, alcohols, thiols, aldehydes, ketones, amides, imides, amines, azo, diazo, azido, hydrazines, carbamates, esters, thioesters, cyanides, ethers, isocyanates, isothiocyanates, sulfides, nitriles, nitrites, nitrates, nitro, peroxides, phosphates, thiophosphates, sulfides, epoxides, anhydrides, halides, acid halides, organometallics, nitrides, phosphides, carbides, and silicides.

23. The method of claim 21, wherein scaffold comprises a scaffold moiety selected from the group consisting of quinazoline, tricyclic quinazoline, purine, pyrimidine, phenylamine-pyrimidine, phthalazine, benzylidene malononitrile, amino acid, tertiary amine, peptide, lactam, sultam, lactone, pyrrole, pyrrolidine, pyrrolinone, oxazole, isoxazole, oxazoline, isoxazoline, oxazolinone, isoxazolinone, thiazole, thiozolidinone, hydantoin, pyrazole, pyrazoline, pyrazolone, imidazole, imidazolidine, imidazolone, triazole, thiadiazole, oxadiazole, furan, benzoffman, isobenzofuran, dihydrobenzofuran, dihydroisobenzofuran, indole, indoline, benzoxazole, oxindole, indolizine, benzimidazole, benzimidazolone, pyridine, piperidine, piperidinone, pyrimidinone, piperazine, piperazinone, diketopiperazine, metathiazanone, morpholine, thiomorpholine, phenol, dihydropyran, quinoline, isoquinoline, quinolinone, isoquinolinone, quinolone, quinazolinone, quinoxalinone, benzopiperazinone, benzodiazepine, quinazolinedione, benzazepine, azepine, tropane, and coumarine.

24. The method of claim 1, wherein the molecule is a branched or cyclical molecule.

25. The method of claim 24, wherein the molecule is cyclical and comprises a ring system selected from a single ring system and a fused ring system.

26. The method of claim 25, wherein one or more heteroatoms are present in either the single ring system or in the fused ring system.

27. The method of claim 25, wherein the single ring system is not directly bonded at more than one ring atom to another closed ring, and wherein the fused ring system is directly bonded at more than one ring atom to another closed ring.

28. The method of claim 1, wherein the molecule is synthesised by one or more reactions selected from the group consisting of amine acylation, reductive alkylation, aromatic reduction, aromatic acylation, aromatic cyclization, aryl-aryl coupling, [3+2] cycloaddition, Mitsunobu reaction, nucleophilic aromatic substitution, sulfonylation, aromatic halide displacement, Michael addition, Wittig reaction, Knoevenagel condensation, reductive amination, Heck reaction, Stille reaction, Suzuki reaction, Aldol condensation, Claisen condensation, amino acid coupling, amide bond formation, acetal formation, Diels-Alder reaction, [2+2] cycloaddition, enamine formation, esterification, Friedel Crafts reaction, glycosylation, Grignard reaction, Horner-Emmons reaction, hydrolysis, imine formation, metathesis reaction, nucleophilic substitution, oxidation, Pictet-Spengler reaction, Sonogashira reaction, thiazolidine formation, thiourea formation and urea formation.

29. The method of claim 1, wherein the one or more chemical reaction site(s) are covalently linked to the one or more priming site(s).

30. A method for the synthesis of a plurality of different bifunctional complexes, said method comprising the steps of
i) providing a plurality of display oligonucleotides each attached to
  a) one or more chemical reaction site(s) comprising one or more reactive groups and
  b) one or more priming site(s) for enzymatic addition of a tag,
ii) providing a plurality of first reactants each comprising one or more chemical entities and one or more reactive groups, each first reactant being capable of reacting with
  c) the one or more chemical reaction site(s) of the display oligonucleotide, and/or
  d) one or more reactive groups of a first further reactant comprising one or more chemical entities, wherein said first further reactant is provided simultaneously or sequentially in any order with the first reactant,
iii) providing a plurality of first oligonucleotide tags each capable of hybridising to part of a first oligonucleotide anti-tag, wherein each first oligonucleotide tag identifies a first reactant and, optionally, a further first reactant,
iv) providing a plurality of first oligonucleotide anti-tags each capable of hybridizing to at least part of a first oligonucleotide tag provided in step iii) and to at least part of a display oligonucleotide provided in step i), v) reacting each of the first reactants provided in step ii) with c) the one or more chemical reaction site(s) of the display oligonucleotides and/or with d) the one or more reactive groups of a first further reactant comprising one or more chemical entities,
   wherein the reaction of complementary reactive groups result in the formation of a covalent bond, and
   wherein one or more reactive group reactions of step v) result in the formation of one or more covalent bond(s) between the one or more chemical reaction site(s) of the display oligonucleotides and at least one chemical entity of at least one reactant selected from the group consisting of a first reactant and a further first reactant, vi) hybridising the first anti-tags to display oligonucleotides and to first oligonucleotide tags, wherein method steps v) and vi) are simultaneous or sequential in any order, vii) enzymatically ligating display oligonucleotides and first oligonucleotide tags to form a plurality of nascent bifunctional complexes, viii) dividing the plurality of nascent bifunctional complexes obtained in step vii) into a plurality of different compartments, ix) providing in each different compartment a plurality of different second reactants each comprising one or more chemical entities and one or more reactive groups capable of reacting with
   c) the one or more chemical reaction site(s) of each of the display oligonucleotides, and/or
   d) one or more reactive groups of one or more reactant(s) having reacted in a previous synthesis round, and/or
   e) one or more reactive groups of a second further reactant comprising one or more chemical entities, wherein said second further reactants are provided simultaneously or sequentially in any order with the second reactants, x) providing in each different compartment a plurality of second oligonucleotide tags each capable of hybridising to part of a second oligonucleotide anti-tag, wherein different second oligonucleotide tags are provided in each different compartment, and wherein each different second oligonucleotide identifies a different second reactant and, optionally, a further second reactant which may be the same or a different further second reactant in each different compartment, xi) providing in each different compartment a plurality of second oligonucleotide anti-tags capable of hybridising to part of a first oligonucleotide tag provided in step iii) and to part of a second oligonucleotide tag provided in step x), xii) reacting in each different compartment each of the different second reactants provided in step ix) with c) the one or more chemical reaction site(s) of a display oligonucleotide and/or d) one or more reactive groups of one or more reactant(s) having reacted in a previous synthesis round and/or e) one or more reactive groups of a further second reactant comprising one or more chemical entities,
   wherein said one or more reactions result in the formation of different bifunctional complexes in each different compartment,
   wherein the reaction of complementary reactive groups result in the formation of a covalent bond, and wherein one or more reactive group reactions of step xii) result in
   f) the formation of one or more covalent bond(s) between the one or more chemical reaction site(s) and at least one chemical entity of at least one reactant selected from the group consisting of second reactants and further second reactants, and/or
   g) the formation of one or more covalent bond(s) between a reactant having reacted in a previous synthesis round and at least one chemical entity of at least one reactant selected from the group consisting of second reactants and further second reactants, xiii) hybridising anti-tags to first oligonucleotide tags and second oligonucleotide tags in each different compartment,
   wherein method steps xii) and xiii) are simultaneous or sequential in any order, xiv) enzymatically ligating in each different compartment first and second oligonucleotide tags in the absence of ligation first and second anti-tag oligonucleotides to provide a bifunctional complex comprising an oligonucleotide identifier having ligated first and second oligonucleotide tags hybridized with unligated first and second anti-tag oligonucleotides xv) displacing in each compartment the unligated anti-tags from the bifunctional complex(es) of step (xiv) to provide bifunctional complexes comprising a molecule and a single stranded oligonucleotide identifier comprising tags identifying the reactants which participated in the synthesis of the molecule, xv) hybridising a primer to the 3'-end of the single stranded oligonucleotide identifier comprising tags identifying the reactants which participated in the synthesis of the molecule, and xvi) extending the primer by a polymerase extension reaction to generate a double stranded identifier oligonucleotide.

31. The method of claim 30 comprising the further step of mixing bifunctional complexes from each different reaction compartment.

32. The method of claim 31, wherein, in any round subsequent to the first round, the end product of the preceding round of reaction is used as the nascent bifunctional complex for obtaining a library of different bifunctional complexes.

33. The method of claim 30, wherein steps viii) to xiv) are repeated once or more than once using different reactants and tags identifying said different reactants.

34. A method for identifying a molecule, said method comprising the steps of subjecting the library produced by the method of claim 30 to assaying conditions resulting in the partitioning of some, but not all molecules, from the remainder of the library, and identifying the molecule(s) by decoding the identifier oligonucleotide of the bifunctional complex.

35. The method of claim 34, wherein the library is contacted with a target and wherein bifunctional complexes having an affinity for the target are partitioned form the remainder of the library.

36. The method of claim 35, wherein the identifier oligonucleotide of the one or more partitioned bifunctional complexes, optionally attached to a molecule, and further optionally provided with one or more chemical reaction sites, is subjected to a method for synthesizing a plurality of molecules, said method comprising the steps of:
(a) forming a first group of subsets of identifier oligonucleotides comprising a plurality of nucleic acid tags, where the identifier oligonucleotides in each subset each has a selected one of a plurality of different first hybridization sequences, a mixture of different second hybridization sequences, and one or more chemical reaction site(s),
(b) reacting the chemical reaction sites in each of the subsets formed in (a) with a selected reagent, thereby forming a reagent-specific molecule intermediate on the associated sequence in each subset,
(c) forming a second group of subsets of the reacted identifier oligonucleotides comprising a plurality of nucleic acid tags, where the identifier oligonucleotides in each subset each have a selected one of a plurality of different second hybridization sequences, and a mixture of different first hybridization sequences; and
(d) reacting the molecule intermediates in the sequences in each of the subsets formed in (c) with a selected reagent.

37. The method of claim 36, wherein each of said forming steps includes hybridizing the identifier oligonucleotides comprising a plurality of nucleic acid tags within a given subset with a plurality of solid phase reagents each having a surface bound oligonucleotide or oligonucleotide analog capable of forming base-specific duplexes with one of the hybridizing sequences in the given subset to bind each nucleic acid tag to one of the reagents.

38. The method of claim 36, for use in forming a plurality of small molecules with different chemical sequences, wherein each of said reacting steps includes adding a selected chemical substituent to each of the subsets of identifier oligonucleotides comprising a plurality of nucleic acid tags under conditions effective to add that substituent to the chemical reaction site or last-added substituent carried thereon.

* * * * *

```
                        SEQUENCE LISTING

<160> NUMBER OF SEQ ID NOS: 540

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1
caagtcacca agaattcatg                                              20

<210> SEQ ID NO 2
<211> LENGTH: 19
<212> TYPE: DNA
<213> ORGANISM: Artificial Sequence
<220> FEATURE:
<223> OTHER INFORMATION: Primer sequence

<400> SEQUENCE: 2
aaggaacatc atcatggat                                               19

<210> SEQ ID NO 3
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Conjugated to 5'-Amino-Modifier 5 (Glen
      Research Catalogue No. 10-1905), Proper name
      2-[2-(4-Monomethoxytrityl)aminoethoxy]ethyl-(2-cyanoethyl)-
      N,N-diisopropyl)-phosphoramidite.

<400> SEQUENCE: 3
tcaaggaagt aggtcacgta                                              20

<210> SEQ ID NO 4
```

```
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Conjugated to Biotion-c-6-.

<400> SEQUENCE: 4
tacgtgacct acttccttga                                              20

<210> SEQ ID NO 5
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on target protein.

<400> SEQUENCE: 5
nnnnnnnnnn nnnnnnnnnn cctaggacca                                   30

<210> SEQ ID NO 6
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on target protein.

<400> SEQUENCE: 6
nnnnnnnnnn nnnnnnnnnn gtgtcactta                                   30

<210> SEQ ID NO 7
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on target protein.

<400> SEQUENCE: 7
nnnnnnnnnn nnnnnnnnnn gtgcacgtgt                                   30

<210> SEQ ID NO 8
<211> LENGTH: 61
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 8
```

```
nnnnnnnnnn nnnnnnnnnn gaattctact ctcctcaagg tgatccatga tgatgttcct    60
t                                                                    61
```

<210> SEQ ID NO 9
<211> LENGTH: 40
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen depending on target protein.

<400> SEQUENCE: 9

```
nnnnnnnnnn nnnnnnnnnn catgaattct tggtgacttg                           40
```

<210> SEQ ID NO 10
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen depending on the target protein.

<400> SEQUENCE: 10

```
nnnnnnnnnn nnnnnnnnnn tggtcctagg                                      30
```

<210> SEQ ID NO 11
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen depending on the target protein.

<400> SEQUENCE: 11

```
nnnnnnnnnn nnnnnnnnnn taagtgacac                                      30
```

<210> SEQ ID NO 12
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen depending on the target protein.

<400> SEQUENCE: 12

```
nnnnnnnnnn nnnnnnnnnn acacgtgcac                                      30
```

<210> SEQ ID NO 13
<211> LENGTH: 30
<212> TYPE: DNA
<213> ORGANISM: Artificial Sequence
<220> FEATURE:

```
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 13
tgttgtccat gatgcttcct cctaggacca                                              30

<210> SEQ ID NO 14
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 14
caacttgatc tccagtcgtc cctaggacca                                              30

<210> SEQ ID NO 15
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 15
ctagtggtcg aagttgcaca gtgtcactta                                              30

<210> SEQ ID NO 16
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 16
cctacgtctt catggacctt gtgtcactta                                              30

<210> SEQ ID NO 17
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 17
ttcgtccatg cacatgatct gtgcacgtgt                                              30

<210> SEQ ID NO 18
<211> LENGTH: 30
<212> TYPE: DNA
<213> ORGANISM: Artificial Sequence
```

```
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 18
cagttcctcc aagcagtagg gtgcacgtgt                                    30

<210> SEQ ID NO 19
<211> LENGTH: 61
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 19
gttcatcgtc ttctaggtgc gaattctact ctcctcaagg tgatccatga tgatgttcct   60
t                                                                   61

<210> SEQ ID NO 20
<211> LENGTH: 61
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 20
tgaggttcga ggttgacgat gaattctact ctcctcaagg tgatccatga tgatgttcct   60
t                                                                   61

<210> SEQ ID NO 21
<211> LENGTH: 40
<212> TYPE: DNA
<213> ORGANISM: Artificial Sequence
<220> FEATURE:
<223> OTHER INFORMATION: Primer sequence

<400> SEQUENCE: 21
aggaagcatc atggacaaca catgaattct tggtgacttg                         40

<210> SEQ ID NO 22
<211> LENGTH: 40
<212> TYPE: DNA
<213> ORGANISM: Artificial Sequence
<220> FEATURE:
<223> OTHER INFORMATION: Primer sequence

<400> SEQUENCE: 22
gacgactgga gatcaagttg catgaattct tggtgacttg                         40

<210> SEQ ID NO 23
<211> LENGTH: 30
<212> TYPE: DNA
<213> ORGANISM: Artificial Sequence
<220> FEATURE:
<223> OTHER INFORMATION: Primer sequence
```

```
<400> SEQUENCE: 23
tgtgcaactt cgaccactag tggtcctagg                                30

<210> SEQ ID NO 24
<211> LENGTH: 30
<212> TYPE: DNA
<213> ORGANISM: Artificial Sequence
<220> FEATURE:
<223> OTHER INFORMATION: Primer sequence

<400> SEQUENCE: 24
aaggtccatg aagacgtagg tggtcctagg                                30

<210> SEQ ID NO 25
<211> LENGTH: 30
<212> TYPE: DNA
<213> ORGANISM: Artificial Sequence
<220> FEATURE:
<223> OTHER INFORMATION: Primer sequence

<400> SEQUENCE: 25
agatcatgtg catggacgaa taagtgacac                                30

<210> SEQ ID NO 26
<211> LENGTH: 30
<212> TYPE: DNA
<213> ORGANISM: Artificial Sequence
<220> FEATURE:
<223> OTHER INFORMATION: Primer sequence

<400> SEQUENCE: 26
cctactgctt ggaggaactg taagtgacac                                30

<210> SEQ ID NO 27
<211> LENGTH: 30
<212> TYPE: DNA
<213> ORGANISM: Artificial Sequence
<220> FEATURE:
<223> OTHER INFORMATION: Primer sequence

<400> SEQUENCE: 27
gcacctagaa gacgatgaac acacgtgcac                                30

<210> SEQ ID NO 28
<211> LENGTH: 30
<212> TYPE: DNA
<213> ORGANISM: Artificial Sequence
<220> FEATURE:
<223> OTHER INFORMATION: Primer sequence

<400> SEQUENCE: 28
atcgtcaacc tcgaacctca acacgtgcac                                30

<210> SEQ ID NO 29
<211> LENGTH: 20
<212> TYPE: DNA
<213> ORGANISM: Artificial Sequence
<220> FEATURE:
<223> OTHER INFORMATION: Primer sequence

<400> SEQUENCE: 29
agtgctcaca cgactgctcg                                           20

<210> SEQ ID NO 30
<211> LENGTH: 20
```

```
<212> TYPE: DNA
<213> ORGANISM: Artificial Sequence
<220> FEATURE:
<223> OTHER INFORMATION: Primer sequence

<400> SEQUENCE: 30
agctacgaca agactaggat                                              20

<210> SEQ ID NO 31
<211> LENGTH: 20
<212> TYPE: DNA
<213> ORGANISM: Artificial Sequence
<220> FEATURE:
<223> OTHER INFORMATION: Primer sequence

<400> SEQUENCE: 31
cgtccactac catcgacgac                                              20

<210> SEQ ID NO 32
<211> LENGTH: 20
<212> TYPE: DNA
<213> ORGANISM: Artificial Sequence
<220> FEATURE:
<223> OTHER INFORMATION: Primer sequence

<400> SEQUENCE: 32
ccaacttgta ggtgaggact                                              20

<210> SEQ ID NO 33
<211> LENGTH: 20
<212> TYPE: DNA
<213> ORGANISM: Artificial Sequence
<220> FEATURE:
<223> OTHER INFORMATION: Primer sequence

<400> SEQUENCE: 33
ctgctgttgg actgcttgta                                              20

<210> SEQ ID NO 34
<211> LENGTH: 20
<212> TYPE: DNA
<213> ORGANISM: Artificial Sequence
<220> FEATURE:
<223> OTHER INFORMATION: Primer sequence

<400> SEQUENCE: 34
cttccaggtc ctcgtagttc                                              20

<210> SEQ ID NO 35
<211> LENGTH: 20
<212> TYPE: DNA
<213> ORGANISM: Artificial Sequence
<220> FEATURE:
<223> OTHER INFORMATION: Primer sequence

<400> SEQUENCE: 35
aacatgctct aggtgtcgtc                                              20

<210> SEQ ID NO 36
<211> LENGTH: 20
<212> TYPE: DNA
<213> ORGANISM: Artificial Sequence
<220> FEATURE:
<223> OTHER INFORMATION: Primer sequence

<400> SEQUENCE: 36
```
acctgcacct ggatggatcg                                              20

<210> SEQ ID NO 37
<211> LENGTH: 20
<212> TYPE: DNA
<213> ORGANISM: Artificial Sequence
<220> FEATURE:
<223> OTHER INFORMATION: Primer sequence

<400> SEQUENCE: 37
aacgaggtca gacgaagcac                                              20

<210> SEQ ID NO 38
<211> LENGTH: 20
<212> TYPE: DNA
<213> ORGANISM: Artificial Sequence
<220> FEATURE:
<223> OTHER INFORMATION: Primer sequence

<400> SEQUENCE: 38
ctctctagtc cacaagatgc                                              20

<210> SEQ ID NO 39
<211> LENGTH: 20
<212> TYPE: DNA
<213> ORGANISM: Artificial Sequence
<220> FEATURE:
<223> OTHER INFORMATION: Primer sequence

<400> SEQUENCE: 39
atctcaagta cgacacatcc                                              20

<210> SEQ ID NO 40
<211> LENGTH: 20
<212> TYPE: DNA
<213> ORGANISM: Artificial Sequence
<220> FEATURE:
<223> OTHER INFORMATION: Primer sequence

<400> SEQUENCE: 40
ccatcacatc agcaggtaga                                              20

<210> SEQ ID NO 41
<211> LENGTH: 20
<212> TYPE: DNA
<213> ORGANISM: Artificial Sequence
<220> FEATURE:
<223> OTHER INFORMATION: Primer sequence

<400> SEQUENCE: 41
tgtgttgtgc ttgaccatcc                                              20

<210> SEQ ID NO 42
<211> LENGTH: 20
<212> TYPE: DNA
<213> ORGANISM: Artificial Sequence
<220> FEATURE:
<223> OTHER INFORMATION: Primer sequence

<400> SEQUENCE: 42
cagacctgtc tccacgtagc                                              20

<210> SEQ ID NO 43
<211> LENGTH: 20
<212> TYPE: DNA
<213> ORGANISM: Artificial Sequence

```
<220> FEATURE:
<223> OTHER INFORMATION: Primer sequence

<400> SEQUENCE: 43
gcacttgtcg atcaagcaga                                               20

<210> SEQ ID NO 44
<211> LENGTH: 20
<212> TYPE: DNA
<213> ORGANISM: Artificial Sequence
<220> FEATURE:
<223> OTHER INFORMATION: Primer sequence

<400> SEQUENCE: 44
tggtccttgc ttgatggagt                                               20

<210> SEQ ID NO 45
<211> LENGTH: 20
<212> TYPE: DNA
<213> ORGANISM: Artificial Sequence
<220> FEATURE:
<223> OTHER INFORMATION: Primer sequence

<400> SEQUENCE: 45
atcgtacaga ctcctcacag                                               20

<210> SEQ ID NO 46
<211> LENGTH: 20
<212> TYPE: DNA
<213> ORGANISM: Artificial Sequence
<220> FEATURE:
<223> OTHER INFORMATION: Primer sequence

<400> SEQUENCE: 46
tccaagcacg tctcgtactc                                               20

<210> SEQ ID NO 47
<211> LENGTH: 20
<212> TYPE: DNA
<213> ORGANISM: Artificial Sequence
<220> FEATURE:
<223> OTHER INFORMATION: Primer sequence

<400> SEQUENCE: 47
ggtcgaccag atggacactt                                               20

<210> SEQ ID NO 48
<211> LENGTH: 20
<212> TYPE: DNA
<213> ORGANISM: Artificial Sequence
<220> FEATURE:
<223> OTHER INFORMATION: Primer sequence

<400> SEQUENCE: 48
catcatctgt acaggatggt                                               20

<210> SEQ ID NO 49
<211> LENGTH: 20
<212> TYPE: DNA
<213> ORGANISM: Artificial Sequence
<220> FEATURE:
<223> OTHER INFORMATION: Primer sequence

<400> SEQUENCE: 49
ttccaactgc aaggtacagg                                               20
```

<210> SEQ ID NO 50
<211> LENGTH: 20
<212> TYPE: DNA
<213> ORGANISM: Artificial Sequence
<220> FEATURE:
<223> OTHER INFORMATION: Primer sequence

<400> SEQUENCE: 50
tagcacctac aagatggagt                                               20

<210> SEQ ID NO 51
<211> LENGTH: 20
<212> TYPE: DNA
<213> ORGANISM: Artificial Sequence
<220> FEATURE:
<223> OTHER INFORMATION: Primer sequence

<400> SEQUENCE: 51
ctcgacacca ggtccagaag                                               20

<210> SEQ ID NO 52
<211> LENGTH: 20
<212> TYPE: DNA
<213> ORGANISM: Artificial Sequence
<220> FEATURE:
<223> OTHER INFORMATION: Primer sequence

<400> SEQUENCE: 52
ggtcatctga gcaacgttgt                                               20

<210> SEQ ID NO 53
<211> LENGTH: 20
<212> TYPE: DNA
<213> ORGANISM: Artificial Sequence
<220> FEATURE:
<223> OTHER INFORMATION: Primer sequence

<400> SEQUENCE: 53
cacaagctag gtacatggac                                               20

<210> SEQ ID NO 54
<211> LENGTH: 20
<212> TYPE: DNA
<213> ORGANISM: Artificial Sequence
<220> FEATURE:
<223> OTHER INFORMATION: Primer sequence

<400> SEQUENCE: 54
tgcagcagct tgctcgtact                                               20

<210> SEQ ID NO 55
<211> LENGTH: 20
<212> TYPE: DNA
<213> ORGANISM: Artificial Sequence
<220> FEATURE:
<223> OTHER INFORMATION: Primer sequence

<400> SEQUENCE: 55
gtccatgtcc aagcatgaag                                               20

<210> SEQ ID NO 56
<211> LENGTH: 20
<212> TYPE: DNA
<213> ORGANISM: Artificial Sequence
<220> FEATURE:
<223> OTHER INFORMATION: Primer sequence

<400> SEQUENCE: 56
tccatctcta ggttgcacac                                               20

<210> SEQ ID NO 57
<211> LENGTH: 20
<212> TYPE: DNA
<213> ORGANISM: Artificial Sequence
<220> FEATURE:
<223> OTHER INFORMATION: Primer sequence

<400> SEQUENCE: 57
atgctacacc actgctgtgc                                               20

<210> SEQ ID NO 58
<211> LENGTH: 20
<212> TYPE: DNA
<213> ORGANISM: Artificial Sequence
<220> FEATURE:
<223> OTHER INFORMATION: Primer sequence

<400> SEQUENCE: 58
caacatggag agtggaacat                                               20

<210> SEQ ID NO 59
<211> LENGTH: 20
<212> TYPE: DNA
<213> ORGANISM: Artificial Sequence
<220> FEATURE:
<223> OTHER INFORMATION: Primer sequence

<400> SEQUENCE: 59
actccatcca cttcacagag                                               20

<210> SEQ ID NO 60
<211> LENGTH: 20
<212> TYPE: DNA
<213> ORGANISM: Artificial Sequence
<220> FEATURE:
<223> OTHER INFORMATION: Primer sequence

<400> SEQUENCE: 60
ctccagacta cctgtggacg                                               20

<210> SEQ ID NO 61
<211> LENGTH: 20
<212> TYPE: DNA
<213> ORGANISM: Artificial Sequence
<220> FEATURE:
<223> OTHER INFORMATION: Primer sequence

<400> SEQUENCE: 61
cgagcaagac atgagcactc                                               20

<210> SEQ ID NO 62
<211> LENGTH: 20
<212> TYPE: DNA
<213> ORGANISM: Artificial Sequence
<220> FEATURE:
<223> OTHER INFORMATION: Primer sequence

<400> SEQUENCE: 62
cctcgtcctg atgttgcatc                                               20

<210> SEQ ID NO 63

```
<211> LENGTH: 20
<212> TYPE: DNA
<213> ORGANISM: Artificial Sequence
<220> FEATURE:
<223> OTHER INFORMATION: Primer sequence

<400> SEQUENCE: 63
tcagaaccat gcacttgacg                                               20

<210> SEQ ID NO 64
<211> LENGTH: 20
<212> TYPE: DNA
<213> ORGANISM: Artificial Sequence
<220> FEATURE:
<223> OTHER INFORMATION: Primer sequence

<400> SEQUENCE: 64
ggaacatgct ggaagaccag                                               20

<210> SEQ ID NO 65
<211> LENGTH: 20
<212> TYPE: DNA
<213> ORGANISM: Artificial Sequence
<220> FEATURE:
<223> OTHER INFORMATION: Primer sequence

<400> SEQUENCE: 65
tacagactga gcttcacttg                                               20

<210> SEQ ID NO 66
<211> LENGTH: 20
<212> TYPE: DNA
<213> ORGANISM: Artificial Sequence
<220> FEATURE:
<223> OTHER INFORMATION: Primer sequence

<400> SEQUENCE: 66
tcctgatggt gtaccacctt                                               20

<210> SEQ ID NO 67
<211> LENGTH: 20
<212> TYPE: DNA
<213> ORGANISM: Artificial Sequence
<220> FEATURE:
<223> OTHER INFORMATION: Primer sequence

<400> SEQUENCE: 67
aagcagctct gtcgagcaat                                               20

<210> SEQ ID NO 68
<211> LENGTH: 20
<212> TYPE: DNA
<213> ORGANISM: Artificial Sequence
<220> FEATURE:
<223> OTHER INFORMATION: Primer sequence

<400> SEQUENCE: 68
atcaaccaag gacatctctg                                               20

<210> SEQ ID NO 69
<211> LENGTH: 20
<212> TYPE: DNA
<213> ORGANISM: Artificial Sequence
<220> FEATURE:
<223> OTHER INFORMATION: Primer sequence

<400> SEQUENCE: 69
```
ccttgtaggt cgtagtgcat					20

<210> SEQ ID NO 70
<211> LENGTH: 20
<212> TYPE: DNA
<213> ORGANISM: Artificial Sequence
<220> FEATURE:
<223> OTHER INFORMATION: Primer sequence

<400> SEQUENCE: 70
accttcacga tcagagctat					20

<210> SEQ ID NO 71
<211> LENGTH: 20
<212> TYPE: DNA
<213> ORGANISM: Artificial Sequence
<220> FEATURE:
<223> OTHER INFORMATION: Primer sequence

<400> SEQUENCE: 71
gatgttgagg acgtagtgtg					20

<210> SEQ ID NO 72
<211> LENGTH: 20
<212> TYPE: DNA
<213> ORGANISM: Artificial Sequence
<220> FEATURE:
<223> OTHER INFORMATION: Primer sequence

<400> SEQUENCE: 72
cttcgtcgaa gactgagtca					20

<210> SEQ ID NO 73
<211> LENGTH: 20
<212> TYPE: DNA
<213> ORGANISM: Artificial Sequence
<220> FEATURE:
<223> OTHER INFORMATION: Primer sequence

<400> SEQUENCE: 73
acgactgtcg tacgagacgt					20

<210> SEQ ID NO 74
<211> LENGTH: 20
<212> TYPE: DNA
<213> ORGANISM: Artificial Sequence
<220> FEATURE:
<223> OTHER INFORMATION: Primer sequence

<400> SEQUENCE: 74
cgatctggtt gacgaacagc					20

<210> SEQ ID NO 75
<211> LENGTH: 20
<212> TYPE: DNA
<213> ORGANISM: Artificial Sequence
<220> FEATURE:
<223> OTHER INFORMATION: Primer sequence

<400> SEQUENCE: 75
ccacgatctt gagtgtacgg					20

<210> SEQ ID NO 76
<211> LENGTH: 20
<212> TYPE: DNA

```
<213> ORGANISM: Artificial Sequence
<220> FEATURE:
<223> OTHER INFORMATION: Primer sequence

<400> SEQUENCE: 76
cactgagcag cttcttccat                                                   20

<210> SEQ ID NO 77
<211> LENGTH: 20
<212> TYPE: DNA
<213> ORGANISM: Artificial Sequence
<220> FEATURE:
<223> OTHER INFORMATION: Primer sequence

<400> SEQUENCE: 77
ctcttggttc ctaggagaca                                                   20

<210> SEQ ID NO 78
<211> LENGTH: 20
<212> TYPE: DNA
<213> ORGANISM: Artificial Sequence
<220> FEATURE:
<223> OTHER INFORMATION: Primer sequence

<400> SEQUENCE: 78
gtcaggacaa ctcagtgcag                                                   20

<210> SEQ ID NO 79
<211> LENGTH: 20
<212> TYPE: DNA
<213> ORGANISM: Artificial Sequence
<220> FEATURE:
<223> OTHER INFORMATION: Primer sequence

<400> SEQUENCE: 79
cgtgctacca cactcacaat                                                   20

<210> SEQ ID NO 80
<211> LENGTH: 20
<212> TYPE: DNA
<213> ORGANISM: Artificial Sequence
<220> FEATURE:
<223> OTHER INFORMATION: Primer sequence

<400> SEQUENCE: 80
tcacatgacc agcacgtgcg                                                   20

<210> SEQ ID NO 81
<211> LENGTH: 20
<212> TYPE: DNA
<213> ORGANISM: Artificial Sequence
<220> FEATURE:
<223> OTHER INFORMATION: Primer sequence

<400> SEQUENCE: 81
cgatcaagct acagaagaag                                                   20

<210> SEQ ID NO 82
<211> LENGTH: 20
<212> TYPE: DNA
<213> ORGANISM: Artificial Sequence
<220> FEATURE:
<223> OTHER INFORMATION: Primer sequence

<400> SEQUENCE: 82
tggactctgt cgaaggtaca                                                   20
```

<210> SEQ ID NO 83
<211> LENGTH: 20
<212> TYPE: DNA
<213> ORGANISM: Artificial Sequence
<220> FEATURE:
<223> OTHER INFORMATION: Primer sequence

<400> SEQUENCE: 83
ctgtagcatc cactccatcc						20

<210> SEQ ID NO 84
<211> LENGTH: 20
<212> TYPE: DNA
<213> ORGANISM: Artificial Sequence
<220> FEATURE:
<223> OTHER INFORMATION: Primer sequence

<400> SEQUENCE: 84
gactgtggtg acacctgact						20

<210> SEQ ID NO 85
<211> LENGTH: 20
<212> TYPE: DNA
<213> ORGANISM: Artificial Sequence
<220> FEATURE:
<223> OTHER INFORMATION: Primer sequence

<400> SEQUENCE: 85
gcttcgacag acatcactcg						20

<210> SEQ ID NO 86
<211> LENGTH: 20
<212> TYPE: DNA
<213> ORGANISM: Artificial Sequence
<220> FEATURE:
<223> OTHER INFORMATION: Primer sequence

<400> SEQUENCE: 86
atggacagtg gacactcatt						20

<210> SEQ ID NO 87
<211> LENGTH: 20
<212> TYPE: DNA
<213> ORGANISM: Artificial Sequence
<220> FEATURE:
<223> OTHER INFORMATION: Primer sequence

<400> SEQUENCE: 87
gcttctcctg gttgatggtc						20

<210> SEQ ID NO 88
<211> LENGTH: 20
<212> TYPE: DNA
<213> ORGANISM: Artificial Sequence
<220> FEATURE:
<223> OTHER INFORMATION: Primer sequence

<400> SEQUENCE: 88
cgtcgatgga cgtgtcgatt						20

<210> SEQ ID NO 89
<211> LENGTH: 20
<212> TYPE: DNA
<213> ORGANISM: Artificial Sequence
<220> FEATURE:

<223> OTHER INFORMATION: Primer sequence

<400> SEQUENCE: 89
cgttccaacc aaccttggag                                                  20

<210> SEQ ID NO 90
<211> LENGTH: 20
<212> TYPE: DNA
<213> ORGANISM: Artificial Sequence
<220> FEATURE:
<223> OTHER INFORMATION: Primer sequence

<400> SEQUENCE: 90
cgaacagaac tagcacgtca                                                  20

<210> SEQ ID NO 91
<211> LENGTH: 20
<212> TYPE: DNA
<213> ORGANISM: Artificial Sequence
<220> FEATURE:
<223> OTHER INFORMATION: Primer sequence

<400> SEQUENCE: 91
gaagttcctc tggtctaggg                                                  20

<210> SEQ ID NO 92
<211> LENGTH: 20
<212> TYPE: DNA
<213> ORGANISM: Artificial Sequence
<220> FEATURE:
<223> OTHER INFORMATION: Primer sequence

<400> SEQUENCE: 92
ggtctagtag catgatcgaa                                                  20

<210> SEQ ID NO 93
<211> LENGTH: 20
<212> TYPE: DNA
<213> ORGANISM: Artificial Sequence
<220> FEATURE:
<223> OTHER INFORMATION: Primer sequence

<400> SEQUENCE: 93
cttcttggaa cctgagctta                                                  20

<210> SEQ ID NO 94
<211> LENGTH: 20
<212> TYPE: DNA
<213> ORGANISM: Artificial Sequence
<220> FEATURE:
<223> OTHER INFORMATION: Primer sequence

<400> SEQUENCE: 94
ttgctcagca tccttgaact                                                  20

<210> SEQ ID NO 95
<211> LENGTH: 20
<212> TYPE: DNA
<213> ORGANISM: Artificial Sequence
<220> FEATURE:
<223> OTHER INFORMATION: Primer sequence

<400> SEQUENCE: 95
tgttcctggt acacgaggag                                                  20

```
<210> SEQ ID NO 96
<211> LENGTH: 40
<212> TYPE: DNA
<213> ORGANISM: Artificial Sequence
<220> FEATURE:
<223> OTHER INFORMATION: Primer sequence

<400> SEQUENCE: 96
tctggtggtc tacgtgctct aaggaacatc atcatggatc                              40

<210> SEQ ID NO 97
<211> LENGTH: 20
<212> TYPE: DNA
<213> ORGANISM: Artificial Sequence
<220> FEATURE:
<223> OTHER INFORMATION: Primer sequence

<400> SEQUENCE: 97
tctggtggtc tacgtgctct                                                    20

<210> SEQ ID NO 98
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 98
nnnnnnnnnn nnnnnnnnnn cctaggacca                                         30

<210> SEQ ID NO 99
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 99
nnnnnnnnnn nnnnnnnnnn gtgtcactta                                         30

<210> SEQ ID NO 100
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 100
nnnnnnnnnn nnnnnnnnnn gtgcacgtgt                                         30

<210> SEQ ID NO 101
<211> LENGTH: 61
<212> TYPE: DNA
<213> ORGANISM: Artificial Sequence
```

```
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 101
nnnnnnnnnn nnnnnnnnnn gaattctact ctcctcaagg tgatccatga tgatgttcct      60
t                                                                     61

<210> SEQ ID NO 102
<211> LENGTH: 40
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 102
nnnnnnnnnn nnnnnnnnnn catgaattct tggtgacttg                            40

<210> SEQ ID NO 103
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 103
nnnnnnnnnn nnnnnnnnnn tggtcctagg                                       30

<210> SEQ ID NO 104
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 104
nnnnnnnnnn nnnnnnnnnn taagtgacac                                       30

<210> SEQ ID NO 105
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(20)
<223> OTHER INFORMATION: n is a, c, g, or t. The sequence may be chosen
      depending on the target protein.

<400> SEQUENCE: 105
```
nnnnnnnnnn nnnnnnnnnn acacgtgcac                                    30

<210> SEQ ID NO 106
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 106
tgttgtccat gatgcttcct cctaggacca                                    30

<210> SEQ ID NO 107
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 107
caacttgatc tccagtcgtc cctaggacca                                    30

<210> SEQ ID NO 108
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 108
ctagtggtcg aagttgcaca gtgtcactta                                    30

<210> SEQ ID NO 109
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 109
cctacgtctt catggacctt gtgtcactta                                    30

<210> SEQ ID NO 110
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 110
ttcgtccatg cacatgatct gtgcacgtgt                                                30

<210> SEQ ID NO 111
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 111
cagttcctcc aagcagtagg gtgcacgtgt                                                30

<210> SEQ ID NO 112
<211> LENGTH: 61
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate

<400> SEQUENCE: 112
gttcatcgtc ttctaggtgc gaattctact ctcctcaagg tgatccatga tgatgttcct             60
t                                                                             61

<210> SEQ ID NO 113
<211> LENGTH: 61
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: Contains a 5' phosphate.

<400> SEQUENCE: 113
tgaggttcga ggttgacgat gaattctact ctcctcaagg tgatccatga tgatgttcct             60
t                                                                             61

<210> SEQ ID NO 114
<211> LENGTH: 40
<212> TYPE: DNA
<213> ORGANISM: Artificial Sequence
<220> FEATURE:
<223> OTHER INFORMATION: Primer sequence

<400> SEQUENCE: 114
aggaagcatc atggacaaca catgaattct tggtgacttg                                    40

<210> SEQ ID NO 115
<211> LENGTH: 40
<212> TYPE: DNA
<213> ORGANISM: Artificial Sequence
<220> FEATURE:
<223> OTHER INFORMATION: Primer sequence

<400> SEQUENCE: 115
gacgactgga gatcaagttg catgaattct tggtgacttg                                    40

<210> SEQ ID NO 116
<211> LENGTH: 30
<212> TYPE: DNA
<213> ORGANISM: Artificial Sequence
<220> FEATURE:
<223> OTHER INFORMATION: Primer sequence

<400> SEQUENCE: 116
tgtgcaactt cgaccactag tggtcctagg                                   30

<210> SEQ ID NO 117
<211> LENGTH: 30
<212> TYPE: DNA
<213> ORGANISM: Artificial Sequence
<220> FEATURE:
<223> OTHER INFORMATION: Primer sequence

<400> SEQUENCE: 117
aaggtccatg aagacgtagg tggtcctagg                                   30

<210> SEQ ID NO 118
<211> LENGTH: 30
<212> TYPE: DNA
<213> ORGANISM: Artificial Sequence
<220> FEATURE:
<223> OTHER INFORMATION: Primer sequence

<400> SEQUENCE: 118
agatcatgtg catggacgaa taagtgacac                                   30

<210> SEQ ID NO 119
<211> LENGTH: 30
<212> TYPE: DNA
<213> ORGANISM: Artificial Sequence
<220> FEATURE:
<223> OTHER INFORMATION: Primer sequence

<400> SEQUENCE: 119
cctactgctt ggaggaactg taagtgacac                                   30

<210> SEQ ID NO 120
<211> LENGTH: 30
<212> TYPE: DNA
<213> ORGANISM: Artificial Sequence
<220> FEATURE:
<223> OTHER INFORMATION: Primer sequence

<400> SEQUENCE: 120
gcacctagaa gacgatgaac acacgtgcac                                   30

<210> SEQ ID NO 121
<211> LENGTH: 30
<212> TYPE: DNA
<213> ORGANISM: Artificial Sequence
<220> FEATURE:
<223> OTHER INFORMATION: Primer sequence

<400> SEQUENCE: 121
atcgtcaacc tcgaacctca acacgtgcac                                   30

<210> SEQ ID NO 122
<211> LENGTH: 20
<212> TYPE: DNA
<213> ORGANISM: Artificial Sequence
<220> FEATURE:

<223> OTHER INFORMATION: Primer sequence

<400> SEQUENCE: 122
gtgctactga gatgttgcag                                           20

<210> SEQ ID NO 123
<211> LENGTH: 20
<212> TYPE: DNA
<213> ORGANISM: Artificial Sequence
<220> FEATURE:
<223> OTHER INFORMATION: Primer sequence

<400> SEQUENCE: 123
gctgatgagt tcgagttcta                                           20

<210> SEQ ID NO 124
<211> LENGTH: 20
<212> TYPE: DNA
<213> ORGANISM: Artificial Sequence
<220> FEATURE:
<223> OTHER INFORMATION: Primer sequence

<400> SEQUENCE: 124
ggtagcaaga tggtactacg                                           20

<210> SEQ ID NO 125
<211> LENGTH: 20
<212> TYPE: DNA
<213> ORGANISM: Artificial Sequence
<220> FEATURE:
<223> OTHER INFORMATION: Primer sequence

<400> SEQUENCE: 125
ccacgacatc aaccatggtg                                           20

<210> SEQ ID NO 126
<211> LENGTH: 20
<212> TYPE: DNA
<213> ORGANISM: Artificial Sequence
<220> FEATURE:
<223> OTHER INFORMATION: Primer sequence

<400> SEQUENCE: 126
gatcacctgt cgatgaacga                                           20

<210> SEQ ID NO 127
<211> LENGTH: 20
<212> TYPE: DNA
<213> ORGANISM: Artificial Sequence
<220> FEATURE:
<223> OTHER INFORMATION: Primer sequence

<400> SEQUENCE: 127
tctacgttca cagatgctcg                                           20

<210> SEQ ID NO 128
<211> LENGTH: 20
<212> TYPE: DNA
<213> ORGANISM: Artificial Sequence
<220> FEATURE:
<223> OTHER INFORMATION: Primer sequence

<400> SEQUENCE: 128
tcatggtctg cactcaggat                                           20

```
<210> SEQ ID NO 129
<211> LENGTH: 20
<212> TYPE: DNA
<213> ORGANISM: Artificial Sequence
<220> FEATURE:
<223> OTHER INFORMATION: Primer sequence

<400> SEQUENCE: 129
cctgtaccaa ctggacatcg                                               20

<210> SEQ ID NO 130
<211> LENGTH: 20
<212> TYPE: DNA
<213> ORGANISM: Artificial Sequence
<220> FEATURE:
<223> OTHER INFORMATION: Primer sequence

<400> SEQUENCE: 130
tgcactgtac gagcaggtct                                               20

<210> SEQ ID NO 131
<211> LENGTH: 20
<212> TYPE: DNA
<213> ORGANISM: Artificial Sequence
<220> FEATURE:
<223> OTHER INFORMATION: Primer sequence

<400> SEQUENCE: 131
taggtcagga gtacaacact                                               20

<210> SEQ ID NO 132
<211> LENGTH: 20
<212> TYPE: DNA
<213> ORGANISM: Artificial Sequence
<220> FEATURE:
<223> OTHER INFORMATION: Primer sequence

<400> SEQUENCE: 132
ctcgttgtcc aacatcacat                                               20

<210> SEQ ID NO 133
<211> LENGTH: 20
<212> TYPE: DNA
<213> ORGANISM: Artificial Sequence
<220> FEATURE:
<223> OTHER INFORMATION: Primer sequence

<400> SEQUENCE: 133
cacacgatgc tgtagctcta                                               20

<210> SEQ ID NO 134
<211> LENGTH: 20
<212> TYPE: DNA
<213> ORGANISM: Artificial Sequence
<220> FEATURE:
<223> OTHER INFORMATION: Primer sequence

<400> SEQUENCE: 134
gaactctagg tggaaggaaa                                               20

<210> SEQ ID NO 135
<211> LENGTH: 20
<212> TYPE: DNA
<213> ORGANISM: Artificial Sequence
<220> FEATURE:
<223> OTHER INFORMATION: Primer sequence
```

```
<400> SEQUENCE: 135
tactgcatgt accaccatga                                              20

<210> SEQ ID NO 136
<211> LENGTH: 20
<212> TYPE: DNA
<213> ORGANISM: Artificial Sequence
<220> FEATURE:
<223> OTHER INFORMATION: Primer sequence

<400> SEQUENCE: 136
acaggaagac gtgcatgtac                                              20

<210> SEQ ID NO 137
<211> LENGTH: 20
<212> TYPE: DNA
<213> ORGANISM: Artificial Sequence
<220> FEATURE:
<223> OTHER INFORMATION: Primer sequence

<400> SEQUENCE: 137
tggtctcgtt ctcgtcacag                                              20

<210> SEQ ID NO 138
<211> LENGTH: 20
<212> TYPE: DNA
<213> ORGANISM: Artificial Sequence
<220> FEATURE:
<223> OTHER INFORMATION: Primer sequence

<400> SEQUENCE: 138
tacagaagca tcgagtagct                                              20

<210> SEQ ID NO 139
<211> LENGTH: 20
<212> TYPE: DNA
<213> ORGANISM: Artificial Sequence
<220> FEATURE:
<223> OTHER INFORMATION: Primer sequence

<400> SEQUENCE: 139
ggtcctctca agatgtggaa                                              20

<210> SEQ ID NO 140
<211> LENGTH: 20
<212> TYPE: DNA
<213> ORGANISM: Artificial Sequence
<220> FEATURE:
<223> OTHER INFORMATION: Primer sequence

<400> SEQUENCE: 140
gtggtgagct tgtggtcgaa                                              20

<210> SEQ ID NO 141
<211> LENGTH: 20
<212> TYPE: DNA
<213> ORGANISM: Artificial Sequence
<220> FEATURE:
<223> OTHER INFORMATION: Primer sequence

<400> SEQUENCE: 141
cgaacctcca gtagcatggt                                              20

<210> SEQ ID NO 142
<211> LENGTH: 20
```

```
<212> TYPE: DNA
<213> ORGANISM: Artificial Sequence
<220> FEATURE:
<223> OTHER INFORMATION: Primer sequence

<400> SEQUENCE: 142
ctcatccacg aggagcaagt                                               20

<210> SEQ ID NO 143
<211> LENGTH: 20
<212> TYPE: DNA
<213> ORGANISM: Artificial Sequence
<220> FEATURE:
<223> OTHER INFORMATION: Primer sequence

<400> SEQUENCE: 143
atcatgcaac ctacgagctt                                               20

<210> SEQ ID NO 144
<211> LENGTH: 20
<212> TYPE: DNA
<213> ORGANISM: Artificial Sequence
<220> FEATURE:
<223> OTHER INFORMATION: Primer sequence

<400> SEQUENCE: 144
ttggaggtac gatccacaca                                               20

<210> SEQ ID NO 145
<211> LENGTH: 20
<212> TYPE: DNA
<213> ORGANISM: Artificial Sequence
<220> FEATURE:
<223> OTHER INFORMATION: Primer sequence

<400> SEQUENCE: 145
ctgcttcgta ccacaagctc                                               20

<210> SEQ ID NO 146
<211> LENGTH: 20
<212> TYPE: DNA
<213> ORGANISM: Artificial Sequence
<220> FEATURE:
<223> OTHER INFORMATION: Primer sequence

<400> SEQUENCE: 146
tcaccacttc cagatcgttc                                               20

<210> SEQ ID NO 147
<211> LENGTH: 20
<212> TYPE: DNA
<213> ORGANISM: Artificial Sequence
<220> FEATURE:
<223> OTHER INFORMATION: Primer sequence

<400> SEQUENCE: 147
ctcttcaacc tgagaacaac                                               20

<210> SEQ ID NO 148
<211> LENGTH: 20
<212> TYPE: DNA
<213> ORGANISM: Artificial Sequence
<220> FEATURE:
<223> OTHER INFORMATION: Primer sequence

<400> SEQUENCE: 148
```
tgtggtggtg ctcgtactgc                                          20

<210> SEQ ID NO 149
<211> LENGTH: 20
<212> TYPE: DNA
<213> ORGANISM: Artificial Sequence
<220> FEATURE:
<223> OTHER INFORMATION: Primer sequence

<400> SEQUENCE: 149
cgttcctctc agaaccagag                                          20

<210> SEQ ID NO 150
<211> LENGTH: 20
<212> TYPE: DNA
<213> ORGANISM: Artificial Sequence
<220> FEATURE:
<223> OTHER INFORMATION: Primer sequence

<400> SEQUENCE: 150
tggaagctac catctcgtgc                                          20

<210> SEQ ID NO 151
<211> LENGTH: 20
<212> TYPE: DNA
<213> ORGANISM: Artificial Sequence
<220> FEATURE:
<223> OTHER INFORMATION: Primer sequence

<400> SEQUENCE: 151
gtggatcgac ctctagcaaa                                          20

<210> SEQ ID NO 152
<211> LENGTH: 20
<212> TYPE: DNA
<213> ORGANISM: Artificial Sequence
<220> FEATURE:
<223> OTHER INFORMATION: Primer sequence

<400> SEQUENCE: 152
ccagtgctag gttgctcgac                                          20

<210> SEQ ID NO 153
<211> LENGTH: 20
<212> TYPE: DNA
<213> ORGANISM: Artificial Sequence
<220> FEATURE:
<223> OTHER INFORMATION: Primer sequence

<400> SEQUENCE: 153
caagttcttg cactcgatct                                          20

<210> SEQ ID NO 154
<211> LENGTH: 20
<212> TYPE: DNA
<213> ORGANISM: Artificial Sequence
<220> FEATURE:
<223> OTHER INFORMATION: Primer sequence

<400> SEQUENCE: 154
tactggacga cgtactaggc                                          20

<210> SEQ ID NO 155
<211> LENGTH: 20
<212> TYPE: DNA
<213> ORGANISM: Artificial Sequence -continued
<220> FEATURE:
<223> OTHER INFORMATION: Primer sequence

<400> SEQUENCE: 155
cctagacgag cttctggttg                                               20

<210> SEQ ID NO 156
<211> LENGTH: 20
<212> TYPE: DNA
<213> ORGANISM: Artificial Sequence
<220> FEATURE:
<223> OTHER INFORMATION: Primer sequence

<400> SEQUENCE: 156
acagtctcat ggtccaagtc                                               20

<210> SEQ ID NO 157
<211> LENGTH: 20
<212> TYPE: DNA
<213> ORGANISM: Artificial Sequence
<220> FEATURE:
<223> OTHER INFORMATION: Primer sequence

<400> SEQUENCE: 157
acagcacctc gtgtaggact                                               20

<210> SEQ ID NO 158
<211> LENGTH: 20
<212> TYPE: DNA
<213> ORGANISM: Artificial Sequence
<220> FEATURE:
<223> OTHER INFORMATION: Primer sequence

<400> SEQUENCE: 158
actgcaagga tgcatctggc                                               20

<210> SEQ ID NO 159
<211> LENGTH: 20
<212> TYPE: DNA
<213> ORGANISM: Artificial Sequence
<220> FEATURE:
<223> OTHER INFORMATION: Primer sequence

<400> SEQUENCE: 159
ccttgacacc aacgtgaagt                                               20

<210> SEQ ID NO 160
<211> LENGTH: 20
<212> TYPE: DNA
<213> ORGANISM: Artificial Sequence
<220> FEATURE:
<223> OTHER INFORMATION: Primer sequence

<400> SEQUENCE: 160
aggaaccagc aacgaggtta                                               20

<210> SEQ ID NO 161
<211> LENGTH: 20
<212> TYPE: DNA
<213> ORGANISM: Artificial Sequence
<220> FEATURE:
<223> OTHER INFORMATION: Primer sequence

<400> SEQUENCE: 161
tactcctcag atcgtacgaa                                               20

```
<210> SEQ ID NO 162
<211> LENGTH: 20
<212> TYPE: DNA
<213> ORGANISM: Artificial Sequence
<220> FEATURE:
<223> OTHER INFORMATION: Primer sequence

<400> SEQUENCE: 162
ttgtctgagg agcttcagga                                              20

<210> SEQ ID NO 163
<211> LENGTH: 20
<212> TYPE: DNA
<213> ORGANISM: Artificial Sequence
<220> FEATURE:
<223> OTHER INFORMATION: Primer sequence

<400> SEQUENCE: 163
cgtcgtcgac gatcctccaa                                              20

<210> SEQ ID NO 164
<211> LENGTH: 20
<212> TYPE: DNA
<213> ORGANISM: Artificial Sequence
<220> FEATURE:
<223> OTHER INFORMATION: Primer sequence

<400> SEQUENCE: 164
caccttgtca ggagtacgtt                                              20

<210> SEQ ID NO 165
<211> LENGTH: 20
<212> TYPE: DNA
<213> ORGANISM: Artificial Sequence
<220> FEATURE:
<223> OTHER INFORMATION: Primer sequence

<400> SEQUENCE: 165
cagttgtacg aggttgcagc                                              20

<210> SEQ ID NO 166
<211> LENGTH: 20
<212> TYPE: DNA
<213> ORGANISM: Artificial Sequence
<220> FEATURE:
<223> OTHER INFORMATION: Primer sequence

<400> SEQUENCE: 166
cgtaccttct tctagcaaca                                              20

<210> SEQ ID NO 167
<211> LENGTH: 20
<212> TYPE: DNA
<213> ORGANISM: Artificial Sequence
<220> FEATURE:
<223> OTHER INFORMATION: Primer sequence

<400> SEQUENCE: 167
agctccagct tcgaagttga                                              20

<210> SEQ ID NO 168
<211> LENGTH: 20
<212> TYPE: DNA
<213> ORGANISM: Artificial Sequence
<220> FEATURE:
<223> OTHER INFORMATION: Primer sequence
```

<400> SEQUENCE: 168
ctcatccact tgtgtgacgc                                               20

<210> SEQ ID NO 169
<211> LENGTH: 20
<212> TYPE: DNA
<213> ORGANISM: Artificial Sequence
<220> FEATURE:
<223> OTHER INFORMATION: Primer sequence

<400> SEQUENCE: 169
atggatggtc ctaccttctc                                               20

<210> SEQ ID NO 170
<211> LENGTH: 20
<212> TYPE: DNA
<213> ORGANISM: Artificial Sequence
<220> FEATURE:
<223> OTHER INFORMATION: Primer sequence

<400> SEQUENCE: 170
tgttccagga cgtcctgcac                                               20

<210> SEQ ID NO 171
<211> LENGTH: 20
<212> TYPE: DNA
<213> ORGANISM: Artificial Sequence
<220> FEATURE:
<223> OTHER INFORMATION: Primer sequence

<400> SEQUENCE: 171
tacctcgaag gtctggatcg                                               20

<210> SEQ ID NO 172
<211> LENGTH: 20
<212> TYPE: DNA
<213> ORGANISM: Artificial Sequence
<220> FEATURE:
<223> OTHER INFORMATION: Primer sequence

<400> SEQUENCE: 172
tgttctagtg gaactcaacg                                               20

<210> SEQ ID NO 173
<211> LENGTH: 20
<212> TYPE: DNA
<213> ORGANISM: Artificial Sequence
<220> FEATURE:
<223> OTHER INFORMATION: Primer sequence

<400> SEQUENCE: 173
agttgaacca tgcactctct                                               20

<210> SEQ ID NO 174
<211> LENGTH: 20
<212> TYPE: DNA
<213> ORGANISM: Artificial Sequence
<220> FEATURE:
<223> OTHER INFORMATION: Primer sequence

<400> SEQUENCE: 174
gaactgatgt gcaagagtct                                               20

<210> SEQ ID NO 175

```
<211> LENGTH: 20
<212> TYPE: DNA
<213> ORGANISM: Artificial Sequence
<220> FEATURE:
<223> OTHER INFORMATION: Primer sequence

<400> SEQUENCE: 175
gatggtacca acgacctaca                                                    20

<210> SEQ ID NO 176
<211> LENGTH: 20
<212> TYPE: DNA
<213> ORGANISM: Artificial Sequence
<220> FEATURE:
<223> OTHER INFORMATION: Primer sequence

<400> SEQUENCE: 176
caacacgaca catccaacct                                                    20

<210> SEQ ID NO 177
<211> LENGTH: 20
<212> TYPE: DNA
<213> ORGANISM: Artificial Sequence
<220> FEATURE:
<223> OTHER INFORMATION: Primer sequence

<400> SEQUENCE: 177
gatgtgctct gcacaccagc                                                    20

<210> SEQ ID NO 178
<211> LENGTH: 20
<212> TYPE: DNA
<213> ORGANISM: Artificial Sequence
<220> FEATURE:
<223> OTHER INFORMATION: Primer sequence

<400> SEQUENCE: 178
ccagtagaac actagaagcg                                                    20

<210> SEQ ID NO 179
<211> LENGTH: 20
<212> TYPE: DNA
<213> ORGANISM: Artificial Sequence
<220> FEATURE:
<223> OTHER INFORMATION: Primer sequence

<400> SEQUENCE: 179
agatcgaaga cgagtgagtg                                                    20

<210> SEQ ID NO 180
<211> LENGTH: 20
<212> TYPE: DNA
<213> ORGANISM: Artificial Sequence
<220> FEATURE:
<223> OTHER INFORMATION: Primer sequence

<400> SEQUENCE: 180
gtaggagagg ttcgatggtg                                                    20

<210> SEQ ID NO 181
<211> LENGTH: 20
<212> TYPE: DNA
<213> ORGANISM: Artificial Sequence
<220> FEATURE:
<223> OTHER INFORMATION: Primer sequence

<400> SEQUENCE: 181
```

```
atccatgtct ggatcagcaa                                                        20

<210> SEQ ID NO 182
<211> LENGTH: 20
<212> TYPE: DNA
<213> ORGANISM: Artificial Sequence
<220> FEATURE:
<223> OTHER INFORMATION: Primer sequence

<400> SEQUENCE: 182
ggtgctccag aacgtacttt                                                        20

<210> SEQ ID NO 183
<211> LENGTH: 20
<212> TYPE: DNA
<213> ORGANISM: Artificial Sequence
<220> FEATURE:
<223> OTHER INFORMATION: Primer sequence

<400> SEQUENCE: 183
ggtaggtacg ttgttctcct                                                        20

<210> SEQ ID NO 184
<211> LENGTH: 20
<212> TYPE: DNA
<213> ORGANISM: Artificial Sequence
<220> FEATURE:
<223> OTHER INFORMATION: Primer sequence

<400> SEQUENCE: 184
gtagcttgca ctggacgtcc                                                        20

<210> SEQ ID NO 185
<211> LENGTH: 20
<212> TYPE: DNA
<213> ORGANISM: Artificial Sequence
<220> FEATURE:
<223> OTHER INFORMATION: Primer sequence

<400> SEQUENCE: 185
ccacttgtgt tccactgatt                                                        20

<210> SEQ ID NO 186
<211> LENGTH: 20
<212> TYPE: DNA
<213> ORGANISM: Artificial Sequence
<220> FEATURE:
<223> OTHER INFORMATION: Primer sequence

<400> SEQUENCE: 186
cgaagaggtg gaacgaccaa                                                        20

<210> SEQ ID NO 187
<211> LENGTH: 20
<212> TYPE: DNA
<213> ORGANISM: Artificial Sequence
<220> FEATURE:
<223> OTHER INFORMATION: Primer sequence

<400> SEQUENCE: 187
gttggtcgat cgagtccaag                                                        20

<210> SEQ ID NO 188
<211> LENGTH: 20
<212> TYPE: DNA
```

```
<213> ORGANISM: Artificial Sequence
<220> FEATURE:
<223> OTHER INFORMATION: Primer sequence

<400> SEQUENCE: 188
tgtccttgtt gcactcctta                                              20

<210> SEQ ID NO 189
<211> LENGTH: 20
<212> TYPE: DNA
<213> ORGANISM: Artificial Sequence
<220> FEATURE:
<223> OTHER INFORMATION: Primer sequence

<400> SEQUENCE: 189
cacatgatgt tctccttggt                                              20

<210> SEQ ID NO 190
<211> LENGTH: 20
<212> TYPE: DNA
<213> ORGANISM: Artificial Sequence
<220> FEATURE:
<223> OTHER INFORMATION: Primer sequence

<400> SEQUENCE: 190
aagtctagtc acacgacacc                                              20

<210> SEQ ID NO 191
<211> LENGTH: 20
<212> TYPE: DNA
<213> ORGANISM: Artificial Sequence
<220> FEATURE:
<223> OTHER INFORMATION: Primer sequence

<400> SEQUENCE: 191
gacctagcat gcttcctagt                                              20

<210> SEQ ID NO 192
<211> LENGTH: 20
<212> TYPE: DNA
<213> ORGANISM: Artificial Sequence
<220> FEATURE:
<223> OTHER INFORMATION: Primer sequence

<400> SEQUENCE: 192
agacacgttc gtggtcgaga                                              20

<210> SEQ ID NO 193
<211> LENGTH: 20
<212> TYPE: DNA
<213> ORGANISM: Artificial Sequence
<220> FEATURE:
<223> OTHER INFORMATION: Primer sequence

<400> SEQUENCE: 193
catccaaggt ctggtctctt                                              20

<210> SEQ ID NO 194
<211> LENGTH: 20
<212> TYPE: DNA
<213> ORGANISM: Artificial Sequence
<220> FEATURE:
<223> OTHER INFORMATION: Primer sequence

<400> SEQUENCE: 194
aggttgaagg tgcaacatgc                                              20
```

<210> SEQ ID NO 195
<211> LENGTH: 20
<212> TYPE: DNA
<213> ORGANISM: Artificial Sequence
<220> FEATURE:
<223> OTHER INFORMATION: Primer sequence

<400> SEQUENCE: 195
cctgagtggt ccttcttgaa                                              20

<210> SEQ ID NO 196
<211> LENGTH: 20
<212> TYPE: DNA
<213> ORGANISM: Artificial Sequence
<220> FEATURE:
<223> OTHER INFORMATION: Primer sequence

<400> SEQUENCE: 196
acctagatgc taggaagcag                                              20

<210> SEQ ID NO 197
<211> LENGTH: 20
<212> TYPE: DNA
<213> ORGANISM: Artificial Sequence
<220> FEATURE:
<223> OTHER INFORMATION: Primer sequence

<400> SEQUENCE: 197
gtagacaagt accactggtc                                              20

<210> SEQ ID NO 198
<211> LENGTH: 20
<212> TYPE: DNA
<213> ORGANISM: Artificial Sequence
<220> FEATURE:
<223> OTHER INFORMATION: Primer sequence

<400> SEQUENCE: 198
gcatggaact tcctgcaggg                                              20

<210> SEQ ID NO 199
<211> LENGTH: 20
<212> TYPE: DNA
<213> ORGANISM: Artificial Sequence
<220> FEATURE:
<223> OTHER INFORMATION: Primer sequence

<400> SEQUENCE: 199
gatcaggact ggttggaagg                                              20

<210> SEQ ID NO 200
<211> LENGTH: 20
<212> TYPE: DNA
<213> ORGANISM: Artificial Sequence
<220> FEATURE:
<223> OTHER INFORMATION: Primer sequence

<400> SEQUENCE: 200
ggacagaagg atcttcagcc                                              20

<210> SEQ ID NO 201
<211> LENGTH: 20
<212> TYPE: DNA
<213> ORGANISM: Artificial Sequence
<220> FEATURE:

<223> OTHER INFORMATION: Primer sequence

<400> SEQUENCE: 201
atctgagttc cttggttctc                                              20

<210> SEQ ID NO 202
<211> LENGTH: 22
<212> TYPE: DNA
<213> ORGANISM: Artificial Sequence
<220> FEATURE:
<223> OTHER INFORMATION: Primer sequence

<400> SEQUENCE: 202
raaactcgtg tcgtctcctt ct                                           22

<210> SEQ ID NO 203
<211> LENGTH: 20
<212> TYPE: DNA
<213> ORGANISM: Artificial Sequence
<220> FEATURE:
<223> OTHER INFORMATION: Primer sequence

<400> SEQUENCE: 203
tctgtgaaca tccaccttcg                                              20

<210> SEQ ID NO 204
<211> LENGTH: 20
<212> TYPE: DNA
<213> ORGANISM: Artificial Sequence
<220> FEATURE:
<223> OTHER INFORMATION: Primer sequence

<400> SEQUENCE: 204
atgtcgatgt agtggtcctc                                              20

<210> SEQ ID NO 205
<211> LENGTH: 20
<212> TYPE: DNA
<213> ORGANISM: Artificial Sequence
<220> FEATURE:
<223> OTHER INFORMATION: Primer sequence

<400> SEQUENCE: 205
gcagttgaac tccacgttgc                                              20

<210> SEQ ID NO 206
<211> LENGTH: 20
<212> TYPE: DNA
<213> ORGANISM: Artificial Sequence
<220> FEATURE:
<223> OTHER INFORMATION: Primer sequence

<400> SEQUENCE: 206
atgtagagtg atgagcttcg                                              20

<210> SEQ ID NO 207
<211> LENGTH: 20
<212> TYPE: DNA
<213> ORGANISM: Artificial Sequence
<220> FEATURE:
<223> OTHER INFORMATION: Primer sequence

<400> SEQUENCE: 207
accaacgtca tcgttgctga                                              20

```
<210> SEQ ID NO 208
<211> LENGTH: 20
<212> TYPE: DNA
<213> ORGANISM: Artificial Sequence
<220> FEATURE:
<223> OTHER INFORMATION: Primer sequence

<400> SEQUENCE: 208
gacgtacaag ttcttggacc                                                20

<210> SEQ ID NO 209
<211> LENGTH: 20
<212> TYPE: DNA
<213> ORGANISM: Artificial Sequence
<220> FEATURE:
<223> OTHER INFORMATION: Primer sequence

<400> SEQUENCE: 209
gttgtaggac caagcaagcg                                                20

<210> SEQ ID NO 210
<211> LENGTH: 20
<212> TYPE: DNA
<213> ORGANISM: Artificial Sequence
<220> FEATURE:
<223> OTHER INFORMATION: Primer sequence

<400> SEQUENCE: 210
tcgaagttca gatcgtgatc                                                20

<210> SEQ ID NO 211
<211> LENGTH: 20
<212> TYPE: DNA
<213> ORGANISM: Artificial Sequence
<220> FEATURE:
<223> OTHER INFORMATION: Primer sequence

<400> SEQUENCE: 211
ctagtgtgaa gtggtccatg                                                20

<210> SEQ ID NO 212
<211> LENGTH: 20
<212> TYPE: DNA
<213> ORGANISM: Artificial Sequence
<220> FEATURE:
<223> OTHER INFORMATION: Primer sequence

<400> SEQUENCE: 212
gcaacagcat cacagatgtt                                                20

<210> SEQ ID NO 213
<211> LENGTH: 20
<212> TYPE: DNA
<213> ORGANISM: Artificial Sequence
<220> FEATURE:
<223> OTHER INFORMATION: Primer sequence

<400> SEQUENCE: 213
cgttcttgaa gctacgacag                                                20

<210> SEQ ID NO 214
<211> LENGTH: 20
<212> TYPE: DNA
<213> ORGANISM: Artificial Sequence
<220> FEATURE:
<223> OTHER INFORMATION: Primer sequence
```

<400> SEQUENCE: 214
gtacctgatc tggatcttgc                                          20

<210> SEQ ID NO 215
<211> LENGTH: 20
<212> TYPE: DNA
<213> ORGANISM: Artificial Sequence
<220> FEATURE:
<223> OTHER INFORMATION: Primer sequence

<400> SEQUENCE: 215
ggactcttct caactgttgt                                          20

<210> SEQ ID NO 216
<211> LENGTH: 20
<212> TYPE: DNA
<213> ORGANISM: Artificial Sequence
<220> FEATURE:
<223> OTHER INFORMATION: Primer sequence

<400> SEQUENCE: 216
gaagtgctcg acatggtcac                                          20

<210> SEQ ID NO 217
<211> LENGTH: 20
<212> TYPE: DNA
<213> ORGANISM: Artificial Sequence
<220> FEATURE:
<223> OTHER INFORMATION: Primer sequence

<400> SEQUENCE: 217
gtactaggac cttcgttgcc                                          20

<210> SEQ ID NO 218
<211> LENGTH: 20
<212> TYPE: DNA
<213> ORGANISM: Artificial Sequence
<220> FEATURE:
<223> OTHER INFORMATION: Primer sequence

<400> SEQUENCE: 218
atcgtacaga ctcctcacag                                          20

<210> SEQ ID NO 219
<211> LENGTH: 20
<212> TYPE: DNA
<213> ORGANISM: Artificial Sequence
<220> FEATURE:
<223> OTHER INFORMATION: Primer sequence

<400> SEQUENCE: 219
ttcgagctac acctgctgac                                          20

<210> SEQ ID NO 220
<211> LENGTH: 20
<212> TYPE: DNA
<213> ORGANISM: Artificial Sequence
<220> FEATURE:
<223> OTHER INFORMATION: Primer sequence

<400> SEQUENCE: 220
ggtccagcaa gagcaccata                                          20

<210> SEQ ID NO 221
<211> LENGTH: 20

```
<212> TYPE: DNA
<213> ORGANISM: Artificial Sequence
<220> FEATURE:
<223> OTHER INFORMATION: Primer sequence

<400> SEQUENCE: 221
ctggtccttc aggaacgtaa                                          20

<210> SEQ ID NO 222
<211> LENGTH: 20
<212> TYPE: DNA
<213> ORGANISM: Artificial Sequence
<220> FEATURE:
<223> OTHER INFORMATION: Primer sequence

<400> SEQUENCE: 222
taggtacctg gtagtgaagt                                          20

<210> SEQ ID NO 223
<211> LENGTH: 20
<212> TYPE: DNA
<213> ORGANISM: Artificial Sequence
<220> FEATURE:
<223> OTHER INFORMATION: Primer sequence

<400> SEQUENCE: 223
ggttgttcct gcttgctcag                                          20

<210> SEQ ID NO 224
<211> LENGTH: 20
<212> TYPE: DNA
<213> ORGANISM: Artificial Sequence
<220> FEATURE:
<223> OTHER INFORMATION: Primer sequence

<400> SEQUENCE: 224
ccagtggact gaccttgtgc                                          20

<210> SEQ ID NO 225
<211> LENGTH: 20
<212> TYPE: DNA
<213> ORGANISM: Artificial Sequence
<220> FEATURE:
<223> OTHER INFORMATION: Primer sequence

<400> SEQUENCE: 225
cgtggttcat ggaagcaacg                                          20

<210> SEQ ID NO 226
<211> LENGTH: 20
<212> TYPE: DNA
<213> ORGANISM: Artificial Sequence
<220> FEATURE:
<223> OTHER INFORMATION: Primer sequence

<400> SEQUENCE: 226
tcctagagac atgcatgcaa                                          20

<210> SEQ ID NO 227
<211> LENGTH: 20
<212> TYPE: DNA
<213> ORGANISM: Artificial Sequence
<220> FEATURE:
<223> OTHER INFORMATION: Primer sequence

<400> SEQUENCE: 227
```
cgagctggat gctacactca                                              20

<210> SEQ ID NO 228
<211> LENGTH: 20
<212> TYPE: DNA
<213> ORGANISM: Artificial Sequence
<220> FEATURE:
<223> OTHER INFORMATION: Primer sequence

<400> SEQUENCE: 228
ggttctctac ctgaagcttc                                              20

<210> SEQ ID NO 229
<211> LENGTH: 20
<212> TYPE: DNA
<213> ORGANISM: Artificial Sequence
<220> FEATURE:
<223> OTHER INFORMATION: Primer sequence

<400> SEQUENCE: 229
ccacttgcag tctgtggaat                                              20

<210> SEQ ID NO 230
<211> LENGTH: 20
<212> TYPE: DNA
<213> ORGANISM: Artificial Sequence
<220> FEATURE:
<223> OTHER INFORMATION: Primer sequence

<400> SEQUENCE: 230
tgaaccagga cactgcttgt                                              20

<210> SEQ ID NO 231
<211> LENGTH: 20
<212> TYPE: DNA
<213> ORGANISM: Artificial Sequence
<220> FEATURE:
<223> OTHER INFORMATION: Primer sequence

<400> SEQUENCE: 231
aagtggaact ggagcactag                                              20

<210> SEQ ID NO 232
<211> LENGTH: 20
<212> TYPE: DNA
<213> ORGANISM: Artificial Sequence
<220> FEATURE:
<223> OTHER INFORMATION: Primer sequence

<400> SEQUENCE: 232
atcctcctac tccagcttca                                              20

<210> SEQ ID NO 233
<211> LENGTH: 20
<212> TYPE: DNA
<213> ORGANISM: Artificial Sequence
<220> FEATURE:
<223> OTHER INFORMATION: Primer sequence

<400> SEQUENCE: 233
accacgtact acctagtctc                                              20

<210> SEQ ID NO 234
<211> LENGTH: 20
<212> TYPE: DNA
<213> ORGANISM: Artificial Sequence

```
<220> FEATURE:
<223> OTHER INFORMATION: Primer sequence

<400> SEQUENCE: 234
ggtacttgga tggtgttcgt                                         20

<210> SEQ ID NO 235
<211> LENGTH: 20
<212> TYPE: DNA
<213> ORGANISM: Artificial Sequence
<220> FEATURE:
<223> OTHER INFORMATION: Primer sequence

<400> SEQUENCE: 235
ggaacttgag tccttgatga                                         20

<210> SEQ ID NO 236
<211> LENGTH: 20
<212> TYPE: DNA
<213> ORGANISM: Artificial Sequence
<220> FEATURE:
<223> OTHER INFORMATION: Primer sequence

<400> SEQUENCE: 236
gaagaggtcg taggaaggaa                                         20

<210> SEQ ID NO 237
<211> LENGTH: 20
<212> TYPE: DNA
<213> ORGANISM: Artificial Sequence
<220> FEATURE:
<223> OTHER INFORMATION: Primer sequence

<400> SEQUENCE: 237
gaggtgcttc gtcgttggta                                         20

<210> SEQ ID NO 238
<211> LENGTH: 20
<212> TYPE: DNA
<213> ORGANISM: Artificial Sequence
<220> FEATURE:
<223> OTHER INFORMATION: Primer sequence

<400> SEQUENCE: 238
ggaaggatct ggtacgtcca                                         20

<210> SEQ ID NO 239
<211> LENGTH: 20
<212> TYPE: DNA
<213> ORGANISM: Artificial Sequence
<220> FEATURE:
<223> OTHER INFORMATION: Primer sequence

<400> SEQUENCE: 239
gcaagttgta gcatcaagga                                         20

<210> SEQ ID NO 240
<211> LENGTH: 20
<212> TYPE: DNA
<213> ORGANISM: Artificial Sequence
<220> FEATURE:
<223> OTHER INFORMATION: Primer sequence

<400> SEQUENCE: 240
caagcagacg atcaaggatt                                         20
```

```
<210> SEQ ID NO 241
<211> LENGTH: 20
<212> TYPE: DNA
<213> ORGANISM: Artificial Sequence
<220> FEATURE:
<223> OTHER INFORMATION: Primer sequence

<400> SEQUENCE: 241
cctcatctct ctctggtcac                                              20

<210> SEQ ID NO 242
<211> LENGTH: 20
<212> TYPE: DNA
<213> ORGANISM: Artificial Sequence
<220> FEATURE:
<223> OTHER INFORMATION: Primer sequence

<400> SEQUENCE: 242
tcgtagcatc cagcaacagt                                              20

<210> SEQ ID NO 243
<211> LENGTH: 20
<212> TYPE: DNA
<213> ORGANISM: Artificial Sequence
<220> FEATURE:
<223> OTHER INFORMATION: Primer sequence

<400> SEQUENCE: 243
tcgaaggtcg ttcaccagtg                                              20

<210> SEQ ID NO 244
<211> LENGTH: 20
<212> TYPE: DNA
<213> ORGANISM: Artificial Sequence
<220> FEATURE:
<223> OTHER INFORMATION: Primer sequence

<400> SEQUENCE: 244
aacgatcaca aggagcagtc                                              20

<210> SEQ ID NO 245
<211> LENGTH: 20
<212> TYPE: DNA
<213> ORGANISM: Artificial Sequence
<220> FEATURE:
<223> OTHER INFORMATION: Primer sequence

<400> SEQUENCE: 245
cacgactagc aactcatggc                                              20

<210> SEQ ID NO 246
<211> LENGTH: 20
<212> TYPE: DNA
<213> ORGANISM: Artificial Sequence
<220> FEATURE:
<223> OTHER INFORMATION: Primer sequence

<400> SEQUENCE: 246
cttgtgtcca cgaagaacat                                              20

<210> SEQ ID NO 247
<211> LENGTH: 20
<212> TYPE: DNA
<213> ORGANISM: Artificial Sequence
<220> FEATURE:
<223> OTHER INFORMATION: Primer sequence
```

<400> SEQUENCE: 247
ctagaggtgg tcctcctgta                                                    20

<210> SEQ ID NO 248
<211> LENGTH: 20
<212> TYPE: DNA
<213> ORGANISM: Artificial Sequence
<220> FEATURE:
<223> OTHER INFORMATION: Primer sequence

<400> SEQUENCE: 248
gaagtagaac gatgcaacgg                                                    20

<210> SEQ ID NO 249
<211> LENGTH: 20
<212> TYPE: DNA
<213> ORGANISM: Artificial Sequence
<220> FEATURE:
<223> OTHER INFORMATION: Primer sequence

<400> SEQUENCE: 249
tacgatgcac acttggttgc                                                    20

<210> SEQ ID NO 250
<211> LENGTH: 20
<212> TYPE: DNA
<213> ORGANISM: Artificial Sequence
<220> FEATURE:
<223> OTHER INFORMATION: Primer sequence

<400> SEQUENCE: 250
gatcacagga tcatgttggc                                                    20

<210> SEQ ID NO 251
<211> LENGTH: 20
<212> TYPE: DNA
<213> ORGANISM: Artificial Sequence
<220> FEATURE:
<223> OTHER INFORMATION: Primer sequence

<400> SEQUENCE: 251
tgcatgagag acatggagat                                                    20

<210> SEQ ID NO 252
<211> LENGTH: 20
<212> TYPE: DNA
<213> ORGANISM: Artificial Sequence
<220> FEATURE:
<223> OTHER INFORMATION: Primer sequence

<400> SEQUENCE: 252
cgttgtgcat gtaccaagtg                                                    20

<210> SEQ ID NO 253
<211> LENGTH: 20
<212> TYPE: DNA
<213> ORGANISM: Artificial Sequence
<220> FEATURE:
<223> OTHER INFORMATION: Primer sequence

<400> SEQUENCE: 253
tgtgtaccta gctgcttggg                                                    20

<210> SEQ ID NO 254

-continued

```
<211> LENGTH: 20
<212> TYPE: DNA
<213> ORGANISM: Artificial Sequence
<220> FEATURE:
<223> OTHER INFORMATION: Primer sequence

<400> SEQUENCE: 254
tctcctgtgg aagcagcagt                                            20

<210> SEQ ID NO 255
<211> LENGTH: 20
<212> TYPE: DNA
<213> ORGANISM: Artificial Sequence
<220> FEATURE:
<223> OTHER INFORMATION: Primer sequence

<400> SEQUENCE: 255
tagcactacg tgatctgaga                                            20

<210> SEQ ID NO 256
<211> LENGTH: 20
<212> TYPE: DNA
<213> ORGANISM: Artificial Sequence
<220> FEATURE:
<223> OTHER INFORMATION: Primer sequence

<400> SEQUENCE: 256
gtcttgaact gatcctacag                                            20

<210> SEQ ID NO 257
<211> LENGTH: 20
<212> TYPE: DNA
<213> ORGANISM: Artificial Sequence
<220> FEATURE:
<223> OTHER INFORMATION: Primer sequence

<400> SEQUENCE: 257
gcagctgcag cagtcgtagt                                            20

<210> SEQ ID NO 258
<211> LENGTH: 20
<212> TYPE: DNA
<213> ORGANISM: Artificial Sequence
<220> FEATURE:
<223> OTHER INFORMATION: Primer sequence

<400> SEQUENCE: 258
ttgcttggag agtgtcactg                                            20

<210> SEQ ID NO 259
<211> LENGTH: 20
<212> TYPE: DNA
<213> ORGANISM: Artificial Sequence
<220> FEATURE:
<223> OTHER INFORMATION: Primer sequence

<400> SEQUENCE: 259
ggagtggttg gtgagagaga                                            20

<210> SEQ ID NO 260
<211> LENGTH: 20
<212> TYPE: DNA
<213> ORGANISM: Artificial Sequence
<220> FEATURE:
<223> OTHER INFORMATION: Primer sequence

<400> SEQUENCE: 260
```

```
aacgaaggtt ctgctctggt                                              20

<210> SEQ ID NO 261
<211> LENGTH: 20
<212> TYPE: DNA
<213> ORGANISM: Artificial Sequence
<220> FEATURE:
<223> OTHER INFORMATION: Primer sequence

<400> SEQUENCE: 261
agtccatctg ctcgtagcat                                              20

<210> SEQ ID NO 262
<211> LENGTH: 20
<212> TYPE: DNA
<213> ORGANISM: Artificial Sequence
<220> FEATURE:
<223> OTHER INFORMATION: Primer sequence

<400> SEQUENCE: 262
cgtgctccaa gcagtagctg                                              20

<210> SEQ ID NO 263
<211> LENGTH: 20
<212> TYPE: DNA
<213> ORGANISM: Artificial Sequence
<220> FEATURE:
<223> OTHER INFORMATION: Primer sequence

<400> SEQUENCE: 263
gtctgatcct accttccata                                              20

<210> SEQ ID NO 264
<211> LENGTH: 20
<212> TYPE: DNA
<213> ORGANISM: Artificial Sequence
<220> FEATURE:
<223> OTHER INFORMATION: Primer sequence

<400> SEQUENCE: 264
aagttctcct gatgctcatc                                              20

<210> SEQ ID NO 265
<211> LENGTH: 20
<212> TYPE: DNA
<213> ORGANISM: Artificial Sequence
<220> FEATURE:
<223> OTHER INFORMATION: Primer sequence

<400> SEQUENCE: 265
ctgatccact gagcacttca                                              20

<210> SEQ ID NO 266
<211> LENGTH: 20
<212> TYPE: DNA
<213> ORGANISM: Artificial Sequence
<220> FEATURE:
<223> OTHER INFORMATION: Primer sequence

<400> SEQUENCE: 266
acgttccaag tcgtcatcgg                                              20

<210> SEQ ID NO 267
<211> LENGTH: 20
<212> TYPE: DNA
```

```
<213> ORGANISM: Artificial Sequence
<220> FEATURE:
<223> OTHER INFORMATION: Primer sequence

<400> SEQUENCE: 267
ggtcacgatg catcctgaca                                              20

<210> SEQ ID NO 268
<211> LENGTH: 20
<212> TYPE: DNA
<213> ORGANISM: Artificial Sequence
<220> FEATURE:
<223> OTHER INFORMATION: Primer sequence

<400> SEQUENCE: 268
tcgtagcaag tgaggaacag                                              20

<210> SEQ ID NO 269
<211> LENGTH: 20
<212> TYPE: DNA
<213> ORGANISM: Artificial Sequence
<220> FEATURE:
<223> OTHER INFORMATION: Primer sequence

<400> SEQUENCE: 269
ggtgcttggt acgaacgtcg                                              20

<210> SEQ ID NO 270
<211> LENGTH: 20
<212> TYPE: DNA
<213> ORGANISM: Artificial Sequence
<220> FEATURE:
<223> OTHER INFORMATION: Primer sequence

<400> SEQUENCE: 270
ctcgaccaac ctgacctgaa                                              20

<210> SEQ ID NO 271
<211> LENGTH: 20
<212> TYPE: DNA
<213> ORGANISM: Artificial Sequence
<220> FEATURE:
<223> OTHER INFORMATION: Primer sequence

<400> SEQUENCE: 271
ttggatcgac aggaccttct                                              20

<210> SEQ ID NO 272
<211> LENGTH: 20
<212> TYPE: DNA
<213> ORGANISM: Artificial Sequence
<220> FEATURE:
<223> OTHER INFORMATION: Primer sequence

<400> SEQUENCE: 272
tacttcgtcc agttccttgc                                              20

<210> SEQ ID NO 273
<211> LENGTH: 20
<212> TYPE: DNA
<213> ORGANISM: Artificial Sequence
<220> FEATURE:
<223> OTHER INFORMATION: Primer sequence

<400> SEQUENCE: 273
atcctcttgc tgtcagtcgc                                              20
```

<210> SEQ ID NO 274
<211> LENGTH: 20
<212> TYPE: DNA
<213> ORGANISM: Artificial Sequence
<220> FEATURE:
<223> OTHER INFORMATION: Primer sequence

<400> SEQUENCE: 274
ggtgaagtac gacaactact                                               20

<210> SEQ ID NO 275
<211> LENGTH: 20
<212> TYPE: DNA
<213> ORGANISM: Artificial Sequence
<220> FEATURE:
<223> OTHER INFORMATION: Primer sequence

<400> SEQUENCE: 275
tcgtacctgt cttgtgtacc                                               20

<210> SEQ ID NO 276
<211> LENGTH: 20
<212> TYPE: DNA
<213> ORGANISM: Artificial Sequence
<220> FEATURE:
<223> OTHER INFORMATION: Primer sequence

<400> SEQUENCE: 276
ctggatgacc agaacttcat                                               20

<210> SEQ ID NO 277
<211> LENGTH: 20
<212> TYPE: DNA
<213> ORGANISM: Artificial Sequence
<220> FEATURE:
<223> OTHER INFORMATION: Primer sequence

<400> SEQUENCE: 277
gatcgacttg cagacgtgca                                               20

<210> SEQ ID NO 278
<211> LENGTH: 20
<212> TYPE: DNA
<213> ORGANISM: Artificial Sequence
<220> FEATURE:
<223> OTHER INFORMATION: Primer sequence

<400> SEQUENCE: 278
agctacgtga gagaagacac                                               20

<210> SEQ ID NO 279
<211> LENGTH: 20
<212> TYPE: DNA
<213> ORGANISM: Artificial Sequence
<220> FEATURE:
<223> OTHER INFORMATION: Primer sequence

<400> SEQUENCE: 279
agtctggtgg tgacgacttt                                               20

<210> SEQ ID NO 280
<211> LENGTH: 20
<212> TYPE: DNA
<213> ORGANISM: Artificial Sequence
<220> FEATURE:

<223> OTHER INFORMATION: Primer sequence

<400> SEQUENCE: 280
gctaggagca ccatcacgat                                               20

<210> SEQ ID NO 281
<211> LENGTH: 20
<212> TYPE: DNA
<213> ORGANISM: Artificial Sequence
<220> FEATURE:
<223> OTHER INFORMATION: Primer sequence

<400> SEQUENCE: 281
tgagaaggat ctcgtacctc                                               20

<210> SEQ ID NO 282
<211> LENGTH: 20
<212> TYPE: DNA
<213> ORGANISM: Artificial Sequence
<220> FEATURE:
<223> OTHER INFORMATION: Primer sequence

<400> SEQUENCE: 282
tagcatcgtt gctccagaca                                               20

<210> SEQ ID NO 283
<211> LENGTH: 20
<212> TYPE: DNA
<213> ORGANISM: Artificial Sequence
<220> FEATURE:
<223> OTHER INFORMATION: Primer sequence

<400> SEQUENCE: 283
aagaactctt cgactccaag                                               20

<210> SEQ ID NO 284
<211> LENGTH: 20
<212> TYPE: DNA
<213> ORGANISM: Artificial Sequence
<220> FEATURE:
<223> OTHER INFORMATION: Primer sequence

<400> SEQUENCE: 284
acgtagtaga gctacaagtc                                               20

<210> SEQ ID NO 285
<211> LENGTH: 20
<212> TYPE: DNA
<213> ORGANISM: Artificial Sequence
<220> FEATURE:
<223> OTHER INFORMATION: Primer sequence

<400> SEQUENCE: 285
cgtcctacca accaagctat                                               20

<210> SEQ ID NO 286
<211> LENGTH: 20
<212> TYPE: DNA
<213> ORGANISM: Artificial Sequence
<220> FEATURE:
<223> OTHER INFORMATION: Primer sequence

<400> SEQUENCE: 286
gttgctcctc cttctcgatt                                               20

```
<210> SEQ ID NO 287
<211> LENGTH: 20
<212> TYPE: DNA
<213> ORGANISM: Artificial Sequence
<220> FEATURE:
<223> OTHER INFORMATION: Primer sequence

<400> SEQUENCE: 287
gacaactgtc ctcgtacact                                              20

<210> SEQ ID NO 288
<211> LENGTH: 20
<212> TYPE: DNA
<213> ORGANISM: Artificial Sequence
<220> FEATURE:
<223> OTHER INFORMATION: Primer sequence

<400> SEQUENCE: 288
gcatgagaac tcttgatcca                                              20

<210> SEQ ID NO 289
<211> LENGTH: 20
<212> TYPE: DNA
<213> ORGANISM: Artificial Sequence
<220> FEATURE:
<223> OTHER INFORMATION: Primer sequence

<400> SEQUENCE: 289
cctccatgct gaagtggaaa                                              20

<210> SEQ ID NO 290
<211> LENGTH: 20
<212> TYPE: DNA
<213> ORGANISM: Artificial Sequence
<220> FEATURE:
<223> OTHER INFORMATION: Primer sequence

<400> SEQUENCE: 290
ggtacgacca tcagtccacc                                              20

<210> SEQ ID NO 291
<211> LENGTH: 20
<212> TYPE: DNA
<213> ORGANISM: Artificial Sequence
<220> FEATURE:
<223> OTHER INFORMATION: Primer sequence

<400> SEQUENCE: 291
tacagttgtc tctggtcttg                                              20

<210> SEQ ID NO 292
<211> LENGTH: 20
<212> TYPE: DNA
<213> ORGANISM: Artificial Sequence
<220> FEATURE:
<223> OTHER INFORMATION: Primer sequence

<400> SEQUENCE: 292
accttgaaca acgactcctg                                              20

<210> SEQ ID NO 293
<211> LENGTH: 20
<212> TYPE: DNA
<213> ORGANISM: Artificial Sequence
<220> FEATURE:
<223> OTHER INFORMATION: Primer sequence
```

```
<400> SEQUENCE: 293
gaccaagtca gtgcaagagc                                              20

<210> SEQ ID NO 294
<211> LENGTH: 20
<212> TYPE: DNA
<213> ORGANISM: Artificial Sequence
<220> FEATURE:
<223> OTHER INFORMATION: Primer sequence

<400> SEQUENCE: 294
ctacacaagt gctagtcttg                                              20

<210> SEQ ID NO 295
<211> LENGTH: 20
<212> TYPE: DNA
<213> ORGANISM: Artificial Sequence
<220> FEATURE:
<223> OTHER INFORMATION: Primer sequence

<400> SEQUENCE: 295
gtctgctgta gcaactcatc                                              20

<210> SEQ ID NO 296
<211> LENGTH: 20
<212> TYPE: DNA
<213> ORGANISM: Artificial Sequence
<220> FEATURE:
<223> OTHER INFORMATION: Primer sequence

<400> SEQUENCE: 296
actgctcaag agatcactca                                              20

<210> SEQ ID NO 297
<211> LENGTH: 20
<212> TYPE: DNA
<213> ORGANISM: Artificial Sequence
<220> FEATURE:
<223> OTHER INFORMATION: Primer sequence

<400> SEQUENCE: 297
gatccacacg ttgcacgttc                                              20

<210> SEQ ID NO 298
<211> LENGTH: 20
<212> TYPE: DNA
<213> ORGANISM: Artificial Sequence
<220> FEATURE:
<223> OTHER INFORMATION: Primer sequence

<400> SEQUENCE: 298
agacctccat cgatggtagg                                              20

<210> SEQ ID NO 299
<211> LENGTH: 20
<212> TYPE: DNA
<213> ORGANISM: Artificial Sequence
<220> FEATURE:
<223> OTHER INFORMATION: Primer sequence

<400> SEQUENCE: 299
tgttctcaca gcttcctaca                                              20

<210> SEQ ID NO 300
<211> LENGTH: 20
```

```
<212> TYPE: DNA
<213> ORGANISM: Artificial Sequence
<220> FEATURE:
<223> OTHER INFORMATION: Primer sequence

<400> SEQUENCE: 300
atcacaagga gatggttctc                                              20

<210> SEQ ID NO 301
<211> LENGTH: 20
<212> TYPE: DNA
<213> ORGANISM: Artificial Sequence
<220> FEATURE:
<223> OTHER INFORMATION: Primer sequence

<400> SEQUENCE: 301
caccttgcac cttgcatcac                                              20

<210> SEQ ID NO 302
<211> LENGTH: 20
<212> TYPE: DNA
<213> ORGANISM: Artificial Sequence
<220> FEATURE:
<223> OTHER INFORMATION: Primer sequence

<400> SEQUENCE: 302
tgttgtcgag tcctccaact                                              20

<210> SEQ ID NO 303
<211> LENGTH: 20
<212> TYPE: DNA
<213> ORGANISM: Artificial Sequence
<220> FEATURE:
<223> OTHER INFORMATION: Primer sequence

<400> SEQUENCE: 303
atccacacca cgacatctaa                                              20

<210> SEQ ID NO 304
<211> LENGTH: 20
<212> TYPE: DNA
<213> ORGANISM: Artificial Sequence
<220> FEATURE:
<223> OTHER INFORMATION: Primer sequence

<400> SEQUENCE: 304
catgtgaaga acctcgtccc                                              20

<210> SEQ ID NO 305
<211> LENGTH: 20
<212> TYPE: DNA
<213> ORGANISM: Artificial Sequence
<220> FEATURE:
<223> OTHER INFORMATION: Primer sequence

<400> SEQUENCE: 305
tctcctgtcc aacagtcctt                                              20

<210> SEQ ID NO 306
<211> LENGTH: 20
<212> TYPE: DNA
<213> ORGANISM: Artificial Sequence
<220> FEATURE:
<223> OTHER INFORMATION: Primer sequence

<400> SEQUENCE: 306
```
gttggacagc aaccagtggt                                                   20

<210> SEQ ID NO 307
<211> LENGTH: 20
<212> TYPE: DNA
<213> ORGANISM: Artificial Sequence
<220> FEATURE:
<223> OTHER INFORMATION: Primer sequence

<400> SEQUENCE: 307
gtaggtacag gtgaggtact                                                   20

<210> SEQ ID NO 308
<211> LENGTH: 20
<212> TYPE: DNA
<213> ORGANISM: Artificial Sequence
<220> FEATURE:
<223> OTHER INFORMATION: Primer sequence

<400> SEQUENCE: 308
aagatgagga gtgcagtaca                                                   20

<210> SEQ ID NO 309
<211> LENGTH: 20
<212> TYPE: DNA
<213> ORGANISM: Artificial Sequence
<220> FEATURE:
<223> OTHER INFORMATION: Primer sequence

<400> SEQUENCE: 309
taccttgaag cacgatggaa                                                   20

<210> SEQ ID NO 310
<211> LENGTH: 20
<212> TYPE: DNA
<213> ORGANISM: Artificial Sequence
<220> FEATURE:
<223> OTHER INFORMATION: Primer sequence

<400> SEQUENCE: 310
atcatgtcct tggatggact                                                   20

<210> SEQ ID NO 311
<211> LENGTH: 20
<212> TYPE: DNA
<213> ORGANISM: Artificial Sequence
<220> FEATURE:
<223> OTHER INFORMATION: Primer sequence

<400> SEQUENCE: 311
gatgctgatg agtgcaacta                                                   20

<210> SEQ ID NO 312
<211> LENGTH: 20
<212> TYPE: DNA
<213> ORGANISM: Artificial Sequence
<220> FEATURE:
<223> OTHER INFORMATION: Primer sequence

<400> SEQUENCE: 312
tacgtcaacg tagatggtga                                                   20

<210> SEQ ID NO 313
<211> LENGTH: 20
<212> TYPE: DNA
<213> ORGANISM: Artificial Sequence

```
<220> FEATURE:
<223> OTHER INFORMATION: Primer sequence

<400> SEQUENCE: 313
cgatctgaca gtccaaggta                                               20

<210> SEQ ID NO 314
<211> LENGTH: 20
<212> TYPE: DNA
<213> ORGANISM: Artificial Sequence
<220> FEATURE:
<223> OTHER INFORMATION: Primer sequence

<400> SEQUENCE: 314
ccacgatctc ctacagactt                                               20

<210> SEQ ID NO 315
<211> LENGTH: 20
<212> TYPE: DNA
<213> ORGANISM: Artificial Sequence
<220> FEATURE:
<223> OTHER INFORMATION: Primer sequence

<400> SEQUENCE: 315
cctcgtcctg atgttgcatc                                               20

<210> SEQ ID NO 316
<211> LENGTH: 20
<212> TYPE: DNA
<213> ORGANISM: Artificial Sequence
<220> FEATURE:
<223> OTHER INFORMATION: Primer sequence

<400> SEQUENCE: 316
ccaacttgga ggttcatgcg                                               20

<210> SEQ ID NO 317
<211> LENGTH: 20
<212> TYPE: DNA
<213> ORGANISM: Artificial Sequence
<220> FEATURE:
<223> OTHER INFORMATION: Primer sequence

<400> SEQUENCE: 317
ttggttctga cactgtagac                                               20

<210> SEQ ID NO 318
<211> LENGTH: 20
<212> TYPE: DNA
<213> ORGANISM: Artificial Sequence
<220> FEATURE:
<223> OTHER INFORMATION: Primer sequence

<400> SEQUENCE: 318
atcaacctac caccaggaaa                                               20

<210> SEQ ID NO 319
<211> LENGTH: 20
<212> TYPE: DNA
<213> ORGANISM: Artificial Sequence
<220> FEATURE:
<223> OTHER INFORMATION: Primer sequence

<400> SEQUENCE: 319
ttctcacgac agcaaccttg                                               20
```

<210> SEQ ID NO 320
<211> LENGTH: 20
<212> TYPE: DNA
<213> ORGANISM: Artificial Sequence
<220> FEATURE:
<223> OTHER INFORMATION: Primer sequence

<400> SEQUENCE: 320
ctctcttgca gctactgaat                                               20

<210> SEQ ID NO 321
<211> LENGTH: 20
<212> TYPE: DNA
<213> ORGANISM: Artificial Sequence
<220> FEATURE:
<223> OTHER INFORMATION: Primer sequence

<400> SEQUENCE: 321
agtcaagtca gagttcgtac                                               20

<210> SEQ ID NO 322
<211> LENGTH: 20
<212> TYPE: DNA
<213> ORGANISM: Artificial Sequence
<220> FEATURE:
<223> OTHER INFORMATION: Primer sequence

<400> SEQUENCE: 322
tagatcgtca ctgacgatcc                                               20

<210> SEQ ID NO 323
<211> LENGTH: 20
<212> TYPE: DNA
<213> ORGANISM: Artificial Sequence
<220> FEATURE:
<223> OTHER INFORMATION: Primer sequence

<400> SEQUENCE: 323
ggacgtgaag gacatcacag                                               20

<210> SEQ ID NO 324
<211> LENGTH: 20
<212> TYPE: DNA
<213> ORGANISM: Artificial Sequence
<220> FEATURE:
<223> OTHER INFORMATION: Primer sequence

<400> SEQUENCE: 324
cactacttgt tctacgtgcc                                               20

<210> SEQ ID NO 325
<211> LENGTH: 20
<212> TYPE: DNA
<213> ORGANISM: Artificial Sequence
<220> FEATURE:
<223> OTHER INFORMATION: Primer sequence

<400> SEQUENCE: 325
atcgttccag tcgagttgat                                               20

<210> SEQ ID NO 326
<211> LENGTH: 20
<212> TYPE: DNA
<213> ORGANISM: Artificial Sequence
<220> FEATURE:
<223> OTHER INFORMATION: Primer sequence

```
<400> SEQUENCE: 326
atcaaccacc tctaccaccg                                                    20

<210> SEQ ID NO 327
<211> LENGTH: 20
<212> TYPE: DNA
<213> ORGANISM: Artificial Sequence
<220> FEATURE:
<223> OTHER INFORMATION: Primer sequence

<400> SEQUENCE: 327
aagctacaac agcagctacg                                                    20

<210> SEQ ID NO 328
<211> LENGTH: 20
<212> TYPE: DNA
<213> ORGANISM: Artificial Sequence
<220> FEATURE:
<223> OTHER INFORMATION: Primer sequence

<400> SEQUENCE: 328
ccagtaggtg atgcaacgta                                                    20

<210> SEQ ID NO 329
<211> LENGTH: 20
<212> TYPE: DNA
<213> ORGANISM: Artificial Sequence
<220> FEATURE:
<223> OTHER INFORMATION: Primer sequence

<400> SEQUENCE: 329
aacaggtcca caacagatgg                                                    20

<210> SEQ ID NO 330
<211> LENGTH: 20
<212> TYPE: DNA
<213> ORGANISM: Artificial Sequence
<220> FEATURE:
<223> OTHER INFORMATION: Primer sequence

<400> SEQUENCE: 330
ccatgtcgta gatcgttcac                                                    20

<210> SEQ ID NO 331
<211> LENGTH: 20
<212> TYPE: DNA
<213> ORGANISM: Artificial Sequence
<220> FEATURE:
<223> OTHER INFORMATION: Primer sequence

<400> SEQUENCE: 331
tcatgtctcg tagacactgc                                                    20

<210> SEQ ID NO 332
<211> LENGTH: 20
<212> TYPE: DNA
<213> ORGANISM: Artificial Sequence
<220> FEATURE:
<223> OTHER INFORMATION: Primer sequence

<400> SEQUENCE: 332
gacgaagcac agcatccata                                                    20

<210> SEQ ID NO 333
```

```
<210> SEQ ID NO 333
<211> LENGTH: 20
<212> TYPE: DNA
<213> ORGANISM: Artificial Sequence
<220> FEATURE:
<223> OTHER INFORMATION: Primer sequence

<400> SEQUENCE: 333
gctgcttctg aggaggatcc                                            20

<210> SEQ ID NO 334
<211> LENGTH: 20
<212> TYPE: DNA
<213> ORGANISM: Artificial Sequence
<220> FEATURE:
<223> OTHER INFORMATION: Primer sequence

<400> SEQUENCE: 334
gcaacagaac tacatgaccg                                            20

<210> SEQ ID NO 335
<211> LENGTH: 20
<212> TYPE: DNA
<213> ORGANISM: Artificial Sequence
<220> FEATURE:
<223> OTHER INFORMATION: Primer sequence

<400> SEQUENCE: 335
ggacagcttc gatgcttcat                                            20

<210> SEQ ID NO 336
<211> LENGTH: 20
<212> TYPE: DNA
<213> ORGANISM: Artificial Sequence
<220> FEATURE:
<223> OTHER INFORMATION: Primer sequence

<400> SEQUENCE: 336
acctagtggt acatcttcct                                            20

<210> SEQ ID NO 337
<211> LENGTH: 20
<212> TYPE: DNA
<213> ORGANISM: Artificial Sequence
<220> FEATURE:
<223> OTHER INFORMATION: Primer sequence

<400> SEQUENCE: 337
cgtgtagaac cacgttcgac                                            20

<210> SEQ ID NO 338
<211> LENGTH: 20
<212> TYPE: DNA
<213> ORGANISM: Artificial Sequence
<220> FEATURE:
<223> OTHER INFORMATION: Primer sequence

<400> SEQUENCE: 338
gtgctaccag aaggatgcaa                                            20

<210> SEQ ID NO 339
<211> LENGTH: 20
<212> TYPE: DNA
<213> ORGANISM: Artificial Sequence
<220> FEATURE:
<223> OTHER INFORMATION: Primer sequence

<400> SEQUENCE: 339
```
ccacacaggt ctcctacatg                                              20

<210> SEQ ID NO 340
<211> LENGTH: 20
<212> TYPE: DNA
<213> ORGANISM: Artificial Sequence
<220> FEATURE:
<223> OTHER INFORMATION: Primer sequence

<400> SEQUENCE: 340
gttgagtcga tccagagtag                                              20

<210> SEQ ID NO 341
<211> LENGTH: 20
<212> TYPE: DNA
<213> ORGANISM: Artificial Sequence
<220> FEATURE:
<223> OTHER INFORMATION: Primer sequence

<400> SEQUENCE: 341
ggttccttcc tgaggttcga                                              20

<210> SEQ ID NO 342
<211> LENGTH: 20
<212> TYPE: DNA
<213> ORGANISM: Artificial Sequence
<220> FEATURE:
<223> OTHER INFORMATION: Primer sequence

<400> SEQUENCE: 342
atcgtccaac gaagcaagtt                                              20

<210> SEQ ID NO 343
<211> LENGTH: 20
<212> TYPE: DNA
<213> ORGANISM: Artificial Sequence
<220> FEATURE:
<223> OTHER INFORMATION: Primer sequence

<400> SEQUENCE: 343
agtacgttgc tagttgacgc                                              20

<210> SEQ ID NO 344
<211> LENGTH: 20
<212> TYPE: DNA
<213> ORGANISM: Artificial Sequence
<220> FEATURE:
<223> OTHER INFORMATION: Primer sequence

<400> SEQUENCE: 344
ggacctacct tgcatgagga                                              20

<210> SEQ ID NO 345
<211> LENGTH: 20
<212> TYPE: DNA
<213> ORGANISM: Artificial Sequence
<220> FEATURE:
<223> OTHER INFORMATION: Primer sequence

<400> SEQUENCE: 345
gatcgacttg aacttcaccc                                              20

<210> SEQ ID NO 346
<211> LENGTH: 20
<212> TYPE: DNA

```
<213> ORGANISM: Artificial Sequence
<220> FEATURE:
<223> OTHER INFORMATION: Primer sequence

<400> SEQUENCE: 346
tcaacgaaca cctgtccacg                                               20

<210> SEQ ID NO 347
<211> LENGTH: 20
<212> TYPE: DNA
<213> ORGANISM: Artificial Sequence
<220> FEATURE:
<223> OTHER INFORMATION: Primer sequence

<400> SEQUENCE: 347
ggtgaagcaa gtgttcaact                                               20

<210> SEQ ID NO 348
<211> LENGTH: 20
<212> TYPE: DNA
<213> ORGANISM: Artificial Sequence
<220> FEATURE:
<223> OTHER INFORMATION: Primer sequence

<400> SEQUENCE: 348
gctagatgtg aaggtcctaa                                               20

<210> SEQ ID NO 349
<211> LENGTH: 20
<212> TYPE: DNA
<213> ORGANISM: Artificial Sequence
<220> FEATURE:
<223> OTHER INFORMATION: Primer sequence

<400> SEQUENCE: 349
aagacagtac cacgatgcta                                               20

<210> SEQ ID NO 350
<211> LENGTH: 20
<212> TYPE: DNA
<213> ORGANISM: Artificial Sequence
<220> FEATURE:
<223> OTHER INFORMATION: Primer sequence

<400> SEQUENCE: 350
gttcgtacca ccttcaagac                                               20

<210> SEQ ID NO 351
<211> LENGTH: 20
<212> TYPE: DNA
<213> ORGANISM: Artificial Sequence
<220> FEATURE:
<223> OTHER INFORMATION: Primer sequence

<400> SEQUENCE: 351
tggagtcgta cagaagcatg                                               20

<210> SEQ ID NO 352
<211> LENGTH: 20
<212> TYPE: DNA
<213> ORGANISM: Artificial Sequence
<220> FEATURE:
<223> OTHER INFORMATION: Primer sequence

<400> SEQUENCE: 352
acctacagta ccaggtggtg                                               20
```

<210> SEQ ID NO 353
<211> LENGTH: 20
<212> TYPE: DNA
<213> ORGANISM: Artificial Sequence
<220> FEATURE:
<223> OTHER INFORMATION: Primer sequence

<400> SEQUENCE: 353
cgagactgtt cctgcactcc                                              20

<210> SEQ ID NO 354
<211> LENGTH: 20
<212> TYPE: DNA
<213> ORGANISM: Artificial Sequence
<220> FEATURE:
<223> OTHER INFORMATION: Primer sequence

<400> SEQUENCE: 354
tactctgcac gtcagttgta                                              20

<210> SEQ ID NO 355
<211> LENGTH: 20
<212> TYPE: DNA
<213> ORGANISM: Artificial Sequence
<220> FEATURE:
<223> OTHER INFORMATION: Primer sequence

<400> SEQUENCE: 355
gctcctgatg tcctggttgc                                              20

<210> SEQ ID NO 356
<211> LENGTH: 20
<212> TYPE: DNA
<213> ORGANISM: Artificial Sequence
<220> FEATURE:
<223> OTHER INFORMATION: Primer sequence

<400> SEQUENCE: 356
tccacatcca gctcgtggtt                                              20

<210> SEQ ID NO 357
<211> LENGTH: 20
<212> TYPE: DNA
<213> ORGANISM: Artificial Sequence
<220> FEATURE:
<223> OTHER INFORMATION: Primer sequence

<400> SEQUENCE: 357
cgagcaccaa gcactgttgt                                              20

<210> SEQ ID NO 358
<211> LENGTH: 20
<212> TYPE: DNA
<213> ORGANISM: Artificial Sequence
<220> FEATURE:
<223> OTHER INFORMATION: Primer sequence

<400> SEQUENCE: 358
aaggaaccac aaccaacctg                                              20

<210> SEQ ID NO 359
<211> LENGTH: 20
<212> TYPE: DNA
<213> ORGANISM: Artificial Sequence
<220> FEATURE:

<223> OTHER INFORMATION: Primer sequence

<400> SEQUENCE: 359
ggatccatcg tctacctcta                    20

<210> SEQ ID NO 360
<211> LENGTH: 20
<212> TYPE: DNA
<213> ORGANISM: Artificial Sequence
<220> FEATURE:
<223> OTHER INFORMATION: Primer sequence

<400> SEQUENCE: 360
aagatggact ctgcaacgtt                    20

<210> SEQ ID NO 361
<211> LENGTH: 20
<212> TYPE: DNA
<213> ORGANISM: Artificial Sequence
<220> FEATURE:
<223> OTHER INFORMATION: Primer sequence

<400> SEQUENCE: 361
tactgacact cgttgctaga                    20

<210> SEQ ID NO 362
<211> LENGTH: 20
<212> TYPE: DNA
<213> ORGANISM: Artificial Sequence
<220> FEATURE:
<223> OTHER INFORMATION: Primer sequence

<400> SEQUENCE: 362
atctgatgga tctgtgctcc                    20

<210> SEQ ID NO 363
<211> LENGTH: 20
<212> TYPE: DNA
<213> ORGANISM: Artificial Sequence
<220> FEATURE:
<223> OTHER INFORMATION: Primer sequence

<400> SEQUENCE: 363
acgagtctct cctaggacaa                    20

<210> SEQ ID NO 364
<211> LENGTH: 20
<212> TYPE: DNA
<213> ORGANISM: Artificial Sequence
<220> FEATURE:
<223> OTHER INFORMATION: Primer sequence

<400> SEQUENCE: 364
tcgttctcgt acttgttgga                    20

<210> SEQ ID NO 365
<211> LENGTH: 20
<212> TYPE: DNA
<213> ORGANISM: Artificial Sequence
<220> FEATURE:
<223> OTHER INFORMATION: Primer sequence

<400> SEQUENCE: 365
gcttgtctag acgttctctg                    20

```
<210> SEQ ID NO 366
<211> LENGTH: 20
<212> TYPE: DNA
<213> ORGANISM: Artificial Sequence
<220> FEATURE:
<223> OTHER INFORMATION: Primer sequence

<400> SEQUENCE: 366
tcctgcttca acctagatgg                                              20

<210> SEQ ID NO 367
<211> LENGTH: 20
<212> TYPE: DNA
<213> ORGANISM: Artificial Sequence
<220> FEATURE:
<223> OTHER INFORMATION: Primer sequence

<400> SEQUENCE: 367
gactacctgg atcgtacata                                              20

<210> SEQ ID NO 368
<211> LENGTH: 20
<212> TYPE: DNA
<213> ORGANISM: Artificial Sequence
<220> FEATURE:
<223> OTHER INFORMATION: Primer sequence

<400> SEQUENCE: 368
aagcaaggag gtgtacgttt                                              20

<210> SEQ ID NO 369
<211> LENGTH: 20
<212> TYPE: DNA
<213> ORGANISM: Artificial Sequence
<220> FEATURE:
<223> OTHER INFORMATION: Primer sequence

<400> SEQUENCE: 369
cctgagctca gagtgtagcc                                              20

<210> SEQ ID NO 370
<211> LENGTH: 20
<212> TYPE: DNA
<213> ORGANISM: Artificial Sequence
<220> FEATURE:
<223> OTHER INFORMATION: Primer sequence

<400> SEQUENCE: 370
agtgagtcct accaagcatg                                              20

<210> SEQ ID NO 371
<211> LENGTH: 20
<212> TYPE: DNA
<213> ORGANISM: Artificial Sequence
<220> FEATURE:
<223> OTHER INFORMATION: Primer sequence

<400> SEQUENCE: 371
tacgagtgtg caagcatgta                                              20

<210> SEQ ID NO 372
<211> LENGTH: 20
<212> TYPE: DNA
<213> ORGANISM: Artificial Sequence
<220> FEATURE:
<223> OTHER INFORMATION: Primer sequence
```

```
<400> SEQUENCE: 372
ctcttgacgt gttgtgctag                                               20

<210> SEQ ID NO 373
<211> LENGTH: 20
<212> TYPE: DNA
<213> ORGANISM: Artificial Sequence
<220> FEATURE:
<223> OTHER INFORMATION: Primer sequence

<400> SEQUENCE: 373
aggagcaagc aaggtacctt                                               20

<210> SEQ ID NO 374
<211> LENGTH: 20
<212> TYPE: DNA
<213> ORGANISM: Artificial Sequence
<220> FEATURE:
<223> OTHER INFORMATION: Primer sequence

<400> SEQUENCE: 374
cgtgtccaga ggttgctgaa                                               20

<210> SEQ ID NO 375
<211> LENGTH: 20
<212> TYPE: DNA
<213> ORGANISM: Artificial Sequence
<220> FEATURE:
<223> OTHER INFORMATION: Primer sequence

<400> SEQUENCE: 375
cctactagca accatggtcg                                               20

<210> SEQ ID NO 376
<211> LENGTH: 20
<212> TYPE: DNA
<213> ORGANISM: Artificial Sequence
<220> FEATURE:
<223> OTHER INFORMATION: Primer sequence

<400> SEQUENCE: 376
ctcacatggt agcacgatgc                                               20

<210> SEQ ID NO 377
<211> LENGTH: 20
<212> TYPE: DNA
<213> ORGANISM: Artificial Sequence
<220> FEATURE:
<223> OTHER INFORMATION: Primer sequence

<400> SEQUENCE: 377
cacttgtacg agaagatcag                                               20

<210> SEQ ID NO 378
<211> LENGTH: 20
<212> TYPE: DNA
<213> ORGANISM: Artificial Sequence
<220> FEATURE:
<223> OTHER INFORMATION: Primer sequence

<400> SEQUENCE: 378
cgttccactc atctgtgctt                                               20

<210> SEQ ID NO 379
<211> LENGTH: 20
```

```
<212> TYPE: DNA
<213> ORGANISM: Artificial Sequence
<220> FEATURE:
<223> OTHER INFORMATION: Primer sequence

<400> SEQUENCE: 379
ccttcacgat cctacagtca                                           20

<210> SEQ ID NO 380
<211> LENGTH: 20
<212> TYPE: DNA
<213> ORGANISM: Artificial Sequence
<220> FEATURE:
<223> OTHER INFORMATION: Primer sequence

<400> SEQUENCE: 380
atctcagaca ccttgatgtg                                           20

<210> SEQ ID NO 381
<211> LENGTH: 20
<212> TYPE: DNA
<213> ORGANISM: Artificial Sequence
<220> FEATURE:
<223> OTHER INFORMATION: Primer sequence

<400> SEQUENCE: 381
tcaggtcttg gtaggatcct                                           20

<210> SEQ ID NO 382
<211> LENGTH: 20
<212> TYPE: DNA
<213> ORGANISM: Artificial Sequence
<220> FEATURE:
<223> OTHER INFORMATION: Primer sequence

<400> SEQUENCE: 382
tacgtcctac cagtccacga                                           20

<210> SEQ ID NO 383
<211> LENGTH: 20
<212> TYPE: DNA
<213> ORGANISM: Artificial Sequence
<220> FEATURE:
<223> OTHER INFORMATION: Primer sequence

<400> SEQUENCE: 383
ccatgctacc agtaccactg                                           20

<210> SEQ ID NO 384
<211> LENGTH: 20
<212> TYPE: DNA
<213> ORGANISM: Artificial Sequence
<220> FEATURE:
<223> OTHER INFORMATION: Primer sequence

<400> SEQUENCE: 384
ggaccttgct tccacacgtc                                           20

<210> SEQ ID NO 385
<211> LENGTH: 20
<212> TYPE: DNA
<213> ORGANISM: Artificial Sequence
<220> FEATURE:
<223> OTHER INFORMATION: Primer sequence

<400> SEQUENCE: 385
```
cacctgacta gacaacaact                                          20

<210> SEQ ID NO 386
<211> LENGTH: 20
<212> TYPE: DNA
<213> ORGANISM: Artificial Sequence
<220> FEATURE:
<223> OTHER INFORMATION: Primer sequence

<400> SEQUENCE: 386
ttggtcgaag gagtcgtgac                                          20

<210> SEQ ID NO 387
<211> LENGTH: 20
<212> TYPE: DNA
<213> ORGANISM: Artificial Sequence
<220> FEATURE:
<223> OTHER INFORMATION: Primer sequence

<400> SEQUENCE: 387
tgcacctgca ctcacgtcct                                          20

<210> SEQ ID NO 388
<211> LENGTH: 20
<212> TYPE: DNA
<213> ORGANISM: Artificial Sequence
<220> FEATURE:
<223> OTHER INFORMATION: Primer sequence

<400> SEQUENCE: 388
acaggagcaa ggaagcaact                                          20

<210> SEQ ID NO 389
<211> LENGTH: 20
<212> TYPE: DNA
<213> ORGANISM: Artificial Sequence
<220> FEATURE:
<223> OTHER INFORMATION: Primer sequence

<400> SEQUENCE: 389
aactggaact caagacagac                                          20

<210> SEQ ID NO 390
<211> LENGTH: 20
<212> TYPE: DNA
<213> ORGANISM: Artificial Sequence
<220> FEATURE:
<223> OTHER INFORMATION: Primer sequence

<400> SEQUENCE: 390
gaagctgaga ccatgagaat                                          20

<210> SEQ ID NO 391
<211> LENGTH: 20
<212> TYPE: DNA
<213> ORGANISM: Artificial Sequence
<220> FEATURE:
<223> OTHER INFORMATION: Primer sequence

<400> SEQUENCE: 391
ctcgaagtag tgttgatggc                                          20

<210> SEQ ID NO 392
<211> LENGTH: 20
<212> TYPE: DNA
<213> ORGANISM: Artificial Sequence

```
<220> FEATURE:
<223> OTHER INFORMATION: Primer sequence

<400> SEQUENCE: 392
ccatcctcga tctcgtgtta                                               20

<210> SEQ ID NO 393
<211> LENGTH: 20
<212> TYPE: DNA
<213> ORGANISM: Artificial Sequence
<220> FEATURE:
<223> OTHER INFORMATION: Primer sequence

<400> SEQUENCE: 393
agtccatctc gtggaacttc                                               20

<210> SEQ ID NO 394
<211> LENGTH: 20
<212> TYPE: DNA
<213> ORGANISM: Artificial Sequence
<220> FEATURE:
<223> OTHER INFORMATION: Primer sequence

<400> SEQUENCE: 394
tgcatccatc atcactaggc                                               20

<210> SEQ ID NO 395
<211> LENGTH: 20
<212> TYPE: DNA
<213> ORGANISM: Artificial Sequence
<220> FEATURE:
<223> OTHER INFORMATION: Primer sequence

<400> SEQUENCE: 395
tagatcctgt caaggttgcc                                               20

<210> SEQ ID NO 396
<211> LENGTH: 20
<212> TYPE: DNA
<213> ORGANISM: Artificial Sequence
<220> FEATURE:
<223> OTHER INFORMATION: Primer sequence

<400> SEQUENCE: 396
gcttggactg tgctgatgcg                                               20

<210> SEQ ID NO 397
<211> LENGTH: 20
<212> TYPE: DNA
<213> ORGANISM: Artificial Sequence
<220> FEATURE:
<223> OTHER INFORMATION: Primer sequence

<400> SEQUENCE: 397
cgtagtagac atctctagca                                               20

<210> SEQ ID NO 398
<211> LENGTH: 20
<212> TYPE: DNA
<213> ORGANISM: Artificial Sequence
<220> FEATURE:
<223> OTHER INFORMATION: Primer sequence

<400> SEQUENCE: 398
actgttctcg atgctagtac                                               20
```

<210> SEQ ID NO 399
<211> LENGTH: 20
<212> TYPE: DNA
<213> ORGANISM: Artificial Sequence
<220> FEATURE:
<223> OTHER INFORMATION: Primer sequence

<400> SEQUENCE: 399
ctcttgtcag acgtgcttcg                                               20

<210> SEQ ID NO 400
<211> LENGTH: 20
<212> TYPE: DNA
<213> ORGANISM: Artificial Sequence
<220> FEATURE:
<223> OTHER INFORMATION: Primer sequence

<400> SEQUENCE: 400
gcagaagtag actgtccacg                                               20

<210> SEQ ID NO 401
<211> LENGTH: 20
<212> TYPE: DNA
<213> ORGANISM: Artificial Sequence
<220> FEATURE:
<223> OTHER INFORMATION: Primer sequence

<400> SEQUENCE: 401
tcgagtgtgt gtaccaagac                                               20

<210> SEQ ID NO 402
<211> LENGTH: 20
<212> TYPE: DNA
<213> ORGANISM: Artificial Sequence
<220> FEATURE:
<223> OTHER INFORMATION: Primer sequence

<400> SEQUENCE: 402
ttggatgcag tccaggagaa                                               20

<210> SEQ ID NO 403
<211> LENGTH: 20
<212> TYPE: DNA
<213> ORGANISM: Artificial Sequence
<220> FEATURE:
<223> OTHER INFORMATION: Primer sequence

<400> SEQUENCE: 403
catctccagt gtcgagcatg                                               20

<210> SEQ ID NO 404
<211> LENGTH: 20
<212> TYPE: DNA
<213> ORGANISM: Artificial Sequence
<220> FEATURE:
<223> OTHER INFORMATION: Primer sequence

<400> SEQUENCE: 404
tacgtgacaa ggatcttcgc                                               20

<210> SEQ ID NO 405
<211> LENGTH: 20
<212> TYPE: DNA
<213> ORGANISM: Artificial Sequence
<220> FEATURE:
<223> OTHER INFORMATION: Primer sequence

<400> SEQUENCE: 405
tgaccatcac cttctgcatt                                              20

<210> SEQ ID NO 406
<211> LENGTH: 20
<212> TYPE: DNA
<213> ORGANISM: Artificial Sequence
<220> FEATURE:
<223> OTHER INFORMATION: Primer sequence

<400> SEQUENCE: 406
aagcacaagc actgagtcgg                                              20

<210> SEQ ID NO 407
<211> LENGTH: 20
<212> TYPE: DNA
<213> ORGANISM: Artificial Sequence
<220> FEATURE:
<223> OTHER INFORMATION: Primer sequence

<400> SEQUENCE: 407
tcctgtcact ccaacctcgg                                              20

<210> SEQ ID NO 408
<211> LENGTH: 20
<212> TYPE: DNA
<213> ORGANISM: Artificial Sequence
<220> FEATURE:
<223> OTHER INFORMATION: Primer sequence

<400> SEQUENCE: 408
atggagagta gtctcctggt                                              20

<210> SEQ ID NO 409
<211> LENGTH: 20
<212> TYPE: DNA
<213> ORGANISM: Artificial Sequence
<220> FEATURE:
<223> OTHER INFORMATION: Primer sequence

<400> SEQUENCE: 409
aagagatgct gactggtagg                                              20

<210> SEQ ID NO 410
<211> LENGTH: 20
<212> TYPE: DNA
<213> ORGANISM: Artificial Sequence
<220> FEATURE:
<223> OTHER INFORMATION: Primer sequence

<400> SEQUENCE: 410
tctctcaagc tacgttggac                                              20

<210> SEQ ID NO 411
<211> LENGTH: 20
<212> TYPE: DNA
<213> ORGANISM: Artificial Sequence
<220> FEATURE:
<223> OTHER INFORMATION: Primer sequence

<400> SEQUENCE: 411
accttggaag taccaagttg                                              20

<210> SEQ ID NO 412

```
<211> LENGTH: 20
<212> TYPE: DNA
<213> ORGANISM: Artificial Sequence
<220> FEATURE:
<223> OTHER INFORMATION: Primer sequence

<400> SEQUENCE: 412
cgtgctacca cactcacaat                                               20

<210> SEQ ID NO 413
<211> LENGTH: 20
<212> TYPE: DNA
<213> ORGANISM: Artificial Sequence
<220> FEATURE:
<223> OTHER INFORMATION: Primer sequence

<400> SEQUENCE: 413
tagtggttca cgtgacctat                                               20

<210> SEQ ID NO 414
<211> LENGTH: 20
<212> TYPE: DNA
<213> ORGANISM: Artificial Sequence
<220> FEATURE:
<223> OTHER INFORMATION: Primer sequence

<400> SEQUENCE: 414
atgtagtcat gctgtccact                                               20

<210> SEQ ID NO 415
<211> LENGTH: 20
<212> TYPE: DNA
<213> ORGANISM: Artificial Sequence
<220> FEATURE:
<223> OTHER INFORMATION: Primer sequence

<400> SEQUENCE: 415
ccttccagta catgcactat                                               20

<210> SEQ ID NO 416
<211> LENGTH: 20
<212> TYPE: DNA
<213> ORGANISM: Artificial Sequence
<220> FEATURE:
<223> OTHER INFORMATION: Primer sequence

<400> SEQUENCE: 416
gatcctcctt gtacctagtg                                               20

<210> SEQ ID NO 417
<211> LENGTH: 20
<212> TYPE: DNA
<213> ORGANISM: Artificial Sequence
<220> FEATURE:
<223> OTHER INFORMATION: Primer sequence

<400> SEQUENCE: 417
tgaggtacct tgtactctca                                               20

<210> SEQ ID NO 418
<211> LENGTH: 20
<212> TYPE: DNA
<213> ORGANISM: Artificial Sequence
<220> FEATURE:
<223> OTHER INFORMATION: Primer sequence

<400> SEQUENCE: 418
```
atggacgagt ctgacgtagc                                               20

<210> SEQ ID NO 419
<211> LENGTH: 20
<212> TYPE: DNA
<213> ORGANISM: Artificial Sequence
<220> FEATURE:
<223> OTHER INFORMATION: Primer sequence

<400> SEQUENCE: 419
ttcgttgagg aacctcacgg                                               20

<210> SEQ ID NO 420
<211> LENGTH: 20
<212> TYPE: DNA
<213> ORGANISM: Artificial Sequence
<220> FEATURE:
<223> OTHER INFORMATION: Primer sequence

<400> SEQUENCE: 420
ctcatggttc ctcctactgt                                               20

<210> SEQ ID NO 421
<211> LENGTH: 20
<212> TYPE: DNA
<213> ORGANISM: Artificial Sequence
<220> FEATURE:
<223> OTHER INFORMATION: Primer sequence

<400> SEQUENCE: 421
gtgttcgttg gtgactcgtg                                               20

<210> SEQ ID NO 422
<211> LENGTH: 20
<212> TYPE: DNA
<213> ORGANISM: Artificial Sequence
<220> FEATURE:
<223> OTHER INFORMATION: Primer sequence

<400> SEQUENCE: 422
ctgtggaacg atggaggagg                                               20

<210> SEQ ID NO 423
<211> LENGTH: 20
<212> TYPE: DNA
<213> ORGANISM: Artificial Sequence
<220> FEATURE:
<223> OTHER INFORMATION: Primer sequence

<400> SEQUENCE: 423
gctcttcctt cgtccttgat                                               20

<210> SEQ ID NO 424
<211> LENGTH: 20
<212> TYPE: DNA
<213> ORGANISM: Artificial Sequence
<220> FEATURE:
<223> OTHER INFORMATION: Primer sequence

<400> SEQUENCE: 424
cctacgatcc acgaagcttc                                               20

<210> SEQ ID NO 425
<211> LENGTH: 20
<212> TYPE: DNA

```
<213> ORGANISM: Artificial Sequence
<220> FEATURE:
<223> OTHER INFORMATION: Primer sequence

<400> SEQUENCE: 425
ggatctacca gcttgtctta                                               20

<210> SEQ ID NO 426
<211> LENGTH: 20
<212> TYPE: DNA
<213> ORGANISM: Artificial Sequence
<220> FEATURE:
<223> OTHER INFORMATION: Primer sequence

<400> SEQUENCE: 426
atgcaagttg gtgctgactc                                               20

<210> SEQ ID NO 427
<211> LENGTH: 20
<212> TYPE: DNA
<213> ORGANISM: Artificial Sequence
<220> FEATURE:
<223> OTHER INFORMATION: Primer sequence

<400> SEQUENCE: 427
tacaacgtcg tgtagtctcc                                               20

<210> SEQ ID NO 428
<211> LENGTH: 20
<212> TYPE: DNA
<213> ORGANISM: Artificial Sequence
<220> FEATURE:
<223> OTHER INFORMATION: Primer sequence

<400> SEQUENCE: 428
gcaactacct gaccaaccat                                               20

<210> SEQ ID NO 429
<211> LENGTH: 20
<212> TYPE: DNA
<213> ORGANISM: Artificial Sequence
<220> FEATURE:
<223> OTHER INFORMATION: Primer sequence

<400> SEQUENCE: 429
gcacgaagat gtcactggtt                                               20

<210> SEQ ID NO 430
<211> LENGTH: 20
<212> TYPE: DNA
<213> ORGANISM: Artificial Sequence
<220> FEATURE:
<223> OTHER INFORMATION: Primer sequence

<400> SEQUENCE: 430
ggttccaagt gtaggaacgc                                               20

<210> SEQ ID NO 431
<211> LENGTH: 20
<212> TYPE: DNA
<213> ORGANISM: Artificial Sequence
<220> FEATURE:
<223> OTHER INFORMATION: Primer sequence

<400> SEQUENCE: 431
tccaaccagc tcctggtaca                                               20
```

<210> SEQ ID NO 432
<211> LENGTH: 20
<212> TYPE: DNA
<213> ORGANISM: Artificial Sequence
<220> FEATURE:
<223> OTHER INFORMATION: Primer sequence

<400> SEQUENCE: 432
acctagctca caaggtggat                                               20

<210> SEQ ID NO 433
<211> LENGTH: 20
<212> TYPE: DNA
<213> ORGANISM: Artificial Sequence
<220> FEATURE:
<223> OTHER INFORMATION: Primer sequence

<400> SEQUENCE: 433
aacttgtcct agactacgag                                               20

<210> SEQ ID NO 434
<211> LENGTH: 20
<212> TYPE: DNA
<213> ORGANISM: Artificial Sequence
<220> FEATURE:
<223> OTHER INFORMATION: Primer sequence

<400> SEQUENCE: 434
atcaggtgta cgactcagtg                                               20

<210> SEQ ID NO 435
<211> LENGTH: 20
<212> TYPE: DNA
<213> ORGANISM: Artificial Sequence
<220> FEATURE:
<223> OTHER INFORMATION: Primer sequence

<400> SEQUENCE: 435
cagaagcaac cagtggtcac                                               20

<210> SEQ ID NO 436
<211> LENGTH: 20
<212> TYPE: DNA
<213> ORGANISM: Artificial Sequence
<220> FEATURE:
<223> OTHER INFORMATION: Primer sequence

<400> SEQUENCE: 436
tgaccacgtg gtaggtcaga                                               20

<210> SEQ ID NO 437
<211> LENGTH: 20
<212> TYPE: DNA
<213> ORGANISM: Artificial Sequence
<220> FEATURE:
<223> OTHER INFORMATION: Primer sequence

<400> SEQUENCE: 437
cgtcgtactt gttgcacgtt                                               20

<210> SEQ ID NO 438
<211> LENGTH: 20
<212> TYPE: DNA
<213> ORGANISM: Artificial Sequence
<220> FEATURE:

<223> OTHER INFORMATION: Primer sequence

<400> SEQUENCE: 438
agtgacacga catgcacgaa                                              20

<210> SEQ ID NO 439
<211> LENGTH: 20
<212> TYPE: DNA
<213> ORGANISM: Artificial Sequence
<220> FEATURE:
<223> OTHER INFORMATION: Primer sequence

<400> SEQUENCE: 439
cgacactctt gtagtcgtgc                                              20

<210> SEQ ID NO 440
<211> LENGTH: 20
<212> TYPE: DNA
<213> ORGANISM: Artificial Sequence
<220> FEATURE:
<223> OTHER INFORMATION: Primer sequence

<400> SEQUENCE: 440
ggttggatct ctctgctctc                                              20

<210> SEQ ID NO 441
<211> LENGTH: 20
<212> TYPE: DNA
<213> ORGANISM: Artificial Sequence
<220> FEATURE:
<223> OTHER INFORMATION: Primer sequence

<400> SEQUENCE: 441
taggtagcaa ccaacgacgt                                              20

<210> SEQ ID NO 442
<211> LENGTH: 20
<212> TYPE: DNA
<213> ORGANISM: Artificial Sequence
<220> FEATURE:
<223> OTHER INFORMATION: Primer sequence

<400> SEQUENCE: 442
accatggtcc tcctggagat                                              20

<210> SEQ ID NO 443
<211> LENGTH: 20
<212> TYPE: DNA
<213> ORGANISM: Artificial Sequence
<220> FEATURE:
<223> OTHER INFORMATION: Primer sequence

<400> SEQUENCE: 443
aggatcctct tcagcactgt                                              20

<210> SEQ ID NO 444
<211> LENGTH: 20
<212> TYPE: DNA
<213> ORGANISM: Artificial Sequence
<220> FEATURE:
<223> OTHER INFORMATION: Primer sequence

<400> SEQUENCE: 444
gcaactggag tgtgatccac                                              20

```
<210> SEQ ID NO 445
<211> LENGTH: 20
<212> TYPE: DNA
<213> ORGANISM: Artificial Sequence
<220> FEATURE:
<223> OTHER INFORMATION: Primer sequence

<400> SEQUENCE: 445
gacaggtcat cagtcgttgc                                               20

<210> SEQ ID NO 446
<211> LENGTH: 20
<212> TYPE: DNA
<213> ORGANISM: Artificial Sequence
<220> FEATURE:
<223> OTHER INFORMATION: Primer sequence

<400> SEQUENCE: 446
ggactgtgaa cgtacacctc                                               20

<210> SEQ ID NO 447
<211> LENGTH: 20
<212> TYPE: DNA
<213> ORGANISM: Artificial Sequence
<220> FEATURE:
<223> OTHER INFORMATION: Primer sequence

<400> SEQUENCE: 447
atccttcagt acgatccatc                                               20

<210> SEQ ID NO 448
<211> LENGTH: 20
<212> TYPE: DNA
<213> ORGANISM: Artificial Sequence
<220> FEATURE:
<223> OTHER INFORMATION: Primer sequence

<400> SEQUENCE: 448
tgatgatctg tggacgatct                                               20

<210> SEQ ID NO 449
<211> LENGTH: 20
<212> TYPE: DNA
<213> ORGANISM: Artificial Sequence
<220> FEATURE:
<223> OTHER INFORMATION: Primer sequence

<400> SEQUENCE: 449
acgactccaa ctgtcctggc                                               20

<210> SEQ ID NO 450
<211> LENGTH: 20
<212> TYPE: DNA
<213> ORGANISM: Artificial Sequence
<220> FEATURE:
<223> OTHER INFORMATION: Primer sequence

<400> SEQUENCE: 450
ccttcatctg gagatgtcga                                               20

<210> SEQ ID NO 451
<211> LENGTH: 20
<212> TYPE: DNA
<213> ORGANISM: Artificial Sequence
<220> FEATURE:
<223> OTHER INFORMATION: Primer sequence
```

```
<400> SEQUENCE: 451
tggtagttcc ttcaggagtc                                                 20

<210> SEQ ID NO 452
<211> LENGTH: 20
<212> TYPE: DNA
<213> ORGANISM: Artificial Sequence
<220> FEATURE:
<223> OTHER INFORMATION: Primer sequence

<400> SEQUENCE: 452
aagaagcagt cctagcacgg                                                 20

<210> SEQ ID NO 453
<211> LENGTH: 20
<212> TYPE: DNA
<213> ORGANISM: Artificial Sequence
<220> FEATURE:
<223> OTHER INFORMATION: Primer sequence

<400> SEQUENCE: 453
tgctggtaga caagacgatt                                                 20

<210> SEQ ID NO 454
<211> LENGTH: 20
<212> TYPE: DNA
<213> ORGANISM: Artificial Sequence
<220> FEATURE:
<223> OTHER INFORMATION: Primer sequence

<400> SEQUENCE: 454
aactcttcga cgtgacactc                                                 20

<210> SEQ ID NO 455
<211> LENGTH: 20
<212> TYPE: DNA
<213> ORGANISM: Artificial Sequence
<220> FEATURE:
<223> OTHER INFORMATION: Primer sequence

<400> SEQUENCE: 455
aacaagacgt gacgttgctg                                                 20

<210> SEQ ID NO 456
<211> LENGTH: 20
<212> TYPE: DNA
<213> ORGANISM: Artificial Sequence
<220> FEATURE:
<223> OTHER INFORMATION: Primer sequence

<400> SEQUENCE: 456
gatctcttga gtggagtccc                                                 20

<210> SEQ ID NO 457
<211> LENGTH: 20
<212> TYPE: DNA
<213> ORGANISM: Artificial Sequence
<220> FEATURE:
<223> OTHER INFORMATION: Primer sequence

<400> SEQUENCE: 457
caccaacctc agacctgaga                                                 20

<210> SEQ ID NO 458
<211> LENGTH: 20
```

```
<212> TYPE: DNA
<213> ORGANISM: Artificial Sequence
<220> FEATURE:
<223> OTHER INFORMATION: Primer sequence

<400> SEQUENCE: 458
ggatgcacag gtacaggaat                                               20

<210> SEQ ID NO 459
<211> LENGTH: 20
<212> TYPE: DNA
<213> ORGANISM: Artificial Sequence
<220> FEATURE:
<223> OTHER INFORMATION: Primer sequence

<400> SEQUENCE: 459
taccacaacc agtccttcct                                               20

<210> SEQ ID NO 460
<211> LENGTH: 20
<212> TYPE: DNA
<213> ORGANISM: Artificial Sequence
<220> FEATURE:
<223> OTHER INFORMATION: Primer sequence

<400> SEQUENCE: 460
atgctgtcaa gcttgtaggg                                               20

<210> SEQ ID NO 461
<211> LENGTH: 20
<212> TYPE: DNA
<213> ORGANISM: Artificial Sequence
<220> FEATURE:
<223> OTHER INFORMATION: Primer sequence

<400> SEQUENCE: 461
cttgcatcaa gcatcgagcg                                               20

<210> SEQ ID NO 462
<211> LENGTH: 20
<212> TYPE: DNA
<213> ORGANISM: Artificial Sequence
<220> FEATURE:
<223> OTHER INFORMATION: Primer sequence

<400> SEQUENCE: 462
aggatcctgt cactagtgga                                               20

<210> SEQ ID NO 463
<211> LENGTH: 20
<212> TYPE: DNA
<213> ORGANISM: Artificial Sequence
<220> FEATURE:
<223> OTHER INFORMATION: Primer sequence

<400> SEQUENCE: 463
ctgcaagcta gacaacagtg                                               20

<210> SEQ ID NO 464
<211> LENGTH: 20
<212> TYPE: DNA
<213> ORGANISM: Artificial Sequence
<220> FEATURE:
<223> OTHER INFORMATION: Primer sequence

<400> SEQUENCE: 464
```
cgacctccac tggtagacct                                           20

<210> SEQ ID NO 465
<211> LENGTH: 20
<212> TYPE: DNA
<213> ORGANISM: Artificial Sequence
<220> FEATURE:
<223> OTHER INFORMATION: Primer sequence

<400> SEQUENCE: 465
tccaagacta cgatgttgag                                           20

<210> SEQ ID NO 466
<211> LENGTH: 20
<212> TYPE: DNA
<213> ORGANISM: Artificial Sequence
<220> FEATURE:
<223> OTHER INFORMATION: Primer sequence

<400> SEQUENCE: 466
cctctgatgg ttcatccagt                                           20

<210> SEQ ID NO 467
<211> LENGTH: 20
<212> TYPE: DNA
<213> ORGANISM: Artificial Sequence
<220> FEATURE:
<223> OTHER INFORMATION: Primer sequence

<400> SEQUENCE: 467
gatgagacat gctacaagag                                           20

<210> SEQ ID NO 468
<211> LENGTH: 20
<212> TYPE: DNA
<213> ORGANISM: Artificial Sequence
<220> FEATURE:
<223> OTHER INFORMATION: Primer sequence

<400> SEQUENCE: 468
gctggaggtg ttcatcaaca                                           20

<210> SEQ ID NO 469
<211> LENGTH: 20
<212> TYPE: DNA
<213> ORGANISM: Artificial Sequence
<220> FEATURE:
<223> OTHER INFORMATION: Primer sequence

<400> SEQUENCE: 469
tggagttcga gtacgagtca                                           20

<210> SEQ ID NO 470
<211> LENGTH: 20
<212> TYPE: DNA
<213> ORGANISM: Artificial Sequence
<220> FEATURE:
<223> OTHER INFORMATION: Primer sequence

<400> SEQUENCE: 470
agttgcagac aggatgaacg                                           20

<210> SEQ ID NO 471
<211> LENGTH: 20
<212> TYPE: DNA
<213> ORGANISM: Artificial Sequence

```
<220> FEATURE:
<223> OTHER INFORMATION: Primer sequence

<400> SEQUENCE: 471
gtagtgaacg accacgagtg                                               20

<210> SEQ ID NO 472
<211> LENGTH: 20
<212> TYPE: DNA
<213> ORGANISM: Artificial Sequence
<220> FEATURE:
<223> OTHER INFORMATION: Primer sequence

<400> SEQUENCE: 472
tacgtcgtcc ttgcagacaa                                               20

<210> SEQ ID NO 473
<211> LENGTH: 20
<212> TYPE: DNA
<213> ORGANISM: Artificial Sequence
<220> FEATURE:
<223> OTHER INFORMATION: Primer sequence

<400> SEQUENCE: 473
gtacaggatc tacgttgagc                                               20

<210> SEQ ID NO 474
<211> LENGTH: 20
<212> TYPE: DNA
<213> ORGANISM: Artificial Sequence
<220> FEATURE:
<223> OTHER INFORMATION: Primer sequence

<400> SEQUENCE: 474
gtgctcaaca gtcaggtgcc                                               20

<210> SEQ ID NO 475
<211> LENGTH: 20
<212> TYPE: DNA
<213> ORGANISM: Artificial Sequence
<220> FEATURE:
<223> OTHER INFORMATION: Primer sequence

<400> SEQUENCE: 475
gcttcgtacg atcatgtacc                                               20

<210> SEQ ID NO 476
<211> LENGTH: 20
<212> TYPE: DNA
<213> ORGANISM: Artificial Sequence
<220> FEATURE:
<223> OTHER INFORMATION: Primer sequence

<400> SEQUENCE: 476
ggtgtgttca gaacaagcac                                               20

<210> SEQ ID NO 477
<211> LENGTH: 20
<212> TYPE: DNA
<213> ORGANISM: Artificial Sequence
<220> FEATURE:
<223> OTHER INFORMATION: Primer sequence

<400> SEQUENCE: 477
ctcgatggag gttgtagcac                                               20
```

```
<210> SEQ ID NO 478
<211> LENGTH: 20
<212> TYPE: DNA
<213> ORGANISM: Artificial Sequence
<220> FEATURE:
<223> OTHER INFORMATION: Primer sequence

<400> SEQUENCE: 478
tagcacgttg agctacgatc                                              20

<210> SEQ ID NO 479
<211> LENGTH: 20
<212> TYPE: DNA
<213> ORGANISM: Artificial Sequence
<220> FEATURE:
<223> OTHER INFORMATION: Primer sequence

<400> SEQUENCE: 479
acagcaagtt cgttcctcta                                              20

<210> SEQ ID NO 480
<211> LENGTH: 20
<212> TYPE: DNA
<213> ORGANISM: Artificial Sequence
<220> FEATURE:
<223> OTHER INFORMATION: Primer sequence

<400> SEQUENCE: 480
tgttcgttgt cagcagttcg                                              20

<210> SEQ ID NO 481
<211> LENGTH: 20
<212> TYPE: DNA
<213> ORGANISM: Artificial Sequence
<220> FEATURE:
<223> OTHER INFORMATION: Primer sequence

<400> SEQUENCE: 481
tcatcgagca aggtgttcgc                                              20

<210> SEQ ID NO 482
<211> LENGTH: 20
<212> TYPE: DNA
<213> ORGANISM: Artificial Sequence
<220> FEATURE:
<223> OTHER INFORMATION: Primer sequence

<400> SEQUENCE: 482
cgagtcttca acttccaagc                                              20

<210> SEQ ID NO 483
<211> LENGTH: 20
<212> TYPE: DNA
<213> ORGANISM: Artificial Sequence
<220> FEATURE:
<223> OTHER INFORMATION: Primer sequence

<400> SEQUENCE: 483
tccatgttcg tacgacgatg                                              20

<210> SEQ ID NO 484
<211> LENGTH: 20
<212> TYPE: DNA
<213> ORGANISM: Artificial Sequence
<220> FEATURE:
<223> OTHER INFORMATION: Primer sequence
```

<400> SEQUENCE: 484
gtgtactcca gacttccttt                                              20

<210> SEQ ID NO 485
<211> LENGTH: 20
<212> TYPE: DNA
<213> ORGANISM: Artificial Sequence
<220> FEATURE:
<223> OTHER INFORMATION: Primer sequence

<400> SEQUENCE: 485
tacttgcacc agacttgtac                                              20

<210> SEQ ID NO 486
<211> LENGTH: 20
<212> TYPE: DNA
<213> ORGANISM: Artificial Sequence
<220> FEATURE:
<223> OTHER INFORMATION: Primer sequence

<400> SEQUENCE: 486
agtacaggac aagacacgtt                                              20

<210> SEQ ID NO 487
<211> LENGTH: 20
<212> TYPE: DNA
<213> ORGANISM: Artificial Sequence
<220> FEATURE:
<223> OTHER INFORMATION: Primer sequence

<400> SEQUENCE: 487
cgatgagagt agtgtctacg                                              20

<210> SEQ ID NO 488
<211> LENGTH: 20
<212> TYPE: DNA
<213> ORGANISM: Artificial Sequence
<220> FEATURE:
<223> OTHER INFORMATION: Primer sequence

<400> SEQUENCE: 488
gcaagctcag agcagaagtg                                              20

<210> SEQ ID NO 489
<211> LENGTH: 20
<212> TYPE: DNA
<213> ORGANISM: Artificial Sequence
<220> FEATURE:
<223> OTHER INFORMATION: Primer sequence

<400> SEQUENCE: 489
cgtgacacgt gttcagcacg                                              20

<210> SEQ ID NO 490
<211> LENGTH: 20
<212> TYPE: DNA
<213> ORGANISM: Artificial Sequence
<220> FEATURE:
<223> OTHER INFORMATION: Primer sequence

<400> SEQUENCE: 490
gtacgtgttg cacaagagca                                              20

<210> SEQ ID NO 491

```
<211> LENGTH: 20
<212> TYPE: DNA
<213> ORGANISM: Artificial Sequence
<220> FEATURE:
<223> OTHER INFORMATION: Primer sequence

<400> SEQUENCE: 491
acgatcacta cgatgaaggt                                               20

<210> SEQ ID NO 492
<211> LENGTH: 20
<212> TYPE: DNA
<213> ORGANISM: Artificial Sequence
<220> FEATURE:
<223> OTHER INFORMATION: Primer sequence

<400> SEQUENCE: 492
taggacgtag cagacaacta                                               20

<210> SEQ ID NO 493
<211> LENGTH: 20
<212> TYPE: DNA
<213> ORGANISM: Artificial Sequence
<220> FEATURE:
<223> OTHER INFORMATION: Primer sequence

<400> SEQUENCE: 493
tctcagtacg ttcgtagtct                                               20

<210> SEQ ID NO 494
<211> LENGTH: 20
<212> TYPE: DNA
<213> ORGANISM: Artificial Sequence
<220> FEATURE:
<223> OTHER INFORMATION: Primer sequence

<400> SEQUENCE: 494
gcaagcaact tcgttggtac                                               20

<210> SEQ ID NO 495
<211> LENGTH: 20
<212> TYPE: DNA
<213> ORGANISM: Artificial Sequence
<220> FEATURE:
<223> OTHER INFORMATION: Primer sequence

<400> SEQUENCE: 495
gtagagagac atccaaccaa                                               20

<210> SEQ ID NO 496
<211> LENGTH: 20
<212> TYPE: DNA
<213> ORGANISM: Artificial Sequence
<220> FEATURE:
<223> OTHER INFORMATION: Primer sequence

<400> SEQUENCE: 496
cctgctagtg cttccttggg                                               20

<210> SEQ ID NO 497
<211> LENGTH: 20
<212> TYPE: DNA
<213> ORGANISM: Artificial Sequence
<220> FEATURE:
<223> OTHER INFORMATION: Primer sequence

<400> SEQUENCE: 497
```
cacacgatct gtagtcctga                                          20

<210> SEQ ID NO 498
<211> LENGTH: 20
<212> TYPE: DNA
<213> ORGANISM: Artificial Sequence
<220> FEATURE:
<223> OTHER INFORMATION: Primer sequence

<400> SEQUENCE: 498
acaccaaggt tcagatgtgt                                          20

<210> SEQ ID NO 499
<211> LENGTH: 20
<212> TYPE: DNA
<213> ORGANISM: Artificial Sequence
<220> FEATURE:
<223> OTHER INFORMATION: Primer sequence

<400> SEQUENCE: 499
ttctactgct gttgaccttg                                          20

<210> SEQ ID NO 500
<211> LENGTH: 20
<212> TYPE: DNA
<213> ORGANISM: Artificial Sequence
<220> FEATURE:
<223> OTHER INFORMATION: Primer sequence

<400> SEQUENCE: 500
cctgtcatcc ttcgtactat                                          20

<210> SEQ ID NO 501
<211> LENGTH: 20
<212> TYPE: DNA
<213> ORGANISM: Artificial Sequence
<220> FEATURE:
<223> OTHER INFORMATION: Primer sequence

<400> SEQUENCE: 501
gttcgaacaa gtctccagag                                          20

<210> SEQ ID NO 502
<211> LENGTH: 20
<212> TYPE: DNA
<213> ORGANISM: Artificial Sequence
<220> FEATURE:
<223> OTHER INFORMATION: Primer sequence

<400> SEQUENCE: 502
ggaaggacca gactgtcacg                                          20

<210> SEQ ID NO 503
<211> LENGTH: 20
<212> TYPE: DNA
<213> ORGANISM: Artificial Sequence
<220> FEATURE:
<223> OTHER INFORMATION: Primer sequence

<400> SEQUENCE: 503
acctacagac acacagatgc                                          20

<210> SEQ ID NO 504
<211> LENGTH: 20
<212> TYPE: DNA

```
<213> ORGANISM: Artificial Sequence
<220> FEATURE:
<223> OTHER INFORMATION: Primer sequence

<400> SEQUENCE: 504
ttctgtagga ccttggaact                                              20

<210> SEQ ID NO 505
<211> LENGTH: 20
<212> TYPE: DNA
<213> ORGANISM: Artificial Sequence
<220> FEATURE:
<223> OTHER INFORMATION: Primer sequence

<400> SEQUENCE: 505
gctccatgga tgtaccttca                                              20

<210> SEQ ID NO 506
<211> LENGTH: 20
<212> TYPE: DNA
<213> ORGANISM: Artificial Sequence
<220> FEATURE:
<223> OTHER INFORMATION: Primer sequence

<400> SEQUENCE: 506
atcctctcca tgctagaggt                                              20

<210> SEQ ID NO 507
<211> LENGTH: 20
<212> TYPE: DNA
<213> ORGANISM: Artificial Sequence
<220> FEATURE:
<223> OTHER INFORMATION: Primer sequence

<400> SEQUENCE: 507
gagaaggaga aggtcgttgc                                              20

<210> SEQ ID NO 508
<211> LENGTH: 20
<212> TYPE: DNA
<213> ORGANISM: Artificial Sequence
<220> FEATURE:
<223> OTHER INFORMATION: Primer sequence

<400> SEQUENCE: 508
tacgtgagta gctactggaa                                              20

<210> SEQ ID NO 509
<211> LENGTH: 20
<212> TYPE: DNA
<213> ORGANISM: Artificial Sequence
<220> FEATURE:
<223> OTHER INFORMATION: Primer sequence

<400> SEQUENCE: 509
taggagtact ccaggatcgc                                              20

<210> SEQ ID NO 510
<211> LENGTH: 20
<212> TYPE: DNA
<213> ORGANISM: Artificial Sequence
<220> FEATURE:
<223> OTHER INFORMATION: Primer sequence

<400> SEQUENCE: 510
tcaagtgtct gacgaagcta                                              20
```

```
<210> SEQ ID NO 511
<211> LENGTH: 20
<212> TYPE: DNA
<213> ORGANISM: Artificial Sequence
<220> FEATURE:
<223> OTHER INFORMATION: Primer sequence

<400> SEQUENCE: 511
gtgatggtag acagctgtaa                                               20

<210> SEQ ID NO 512
<211> LENGTH: 20
<212> TYPE: DNA
<213> ORGANISM: Artificial Sequence
<220> FEATURE:
<223> OTHER INFORMATION: Primer sequence

<400> SEQUENCE: 512
aagtggagtt ggatgcacct                                               20

<210> SEQ ID NO 513
<211> LENGTH: 20
<212> TYPE: DNA
<213> ORGANISM: Artificial Sequence
<220> FEATURE:
<223> OTHER INFORMATION: Primer sequence

<400> SEQUENCE: 513
ttcctggttg gactcgtcgg                                               20

<210> SEQ ID NO 514
<211> LENGTH: 20
<212> TYPE: DNA
<213> ORGANISM: Artificial Sequence
<220> FEATURE:
<223> OTHER INFORMATION: Primer sequence

<400> SEQUENCE: 514
cctgcacgaa cacttgcaca                                               20

<210> SEQ ID NO 515
<211> LENGTH: 20
<212> TYPE: DNA
<213> ORGANISM: Artificial Sequence
<220> FEATURE:
<223> OTHER INFORMATION: Primer sequence

<400> SEQUENCE: 515
tgagttgctg cactgttgct                                               20

<210> SEQ ID NO 516
<211> LENGTH: 20
<212> TYPE: DNA
<213> ORGANISM: Artificial Sequence
<220> FEATURE:
<223> OTHER INFORMATION: Primer sequence

<400> SEQUENCE: 516
cttgtcaagc agtcactaga                                               20

<210> SEQ ID NO 517
<211> LENGTH: 20
<212> TYPE: DNA
<213> ORGANISM: Artificial Sequence
<220> FEATURE:
```

<223> OTHER INFORMATION: Primer sequence

<400> SEQUENCE: 517
tcacatgacc agcacgtgcg                                              20

<210> SEQ ID NO 518
<211> LENGTH: 20
<212> TYPE: DNA
<213> ORGANISM: Artificial Sequence
<220> FEATURE:
<223> OTHER INFORMATION: Primer sequence

<400> SEQUENCE: 518
cgatcaagct acagaagaag                                              20

<210> SEQ ID NO 519
<211> LENGTH: 20
<212> TYPE: DNA
<213> ORGANISM: Artificial Sequence
<220> FEATURE:
<223> OTHER INFORMATION: Primer sequence

<400> SEQUENCE: 519
tggactctgt cgaaggtaca                                              20

<210> SEQ ID NO 520
<211> LENGTH: 20
<212> TYPE: DNA
<213> ORGANISM: Artificial Sequence
<220> FEATURE:
<223> OTHER INFORMATION: Primer sequence

<400> SEQUENCE: 520
ctgtagcatc cactccatcc                                              20

<210> SEQ ID NO 521
<211> LENGTH: 20
<212> TYPE: DNA
<213> ORGANISM: Artificial Sequence
<220> FEATURE:
<223> OTHER INFORMATION: Primer sequence

<400> SEQUENCE: 521
gactgtggtg acacctgact                                              20

<210> SEQ ID NO 522
<211> LENGTH: 20
<212> TYPE: DNA
<213> ORGANISM: Artificial Sequence
<220> FEATURE:
<223> OTHER INFORMATION: Primer sequence

<400> SEQUENCE: 522
gcttcgacag acatcactcg                                              20

<210> SEQ ID NO 523
<211> LENGTH: 20
<212> TYPE: DNA
<213> ORGANISM: Artificial Sequence
<220> FEATURE:
<223> OTHER INFORMATION: Primer sequence

<400> SEQUENCE: 523
atggacagtg gacactcatt                                              20

```
<210> SEQ ID NO 524
<211> LENGTH: 20
<212> TYPE: DNA
<213> ORGANISM: Artificial Sequence
<220> FEATURE:
<223> OTHER INFORMATION: Primer sequence

<400> SEQUENCE: 524
gcttctcctg gttgatggtc                                            20

<210> SEQ ID NO 525
<211> LENGTH: 20
<212> TYPE: DNA
<213> ORGANISM: Artificial Sequence
<220> FEATURE:
<223> OTHER INFORMATION: Primer sequence

<400> SEQUENCE: 525
cgtggaaggt tgagctcaac                                            20

<210> SEQ ID NO 526
<211> LENGTH: 20
<212> TYPE: DNA
<213> ORGANISM: Artificial Sequence
<220> FEATURE:
<223> OTHER INFORMATION: Primer sequence

<400> SEQUENCE: 526
acatctagtc caggtggttt                                            20

<210> SEQ ID NO 527
<211> LENGTH: 20
<212> TYPE: DNA
<213> ORGANISM: Artificial Sequence
<220> FEATURE:
<223> OTHER INFORMATION: Primer sequence

<400> SEQUENCE: 527
cctcgaacct tgctacagcg                                            20

<210> SEQ ID NO 528
<211> LENGTH: 20
<212> TYPE: DNA
<213> ORGANISM: Artificial Sequence
<220> FEATURE:
<223> OTHER INFORMATION: Primer sequence

<400> SEQUENCE: 528
cgacgagcac actctctcag                                            20

<210> SEQ ID NO 529
<211> LENGTH: 20
<212> TYPE: DNA
<213> ORGANISM: Artificial Sequence
<220> FEATURE:
<223> OTHER INFORMATION: Primer sequence

<400> SEQUENCE: 529
atgcttgcac tgtgatgaca                                            20

<210> SEQ ID NO 530
<211> LENGTH: 20
<212> TYPE: DNA
<213> ORGANISM: Artificial Sequence
<220> FEATURE:
<223> OTHER INFORMATION: Primer sequence
```

<400> SEQUENCE: 530
gtgtactgag tgcagcatgg                                             20

<210> SEQ ID NO 531
<211> LENGTH: 20
<212> TYPE: DNA
<213> ORGANISM: Artificial Sequence
<220> FEATURE:
<223> OTHER INFORMATION: Primer sequence

<400> SEQUENCE: 531
tacgagcaag gtagctggtg                                             20

<210> SEQ ID NO 532
<211> LENGTH: 20
<212> TYPE: DNA
<213> ORGANISM: Artificial Sequence
<220> FEATURE:
<223> OTHER INFORMATION: Primer sequence

<400> SEQUENCE: 532
cgttctagga agtgaagctg                                             20

<210> SEQ ID NO 533
<211> LENGTH: 27
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(27)
<223> OTHER INFORMATION: n is a, c, g, or t. The sequence may be chosen
      depending on the target protein.

<400> SEQUENCE: 533
caagtcacca agaattcatg nnnnnnn                                     27

<210> SEQ ID NO 534
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (20)..(20)
<223> OTHER INFORMATION: Conjugated to Biotin

<400> SEQUENCE: 534
catgaattct tggtgacttg                                             20

<210> SEQ ID NO 535
<211> LENGTH: 12
<212> TYPE: DNA
<213> ORGANISM: Artificial Sequence
<220> FEATURE:
<223> OTHER INFORMATION: Primer sequence

<400> SEQUENCE: 535
caagtcacca ag                                                     12

<210> SEQ ID NO 536
<211> LENGTH: 17
<212> TYPE: DNA
<213> ORGANISM: Artificial Sequence
<220> FEATURE:

```
<223> OTHER INFORMATION: Primer sequence
<220> FEATURE:
<221> NAME/KEY: misc_feature
<222> LOCATION: (20)..(20)
<223> OTHER INFORMATION: Conjugated to biotin.

<400> SEQUENCE: 536
caattcttgg tgacttg                                                    17

<210> SEQ ID NO 537
<211> LENGTH: 4
<212> TYPE: PRT
<213> ORGANISM: Artificial Sequence
<220> FEATURE:
<223> OTHER INFORMATION: Cleavage site for Enterokinase
<220> FEATURE:
<221> NAME/KEY: SITE
<222> LOCATION: (1)..(4)
<223> OTHER INFORMATION: Cleavage site for Enterokinase

<400> SEQUENCE: 537

Asp Asp Asp Lys
1

<210> SEQ ID NO 538
<211> LENGTH: 7
<212> TYPE: PRT
<213> ORGANISM: Artificial Sequence
<220> FEATURE:
<223> OTHER INFORMATION: Cleavage site for Nuclear Inclusion Protease
      from Tobacco ETCHvirus.
<220> FEATURE:
<221> NAME/KEY: SITE
<222> LOCATION: (1)..(7)
<223> OTHER INFORMATION: Cleavage site Nuclear Inclusion protease from
      Tobacco etch virus.
<220> FEATURE:
<221> NAME/KEY: misc_feature
<222> LOCATION: (7)..(7)
<223> OTHER INFORMATION: X can be either G or S

<400> SEQUENCE: 538

Glu Asn Leu Tyr Phe Gln Xaa
1               5

<210> SEQ ID NO 539
<211> LENGTH: 6
<212> TYPE: PRT
<213> ORGANISM: Artificial Sequence
<220> FEATURE:
<223> OTHER INFORMATION: Cleavage site for thrombin
<220> FEATURE:
<221> NAME/KEY: SITE
<222> LOCATION: (1)..(6)
<223> OTHER INFORMATION: Cleavage site for thrombin

<400> SEQUENCE: 539

Leu Val Pro Ala Gly Ser
1               5

<210> SEQ ID NO 540
<211> LENGTH: 4
<212> TYPE: PRT
<213> ORGANISM: Artificial Sequence
<220> FEATURE:
<223> OTHER INFORMATION: Cleavage stite for Coagulation factor FX
<220> FEATURE:
<221> NAME/KEY: SITE
<222> LOCATION: (1)..(4)
<223> OTHER INFORMATION: Cleavage stite for Coagulation factor FX.
```

<400> SEQUENCE: 540

Ile Glu Gly Arg
1